US008299056B2

(12) United States Patent
Bahmanyar et al.

(10) Patent No.: US 8,299,056 B2
(45) Date of Patent: Oct. 30, 2012

(54) AMINOTRIAZOLOPYRIDINES, COMPOSITIONS THEREOF, AND METHODS OF TREATMENT THEREWITH

(75) Inventors: Sogole Bahmanyar, San Diego, CA (US); R.J. Bates, Oceanside, CA (US); Kate Blease, San Diego, CA (US); Andrew Calabrese, San Diego, CA (US); Thomas Daniel, San Diego, CA (US); Mercedes Delgado, San Diego, CA (US); Jan Elsner, San Diego, CA (US); Paul Erdman, San Diego, CA (US); Bruce Fahr, San Diego, CA (US); Gregory Ferguson, San Diego, CA (US); Branden Lee, Encinitas, CA (US); Lisa Nadolny, San Diego, CA (US); Garrick Packard, San Diego, CA (US); Patrick Papa, Carlsbad, CA (US); Veronique Plantevin-Krenitsky, San Diego, CA (US); Jennifer Riggs, Cardiff, CA (US); Patricia Rohane, Florham Park, NJ (US); Sabita Sankar, San Diego, CA (US); John Sapienza, Chula Vista, CA (US); Yoshitaka Satoh, Poway, CA (US); Victor Sloan, Flemington, NJ (US); Randall Stevens, Plainfield, NJ (US); Lida Tehrani, San Diego, CA (US); Jayashree Tikhe, San Diego, CA (US); Eduardo Torres, San Diego, CA (US); Andrew Wallace, San Diego, CA (US); Brandon Wade Whitefield, San Diego, CA (US); Jingjing Zhao, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 411 days.

(21) Appl. No.: 12/555,018

(22) Filed: Sep. 8, 2009

(65) Prior Publication Data

US 2010/0093698 A1 Apr. 15, 2010

Related U.S. Application Data

(60) Provisional application No. 61/095,217, filed on Sep. 8, 2008, provisional application No. 61/230,479, filed on Jul. 31, 2009.

(51) Int. Cl.
*A61K 31/437* (2006.01)
*A61K 31/5377* (2006.01)
*A61K 31/497* (2006.01)
*A61K 31/55* (2006.01)
*C07D 471/02* (2006.01)

(52) U.S. Cl. ........ 514/210.21; 514/303; 514/233.2; 514/253.04; 514/217.07; 546/119; 544/125; 544/362; 540/597

(58) Field of Classification Search ............ 514/210.21, 514/303, 233.2, 253.04, 217.07; 546/119; 544/125, 362; 540/597
See application file for complete search history.

(56) References Cited

U.S. PATENT DOCUMENTS

| 5,434,150 A | 7/1995 | Austel et al. |
| 7,863,291 B2 * | 1/2011 | Cook et al. ............. 514/305 |
| 2011/0065700 A1 | 3/2011 | De Peretti et al. |

FOREIGN PATENT DOCUMENTS

| EP | 0 547 568 | 6/1993 |
| EP | 1894931 | 3/2008 |
| JP | 57206685 | 12/1982 |
| JP | 4190232 | 7/1992 |
| WO | WO 92/16497 | 10/1991 |
| WO | WO 98/21178 | 5/1998 |
| WO | WO 98/30564 | 7/1998 |
| WO | WO 03/010167 | 2/2003 |
| WO | WO 03/057695 | 7/2003 |
| WO | WO 2004/026865 | 4/2004 |
| WO | WO 2005/097052 | 10/2005 |
| WO | WO 2006/018735 | 2/2006 |
| WO | WO 2006/038116 | 4/2006 |
| WO | WO 2007/138072 | 12/2007 |
| WO | 2009047514 | * 4/2009 |
| WO | WO 2009/047514 | 4/2009 |
| WO | 2009131926 | * 10/2009 |
| WO | 2009155565 | * 12/2009 |
| WO | WO 2009/155551 | 12/2009 |
| WO | WO 2009/155565 | 12/2009 |

(Continued)

OTHER PUBLICATIONS

Zhao et al., 2007, *Molecules* 12:1136-1146.
Richardson et al., 2006, *Bioorg. Med. Chem. Lett.* 16(50:1353-1357.
Chan et al., 1999, "The central and multiple roles of B cells in lupus pathogenesis," Immunological Reviews, vol. 169:107-121.
Cohen, 2001, "The role of protein phosphorylation in human health and disease," Eur. J. Biochem., vol. 268:5001-5010.
Cohen, 2002, "Proteins kinase—the major drug targets of the twenty-first century?" Nat. Rev. Drug Discov., vol. 1:309-315.

(Continued)

*Primary Examiner* — Niloofar Rahmani
(74) *Attorney, Agent, or Firm* — Jones Day

(57) ABSTRACT

Provided herein are Heteroaryl Compounds of formula (I):

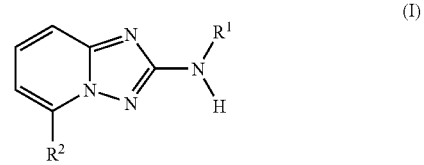

wherein $R^1$ and $R^2$ are as defined herein, compositions comprising an effective amount of a Heteroaryl Compound and methods for treating or preventing inflammatory conditions or cancer, and conditions treatable or preventable by inhibition of a kinase or a kinase pathway comprising administering an effective amount of a Heteroaryl Compound to a subject in need thereof.

31 Claims, No Drawings

FOREIGN PATENT DOCUMENTS

| | | | |
|---|---|---|---|
| WO | 2010010188 | * | 1/2010 |
| WO | 2010010189 | * | 1/2010 |

OTHER PUBLICATIONS

Combs et al., 1999, "Identification of microglial signal transduction pathways mediating a neurotoxic response to amyloidogenic fragments of β-amyloid and prion proteins," J. Neurosci., vol. 19(3):928-939.

Frank, 1999, "Stat signaling in the pathogenesis and treatment of cancer," Mol. Med., vol. 5:432-456.

Gause et al., 2001, "Role of B cells in the pathogenesis of rheumatoid arthritis," BioDrugs, vol. 15(2):73-79.

Gilliland et al., 2002, "The roles of FLT3 in hematopoiesis and leukemia," Blood, vol. 100(5):1532-1542.

Kelly et al., 2002, "CT53518, a novel selective FLT3 antagonist for the treatment of acute myelogenous leukemia (AML)," Cancer Cell, vol. 1:421-432.

Kuno et al., 2001, "Constitutive kinase activation of the TEL-Syk fusion gene in myelodysplastic syndrome with t(9;12)(q22;p12)," Blood, vol. 97(4):1050-1055.

Levis et al., 2005, "FLT3 tyrosine kinase inhibitors," Int. J. Hematol., vol. 52:100-107.

Levis et al., 2002, "A FLT3-targeted tyrosine kinase inhibitor is cytotoxic to leukemia cells in vitro and in vivo," Blood, vol. 99(11):3885-3891.

Malempati et al., 2004, "Outcome after relapse among children with standard risk (SR) all treated on CCG-1952," Blood, vol. 104(11):151a, Abstract #520.

Park et al., 2000, "A novel mechanism of TRAF signaling revealed by structural and functional analyses of the TRADD-TRAF2 interaction," Cell, vol. 101:777-787.

Rivera et al., 1995, "Clustetring of Syk is sufficient to induce tyrosine phosphorylation and release of allergic mediators from rat basophilic leukemia cells," Mol. And Cell. Biol., vol. 15(3):1582-1590.

Seidel et al., 2000, "Pharmaceutical intervention in the JAK/STAT signaling pathway," Oncogene, vol. 19:2645-2656.

Sridhar et al., 2000, "Protein kinases as therapeutic targets," Pharmaceutical Research, vol. 17(11):1345-1353.

Stirewalt et al., 2003, "The role of FLT3 in haematopoietic malignancies," Nat. Rev. Cancer, vol. 3:650-665.

Taylor et al., 1995, "Activation of the high-affinity immunoglobulin E receptor FCεRI in RBL-2H3 cells in inhibited by Syk SH2 domains," Mol. and Cell. Biol., vol. 15(8):4149-4157.

Turner et al., 2000, "Tyrosine kinase SYK: essential functions for immunoreceptor signalling," Immunology Today, vol. 21(3):148-154.

Weisberg et al., 2002, "Inhibition of mutant FLT3 receptors in leukemia cells by the small molecule tyrosine kinase inhibitor," Cancer Cell., vol. 1:433-443.

Yee et al., 2002, "SU5416 and SU5614 inhibit kinase activity of wild-type and mutant FLT3 receptor tyrosine kinase," Blood, vol. 100(8):2941-2949.

* cited by examiner

AMINOTRIAZOLOPYRIDINES, COMPOSITIONS THEREOF, AND METHODS OF TREATMENT THEREWITH

This application claims the benefit of U.S. Provisional Application No. 61/095,217, filed Sep. 8, 2008, and U.S. Provisional Application No. 61/230,479, filed Jul. 31, 2009, the entire contents of which are incorporated herein by reference.

1. FIELD

Provided herein are certain heteroaryl compounds, compositions comprising an effective amount of one or more such compounds and methods for treating or preventing cancer, inflammatory conditions, immunological conditions, metabolic conditions and conditions treatable or preventable by inhibition of a kinase or a kinase pathway, comprising administering an effective amount of a heteroaryl compound to a subject in need thereof.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, inflammation, and angiogenesis. Malfunctions of cellular signaling have been associated with many diseases, the most characterized of which include inflammation, cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research*, 17(11):1345-1353 (2000). Viral infections and the conditions related thereto have also been associated with the regulation of protein kinases. Park et al. *Cell* 101 (7): 777-787 (2000).

Protein kinases can be divided into broad groups based upon the identity of the amino acid(s) that they target (serine/threonine, tyrosine, lysine, and histidine). For example, tyrosine kinases include receptor tyrosine kinases (RTKs), such as growth factors and non-receptor tyrosine kinases, such as the src kinase family. There are also dual-specific protein kinases that target both tyrosine and serine/threonine, such as cyclin dependent kinases (CDKs) and mitogen-activated protein kinases (MAPKs).

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

One of the key events in the signaling pathway following the activation of mast cells is activation of the tyrosine kinase Syk. Mast cells play a critical role in asthma and allergic disorders by releasing pro-inflammatory mediators and cytokines Antigen-mediated aggregation of FcɛRI, the high-affinity receptor for IgE, results in activation of mast cells. This triggers a series of signaling events resulting in the release of mediators, including histamine, proteases, leukotrienes and cytokines. These mediators cause increased vascular permeability, mucus production, bronchoconstriction, tissue degradation and inflammation, thus playing key roles in the etiology and symptoms of asthma and allergic disorders. Syk kinase acts as a central initiator of all subsequent signaling leading to mediator release. The critical role of Syk kinase in the signaling path was demonstrated by the complete inhibition of mediator release by a protein containing the SH2 domains of Syk kinase that functioned as an inhibitor of Syk kinase (J. A. Taylor et al., *Molec. and Cell Biol.*, 15: 4149-4157 (1995). Furthermore, direct clustering of Syk, introduced into a mast cell line as part of a chimeric transmembrane protein, was found to be sufficient to stimulate the events leading to mediator release normally induced by clustering of FcɛRI (V. M. Rivera et al, *Molec. and Cell. Biol.*, 15: 1582-1590 (1995).

Activation and activity of Syk kinase is required for FIɛRI-mediated release of mediators from mast cells. Therefore, agents that block the activity of Syk kinase act to block the release of allergic and pro-inflammatory mediators and cytokines. These agents have potential utility in treating inflammatory and allergic disorders including asthma, chronic obstructive pulmonary disease (COPD), adult or acute respiratory distress syndrome (ARDS), ulcerative colitis, Crohn's disease, bronchitis, conjunctivitis, psoriasis, scleroderma, urticaria, dermatitis and allergic rhinitis.

In addition to mast cells, Syk is expressed in other hematopoietic cells including B cells, where it is thought to play an essential role in transducing signals required for the transition of immature B cells into mature recirculating B cells (M. Turner et al., *Immunology Today*, 21: 148 (2000). B cells are reported to play an important role in some inflammatory conditions such as lupus (O. T. Chan et al., *Immunological Rev*, 169: 107-121 (1999) and rheumatoid arthritis (A. Gause et al, *Biodrugs*, 15(2): 73-79 (2001).

Syk was also reported to be an element of the signaling cascade in beta-amyloid and prion fibrils leading to production of neurotoxic products (C. K. Combs et al., *J. Neurosci.*, 19: 928-939 (1999). Furthermore, an inhibitor of Syk blocked the production of these neurotoxic products. Thus Heteroaryl Compound would potentially be useful in the treatment of Alzheimer's disease and related neuroinflammatory diseases. Another report (Y. Kuno et al., *Blood*, 97, 1050-1055 (2001) demonstrates that Syk plays an important role in malignant progression. A TEL-Syk fusion protein was found to transform hematopoietic cells suggesting a role in the pathogenesis of hematopoietic malignancies. Therefore Heteroaryl Compound may be useful in the treatment of certain types of cancers.

Other protein tyrosine kinases involved in hematologic malignancies include ABL (ABL1), ARG (ABL2), PDGFβR, PDGFaR, JAK2, TRKC, FGFR1, FGFR3, FLT3, and FRK. The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas (for a review of the pharmaceutical intervention of the JAK/STAT pathway see Frank, *Mol. Med.* 5, 432:456 (1999), and Seidel et al, *Oncogene* 19, 2645-2656 (2000). JAK2 is a well validated target with strong potential in the treatment of myeloproliferative disorders (MPDs), which include polycythemia vera (PV), essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

Fms-like tyrosine kinase 3 (FLT3), which is also known as FLK-2 (fetal liver kinase 2) and STK-I (stem cell kinase 1), plays an important role in the proliferation and differentiation of hematopoietic stem cells. FLT3 receptor kinase is expressed in normal hematopoietic cells, placenta, gonads, and brain. However, this enzyme is expressed at very high levels on the cells of more than 80% of myelogenous patients and of a fraction of acute lymphoblastic leukemia cells. Furthermore, the enzyme can also be found on cells from patients with chronic myelogenous leukemia in lymphoid blast crisis. It has been reported that FLT3 kinase is mutated in 30% of acute myeloid leukemia (AML) and in a subset of acute lymphoblastic leukemia (ALL) as well (Gilliland et al, *Blood* 100, 1532-1542 (2002); Stirewalt et al., *Nat. Rev. Cancer*, 3, 650-665 (2003). The most common activating mutations in FLT3 are internal tandem duplications within the juxtamembrane region, while point mutations, insertions, or deletions in the kinase domain are less common. Some of these mutant FLT3 kinases are constitutively active. FLT3 mutations have been associated with a poor prognosis (Malempati et al., *Blood*, 104, 11 (2004). More than a dozen known FLT3 inhibitors are being developed and some have shown promising clinical effects against AML (Levis et at Int. *J. Hematol.*, 52, 100-107 (2005). It has been reported that some of small-molecule FLT3 inhibitors are effective in inducing apoptosis in cell lines with FLT3-activating mutations and prolonging survival of mice that express mutant FLT3 in their bone marrow cells (Levis et al, *Blood*, 99, 3885-3891 (2002); Kelly et al, *Cancer Cell*, 1, 421-432 (2002); Weisberg et al, *Cancer Cell*, 1, 433-443 (2002); Yee et al, *Blood*, 100, 2941-2949 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

Citation or identification of any reference in Section 2 of this application is not to be construed as an admission that the reference is prior art to the present application.

3. SUMMARY

Provided herein are Heteroaryl Compounds having the following formula (I):

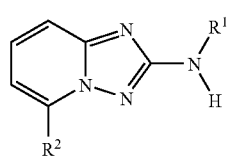

(I)

and pharmaceutically acceptable salts, tautomers, stereoisomers, solvates, or prodrugs thereof, wherein $R^1$ and $R^2$ are as defined herein.

In one aspect, provided herein are Heteroaryl Compounds shown in Table 1 of the instant disclosure and pharmaceutically acceptable salts, tautomers, stereoisomers, solvates and prodrugs thereof.

In one aspect, provided herein are pharmaceutical compositions comprising an effective amount of a Heteroaryl Compound as described herein or pharmaceutically acceptable salt, tautomer, stereoisomer, solvate or prodrug thereof, and a pharmaceutically acceptable carrier, excipient or vehicle. In some embodiments the pharmaceutical composition is suitable for oral, parenteral, mucosal, transdermal or topical administration.

In one aspect, provided herein are methods for treating or preventing inflammatory conditions, immunological conditions, autoimmune conditions, allergic conditions, rheumatic conditions, thrombotic conditions, cancer, infections, neurodegenerative diseases, neuroinflammatory diseases, cardiovascular diseases, and metabolic conditions, comprising administering to a subject in need thereof an effective amount of a Heteroaryl Compound as described herein or a pharmaceutically acceptable salt, tautomer, stereoisomer, solvate or prodrug thereof and a pharmaceutically acceptable carrier, excipient or vehicle. In some embodiments, the methods further include administration of additional therapeutic ingredients as described herein.

In one aspect, provided herein are methods for inhibiting a kinase in a cell expressing said kinase, comprising contacting said cell with an effective amount of a Heteroaryl Compound as described herein or a pharmaceutically acceptable salt, tautomer, stereoisomer, solvate or prodrug thereof.

In one aspect, provided herein are methods for the treatment or prevention of cancer, comprising administering to a subject having cancer an amount of a Heteroaryl Compound as described herein or a pharmaceutically acceptable salt, tautomer, stereoisomer, solvate or prodrug thereof.

The present embodiments can be understood more fully by reference to the detailed description and examples, which are intended to exemplify non-limiting embodiments.

4. DETAILED DESCRIPTION

4.1 Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tent-butyl, -isopentyl, 2-methylpentyl, 3-methylpentyl, 4-methylpentyl, 2,3-dimethylbutyl and the like. Examples of unsaturared alkyl groups include, but are not limited to, vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, —C≡CH, —C≡C(CH$_3$), —C≡C(CH$_2$CH$_3$), —CH$_2$C≡CH, —CH$_2$C≡C(CH$_3$) and —CH$_2$C≡C(CH$_7$CH$_3$), among others. An alkyl group can be substituted or unsubstituted.

A "cycloalkyl" group is a saturated, partially saturated, or unsaturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like. Examples of unsaturared cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanone and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl (e.g., imidazolidin-4-one or imidazolidin-2,4-dionyl) groups. The phrase heterocyclyl includes fused ring species, including those comprising fused aromatic and non-aromatic groups, such as, for example, benzotriazolyl (e.g., 1H-benzo[d][1,2,3]triazolyl), benzimidazolyl (e.g., 1H-benzo[d]imidazolyl), 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, benzisoxazolyl (e.g., benzo[d]isoxazolyl), thiazolyl, thiazolinyl, isothiazolyl, thiadiazolyl, oxadiazolyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dioxyl, dithianyl, pyranyl, pyridyl, pyrimidyl, pyridazinyl, pyrazinyl, triazinyl, dihydropyridyl, dihydrodithiinyl, dihydrodithionyl, homopiperazinyl, quinuclidyl, indolyl (e.g., indolyl-2-onyl or isoindolin-1-onyl), indolinyl, isoindolyl, isoindolinyl, azaindolyl (pyrrolopyridyl or 1H-pyrrolo[2,3-b]pyridyl), indazolyl, indolizinyl, benzotriazolyl (e.g. 1H-benzo[d][1,2,3]triazolyl), benzimidazolyl (e.g., 1H-benzo[d]imidazolyl or 1H-benzo[d]imidazol-2(3H)-onyl), benzofuranyl, benzothiophenyl, benzothiazolyl, benzoxadiazolyl, benzoxazinyl, benzodithiinyl, benzoxathiinyl, benzothiazinyl, benzoxazolyl (i.e., benzo[d]oxazolyl), benzothiazolyl, benzothiadiazolyl, benzo[1,3]dioxolyl, pyrazolopyridyl (for example, 1H-pyrazolo[3,4-b]pyridyl, 1H-pyrazolo[4,3-b]pyridyl), imidazopyridyl (e.g., azabenzimidazolyl or 1H-imidazo[4,5-b]pyridyl), triazolopyridyl, isoxazolopyridyl, purinyl, xanthinyl, adeninyl, guaninyl, quinolinyl, isoquinolinyl (e.g., 3,4-dihydroisoquinolin-1(2H)-onyl), quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, tetrahydropyrimidin-2(1H)-one and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyrdine-3-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: —$NH_2$.

An "alkylamino" group is a radical of the formula: —NH-alkyl or —N(alkyl)$_2$, wherein each alkyl is independently as defined above.

A "carboxy" group is a radical of the formula: —C(O)OH.

An "aminocarbonyl" group is a radical of the formula: —C(O)N(R$^\#$)$_2$, —C(O)NH(R$^\#$) or —C(O)NH$_2$, wherein each R$^\#$ is independently a substituted or unsubstituted alkyl, cycloalkyl, aryl, aralkyl, heterocyclyl or heterocyclyl group as defined herein.

An "acylamino" group is a radical of the formula: —NHC(O)(R$^\#$) or —N(alkyl)C(O)(R$^\#$), wherein each alkyl and R$^\#$ are independently as defined above.

A "sulfonylamino" group is a radical of the formula: —NHSO$_2$(R$^\#$) or —N(alkyl)SO$_2$(R$^\#$), wherein each alkyl and R$^\#$ are defined above.

A "urea" group is a radical of the formula: —N(alkyl)C(O)N(R$^{14}$)$_2$, —N(alkyl)C(O)NH(R$^\#$), —N(alkyl)C(O)NH$_2$, —NHC(O)N(R$^\#$)$_2$, —NHC(O)NH(R$^\#$), or —NH(CO)NHR$^\#$, wherein each alkyl and R$^\#$ are independently as defined above.

In one embodiment, when the groups described herein are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl)aryloxy; aralkyloxy; heterocyclyloxy; and heterocyclyl alkoxy.

As used herein, the term "Heteroaryl Compound" refers to compounds of formula (I) as well as to further embodiments provided herein. In one embodiment, a "Heteroaryl Compound" is a compound set forth in Table 1. The term "Heteroaryl Compound" includes pharmaceutically acceptable salts, tautomers, stereoisomers, solvates and prodrugs of the compounds provided herein.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Heteroaryl Compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride and mesylate salts. Others are well-known in the art, see for example, *Remington's Pharmaceutical Sciences,* 18$^{th}$ eds., Mack Publishing, Easton Pa. (1990) or *Remington: The Science and Practice of Pharmacy,* 19$^{th}$ eds., Mack Publishing, Easton Pa. (1995).

As used herein and unless otherwise indicated, the term "solvate" means a Heteroaryl Compound, or a salt thereof, that further includes a stoichiometric or non-stoichiometric amount of a solvent bound by non-covalent intermolecular forces. In some embodiments, the solvate is a hydrate. As used herein and unless otherwise indicated, the term "hydrate" means a Heteroaryl Compound, or a salt thereof, that further includes a stoichiometric or non-stoichiometric amount of water bound by non-covalent intermolecular forces.

As used herein and unless otherwise indicated, the term "prodrug" means a Heteroaryl Compound derivative that can hydrolyze, oxidize, or otherwise react under biological conditions (in vitro or in vivo) to provide an active compound, particularly a Heteroaryl Compound. Examples of prodrugs include, but are not limited to, derivatives and metabolites of a Heteroaryl Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a Heteroaryl Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Heteroaryl Compounds can have chiral centers and can occur as racemates, individual enantiomers or diastereomers, and mixtures thereof. All such isomeric forms are included within the embodiments disclosed herein, including mixtures thereof.

The use of stereomerically pure forms of such Heteroaryl Compounds, as well as the use of mixtures of those forms are encompassed by the embodiments disclosed herein. For example, mixtures comprising equal or unequal amounts of the enantiomers of a particular Heteroaryl Compound may be used in methods and compositions disclosed herein. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

It should also be noted the Heteroaryl Compounds can include E and Z isomers, or a mixture thereof, and cis and trans isomers or a mixture thereof. In certain embodiments, the Heteroaryl Compounds are isolated as either the E or Z isomer. In other embodiments, the Heteroaryl Compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

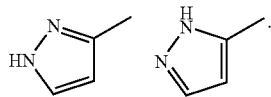

As readily understood by one skilled in the art, a wide variety of functional groups and other structures may exhibit tautomerism and all tautomers of compounds of formula (I) are within the scope of the present invention.

It should also be noted the Heteroaryl Compounds can contain unnatural proportions of atomic isotopes at one or more of the atoms. For example, the compounds may be radiolabeled with radioactive isotopes, such as for example tritium (3H), iodine-125 ($^{125}$I), sulfur-35 ($^{35}$S), or carbon-14 ($^{14}$C), or may be isotopically enriched, such as with deuterium ($^{2}$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Heteroaryl Compounds as described herein, whether radioactive or not, are intended to be encompassed within the scope of the embodiments provided herein. In some embodiments, there are provided isotopologues of the Heteroaryl Compounds, for example, the isotopologues are deuterium, carbon-13, or nitrogen-15 enriched Heteroaryl Compounds.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with an Heteroaryl Compound can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer, metabolic conditions or conditions treatable or preventable by inhibition of a kinase or a kinase pathway, in one embodiment, the Syk, FLT-3, JAK1 and/or JAK2 pathway. In one embodiment an effective amount of a Heteroaryl Compound is an amount that inhibits a kinase in a cell, such as, for example, in vitro or in vivo. In some embodiments, the effective amount of the Heteroaryl Compound inhibits the kinase in a cell by 10%, 20%, 30%, 40%, 50%, 60%, 70%, 80%, 90% or 99%, compared to the activity of the kinase in an untreated cell. The effective amount of the Heteroaryl Compound, for example in a pharmaceutical composition, may be at a level that will exercise the desired effect; for example, about 0.005 mg/kg of a subject's body weight to about 10 mg/kg of a subject's body weight in unit dosage for both oral and parenteral administration.

A "kinase inhibitor" within the instant context is a compound which at a concentration of 10 μM inhibits the phosphorylating ability of the kinase enzyme by about 50% or greater than 50%, as determined by the HTRF enzyme assays as described herein. In some embodiments, the kinase is Syk kinase, in others the kinase is Syk, FLT3, JAK1, and/or JAK2.

"Fc Receptor" refers to a member of the family of cell surface molecules that binds the Fc portion (containing the specific constant region) of an immunoglobulin. Each Fc receptor binds immunoglobulins of a specific type. For example the Fc alpha receptor ("FcαR") binds IgA, the FcεR binds IgE and the FcγR binds IgG.

The FcαR family includes the polymeric Ig receptor involved in epithelial transport of IgA/IgM, the myeloid specific receptor RcαRI (also called CD89), the Fcα/μIR and at least two alternative IgA receptors (for a recent review see Monteiro & van de Winkel, 2003, Annu Rev. Immunol, advanced e-publication. The FcαRI is expressed on neutrophils, eosinophils, moncytes/macrophages, dendritic cells and kupfer cells. The FcαRI includes one alpha chain and the FcR gamma homodimer that bears an activation motif (ITAM) in the cytoplasmic domain and phosphorylates Syk kinase.

The FcεR family includes two types, designated FcεRI and FcεRII (also known as CD23). FcεRI is a high affinity receptor found on mast, basophil and eosinophil cells that anchors monomeric IgE to the cell surface. The FcεRI possesses one alpha chain, one beta chain and the gamma chain homodimer discussed above. The FcεRII is a low affinity receptor expressed on mononuclear phagocytes, B lymphocytes, eosinophils and platelets. The FcεRII comprises a single polypeptide chain and does not include the gamma chain homodimer.

The FcγR family includes three types, designated FcγRI (also known as CD64), FcγRII (also known as CD32) and FcγRIII (also known as CD16). FcγRI is a high affinity receptor found on mast, basophil, mononuclear, neutrophil, eosinophil, deudritic and phagocyte cells that anchors nomomeric IgG to the cell surface. The FcγRI includes one alpha chain and the gamma chain dimer shared by FcαRI and FcεRI.

The FcγRII is a low affinity receptor expressed on neutrophils, monocytes, eosinophils, platelets and B lymphocytes. The FcγRII includes one alpha chain, and does not include the gamma chain homodimer discussed above.

The FcγRIII is a low affinity expressed on NK, eosinophil, macrophage, neutrophil and mast cells. It comprises one alpha chain and the gamma homodimer shared by FcαRI, FcεRI and FcγRI.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

"Hematopoietic neoplasm" refers to a cell proliferative disorder arising from cells of the hematopoietic lineage. Generally, hematopoiesis is the physiological process whereby undifferentiated cells or stem cells develop into various cells found in the peripheral blood. In the initial phase of development, hematopoietic stem cells, typically found in the bone marrow, undergo a series of cell divisions to form multipotent progenitor cells that commit to two main developmental pathways: the lymphoid lineage and the myeloid lineage. The committed progenitor cells of the myeloid lineage differentiate into three major sub-branches comprised of the erythroid, megakaryocyte, and granulocyte/monocyte developmental pathways. An additional pathway leads to formation of dendritic cells, which are involved in antigen presentation. The erythroid lineage gives rise to red blood cells while the megakaryocytic lineage gives rise to blood platelets. Committed cells of the granulocyte/monocyte lineage split into granulocyte or monocyte developmental pathways, the former pathway leading to formation of neutrophils, eosinophils, and basophils and the latter pathway giving rise to blood monocytes and macrophages.

"Lymphoid neoplasm" refers a proliferative disorder involving cells of the lymphoid lineage of hematopoiesis. Lymphoid neoplasms can arise from hematopoietic stem cells as well as lymphoid committed progenitor cells, precursor cells, and terminally differentiated cells. These neoplasms can be subdivided based on the phenotypic attributes of the aberrant cells or the differentiated state from which the abnormal cells arise. Subdivisions include, among others, B cell neoplasms, T cell neoplasms, NK cell neoplasms, and Hodgkin's lymphoma.

"Myeloid neoplasm" refers to proliferative disorder of cells of the myeloid lineage of hematopoiesis. Neoplasms can arise from hematopoietic stem cells, myeloid committed progenitor cells, precursor cells, and terminally differentiated cells. Myeloid neoplasms can be subdivided based on the phenotypic attributes of the aberrant cells or the differentiated state from which the abnormal cells arise. Subdivisions include, among others, myeloproliferative diseases, myelodysplastic/myeloproliferative diseases, myelodysplastic syndromes, acute myeloid leukemia, and acute biphenotypic leukemia.

"Virally mediated tumor" refers to a neoplasm or tumor associated with viral infection or an activity of a virally encoded product. The neoplasm can arise from presence of a latent virus integrated into the cellular genome or arise from activity of a virally associated gene product. Infection with the virus need not be tightly correlated in time with tumor formation in that incubation periods can extend from months to years before development of a tumor phenotype. Because in some embodiments, the treatments herein are directed to the use of Syk inhibitory Heteroaryl Compounds, the applicable virally associated tumors are those in which viral modulation of Syk activity is correlated with aberrant cell proliferation. Any virus, including RNA and DNA viruses and viruses that reside episomally or integrate into the cellular genome, in which activation of Syk is a consequence of virus infection can be targeted using the methods herein.

"Tumor metastasis" refers to the capability of tumor cells to migrate from the original tumor site and colonize in other tissues. Tumors formed from cells that have spread are referred to as "secondary tumors" and contain cells that are similar to those in the original "primary" tumor. Metastatic tumors typically form by migration of tumor cells from the original tumor site through the blood and lymph system to other tissues.

The terms "patient" and "subject" include an animal, including, but not limited to, an animal such as a cow, monkey, horse, sheep, pig, chicken, turkey, quail, cat, dog, mouse, rat, rabbit or guinea pig. In one embodiment the subject is a mammal, in another a human. In certain embodiments, a patient or subject "in need thereof" is a patient or subject having a certain disease or disorder or at risk for having a disease or disorder.

4.2 Heteroaryl Compounds

Provided herein are Heteroaryl Compounds having the following formula (I):

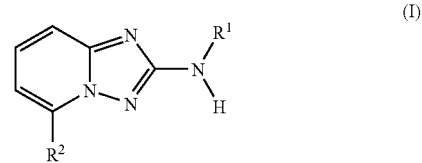

and pharmaceutically acceptable salts, tautomers, stereoisomers, solvates and prodrugs thereof, wherein:

$R^1$ is a substituted or unsubstituted aryl, or a substituted or unsubstituted heterocyclyl;

$R^2$ is a substituted or unsubstituted $C_{1-8}$ alkyl, a substituted or unsubstituted cycloalkyl, a substituted or unsubstituted heterocyclylalkyl, a substituted or unsubstituted aralkyl, —$NR^3R^4$, —$OR^3$, —$C(=O)R^5$, —$C(=O)NR^3R^4$, —NHC(=O)$R^3$, —$(CH_2)_{0-2}CR^6(OR^3)R^4$, or a substituted or unsubstituted heterocyclyl selected from azetidinyl, pyrrolidyl, piperidyl, morpholinyl, piperazin-2-onyl, 1,2,3,6-tetrahydropyridyl, isoxazolyl, imidazolyl, indazolyl, benzimidazolyl, 1H-benzo[d][1,2,3]triazolyl, benzisoxazolyl, benzo[d]oxazolyl, isoindolin-1-onyl, 1H-imidazo[4,5-b]pyridyl, isoquinolinyl, or quinolyl; or $R^2$ is pyridyl, provided $R^1$ is not (2-(pyrrolidin-1-yl)ethoxy)phenyl-4-yl;

$R^3$ and $R^4$ are at each occurrence independently —H, a substituted or unsubstituted $C_{1-8}$ alkyl, a substituted or unsubstituted aryl, a substituted or unsubstituted heteroaryl, a substituted or unsubstituted cycloalkyl, a substituted or unsubstituted heterocyclyl, a substituted or unsubstituted aralkyl, or a substituted or unsubstituted heterocyclylalkyl;

$R^5$ is substituted or unsubstituted $C_{1-8}$ alkyl, a substituted or unsubstituted aryl, a substituted or unsubstituted heteroaryl, a substituted or unsubstituted cycloalkyl, a substituted or unsubstituted heterocyclyl, a substituted or unsubstituted aralkyl, or a substituted or unsubstituted heterocyclylalkyl; and $R^6$ is —H, or a substituted or unsubstituted $C_{1-8}$ alkyl, or together with $R^4$ and the atoms to which they are attached form a substituted or unsubstituted heterocyclyl;

provided the compound is not $N^5$-cyclopentyl-$N^2$-(4-(2-(pyrrolidin-1-yl)ethoxy)phenyl)-[1,2,4]triazolo[1,5-a]pyridine-2,5-diamine, shown below:

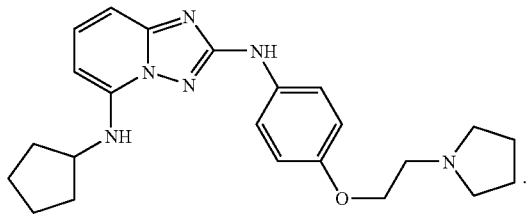

In one embodiment, the Heteroaryl Compound is a compound of formula (I), wherein $R^1$ is a substituted or unsubstituted aryl, for example, a substituted or unsubstituted phenyl. In some such embodiments, $R^1$ is phenyl, substituted with one or more substituted or unsubstituted $C_{1-4}$ alkyl, substituted or unsubstituted heterocyclyl, halogen, hydroxyl, alkoxy, carboxy, —CN, —($C_{0-4}$alkyl)$NR_2$, —O($C_{1-4}$alkyl)$NR_2$, —$NR_2$, or —C(=O)$NR_2$, wherein each R is independently H, a substituted or unsubstituted $C_{1-6}$ alkyl, or a substituted or unsubstituted heterocyclyl. For example, in certain embodiments, $R^1$ is phenyl, substituted with one or more —F, —Cl, —$CF_3$, —CN, hydroxyl, carboxy, methyl, —($C_{0-4}$alkyl)$NH_2$, —($C_{0-4}$ alkyl)NH($C_{1-4}$alkyl), —O($C_{1-4}$alkyl), —O($C_{1-4}$alkyl)O($C_{1-4}$ alkyl), —O($C_{1-4}$alkyl)$NH_2$, —N($C_{1-4}$alkyl)$_2$, —C(=O)$NH_2$, —C(=O)NH($C_{1-4}$alkyl), —C(=O)NH (substituted or unsubstituted piperidyl), or a substituted or unsubstituted heterocyclyl selected from morpholinyl, triazolyl, pyrrolidyl, imidazolyl or pyrrolidinonyl.

In some embodiments, the Heteroaryl Compound is a compound of formula (I), wherein $R^1$ is a substituted or unsubstituted heterocyclyl. For example, in certain embodiments, $R^1$ is a substituted or unsubstituted heterocyclyl selected from isoindolin-1-onyl, pyridyl, pyrimidyl, indazolyl, indolinyl, isoindolinyl, indolin-2-onyl, quinolinyl, dihydroisoquinolin-1-onyl, benzotriazolyl, benzimidazolyl, 1H-pyrazolo[3,4-b]pyridyl, 1H-pyrazolo[4,3-b]pyridyl, 1H-benzo[d]imidazol-2(3H)-onyl, benzisoxazolyl, isoquinolinyl, dihydrobenziisothiazole-1,1-dionyl or pyrrolopyridyl. In some such embodiments, $R^1$ is substituted with one or more substituted or unsubstituted $C_{1-4}$alkyl, substituted or unsubstituted heterocyclyl, halogen, hydroxyl, hydroxyalkyl, alkoxy, —CN, —OR, —$NR_2$, —($C_{1-4}$alkyl)$NR_2$, —C(=O)$NR_2$ or —C(O)R, wherein each R is independently —H, a substituted or unsubstituted $C_{1-6}$ alkyl, a substituted or unsubstituted heterocyclyl or a substituted or unsubstituted heterocyclylalkyl.

In some such embodiments, $R^1$ is

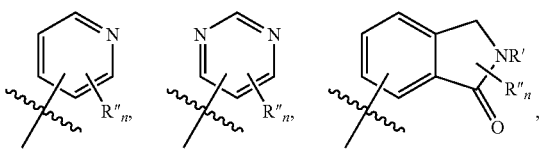

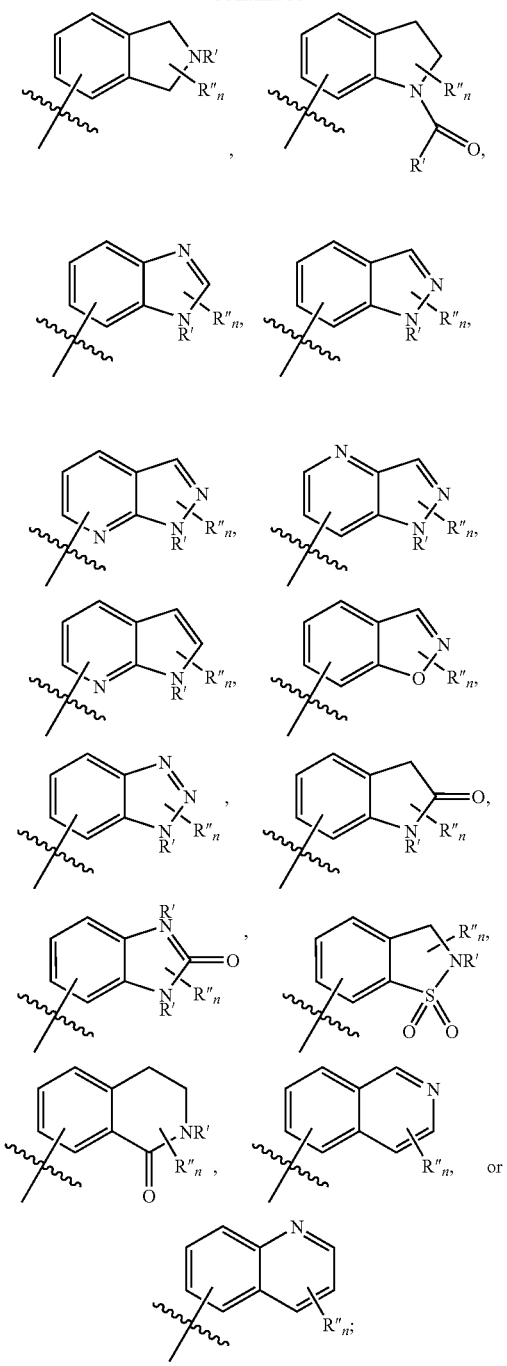

wherein R' is —H, or a substituted or unsubstituted $C_{1-6}$ alkyl; each R" is independently a substituted or unsubstituted $C_{1-4}$alkyl, substituted or unsubstituted heterocyclyl, unsubstituted heterocyclylalkyl, hydroxyl, halogen, alkoxy, —CN, —OR, —$NR_2$, —($C_{1-4}$ alkyl)$NR_2$, —C(=O)$NR_2$, wherein each R is independently —H, a substituted or unsubstituted $C_{1-6}$ alkyl, a substituted or unsubstituted heterocyclyl, or a substituted or unsubstituted heterocyclylalkyl; and n is 0-2.

It will be understood by those of skill in the art that any of the substitutents R" may be attached to any suitable atom of any of the rings in the fused ring systems. For example, in some embodiments, $R^1$ is

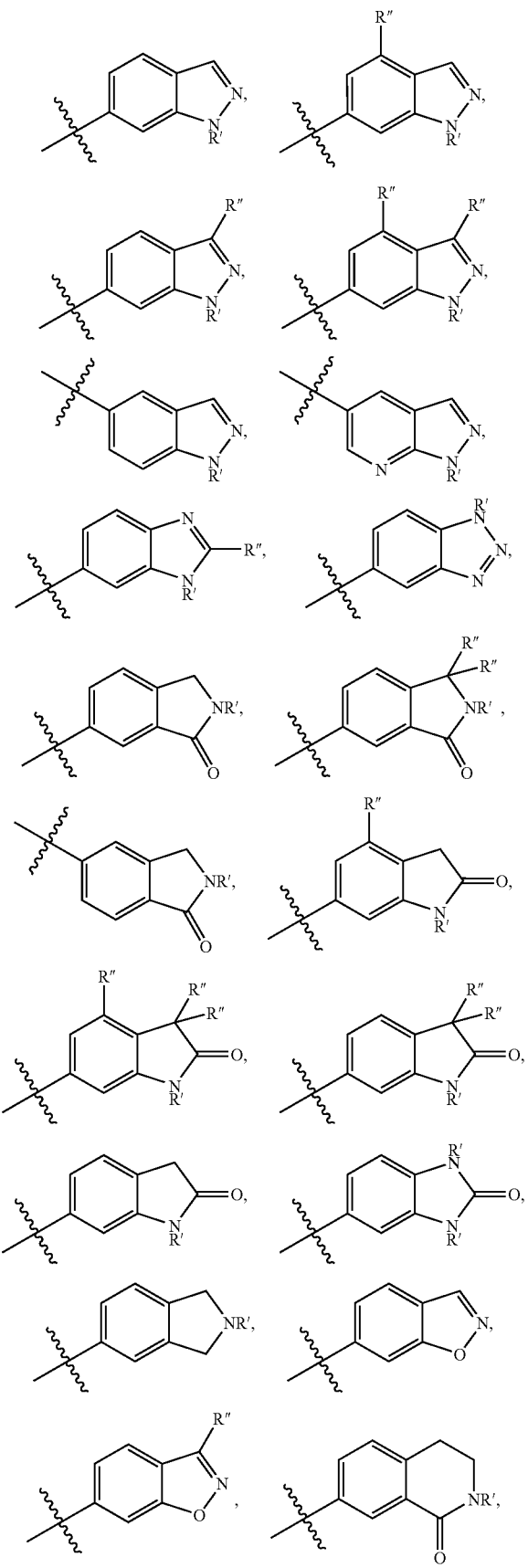

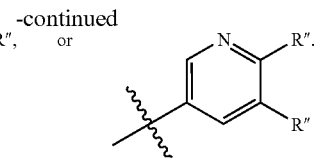

In some embodiments, R' is —H, —CH$_3$, —CH$_2$CH$_3$, isopropyl, —(CH$_2$)$_2$OH, —(CH$_2$)$_2$NH$_2$, or —(CH$_2$)$_2$OCH$_3$. In other embodiments, R" is —F, —CH$_3$, —CH$_2$CH$_3$, isopropyl, —NH(Cl$_{1-3}$ alkyl)NH$_2$, —NH(CH$_2$)$_2$OH, —CF$_3$, —OH, —OCH$_3$, —O(CH$_2$)$_2$OCH$_3$, —O(CH$_2$)$_2$OH, —O(CH$_2$)$_2$NH$_2$, —O(CH$_2$)$_2$pyrrolidyl, —CH$_2$OH, —(CH$_2$)$_2$OH, —CH$_2$OCH$_3$, —(CH$_2$)$_2$OCH$_3$, —CH$_2$NH$_2$, —CH$_2$NHCH$_3$, —CH$_2$N(CH$_3$)$_2$, —C(CH$_3$)$_2$OH, —CN, —NH$_2$, —NHCH$_3$, —N(CH$_3$)$_2$, —NH(CH$_2$)$_2$NH$_2$, —C(=O)NH$_2$, —C(=O)NHCH$_3$, —NH(CH$_2$)$_2$pyrrolidyl, —NH (substituted or unsubstituted piperidyl), substituted or unsubstituted piperidyl, —NH (substituted or unsubstituted tetrahydropyranyl), or substituted or unsubstituted morpholinyl.

In some embodiments, the Heteroaryl Compound is a compound of formula (I), wherein R$^2$ is pyridyl, provided R$^1$ is not (2-(pyrrolidin-1-yl)ethoxy)phenyl-4-yl, that is, R$^1$ is not

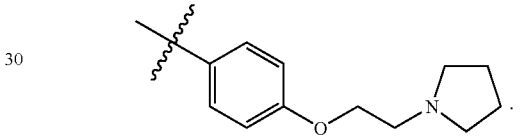

In some embodiments, the Heteroaryl Compound is a compound of formula (I), wherein R$^2$ is a substituted or unsubstituted C$_{1-6}$ alkyl. For example, in certain embodiments, R$^2$ is methyl, ethyl, n-propyl, isopropyl, n-butyl, sec-butyl, isobutyl, or tert-butyl, optionally substituted with one or more —OH, —C(O)NH$_2$, —NH$_2$, alkylamino, —NHCH$_2$C(=O)NH$_2$, cyclopentyl, cyclopentanol, cyclohexyl, cyclohexanol, or 1-methylcyclohexanol-4-yl. In some embodiments, R$^2$ is a substituted or unsubstituted cycloalkyl, for example, R$^2$ is cyclohexyl. In other embodiments, R$^2$ is a substituted or unsubstituted heterocyclylalkyl, for example, —CH$_2$-azetidinyl, —CH$_2$-piperidyl, —CH$_2$-pyridin-2(1H)-onyl, —CH$_2$-pyridyl, —CH$_2$-piperazin-2-onyl, —CH$_2$-piperazin-2,6-dionyl, —CH$_2$-piperazinyl, —CH$_2$-pyrrolidyl, —CH$_2$-1,4-dioxanyl, —CH$_2$-piperidin-2,6-dionyl, —CH$_2$-imidazolidinyl, —CH$_2$-imidazolidin-4-onyl, —CH$_2$-morpholinyl, —CH$_2$-tetrahydropyrimidin-2(1H)-onyl, —CH$_2$-1,4-diazepan-5-onyl, —CH$_2$-tetrahydro-2H-pyranyl or —CH$_2$-imidazolidin-2,4-dionyl; wherein the heterocyclylalkyl is optionally substituted with one or more methyl, ethyl, isopropyl, halogen, —OH, —(CH$_2$)OH, or —C(=O)NH$_2$. For example, in some embodiments, R$^2$ is —CF$_2$—(tetrahydro-2H-pyran-4-yl) or —CF$_2$-(1,4-dioxan-2-yl).

In some embodiments, the Heteroaryl Compound is a compound of formula (I), wherein R$^2$ is —NR$^3$R$^4$. For example, in certain embodiments, R$^2$ is —NH(C$_{1-6}$ alkyl), —N(C$_{1-6}$ alkyl)$_2$, —N(C$_{1-6}$alkyl)(cycloalkyl), —NH(aryl), —NH(heteroaryl), —NH(cycloalkyl), —NH(cycloalkylalkyl), —NH(heterocyclyl), —N(C$_{1-6}$ alkyl)(heterocyclyl), or —NH(heterocyclylalkyl), wherein each alkyl, aryl, heteroaryl, cycloalkyl, cycloalkylalkyl, heterocyclyl and heterocyclylalkyl is independently substituted or unsubstituted. In some embodiments, R$^2$ is —NH(methyl), —N(methyl)$_2$, —N(methyl)(ethyl), —NH(ethyl), —NH(propyl), —NH(isopropyl), —NH(cyclopentyl), —NH(cyclohexyl), —N(cyclohexyl)(methyl), —NHCH$_2$(cyclopentyl), —NHCH$_2$(cyclohexyl), —NH(phenyl), —NH(pyridyl), —NH(piperidyl), —NH(tetrahydro-2H-pyranyl), —N(methyl)(tetrahydro-2H-pyranyl), —NH(azepanyl), —NH(tetrahydrofuranyl), —N(methyl)(tetrahydrofuranyl), —NH(pyrrolidyl), or —NHCH$_2$(tetrahydro-2H-pyranyl), wherein each methyl, ethyl, propyl, isopropyl, cyclopentyl, cyclohexyl, phenyl, pyridyl, piperidyl, pyrrolidyl, tetrahydro-2H-pyranyl, azepanyl, or tetrahydrofuranyl is independently substituted or unsubstituted. In some such embodiments, the methyl, ethyl, propyl, isopropyl, cyclopentyl, cyclohexyl, phenyl, pyridyl, piperidyl, pyrrolidyl, tetrahydro-2H-pyranyl, azepanyl, or tetrahydrofuranyl, is substituted with one or more phenyl, C$_{1-4}$alkyl, hydroxyalkyl, —NR$_2$, —OR, or —C(=O)NR$_2$, wherein each R is independently —H, a substituted or unsubstituted C$_{1-6}$ alkyl, a substituted or unsubstituted heterocyclyl or a substituted or unsubstituted heterocyclylalkyl.

In some embodiments, the Heteroaryl Compound is a compound of formula (I), wherein R$^2$ is —NHC(=O)R$^3$, wherein R$^3$ is a substituted or unsubstituted C$_{1-4}$ alkyl. In others, R$^2$ is —C(=O)NR$^3$R$^4$, and R$^3$ and R$^4$ are independently —H, or a substituted or unsubstituted C$_{1-4}$ alkyl, or a substituted or unsubstituted heterocyclyl. In still others, R$^2$ is —OR$^3$. In some such embodiments, R$^3$ is cyclohexyl, methyl, ethyl, propyl, piperidyl, tetrahydro-2H-pyranyl, tetrahydrofuranyl, —CH$_2$(pyrrolidyl), or phenyl, optionally substituted with one or more —OH, —NH$_2$, or —(C=O)NH$_2$. In still other embodiments, R$^2$ is —C(=O)R$^5$. For example, in certain embodiments, R$^5$ is phenyl.

In some embodiments, the Heteroaryl Compound is a compound of formula (I), wherein R$^2$ is —(CH$_2$)$_{0-2}$CR$^6$(OR$^3$)R$^4$. For example, in certain embodiments, R$^2$ is —CH(OR$^3$)R$^4$. In some such embodiments, R$^3$ is —H and R$^4$ is phenyl, piperidyl, pyridyl, pyrimidin-4(3H)-onyl, or tetrahydrofuranyl. In some other embodiments, R$^3$ is —H, and R$^4$ and R$^6$, together with the atoms to which they are bound, form a piperidyl.

In some embodiments, the Heteroaryl Compound is a compound of formula (I), wherein R$^2$ is a substituted or unsubstituted heterocyclyl selected from azetidinyl, pyrrolidyl, piperidyl, morpholinyl, piperazin-2-onyl, 1,2,3,6-tetrahydropyridyl, isoxazolyl, imidazolyl, pyridyl, indazolyl, benzimidazolyl, 1H-benzo[d][1,2,3]triazolyl, benzisoxazolyl, benzo[d]oxazolyl, isoindolin-1-onyl, 1H-imidazo[4,5-b]pyridyl, quinolinyl, or isoquinolinyl. In some such embodiments, R$^2$ is substituted with one or more substituted or unsubstituted C$_{1-4}$ alkyl, substituted or unsubstituted heterocyclylalkyl, hydroxyl, —OR, —NR$^2$, or —C(=O)NR$^2$, wherein each R is independently —H, a substituted or unsubstituted C$_{1-6}$ alkyl, a substituted or unsubstituted heterocyclyl, or a substituted or unsubstituted heterocyclylalkyl.

In some embodiments, R$^2$ is

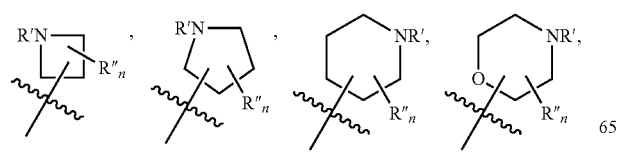

-continued wherein R' is —H, or a substituted or unsubstituted C$_{1-6}$ alkyl; each R'' is independently a substituted or unsubstituted C$_{1-4}$ alkyl, substituted or unsubstituted heterocyclyl, a substituted or unsubstituted heterocyclylalkyl, hydroxyl, halogen, alkoxy, —CN, —OR, —NR$_2$, —(C$_{1-4}$ alkyl)NR$_2$, —C(=O)NR$_2$, wherein each R is independently —H, a substituted or unsubstituted C$_{1-6}$ alkyl, a substituted or unsubstituted heterocyclyl or a substituted or unsubstituted heterocyclylalkyl; and n=0-2. For example, in certain embodiments, R'' is —CH$_3$, —CH$_2$CH$_3$, isopropyl, —CH$_2$OH, —CH$_2$OCH$_3$, —CH(CH$_3$)OH, —(CH$_2$)$_2$NH$_2$, —CH$_2$NHCH$_3$, —CH$_2$N(CH$_3$)$_2$, —OH, —OCH$_3$, —O(CH$_2$)$_2$NH$_2$, —NH$_2$, —NHCH$_3$, —N(CH$_3$)$_2$, —NH(CH$_2$)$_2$OH, —NH(CH$_2$)$_2$NH$_2$, —C(=O)NH$_2$, —CH$_2$(pyrrolidyl), or substituted or unsubstituted piperazinyl.

It will be understood by those of skill in the art that any of the substitutents R'' may be attached to any suitable atom of any of the rings in the fused ring systems. For example, in some embodiments, R$^2$ is —(C$_{1-4}$ alkyl), —(C$_{1-4}$ alkyl)OH,

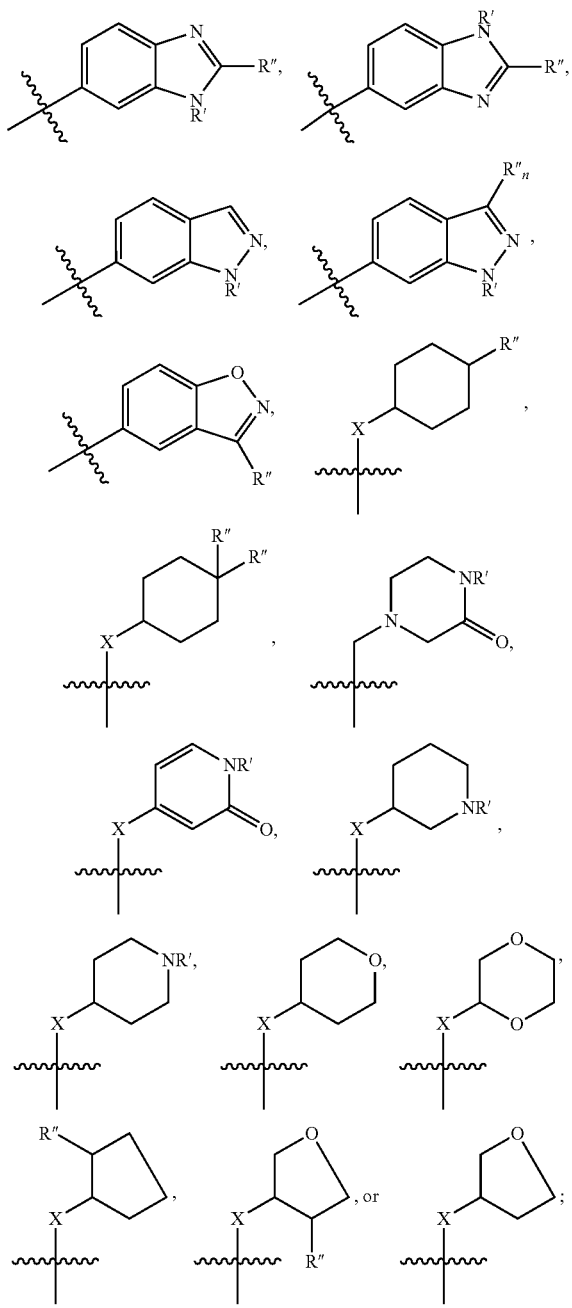
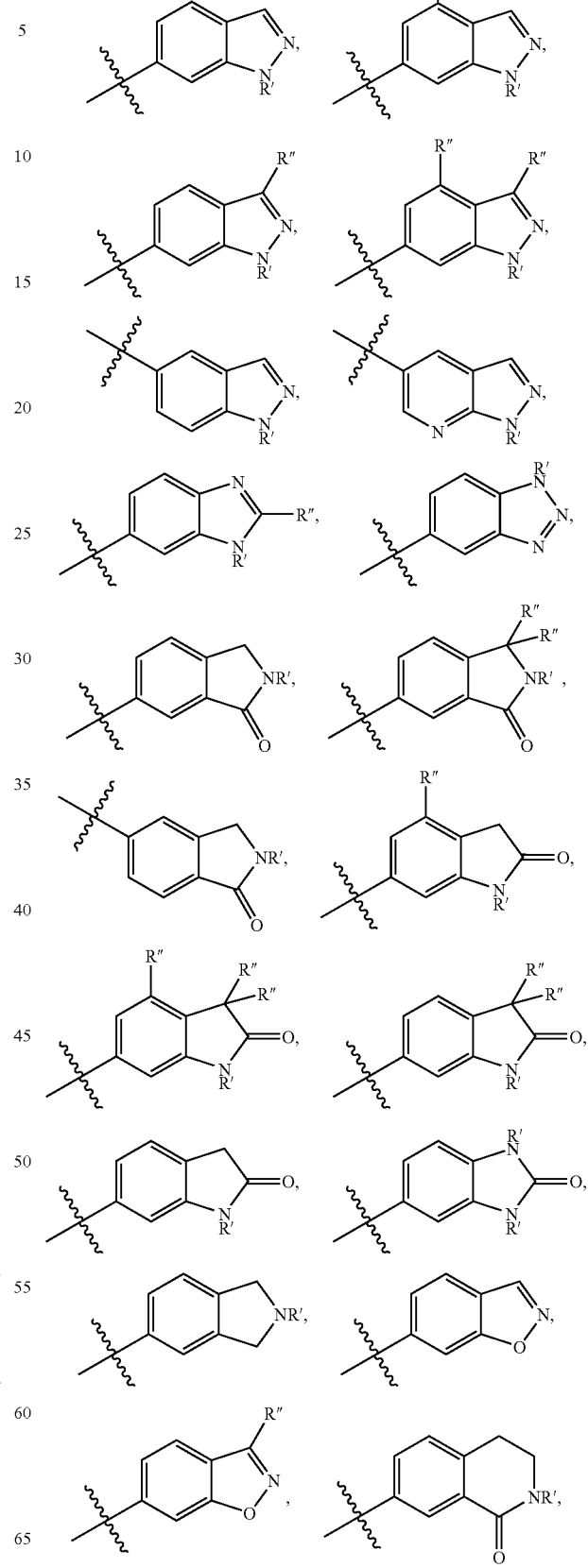

wherein R' is —H, or a substituted or unsubstituted $C_{1-6}$ alkyl; each R" is independently a substituted or unsubstituted $C_{1-4}$ alkyl, substituted or unsubstituted heterocyclyl, a substituted or unsubstituted heterocyclylalkyl, hydroxyl, halogen, alkoxy, —CN, —OR, —$NR_2$, —($C_{1-4}$ alkyl)$NR_2$, —C(=O)$NR_2$, wherein each R is independently —H, a substituted or unsubstituted $C_{1-6}$ alkyl, a substituted or unsubstituted heterocyclyl or a substituted or unsubstituted heterocyclylalkyl; and X=$CH_2$, $CF_2$ or NR'.

In certain embodiments, the Heteroaryl Compounds have an $R^1$ group set forth herein and an $R^2$ group set forth herein. In some such embodiments where $R^2$ is as described herein, $R^1$ is -continued

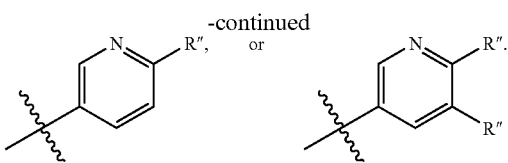

wherein R' is —H, or a substituted or unsubstituted $C_{1-6}$ alkyl; each R" is independently a substituted or unsubstituted $C_{1-4}$ alkyl, substituted or unsubstituted heterocyclyl, substituted or unsubstituted heterocyclylalkyl, hydroxyl, halogen, alkoxy, —CN, —OR, —$NR_2$, —($C_{1-4}$ alkyl)$NR_2$, —C(=O) $NR_2$, wherein each R is independently —H, a substituted or unsubstituted $C_{1-6}$ alkyl, a substituted or unsubstituted heterocyclyl or a substituted or unsubstituted heterocyclylalkyl; and n is 0-2. In some such embodiments, R" is —F, —$CH_3$, —$CH_2CH_3$, isopropyl, —NH($C_{1-3}$ alkyl)$NH_2$, —NH$(CH_2)_2$OH, —$CF_3$, —OH, —$OCH_3$, —$O(CH_2)_2OCH_3$, —$O(CH_2)_2$OH, —$O(CH_2)_2NH_2$, —$O(CH_2)_2$pyrrolidyl, —$CH_2$OH, —$(CH_2)_2$OH, —$CH_2OCH_3$, —$(CH_2)_2OCH_3$, —CH($CH_3$)OH, —$CH_2NH_2$, —$(CH_2)_2NH_2$, —$CH_2NHCH_3$, —$CH_2N(CH_3)_2$, —C($CH_3)_2$OH, —CN, —$NH_2$, —$NHCH_3$, —N($CH_3)_2$, —NH$(CH_2)_2NH_2$, —NH$(CH_2)_2$OH, —C(=O)$NH_2$, —C(=O)$NHCH_3$, —NH$(CH_2)_2$pyrrolidyl, —NH (substituted or unsubstituted piperidyl), —NH (substituted or unsubstituted tetrahydropyranyl), —$CH_2$(pyrrolidyl), substituted or unsubstituted piperidyl, substituted or unsubstituted morpholinyl, or substituted or unsubstituted piperazinyl.

In one embodiment, the Heteroaryl Compound is a compound as described herein, wherein the compound at a concentration of 10 µM inhibits Syk by at least about 50%.

Further embodiments provided herein include combinations of one or more of the particular embodiments set forth above.

In some embodiments, the Heteroaryl Compound is:
1-methyl-$N^3$-(tetrahydro-2H-pyran-4-yl)-$N^6$-(5-((tetrahydro-2H-pyran-4-yl)methyl)-[1,2,4]triazolo[1,5-a]pyridin-2-yl)-1H-indazole-3,6-diamine;
$N^3$-(tetrahydro-2H-pyran-4-yl)-$N^6$-(5-((tetrahydro-2H-pyran-4-yl)methyl)-[1,2,4]triazolo[1,5-a]pyridin-2-yl)-1H-indazole-3,6-diamine;
1-methyl-$N^3$-(piperidin-4-yl)-$N^6$-(5-((tetrahydro-2H-pyran-4-yl)methyl)-[1,2,4]triazolo[1,5-a]pyridin-2-yl)-1H-indazole-3,6-diamine;
cis-6-(5-(4-hydroxycyclohexylamino)-[1,2,4]triazolo[1,5-a]pyridin-2-ylamino)-1H-pyrrolo[3,2-b]pyridin-2(3H)-one;
cis-6-(5-(4-hydroxy-4-methylcyclohexylamino)-[1,2,4]triazolo[1,5-a]pyridin-2-ylamino)-1,3,3-trimethylindolin-2-one;
N-(3-(methoxymethyl)-1H-indazol-6-yl)-5-((tetrahydro-2H-pyran-4-yl)methyl)-[1,2,4]triazolo[1,5-a]pyridin-2-amine;
cis-4-(2-(5-methyl-6-morpholinopyridin-3-ylamino)-[1,2,4]triazolo[1,5-a]pyridin-5-ylamino)cyclohexanol;
N-(5-((tetrahydro-2H-pyran-4-yl)methyl)-[1,2,4]triazolo[1,5-a]pyridin-2-yl)-1H-pyrazolo[4,3-b]pyridin-6-amine;
cis-4-(2-(1H-pyrazolo[4,3-b]pyridin-6-ylamino)-[1,2,4]triazolo[1,5-a]pyridin-5-ylamino)cyclohexanol;
$N^2$-(3,4-dimethyl-1H-indazol-6-yl)-$N^5$-(tetrahydro-2H-pyran-4-yl)-[1,2,4]triazolo[1,5-a]pyridine-2,5-diamine;
cis-6-(5-(4-hydroxycyclohexylamino)-[1,2,4]triazolo[1,5-a]pyridin-2-ylamino)-3,3,4-trimethylindolin-2-one;
trans-6-(5-(4-hydroxy-4-methylcyclohexylamino)-[1,2,4]triazolo[1,5-a]pyridin-2-ylamino)-1,3,3-trimethylindolin-2-one;
$N^2$-(1H-pyrazolo[4,3-b]pyridin-6-yl)-$N^5$-(tetrahydro-2H-pyran-4-yl)-[1,2,4]triazolo[1,5-a]pyridine-2,5-diamine;
cis-4-(2-(imidazo[1,2-a]pyridin-7-ylamino)-[1,2,4]triazolo[1,5-a]pyridin-5-ylamino)cyclohexanol;
3,3-dimethyl-6-(5-((tetrahydro-2H-pyran-4-yl)methyl)-[1,2,4]triazolo[1,5-a]pyridin-2-ylamino)isoindolin-1-one;
6-(5-(4-hydroxypiperidin-1-yl)-[1,2,4]triazolo[1,5-a]pyridin-2-ylamino)-3,3-dimethylindolin-2-one;
(R)—$N^2$-(3-methyl-1H-indazol-5-yl)-$N^5$-(tetrahydrofuran-3-yl)-[1,2,4]triazolo[1,5-a]pyridine-2,5-diamine;
N-(3-methyl-1H-indazol-5-yl)-5-((tetrahydro-2H-pyran-4-yl)methyl)-[1,2,4]triazolo[1,5-a]pyridin-2-amine;
$N^2$-(3-methyl-1H-indazol-5-yl)-$N^5$-(tetrahydro-2H-pyran-4-yl)-[1,2,4]triazolo[1,5-a]pyridine-2,5-diamine;
1-methyl-6-(5-((tetrahydro-2H-pyran-4-yl)methyl)-[1,2,4]triazolo[1,5-a]pyridin-2-ylamino)indolin-2-one;
1-methyl-6-(5-(tetrahydro-2H-pyran-4-ylamino)-[1,2,4]triazolo[1,5-a]pyridin-2-ylamino)indolin-2-one;
cis-6-(5-(4-hydroxycyclohexylamino)-[1,2,4]triazolo[1,5-a]pyridin-2-ylamino)-3,3-dimethylisoindolin-1-one;
(S)-3,3-dimethyl-6-(5-(methyl(tetrahydrofuran-3-yl)amino)-[1,2,4]triazolo[1,5-a]pyridin-2-ylamino)indolin-2-one;
(R)-3,3-dimethyl-6-(5-(methyl(tetrahydrofuran-3-yl)amino)-[1,2,4]triazolo[1,5-a]pyridin-2-ylamino)indolin-2-one;
(R)-1,3,3-trimethyl-6-(5-(tetrahydrofuran-3-ylamino)-[1,2,4]triazolo[1,5-a]pyridin-2-ylamino)indolin-2-one;
4-((2-(4-methyl-1H-indazol-6-ylamino)-[1,2,4]triazolo[1,5-a]pyridin-5-yl)methyl)pyridine-2-ol;
3,3,4-trimethyl-6-(5-(tetrahydro-2H-pyran-4-ylamino)-[1,2,4]triazolo[1,5-a]pyridin-2-ylamino)indolin-2-one;
3,3,4-trimethyl-6-(5-((tetrahydro-2H-pyran-4-yl)methyl)-[1,2,4]triazolo[1,5-a]pyridin-2-ylamino)indolin-2-one;
trans-4-(2-(3-methyl-1H-indazol-5-ylamino)-[1,2,4]triazolo[1,5-a]pyridin-5-ylamino)cyclohexanol;
3,3-dimethyl-6-(5-(tetrahydro-2H-pyran-4-ylamino)-[1,2,4]triazolo[1,5-a]pyridin-2-ylamino)isoindolin-1-one;
$N^5$-(tetrahydro-2H-pyran-4-yl)-$N^2$-(3-(trifluoromethyl)-1H-indazol-6-yl)-[1,2,4]triazolo[1,5-a]pyridine-2,5-diamine;
4-((2-(2-(methoxymethyl)-1H-benzo[d]imidazol-6-ylamino)-[1,2,4]triazolo[1,5-a]pyridin-5-yl)methyl)pyridine-2-ol;
(R)-3,3-dimethyl-6-(5-(piperidin-3-ylamino)-[1,2,4]triazolo[1,5-a]pyridin-2-ylamino)indolin-2-one;
N-(2-(methoxymethyl)-1H-benzo[d]imidazol-6-yl)-5-((tetrahydro-2H-pyran-4-yl)methyl)-[1,2,4]triazolo[1,5-a]pyridin-2-amine;
(S)-3,3-dimethyl-6-(5-(tetrahydrofuran-3-yloxy)-[1,2,4]triazolo[1,5-a]pyridin-2-ylamino)indolin-2-one;
(R)-3,3-dimethyl-6-(5-(tetrahydrofuran-3-yloxy)-[1,2,4]triazolo[1,5-a]pyridin-2-ylamino)indolin-2-one;
cis-5-(5-(4-hydroxycyclohexylamino)-[1,2,4]triazolo[1,5-a]pyridin-2-ylamino)-2-methylisoindolin-1-one;
1,3,3-trimethyl-6-(5-((3-oxopiperazin-1-yl)methyl)-[1,2,4]triazolo[1,5-a]pyridin-2-ylamino)indolin-2-one;
trans-6-(5-(4-hydroxycyclohexylamino)-[1,2,4]triazolo[1,5-a]pyridin-2-ylamino)-3,3-dimethylisoindolin-1-one;
3,3-dimethyl-6-(5-(piperidin-4-ylmethyl)-[1,2,4]triazolo[1,5-a]pyridin-2-ylamino)indolin-2-one;
cis-4-(2-(1-methyl-1H-pyrazolo[3,4-b]pyridin-5-ylamino)-[1,2,4]triazolo[1,5-a]pyridin-5-ylamino)cyclohexanol;
cis-6-(5-((4-hydroxy-4-methylcyclohexyl)methyl)-[1,2,4]triazolo[1,5-a]pyridin-2-ylamino)-3,3-dimethylindolin-2-one;

trans-6-(5-((4-hydroxy-4-methylcyclohexyl)methyl)-[1,2,4]triazolo[1,5-a]pyridin-2-ylamino)-3,3-dimethylindolin-2-one;

$N^2$-(2-(methoxymethyl)-1H-benzo[d]imidazol-6-yl)-$N^5$-(tetrahydro-2H-pyran-4-yl)-[1,2,4]triazolo[1,5-a]pyridine-2,5-diamine;

1,3,3-trimethyl-6-(5-((tetrahydro-2H-pyran-4-yl)methyl)-[1,2,4]triazolo[1,5-a]pyridin-2-ylamino)indolin-2-one;

2-methyl-5-(5-(tetrahydro-2H-pyran-4-ylamino)-[1,2,4]triazolo[1,5-a]pyridin-2-ylamino)isoindolin-1-one;

2-methyl-5-(5-((tetrahydro-2H-pyran-4-yl)methyl)-[1,2,4]triazolo[1,5-a]pyridin-2-ylamino)isoindolin-1-one;

trans-6-(5-(4-hydroxycyclohexylamino)-[1,2,4]triazolo[1,5-a]pyridin-2-ylamino)-1,3,3-trimethylindolin-2-one;

N-(1,4-dimethyl-1H-indazol-6-yl)-5-((tetrahydro-2H-pyran-4-yl)methyl)-[1,2,4]triazolo[1,5-a]pyridin-2-amine;

$N^2$-(1,4-dimethyl-1H-indazol-6-yl)-$N^5$-(tetrahydro-2H-pyran-4-yl)-[1,2,4]triazolo[1,5-a]pyridine-2,5-diamine;

cis-4-(2-(4-fluoro-1,3-dimethyl-1H-indazol-6-ylamino)-[1,2,4]triazolo[1,5-a]pyridin-5-ylamino)cyclohexanol;

(R)-3,3-dimethyl-6-(5-(tetrahydrofuran-3-ylamino)-[1,2,4]triazolo[1,5-a]pyridin-2-ylamino)indolin-2-one;

1,3,3-trimethyl-6-(5-(tetrahydro-2H-pyran-4-ylamino)-[1,2,4]triazolo[1,5-a]pyridin-2-ylamino)indolin-2-one;

cis-6-(5-(4-hydroxycyclohexylamino)-[1,2,4]triazolo[1,5-a]pyridin-2-ylamino)-1,3,3-trimethylindolin-2-one;

6-(5-((2-hydroxyethyl)(methyl)amino)-[1,2,4]triazolo[1,5-a]pyridin-2-ylamino)-3,3-dimethylindolin-2-one;

(S)-3,3-dimethyl-6-(5-(piperidin-3-ylamino)-[1,2,4]triazolo[1,5-a]pyridin-2-ylamino)indolin-2-one;

4-((2-(3-(trifluoromethyl)-1H-indazol-6-ylamino)-[1,2,4]triazolo[1,5-a]pyridin-5-yl)methyl)piperazin-2-one;

3,3-dimethyl-6-(5-((2-oxo-1,2-dihydropyridin-4-yl)methyl)-[1,2,4]triazolo[1,5-a]pyridin-2-ylamino)indolin-2-one;

5-(5-((2-hydroxypyridin-4-yl)methyl)-[1,2,4]triazolo[1,5-a]pyridin-2-ylamino)isoindolin-1-one;

3,3-dimethyl-6-(5-(methyl(tetrahydro-2H-pyran-4-yl)amino)-[1,2,4]triazolo[1,5-a]pyridin-2-ylamino)indolin-2-one;

3,3-dimethyl-6-(5-(1-(tetrahydro-2H-pyran-4-yl)ethyl)-[1,2,4]triazolo[1,5-a]pyridin-2-ylamino)indolin-2-one;

N-(1-methyl-1H-indazol-6-yl)-5-((tetrahydro-2H-pyran-4-yl)methyl)-[1,2,4]triazolo[1,5-a]pyridin-2-amine;

$N^2$-(1-methyl-1H-indazol-6-yl)-$N^5$-(tetrahydro-2H-pyran-4-yl)-[1,2,4]triazolo[1,5-a]pyridine-2,5-diamine;

trans-6-(5-(4-hydroxy-4-methylcyclohexylamino)-[1,2,4]triazolo[1,5-a]pyridin-2-ylamino)-3,3-dimethylindolin-2-one;

cis-6-(5-(4-hydroxy-4-methylcyclohexylamino)-[1,2,4]triazolo[1,5-a]pyridin-2-ylamino)-3,3-dimethylindolin-2-one;

cis-4-(2-(4-fluoro-3-methyl-1H-indazol-6-ylamino)-[1,2,4]triazolo[1,5-a]pyridin-5-ylamino)cyclohexanol;

(±)-cis-4-(2-(3-methyl-1H-indazol-6-ylamino)-[1,2,4]triazolo[1,5-a]pyridin-5-yloxy)tetrahydrofuran-3-ol;

(±)-trans-4-(2-(3-methyl-1H-indazol-6-ylamino)-[1,2,4]triazolo[1,5-a]pyridin-5-ylamino)tetrahydrofuran-3-ol;

(R)—$N^2$-(3-methyl-1H-indazol-6-yl)-$N^5$-(tetrahydrofuran-3-yl)-[1,2,4]triazolo[1,5-a]pyridine-2,5-diamine;

3,3-dimethyl-6-(5-(tetrahydro-2H-pyran-4-yloxy)-[1,2,4]triazolo[1,5-a]pyridin-2-ylamino)indolin-2-one;

3-methyl-1-((2-(3-methyl-1H-indazol-6-ylamino)-[1,2,4]triazolo[1,5-a]pyridin-5-yl)methyl)azetidin-3-ol;

6-(5-(3-hydroxyazetidin-1-yl)-[1,2,4]triazolo[1,5-a]pyridin-2-ylamino)-3,3-dimethylindolin-2-one;

6-(5-(3-hydroxy-3-methylazetidin-1-yl)-[1,2,4]triazolo[1,5-a]pyridin-2-ylamino)-3,3-dimethylindolin-2-one;

3,3-dimethyl-6-(5-((3-oxopiperazin-1-yl)methyl)-[1,2,4]triazolo[1,5-a]pyridin-2-ylamino)indolin-2-one;

6-(5-(hydroxy(tetrahydro-2H-pyran-4-yl)methyl)-[1,2,4]triazolo[1,5-a]pyridin-2-ylamino)-3,3-dimethylindolin-2-one;

cis-5-(5-(4-hydroxycyclohexylamino)-[1,2,4]triazolo[1,5-a]pyridin-2-ylamino)-2-(2-methoxyethyl)isoindolin-1-one;

trans-6-(5-(4-hydroxycyclohexylamino)-[1,2,4]triazolo[1,5-a]pyridin-2-ylamino)-3,3-dimethylindolin-2-one;

3,3-dimethyl-6-(5-((tetrahydro-2H-pyran-4-yl)methyl)-[1,2,4]triazolo[1,5-a]pyridin-2-ylamino)indolin-2-one;

3,3-dimethyl-6-(5-(tetrahydro-2H-pyran-4-ylamino)-[1,2,4]triazolo[1,5-a]pyridin-2-ylamino)indolin-2-one;

(1S,3R)-3-((2-(3-methyl-1H-indazol-6-ylamino)-[1,2,4]triazolo[1,5-a]pyridin-5-ylamino)methyl)cyclopentanol;

(1R,3R)-3-((2-(3-methyl-1H-indazol-6-ylamino)-[1,2,4]triazolo[1,5-a]pyridin-5-ylamino)methyl)cyclopentanol;

(1R,3S)-3-((2-(3-methyl-1H-indazol-6-ylamino)-[1,2,4]triazolo[1,5-a]pyridin-5-ylamino)methyl)cyclopentanol;

(1S,3S)-3-((2-(3-methyl-1H-indazol-6-ylamino)-[1,2,4]triazolo[1,5-a]pyridin-5-ylamino)methyl)cyclopentanol;

(S)—$N^2$-(3-methyl-1H-indazol-6-yl)-$N^5$-(tetrahydrofuran-3-yl)-[1,2,4]triazolo[1,5-a]pyridine-2,5-diamine;

4-((2-(3-methyl-1H-indazol-6-ylamino)-[1,2,4]triazolo[1,5-a]pyridin-5-yl)methyl)pyridin-2(1H)-one;

5-((3,3-difluoropiperidin-1-yl)methyl)-N-(3-methyl-1H-indazol-6-yl)-[1,2,4]triazolo[1,5-a]pyridin-2-amine;

cis-6-(5-(4-hydroxycyclohexylamino)-[1,2,4]triazolo[1,5-a]pyridin-2-ylamino)-1-(2-hydroxyethyl)indolin-2-one;

2-((2-(3-methyl-1H-indazol-6-ylamino)-[1,2,4]triazolo[1,5-a]pyridin-5-yl)methylamino)acetamide;

cis-1-(methoxymethyl)-4-((2-(4-(trifluoromethyl)phenylamino)-[1,2,4]triazolo[1,5-a]pyridin-5-yl)methyl)cyclohexanol;

4-((2-(1-isopropyl-1H-indazol-6-ylamino)-[1,2,4]triazolo[1,5-a]pyridin-5-yl)methyl)piperazin-2-one;

$N^5$-methyl-$N^2$-(3-methyl-1H-indazol-6-yl)-$N^5$-(tetrahydro-2H-pyran-4-yl)-[1,2,4]triazolo[1,5-a]pyridine-2,5-diamine;

2-(methyl(2-(3-methyl-1H-indazol-6-ylamino)-[1,2,4]triazolo[1,5-a]pyridin-5-yl)amino)ethanol;

cis-4-(2-(1-(2-hydroxyethyl)-3-methyl-1H-indazol-6-ylamino)-[1,2,4]triazolo[1,5-a]pyridin-5-ylamino)cyclohexanol;

cis-6-(5-(4-hydroxycyclohexylamino)-[1,2,4]triazolo[1,5-a]pyridin-2-ylamino)-1-methylindolin-2-one;

6-(hydroxy(2-(4-(trifluoromethyl)phenylamino)-[1,2,4]triazolo[1,5-a]pyridin-5-yl)methyl)pyrimidin-4(3H)-one;

cis-4-(2-(1-(2-methoxyethyl)-3-methyl-1H-indazol-6-ylamino)-[1,2,4]triazolo[1,5-a]pyridin-5-ylamino)cyclohexanol;

cis-4-(2-(2-(hydroxymethyl)-1H-benzo[d]imidazol-6-ylamino)-[1,2,4]triazolo[1,5-a]pyridin-5-ylamino)cyclohexanol;

cis-4-(2-(2-(methoxymethyl)-1H-benzo[d]imidazol-6-ylamino)-[1,2,4]triazolo[1,5-a]pyridin-5-ylamino)cyclohexanol;

cis-4-(2-(1-ethyl-3-methyl-1H-indazol-6-ylamino)-[1,2,4]triazolo[1,5-a]pyridin-5-ylamino)cyclohexanol;

cis-5-(5-(4-hydroxycyclohexylamino)-[1,2,4]triazolo[1,5-a]pyridin-2-ylamino)-2-(2-hydroxyethyl)isoindolin-1-one;

N-(3-methyl-1H-indazol-6-yl)-5-((tetrahydro-2H-pyran-4-yl)methyl)-[1,2,4]triazolo[1,5-a]pyridin-2-amine;

(2-(3-methyl-1H-indazol-6-ylamino)-[1,2,4]triazolo[1,5-a]pyridin-5-yl)(tetrahydro-2H-pyran-4-yl)methanol;

trans-4-(2-(3-methyl-1H-indazol-6-ylamino)-[1,2,4]triazolo [1,5-a]pyridin-5-ylamino)cyclohexanol;
cis-6-(5-(4-hydroxycyclohexylamino)-[1,2,4]triazolo[1,5-a] pyridin-2-ylamino)-3,3-dimethylindolin-2-one;
cis-6-(5-(4-hydroxycyclohexylamino)-[1,2,4]triazolo[1,5-a] pyridin-2-ylamino)-3,4-dihydroisoquinolin-1(2H)-one;
cis-4-(2-(4-methyl-1H-indazol-6-ylamino)-[1,2,4]triazolo [1,5-a]pyridin-5-ylamino)cyclohexanol;
(R)-3-((2-(4-(trifluoromethyl)phenylamino)-[1,2,4]triazolo [1,5-a]pyridin-5-yl)methylamino)pyrrolidin-2-one;
cis-6-(5-(4-hydroxycyclohexylamino)-[1,2,4]triazolo[1,5-a] pyridin-2-ylamino)-2-(2-hydroxyethyl)isoindolin-1-one;
(±)-3-((2-(4-(trifluoromethyl)phenylamino)-[1,2,4]triazolo [1,5-a]pyridin-5-yl)methylamino)pyrrolidin-2-one;
4-((2-(3-amino-1H-indazol-6-ylamino)-[1,2,4]triazolo[1,5-a]pyridin-5-yl)methyl)cyclohexanol;
$N^2$-(3-methyl-1H-indazol-6-yl)-$N^5$-(tetrahydro-2H-pyran-4-yl)-[1,2,4]triazolo[1,5-a]pyridine-2,5-diamine;
cis-4-(2-(4-fluoro-3-(2-methoxyethoxy)phenylamino)-[1,2, 4]triazolo[1,5-a]pyridin-5-ylamino)cyclohexanol;
4-(1-(2-(4-(trifluoromethyl)phenylamino)-[1,2,4]triazolo[1, 5-a]pyridin-5-yl)ethyl)pyridin-2(1H)-one;
(1S,2S)-2-(2-(3-methyl-1H-indazol-6-ylamino)-[1,2,4]triazolo[1,5-a]pyridin-5-ylamino)cyclopentanol;
N-methyl-2-((2-(4-(trifluoromethyl)phenylamino)-[1,2,4] triazolo[1,5-a]pyridin-5-yl)methylamino)acetamide;
4-(5-((3-hydroxycyclopentyl)methyl)-[1,2,4]triazolo[1,5-a] pyridin-2-ylamino)-N-methylbenzamide (diastereomer 2);
1-(2-(3-methyl-1H-indazol-6-ylamino)-[1,2,4]triazolo[1,5-a]pyridin-5-yl)azetidin-3-ol;
cis-4-(2-(3-amino-1H-indazol-6-ylamino)-[1,2,4]triazolo[1, 5-a]pyridin-5-ylamino)cyclohexanol;
cis-4-(2-(2,3-dimethyl-2H-indazol-6-ylamino)-[1,2,4]triazolo[1,5-a]pyridin-5-ylamino)cyclohexanol;
cis-4-(2-(1,3-dimethyl-1H-indazol-6-ylamino)-[1,2,4]triazolo[1,5-a]pyridin-5-ylamino)cyclohexanol;
4-((2-(4-fluoro-3-methylphenylamino)-[1,2,4]triazolo[1,5-a]pyridin-5-yl)methyl)pyridin-2-ol;
$N^2$-(3-methyl-1H-indazol-6-yl)-$N^5$-((tetrahydro-2H-pyran-4-yl)methyl)-[1,2,4]triazolo[1,5-a]pyridine-2,5-diamine;
4-((2-(6-(4-hydroxypiperidin-1-yl)pyridin-3-ylamino)-[1,2, 4]triazolo[1,5-a]pyridin-5-yl)methyl)piperazin-2-one;
(S)-2-((2-(4-(trifluoromethyl)phenylamino)-[1,2,4]triazolo [1,5-a]pyridin-5-yl)methylamino)propanamide;
cis-3-(2-(4-(trifluoromethyl)phenylamino)-[1,2,4]triazolo [1,5-a]pyridin-5-ylamino)cyclohexanol (enantiomer 1);
cis-3-(2-(4-(trifluoromethyl)phenylamino)-[1,2,4]triazolo [1,5-a]pyridin-5-ylamino)cyclohexanol (enantiomer 2);
trans-3-(2-(4-(trifluoromethyl)phenylamino)-[1,2,4]triazolo [1,5-a]pyridin-5-ylamino)cyclohexanol (enantiomer 1);
trans-3-(2-(4-(trifluoromethyl)phenylamino)-[1,2,4]triazolo [1,5-a]pyridin-5-ylamino)cyclohexanol (enantiomer 2);
cis-1-(hydroxymethyl)-4-(2-(4-(trifluoromethyl)phenylamino)-[1,2,4]triazolo[1,5-a]pyridin-5-ylamino)cyclohexanol;
4-((2-(4-fluoro-3-methylphenylamino)-[1,2,4]triazolo[1,5-a]pyridin-5-yl)methyl)piperazin-2-one;
4-((2-(1H-pyrrolo[2,3-b]pyridin-5-ylamino)-[1,2,4]triazolo [1,5-a]pyridin-5-yl)methyl)piperazin-2-one;
(±)-5-isopropyl-4-((2-(4-(trifluoromethyl)phenylamino)-[1, 2,4]triazolo[1,5-a]pyridin-5-yl)methyl)piperazin-2-one;
cis-4-(2-(3-(methoxymethyl)-1H-indazol-6-ylamino)-[1,2, 4]triazolo[1,5-a]pyridin-5-ylamino)cyclohexanol;
4-(5-((3-hydroxycyclopentyl)methyl)-[1,2,4]triazolo[1,5-a] pyridin-2-ylamino)-N-methylbenzamide (diastereomer 1);

(±)-2-((2-(4-(trifluoromethyl)phenylamino)-[1,2,4]triazolo [1,5-a]pyridin-5-yl)methylamino)propanamide;
1-(3-methyl-1H-indazol-6-yl)-4-((2-(3-methyl-1H-indazol-6-ylamino)-[1,2,4]triazolo[1,5-a]pyridin-5-yl)methyl) piperazin-2-one;
4-((2-(3-methyl-1H-indazol-6-ylamino)-[1,2,4]triazolo[1,5-a]pyridin-5-yl)methyl)piperazin-2-one;
cis-4-(2-(1-methyl-1H-indazol-5-ylamino)-[1,2,4]triazolo [1,5-a]pyridin-5-ylamino)cyclohexanol;
cis-4-(2-(1H-benzo[d][1,2,3]triazol-5-ylamino)-[1,2,4]triazolo[1,5-a]pyridin-5-ylamino)cyclohexanol;
cis-6-(5-(4-hydroxycyclohexylamino)-[1,2,4]triazolo[1,5-a] pyridin-2-ylamino)indolin-2-one;
cis-4-((2-(3-methyl-1H-indazol-6-ylamino)-[1,2,4]triazolo [1,5-a]pyridin-5-yl)methyl)cyclohexanol;
trans-4-((2-(3-methyl-1H-indazol-6-ylamino)-[1,2,4]triazolo[1,5-a]pyridin-5-yl)methyl)cyclohexanol;
4-(5-(1H-imidazol-1-yl)-[1,2,4]triazolo[1,5-a]pyridin-2-ylamino)-N-methylbenzamide;
4-(5-(4-hydroxypiperidin-1-yl)-[1,2,4]triazolo[1,5-a]pyridin-2-ylamino)-N-methylbenzamide;
cis-4-(2-(1-isopropyl-1H-indazol-6-ylamino)-[1,2,4]triazolo[1,5-a]pyridin-5-ylamino)cyclohexanol;
N-methyl-4-(5-(2-methyl-1H-benzo[d]imidazol-6-yl)-[1,2, 4]triazolo[1,5-a]pyridin-2-ylamino)benzamide;
cis-4-(2-(3-ethyl-1H-indazol-6-ylamino)-[1,2,4]triazolo[1, 5-a]pyridin-5-ylamino)cyclohexanol;
(1R,2R)-2-(4-(2-(4-(trifluoromethyl)phenylamino)-[1,2,4] triazolo[1,5-a]pyridin-5-yl)pyridin-2-ylamino)cyclopentanol;
N-methyl-4-(5-(piperidin-1-yl)-[1,2,4]triazolo[1,5-a]pyridin-2-ylamino)benzamide; (±)-trans-3-(2-(4-(trifluoromethyl)phenylamino)-[1,2,4]triazolo[1,5-a]pyridin-5-ylamino)cyclohexanol;
(S)-4-(5-(3-hydroxypyrrolidin-1-yl)-[1,2,4]triazolo[1,5-a] pyridin-2-ylamino)-N-methylbenzamide;
(R)-4-(5-(3-hydroxypyrrolidin-1-yl)-[1,2,4]triazolo[1,5-a] pyridin-2-ylamino)-N-methylbenzamide;
N-methyl-4-(5-(pyrrolidin-1-yl)-[1,2,4]triazolo[1,5-a]pyridin-2-ylamino)benzamide;
1-((2-(4-(trifluoromethyl)phenylamino)-[1,2,4]triazolo[1,5-a]pyridin-5-yl)methyl)imidazolidine-2,4-dione;
cis-5-(5-(4-hydroxycyclohexylamino)-[1,2,4]triazolo[1,5-a] pyridin-2-ylamino)isoindolin-1-one;
N-methyl-4-(5-(2-(piperidin-4-yl)ethyl)-[1,2,4]triazolo[1,5-a]pyridin-2-ylamino)benzamide;
cis-4-(5-(4-hydroxycyclohexylamino)-[1,2,4]triazolo[1,5-a] pyridin-2-ylamino)picolinamide;
cis-4-(5-(4-hydroxycyclohexylamino)-[1,2,4]triazolo[1,5-a] pyridin-2-ylamino)picolinonitrile;
1-((2-(4-(trifluoromethyl)phenylamino)-[1,2,4]triazolo[1,5-a]pyridin-5-yl)methyl)piperidine-3-carboxamide;
5-methyl-4-((2-(4-(trifluoromethyl)phenylamino)-[1,2,4] triazolo[1,5-a]pyridin-5-yl)methyl)piperazin-2-one;
(1-(2-(4-(trifluoromethyl)phenylamino)-[1,2,4]triazolo[1,5-a]pyridin-5-yl)azetidin-3-yl)methanol;
cis-6-(5-(4-hydroxycyclohexylamino)-[1,2,4]triazolo[1,5-a] pyridin-2-ylamino)isoindolin-1-one;
cis-4-(2-(2,6-dimethylpyridin-4-ylamino)-[1,2,4]triazolo[1, 5-a]pyridin-5-ylamino)cyclohexanol;
4-(5-((4-aminocyclohexyl)methyl)-[1,2,4]triazolo[1,5-a]pyridin-2-ylamino)-N-methylbenzamide;
4-(1-(2-(4-(trifluoromethyl)phenylamino)-[1,2,4]triazolo[1, 5-a]pyridin-5-yl)ethyl)piperazin-2-one;
4-((2-(4-(trifluoromethyl)phenylamino)-[1,2,4]triazolo[1,5-a]pyridin-5-yl)methyl)piperazine-2,6-dione;

cis-N⁵-(4-methoxycyclohexyl)-N⁵-methyl-N²-(4-(trifluoromethyl)phenyl)-[1,2,4]triazolo[1,5-a]pyridine-2,5-diamine;
cis-4-(methyl(2-(4-(trifluoromethyl)phenylamino)-[1,2,4]triazolo[1,5-a]pyridin-5-yl)amino)cyclohexanol;
N-methyl-4-(5-(pyrrolidin-3-ylmethyl)-[1,2,4]triazolo[1,5-a]pyridin-2-ylamino)benzamide;
5-(5-(2-(hydroxymethyl)-1H-benzo[d]imidazol-6-yl)-[1,2,4]triazolo[1,5-a]pyridin-2-ylamino)pyridin-2-ol;
1-((2-(4-(trifluoromethyl)phenylamino)-[1,2,4]triazolo[1,5-a]pyridin-5-yl)methyl)-1,4-diazepan-5-one;
(1S,2R)-2-(2-(4-(trifluoromethyl)phenylamino)-[1,2,4]triazolo[1,5-a]pyridin-5-ylamino)cyclohexanol;
(S)-(1-((2-(4-(trifluoromethyl)phenylamino)-[1,2,4]triazolo[1,5-a]pyridin-5-yl)methyl)pyrrolidin-2-yl)methanol;
(R)-(1-((2-(4-(trifluoromethyl)phenylamino)-[1,2,4]triazolo[1,5-a]pyridin-5-yl)methyl)pyrrolidin-2-yl)methanol;
(1-((2-(4-(trifluoromethyl)phenylamino)-[1,2,4]triazolo[1,5-a]pyridin-5-yl)methyl)piperidin-3-yl)methanol;
(1-((2-(4-(trifluoromethyl)phenylamino)-[1,2,4]triazolo[1,5-a]pyridin-5-yl)methyl)piperidin-4-yl)methanol;
(S)-3-methyl-4-((2-(4-(trifluoromethyl)phenylamino)-[1,2,4]triazolo[1,5-a]pyridin-5-yl)methyl)piperazin-2-one;
N-methyl-4-(5-(piperidin-4-ylmethyl)-[1,2,4]triazolo[1,5-a]pyridin-2-ylamino)benzamide;
cis-4-(2-(2-(2-hydroxyethoxy)pyridin-4-ylamino)-[1,2,4]triazolo[1,5-a]pyridin-5-ylamino)cyclohexanol;
cis-4-(2-(2-(2-(pyrrolidin-1-yl)ethylamino)pyridin-4-ylamino)-[1,2,4]triazolo[1,5-a]pyridin-5-ylamino)cyclohexanol;
cis-4-(2-(4-fluoro-3,5-dimethylphenylamino)-[1,2,4]triazolo[1,5-a]pyridin-5-ylamino)cyclohexanol;
(6-(2-(6-methoxypyridin-3-ylamino)-[1,2,4]triazolo[1,5-a]pyridin-5-yl)-1H-benzo[d]imidazol-2-yl)methanol;
3-methyl-4-((2-(4-(trifluoromethyl)phenylamino)-[1,2,4]triazolo[1,5-a]pyridin-5-yl)methyl)piperazin-2-one;
6-methyl-4-((2-(4-(trifluoromethyl)phenylamino)-[1,2,4]triazolo[1,5-a]pyridin-5-yl)methyl)piperazin-2-one;
cis-4-(5-(4-aminocyclohexyloxy)-[1,2,4]triazolo[1,5-a]pyridin-2-ylamino)-N-methylbenzamide;
N-methyl-4-(5-(piperidin-4-yloxy)-[1,2,4]triazolo[1,5-a]pyridin-2-ylamino)benzamide;
(6-(2-(6-methylpyridin-3-ylamino)-[1,2,4]triazolo[1,5-a]pyridin-5-yl)-1H-benzo[d]imidazol-2-yl)methanol;
1-((2-(4-(trifluoromethyl)phenylamino)-[1,2,4]triazolo[1,5-a]pyridin-5-yl)methyl)tetrahydropyrimidin-2(1H)-one;
1-(2-(4-(trifluoromethyl)phenylamino)-[1,2,4]triazolo[1,5-a]pyridin-5-yl)azetidin-3-ol;
(R)-(1-(2-(4-(trifluoromethyl)phenylamino)-[1,2,4]triazolo[1,5-a]pyridin-5-yl)pyrrolidin-2-yl)methanol;
(S)-(1-(2-(4-(trifluoromethyl)phenylamino)-[1,2,4]triazolo[1,5-a]pyridin-5-yl)pyrrolidin-2-yl)methanol;
2-((2-(4-(trifluoromethyl)phenylamino)-[1,2,4]triazolo[1,5-a]pyridin-5-yl)methylamino)acetamide;
trans-4-(5-(4-aminocyclohexyloxy)-[1,2,4]triazolo[1,5-a]pyridin-2-ylamino)-N-methylbenzamide;
4-(5-(3-hydroxybenzyl)-[1,2,4]triazolo[1,5-a]pyridin-2-ylamino)-N-methylbenzamide;
cis-4-(2-(2-(2-(pyrrolidin-1-yl)ethoxy)pyridin-4-ylamino)-[1,2,4]triazolo[1,5-a]pyridin-5-ylamino)cyclohexanol;
cis-1-(5-(5-(4-hydroxycyclohexylamino)-[1,2,4]triazolo[1,5-a]pyridin-2-ylamino)pyridin-2-yl)piperidin-4-ol;
cis-4-(2-(6-(methylamino)pyridin-3-ylamino)-[1,2,4]triazolo[1,5-a]pyridin-5-ylamino)cyclohexanol;
5-(2-aminoethoxy)-N-(4-(trifluoromethyl)phenyl)-[1,2,4]triazolo[1,5-a]pyridin-2-amine;
cis-4-(2-(1H-pyrrolo[2,3-b]pyridin-5-ylamino)-[1,2,4]triazolo[1,5-a]pyridin-5-ylamino)cyclohexanol;
(6-(2-(6-(dimethylamino)pyridin-3-ylamino)-[1,2,4]triazolo[1,5-a]pyridin-5-yl)-1H-benzo[d]imidazol-2-yl)methanol;
(R)-1-((2-(4-(trifluoromethyl)phenylamino)-[1,2,4]triazolo[1,5-a]pyridin-5-yl)methyl)piperidin-3-ol;
(S)-1-((2-(4-(trifluoromethyl)phenylamino)-[1,2,4]triazolo[1,5-a]pyridin-5-yl)methyl)piperidin-3-ol;
1-((2-(4-(trifluoromethyl)phenylamino)-[1,2,4]triazolo[1,5-a]pyridin-5-yl)methyl)imidazolidin-4-one;
(R)-5-(pyrrolidin-2-ylmethoxy)-N-(4-(trifluoromethyl)phenyl)-[1,2,4]triazolo[1,5-a]pyridin-2-amine;
(S)-5-(pyrrolidin-2-ylmethoxy)-N-(4-(trifluoromethyl)phenyl)-[1,2,4]triazolo[1,5-a]pyridin-2-amine;
3-(2-(4-(trifluoromethyl)phenylamino)-[1,2,4]triazolo[1,5-a]pyridin-5-yloxy)propan-1-ol;
cis-6-(5-(4-hydroxycyclohexylamino)-[1,2,4]triazolo[1,5-a]pyridin-2-ylamino)pyridin-2-ol;
4-(5-(2-hydroxy-2-(piperidin-4-yl)ethyl)-[1,2,4]triazolo[1,5-a]pyridin-2-ylamino)-N-methylbenzamide;
5-(pyrrolidin-1-yl)-N-(4-(trifluoromethyl)phenyl)-[1,2,4]triazolo[1,5-a]pyridin-2-amine;
5-(morpholinomethyl)-N-(4-(trifluoromethyl)phenyl)-[1,2,4]triazolo[1,5-a]pyridin-2-amine;
(R)-1-(2-(4-(trifluoromethyl)phenylamino)-[1,2,4]triazolo[1,5-a]pyridin-5-yl)piperidin-3-ol;
(S)-1-(2-(4-(trifluoromethyl)phenylamino)-[1,2,4]triazolo[1,5-a]pyridin-5-yl)piperidin-3-ol;
cis-4-(2-(3,4-difluorophenylamino)-[1,2,4]triazolo[1,5-a]pyridin-5-ylamino)cyclohexanol;
2-(4-(2-(4-(trifluoromethyl)phenylamino)-[1,2,4]triazolo[1,5-a]pyridin-5-yl)pyridin-2-ylamino)ethanol;
cis-4-(2-(6-morpholinopyridin-3-ylamino)-[1,2,4]triazolo[1,5-a]pyridin-5-ylamino)cyclohexanol;
cis-4-(2-(3,5-dimethylphenylamino)-[1,2,4]triazolo[1,5-a]pyridin-5-ylamino)cyclohexanol;
2-(2-(4-(trifluoromethyl)phenylamino)-[1,2,4]triazolo[1,5-a]pyridin-5-yloxy)ethanol;
cis-3-(5-(4-hydroxycyclohexylamino)-[1,2,4]triazolo[1,5-a]pyridin-2-ylamino)-N-methylbenzamide;
4-((2-(4-(trifluoromethyl)phenylamino)-[1,2,4]triazolo[1,5-a]pyridin-5-yl)methyl)pyridin-2(1H)-one;
cis-2-fluoro-5-(5-(4-hydroxycyclohexylamino)-[1,2,4]triazolo[1,5-a]pyridin-2-ylamino)benzamide;
cis-4-(2-(4-fluorophenylamino)-[1,2,4]triazolo[1,5-a]pyridin-5-ylamino)cyclohexanol;
cis-4-(2-(4-fluoro-3-methylphenylamino)-[1,2,4]triazolo[1,5-a]pyridin-5-ylamino)cyclohexanol;
5-(3-aminopropoxy)-N-(4-(trifluoromethyl)phenyl)-[1,2,4]triazolo[1,5-a]pyridin-2-amine;
cis-4-(2-(2-fluoropyridin-3-ylamino)-[1,2,4]triazolo[1,5-a]pyridin-5-ylamino)cyclohexanol;
(R)-(1-((2-(4-(trifluoromethyl)phenylamino)-[1,2,4]triazolo[1,5-a]pyridin-5-yl)methyl)pyrrolidin-3-yl)methanol;
(S)-(1-((2-(4-(trifluoromethyl)phenylamino)-[1,2,4]triazolo[1,5-a]pyridin-5-yl)methyl)pyrrolidin-3-yl)methanol;
N-methyl-4-(5-(pyridin-3-yl)-[1,2,4]triazolo[1,5-a]pyridin-2-ylamino)benzamide;
(R)-(1-(2-(4-(trifluoromethyl)phenylamino)-[1,2,4]triazolo[1,5-a]pyridin-5-yl)pyrrolidin-3-yl)methanol;
(S)-(1-(2-(4-(trifluoromethyl)phenylamino)-[1,2,4]triazolo[1,5-a]pyridin-5-yl)pyrrolidin-3-yl)methanol;
(R)-2-(2-(4-(trifluoromethyl)phenylamino)-[1,2,4]triazolo[1,5-a]pyridin-5-ylamino)propan-1-ol;
(S)-2-(2-(4-(trifluoromethyl)phenylamino)-[1,2,4]triazolo[1,5-a]pyridin-5-ylamino)propan-1-ol;

$N^5$-isopropyl-$N^2$-(4-(trifluoromethyl)phenyl)-[1,2,4]triazolo[1,5-a]pyridine-2,5-diamine;

cis-4-(5-(4-hydroxycyclohexylamino)-[1,2,4]triazolo[1,5-a]pyridin-2-ylamino)pyridin-2-ol;

(R)-1-(2-(4-(trifluoromethyl)phenylamino)-[1,2,4]triazolo[1,5-a]pyridin-5-yl)pyrrolidin-3-ol;

(S)-1-(2-(4-(trifluoromethyl)phenylamino)-[1,2,4]triazolo[1,5-a]pyridin-5-yl)pyrrolidin-3-ol;

(1S,2S)-2-(2-(4-(trifluoromethyl)phenylamino)-[1,2,4]triazolo[1,5-a]pyridin-5-ylamino)cyclohexanol;

(R)-1-((2-(4-(trifluoromethyl)phenylamino)-[1,2,4]triazolo[1,5-a]pyridin-5-yl)methyl)pyrrolidin-3-ol;

(S)-1-((2-(4-(trifluoromethyl)phenylamino)-[1,2,4]triazolo[1,5-a]pyridin-5-yl)methyl)pyrrolidin-3-ol;

cis-3-(5-(4-hydroxycyclohexylamino)-[1,2,4]triazolo[1,5-a]pyridin-2-ylamino)benzamide;

cis-4-(2-(3-methoxyphenylamino)-[1,2,4]triazolo[1,5-a]pyridin-5-ylamino)cyclohexanol;

cis-4-(2-(2-methoxyphenylamino)-[1,2,4]triazolo[1,5-a]pyridin-5-ylamino)cyclohexanol;

cis-3-fluoro-4-(5-(4-hydroxycyclohexylamino)-[1,2,4]triazolo[1,5-a]pyridin-2-ylamino)benzamide;

cis-3-fluoro-4-(5-(4-hydroxycyclohexylamino)-[1,2,4]triazolo[1,5-a]pyridin-2-ylamino)benzonitrile;

cis-4-(2-(6-methoxypyridin-2-ylamino)-[1,2,4]triazolo[1,5-a]pyridin-5-ylamino)cyclohexanol;

cis-4-(2-(p-tolylamino)-[1,2,4]triazolo[1,5-a]pyridin-5-ylamino)cyclohexanol;

cis-4-(2-(4-(trifluoromethyl)phenylamino)-[1,2,4]triazolo[1,5-a]pyridin-5-yloxy)cyclohexanecarboxamide;

1-(2-(4-(trifluoromethyl)phenylamino)-[1,2,4]triazolo[1,5-a]pyridin-5-yl)piperidin-4-ol;

(1-(2-(4-(trifluoromethyl)phenylamino)-[1,2,4]triazolo[1,5-a]pyridin-5-yl)piperidin-4-yl)methanol;

cis-2-fluoro-4-(5-(4-hydroxycyclohexylamino)-[1,2,4]triazolo[1,5-a]pyridin-2-ylamino)benzamide;

cis-3-(5-(4-hydroxycyclohexylamino)-[1,2,4]triazolo[1,5-a]pyridin-2-ylamino)benzonitrile;

cis-4-(2-(pyridin-2-ylamino)-[1,2,4]triazolo[1,5-a]pyridin-5-ylamino)cyclohexanol;

cis-4-(2-(m-tolylamino)-[1,2,4]triazolo[1,5-a]pyridin-5-ylamino)cyclohexanol;

cis-4-(2-(3-methyl-1H-indazol-6-ylamino)-[1,2,4]triazolo[1,5-a]pyridin-5-ylamino)cyclohexanol;

5-(piperidin-4-yloxy)-N-(4-(trifluoromethyl)phenyl)-[1,2,4]triazolo[1,5-a]pyridin-2-amine;

cis-4-(2-(4-chlorophenylamino)-[1,2,4]triazolo[1,5-a]pyridin-5-ylamino)cyclohexanol;

cis-4-(2-(3-chlorophenylamino)-[1,2,4]triazolo[1,5-a]pyridin-5-ylamino)cyclohexanol;

cis-4-(2-(3-fluorophenylamino)-[1,2,4]triazolo[1,5-a]pyridin-5-ylamino)cyclohexanol;

(1S,2R)-(2-(2-(4-(trifluoromethyl)phenylamino)-[1,2,4]triazolo[1,5-a]pyridin-5-ylamino)cyclohexyl)methanol;

cis-4-(2-(2-fluorophenylamino)-[1,2,4]triazolo[1,5-a]pyridin-5-ylamino)cyclohexanol;

2-methyl-2-(2-(4-(trifluoromethyl)phenylamino)-[1,2,4]triazolo[1,5-a]pyridin-5-ylamino)propan-1-ol;

cis-4-(2-(6-(2-hydroxypropan-2-yl)pyridin-3-ylamino)-[1,2,4]triazolo[1,5-a]pyridin-5-ylamino)cyclohexanol;

4-(5-(cis-4-aminocyclohexylamino)-[1,2,4]triazolo[1,5-a]pyridin-2-ylamino)-N-methylbenzamide;

(R)-5-(piperidin-3-yloxy)-N-(4-(trifluoromethyl)phenyl)-[1,2,4]triazolo[1,5-a]pyridin-2-amine;

(S)-5-(piperidin-3-yloxy)-N-(4-(trifluoromethyl)phenyl)-[1,2,4]triazolo[1,5-a]pyridin-2-amine;

4-(5-(cis-4-hydroxycyclohexylamino)-[1,2,4]triazolo[1,5-a]pyridin-2-ylamino)benzonitrile;

cis-4-(2-(1-methyl-1H-indazol-6-ylamino)-[1,2,4]triazolo[1,5-a]pyridin-5-ylamino)cyclohexanol;

cis-4-(2-(1H-indazol-6-ylamino)-[1,2,4]triazolo[1,5-a]pyridin-5-ylamino)cyclohexanol;

cis-4-(2-(2-(methylamino)pyridin-4-ylamino)-[1,2,4]triazolo[1,5-a]pyridin-5-ylamino)cyclohexanol;

cis-4-(2-(2-methylpyridin-4-ylamino)-[1,2,4]triazolo[1,5-a]pyridin-5-ylamino)cyclohexanol;

cis-4-(2-(5-methoxypyridin-3-ylamino)-[1,2,4]triazolo[1,5-a]pyridin-5-ylamino)cyclohexanol;

cis-5-(5-(4-hydroxycyclohexylamino)-[1,2,4]triazolo[1,5-a]pyridin-2-ylamino)nicotinamide;

cis-5-(5-(4-hydroxycyclohexylamino)-[1,2,4]triazolo[1,5-a]pyridin-2-ylamino)picolinamide;

cis-5-(5-(4-hydroxycyclohexylamino)-[1,2,4]triazolo[1,5-a]pyridin-2-ylamino)pyridin-2-ol;

5-(pyridin-4-ylmethyl)-N-(4-(trifluoromethyl)phenyl)-[1,2,4]triazolo[1,5-a]pyridin-2-amine;

(±)-trans-3-(2-(4-(trifluoromethyl)phenylamino)-[1,2,4]triazolo[1,5-a]pyridin-5-ylamino)cyclohexanol;

(1S,2S)-2-(2-(4-(trifluoromethyl)phenylamino)-[1,2,4]triazolo[1,5-a]pyridin-5-ylamino)cyclopentanol;

trans-4-((2-(4-(trifluoromethyl)phenylamino)-[1,2,4]triazolo[1,5-a]pyridin-5-ylamino)methyl)cyclohexanol;

(1S,2R)-2-(2-(4-(trifluoromethyl)phenylamino)-[1,2,4]triazolo[1,5-a]pyridin-5-ylamino)cyclopentanol;

(1R,2R)-2-(2-(4-(trifluoromethyl)phenylamino)-[1,2,4]triazolo[1,5-a]pyridin-5-ylamino)cyclopentanol;

cis-4-(2-(2-methoxypyridin-4-ylamino)-[1,2,4]triazolo[1,5-a]pyridin-5-ylamino)cyclohexanol;

2-(6-(2-(4-(trifluoromethyl)phenylamino)-[1,2,4]triazolo[1,5-a]pyridin-5-yl)-1H-benzo[d]imidazol-2-yl)propan-2-ol;

5-(1H-imidazo[4,5-b]pyridin-6-yl)-N-(4-(trifluoromethyl)phenyl)-[1,2,4]triazolo[1,5-a]pyridin-2-amine;

cis-5-(5-(4-hydroxycyclohexylamino)-[1,2,4]triazolo[1,5-a]pyridin-2-ylamino)picolinonitrile;

cis-4-((2-(4-(trifluoromethyl)phenylamino)-[1,2,4]triazolo[1,5-a]pyridin-5-ylamino)methyl)cyclohexanol;

trans-1-methyl-4-(2-(4-(trifluoromethyl)phenylamino)-[1,2,4]triazolo[1,5-a]pyridin-5-ylamino)cyclohexanol;

cis-1-methyl-4-(2-(4-(trifluoromethyl)phenylamino)-[1,2,4]triazolo[1,5-a]pyridin-5-ylamino)cyclohexanol;

cis-2-(4-(2-(4-(trifluoromethyl)phenylamino)-[1,2,4]triazolo[1,5-a]pyridin-5-ylamino)cyclohexyl)propan-2-ol;

cis-4-(5-(4-hydroxycyclohexylamino)-[1,2,4]triazolo[1,5-a]pyridin-2-ylamino)-N-methylbenzamide;

trans-4-(5-(4-hydroxycyclohexylamino)-[1,2,4]triazolo[1,5-a]pyridin-2-ylamino)-N-methylbenzamide;

4-((2-(4-(trifluoromethyl)phenylamino)-[1,2,4]triazolo[1,5-a]pyridin-5-yl)methyl)piperazin-2-one;

cis-4-(2-(pyridin-4-ylamino)-[1,2,4]triazolo[1,5-a]pyridin-5-ylamino)cyclohexanol;

cis-4-(2-(5-methylpyridin-3-ylamino)-[1,2,4]triazolo[1,5-a]pyridin-5-ylamino)cyclohexanol;

cis-4-(2-(6-methoxypyridin-3-ylamino)-[1,2,4]triazolo[1,5-a]pyridin-5-ylamino)cyclohexanol;

cis-4-(2-(6-(dimethylamino)pyridin-3-ylamino)-[1,2,4]triazolo[1,5-a]pyridin-5-ylamino)cyclohexanol;

5-(piperazin-1-ylmethyl)-N-(4-(trifluoromethyl)phenyl)-[1,2,4]triazolo[1,5-a]pyridin-2-amine;

trans-4-(5-(4-aminocyclohexylamino)-[1,2,4]triazolo[1,5-a]pyridin-2-ylamino)-N-methylbenzamide;

5-(piperidin-4-ylmethyl)-N-(4-(trifluoromethyl)phenyl)-[1,2,4]triazolo[1,5-a]pyridin-2-amine;

1-((2-(4-(trifluoromethyl)phenylamino)-[1,2,4]triazolo[1,5-a]pyridin-5-yl)methyl)piperidin-4-ol;
trans-2-(4-(2-(4-(trifluoromethyl)phenylamino)-[1,2,4]triazolo[1,5-a]pyridin-5-ylamino)cyclohexyl)propan-2-ol;
trans-4-((2-(4-(trifluoromethyl)phenylamino)-[1,2,4]triazolo[1,5-a]pyridin-5-yl)methyl)cyclohexanol;
cis-4-((2-(4-(trifluoromethyl)phenylamino)-[1,2,4]triazolo[1,5-a]pyridin-5-yl)methyl)cyclohexanol;
4-(5-(cyclopentylamino)-[1,2,4]triazolo[1,5-a]pyridin-2-ylamino)-N-methylbenzamide;
5-(2-(methoxymethyl)-1H-benzo[d]imidazol-6-yl)-N-(4-(trifluoromethyl)phenyl)-[1,2,4]triazolo[1,5-a]pyridin-2-amine;
1-(6-(2-(4-(trifluoromethyl)phenylamino)-[1,2,4]triazolo[1,5-a]pyridin-5-yl)-1H-benzo[d]imidazol-2-yl)ethanol;
cis-4-(2-(6-methylpyridin-3-ylamino)-[1,2,4]triazolo[1,5-a]pyridin-5-ylamino)cyclohexanol;
(S)—$N^2$-(2-(2-aminoethoxy)pyridin-4-yl)-$N^5$-(piperidin-3-yl)-[1,2,4]triazolo[1,5-a]pyridine-2,5-diamine;
trans-4-(2-(4-(trifluoromethyl)phenylamino)-[1,2,4]triazolo[1,5-a]pyridin-5-yloxy)cyclohexanecarboxamide;
(1R,2S)-2-(2-(4-(trifluoromethyl)phenylamino)-[1,2,4]triazolo[1,5-a]pyridin-5-ylamino)cyclopentanol;
5-((1-ethylpiperidin-4-yl)methyl)-N-(4-(trifluoromethyl)phenyl)-[1,2,4]triazolo[1,5-a]pyridin-2-amine;
6-(2-(4-(trifluoromethyl)phenylamino)-[1,2,4]triazolo[1,5-a]pyridin-5-yl)-1H-benzo[d]imidazole-2-carboxamide;
(6-(2-(4-(trifluoromethyl)phenylamino)-[1,2,4]triazolo[1,5-a]pyridin-5-yl)-1H-benzo[d]imidazol-2-yl)methanol;
cis-(4-(2-(4-(trifluoromethyl)phenylamino)-[1,2,4]triazolo[1,5-a]pyridin-5-ylamino)cyclohexyl)methanol;
(S)—$N^2$-(6-morpholinopyridin-3-yl)-$N^5$-(piperidin-3-yl)-[1,2,4]triazolo[1,5-a]pyridine-2,5-diamine;
(R)-2-phenyl-2-(2-(4-(trifluoromethyl)phenylamino)-[1,2,4]triazolo[1,5-a]pyridin-5-ylamino)ethanol;
(S)-2-phenyl-2-(2-(4-(trifluoromethyl)phenylamino)-[1,2,4]triazolo[1,5-a]pyridin-5-ylamino)ethanol;
trans-(4-(2-(4-(trifluoromethyl)phenylamino)-[1,2,4]triazolo[1,5-a]pyridin-5-ylamino)cyclohexyl)methanol;
4-(2-(4-(trifluoromethyl)phenylamino)-[1,2,4]triazolo[1,5-a]pyridin-5-ylamino)pyridin-2-ol;
4-(2-(4-fluorophenylamino)-[1,2,4]triazolo[1,5-a]pyridin-5-yl)picolinamide;
cis-4-(2-(4-fluorophenylamino)-[1,2,4]triazolo[1,5-a]pyridin-5-yloxy)cyclohexanol;
(1S,3R)-3-(2-(4-(trifluoromethyl)phenylamino)-[1,2,4]triazolo[1,5-a]pyridin-5-ylamino)cyclopentanol;
(1S,3S)-3-(2-(4-(trifluoromethyl)phenylamino)-[1,2,4]triazolo[1,5-a]pyridin-5-ylamino)cyclopentanol;
(1R,3R)-3-(2-(4-(trifluoromethyl)phenylamino)-[1,2,4]triazolo[1,5-a]pyridin-5-ylamino)cyclopentanol;
(1R,3S)-3-(2-(4-(trifluoromethyl)phenylamino)-[1,2,4]triazolo[1,5-a]pyridin-5-ylamino)cyclopentanol;
trans-5-(4-aminocyclohexyloxy)-N-(4-(trifluoromethyl)phenyl)-[1,2,4]triazolo[1,5-a]pyridin-2-amine;
cis-5-(4-aminocyclohexyloxy)-N-(4-(trifluoromethyl)phenyl)-[1,2,4]triazolo[1,5-a]pyridin-2-amine;
5-(2-((methylamino)methyl)benzo[d]oxazol-6-yl)-N-phenyl-[1,2,4]triazolo[1,5-a]pyridin-2-amine;
2-(2-(4-fluorophenylamino)-[1,2,4]triazolo[1,5-a]pyridin-5-yl)-1-(piperidin-4-yl)ethanol;
4-(5-(1H-indazol-5-yl)-[1,2,4]triazolo[1,5-a]pyridin-2-ylamino)-N-methylbenzamide;
$N^5$-(azepan-3-yl)-$N^2$-(4-fluorophenyl)-[1,2,4]triazolo[1,5-a]pyridine-2,5-diamine;
N-phenyl-5-(2-(pyrrolidin-1-ylmethyl)-1H-benzo[d]imidazol-6-yl)-[1,2,4]triazolo[1,5-a]pyridin-2-amine;
cis-4-(5-(4-hydroxycyclohexylamino)-[1,2,4]triazolo[1,5-a]pyridin-2-ylamino)benzamide;
4-((2-(4-fluorophenylamino)-[1,2,4]triazolo[1,5-a]pyridin-5-yl)methyl)piperidin-4-ol;
2-(2-(4-fluorophenylamino)-[1,2,4]triazolo[1,5-a]pyridin-5-yl)-1-phenylethanol;
4-(5-(1H-benzo[d][1,2,3]triazol-6-yl)-[1,2,4]triazolo[1,5-a]pyridin-2-ylamino)-N-methylbenzamide;
(S)—$N^5$-(piperidin-3-yl)-$N^2$-(pyridin-3-yl)-[1,2,4]triazolo[1,5-a]pyridine-2,5-diamine;
(R)—$N^5$-(piperidin-3-yl)-$N^2$-(pyridin-3-yl)-[1,2,4]triazolo[1,5-a]pyridine-2,5-diamine;
5-(4-methylisoxazol-3-yl)-N-phenyl-[1,2,4]triazolo[1,5-a]pyridin-2-amine;
N-(4-fluorophenyl)-5-(1H-indazol-6-yl)-[1,2,4]triazolo[1,5-a]pyridin-2-amine;
N-(4-fluorophenyl)-5-(2-((methylamino)methyl)-1H-benzo[d]imidazol-6-yl)-[1,2,4]triazolo[1,5-a]pyridin-2-amine;
$N^2$-phenyl-$N^5$-(tetrahydro-2H-pyran-4-yl)-[1,2,4]triazolo[1,5-a]pyridine-2,5-diamine;
5-(3-amino-1H-indazol-6-yl)-N-phenyl-[1,2,4]triazolo[1,5-a]pyridin-2-amine;
5-(2-((methylamino)methyl)-1H-benzo[d]imidazol-6-yl)-N-(4-(trifluoromethyl)phenyl)-[1,2,4]triazolo[1,5-a]pyridin-2-amine;
N-methyl-4-(5-(tetrahydrofuran-3-ylamino)-[1,2,4]triazolo[1,5-a]pyridin-2-ylamino)benzamide;
3-((2-(phenylamino)-[1,2,4]triazolo[1,5-a]pyridin-5-yl)methyl)benzamide;
2-(4-(2-(phenylamino)-[1,2,4]triazolo[1,5-a]pyridin-5-yl)pyridin-2-ylamino)ethanol;
5-(2-(2-aminoethoxy)pyridin-4-yl)-N-phenyl-[1,2,4]triazolo[1,5-a]pyridin-2-amine;
5-(2-aminopyridin-4-yl)-N-phenyl-[1,2,4]triazolo[1,5-a]pyridin-2-amine;
5-(2-(dimethylamino)pyridin-4-yl)-N-phenyl-[1,2,4]triazolo[1,5-a]pyridin-2-amine;
$N^1$-(4-(2-(phenylamino)-[1,2,4]triazolo[1,5-a]pyridin-5-yl)pyridin-2-yl)ethane-1,2-diamine;
(R)—$N^2$-(isoindolin-5-yl)-$N^5$-(piperidin-3-yl)-[1,2,4]triazolo[1,5-a]pyridine-2,5-diamine;
(S)—$N^2$-(isoindolin-5-yl)-$N^5$-(piperidin-3-yl)-[1,2,4]triazolo[1,5-a]pyridine-2,5-diamine;
(R)—$N^2$-(3-amino-1H-indazol-6-yl)-$N^5$-(piperidin-3-yl)-[1,2,4]triazolo[1,5-a]pyridine-2,5-diamine;
(S)—$N^2$-(3-amino-1H-indazol-6-yl)-$N^5$-(piperidin-3-yl)-[1,2,4]triazolo[1,5-a]pyridine-2,5-diamine;
4-((2-(phenylamino)-[1,2,4]triazolo[1,5-a]pyridin-5-yl)methyl)benzamide;
cis-4-(2-(4-(trifluoromethyl)phenylamino)-[1,2,4]triazolo[1,5-a]pyridin-5-ylamino)cyclohexanol;
(S)—$N^2$-(1H-benzo[d][1,2,3]triazol-6-yl)-$N^5$-(piperidin-3-yl)-[1,2,4]triazolo[1,5-a]pyridine-2,5-diamine;
(R)—$N^2$-(1H-benzo[d][1,2,3]triazol-6-yl)-$N^5$-(piperidin-3-yl)-[1,2,4]triazolo[1,5-a]pyridine-2,5-diamine;
N-methyl-4-(5-(tetrahydro-2H-pyran-4-ylamino)-[1,2,4]triazolo[1,5-a]pyridin-2-ylamino)benzamide;
5-(2-(phenylamino)-[1,2,4]triazolo[1,5-a]pyridin-5-yl)benzo[d]isoxazol-3-amine;
(R)-5-(3-amino-2-methylpropyl)-N-phenyl-[1,2,4]triazolo[1,5-a]pyridin-2-amine;
(S)-5-(3-amino-2-methylpropyl)-N-phenyl[1,2,4]triazolo[1,5-a]pyridin-2-amine;
(R)-2-methyl-3-(2-(phenylamino)-[1,2,4]triazolo[1,5-a]pyridin-5-yl)propanamide;
(S)-2-methyl-3-(2-(phenylamino)-[1,2,4]triazolo[1,5-a]pyridin-5-yl)propanamide;

(R)—N²-(4-fluorophenyl)-N⁵-(piperidin-3-yl)-[1,2,4]triazolo[1,5-a]pyridine-2,5-diamine;
(R)—N²-(1-methyl-1H-indazol-6-yl)-N⁵-(piperidin-3-yl)-[1,2,4]triazolo[1,5-a]pyridine-2,5-diamine;
(S)—N²-(1H-indazol-6-yl)-N⁵-(piperidin-3-yl)-[1,2,4]triazolo[1,5-a]pyridine-2,5-diamine;
(S)—N²-(4-fluorophenyl)-N⁵-(piperidin-3-yl)-[1,2,4]triazolo[1,5-a]pyridine-2,5-diamine;
(S)—N²-(1-methyl-1H-indazol-6-yl)-N⁵-(piperidin-3-yl)-[1,2,4]triazolo[1,5-a]pyridine-2,5-diamine;
(R)—N²-(1H-indazol-6-yl)-N⁵-(piperidin-3-yl)-[1,2,4]triazolo[1,5-a]pyridine-2,5-diamine;
(R)—N⁵-(piperidin-3-yl)-N²-(4-(trifluoromethyl)phenyl)-[1,2,4]triazolo[1,5-a]pyridine-2,5-diamine;
(S)—N⁵-(piperidin-3-yl)-N²-(4-(trifluoromethyl)phenyl)-[1,2,4]triazolo[1,5-a]pyridine-2,5-diamine;
trans-4-(2-(phenylamino)-[1,2,4]triazolo[1,5-a]pyridin-5-ylamino)cyclohexanol;
cis-4-(2-(phenylamino)-[1,2,4]triazolo[1,5-a]pyridin-5-ylamino)cyclohexanol;
N⁵-methyl-N²,N⁵-diphenyl-[1,2,4]triazolo[1,5-a]pyridine-2,5-diamine;
5-(5-methylisoxazol-3-yl)-N-phenyl-[1,2,4]triazolo[1,5-a]pyridin-2-amine;
(R)—N²-phenyl-N⁵-(pyrrolidin-3-yl)-[1,2,4]triazolo[1,5-a]pyridine-2,5-diamine;
(S)—N²-phenyl-N⁵-(pyrrolidin-3-yl)-[1,2,4]triazolo[1,5-a]pyridine-2,5-diamine;
(R)-4-(5-(piperidin-3-ylamino)-[1,2,4]triazolo[1,5-a]pyridin-2-ylamino)benzamide;
N⁵,N⁵-dimethyl-N²-phenyl-[1,2,4]triazolo[1,5-a]pyridine-2,5-diamine;
N-phenyl-5-(piperidin-3-ylmethyl)-[1,2,4]triazolo[1,5-a]pyridin-2-amine;
(R)-2-methyl-3-(2-(phenylamino)-[1,2,4]triazolo[1,5-a]pyridin-5-yl)propan-1-ol;
(S)-2-methyl-3-(2-(phenylamino)-[1,2,4]triazolo[1,5-a]pyridin-5-yl)propan-1-ol;
5-(2-(methylamino)-1H-benzo[d]imidazol-5-yl)-N-phenyl-[1,2,4]triazolo[1,5-a]pyridin-2-amine;
N-phenyl-5-(piperidin-4-ylmethyl)-[1,2,4]triazolo[1,5-a]pyridin-2-amine;
(S)-4-(5-(piperidin-3-ylamino)-[1,2,4]triazolo[1,5-a]pyridin-2-ylamino)benzamide;
N²-phenyl-N⁵-(pyridin-2-yl)-[1,2,4]triazolo[1,5-a]pyridine-2,5-diamine;
5-(1H-indazol-6-yl)-N-phenyl-[1,2,4]triazolo[1,5-a]pyridin-2-amine;
5-(2-((dimethylamino)methyl)-1H-benzo[d]imidazol-5-yl)-N-phenyl-[1,2,4]triazolo[1,5-a]pyridin-2-amine;
5-(2-((methylamino)methyl)-1H-benzo[d]imidazol-5-yl)-N-phenyl-[1,2,4]triazolo[1,5-a]pyridin-2-amine;
N-phenyl-5-(pyridin-2-yl)-[1,2,4]triazolo[1,5-a]pyridin-2-amine;
7-(2-(phenylamino)-[1,2,4]triazolo[1,5-a]pyridin-5-yl)isoquinolin-1-amine;
5-(1-(2-aminoethyl)-1H-benzo[d]imidazol-5-yl)-N-phenyl-[1,2,4]triazolo[1,5-a]pyridin-2-amine;
(1-benzylpiperidin-4-yl)(2-(phenylamino)-[1,2,4]triazolo[1,5-a]pyridin-5-yl)methanol;
trans-4-(5-(4-aminocyclohexylamino)-[1,2,4]triazolo[1,5-a]pyridin-2-ylamino)benzamide;
cis-4-(5-(4-aminocyclohexylamino)-[1,2,4]triazolo[1,5-a]pyridin-2-ylamino)benzamide;
2-(aminoethyl)-5-(2-(phenylamino)-[1,2,4]triazolo[1,5-a]pyridin-5-yl)-isoindolin-1-one;
2-(2-aminoethyl)-6-(2-(phenylamino)-[1,2,4]triazolo[1,5-a]pyridin-5-yl)-isoindolin-1-one;
5-(2-(phenylamino)-[1,2,4]triazolo[1,5-a]pyridin-5-yl)isoindolin-1-one;
(R)—N²-phenyl-N⁵-(piperidin-3-yl)-[1,2,4]triazolo[1,5-a]pyridine-2,5-diamine;
5-(3-aminopropyl)-N-phenyl-[1,2,4]triazolo[1,5-a]pyridin-2-amine;
4-(2-(phenylamino)-[1,2,4]triazolo[1,5-a]pyridin-5-yl)isoindolin-1-one;
6-(2-(phenylamino)-[1,2,4]triazolo[1,5-a]pyridin-5-yl)isoindolin-1-one;
(2-(phenylamino)-[1,2,4]triazolo[1,5-a]pyridin-5-yl)(pyridin-3-yl)methanol;
(2-(phenylamino)-[1,2,4]triazolo[1,5-a]pyridin-5-yl)(piperidin-4-yl)methanol;
5-phenoxy-N-phenyl-[1,2,4]triazolo[1,5-a]pyridin-2-amine;
(S)-2-(phenylamino)-N-(piperidin-3-yl)-[1,2,4]triazolo[1,5-a]pyridine-5-carboxamide;
5-(4-aminobutyl)-N-phenyl-[1,2,4]triazolo[1,5-a]pyridin-2-amine;
5-benzyl-N-phenyl-[1,2,4]triazolo[1,5-a]pyridin-2-amine;
(S)—N²-phenyl-N⁵-(piperidin-3-yl)-[1,2,4]triazolo[1,5-a]pyridine-2,5-diamine;
cis-N⁵-(4-aminocyclohexyl)-N²-phenyl-[1,2,4]triazolo[1,5-a]pyridine-2,5-diamine;
phenyl(2-(phenylamino)-[1,2,4]triazolo[1,5-a]pyridin-5-yl)methanone;
5-(cyclohexyloxy)-N-phenyl-[1,2,4]triazolo[1,5-a]pyridin-2-amine;
5-(3-amino-1H-indazol-5-yl)-N-phenyl-[1,2,4]triazolo[1,5-a]pyridin-2-amine;
N-phenyl-5-(piperidin-4-yl)-[1,2,4]triazolo[1,5-a]pyridin-2-amine;
N-phenyl-5-(1,2,3,6-tetrahydropyridin-4-yl)-[1,2,4]triazolo[1,5-a]pyridin-2-amine;
5-(1H-benzo[d]imidazol-6-yl)-N-phenyl-[1,2,4]triazolo[1,5-a]pyridin-2-amine;
5-(1-(2-aminoethyl)-1H-benzo[d]imidazol-6-yl)-N-phenyl-[1,2,4]triazolo[1,5-a]pyridin-2-amine;
4-(5-(piperidin-4-ylamino)-[1,2,4]triazolo[1,5-a]pyridin-2-ylamino)benzamide;
4-(2-(phenylamino)-[1,2,4]triazolo[1,5-a]pyridin-5-yl)pyridin-2-ol;
trans-N⁵-(4-aminocyclohexyl)-N²-phenyl-[1,2,4]triazolo[1,5-a]pyridine-2,5-diamine;
cis-4-(2-(phenylamino)-[1,2,4]triazolo[1,5-a]pyridin-5-ylamino)cyclohexanecarboxamide;
N-phenyl-5-(2-(piperazin-1-yl)pyridin-4-yl)-[1,2,4]triazolo[1,5-a]pyridin-2-amine;
5-(2-methoxypyridin-4-yl)-N-phenyl-[1,2,4]triazolo[1,5-a]pyridin-2-amine;
5-(1H-indazol-5-yl)-N-phenyl-[1,2,4]triazolo[1,5-a]pyridin-2-amine;
N²-phenyl-N⁵-(piperidin-4-yl)-[1,2,4]triazolo[1,5-a]pyridine-2,5-diamine;
N-phenyl-5-(pyridin-3-yl)-[1,2,4]triazolo[1,5-a]pyridin-2-amine;
5-cyclohexyl-N-phenyl-[1,2,4]triazolo[1,5-a]pyridin-2-amine;
N-(2-(phenylamino)-[1,2,4]triazolo[1,5-a]pyridin-5-yl)isobutyramide;
N-(2-(phenylamino)-[1,2,4]triazolo[1,5-a]pyridin-5-yl)acetamide;
N-phenyl-5-(pyridin-4-yl)-[1,2,4]triazolo[1,5-a]pyridin-2-amine;
N²,N⁵-diphenyl-[1,2,4]triazolo[1,5-a]pyridine-2,5-diamine;

$N^5$-isopropyl-$N^2$-phenyl-[1,2,4]triazolo[1,5-a]pyridine-2,5-diamine;
$N^2$-(3-methylbenzo[d]isoxazol-6-yl)-$N^5$-(tetrahydro-2H-pyran-4-yl)-[1,2,4]triazolo[1,5-a]pyridine-2,5-diamine;
1-methyl-5-(5-((tetrahydro-2H-pyran-4-yl)methyl)-[1,2,4]triazolo[1,5-a]pyridin-2-ylamino)-1H-benzo[d]imidazol-2(3H)-one;
4-((2-(3-(methoxymethyl)-1H-indazol-6-ylamino)-[1,2,4]triazolo[1,5-a]pyridin-5-yl)methyl)piperazin-2-one;
$N^2$-(3-methyl-[1,2,4]triazolo[4,3-a]pyridin-7-yl)-$N^5$-(tetrahydro-2H-pyran-4-yl)-[1,2,4]triazolo[1,5-a]pyridine-2,5-diamine;
N-(5-methyl-6-morpholinopyridin-3-yl)-5-((tetrahydro-2H-pyran-4-yl)methyl)-[1,2,4]triazolo[1,5-a]pyridin-2-amine;
6-(5-(difluoro(tetrahydro-2H-pyran-4-yl)methyl)-[1,2,4]triazolo[1,5-a]pyridin-2-ylamino)-3,3-dimethylindolin-2-one;
3-methyl-N-(5-((tetrahydro-2H-pyran-4-yl)methyl)-[1,2,4]triazolo[1,5-a]pyridin-2-yl)benzo[d]isoxazol-6-amine;
3-methyl-N-(5-((tetrahydro-2H-pyran-4-yl)methyl)-[1,2,4]triazolo[1,5-a]pyridin-2-yl)-[1,2,4]triazolo[4,3-a]pyridin-7-amine;
$N^2$-(3-methyl-1H-pyrazolo[3,4-b]pyridin-5-yl)-$N^5$-(tetrahydro-2H-pyran-4-yl)-[1,2,4]triazolo[1,5-a]pyridine-2,5-diamine;
5-((tetrahydro-2H-pyran-4-yl)methyl)-N-(3-(trifluoromethyl)-1H-indazol-6-yl)-[1,2,4]triazolo[1,5-a]pyridin-2-amine;
cis-4-(2-(3-methyl-1H-pyrazolo[3,4-b]pyridin-5-ylamino)-[1,2,4]triazolo[1,5-a]pyridin-5-ylamino)cyclohexanol;
$N^5$-methyl-$N^2$-(1-methyl-1H-indazol-5-yl)-$N^5$-(tetrahydro-2H-pyran-4-yl)-[1,2,4]triazolo[1,5-a]pyridine-2,5-diamine;
cis-4-(2-(3-methylbenzo[d]isoxazol-6-ylamino)-[1,2,4]triazolo[1,5-a]pyridin-5-ylamino)cyclohexanol;
3-methyl-N-(5-((tetrahydro-2H-pyran-4-yl)methyl)-[1,2,4]triazolo[1,5-a]pyridin-2-yl)-1H-pyrazolo[3,4-b]pyridin-5-amine; cis-tert-butyl 6-(5-(4-hydroxycyclohexylamino)-[1,2,4]triazolo[1,5-a]pyridin-2-ylamino)-3,3-dimethyl-2-oxoindoline-1-carboxylate;
3,3,4-trimethyl-6-(5-((3-oxopiperazin-1-yl)methyl)-[1,2,4]triazolo[1,5-a]pyridin-2-ylamino)indolin-2-one;
$N^2$-(5-methyl-6-morpholinopyridin-3-yl)-$N^5$-(tetrahydro-2H-pyran-4-yl)-[1,2,4]triazolo[1,5-a]pyridine-2,5-diamine;
N-(3,4-dimethyl-1H-indazol-6-yl)-5-((tetrahydro-2H-pyran-4-yl)methyl)-[1,2,4]triazolo[1,5-a]pyridin-2-amine;
6-(5-(isopropylamino)-[1,2,4]triazolo[1,5-a]pyridin-2-ylamino)-3,3-dimethylindolin-2-one;
N-(1-methyl-1H-indazol-5-yl)-5-((tetrahydro-2H-pyran-4-yl)methyl)-[1,2,4]triazolo[1,5-a]pyridin-2-amine;
$N^2$-(1-methyl-1H-indazol-5-yl)-$N^5$-(tetrahydro-2H-pyran-4-yl)-[1,2,4]triazolo[1,5-a]pyridine-2,5-diamine;
N-(3-(methoxymethyl)-1H-indazol-6-yl)-5-((tetrahydro-2H-pyran-4-yl)methyl)-[1,2,4]triazolo[1,5-a]pyridin-2-amine;
cis-4-(2-(1H-pyrazolo[4,3-b]pyridin-6-ylamino)-[1,2,4]triazolo[1,5-a]pyridin-5-ylamino)cyclohexanol;
cis-4-(5-(4-hydroxycyclohexylamino)-[1,2,4]triazolo[1,5-a]pyridin-2-ylamino)-1,6-dimethylindolin-2-one;
(S)-2-methyl-3-(2-(3-methyl-1-indazol-6-ylamino)-[1,2,4]triazolo[1,5-a]pyridin-5-yl)propan-1-ol;
cis-6-(5-(4-hydroxycyclohexylamino)-[1,2,4]triazolo[1,5-a]pyridin-2-ylamino)-1,4-dimethylindolin-2-one;
N-(4-(1H-1,2,4-triazol-3-yl)phenyl)-5-((tetrahydro-2H-pyran-4-yl)methyl)-[1,2,4]triazolo[1,5-a]pyridin-2-amine;
3,3-dimethyl-6-(5-((tetrahydrofuran-3-yl)methyl)-[1,2,4]triazolo[1,5-a]pyridin-2-ylamino)indolin-2-one;
6-(5-(2-methoxypyridin-4-yl)-[1,2,4]triazolo[1,5-a]pyridin-2-ylamino)-3,3-dimethylindolin-2-one;
4-(5-(cyclohexylamino)-[1,2,4]triazolo[1,5-a]pyridin-2-ylamino)benzamide
3,3-dimethyl-6-(5-((tetrahydrofuran-3-yl)methyl)-[1,2,4]triazolo[1,5-a]pyridin-2-ylamino)indolin-2-one;
5-(difluoro(tetrahydro-2H-pyran-4-yl)methyl)-N-(3-methyl-1H-indazol-6-yl)-[1,2,4]triazolo[1,5-a]pyridin-2-amine;
5-((1,4-dioxan-2-yl)difluoromethyl)-N-(3-methyl-1H-indazol-6-yl)-[1,2,4]triazolo[1,5-a]pyridin-2-amine;
3,3-dimethyl-6-(5-methyl-[1,2,4]triazolo[1,5-a]pyridin-2-ylamino)indolin-2-one
$N^2$-(4-(1H-1,2,4-triazol-3-yl)phenyl)-$N^5$-(tetrahydro-2H-pyran-4-yl)-[1,2,4]triazolo[1,5-a]pyridine-2,5-diamine;
6-(5-(dimethylamino)-[1,2,4]triazolo[1,5-a]pyridin-2-ylamino)-3,3-dimethylindolin-2-one cis-4-(2-(4-(1H-1,2,4-triazol-3-yl)phenylamino)-[1,2,4]triazolo[1,5-a]pyridin-5-ylamino)cyclohexanol;
cis-4-(2-(3-methyl-[1,2,4]triazolo[4,3-a]pyridin-7-ylamino)-[1,2,4]triazolo[1,5-a]pyridin-5-ylamino)cyclohexanol;
1-methyl-5-(5-(tetrahydro-2H-pyran-4-ylamino)-[1,2,4]triazolo[1,5-a]pyridin-2-ylamino)-1H-benzo[d]imidazol-2(3H)-one;
cis-5-(5-(4-hydroxycyclohexylamino)-[1,2,4]triazolo[1,5-a]pyridin-2-ylamino)-1-methyl-1H-benzo[d]imidazol-2(3H)-one; or
3,3-dimethyl-6-(5-morpholino-[1,2,4]triazolo[1,5-a]pyridin-2-ylamino)indolin-2-one.

Further provided are the following Heteroaryl Compounds:
N-(2-((dimethylamino)methyl)-1H-benzo[d]imidazol-6-yl)-5-(3-fluorophenyl)-[1,2,4]triazolo[1,5-a]pyridin-2-amine;
5-(3-fluorophenyl)-N-(1H-indazol-5-yl)-[1,2,4]triazolo[1,5-a]pyridin-2-amine;
(6-(5-(3-fluorophenyl)-[1,2,4]triazolo[1,5-a]pyridin-2-ylamino)-1H-benzo[d]imidazol-2-yl)methanol;
5-(3-fluorophenyl)-N-(1-methyl-1H-benzo[d]imidazol-6-yl)-[1,2,4]triazolo[1,5-a]pyridin-2-amine;
3'-chloro-5'-(2-(4-(methylcarbamoyl)phenylamino)-[1,2,4]triazolo[1,5-a]pyridin-5-yl)biphenyl-2-carboxamide;
4-(5-(3-(3-aminopropyl)-5-chlorophenyl)-[1,2,4]triazolo[1,5-a]pyridin-2-ylamino)-N-methylbenzamide;
4-(5-(3-(1H-imidazol-5-yl)phenyl)-[1,2,4]triazolo[1,5-a]pyridin-2-ylamino)-N-methylbenzamide;
4-(5-(3-(3-aminopropyl)phenyl)-[1,2,4]triazolo[1,5-a]pyridin-2-ylamino)-N-methylbenzamide;
4-(5-(4-(1H-imidazol-4-yl)phenyl)-[1,2,4]triazolo[1,5-a]pyridin-2-ylamino)-N-methylbenzamide;
3-(2-(2-methyl-1H-benzo[d]imidazol-6-ylamino)-[1,2,4]triazolo[1,5-a]pyridin-5-yl)phenol;
4-(5-(3-(2-aminoethyl)phenyl)-[1,2,4]triazolo[1,5-a]pyridin-2-ylamino)-N-methylbenzamide;
4-(5-(3-fluorophenyl)-[1,2,4]triazolo[1,5-a]pyridin-2-ylamino)-N-methylbenzamide;
4-(5-(3-chlorophenyl)-[1,2,4]triazolo[1,5-a]pyridin-2-ylamino)-N-methylbenzamide;
3-(2-(benzo[d]isoxazol-6-ylamino)-[1,2,4]triazolo[1,5-a]pyridin-5-yl)phenol;
4-(5-(3-hydroxyphenyl)-[1,2,4]triazolo[1,5-a]pyridin-2-ylamino)-3-methoxy-N-methylbenzamide;
3-(2-(4-(1H-imidazol-2-yl)phenylamino)-[1,2,4]triazolo[1,5-a]pyridin-5-yl)phenol;

$N^6$-(5-phenyl-[1,2,4]triazolo[1,5-a]pyridin-2-yl)quinoline-2,6-diamine;
4-(5-(3-carbamoylphenyl)-[1,2,4]triazolo[1,5-a]pyridin-2-ylamino)-N-methylbenzamide;
3-(2-(1-methyl-1H-indazol-6-ylamino)-[1,2,4]triazolo[1,5-a]pyridin-5-yl)phenol;
4-(5-(3-methoxyphenyl)-[1,2,4]triazolo[1,5-a]pyridin-2-ylamino)-N-methylbenzamide;
4-(5-(2-fluorophenyl)-[1,2,4]triazolo[1,5-a]pyridin-2-ylamino)-N-methylbenzamide;
4-(5-(2-chlorophenyl)-[1,2,4]triazolo[1,5-a]pyridin-2-ylamino)-N-methylbenzamide;
$N^6$-(5-phenyl-[1,2,4]triazolo[1,5-a]pyridin-2-yl)-$N^3$-(piperidin-4-yl)-1H-indazole-3,6-diamine;
3-(2-(4-(aminomethyl)phenylamino)-[1,2,4]triazolo[1,5-a]pyridin-5-yl)phenol;
4-(5-(3-hydroxyphenyl)-[1,2,4]triazolo[1,5-a]pyridin-2-ylamino)benzoic acid;
6-(5-phenyl-[1,2,4]triazolo[1,5-a]pyridin-2-ylamino)quinolin-2-ol;
3-(2-(1H-indazol-6-ylamino)-[1,2,4]triazolo[1,5-a]pyridin-5-yl)phenol;
3-(2-(1-methyl-1H-benzo[d][1,2,3]triazol-6-ylamino)-[1,2,4]triazolo[1,5-a]pyridin-5-yl)phenol;
4-(2-(4-(methylcarbamoyl)phenylamino)-[1,2,4]triazolo[1,5-a]pyridin-5-yl)benzoic acid;
3-(2-(4-(methylcarbamoyl)phenylamino)-[1,2,4]triazolo[1,5-a]pyridin-5-yl)benzoic acid;
N-(2-((dimethylamino)methyl)-1H-benzo[d]imidazol-6-yl)-5-phenyl-[1,2,4]triazolo[1,5-a]pyridin-2-amine;
3-(2-(4-morpholinophenylamino)-[1,2,4]triazolo[1,5-a]pyridin-5-yl)phenol;
4-(5-(3-(aminomethyl)phenyl)-[1,2,4]triazolo[1,5-a]pyridin-2-ylamino)-N-methylbenzamide;
4-(5-(3-hydroxyphenyl)-[1,2,4]triazolo[1,5-a]pyridin-2-ylamino)-N-(1-methylpiperidin-4-yl)benzamide;
1-methyl-$N^6$-(5-phenyl-[1,2,4]triazolo[1,5-a]pyridin-2-yl)-1H-indazole-3,6-diamine;
4-(5-(3-hydroxyphenyl)-[1,2,4]triazolo[1,5-a]pyridin-2-ylamino)-N-methylbenzamide;
N-(5-phenyl-[1,2,4]triazolo[1,5-a]pyridin-2-yl)-2,3-dihydrobenzo[d]isothiazol-6-amine dione;
N-(5-methoxypyridin-3-yl)-5-phenyl-[1,2,4]triazolo[1,5-a]pyridin-2-amine;
$N^2$-(2-aminoethyl)-$N^4$-(5-phenyl-[1,2,4]triazolo[1,5-a]pyridin-2-yl)pyridine-2,4-diamine;
$N^4$-(5-phenyl-[1,2,4]triazolo[1,5-a]pyridin-2-yl)pyridine-2,4-diamine;
N-(6-morpholinopyridin-3-yl)-5-phenyl-[1,2,4]triazolo[1,5-a]pyridin-2-amine;
$N^5$-(5-phenyl-[1,2,4]triazolo[1,5-a]pyridin-2-yl)benzo[d]isoxazole-3,5-diamine;
N-(5-phenyl-[1,2,4]triazolo[1,5-a]pyridin-2-yl)benzo[d]isoxazol-5-amine;
$N^6$-(5-phenyl-[1,2,4]triazolo[1,5-a]pyridin-2-yl)benzo[d]isoxazole-3,6-diamine;
2-(2-aminoethyl)-5-(5-phenyl-[1,2,4]triazolo[1,5-a]pyridin-2-ylamino)isoindolin-1-one;
N-(2-methyl-1H-benzo[d]imidazol-5-yl)-5-phenyl-[1,2,4]triazolo[1,5-a]pyridin-2-amine;
N-(1-methyl-1H-benzo[d]imidazol-6-yl)-5-phenyl-[1,2,4]triazolo[1,5-a]pyridin-2-amine;
N-(5-phenyl-[1,2,4]triazolo[1,5-a]pyridin-2-yl)benzo[d]isoxazol-6-amine;
N-(5-phenyl-[1,2,4]triazolo[1,5-a]pyridin-2-yl)-1H-benzo[d][1,2,3]triazol-6-amine;
1-(4-(5-phenyl-[1,2,4]triazolo[1,5-a]pyridin-2-ylamino)phenyl)pyrrolidin-2-one;
4-(5-phenyl-[1,2,4]triazolo[1,5-a]pyridin-2-ylamino)picolinamide;
4-(5-phenyl-[1,2,4]triazolo[1,5-a]pyridin-2-ylamino)picolinonitrile;
N-(isoindolin-5-yl)-5-phenyl-[1,2,4]triazolo[1,5-a]pyridin-2-amine;
N-(1-methyl-1H-indazol-6-yl)-5-phenyl-[1,2,4]triazolo[1,5-a]pyridin-2-amine;
N-(1-methyl-1H-benzo[d]imidazol-5-yl)-5-phenyl-[1,2,4]triazolo[1,5-a]pyridin-2-amine;
N-(4-(1H-1,2,4-triazol-5-yl)phenyl)-5-phenyl-[1,2,4]triazolo[1,5-a]pyridin-2-amine;
$N^6$-(5-phenyl-[1,2,4]triazolo[1,5-a]pyridin-2-yl)-1H-indazole-3,6-diamine;
5-phenyl-N-(pyridin-4-yl)-[1,2,4]triazolo[1,5-a]pyridin-2-amine;
N-(5-phenyl-[1,2,4]triazolo[1,5-a]pyridin-2-yl)quinolin-6-amine;
1-(5-(5-phenyl-[1,2,4]triazolo[1,5-a]pyridin-2-ylamino)indolin-1-yl)ethanone;
N-(1H-indazol-5-yl)-5-phenyl-[1,2,4]triazolo[1,5-a]pyridin-2-amine;
5-(3-(1H-1,2,4-triazol-5-yl)phenyl)-N-phenyl-[1,2,4]triazolo[1,5-a]pyridin-2-amine;
4-(5-(3-cyanophenyl)-[1,2,4]triazolo[1,5-a]pyridin-2-ylamino)benzamide;
4-(5-(3-hydroxyphenyl)-[1,2,4]triazolo[1,5-a]pyridin-2-ylamino)benzamide;
2-fluoro-5-(5-phenyl-[1,2,4]triazolo[1,5-a]pyridin-2-ylamino)benzamide;
3-(5-phenyl-[1,2,4]triazolo[1,5-a]pyridin-2-ylamino)benzonitrile;
3-(5-phenyl-[1,2,4]triazolo[1,5-a]pyridin-2-ylamino)benzamide;
N-(1H-indazol-6-yl)-5-phenyl-[1,2,4]triazolo[1,5-a]pyridin-2-amine;
5-(5-phenyl-[1,2,4]triazolo[1,5-a]pyridin-2-ylamino)isoindolin-1-one;
5-(5-phenyl-[1,2,4]triazolo[1,5-a]pyridin-2-ylamino)pyridine-2-ol;
N-(6-methoxypyridin-3-yl)-5-phenyl-[1,2,4]triazolo[1,5-a]pyridin-2-amine;
5-(5-phenyl-[1,2,4]triazolo[1,5-a]pyridin-2-ylamino)picolinamide;
2-fluoro-4-(5-phenyl-[1,2,4]triazolo[1,5-a]pyridin-2-ylamino)benzamide;
5-phenyl-N-(pyrimidin-5-yl)-[1,2,4]triazolo[1,5-a]pyridin-2-amine;
5-phenyl-N-(pyridin-3-yl)-[1,2,4]triazolo[1,5-a]pyridin-2-amine;
4-(2-(phenylamino)-[1,2,4]triazolo[1,5-a]pyridin-5-yl)benzonitrile;
4-(5-phenyl-[1,2,4]triazolo[1,5-a]pyridin-2-ylamino)-N-(piperidin-4-yl)benzamide;
N-(3-(2-(phenylamino)-[1,2,4]triazolo[1,5-a]pyridin-5-yl)phenyl)acetamide;
N-(4-(2-(phenylamino)-[1,2,4]triazolo[1,5-a]pyridin-5-yl)phenyl)acetamide;
5-(2-fluorophenyl)-N-phenyl[1,2,4]triazolo[1,5-a]pyridin-2-amine;
5-(3-fluorophenyl)-N-phenyl[1,2,4]triazolo[1,5-a]pyridin-2-amine;
5-(4-aminophenyl)-N-phenyl-[1,2,4]triazolo[1,5-a]pyridin-2-amine;

3-(2-(phenylamino)-[1,2,4]triazolo[1,5-a]pyridin-5-yl)benzonitrile;

5-(3-(aminomethyl)phenyl)-N-phenyl-[1,2,4]triazolo[1,5-a]pyridin-2-amine;

4-(2-(phenylamino)-[1,2,4]triazolo[1,5-a]pyridin-5-yl)benzamide;

3-(2-(phenylamino)-[1,2,4]triazolo[1,5-a]pyridin-5-yl)benzamide;

5-(3-aminophenyl)-N-phenyl-[1,2,4]triazolo[1,5-a]pyridin-2-amine;

4-(5-phenyl-[1,2,4]triazolo[1,5-a]pyridin-2-ylamino)benzamide;

5-(4-fluorophenyl)-N-phenyl[1,2,4]triazolo[1,5-a]pyridin-2-amine;

4-(2-(phenylamino)-[1,2,4]triazolo[1,5-a]pyridin-5-yl)phenol;

2-(2-(phenylamino)-[1,2,4]triazolo[1,5-a]pyridin-5-yl)phenol;

3-(2-(phenylamino)-[1,2,4]triazolo[1,5-a]pyridin-5-yl)phenol;

N-(4-morpholinophenyl)-5-phenyl-[1,2,4]triazolo[1,5-a]pyridin-2-amine;

$N^1,N^1$-dimethyl-$N^4$-(5-phenyl-[1,2,4]triazolo[1,5-a]pyridin-2-yl)benzene-1,4-diamine;

N-(3,4-dimethoxyphenyl)-5-phenyl-[1,2,4]triazolo[1,5-a]pyridin-2-amine;

5-(furan-3-yl)-N-phenyl-[1,2,4]triazolo[1,5-a]pyridin-2-amine;

5-(3-chlorophenyl)-N-phenyl-[1,2,4]triazolo[1,5-a]pyridin-2-amine; or

N,5-diphenyl-[1,2,4]triazolo[1,5-a]pyridin-2-amine;

and pharmaceutically acceptable salts, tautomers, stereoisomers, solvates or prodrugs thereof.

4.3 Methods for Making Heteroaryl Compounds

The Heteroaryl Compounds can be made by one skilled in the art using conventional organic syntheses and commercially available materials. By way of example and not limitation, Heteroaryl Compounds can be prepared as outlined in Schemes 1-12 shown below, as well as in the examples set forth in Section 5.1. It should be noted that one skilled in the art can modify the procedures set forth in the illustrative schemes and examples to arrive at the desired product.

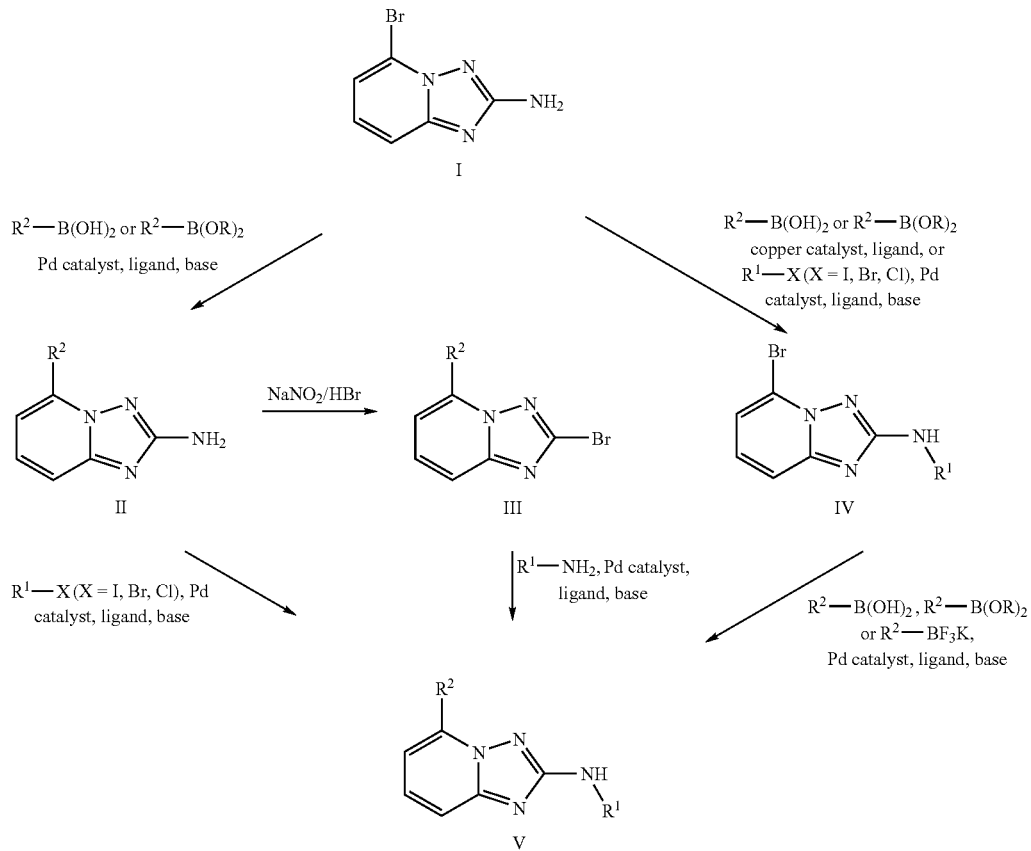

Heteroaryl Compounds can be synthesized from compound I, by treatment with an appropriate boronic acid or boronate ester in the presence of a palladium catalyst (such as palladium acetate), ligand (such as triphenylphosphine or tricyclohexylphosphine) and base (such as potassium phosphate or cesium fluoride) to introduce the $R^2$ substituent (see compound II). The resulting compound can then be reacted with an appropriate halo-compound in the presence of a palladium catalyst (such as tris(dibenzylideneacetone)dipalladium (0)), ligand (such as 4,5-bis(diphenylphosphino)-9,9-dimethylxanthene or (R)-(+)-2,2'-bis(diphenylphosphino) 1,1'-binaphthyl) and base (such as cesium carbonate, sodium tert-butoxide or potassium tert-butoxide) to introduce the $R^1$ substituent.

Alternatively, compound II can be reacted with sodium nitrite in hydrobromic acid to obtain compound III, which can then be reacted with an appropriate amine, in the presence of a palladium catalyst (such as tris(dibenzylideneacetone)dipalladium (0)), ligand (such as 4,5-bis(diphenylphosphino)-9,9-dimethylxanthene or (R)-(+)-2,2'-bis(diphenylphosphino) and base (such as cesium carbonate, sodium tert-butoxide or potassium tert-butoxide).

Alternatively, the $R^1$ substituent can be introduced first via coupling of compound I with an appropriate boronic acid or boronate ester in the presence of a copper catalyst (such as copper acetate (II)) and ligand (such as bipyridine), or by reaction with an appropriate halo-compound in the presence of a palladium catalyst (such as tris(dibenzylideneacetone) dipalladium (0)), ligand (such as 4,5-bis(diphenylphosphino)-9,9-dimethylxanthene or (R)-(+)-2,2'-bis(diphenylphosphino) and base (such as cesium carbonate, sodium tert-butoxide or potassium tert-butoxide). Compound IV can then be reacted with an appropriate boronic acid, boronate ester, or potassium trifluoroborate in the presence of a palladium catalyst (such as such as 1-1'-bis(diphenylphosphino) ferrocene palladium dichloride or tetrakis(triphenylphosphine)palladium (0) or palladium diacetate) and base (such as sodium or potassium carbonate, potassium phosphate or potassium acetate) to introduce the $R^2$ substituent.

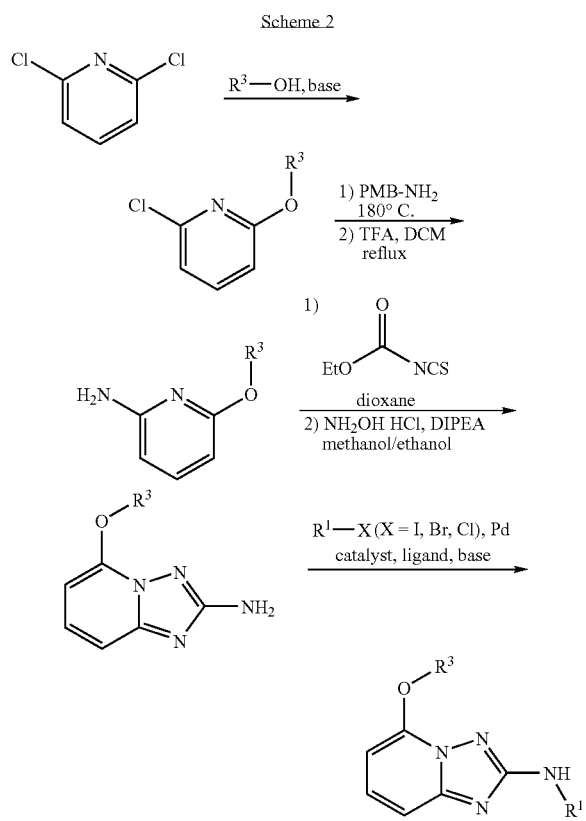

Compounds wherein $R^2=OR^3$ can be prepared as shown in Scheme 2. 2,6-Dichloropyridine is reacted with an appropriately substituted alcohol in the presence of a base (such as sodium hydroxide or sodium metal) and the second chlorine atom can be converted to an amino group via treatment with para-methoxybenzylamine and subsequent deprotection with an acid, such as trifluoroacetic acid. The resulting compound can be treated sequentially with ethoxycarbonyl isothiocyanate in dioxane and hydroxylamine to obtain the cyclized compound, which can then be reacted with an appropriate halo-compound in the presence of a palladium catalyst (such as tris(dibenzylideneacetone) dipalladium (0)), ligand (such as 4,5-bis(diphenylphosphino)-9,9-dimethylxanthene or (R)-(+)-2,2'-bis(diphenylphosphino)1,1'-binaphthyl) and base (such as cesium carbonate, sodium tert-butoxide or potassium tert-butoxide) to introduce the $R^1$ substituent.

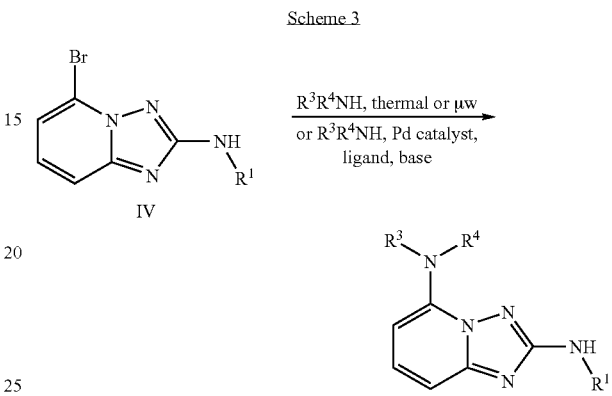

Compounds wherein $R^2=NR^3R^4$ can be prepared as shown in Scheme 3. Compound IV can be reacted with a secondary amine under thermal conditions, microwave irradiation or by reacting with a palladium catalyst (such as tris(dibenzylideneacetone)dipalladium (0)), ligand (such as 4,5-bis(diphenylphosphino)-9,9-dimethylxanthene or (R)-(+)-2,2'-bis(diphenylphosphino)1,1'-binaphthyl)) and base (such as cesium carbonate, sodium tert-butoxide or potassium tert-butoxide).

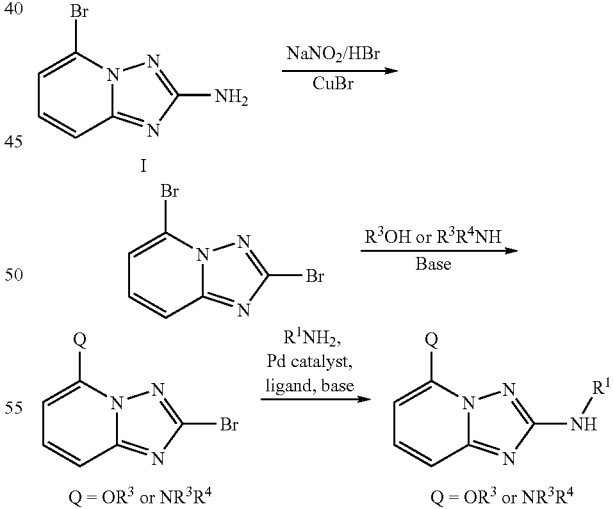

Compounds wherein $R^2$ is —$OR^3$ or —$NR^3R^4$ (wherein $R^4$ can be H) can be prepared as shown in Scheme 4. Compound I can be reacted with sodium nitrite and hydrogen hydrobromide in the presence of copper (I) bromide. The resulting dibromo compound can then be treated with an appropriate alcohol or amine in the presence of a base, such as sodium hydride or N,N-diisopropylethylamine. The $R^1$ substituent can then be installed by reaction with an appropriate amine in the presence of a palladium catalyst (such as tris(dibenzylideneacetone)dipalladium (0)), ligand (such as 4,5-bis(diphenylphosphino)-9,9-dimethylxanthene or (R)-(+)-2,2'-bis(diphenylphosphino)1,1'-binaphthyl) and base (such as cesium carbonate, sodium tert-butoxide or potassium tert-butoxide).

Scheme 5

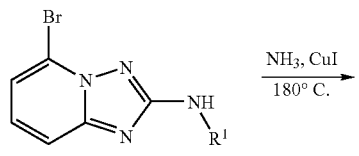

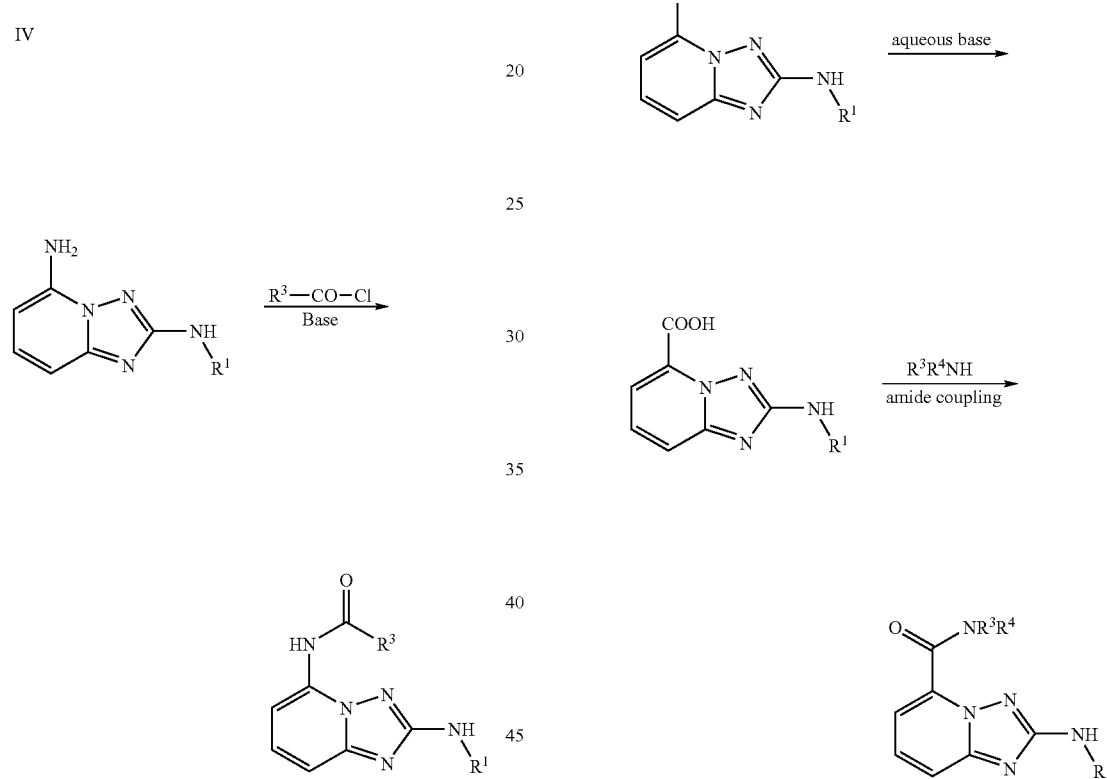

Compounds wherein $R^2$=NHC(O)$R^3$ can be prepared as shown in Scheme 5. Compound IV can be reacted with ammonia and copper iodide to introduce the amino group that can then be reacted with an appropriate acetyl chloride in the presence of a base such as triethylamine.

Scheme 6

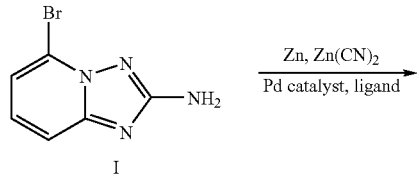

Compounds wherein $R^2$=C(O)N$R^3R^4$ can be prepared as shown in Scheme 6. Compound I can be reacted with zinc dust and zinc cyanide in the presence of a palladium catalyst (such as tris(dibenzylideneacetone)dipalladium(0)) and a ligand (such as 1,1'-bis(diphenylphosphino)ferrocene). The resulting compound can then be treated with an appropriate boronic acid or boronate ester in the presence of a copper catalyst (such as copper acetate (II)) and ligand (such as bipyridine) or by reaction with an appropriate halo-compound in the presence of a palladium catalyst (such as tris (dibenzylideneacetone)dipalladium (0)), ligand (such as 4,5-bis(diphenylphosphino)-9,9-dimethylxanthene or (R)-(+)-2,2'-bis(diphenylphosphino)1,1'-binaphthyl)) and base (such as cesium carbonate, sodium tert-butoxide or potassium tert-butoxide). The cyano group is then hydrolyzed with base (such sodium hydroxide) and the resulting acid is reacted with an appropriate amine under standard amide coupling conditions.

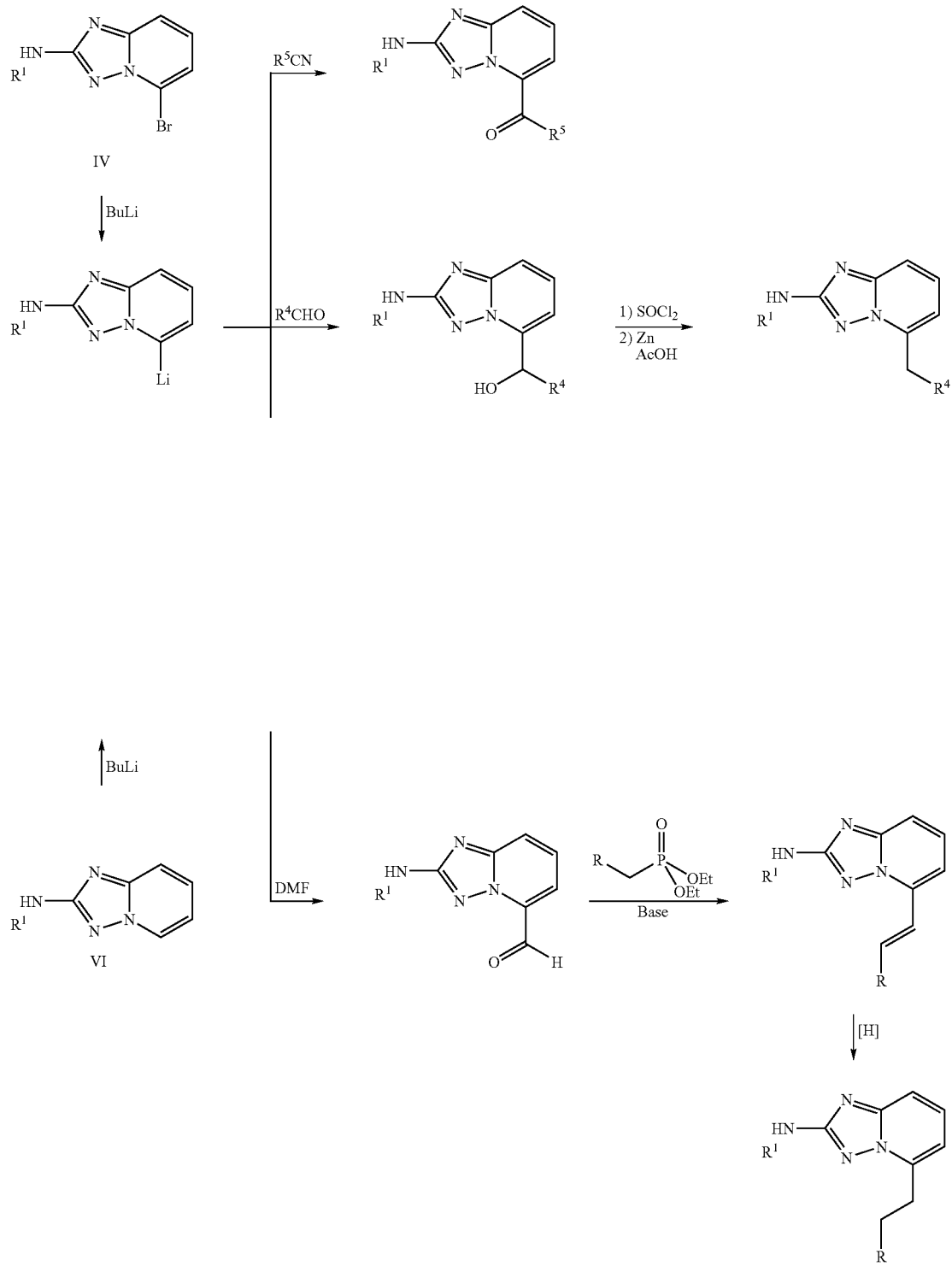

Scheme 7

Compounds wherein $R^2$=C(O)$R^5$, CH(OH)$R^4$ or a substituted or unsubstituted alkyl can be prepared as shown in Schemes 7, 8, 9 and/or 11. Compound IV can be reacted with butyllithium to generate the lithiated intermediate that can then be reacted with an appropriate nitrile or aldehyde. When it is reacted with an aldehyde, the resulting alcohol can be reduced with thionyl chloride and zinc dust. Alternatively, the lithium species can be reacted with N,N-dimethylformamide to generate an aldehyde that can then be reacted with an appropriate ylide (obtained from a phosphonate and a base such as aqueous sodium hydroxide). The double bond can then be reduced via catalytic hydrogenation using a catalyst such as palladium on carbon under hydrogen.

Scheme 8

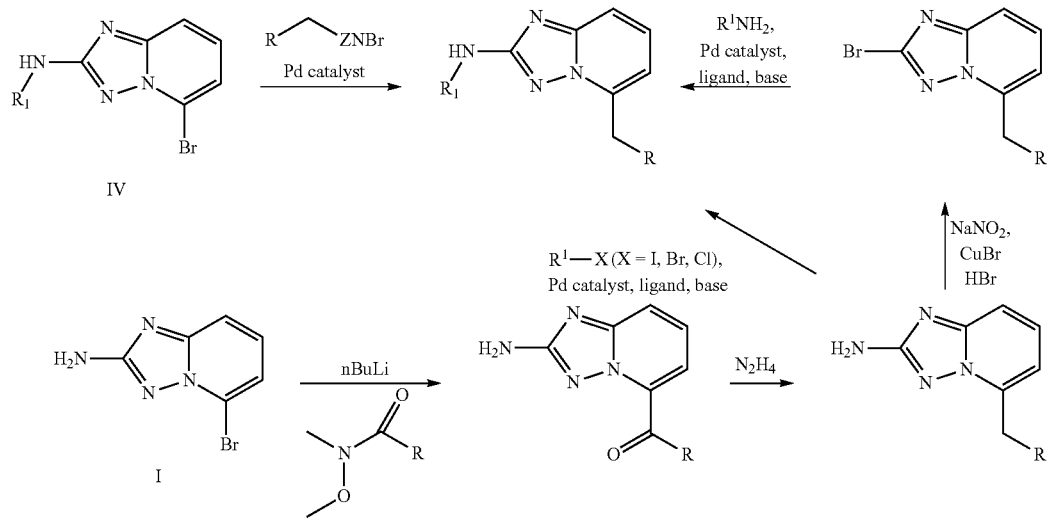

Compounds wherein R²=—CH₂—R can be prepared as shown in Scheme 8. Compound IV can be reacted with an appropriate zinc bromide in the presence of a palladium catalyst (such as tetrakis(triphenylphosphine)palladium (0)). Alternatively, compound I can be reacted with n-butyllithium and condensed with an appropriate Weinreb amide. The resulting ketone can then be reduced with a reducing agent such as hydrazine. The R¹ substituent can be introduced by coupling with an appropriate halo-compound in the presence of a palladium catalyst (such as tris(dibenzylideneacetone) dipalladium (0)), ligand (such as 4,5-bis(diphenylphosphino)-9,9-dimethylxanthene or (R)-(+)-2,2'-bis(diphenylphosphino)1,1'-binaphthyl) and base (such as cesium carbonate, sodium tert-butoxide or potassium tert-butoxide) or by converting the amine to the bromo compound via treatment with sodium nitrite and copper(I) bromide in hydrobromic acid and then coupling with an appropriate amine in the presence of a palladium catalyst (such as tris(dibenzylideneacetone)dipalladium (0)), ligand (such as 4,5-bis(diphenylphosphino)-9,9-dimethylxanthene or (R)-(+)-2,2'-bis (diphenylphosphino)1,1'-binaphthyl) and base (such as cesium carbonate, sodium tert-butoxide or potassium tert-butoxide).

Scheme 9

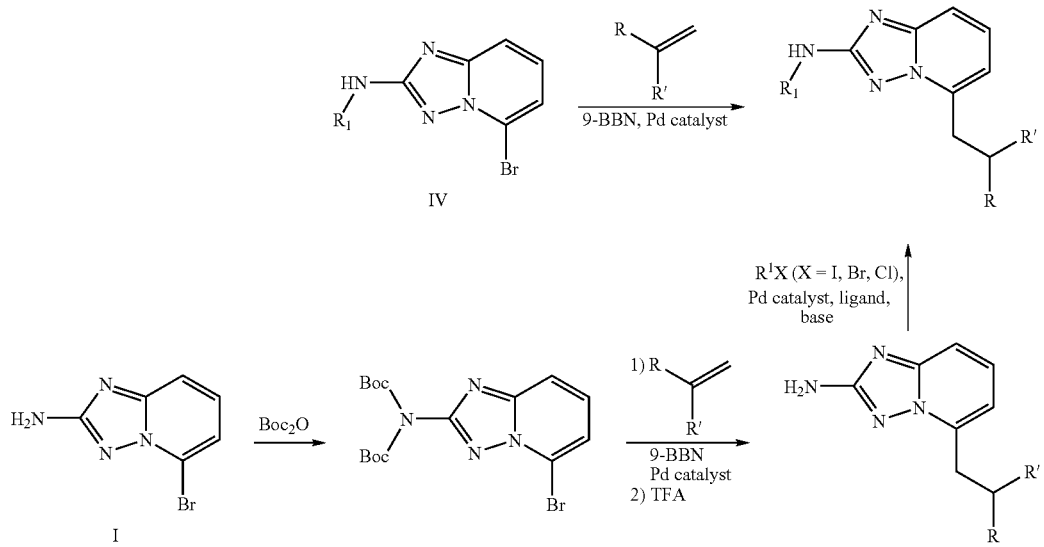

Compounds wherein R²=—(CH₂)—CHRR' can be prepared as shown in scheme 9. Compound IV can be reacted with an appropriate alkene in the presence of a borane (such as (1S,5S)-9-borabicyclo[3.3.1]nonane), a palladium catalyst (such as [1,1'-bis(diphenylphosphino) ferrocene]dichloropalladium(II) complex with dichloromethane) and a base such as potassium carbonate. Alternatively, compound I can be reacted with di-tent-butyl dicarbonate and then treated with an appropriate alkene in the presence of a borane (such as (1S,5S)-9-borabicyclo[3.3.1]nonane), a palladium catalyst (such as [1,1'-bis(diphenylphosphino) ferrocene]dichloropalladium(II) complex with dichloromethane) and a base such as potassium carbonate. The R¹ substituent can then be introduced by reaction with an appropriate halo-compound in the presence of a palladium catalyst (such as tris(dibenzylideneacetone)dipalladium (0)), ligand (such as 4,5-bis(diphenylphosphino)-9,9-dimethylxanthene or (R)-(+)-2,2'-bis(diphenylphosphino)1,1'-binaphthyl) and base (such as cesium carbonate, sodium tert-butoxide or potassium tert-butoxide).

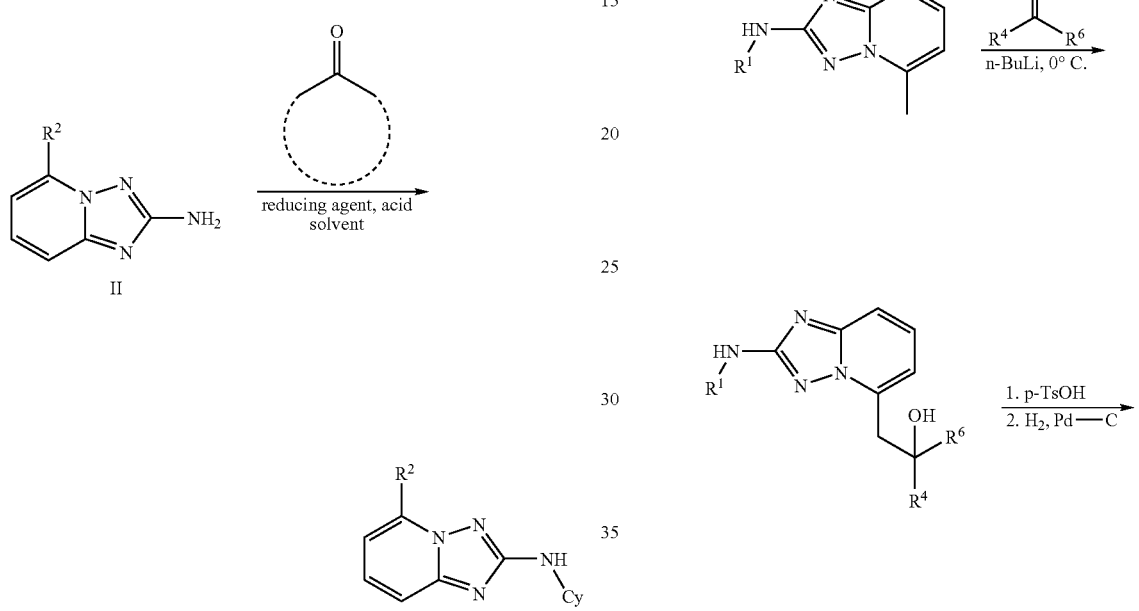

Compounds wherein R¹ is a substituted or unsubstituted cycloalkyl can be prepared as shown in Scheme 10. Compound II can be reacted with an appropriately substituted cyclic ketone in the presence of a reducing agent such as sodium triacetoxyborohydride in the presence of acid (such as acetic acid).

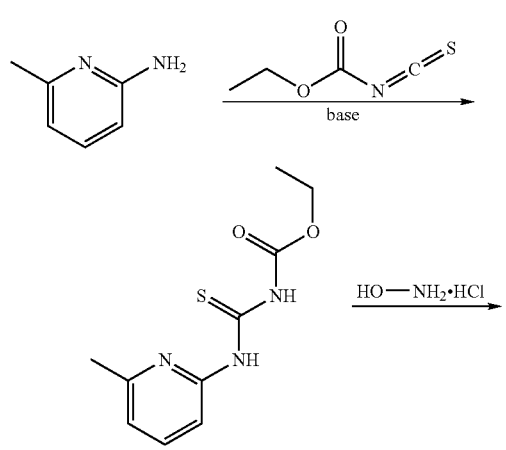

Compounds wherein R² is —(CH₂)CR⁶(OR³)R⁴ or alkyl can be prepared as shown in Scheme 11. 6-Methylpyridin-2-amine can be reacted sequentially with ethoxycarbonyl isothiocyanate and hydroxylamine in the presence of N,N-diisopropylethylamine. The cyclized compound can then be reacted with an appropriate halo-compound in the presence of a palladium catalyst (such as tris(dibenzylideneacetone)dipalladium (0)), ligand (such as 4,5-bis(diphenylphosphino)-9,9-dimethylxanthene or (R)-(+)-2,2'-bis(diphenylphosphino)1,1'-binaphthyl) and base (such as cesium carbonate, sodium tert-butoxide or potassium tert-butoxide). The lithiated intermediate can then be generated by treatment with butyllithium and can be reacted with an appropriate aldehyde or ketone. When a ketone is used, the resulting tertiary alcohol can be treated with acid (such as p-toluenesulfonic acid) to form the corresponding alkene that can then be reduced to the corresponding alkane via catalytic hydrogenation.

Scheme 12

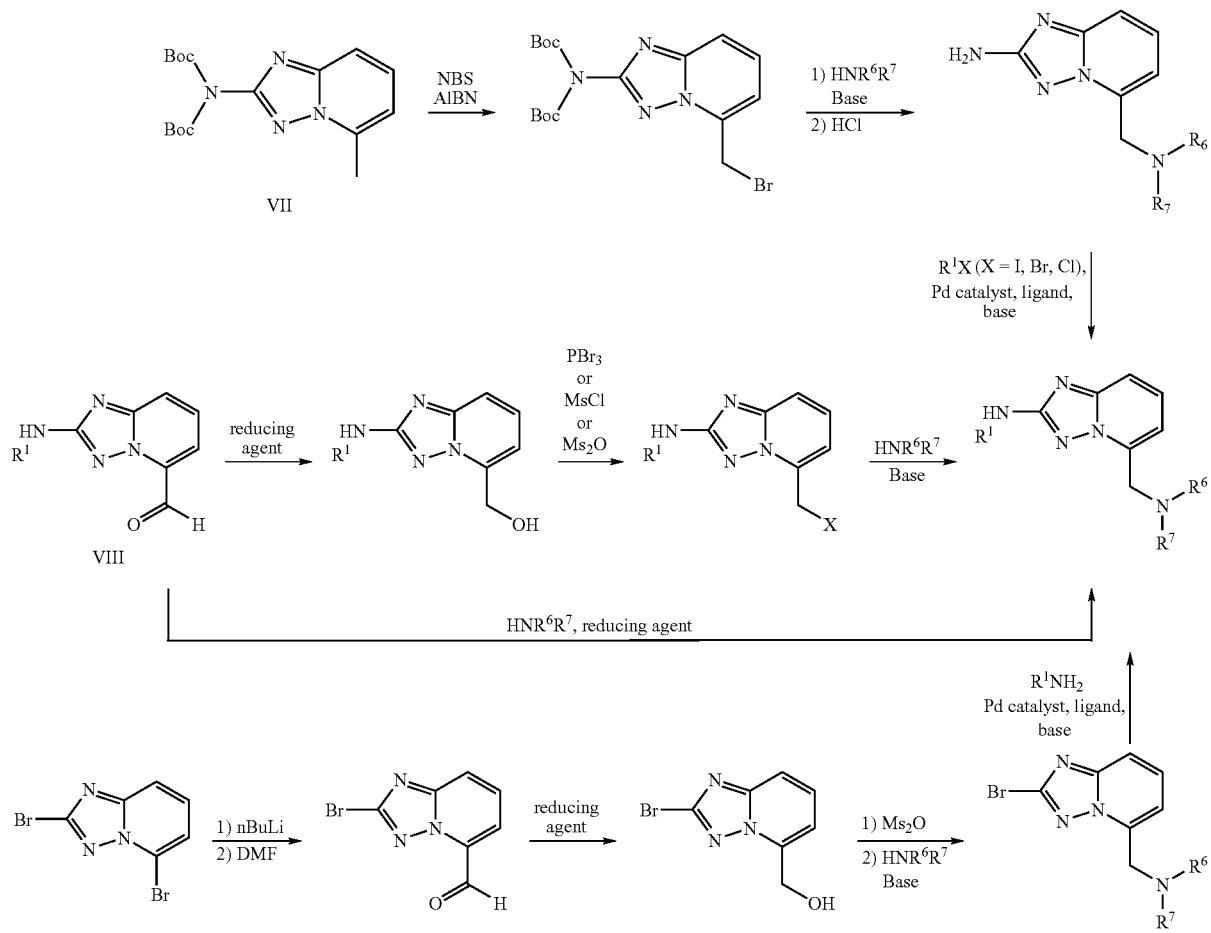

Compounds wherein R² is —(CH₂)—NR⁶R⁷ can be synthesized as shown in Scheme 12. Compound VII can be reacted with N-bromosuccinimide and 2,2'-azobis(2-methylpropionitrile), followed by reaction with the appropriate amine in the presence of a base, such as potassium carbonate. The R¹ substituent can be introduced by coupling with an appropriate halo-compound in the presence of a palladium catalyst (such as tris(dibenzylideneacetone)dipalladium(0)), ligand (such as 4,5-bis(diphenylphosphino)-9,9-dimethylxanthene or (R)-(+)-2,2'-bis(diphenylphosphino)1,1'-binaphthyl) and a base (such as cesium carbonate, sodium tert-butoxide or potassium tert-butoxide). Alternatively, compound VIII can be reduced to the alcohol with a reducing agent such as sodium borohydride or sodium triacetoxyborohydride, and subsequently converted to a leaving group such as bromide or mesylate via treatment with phosphorus tribromide, methanesulfonyl chloride or methanesulfonic anhydride. The resulting compound can be reacted with the appropriate amine in the presence of base such as potassium carbonate. Alternatively, these compounds can be obtained in one step from compound VIII by reaction with an appropriate amine in the presence of a reducing agent such as sodium triacetoxyborohydride. Alternatively, 2,5-dibromo-[1,2,4]triazolo[1,5-a]pyridine can be treated with n-butyllithium, followed by N,N-dimethylformamide. The resulting aldehyde can then be reacted with a reducing agent such as sodium borohydride to yield the corresponding alcohol, which in turn is treated with methanesulfonic anhydride and an appropriate amine. The R¹ group can the be installed by reaction with an appropriate amino-compound in the presence of a palladium catalyst (such as tris(dibenzylideneacetone)dipalladium(0)), ligand (such as 4,5-bis(diphenylphosphino)-9,9-dimethylxanthene or (R)-(+)-2,2'-bis(diphenylphosphino)1,1'-binaphthyl) and a base (such as cesium carbonate, sodium tert-butoxide or potassium tert-butoxide).

Pharmaceutically acceptable salts of the Heteroaryl Compounds can be formed by conventional and known techniques, such as by reacting a Heteroaryl Compound with a suitable acid as disclosed above. Such salts are typically formed in high yields at moderate temperatures, and often are prepared by merely isolating the compound from a suitable acidic wash in the final step of the synthesis. The salt-forming acid may be dissolved in an appropriate organic solvent, or aqueous organic solvent, such as an alkanol, ketone or ester. On the other hand, if the Heteroaryl Compound is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

4.4 Methods of Use

In one aspect provided herein are methods for treating or preventing an inflammatory condition, immunological condition, autoimmune condition, allergic condition, rheumatic condition, thrombotic condition, cancer, infection, neurodegenerative disease, neuroinflammatory disease, cardiovascular disease or metabolic condition, comprising administering to a subject in need thereof an effective amount of a Heteroaryl Compound or a pharmaceutically acceptable salt, tautomer, stereoisomer, solvate or prodrug thereof. In some embodiments, the methods further include administration of additional therapeutic ingredients as described herein.

In another aspect provided herein are methods of inhibiting a kinase in a cell expressing said kinase, comprising contacting said cell with an effective amount of a Heteroaryl Compound or a pharmaceutically acceptable salt, tautomer, stereoisomer, solvate or prodrug thereof. In one embodiment the kinase is Syk, FLT3, JAK1 or JAK2, or mutants or isoforms thereof, or combinations of two or more thereof. For example, the Heteroaryl Compound is a compound from Table 1.

Heteroaryl Compounds described herein have utility as pharmaceuticals to treat or prevent disease in subjects such as animals or humans. Further, Heteroaryl Compounds described herein are active against kinases (e.g., protein kinases), including those involved in inflammatory conditions, immunological conditions, autoimmune conditions, allergic conditions, rheumatic conditions, thrombotic conditions, cancer, infections, neurodegenerative diseases, neuroinflammatory diseases, cardiovascular diseases and metabolic conditions. Without being limited by theory, it is thought the Heteroaryl Compounds are effective for treating and preventing inflammatory conditions, immunological conditions, autoimmune conditions, allergic conditions, rheumatic conditions, thrombotic conditions, cancer, infections, neurodegenerative diseases, neuroinflammatory diseases, cardiovascular diseases, and metabolic conditions due to their ability to modulate (e.g., inhibit) kinases which are involved in the etiology of these conditions. Accordingly, provided herein are many uses of the Heteroaryl Compounds, including the treatment or prevention of those diseases set forth below. The methods provided herein comprise the administration of an effective amount of one or more Heteroaryl Compounds to a subject in need thereof. In some embodiments a Heteroaryl Compound is administered in combination with another active agent.

Representative immunological conditions that Heteroaryl Compounds are useful for treating or preventing include, but are not limited to, Behcet's syndrome, non-allergy mast cell diseases (e.g., mastocytosis and treatment of anaphylaxis), ankylosing spondylitis, osteoarthritis, rheumatoid arthritis (RA), multiple sclerosis, lupus, inflammatory bowel disease, ulcerative colitis, Crohn's disease, myasthenia gravis, Grave's disease, transplant rejection, humoral transplant rejection, non-humoral transplant rejection, cellular transplant rejection, immune thrombocytopenic purpura (ITP), idiopathic thrombocytopenic purpura, diabetes, immunological response to bacterial, parasitic, helminth infestation or viral infection, eczema, dermatitis, graft versus host disease, Goodpasture's disease, hemolytic disease of the newborn, autoimmune hemolytic anemia, anti-phospholipid syndrome, ANCA-associated vasculitis, Churg-Strauss syndrome, Wegeners granulomatosis, pemphigus vulgaris, serum sickness, mixed cryoglobulinemia, peripheral neuropathy associated with IgM antibody, microscopic polyangiitis, Hashimoto's thyroiditis, Sjogrens syndrome, fibrosing conditions (such as those dependent on the innate or adaptive immune systems or local mesenchyma cells) or primary billary cirrhosis.

Representative autoimmune conditions that Heteroaryl Compounds are useful for treating or preventing include, but are not limited to, autoimmune hemolytic anemia (AIHA), Behcet's syndrome, Crohn's disease, type I diabetes, Goodpasture's disease, Grave's disease, Hashimoto's thyroiditis, idiopathic thrombocytopenic purpura, lupus, multiple sclerosis, amyotrophic lateral sclerosis, myasthenia gravis, pemphigus vulgaris, primary billary cirrhosis, rheumatoid arthritis, scleroderma, Sjogren's syndrome, ulcerative colitis, or Wegeners granulomatosus.

Representative allergic conditions that Heteroaryl Compounds are useful for treating or preventing include, but are not limited to, anaphylaxis, hay fever, allergic conjunctivitis, allergic rhinitis, allergic asthma, atopic dermatitis, eczema, urticaria, mucosal disorders, tissue disorders and certain gastrointestinal disorders.

Representative rheumatic conditions that Heteroaryl Compounds are useful for treating or preventing include, but are not limited to, rheumatoid arthritis, gout, ankylosing spondylitis, or osteoarthritis.

Representative inflammatory conditions that Heteroaryl Compounds are useful for treating or preventing include, but are not limited to, non-ANCA (anti-neutrophil cytoplasmic autoantibody) vasculitis (e.g., wherein Syk function is associated with neutrophil adhesion, diapedesis and/or activation), psoriasis, asthma, allergic rhinitis, allergic conjunctivitis, chronic urticaria, hives, anaphylaxis, bronchitis, chronic obstructive pulmonary disease, cystic fibrosis, inflammatory bowel disease, irritable bowel syndrome, gout, Crohn's disease, mucous colitis, ulcerative colitis, allergy to intestinal antigens (such as gluten enteropathy), diabetes (e.g., Type I diabetes and Type II diabetes) and obesity. In some embodiments, the inflammatory condition is a dermatologic condition, such as, for example, psoriasis, urticaria, hives, eczema, scleroderma, or dermatitis. In other embodiments, the inflammatory condition is an inflammatory pulmonary condition, such as, for example, asthma, bronchitis, chronic obstructive pulmonary disease (COPD), or adult/acute respiratory distress syndrome (ARDS). In other embodiments, the inflammatory condition is a gastrointestinal condition, such as, for example, inflammatory bowel disease, ulcerative colitis, Crohn's disease, idiopathic inflammatory bowel disease, irritable bowel syndrome, or spastic colon.

Representative infections that Heteroaryl Compounds are useful for treating or preventing include, but are not limited to, bacterial, parasitic, prion, viral infections or helminth infestation.

Representative cancers that Heteroaryl Compounds are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Representative cardiovascular diseases that Heteroaryl Compounds are useful for treating or preventing include, but are not limited to, restenosis, atherosclerosis and its consequences such as stroke, myocardial infarction, ischemic damage to the heart, lung, gut, kidney, liver, pancreas, spleen or brain.

Representative metabolic conditions that Heteroaryl Compounds are useful for treating or preventing include, but are not limited to, obesity and diabetes (e.g., Type I and II diabetes). In a particular embodiment, provided herein are methods for the treatment or prevention of insulin resistance. In certain embodiments, provided herein are methods for the treatment or prevention of insulin resistance that leads to diabetes (e.g., Type II diabetes). In another embodiment, provided herein are methods for the treatment or prevention of syndrome X or metabolic syndrome. In another embodiment, provided herein are methods for the treatment or prevention of Type II diabetes, Type I diabetes, slow-onset Type I diabetes, diabetes insipidus (e.g., neurogenic diabetes insipidus, nephrogenic diabetes insipidus, dipsogenic diabetes insipidus, or gestagenic diabetes insipidus), diabetes mellitus, gestational diabetes mellitus, polycystic ovarian syndrome, maturity-onset diabetes, juvenile diabetes, insulin-dependant diabetes, non-insulin dependant diabetes, malnutrition-related diabetes, ketosis-prone diabetes, pre-diabetes (e.g., impaired glucose metabolism), cystic fibrosis related diabetes, hemochromatosis and ketosis-resistant diabetes.

Representative neurodegenerative and neuroinflammatory diseases that Heteroaryl Compounds are useful for treating or preventing include, but are not limited to, Huntington's disease, Alzheimer's disease, viral (e.g., HIV) or bacterial-associated encephalitis and damage.

In another embodiment, provided herein are methods for the treatment or prevention of fibrotic diseases and disorders. In a particular embodiment, provided herein are methods for the treatment or prevention of idiopathic pulmonary fibrosis, myelofibrosis, hepatic fibrosis, steatofibrosis and steatohepatitis.

In another embodiment, provided herein are methods for the treatment or prevention of diseases associated with thrombotic events such as but not limited to atherosclerosis, myocardial infarction and ischemic stroke.

Provided also are methods that permit the regulation of, and in particular the inhibition of, downstream processes that result as a consequence of activating the Fc receptor signaling cascade(s). Such downstream processes include, but are not limited to, FIεRI-mediated and/or FcγRI-mediated degranulation, cytokine production and/or the production and/or release of lipid mediators such as leukotrienes and prostaglandins. The method generally involves contacting a cell expressing an Fc receptor, such as one of the cell types discussed above, with an amount of a Heteroaryl Compound as described herein, effective to regulate or inhibit the Fc receptor signaling cascade and/or a downstream process effected by the activation of this signaling cascade. The method may be practiced in in vitro contexts or in in vivo contexts as a therapeutic approach towards the treatment or prevention of diseases characterized by, caused by or associated with the Fc receptor signaling cascade, such as diseases effected by the release of granule specific chemical mediators upon degranulation, the release and/or synthesis of cytokines and/or the release and/or synthesis of lipid mediators such as leukotrienes and prostaglandins.

In yet another aspect, there are also provided methods for the treatment or prevention of diseases characterized by, caused by or associated with the release of chemical mediators as a consequence of activating Fc receptor signaling cascades, such as FcεRI and/or FcγRI-signaling cascades. The methods generally involve administering to a subject an amount of a Heteroaryl Compound, effective to treat or prevent the disease. As discussed previously, activation of the FcεRI or FcγRI receptor signaling cascade in certain immune cells leads to the release and/or synthesis of a variety of chemical substances that are pharmacological mediators of a wide variety of diseases. Any of these diseases may be treated or prevented according to the methods as described herein.

For example, in mast cells and basophil cells, activation of the FcεRI or FcγRI signaling cascade leads to the immediate (i.e., within 1-3 min. of receptor activation) release of preformed mediators of atopic and/or Type I hypersensitivity reactions (e.g., histamine, proteases such as tryptase, etc.) via the degranulation process. Such atopic or Type I hypersensitivity reactions include, but are not limited to, anaphylactic reactions to environmental and other allergens (e.g., pollens, insect and/or animal venoms, foods, drugs, contrast dyes, etc.), anaphylactoid reactions, hay fever, allergic conjunctivitis, allergic rhinitis, allergic asthma, atopic dermatitis, eczema, urticaria, mucosal disorders, tissue disorders and certain gastrointestinal disorders. The immediate release of the preformed mediators via degranulation is followed by the release and/or synthesis of a variety of other chemical mediators, including, among other things, platelet activating factor (PAF), prostaglandins and leukotrienes (e.g., LTC4) and the de novo synthesis and release of cytokines such as TNFα, IL-4, IL-5, IL-6, IL-13, etc. The first of these two processes occurs approximately 3-30 min. following receptor activation; the latter approximately 30 min.-7 hrs. following receptor activation. These "late stage" mediators are thought to be in part responsible for the chronic symptoms of the above-listed atopic and Type I hypersensitivity reactions, and in addition are chemical mediators of inflammation and inflammatory diseases (e.g., osteoarthritis, inflammatory bowel disease, ulcerative colitis, Crohn's disease, idiopathic inflammatory bowel disease, irritable bowel syndrome, spastic colon, etc.), low grade scarring (e.g., scleroderma, increased fibrosis, keloids, post-surgical scars, pulmonary fibrosis, vascular spasms, migraine, reperfusion injury and post myocardial infarction), and sicca complex or syndrome. All of these diseases may be treated or prevented according to the methods as described herein.

Additional diseases which can be treated or prevented according to the methods as described herein include diseases associated with basophil cell and/or mast cell pathology. Examples of such diseases include, but are not limited to, diseases of the skin such as scleroderma, cardiac diseases such as post myocardial infarction, pulmonary diseases such as pulmonary muscle changes or remodeling, chronic obstructive pulmonary disease (COPD) and diseases of the gut such as inflammatory bowel syndrome (spastic colon).

The Heteroaryl compounds as described herein are also potent inhibitors of the tyrosine kinase Syk kinase. Thus, in still another aspect, there are provided methods of regulating, and in particular inhibiting, Syk kinase activity. The method generally involves contacting a Syk kinase or a cell comprising a Syk kinase with an amount of a Heteroaryl Compound, effective to regulate or inhibit Syk kinase activity. In one embodiment, the Syk kinase is an isolated or recombinant Syk kinase. In another embodiment, the Syk kinase is an endogenous or recombinant Syk kinase expressed by a cell, for example a mast cell or a basophil cell. The method may be practiced in in vitro contexts or in in vivo contexts as a therapeutic approach towards the treatment or prevention of diseases characterized by, caused by or associated with Syk kinase activity.

In one embodiment, provided herein are methods of inhibiting a Syk kinase in a cell expressing said Syk kinase, comprising contacting said cell with an effective amount of a Heteroaryl Compound, wherein the compound is not cis-4-(2-(phenylamino)-[1,2,4]triazolo[1,5-a]pyridin-5-ylamino)cyclohexanecarboxamide.

Syk kinase is known to play a critical role in other signaling cascades. For example, Syk kinase is an effector of B-cell receptor (BCR) signaling (Turner et al., *Immunology Today* 21:148-154 (2000) and is an essential component of integrin beta(1), beta(2) and beta(3) signaling in neutrophils (Mocsai et al., *Immunity* 16:547-558 (2002). As the Heteroaryl compounds described herein are potent inhibitors of Syk kinase, they can be used to regulate, and in particular inhibit, any signaling cascade where Syk plays a role, such as, for example, the Fc receptor, BCR and integrin signaling cascades, as well as the cellular responses elicited through these signaling cascades. The particular cellular response regulated or inhibited will depend, in part, on the specific cell type and receptor signaling cascade, as is well known in the art. Non-limiting examples of cellular responses that may be regulated or inhibited with the Heteroaryl compounds include a respiratory burst, cellular adhesion, cellular degranulation, cell spreading, cell migration, phagocytosis (e.g., in macrophages), calcium ion flux (e.g., in mast, basophil, neutrophil, eosinophil and B-cells), platelet aggregation, and cell maturation (e.g., in B-cells).

Thus, in another aspect, there are provided methods of regulating, and in particular inhibiting, signal transduction cascades in which Syk plays a role. The method generally involves contacting a Syk-dependent receptor or a cell expressing a Syk-dependent receptor with an amount of a Heteroaryl Compound as described herein, effective to regulate or inhibit the signal transduction cascade. The methods may also be used to regulate, and in particular inhibit, downstream processes or cellular responses elicited by activation of the particular Syk-dependent signal transduction cascade. The methods may be practiced to regulate any signal transduction cascade where Syk is not known or later discovered to play a role. The methods may be practiced in in vitro contexts or in in vivo contexts as a therapeutic approach towards the treatment or prevention of diseases characterized by, caused by or associated with activation of the Syk-dependent signal transduction cascade. Non-limited examples of such diseases include those previously discussed.

These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system.

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B cell neoplasms, T and NK-cell neoplasms, Hodgkin's lymphoma and non-Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-I), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with a Heteroaryl Compound include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. The forth member of lymphoid neoplasms is non-Hodgkin's lymphoma, also referred to as non-Hodgkin's disease. Exemplary disorders of this class that can be treated with a Heteroaryl Compound include, among others Waldenstrom's macroglobulinemia; monoclonal gammopathy of undetermined significance; benign monoclonal gammopathy; heavy chain disease, mantle cell lymphoma, MCL, lymphocytic lymphoma of intermediate differentiation, intermediate lymphocytic lymphoma, ILL, diffuse poorly differentiated lymphocytic lymphoma, PDL, centrocytic lymphoma, diffuse small-cleaved cell lymphoma, DSCCL, follicular lymphoma, and any type of the mantle cell lymphomas that can be seen under the microscope (nodular, diffuse, blastic and mentle zone lymphoma). In various embodiments, any of the lymphoid neoplasms that are associated with aberrant Syk activity can be treated with the Heteroaryl Compounds.

In some embodiments, the hematopoietic neoplasm treated is a myeloid neoplasm. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q1 1)), chronic neutrophilic leukemia, chronic eosinophilic leukemia/hypereosinophilic syndromes, chronic idiopathic myelofibrosis, polycythemia vera and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, multiple myelomas such as but not limited to smoldering multiple myeloma, nonsecretory myeloma, osteosclerotic myeloma, plasma cell leukemia, solitary plasmacytoma and extramedullary plasmacytoma, refractory anemia (myelodysplastic syndrome) with excess blasts, 5q-syndrome, and myelodysplastic syndrome with t(9;12)(q22;p12) (TEL-Syk fusion; see, e.g., Kuno et al., Blood 97:1050 (2001). In various embodiments, any of the myeloid neoplasms that are associated with aberrant Syk activity can be treated with the Heteroaryl Compounds as described herein.

In some embodiments, the Heteroaryl Compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22; q22), AML1(CBF-alpha)/ETO, Acute promyelocytic leukemia (AML with t(15;17)(q22;q11-12) and variants, PML/R AR— alpha), AML with abnormal bone marrow eosinophils (inv(16)(p13q22) or t(16;16)(p13;q11), CBFb/MYH1 1X), and AML with I lq23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

In some embodiments, the Heteroaryl Compounds can be used to treat bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; breast cancer, including, but not limited to, adenocarcinoma, lobular (small cell) carcinoma, intraductal carcinoma, medullary breast cancer, mucinous breast cancer, tubular breast cancer, papillary breast cancer, primary breast cancers, Paget's disease, and inflammatory breast cancer; squamous cell carcinoma; and carcinoma of the head and neck.

In other aspects, cell proliferative disorders that can be targeted with the Heteroaryl Compounds comprise virally mediated tumors. These can arise from infection of cells by an oncogenic virus that has the capability of transforming a normal cell into a tumor cell. In some embodiments, the virally mediated tumor treatable with the compounds disclosed herein is associated with any virus that encodes an immunoreceptor tyrosine based activation motif (ITAM) capable of modulating Syk activity. This motif refers to a conserved amino acid sequence motif that functions by interacting with and activating nonreceptor tyrosine kinases. ITAM motifs are found in, among others, the β and γ chains of FϵERI, the ϵ subunit of the T cell receptor, and immunoglobulin 0 (Igβ) and Igα of the B cell receptor. The canonical sequence motif is typically Yxx(L/I)$x_{6-8}$ Yxx(L/I), where x represents any amino acid. Generally, the tyrosine residues in the motif are involved in ITAM signaling and are substrates for phosphorylation by Src family of kinases. The phosphorylated form of ITAMs function as interaction sites for SH2 (src homology domain) containing signaling proteins, such as Syk/ZAP-70 kinases. In addition to its presence in a variety of cellular cell surface molecules, the ITAM sequences have been identified in virally encoded proteins. In view of the descriptions herein indicating function of Syk kinase as an oncogene, tumors associated with viruses carrying genes encoding proteins with ITAM sequences can be treated with the Heteroaryl Compounds.

Accordingly, in some embodiments, the virally mediated tumor treatable with the Heteroaryl Compounds is associated with Kaposi's sarcoma (KS) associated herpes virus, a lymphotropic virus implicated in Kaposi's sarcoma, a rare malignancy found at higher incidence among HIV infected population. In some embodiments, the virally mediated tumor is associated with Epstein Barr Virus (EBV).

In some embodiments, the virally mediated tumor to be treated with the Heteroaryl Compound is associated with Human T-cell Lymphotropic Virus (HTLV-I virus), a retrovirus in the same class of virus as the AIDS virus, HIV-I.

In some embodiments, the virally mediated tumor is associated with mammary tumor virus (MTV). ITAM sequences are found within the Env gene of murine mammary tumor virus (MMTV), a B type retrovirus identified as an etiological agent for breast cancer in mice.

It is to be understood that use of Heteroaryl Compounds for treating virally mediated tumors is not limited to tumors associated with the viruses specified above. As noted, any tumors associated with an oncogenic virus in which Syk is activated as part of its oncogenic mechanism, whether or not it involves ITAM sequences, can be targeted using the Heteroaryl Compounds.

In other aspects, the present disclosure is directed to the treatment of tumor metastasis by use of the Heteroaryl Compounds. Metastasis is a characteristic of malignant tumor cells whereby tumor cells detach from its site of origin and then spread to colonize at other sites. These secondary tumors can form in tissues unrelated to the cells from which the tumor cells originate. It is the formation of these secondary tumors by metastasis that appears to be the primary cause of mortality from malignant forms of cancer. Metastasis begins when malignant cells break off from the primary tumor and enter the blood or lymphatic system, and then migrate to other colonization sites. Generally, normal cells do not detach and invade other tissues because of various signals that inhibit dissimilar cells from adhering to each other, as well as signals between cells that inhibit cell growth. Cell transformation, however, alters these normal regulatory programs such that tumor cells interact with local tissue cells to modify the local extracellular matrix, stimulate migration, and promote proliferation and survival. Alterations of cell adhesion molecule (CAMs), such as those members of the immunoglobulin and calcium-dependent cadherin families and integrins, appear to play critical role in invasion and metastasis. For instance, alteration of N-CAM from a highly adhesive isoform to a poorly adhesive form, which along with its down regulation, may lead to invasive pancreatic cancer.

Syk kinase activity is associated with various integrins expressed on cells of the hematopoietic lineage, but also in non-hematopoietic cells. Syk kinase is implicated in β1 integrin signaling of lung epithelial cells (Ulanova et al., *Am. J. Physiol. Lung Cell Mol. Physiol.* 288:L497-L507 (2004) and monocytes (Lin et al., *Biol. Chem.* 270(27):16189-97 (1995), β2 integrin signaling in granulocytes/neutrophils (Miura et al., *Blood* 96(5): 1733-9 (2000); Kusumoto et al., *Microbiol. Immunol.* 45(3):241-8 (2001), and β3 integrin signaling in platelet activation and cell adhesion (Gao et al., *EMBO J.* 16(21):6414-25 (1997). Given the connection provided herein between Syk kinase activity and tumorigenesis, the use of the Syk-inhibitory Heteroaryl Compounds in attenuating the invasiveness and metastatic properties of tumors is indicated through the link between Syk kinase activity and certain integrins (Mocsai et al., *Immunity* 16(4):547-58 (2002). Thus, in some embodiments, the Heteroaryl Compounds can be used to modulate metastatic properties of tumors mediated via integrin activity. In some embodiments, the Heteroaryl Compounds can be used to attenuate tumor cell tissue invasiveness and metastatic potential affected by β1 integrins (Lin et al., *Biol. Chem.* 270:16189-16197 (1995); Kusumoto et al., *Microbiol Immunol.*, 45(3):241-8 (2001); Ortiz-Stern et al., *J Leukoc Biol.* 77(5):787-99 (2005). An exemplary integrin of this type is integrin $\alpha_2\beta_1$.

In some embodiments, the Heteroaryl Compounds can be used to attenuate tumor cell tissue invasiveness and metastatic potential affected by the activity of β2 integrins (CD 18)

(Willeke et al., *J. Leukoc. Biol.* 74(2):260-9 (2003). These include, among others, CD11a/CD18, CD11b/CD18, CD11c/CD18, and CD11d/CD18. In further embodiments, the Heteroaryl Compounds can be used to attenuate tumor cell tissue invasiveness and metastatic potential affected by the activity of β3 integrins. Exemplary integrins of this type are $α_{IIb}β_3$ and $α_vβ_3$.

Various tumor types capable of metastasis can be treated with the Heteroaryl Compounds. Such tumors include, by way of example and not limitation, breast cancer, ovarian cancer, renal cancer, gastrointestinal cancer, kidney cancer, bladder cancer, pancreatic cancer, lung squamous carcinoma, and adenocarcinoma (see, e.g., Felding-Habermann et al., *Proc Natl Acad Sci USA* 98(4): 1853-8 (2001). Therapeutic treatment to attenuate the metastasis of established tumors can follow a diagnosis of metastasis. If no diagnosis of metastasis has been made, the Heteroaryl Compound can be administered prophylactically to reduce the probability of metastasis.

In another embodiment, the methods and compositions provided herein are also useful for administration to subjects in need of a bone marrow transplant to treat a malignant disease (e.g., subjects suffering from acute lymphocytic leukemia, acute myelogenous leukemia, chronic myelogenous leukemia, chronic lymphocytic leukemia, myelodysplastic syndrome ("preleukemia"), monosomy 7 syndrome, non-Hodgkin's lymphoma, neuroblastoma, brain tumors, multiple myeloma, testicular germ cell tumors, breast cancer, lung cancer, ovarian cancer, melanoma, glioma, sarcoma or other solid tumors), those in need of a bone marrow transplant to treat a non-malignant disease (e.g., subjects suffering from hematologic disorders, congenital immunodeficiencies, mucopolysaccharidoses, lipidoses, osteoporosis, Langerhan's cell histiocytosis, Lesch-Nyhan syndrome or glycogen storage diseases), those undergoing chemotherapy or radiation therapy, those preparing to undergo chemotherapy or radiation therapy and those who have previously undergone chemotherapy or radiation therapy.

In another embodiment, provided herein are methods for the treatment of cancer or tumors resistant to other kinase inhibitors such as imatinib mesylate (STI-571 or Gleevec™) treatment, comprising administering to a subject in need thereof an effective amount of a Heteroaryl Compound or a composition thereof. In a particular embodiment, provided herein are methods for the treatment of leukemias, including, but not limited to, gastrointestinal stromal tumor (GIST), acute lymphocytic leukemia or chronic myelocytic leukemia resistant to imatinib mesylate (STI-571 or Gleevec™) treatment, comprising administering to a subject in need thereof an effective amount of a Heteroaryl Compound or a composition thereof.

In a specific embodiment, provided herein are methods for treating or preventing leukemia (i.e., malignant neoplasms of the blood-forming tissues) including, but not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where subjects who have had a remission of leukemia after therapy have a return of leukemia cells in the marrow and a decrease in normal blood cells. The term "refractory or resistant" refers to a circumstance where subjects, even after intensive treatment, have residual leukemia cells in their marrow.

Further provide herein are methods for treating subjects who have been previously treated for cancer, but are non-responsive to standard therapies, as well as those who have not previously been treated. Also provided herein are methods for treating subjects regardless of subject's age, although some cancers are more common in certain age groups. Still further provided herein are methods for treating subjects who have undergone surgery in an attempt to treat the cancer at issue, as well as those who have not. Because subjects with cancer have heterogenous clinical manifestations and varying clinical outcomes, the treatment given to a subject may vary, depending on his/her prognosis. The skilled clinician will be able to readily determine without undue experimentation specific secondary agents, types of surgery, and types of non-drug based standard therapy that can be effectively used to treat an individual subject with cancer.

It is to be understood that the Heteroaryl Compounds can be used independently of any other treatment, or used in combination with other cancer treatment regimens, including surgery, radiology, or other chemotherapies. A Heteroaryl Compound can be combined with other pharmacologically active compounds ("second active agents") in methods and compositions described herein. It is believed that certain combinations may work synergistically in the treatment of particular types diseases or disorders, and conditions and symptoms associated with such diseases or disorders. A Heteroaryl Compound can also work to alleviate adverse effects associated with certain second active agents, and vice versa.

Accordingly, in some embodiments, the Heteroaryl Compounds can be used in combination with other chemotherapeutic agents. Combination treatments with the Heteroaryl Compounds can target different cellular components by appropriate choice of the second chemotherapeutic agent. For instance, the Heteroaryl Compounds can be used in some embodiments to limit the metastatic potential of tumor cells while another chemotherapeutic agent can be used to eliminate or kill aberrant cells.

Various chemotherapeutic agents can be used in combination with the Heteroaryl Compounds to treat cell proliferative disorders. These chemotherapeutic agents can be general cytotoxic agents or target a specific cellular molecule. Various classes of cancer chemotherapeutic agents include, among others, antimetabolites, agents that react with DNA {e.g., alkylating agents, coordination compounds, etc), inhibitors of transcription enzymes, topoisomerase inhibitors, DNA minor-groove binding compounds, antimitotic agents {e.g., vinca alkyloids), antitumor antibiotics, hormones, and enzymes. Exemplary alkylating agents include, by way of example and not limitation, mechlorothamine, cyclophosphamide, ifosfamide, melphalan, chlorambucil, ethyleneimines, methylmelamines, alkyl sulfonates {e.g., busulfan), and carmustine. Exemplary antimetabolites include, by way of example and not limitation, folic acid analog methotrexate; pyrimidine analogs fluorouracil, cytosine arabinoside; and purine analogs mercaptopurine, thioguanine, and azathioprine. Exemplary vinca alkyloids include, by way of example and not limitation, vinblastine, vincristine, paclitaxel, and colchicine. Exemplary antitumor antibiotics include, by way of example and not limitation, actinomycin D, daunorubicin, and bleomycin. An exemplary enzyme effective as anti-neoplastic agent is L-asparaginase. Exemplary coordination compounds include, by way of example and not limitation, cisplatin and carboplatin. Exemplary hormones and hormone related compounds include, by way of example and not limitation, adrenocorticosteroids prednisone, and dexamethasone; aromatase inhibitors amino glutethimide, formestane, and anastrozole; progestin compounds hydroxyprogesteron caproate, medroxyprogesterone; and anti-estrogen compound tamoxifen. Exemplary topoisomerase inhibitors include, by way of example and not limitation, amsacrine (m-AMSA); mitoxantrone, topotecan, irinotecan, and camptothecin.

These and other useful anti-cancer compounds are described in Merck Index, 13th Ed. (O'Neil, M J. Et al., ed) Merck Publishing Group (2001) and Goodman and Gilman's *The Pharmacological Basis of Therapeutics*, 10th Edition, Hardman, J. G. and Limbird, L. E. eds., pg. 1381-1287, McGraw Hill, (1996), both of which are incorporated herein by reference.

Typically, any chemotherapeutic agent that has activity versus a neoplasm being treated may be utilized in combination with the Heteroaryl Compounds as described herein provided that the particular agent is clinically compatible with therapy employing a Heteroaryl Compound as described herein. Typical antineoplastic agents useful in the methods described herein include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracycline, actinomycins and bleomycins; topoisomerase II inhibitors such as epipodophyilotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesls Inhibitors; immunotherapeutic agents; proapoptotic agents; and cell cycle signaling inhibitors.

Signal transduction pathway inhibitors are those inhibitors which block or inhibit a chemical process which evokes an intracellular change. As used herein this change is cell proliferation, survival, angiogenesis or differentiation. Signal transduction inhibitors useful in the present methdos include inhibitors of receptor tyrosine kinases, non-receptor tyrosine kinases, SH2/SH3 domain blockers, serine/threonine kinases, phosphatidyl inositol-3 kinases, myoinositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are sometimes termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr, ErbB2 and ErbB4), platelet derived growth factor receptor (PDGFR), vascular endothelial growth factor receptor (VEGFR), tyrosine kinase with immunoglobin-like and epidermal growth factor homology domains (Tie-2), insulin growth factor-I receptor (IGF-I), macrophage colony stimulating factor (MCSF), BTK, ckit, cmet, fibroblast growth factor (FGF) receptors, Trk receptors (TrkA, TrkB, and TrkC), ephrin (eph) receptors, and the RET protooncogene. Several inhibitors of growth factor receptors are under development and include ligand antagonists, antibodies, tyrosine kinase inhibitors, anti-sense oligonucleotides and aptamers. Growth factor receptors and agents that inhibit growth factor receptor function are described, for instance, in Kath, John C, *Exp. Opin. Ther. Patents* 10 {8):803-818 (2000); and Lofts, F. J. et al, "*Growth Factor Receptors as Targets*", New Molecular Targets for Cancer Chemotherapy, Ed. Workman, Paul and Kerr, David, CRC Press 1994, London.

Tyrosine kinases, which are not growth factor receptor kinases are termed non-receptor tyrosine kinases. Non-receptor tyrosine kinases useful in the present methods are targets or potential targets of antineoplastic drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. et al., *J. Hematother. Stem Cell Res.* 8 (5): 485-80 (1999); and Bolen, J. B. et al., *Ann. Rev. Immunol.* 15: 371-404 (1997).

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods 34(3) 125-32.

Inhibitors of Serine/Threonine Kinases including MAP kinase cascade blockers which include blockers of Raf kinases (Rafk), Mitogen or Extracellular Regulated Kinase (MEKs), and Extracellular Regulated Kinases (ERKs); and Protein kinase C family member blockers including blockers of subtypes of PKCs (alpha, beta, gamma, epsilon, mu, lambda, iota, zeta), IkB kinase family (IKKa, IKKb), PKB family kinases, Akt kinase family members, and TGF beta receptor kinases. Such Serine/Threonine kinases and inhibitors thereof are described in Yamamoto, T. et al, *J. Biochem.* 126(5): 799-803 (1999); Brodt, P. et al. *Biochem. Pharmacol.* 60: 1101-1107 (2000); Massague, J. et al. *Cancer Surveys* 27:41-64 (1988); Philip, P A. et al., *Cancer Treat. Res.* 78: 3-27 (1995), Lackey, K. et al. Bioorg. Med. Chem. Lett. 10: 223-228 (2000); and Martinez-Lacaci, L., et al, *Int. J. Cancer* 88(1): 44-52 (2000).

Inhibitors of Phosphatidyl Inositol-3 Kinase family members including blockers of PI3-kinase, ATM, DNA-PK, and Ku are also useful in combination with the compounds described herein. Such kinases are discussed in Abraham, R T. *Curr. Op. Immunol.* 8(3):412-8 (1996); Canman, C. E. et al. *Oncogene* 17(25):3301-3308 (1998); Jackson, S P. *Int. J. Biochem. Cell Biol.* 29(7):935-938 (1997); and Zhong, H. et al, *Cancer Res.* 60(6):1541-1545 (2000).

Also useful in combination with the Heteroaryl Compounds described herein are Myo-inositol signaling inhibitors such as phospholipase C blockers and Myoinositol analogues. Such signal inhibitors are described in Powis, G. et al. *New Molecular Targets for Cancer Chemotherapy* ed., Paul Workman and David Kerr, CRC Press 1994, London.

Another group of signal transduction pathway inhibitors useful in combination with the Heteroaryl Compounds are inhibitors of Ras Oncogene. Such inhibitors include inhibitors of farnesyltransferase, geranyl-geranyl transferase, and CAAX proteases as well as anti-sense oligonucleotides, rybozymes and immunotherapy. Such inhibitors have been shown to block Ras activation in cells containing wild type mutant Ras, thereby acting as antiproliferation agents. Ras oncogene inhibition is discussed in Scharovsky, C G. et al. *J. Biomed. Sci.* 7(4) 292-298 (2000): Ashby, M M, *Curr. Op. Lipid.* 9(2)99-102 (1998); and Oliff, A., *Biochim. Biophys. Acta,* 1423(3): C19-C30 (1999).

As mentioned above, antibodies to receptor kinase ligand binding may also serve as signal transduction inhibitors. This group of signal transduction pathway inhibitors includes the use of humanized antibodies to the extracellular ligand binding domain of receptor tyrosine kinases. For example, Imclone C225 EGFR specific antibody (see Green, M. C. et al. *Cancer Treat. Rev.,* 26(4), 280-286 (2000)); Herceptin® ErbB2 antibody (see Stern, D F *Breast Cancer Res.,* 2(3), 176-183 (2000)); and 2CB VEGFR2 specific antibody (see Brekken, R A et al, *Cancer Res.* 80, 5117-5124 (2000)).

Receptor kinase angiogenesis inhibitors may also find use in the present methods. Inhibitors of angiogenesis related VEGFR and TIE2 are discussed above in regard to signal transduction inhibitors (both receptors are receptor tyrosine kinases). Other inhibitors may be used in combination with the Heteroaryl Compounds described herein. For example, anti-VEGF antibodies, which do not recognize VEGFR (the receptor tyrosine kinase), but bind to the ligand; small molecule inhibitors of Integrin (alpha$_v$ beta$_3$) that will inhibit angiogenesis: endostatin and angiostatin (non-RTK) may also prove useful in combination with PLK inhibitors.

Agents used in immunotherapeutic regimens may also be useful in combination with the Heteroaryl Compound as described herein.

Agents used in proapoptotic regimens (e.g., bcl-2 antisense oligonucleotides) may also be used in the combinations provided herein, Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mc1-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al, *J. Clin. Oncol* 18:1812-1823 (2000); and Kitada S et al, *Antisense Res. Dev.* 4:71-79 (1994).

Cell cycle signaling inhibitors inhibit molecules involved in the control of the cell cycle. Cyclin dependent kinases (CDKs) and their interaction with cyclins control progression through the eukaryotic cell cycle. The coordinated activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania, et al., *Exp. Opin Ther, Patents* 10(2):215-230 (2000).

Other anti-proliferative compounds useful in combination with the Heteroaryl Compounds include, by way of example and not limitation, antibodies directed against growth factor receptors {e.g., anti-Her2); cytokines such as interferon-α and interferon-γ, interleukin-2, and GM-CSF; and antibodies for cell surface markers {e.g., anti-CTLA-4. anti-CD20 (rituximab); anti-CD33). When antibodies against cell surface markers are used, a chemotherapeutic agent can be conjugated to it for specific targeting to the tumor cell. Suitable conjugates include radioactive compounds {e.g., radioactive metal bound to an antibody conjugated chelator), cytotoxic compounds, and drug activating enzymes {e.g., allinase, peptidases, esterases, catalytic antibodies, etc.) (see, e.g., Arditti et al., *Mol. Cancer Therap.* 4(2):325-331 (2005); U.S. Pat. No. 6,258,360; incorporated herein by reference).

In some embodiments, the Heteroaryl Compounds can be used with a second kinase inhibitor that targets an oncogenic kinase different from Syk. Given that the Heteroaryl Compounds are disclosed herein for the treatment of hematopoietic neoplasms, other compatible kinase inhibitors used for treating hematopoietic neoplasms can also be used. In some embodiments, the second kinase inhibitor is an inhibitor of Abl kinase. Chronic myelogenous leukemia is a myeloid neoplasm characterized by malignant proliferation of leukemic stem cells in the bone marrow. The majority of chronic myelogenous leukemia are associated with a cytogenetic abnormality defined by a reciprocal translocation t(9;22) (q34;q1 1). This chromosomal aberration results in generation of a BCR/ABL fusion protein with activated kinase activity. Inhibitors of the fusion protein kinase activity can be effective in treating chronic myelogenous leukemia although resistant forms can develop upon continued treatment. Use of the Heteroaryl Compound in combination with Abl kinase inhibitors can lessen the chances of resistant cells by targeting a different cellular process than targeted by the second kinase inhibitor. An exemplary Abl kinase inhibitor is 2-phenylaminopyrimidine, also known as imatinib mesylate and Gleevec®. Thus, in some embodiments, the Heteroaryl Compounds can be used in combination with Abl kinase inhibitor 2-phenylaminopyrimidine and its derivatives. In other embodiments, the second kinase inhibitor can be pyridol[2-3-d]pyrimidine and its derivatives, which was originally identified as inhibitors of Src kinase. In still other embodiments, the second kinase inhibitor can be tyrphostins and its derivatives (e.g., adaphostin), which can affect the association of the kinase with its substrates. Other kinase inhibitor compounds will be apparent to the skilled artisan.

Other second active agents useful in combination with Heteroaryl Compounds have activity against Syk kinase include, by way of example and not limitation, Fc-domain containing therapeutic antibodies or fusion proteins, such as infliximab or etanercept. In one embodiment, provided herein are methods for the treatment or prevention of an autoimmune disorder, such as those known in the art or recited herein, comprising administering to a subject in need thereof a combination of a Heteroaryl Compound having activity against Syk kinase and a Fc-domain containing antibody, such as infliximab or etanercept. In one embodiment, provided herein are methods for the treatment or prevention of an inflammatory disorder, such as those known in the art or recited herein, comprising administering to a subject in need thereof a combination of a Heteroaryl Compound having activity against Syk kinase and a Fc-domain containing antibody, such as infliximab. In a particular embodiment, the Heteroaryl Compound is administered as a chronic therapy, starting before or immediately after the initial administration of the Fc-domain containing therapeutic antibody or fusion protein. Without being limited by theory, it is thought that a Heteroaryl Compound with activity against Syk kinase can extend the serum half-life of Fc-domain containing therapeutic antibodies and fusion proteins in a subject.

One or more second active ingredients or agents can be used in the methods and compositions described herein. Second active agents can be large molecules (e.g., proteins) or small molecules (e.g., synthetic inorganic, organometallic, or organic molecules).

Examples of large molecule second active agents include, but are not limited to, hematopoietic growth factors, cytokines, and monoclonal and polyclonal antibodies. Specific examples of the active agents are thrombopoietin mimetics or receptor agonists such as Rombiplosim and Promacta, anti-CD40 monoclonal antibodies (such as, for example, SGN-40); histone deacetylyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan), tositumomab (Bexxar), edrecolomab (Panorex®) and G250); and anti-TNF-α antibodies. Examples of small molecule active agents include, but are not limited to, small molecule anti-cancer agents and antibiotics (e.g., clarithromycin).

Specific second active compounds that can be combined with a Heteroaryl Compound vary depending on the specific indication to be treated, prevented or managed.

For instance, for the treatment, prevention or management of inflammatory, autoimmune disease or cancer, second active agents include, but are not limited to: semaxanib; cyclosporine; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; corticosteroids; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clathromycin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; j asplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin;

lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), bortezomib, statins, semaxanib, cyclosporine, etanercept, doxycycline, bortezomib, oblimersen (Genasense), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Similarly, examples of specific second agents according to the indications to be treated, prevented, or managed can be found in the following references, all of which are incorporated herein in their entireties: U.S. Pat. Nos. 7,189,740, 6,281,230 and 5,635,517; U.S. application Ser. Nos. 11/085,905, 11/111,188, 11/271,963, 11/284,403, 11/289,723, 11/022,075, 10/411,656, 10/693,794, 10/699,154, and 10/981,189.

Examples of additional second active agents include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Enbrel®, ketamine, gabapentin (Neurontin®), phenyloin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®), mexiletine, nifedipine, propranolol, tramadol, lamotrigine, ziconotide, ketamine, dextromethorphan, benzodiazepines, baclofen, tizanidine and phenoxybenzamine.

Examples of additional second active agents include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2α, pentoxifylline, tin etiopurpurin, motexafin lutetium, 9-fluoro-11, 21-dihydroxy-16,17-1-methylethylidine-bis(oxy)pregna-1, 4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O—Ac genistin, daidzein, daidzin, 6'-O-Mal daidzin, 6'-O—Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, lenalidomide and pomalidomide or an IMiDs® brand Immunomodulatory product, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited above are incorporated herein in their entireties by reference.

Examples of additional second active agents include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin 12 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Clalis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of additional second active agents include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), pacli-taxel, ganciclovir, adriamycin, bleomycin, hyaluronidase, mitomycin C, mepacrine, thiotepa, tetracycline and gemcitabine.

Examples of additional second active agents include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stibogluconate), interferon gamma, itraconazole, a combination of dead promastigotes and BCG, leucovorin, corticosteroids, sulfonamide, spiramycin, IgG (serology), trimethoprim, and sulfamethoxazole.

Examples of additional second active agents include, but are not limited to: antibiotics (therapeutic or prophylactic) such as, but not limited to, ampicillin, clarithromycin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-β), antibodies (e.g., anti-CD40 and IgM), oligonucleotides containing unmethylated CpG motifs, and vaccines (e.g., viral and tumor peptide vaccines).

Examples of additional second active agents include, but are not limited to: a dopamine agonist or antagonist, such as, but not limited to, Levodopa, L-DOPA, cocaine, α-methyltyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet C, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of additional second active agents include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in subjects with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methylphenidate, dl-threo-methylphenidate, 1-erythro-methylphenidate, d-erythro-methylphenidate, dl-erythro-methylphenidate, and a mixture thereof; and a diuretic agent such as, but not limited to, mannitol, furosemide, glycerol, and urea.

Examples of additional second active agents include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-nl, interferon alfa-n3, interferon beta-I a, and interferon gamma-I b; and G-CSF; hydroxyurea; butyrates or butyrate derivatives; nitrous oxide; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Some Heteroaryl Compounds described herein are inhibitors of PLK, in particular, PLK1. By PLK inhibitor is meant a compound which exhibits an $IC_{50}$ less than 10 μM in the PLK Inhibition assay described below in the examples or an $IC_{50}$ less than 10 μM in the Cell-Titer Glo or p-TCTP biomarker assays described below in the examples; more particularly a PLK inhibitor is a compound which exhibits an $IC_{50}$ less than 10 μM in the PLK Inhibition assay or an $IC_{50}$ less than 1 μM in the Cell-liter Glo or p-TCTP biomarker assay using the methods described in the examples below.

As described herein, there are provided methods of regulating, modulating, binding, or inhibiting PLK for the treatment of conditions mediated by PLK particularly PLK1. "Regulating, modulating, binding or inhibiting PLK" refers to regulating, modulating, binding or inhibiting PLK, particularly PLK1 activity, as well as regulating, modulating, binding or inhibiting overexpression of PLK, particularly PLK1. Such conditions include certain neoplasms (including cancers and tumors) which have been associated with PLK, particularly PLK1, and conditions characterized by inappropriate cellular proliferation.

Also provided are methods for treating a PLK susceptible neoplasm (cancer or tumor) in a subject such as a mammal (e.g., a human) in need thereof, which method comprises administering to the subject a therapeutically effective amount of a Heteroaryl Compound described herein. "PLK susceptible neoplasm" as used herein refers to neoplasms which are susceptible to treatment with a PLK, particularly PLK1, inhibitor. Neoplasms which have been associated with PLK and are therefore susceptible to treatment with a PLK inhibitor are known in the art, and include both primary and metastatic tumors and cancers. See e.g., M. Whitfield et al, Nature Reviews/Cancer, 6:99 (2006). For example, PLK susceptible neoplasms include but are not limited to breast cancer, colon cancer, lung cancer (including small cell lung cancer and non-small cell lung cancer), prostate cancer, endometrial cancer, gastric cancer, melanoma, ovarian cancer, pancreatic cancer, squamous cell carcinoma, carcinoma of the head and neck, esophageal carcinoma, hepatocellular carcinoma, renal cell cancer, sarcoma {including cancers of connective tissue), bladder cancer, glioma and hematologic malignancies such as lymphoma including aggressive lymphomas and non-Hodgkins lymphoma, and leukemia including acute leukemias. In one particular embodiment, a method is provided of treating breast cancer in a subject, such as a mammal (e.g., a human} in need thereof by administering a therapeutically effective amount of a Heteroaryl Compound as described herein. In another particular embodiment, there is provided a method of treating ovarian cancer in a subject, such as a mammal (e.g. a human) in need thereof by administering a therapeutically effective amount of a Heteroaryl Compound as described herein. In another particular embodiment, there is provided a method of treating non-small cell lung cancer in a subject, such as a mammal (e.g., a human) in need thereof by administering a therapeutically effective amount of a Heteroaryl Compound as described herein. In another particular embodiment, there is provided a method of treating prostate cancer in a subject, such as a mammal (e.g., a human) in need thereof by administering a therapeutically effective amount of a Heteroaryl Compound as described herein. In another particular embodiment, there is provided a method of treating hematologic malignancies including lymphoma, such as aggressive lymphoma and non-Hodgkins lymphoma, and leukemia such as acute leukemia in a subject, such as a mammal (e.g., a human) in need thereof by administering a therapeutically effective amount of a Heteroaryl Compound as described herein. "Acute leukemias" includes both acute myeloid leukemias and acute lymphoid leukemias. See, H. Harris, et al, *J Clin. Onc.* 17(12):3835-3849, (1999). "Aggressive lymphomas" is a term of art, See, J. Chan, *Hematological One.* 19:128-150 (2001).

Also provided are methods for treating a condition characterized by inappropriate cellular proliferation in a subject, such as a mammal (e.g., a human) in need thereof. The method comprises administering a therapeutically effective amount of a Heteroaryl Compound as described herein. By "inappropriate cellular proliferation" is meant cellular proliferation resulting from inappropriate cell growth, cellular proliferation resulting from excessive cell division, cellular proliferation resulting from cell division at an accelerated rate, cellular proliferation resulting from inappropriate cell survival, and/or cellular proliferation in a normal cell occurring at a normal rate, which is nevertheless undesired. Conditions characterized by inappropriate cellular proliferation include but are not limited to neoplasms, blood vessel proliferative disorders, fibrotic disorders, mesangial cell proliferative disorders and inflammatory/immune-mediated diseases. Blood vessel proliferative disorders include arthritis and restenosis. Fibrotic disorders include hepatic cirrhosis and atherosclerosis. Mesangial cell proliferative disorders include glomerulonephritis, malignant nephrosclerosis and glomerulopathies. Inflammatory/immune-mediated disorders include psoriasis, chronic wound healing, organ transplant rejection, thrombotic microangiopathy syndromes, and neurodegenerative diseases. Osteoarthritis and other osteoclast proliferation dependent diseases of excess bone resorption are examples of conditions characterized by inappropriate cellular proliferation in which the cellular proliferation occurs in normal cells at a normal rate, but is nevertheless undesired.

Also provided are methods for inhibiting proliferation of a cell which methods comprise contacting the cell with an amount of a Heteroaryl Compound as described herein sufficient to inhibit proliferation of the cell. In one particular embodiment the cell is a neoplastic cell. In one particular embodiment, the cell is an inappropriately proliferative cell. The term "inappropriately proliferative cell" as used herein refers to cells that grow inappropriately (abnormally), cells that divide excessively or at an accelerated rate, cells that inappropriately (abnormally) survive and/or normal cells that proliferate at a normal rate but for which proliferation is undesired. Neoplastic cells (including cancer cells) are an example of inappropriately proliferative cells but are not the only inappropriately proliferative cells.

PLK is essential for cellular mitosis and accordingly, the compounds as described herein are believed to be effective for inhibiting mitosis "Inhibiting mitosis" refers to inhibiting the entry into the M phase of the cell cycle, inhibiting the normal progression of the M phase of the cell cycle once M phase has been entered and inhibiting the normal exit from the M phase of the cell cycle. Thus, Heteroaryl Compounds as described herein may inhibit mitosis by inhibiting the cell's entry into mitosis, by inhibiting the cell's progression through mitosis or by inhibiting the cell's exit from mitosis. As one aspect, provided are methods for inhibiting mitosis in a cell, which methods comprise administering to the cell an amount of a compound as described herein sufficient to inhibit mitosis, and in one particular embodiment, the cell is a neoplastic cell. In one particular embodiment, the cell is an inappropriately proliferative cell.

Further provided are the use of a Heteroaryl Compound as described herein for the preparation of a medicament for the treatment of condition mediated by PLK, particularly PLK1, in a subject, such as a mammal {e.g., a human). Still further provided are the use of a Heteroaryl Compound for the preparation of a medicament for the treatment of a PLK susceptible neoplasm in a subject, particularly a mammal (e.g., a human). In particular, provided are the use of a Heteroaryl Compound for the preparation of a medicament for the treatment of breast cancer. In addition, also provided are the use of a Heteroaryl Compound for the preparation of a medicament for the treatment of ovarian cancer, the use of a Heteroaryl Compound for the preparation of a medicament for the treatment of non-small cell lung cancer, the use of a Heteroaryl Compound for the preparation of a medicament for the treatment of prostate cancer, and the use of a Heteroaryl Compound for the preparation of a medicament for the treatment of hematologic malignancies, such as acute leukemias, aggressive lymphomas and non-Hodgkins lymphomas. Further provided are the use of a Heteroaryl Compound for the preparation of a medicament for the treatment of a condition characterized by inappropriate cellular proliferation, for the use of a Heteroaryl Compound for the preparation of a medicament for inhibiting proliferation of a cell, and for the use of a Heteroaryl Compound for the preparation of a medicament for inhibiting mitosis in a cell.

In the above-described methods of treatment and uses, a compound as described herein may be employed alone, in combination with one or more other compounds ad described herein or in combination with other therapeutic agents and/or in combination with other antineoplastic therapies. In particular, in methods of treating conditions mediated by PLK and methods of treating PLK susceptible neoplasms, combination with other chemotherapeutic agents is envisaged as well as combination with surgical therapy and radiation therapy. The term "chemotherapeutic" as used herein refers to any chemical agent having a therapeutic effect on the subject to which it is administered. "Chemotherapeutic" agents include but are not limited to antineoplastic agents, analgesics and anti-emetics. As used herein, "antineoplastic agents" include both cytostatic and cytotoxic agents such as but not limited to cytotoxic chemotherapy, hormonal therapy, targeted kinase inhibitors and therapeutic monoclonal antibodies. Combination therapies as described herein thus comprise the administration of at least one Heteroaryl Compound as described herein and the use of at least one other cancer treatment method. In one embodiment, combination therapies as provided herein comprise the administration of at least one compound as described herein and at least one other chemotherapeutic agent. One particular embodiment comprises the administration of at least one Heteroaryl Compound as described herein and at least one antineoplastic agent. As an additional aspect, also provided are the methods of treatment and uses as described above, which comprise administering a Heteroaryl Compound as described herein together with at least one chemotherapeutic agent. In one particular embodiment, the chemotherapeutic agent is an antineoplastic agent. In another embodiment, provided herein is a pharmaceutical composition as described above further comprising at least one other chemotherapeutic agent, more particularly, the chemotherapeutic agent is an anti-neoplastic agent.

As further described herein, the administration of other chemotherapeutic agents can be done in the form of a composition, or administered adjunctively in combination with the Heteroaryl Compound. When provided adjunctively, the chemotherapeutic agents can be administered simultaneously with or sequentially with administration of the Heteroaryl Compound.

The methods and uses employing these combinations may comprise the administration of the Heteroaryl Compound as described herein and the second active agent either sequentially in any order or simultaneously in separate or combined pharmaceutical compositions. When combined in the same formulation it will be appreciated that the two compounds must be stable and compatible with each other and the other components of the formulation and may be formulated for administration.

Administration of a Heteroaryl Compound and a second active agent to a subject can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One route of administration for Heteroaryl Compounds is oral. Preferred routes of administration for the second active agents or ingredients as described herein are known to those of ordinary skill in the art. See, e.g., Physicians' Desk Reference, 1755-1760 ($56^{th}$ ed., 2002).

In one embodiment, the second active agent is administered intravenously or subcutaneously. In another embodiment, the second active agent is administered intravenously or subcutaneously once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of a Heteroaryl Compound and any optional additional active agents concurrently administered to the subject.

Further provided herein are methods of reducing, treating and/or preventing adverse or undesired effects associated with conventional therapy including, but not limited to, surgery, chemotherapy, radiation therapy, hormonal therapy, biological therapy and immunotherapy. Heteroaryl Compounds and other active ingredients can be administered to a subject prior to, during, or after the occurrence of the adverse effect associated with conventional therapy.

4.5 Pharmaceutical Compositions and Routes of Administration

In one aspect provided herein are pharmaceutical compositions comprising an effective amount of a Heteroaryl Compound or a pharmaceutically acceptable salt, tautomer, stereoisomer, solvate or prodrug thereof; and a pharmaceutically acceptable carrier, excipient or vehicle.

In one embodiment provided herein are pharmaceutical compositions suitable for oral, parenteral, mucosal, transdermal or topical administration.

The Heteroaryl Compounds can be administered to a subject orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Heteroaryl Compound in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a Heteroaryl Compound to be administered to a subject is rather widely variable and can be subject to the judgment of a health-care practitioner. In general, the Heteroaryl Compounds can be administered one to four times a day in a dose of about 0.005 mg/kg of a subject's body weight to about 10 mg/kg of a subject's body weight in a subject, but the above dosage may be properly varied depending on the age, body weight and medical condition of the subject and the type of administration. In one embodiment, the dose is about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the Heteroaryl Compound administered will depend on such factors as the solubility of the active component, the formulation used and the route of administration.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a Heteroaryl Compound to a subject in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Heteroaryl Compound to a subject in need thereof. In a particular embodiment, the methods disclosed herein comprise the administration of 400 mg/day, 600 mg/day or 800 mg/day of a Heteroaryl Compound to a subject in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of a Heteroaryl Compound.

In a particular embodiment, provided herein are unit dosage formulation comprising about 100 mg or 400 mg of a Heteroaryl Compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Heteroaryl Compound.

A Heteroaryl Compound can be administered once, twice, three, four or more times daily. In a particular embodiment, doses of 600 mg or less are administered as a once daily dose and doses of more than 600 mg are administered twice daily in an amount equal to one half of the total daily dose.

A Heteroaryl Compound can be administered orally for reasons of convenience. In one embodiment, when administered orally, a Heteroaryl Compound is administered with a meal and water. In another embodiment, the Heteroaryl Compound is dispersed in water or juice (e.g., apple juice or orange juice) and administered orally as a suspension.

The Heteroaryl Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Heteroaryl Compound without an additional carrier, excipient or vehicle.

In another embodiment, provided herein are compositions comprising an effective amount of a Heteroaryl Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Heteroaryl Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Heteroaryl Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Heteroaryl Compound can be delayed or prolonged by proper formulation. For example, a slowly soluble pellet of the Heteroaryl Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Heteroaryl Compound in oily or emulsified vehicles that allow it to disperse slowly in the serum.

5. EXAMPLES

The following abbreviations were used in descriptions and examples:

| 9-BBN | 9-Borabicyclo[3.3.1]nonane |
|---|---|
| ATP | Adenosine triphosphate |
| BSA | Bovine serum albumin |
| DPBS | Dulbecco's phosphate buffered saline |
| DCM | Dichloromethane |
| DIPEA | N,N-Diisopropylethylamine |
| DMF | N,N-Dimethylformamide |
| DMSO | Dimethylsulfoxide |
| DNP | 2,4-Dinitrophenol |
| DTT | Dithiothreitol |
| EDTA | Ethylenediaminetetraacetic acid |
| ESI | Electrospray ionization |
| FBS | Fetal bovine serum |
| HEPES | (4-(2-Hydroxyethyl)-1-piperazineethanesulfonic acid |
| HPLC | High performance liquid chromatography |

-continued

| HTRF | Homogeneous time resolved fluorescence |
|---|---|
| LCMS | Liquid chromatography mass spectrometry |
| MS | Mass spectrometry |
| n-BuLi | n-Butyllithium |
| NMR | Nuclear magnetic resonance |
| p-TsOH | Para-toluene sulfonic acid |
| RPMI | Roswell Park Memorial Institute medium |
| SN | Supernatant |
| TFA | Trifluoracetic acid |
| TLC | Thin layer chromatography |
| TsCl | 4-Methyl benzenesulfonyl chloride |
| µw | Microwave |

Compounds are named using the automatic name generating tool provided in Chemdraw Ultra 9.0 (Cambridgesoft), which generates systematic names for chemical structures, with support for the Cahn-Ingold-Prelog rules for stereochemistry.

The following Examples are presented by way of illustration, not limitation.

5.1 Synthetic Examples

5.1.1 Synthesis of Intermediates

Intermediate 1: tert-Butyl 5-bromo-1-oxoisoindoline-2-carboxylate

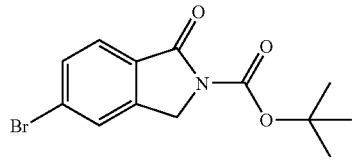

A. Methyl 4-bromo-2-methylbenzoate. To a stirred solution of 4-bromo-2-methylbenzoic acid (1 g, 4.7 mmol) in methanol (20 mL) was added dropwise sulfurous dichloride (1.4 g, 11.7 mmol) at 0° C., and the resulting mixture was refluxed for 2 h. After TLC (ethyl acetate) indicated the starting material was consumed, the solvent was removed under reduced pressure, and the residue was dissolved in ethyl acetate and water. Layers were separated and the aqueous phase was extracted with ethyl acetate. The combined organic layers were washed with brine, dried over anhydrous sodium sulfate, and evaporated in vacuo to give methyl 4-bromo-2-methylbenzoate (0.8 g, 75% yield). $^1$H-NMR (400 MHz, CHLOROFORM-d) δ (ppm) 7.80 (d, J=8.4 Hz, 1H), 7.46-7.38 (m, 2H), 3.90 (s, 3H), 2.60 (s, 3H).

B. Methyl 4-bromo-2-(bromomethyl)benzoate. A suspension of methyl 4-bromo-2-methylbenzoate (0.8 g, 3.5 mmol), N-bromosuccinimide (0.69 g, 3.8 mmol), benzoyl peroxide (15 mg, 0.06 mmol) in tetrachloromethane (10 mL) was refluxed for 5 h. When TLC (ethyl acetate) indicated the starting material was consumed, the mixture was cooled down to room temperature. The precipitate was filtered off, and the filtrate was concentrated to give methyl 4-bromo-2-(bromomethyl)benzoate (0.9 g, 84% yield). $^1$H-NMR (400 MHz, CHLOROFORM-d) δ (ppm) 7.86 (d, J=8.8 Hz, 1H), 7.65 (s, 1H), 7.52 (dd, J=8.4 Hz, J=2.0 Hz, 1H), 4.91 (s, 2H), 3.95 (s, 3H).

C. 5-Bromoisoindolin-1-one. To a solution of methyl 4-bromo-2-(bromomethyl)benzoate (0.8 g, 2.6 mmol) in tetrahydrofuran (40 mL) was added an aqueous solution of ammonia (5 mL) in a sealed vessel, and the reaction mixture was stirred at 40° C. for 3 days. The precipitate was collected and dried in vacuo to give 5-bromoisoindolin-1-one (220 mg, 40% yield) as a white solid. $^1$H-NMR (400 MHz, DMSO-d$_6$) δ (ppm) 8.62 (br s, 1H), 7.81 (s, 1H), 7.64 (d, J=8 Hz, 1H), 7.57 (d, J=8 Hz, 1H), 4.34 (s, 2H).

D. tert-Butyl 5-bromo-1-oxoisoindoline-2-carboxylate. A mixture of 5-bromoisoindolin-1-one (40 mg, 0.19 mmol), di-tert-butyl dicarbonate (41 mg, 0.19 mmol), N,N-dimethylpyridin-4-amine (2.3 mg, 0.02 mmol) in dichloromethane (3 mL) was stirred at room temperature overnight. When TLC (ethyl acetate) indicated the starting material was consumed, the reaction mixture was washed with water and brine, dried over anhydrous sodium sulfate, and evaporated in vacuo to give tert-butyl 5-bromo-1-oxoisoindoline-2-carboxylate (30 mg, 51% yield) as a white solid. $^1$H-NMR (400 MHz, DMSO-d$_6$) δ (ppm) 7.89 (s, 1H), 7.71-7.65 (m, 2H), 4.75 (s, 2H), 1.49 (s, 9H).

Intermediate 2: tert-Butyl 4-(4-(4,4,5,5-tetramethyl-1,3,2-dioxaborolan-2-yl)pyridin-2-yl)piperazine-1-carboxylate

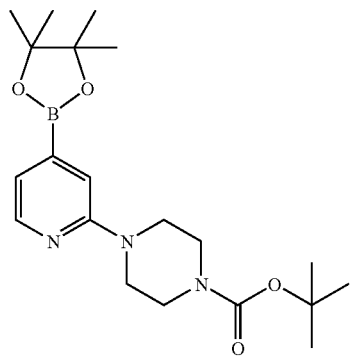

A. tert-Butyl 4-(4-(4,4,5,5-tetramethyl-1,3,2-dioxaborolan-2-yl)pyridin-2-yl)piperazine-1-carboxylate. A solution of 1-(4-(4,4,5,5-tetramethyl-1,3,2-dioxaborolan-2-yl)pyridin-2-yl)piperazine (0.5 g, 1.729 mmol) in dichloromethane (13 mL) was cooled to 0° C. and treated with triethylamine (0.265 mL, 1.902 mmol) followed by di-tert-butyl dicarbonate (0.377 g, 1.73 mmol). The reaction was slowly warmed to room temperature. The reaction mixture was washed with water. The organic phase was dried over magnesium sulfate and evaporated to dryness. The product was dried overnight under vacuum at room temperature. tert-Butyl 4-(4-(4,4,5,5-tetramethyl-1,3,2-dioxaborolan-2-yl)pyridin-2-yl)piperazine-1-carboxylate (0.606 g, 1.557 mmol, 90% yield) was isolated as a white solid. MS (ESI) m/z 290 [M-Boc+1]$^+$.

Intermediate 3: 4-(5-Bromopyrimidin-2-yl)morpholine

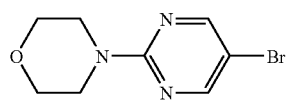

A. 4-(5-Bromopyrimidin-2-yl)morpholine. A solution of 5-bromo-2-chloropyrimidine (0.5 g, 2.58 mmol) in acetonitrile (10.5 mL) was treated with morpholine (0.225 g, 2.58 mmol) and diisopropylethyl amine (0.677 mL, 3.88 mmol) and was stirred at room temperature overnight. The solvent was removed under reduced pressure (white sticky solid). The residue could not be partitioned between water and ethyl acetate but a white solid formed upon suspending the mixture in a saturated aqueous solution of ammonium chloride that was collected by filtration and washed with water. 4-(5-Bromopyrimidin-2-yl)morpholine (0.550 g, 2.253 mmol, 87% yield) was isolated as a white solid. MS (ESI) m/z 244 [M]$^+$ 246 [M+2]$^+$.

Intermediate 4: tert-Butyl 2-(6-(4,4,5,5-tetramethyl-1,3,2-dioxaborolan-2-yl)-1H-Benzo[d]Imidazol-1-yl) ethylcarbamate

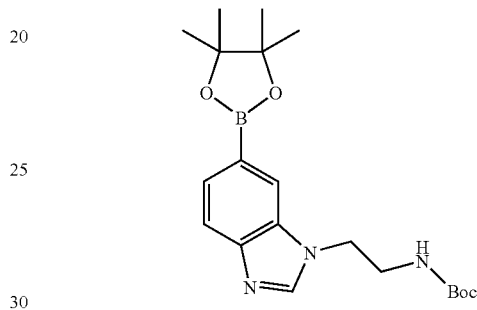

A. tert-Butyl 2-(5-bromo-2-nitrophenylamino)ethylcarbamate. To a stirred solution of 4-bromo-2-fluoro-1-nitrobenzene (3 g, 13.7 mmol), tert-butyl 2-aminoethylcarbamate (2.2 g, 13.7 mmol) and triethylamine (2.78 g, 27.4 mmol) in N,N-dimethylacetamide (25 mL) was stirred at room temperature overnight. The reaction mixture was concentrated under reduced pressure give the crude product, which was purified on silica gel column (eluting with 5-15% ethyl acetate in petroleum ether) to give tert-butyl 2-(5-bromo-2-nitrophenylamino)ethylcarbamate as a yellow solid. (3.1 g, 63% yield). $^1$H NMR (400 MHz, CHLOROFORM-d) δ (ppm) 8.24 (br s, 1H), 8.07 (d, J=9.2 Hz, 1H), 7.10 (s, 1H), 6.82 (d, J=9.2 Hz, 1H), 4.82 (br s, 1H), 3.47 (s, 4H), 1.48 (s, 9H).

B. tert-Butyl 2-(2-amino-5-bromophenylamino)ethylcarbamate. A mixture of tert-butyl 2-(5-bromo-2-nitrophenylamino)ethylcarbamate (2.0 g, 5.57 mmol), zinc dust (3.64 g, 55.70 mmol), and ammonium chloride (3.0 g, 55.7 mmol) in a mixture of tetrahydrofuran and methanol (1:1, 30 mL) was stirred at room temperature for 1 h. The reaction mixture was filtered, and the filtrate was concentrated under reduced pressure. The residue was partitioned between water and ethyl acetate, and the aqueous was extracted with ethyl acetate for three times. The organic layer was washed with brine, dried over sodium sulfate, and concentrated in vacuo to give tert-butyl 2-(2-amino-5-bromophenylamino)ethylcarbamate (1.65 g, 90% yield) as a yellow solid. $^1$H NMR (400 MHz, CHLOROFORM-d) δ (ppm) 6.79 (dd, J$_1$=8.1 Hz, J$_2$=2.1 Hz, 1H), 6.71 (d, J=2.1 Hz, 1H), 6.59 (d, J=8.1 Hz, 1H), 4.87 (br s, 1H), 3.46 (s, 4H), 3.24 (br s, 2H), 1.48 (s, 9H).

C. tert-Butyl 2-(6-bromo-1H-benzo[d]imidazol-1-yl)ethylcarbamate. To a mixture of tert-butyl 2-(2-amino-5-bromophenylamino)ethylcarbamate (1.55 g, 4.7 mmol) in acetic acid (1 mL) was added triethyl orthoformate (65 mL) dropwise at room temperature, and the resulting mixture was refluxed for 0.5 h. Triethyl orthoformate was removed under reduced pressure, and the residue was diluted with water, and extracted with ethyl acetate. The organic layer was washed with brine, dried and evaporated to give tert-butyl 2-(6-bromo-1H-benzo[d]imidazol-1-yl)ethylcarbamate (1.4 g, 87% yield). $^1$H NMR (400 MHz, CHLOROFORM-d) δ (ppm) 7.77 (s, 1H), 7.53 (dd, $J_1$=8.0 Hz, $J_2$=2.0 Hz, 1H), 7.28 (d, J=8.0 Hz, 1H), 7.19 (d, J=2.0 Hz, 1H), 4.84 (br s, 1H), 4.24 (t, J=6.0 Hz, 2H), 3.45 (t, J=6.0 Hz, 2H), 1.38 (s, 9H); MS (ESI): m/z 339.9 [M+1]$^+$.

D. tert-Butyl 2-(6-(4,4,5,5-tetramethyl-1,3,2-dioxaborolan-2-yl)-1H-benzo[d]imidazol-1-yl)ethylcarbamate. After a mixture of tert-butyl 2-(6-bromo-1H-benzo[d]imidazol-1-yl)ethylcarbamate (1.29 g, 3.81 mmol), 4,4,4',4',5,5,5',5'-octamethyl-2,2'-bi(1,3,2-dioxaborolane) (1.45 g, 5.71 mmol) and potassium acetate (0.93 g, 9.51 mmol) in N,N-dimethylformamide (10 mL) was degassed for three times, 1,1'-bis(diphenylphosphino)ferrocene palladium dichloride (0.129 g, 0.17 mmol) was added, and the resulting mixture was heated at 100° C. overnight. The solvent was removed under reduced pressure, and the residue was purified on silica gel column (eluting with 10% ethyl acetate in petroleum ether) to give tert-butyl 2-(6-(4,4,5,5-tetramethyl-1,3,2-dioxaborolan-2-yl)-1H-benzo[d]imidazol-1-yl)ethylcarbamate (0.89 g, 59.3% yield) as a solid. $^1$H NMR (400 MHz, CHLOROFORM-d) δ (ppm) 8.33 (s, 1H), 7.95 (s, 1H), 7.89-7.82 (m, 2H), 4.81 (br s, 1H), 4.47 (t, J=6.0 Hz, 2H), 3.62 (t, J=6.0 Hz, 2H), 1.38 (s, 2H); MS (ESI): m/z 388.1 [M+1]$^+$.

Intermediate 5: 2-Nitro-4-(4,4,5,5-tetramethyl-1,3,2-dioxaborolan-2-yl)aniline

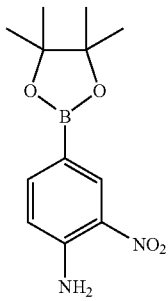

A. 2-Nitro-4-(4,4,5,5-tetramethyl-1,3,2-dioxaborolan-2-yl)aniline. After a mixture of 4-bromo-2-nitro-phenylamine (3.09 g, 13.89 mmol), 4,4,4',4',5,5,5',5'-octamethyl-2,2'-bi(1,3,2-dioxaborolane) (3.9 g, 15.28 mmol) and potassium acetate (2.7 g, 27.8 mmol) in N,N-dimethylformamide (20 mL) was degassed three times, 1,1'-bis(diphenylphosphino)-ferrocene palladium dichloride (0.3 g, 0.40 mmol) was added, and the resulting mixture was heated at 100° C. overnight. The solvent was removed under reduced pressure, and the residue was purified on silica gel column (eluting with 10-15% ethyl acetate in petroleum ether) to give 2-nitro-4-(4,4,5,5-tetramethyl-1,3,2-dioxaborolan-2-yl)aniline (3.0 g, 81% yield). $^1$H NMR (400 MHz, DMSO-$d_6$) δ (ppm) 8.24 (s, 1H), 7.68 (br s, 2H), 7.54 (d, J=8.4 Hz, 1H), 6.96 (d, J=8.4 Hz, 1H), 1.25 (s, 12H); MS (ESI): m/z 265.0 [M+1]$^+$.

Intermediate 6: 1-(Tetrahydro-2H-pyran-2-yl)-1H-indazol-6-amine

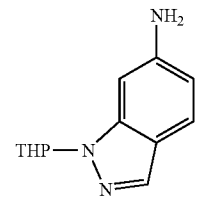

A. 6-Nitro-1H-indazole. To a stirred solution of 2-methyl-5-nitro-phenylamine (50 g, 0.33 mol) in acetic acid (500 mL) was added dropwise a solution of sodium nitrite (34 g, 0.49 mol) in water (100 mL) at 0° C., and the reaction mixture was stirred at room temperature for 1 hour. When the starting material was consumed, the reaction mixture was poured into water. The precipitate was collected by filtration, and purified on silica gel column (eluting with dichloromethane) to give 6-nitro-1H-indazole (40 g, 75% yield) as a solid. $^1$H NMR (400 MHz, METHANOL-$d_4$) δ (ppm) 8.50 (s, 1H), 8.23 (s, 1H), 8.02-7.95 (m, 2H); MS (ESI): m/z 164.1 [M+1]$^+$.

B. 6-Nitro-1-(tetrahydro-pyran-2-yl)-1H-indazole. A stirred mixture of 6-nitro-1H-indazole (5.0 g, 30 mmol), 3,4-dihydro-2H-pyran (5.2 g, 60 mmol) and 4-methylbenzenesulfonic acid (516 mg, 3 mmol) in tetrahydrofuran (25 mL) was refluxed overnight. After removal of the solvent, the residue was purified by column chromatography on silica gel (eluting with 10% ethyl acetate in petroleum ether) to give 6-nitro-1-(tetrahydro-2H-pyran-2-yl)-1H-indazole (4 g, 52% yield) as a yellow solid. MS (ESI): m/z 248.1 [M+1]$^+$.

C. 1-(Tetrahydro-2H-pyran-2-yl)-1H-indazol-6-amine. To a solution of 6-nitro-1-(tetrahydro-2H-pyran-2-yl)-1H-indazole (1.0 g, 4.0 mmol) in a mixture of tetrahydrofuran and methanol (v/v, 1:1, 20 mL) was added zinc dust (2.6 g, 40 mmol) and ammonium chloride (2.2 g, 40 mmol) under nitrogen atmosphere. The mixture was stirred at room temperature overnight, and TLC (50% ethyl acetate in petroleum ether) showed starting material was consumed. The reaction mixture was filtered, and the filtrate was concentrated. The residue was diluted with water and the aqueous layer was extracted with ethyl acetate. The organic layer was washed with brine, dried over anhydrous sodium sulfate, and concentrated under reduced pressure to give 1-(tetrahydro-2H-pyran-2-yl)-1H-indazol-6-amine (750 mg, 85% yield). MS (ESI): m/z 218.1 [M+1]$^+$.

Intermediate 7: tert-Butyl 5-bromoisoindoline-2-carboxylate

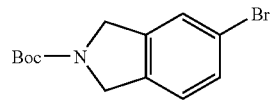

A. 5-Bromoisoindoline. To a stirred solution of 5-bromoisoindoline-1,3-dione (10 g, 0.044 mol) in anhydrous tetrahydrofuran (500 mL) at 0° C. was added sodium borohydride (17.5 g, 0.46 mol) in portions. The reaction mixture was cooled to −10° C., and boron trifluoride diethyl ether complex (63 mL, 0.5 mol) was added dropwise. After the addition, the reaction mixture was refluxed for 4 hours. After being cooled to room temperature, the reaction mixture was poured slowly into cold water (100 mL) at 0-5° C. The mixture was diluted with ethyl acetate (480 mL), and basified with the addition of a 6 N aqueous sodium hydroxide solution at 0-5° C. to pH=10. The organic layer was washed with brine (4×100 mL), dried over sodium sulfate, and concentrated under reduced pressure. The resulting oil was diluted with diethyl ether (100 mL), and acidified (pH ~2) with 6 N hydrochloric acid aqueous solution at 0° C. The aqueous layer was basified with 6 N aqueous solution of sodium hydroxide, and extracted with ethyl acetate (400 mL). The organic layer was washed with brine (3×150 mL), dried over sodium sulfate, and concentrated under reduced pressure to afford crude 5-bromoisoindoline (4 g, 46% yield) as a brown oil. MS (ESI): m/z 199.7 [M+1]+.

B. tert-Butyl 5-bromoisoindoline-2-carboxylate. To a mixture of 5-bromoisoindoline (4.0 g, 20 mmol) and triethylamine (10.1 g, 100 mmol) in dichloromethane (20 mL) was added a solution of di-tert-butyl dicarbonate (6.54 g, 30 mmol) in dichloromethane (30 mL) at 0° C., and the reaction mixture was stirred at room temperature for 3 h. The reaction mixture was concentrated, and the residue was purified by chromatography on silica gel (eluting with 10% ethyl acetate in petroleum) to give tert-butyl 5-bromoisoindoline-2-carboxylate (3.9 g, 65% yield). MS (ESI): m/z 297.7 [M+1]+.

Intermediate 8: 6-(4,4,5,5-Tetramethyl-1,3,2-dioxaborolan-2-yl)isoindolin-1-one

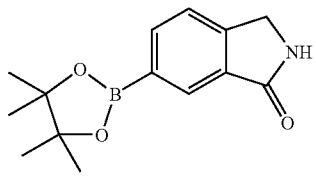

A. 6-(4,4,5,5-Tetramethyl-1,3,2-dioxaborolan-2-yl)isoindolin-1-one. A degassed mixture of 6-bromoisoindolin-1-one (2.8 g, 13.6 mmol), 4,4,4',4',5,5,5',5'-octamethyl-2,2'-bi(1,3,2-dioxaborolane) (6.9 g, 27 mmol), potassium acetate (3.33 g, 34 mmol) and 1,1'-bis(diphenylphosphino)ferrocene palladium dichloride (1 g, 1.3 mmol) in dioxane (50 mL) was heated at 90° C. under nitrogen overnight. After being cooled to room temperature, the reaction mixture was filtered, and the filtrate was concentrated under reduced pressure to give the crude product, which was purified on silica gel column (eluting with 10% ethyl acetate in petroleum ether) to give 6-(4,4,5,5-tetramethyl-1,3,2-dioxaborolan-2-yl)isoindolin-1-one (2.2 g, 62% yield) as a white solid. MS (ESI): m/z 259.9 [M+1]+.

Intermediate 9: 5-(4,4,5,5-Tetramethyl-1,3,2-dioxaborolan-2-yl)isoindolin-1-one

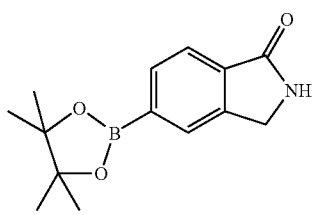

A. Methyl 4-bromo-2-(bromomethyl)benzoate. A mixture of methyl 4-bromo-2-methylbenzoate (22.8 g, 0.1 mol), 2,2'-azobis(2-methylpropionitrile) (1.64 g, 0.01 mol), and N-bromosuccinimide (17.7 g, 0.1 mol) was refluxed overnight. The solvent was removed, and the residue was partitioned between water and dichloromethane. The organic layer was separated, and the aqueous layer was extracted with dichloromethane. The combined organic layer was dried and evaporated to afford the crude methyl 4-bromo-2-(bromomethyl)benzoate (30 g), which was used in the next step without further purification. 1H NMR (400 MHz, CHLOROFORM-d) δ (ppm) 7.83 (m, 1H), 7.63 (s, 1H), 7.51 (m, 1H), 4.90 (s, 2H), 3.94 (s, 3H).

B. 5-Bromoisoindolin-1-one. To a solution of methyl 4-bromo-2-(bromomethyl)benzoate (15 g, 0.05 mol) in methanol (20 mL) was added ammonium hydroxide (200 mL), and the mixture was stirred at room temperature for 18 hours. The solvent was removed, and the residue was washed with ethyl acetate and methanol (v/v, 10:1, 110 mL) to give 5-bromoisoindolin-1-one (4.5 g, 42% yield). 1H NMR (400 MHz, CHLOROFORM-d) δ (ppm) 8.65 (br s, 1H), 7.84 (s, 1H), 7.65 (m, 1H), 7.59 (m, 1H), 4.37 (s, 2H).

C. 5-(4,4,5,5-Tetramethyl-1,3,2-dioxaborolan-2-yl)isoindolin-1-one. A degassed mixture of 5-bromoisoindolin-1-one (1.05 g, 5.0 mmol), 4,4,4',4',5,5,5',5'-octamethyl-2,2'-bi(1,3,2-dioxaborolane) (2.54 g, 10 mmol), potassium acetate (1.20 g, 12.5 mmol) and 1,1'-bis(diphenylphosphino)ferrocenepalladium dichloride (0.38 g, 0.5 mmol) in dioxane (50 mL) was heated to 80° C. under nitrogen overnight. After being down cooled to room temperature, the reaction mixture was filtered, and the filtrate was concentrated under reduced pressure to give the crude product, which was purified by silica gel column (eluting with 10% ethyl acetate in petroleum ether) to give 5-(4,4,5,5-tetramethyl-1,3,2-dioxaborolan-2-yl)isoindolin-1-one (400 mg, 31% yield) as a white solid. MS (ESI): m/z 259.9 [M+1]+.

Intermediate 10: 1-Oxoisoindolin-4-ylboronic acid

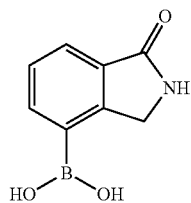

A. 1-Oxoisoindolin-4-ylboronic acid. To a solution of 4-bromoisoindolin-1-one (3.0 g, 14.2 mmol) in anhydrous tetrahydrofuran (50 mL) was added dropwise n-butyllithium (2.5 M in hexane, 12 mL, 30 mmol) at −78° C. under nitrogen. After being stirred for 1 h at this temperature, a solution of trimethyl borate (4.41 g, 40.0 mmol) in anhydrous tetrahydrofuran (20 mL) was added dropwise. The reaction mixture was stirred at −78° C. for 2 h, and at room temperature overnight. The reaction was quenched by the addition of 1 N aqueous hydrochloric acid, and the precipitate was collected and washed with water to give 1-oxoisoindolin-4-ylboronic acid (400 mg, 16% yield) as a solid. MS (ESI): m/z 178.1 [M+1]+.

Intermediate 11: tert-Butyl 2-(1-oxo-6-(4,4,5,5-tetramethyl-1,3,2-dioxaborolan-2-yl)isoindolin-2-yl)ethylcarbamate

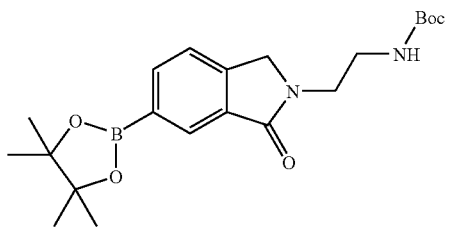

A. tert-Butyl 2-(6-bromo-1-oxoisoindolin-2-yl)ethylcarbamate. A solution of methyl 5-bromo-2-(bromomethyl)benzoate (3 g, 0.01 mol) and tert-butyl 2-aminoethylcarbamate (3.15 g, 0.02 mmol) in methanol (50 mL) was refluxed under nitrogen overnight. After being cooled down to room temperature, the reaction mixture was filtered, and the filtrate was concentrated in vacuo to give the crude product, which was purified on silica gel column (eluting with 50% ethyl acetate in petroleum ether) to give tert-butyl 2-(6-bromo-1-oxoisoindolin-2-yl)ethylcarbamate (2.5 g, 71% yield) as a solid. 1H-NMR (400 MHz, METHANOL-d4) δ (ppm) 7.85 (s, 1H), 7.72 (d, J=8.0 Hz, 1H), 7.49 (d, J=7.6 Hz, 1H), 4.52 (s, 2H), 3.68 (t, J=5.6 Hz, 2H), 3.34 (t, J=5.6 Hz, 2H), 1.30 (s, 9H).

B. tert-Butyl 2-(1-oxo-6-(4,4,5,5-tetramethyl-1,3,2-dioxaborolan-2-yl)isoindolin-2-yl)ethylcarbamate. A degassed solution of tert-butyl 2-(6-bromo-1-oxoisoindolin-2-yl)ethylcarbamate (750 mg, 2.11 mmol), 4,4,4',4',5,5,5',5'-octamethyl-2,2'-bi(1,3,2-dioxaborolane) (1.07 g, 4.22 mmol), potassium acetate (409 mg, 4.22 mmol) and 1,1'-bis(diphenylphosphino)ferrocene palladium dichloride (153 mg, 0.2 mmol) in dioxane (20 mL) was heated to 90° C. under nitrogen overnight. After being cooled down to room temperature, the reaction mixture was filtered, and the filtrate was concentrated in vacuo to give the crude product, which was purified on silica gel chromatography (eluting with 50% ethyl acetate in petroleum ether) to give tert-butyl 2-(1-oxo-6-(4,4,5,5-tetramethyl-1,3,2-dioxaborolan-2-yl)isoindolin-2-yl)ethylcarbamate (600 mg, 71% yield) as a solid. 1H-NMR (400 MHz, METHANOL-d4) δ (ppm) 8.12 (s, 1H), 7.95 (d, J=7.6 Hz, 1H), 7.56 (d, J=7.2 Hz, 1H), 4.58 (s, 2H), 3.70 (t, J=5.6 Hz, 2H), 3.35 (t, J=5.6 Hz, 2H), 1.36 (s, 9H), 1.30 (s, 6H), 1.24 (s, 6H).

Intermediate 12: tert-Butyl 2-(1-oxo-5-(4,4,5,5-tetramethyl-1,3,2-dioxaborolan-2-yl)isoindolin-2-yl)ethylcarbamate

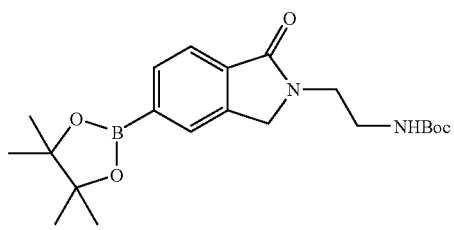

A. tert-Butyl 2-(5-bromo-1-oxoisoindolin-2-yl)ethylcarbamate. To a solution of methyl 4-bromo-2-(bromomethyl)benzoate (5 g, 16.3 mmol) in methanol (50 mL) was added tert-butyl 2-aminoethylcarbamate (5.12 g, 32 mmol), and the mixture was stirred at 65° C. overnight. The solvent was removed, and the residue was purified on silica gel column to give tert-butyl 2-(5-bromo-1-oxoisoindolin-2-yl)ethylcarbamate (3.58 g, 63% yield). 1H NMR (400 MHz, DMSO-d6) δ (ppm) 7.85 (s, 1H), 7.63 (d, J=8.0 Hz, 1H), 7.56 (d, J=8.0 Hz, 1H), 6.92 (br s, 1H), 4.46 (s, 2H), 3.50 (t, J=6.0 Hz, 2H), 3.14 (t, J=6.0 Hz, 2H), 1.26 (s, 9H).

B. tert-Butyl 2-(1-oxo-5-(4,4,5,5-tetramethyl-1,3,2-dioxaborolan-2-yl)isoindolin-2-yl)ethylcarbamate. A degassed mixture of tert-butyl 2-(5-bromo-1-oxoisoindolin-2-yl)ethylcarbamate (0.89 g, 2.5 mmol), 4,4,4',4',5,5,5',5'-octamethyl-2,2'-bi(1,3,2-dioxaborolane) (1.27 g, 5.0 mmol), 1,1'-bis(diphenylphosphino)ferrocene palladium dichloride (0.19 g, 0.25 mmol) and potassium acetate (0.61 g, 6.25 mmol) in dioxane (25 mL) was heated at 80° C. under nitrogen overnight. After being cooled down to room temperature, the reaction mixture was filtered, and the filtrate was concentrated under reduced pressure to give the crude product, which was purified on silica gel chromatography (eluting with 10% ethyl acetate in petroleum ether) to give tert-butyl 2-(1-oxo-5-(4,4,5,5-tetramethyl-1,3,2-dioxaborolan-2-yl)

isoindolin-2-yl)ethylcarbamate (600 mg, 60% yield) as a white solid. MS (ESI): m/z 303.0 [M-99]⁺.

Intermediate 13: tert-Butyl 2-(5-(4,4,5,5-tetramethyl-1,3,2-dioxaborolan-2-yl)-1H-benzo[d]imidazol-1-yl)ethylcarbamate

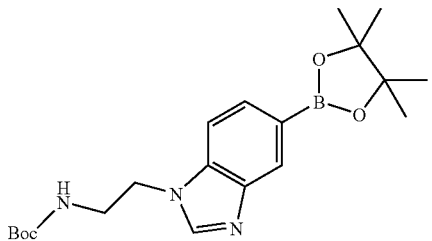

A. tert-Butyl 2-(4-bromo-2-nitrophenylamino)ethylcarbamate. A solution of 4-bromo-1-fluoro-2-nitro-benzene (3.2 g, 13.7 mmol), tert-butyl 2-aminoethylcarbamate (4.8 g, 30.0 mmol) in N,N-dimethylformamide (100 mL) was stirred at 120° C. overnight. The reaction mixture was concentrated under reduced pressure to give the crude product which was purified on silica gel column (eluting with 10% ethyl acetate in petroleum ether) to give crude tert-butyl 2-(4-bromo-2-nitrophenylamino)ethylcarbamate (5.4 g, 100% yield) as a yellow solid. MS (ESI): m/z 305.8 [M+1]⁺.

B. tert-Butyl 2-(2-amino-4-bromophenylamino)ethylcarbamate. A solution of tert-butyl 2-(4-bromo-2-nitrophenylamino)ethylcarbamate (5.4 g, 15 mmol), zinc dust (9.80 g, 150 mmol), and ammonium chloride (8.10 g, 150 mmol) in a mixture of tetrahydrofuran and methanol (v/v, 1:1, 100 mL) was stirred at room temperature for 12 hours. After filtration, the filtrate was concentrated under reduced pressure, and the residue was dissolved in ethyl acetate. The organic solution was washed with water for three times, dried over sodium sulfate, and concentrated in vacuo to give tert-butyl 2-(2-amino-4-bromophenylamino)ethylcarbamate (4.8 g, 97% yield) as a yellow solid. MS (ESI): m/z 329.9 [M+1]⁺.

C. tert-Butyl 2-(5-bromo-1H-benzo[d]imidazol-1-yl)ethylcarbamate. A mixture of tert-butyl 2-(2-amino-4-bromophenylamino)ethylcarbamate (1.55 g, 4.7 mmol) in triethyl orthoformate (100 mL) was heated at 100° C. for 1.5 hours. Triethyl orthoformate was removed under reduced pressure, and the residue was purified on silica gel column (eluting with 5% ethyl acetate in petroleum ether) to give tert-butyl 2-(5-bromo-1H-benzo[d]imidazol-1-yl)ethylcarbamate (3.0 g, 61% yield). MS (ESI): m/z 341.7 [M+1]⁺.

D. tert-Butyl 2-(5-(4,4,5,5-tetramethyl-1,3,2-dioxaborolan-2-yl)-1H-benzo[d]imidazol-1-yl)ethylcarbamate. A degassed mixture of tert-butyl 2-(5-bromo-1H-benzo[d]imidazol-1-yl)ethylcarbamate (1.02 g, 3.00 mmol), 4,4,4',4',5,5,5',5'-octamethyl-2,2'-bi(1,3,2-dioxaborolane) (2.29 g, 9.00 mmol), 1,1'-bis(diphenylphosphino)ferrocene palladium dichloride (0.23 g, 0.30 mmol) and potassium acetate (0.74 g, 7.50 mmol) in 1,4-dioxane (30 mL) was heated at 100° C. overnight under nitrogen. The solvent was removed under reduced pressure, and the residue was purified on silica gel column (eluting with ethyl acetate) to give tert-butyl 2-(5-(4,4,5,5-tetramethyl-1,3,2-dioxaborolan-2-yl)-1H-benzo[d]imidazol-1-yl)ethylcarbamate (0.90 g, 77% yield) as a solid. MS (ESI): m/z 388.2 [M+1]⁺.

Intermediate 14: N-Methyl-6-(4,4,5,5-tetramethyl-1,3,2-dioxaborolan-2-yl)-1H-benzo[d]imidazol-2-amine

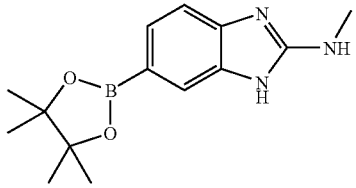

A. 5-Bromo-1H-benzo[d]imidazol-2(3H)-one. A solution of 4-bromobenzene-1,2-diamine (5 g, 27.0 mmol), triethylamine (8.1 g, 81.0 mmol) and triphosgene (3.96 g, 14.0 mmol) in dioxane (20 mL) was stirred at 120° C. overnight. The precipitate was collected and washed with water to give the 5-bromo-1H-benzo[d]imidazol-2(3H)-one (3 g, 52% yield) as a solid. ¹H NMR (400 MHz, DMSO-d₆) δ (ppm) 10.75 (br s, 2H), 7.04 (d, J=8.4 Hz, 1H), 7.02 (s, 1H), 6.84 (d, J=8.0 Hz, 1H); MS (ESI): m/z 212.8 [M+1]⁺.

B. 6-Bromo-2-chloro-1H-benzo[d]imidazole. A mixture of 5-bromo-1H-benzo[d]imidazol-2(3H)-one (2 g, 9.4 mmol) in phosphoryl trichloride (20 mL) was refluxed overnight. The reaction mixture was concentrated in vacuo. Ice water was added to the residue, and the aqueous layer was extracted with ethyl acetate, and the combined organic layer was dried over sodium sulfate. The solution was removed in vacuo to give 6-bromo-2-chloro-1H-benzo[d]imidazole (1.5 g, 69% yield) as a solid. MS (ESI): m/z 232.7 [M+1]⁺.

C. 6-Bromo-N-methyl-1H-benzo[d]imidazol-2-amine. A solution of 6-bromo-2-chloro-1H-benzo[d]imidazole (1 g, 4.35 mmol), triethylamine (1.4 g, 13.8 mmol) and methyl amine hydrochloride (430 g, 6.42 mmol) in 1-methyl-2-pyrrolidinone (10 mL) was stirred at 120° C. overnight. After being cooled down to room temperature, the reaction mixture was extracted with ethyl acetate. The combined organic layer was dried over sodium sulfate, and concentrated to give the crude product, which was purified on silica gel column (eluting with 50% ethyl acetate in petroleum ether) to give 6-bromo-N-methyl-1H-benzo[d]imidazol-2-amine (400 mg, 43% yield). MS (ESI): m/z 227.8 [M+1]⁺.

D. N-Methyl-6-(4,4,5,5-tetramethyl-1,3,2-dioxaborolan-2-yl)-1H-benzo[d]imidazol-2-amine. A mixture of 6-bromo-N-methyl-1H-benzo[d]imidazol-2-amine (500 mg, 2.2 mmol), 4,4,4',4',5,5,5',5'-octamethyl-2,2'-bi(1,3,2-dioxaborolane) (1.13 g, 4.4 mmol) and potassium acetate (540 g, 5.5 mmol) in dioxane (5 mL) was degassed for three times, and followed by the addition of 1,1'-bis(diphenylphosphino)ferrocene palladium dichloride (170 g, 0.22 mmol). The resulting mixutre was heated at 100° C. under nitrogen overnight, and the solvent was removed under reduced pressure. The residue was purified on silica gel column (eluting with 50% ethyl acetate in petroleum ether) to give N-methyl-6-(4, 4,5,5-tetramethyl-1,3,2-dioxaborolan-2-yl)-1H-benzo[d]imidazol-2-amine (500 mg, 83% yield) as a solid. MS (ESI): m/z 273.9 [M+1]+.

Intermediate 15: 1-Chloroisoquinolin-7-ylboronic acid

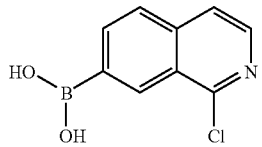

A. 1-Chloroisoquinolin-7-ylboronic acid. A solution of 7-bromo-1-chloroisoquinoline (1 g, 4.1 mmol) in tetrahydrofuran (5 mL) was cooled to −78° C. under nitrogen, and triisopropylborate (2.4 g, 11.5 mmol) was added, followed by dropwise addition of n-butyllithium (5 mL, 1.5 M). The reaction mixture was warmed to −20° C. over 30 min., quenched with 1 M aqueous hydrochloric acid, and neutralized with triethylamine to pH=7. The residue was partitioned between water and ethyl acetate, the aqueous layer was extracted with ethyl acetate. The organic layer was washed with brine, dried with anhydrous magnesium sulfate, and concentrated to give the crude product, which was purified on silica gel column (eluting with ethyl acetate) to give 1-chloroisoquinolin-7-ylboronic acid (0.5 g, 58.8% yield) as a solid. $^1$H NMR (400 MHz, DMSO-$d_6$) δ (ppm) 8.74 (s, 1H), 8.58 (br s, 2H), 8.28 (d, J=5.2 Hz, 1H), 8.19 (d, J=8.4 Hz, 1H), 7.98 (d, J=8.4 Hz, 1H), 7.85 (d, J=5.6 Hz, 1H); MS (ESI): m/z 208.1 [M+1]+.

Intermediate 16: tert-Butyl 6-bromobenzo[d]isoxazol-3-ylcarbamate

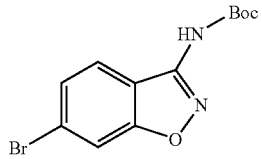

A. 4-Bromo-2-(propan-2-ylideneaminooxy)benzonitrile. A mixture of propan-2-one oxime (730 mg, 10 mmol) and potassium tert-butoxide (24 mg, 0.58 mmol) in tetrahydrofurane (10 mL) was stirred at 0° C. for 1 h, and 4-bromo-2-fluorobenzonitrile (1.0 g, 5.02 mmol) was added at 0° C. The mixture was heated at 55° C. for 2 h. After being cooled down to room temperature, the reaction mixture was diluted with water, and the mixture was extracted with ethyl acetate. The organic layer was washed with brine, dried over anhydrous sodium sulfate, and concentrated under reduced pressure to give 4-bromo-2-(propan-2-ylideneaminooxy)benzonitrile (1.2 g, 94% yield) as a solid. $^1$H NMR (400 MHz, CHLOROFORM-d) δ (ppm) 7.75 (s, 1H), 7.53 (d, J=8.0 Hz, 1H), 7.27 (d, J=8.0 Hz, 1H), 2.14 (s, 3H), 2.07 (s, 3H); MS (ESI): m/z 254.8 [M+1]+.

B. 6-Bromobenzo[d]isoxazol-3-amine. A solution of 4-bromo-2-(propan-2-ylideneaminooxy)benzonitrile (1.2 g, 4.76 mmol) in a mixture of hydrochloric acid (5 M, 1 mL) and 2,2,2-trifluoroacetic acid (4 mL) was stirred at room temperature overnight. The solvent was evaporated under reduced pressure to give 6-bromobenzo[d]isoxazol-3-amine (900 mg, 90% yield) as a hydrochloride salt. $^1$H NMR (400 MHz, DMSO-$d_6$) δ (ppm) 7.76 (m, 2H), 7.41 (m, 1H), 6.50 (br s, 2H).

C. tert-Butyl 6-bromobenzo[d]isoxazol-3-ylcarbamate. A mixture of 6-bromobenzo[d]isoxazol-3-amine (900 mg, 4.25 mmol), di-tert-butyl dicarbonate (1.2 g, 5.1 mmol), triethylamine (686 mg, 6.8 mmol) and N,N-dimethylpyridin-4-amine (72 mg, 0.6 mmol) in dichloromethane (10 mL) was stirred at room temperature overnight. Water was added, and the organic layer was separated, the aqueous phase was extracted with dichloromethane. The combined organic layer was washed with brine, dried over sodium sulfate and evaporated under reduced pressure. The crude product was purified on silica gel column to give tert-butyl 6-bromobenzo[d]isoxazol-3-ylcarbamate (900 mg, 68% yield) as a solid. MS (ESI): m/z 313.9 [M+1]+.

Intermediate 17: 6-Bromo-1-methyl-1H-benzo[d]imidazole

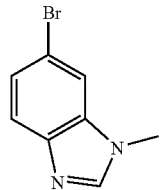

A. 5-Bromo-N-methyl-2-nitroaniline. To a solution of 4-bromo-2-fluoro-1-nitrobenzene (10 g, 0.043 mol) in ethanol (100 mL) was added methyl amine alcoholic solution (3 g, 0.1 mol) slowly at 0° C., and the mixture was stirred at room temperature for 3 h. The mixture was concentrated to give 5-bromo-N-methyl-2-nitroaniline as a white solid (9 g, 85.7%). $^1$H NMR (400 MHz, DMSO-$d_6$) δ (ppm) 8.23 (s, 1H), 7.98 (d, J=8.8 Hz, 1H), 7.14 (s, 1H), 6.80 (dd, $J_1$=9.2 Hz, $J_2$=2.0 Hz, 1H), 2.92 (d, J=4.8 Hz, 3H); MS (ESI): m/z 231.1 [M+1]+.

B. 5-Bromo-N-methylbenzene-1,2-diamine. 5-Bromo-N-methyl-2-nitroaniline (9 g, 0.039 mol), ammonium chloride (53 g, 0.39 mol) and zinc powder (21 g, 0.39 mol) were mixed in methanol and tetrahydrofuran (v/v, 1:1, 80 mL) and the mixture was stirred at room temperature for 4 h. The solution was filtered and the filtrate was concentrated to give the crude product, which was partitioned between ethyl acetate and water, the aqueous layer was extracted with ethyl acetate. The combined organic layer was washed with saturated sodium chloride aqueous solution, dried over sodium sulfate, and concentrated to give 5-bromo-N-methylbenzene-1,2-diamine as a solid (7.5 g, 60% yield). $^1$H NMR (400 MHz, DMSO-$d_6$) δ (ppm) 6.50 (d, J=8.0 Hz, 1H), 6.42 (d, J=8.4 Hz, 1H), 6.38 (s, 1H), 4.87 (d, J=4.8 Hz, 1H), 4.59 (br s, 2H), 2.66 (d, J=5.2 Hz, 3H); MS (ESI): m/z 201.1 [M+1]+.

C. 6-Bromo-1-methyl-1H-benzo[d]imidazole. A solution of 5-bromo-N-methylbenzene-1,2-diamine (7.5 g, 0.037 mmol) in formic acid (25 mL) was refluxed overnight. The solvent was removed under reduced pressure to give the crude product, which was purified on silica gel column (eluting with 20-30% ethyl acetate in petroleum ether) to give 6-bromo-1-methyl-1H-benzo[d]imidazole as a solid (6.5 g, 86% yield). $^1$H NMR (400 MHz, DMSO-$d_6$) δ (ppm) 8.21 (s, 1H), 8.85 (s, 1H), 7.55 (d, J=8.0 Hz, 1H), 7.32 (d, J=8.4 Hz, 3H), 3.81 (s, 3H); MS (ESI): m/z 211.1 [M+1]⁺.

Intermediate 18: 6-Bromo-2-methyl-1-((2-(trimethylsilyl)ethoxy)methyl)-1H-benzo[d]imidazole

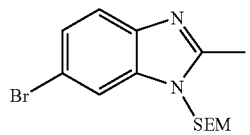

A. 6-Bromo-2-methyl-1H-benzo[d]imidazole. A solution of 4-bromobenzene-1,2-diamine (3 g, 0.02 mmol) in acetic acid (20 mL) was stirred at 120° C. overnight. When TLC (3% dichloromethane in methanol) showed the starting material was consumed, the mixture was adjusted to pH=7 with aqueous sodium carbonate solution, and the aqueous layer was extracted with ethyl acetate. The combined organic layer was dried over sodium sulfate, and concentrated to give 6-bromo-2-methyl-1H-benzo[d]imidazole (2.8 g, 83% yield) as a solid. ¹H NMR (400 MHz, DMSO-d₆) δ (ppm) 12.34 (br s, 1H), 7.60 (s, 1H), 7.37 (d, J=8.8 Hz, 1H), 7.20 (dd, J₁=8.4 Hz, J₂=2.0 Hz, 1H), 2.44 (s, 3H).

B. 6-Bromo-2-methyl-1-((2-(trimethylsilyl)ethoxy)methyl)-1H-benzo[d]imidazole. A mixture of 6-bromo-2-methyl-1H-benzo[d]imidazole (1 g, 4.76 mmol) and sodium hydride (60% in mineral oil, 226 mg, 5.17 mmol) in N,N-dimethylformamide (10 mL) was stirred at 0° C. for 1 h. A solution of (2-(chloromethoxy)ethyl)trimethylsilane (948 mg, 5.17 mmol) in N,N-dimethylformamide (2 mL) was added dropwise at this temperature, and the resulting mixture was stirred at room temperature overnight. Water was added, and the mixture was extracted with ethyl acetate. The organic layer was dried, concentrated under vacuum, and purified by silica gel chromatography (eluting with 50% ethyl acetate in petroleum ether) to give 6-bromo-2-methyl-1-((2-(trimethylsilyl)ethoxy)methyl)-1H-benzo[d]imidazole (1.2 g, 75% yield) as a solid. MS (ESI): m/z 341.9 [M+1]⁺.

Intermediate 19: tert-Butyl 5-bromobenzo[d]isoxazol-3-ylcarbamate

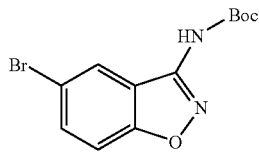

A. 5-Bromo-2-(propan-2-ylideneaminooxy)benzonitrile. A mixture of propan-2-one oxime (730 mg, 10 mmol) and potassium tert-butoxide (1.12 g, 10 mmol) in tetrahydrofurane (10 mL) was stirred at 0° C. for 1 h, and 5-bromo-2-fluorobenzonitrile (1.0 g, 5.02 mmol) was added at 0° C. The resulting mixture was heated at 55° C. for 2 h. After cooling down to room temperature, the reaction mixture was diluted with water, and the mixture was extracted with ethyl acetate. The organic layer was washed with brine, dried over anhydrous sodium sulfate, and concentrated under reduced pressure to give 5-bromo-2-(propan-2-ylideneaminooxy)benzonitrile (800 mg, 64% yield) as a solid. ¹H NMR (400 MHz, CHLOROFORM-d) δ (ppm) 7.64 (m, 2H), δ (ppm) 7.47 (d, J=9.2 Hz, 1H), δ (ppm) 2.17 (s, 3H), δ (ppm) 2.07 (s, 3H); MS (ESI): m/z 254.7 [M+1]⁺.

B. 5-Bromobenzo[d]isoxazol-3-amine. A solution of 5-bromo-2-(propan-2-ylideneaminooxy)benzonitrile (504 mg, 2.0 mmol) in a mixture of hydrochloric acid (5 M, 1 mL) and 2,2,2-trifluoroacetic acid (4 mL) was stirred at room temperature overnight. The solvent was evaporated under reduced pressure to give 5-bromobenzo[d]isoxazol-3-amine (324 mg, 76% yield). ¹H NMR (400 MHz, CHLOROFORM-d) δ (ppm) 7.70 (d, J=1.6 Hz, 1H), δ (ppm) 7.62 (dd, J₁=2.0 Hz, J₂=8.8 Hz, 1H), δ (ppm) 7.35 (d, J=9.2 Hz, 1H), 4.43 (br s, 2H).

C. tert-Butyl 5-bromobenzo[d]isoxazol-3-ylcarbamate. A mixture of 5-bromobenzo[d]isoxazol-3-amine (424 mg, 2.0 mmol), di-tert-butyl dicarbonate (654 mg, 3.0 mmol), triethylamine (808 mg, 8.0 mmol) and N,N-dimethylpyridin-4-amine (24 mg, 0.2 mmol) in dichloromethane (10 mL) was stirred at room temperature overnight. Water was added, the organic layer was separated, and the aqueous phase was extracted with dichloromethane. The combined organic layer was washed with brine, dried over sodium sulfate, and evaporated under reduced pressure. The crude product was purified on silica gel column (eluting with 10% ethyl acetate in petroleum ether) to give tert-butyl 5-bromobenzo[d]isoxazol-3-ylcarbamate (476 mg, 76% yield) as a solid. MS (ESI): m/z 313.9 [M+1]⁺.

Intermediate 20: 2-Fluoro-5-(4,4,5,5-tetramethyl-1,3,2-dioxaborolan-2-yl)benzonitrile

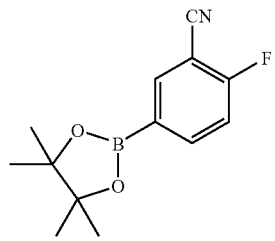

A. 2-Fluoro-5-(4,4,5,5-tetramethyl-1,3,2-dioxaborolan-2-yl)benzonitrile. A mixture of 5-bromo-2-fluorobenzonitrile (3 g, 0.015 mol), 4,4,4',4',5,5,5',5'-octamethyl-2,2'-bi(1,3,2-dioxaborolane) (7.6 g, 0.03 mol) and potassium acetate (3.6 g, 0.038 mmol) in dioxane (10 mL) was degassed for three times, and 1,1'-bis(diphenylphosphino) ferrocene palladium dichloride (1.1 g, 1.5 mmol) was added. The resulting mixture was heated at 100° C. overnight, and the solvent was removed under reduced pressure. The residue was purified on silica gel column (eluting with 25% ethyl acetate in petroleum ether) to give 2-fluoro-5-(4,4,5,5-tetramethyl-1,3,2-dioxaborolan-2-yl)benzonitrile (1 g, 27.0% yield) as a solid. ¹H NMR (400

MHz, METHANOL-d$_4$) δ (ppm) 8.05 (m, 2H), 7.37 (t, J=9.2 Hz, 1H), 1.37 (s, 12H); MS (ESI): m/z 248.1 [M+1]$^+$.

Intermediate 21: 6-Iodo-1-((2-(trimethylsilyl)ethoxy)methyl)-1H-indazole

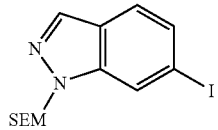

A. 6-Nitro-1H-indazole. To a solution of 2-methyl-5-nitrophenylamine (50 g, 329 mmol) in hydrochloric acid (5 M, 200 mL) was added a solution of sodium nitrite (45 g, 658 mmol) at 0° C., and the reaction mixture was heated at 60° C. overnight. The precipitate was collected by filtration, washed with water, and dried in vacuo to give 6-nitro-1H-indazole (40 g, 75% yield) as a hydrochloride salt.

B. 6-Nitro-1-((2-(trimethylsilyl)ethoxy)methyl)-1H-indazole. To a solution of 6-nitro-1H-indazole (8 g, 49 mmol) in N,N-dimethylformamide (80 mL) was added sodium hydride (60% in mineral oil, 4 g, 100 mmol) in portions at 0° C. After being stirred at this temperature for 1 h, a solution of (2-chloromethoxy-ethyl)-trimethyl-silane (8.3 g, 50 mmol) in N,N-dimethylformamide (30 mL) was added dropwise, and the resulting mixture was stirred at room temperature overnight. The solvent was evaporated under reduced pressure, and the residue was purified by column chromatography on silica gel (eluting with 5-20% ethyl acetate in petroleum ether) to give 6-nitro-1-((2-(trimethylsilyl)ethoxy)methyl)-1H-indazole (5.8 g, 40% yield). MS (ESI): m/z 293.9 [M+1]$^+$.

C. 1-((2-(Trimethylsilyl)ethoxy)methyl)-1H-indazol-6-amine. To a mixture of 6-nitro-1-((2-(trimethylsilyl)ethoxy)methyl)-1H-indazole (5.8 g, 19.8 mmol) and ammonium chloride (53.5 g, 198 mmol) in a mixture of methanol and tetrahydrofuran (100 mL, v/v=1:1) was added zinc dust (13 g, 198 mmol) at 0° C., and the reaction mixture was stirred at room temperature overnight. The reaction mixture was filtered, and the filtrate was concentrated to give the crude product, which was purified on silica gel column (eluting with 5% ethyl acetate in petroleum ether) to give 1-((2-(trimethylsilyl)ethoxy)methyl)-1H-indazol-6-amine (3.5 g, 67% yield) as a solid. MS (ESI): m/z 263.9 [M+1]$^+$.

D. 6-Iodo-1-((2-(trimethylsilyl)ethoxy)methyl)-1H-indazole. To a solution of 1-((2-(trimethylsilyl)ethoxy)methyl)-1H-indazol-6-amine (3.4 g, 13 mmol) in hydrochloric acid (20 mL, 6 M) was added a solution of sodium nitrite (0.9 g, 13 mmol) in water (5 mL) at 0° C. After being stirred for 30 min., a solution of potassium iodide (2.2 g, 13 mmol) in water (10 mL) was added over 30 min, and the reaction mixture was stirred at room temperature overnight. The precipitate was collected by filtration, washed with water, and dried in vacuo to give 6-iodo-1-((2-(trimethylsilyl)ethoxy)methyl)-1H-indazole (1.64 g, 33% yield) as a solid. MS (ESI): m/z 375.1 [M+1]$^+$.

Intermediate 22: 6-Iodo-1-((2-(trimethylsilyl)ethoxy)methyl)-1H-benzo[d][1,2,3]triazole

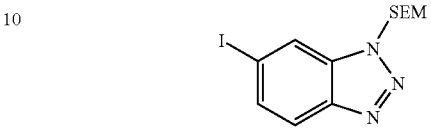

A. 4-Iodobenzene-1,2-diamine. To a mixture of 4-iodo-2-nitroaniline (10 g, 37.8 mmol) and ammonium chloride (20 g, 378 mmol) in a mixture of methanol and tetrahydrofuran (400 mL, v/v=1:1) was added zinc dust (24.6 g, 378 mmol) in portions at 0° C., and the reaction mixture was stirred at room temperature overnight. The mixture was filtered, and the organic layer was concentrated to give the crude product, which was purified on silica gel column (eluting with 1% methanol in dichloromathane) to give 4-iodobenzene-1,2-diamine (7.6 g, 88% yield) as a solid. $^1$H NMR (400 MHz, DMSO-d$_6$) δ (ppm) 6.75 (s, 1H), 6.58 (m, 1H), 6.21 (m, 1H), 4.59 (br s, 4H).

B. 6-Iodo-1H-benzo[d][1,2,3]triazole. To a solution of 4-iodobenzene-1,2-diamine (6 g, 25.6 mmol) in aqueous sulfuric acid (23.7 mL, 40%) was added dropwise a solution of sodium nitrite (2.36 g, 34.3 mmol) in water (10 mL) at 0° C. The mixture was stirred at room temperature for 3 hours. The precipitate was collected by filtration, washed with water and dried under high vacuum to give 6-iodo-1H-benzo[d][1,2,3]triazole (5.6 g, 90% yield) as a sulfate salt. $^1$H NMR (400 MHz, DMSO-d$_6$) δ (ppm) 8.32 (s, 1H), 7.72 (d, J=8 Hz, 1H), 7.65 (d, J=8 Hz, 1H).

C. 6-Iodo-1-((2-(trimethylsilyl)ethoxy)methyl)-1H-benzo[d][1,2,3]triazole. To a mixture of 6-iodo-1H-benzo[d][1,2,3]triazole (5.6 g, 20 mmol) in N,N-dimethylformamide (100 mL) was added sodium hydride (60% in mineral oil, 1.44 g, 36 mmol) in portions at 0° C. After being stirred at 0° C. for 1 h, a solution of (2-chloromethoxy-ethyl)-trimethyl-silane (3.98 g, 24 mmol) in N,N-dimethylformamide (10 mL) was added dropwise, and the reaction mixture was stirred at room temperature overnight. The solvent was evaporated under reduced pressure, and the residue was purified by column chromatography on silica gel (eluting with 5-15% ethyl acetate in petroleum ether) to give 6-iodo-1-((2-(trimethylsilyl)ethoxy)methyl)-1H-benzo[d][1,2,3]triazole (6.6 g, 88% yield). MS (ESI): m/z 376.2 [M+1]$^+$.

Intermediate 23: 6-Iodo-1-methyl-1H-indazole

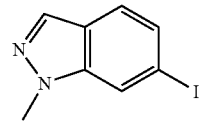

A. 1-Methyl-6-nitro-1H-indazole. To a solution of 6-nitro-1H-indazole (20 g, 0.1 mol) in N,N-dimethylformamide (250 mL) was added sodium hydride (60% in mineral oil, 6.0 g, 0.15 mol) in portions at 0° C. After the addition, the mixture was stirred for 30 min at 0° C., and iodomethane (14.2 g, 0.1 mmol) was added. The resulting mixture was stirred at room temperature overnight. The reaction was quenched by the addition of water (500 mL), and the mixture was extracted with ethyl acetate. The combined organic layer was washed with brine, dried over sodium sulfate and evaporated. The residue was purified on silica gel column (eluting with 5-10% ethyl acetate in petroleum ether) to give 1-methyl-6-nitro-1H-indazole (11 g, 62% yield) as yellow solid. MS (ESI): m/z 178.7 [M+1]$^+$.

B. 1-Methyl-1H-indazol-6-amine. To a mixture of 1-methyl-6-nitro-1H-indazole (1.77 g, 10 mmol) and ammonium chloride (5.3 g, 100 mmol) in a mixture of methanol and tetrahydrofuran (25 mL, v/v=1:1) was added zinc dust (6.5 g, 100 mmol) in portions at 0° C. After the addition, the reaction mixture was stirred at room temperature overnight. The reaction mixture was filtered, and the filtrate was concentrated to give the crude product, which was purified on silica gel column (eluting with 1% methanol in dichloromethane) to give 1-methyl-1H-indazol-6-amine (1.1 g, 74.8% yield) as a solid. $^1$H NMR (400 MHz, DMSO-d$_6$) δ (ppm) 7.65 (s, 1H), 7.31 (d, J=8.0 Hz, 1H), 6.48 (d, J=8.0 Hz, 1H), 6.42 (s, 1H), 5.30 (br s, 2H), 3.78 (s, 3H).

C. 6-Iodo-1-methyl-1H-indazole. To a solution of 1-methyl-1H-indazol-6-amine (1.0 g, 7 mmol) in hydrochloric acid (15 mL, 6 M) was added dropwise a solution sodium nitrite (0.48 g, 7 mmol) in water (2 mL) at 0° C. After being stirred at this temperature for 30 min, a solution of potassium iodide (1.16 g, 7 mmol) in water (10 mL) was added, and the reaction mixture was stirred at room temperature overnight. The precipitate was collected by filtration, washed with water to give 6-iodo-1-methyl-1H-indazole (0.8 g, 44% yield) as a solid. $^1$H NMR (400 MHz, CHLOROFORM-d) δ (ppm) 7.95 (s, 1H), 7.84 (s, 1H), 7.48 (d, J=8.0 Hz, 1H), 7.42 (d, J=8.0 Hz, 1H), 4.06 (s, 3H).

Intermediate 24: tert-Butyl 5-iodoisoindoline-2-carboxylate

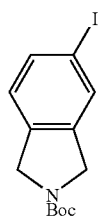

A. 5-Iodoisoindoline-1,3-dione. To a solution of 5-aminoisoindoline-1,3-dione (5 g, 0.03 mol) in 2 N hydrochloric acid (20 mL) was added dropwise a solution of sodium nitrite (2.1 g, 0.03 mol) in water (10 mL) at 0° C., and the mixture was stirred at this temperature for 0.5 h. A solution of sodium iodide (5.1 g, 0.03 mol) was added, and the reaction mixture was stirred at room temperature overnight. The precipitate was collected by filtration, washed with water to give 5-iodoisoindoline-1,3-dione (4 g, 48% yield) as a solid. $^1$H NMR (400 MHz, DMSO-d$_6$) δ (ppm) 11.38 (s, 1H), 8.17 (d, J=7.6 Hz, 1H), 8.11 (s, 1H), 7.56 (d, J=8.0 Hz, 1H), 2.07 (s, 3H).

B. 5-Iodoisoindoline. To a stirred solution of 5-iodoisoindoline-1,3-dione (700 mg, 2.57 mmol) in anhydrous tetrahydrofuran (20 mL) at 0° C. was added sodium borohydride (974 g, 25.7 mmol) in portions, and the reaction mixture was chilled to –10° C. Boron trifluoride diethyl ether complex (3.9 mL, 25.7 mmol) was added dropwise. The reaction mixture was refluxed overnight. After being cooled to room temperature, the reaction mixture was poured slowly into cold water (100 mL) at 0-5° C. The mixture was diluted with ethyl acetate (480 mL), and the mixture was basified with aqueous sodium hydroxide solution (6 M) at 0-5° C. to pH=10. The organic layer was separated and washed with brine (4×100 mL), dried over sodium sulfate, and concentrated under reduced pressure. The resulting oil was diluted with diethyl ether (100 mL), and acidified (pH~2) with hydrochloric acid aqueous solution (6 M) at 0° C. The aqueous layer was separated and basified with aqueous sodium hydroxide solution (6 N), the mixture was extracted with ethyl acetate (400 mL). The organic layer was washed with brine (3×150 mL), dried over sodium sulfate, and concentrated under reduced pressure to give 5-iodoisoindoline (300 mg, 48% yield) as a solid. MS (ESI): m/z 245.7 [M+1]$^+$.

C. tert-Butyl 5-iodoisoindoline-2-carboxylate. A mixture of 5-iodoisoindoline (730 mg, 2.95 mmol), di-tert-butyl dicarbonate (1.2 g, 5.95 mmol), triethylamine (600 mg, 5.95 mmol) and N,N-dimethylpyridin-4-amine (72 mg, 0.6 mmol) in dichloromethane (10 mL) was stirred at room temperature overnight. Water was added, and the organic layer was separated. The aqueous phase was extracted with dichloromethane. The combined organic layer was washed with brine, dried over sodium sulfate, and evaporated under reduced pressure. The crude product was purified on silica gel column to give tert-butyl 5-iodoisoindoline-2-carboxylate (800 mg, 79% yield) as a solid.

Intermediate 25: N-(4-Chloropyridin-2-yl)pivalamide

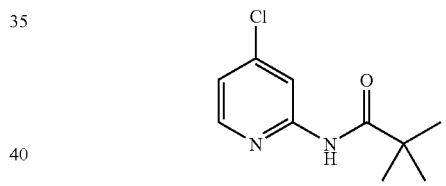

A. N-(4-Chloropyridin-2-yl)pivalamide. To a mixture of 4-chloropyridin-2-amine (1.7 g, 13.28 mmol) and triethylamine (1.61 g, 15.94 mmol) in dichloromethane (30 mL) was added dropwise pivaloyl chloride (1.91 g, 15.94 mmol) at 0° C. After the addition was complete, the mixture was stirred at room temperature overnight. The mixture was washed with water for three times, the organic layer was dried over anhydrous sodium sulfate and concentrated. The residue was dried in vacuo to give N-(4-chloropyridin-2-yl)pivalamide (2.67 g, 95.0% yield) as a white solid. MS (ESI) m/z: 212.8 [M+1]$^+$.

Intermediate 26: 4-Iodo-N-methylbenzamide

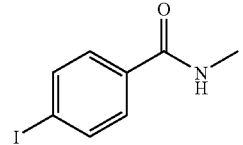

A. 4-Iodo-N-methylbenzamide. To a solution of methanamine (15 mL) in water (15 mL) was added dropwise 4-iodo-benzoyl chloride (6 g, 22.6 mmol) at 0° C. The mixture was stirred at room temperature and monitored by TLC. After 5 h, the reaction mixture was extracted with dichloromethane, the organic layer was dried over sodium sulfate and evaporated to give 4-iodo-N-methylbenzamide (4.0 g, 68% yield), which was used without further purification. MS (ESI): m/z 262.1 [M+1]+.

Intermediate 27:
4-Iodo-N-(1-methylpiperidin-4-yl)benzamide

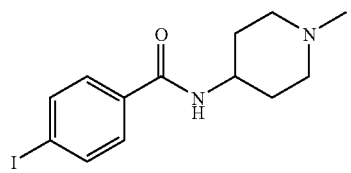

A. 4-Iodo-N-(1-methyl-piperidin-4-yl)-benzamide. To a solution of 1-methylpiperidin-4-amine (0.91 g, 8 mmol) and triethylamine (1.21 g, 12 mmol) in dichloromethane (10 mL) was added dropwise 4-iodo-benzoyl chloride (1.06 g, 4 mmol) at 0° C. under nitrogen. The mixture was warmed slowly to room temperature and stirred overnight. The reaction mixture was poured into ice-water, and the organic layer was separated, the aqueous phase was extracted with dichloromethane. The combined organic layer was dried over sodium sulfate and evaporated to give 4-iodo-N-(1-methyl-piperidin-4-yl)-benzamide (1.10 g, 79.7% yield), which was used without further purification. $^1$H-NMR (400 MHz, CHLOROFORM-d) δ (ppm) 7.72 (m, 2H), 7.42 (d, J=8.4 Hz, 2H), 5.92 (br s, 1H), 3.92 (m, 1H), 2.79 (d, J=11.2 Hz, 2H), 2.24 (s, 3H), 2.12 (t, J=11.2 Hz, 2H), 1.97 (d, J=11.2 Hz, 2H), 1.57 (m, 3H).

Intermediate 28: tert-Butyl
6-bromo-1-methyl-1H-indazol-3-ylcarbamate

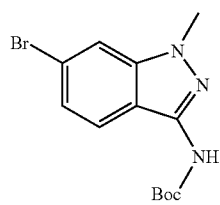

A. 6-Bromo-1H-indazol-3-amine. To a solution of 4-bromo-2-fluorobenzonitrile (2 g, 10 mmol) in butan-1-ol (30 mL) was added dropwise hydrazine hydrate (2 mL, 40 mmol), and the reaction mixture was heated at 100° C. overnight. The solvent was removed under reduced pressure, and the precipitate was collected by filtration, washed with water, and dried in vacuo to give 6-bromo-1H-indazol-3-amine (2.11 g, 98% yield) as a white solid. $^1$H NMR (400 MHz, DMSO-d$_6$) δ (ppm) 11.47 (s, 1H), 7.32 (d, J=8.4 Hz, 1H), 7.39 (s, 1H), 6.99 (d, J=8.4 Hz, 1H), 5.42 (br s, 2H).

B. 6-Bromo-1-methyl-1H-indazol-3-amine. To a solution of 6-bromo-1H-indazol-3-amine (2.11 g, 10 mmol) in N,N-dimethylformamide (10 mL) was added sodium hydride (60% in mineral oil, 0.4 g, 10 mmol) in portions at 0° C. After the addition, the mixture was stirred for 30 min. at 0° C., and iodomethane (1.42 g, 10 mmol) was added. The resulting mixture was stirred at room temperature overnight. The reaction was quenched by the addition of water (50 mL), and the mixture was extracted with ethyl acetate. The combined organic layer was washed with brine, dried over sodium sulfate and evaporated. The residue was purified on silica gel column (eluting with 10-25% ethyl acetate in petrol ether) to give 6-bromo-1-methyl-1H-indazol-3-amine (1.36 g, 61% yield) as a yellow solid. $^1$H NMR (400 MHz, DMSO-d$_6$) δ (ppm) 7.60 (m, 2H), 6.99 (d, J=8.0 Hz, 1H), 5.52 (s, 2H), 3.68 (s, 3H); MS (ESI): m/z 326.1 [M+1]+.

C. tert-Butyl 6-bromo-1-methyl-1H-indazol-3-ylcarbamate. A mixture of 6-bromo-1-methyl-1H-indazol-3-amine (1.36 g, 6 mmol), di-tert-butyl dicarbonate (2.62 g, 12 mmol), triethylamine (1.22 g, 12 mmol) and N,N-dimethylpyridin-4-amine (24 mg, 0.2 mmol) in dichloromethane (40 mL) was stirred at room temperature overnight. Water was added, and the organic layer was separated, the aqueous phase was extracted with dichloromethane. The combined organic layer was washed with brine, dried over sodium sulfate and evaporated under reduced pressure. The crude product was purified on silica gel column (eluting with 10% ethyl acetate in petroleum ether) to give tert-butyl 6-bromo-1-methyl-1H-indazol-3-ylcarbamate (480 mg, 25% yield) as a solid. $^1$H NMR (400 MHz, DMSO-d$_6$) δ (ppm) 7.80 (s, 1H), 7.29 (d, J=8.4 Hz, 1H), 7.16 (d, J=8.4 Hz, 1H), 3.98 (s, 3H), 1.41 (s, 9H); MS (ESI): m/z 426.1 [M+1]+.

Intermediate 29: Mixture of 1-(tetrahydro-2H-pyran-2-yl)-6-(4,4,5,5-tetramethyl-1,3,2-dioxaborolan-2-yl)-1H-benzo[d]imidazole and 1-(tetrahydro-2H-pyran-2-yl)-5-(4,4,5,5-tetramethyl-1,3,2-dioxaborolan-2-yl)-1H-benzo[d]imidazole

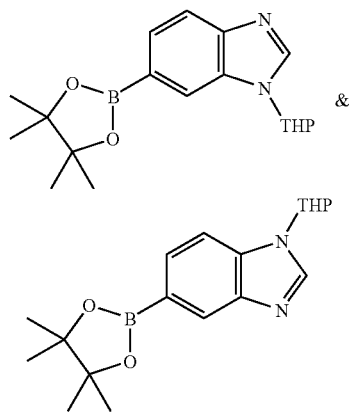

A. 6-Bromo-1H-benzo[d]imidazole. A mixture of 4-bromobenzene-1,2-diamine (2 g, 0.011 mol), triethyl orthoformate (10 mL) and pyridinium p-toluenesulfonate (300 mg, 0.001 mol) was refluxed overnight. The mixture was evaporated in vacuo. The residue was purified on silica gel column (eluting with 10-20% ethyl acetate in petroleum ether) to give 6-bromo-1H-benzo[d]imidazole (1.3 g, 65% yield). $^1$H NMR (300 MHz, DMSO-d$_6$) δ (ppm) 12.60 (br s, 1H), 8.24 (s, 1H), 7.83 (m, 1H), 7.60 (m, 1H), 7.32 (m, 1H).

B. 6-Bromo-1-(tetrahydro-2H-pyran-2-yl)-1H-benzo[d]imidazole and 5-bromo-1-(tetrahydro-2H-pyran-2-yl)-1H-benzo[d]imidazole. A mixture of 6-bromo-1H-benzo[d]imidazole (1.3 g, 6.6 mmol), 3,4-dihydro-2H-pyran (7 mL) and p-toluenesulfonic acid (300 mg, 1.57 mmol) in tetrahydrofuran (50 mL) was heated at 60° C. overnight. The reaction mixture was poured into ice water and the aqueous phase was extracted with ethyl acetate. The organic layer was dried over sodium sulfate, filtered, and the filtrate was evaporated under reduced pressure. The residue was purified on silica gel column (eluting with 2-10% ethyl acetate in petroleum ether) to give a mixture of 6-bromo-1-(tetrahydro-2H-pyran-2-yl)-1H-benzo[d]imidazole and 5-bromo-1-(tetrahydro-2H-pyran-2-yl)-1H-benzo[d]imidazole (800 mg, 44% yield).

C. 1-(Tetrahydro-2H-pyran-2-yl)-6-(4,4,5,5-tetramethyl-1,3,2-dioxaborolan-2-yl)-1H-benzo[d]imidazole and 1-(tetrahydro-2H-pyran-2-yl)-5-(4,4,5,5-tetramethyl-1,3,2-dioxaborolan-2-yl)-1H-benzo[d]imidazole. A degassed mixture of 6-bromo-1-(tetrahydro-2H-pyran-2-yl)-1H-benzo[d]imidazole and 5-bromo-1-(tetrahydro-2H-pyran-2-yl)-1H-benzo[d]imidazole (800 mg, 2.8 mmol), 4,4,4',4',5,5,5',5'-octamethyl-2,2'-bi(1,3,2-dioxaborolane) (1.4 g, 5.6 mmol), palladium acetate (65 mg, 0.28 mmol), triphenylphosphine (220 mg, 0.84 mmol) and potassium phosphate (1 g, 4.7 mmol) in 1,2-dimethoxyethane (15 mL) was heated at 100° C. under nitrogen overnight. After being cooled to room temperature, the mixture was filtered and the filtrate was evaporated under pressure. The residue was purified on silica gel column to give a mixture of 1-(tetrahydro-2H-pyran-2-yl)-6-(4,4,5,5-tetramethyl-1,3,2-dioxaborolan-2-yl)-1H-benzo[d]imidazole and 1-(tetrahydro-2H-pyran-2-yl)-5-(4,4,5,5-tetramethyl-1,3,2-dioxaborolan-2-yl)-1H-benzo[d]imidazole (470 mg, yield 51%). $^1$H NMR (400 MHz, DMSO-d$_6$) δ (ppm) 8.48 (s, 0.55H), 8.42 (s, 0.45H), 7.95 (s, 0.45H), 7.93 (s, 0.55H), 7.60-7.54 (m, 2H), 5.79 (dd, J$_1$=10.4 Hz, J$_2$=2.0 Hz, 0.55H), 5.69 (dd, J$_1$=10.4 Hz, J$_2$=2.0 Hz, 0.45H), 3.99 (m, 1H), 3.77 (m, 1H), 2.20-1.60 (m, 6H), 1.32 (s, 12H).

Intermediate 30: 1-(Tetrahydro-2H-pyran-2-yl)-6-(4,4,5,5-tetramethyl-1,3,2-dioxaborolan-2-yl)-1H-indazole

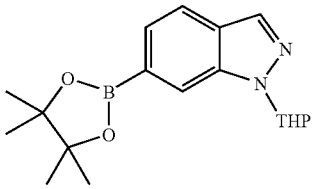

A. 6-Bromo-1H-indazole. A mixture of 4-bromo-2-fluorobenzaldehyde (2 g, 10 mmol) and aqueous hydrazine (10 mL, 85%) was refluxed overnight. After being cooled to room temperature, the reaction mixture was extracted with ethyl acetate. The organic layer was dried over sodium sulfate and evaporated under reduced pressure. The crude product was purified on silica gel column (eluting with 10-20% ethyl acetate in petroleum ether) to give 6-bromo-1H-indazole (1.3 g, 68% yield) as a solid. $^1$H NMR (400 MHz, DMSO-d$_6$) δ (ppm) 13.17 (br s, 1H), 8.09 (s, 1H), 7.75 (s, 1H), 7.73 (d, J=8.8 Hz, 1H), 7.23 (dd, J$_1$=8.8 Hz, J$_2$=1.6 Hz, 1H).

B. 6-Bromo-1-(tetrahydro-2H-pyran-2-yl)-1H-indazole. A mixture of 6-bromo-1H-indazole (1.3 g, 6.6 mmol), 3,4-dihydro-2H-pyran (7 mL) and p-toluenesulfonic acid (300 mg, 1.57 mmol) in tetrahydrofuran (50 mL) was heated at 60° C. overnight. The reaction mixture was poured into ice water and the aqueous phase was extracted with ethyl acetate. The organic layer was dried over sodium sulfate, and filtered. The filtrate was evaporated under reduced pressure. The residue was purified on silica gel column (eluting with 5-15% ethyl acetate in petroleum ether) to give 6-bromo-1-(tetrahydro-2H-pyran-2-yl)-1H-indazole (800 mg, yield 44%). $^1$H NMR (400 MHz, DMSO-d$_6$) δ (ppm) 8.13 (s, 1H), 8.03 (s, 1H), 7.74 (d, J=8.4 Hz, 1H), 7.32 (dd, J$_1$=8.4 Hz, J$_2$=1.6 Hz, 1H), 5.88 (dd, J$_1$=9.6 Hz, J$_2$=2.4 Hz, 1H), 3.90-3.70 (m, 2H), 2.40 (m, 1H), 2.05-1.90 (m, 2H), 1.65 (m, 1H), 1.53-1.45 (m, 2H).

C. 1-(Tetrahydro-2H-pyran-2-yl)-6-(4,4,5,5-tetramethyl-1,3,2-dioxaborolan-2-yl)-1H-indazole. A degassed mixture of 6-bromo-1-(tetrahydro-2H-pyran-2-yl)-1H-indazole (800 mg, 2.8 mmol), 4,4,4',4',5,5,5',5'-octamethyl-2,2'-bi(1,3,2-dioxaborolane) (1.4 g, 5.6 mmol), palladium acetate (65 mg, 0.28 mmol), triphenylphosphine (220 mg, 0.84 mmol) and potassium phosphate (1 g, 4.7 mmol) in 1,2-dimethoxyethane (15 mL) was heated at 100° C. under nitrogen overnight. After being cooled to room temperature, the mixture was filtered, and the filtrate was evaporated under reduced pressure. The residue was purified on silica gel column (eluting with 5-15% ethyl acetate in petroleum ether) to give 1-(tetrahydro-2H-pyran-2-yl)-6-(4,4,5,5-tetramethyl-1,3,2-dioxaborolan-2-yl)-1H-indazole (470 mg, 51% yield) as a solid. $^1$H NMR (400 MHz, DMSO-d$_6$) δ (ppm) 8.13 (s, 1H), 7.99 (s, 1H), 7.77 (d, J=8.4 Hz, 1H), 7.45 (d, J=8.0 Hz, 1H), 5.98 (dd, J$_1$=9.6 Hz, J$_2$=2.4 Hz, 1H), 3.83-3.77 (m, 2H), 239 (m, 1H), 2.01-1.96 (m, 2H), 1.81 (m, 1H), 1.58-1.56 (m, 2H), 1.32 (s, 12H).

Intermediate 31: 1-(6-Bromo-1-((2-(trimethylsilyl)ethoxy)methyl)-1H-benzo[d]imidazol-2-yl)-N,N-dimethylmethanamine

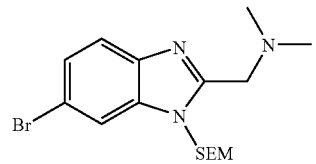

A. 6-Bromo-2-(chloromethyl)-1H-benzo[d]imidazole. A mixture of 4-bromobenzene-1,2-diamine (1.8 g, 0.01 mol) and ethyl 2-chloroacetimidate hydrochloride (1.59 g, 0.01 mol) in anhydrous ethanol (20 mL) was stirred at room temperature for 4 h. The solvent was removed under reduced pressure, the residue was poured into water, and the aqueous layer was extracted with ethyl acetate. The organic layer was dried over sodium sulfate, filtered and the filtrate was concentrated in vacuo to provide 6-bromo-2-(chloromethyl)-1H-benzo[d]imidazole (2.0 g, 82% yield) as a solid. MS (ESI): m/z 246.7 [M+1]$^+$.

B. 1-(6-Bromo-1H-benzo[d]imidazol-2-yl)-N,N-dimethylmethanamine. A mixture of 6-bromo-2-(chloromethyl)-1H-benzo[d]imidazole (2.0 g, 8.23 mmol) and dimethylamine aqueous solution (6.7 g, 0.04 mol) in acetonitrile (25 mL) was stirred at room temperature overnight. The solvent was removed under reduced pressure to give the crude product, which was purified by silica gel chromatography (eluting with ethyl acetate) to give 1-(6-bromo-1H-benzo[d]imidazol-2-yl)-N,N-dimethylmethanamine (1.2 g, 57.7% yield) as a solid. MS (ESI): m/z 255.8 [M+1]$^+$.

C. 1-(6-Bromo-1-((2-(trimethylsilyl)ethoxy)methyl)-1H-benzo[d]imidazol-2-yl)-N,N-dimethylmethanamine. To a solution of 1-(6-bromo-1H-benzo[d]imidazol-2-yl)-N,N-dimethylmethanamine (1.1 g, 4.35 mmol) in N,N-dimethylformamide (10 mL) at 0° C. was added sodium hydride (191 mg, 4.78 mmol) in portions under nitrogen. After the addition, the mixture was stirred at 0° C. for 30 min., (2-(chloromethoxy)ethyl)trimethylsilane (794 mg, 4.78 mmol) was added and the resulting mixture was stirred at 0° C. for 1 h, then warmed to room temperature and stirred overnight. Water was added, and the resulting mixture was extracted with ethyl acetate. The organic layer was concentrated under vacuum, and the residue was purified by silica gel column (eluting with 50% ethyl acetate in petroleum ether) to give 1-(6-bromo-1-((2-(trimethylsilyl)ethoxy)methyl)-1H-benzo[d]imidazol-2-yl)-N,N-dimethylmethanamine (1.2 g, 72.3% yield) as a solid. MS (ESI): m/z 385.9 [M+1]$^+$.

Intermediate 32: 6-Bromo-2-methoxy-quinoline

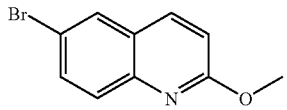

A. 3,4-Dihydroquinolin-2(1H)-one. A mixture of (E)-3-(2-nitrophenyl)acrylic acid (60 g, 0.31 mol) and palladium on charcoal (10% w/w, 6 g) in methanol (1 L) was hydrogenated under 50 psi of hydrogen at room temperature overnight. The catalyst was filtered off, and the filtrate was concentrated to give 3,4-dihydroquinolin-2(1H)-one (36 g, 79% yield) as a yellow solid. $^1$H NMR (400 MHz, DMSO-d$_6$) δ (ppm) 10.01 (s, 1H), 7.07 (m, 2H), 6.84 (m, 1H), 6.79 (m, 1H), 2.80 (t, J=7.2 Hz, 2H), 2.38 (t, J=7.2 Hz, 2H).

B. 6-Bromo-3,4-dihydroquinolin-2(1H)-one. A mixture of 3,4-dihydroquinolin-2(1H)-one (10 g, 0.068 mol) and N-bromosuccinimide (4.3 g, 0.075 mol) in dichloromethane (300 mL) was heated at 80° C. overnight. After cooling to room temperature, the precipitate was filtered off, and the filtrate was concentrated. The residue was purified on silica gel column (eluting with 10% ethyl acetate in petroleum ether) to give 6-bromo-3,4-dihydroquinolin-2(1H)-one (9.5 g, 62% yield) as a solid. MS (ESI): m/z 226.1 [M+1]$^+$.

C. 6-Bromo-2-chloroquinoline. A mixture of 6-bromo-3,4-dihydroquinolin-2(1H)-one (1 g, 4.4 mmol), 2,3-dichloro-5,6-dicyano-1,4-benzoquinone (DDQ) (1 g, 4.5 mmol) and phosphorous oxytrichloride (3 mL) in toluene (10 mL) was stirred at 90° C. overnight. The solvent was evaporated in vacuo, the residue was diluted with water, and the resulting mixture was extracted with ethyl acetate. The organic layer was dried over anhydrous sodium sulfate and evaporated under reduced pressure to give the crude product, which was purified on silica gel column (eluting with 10-15% ethyl acetate in petroleum ether) to give 6-bromo-2-chloroquinoline (960 mg, 91% yield) as a solid. $^1$H NMR (400 MHz, DMSO-d$_6$) δ (ppm) 8.38 (d, J=8.8 Hz, 1H), 8.32 (s, 1H), 7.91 (d, J=8.8 Hz, 1H), 7.85 (d, J=8.8 Hz, 1H), 7.62 (d, J=8.8 Hz, 1H).

D. 6-Bromo-2-methoxyquinoline. Metal sodium (95 mg, 4.1 mmol) was dissolved in anhydrous methanol (50 mL), and 6-bromo-2-chloroquinoline (500 mg, 2.1 mmol) was added, then the mixture was heated to 80° C. for 5 h. The solvent was evaporated under reduced pressure, and the residue was diluted with water. The resulting mixture was extracted with ethyl acetate. The organic layer was dried over anhydrous sodium sulfate and evaporated under reduced pressure to give 6-bromo-2-methoxyquinoline (483 mg, 98% yield) as a white solid. $^1$H NMR (400 MHz, DMSO-d$_6$) δ (ppm) 8.10 (d, J=9.2 Hz, 1H), 8.04 (s, 1H), 7.65 (d, J=8.8 Hz, 1H), 7.59 (d, J=8.8 Hz, 1H), 6.96 (d, J=9.2 Hz, 1H), 3.86 (s, 3H).

Intermediate 33: 6-Bromo-1-methyl-1H-benzotriazole

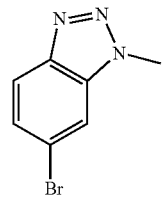

A. 6-Bromo-1-methyl-1H-benzo[d][1,2,3]triazole. To a solution of 5-bromo-N$^1$-methylbenzene-1,2-diamine (1.6 g, 8 mmol) in hydrochloric acid (5 M, 20 mL) was added a solution of sodium nitrite (1.1 g, 16 mmol) at 0° C., and the reaction mixture was stirred at room temperature for 2 h. The solution was neutralized to pH=7~8 with saturated sodium bicarbonate, and the mixture was extracted with ethyl acetate (20 mL×3). The organic layer was dried over anhydrous sodium sulfate, concentrated under vacuum to give the crude product, which was purified on silica gel column (eluting with 0-10% ethyl acetate in petroleum ether) to give 6-bromo-1-methyl-1H-benzo[d][1,2,3]triazole (800 mg, 47% yield) as a solid. $^1$H NMR (400 MHz, CHLOROFORM-d) δ (ppm) 7.85 (d, J=8.8 Hz, 1H), 7.64 (d, J=1.6 Hz, 1H), 7.40 (dd, J$_1$=8.8 Hz J$_2$=1.6 Hz, 1H), 4.19 (s, 3H); MS (ESI): m/z 212.2 [M+1]$^+$.

Intermediate 34: (±)-cis-3-Aminocyclohexanol hydrochloride

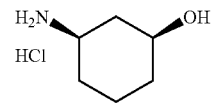

A. 2-(Cyclohex-2-enyl)isoindoline-1,3-dione. Triphenylphosphine-resin supported (12.01 g, 30.6 mmol), isoindoline-1,3-dione (5.01 g, 34.1 mmol), and cyclohex-2-enol (3.05 mL, 30.6 mmol) were weighed into a 200 mL flask. Tetrahydrofuran (60 mL) was added. The mixture was stirred and cooled to 0° C., then diisopropylazodicarboxylate (DIAD) (6.5 mL, 33.4 mmol) was added dropwise over 2 minutes. The reaction was stirred and allowed to warm slowly to room temperature. After 20 h, the reaction was filtered through celite using ethyl acetate, then concentrated to a yellow solid. The material was dissolved into hot ethyl acetate (~40 mL), and hexanes were added (~15 mL) to initiate cause crystallization of the byproduct. The yellow supernatant was decanted, concentrated, then redissolved in tetrahydrofuran and purified by flash chromatography over silica gel (0-20% ethyl acetate in hexanes) to provide 2-(cyclohex-2-enyl)isoindoline-1,3-dione (3.2053 g, 14.10 mmol, 46.1% yield). (ESI): m/z 228.6 [M+1]$^+$.

B. Intermediate A. Into a 200 mL flask were added 2-(cyclohex-2-enyl)isoindoline-1,3-dione (3.2053 g, 14.10 mmol), chloroform (50 mL) and ethanol (2.0 mL). The solution was stirred at room temperature, and N-bromosuccinimide (3.19 g, 17.92 mmol) (freshly recrystallized from hot water) was added. The flask was capped and the reaction stirred at room temperature. After 16 h the reaction was quenched by addition of 10% sodium bisulfite solution, then diluted with ethyl acetate and water. The organic layer was removed, and the aqueous layer extracted with ethyl acetate. The combined organic solution was dried over magnesium sulfate, filtered and concentrated, then redissolved into dichloromethane and applied to a Biotage 40+M column. The product was eluted using 0-20% ethyl acetate/hexanes, yielding the desired Intermediate A (1.975 g, 5.61 mmol, 39.8% yield) as a colorless oil. $^1$H NMR (400 MHz, CHLOROFORM-d) δ (ppm) 7.78 (d, J=7.03 Hz, 1H), 7.59-7.66 (m, 1H), 7.50-7.57 (m, 2H), 5.58 (br s, 1H), 4.57 (br s, 1H), 4.38 (br s, 1H), 3.33-3.49 (m, 1H), 2.98-3.11 (m, 1H), 2.57 (d, J=14.45 Hz, 1H), 2.06-2.30 (m, 2H), 1.67 (d, J=14.84 Hz, 1H), 1.30-1.43 (m, 2H), 1.15 (t, J=7.03 Hz, 3H).

C. (±)-2-((1S,2R,3R)-2-Bromo-3-hydroxycyclohexyl)isoindoline-1,3-dione. Intermediate A (1.975 g, 5.61 mmol) was dissolved into methanol (25 mL), and 2N hydrochloric acid (aq.) (5 mL, 10.00 mmol) was added. The reaction was stirred at room temperature for 5 h, then filtered through a medium frit, and the white solid was washed with water. The solid was dried at rt in vacuo to provide (±)-2-1S,2R,3R)-2-bromo-3-hydroxycyclohexypisoindoline-1,3-dione (1.2218 g, 3.77 mmol, 67.2% yield). $^1$H NMR (400 MHz, DMSO-d$_6$) δ (ppm) 7.68-8.13 (m, 4H), 5.39 (d, J=6.64 Hz, 1H), 4.42-4.78 (m, 1H), 4.25 (td, J=11.71, 4.30 Hz, 1H), 3.47-3.71 (m, 1H), 1.90-2.12 (m, 2H), 1.79-1.89 (m, 1H), 1.67-1.77 (m, 1H), 1.40-1.56 (m, 1H), 1.25-1.40 (m, 1H). (ESI): m/z 326.5 [M+1]$^+$.

D. (±)-cis-2-(3-Hydroxycyclohexyl)isoindoline-1,3-dione. (±)-2-((1S,2R,3R)-2-Bromo-3-hydroxycyclohexyl)isoindoline-1,3-dione (1.0933 g, 3.37 mmol), tributylstannane (1.10 mL, 4.15 mmol), toluene (18 mL), methanol (2 mL), and (E)-2,2'-(diazene-1,2-diyl)bis(2-methylpropanenitrile) (AIBN) (0.039 g, 0.236 mmol) were added to a 100 mL flask. The flask was equipped with a reflux condenser and a nitrogen inlet, and the apparatus flushed with nitrogen. The flask was then placed into a 120° C. oil bath to stir. After 16 h, LCMS analysis showed a ratio of ~1:1 product:starting material. Another portion of tributylstannane (1.1 mL, 3.37 mmol) and (E)-2,2'-(diazene-1,2-diyl)bis(2-methylpropanenitrile) (AIBN) (0.051 g, 0.311 mmol) were added to the reaction, and the cooled solution was heated to reflux for 24 h. The cooled reaction was then concentrated to a white semi-solid, redissolved into tetrahydrofuran and methanol, and applied to a Biotage 40+M column. Flash chromatography in 10-60% ethyl acetate/hexanes provided the desired (±)-cis-2-(3-hydroxycyclohexyl)isoindoline-1,3-dione (0.5213 g, 2.125 mmol, 63.0% yield). $^1$H NMR (400 MHz, CHLOROFORM-d) δ (ppm) 7.78-7.91 (m, 2H), 7.66-7.76 (m, 2H), 4.18 (t, J=12.49 Hz, 1H), 3.71 (td, J=10.25, 5.27 Hz, 1H), 2.27 (q, J=11.84 Hz, 1H), 1.98-2.19 (m, 3H), 1.85-1.96 (m, 1H), 1.69 (d, J=12.49 Hz, 1H), 1.51 (d, J=5.47 Hz, 1H), 1.25-1.44 (m, 3H). (ESI): m/z 246.4 [M+1]$^+$.

E. (±)-cis-3-Aminocyclohexanol hydrochloride. Into a flask containing (±)-cis-2-(3-hydroxycyclohexyl)isoindoline-1,3-dione (0.5213 g, 2.125 mmol) were added ethanol (10 mL), then hydrazine hydrate (0.12 mL, 2.474 mmol). The flask was capped and placed to stir in an 80° C. oil bath. Within 5 h all had dissolved. After 20 h, more hydrazine (0.04 mL) was added to the reaction, and the reaction was heated to reflux for another 5 h, at which point TLC showed consumption of starting material. The reaction was concentrated to approximately half volume, then 1 mL of concentrated HCl was added. The slurry was concentrated to a solid, and the solid was triturated with water, filtering to remove the solid precipitate. The filtrate was concentrated to provide the desired (±)-cis-3-aminocyclohexanol hydrochloride (0.3338 g, 2.201 mmol, 104% yield) as an HCl salt. $^1$H NMR (400 MHz, DMSO-d$_6$) δ (ppm) 8.04 (br s, 3H), 3.32-3.54 (m, 1H), 2.96 (d, J=4.69 Hz, 1H), 2.11 (d, J=11.71 Hz, 1H), 1.57-1.90 (m, 3H), 1.08-1.33 (m, 3H), 0.93-1.07 (m, 1H).

Intermediate 35:
trans-(4-Aminocyclohexyl)methanol hydrochloride

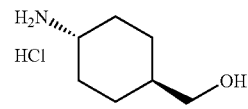

A. trans-(4-Aminocyclohexyl)methanol hydrochloride. trans-4-(tert-Butoxycarbonylamino)cyclohexanecarboxylic acid (2.5 g, 10.28 mmol) was dissolved in tetrahydrofuran (100 mL) and then added with 1M borane tetrahydrofuran complex (10.28 mL, 10.28 mmol). The solution was heated to 60° C. and then methanol (25 mL) was added dropwise to the reaction. The reaction was stirred 30 min and then concentrated. The residue was added with 4N hydrogen chloride in dioxane, stirred for 5 min and then concentrated. The solid was triturated in 10% methanol in ethyl acetate to give a white solid (1.11 g, 6.70 mmol, 65.2% yield). MS (ESI) m/z 230.4 [M]$^+$.

Intermediate 36: cis-(4-Aminocyclohexyl)methanol hydrochloride

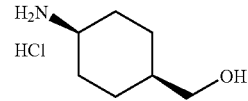

A. cis-(4-Aminocyclohexyl)methanol hydrochloride. cis-4-Aminocyclohexanecarboxylic acid (2 g, 13.97 mmol) was added with tetrahydrofuran (100 mL) and borane-methyl sulfide complex (13.26 mL, 140 mmol). The solution was heated to 60° C. for 24 h under nitrogen. The reaction was quenched with methanol and then concentrated. The residue was purified on silica gel column (0-100% ethyl acetate in hexanes). The product fractions were concentrated and then added with 4N hydrogen chloride in dioxane. The solution was concentrated and then triturated with 10% methanol in ethyl acetate to give a white solid (1.6 g, 9.66 mmol, 69.1% yield). MS (ESI) m/z 130.1 [M]$^+$.

Intermediate 37:
trans-2-(4-Aminocyclohexyl)propan-2-ol hydrochloride

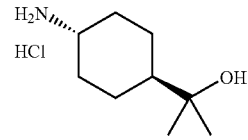

A. trans-Methyl 4-(tert-butoxycarbonylamino)cyclohexanecarboxylate. trans-4-(tert-Butoxycarbonylamino)cyclohexanecarboxylic acid (2 g, 8.22 mmol), iodomethane (0.771 mL, 12.33 mmol), potassium carbonate (3.41 g, 24.66 mmol), and acetone (20 mL) were heated in a pressure flask to 70° C. for 16 h. The reaction was filtered, concentrated, and the purified on silica gel column (eluting with 0-20% ethyl acetate in hexanes). The product fractions were concentrated and then triturated in hexanes to give a white solid (1.08 g, 4.20 mmol, 51.1% yield). MS (ESI) m/z 258.4 [M]$^+$.

B. trans-2-(4-Aminocyclohexyl)propan-2-ol hydrochloride. trans-Methyl 4-(tert-butoxycarbonylamino)cyclohexanecarboxylate (0.5 g, 1.943 mmol) was dissolved in tetrahydrofuran (3 mL) and then cooled in −78° C. under nitrogen. Methylmagnesium bromide (6.48 mL, 19.43 mmol, 3M in diethyl ether) was added and the reaction was allowed to warm to room temperature over 18 h. The reaction was quenched by addition of saturated ammonium chloride and then extracted with ethyl acetate. The organic layer was dried over magnesium sulfate, filtered, and then concentrated. The residue was treated with 4N hydrogen chloride in dioxane at room temperature for 4 h and then concentrated to give a white solid. MS (ESI) m/z 158.3 [M+1]$^+$.

Intermediate 38: N$^2$-(4-methoxybenzyl)-quinoline-2,6-diamine

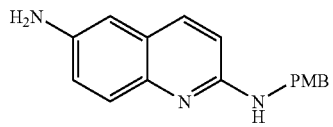

A. 2-Chloro-6-nitroquinoline. To a mixture of 6-nitro-3,4-dihydroquinolin-2(1H)-one (1.5 g, 7.8 mmol) and 2,3-dichloro-5,6-dicyano-1,4-benzoquinone (DDQ) (1.77 g, 7.8 mmol) in toluene (20 mL) was added dropwise phosphorus oxychloride (3.75 mmol), and the resulting solution was heated at 90° C. for 3 h. After cooling to room temperature, the reaction was quenched by the addition of 50 mL of ice-water. The mixture was basified with 4N aqueous sodium hydroxide solution to pH=7. The precipitate was collected by filtration, washed with ethyl ether, and dried under high vacuum to give 2-chloro-6-nitroquinoline (550 mg, 34% yield). $^1$H NMR (400 MHz, DMSO-d$_6$) δ (ppm) 9.15 (s, 1H), 8.76 (d, J=8.8 Hz, 1H), 8.51 (m, 1H), 8.15 (d, J=9.2 Hz, 1H), 7.81 (d, J=8.4 Hz, 1H).

B. N-(4-Methoxybenzyl)-6-nitroquinolin-2-amine. A mixture of 2-chloro-6-nitroquinoline (500 mg, 2.4 mmol) and 4-methoxybenzylamine (10 mL) was heated at 120° C. overnight. The mixture was cooled down to room temperature, diluted with ethyl acetate (50 mL), and the organic layer was washed with water for 3 times, dried over anhydrous sodium sulfate, and concentrated. The residue was purified on silica gel column (eluting with 2-10% ethyl acetate in petroleum ether) to give N-(4-methoxybenzyl)-6-nitroquinolin-2-amine (96 mg, 13% yield) as a ropy liquid. MS (ESI): m/z 309.9 [M+1]$^+$.

C. N$^2$-(4-Methoxybenzyl)quinoline-2,6-diamine. To a solution of N-(4-methoxybenzyl)-6-nitroquinolin-2-amine (96 mg, 0.31 mmol) in a mixture of tetrahydrofuran and methanol (v/v, 1:1, 20 mL) were added zinc power (202 mg, 3.1 mmol) and ammonium chloride (167 mg, 3.1 mmol) at room temperature, and the mixture was stirred at room temperature overnight. TLC and LCMS analysis showed the reaction was completed. After filtration, the filtrate was concentrated, and the residue was purified on silica gel column (eluting with 10-50% ethyl acetate in petroleum ether) to give N$^2$-(4-methoxybenzyl)quinoline-2,6-diamine (50 mg, 57.7% yield) as a liquid. MS (ESI): m/z 279.9 [M+1]$^+$.

Intermediate 39: (±)-tert-Butyl 3-aminoazepane-1-carboxylate

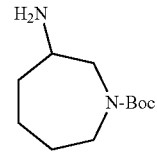

A. (±)-Azepan-3-amine. To a solution of (±)-3-aminoazepan-2-one (3.65 g, 28.5 mmol) in tetrahydrofuran (30 mL) at 0° C. under nitrogen was added lithium aluminium tetrahydride (2.71 g, 71.3 mmol) in portions. After the addition, the reaction mixture was allowed to warm up to room temperature, then refluxed for 5 days. Water was added slowly, and the reaction mixture was filtered, the filter cake was washed with tetrahydrofuran (3×100 mL). The combined tetrahydrofuran phase was evaporated in vacuo to give azepan-3-amine (2.28 g, 69.5% yield) as a yellow oil, which was used for the next step directly. $^1$H NMR (400 MHz, CHLOROFORM-d) δ (ppm) 2.85 (m, 2H), 2.75 (m, 2H), 1.76 (m, 1H), 1.60 (m, 9H); MS (ESI): m/z 115.3 [M+1]$^+$.

B. (±)-N-Benzylideneazepan-3-amine. To a solution of (±)-azepan-3-amine (2.28 g, 0.02 mol) in dichloromethane (100 mL) was added benzaldehyde (2.54 g, 0.024 mol), followed by anhydrous sodium sulfate (3.41 g, 0.024 mmol). The resulting mixture was stirred at room temperature for 24 h. The reaction mixture was filtered, and the filtrate was concentrated to give the crude (±)-N-benzylideneazepan-3-amine (4.61 g), which was used in the next step directly. MS (ESI): m/z 203.4 [M+1]$^+$.

C. (±)-tert-Butyl 3-(benzylideneamino)azepane-1-carboxylate. To a mixture of (±)-N-benzylideneazepan-3-amine (4.04 g, 0.02 mmol) and triethylamine (6.06 g, 0.06 mmol) in dichloromethane (60 mL) was added dropwise a solution of di-tert-butyl dicarbonate (5.18 g, 0.024 mmol) in dichloromethane (20 mL), and the mixture was stirred at room temperature overnight. Water was added, and the mixture was extracted with dichloromethane (3×50 mL). The organic layer was dried over anhydrous sodium sulfate, and concentrated to give the crude (±)-tert-butyl 3-(benzylideneamino) azepane-1-carboxylate (4.98 g) as a ropy liquid. MS (ESI): m/z 303.2 [M+1]$^+$.

D. (±)-tert-Butyl 3-aminoazepane-1-carboxylate. A solution of tert-butyl 3-(benzylideneamino)azepane-1-carboxylate (1 g, 3.31 mmol) in a mixture of acetic acid and dichloromethane (1:4, 20 mL) was stirred at room temperature for 24 h. The solvent was removed, and the residue was basified with sodium bicarbonate solution, the mixture was extracted with ethyl acetate for three times. The organic layer was dried over anhydrous sodium sulfate, and concentrated to give the crude product, which was purified on silica gel column (eluting with 5% methanol in dichloromethane) to give (±)-tert-butyl 3-aminoazepane-1-carboxylate (360 mg, 42% yield for three steps). $^1$H NMR (400 MHz, CHLOROFORM-d) δ

(ppm) 2.87 (m, 1H), 2.77 (m, 1H), 2.52 (m, 1H), 1.80-1.30 (m, 8H); MS (ESI): m/z 215.4 [M+1]+.

Intermediate 40: cis-4-(tert-Butyldimethylsilyloxy)cyclohexanol

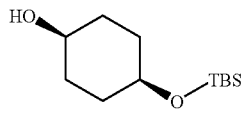

A. cis-4-(tert-butyldimethylsilyloxy)cyclohexanol. To a solution of cis-cyclohexane-1,4-diol (500 mg, 4.31 mmol) and tert-butylchlorodimethylsilane (650 mg, 4.31 mmol) in N,N-dimethylformamide (3 mL) was added dropwise a solution of triethylamine (436 mg, 4.31 mmol) and 4-(dimethylamino)pyridine (21 mg) in N,N-dimethylformamide (1 mL) at 0° C. After the addition, the mixture was stirred at 0° C. for an additional 1 h. The reaction mixture was diluted with ethyl acetate, and the organic layer was washed saturated aqueous sodium chloride solution, and dried over anhydrous sodium sulfate. The solvent was evaporated under reduced pressure, and the residue was purified on silica gel column (eluting with 20% ethyl acetate in petroleum ether) to give cis-4-(tert-butyldimethylsilyloxy)-cyclohexanol (420 mg, 42.4% yield) as a liquid. $^1$H NMR (400 MHz, CHLOROFORM-d) δ (ppm) 3.81 (m, 2H), 1.84 (m, 8H), 0.90 (s, 9H), 0.03 (s, 6H).

Intermediate 41: 2-(4-Iodophenyl)-1-((2-(trimethylsilyl)ethoxy)methyl)-1H-imidazole

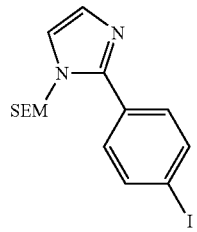

A. 2-(4-Iodophenyl)-1H-imidazole. To a solution 4-iodobenzaldehyde (500 mg, 2.16 mmol) in methanol (20 mL) were added oxalaldehyde (40%) (5 mL) and 25% aqueous solution of ammonium hydroxide (5 mL), and the mixture was stirred at room temperature overnight. The precipitate was collected by filtration, washed with petroleum ester, and dried under high vacuum to give 2-(4-iodophenyl)-1H-imidazole (500 mg, 86% yield). MS (ESI): m/z 270.9 [M+1]+.

B. 2-(4-Iodophenyl)-1-((2-(trimethylsilyl)ethoxy)methyl)-1H-imidazole. To a solution of 2-(4-iodophenyl)-1H-imidazole (268 mg, 1 mmol) in N,N-dimethylformamide (10 mL) was added sodium hydride (60 mg, 1.5 mmol) at 0° C. in portions. After the mixture was stirred at room temperature for one hour, (2-(chloromethoxy)ethyl)trimethyl-silane (196 mg, 1.2 mmol) was added dropwise, and the mixture was stirred at room temperature overnight. Water was added, the mixture was extracted with ethyl acetate for 3 times, the organic layer was concentrated and washed with saturated sodium chloride solution for 3 times. The organic layer was dried over anhydrous sodium sulfate, and concentrated to give 2-(4-iodophenyl)-1-((2-trimethylsilyl)ethoxy)methyl)-1H-imidazole (217 mg, 54.7% yield) as a liquid, which was used to the next step directly. MS (ESI): m/z 400.9 [M+1]+.

Intermediate 42: 6-Morpholinopyridin-3-amine

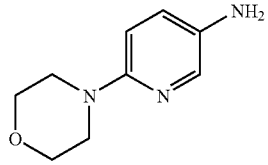

A. 4-(5-Nitropyridin-2-yl)morpholine. 2-Bromo-5-nitropyridine (1 g, 5 mmol) was dissolved in morpholine (5 mL), and the mixture was stirred at room temperature for 3 h. The precipitate was collected by filtration, washed with n-hexane, dried under high vacuum to give 4-(5-nitropyridin-2-yl)morpholine (0.9 g, 90% yield). $^1$H NMR (400 MHz, CHLOROFORM-d) δ (ppm) 9.04 (s, 1H), 8.23 (d, J=6.8 Hz, 1H), 8.51 (d, J=9.2 Hz, 1H), 3.83 (m, 4H), 3.75 (m, 4H).

B. 6-Morpholinopyridin-3-amine. To a solution of 4-(5-nitro-pyridin-2-yl)-morpholine (0.8 g, 3.83 mmol) in a mixture of methanol and tetrahydrofuran (v/v, 1:1, 40 mL) at room temperature was added ammonium chloride (2.07 g, 38.3 mmol), followed by zinc dust (2.49 g, 38.3 mmol), then the mixture was stirred at room temperature overnight. The reaction mixture was filtered on celite and rinsed with methanol. The combined filtrates were concentrated, and the residue was diluted with brine (20 mL) and extracted with ethyl acetate (15 mL×3). The organic layers were dried over sodium sulfate, and concentrated to afford the crude product, which was purified on silica gel column (eluting with 10-70% ethyl acetate in petroleum ether) to give 6-morpholinopyridin-3-amine (330 mg, 48.2% yield) as a black solid. $^1$H NMR (400 MHz, DMSO-$d_6$) δ (ppm) 7.59 (s, 1H), 6.91 (m, 1H), 6.60 (d, J=8.8 Hz, 1H), 4.57 (br s, 2H), 3.66 (m, 4H), 3.16 (m, 4H); MS (ESI): m/z 180.0 [M+1]+.

Intermediate 43: cis-4-Amino-1-methylcyclohexanol

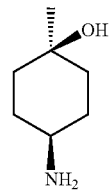

A. trans-4-(Dibenzylamino)cyclohexanol. trans-4-Aminocyclohexanol (15.69 g, 136 mmol) and sodium bicarbonate (37.8 g, 450 mmol) were suspended in ethanol (300 mL), treated with benzyl chloride (45.9 mL, 395 mmol) and stirred at 75° C. for 16 h. The suspension was filtered and the resulting filtrate was concentrated to give a yellow waxy solid. The solid was then dissolved in methylene chloride (400 mL) and washed with 1N sodium hydroxide (2×100 mL), brine (1×100 mL), dried over magnesium sulfate and concentrated to give an off-white waxy solid that upon standing at room temperature formed a yellow liquid containing waxy solid which showed both the product and the excess benzyl chloride by TLC. This material was dissolved in ether (300 mL) and the desired product was extracted as the amine salt with 1N aqueous hydrochloric acid (1×300 mL). TLC indicated benzyl chloride in ethereal layer and product in aqueous layer. The aqueous layer was then washed with ethyl acetate (200 mL) before it was neutralized using 6N aqueous sodium hydroxide, followed by 1N aqueous sodium hydroxide and extracted as the free amine using ethyl acetate (300 mL). The organic layer was then dried over magnesium sulfate and concentrated to give the product as a white solid (37.12 g, 92%). $^1$H NMR (400 MHz, DMSO-$d_6$) δ (ppm) 7.31 (dt, J=7.26, 14.47 Hz, 8H), 7.17-7.23 (m, 2H), 4.42-4.46 (m, 1H), 3.55 (s, 4H), 3.26-3.33 (m, 1H), 2.29-2.41 (m, 1H), 1.71-1.88 (m, 5H), 1.34-1.46 (m, 2H), 0.91-1.12 (m, 3H). $R_f$=0.11 (TLC, 20% ethyl acetate in hexane); MS (ESI) m/z 296.5 [M+1]$^+$.

B. 4-(Dibenzylamino)cyclohexanone. A solution of dimethyl sulfoxide (5.77 mL, 81 mmol) in methylene chloride (20 mL) was added dropwise, to a solution of oxalyl chloride (3.26 mL, 37.2 mmol) in methylene chloride (150 mL) stirring at –78° C. After stirring for 15 min at –78° C., a solution of trans-4-(dibenzylamino)cyclohexanol (10.0 g, 33.9 mmol) in methylene chloride (100 mL) was added dropwise. After stirring at –78° C. for another 15 min, triethylamine (23.59 mL, 169 mmol) was added dropwise and the reaction was allowed to warm to room temperature and stirred for 16 h. The reaction mixture appeared as a suspension and was washed with brine (100 mL). The organic layer was separated, dried over magnesium sulfate and concentrated to give a colorless oil that was purified using silica gel flash column chromatography (5-100% ethyl acetate in hexanes) to give the title compound as a colorless oil (8.11 g, 82% yield). $^1$H NMR (400 MHz, DMSO-$d_6$) δ (ppm) 7.35-7.39 (m, 4H), 7.28-7.33 (m, 4H), 7.18-7.24 (m, 2H), 3.61 (s, 4H), 2.89-2.99 (m, 1H), 2.26-2.38 (m, 2H), 2.14-2.24 (m, 2H), 2.06 (td, J=2.81, 6.43 Hz, 2H), 1.81 (qd, J=4.27, 12.49 Hz, 2H). $R_f$=0.36 (TLC, 20% ethyl acetate in hexane); MS (ESI) m/z 294.4 [M+1]$^+$.

C. cis-4-(Dibenzylamino)-1-methylcyclohexanol and trans-4-(dibenzylamino)-1-methylcyclohexanol. A solution of 3.0 M methylmagnesium bromide/ether (11.95 mL, 35.8 mmol) in dry ether (100 mL) was added dropwise over 15 min to a solution of 4-(dibenzylamino)cyclohexanone (8.09 g, 27.6 mmol) in dry ether (200 mL). The cloudy reaction mixture was stirred at room temperature for 16 h. The reaction was found to be only 75% complete by NMR and LCMS (using TIC). Additional 3.0 M methylmagnesium bromide/ether (3 mL, 9 mmol) was added and the mixture was stirred another 20 h. The reaction mixture was quenched when poured cautiously into a solution of aqueous ammonium chloride (250 mL), causing a precipitate to form. Both layers (and suspension) were stirred for 10 min, causing all precipitate to go into solution. The ethereal layer was separated, dried over magnesium sulfate and concentrated to give a colorless oil that was purified by using silica gel flash column chromatography (0-50% ethyl acetate in hexanes) to separate the cis and trans isomers (cis: $R_f$=0.33; trans: $R_f$=0.20, 20% ethyl acetate in hexanes). Both isomers required additional chromatography. The fractions containing the cis material were purified by using silica gel flash column chromatography (0-20% ethyl acetate in hexane) to give the product as a white solid (1.54 g, 18%). $^1$H NMR (400 MHz, DMSO-$d_6$) δ (ppm) 7.32-7.37 (m, 4H), 7.25-7.32 (m, 4H), 7.16-7.22 (m, 2H), 4.00 (s, 1H), 3.59 (s, 4H), 2.29-2.40 (m, 1H), 1.66-1.79 (m, 2H), 1.54 (d, 4H), 1.07-1.19 (m, 2H), 1.02 (s, 3H). The trans isomer also needed additional column chromatography (0-20% ethyl acetate in hexane) to give the trans isomer as a white solid (1.70 g, 20%). $^1$H NMR (400 MHz, DMSO-$d_6$) δ (ppm) 7.32-7.37 (m, 4H), 7.26-7.32 (m, 4H), 7.16-7.24 (m, 2H), 4.18 (s, 1H), 3.57 (s, 4H), 2.33-2.44 (m, 1H), 1.69 (d, J=10.15 Hz, 2H), 1.55 (d, J=12.20 Hz, 2H), 1.36-1.49 (m, 2H), 1.16-1.29 (m, 2H), 1.09 (s, 3H). MS (ESI) m/z 310.5 [M+1]$^+$.

D. cis-4-Amino-1-methylcyclohexanol. cis-4-(Dibenzylamino)-1-methylcyclohexanol (0.770 g, 2.488 mmol) was dissolved in ethanol (25 mL), treated with 20% palladium hydroxide on carbon (0.349 g, 2.488 mmol) and stirred under a balloon filled with hydrogen for 2 days. The suspension was filtered through Celite and the resulting filtrate was concentrated to give the product as a pale gray solid (0.308 g, 96% yield). $^1$H NMR (400 MHz, DMSO-$d_6$) δ (ppm) 2.42 (tt, 1H), 1.29-1.54 (m, 6H), 1.18-1.29 (m, 2H). MS (ESI) m/z 130.1 [M+1]$^+$.

Intermediate 44:
trans-4-Amino-1-methylcyclohexanol

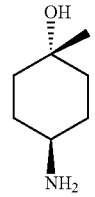

A. trans-4-Amino-1-methylcyclohexanol. trans-4-(Dibenzylamino)-1-methylcyclohexanol (0.787 g, 2.54 mmol) was dissolved in ethanol (25 mL), treated with 20% palladium hydroxide on carbon (0.357 g, 2.54 mmol) and stirred under a balloon filled with hydrogen for 16 h. The suspension was filtered through a pad of Celite and concentrated to give the product as an off-white solid (0.311 g, 95% yield). $^1$H NMR (400 MHz, DMSO-$d_6$) δ (ppm) 3.44 (q, J=6.98 Hz, 2H), 2.55-2.66 (m, 1H), 1.64 (dd, J=3.83, 12.96 Hz, 2H), 1.50 (d, J=13.03 Hz, 2H), 1.25-1.38 (m, 2H), 1.00-1.15 (m, 6H). MS (ESI) m/z 130.1 [M+1]$^+$.

Intermediate 45: tert-Butyl
4-methylenepiperidine-1-carboxylate

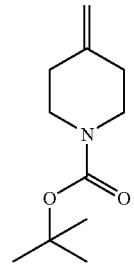

A. tert-Butyl 4-methylenepiperidine-1-carboxylate. To a solution of 1-benzyl-4-methylenepiperidine (1.0 g, 5.34 mmol) in dichloromethane (53.4 mL) at 0° C. was added dropwise 1-chloroethyl carbonochloridate (0.840 g, 5.87 mmol). The reaction was then heated to reflux temperature of the solvent for 2 h. The solvent was removed under reduced pressure and replaced with methanol (20 mL). The solution was then heated to 75° C. for 4 h. The solvent was removed under reduced pressure and the residue was dissolved in 5 mL of a 0.5 N aqueous solution of HCl. The solution was washed with diethyl ether 3 times and the aqueous phase was evaporated to dryness. Water was azeotroped with methanol (2×5 mL). LCMS analysis confirmed the consumption of the starting material. The material (colorless needles) was used without further purification.

A solution of 4-methylenepiperidine hydrochloride (0.714 g, 5.34 mmol) in dichloromethane (39.6 mL) was cooled to 0° C. and treated with triethyl amine (1.563 mL, 11.21 mmol) followed by di-tert-butyl dicarbonate (1.240 mL, 5.34 mmol). The bath was removed and the reaction was stirred at room temperature for 3 h. The reaction was washed with water and the organic phase was dried over magnesium sulfate and evaporated to dryness. The residue was purified by silica gel column chromatography (5-20% ethyl acetate in hexanes). tert-Butyl 4-methylenepiperidine-1-carboxylate (0.974 g, 4.94 mmol, 92% yield) was isolated as a colorless oil. $^1$H NMR (400 MHz, METHANOL-$d_4$) δ (ppm) 4.75 (s, 2H), 3.40 (t, J=5.86 Hz, 4H), 2.11-2.21 (m, 4H), 1.40-1.47 (m, 9H).

Intermediate 46:
tert-Butyldimethyl(4-methylenecyclohexyloxy)silane

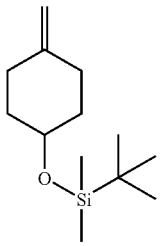

A. tert-Butyldimethyl(4-methylenecyclohexyloxy)silane. To a suspension of methyltriphenylphosphonium bromide (6.26 g, 17.51 mmol) in tetrahydrofuran (88 mL) at 0° C. was added dropwise a solution of n-butyl lithium in hexanes (2.5 M, 7.29 mL, 18.21 mmol) with vigorous stirring. The suspension became bright orange. The reaction was warmed to room temperature before a solution of 4-(tert-butyldimethylsilyloxy)cyclohexanone (4.0 g, 17.51 mmol) in dry tetrahydrofuran (10 mL) was added at room temperature. Upon addition, a yellow precipitate formed and became more abundant by the end of the addition. The reaction was stirred at room temperature for 24 h. The reaction was then decanted and filtered. The solid was washed with hexanes and the filtrate was evaporated to dryness. The residue was purified by column chromatography (2 columns, sample loaded as a solution in dichloromethane) and eluted with 5-10% ethyl acetate in hexanes. tert-Butyldimethyl(4-methylenecyclohexyloxy)silane (3.339 g, 14.75 mmol, 84% yield) was isolated as a light yellow-green oil. $^1$H NMR (400 MHz, METHANOL-$d_4$) δ (ppm) 4.52 (s, 2H), 3.76-3.86 (m, 1H), 2.23-2.32 (m, 2H), 1.92-2.03 (m, 2H), 1.61-1.74 (m, 2H), 1.35-1.49 (m, 2H), 0.78-0.85 (m, 9H), −0.04-0.03 (m, 6H).

Intermediate 47:
2-(5-Bromopyridin-2-yl)propan-2-ol

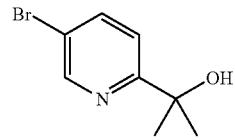

A. 2-(5-Bromopyridin-2-yl)propan-2-ol. 2,5-Dibromopyridine (15 g, 63.3 mmol) was dissolved in toluene (750 mL) and then cooled to −78° C. under nitrogen. n-Butyl lithium (1.7 M in pentane, 30.4 mL, 76 mmol) was added dropwise to the solution and then stirred for 2 h. To the solution was added acetone (5.58 mL, 76 mmol) and then stirred for 1 h at −78° C. The reaction was allowed to warm to −10° C. and then added with saturated ammonium chloride (150 mL). The reaction was extracted with ethyl acetate and water. The organic layer was dried over magnesium sulfate, filtered, and then concentrated. The residue was purified by silica gel chromatography (0-30% ethyl acetate in hexanes) to give a clear lightly color oil (11.6 g, 53.7 mmol, 85% yield). MS (ESI) m/z 216.1 [M]$^+$.

Intermediate 48: $N^2,N^2$-Dimethylpyridine-2,5-diamine

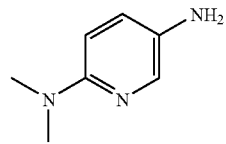

A. N,N-Dimethyl-5-nitropyridin-2-amine. 2-Bromo-5-nitropyridine (5 g, 24.8 mmol) in aqueous dimethylamine solution (33%, 20 mL) was stirred at room temperature overnight. The precipitate was collected by filtration and recrystallized from methanol to give N,N-dimethyl-5-nitropyridin-2-amine (2.6 g, 63% yield) as a solid. $^1$H NMR (400 MHz, DMSO-$d_6$) δ (ppm) 8.95 (d, J=2.0 Hz, 1H), 8.18 (dd, $J_1$=9.6 Hz, $J_2$=2.0 Hz, 1H), 6.73 (d, J=9.6 Hz, 1H), 3.18 (s, 6H).

B. $N^2,N^2$-Dimethylpyridine-2,5-diamine. A mixture of N,N-dimethyl-5-nitropyridin-2-amine (500 mg, 3 mmol) and 10% palladium on carbon (10% w/w, 50 mg) in ethanol (20 mL) was hydrogenated under 1 atm of hydrogen at room temperature for 1 h. The catalyst was filtered off, and the filtrate was concentrated to give N²,N²-dimethylpyridine-2,5-diamine (340 mg, 83% yield) as a ropy liquid. MS (ESI): m/z 138.1 [M+1]⁺.

Intermediate 49: 5-Aminonicotinamide

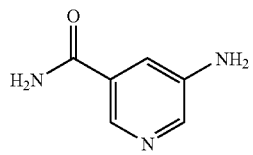

A. 5-Aminonicotinamide. A mixture of methyl 5-aminonicotinate (500 mg, 3.28 mmol) in a mixture of methanol (5 mL) and ammonium hydroxide (5 mL) was stirred at room temperature overnight. Water was added (30 mL), and the mixture was extracted with dichloromethane (15 mL×4). The combined organic layer was washed with brine (25 mL), dried over sodium sulfate and evaporated under reduced pressure to give 5-aminonicotinamide (300 mg, 67% yield) as a solid.

Intermediate 50: 5-Methoxypyridin-3-amine

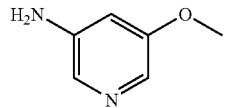

A. 2,6-Dibromopyridin-3-ol. An ice-cold solution of bromine (50 g, 320 mol) in 10% aqueous sodium hydroxide (320 mL) was added dropwise to a stirred solution of pyridin-3-ol (10 g, 105 mmol) in 10% aqueous sodium hydroxide (110 mL). The solution was stirred at 0° C. for 1 h and then at room temperature for 4 h. A small amount of white solid was filtered off. The filtrate was cooled, and concentrated hydrochloric acid was added until pH=1. The solid was filtered, washed with water, dried, and recrystallized from carbon tetrachloride to give 2,6-dibromo-pyridin-3-ol (9.93 g, 37% yield) as a solid. ¹H NMR (400 MHz, DMSO-d₆) δ (ppm) 11.17 (s, 1H), 7.47 (m, 1H), 7.25 (m, 1H); MS (ESI): m/z 253.7 [M+H]⁺.

B. 2,6-Dibromo-3-methoxypyridine. A mixture of 2,6-dibromopyridin-3-ol (9.49 g, 37.5 mmol), potassium carbonate (4.75 g, 34.4 mmol), dimethylsulfoxide (16 mL) and methyl iodide (8 mL) was refluxed for 2 h. The reaction mixture was poured into water (50 mL), the mixture was warmed gently with stirring, until the residual methyl iodide had evaporated. The methoxypyridine precipitated when the aqueous solution was cooled, and the solid was recrystallized from hexane to give 2,6-dibromo-3-methoxypyridine (4.0 g, 40% yield) as a solid. ¹H NMR (400 MHz, DMSO-d₆) δ (ppm) 7.66 (d, J=8.0 Hz, 1H), 7.52 (d, J=8.4 Hz, 1H), 3.89 (s, 3H); MS (ESI): m/z 267.6 [M+H]⁺.

C. 2,6-Dibromo-3-methoxy-5-nitropyridine. To a solution of 2,6-dibromo-3-methoxypyridine (4.0 g, 0.015 mol) in sulfuric acid (20 mL) was added a mixture of sulfuric acid and nitric acid (v/v, 1:1) (40 mL) at 0° C. The mixture was heated at 60-65° C. overnight, cooled, and neutralized with saturated aqueous sodium carbonate solution. The resulting mixture was extracted with ethyl acetate (50 mL×3). The combined organic layer was dried over sodium sulfate, and concentrated to give 2,6-dibromo-3-methoxy-5-nitropyridine (1.3 g, 28% yield) as a solid. ¹H NMR (400 MHz, DMSO-d₆) δ (ppm) 8.24 (s, 1H), 3.99 (s, 3H).

D. 5-Methoxypyridin-3-amine. A mixture of 2,6-dibromo-3-methoxy-5-nitropyridine (0.3 g, 0.98 mmol), 10% palladium on carbon (50% w/w, 30 mg) in methanol (20 mL) was hydrogenated under 1 atmosphere of hydrogen at room temperature overnight. The catalyst was filtered off, and the filtrate was concentrated under vacuum to give 5-methoxypyridin-3-amine (0.1 g, 92% yield). ¹H NMR (400 MHz, DMSO-d₆) δ (ppm) 7.54 (d, J=2.0 Hz, 1H), 7.45 (d, J=2.8 Hz, 1H), 6.48 (t, J=2.4 Hz, 1H), 5.31 (s, 2H), 3.71 (s, 3H).

Intermediate 51: 6-(4,4,5,5-Tetramethyl-1,3,2-dioxaborolan-2-yl)-1-(2-(trimethylsilyl)ethoxy)methyl)-1H-imidazo[4,5-b]pyridine

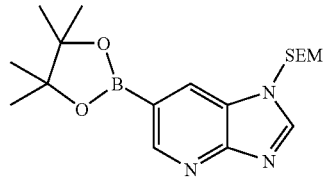

A. 6-Bromo-1H-imidazo[4,5-b]pyridine. A solution of 4-bromobenzene-1,2-diamine (2 g, 11 mmol) in formic acid (20 mL) was refluxed for 3 h. The reaction mixture was concentrated under reduced pressure to give 6-bromo-1H-imidazo[4,5-b]pyridine as a brown solid (2 g, 94% yield).

B. 6-Bromo-1-((2-(trimethylsilyl)ethoxy)methyl)-1H-imidazo[4,5-b]pyridine. To a solution of 6-bromo-1H-imidazo[4,5-b]pyridine (1 g, 5 mmol) in N,N-dimethylformamide (10 mL) was added sodium hydride (300 mg, 7.5 mmol) in portions at 0° C. After stirring for 0.5 h, (2-chloromethoxyethyl)-trimethylsilane (996 mg, 6 mmol) was added dropwise. The resulting mixture was stirred at room temperature overnight. Saturated aqueous ammonium chloride solution (20 mL) was added, and the mixture was extracted with ethyl acetate (15 mL×3). The combined organic layer was washed with brine (20 mL), dried over sodium sulfate, and concentrated. The residue was purified on silica gel column (eluting with 10-15% ethyl acetate in petroleum ether) to give 6-bromo-1-((2-(trimethylsilyl)ethoxy)methyl)-1H-imidazo[4,5-b]pyridine (600 mg, 36.6% yield) as a pale yellow oil. ¹H NMR (400 MHz, CHLOROFORM-d) δ (ppm) 8.47 (s, 1H), 8.23 (s 1H), 8.19 (s, 1H), 5.65 (s, 2H), 3.61 (m, 2H), 0.93 (m, 2H), 0.04 (s, 9H).

C. 6-(4,4,5,5-Tetramethyl-1,3,2-dioxaborolan-2-yl)-1-((2-(trimethylsilyl)ethoxy)methyl)-1H-imidazo[4,5-b]pyridine. A mixture of 6-bromo-1-((2-(trimethylsilyl)ethoxy)methyl)-1H-imidazo[4,5-b]pyridine (400 mg, 1.22 mmol), bis(pinacolato)diboron (466 mg, 1.83 mmol), tricyclohexylphosphine (68 mg, 0.24 mmol), tris(dibenzylideneacetone)palladium(0) (112 mg, 0.12 mmol) and potassium acetate (240 mg, 2.4 mmol) in dioxane (10 mL) was degassed and heated at 100° C. under nitrogen overnight. The reaction mixture was filtered, and the filtrate was concentrated under vacuo to give the crude product, which was purified on silica gel column (eluting with 0-1% methanol in dichloromethane) to give 6-(4,4,5,5-tetramethyl-1,3,2-dioxaborolan-2-yl)-1-((2-(trimethylsilyl)ethoxy)methyl)-1H-imidazo[4,5-b]pyridine (330 mg, 72% yield) as an oil. ¹H NMR (400 MHz, CHLOROFORM-d) δ (ppm) 8.78 (s, 1H), 8.49 (s, 1H), 8.21 (s, 1H), 5.70 (s, 2H), 3.61 (t, J=8.0 Hz, 2H), 1.36 (s, 12H), 0.92 (t, J=8.0 Hz, 2H), 0 (s, 9H); MS (ESI): m/z 376.1 [M+1]$^+$.

Intermediate 52: 2-Methylpyridin-4-amine

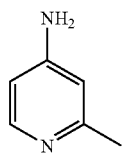

A. 2-Methylpyridin-4-amine. A mixture of 2-methyl-4-nitropyridine (500 mg, 3.6 mmol) and iron dust (1 g, 18 mmol) in acetic acid (20 mL) was stirred 110° C. for 4 h. The reaction mixture was filtered, and the filtrate was concentrated under reduced pressure. The residue was purified by preparative TLC (eluting with 5% methanol in dichloromethane) to give 2-methylpyridin-4-amine (100 mg, 26% yield) as a solid. $^1$H NMR (400 MHz, DMSO-d$_6$) δ (ppm) 7.81 (d, J=5.6 Hz, 1H), 6.28 (s, 1H), 6.25 (d, J=5.6 Hz, 1H), 5.82 (br s, 2H), 2.19 (s, 3H).

Intermediate 53: 2-(Benzyloxy)pyridin-4-amine

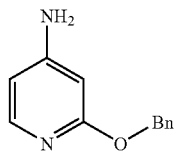

A. 2-(Benzyloxy)pyridin-4-amine. To a solution of benzyl alcohol (2.53 g, 23.4 mmol) in dioxane (10 mL) was added sodium hydride (1.15 g, 28.75 mmol) at room temperature, and the mixture was refluxed for 1.5 h. After cooling down to room temperature, 2-chloropyridin-4-amine (1.5 g, 11.7 mmol) was added and the mixture was heated to 160° C. for 12 h under nitrogen. After cooling down to room temperature, the reaction mixture was poured into water (30 mL), and the mixture was extracted with ethyl acetate (20 mL×3). The organic layer was concentrated under reduced pressure, and the residue was purified on silica gel column (eluting with 10% methanol in ethyl acetate) to give 2-(benzyloxy)pyridin-4-amine (800 mg, 34.1% yield) as a solid. $^1$H NMR (400 MHz, CHLOROFORM-d) δ (ppm) 7.95 (d, J=5.6 Hz, 1H), 7.51 (br s, 5H), 6.27 (s, 1H), 6.01 (s, 1H), 5.39 (s, 2H), 4.11 (br s, 2H).

Intermediate 54: 2-Methoxypyridin-4-amine

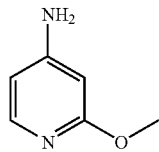

A. 2-Methoxypyridin-4-amine. A mixture of methanol (10 mL) and sodium hydride (60% in mineral oil, 624 mg, 15.6 mmol) was refluxed for 1.5 h. The mixture was cooled down to room temperature, and 2-chloropyridin-4-amine (1.0 g, 7.8 mmol) was added. The reaction mixture was heated to 160° C. for 12 h under nitrogen. After cooling down to room temperature, the reaction mixture was poured into water (30 mL), and the mixture was extracted with ethyl acetate (15 mL×3). The combined organic layer was concentrated under reduced pressure, and the residue was purified on silica gel column (eluting with 10% methanol in ethyl acetate) to give 2-methoxypyridin-4-amine (210 mg, 21.6% yield) as a solid. $^1$H NMR (400 MHz, CHOLOROFORM-d) δ (ppm) 7.83 (d, J=6.0 Hz, 1H), 6.21 (dd, J$_1$=2.0 Hz, J$_1$=6.0 Hz, 1H), 5.93 (d, J=1.6 Hz, 1H), 4.07 (br s, 2H), 3.87 (s, 3H).

Intermediate 55: N$^2$-(4-Methoxybenzyl)-N$^2$-methylpyridine-2,4-diamine

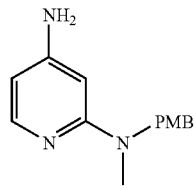

A. N-(4-Methoxybenzyl)-N-methyl-4-nitropyridin-2-amine. A solution of 2-chloro-4-nitropyridine (1.0 g, 6.3 mmol) and 1-(4-methoxyphenyl)-N-methylmethanamine (1.5 g, 9.6 mmol) in dimethoxyethane (15 mL) was stirred at 100° C. for 4 h. The solvent was evaporated under reduced pressure to give the crude product, which was purified on silica gel column (eluting with petroleum ether) to give N-(4-methoxybenzyl)-N-methyl-4-nitropyridin-2-amine (0.65 g, 38% yield). $^1$H NMR (400 MHz, DMSO-d$_6$) δ (ppm) 8.39 (d, J=4.2 Hz, 1H), 7.22 (m, 2H), 7.16 (d, J=8.8 Hz, 2H), 6.88 (d, J=8.4 Hz, 2H), 4.80 (s, 2H), 3.71 (s, 3H), 3.10 (s, 3H).

B. N$^2$-(4-Methoxybenzyl)-N$^2$-methylpyridine-2,4-diamine. A mixture of N-(4-methoxybenzyl)-N-methyl-4-nitropyridin-2-amine (0.5 g, 1.83 mmol) and 10% palladium on carbon (50 mg, 50% w/w) in methanol (20 mL) under 1 atmosphere of hydrogen was stirred at room temperature overnight. The reaction mixture was filtered, and the filtrate was concentrated to give N$^2$-(4-methoxy-benzyl)-N$^2$-methyl-pyridine-2,4-diamine (0.41 g, 92% yield). $^1$H NMR (400 MHz, DMSO-d$_6$) δ (ppm) 7.60 (d, J=5.6 Hz, 1H), 7.10 (d, J=8.4 Hz, 2H), 6.85 (d, J=8.8 Hz, 2H), 5.86 (m, 1H), 5.69 (d, J=1.6 Hz, 1H), 5.60 (s, 2H), 4.62 (s, 2H), 3.71 (s, 3H) 2.84 (s, 3H); MS (ESI): m/z 244.0 [M+1]$^+$.

Intermediate 56: 1-Methyl-1H-indazol-6-amine

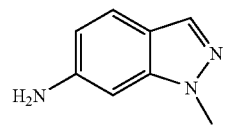

A. 1-Methyl-6-nitro-1H-indazole. A mixture of 6-nitro-1H-indazole (3.3 g, 20 mmol) and sodium hydride (60% in mineral oil, 1.2 g, 30 mmol) in N,N-dimethylformamide (15 mL) was stirred at 0° C. for 1 h. Methyl iodide (8.52, 60 mmol) was added, and the reaction mixture was stirred at room temperature overnight. The reaction mixture was quenched with water (50 mL) and extracted with ethyl acetate (50 mL×3). The combined organic layer was dried over anhydrous sodium sulfate, filtered and concentrated under reduced pressure. The residue was purified on silica gel column (eluting with 2-5% ethyl acetate in petroleum ether) to give 1-methyl-6-nitro-1H-indazole (1.9 g, 53% yield). $^1$H NMR (400 MHz, DMSO-$d_6$) δ (ppm) 8.52 (m, 1H), 8.08 (d, J=1.2 Hz, 1H), 7.81 (m, 2H), 3.98 (s, 3H).

B. 1-Methyl-1H-indazol-6-amine. A mixture of 1-methyl-6-nitro-1H-indazole (1 g, 5.6 mmol) in ethanol (50 mL) and 10% palladium on carbon (50% w/w, 100 mg) was hydrogenated under 1 atmosphere of hydrogen at room temperature for 2 h. The catalyst was filtered off, and the filtrate was evaporated to afford 1-methyl-1H-indazol-6-ylamine (790 mg, 95.1%) as a solid. $^1$H NMR (400 MHz, DMSO-$d_6$) δ (ppm) 7.67 (s, 1H), 7.33 (d, J=8.4 Hz, 1H), 7.49 (m, 2H), 5.31 (br s, 2H), 3.80 (s, 3H).

Intermediate 57: 3-Methyl-1-((2-(trimethylsilyl)ethoxy)methyl)-1H-indazol-6-amine

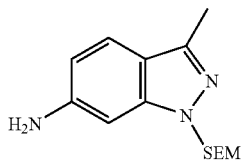

A. 3-Iodo-6-nitro-1H-indazole. A solution of 6-nitro-1H-indazole (2.0 g, 12 mmol) in a mixture of 1,4-dioxane (50 mL) and aqueous sodium hydroxide solution (7.5 mL, 2 M) was stirred at room temperature for about 1 h. Iodine crystals (3.8 g, 15 mmol) were added, and the reaction mixture was stirred at room temperature for 12 h. The reaction mixture was quenched with 10% citric acid aqueous solution, and extracted with ethyl acetate (100 mL×3). The organic layer was washed with 10% sodium bicarbonate aqueous (100 mL), and brine (100 mL), dried over sodium sulfate, filtered, and concentrated to provide 3-iodo-6-nitro-1H-indazole (3.2 g, 92% yield) as an orange solid. MS (ESI): m/z 289.9 [M+1]$^+$.

B. 3-Iodo-6-nitro-1-((2-(trimethylsilyl)ethoxy)methyl)-1H-indazole. To a solution of 3-iodo-6-nitro-1H-indazole (1.45 g, 5 mmol) in N,N-dimethylformamide (10 mL) was added sodium hydride (60% in mineral oil, 0.24 g, 6 mmol) at 0° C. After stirring for 1 h, (2-chloromethoxyethyl)trimethylsilane (1.0 g, 6 mmol) was added dropwise to the above mixture at 0° C., and the reaction mixture was stirred at room temperature overnight. Water (50 mL) was added, and the mixture was extracted with ethyl acetate (30 mL×4). The combined organic layer was dried and evaporated under reduced pressure, and the residue was purified on silica gel column (eluting with 2-5% ethyl acetate in petroleum ether) to give 3-iodo-6-nitro-1-((2-(trimethylsilyl)ethoxy)methyl)-1H-indazole (0.78 g, 37% yield). MS (ESI): m/z 420.9 [M+1]$^+$.

This reaction was also carried out using tetrahydrofuran as solvent, providing a yield of 57% of 3-iodo-6-nitro-1-((2-(trimethylsilyl)ethoxy)methyl)-1H-indazole.

C. 3-Methyl-6-nitro-1-((2-(trimethylsilyl)ethoxy)methyl)-1H-indazole. A degassed mixture of 3-iodo-6-nitro-1-((2-(trimethylsilyl)ethoxy)methyl)-1H-indazole (754 mg, 1.8 mmol), methylboronic acid in tetrahydrofuran (432 mg, 3.6 mmol), aqueous solution of potassium phosphate (2 M, 5 mL), and tetrakis(triphenylphosphine)palladium(0) (104 mg, 0.09 mmol) in dioxane (5 mL) was heated at 100° C. overnight. The solvent was removed under reduced pressure, and the residue was purified on silica gel column (eluting with 25-50% ethyl acetate in petroleum ether) to give 3-methyl-6-nitro-1-((2-(trimethylsilyl)ethoxy)methyl)-1H-indazole (0.48 g, crude). MS (ESI): m/z 308.1 [M+1]$^+$.

This reaction can also be carried out in anhydrous dioxane using 3 equivalents of methylboronic acid, 3 equivalents of cesium carbonate as base and 0.1 equivalents of tetrakis(triphenylphosphine)palladium(0) at 90° C. overnight. Following this procedure, 3-methyl-6-nitro-1-((2-(trimethylsilyl)ethoxy)methyl)-1H-indazole was obtained in 82% yield after chromatography.

D. 3-Methyl-1-((2-(trimethylsilyl)ethoxy)methyl)-1H-indazol-6-amine. To a solution of 3-methyl-6-nitro-1-((2-(trimethylsilyl)ethoxy)methyl)-1H-indazole (0.48 g, crude) in methanol (5 mL) was added 10% palladium on carbon (0.3 g, 50% w/w), and the mixture was hydrogenated under 1 atmosphere of hydrogen at room temperature for 30 min. The catalyst was filtered off, and the filtrate was concentrated. The residue was purified on silica gel column (eluting with 3-5% ethyl acetate in petroleum ether) to give 3-methyl-1-((2-(trimethylsilyl)ethoxy)methyl)-1H-indazol-6-amine (138 mg, 32% yield). $^1$H NMR (400 MHz, CHLOROFORM-d) δ (ppm) 7.42 (d, J=8.4 Hz, 1H), 6.66 (d, J=2.0 Hz, 1H), 6.58 (dd, $J_1$=2.0 Hz, $J_2$=8.4 Hz, 1H), 5.54 (s, 2H), 5.34 (s, 2H), 3.89 (br s, 2H), 3.56 (t, J=8.0 Hz, 2H), 2.48 (s, 3H), 0.91 (m, 2H), −0.05 (d, J=3.2 Hz, 9H).

The yield of this step was increased to 100% when purified 3-methyl-6-nitro-1-((2-(trimethylsilyl)ethoxy)methyl)-1H-indazole was used, eliminating the need for chromatography.

Intermediate 58: 4-(4-(4,4,5,5-Tetramethyl-1,3,2-dioxaborolan-2-yl)phenyl)-14(2-(trimethylsilyl)ethoxy)methyl)-1H-imidazole

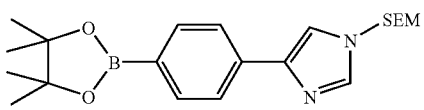

A. 4-(4-Bromophenyl)-1-((2-(trimethylsilyl)ethoxy)methyl)-1H-imidazole. To a stirred solution of 4-(4-bromophenyl)-1H-imidazole (446 mg, 2 mmol) in anhydrous N,N-dimethylformamide (10 mL) was added sodium hydride (60% in mineral oil, 96 mg, 2.4 mmol) at 0° C., and the mixture was stirred at this temperature for 2 h. A solution of (2-(chloromethoxy)ethyl)trimethylsilane (545 mg, 3 mmol) in N,N-dimethylformamide (5 mL) was added dropwise, and the resulting mixture was stirred at room temperature for 4 h. When the starting material was consumed, the reaction was quenched with water (50 mL), and the mixture was extracted with ethyl acetate (15 mL×3). The combined organic layer was washed with brine (20 mL), dried over anhydrous sodium sulfate, and evaporated in vacuo. The residue was purified on silica gel column (eluting with 5-10% ethyl acetate in petroleum ether) to give 4-(4-bromophenyl)-1-((2-(trimethylsilyl)ethoxy)methyl)-1H-imidazole (440 mg, 62% yield). $^1$H NMR (400 MHz, DMSO-$d_6$) δ (ppm) 7.80-7.84 (m, 2H), 7.71 (d, J=8.4 Hz, 2H), 7.52 (d, J=8.4 Hz, 2H), 5.32 (s, 2H), 3.49 (t, J=8.0 Hz, 2H), 0.84 (t, J=8.0 Hz, 2H), −0.06 (s, 9H); MS (ESI): m/z 353.0 [M+1]$^+$.

B. 4-(4-(4,4,5,5-Tetramethyl-1,3,2-dioxaborolan-2-yl)phenyl)-1-((2-(trimethylsilyl)ethoxy)methyl)-1H-imidazole. A degassed mixture of 4-(4-bromophenyl)-1-((2-(trimethylsilyl)ethoxy)methyl)-1H-imidazole (200 mg, 0.56 mmol), bis(pinacolato)diboron (158 mg, 0.62 mmol), potassium acetate (139 mg, 1.42 mmol) and [1,1'-bis(diphenylphosphino)ferrocene]dichloropalladium(II) (42 mg, 0.06 mmol) in N,N-dimethylformamide (5 mL) was stirred at 80° C. overnight. The reaction mixture was poured into ice water (30 mL), and the mixture was extracted with ethyl acetate (15 mL×2). The organic layer was dried over sodium sulfate and evaporated in vacuo. The residue was purified on silica gel column (eluting with 10-20% ethyl acetate in petroleum ether) to give 4-(4-(4,4,5,5-tetramethyl-1,3,2-dioxaborolan-2-yl)phenyl)-1-((2-(trimethylsilyl)ethoxy)methyl)-1H-imidazole (120 mg, 62% yield). $^1$H NMR (400 MHz, CHLOROFORM-d) δ (ppm) 7.90 (s, 1H), 7.77 (s, 4H), 7.69 (s, 1H), 5.42 (s, 2H), 3.62 (t, J=8.0 Hz, 2H), 1.37 (s, 12H), 0.94 (t, J=8.0 Hz, 2H), 0.01 (s, 9H); MS (ESI): m/z 386.2 [M+1]$^+$.

Intermediate 59: tert-Butyl 3-(4,4,5,5-tetramethyl-1,3,2-dioxaborolan-2-yl)phenethylcarbamate

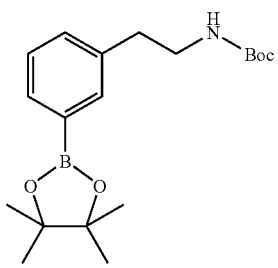

A. tert-Butyl 3-bromophenethylcarbamate. A mixture of 2-(3-bromophenyl)ethanamine (1 g, 5.03 mmol), di-tert-butyl dicarbonate (1.64 mg, 7.5 mmol) in dichloromethane (20 mL) was stirred at room temperature for 1 h. The solvent was removed to give tert-butyl 3-bromophenethylcarbamate (1.5 g, 99.1% yield) as a solid. $^1$H NMR (400 MHz, DMSO-d$_6$) δ (ppm) 7.37 (d, J=7.6 Hz, 2H), 7.23 (m, 2H), 6.87 (t, J=5.6 Hz, 1H), 3.13 (m, 2H), 2.69 (t, J=7.2 Hz, 2H), 1.35 (s, 9H).

B. tert-Butyl 3-(4,4,5,5-tetramethyl-1,3,2-dioxaborolan-2-yl)phenethylcarbamate. A degassed mixture of tert-butyl 3-bromophenethylcarbamate (1.9 g, 6.35 mmol), bis(pinacolato)diboron (2.4 g, 9.53 mmol), potassium acetate (1.56 g, 19 mmol), and[1,1'-bis(diphenylphosphino)ferrocene]dichloropalladium(II) (475 mg, 0.64 mmol) in dioxane (20 mL) was heated at 100° C. under nitrogen for 2 h. The reaction mixture was poured into water (50 mL), and the mixture was extracted with ethyl acetate (20 mL×2). The combined organic layer was dried over anhydrous sodium sulfate, and evaporated under reduced pressure. The residue was purified on silica gel column (eluting with 0-5% ethyl acetate in petroleum ether) to give tert-butyl 3-(4,4,5,5-tetramethyl-1,3,2-dioxaborolan-2-yl)phenethylcarbamate (1.9 g, 86.4% yield) as a solid. $^1$H NMR (400 MHz, DMSO-d$_6$) δ (ppm) 7.48 (m, 2H), 7.30 (m, 2H), 6.86 (t, J=5.6 Hz, 1H), 3.10 (m, 2H), 2.68 (t, J=7.2 Hz, 1H), 1.29 (s, 12H), 1.16 (s, 9H).

Intermediate 60: 3-(3-(4,4,5,5-Tetramethyl-1,3,2-dioxaborolan-2-yl)phenyl)propanenitrile

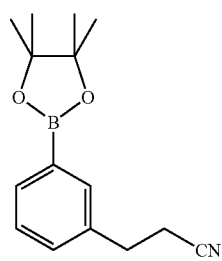

A. 3-(3-(4,4,5,5-Tetramethyl-1,3,2-dioxaborolan-2-yl)phenyl)propanenitrile. A degassed mixture of 3-(3-bromophenyl)propanenitrile (1.05 g, 5 mmol), bis(pinacolato)diboron (1.9 g, 7.5 mmol), potassium acetate (1.47 g, 15 mmol) and [1,1'-bis(diphenylphosphino)ferrocene]dichloropalladium(II) (0.37 g, 0.5 mmol) in dioxane (10 mL) was heated at 120° C. under nitrogen for 4 h. The reaction mixture was filtered, and the filtrate was concentrated. The residue was purified by column chromatography on silica gel (eluting with 5% ethyl acetate in petroleum ether) to give 3-(3-(4,4,5,5-tetramethyl-1,3,2-dioxaborolan-2-yl)phenyl)propanenitrile (1 g, 74% yield) as a colorless oil. $^1$H NMR (400 MHz, CHLOROFORM-d) δ (ppm) 7.73-7.70 (m, 2H), 7.64 (s, 1H), 7.36-7.32 (m, 2H), 2.97 (t, J=7.6 Hz, 2H), 2.63 (t, J=7.6 Hz, 2H), 1.35 (s, 12H).

Intermediate 61: 6-Methoxypyridin-2-amine

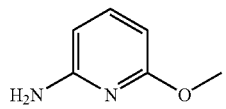

A. 6-Methoxypyridin-2-amine. A mixture of sodium (0.8 g, 34.8 mmol) in methanol (20 mL) was refluxed at 80° C. After the sodium was consumed, 6-bromopyridin-2-amine (3 g, 17.4 mmol) was added and the reaction mixture was heated to 160° C. in an autoclave for 3 h. After cooling down to room temperature, ethyl acetate (30 mL) was added, and the mixture was filtered. The filtrate was concentrated in vacuo to give 6-methoxypyridin-2-amine (1.4 g, 63.6% yield). $^1$H NMR (400 MHz, CHLOROFORM-d) δ (ppm) 7.33 (t, J=8.0 Hz, 1H), 6.06 (m, 2H), 3.83 (s, 1H).

Intermediate 62: 4-(4,4,5,5-Tetramethyl-1,3,2-dioxaborolan-2-yl)picolinonitrile

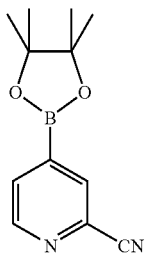

A. 4-Bromopyridine 1-oxide. To a suspension of 4-bromopyridine hydrochloride (5.0 g, 25.9 mmol) in dichloromethane (50 mL) was added triethylamine (2.62 g, 25.9 mmol) at room temperature. After stirring for 0.5 h, 3-chlorobenzoperoxoic acid (4.46 g, 25.9 mmol) was added in portions, and the reaction mixture was stirred at room temperature for 5 h. The solution was washed with saturated aqueous sodium thiosulfate solution (30 mL), saturated aqueous sodium carbonate solution (30 mL) and brine (30 mL), and dried over sodium sulfate. The solvent was removed under reduced pressure to give the crude product, which was purified on silica gel column (eluting with 50-100% ethyl acetate in methanol) to give 4-bromopyridine 1-oxide as a solid (2.1 g, 44.8% yield).

B. 4-Bromopicolinonitrile. A mixture of 4-bromopyridine 1-oxide (2.0 g, 11.56 mmol), trimethylsilyl cyanide (3.43 g, 34.68 mmol) and triethylamine (2.34 g, 23.12 mmol) in acetonitrile (10 mL) was stirred at 110° C. under nitrogen for 3 h. The reaction mixture was concentrated under reduced pressure, and the residue was purified on silica gel column (eluting with 20% ethyl acetate in petroleum ether) to give 4-bromopicolinonitrile (1.52 g, 72.4% yield). $^1$H NMR (400 MHz, CHLOROFORM-d) δ (ppm) 8.56 (d, J=4.2 Hz, 1H), 7.88 (s, 1H), 7.73 (d, J=4.2 Hz, 1H).

C. 4-(4,4,5,5-Tetramethyl-1,3,2-dioxaborolan-2-yl)picolinonitrile. A degassed mixture of 4-bromopicolinonitrile (1.50 g, 8.24 mmol), bis(pinacolato)diboron (4.19 g, 16.48 mmol), [1,1'-bis(diphenylphosphino)ferrocene]dichloropalladium (II) (600 mg, 0.82 mmol) and potassium acetate (2.0 g, 20.6 mmol) in dioxane (10 mL) was heated at 100° C. under nitrogen overnight. The reaction mixture was filtered, and the filtrate was concentrated in vacuo to give the crude product, which was purified on silica gel chromatography (eluting with 0-30% of ethyl acetate in petroleum ether) to give 4-(4,4,5,5-tetramethyl-1,3,2-dioxaborolan-2-yl)picolinonitrile (1.8 g, 9.2% yield) as a solid. $^1$H NMR (400 MHz, CHLOROFORM-d) δ (ppm) 8.73 (d, J=3.3 Hz, 1H), 8.02 (s, 1H), 7.83 (d, J=3.6 Hz, 1H), 1.35 (s, 12H).

Intermediate 63: tert-Butyl 2-(4-aminopyridin-2-yloxy)ethylcarbamate

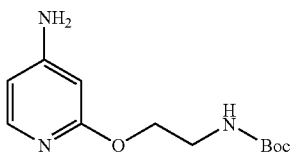

A. 2-Chloropyridin-4-amine. To a solution of 2-chloro-4-nitropyridine (13 g, 82.3 mmol) in a mixture of 80% aqueous ethanol (50 mL) and concentrated hydrochloric acid (5 mL) was added iron powder (20 g, 357.1 mmol) and the mixture was refluxed for 3 h. Sodium carbonate was added to neutralize the residual acid. The resulting mixture was filtered through Celite and was concentrated. The residue was purified on silica gel column (eluting with 0-10% methanol in dichloromethane) to give 2-chloropyridin-4-amine (6.8 g, 53.1 mmol, 64.5% yield) as a solid. $^1$H NMR (400 MHz, CHLOROFORM-d) δ (ppm) 7.92 (t, J=7.6 Hz, 1H), 6.47 (d, J=2.0 Hz, 1H), 6.38 (dd, J$_1$=7.6 Hz, J$_2$=2.0 Hz, 1H), 4.36 (br s, 2H).

B. 2-(2-Aminoethoxy)-pyridin-4-amine. A mixture of 2-aminoethanol (2.1 g, 34.4 mmol) and sodium hydride (825 mg, 34.4 mmol) in dioxane (20 mL) was refluxed for 1.5 h, and the mixture was cooled down to room temperature, and 2-chloropyridin-4-amine (4.0 g, 31.3 mmol) was added. The resulting mixture was heated to 160° C. under nitrogen for 12 h. After cooling down to room temperature, the reaction mixture was poured into water (50 mL). The mixture was extracted with ethyl acetate (30 mL×3), the organic layer was combined, dried and concentrated under reduced pressure. The residue was purified on silica gel column (eluting with 10% methanol in ethyl acetate) to give 2-(2-aminoethoxy)-pyridin-4-amine (1.0 g, 20.9% yield) as a solid. MS (ESI): m/z 154.2 [M+1]$^+$.

C. tert-Butyl 2-(4-aminopyridin-2-yloxy)ethylcarbamate. A mixture of 2-(2-aminoethoxy)-pyridin-4-amine (1.0 mg, 6.54 mmol), di-tert-butyl dicarbonate (1.42 mg, 6.54 mmol) in dichloromethane (20 mL) was stirred at room temperature for 1 h. The solvent was removed, and the residue was purified on silica gel column chromatography (eluting with 30-50% ethyl acetate in petroleum ether) to give tert-butyl 2-(4-aminopyridin-2-yloxy)ethylcarbamate (900 mg, 54.5% yield) as a solid. $^1$H NMR (400 MHz, DMSO-d$_6$) δ (ppm) 7.59 (d, J=6.0 Hz, 1H), 6.90 (br s, 1H), 6.15 (dd, J$_1$=2.0 Hz, J$_2$=5.6 Hz, 1H), 5.90 (br s, 2H), 5.78 (d, J=1.6 Hz, 1H), 4.10 (t, J=6.0 Hz, 2H), 3.22 (m, J=6.0 Hz, 2H), 1.37 (s, 9H).

Intermediate 64: 6-(Benzyloxy)pyridin-2-amine

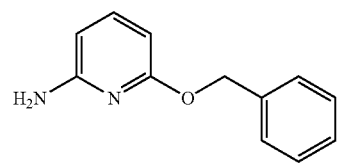

A. 6-(Benzyloxy)pyridin-2-amine. A mixture of sodium (0.54 g, 23.2 mmol) and benzyl alcohol (2.5 g, 23.2 mmol) in dioxane (20 mL) was refluxed. When the sodium was consumed, the dioxane was removed, and 6-bromopyridin-2-amine (2 g, 11.6 mmol) was added. The mixture was heated at 160° C. for 3 h. After cooling down to room temperature, the reaction mixture was diluted with ethyl acetate, washed with water and brine, dried over anhydrous sodium sulfate, and evaporated under reduced pressure. The residue was purified on silica gel column (eluting with 10-100% ethyl acetate in petroleum ether) to give 6-(benzyloxy)pyridin-2-amine (0.6 g, 26% yield). $^1$H NMR (400 MHz, METHANOL-d$_4$) δ (ppm) 7.83 (t, J=8.8 Hz, 1H), 7.45 (d, J=7.2 Hz, 2H), 7.37 (d, J=7.6 Hz, 2H), 7.28 (d, J=6.4 Hz, 1H), 6.49 (d, J=8.8 Hz, 1H), 6.39 (d, J=8.4 Hz, 1H), 5.29 (s, 2H).

Intermediate 65: 2-Fluoropyridin-3-amine

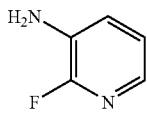

A. 2-Fluoropyridin-3-amine. To a solution of 2-fluoro-3-nitropyridine (600 mg, 4.2 mmol) in 80% aqueous ethanol (50 mL) and concentrated hydrochloric acid (1 mL) was added iron powder (2.4 g, 42 mmol), and the mixture was refluxed for 3 h. Sodium carbonate was added to neutralize the residual acid, and the resulting mixture was filtered through Celite. The filtrate was concentrated to dryness, and the residue was purified on silica gel column (eluting with 0-10% methanol in dichloromethane) to give 2-fluoropyridin-3-amine (300 mg, 63% yield) as a solid. MS (ESI): m/z 112.9 [M+1]$^+$.

Intermediate 66: 1-((2-(Trimethylsilyl)ethoxy)methyl)-1H-pyrrolo[2,3-b]pyridin-5-amine

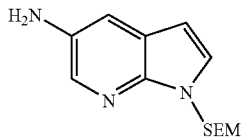

A. 1-((2-(Trimethylsilyl)ethoxy)methyl)-1H-pyrrolo[2,3-b]pyridin-5-amine. To a solution of 1H-pyrrolo[2,3-b]pyridin-5-amine (250 mg, 1.88 mmol) in N,N-dimethylformamide (10 mL) was added sodium hydride (75 mg, 1.88 mmol) in portions at 0° C. under nitrogen. The reaction mixture was stirred at this temperature for 1 h, 2-(trimethylsilyl)ethoxymethyl chloride (312 g, 1.88 mmol) was added dropwise, and the resulting mixture was stirred at room temperature overnight. When TLC indicated the starting material was consumed, the solvent was removed under reduced pressure. The residue was diluted with ethyl acetate, the organic layer was washed with water and brine, dried, and evaporated. The crude product was purified on silica gel column (eluting with 10% ethyl acetate in petroleum ether) to give 14(2-(trimethylsilyl)ethoxy)methyl)-1H-pyrrolo[2,3-b]pyridin-5-amine (300 mg, 67.6% yield) as a solid. $^1$H NMR (400 MHz, CHOLOROFORM-d) δ (ppm) 7.93 (d, J=2.4 Hz, 1H), 7.27 (m, 2H), 6.34 (d, J=3.6 Hz, 1H), 5.60 (s, 2H), 3.54 (m, 4H), 0.92 (m, 2H), −0.05 (s, 9H).

Intermediate 67: tert-Butyl 3-hydroxypropylcarbamate

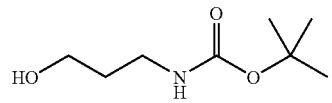

A. tert-Butyl 3-hydroxypropylcarbamate. To a solution of 3-aminopropan-1-ol (4.6 g, 61 mmol) in dichloromethane (40 mL) was added a solution of di-tert-butyl dicarbonate (14 g, 64 mmol) in dichloromethane (40 mL) in 30 min, and the mixture was stirred at room temperature for 5 h. The reaction mixture was washed with water and brine, dried over sodium sulfate, and concentrated under reduced pressure to give the crude product, which was washed with petroleum ester and dried to give tert-butyl 3-hydroxypropylcarbamate (8.9 g, 83.1% yield) as a colorless oil.

Intermediate 68: N$^2$-Methylpyridine-2,5-diamine

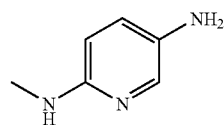

A. N-Methyl-5-nitropyridin-2-amine. A solution of 2-bromo-5-nitropyridine (1.2 g, 5.9 mmol) in methylamine (aqueous solution, 10 mL) was stirred at room temperature for 5 h. Brine was added, and the precipitate was collected and washed with water to give N-methyl-5-nitropyridin-2-amine (870 mg, 96% yield) as a solid.
B. N$^2$-Methylpyridine-2,5-diamine. A mixture of N-methyl-5-nitropyridin-2-amine (870 mg, 5.7 mmol) and 10% palladium on charcoal (50% wet, w/w, 170 mg) in methanol was hydrogenated under 1 atmosphere of hydrogen for 4 h. The catalyst was filtered off, and the filtrate was concentrated. The residue was purified on silica gel column (eluting with 10-33% ethyl acetate in petroleum ether) to afford N$^2$-methylpyridine-2,5-diamine (300 mg, 42% yield) as an oil. $^1$H NMR (400 MHz, CHLOROFORM-d) δ (ppm) 7.63 (s, 1H), 6.90 (d, J=8.4 Hz, 1H), 6.25 (d, J=8.4 Hz, 1H), 4.05 (br s, 1H), 3.15 (br s, 1H), 2.77 (s, 3H).

Intermediate 69: 6-(4-(tert-Butyldimethylsilyloxy)piperidin-1-yl)pyridin-3-amine

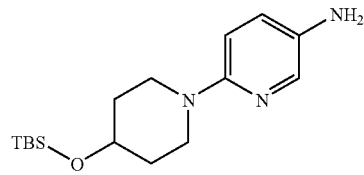

A. 1-(5-Nitropyridin-2-yl)piperidin-4-ol. A mixture of 2-bromo-5-nitropyridine (1 g, 4.98 mmol), piperidin-4-ol (503 mg, 4.98 mmol), triethylamine (503 mg, 4.98 mmol) in N,N-dimethylformamide (10 mL) was stirred at room temperature for 3 h. The reaction mixture was concentrated in vacuo to give the crude product, which was purified on silica gel chromatography (eluting with 10% ethyl acetate in petroleum ether) to give 1-(5-nitropyridin-2-yl)piperidin-4-ol (1 g, 90.5% yield).

B. 2-(4-(tert-Butyldimethylsilyloxy)piperidin-1-yl)-5-nitropyridine. To a solution of 1-(5-nitropyridin-2-yl)piperidin-4-ol (2 g, 8.96 mmol) and tert-butylchlorodimethylsilane (1.34 g, 8.96 mmol) in N,N-dimethylformamide (15 mL) was added dropwise a solution of triethylamine (0.9 g, 8.96 mmol) and 4-(dimethylamino)pyridine (110 mg, 0.896 mmol) in N,N-dimethylformamide (5 mL) at 0° C. After stirring for one hour, the reaction mixture was partitioned between water and ethyl acetate. The organic layer was separated, washed with water and saturated sodium chloride aqueous solution, and dried over anhydrous sodium sulfate. The solvent was removed under reduced pressure, and the residue was purified on silica gel column (eluting with 20% ethyl acetate in petroleum ether) to give 2-4-(tert-butyldimethylsilyloxy)piperidin-1-yl-5-nitropyridine (2 g, 75% yield).

C. 6-(4-(tert-Butyldimethylsilyloxy)piperidin-1-yl)pyridin-3-amine. A mixture of 2-(4-(tert-butyldimethylsilyloxy) piperidin-1-yl)-5-nitropyridine (500 mg, 1.48 mmol), 10% palladium on carbon (50% wet, 50 mg) in methanol (2 mL) was hydrogenated under 1 atmosphere of hydrogen at room temperature overnight. The reaction mixture was filtered, and the filtrate was concentrated under vacuum to give the crude product, which was purified on silica gel column (eluting with 50% ethyl acetate in petroleum ether) to give 6-(4-(tert-butyldimethylsilyloxy)piperidin-1-yl)pyridin-3-amine (200 mg, 44.0% yield).

Intermediate 70:
2-(2-(Pyrrolidin-1-yl)ethoxy)pyridin-4-amine

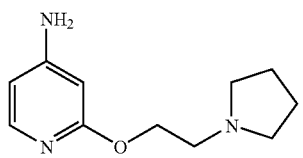

A. 2-(2-(Pyrrolidin-1-yl)ethoxy)pyridin-4-amine. A mixture of sodium hydride (0.4 g, 8.6 mmol) and 2-(pyrrolidin-1-yl)ethanol (0.98 g, 8.6 mmol) in dioxane (20 mL) was refluxed for 1 h (110° C.). When sodium was consumed, the mixture was concentrated to remove dioxane. 2-Chloropyridin-4-amine (1 g, 7.8 mmol) was added, and the mixture was heated to 160° C. for 3 h. After cooling down to room temperature, the reaction mixture was diluted with ethyl acetate, and the organic layer was washed with water and brine, dried over anhydrous sodium sulfate, and evaporated under reduced pressure. The residue was purified on silica gel column (eluting with 33-100% ethyl acetate in petroleum ether) to give 2-(2-(pyrrolidin-1-yl)ethoxy)pyridin-4-amine (0.5 g, 31.3%). $^1$H NMR (400 MHz, METHANOL-$d_4$) δ (ppm) 7.58 (d, J=6.0 Hz, 1H), 6.23 (m, 1H), 5.95 (d, J=1.6 Hz, 1H), 4.25 (t, J=6.0 Hz, 2H), 2.89 (t, J=6.0 Hz, 2H), 2.67 (m, 4H), 1.82 (m, 4H).

Intermediate 71: $N^2$-(2-Pyrrolidin-1-yl-ethyl)-pyridine-2,4-diamine

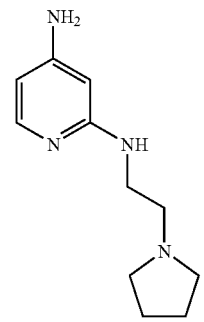

A. 2-Chloropyridine 1-oxide. To a solution of 2-chloropyridine (5 g, 0.04 mol) in dichloromethane (50 mL) was added 3-chlorobenzoperoxoic acid (15.2 g, 0.08 mmol) in portions at room temperature. The mixture was stirred at room temperature for 1 h. After the starting material was consumed, saturated sodium thiosulfate aqueous solution was added. The organic layer was separated and washed with brine, dried over sodium sulfate, and concentrated under reduced pressure to give 2-chloropyridine 1-oxide (4 g, 71% yield) as a solid.

B. 2-Chloro-4-nitropyridine 1-oxide. 2-Chloropyridine 1-oxide (4 g, 0.03 mol) was mixed with sulfuric acid (16 g, 0.18 mol) and fuming nitric acid (9 g, 0.15 mol), and the mixture was stirred at 90° C. for 2.5 h. After cooling to room temperature, the reaction mixture was poured slowly into the cold water (100 mL) at 0-5° C. The mixture was diluted with ethyl acetate (480 mL), and basified by the addition of a 6N aqueous sodium hydroxide solution at 0-5° C. to pH=10. The organic layer was separated, washed with brine (100 mL×4), dried over sodium sulfate, and concentrated under reduced pressure to give 2-chloro-4-nitropyridine 1-oxide (1.2 g, 24% yield) as a solid.

C. 4-Nitro-2-(2-(pyrrolidin-1-yl)ethylamino)pyridine 1-oxide. A mixture of 2-chloro-4-nitropyridine 1-oxide (400 mg, 2.3 mmol) and 2-(pyrrolidin-1-yl)ethanamine (524 mg, 4.6 mmol) in ethanol (5 mL) was heated at 80° C. overnight. The reaction mixture was concentrated in vacuo, and the residue was purified on silica gel column (10% methanol in ethyl acetate) to give 4-nitro-2-(2-(pyrrolidin-1-yl)ethylamino)pyridine 1-oxide (300 mg, 51% yield) as a solid. $^1$H NMR (400 MHz, METHANOL-$d_4$) δ (ppm) 8.33 (d, J=7.2 Hz, 1H), 7.71 (d, J=4.2 Hz, 1H), 7.50 (dd, $J_1$=7.2 Hz, $J_2$=2.8 Hz, 1H), 3.64 (t, J=6.4 Hz, 2H), 2.96 (s, 2H), 2.80 (s, 4H), 1.90 (s, 4H).

D. $N^2$-(2-Pyrrolidin-1-yl-ethyl)-pyridine-2,4-diamine. A mixture of 4-nitro-2-(2-(pyrrolidin-1-yl)ethylamino)pyridine 1-oxide (300 mg, 1.19 mmol) and Raney-Ni (50 mg) in methanol (10 mL) was hydrogenated under 1 atm of hydrogen for 1 h. The catalyst was filtered off, and the filtrate was concentrated to give N²-(2-(pyrrolidin-1-yl)ethyl)pyridine-2,4-diamine (210 mg, 85% yield). MS (ESI): m/z 206.9 [M+1]⁺.

Intermediate 72: 2,6-Dimethylpyridin-4-amine

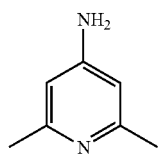

A. 2,6-Dimethylpyridine 1-oxide. To a solution of 2,6-dimethylpyridine (10.7 g, 0.1 mol) in dichloromethane (100 mL) was added 3-chlorobenzoperoxoic acid (32.4 g, 0.15 mmol) in portions at room temperature. The mixture was stirred at room temperature for 1 h. After the starting material was consumed, saturated sodium thiosulfate aqueous solution was added. The organic layer was separated, washed with brine, dried over sodium sulfate, and concentrated under reduced pressure to give 2,6-dimethylpyridine 1-oxide (12 g, 97% yield) as a solid.

B. 2,6-Dimethyl-4-nitropyridine 1-oxide. To a solution of 2,6-dimethylpyridine 1-oxide (7 g, 0.057 mol) in sulfuric acid (20 mL) was added a mixture of sulfuric acid and nitric acid (v/v, 1:1, 50 mL) at 0° C. The mixture was heated at 100° C. until the starting material was consumed. The mixture was cooled, neutralized with saturated sodium carbonate solution, and extracted with ethyl acetate. The combined organic layers were dried over sodium sulfate, and concentrated to give 2,6-dimethyl-4-nitropyridine 1-oxide (3.1 g, 33% yield) as a solid. ¹H NMR (400 MHz, CHLOROFORM-d) δ (ppm) 8.01 (s, 2H), 2.57 (s, 6H).

C. 2,6-Dimethylpyridin-4-ylamine. A solution of 2,6-dimethyl-4-nitropyridine 1-oxide (2 g, 11.9 mmol) in glacial acetic acid was added 10% palladium on activated carbon (0.2 g), and the mixture was hydrogenated at 45 psi of hydrogen at 50° C. for 19 h. The reaction mixture was filtered, and the filtrate was adjusted to pH=12 with 6N sodium hydroxide solution. The mixture was extracted with chloroform, dried, filtered, and evaporated to give 2,6-dimethylpyridin-4-ylamine (600 mg, 47% yield). MS (ESI): m/z 113.1 [M+1]⁺.

Intermediate 73: tert-Butyl 6-amino-1-oxoisoindoline-2-carboxylate

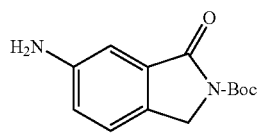

A. Methyl 2-methyl-5-nitrobenzoate. To a stirred solution of 2-methyl-5-nitrobenzoic acid (2 g, 11 mmol) in methanol was added dropwise thionyl chloride (3.2 g, 27.5 mmol) at 0° C., and the resulting mixture was refluxed for 2 h. After thin layer chromatography indicated the starting material was consumed, the solvent was removed under reduced pressure, and the residue was dissolved in the mixture of ethyl acetate and water. The organic layer was separated, and the aqueous phase was extracted with ethyl acetate for three times. The combined organic layer was dried over sodium sulfate, and evaporated under reduced pressure to give methyl 2-methyl-5-nitrobenzoate (2.08 g, 96.7% yield) as a solid. ¹H NMR (400 MHz, CHLOROFORM-d) δ (ppm) 8.69 (s, 1H), 8.16 (d, J=6.0 Hz, 1H), 7.36 (d, J=8.4 Hz, 1H), 3.89 (s, 3H), 2.65 (s, 3H).

B. Methyl 2-(bromomethyl)-5-nitrobenzoate. A suspension of methyl 2-methyl-5-nitrobenzoate (2.08 g, 10.67 mmol), N-bromosuccinimide (2.06 g, 11.58 mmol), 2,2'-azo-bis(2-methylpropionitrile) (AIBN) (40 mg, 0.244 mmol) in tetrachloromethane (25 mL) was refluxed for 5 h. When thin layer chromatography indicated the starting material was consumed, the mixture was cooled down to room temperature. The precipitate was filtered off, and the filtrate was evaporated to give methyl 2-(bromomethyl)-5-nitrobenzoate (2.2 g), which was used in the next step directly.

C. 6-Nitroisoindolin-1-one. Crude methyl 2-(bromomethyl)-5-nitrobenzoate (2.2 g) was dissolved in methanolic ammonia solution (7N), and the mixture was stirred at room temperature overnight. The precipitate was filtered off and washed with ethanol to give 6-nitroisoindolin-1-one (616 mg, 32% yield for two steps) as a solid. ¹H NMR (400 MHz, DMSO-d₆) δ (ppm) 8.97 (s, 1H), 8.44 (d, J=2.0 Hz, 1H), 8.33 (s, 1H), 7.86 (d, J=8.4 Hz, 1H), 4.53 (s, 2H).

D. tert-Butyl 6-nitro-1-oxoisoindoline-2-carboxylate. A mixture of 6-nitroisoindolin-1-one (500 mg, 2.8 mmol) and di-tert-butyl dicarbonate (610 mg, 228 mmol) in dichloromethane (50 mL) was added N,N-dimethylpyridin-4-amine (34 mg, 0.28 mmol), and the resulting mixture was stirred at room temperature for 30 min. The reaction mixture was washed with water and brine, dried over anhydrous sodium sulfate, and concentrated under reduced pressure to give tert-butyl 6-nitro-1-oxoisoindoline-2-carboxylate (778 mg, 90.6% yield) as a solid.

E. tert-Butyl 6-amino-1-oxoisoindoline-2-carboxylate. A mixture of tert-butyl 6-nitro-1-oxoisoindoline-2-carboxylate (426 mg, 1.53 mmol) and 10% palladium on activated carbon (40 mg) in methanol (50 mL) was hydrogenated under 1 atmosphere of hydrogen at room temperature for 40 min. The catalyst was filtered off, and the filtrate was concentrated to give tert-butyl 6-amino-1-oxoisoindoline-2-carboxylate (273 mg, 64% yield). MS (ESI): m/z 249.2 [M+1]⁺.

tert-Butyl 5-amino-1-oxoisoindoline-2-carboxylate was prepared following the same procedure used for the preparation of tert-butyl 6-amino-1-oxoisoindoline-2-carboxylate using 2-methyl-4-nitrobenzoic acid as starting material.

Intermediate 74: 3-Ethyl-1-((2-(trimethylsilyl)ethoxy)methyl)-1H-indazol-6-amine

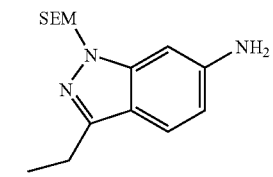

A. 6-Nitro-1-((2-(trimethylsilyl)ethoxy)methyl)-3-vinyl-1H-indazole. A degassed mixture of 3-iodo-6-nitro-1-((2-(trimethylsilyl)ethoxy)methyl)-1H-indazole (1.1 g, 2.63 mmol), 4,4,5,5-tetramethyl-2-vinyl-1,3,2-dioxaborolane (486 mg, 3.16 mmol), sodium carbonate (558 mg, 5.26 mmol), and 1,1'-bis(diphenylphosphino)ferrocene palladium dichloride (191 mg, 0.26 mmol) in a mixture of dioxane and water (v/v, 3:1, 24 mL) was heated at 100° C. overnight under nitrogen. The reaction mixture was poured into water, and extracted with ethyl acetate. The combined organic layers were dried over anhydrous sodium sulfate, evaporated under reduced pressure, and purified on silica gel column (eluting with 0-2% ethyl acetate in petroleum ether) to give 6-nitro-1-((2-(trimethylsilyl)ethoxy)methyl)-3-vinyl-1H-indazole (610 mg, 72.8% yield). $^1$H NMR (400 MHz, DMSO-$d_6$) δ (ppm) 8.79 (t, J=1.6 Hz, 1H), 8.30 (d, J=9.2 Hz, 1H), 8.04 (m, 1H), 7.08 (m, 1H), 6.23 (m, 1H), 5.91 (s, 2H), 5.63 (m, 1H), 3.55 (t, J=8.0 Hz, 2H), 0.80 (t, J=7.6 Hz, 2H), −0.12 (s, 9H).

B. 3-Ethyl-1-((2-(trimethylsilyl)ethoxy)methyl)-1H-indazol-6-amine. A mixture of 6-nitro-1-((2-(trimethylsilyl)ethoxy)methyl)-3-vinyl-1H-indazole (610 mg, 1.91 mmol) and 10% palladium on activated carbon (30 mg) in methanol (10 mL) was hydrogenated under 1 atmosphere of hydrogen at room temperature overnight. The catalyst was filtered off, and the filtrate was concentrated under vacuum, the crude product was purified on silica gel column (eluting with 4-20% ethyl acetate in petroleum ether) to give 3-ethyl-1-((2-(trimethylsilyl)ethoxy)methyl)-1H-indazol-6-amine (390 mg, 69.9% yield). $^1$H NMR (400 MHz, METHANOL-$d_4$) δ (ppm) 7.43 (m, 1H), 6.70 (t, J=0.8 Hz, 1H), 6.63 (m, 1H), 5.51 (s, 2H), 3.51 (t, J=7.6 Hz, 2H), 2.86 (m, 2H), 1.32 (q, J=7.6 Hz, 1H), 0.82 (t, J=8.0 Hz, 8H), 0.09 (m, 9H); MS (ESI): m/z 292.18 [M+1]$^+$.

Intermediate 75: 1-Isopropyl-1H-indazol-6-amine

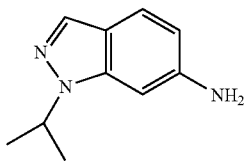

A. 1-Isopropyl-6-nitro-1H-indazole. To a solution of 6-nitro-1H-indazole (5 g, 31 mmol) in N,N-dimethylformamide (75 mL) was added sodium hydride (60% in mineral oil, 1.4 g, 34 mmol) in portions at 0° C. After the addition, the mixture was stirred for 30 min at 0° C., and 2-iodo-2-methylpropane (27.6 g, 150 mmol) was added. The resulting mixture was stirred at room temperature overnight, quenched by the addition of water (250 mL), and extracted with ethyl acetate. The combined organic layers were washed with brine, dried over sodium sulfate, and evaporated. The residue was purified on silica gel column (eluting with 5-10% ethyl acetate in petrol ether) to give 1-isopropyl-6-nitro-1H-indazole (2.48 g, 40% yield) as a yellow solid. $^1$H NMR (400 MHz, METHANOL-$d_4$) δ (ppm) 8.50 (s, 1H), 8.08 (d, J=8.0 Hz, 1H), 7.86 (d, J=8.0 Hz, 1H), 7.82 (s, 1H), 5.02 (m, 1H), 1.47 (d, J=4.0 Hz, 6H).

B. 1-Isopropyl-1H-indazol-6-amine. To a mixture of 1-isopropyl-6-nitro-1H-indazole (1 g, 4.88 mmol) and ammonium chloride (2.6 g, 4.88 mmol) in methanol (30 mL) was added zinc dust (3.18 g, 4.88 mmol) in portions at 0° C. After the addition, the reaction mixture was stirred at room temperature overnight, filtered, concentrated, and purified on silica gel column (eluting with 1% methanol in dichloromethane) to give 1-isopropyl-1H-indazol-6-amine (0.56 g, 65.9% yield) as a solid. $^1$H NMR (400 MHz, DMSO-$d_6$) δ (ppm) 7.75 (s, 1H), 7.41 (d, J=8.0 Hz, 1H), 6.56 (d, J=8.0 Hz, 2H), 5.33 (br s, 2H), 4.68 (m, 1H), 1.50 (s, 6H).

Intermediate 76: 1-((2-(Trimethylsilyl)ethoxy)methyl)-1H-benzo[d][1,2,3]triazol-5-amine

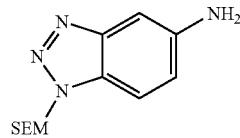

A. 1-((2-(Trimethylsilyl)ethoxy)methyl)-1H-benzo[d][1,2,3]triazol-5-amine. To a solution of 1H-benzo[d][1,2,3]triazol-5-amine (500 mg, 3.73 mmol) in N,N-dimethylformamide (15 mL) was added sodium hydride (149 mg, 3.73 mmol, 60% in mineral oil) at 0° C. under nitrogen, and the mixture was stirred for 1 h at room temperature. (2-(Chloromethoxy)ethyl)trimethylsilane (619 mg, 3.73 mmol) was added dropwise at 0° C., and the resulting mixture was continued to stir for another 2 h at room temperature. The reaction mixture was poured into ice-water (50 mL), extracted with ethyl acetate (100 mL×3). The combined organic layers were dried over anhydrous sodium sulfate, and evaporated under reduced pressure to give the crude product, which was purified on silica gel column (eluting with 5-10% ethyl acetate in petroleum ether) to give 142-(trimethylsilyl)ethoxy)methyl)-1H-benzo[d][1,2,3]triazol-5-amine (400 mg, 40.6% yield), which was obtained as an oil. $^1$H NMR (400 MHz, METHANOL-$d_4$) δ (ppm) 7.60 (d, J=9.2 Hz, 1H), 6.98 (m, 1H), 6.83 (d, J=1.6 Hz, 1H), 5.81 (s, 2H), 3.68 (t, J=8.0 Hz, 2H), 0.88 (t, J=8.0 Hz, 2H), −0.07 (s, 9H); MS (ESI): m/z 265.2 [M+1]$^+$.

Intermediates 77 and 78: 6-Bromo-1,3-dimethyl-1H-indazole and 6-bromo-2,3-dimethyl-2H-indazole

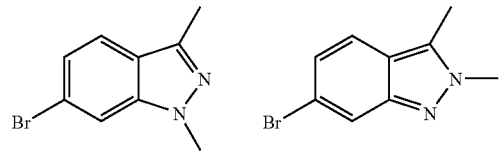

A. 6-Bromo-1,3-dimethyl-1H-indazole and 6-bromo-2,3-dimethyl-2H-indazole. 6-Bromo-3-methyl-1H-indazole (3 g, 14.21 mmol) was dissolved in 20 mL of N,N-dimethylformamide, and sodium hydride (60% dispersion in mineral oil, 0.682 g; 17.06 mmol) was added at 0° C. under nitrogen. The reaction mixture was stirred at 0° C. for 1 h and iodomethane (1.06 mL, 17.06 mmol.) was added. The reaction mixture was stirred at room temperature overnight under nitrogen. Upon completion of reaction as indicated by LCMS the reaction mixture was poured into water/brine, and extracted with ethyl acetate several times. The combined organic layer was dried over anhydrous magnesium sulfate and concentrated. The crude mixture was purified by chromatography using a gradient of 0-100% ethyl acetate in hexanes to give 6-bromo-1,3-dimethyl-1H-indazole as a yellow solid (2.04 g, 64% yield) and 6-bromo-2,3-dimethyl-2H-indazole as a yellow solid (1.02 g, 32% yield).

$^1$H NMR of 6-bromo-1,3-dimethyl-1H-indazole (400 MHz, DMSO-$d_6$) δ (ppm) 7.88-7.92 (m, 1H), 7.64-7.69 (m, 1H), 7.21 (dd, J=1.64, 8.52 Hz, 1H), 3.94 (s, 3H), 2.46 (s, 3H). MS (ESI) m/z 226 [M+1]$^+$ $^1$H NMR of 6-bromo-2,3-dimethyl-2H-indazole (400 MHz DMSO-d$_6$) δ (ppm) 7.71-7.77 (m, 1H), 7.62-7.68 (m, 1H), 7.05 (dd, J=1.68, 8.81 Hz, 1H), 4.03 (s, 3H), 2.60 (s, 3H). MS (ESI) m/z 226 [M+1]$^+$

Intermediate 79: 4-Fluoro-3-(2-methoxyethoxy)aniline

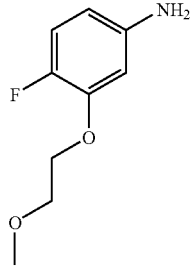

A. 1-Fluoro-2-(2-methoxyethoxy)-4-nitrobenzene. Diisopropyl azodicarboxylate (1.356 mL, 7.00 mmol) was added dropwise to a stirred solution of 2-fluoro-5-nitrophenol (1.00 g, 6.37 mmol), triphenylphosphine (1.837 g, 7.00 mmol), and 2-methoxyethanol (0.533 g, 7.00 mmol) in tetrahydrofuran (10 mL) cooled with a water bath. The resulting dark red mixture was stirred at room temperature under nitrogen for 1.5 h. The resulting mixture was purified using flash chromatography (Biotage) (0-30% ethyl acetate in hexane). Fractions containing the desired product were combined and washed twice with water and once with brine. The organics were dried over magnesium sulfate, filtered, and concentrated on a rotary evaporator nearly to dryness. The residue was diluted with cold hexane. Solids were collected by vacuum filtration, washed with cold hexane, and dried under high vacuum to give the desired product (0.865 g, 4.02 mmol, 63% yield) as slightly yellow needles. $^1$H NMR (400 MHz, DMSO-d$_6$) δ (ppm) 8.01 (dd, J=2.73, 7.42 Hz, 1H), 7.91 (ddd, J=2.73, 3.90, 8.98 Hz, 1H), 7.54 (dd, J=8.98, 10.93 Hz, 1H), 4.31-4.39 (m, 2H), 3.67-3.76 (m, 2H), 3.32 (s, 3H); MS (ESI) m/z 216.3 [M+1]$^+$.

B. 4-Fluoro-3-(2-methoxyethoxy)aniline. 1-Fluoro-2-(2-methoxyethoxy)-4-nitrobenzene (0.862 g, 4.01 mmol) was dissolved in ethyl acetate (5 mL) and ethanol (15 mL) with stirring at room temperature. A combination vacuum/nitrogen/hydrogen manifold was attached. The atmosphere in the flask was removed and replaced with nitrogen twice. Palladium (10 wt. % on activated carbon) (0.213 g, 0.200 mmol) was added and the atmosphere in the flask was removed and replaced with hydrogen three times. The resulting mixture was stirred vigorously under a hydrogen balloon at room temperature for 2.5 h. The resulting black mixture was filtered through Celite and the filter cake washed thoroughly with methanol. The filtrate was concentrated on a rotary evaporator and dried under high vacuum to give the desired product (0.731 g, 3.95 mmol, 99% yield) as an amber solid. $^1$H NMR (400 MHz, DMSO-d$_6$) δ (ppm) 6.81 (dd, J=8.59, 11.71 Hz, 1H), 6.32 (dd, J=2.73, 7.42 Hz, 1H), 6.01-6.09 (m, 1H), 4.92 (s, 2H), 3.99-4.05 (m, 2H), 3.61-3.67 (m, 2H), 3.31 (s, 3H); $^{19}$F NMR (376 MHz, DMSO-d$_6$) δ (ppm)-151.45 (m, 1F); MS (ESI) m/z 186.2 [M+1]$^+$.

Intermediate 80: 2-(2-(tert-Butyldimethylsilyloxy)ethoxy)pyridin-4-amine

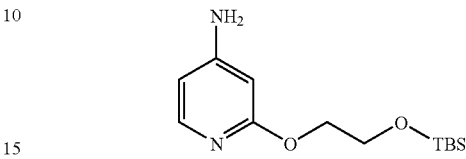

A. 2-(tert-Butyldimethylsilyloxy)ethanol. A mixture of ethane-1,2-diol (6.2 g, 0.1 mol), imidazole (10 g, 0.15 mol), and tert-butylchlorodimethylsilane (10 g, 0.15 mol) in N,N-dimethylformamide (15 mL) was stirred at room temperature overnight. The reaction was quenched by the addition of water, and the mixture was extracted with ethyl acetate. The organic layer was dried over sodium sulfate, and concentrated to give 2-(tert-butyldimethylsilyloxy)ethanol as an oil (10 g, 56.8% yield).

B. 2-(2-(tert-Butyldimethylsilyloxy)ethoxy)pyridin-4-amine. To a solution of 2-(tert-butyldimethylsilyloxy)ethanol (4.1 g, 23.3 mmol) in dioxane (20 mL) was added sodium hydride (60% in mineral oil, 0.96 g, 24 mmol). The mixture was refluxed for 1.5 h. When the reaction mixture was cooled down to room temperature, 2-chloropyridin-4-amine (2.0 g, 15.5 mmol) was added, and the reaction mixture was heated at 160° C. for 7 h under nitrogen. After being cooled down to room temperature, the reaction mixture was poured into water, and the resulting mixture was extracted with ethyl acetate. The organic layer was concentrated under reduced pressure, and purified on silica gel column (eluting with 1-10% ethyl acetate in petroleum ether) to give 2-(2-(tert-butyldimethylsilyloxy)ethoxy)pyridin-4-amine (180 mg, 4.4% yield) as a solid. MS (ESI): m/z 268.9 [M+1]$^+$.

Intermediate 81: cis-4-Amino-1-((tert-butyldiphenylsilyloxy)methyl)cyclohexanol

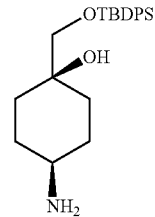

A. cis-tert-Butyl-1-oxaspiro[2.5]octan-6-ylcarbamate. To a solution of trimethylsulfoxonium iodide (12.5 g, 57 mmol) in N,N-dimethylformamide (100 mL) was added sodium hydride (2.5 g, 62.5 mmol, 60% in mineral oil) at 10° C., and the mixture was stirred at room temperature for 40 min. The mixture was cooled to 10° C., added tert-butyl 4-oxocyclohexylcarbamate (9.5 g, 44.6 mmol), and stirred at room temperature for another 2 h. Water (150 mL) was added, and the mixture was extracted with ethyl acetate (200 mL). The organic phase was dried over anhydrous sodium sulfate, concentrated, and purified by column chromatography on silica gel (eluting with 10% ethyl acetate in petroleum ether) to give cis-tert-butyl-1-oxaspiro[2.5]octan-6-ylcarbamate (5 g, 50% yield) as a white powder. $^1$H NMR (400 MHz, DMSO-$d_6$) δ (ppm) 6.78 (d, J=7.6 Hz, 1H), 3.39 (m, 1H), 2.56 (s, 2H), 1.87 (m, 4H), 1.45 (m, 11H), 1.22 (m, 2H).

B. cis-tert-Butyl-4-hydroxy-4-(hydroxymethyl)cyclohexylcarbamate. To a solution of cis-tert-butyl-1-oxaspiro [2.5]octan-6-ylcarbamate (4.54 g, 20 mmol) in 1,2-dimethoxyethane (50 mL) was added potassium hydroxide (5.6 g, 100 mmol) in 200 mL of water. The mixture was stirred at reflux for 10 h, concentrated until 150 mL of solvent was left. After filtration. the filter cake was washed with water (50 mL) and ether (20 mL) to give cis-tert-butyl-4-hydroxy-4-(hydroxymethyl)cyclohexylcarbamate (2.8 g, 57% yield) as a white powder. $^1$H NMR (400 MHz, DMSO-$d_6$) δ (ppm) 6.70 (d, J=8.0 Hz, 1H), 4.49 (br s, 1H), 3.83 (br s, 1H), 3.15 (m, 3H), 1.50 (m, 17H).

C. cis-tert-Butyl-4-((tert-butyldiphenylsilyloxy)methyl)-4-hydroxycyclohexyl carbamate. A mixture of cis-tert-butyl-4-hydroxy-4-(hydroxymethyl)cyclohexylcarbamate (735 mg, 3 mmol), and imidazole (340 mg, 5 mmol) in N,N-dimethylformamide (10 mL) was added tert-butylchlorodiphenylsilane (2.2 g, 8 mmol), and the mixture was stirred at 50° C. for 12 h. Water (30 mL) was added, and the solution was extracted with ethyl acetate (30 mL). The organic phase was dried over sodium sulfate, concentrated, and purified by column chromatography on silica gel (eluting with 7-10% ethyl acetate in petroleum ether) to give cis-tert-butyl-4-((tert-butyldiphenylsilyloxy)methyl)-4-hydroxycyclo hexylcarbamate (420 mg, 29% yield). $^1$H NMR (400 MHz, DMSO-$d_6$) δ (ppm) 7.62 (m, 4H), 7.49 (m, 6H), 6.74 (d, J=7.6 Hz, 1H), 4.09 (s, 1H), 3.31 (s, 2H), 3.12 (br s, 1H), 1.58 (m, 6H), 1.44 (m, 11H), 1.00 (s, 9H).

D. cis-4-Amino-1-((tert-butyldiphenylsilyloxy)methyl) cyclohexanol. To a stirred solution of cis-tert-butyl-4-((tert-butyldiphenylsilyloxy)methyl)-4-hydroxy cyclohexylcarbamate (966 mg, 2 mmol) in dichloromethane (15 mL) was added dropwise trifluoroacetic acid (2 mL) at –5° C., and the mixture was stirred at 0° C. for 2 h. When the LC-MS showed 70% of the starting material remained, additional 2 mL of trifluoroacetic acid was added, and the mixture was stirred for another 6 h at 0° C. until the starting material was consumed. The mixture was adjusted to pH=8 with saturated sodium carbonate aqueous solution, and the resulting mixture was extracted with ethyl acetate (20 mL). The organic phase was dried with sodium sulfate, and concentrated to give the crude cis-4-amino-1-((tert-butyldiphenylsilyloxy)methyl)cyclohexanol, which was used directly without further purification.

Intermediate 82:
6-Bromo-1-methylindoline-2,3-dione

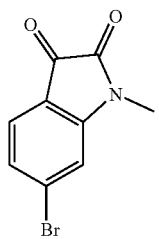

A. 6-Bromo-1-methylindoline-2,3-dione. To a solution of 6-bromoindoline-2,3-dione (4.5 g, 20 mmol) in N,N-dimethylformamide (20 mL) was added potassium carbonate (4.14 g, 30 mmol) and dimethyl sulfate (3.15 g, 25 mmol) was added dropwise with stirring. After stirring at room temperature for 2 h, the reaction mixture was poured into ice water (400 mL), and extracted with ethyl acetate (200 mL). The organic layer was dried with sodium sulfate, concentrated, and purified with column chromatography on silica gel (eluting with 15% ethyl acetate in petroleum ether) to give 6-bromo-1-methylindoline-2,3-dione (3.7 g, 77% yield) as a red solid.

Intermediate 83: 3-(Methoxymethyl)-1-((2-(trimethylsilyl)ethoxy)methyl)-1H-indazol-6-amine

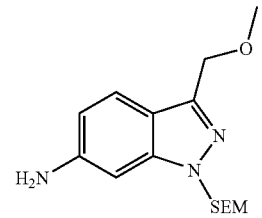

A. Methyl 6-nitro-1-((2-(trimethylsilyl)ethoxy)methyl)-1H-indazole-3-carboxylate. A degassed mixture of 3-iodo-6-nitro-1-((2-(trimethylsilyl)ethoxy)methyl)-1H-indazole (4.62 g, 11 mmol), potassium carbonate (4.55 g, 33 mmol), palladium acetate (250 mg, 1.1 mmol), and 1,1'-bis(diphenylphosphino)ferrocene (610 mg, 1.1 mmol) in a mixture of methanol (25 mL) and N,N-dimethylformamide (25 mL) was vigorously stirred, and heated at 80° C. under carbon monoxide (50 psi) for 24 h. After cooling to room temperature, the reaction mixture was filtered, and the filtrate was diluted with water (100 mL). The aqueous mixture was extracted with ethyl acetate (250 mL×3). The extracts were washed with water and brine, dried over sodium sulfate, concentrated in vacuo, and purified on silica gel column (eluting with 10-25% ethyl acetate in petroleum ether) to give methyl 6-nitro-1-((2-(trimethylsilyl)ethoxy)methyl)-1H-indazole-3-carboxylate as an orange oil (1.8 g, 47% yield). $^1$H NMR (400 MHz, CHLOROFORM-d) δ (ppm) 8.36 (d, J=8.8 Hz, 1H), 8.29 (s, 1H), 8.04 (d, J=8.8 Hz, 1H), 5.93 (s, 2H), 4.09 (s, 3H), 3.63 (t, J=8.4 Hz, 2H), 0.92 (t, J=8.4 Hz, 2H), –0.06 (s, 9H).

B. (6-Nitro-1-((2-(trimethylsilyl)ethoxy)methyl)-1H-indazol-3-yl)methanol. To a solution of methyl 6-nitro-1-((2-(trimethylsilyl)ethoxy)methyl)-1H-indazole-3-carboxylate (1.8 g, 5.1 mmol) in anhydrous tetrahydrofuran (100 mL) was added aluminium lithium hydride (5.81 g, 15.3 mmol) in portions at 0° C. When the starting material was consumed, the reaction mixture was quenched with aqueous sodium hydroxide solution (0.15 M, 100 mL), and filtered. The filtrate was extracted with ethyl acetate (150 mL×3). The extracts were washed with brine, dried over sodium sulfate, and concentrated in vacuo to give (6-nitro-1-((2-(trimethylsilyl) ethoxy)methyl)-1H-indazol-3-yl)methanol (800 mg, 48% yield) as an orange oil. $^1$H NMR (400 MHz, CHLOROFORM-d) δ (ppm) 8.16 (s, 1H), 7.90 (m, 2H), 5.78 (s, 2H), 5.10 (s, 2H), 3.61 (m, 2H), 0.93 (m, 2H), –0.05 (s, 9H).

C. 3-(Methoxymethyl)-6-nitro-1-((2-(trimethylsilyl) ethoxy)methyl)-1H-indazole. To a solution of (6-nitro-1-((2-(trimethylsilyl)ethoxy)methyl)-1H-indazol-3-yl)methanol (800 mg, 2.47 mmol) in N,N-dimethylformamide (15 mL) was added sodium hydride (60% in mineral oil, 148 mg, 3.71 mmol) in portions at 0° C., and the mixture was stirred at 0°

C. for 30 min. Iodomethane (527 mg, 3.71 mmol) was added, and the reaction mixture was stirred at room temperature for 2 h. Water (50 mL) was added, and the aqueous mixture was extracted with ethyl acetate (50 mL×3). The extracts were washed with water and brine, dried over sodium sulfate, concentrated in vacuo, and purified on silica gel column (eluting with 20-30% ethyl acetate in petroleum ether) to give 3-(methoxymethyl)-6-nitro-1-((2-(trimethylsilyl)ethoxy)methyl)-1H-indazole (500 mg, 60% yield). $^1$H NMR (400 MHz, CHLOROFORM-d) δ (ppm) 8.18 (s, 1H), 7.95 (d, J=8.0 Hz, 1H), 7.90 (d, J=8.0 Hz, 1H), 5.81 (s, 2H), 4.88 (s, 2H), 3.62 (m, 2H), 3.46 (s, 3H), 0.93 (m, 2H), −0.05 (s, 9H).

D. 3-(Methoxymethyl)-1-((2-(trimethylsilyl)ethoxy)methyl)-1H-indazol-6-amine. A degassed mixture of 3-(methoxymethyl)-6-nitro-1-((2-(trimethylsilyl)ethoxy)methyl)-1H-indazole (500 mg, 1.48 mmol) and Raney nickel (100 mg) in methanol (150 mL) was stirred at room temperature under 1 atmosphere of hydrogen overnight. The catalyst was filtered off, and the solution was concentrated in vacuo to give 3-(methoxymethyl)-1-((2-(trimethylsilyl)ethoxy)methyl)-1H-indazol-6-amine (380 mg, 83% yield). $^1$H NMR (400 MHz, DMSO-$d_6$) δ (ppm) 7.39 (d, J=8.4 Hz, 1H), 6.53 (m, 2H), 5.47 (s, 2H), 5.43 (s, 2H), 4.56 (s, 2H), 3.46 (t, J=8.0 Hz, 2H), 3.23 (s, 3H), 0.78 (t, J=8.0 Hz, 2H), −0.10 (s, 9H); MS (ESI): m/z 308.1 [M+1]$^+$.

Intermediate 84: tert-Butyl 6-bromo-1-oxo-3,4-dihydroisoquinoline-2(1H)-carboxylate

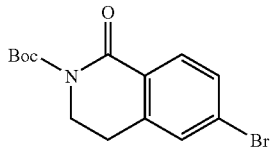

A. 6-Bromo-3,4-dihydroisoquinolin-1(2H)-one. To a stirred solution of 5-bromo-2,3-dihydro-1H-inden-1-one (10 g, 47.6 mmol) in a mixture of methyl sulfonic acid and dichloromethane (v/v=1:1, 100 mL) was added sodium azide (6 g, 95.2 mmol) in portionwise between 22° C. and 29° C. When the addition was completed, the mixture was stirred at room temperature for 16 h, cooled to 0° C., and neutralized by the addition of 5N sodium hydroxide aqueous solution. The aqueous layer was extracted with dichloromethane (250 mL×3). The combined organic layers were washed with water (100 mL×3) and brine (100 mL×3), dried over anhydrous sodium sulfate, concentrated, and purified on silica gel column (eluting with 10-33.3% ethyl acetate in petroleum ether) to give 6-bromo-3,4-dihydroisoquinolin-1(2H)-one (2.1 g, 19.6% yield). $^1$H NMR (400 MHz, DMSO-$d_6$) δ (ppm) 8.03 (s 1H), 7.75 (d, J=8.0 Hz, 1H), 7.54 (d, J=8.0 Hz, 1H), 7.51 (s, 1H), 3.35 (t, J=6.4 Hz, 2H), 2.90 (d, J=6.4 Hz, 2H).

B. tert-Butyl 6-bromo-1-oxo-3,4-dihydroisoquinoline-2(1H)-carboxylate. A mixture of 6-bromo-3,4-dihydroisoquinolin-1(2H)-one (600 mg, 2.67 mmol) and di-tert-butyl dicarbonate (872 mg, 4.0 mmol) in dichloromethane (50 mL) was added N,N-dimethylpyridin-4-amine (49 mg, 0.40 mmol), and the resulting mixture was stirred at room temperature overnight. The reaction mixture was concentrated under reduced pressure, and the residue was purified on silica gel column (eluting with 10% ethyl acetate in petroleum ether) to give tert-butyl 6-bromo-1-oxo-3,4-dihydroisoquinoline-2(1H)-carboxylate (730 mg, 84.2% yield) as a solid. $^1$H NMR (400 MHz, DMSO-$d_6$) δ (ppm) 7.86 (d, J=8.8 Hz, 1H), 7.61 (d, J=8.0 Hz, 1H), 7.58 (s, 1H), 3.88 (t, J=7.2 Hz, 2H), 3.00 (d, J=6.0 Hz, 2H), 1.49 (s, 9H).

Intermediate 85: 5-Amino-2-(2-(tert-butyldimethylsilyloxy)ethyl)isoindolin-1-one

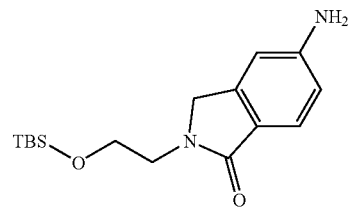

A. 2-(tert-Butyldimethylsilyloxy)ethanamine. To a solution of 2-aminoethanol (6.12 g, 0.1 mol) and tert-butylchlorodimethylsilane (18.22 g, 0.12 mol) in dichloromethane (200 mL) was added dropwise a solution of triethylamine (46 mL, 0.3 mol) and 4-(dimethylamino)pyridine (68 mg) in dichloromethane (100 mL) at 0° C. After the addition, the mixture was stirred at room temperature for 24 h. Water was added, and the organic layer was washed with saturated aqueous sodium chloride solution, and dried over anhydrous sodium sulfate. The solvent was evaporated under reduced pressure to give the crude product, which was used for the next step directly.

B. 2-(2-(tert-Butyldimethylsilyloxy)ethyl)-5-nitroisoindolin-1-one. To a mixture of methyl 2-(bromomethyl)-4-nitrobenzoate (2.0 g, 7.3 mmol) in methanol (30 mL) was added 2-(tert-butyldimethylsilyloxy)ethanamine (3.5 g, 20 mmol). The mixture was refluxed for 6 h. The reaction mixture was concentrated, and the residue was purified by column chromatography on silica gel (eluting with 10% ethyl acetate in petroleum ether) to give 2-(2-(tert-butyldimethylsilyloxy)ethyl)-5-nitroisoindolin-1-one as a white solid (1.1 g, 44.9% yield).

C. 5-Amino-2-(2-(tert-butyldimethylsilyloxy)ethyl)isoindolin-1-one. A mixture of 2-(2-(tert-butyldimethylsilyloxy)ethyl)-5-nitroisoindolin-1-one (1.1 g, 3.27 mmol) and 10% palladium on activated carbon (0.2 g) in methanol (10 mL) was hydrogenated under 1 atmosphere of hydrogen (using a balloon) at 30° C. for 1.5 h. The reaction mixture was filtered, and the filtrate was concentrated under reduced pressure. The residue was purified by column chromatography on silica gel (eluting with 20-30% ethyl acetate in petroleum ether) to give 5-amino-2-(2-(tert-butyldimethyl silyloxy)ethyl)isoindolin-1-one (600 mg, 60% yield). $^1$H NMR (400 MHz, DMSO-$d_6$)

δ (ppm) 7.29 (d, J=8.0 Hz, 1H), 6.61 (m, 2H), 5.71 (s, 2H), 4.34 (s, 2H), 3.74 (t, J=6.4 Hz, 2H), 3.50 (t, J=6.4 Hz, 2H), 0.83 (s, 9H), 0.00 (s, 6H).

Intermediate 86: 6-Amino-2-(2-(tert-butyldimethylsilyloxy)ethyl)isoindolin-1-one

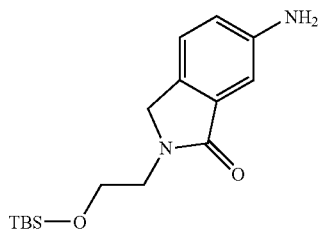

A. 2-(2-(tert-Butyldimethylsilyloxy)ethyl)-6-nitroisoindolin-1-one. The crude methyl 2-(bromomethyl)-5-nitrobenzoate (2.2 g), 2-(tert-butyldimethylsilyloxy)ethanamine (10.5 g, 60 mmol) was dissolved in methanol, and the mixture was stirred at room temperature overnight. The precipitates were filtered and washed with ethanol to give 2-(2-(tert-butyldimethylsilyloxy)ethyl)-6-nitroisoindolin-1-one (800 mg, 32% yield) as a solid. MS (ESI): m/z 337.1 [M+1]$^+$.

B. 6-Amino-2-(2-(tert-butyldimethylsilyloxy)ethyl)isoindolin-1-one. A mixture of 2-(2-(tert-butyldimethylsilyloxy)ethyl)-6-nitroisoindolin-1-one (900 mg, 2.67 mmol) and 10% palladium on activated carbon (90 mg) in methanol (50 mL) was hydrogenated under 1 atmosphere of hydrogen at room temperature overnight. The catalyst was filtered off, and the filtrate was concentrated to give 6-amino-2-(2-(tert-butyldimethylsilyloxy)ethyl)isoindolin-1-one (500 mg, 60.9% yield). MS (ESI): m/z 307.2 [M+1]$^+$.

Intermediate 87: 6-Bromo-1-(2-(tert-butyldimethylsilyloxy)ethyl)indoline-2,3-dione

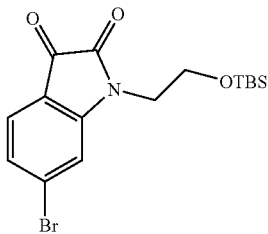

A. 6-Bromo-1-(2-(tert-butyldimethylsilyloxy)ethyl)indoline-2,3-dione. A solution of 6-bromoindoline-2,3-dione (4.5 g, 20 mmol) in N,N-dimethylformamide (20 mL) was added potassium carbonate (4.14 g, 30 mmol), and (2-bromoethoxy)(tert-butyl)dimethylsilane (5.95 g, 25 mmol) dropwise with stirring. After stirring for 2 h, the reaction mixture was poured into ice water (400 mL), and extracted with ethyl acetate (200 mL). The organic layer was dried with sodium sulfate, concentrated, and purified with column chromatography on silica gel (eluting with 10% ethyl acetate in petroleum ether) to give 6-bromo-1-(2-(tert-butyldimethylsilyloxy)ethyl)indoline-2,3-dione (3.2 g, 41.7% yield) as a red solid.

Intermediate 88: 6-Bromo-1-ethyl-3-methyl-1H-indazole

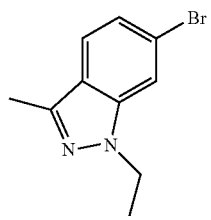

A. 6-Bromo-1-ethyl-3-methyl-1H-indazole. To a solution of 6-bromo-3-methyl-1H-indazole (2 g, 9.5 mmol) in N,N-dimethylformamide (30 mL) was added sodium hydride (60% in mineral oil, 0.23 g, 11.4 mmol) in portions at 0° C. After the addition, the mixture was stirred for 30 min. at 0° C., iodoethane (1.48 g, 19.4 mmol) was added, and the resulting mixture was stirred at room temperature overnight. The reaction was quenched by the addition of water (50 mL), and the mixture was extracted with ethyl acetate. The combined organic layers were washed with brine, dried over sodium sulfate, evaporated, and purified on silica gel column (eluting with 5-10% ethyl acetate in petroleum ether) to give 6-bromo-1-ethyl-3-methyl-1H-indazole (1.2 g, 53% yield) as yellow oil. $^1$H NMR (400 MHz, CHLOROFORM-d) δ (ppm) 7.39 (m, 2H), 7.07 (m, 1H), 4.20 (s, 2H), 2.40 (s, 3H), 1.32 (s, 3H).

Intermediate 89: 6-Bromo-1-(2-(tert-butyldimethylsilyloxy)ethyl)-3-methyl-1H-indazole

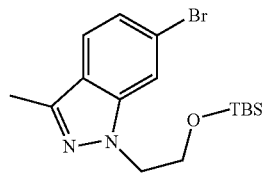

A. 6-Bromo-1-(2-(tert-butyldimethylsilyloxy)ethyl)-3-methyl-1H-indazole. To a solution of 6-bromo-3-methyl-1H-indazole (2.1 g, 10 mmol) in N,N-dimethylformamide (50 mL) was added sodium hydride (440 mg, 11 mmol) in portions at 0° C. After stirring for 0.5 h, (2-bromoethoxy)(tert-butyl)dimethylsilane (2.38 g, 10 mmol) was added. The reaction mixture was stirred at room temperature overnight. Water (100 mL) was added, and the mixture was extracted with ethyl acetate (100 mL×3). The combined organic layer was washed with brine (200 mL), dried over sodium sulfate, concentrated, and purified on silica gel chromatography (eluting with 0-10% ethyl acetate in petroleum ether) to give 6-bromo-1-

(2-(tert-butyldimethylsilyloxy)ethyl)-3-methyl-1H-indazole (1.5 g, 40.7% yield). MS (ESI): m/z 371.0 [M+1]+.

Intermediate 90: 6-Iodo-4-methyl-1-(tetrahydro-2H-pyran-2-yl)-1H-indazole

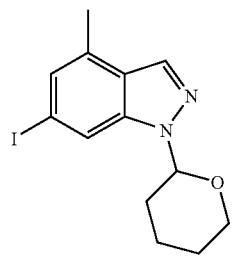

A. 6-Iodo-4-methyl-1-(tetrahydro-2H-pyran-2-yl)-1H-indazole. 6-Iodo-4-methyl-1H-indazole (0.250 g, 0.969 mmol) was dissolved in tetrahydrofuran (10 mL) and 3,4-dihydro-2H-pyran (0.133 mL, 1.453 mmol) and methane sulfonic acid (9.44 µl, 0.145 mmol) was added at room temperature under nitrogen. The reaction mixture was stirred at 75° C. overnight. Upon completion of reaction as indicated by LCMS the reaction mixture was diluted with triethylamine (0.5 mL) and condensed under reduced pressure. The crude mixture was purified by chromatography using a gradient of 0-50% ethyl acetate in hexanes to give 6-iodo-4-methyl-1-(tetrahydro-2H-pyran-2-yl)-1H-indazole as a white solid (0.336 g, 99% yield); $^1$H NMR (400 MHz, DMSO-$d_6$) δ (ppm) 8.16 (dd, J=0.10, 0.93 Hz, 1H), 7.96-8.03 (m, 1H), 7.29 (dd, J=0.63, 1.71 Hz, 1H), 5.84 (dd, J=2.64, 9.71 Hz, 1H), 3.83-3.90 (m, 1H), 3.71-3.81 (m, 1H), 2.29-2.43 (m, 1H), 1.99-2.06 (m, 1H), 1.88-1.97 (m, 1H), 1.65-1.80 (m, 1H), 1.52-1.62 (m, 2H); MS (ESI) m/z 343 [M+1]+

Intermediate 91: 2-(Methoxymethyl)-1-tosyl-1H-benzo[d]imidazol-6-amine

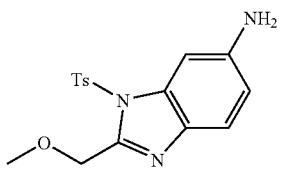

A. 2-(Methoxymethyl)-6-nitro-1H-benzo[d]imidazole. 4-Nitrobenzene-1,2-diamine (1.5 g, 9.80 mmol) and 2-methoxyacetic acid (0.882 g, 9.80 mmol) were dissolved in 4 M hydrochloric acid (20 mL, 80 mmol) and heated to 100° C. for 2 h. The reaction was cooled to 0° C. and neutralized with 1M sodium hydroxide (80 mL). The resulting precipitate was filtered, and dried to give desire product as a light yellow solid which was then further purified by crystallization from ethyl acetate and hexane. The resulting solid was dried under high vacuum at 50° C. to give desired product as white solid (1.23 g, 60.6% yield). MS (ESI) m/z 207.9 [M+1]+.

B. 2-(Methoxymethyl)-5-nitro-1-tosyl-1H-benzo[d]imidazole. 2-(Methoxymethyl)-5-nitro-1H-benzo[d]imidazole (1.23 g, 5.94 mmol) and 4-methylbenzene-1-sulfonyl chloride (1.358 g, 7.12 mmol) were dissolved in tetrahydrofuran (50 mL) and sodium tert-butoxide (1.141 g, 11.87 mmol) was added. The mixture was stirred at room temperature for 16 h. The reaction mixture was poured into a separatory funnel containing water and 50% ethyl acetate. The organic layer was concentrated on a rotary evaporator nearly to dryness and purified on silica column eluting with 0-50% ethyl acetate in hexane. The fractions containing product were concentrated on a rotary evaporator to give the desired product as white solid (0.9 g, 42% yield). MS (ESI) m/z 362.3 [M+1]+.

C. 2-(Methoxymethyl)-1-tosyl-1H-benzo[d]imidazol-5-amine. 2-(Methoxymethyl)-5-nitro-1-tosyl-1H-benzo[d]imidazole (0.9 g, 2.491 mmol) were dissolved in ethanol and purged with nitrogen. Palladium on activated carbon was added (0.530 g, 0.498 mmol), the nitrogen was evacuated and the reaction was stirred under 1 atmosphere of hydrogen for 16 h. The reaction mixture was filtrated through Celite and washed with ethanol. The organic layer was concentrated on a rotary evaporator to dryness to give desired product as purple solid, which was then crystallized from ethyl acetate in hexane to give the desired compound as a white solid (0.7 g, 85% yield). MS (ESI) m/z 332.2 [M+1]+.

Intermediate 92: 6-Bromo-1-isopropyl-1H-indazole

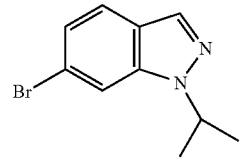

A. 6-Bromo-1-isopropyl-1H-indazole. A solution/suspension of 6-bromo-1H-indazole (1 g, 5.08 mmol), in N,N-dimethylformamide (5 mL) was cooled to 0° C. followed by the addition of sodium hydride (0.244 g, 6.09 mmol). The reaction was left to stir for 10 min, then 2-iodopropane (0.609 mL, 6.09 mmol) was added. The reaction mixture was allowed to warm up to room temperature and stirred overnight. LCMS analysis showed only product. Water was added to the reaction mixture and the product was extracted with ethyl acetate twice, the organics were washed with brine then dried over sodium sulfate. The solvent was removed under vacuum. The crude oil was loaded onto a Biotage column and eluted with 0-100% ethyl acetate in hexanes. The two regioisomers were collected and a series of NOEs were taken to determine the regioselectivity. The first peak to come out was the desired regioisomer 6-bromo-1-isopropyl-1H-indazole (638 mg, 2.67 mmol, 52.6% yield) was collected as a clear oil. $^1$H NMR (400 MHz, DMSO-$d_6$) δ (ppm) 8.10 (s, 1H), 8.04 (s, 1H), 7.72 (d, J=8.59 Hz, 1H), 7.25 (dd, J=1.76, 8.39 Hz, 1H), 5.02 (s, 1H), 1.46 (d, J=6.64 Hz, 6H). MS (ESI): m/z 241.2 [M+1]+.

Intermediate 93:
6-Amino-2,3-dihydro-1,2-benzisothiazol-1,1-dioxide

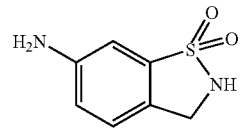

A. 6-Nitro-1,2-benzisothiazol-3(2H)-one-1,1-dioxide. A mixture of periodic acid dihydrate (42 g, 0.184 mol), chromium (VI) oxide (0.23 g, 2.3 mmol) and 2-methyl-5-nitrobenzenesulfonamide (5 g, 0.023 mol) in acetonitrile (100 mL) was refluxed until the oxidation was complete (monitored by TLC). Isopropyl alcohol (25 mL) was added dropwise. After the addition was complete, the mixture was heated to reflux for an additional 10 min, the mixture was cooled to room temperature, filtered, and the solids were washed with acetone (60 mL). The filtrates were combined and concentrated under reduced pressure. The residue was triturated with sulfuric acid solution (2 N, 69 mL) and 6-nitro-1,2-benzisothiazol-3(2H)-one-1,1-dioxide (2.5 g, 47.2% yield) was collected by filtration. $^1$H NMR (400 MHz, DMSO-d$_6$) δ (ppm) 8.82 (s, 1H), 8.57 (dd, J$_1$=8.4 Hz, J$_2$=2.0 Hz, 1H), 8.0 (d, J=8.0 Hz, 1H); MS (ESI): m/z 228.9 [M+1]$^+$.

B. 6-Amino-1,2-benzisothiazol-3(2H)-one-1,1-dioxide. Platinum dioxide (259 mg, 1.2 mmol) and 6-nitro-1,2-benzisothiazol-3(2H)-one-1,1-dioxide (1 g, 4.4 mmol) were suspended in a mixture of ethanol (52 mL) and dimethylformamide (4 mL), and the mixture was stirred under atmosphere of hydrogen overnight. The mixture was filtered through celite, and the filtrate was evaporated under vacuum to give 6-amino-1,2-benzisothiazol-3(2H)-one-1,1-dioxide (700 mg, 80.6% yield).

C. 6-Amino-2,3-dihydro-1,2-benzisothiazol-1,1-dioxide. To a suspension of 6-amino-1,2-benzisothiazol-3(2H)-one-1, 1-dioxide (700 mg, 3.53 mmol) in a mixture of ethanol (39 mL), dimethylformamide (3 mL) and concentrated hydrochloric acid (10 mL) was added zinc dust (2.95 g, 31.8 mmol) in portions, and the reaction mixture was stirred at room temperature overnight. The mixture was basified with saturated sodium bicarbonate aqueous solution and solid sodium bicarbonate carefully, and the resulting mixture was extracted with ethyl acetate for three times. The combined organic layers was dried over anhydrous sodium sulfate and concentrated to give 6-amino-2,3-dihydro-1,2-benzisothiazol-1,1-dioxide as a solid (250 mg, 38.5% yield). $^1$H NMR (400 MHz, DMSO-d$_6$): δ (ppm) 7.53 (s, 1H), 7.12 (d, J=8.4 Hz, 1H), 6.82 (dd, J$_1$=8.4 Hz, J$_2$=2.0 Hz, 1H), 6.77 (s, 2H), 4.16 (d, J=3.2 Hz, 2H); MS (ESI): m/z 184.9 [M+1]$^+$.

Intermediate 94: tert-Butyl 6-amino-3,3-dimethyl-2-oxoindoline-1-carboxylate

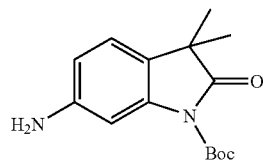

A. 2-Bromo-5-nitroaniline. To a solution of 2-bromoaniline (20 g, 0.117 mol) in concentrated sulfuric acid solution (120 mL) was added potassium nitrate (11.8 g, 0.117 mol) at 0° C. in portions during 1.5 h. The mixture was stirred at the same temperature for 0.5 h, and neutralized with ammonia water (800 mL) to pH>5. The yellow precipitate was collected by filtration, washed with water (300 mL×3), and dried in vacuo to give 2-bromo-5-nitroaniline (25 g, 100% yield) as a yellow solid. $^1$H NMR (400 MHz, CHLOROFORM-d) δ (ppm) 7.62 (m, 2H), 7.49 (dd, J$_1$=2.4 Hz, J$_2$=8.4 Hz, 1H), 4.46 (br s, 2H).

B. N-(2-Bromo-5-nitrophenyl)methacrylamide. To a stirred solution of methacrylic acid (2.0 g, 23 mmol) in N,N-dimethyl-acetamide (15 mL) was added dropwise thionyl chloride (2.77 g, 23 mmol) at 0° C. under nitrogen, and the mixture was stirred for 0.5 h at this temperature. 2-Bromo-5-nitroaniline (5.0 g, 23 mmol) was added. The resulting mixture was stirred at room temperature overnight. Water (150 mL) was added. The yellow precipitate was collected by filtration, washed with water (50 mL×3), and dried in vacuo to give N-(2-bromo-5-nitrophenyl)methacrylamide (5.2 g, 80% yield) as a yellow solid. $^1$H-NMR (400 MHz, DMSO-d$_6$) δ (ppm) 9.78 (s 1H), 8.50 (s 1H), 8.07 (m, 2H), 6.03 (s, 1H), 5.69 (s, 1H), 2.06 (s, 3H).

C. 3,3-Dimethyl-6-nitroindolin-2-one. A solution of N-(2-bromo-5-nitrophenyl)methacrylamide (5.0 g, 17.6 mmol), diacetoxypalladium(II) (79 mg, 0.35 mmol), tetrabutylammonium bromide (5.7 g, 17.6 mmol), and triethylamine (6.1 mL, 44 mmol) in dry N,N-dimethylformamide (150 mL) under nitrogen was heated at 80° C. for 1 h. Sodium formate (1.2 g, 17.6 mmol) was added, and the mixture was stirred at 80° C. for 10 h. Water (600 mL) was added, and the mixture was extracted with ethyl acetate (400 mL×3). The combined organic layer was washed with brine, dried over sodium sulfate, concentrated, and purified by column chromatography on silica gel (eluting with 10-25% ethyl acetate in petroleum ether) to give 3,3-dimethyl-6-nitroindolin-2-one (2.5 g, 69% yield) as a solid. $^1$H-NMR (400 MHz, DMSO-d$_6$) δ (ppm) 10.73 (s, 1H), 7.87 (m, 1H), 7.55 (m, 2H), 1.28 (s, 6H).

D. tert-Butyl 3,3-dimethyl-6-nitro-2-oxoindoline-1-carboxylate. To a solution of 3,3-dimethyl-6-nitroindolin-2-one (250 mg, 1.21 mmol) in a solution of sodium bicarbonate (204 mg, 2.43 mmol) in tetrahydrofuran (10 mL) was added di-tert-butyl dicarbonate (529 mg, 2.43 mmol) at 0° C. under nitrogen, and the mixture was stirred for 6 h at room temperature. The reaction mixture was poured into water, and the resulting mixture was extracted with ethyl acetate. The combined organic layer was washed with brine, dried over anhydrous sodium sulfate, and evaporated under reduced pressure. The residue was purified on silica gel column (eluting with 1-10% ethyl acetate in petroleum ether) to give tert-butyl 3,3-dimethyl-6-nitro-2-dimethyl-6-nitro-2-oxoindoline-1-carboxylate (290 mg, 78.4% yield). $^1$H NMR (400 MHz, CHLOROFORM-d) δ (ppm) 8.70 (d, J=1.6 Hz, 1H), 8.04 (dd, J$_1$=2.0 Hz, J$_2$=8.0 Hz, 1H), 7.30 (d, J=8.0 Hz, 1H), 1.61 (s, 9H), 1.40 (s, 6H).

E. tert-Butyl 6-amino-3,3-dimethyl-2-oxoindoline-1-carboxylate. To a solution of tert-butyl 3,3-dimethyl-6-nitro-2-oxoindoline-1-carboxylate (0.29 g, 0.95 mmol) in methanol (5 mL) was added 10% palladium on activated carbon (0.15 g), and the mixture was hydrogenated under 1 atmosphere of hydrogen at room temperature for 3 h. When TLC (50% ethyl acetate in petroleum ether) showed the starting material was consumed, the reaction mixture was filtered, and the filtrate was concentrated to give tert-butyl 6-amino-3,3-dimethyl-2-oxoindoline-1-carboxylate (230 mg, 88% yield). MS (ESI): m/z 277.1 [M+1]$^+$.

Intermediate 95: 6-Iodo-3,3-dimethyl-1-((2-(trimethylsilyl)ethoxy)methyl)indolin-2-one

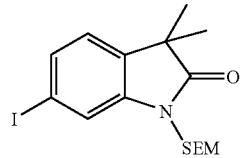

A. 6-Amino-3,3-dimethylindolin-2-one. A mixture of 3,3-dimethyl-6-nitroindolin-2-one (2.5 g, 12.1 mmol) and 10% palladium on carbon (50% wet, w/w, 250 mg) in a mixture of methanol and ethyl acetate (v:v=1:1, 20 mL) was hydrogenated under 1 atmosphere of hydrogen at room temperature for 3 h. The catalyst was filtered off, and the filtrate was concentrated under vacuum to give 6-amino-3,3-dimethylindolin-2-one (2.0 g, 95% yield).

B. 6-Iodo-3,3-dimethylindolin-2-one. To a solution of 6-amino-3,3-dimethylindolin-2-one (1.04 g, 5.9 mmol) in hydrochloric acid (3 M, 30 mL) was added sodium nitrite (406 mg, 5.9 mmol) at 0° C. After stirring for 0.5 h, a solution of potassium iodide (978 mg, 5.9 mmol) was added dropwise, and the reaction mixture was stirred at 0° C. for 2 h. The reaction mixture was neutralized with sodium carbonate, and extracted with ethyl acetate. The organic layer was combined, dried over sodium sulfate, filtered, and concentrate to give the crude product, which was purified by chromatography on silica gel (eluting with 10% ethyl acetate in petroleum ether) to give 6-iodo-3,3-dimethylindolin-2-one as a pale yellow solid (780 mg, yield 46%); MS (ESI): m/z 287.9 [M+1]$^+$.

C. 6-Iodo-3,3-dimethyl-1-((2-(trimethylsilyl)ethoxy)methyl)indolin-2-one. To a solution of 6-iodo-3,3-dimethylindolin-2-one (780 mg, 2.7 mmol) in N,N-dimethylformamide (20 mL) was added sodium hydride (162 mg, 4.1 mmol, 60% in mineral oil) in portions at 0° C. The mixture was stirred for 0.5 h at 0° C., and (2-(chloromethoxy)ethyl)trimethylsilane (678 mg, 4.1 mmol) was added. The resulting mixture was stirred at room temperature for 2 h. The reaction was quenched by the addition of ammonium chloride solution (30 mL), and the mixture was extracted with ethyl acetate. The combined organic layer was washed with brine, dried over sodium sulfate, and evaporated. The residue was purified on silica gel column (eluting with 10% ethyl acetate in petroleum ether) to give 6-iodo-3,3-dimethyl-1-((2-(trimethylsilyl)ethoxy)methyl)indolin-2-one (950 mg, 84% yield) as yellow oil. $^1$H NMR (300 MHz, CHLOROFORM-d) δ (ppm) 7.47 (d, J=7.8 Hz, 1H), 7.44 (s, 1H), 6.99 (d, J=7.8 Hz, 1H), 5.16 (s, 2H), 3.57 (t, J=8.1 Hz, 2H), 1.41 (s, 6H), 0.96 (t, J=8.1 Hz, 2H), 0 (s, 9H).

Intermediate 96:
4-Iodo-3-methoxy-N-methylbenzamide

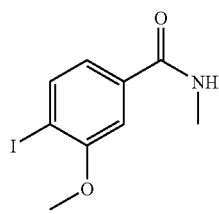

A. 4-Iodo-3-methoxybenzoic acid. A solution of sodium nitrite (1.7 g, 24.4 mmol) in water (3.5 mL) was added slowly to a stirred solution of 4-amino-3-methoxybenzoic acid (4.0 g, 23.9 mmol) in a mixture of water (61 mL) and concentrated hydrochloric acid (18 mL) at 0° C. After stirring for 1 h at 0° C., sodium iodide (3.67 g, 24.4 mmol) was added. The resultant mixture was warmed slowly to room temperature for 5 min., and heated at 60° C. for 2 h. After cooling down to room temperature, the precipitate was collected by filtration and washed with water to give 4-iodo-3-methoxybenzoic acid (4.0 g, 60.1% yield). $^1$H NMR (400 MHz, DMSO-d$_6$) δ (ppm) 7.92 (d, J=8.0 Hz, 1H), 7.42 (d, J=1.6 Hz, 1H), 7.31 (dd, J$_1$=7.6 Hz, J$_2$=1.6 Hz, 1H), 2.27 (s, 3H).

B. 4-Iodo-3-methoxy-N-methylbenzamide. N,N-Dimethylformamide (0.1 mL) was added to a solution of 4-iodo-3-methoxybenzoic acid (2.0 g, 7.2 mmol) in sulfuryl dichloride (20 mL), and the mixture was heated to reflux for 2 h. The excess sulfuryl dichloride was removed under reduced pressure to give the crude product 4-iodo-3-methoxy-benzoyl chloride. To a solution of methyl amine (0.72 g, 10.8 mmol) and triethylamine (2.18 g, 21.6 mmol) in dichloromethane (20 mL) was added dropwise a solution of the above 4-iodo-3-methoxy-benzoyl chloride in dichloromethane (15 mL) at 0° C. After the reaction was completed, water was added, the organic layer was separated, dried over sodium sulfate evaporated to give the crude product, which was purified on silica gel column (eluting with 10-17% ethyl acetate in petroleum ether) to give 4-iodo-3-methoxy-N-methylbenzamide (0.92 g, 46% yield). $^1$H NMR (400 MHz, DMSO-d$_6$) δ (ppm) 7.92 (d, J=8.0 Hz, 1H), 7.42 (d, J=5.6 Hz, 1H), 7.31 (dd, J$_1$=8.0 Hz, J$_2$=2.0 Hz, 1H), 3.88 (s, 3H).

Intermediate 97: 5-(3-Bromophenyl)-1-((2-(trimethylsilyl)ethoxy)methyl)-1H-imidazole

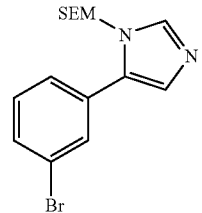

5-(3-Bromophenyl)-1-((2-(trimethylsilyl)ethoxy)methyl)-1H-imidazole. To a stirred solution of 5-(3-bromophenyl)-1H-imidazole (1 g, 4.5 mmol) in anhydrous N,N-dimethylformamide (20 mL) was added sodium hydride (60% in mineral oil, 160 mg, 4.7 mmol) at 0° C., and the mixture was stirred at this temperature for 0.5 h. A solution of (2-(chloromethoxy)ethyl)trimethylsilane (0.9 mL, 5.36 mmol) in N,N-dimethylformamide (5 mL) was added dropwise, and the resulting mixture was stirred at room temperature for 4 h. When the starting material was consumed, the reaction was quenched with water. The mixture was extracted with ethyl acetate, and the combined organic layer was washed with brine, dried over anhydrous sodium sulfate, and evaporated in vacuo. The residue was purified on silica gel column (eluting with 5-10% ethyl acetate in petroleum ether) to give 5-(3-bromophenyl)-1-((2-(trimethylsilyl)ethoxy)methyl)-1H-imidazole (1.1 mg, 69.6% yield) as a yellow solid. MS (ESI): m/z 353.0 [M+1]$^+$.

Intermediate 98: (R)-Piperidin-3-ylmethanol

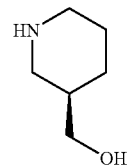

A. (R)-Piperidin-3-ylmethanol. (R)-Piperidine-3-carboxylic acid (2 g, 15.49 mmol) was added to tetrahydrofuran (20 mL). To the suspension was added lithium aluminum hydride (23.23 mL, 23.23 mmol, 1M solution in tetrahydrofuran) dropwise and then heated to 60° C. for 18 h under nitrogen. The reaction was cooled and quenched with sodium sulfate hepta-hydrate (0.5 g). The mixture was stirred at room temperature for 2 h and then filtered. The filtrate was past through ion-exchange column (Strata-XC) and then released with 2M ammonia in methanol. The solution was concentrated to give a clear oil, (0.55 g, 4.78 mmol, 30.8% yield). MS (ESI) m/z 116.2 [M+1]+.

(S)-Piperidin-3-ylmethanol was synthesized following the same procedure starting with (S)-piperidine-3-carboxylic acid.

Intermediate 99: (S)-Piperidine-3-carboxamide hydrochloride

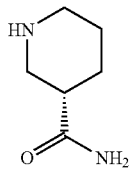

A. (S)-1-(tert-Butoxycarbonyl)piperidine-3-carboxylic acid. (S)-Piperidine-3-carboxylic acid (1 g, 7.74 mmol) was added with ethanol (50 mL) and N,N-dimethylformamide (1 mL) follow with di-tert-butyl dicarbonate (2.157 mL, 9.29 mmol) and then stirred at room temperature for 16 h. The reaction was concentrated and then purified by silica gel chromatography (0-100% ethyl acetate in hexanes) to give a white solid, (1.6 g, 6.98 mmol, 90% yield). MS (ESI) m/z 230.4 [M+1]+.

B. (S)-Piperidine-3-carboxamide hydrochloride. (S)-1-(tert-Butoxycarbonyl)piperidine-3-carboxylic acid (1.6 g, 6.98 mmol) was added with acetonitrile (70 mL), triethylamine (2.92 mL, 20.94 mmol), and O-benzotriazole-N,N,N',N'-tetramethyl-uronium-hexafluoro-phosphate (2.91 g, 7.68 mmol). The reaction and stirred at room temperature for 5 min. Then ammonium chloride (0.747 g, 13.96 mmol) was added and stirred at room temperature for 20 min. The reaction was concentrated under vacuo and then purified by silica gel chromatography (0-100% ethyl acetate in hexanes). Product fractions were concentrated and then treated with 4N hydrogen chloride in dioxane (5 mL). The solution was stirred at room temperature for 1 h and then concentrated. The residue was filtered and rinsed with ethyl acetate to give a white solid (0.32 g, 1.944 mmol, 27.9% yield). MS (ESI) m/z 129.0 [M+1]+.

(R)-Piperidine-3-carboxamide hydrochloride was synthesized following the same procedure using (R)-piperidine-3-carboxylic acid as starting material.

Intermediate 100: 5-Bromo-1-tosyl-1H-pyrrolo[2,3-b]pyridine

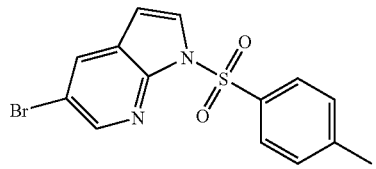

A. 5-Bromo-1-tosyl-1H-pyrrolo[2,3-b]pyridine. A stirred solution of 5-bromo-1H-pyrrolo[2,3-b]pyridine (0.682 g, 3.46 mmol) in tetrahydrofuran (10 mL) was cooled to −50° C. under nitrogen. p-Toluenesulfonyl chloride (0.693 g, 3.63 mmol) was added and the resulting mixture was stirred at −50° C. until all of the p-toluenesulfonyl chloride had dissolved. Sodium hydride (0.100 g, 4.15 mmol) was added to give a cloudy orange mixture. The resulting mixture was slowly warmed to 0° C. over 40 min and then aqueous ammonium hydroxide was added to quench the reaction. The resulting mixture was diluted with water and ethyl acetate and shaken in a separatory funnel. The layers were separated and the organics were washed with brine, dried over magnesium sulfate, filtered, and concentrated on a rotary evaporator. The residue was dissolved in dichloromethane and purified using flash chromatography (Biotage) (2-40% ethyl acetate in hexane) to give the desired product (1.133 g, 3.23 mmol, 93% yield) as a white solid. $^1$H NMR (400 MHz, DMSO-d$_6$) δ (ppm) 8.47 (d, J=2.34 Hz, 1H), 8.33 (d, J=2.34 Hz, 1H), 7.92-8.02 (m, 3H), 7.43 (d, J=8.20 Hz, 2H), 6.80 (d, J=3.90 Hz, 1H), 2.35 (s, 3H); MS (ESI) m/z 351.1 [M]+, 353.2 [M+2]+.

Intermediate 101: 6-Bromo-3-methyl-1-(tetrahydro-2H-pyran-2-yl)-1H-indazole

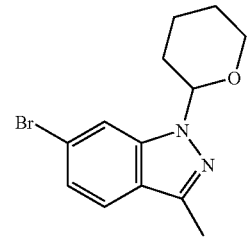

A. 6-Bromo-3-methyl-1-(tetrahydro-2H-pyran-2-yl)-1H-indazole. 6-Bromo-3-methyl-1H-indazole (2.5 g, 11.85 mmol), tetrahydrofuran (20.0 mL), p-toluenesulfonic acid monohydrate (0.113 g, 0.592 mmol), 3,4-dihydro-2H-pyran (1.625 mL, 17.77 mmol), and magnesium sulfate (1.426 g, 11.85 mmol) were added to a microwave vial, sealed, and heated to 70° C. for 4 h. The reaction was filtered, concentrated, and then purified via silica gel chromatography on an Emrys Biotage SP1 (eluting with 0-50% ethyl acetate in hexanes). The desired fractions were combined and organic volatiles removed under reduced pressure to afford 6-bromo-3-methyl-1-(tetrahydro-2H-pyran-2-yl)-1H-indazole (1.6103 g, 5.46 mmol, 46.1% yield), as a white solid. MS (ESI) m/z 295.2 [M]+, 297.2 [M+2]+.

Intermediate 102:
6-Bromo-3-methyl-1-tosyl-1H-indazole

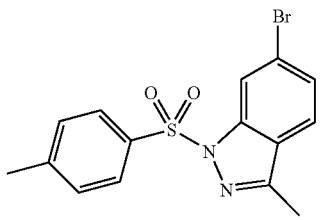

A. 6-Bromo-3-methyl-1-tosyl-1H-indazole. A stirred mixture of 6-bromo-3-methyl-1H-indazole (2.33 g, 11.04 mmol) and p-toluenesulfonyl chloride (2.126 g, 11.15 mmol) in 1,4-dioxane (25 mL) under nitrogen was heated briefly with a heat gun until all the solids dissolved. The resulting clear amber-colored solution was cooled with an ice water bath. Sodium hydride (0.318 g, 13.25 mmol) was added, the cold bath was removed, and the resulting mixture was stirred at room temperature under nitrogen for 1 h. Saturated aqueous ammonium chloride (2 mL) was added followed by water (40 mL). Solids were collected by vacuum filtration and washed with water. The solids were then washed with 50% diethyl ether in hexane (50 mL) and dried under vacuum to give the desired product (3.66 g, 10.02 mmol, 91% yield) as an off-white solid. $^1$H NMR (400 MHz, DMSO-$d_6$) δ (ppm) 8.23 (d, J=1.56 Hz, 1H), 7.76-7.87 (m, 3H), 7.60 (dd, J=1.56, 8.59 Hz, 1H), 7.41 (d, J=8.20 Hz, 2H), 2.48 (s, 3H), 2.34 (s, 3H); MS (ESI) m/z 365.2 [M]+, 367.1 [M+2]+.

Intermediate 103:
8-Methylene-1,4-dioxaspiro[4.5]decane

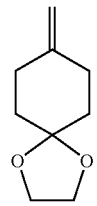

A. 8-Methylene-1,4-dioxaspiro[4.5]decane. To a suspension of methyltriphenylphosphonium bromide (9.15 g, 25.6 mmol) in dry tetrahydrofuran (88 mL) at 0° C. was added dropwise n-butyl lithium (16.65 mL, 26.6 mmol, 1.6 M solution in hexanes) with vigorous stirring. The suspension became bright orange and clear. The reaction was warmed to room temperature over 1 h before a solution of 1,4-dioxaspiro[4.5]decan-8-one (4.0 g, 25.6 mmol) in dry tetrahydrofuran (10 mL) was added at room temperature. After addition, a yellow precipitate formed slowly. The reaction was stirred overnight at room temperature. The reaction mixture was filtered and the solid was washed with hexanes. The filtrate was evaporated to dryness and the residue was purified by biotage column chromatography (eluting with 5-15% ethyl acetate in hexanes). 8-Methylene-1,4-dioxaspiro[4.5]decane (3.1 g, 20.10 mmol, 78% yield) was isolated as a colorless oil.

$^1$H NMR (400 MHz, DMSO-$d_6$) δ (ppm) 4.66 (s, 2H), 3.87 (s, 4H), 2.11-2.25 (m, 4H), 1.50-1.66 (m, 4H).

Intermediate 104: 3-Chloro-5-hydroxyphenylboronic acid

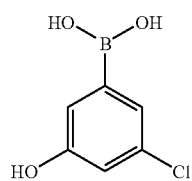

A. 1-Bromo-3-chloro-5-methoxybenzene. To a solution of 1-bromo-3-chloro-5-fluorobenzene (10 g, 48 mmol) in methanol (250 mL) was added sodium methoxide (5.18 g, 96 mmol) at room temperature under nitrogen, and the mixture was refluxed for 24 h. The reaction mixture was evaporated under reduced pressure and the residue was dissolved in ethyl acetate. The organic solution was washed with water and brine, dried over anhydrous sodium sulfate, and evaporated in vacuo to give 1-bromo-3-chloro-5-methoxybenzene (4 g, 36% yield) as a white solid.

B. 3-Chloro-5-methoxyphenylboronic acid. To a stirred solution of 1-bromo-3-chloro-5-methoxybenzene (4.0 g, 18 mmol) in tetrahydrofuran (50 mL) was added dropwise n-butyllithium (0.76 mL, 1.9 mmol, 2.5 M in hexane) at −78° C. under nitrogen. After the mixture was stirred for 1 h at this temperature, trimethyl borate (5.68 g, 54 mmol) was added. The resulting mixture was stirred at room temperature overnight. Water (100 mL) was added dropwise, then concentrated hydrochloric acid was added to adjust the pH=3. The organic solution was removed in vacuo, and the aqueous layer was extracted with ethyl acetate. The combined organic layer was washed with brine, dried over anhydrous sodium sulfate, and evaporated in vacuo to give the crude product, which was washed with ether to afford 3-chloro-5-methoxyphenylboronic acid (1.2 g, 36% yield) as a white solid. $^1$H-NMR (400 MHz, DMSO-$d_6$) δ (ppm) 8.26 (br s 1H), 7.36 (s, 1H), 7.30 (s, 1H), 7.04 (m, 1H), 3.74 (s, 3H).

C. 3-Chloro-5-hydroxyphenylboronic acid. To a stirred solution of 3-chloro-5-methoxyphenylboronic acid (1.2 g, 66 mmol) in dichloromethane (20 mL) was added dropwise tribromoborane (4.8 g, 20 mmol) at −78° C., and the mixture was stirred at room temperature overnight. The mixture was quenched with methanol at −78° C., warmed to room temperature, and concentrated in vacuo. The residue was diluted with water, and the aqueous layer was extracted with ethyl acetate. The combined organic layer was washed with brine, dried over anhydrous sodium sulfate, and evaporated in vacuo to give 3-chloro-5-hydroxyphenylboronic acid (1.08 g, 95% yield) as a white solid. ¹H-NMR (400 MHz, DMSO-d₆) δ (ppm) 9.71 (br s 1H), 8.14 (br s, 2H), 7.35 (s, 1H), 7.21 (s, 1H), 6.82 (s, 1H).

Intermediate 105:
5-Methyl-6-morpholinopyridin-3-amine

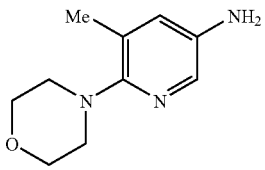

A. 4-(3-Methyl-5-nitropyridin-2-yl)morpholine. 2-Chloro-3-methyl-5-nitropyridine (5 g, 29.0 mmol), potassium carbonate (8.01 g, 57.9 mmol), dimethylsulfoxide (20 mL), and morpholine (5.05 mL, 57.9 mmol) were heated together to 80° C. for 16 h. The reaction was diluted with water, filtered, and then dried to give 4-(3-methyl-5-nitropyridin-2-yl)morpholine (7.1 g, 31.8 mmol, 110% yield) as bright yellow solid. ¹H NMR (400 MHz, DMSO-d₆) δ (ppm) 8.91 (d, J=2.7 Hz, 1H), 8.24 (dd, J=0.8, 2.7 Hz, 1H), 3.67-3.76 (m, 4H), 3.44 (m, 4H), 2.34 (s, 3H). MS (ESI) m/z 224.2 [M+1]⁺.

B. 5-Methyl-6-morpholinopyridin-3-amine. 4-(3-Methyl-5-nitropyridin-2-yl)morpholine (6.47 g, 29 mmol) was added with 4N hydrogen chloride in dioxane (4 mL), 10% palladium on carbon (100 mg), methanol (60 mL), and then shaken in a Parr hydrogenator under 40 psi of hydrogen for 16 h. The reaction was filtered through celite, concentrated, and then purified over silica gel (0-100% methanol in ethyl acetate) and dried to a tan solid to provide 5-methyl-6-morpholinopyridin-3-amine, as a hydrochloride salt (2.7 g, 11.75 mmol, 40.5% yield). ¹H NMR (400 MHz, DMSO-d₆) δ (ppm) 2.29 (s, 3H) 3.08-3.16 (m, 4H) 3.69-3.79 (m, 4H) 7.51 (d, J=2.34 Hz, 1H) 7.78 (br s, 1H). MS (ESI) m/z 194.1 [M+1]⁺.

Intermediate 106: tert-Butyl 6-amino-3,3,4-trimethyl-2-oxoindoline-1-carboxylate

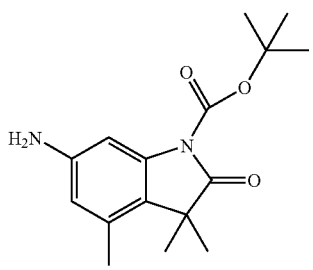

A. 2-Bromo-3-methyl-5-nitroaniline. 2-Bromo-3-methylaniline (4.420 g, 23.76 mmol) was dissolved into sulfuric acid (25 mL, 469 mmol) at room temperature using sonication. The solution was cooled to 0° C., and potassium nitrate (2.62 g, 25.9 mmol) was added in one portion. The solution became brown over time. LCMS after 45 min showed ~10:1 product:starting material. Another portion of potassium nitrate (240 mg, 2.374 mmol) was added. After 2 h, the reaction was poured slowly into a mixture of 100 mL ammonium hydroxide solution and crushed ice, maintaining the temperature below room temperature using additional crushed ice. The reddish-yellow solid was collected by filtration and dried in a vacuum oven at 60° C. for 16 h to provide the desired 2-bromo-3-methyl-5-nitroaniline (5.3792 g, 23.28 mmol, 98% yield). ¹H NMR of the crude product showed two regioisomers of nitration, with the desired regioisomer being ~85% of the mixture. The crude nitroaniline was carried on directly to the next reaction. ¹H NMR (400 MHz, CHLOROFORM-d) δ (ppm) 8.94 (s, 1H), 7.85 (d, J=8.98 Hz, 1H), 7.48 (d, J=2.34 Hz, 1H), 7.44 (d, J=2.73 Hz, 1H), 4.46 (br s, 2H), 2.46 (s, 3H); MS (ESI): m/z 233.2 [M+1]⁺.

B. N-(2-Bromo-3-methyl-5-nitrophenyl)methacrylamide. Methacrylic acid (1.961 mL, 23.12 mmol) was weighed into a 200 mL flask and dissolved into dry N,N-dimethylacetamide (30 mL). The solution was cooled to 0° C. and thionyl chloride (1.70 mL, 23.29 mmol) was added dropwise over 1 min. The solution was stirred for 20 min, and 2-bromo-3-methyl-5-nitroaniline (3.8150 g, 16.51 mmol) was then added as a solid. After 30 min, the cold bath was removed. After 1 h, LCMS analysis showed a strong product peak. Water (~100 mL) was added causing precipitation of brown solid. The solid was collected by vacuum filtration in a 60 mL medium fitted funnel, then dried in a vacuum oven at 60° C. for 2 h to provide the crude N-(2-bromo-3-methyl-5-nitrophenyl)methacrylamide (4.5198 g, 15.11 mmol, 92% yield). MS (ESI): m/z 299.4 [M+1]⁺.

C. 3,3,4-Trimethyl-6-nitroindolin-2-one. N-(2-bromo-3-methyl-5-nitrophenyl)methacrylamide (2.5451 g, 8.51 mmol), palladium (II) acetate (106.4 mg, 0.474 mmol), tetrabutylammonium bromide (2.80 g, 8.69 mmol), and N,N-dimethylformamide (24 mL) were added to a 200 mL flask, which was then capped with a septum and flushed with nitrogen. N,N-dimethylformamide (24 mL) was added via syringe, and nitrogen was bubbled through the solution through a needle for 5 min. Triethylamine (3.0 mL, 21.52 mmol) was added via syringe, and the vial was placed to stir in an 80° C. oil bath for 30 min. The cap was then briefly removed and sodium formate (0.675 g, 9.93 mmol) was added to the hot reaction. The vial was then capped, nitrogen was bubbled through the solution for 2 min using a needle, and the reaction was placed to stir at 80° C. for 15 h. The reaction was filtered through celite and concentrated to a brown oil. Flash chromatography over silica gel provided the desired 3,3,4-trimethyl-6-nitroindolin-2-one (0.9092 g, 4.13 mmol, 48.5% yield). ¹H NMR (400 MHz, CHLOROFORM-d) δ (ppm) 8.44 (br s, 1H), 7.76 (d, J=1.56 Hz, 1H), 7.61 (d, J=1.95 Hz, 1H), 2.50 (s, 3H), 1.52 (s, 6H). MS (ESI): m/z 221.4 [M+1]⁺.

D. tert-Butyl 3,3,4-trimethyl-6-nitro-2-oxoindoline-1-carboxylate. 3,3,4-Trimethyl-6-nitroindolin-2-one (0.9092 g, 4.13 mmol), di-tert-butyl dicarbonate (1.602 mL, 6.90 mmol), tetrahydrofuran (10 mL) and sodium bicarbonate (748.8 mg, 8.91 mmol) were placed in a 100 mL flask. 4-(Dimethylamino)pyridine (51.8 mg, 0.424 mmol) was added, and the loosely capped flask was left to stir hard at 60° C. in an oil bath. After 1.5 h, the reaction was diluted with ethyl acetate and 10% citric acid. Using some brine to break up the emulsion, the organic layer was removed and the aqueous layer extracted with ethyl acetate. The combined organic solutions were dried over magnesium sulfate, filtered and concentrated. Flash chromatography over silica gel eluting 0-25% ethyl acetate in hexanes provided the desired tert-butyl 3,3,4-trimethyl-6-nitro-2-oxoindoline-1-carboxylate (1.1263 g, 3.52 mmol, 85% yield). ¹H NMR (400 MHz, CHLOROFORM-d) δ (ppm) 8.64 (d, J=1.95 Hz, 1H), 7.87 (d, J=1.56 Hz, 1H), 2.52 (s, 3H), 1.68 (s, 9H), 1.55 (s, 6H). MS (ESI): m/z 265.2 [M+1]⁺.

E. tert-Butyl 6-amino-3,3,4-trimethyl-2-oxoindoline-1-carboxylate. 10% Palladium on carbon (72.3 mg, 0.068 mmol) and tert-butyl 3,3,4-trimethyl-6-nitro-2-oxoindoline-1-carboxylate (1.1263 g, 3.52 mmol) were dissolved into ethyl acetate (15 mL). The flask was flushed with hydrogen and left to stir under a hydrogen balloon for 3 days, then filtered through celite and concentrated to provide the desired tert-butyl 6-amino-3,3,4-trimethyl-2-oxoindoline-1-carboxylate (1.0589 g, 3.65 mmol, 104% yield). MS (ESI): m/z 291.1 [M+1]$^+$.

Intermediate 107: 6-Aminoindolin-2-one

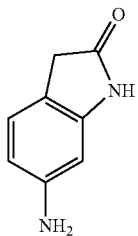

A. Methyl 2-(2,4-dinitrophenyl)acetate. To a stirred solution of 2-(2,4-dinitrophenyl)acetic acid (11.3 g, 0.5 mol) in methanol (150 mL) was added concentrated sulfuric acid (2 mL), and the mixture was stirred at reflux for 10 h. The reaction mixture was concentrated under vacuum, and the residue was washed by water to give methyl 2-(2,4-dinitrophenyl)acetate (9.4 g, 78.3% yield) as a off-white solid. $^1$H NMR (400 MHz, DMSO-d$_6$) δ (ppm) 8.73 (d, J=2.4 Hz, 1H), 8.51 (dd, J=2.4, 8.4 Hz, 1H), 7.83 (d, J=8.4 Hz, 1H), 4.19 (s, 2H), 3.57 (s, 3H); MS (ESI): m/z: 241.0 [M+H]$^+$.

B. 6-Aminoindolin-2-one. A mixture of methyl 2-(2,4-dinitrophenyl)acetate (4.8 g, 20 mmol) and 10% palladium on carbon (50% wet, w/w, 100 mg) in methanol (50 mL) was hydrogenated under 1 atmosphere of hydrogen at room temperature overnight. The suspension was filtered off, the filtrate was heated at 60° C. for 12 h. The mixture was cooled to room temperature and concentrated. The residue was purified by column chromatography on silica gel (eluting with 60% ethyl acetate in petroleum) to give 6-aminoindolin-2-one (220 mg, 7.4% yield) as a grey solid. $^1$H NMR (400 MHz, DMSO-d$_6$) δ (ppm) 6.80 (d, J=8.4 Hz, 1H), 6.12 (m, 2H), 5.01 (s, 2H), 3.24 (s, 2H).

Intermediate 108: 6-Bromo-3-ethyl-1-(tetrahydro-2H-pyran-2-yl)-1H-indazole

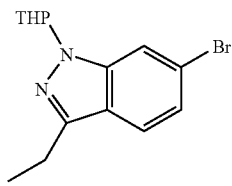

A. 1-(4-Bromo-2-fluorophenyl)propan-1-ol. Ethylmagnesium bromide (64.3 mL, 192.9 mmol, 3 M solution in tetrahydrofuran) was added dropwise to a solution of 4-bromo-2-fluorobenzaldehyde (30.0 g, 148 mmol) in tetrahydrofuran (500 mL) under nitrogen at 0° C. over 30 min. The resulting mixture was warmed to room temperature over 2 h, quenched with aqueous ammonium chloride solution, and extracted with ethyl acetate. The combined organic layer was dried over sodium sulfate, evaporated under reduced pressure, and dried under vacuum to give 1-(4-bromo-2-fluorophenyl)propan-1-ol (16 g, 47%) as an oil. $^1$H NMR (400 MHz, DMSO-d$_6$) δ (ppm) 7.45 (m, 3H), 5.36 (s, 1H), 4.70 (t, J=6.4 Hz, 1H), 1.63 (q, J=7.2 Hz, 2H), 0.80 (m, 3H).

B. 1-(4-Bromo-2-fluorophenyl)propan-1-one. A mixture of 1-(4-bromo-2-fluorophenyl)propan-1-ol (15 g, 64.6 mmol) and manganese (IV) oxide (22.5 g, 258 mmol) in dichloromethane (250 mL) was refluxed overnight. After cooling to room temperature, the reaction mixture was filtered, and the filtrate was removed under reduced pressure to give 1-(4-bromo-2-fluorophenyl)propan-1-one (9 g, 60.5%) as a solid. MS (ESI): m/z 230.8 [M+1]$^+$.

C. 6-Bromo-3-ethyl-1H-indazole. A mixture of 1-(4-bromo-2-fluorophenyl)propan-1-one (9 g, 39.0 mmol) and aqueous hydrazine (50 mL, 85%) was refluxed overnight. After cooling to room temperature, the reaction mixture was filtered, and the filter cake was dried under vacuum to give 6-bromo-3-ethyl-1H-indazole (4.4 g, 50.3% yield) as a solid. MS (ESI): m/z 224.8 [M+1]$^+$.

D. 6-Bromo-3-ethyl-1-(tetrahydro-2H-pyran-2-yl)-1H-indazole. A mixture of 6-bromo-3-ethyl-1H-indazole (4.4 g, 19.5 mmol), 3,4-dihydro-2H-pyran (3.3 g, 39 mmol), and p-toluenesulfonic acid (374 mg, 1.95 mmol) in tetrahydrofuran (60 mL) was heated at 60° C. overnight. The reaction mixture was poured into ice water, and the aqueous phase was extracted with ethyl acetate. The organic layer was dried over sodium sulfate, filtered, and evaporated under reduced pressure. The residue was purified on silica gel column to give 6-bromo-3-ethyl-1-(tetrahydro-2H-pyran-2-yl)-1H-indazole (4.4 g, 73.2% yield). MS (ESI): m/z 310.8 [M+3]$^+$.

Intermediate 109:
5-Bromo-2-(2-methoxyethyl)isoindolin-1-one

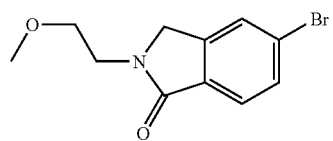

A. 5-Bromo-2-(2-methoxyethyl)isoindolin-1-one. A mixture of methyl 4-bromo-2-(bromomethyl)benzoate (2.4 g, 7.8 mmol) and 2-methoxyethanamine (2.9 g, 39 mmol) in methanol (20 mL) was stirred at room temperature overnight. The reaction mixture was concentrated, and purified by column chromatography on silica gel (eluting with 5-20% ethyl acetate in petroleum ether) to give 5-bromo-2-(2-methoxyethyl)isoindolin-1-one as a white solid (1.2 g, 57% yield). $^1$H NMR (400 MHz, CHLOROFORM-d) δ (ppm) 7.71 (d, J=7.6

Hz, 1H), 7.59 (m, 2H), 7.45 (s, 2H), 3.78 (t, J=6.4 Hz, 2H), 3.63 (t, J=6.4 Hz, 2H), 3.39 (s, 3H).

Intermediate 110: 6-Bromo-4-fluoro-3-methyl-1-(tetrahydro-2H-pyran-2-yl)-1H-indazole

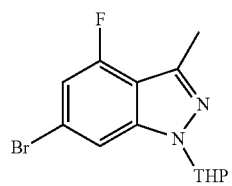

A. (4-Bromo-2,6-difluorophenyl)methanol. To a solution of 4-bromo-2,6-difluorobenzoic acid (5 g, 21 mmol) in tetrahydrofuran (200 mL) was added dropwise a solution of borane dimethyl sulfide complex (16.1 g, 212 mmol) in tetrahydrofuran (100 mL) at 0° C. under nitrogen, and the resulting mixture was stirred at room temperature for 3 h. Methanol (300 mL) was added to quench the reaction, and the solvent was removed under reduced pressure. The residue was dissolved in ethyl acetate, the solution was washed with brine, dried over anhydrous sodium sulfate, and evaporated in vacuo to give (4-bromo-2,6-difluorophenyl)methanol (4.56 g, 97% yield). $^1$H NMR (400 MHz, CHLOROFORM-d) δ (ppm) 7.13 (d, J=8.8 Hz, 2H), 4.75 (s, 2H).

B. 4-Bromo-2,6-difluorobenzaldehyde. A mixture of (4-bromo-2,6-difluorophenyl)methanol (4.56 g, 20.5 mmol) and manganese (IV) dioxide (7.14 g, 82.2 mmol) in dichloromethane (200 mL) was refluxed overnight. After cooling to room temperature, the reaction mixture was filtered, and the filtrate was concentrated under reduced pressure to give 4-bromo-2,6-difluorobenzaldehyde (3.54 g, 78%) as a solid. $^1$H NMR (400 MHz, CHLOROFORM-d) δ (ppm) 10.22 (s, 1H), 7.19-7.14 (m, J=8.8 Hz, 2H).

C. 1-(4-Bromo-2,6-difluorophenyl)ethanol. Methylmagnesium bromide (6.4 mL, 19.3 mmol, 3 M solution in tetrahydrofuran) was added dropwise to a solution of 4-bromo-2,6-difluorobenzaldehyde (3.54 g, 16.1 mmol) in tetrahydrofuran (100 mL) under nitrogen at 0° C. over 30 min. The resulting mixture was warmed to room temperature over 2 h, quenched with aqueous ammonium chloride solution, and extracted with ethyl acetate. The combined organic layer was dried over sodium sulfate, evaporated under reduced pressure, and dried under vacuum to give 1-(4-bromo-2,6-difluorophenyl)ethanol (2.2 g, 58%) as an oil. $^1$H NMR (400 MHz, CHLOROFORM-d) δ (ppm) 7.12 (m, 2H), 5.14 (m, 1H), 1.54 (m, 3H).

D. 1-(4-Bromo-2,6-difluorophenyl)ethanone. A mixture of 1-(4-Bromo-2,6-difluorophenyl)ethanol (2.2 g, 9.3 mmol) and manganese (IV) dioxide (3.2 g, 37.3 mmol) in dichloromethane (50 mL) was refluxed overnight. After cooling to room temperature, the reaction mixture was filtered, and the filtrate was concentrated under reduced pressure to give 1-(4-bromo-2,6-difluorophenyl)ethanone (1.7 g, 78%) as an oil. $^1$H NMR (400 MHz, CHLOROFORM-d) δ (ppm) 7.14 (m, 2H), 1.54 (s, 3H).

E. 6-Bromo-4-fluoro-3-methyl-1H-indazole. A mixture of 1-(4-bromo-2,6-difluorophenyl)ethanone (1.1 g, 4.7 mmol) and aqueous hydrazine (235 mg, 4.7 mmol, 85%) in tetrahydrofuran was refluxed overnight. After cooling to room temperature, the reaction mixture was concentrated, and the residue was dissolved with ethyl acetate, the solution was washed with brine, dried over anhydrous sodium sulfate, evaporated under reduced pressure, and purified on silica gel column to give 6-bromo-4-fluoro-3-methyl-1H-indazole (510 mg, 47.7% yield). $^1$H NMR (400 MHz, CHLOROFORM-d) δ (ppm) 9.85 (br s, 1H), 7.31 (d, J=0.8 Hz, 1H), 6.86 (dd, J$_1$=1.2 Hz, J$_2$=9.2 Hz, 1H), 2.60 (s, 3H).

F. 6-Bromo-4-fluoro-3-methyl-1-(tetrahydro-2H-pyran-2-yl)-1H-indazole. A mixture of 6-bromo-4-fluoro-3-methyl-1H-indazole (510 mg, 2.24 mmol), 3,4-dihydro-2H-pyran (376 mg, 4.47 mmol), and p-toluenesulfonic acid (42.5 mg, 0.224 mmol) in tetrahydrofuran (20 mL) was heated at 80° C. overnight. The reaction mixture was poured into ice water, and the aqueous phase was extracted with ethyl acetate. The organic layer was dried over sodium sulfate, evaporated under reduced pressure, and purified on silica gel column to give 6-bromo-4-fluoro-3-methyl-1-(tetrahydro-2H-pyran-2-yl)-1H-indazole (590 mg, 84.5% yield). $^1$H NMR (300 MHz, DMSO-d$_6$) δ (ppm) 7.85 (s, 1H), 7.20 (d, J=8.7 Hz, 1H), 5.81 (d, J=9.2 Hz, 1H), 3.88 (m, 2H), 2.55 (s, 3H), 1.98-1.91 (m, 2H), 1.67-1.47 (m, 4H).

Intermediate 111: 6-Bromo-4-fluoro-1,3-dimethyl-1H-indazole

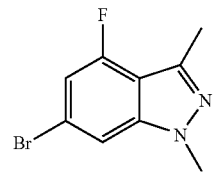

A. 6-Bromo-4-fluoro-1,3-dimethyl-1H-indazole. To a solution of 6-bromo-4-fluoro-3-methyl-1H-indazole (500 mg, 2.19 mmol) in N,N-dimethylformamide (15 mL) was added sodium hydride (100 mg, 2.49 mmol, 60% in mineral oil) in portions at 0° C. After the addition, the mixture was stirred for 30 min at 0° C., iodomethane (1.25 g, 8.8 mmol) was added, and the resulting mixture was stirred at room temperature for 2 h. The reaction was quenched by the addition of water (10 mL), and the mixture was extracted with ethyl acetate. The combined organic layer was washed with brine, dried over sodium sulfate, evaporated, and purified on silica gel column (eluting with 5% ethyl acetate in petrol ether) to give 6-bromo-4-fluoro-1,3-dimethyl-1H-indazole (426 mg, 80% yield) as a white solid. $^1$H NMR (300 MHz, CHLOROFORM-d) δ (ppm) 7.19 (d, J=1.2 Hz, 1H), 6.80 (dd, J$_1$=1.5 Hz, J$_2$=9.6 Hz, 1H), 3.87 (s, 3H), 2.54 (s, 3H).

Intermediate 112: Diethyl 2-(5-bromo-3-nitropyridin-2-yl)malonate

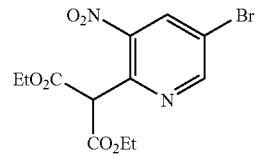

A. Diethyl 2-(5-bromo-3-nitropyridin-2-yl)malonate. To a solution of diethylmalonate (6.35 g, 40 mmol) in N,N-dimethylformamide (30 mL) was added sodium hydride (2.0 g, 50 mol, 60% in mineral oil) at 0-2° C. under nitrogen atmosphere. Once the addition was completed, the reaction mixture was stirred at the same temperature for 10 minutes.

A solution of 5-bromo-2-chloro-3-nitropyridine (5 g, 21 mmol) in N,N-dimethylformamide (10 mL) was added slowly, and the reaction mixture was maintained approximately at 40° C. for 1 hour. The reaction was quenched with water (50 mL), extracted with diethyl ether (150 mL×3), dried over sodium sulfate, and evaporated in vacuo to yield a brown oil, which was purified on silica gel column (eluting with 0-10% ethyl acetate in petroleum ether) to give diethyl 2-(5-bromo-3-nitropyridin-2-yl)malonate (5 g, 65.6% yield). $^1$H-NMR (400 MHz, CHLOROFORM-d) δ (ppm) 8.87 (d, J=2.0 Hz, 1H), 8.62 (d, J=2.0 Hz, 1H), 5.45 (s, 1H), 4.32 (m, 4H), 1.30 (m, 6H).

Intermediate 113:
1-Methyl-1H-pyrazolo[3,4-b]pyridin-5-amine

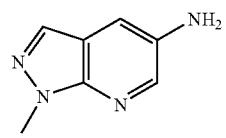

A. 5-Bromo-1-methyl-1H-pyrazolo[3,4-b]pyridine. To a solution of 1-methyl-1H-pyrazol-5-amine (5 g, 51.5 mmol) in acetic acid (50 mL) was added 2-bromomalonaldehyde (7.5 g, 50 mmol) and concentrated sulfuric acid (0.5 mL), and the mixture was refluxed for 2 days. The solution was concentrated, and partitioned between water (100 mL) and ethyl acetate (100 mL). The aqueous layer was extracted with ethyl acetate (100 mL×2). The combined organic layers were dried, concentrated, and purified by column chromatography on silica gel (eluting with 10% ethyl acetate in petroleum ether) to give 5-bromo-1-methyl-1H-pyrazolo[3,4-b]pyridine (3.0 g, 27% yield) as a white powder. $^1$H NMR (400 MHz, DMSO-d$_6$) δ (ppm) 8.63 (d, J=2.0 Hz, 1H), 8.53 (d, J=2.0 Hz, 1H), 8.13 (s, 1H), 4.05 (s, 3H).

B. 1-Methyl-1H-pyrazolo[3,4-b]pyridin-5-amine. A degassed mixture of 5-bromo-1-methyl-1H-pyrazolo[3,4-b]pyridine (880 mg, 4 mmol), diphenylmethanimine (1.08 g, 6 mmol), tris(dibenzylideneacetone)palladium (0) (734 mg, 0.8 mmol), (R)-(+)-2,2'-bis(diphenylphosphino)-1,1'-binaphthyl (1.24 g, 2 mmol), and sodium tert-butoxide (576 mg, 6 mmol) in toluene (18 mL) was heated at 115° C. under nitrogen overnight. The reaction mixture was purified by column chromatography on silica gel (eluting with 4% ethyl acetate in petroleum ether) to give N-(diphenylmethylene)-1-methyl-1H-pyrazolo[3,4-b]pyridin-5-amine (1.2 g, crude). The crude N-(diphenylmethylene)-1-methyl-1H-pyrazolo[3,4-b]pyridin-5-amine was dissolved in tetrahydrofuran (10 mL), and hydrochloric acid (2 N, 5 mL) was added. The mixture was stirred at room temperature for 2 h. The mixture was adjusted to pH=8 with saturated sodium carbonate solution, and extracted with ethyl acetate. The organic phase was dried, concentrated, and purified by column chromatography on silica gel (eluting with 33% ethyl acetate in petroleum ether) to give 1-methyl-1H-pyrazolo[3,4-b]pyridin-5-amine (420 mg, 68.4% yield) as an off-white solid.

Intermediate 114: 3-(Trifluoromethyl)-1-((2-(trimethylsilyl)ethoxy)methyl)-1H-indazol-6-amine

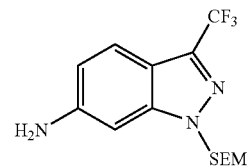

A. 6-Nitro-3-(trifluoromethyl)-1-((2-(trimethylsilyl)ethoxy)methyl)-1H-indazole. To a stirred solution of 3-iodo-6-nitro-1-((2-(trimethylsilyl)ethoxy)methyl)-1H-indazole (15 g, 35.8 mmol), methyl 2,2-difluoro-2-(fluorosulfonyl)acetate (3.4 g, 17.9 mmol), and copper (I) iodide (1.36 g, 7.2 mmol) in dimethylsulfoxide (50 mL) was heated at 120° C. for 3 hours under nitrogen atmosphere. More methyl 2,2-difluoro-2-(fluorosulfonyl)acetate (1.72 g, 8.95 mmol) was added, and the mixture was heated at 120° C. for 16 h. The reaction mixture was concentrated under vacuum, and purified by silica gel column (eluting with 1% ethyl acetate in petroleum ether) to give 6-nitro-3-(trifluoromethyl)-1-((2-(trimethylsilyl)ethoxy)methyl)-1H-indazole (2.0 g, 15.5% yield) as an oil. $^1$H NMR (400 MHz, CHLOROFORM-d) δ (ppm) 8.63 (s, 1H), 8.22 (d, J=8.8 Hz, 1H), 8.01 (d, J=8.8 Hz, 1H), 5.87 (s, 2H), 3.62 (t, J=8.4 Hz, 1H), 0.93 (t, J=8.4 Hz, 1H), −0.05 (s, 9H).

B. 3-(Trifluoromethyl)-1-((2-(trimethylsilyl)ethoxy)methyl)-1H-indazol-6-amine. A mixture of 6-nitro-3-(trifluoromethyl)-1-((2-(trimethylsilyl)ethoxy)methyl)-1H-indazole (1.0 g, 2.77 mmol) and 10% palladium on carbon (50% wet, w/w, 100 mg) in methanol (10 mL) was hydrogenated under 1 atmosphere of hydrogen at room temperature for 2 h. The suspension was filtered off, and the filtrate was concentrated to give 3-(trifluoromethyl)-1-((2-(trimethylsilyl)ethoxy)methyl)-1H-indazol-6-amine (900 mg, 98% yield) as a solid. $^1$H NMR (400 MHz, CHLOROFORM-d) δ (ppm) 7.57 (d, J=8.4 Hz, 1H), 6.71 (m, 2H), 5.62 (s, 2H), 4.00 (br s, 2H), 3.56 (t, J=8.4 Hz, 2H), 0.88 (t, J=8.4 Hz, 2H), −0.05 (s, 9H).

Intermediate 115: tert-Butyl 4-(6-bromo-1-methyl-1H-indazol-3-ylamino)piperidine-1-carboxylate

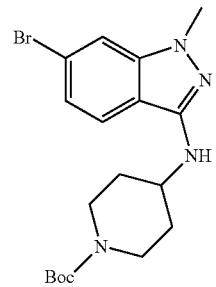

A. tert-Butyl 4-(6-bromo-1-methyl-1H-indazol-3-ylamino)piperidine-1-carboxylate. To 6-bromo-1-methyl-1H-indazol-3-amine (400 mg, 1.77 mmol) in a mixture of acetic acid (2 mL) and methanol (40 mL) was added tert-butyl 4-oxopiperidine-1-carboxylate (525 mg, 2.65 mmol), and the mixture was stirred at room temperature for 10 min. The mixture was cooled to 0° C., and sodium cyanoborohydride (223 mg, 3.54 mmol) was added. The reaction mixture was stirred at room temperature overnight, concentrated under reduced pressure, and purified on silica gel column (eluting with 5-25% ethyl acetate in petroleum ether) to give tert-butyl 4-(6-bromo-1-methyl-1H-indazol-3-ylamino)piperidine-1-carboxylate (700 mg, 97% yield) as a solid. MS (ESI): m/z 309.0 [M+1]+.

Intermediate 116: 6-Bromo-1-(tetrahydro-2H-pyran-2-yl)-N-(tetrahydro-2H-pyran-4-yl)-1H-indazol-3-amine

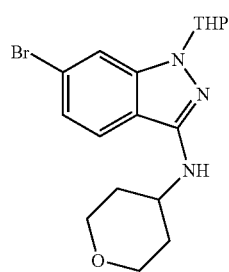

A. 6-Bromo-N-(tetrahydro-2H-pyran-4-yl)-1H-indazol-3-amine. A solution of 6-bromo-1H-indazol-3-amine (915 mg, 4.34 mmol) in a mixture of acetic acid (4 mL) and methanol (80 mL) was added dihydro-2H-pyran-4(3H)-one (650 mg, 6.50 mmol), and the mixture was stirred at room temperature for 10 min. The mixture was cooled to 0° C., and sodium cyanoborohydride (547 mg, 8.68 mmol) was added. The reaction mixture was stirred at room temperature overnight, concentrated under reduced pressure, and purified on silica gel column (eluting with 5-25% ethyl acetate in petroleum ether) to give 6-bromo-N-(tetrahydro-2H-pyran-4-yl)-1H-indazol-3-amine (860 mg, 67% yield) as a solid. MS (ESI): m/z 295.9 [M+1]+.

B. 6-Bromo-1-(tetrahydro-2H-pyran-2-yl)-N-(tetrahydro-2H-pyran-4-yl)-1H-indazol-3-amine. A mixture of 6-bromo-N-(tetrahydro-2H-pyran-4-yl)-1H-indazol-3-amine (860 mg, 2.91 mmol) and p-toluensulfonic acid (50 mg, 0.29 mmol) in tetrahydrofuran (40 mL) was added 3,4-dihydro-2H-pyran (489 mg, 5.82 mmol), and the mixture was refluxed at 70° C. under nitrogen overnight. The reaction mixture was concentrated, and purified on silica gel column (eluting with 5-25% ethyl acetate in petroleum ether) to give 6-bromo-1-(tetrahydro-2H-pyran-2-yl)-N-(tetrahydro-2H-pyran-4-yl)-1H-indazol-3-amine.

Intermediate 117: 6-Bromo-1-methyl-N-(tetrahydro-2H-pyran-4-yl)-1H-indazol-3-amine

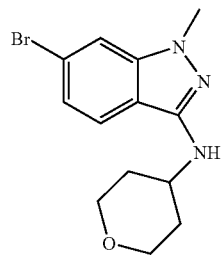

A. 6-Bromo-1-methyl-N-(tetrahydro-2H-pyran-4-yl)-1H-indazol-3-amine. To a mixture of 6-bromo-1-methyl-1H-indazol-3-amine (420 mg, 1.86 mmol) in a mixture of acetic acid (2 mL) and methanol (40 mL) was added dihydro-2H-pyran-4(3H)-one (279 mg, 2.79 mmol), and the mixture was stirred at room temperature for 10 min. The mixture was cooled to 0° C., sodium cyanoborohydride (234 mg, 3.72 mmol) was added. The reaction mixture was stirred at room temperature overnight, concentrated under reduced pressure, and purified on silica gel column (eluting with 5-25% ethyl acetate in petroleum ether) to give 6-bromo-1-methyl-N-(tetrahydro-2H-pyran-4-yl)-1H-indazol-3-amine (570 mg, 84% yield, 85% purity) as a solid. MS (ESI): m/z 309.9 [M+1]+.

Intermediate 118: tert-Butyl 5-amino-3-methyl-1H-indazole-1-carboxylate

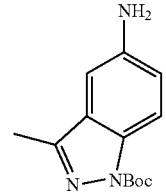

A. tert-Butyl 3-methyl-5-nitro-1H-indazole-1-carboxylate. To a solution of 3-methyl-5-nitro-1H-indazole (0.95 g, 5.36 mmol) in ethanol (12 mL) was added di-tert-butyl dicarbonate (1.755 g, 8.04 mmol). The reaction was stirred at 50° C. for 5 h. The reaction mixture was cooled down to room temperature and the solvent was removed under reduced pressure. The crude was diluted with ethyl acetate (150 mL), washed with saturated sodium bicarbonate (100 mL), and brine (100 mL). The organic layer was dried over magnesium sulfate, filtered and concentrated down to give the title compound as an off-white solid, which was used in the next step without further purification. MS (ESI) m/z 278.4 [M+1]+.

B. tert-Butyl 5-amino-3-methyl-1H-indazole-1-carboxylate. To a solution of tert-butyl 3-methyl-5-nitro-1H-indazole-1-carboxylate (1.486 g, 5.36 mmol) in ethanol (25 mL) was added palladium on carbon (0.057 g, 0.536 mmol) and the reaction was stirred at room temperature for 16 h under 1 atmosphere of hydrogen. The reaction mixture was filtered through Celite and concentrated down. The crude was purified by column chromatography (Biotage, eluting with 0-100% ethyl acetate in hexane) to give the desired compound as yellow solid (1 g, 75% yield). MS (ESI) m/z 248.9 [M+1]+.

Intermediate 119:
6-Amino-3,3-dimethylisoindolin-1-one

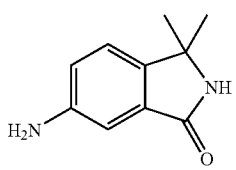

A. 3,3-Dimethylisoindolin-1-one. 2-Cyanobenzoic acid (3 g, 20.39 mmol) was dissolved in tetrahydrofuran (300 mL) and then cooled to −78° C. Methyllithium (127 mL, 204 mmol) was added dropwise and the reaction was slowly warmed to room temperature over 2 hours. The reaction was quenched with brine then extracted twice with ethyl acetate. The combined organics were washed with 1 N HCl, saturated sodium bicarbonate and water, dried over magnesium sulfate and concentrated. The residue was purified by column chromatography to give the desired product. $^1$H NMR (400 MHz, DMSO-$d_6$) δ (ppm) 8.58-8.69 (m, 1H), 7.53-7.66 (m, 3H), 7.45 (dd, J=1.56, 7.42 Hz, 1H), 1.44 (s, 6H). MS (ESI) m/z 162.2 [M+1]+.

B. 3,3-Dimethyl-6-nitroisoindolin-1-one. 3,3-Dimethylisoindolin-1-one (0.600 g, 3.72 mmol) was dissolved in sulfuric acid (6.7 mL) and then cooled to 0° C. Potassium nitrate (0.587 g, 5.81 mmol) was added to the solution. The mixture was stirred overnight while gradually raising the temperature to room temperature. The reaction solution was poured into ice water, and then extracted with ethyl acetate. The extract was washed with water, saturated aqueous sodium bicarbonate solution, and brine. The organic layer was dried and evaporated to give 3,3-dimethyl-6-nitroisoindolin-1-one (0.700 g, 3.39 mmol, 91% yield). $^1$H NMR (400 MHz, CHLOROFORM-d) δ (ppm) 8.67 (d, J=1.95 Hz, 1H), 8.47 (dd, J=2.15, 8.40 Hz, 1H), 7.59 (d, J=8.20 Hz, 1H), 7.08-7.25 (m, 1H), 1.63 (s, 6H).

C. 3,3-Dimethyl-6-aminoisoindolin-1-one. 3,3-Dimethyl-6-nitroisoindolin-1-one (1.5 g, 7.27 mmol) was taken up in methanol (60 mL) and a catalytic amount of palladium on carbon was added. The reaction was then stirred under 1 atmosphere of hydrogen gas for 18 hours. The reaction mixture was filtered through celite and the solvent was removed under reduced pressure to give 6-amino-3,3-dimethylisoindolin-1-one (1.218 g, 6.91 mmol, 95% yield). MS (ESI) m/z 177.1 [M+1]+.

Intermediate 120: 3,4-Dimethyl-1-(tetrahydro-2H-pyran-2-yl)-1H-indazol-6-amine

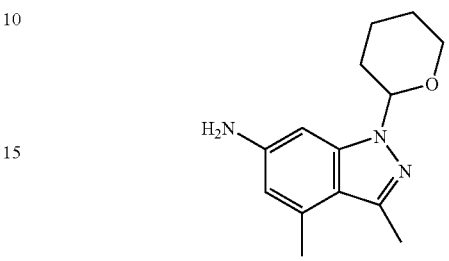

A. 2,3-Dimethyl-5-nitroaniline. To a 250 mL round-bottom flask was added concentrated sulfuric acid (40 mL, 750 mmol) at 0° C. To this was added 2,3-dimethylaniline (5 g, 41.3 mmol) in small portions and after the addition was over the flask was cooled to −10° C.

A mixture of fuming nitric acid (2.2 mL, 49.2 mmol) and concentrated sulfuric acid (6.6 mL) was added over 45 min and the mixture was stirred for an additional hour at 0° C. The mixture was poured onto ice water, the resulting precipitate was filtered, washed with water and dried under vacuum to afford 2,3-dimethyl-5-nitroaniline (3.63 g, 21.84 mmol, 52.9% yield) as a yellow solid. MS (ESI) m/z 167.4 [M+1]+.

B. 4-Methyl-6-nitro-1H-indazole. A solution of sodium nitrite (0.415 g, 6.02 mmol) in water (1.4 mL) was added to a solution of 2,3-dimethyl-5-nitroaniline (1 g, 6.02 mmol) in acetic acid (137 mL). The resulting solution was stirred at room temperature for 24 h. The solvents were removed in vacuo affording a solid that was dissolved in ethyl acetate and filtered through a plug of silica. The ethyl acetate was finally removed to give 4-methyl-6-nitro-1H-indazole (0.900 g, 5.08 mmol, 84% yield) as a yellow solid. MS (ESI) m/z 178.2 [M+1]+.

C. 3-Iodo-4-methyl-6-nitro-1H-indazole. A solution of 4-methyl-6-nitro-1H-indazole (0.900 g, 5.08 mmol) in a mixture of dioxane (25 mL) and sodium hydroxide (2 N in water, 3.81 mL, 7.62 mmol) was stirred at room temperature for 1 h. Iodine (1.547 g, 6.10 mmol) was added, and the reaction mixture was stirred at room temperature for 12 h. The aqueous layer was neutralized with hydrogen chloride (6 N in water) and extracted three times with ethyl acetate. After that the combined organic layers were washed with a saturated aqueous sodium thiosulfate solution, water and brine, dried over magnesium sulfate and concentrated to afford 3-iodo-4-methyl-6-nitro-1H-indazole (1.38 g, 4.55 mmol, 90% yield). MS (ESI) m/z 304.2 [M+1]+.

D. 3-Iodo-4-methyl-6-nitro-1-(tetrahydro-2H-pyran-2-yl)-1H-indazole. 3-Iodo-4-methyl-6-nitro-1H-indazole (1.38 g, 4.55 mmol), 3,4-dihydro-2H-pyran (0.457 mL, 5.01 mmol) and methanesulfonic acid (0.035 mL, 0.546 mmol) were dissolved in tetrahydrofuran (15 mL) and stirred at 75° C. After 6 h, the solution was diluted with triethylamine (0.5 mL) and condensed under reduced pressure. The residue was purified by silica gel chromatography (0-15% ethyl acetate in hexanes) to afford 3-iodo-4-methyl-6-nitro-1-(tetrahydro-2H-pyran-2-yl)-1H-indazole (1.4 g, 3.62 mmol, 79% yield). MS (ESI) m/z 388.2 [M+1]+.

E. 3,4-Dimethyl-6-nitro-1-(tetrahydro-2H-pyran-2-yl)-1H-indazole. A mixture of 3-iodo-4-methyl-6-nitro-1-(tetrahydro-2H-pyran-2-yl)-1H-indazole (1.4 g, 3.62 mmol), methylboronic acid (0.649 g, 10.85 mmol), tetrakis(triphenylphosphine)-palladium(0) (0.418 g, 0.362 mmol) and cesium carbonate (3.53 g, 10.85 mmol) in dioxane (15 mL) was degassed and heated to 90° C. overnight. After cooling to room temperature the mixture was filtered over Celite, the solvent was removed under reduced pressure and the residue was purified by silica gel chromatography (0-20% ethyl acetate in hexanes) to afford 3,4-dimethyl-6-nitro-1-(tetrahydro-2H-pyran-2-yl)-1H-indazole (0.897 g, 3.26 mmol, 90% yield). MS (ESI) m/z 276.5 [M+1]⁺.

F. 3,4-Dimethyl-1-(tetrahydro-2H-pyran-2-yl)-1H-indazol-6-amine. 3,4-Dimethyl-6-nitro-1-(tetrahydro-2H-pyran-2-yl)-1H-indazole (0.897 g, 3.26 mmol) was dissolved in ethyl acetate (60 mL) and methanol (10 mL) and flushed with nitrogen, treated with 10% palladium on activated charcoal (0.173 g, 1.629 mmol) and stirred under a hydrogen filled balloon for 24 h. The reaction mixture was filtered through a pad of Celite and concentrated to give a dark orange solid which purified using reverse-phase preparatory HPLC (10-80% acetonitrile+0.1% trifluoroacetic acid in water+0.1% trifluoroacetic acid, over 30 min) to afford 3,4-dimethyl-1-(tetrahydro-2H-pyran-2-yl)-1H-indazol-6-amine (0.528 g, 2.150 mmol, 66% yield). MS (ESI) m/z 246.5 [M+1]⁺.

Intermediate 121:
6-Amino-1,3,3-trimethylindolin-2-one

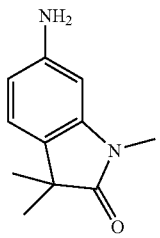

A. 1,3,3-Trimethyl-6-nitroindolin-2-one. To a brown suspension of 3,3-dimethyl-6-nitroindolin-2-one (1.82 g, 8.83 mmol) in N,N-dimethylformamide (15 mL) at room temperature, was added potassium carbonate (1.830 g, 13.24 mmol), followed by dimethyl sulfate (1.054 mL, 11.03 mmol) dropwise (neat). After stirring for 24 h, the reaction was incomplete when checked by TLC. Additional dimethyl sulfate (0.5 mL, 5.5 mmol) was added and the reaction was stirred overnight. The reaction mixture was partitioned between ethyl acetate (100 mL) and water (30 mL). The organic layer was separated, dried over magnesium sulfate and concentrated to give a brown oil that was purified using silica gel flash column chromatography (eluting with 100% dichloromethane) to give the product as a yellow solid (1.46 g, 54%). ¹H NMR (400 MHz, DMSO-d₆) δ (ppm) 7.98 (dd, 1H), 7.83 (d, J=2.15 Hz, 1H), 7.66 (d, J=8.10 Hz, 1H), 3.23 (s, 3H), 1.32 (s, 6H); R$_f$=0.50, (33% ethyl acetate in hexanes).

B. 6-Amino-1,3,3-trimethylindolin-2-one. 1,3,3-Trimethyl-6-nitroindolin-2-one (1.42 g, 6.45 mmol) was suspended in ethyl acetate (30 mL) and methanol (5 mL), and 10% palladium on carbon (0.343 g, 3.22 mmol) was added. The reaction mixture was stirred under 1 atmosphere of hydrogen at 30° C. for 1 h then at room temperature for 4 h. The reaction mixture was flushed with nitrogen and filtered through a pad of Celite, washing with ethyl acetate and methanol. The filtrate was concentrated to give 6-amino-1,3,3-trimethylindolin-2-one as a pale grey solid (0.997 g, 81% yield). ¹H NMR (400 MHz, DMSO-d₆) δ (ppm) 6.83-6.99 (m, 1H), 6.12-6.27 (m, 2H), 5.10 (s, 2H), 3.03 (s, 3H), 1.17 (s, 6H); MS (ESI) m/z 191.0 [M+1]⁺.

Intermediate 122:
N,2-Dimethoxy-N-methylisonicotinamide

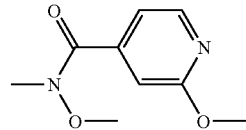

A. N,2-Dimethoxy-N-methylisonicotinamide. Oxalyl chloride (6.27 mL, 71.8 mmol) was added dropwise slowly to a stirred suspension of 2-methoxyisonicotinic acid (10.00 g, 65.3 mmol) and N,N-dimethylformamide (0.101 mL, 1.306 mmol) in dichloromethane (300 mL). The resulting white mixture was stirred at room temperature under nitrogen for 2 h. Evolution of gas was observed but no heat was generated. The resulting mixture was cooled to 0° C. under nitrogen. N,O-dimethylhydroxylamine hydrochloride (9.56 g, 98 mmol) was added followed by triethylamine (45.5 mL, 327 mmol) slowly. The resulting thick slurry was stirred at room temperature under nitrogen. LCMS after 10 min showed complete conversion to the desired product. Water was added and the reaction was extracted with dichloromethane. The combined organic layers were dried over magnesium sulfate, filtered, and concentrated on a rotary evaporator. The residue was purified using flash chromatography (5-60% ethyl acetate in hexane) to give N,2-dimethoxy-N-methylisonicotinamide (11.0 g, 56. mmol, 86% yield) as a yellow oil. MS (ESI) m/z 197.3 [M+1]⁺.

Intermediate 123:
5-Amino-2-(2,4-dimethoxybenzyl)isoindolin-1-one

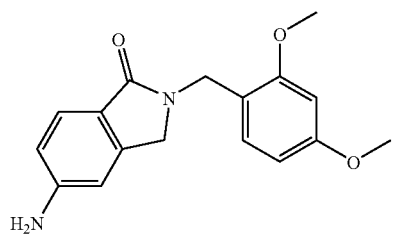

A. Methyl 2-(bromomethyl)-4-nitrobenzoate. Methyl 2-methyl-4-nitrobenzoate (5 g, 25.6 mmol) was dissolved in carbon tetrachloride (60 mL) and then purged with nitrogen for 10 min. N-bromosuccinimide (5.47 g, 30.7 mmol) and benzoyl peroxide (0.124 g, 0.512 mmol) were added to the solution and then heated to 70° C. for 16 h. The reaction was concentrated and then purified via silica gel chromatography (0-60% ethyl acetate in hexanes) to give an orange solid (3.5 g, 12.77 mmol, 49.8% yield). ¹H NMR (400 MHz, CHLOROFORM-d) δ (ppm) 8.35 (d, J=2.34 Hz, 1H), 8.16-8.25 (m, 1H), 8.12 (d, J=8.59 Hz, 1H), 4.98 (s, 2H), 3.97-4.09 (m, 3H).

B. 2-(2,4-Dimethoxybenzyl)-5-nitroisoindolin-1-one. A mixture of methyl 2-(bromomethyl)-4-nitrobenzoate (2.5 g, 9.12 mmol), (2,4-dimethoxyphenyl)methanamine (1.525 g, 9.12 mmol), triethylamine (3.81 mL, 27.4 mmol) in methanol (25 mL) was refluxed for 16 h. The mixture was diluted with ethyl acetate, washed with dilute hydrochloric acid and brine, dried over magnesium sulfate, filtered, and concentrated on a rotary evaporator to dryness. Flash chromatography (30-50% ethyl acetate in hexane) gave the desired product as a yellow solid (2.5 g, 7.68 mmol, 84% yield). MS (ESI) m/z 329.9 [M+1]$^+$.

C. 5-Amino-2-(2,4-dimethoxybenzyl)isoindolin-1-one. 2-(2,4-Dimethoxybenzyl)-5-nitroisoindolin-1-one (1 g, 3.05 mmol) was dissolved in ethanol and purged with nitrogen. Palladium on carbon (0.530 g, 0.498 mmol) was added and the reaction mixture was stirred under 1 atmosphere of hydrogen for 16 h. The reaction mixture was filtered through Celite and washed with ethanol. The organic layer was concentrated on a rotary evaporator to dryness to give desired product as purple solid. The crude material was crystallized from ethyl acetate and hexane to give 5-amino-2-(2,4-dimethoxybenzyl) isoindolin-1-one as a white solid (0.9 g, 3.02 mmol, 99%). MS (ESI) m/z 299.2 [M+1]$^+$.

Intermediate 124: N-Methoxy-N-methyltetrahydro-2H-pyran-4-carboxamide

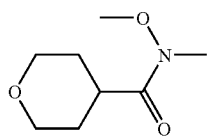

A. N-Methoxy-N-methyltetrahydro-2H-pyran-4-carboxamide. N-Methoxy-N-methyltetrahydro-2H-pyran-4-carboxamide was prepared according to the procedure described for N,2-dimethoxy-N-methylisonicotinamide from tetrahydro-2H-pyran-4-carboxylic acid (10 g, 77 mmol), oxalyl chloride (7.40 mL, 85 mmol), N,O-dimethylhydroxylamine hydrochloride (9.4 g, 115 mmol) and triethyl amine (53.5 mL, 384 mmol). After purification via flash chromatography (eluting with 30-70% ethyl acetate in hexane), N-methoxy-N-methyltetrahydro-2H-pyran-4-carboxamide was obtained as a yellow oil (11.3 g, 65.2 mmol, 85% yield). $^1$H NMR (400 MHz, CHLOROFORM-d) δ (ppm) 4.02 (ddd, J=11.52, 4.10, 1.95 Hz, 2H), 3.73 (s, 3H), 3.47 (td, J=11.81, 2.15 Hz, 2H), 3.19 (s, 3H), 2.81-2.98 (m, 1H), 1.75-1.97 (m, 2H), 1.66 (dd, 2H); MS (ESI) m/z 174.2 [M+1]$^+$.

Intermediate 125: 1-(Tetrahydro-2H-pyran-2-yl)-1H-pyrazolo[4,3-b]pyridin-6-amine

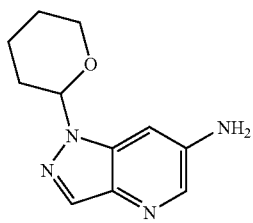

A. 6-Nitro-1H-pyrazolo[4,3-b]pyridine. A solution of sodium nitrite (2.163 g, 31.3 mmol) in water (20 mL) was added to a stirred solution of 2-methyl-5-nitropyridin-3-amine (4 g, 26.1 mmol) in acetic acid (70 mL). The resulting orange solution was stirred at room temperature for 16 h. The reaction was cooled to 0° C. and the reaction mixture was brought to pH=7 via addition of aqueous sodium hydroxide (6 M). Water and ethyl acetate were added. The resulting mixture was shaken in a reparatory funnel and the layers were separated. The organics were washed with water and brine, dried over magnesium sulfate, filtered, and concentrated on a rotary evaporator. The residue was triturated with diethyl ether. Solids were collected by vacuum filtration, washed with diethyl ether, and dried under high vacuum to give the desired product, as a dark orange solid (2.3 g, 14.01 mmol, 53.7% yield). $^1$H NMR (400 MHz, DMSO-d$_6$) δ (ppm) 9.29 (d, J=2.34 Hz, 1H), 8.91 (br s, 1H), 8.59 (br s, 1H). MS (ESI) m/z 165.2 [M+1]$^+$.

B. 6-Nitro-1-(tetrahydro-2H-pyran-2-yl)-1H-pyrazolo[4,3-b]pyridine. A solution of 6-nitro-1H-pyrazolo[4,3-b]pyridine (2 g, 12.19 mmol), 3,4-dihydro-2H-pyran (1.538 g, 18.28 mmol) and methanesulfonic acid (0.119 mL, 1.828 mmol) in tetrahydrofuran (100 mL) was heated to 70° C. overnight. The reaction was cooled and neutralized with aqueous sodium bicarbonate to pH 7, and then extracted with ethyl acetate. The combined organics were dried over magnesium sulfate, filtered, concentrated on a rotary evaporator. Flash chromatography (eluting with 0-50% ethyl acetate in hexane) gave the desired product as an off white solid (1.3 g, 5.24 mmol, 43.0% yield). (ESI) m/z 249.3 [M+1]$^+$.

C. 1-(Tetrahydro-2H-pyran-2-yl)-1H-pyrazolo[4,3-b]pyridin-6-amine. 6-Nitro-1-(tetrahydro-2H-pyran-2-yl)-1H-pyrazolo[4,3-b]pyridine (1 g, 4.03 mmol) was dissolved in 50% ethanol in ethyl acetate and the reaction mixture was purged with nitrogen. Palladium on carbon (0.6 g, 0.564 mmol) was added and the reaction was stirred under 1 atmosphere of hydrogen for 16 h. The reaction mixture was filtrated through Celite and washed with ethanol. The organic layer was concentrated on a rotary evaporator to dryness to give desired product as purple solid, which was purified by crystallization from ethyl acetate in hexane to give 1-(tetrahydro-2H-pyran-2-yl)-1H-pyrazolo[4,3-b]pyridin-6-amine (0.8 g, 3.67 mmol, 91% yield) as a white solid. (ESI) m/z 219.4 [M+1]$^+$.

Intermediate 126: 1,4-Dimethyl-1H-indazol-6-amine

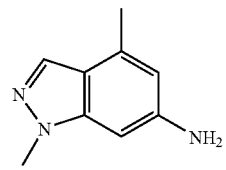

A. 1,4-Dimethyl-6-nitro-1H-indazole. 4-Methyl-6-nitro-1H-indazole (0.75 g, 4.23 mmol) was dissolved in N,N-dimethylformamide (10 mL). Sodium hydride (0.203 g, 5.08 mmol, 60% dispersion in mineral oil) was then added at ambient temperature. After 15 minutes, methyl iodide (0.318 mL, 5.08 mmol) in N,N-dimethylformamide (0.5 mL) was added dropwise to the solution and allowed to stir at ambient temperature. After 2 h, LCMS analysis showed two peaks in the UV trace, both with the same product masses as geometric isomers. The solution was condensed under reduced pressure to give a brown solid. The solid was diluted with water (25 mL) and sonicated for 5 minutes. The resultant solid was filtered and washed with additional water followed by hexanes to afford a tan solid. The solid was purified via column chromatography (Biotage, eluting with 0-100% ethyl acetate in hexanes) to afford the title compound (0.480 g, 2.51 mmol, 59% yield) as verified via $^1$H NMR and NOE NMR. NOE-NMR (400 MHz, DMSO-$d_6$) δ (ppm) 4.18 (Irradiate peak). $^1$H NMR (400 MHz, DMSO-$d_6$) δ (ppm) 8.55 (s, 1H), 8.35 (s, 1H), 7.77 (s, 1H), 4.18 (s, 3H), 2.66 (s, 3H); MS (ESI) m/z 192.4 [M+1]$^+$.

B. 1,4-Dimethyl-1H-indazol-6-amine. 1,4-Dimethyl-6-nitro-1H-indazole (0.49 g, 2.56 mmol) was diluted with ethanol (20 mL) followed by palladium on carbon (0.049 g, 0.460 mmol). The solution was evacuated and purged with hydrogen gas twice. The solution was allowed to stir at ambient temperature. After 1 h, LCMS analysis showed majority as starting materials, with some hydroxylamine intermediate seen. Solution was kept stirring at ambient temperature. After 4 h, LCMS analysis showed complete consumption of starting materials. Solution was filtered through celite and the filtrant condensed under reduced pressure to afford a reddish solid (0.409 g, 2.54 mmol, 99% yield). MS (ESI) m/z 162.5 [M+1]$^+$.

Intermediate 127:
5-Amino-2-methylisoindolin-1-one

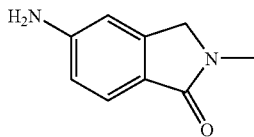

A. 2-Methyl-5-nitroisoindolin-1-one. To a solution/suspension of methyl 2-(bromomethyl)-4-nitrobenzoate (7 g, 25.5 mmol) in methanol (50 mL), methanamine hydrochloride (1.724 g, 25.5 mmol) and triethylamine (17.80 mL, 128 mmol) were added. The reaction mixture was heated to 70° C. and stirred overnight. The reaction was cooled to room temperature, and crystals of product formed. The product was then left to crystallize over the weekend at 0° C. The solids formed were filtered and dissolved in dichloromethane. This crude solution was loaded in to a column and purified by column chromatography (eluting with 0-10% methanol in dichloromethane). The fractions containing product were combined and the solvent was removed under vacuum. 2-Methyl-5-nitroisoindolin-1-one (3 g, 15.61 mmol, 61.1% yield) was obtained as an impure orange yellow solid. This solid was used in the next reaction without further purification. MS (ESI): m/z 193.0 [M+1]$^+$.

B. 5-Amino-2-methylisoindolin-1-one. To a solution/suspension of 2-methyl-5-nitroisoindolin-1-one (3 g, 15.61 mmol) in methanol (50 mL) and ethanol (50.0 mL), palladium on carbon was added. A balloon filled with hydrogen gas was placed and the reaction was stirred overnight. The reaction was filtered and the solvent was removed under vacuum. 5-Amino-2-methylisoindolin-1-one (2 g, 12.33 mmol, 79% yield) was obtained as a light yellow solid. $^1$H NMR (400 MHz, DMSO-$d_6$) δ (ppm) 7.27 (d, J=7.81 Hz, 1H), 6.47-6.66 (m, 2H), 5.70 (s, 2H), 4.24 (s, 2H), 2.96 (s, 3H); MS (ESI): m/z 163.0 [M+1]$^+$.

Intermediate 128: 6-Bromo-3-methylbenzo[d]isoxazole

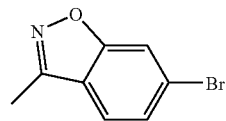

A. (E)-1-(4-Bromo-2-hydroxyphenyl)ethanone oxime. To a solution of 1-(4-bromo-2-hydroxyphenyl)ethanone (2.8 g, 13.02 mmol) and water (10 mL) was added sodium acetate (1.602 g, 19.53 mmol) and hydroxylamine hydrochloride (1.176 g, 16.93 mmol). The mixture was allowed to stir at ambient temperature for 16 h. The solution was condensed under reduced pressure and diluted with water and sonicated. The resultant solid was filtered and dried under vacuum oven conditions to afford the title compound (1.90 g, 8.26 mmol, 63.4% yield). MS (ESI) m/z 230.3 [M]$^+$, 232.4 [M+2]$^+$.

B. (E)-1-(4-Bromo-2-hydroxyphenyl)ethanone O-acetyl oxime. (E)-1-(4-Bromo-2-hydroxyphenyl)ethanone oxime (0.75 g, 3.26 mmol) was diluted with acetic anhydride (7.69 mL, 82 mmol). The solution was allowed to stir at 110° C. in a screw capped flask. After 5 minutes, the mixture was allowed to stir at ambient temperature for 30 minutes. The solution was condensed under reduced pressure and partitioned between pH 7 phosphate buffer and ethyl acetate (2×). The organics were dried over sodium sulfate, filtered and solvent removed under reduced pressure to afford the acetate of the oxime as a white solid (0.880 g). LCMS analysis of this material showed what looks to be 2 different peaks both with product mass, however they both show different higher mass Br splittings. The solid was purified via biotage column chromatography (100% hexanes (100 mL), then 0-45% ethyl acetate in hexanes (700 mL), then 45-100% ethyl acetate (100 mL)) to afford two cleanly resolved products. $^1$H-NMR confirmed (E)-1-(4-bromo-2-hydroxyphenyl)ethanone O-acetyl oxime as the first elutant (0.252 g, 0.926 mmol, 28% yield) and the bis-acetate as the second elutant (0.487 g, 1.550 mmol, 48% yield). First elutant: $^1$H NMR (400 MHz, CHLOROFORM-d) δ (ppm) 11.46 (s, 1H), 7.32 (d, J=8.59 Hz, 1H), 7.22 (d, J=1.95 Hz, 1H), 7.05 (dd, J=8.59, 1.95 Hz, 1H), 2.43 (s, 3H), 2.26 (s, 3H); Second elutant: $^1$H NMR (400 MHz, CHLOROFORM-d) δ (ppm) 7.41-7.46 (m, 1H), 7.37 (s, 1H), 7.34-7.36 (m, 1H), 2.31 (s, 3H), 2.30 (s, 3H), 2.23 (s, 3H).

C. 6-Bromo-3-methylbenzo[d]isoxazole. (E)-1-(4-Bromo-2-hydroxyphenyl)ethanone O-acetyl oxime (1.6 g, 6.95 mmol) was diluted with pyridine (10 mL) in a screw capped flask and heated to 125° C. for 16 h. TLC (40% ethyl acetate in hexanes) confirms starting material consumption and product formation. The solution was condensed under reduced pressure and the oil purified via biotage column chromatography (100% hexanes (100 mL), then 0-50% ethyl acetate in hexanes (750 mL)) to afford 6-bromo-3-methylbenzo[d]isoxazole (1.19 g, 5.6 mmol, 68% yield). $^1$H NMR (400 MHz, CHLOROFORM-d) δ 7.75 (d, J=1.17 Hz, 1H), 7.48-7.52 (m, 1H), 7.42-7.47 (m, 1H), 2.58 (s, 3H); MS (ESI) m/z 212.2 [M]+, 214.2 [M+2]+.

Intermediate 129: 1-Methyl-1H-indazol-5-amine

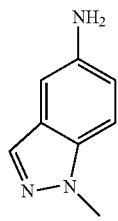

A. 1-Methyl-1H-indazol-5-amine. To a solution of 1-methyl-5-nitro-1H-indazole (1 g, 5.64 mmol) in ethanol (10 mL) was added palladium on carbon (0.060 g, 0.564 mmol) and the reaction was stirred at room temperature for 16 h under 1 atmosphere of hydrogen. The reaction mixture was filtered through Celite and concentrated down. The crude was triturated with ethyl acetate and dichlomethane to give the title compound as a light purple solid (0.65 g, 78% yield). MS (ESI) m/z 148.2 [M+1]+.

Intermediate 130: tert-Butyl 3-methyl-6-amino-2-oxo-3-hydrobenzimidazolecarboxylate

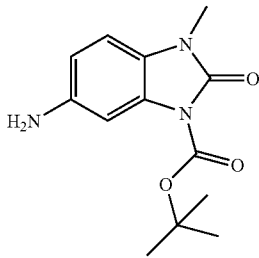

A. (2-Amino-4-nitrophenyl)methylamine. 2-Fluoro-5-nitroaniline (2 g, 12.81 mmol) was added to a sealed tube with methylamine (5 mL, 40% in water) and the reaction mixture was heated at 95° C. overnight. The reaction was evaporated and the residue was purified with silica gel (0 to 85% ethyl acetate in hexanes) to give (2-amino-4-nitrophenyl)methylamine as a red-orange solid. MS (ESI) m/z 168.2 [M+1]+.

B. 1-Methyl-5-nitro-3-hydrobenzimidazol-2-one. A solution of (2-amino-4-nitrophenyl)methylamine (1.62 g, 9.69 mmol) and di(1H-imidazol-1-yl)methanone (1.571 g, 9.69 mmol) in tetrahydrofuran (25 mL) was stirred at 65° C. for 18 hours. The reaction mixture was then cooled to 0° C. The resulting precipitate was filtered off and dried to give 1-methyl-5-nitro-3-hydrobenzimidazol-2-one (1.81 g, 9.37 mmol, 97% yield) as a clean, beige solid. 1H NMR (400 MHz, DMSO-d6) δ (ppm) 11.36-11.49 (m, 1H), 8.03 (dd, J=2.34, 8.59 Hz, 1H), 7.76 (d, J=2.34 Hz, 1H), 7.31 (d, J=8.98 Hz, 1H), 3.36 (s, 3H); MS (ESI) m/z 194.5 [M+1]+.

C. tert-Butyl 3-methyl-6-nitro-2-oxo-3-hydrobenzimidazolecarboxylate. A mixture of 1-methyl-5-nitro-1H-benzo[d]imidazol-2(3H)-one (1 g, 5.18 mmol), di-tert-butyl dicarbonate (2.404 mL, 10.35 mmol), and sodium bicarbonate (0.870 g, 10.35 mmol) in tetrahydrofuran (37 mL) was stirred at room temperature for 3 days. The resulting white solid was filtered, washed with water and tetrahydrofuran and dried to give tert-butyl 3-methyl-6-nitro-2-oxo-3-hydrobenzimidazolecarboxylate (1.39 g, 4.74 mmol, 92% yield). 1H NMR (400 MHz, DMSO-d6) δ (ppm) 8.52 (d, J=2.34 Hz, 1H), 8.22 (dd, J=2.34, 8.59 Hz, 1H), 7.43 (d, J=8.59 Hz, 1H), 3.37 (s, 3H), 1.62 (s, 9H).

D. tert-Butyl 3-methyl-6-amino-2-oxo-3-hydrobenzimidazolecarboxylate. tert-Butyl 3-methyl-6-nitro-2-oxo-2,3-dihydro-1H-benzo[d]imidazole-1-carboxylate (1.38 g, 4.71 mmol) was taken up in methanol (30 mL) and a catalytic amount of palladium on carbon was added. The reaction mixture was stirred under hydrogen gas for 18 hours, filtered through celite and then evaporated to give tert-butyl 3-methyl-6-amino-2-oxo-3-hydrobenzimidazolecarboxylate (1.12 g, 4.25 mmol, 90% yield). MS (ESI) m/z 264.2 [M+1]+.

Intermediate 131: 3-Methyl-[1,2,4]triazolo[4,3-a]pyridin-7-amine

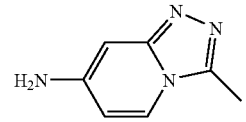

A. Di-tert-butyl 1-(4-nitropyridin-2-yl)hydrazine-1,2-dicarboxylate. A tube was charged with tris(dibenzylideneacetone)dipalladium(0) (0.695 g, 0.759 mmol), 1,1'-bis(diphenylphosphino)ferrocene (1.277 g, 2.278 mmol), cesium carbonate (6.19 g, 18.99 mmol) and di-tert-butyl hydrazine-1,2-dicarboxylate (3.53 g, 15.19 mmol). The tube was purged with argon, and then toluene (20 mL) and 2-chloro-4-nitropyridine (3.01 g, 18.99 mmol) were added. The reaction mixture was heated at 100° C. with stirring for 16 hours. The reaction mixture was cooled, filtered over Celite and concentrated in vacuo. The crude residue was purified by silica gel chromatography (0-20% ethyl acetate in hexanes) to afford di-tert-butyl 1-(4-nitropyridin-2-yl)hydrazine-1,2-dicarboxylate (4.5 g, 12.70 mmol, 66.9% yield). MS (ESI) m/z 355.2 [M+1]+.

B. 2-Hydrazinyl-4-nitropyridine dihydrochloride. To a stirred mixture of di-tert-butyl 1-(4-nitropyridin-2-yl)hydrazine-1,2-dicarboxylate (6.7 g, 18.91 mmol) in ethanol (30 mL) at room temperature was added hydrogen chloride (142 mL, 567 mmol, 4 N in dioxane). The resulting mixture was stirred under nitrogen for 16 h. The resulting suspension was concentrated by half on a rotary evaporator, filtered and washed with a small amount of diethylether to afford 2-hydrazinyl-4-nitropyridine dihydrochloride (3.09 g, 13.61 mmol, 72% yield) as a yellow solid. MS (ESI) m/z 155.2 [M+1]+.

C. N'-(4-Nitropyridin-2-yl)acetohydrazide. To a stirred mixture of 2-hydrazinyl-4-nitropyridine dihydrochloride (1.6 g, 7.05 mmol) in pyridine (54 mL) at room temperature was added acetic anhydride (0.799 mL, 8.46 mmol). The resulting mixture was stirred under nitrogen at 50° C. for 16 h. The resulting suspension was concentrated on a rotary evaporator, and the residue was purified using flash chromatography (0-10% methanol in dichloromethane) to afford N'-(4-nitropyridin-2-yl)acetohydrazide (0.646 g, 3.29 mmol, 46.7% yield) as a yellow solid. MS (ESI) m/z 197.3 [M+1]+.

D. 3-Methyl-7-nitro-[1,2,4]triazolo[4,3-a]pyridine. To a solution of N'-(4-nitropyridin-2-yl)acetohydrazide (0.641 g, 3.27 mmol) in tetrahydrofuran (25 mL) was added (methoxycarbonylsulfamoyl)triethylammonium hydroxide, inner salt (2.336 g, 9.80 mmol) at room temperature. The mixture was heated at 65° C. for 18 h and cooled to room temperature. The reaction mixture was concentrated and the residue was loaded on a biotage column and purified by flash chromatography (0-10% methanol in dichloromethane) to afford 3-methyl-7-nitro-[1,2,4]triazolo[4,3-a]pyridine (0.467 g, 2.62 mmol, 80% yield) as a yellow-white solid. MS (ESI) m/z 179.2 [M+1]$^+$.

E. 3-Methyl-[1,2,4]triazolo[4,3-a]pyridin-7-amine. 3-Methyl-7-nitro-[1,2,4]triazolo[4,3-a]pyridine (0.467 g, 2.62 mmol) was suspended in methanol (10 mL) followed by addition of platinum, 1% on activated carbon, vanadium doped (50% wetted powder) Evonik F4 (0.100 g). The solution was evacuated and purged with fresh hydrogen gas three times and the mixture was allowed to stir at ambient temperature for 4 h. The solution was filtered through Celite and the solvent was removed under reduced pressure to give 3-methyl-[1,2,4]triazolo[4,3-a]pyridin-7-amine (0.388 g, 2.62 mmol, 100% yield) as a brown solid. MS (ESI) m/z 149.3 [M+1]$^+$.

Intermediate 132: 3-Methyl-1-((2-(trimethylsilyl)ethoxy)methyl)-1H-pyrazolo[3,4-b]pyridin-5-amine

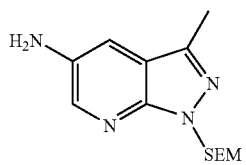

A. 5-Bromo-2-chloro-N-methoxy-N-methylnicotinamide. To a mixture of 5-bromo-2-chloronicotinic acid (6 g, 25.5 mmol) in thionyl chloride (30 mL) was added a drop of N,N-dimethylformamide, and the reaction mixture was heated at 80° C. for 2 h. The mixture was cooled to room temperature, and concentrated to give crude 5-bromo-2-chloronicotinoyl chloride. A solution of O,N-dimethyl-hydroxylamine hydrochloride salt (3.45 g, 35.6 mmol) and triethylamine (7.48 g, 74.1 mmol) in dichloromethane (80 mL), and a solution of the above 5-bromo-2-chloronicotinoyl chloride in dichloromethane (20 mL) were added, and the reaction mixture was stirred overnight. The mixture was poured into water, and extracted with dichloromethane (50 mL×3). The combined organic layer was concentrated under reduced pressure, and purified on silica gel column (eluting with 5-10% ethyl acetate in petroleum ether) to give 5-bromo-2-chloro-N-methoxy-N-methylnicotinamide as a solid (6.2 g, 71.4% yield). $^1$H NMR (400 MHz, DMSO-d$_6$) δ (ppm) 8.65 (s, 1H), 8.39 (s, 1H), 3.49 (s, 3H), 3.30 (s, 3H).

B. 1-(5-Bromo-2-chloropyridin-3-yl)ethanone. Methylmagnesium bromide (6.0 mL, 18 mmol, 3 M solution in tetrahydrofuran) was added dropwise to a solution of 5-bromo-2-chloro-N-methoxy-N-methylnicotinamide (5 g, 18 mmol) in tetrahydrofuran (80 mL) under nitrogen at 0° C. over 30 min. The resulting mixture was warmed to room temperature over 2 h, quenched with aqueous ammonium chloride solution, and extracted with ethyl acetate. The combined organic layer was dried over sodium sulfate, evaporated under reduced pressure, and dried under vacuum to give 1-(5-bromo-2-chloropyridin-3-yl)ethanone (3.1 g, 73.8% yield) as an oil. $^1$H NMR (400 MHz, CHLOROFORM-d) δ (ppm) 8.54 (s, 1H), 8.00 (s, 1H), 2.69 (s, 3H).

C. 5-Bromo-3-methyl-1H-pyrazolo[3,4-b]pyridine. A mixture of 1-(5-bromo-2-chloropyridin-3-yl)-ethanone (3.1 g, 13.3 mmol), aqueous hydrazine (782 mg, 13.3 mmol, 85%), and potassium carbonate (1.83 g, 13.3 mmol) in tetrahydrofuran (20 mL) was refluxed overnight. After cooling to room temperature, the reaction mixture was concentrated, and the residue was dissolved in ethyl acetate. The organic solution was washed with brine, dried over anhydrous sodium sulfate, evaporated under reduced pressure, and purified on silica gel column to give 5-bromo-3-methyl-1H-pyrazolo[3,4-b]pyridine (2.0 g, 71.4% yield). $^1$H NMR (400 MHz, CHLOROFORM-d) δ (ppm) 12.33 (br s, 1H), 8.58 (s, 1H), 8.16 (s, 1H), 2.58 (s, 3H).

D. 5-Bromo-3-methyl-1-((2-(trimethylsilyl)ethoxy)methyl)-1H-pyrazolo[3,4-b]pyridine. To a solution of 5-bromo-3-methyl-1H-pyrazolo[3,4-b]pyridine (2.0 g, 9.47 mmol) in N,N-dimethylformamide (15 mL) was added sodium hydride (455 mg, 11.4 mmol, 60% in mineral oil) at 0° C. under nitrogen, and the mixture was stirred for 1 h at 0° C. Subsequently (2-(chloromethoxy)ethyl)trimethylsilane (1.88 g, 11.4 mmol) was added dropwise, the mixture was continued to stir for 1 h at 0° C., and poured into ice-water (50 mL), and extracted with ethyl acetate (100 mL×3). The combined organic layer was dried over anhydrous sodium sulfate, evaporated under reduced pressure, and purified on silica gel column (eluting with 20-25% ethyl acetate in petroleum ether) to give 5-bromo-3-methyl-1-((2-(trimethylsilyl)ethoxy)methyl)-1H-pyrazolo[3,4-b]pyridine (1.6 g, 50% yield) as an oil. $^1$H NMR (400 MHz, CHLOROFORM-d) δ (ppm) 8.55 (s, 1H), 8.12 (s, 1H), 5.76 (s, 2H), 3.62 (t, J=8.8 Hz, 2H), 2.55 (s, 3H), 0.93 (t, J=8.4 Hz, 2H), −0.06 (s, 9H); MS (ESI): m/z 341.9 [M+1]$^+$.

E. 3-Methyl-1-((2-(trimethylsilyl)ethoxy)methyl)-1H-pyrazolo[3,4-b]pyridin-5-amine. A degassed mixture of 5-bromo-3-methyl-1-((2-(trimethylsilyl)ethoxy)methyl)-1H-pyrazolo[3,4-b]pyridine (1.7 g, 5 mmol), diphenylmethanimine (1.36 g, 7.5 mmol), tris(dibenzylideneacetone)palladium (0) (920 mg, 1 mmol), (R)-(+)-2,2'-bis(diphenylphosphino)-1,1'-binaphthyl (1.55 g, 2.5 mmol), and sodium tert-butoxide (720 mg, 7.5 mmol) in toluene (30 mL) was heated at 115° C. under nitrogen overnight. The reaction mixture was concentrated, and purified by column chromatography on silica gel (eluting with 5-20% ethyl acetate in petroleum ether) to give N-(diphenylmethylene)-3-methyl-1-((2-(trimethylsilyl)ethoxy)methyl)-1H-pyrazolo[3,4-b]pyridin-5-amine (2.5 g, crude), which was dissolved in tetrahydrofuran (10 mL), and hydrochloric acid (2 N, 10 mL) was added. The mixture was stirred at room temperature for 2 h. The mixture was adjusted to pH=8 with saturated sodium carbonate solution, extracted with ethyl acetate, dried, concentrated, and purified by column chromatography on silica gel (eluting with 10-25% ethyl acetate in petroleum ether) to give 3-methyl-1-((2-(trimethylsilyl)ethoxy)methyl)-1H-pyrazolo[3,4-b]pyridin-5-amine (1.1 g, 79.1% yield) as an oil. $^1$H NMR (400 MHz, CHLOROFORM-d) δ (ppm) 8.10 (s, 1H), 7.18 (s, 1H), 5.7 (s, 1H), 3.58 (d, J=11.2 Hz, 2H), 3.34 (s, 2H), 2.47 (s, 3H), 0.90 (t, J=11.2 Hz, 2H), −0.09 (s, 9H).

Intermediate 133:
N-Methoxy-N-methyltetrahydrofuran-3-carboxamide

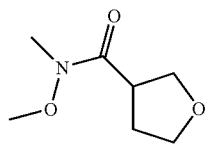

A. N-Methoxy-N-methyltetrahydrofuran-3-carboxamide. A mixture of tetrahydrofuran-3-carboxylic acid (5 g, 43 mmol), N,O-dimethylhydroxylamine hydrochloride (4.58 g, 48 mmol), N-(3-dimethylaminopropyl)-N′-ethylcarbodiimide hydrochloride (9.55 g, 50 mmol), 1-hydroxybenzotriazole (6.75 g, 50 mmol), and 4-methylmorpholine (10.1 g, 100 mmol) in anhydrous dichloromethane (200 mL) was stirred at 0° C. for 1 h. The mixture was warmed to room temperature, stirred overnight, and poured into water (200 mL). The organic layer was separated, the aqueous layer was extracted with dichloromethane. The combined organic phase was dried over sodium sulfate, concentrated under vacuum, and purified with column chromatography on silica gel (eluting with 8% ethyl acetate in petroleum ether) to give N-methoxy-N-methyltetrahydrofuran-3-carboxamide (3 g, 44.1% yield) as a colorless oil.

Intermediate 134: 4-(1-(Tetrahydro-2H-pyran-2-yl)-1H-1,2,4-triazol-3-yl)aniline

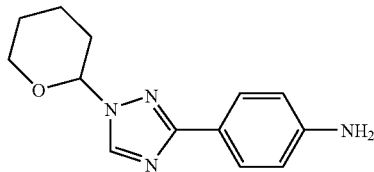

A. 3-Bromo-1-(tetrahydro-2H-pyran-2-yl)-1H-1,2,4-triazole. To a solution/suspension of 3,4-dihydro-2H-pyran (0.674 mL, 7.43 mmol), 3-bromo-1H-1,2,4-triazole (1 g, 6.76 mmol) in tetrahydrofuran (15 mL), methanesulfonic acid (0.053 mL, 0.811 mmol) was added. The reaction mixture was refluxed for 2 hours at 75° C. The reaction mixture was then cooled and the solvent was removed under vacuum. Water was added to mixture, and the mixture was extracted three times with ethyl acetate. The organics were combined and dried over sodium sulfate. The solvent was removed under vacuum to afford 3-bromo-1-(tetrahydro-2H-pyran-2-yl)-1H-1,2,4-triazole (1.493 g, 6.43 mmol, 95% yield) as an oil which was taken to the next step without further purification. MS (ESI): m/z 232.0 [M+1]+.

B. 3-(4-Nitrophenyl)-1-(tetrahydro-2H-pyran-2-yl)-1H-1,2,4-triazole. To a suspension/solution of 4-nitrophenylboronic acid (1 g, 5.99 mmol) in dimethoxyethane (20 mL) and water (10 mL), 3-bromo-1-(tetrahydro-2H-pyran-2-yl)-1H-1,2,4-triazole (1.390 g, 5.99 mmol) followed by potassium carbonate was added. Nitrogen was bubbled into the reaction mixture for 3 minutes. Tetrakis(triphenylphosphine)palladium (0) (0.346 g, 0.300 mmol) was added, and the sealed reaction flask was stirred at 120° C. overnight. The reaction was cooled down and water (50 mL) was added. The mixture was extracted three times with ethyl acetate. The organics were combined, washed with brine and dried over anhydrous sodium sulfate. The solvent was removed under vacuum. The residue was purified by column chromatography (eluting with 0-100% ethyl acetate in hexanes) to afford 3-(4-nitrophenyl)-1-(tetrahydro-2H-pyran-2-yl)-1H-1,2,4-triazole (400 mg, 1.458 mmol, 24.34% yield) as yellow solid. [1] NMR (400 MHz, DMSO-$d_6$) δ (ppm) 8.91 (s, 1H), 8.31-8.38 (m, 2H), 8.22-8.30 (m, 2H), 5.66 (dd, J=2.73, 9.76 Hz, 1H), 3.98 (dtd, 1H), 3.58-3.80 (m, 1H), 1.86-2.35 (m, 3H), 1.48-1.83 (m, 3H). MS (ESI): m/z 275.2 [M+1]+.

C. 4-(1-(Tetrahydro-2H-pyran-2-yl)-1H-1,2,4-triazol-3-yl)aniline. To a degassed solution of 3-(4-nitrophenyl)-1-(tetrahydro-2H-pyran-2-yl)-1H-1,2,4-triazole (400 mg, 1.458 mmol) in methanol (100 mL) was added palladium on carbon (155 mg, 1.458 mmol). The reaction mixture was stirred at room temperature under 1 atmosphere of hydrogen overnight. The solution was filtered and the solvent was removed under vacuum to afford 4-(1-(tetrahydro-2H-pyran-2-yl)-1H-1,2,4-triazol-3-yl)aniline (0.356 g, 1.458 mmol, 100% yield) which was used for the next step without further purification. MS (ESI): m/z 245.0 [M+1]+.

Intermediate 135:
N-Methoxy-N-methyl-1,4-dioxane-2-carboxamide

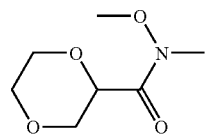

A. 1,4-Dioxane-2-carbonitrile. 4 M Hydrogen chloride in 1,4-dioxane (23 mL, 93 mmol) was added dropwise to a stirred solution of 2,3-dihydro-1,4-dioxine (8 g, 93 mmol) in toluene (20 mL) at room temperature under nitrogen. After 15 min the colorless solution was transferred to a dropping funnel and added dropwise to a stirred suspension of cyanosilver (12.44 g, 93 mmol) in toluene (100 mL) at room temperature under nitrogen. After the addition was completed, the resulting mixture was heated at 115° C. under a reflux condenser under nitrogen for 16 h. The mixture was cooled to room temperature and filtered through Celite and the filter cake washed with diethyl ether. The filtrate was concentrated on a rotary evaporator and purified using flash chromatography (eluting with 0-100% ethyl acetate in hexanes). Fractions containing the desired product were combined and the solvent was removed on a rotary evaporator. The residue was diluted with hexane and concentrated on a rotary evaporator three times to give the desired product (6.2 g, 54.8 mmol, 59.0% yield) as a clear oil. $^1$H NMR (400 MHz, CHLOROFORM-d) δ (ppm) 4.55 (t, J=3.32 Hz, 1H) 4.04 (ddd, J=12.59, 9.27, 2.73 Hz, 1H) 3.87 (d, J=3.12 Hz, 2H) 3.77-3.84 (m, 1H) 3.70-3.77 (m, 2H.).

B. 1,4-Dioxane-2-carboxylic acid. A solution of sodium hydroxide (5.0 g, 125 mmole) in distilled water (45 mL) was added to 1,4-dioxane-2-carbonitrile (6.5 g, 57 mmole). The mixture was refluxed for four hours, acidified with 6 N sulfuric acid (15 mL) and extracted with ether (3×30 mL). The water solution was evaporated at low pressure and extracted with ether. The ether solution, dried over anhydrous sodium sulfate, was evaporated, leaving a clear oil which crystallized when chilled. Recrystallization from carbon tetrachloride afforded 1,4-dioxane-2-carboxylic acid (4.1 g, 31.0 mmol, 54% yield). $^1$H NMR (400 MHz, CHLOROFORM-d) δ (ppm) 8.88 (br s, 1H) 4.32 (dd, J=8.59, 3.12 Hz, 1H) 4.07 (dd, J=11.52, 3.32 Hz, 1H) 4.00 (dt, J=11.71, 2.93 Hz, 1H) 3.64-3.83 (m, 4H).

C. N-Methoxy-N-methyl-1,4-dioxane-2-carboxamide. Oxalyl chloride (1.093 mL, 12.49 mmol) was added dropwise to a stirred solution of 1,4-dioxane-2-carboxylic acid (1.5 g, 11.35 mmol) and N,N-dimethylformamide (0.018 mL, 0.227 mmol) in dichloromethane (50 mL). The resulting colorless solution was stirred at room temperature under nitrogen for 2 h. The resulting mixture was cooled to 0° C. under nitrogen then N,O-dimethylhydroxylamine hydrochloride (1.7 g, 17.03 mmol) was added. The thick slurry mixture was stirred at room temperature under nitrogen for 10 min. The resulting mixture was diluted with dichloromethane and washed with saturated aqueous sodium bicarbonate. The organics were washed with brine and then dried over magnesium sulfate, filtered, and concentrated on a rotary evaporator. The residue was purified using flash chromatography (30-70% ethyl acetate in hexane) to give the title compound (1.5 g, 8.56 mmol, 75%) as clear oil. MS (ESI) m/z 176.4 [M+1]$^+$.

Intermediates 136 and 137: 6-Bromo-1,4-dimethylindoline-2,3-dione and 4-bromo-1,6-dimethylindoline-2,3-dione

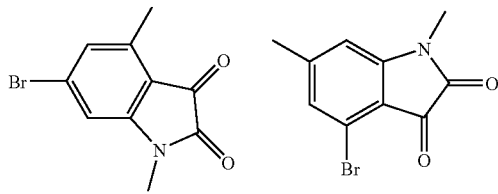

A. 3-Bromo-N,N,5-trimethylaniline. To a solution of 3-bromo-5-methylaniline hydrochloride salt (0.419 g, 2.25 mmol) in 1,2-dimethoxyethane (6 mL) was added sodium hydride (0.162 g, 6.75 mmol) and the reaction mixture was stirred at room temperature for 15 min. Iodomethane (0.7 mL, 11.25 mmol) was added and the reaction mixture was stirred at room temperature for 17 h. Water was added and the reaction mixture was extracted with ethyl acetate (3×50 mL). The organic layers were washed with saturated ammonium chloride solution (100 mL) and brine, dried over magnesium sulfate, filtered and concentrated down. The crude was purified by column chromatography (eluting with 0-40% ethyl acetate in hexane) to afford 3-bromo-N,N,5-trimethylaniline (0.31 g, 66.4% yield) as yellow liquid. $^1$H NMR (400 MHz, DMSO-d$_6$) δ (ppm) 6.62 (d, J=1.95 Hz, 2H), 6.51 (s, 1H), 2.88 (s, 6H), 2.22 (s, 3H). MS (ESI) m/z 213.9 [M+2]$^+$.

B. 6-Bromo-1,4-dimethylindoline-2,3-dione and 4-bromo-1,6-dimethylindoline-2,3-dione. A solution of 1,4-diazabicyclo[2.2.2]octane (DABCO) (1.912 g, 17.05 mmol) in chloroform (5 mL) was cooled down to 0° C. under nitrogen gas and oxalyl chloride (1.492 mL, 17.05 mmol) was added dropwise, to form a pale yellow solid. To this solid was added slowly 3-bromo-N,N,5-trimethylaniline (0.73 g, 3.41 mmol) in chloroform (3 mL) at 0° C. The reaction mixture changed from a yellow suspension to a brown suspension. The reaction mixture was then warmed to room temperature, transferred into a sealed tube and heated at 90° C. for 3 h. The reaction mixture was neutralized with 10% sodium hydroxide solution to pH 8-9. The water layer was extracted with ethyl acetate (3×100 mL), washed with saturated ammonium chloride and brine, dried over magnesium sulfate, filtered and concentrated down to give the mixture of regioisomers as a red-brown solid. The regioisomers were separated by column chromatography (eluting with 0-100% ethyl acetate in hexane). The least polar compound was identified as 6-bromo-1,4-dimethylindoline-2,3-dione (0.34 g, 39.2%). $^1$H NMR (400 MHz, DMSO-d$_6$) δ (ppm) 7.27 (s, 1H), 7.21 (s, 1H), 3.12 (s, 3H), 2.44 (s, 3H). MS (ESI) m/z 256.1 [M+2]$^+$. The regiochemistry was confirmed by NOE (NOE-NMR (400 MHz, DMSO-d$_6$) δ (ppm) 2.44 (irradiated peak suppressed one major peak at 7.21 ppm). The most polar compound spot was identified as 4-bromo-1,6-dimethylindoline-2,3-dione and was further purified by trituration with methanol (0.146 g, 17%). $^1$H NMR (400 MHz, DMSO-d$_6$) δ (ppm) 7.16 (s, 1H), 7.02 (s, 1H), 3.11 (s, 3H), 2.38 (s, 3H). MS (ESI) m/z 256.1 [M+2]$^+$. The regiochemistry was confirmed by nOE (NOE-NMR (400 MHz, DMSO-d$_6$) δ (ppm) 2.38 (irradiated peak suppressed two major peaks at 7.02 and 7.16 ppm).

EXAMPLES

Example 1

N,5-Diphenyl-[1,2,4]triazolo[1,5-a]pyridin-2-amine

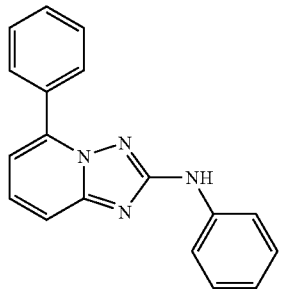

A. 2-(3-Ethoxycarbonyl-2-thioureido)-6-bromopyridine. To a solution of 2-amino-6-bromopyridine (8 g, 46.5 mmol) in dioxane (160 mL) was added dropwise ethoxycarbonyl isothiocyanate (6.09 g, 46.5 mmol) under nitrogen at room temperature, and the reaction mixture was stirred at room temperature for 2 h. The reaction mixture was monitored by TLC (petroleum ether: ethyl acetate=5:1). When the starting material was consumed, dioxane was removed under reduced pressure to give crude 2-(3-ethoxycarbonyl-2-thioureido)-6-bromopyridine (14.81 g) as a solid. $^1$H NMR (300 MHz, DMSO-d$_6$) δ (ppm) 12.16 (br s, 1H), 11.65 (br s, 1H), 8.65 (d, J=8.1 Hz, 1H), 7.84 (dd, J$_1$=8.1, J$_2$=7.2 Hz, 1H), 7.49 (d, J=7.2 Hz, 1H), 4.24 (q, J=7.2 Hz, 2H), 1.27 (t, J=7.2 Hz, 3H); MS (ESI): m/z 303.9 [M+1]$^+$.

B. 5-Bromo-[1,2,4]triazolo[1,5-a]pyridin-2-amine. To a solution of hydroxylamine hydrochloride (16.16 g, 232.5 mmol) and N,N-diisopropylethylamine (23.89 mL, 139.5 mmol) in a mixture of methanol and ethanol (v/v, 1:1, 95 mL) was added 2-(3-ethoxycarbonyl-2-thioureido)-6-bromopyridine (14.81 g, 46.5 mmol) in one portion at room temperature. After being stirred at room temperature for 2 h, the reaction mixture was heated at 60° C. overnight. TLC (ethyl acetate: methanol=20:1) indicated the starting material was consumed. The volatiles were removed under reduced pressure and the residue was treated with water. The precipitate was collected by filtration, washed with a mixture of methanol and diethyl ether (4:1, 18.5 mL). After being dried under high vacuum, 5-bromo-[1,2,4]triazolo[1,5-a]pyridin-2-amine (7.29 g, overall yield 74% for two steps) was obtained as a off-white solid. $^1$H NMR (300 MHz, DMSO-d$_6$) δ (ppm) 7.34 (m, 2H), 7.20 (m, 1H), 6.24 (br s, 2H); MS (ESI): m/z 213.0 [M+1]$^+$.

C. 5-Phenyl-[1,2,4]triazolo[1,5-a]pyridin-2-amine. A mixture of 5-bromo-[1,2,4]triazolo[1,5-a]pyridin-2-amine (2.5 g, 11.8 mmol), phenyl boronic acid (2.88 g, 23.6 mmol), triphenylphosphine (618 mg, 2.36 mmol) and potassium phosphate (5.00 g, 23.6 mmol) in 1,2-dimethoxyethane (35 mL) was degassed, and palladium acetate (0.5 g, 1.77 mmol) was added under nitrogen. The reaction mixture was refluxed under nitrogen overnight. After being cooled to room temperature, the reaction mixture was partitioned between ethyl acetate (50 mL) and water (50 mL), and the aqueous layer was extracted with ethyl acetate (30 mL×3). The combined organic layer was washed with brine, dried over sodium sulfate, and evaporated. The residue was purified by silica gel column (eluting with 15-25% ethyl acetate in petroleum ether) to give 5-phenyl-[1,2,4]triazolo[1,5-a]pyridin-2-amine (1.7 g, 68.5% yield) as a solid. $^1$H NMR (400 MHz, METHANOL-d$_4$) δ (ppm) 7.92 (m, 2H), 7.59-7.34 (m, 5H), 7.40 (d, J=7.2, 1H); MS (ESI): m/z 211.0 [M+1]$^+$.

D. N,5-Diphenyl-[1,2,4]triazolo[1,5-a]pyridin-2-amine. A mixture of 5-phenyl-[1,2,4]triazolo[1,5-a]pyridin-2-amine (200 mg, 0.94 mmol), phenyl bromide (163 mg, 1.03 mmol), 4,5-bis(diphenylphosphino)-9,9-dimethylxanthene (54 mg, 0.094 mmol) and cesium carbonate (430 mg, 1.32 mmol) in dioxane (8 mL) was degassed, and tris(dibenzylideneacetone)-dipalladium (0) (43 mg, 0.047 mmol) was added under nitrogen. The reaction mixture was heated at 120° C. with stirring overnight. The reaction mixture was quenched by the addition of water and the mixture was extracted with ethyl acetate (25 mL×3). The combined organic layer was washed with brine, dried over sodium sulfate, concentrated. The residue was purified by preparative TLC (eluting with 25% ethyl acetate in petroleum ether) to give N,5-diphenyl-[1,2,4]triazolo[1,5-a]pyridin-2-amine (130 mg, 48% yield). $^1$H NMR (400 MHz, DMSO-d$_6$) δ (ppm) 9.62 (s, 1H), 8.04 (d, J=8.4 Hz, 2H), 7.68-7.51 (m, 6H), 7.22 (t, J=7.6 Hz, 2H), 7.18 (d, J=8.4 Hz, 1H), 6.83 (t, J=7.6 Hz, 1H); MS (ESI): m/z 286.9 [M+1]$^+$. Iodides or chlorides may be used in place of bromides for this coupling reaction.

Example 2

N-(4-Morpholinophenyl)-5-phenyl-[1,2,4]triazolo[1,5-a]pyridin-2-amine

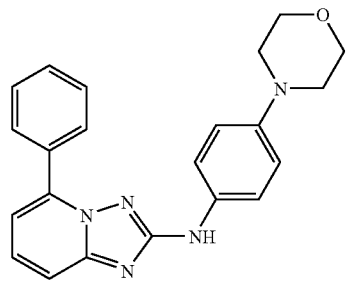

A. N-(4-Morpholinophenyl)-5-phenyl-[1,2,4]triazolo[1,5-a]pyridin-2-amine. After the mixture of 5-phenyl-[1,2,4]triazolo[1,5-a]pyridin-2-amine (100 mg, 0.47 mmol), 4-(4-bromo-phenyl)-morpholine (137 mg, 0.57 mmol), 4,5-bis(diphenylphosphino)-9,9-dimethylxanthene (27 mg, 0.047 mmol) and potassium tert-butoxide (105 mg, 0.94 mmol) in dioxane (6 mL) was degassed, tris(dibenzylideneacetone)-dipalladium (0) (21.6 mg, 0.024 mmol) was added under nitrogen, and the reaction mixture was heated at 80° C. with stirring under nitrogen overnight. The reaction mixture was quenched by the addition of water, and the mixture was extracted with ethyl acetate (15 mL×3). The combined organic layer was washed with brine, dried over sodium sulfate and concentrated. The residue was purified by preparative TLC (eluting with 25% ethyl acetate in petroleum ether) to give N-(4-morpholinophenyl)-5-phenyl-[1,2,4]triazolo[1,5-a]pyridin-2-amine as free base, which was converted to the corresponding hydrochloride salt with methanolic hydrochloride solution (28 mg, 15.8% yield). $^1$H NMR (400 MHz, DMSO-d$_6$) δ (ppm) 9.91 (br s, 1H), 8.02 (d, J=8.0 Hz, 2H), 7.75-7.52 (m, 9H), 7.20 (d, J=6.8 Hz, 1H), 3.97 (s, 4H), 3.45 (s, 4H); MS (ESI): m/z 372.2 [M+1]$^+$.

Example 3

5-(Furan-3-yl)-N-phenyl-[1,2,4]triazolo[1,5-a]pyridin-2-amine

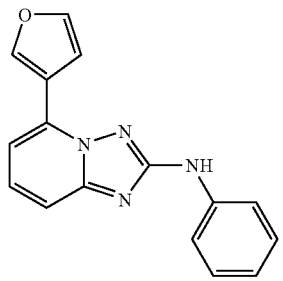

Example 4

5-(2-Fluorophenyl)-N-phenyl-[1,2,4]triazolo[1,5-a]pyridin-2-amine

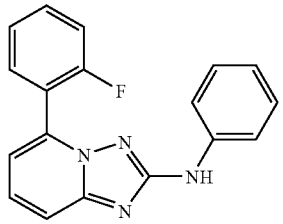

A. 5-(2-Fluorophenyl)-N-phenyl-[1,2,4]triazolo[1,5-a]pyridin-2-amine. 542-Fluorophenyl)-[1,2,4]triazolo[1,5-a]pyridin-2-amine was prepared from 5-bromo-[1,2,4]triazolo[1,5-a]pyridin-2-amine and 2-fluorophenylboronic acid, following the procedure described for the synthesis of 5-(furan-3-yl)-[1,2,4]triazolo[1,5-a]pyridin-2-amine. A degassed mixture of 5-(2-fluorophenyl)-[1,2,4]triazolo[1,5-a]pyridin-2-amine (73 mg, 0.3 mmol), 4,5-bis(diphenylphosphino)-9,9-dimethylxanthene (37 mg, 0.064 mmol), tris(dibenzylideneacetone)dipalladium(0) (29 mg, 0.032 mmol), bromobenzene (47 mg, 0.3 mmol) and potassium tert-butoxide (72 mg, 0.64 mmol) in dioxane (5 mL) was heated at 120°

C. under nitrogen overnight. After being cooled to room temperature, ethyl acetate (30 mL) and water (30 mL) were added. The organic layer was separated and then the aqueous phase was extracted with ethyl acetate (30 mL×3). The combined organic layer was dried over anhydrous sodium sulfate and filtered. The filtrate was evaporated under reduced pressure. The residue was purified by reverse-phase preparative HPLC (40-70% acetonitrile+0.1% trifluoroacetic acid in water+0.1% trifluoroacetic acid, over 15 min) to give 5-(2-fluorophenyl)-N-phenyl-[1,2,4]triazolo[1,5-a]pyridin-2-amine as a trifluoroacetic acid salt, which was converted to the corresponding hydrochloride salt with methanolic hydrochloride solution (23 mg, 24% yield). $^1$H NMR (400 MHz, METHANOL-$d_4$) δ (ppm) 8.10 (t, J=8.0 Hz, 1H), 7.81 (m, 2H), 7.71 (m, 1H), 7.58 (m, 1H), 7.50 (m, 2H), 7.42 (m, 2H), 7.32 (m, 2H), 7.07 (m, 1H); MS (ESI): m/z 305.1 [M+1]$^+$.

Example 5

N-(5-Methoxypyridin-3-yl)-5-phenyl-[1,2,4]triazolo[1,5-a]pyridin-2-amine

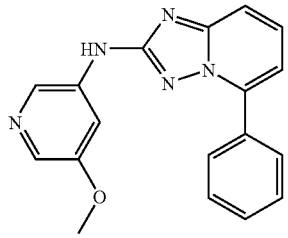

A. N-(5-Methoxypyridin-3-yl)-5-phenyl-[1,2,4]triazolo[1,5-a]pyridin-2-amine. A mixture of 5-phenyl-[1,2,4]triazolo[1,5-a]pyridin-2-amine (303 mg, 1.44 mmol), 3-bromo-5-methoxy-pyridine (245 mg, 1.31 mmol), (R)-(+)-2,2'-bis(diphenylphosphino) 1,1'-binaphthyl (162 mg, 0.26 mmol) and sodium tert-butoxide (252 mg, 2.88 mmol) in toluene (10 mL) was degassed, and tris(dibenzylideneacetone)dipalladium(0) (119 mg, 0.13 mmol) was added. The reaction mixture was heated at 80° C. under nitrogen with stirring overnight. Toluene was removed under reduced pressure, and the residue was purified on silica gel column (eluting with 5-30% ethyl acetate in petroleum ether) to give the crude product, which was recrystallized from methanol to give N-(5-methoxypyridin-3-yl)-5-phenyl-[1,2,4]triazolo[1,5-a]pyridin-2-amine (170 mg, 41.0% yield) as a white solid. $^1$H NMR (400 MHz, DMSO-$d_6$) δ (ppm) 9.94 (s, 1H), 8.30 (d, J=2.0 Hz, 1H), 8.01 (d, J=2.0 Hz, 2H), 7.94 (s, 1H), 7.78 (d, J=2.4 Hz, 1H), 7.65 (m, 1H), 7.61 (s, 1H), 7.55 (m, 3H), 7.28 (d, 1H), 3.76 (s, 3H); MS (ESI): m/z 318.1 [M+1]$^+$.

Example 6

N$^2$-(2-Aminoethyl)-N$^4$-(5-phenyl-[1,2,4]triazolo[1,5-a]pyridin-2-yl)pyridine-2,4-diamine

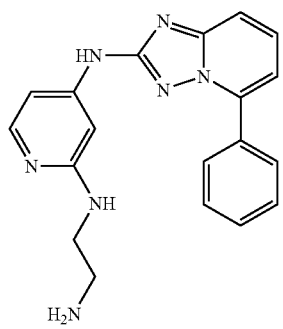

A. N-(2-Chloropyridin-4-yl)-5-phenyl-[1,2,4]triazolo[1,5-a]pyridin-2-amine. A degassed mixture of 5-phenyl-[1,2,4]triazolo[1,5-a]pyridin-2-amine (420 mg, 2.0 mmol), 2-chloro-4-iodo-pyridine (478 mg, 2.0 mmol), tris(dibenzylideneacetone) dipalladium(0) (180 mg, 0.2 mmol), 4,5-bis(diphenylphosphino)-9,9-dimethylxanthene (230 mg, 0.4 mmol) and cesium carbonate (1.3 g, 4.0 mmol) in dioxane (5 mL) was heated at 80° C. under nitrogen overnight. After being cooled to room temperature, the reaction mixture was filtered, and the filtrate was concentrated in vacuo. The crude product was washed with water (10 mL) and methanol (20 mL), and dried under vacuum to give N-(2-chloropyridin-4-yl)-5-phenyl-[1,2,4]triazolo[1,5-a]pyridin-2-amine (502 mg, 78% yield) as a solid which was used without further purification. MS (ESI): m/z 321.9 [M+H]$^+$.

B. N$^2$-(2-Aminoethyl)-N$^4$-(5-phenyl-[1,2,4]triazolo[1,5-a]pyridin-2-yl)pyridine-2,4-diamine. A mixture of N-(2-chloropyridin-4-yl)-5-phenyl-[1,2,4]triazolo[1,5-a]pyridin-2-amine (160 mg, 0.5 mmol), ethane-1,2-diamine (5 mL) and copper (I) iodide (10 mg, 0.05 mmol) in a sealed tube was irradiated in a microwave (150 W) at 150° C. under nitrogen for 45 min. Water was added, and the mixture was extracted with dichloromethane. The combined organic layer was washed with brine, dried over sodium sulfate, and evaporated under reduced pressure. The crude product was purified by reverse-phase preparative HPLC (24-54%: acetonitrile+0.1% trifluoroacetic acid in water+0.1% trifluoroacetic acid, over 20 min) to give N$^2$-(2-aminoethyl)-N$^4$-(5-phenyl-[1,2,4]triazolo[1,5-a]pyridin-2-yl)pyridine-2,4-diamine as a trifluoroacetic acid salt, which was converted to a hydrochloride salt with methanolic hydrochloride solution (35 mg, 20% yield) as a solid. $^1$H NMR (400 MHz, METHANOL-$d_4$) δ (ppm) 7.92 (m, 2H), 7.71 (m, 2H), 7.59 (m, 1H), 7.51 (m, 4H), 7.21

(dd, J$_1$=1.2 Hz, J$_2$=7.6 Hz, 1H), 6.9 (d, J=1.2 Hz, 1H), 3.55 (t, J=6.0 Hz, 2H), 3.02 (t, J=6.0, 2H); MS (ESI): m/z 346.1 [M+1].

Example 7

3-(2-(Phenylamino)-[1,2,4]triazolo[1,5-a]pyridin-5-yl)phenol

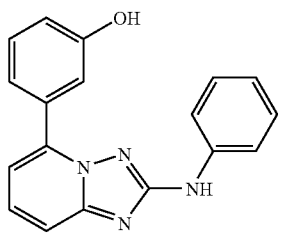

A. 5-Bromo-N-phenyl-[1,2,4]triazolo[1,5-a]pyridin-2-amine. To a solution of 5-bromo-[1,2,4]triazolo[1,5-a]pyridin-2-amine (2 g, 9.39 mmol) in 100 mL of dioxane was added iodobenzene (3.83 g, 18.78 mmol), sodium tert-butoxide (1.804 g, 18.78 mmol), 4,5-bis(diphenylphosphino)-9,9-dimethylxanthene (1.086 g, 1.878 mmol) and tris(dibezylideneacetone)palladium (0.903 g, 0.986 mmol) at room temperature under nitrogen. The reaction mixture was heated at 100° C. for 2 h. Upon completion of the reaction, as indicated by LCMS, the reaction mixture was poured into water/brine, and extracted with ethyl acetate several times. The combined organic layers were dried over anhydrous magnesium sulfate and concentrated. The crude mixture was purified by silica gel column chromatography (eluting with 0-80% ethyl acetate in hexanes) to give the title compound as a brown solid (1.3 g, 48% yield). $^1$H NMR (400 MHz DMSO-d$_6$) δ (ppm) 9.84 (s, 1H), 7.74-7.71 (m, 2H), 7.62-7.60 (m, 1H), 7.52-7.48 (m, 1H), 7.40-7.38 (m, 1H), 7.32-7.28 (m, 2H), 6.92-6.88 (m, 1H); MS (ESI) m/z 290.13 [M+1]$^+$ B. 3-(2-(Phenylamino)-[1,2,4]triazolo[1,5-a]pyridin-5-yl)phenol. A degassed solution of 5-bromo-N-phenyl-[1,2,4]triazolo[1,5-a]pyridin-2-amine (60 mg, 0.286 mmol), 3-hydroxy-phenylboronic acid (43 mg, 0.312 mmol), 1-1'-bis(diphenylphosphino)ferrocene palladium dichloride (15 mg, 0.020 mmol) and aqueous solution of sodium carbonate (2 M, 1 mL) in dioxane (3 mL) was refluxed for 2 h under nitrogen. The reaction mixture was filtered, and the filtrate was partitioned between ethyl acetate and water. The aqueous layer was extracted with ethyl acetate. The organic layers were combined, dried with sodium sulfate, and evaporated in vacuo. The residue was purified by preparative TLC (eluting with 15-20% ethyl acetate in petroleum ether) give 3-(2-(phenylamino)-[1,2,4]triazolo[1,5-a]pyridin-5-yl)phenol (45 mg, 52% yield) as a solid. $^1$H NMR (400 MHz, DMSO-d$_6$) δ (ppm) 9.81 (br s, 1H), 9.62 (br s, 1H), 7.68-7.56 (m, 4H), 7.42-7.35 (m, 3H), 7.24 (t, J=8.0 Hz, 2H), 7.11 (d, J=6.8 Hz, 1H), 6.93 (m, 1H), 6.83 (m, 1H); MS (ESI): m/z 303.0 [M+1]$^+$.

Example 8

5-(1H-Indazol-5-yl)-N-phenyl-[1,2,4]triazolo[1,5-a]pyridin-2-amine

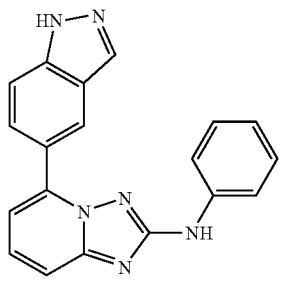

A. 5-(1H-Indazol-5-yl)-N-phenyl-[1,2,4]triazolo[1,5-a]pyridin-2-amine. A mixture of 5-bromo-N-phenyl-[1,2,4]triazolo[1,5-a]pyridin-2-amine (180 mg, 0.625 mmol), tert-butyl 5-(4,4,5,5-tetramethyl-1,3,2-dioxaborolan-2-yl)-1H-indazole-1-carboxylate (258 mg, 0.72 mmol), tetrakis(triphenylphosphine)palladium (0) (72 mg, 0.06 mmol) and an aqueous solution of potassium phosphate (2 M, 0.625 mL, 1.3 mmol) in dimethylsulfoxide (5 mL) in a tube was heated at 85° C. with stirring under nitrogen overnight. A saturated sodium chloride aqueous solution was added, and the precipitated was collected by filtration. The pale yellow solid was dissolved in ethyl acetate (5 mL) and methanolic hydrochloride solution (2 M, 2 mL) was added dropwise. The mixture was concentrated under vacuum, and the residue was washed with ethyl acetate to give 5-(1H-indazol-5-yl)-N-phenyl-[1,2,4]triazolo[1,5-a]pyridin-2-amine (82 mg, 41% yield) as a hydrochloride salt. $^1$H NMR (400 MHz, DMSO-d$_6$) δ (ppm) 9.65 (br s, 1H), 8.49 (s, 1H), 8.23 (s, 1H), 7.98 (d, J=8.8 Hz, 1H), 7.68 (m, 4H), 7.56 (d, J=8.8 Hz, 1H), 7.22 (m, 3H), 6.83 (t, J=7.2 Hz. 1H); MS (ESI): m/z 327.1 [M+1]$^+$. Alternatively, this reaction can be run in N,N-dimethylformide as solvent and at a temperature of 100° C.

Example 9

5-(2-((Methylamino)methyl)-1H-benzo[d]imidazol-5-yl)-N-phenyl-[1,2,4]triazolo[1,5-a]pyridin-2-amine

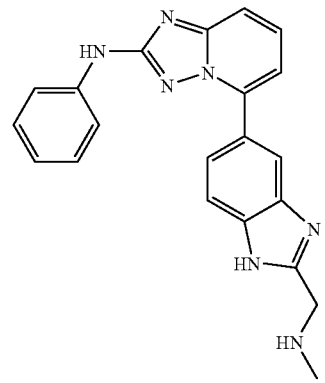

A. 5-(4-Amino-3-nitrophenyl)-N-phenyl-[1,2,4]triazolo[1,5-a]pyridin-2-amine. A degassed mixture of 2-nitro-4-(4,4,5,5-tetramethyl-1,3,2-dioxaborolan-2-yl)aniline (0.5 g mg, 1.89 mmol), 5-bromo-N-phenyl-[1,2,4]triazolo[1,5-a]pyridin-2-amine (0.54 g, 1.89 mmol), sodium carbonate (0.4 g, 3.78 mmol), and tetrakis(triphenyl-phosphine)palladium (0) (50 mg, 0.043 mmol) in 1,2-dimethoxyethane and water (v/v, 3:1, 12 mL) was heated to 85° C. overnight. The reaction mixture was extracted with ethyl acetate, and the organic layer was evaporated. The crude product was purified on silica gel column (eluting with 15% ethyl acetate in petroleum ether) to 5-(4-amino-3-nitrophenyl)-N-phenyl-[1,2,4]triazolo[1,5-a]pyridin-2-amine (0.39 g, 60% yield). $^1$H NMR (400 MHz, DMSO-$d_6$) δ (ppm) 9.63 (br s, 1H), 9.23 (br s, 1H), 8.08-8.06 (dd, $J_1$=9.2 Hz, $J_2$=2.4 Hz, 1H), 7.82 (s, 2H), 7.73 (d, J=7.6 Hz, 2H), 7.63 (d, J=8.8 Hz, 1H), 7.51 (d, J=8.8 Hz, 1H), 7.29-7.23 (m, 3H), 7.18 (d, J=8.8 Hz, 1H), 6.85 (t, J=7.2 Hz, 1H); MS (ESI): m/z 347.0 [M+1]$^+$.

B. 4-(2-Phenylamino-[1,2,4]triazolo[1,5-a]pyridin-5-yl)-benzene-1,2-diamine. A mixture of 5-(4-amino-3-nitrophenyl)-N-phenyl-[1,2,4]triazolo[1,5-a]pyridin-2-amine (0.59 g, 1.72 mmol), zinc dust (1.12 g, 17.2 mmol), and ammonium chloride (0.92 g, 17.2 mmol) in a mixture of tetrahydrofuran and methanol (1:1, 30 mL) was stirred at room temperature for 1 h. The reaction mixture was filtered, and filtrate was concentrated under reduced pressure. The residue was partitioned between water and ethyl acetate, and the aqueous solution was extracted with ethyl acetate for three times. The organic layer was washed with brine, dried over sodium sulfate, and concentrated in vacuo to give 4-(2-phenylamino-[1,2,4]triazolo[1,5-a]pyridin-5-yl)-benzene-1,2-diamine (0.36 g, 61% yield) as a yellow solid. $^1$H NMR (400 MHz, DMSO-$d_6$) δ (ppm) 9.54 (br s, 1H), 7.70 (m, 2H), 7.55 (m, 1H), 7.39 (m, 1H), 7.25-7.21 (m, 4H), 6.95 (d, J=7.2 Hz, 1H), 6.84 (m, 1H), 6.63 (d, J=6.8 Hz, 1H), 4.99 (br s, 2H), 4.63 (br s, 2H); MS (ESI): m/z 317.0 [M+1]$^+$.

C. 5-(2-(Chloromethyl)-1H-benzo[d]imidazol-5-yl)-N-phenyl-[1,2,4]triazolo[1,5-a]pyridin-2-amine. A mixture of 4-(2-phenylamino-[1,2,4]triazolo[1,5-a]pyridin-5-yl)-benzene-1,2-diamine (0.34 g, 1.1 mmol) and ethyl 2-chloroacetimidate hydrochloride (0.17 g, 1.1 mol) in anhydrous ethanol (50 mL) was stirred at room temperature for 4 h. The solvent was removed under reduced pressure, and the residue was poured into water. The aqueous layer was extracted with ethyl acetate. The organic layer was dried over sodium sulfate, filtered and the filtrate was concentrated in vacuo to provide 5-(2-(chloromethyl)-1H-benzo[d]imidazol-5-yl)-N-phenyl-[1,2,4]triazolo[1,5-a]pyridin-2-amine (0.34 g, 84% yield). $^1$H NMR (400 MHz, DMSO-$d_6$) δ (ppm) 13.03 (br s, 1H), 9.61 (br s, 1H), 8.33-8.25 (m, 1H), 7.88-7.51 (m, 6H), 7.39-7.21 (m, 3H), 6.64 (d, J=7.6 Hz, 1H), 4.97 (s, 2H); MS (ESI): m/z 375.0 [M+1]$^+$.

D. 5-(2-((Methylamino)methyl)-1H-benzo[d]imidazol-5-yl)-N-phenyl-[1,2,4]triazolo[1,5-a]pyridin-2-amine. A mixture of 5-(2-(chloromethyl)-1H-benzo[d]imidazol-5-yl)-N-phenyl-[1,2,4]triazolo[1,5-a]pyridin-2-amine (0.18 g, 0.4 mmol) and methylamine aqueous solution (0.24 g, 2.0 mmol) in acetonitrile (25 mL) was stirred at room temperature overnight. The solvent was removed under reduced pressure to give the crude product, which was purified by reverse-phase preparative HPLC (20-54% acetonitrile+0.1% trifluoroacetic acid in water+0.1% trifluoroacetic acid, over 15 min) to give 542-((methylamino)methyl)-1H-benzo[d]imidazol-5-yl)-N-phenyl-[1,2,4]triazolo[1,5-a]pyridin-2-amine as a trifluoroacetic acid salt, which was converted to the hydrochloride salt with methanolic hydrochloride solution (0.65 g, 37% yield). $^1$H NMR (400 MHz, METHANOL-$d_4$) δ (ppm) 8.53 (s, 1H), 8.21-8.13 (m, 2H), 8.03 (d, J=8.4 Hz, 1H), 7.85 (d, J=8.4 Hz, 1H), 7.78 (d, J=7.6 Hz, 1H), 7.57 (d, J=7.6 Hz, 2H), 7.40 (t, J=8.0 Hz, 2H), 7.14 (t, J=7.6 Hz, 1H), 4.69 (s, 2H), 2.97 (s, 3H); MS (ESI): m/z 370.1 [M+1]$^+$.

Example 10

7-(2-(Phenylamino)-[1,2,4]triazolo[1,5-a]pyridin-5-yl)isoquinolin-1-amine

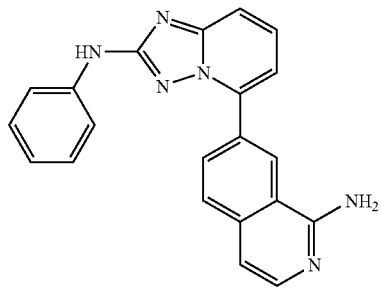

A. 5-(1-Chloroisoquinolin-7-yl)-N-phenyl-[1,2,4]triazolo[1,5-a]pyridine-2-amine. A degassed mixture of 1-chloroisoquinolin-7-ylboronic acid (288 mg, 1.38 mmol), 5-bromo-N-phenyl-[1,2,4]triazolo[1,5-a]pyridine-2-amine (400 mg, 1.38 mmol), potassium phosphate (296 mg, 2.76 mmol) and tetrakis (triphenylphosphine)palladium(0) (160 mg, 0.138 mmol) in dimethylsulfoxide (10 mL) was heated at 90° C. under nitrogen overnight. After being cooled down to room temperature, the reaction mixture was filtered, and the filtrate was concentrated in vacuo to give the crude product, which was washed with ethyl acetate to give 541-chloroisoquinolin-7-yl)-N-phenyl-[1,2,4]triazolo[1,5-a]pyridine-2-amine (200 mg, 38.7% yield) as a solid. $^1$H NMR (400 MHz, DMSO-$d_6$) δ (ppm) 9.68 (br s, 1H), 9.23 (s, 1H), 8.45 (d, J=8.4 Hz, 1H), 8.41 (d, J=5.2 Hz, 1H), 8.27 (d, J=8.8 Hz, 1H), 8.01 (d, J=5.6 Hz, 1H), 7.69 (m, 4H), 7.44 (d, J=6.0 Hz, 1H), 7.23 (t, J=7.6 Hz, 2H), 6.85 (t, J=7.2 Hz, 1H); MS (ESI) m/z: 372.1 [M+1].$^+$ B. N-(4-Methoxybenzyl)-7-(2-(phenylamino)[1,2,4]triazolo[1,5-a]pyridin-5-yl)isoquinolin-1-amine. A mixture of 5-(1-chloroisoquinolin-7-yl)-N-phenyl-[1,2,4]triazolo[1,5-a]pyridine-2-amine (200 mg, 0.54 mmol) and (4-methoxyphenyl)-methanamine (20 mL) was heated at 180° C. for 6 h. Then the reaction mixture was concentrated in vacuo to give the crude product, which was purified by reverse-phase preparative HPLC (34-54%: acetonitrile+0.1% trifluoroacetic acid in water, over 15 min) to give N-(4-methoxybenzyl)-7-(2-(phenylamino)-[1,2,4]triazolo[1,5-a]pyridin-5-yl)isoquinolin-1-amine as a trifluoroacetic acid salt, which was converted to the hydrochloride salt with methanolic hydrochloride solution (120 mg, 47% yield). $^1$H-NMR (400 MHz, DMSO-$d_6$) δ (ppm) 9.67 (br s, 1H), 9.19 (s, 1H), 8.65 (m, 1H), 8.14 (m, 1H), 7.72 (m, 5H), 7.35 (m, 4H), 7.21 (t, J=7.6 Hz, 2H), 6.89 (m, 2H), 6.83 (t, J=6.8 Hz, 1H), 4.76 (d, J=5.2 Hz, 2H), 3.70 (s, 3H); MS (ESI): m/z 473.1 [M+1]$^+$.

C. 7-(2-(Phenylamino)-[1,2,4]triazolo[1,5-a]pyridin-5-yl)isoquinolin-1-amine. A solution of N-(4-methoxybenzyl)-7-(2-(phenylamino)-[1,2,4]triazolo[1,5-a]pyridin-5-yl)isoquinolin-1-amine (120 mg, 0.25 mmol) in trifluoroacetic acid (20 mL) was refluxed for 6 h. The reaction mixture was concentrated in vacuo to give the crude product which was purified by reverse-phase preparative HPLC (30-50%: acetonitrile+0.1% trifluoroacetic acid in water+0.1% trifluoroacetic acid, over 12 min) to give 7-(2-(phenylamino)-[1,2,4]triazolo[1,5-a]pyridin-5-yl)isoquinolin-1-amine as a trifluoroacetic acid salt, which was converted to the hydrochloride salt with methanolic hydrochloride solution (28 mg, 31.5% yield). $^1$H-NMR (400 MHz, DMSO-$d_6$) δ (ppm) 9.18 (br s, 1H), 8.67 (d, J=6.8 Hz, 1H), 8.15 (d, J=8.4 Hz, 1H), 7.96 (m, 1H), 7.71 (m, 2H), 7.58 (m, 3H), 7.36 (d, J=7.2 Hz, 1H), 7.31 (m, 2H), 7.01 (m, 1H); MS (ESI): m/z 353.1 [M+1]$^+$.

Example 11

5-(2-(Phenylamino)-[1,2,4]triazolo[1,5-a]pyridin-5-yl)benzo[d] isoxazol-3-amine

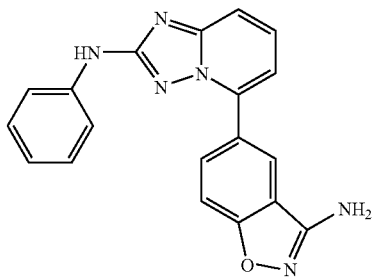

A. 2-Fluoro-5-(2-(phenylamino)-[1,2,4]triazolo[1,5-a]pyridin-5-yl)benzonitrile. To a degassed mixture of 2-fluoro-5-(4,4,5,5-tetramethyl-1,3,2-dioxaborolan-2-yl)benzonitrile (700 mg, 2.8 mmol), 5-bromo-N-phenyl-[1,2,4]triazolo[1,5-a]pyridin-2-amine (400 mg, 1.4 mmol) and potassium acetate (317 mg, 9.51 mmol) in dioxane (10 mL) was added 1,1'-bis(diphenylphosphino)ferrocene palladium dichloride (104 mg, 0.14 mmol), and the resulting mixutre was heated at 100° C. under nitrogen overnight. The reaction mixture was filtered, and the filtrate was evaporated under reduced pressure. The residue was washed with ethyl acetate to give 2-fluoro-5-(2-(phenylamino)-[1,2,4]triazolo[1,5-a]pyridin-5-yl)benzonitrile (300 mg, 65% yield) as a solid. $^1$H NMR (400 MHz, DMSO-$d_6$) δ (ppm) 9.70 (s, 1H), 8.34 (d, J=1.2 Hz, 1H), 8.16 (m, 2H), 7.69 (m, 3H), 7.37 (t, J=4.4 Hz, 1H), 7.25 (m, 2H), 6.86 (m, 1H); MS (ESI): m/z 330.0 [M+1]$^+$.

B. 5-(2-(Phenylamino)-[1,2,4]triazolo[1,5-a]pyridin-5-yl)-2-(propan-2-ylideneaminooxy)benzonitrile. Propan-2-one oxime (131 mg, 1.8 mmol) was added to a solution of potassium tert-butoxide (202 mg, 1.8 mmol) in tetrahydrofuran (15 mL), and the mixture was stirred for 1 h at room temperature. 2-Fluoro-5-(2-(phenylamino)-[1,2,4]triazolo[1,5-a]pyridin-5-yl)benzonitrile (300 mg, 0.9 mmol) was added, and the resulting mixture was stirred at room temperature for 1 h. The mixture was extracted with ethyl acetate, and the combined organic layer was dried over sodium sulfate and filtered. The filtrate was evaporated under reduced pressure, and the residue was purified by reverse-phase preparative HPLC (30-60%: acetonitrile+0.1% trifluoroacetic acid in water+0.1% trifluoroacetic acid, over 25 min) to give 5-(2-(phenylamino)-[1,2,4]triazolo[1,5-a]pyridin-5-yl)-2-(propan-2-ylideneaminooxy)-benzonitrile as a trifluoroacetic acid salt (150 mg, 43.7% yield). $^1$H NMR (400 MHz, DMSO-$d_6$) δ (ppm) 9.52 (s, 1H), 8.19 (s, 1H), 7.81 (d, J=8.0 Hz, 1H), 7.56 (d, J=8.4 Hz, 1H), 7.51 (m, 4H), 7.12 (dd, $J_1$=6.4 Hz, $J_2$=2.0 Hz, 1H), 7.05 (t, J=8.0 Hz, 2H), 6.68 (t, J=7.2 Hz, 1H), 1.98 (s, 3H), 1.80 (s, 3H); MS (ESI): m/z 383.0 [M+1]$^+$.

C. 5-(2-(Phenylamino)-[1,2,4]triazolo[1,5-a]pyridin-5-yl)benzo[d] isoxazol-3-amine. A solution of 5-(2-(phenylamino)-[1,2,4]triazolo[1,5-a]pyridin-5-yl)-2-(propan-2-ylideneaminooxy)benzonitrile (150 mg, 0.39 mmol) in trifluoroacetic acid and 5 N hydrochloric acid (4:1, 50 mL) was stirred at room temperature under nitrogen overnight. The solvent was concentrated in vacuo to give the crude product, which was purified by a reverse-phase preparative HPLC (27-57%: acetonitrile+0.1% trifluoroacetic acid in water+0.1% trifluoroacetic acid, over 15 min) to give 5-(2-(phenylamino)-[1,2,4]triazolo[1,5-a]pyridin-5-yl)benzo[d]isoxazol-3-amine as a trifluoroacetic acid salt, which was converted to the hydrochloride salt (67 mg, 47.0% yield) as a solid. $^1$H NMR (400 MHz, DMSO-$d_6$) δ (ppm) 9.67 (s, 1H), 8.18 (s, 1H), 8.00 (d, J=8.0 Hz, 1H), 7.89 (d, J=8.4 Hz, 1H), 7.65 (m, 4H), 7.31 (d, J=7.2 Hz, 1H), 7.24 (t, J=8.0 Hz, 2H), 6.86 (t, J=7.6 Hz, 1H); MS (ESI): m/z 343.0 [M+1]$^+$.

Example 12

4-(5-(3-Hydroxyphenyl)-[1,2,4]triazolo[1,5-a]pyridin-2-ylamino)benzamide

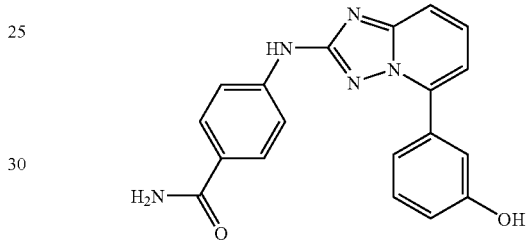

A. 4-(5-Bromo-[1,2,4]triazolo[1,5-a]pyridin-2-ylamino)benzonitrile. To an orange solution of 5-bromo-[1,2,4]triazolo[1,5-a]pyridin-2-amine (2.00 g, 9.39 mmol) in dioxane (100 mL) was added 4-iodobenzonitrile (4.30 g, 18.78 mmol), cesium carbonate (6.12 g, 18.78 mmol), 4,5-bis(diphenylphosphino)-9,9-dimethylxanthene (1.086 g, 1.878 mmol) and tris(dibezylideneacetone)palladium (0.903 g, 0.986 mmol) at room temperature under nitrogen. The reaction mixture was heated at 100° C. for 18 h under nitrogen. Upon completion of the reaction, as indicated by LCMS, the reaction mixture was poured into water/brine, and extracted with ethyl acetate several times. The combined organic layers were dried over anhydrous magnesium sulfate and concentrated. The crude mixture was triturated with ethyl acetate to give the title compound as a brownish yellow solid (0.565 g, 20% yield). $^1$H NMR (400 MHz, DMSO-$d_6$) δ (ppm) 10.55 (s, 1H), 7.89-7.87 (m, 2H), 7.77-7.75 (m, 2H), 7.71-7.69 (m, 1H), 7.58-7.54 (m, 1H), 7.49-7.46 (m, 1H); MS (ESI) m/z 315.14 [M+1]$^+$ B. 4-(5-Bromo-[1,2,4]triazolo[1,5-a]pyridin-2-ylamino)benzamide. A pale yellow solution of 4-(5-bromo-[1,2,4]triazolo[1,5-a]pyridin-2-ylamino)benzonitrile (0.909 g, 2.89 mmol) in 85% phosphoric acid (15 mL) was heated at 100° C. for 2 h. Upon completion of the reaction as indicated by LCMS the reaction mixture was poured into minimum water, and made neutral with 1N sodium hydroxide (pH 6-7). The mixture was extracted with 20% isopropanol in chloroform several times. The combined organic layers were dried over anhydrous magnesium sulfate and concentrated. The crude mixture was purified by silica gel chromatography using a gradient of 0-8% of saturated methanolic ammonia in chloroform to give the title compound as a pale yellow solid (0.677 g, 71% yield). $^1$H NMR (400 MHz, DMSO-$d_6$) δ

(ppm) 10.20 (s, 1H), 7.84 (d, 2H, J=8 Hz), 7.78-7.75 (m, 3H), 7.66 (d, 1H, J=8 Hz), 7.53 (t, 1H, J=8 Hz), 7.7.45-7.42 (m, 1H), 7.16 (br s, 1H); MS (ESI) m/z 332.16 and 334.16 [M]+ and [M+2]+

C. 4-(5-(3-Hydroxyphenyl)-[1,2,4]triazolo[1,5-a]pyridin-2-ylamino)benzamide. To a colorless solution of 4-(5-bromo-[1,2,4]triazolo[1,5-a]pyridin-2-ylamino)benzamide (0.150 g, 0.452 mmol) in dioxane (10 mL) was added 3-hydroxyphenylboronic acid (0.069 g, 0.497 mmol), sodium carbonate (0.020 g, 0.189 mmol) dissolved in minimum amount of water and [1,1'-bis(diphenylphosphino)ferrocene]dichloropalladium(II) (0.026 g, 0.032 mmol) at room temperature under nitrogen. The reaction mixture was heated at 100° C. for 18 h under nitrogen. Upon completion of the reaction as indicated by LCMS the reaction mixture was poured into water/brine, and extracted with ethyl acetate several times. The combined organic layers were dried over anhydrous magnesium sulfate and concentrated. The crude mixture was purified by silica gel chromatography using a gradient of 0-15% saturated methanolic ammonia in chloroform to give a pale yellow solid. This solid was washed with methanol and the filtrate was concentrated to give the pure title compound as a brownish colored solid (92.1% pure, 0.036 g, 23% yield). $^1$H NMR (400 MHz, DMSO-$d_6$) δ (ppm) 10.01 (s, 1H), 9.78 (s, 1H), 7.82-7.76 (m, 3H), 7.74-7.71 (m, 2H), 7.69-7.61 (m, 2H), 7.43-7.37 (m, 3H), 7.17 (d, 1H, J=8 Hz), 7.12 (br s, 1H), 6.97-6.95 (m, 1H); MS (ESI) m/z 346.35 [M+1]+

Example 13

$N^5$-Isopropyl-$N^2$-phenyl-[1,2,4]triazolo[1,5-a]pyridine-2,5-diamine

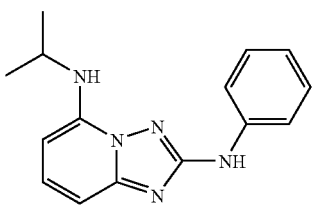

A. $N^5$-Isopropyl-$N^2$-phenyl-[1,2,4]triazolo[1,5-a]pyridine-2,5-diamine. A mixture of 5-bromo-N-phenyl-[1,2,4]triazolo[1,5-a]pyridin-2-amine (60 mg, 0.286 mmol) and isopropylamine (5 mL) in a sealed vessel was heated at 120° C. overnight. The solvent was removed under reduced pressure, and the crude product was purified by preparative TLC (eluting with 15-20% ethyl acetate in petroleum ether) to afford $N^5$-isopropyl-$N^2$-phenyl-[1,2,4]triazolo[1,5-a]pyridine-2,5-diamine (20 mg, 35.9%) as a solid. $^1$H NMR (300 MHz, METHANOL-$d_4$) δ (ppm) 7.63 (m, 2H), 7.46 (m, 1H), 7.32-7.27 (m, 2H), 6.95 (m, 1H), 6.71 (m, 1H), 6.15 (d, J=7.8 Hz, 1H), 3.86 (m, 1H), 1.38 (d, J=6.6 Hz, 6H); MS (ESI): m/z 268.2 [M+1]+.

Example 14 cis-4-(2-(4-(Trifluoromethyl)phenylamino)-[1,2,4]triazolo[1,5-a]pyridin-5-ylamino)cyclohexanol

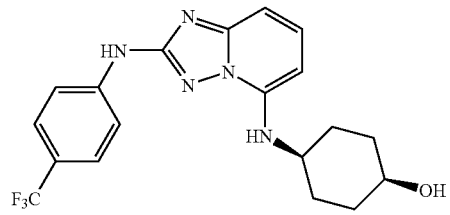

A. 5-Bromo-N-(4-(trifluoromethyl)phenyl)-[1,2,4]triazolo[1,5-a]pyridin-2-amine. To an orange solution of 5-bromo-[1,2,4]triazolo[1,5-a]pyridin-2-amine (1.00 g, 4.69 mmol) in dioxane (40 mL) was added 1-iodo-4-(trifluoromethyl)benzene (2.55 g, 1.3 mL, 9.39 mmol), sodium tert-butoxide (0.902 g, 9.39 mmol), 4,5-bis(diphenylphosphino)-9,9-dimethylxanthene (0.543 g, 0.939 mmol) and tris(dibezylideneacetone)dipalladium (0) (0.451 g, 0.492 mmol) at room temperature under nitrogen. The reaction mixture was heated at 100° C. for 1 h under nitrogen. Upon completion of reaction as indicated by LCMS the reaction mixture was poured into water/brine, and extracted with ethyl acetate several times. The combined organic layer was dried over anhydrous magnesium sulfate and concentrated. The crude mixture was purified by silica gel column chromatography (eluting with 0-50% ethyl acetate in hexanes) to give 5-bromo-N-(4-(trifluoromethyl)phenyl)-[1,2,4]triazolo[1,5-a]pyridin-2-amine as a yellowish brown solid (0.306 g, 18% yield). $^1$H-NMR (400 MHz, DMSO-$d_6$) δ (ppm) 10.39 (s, 1H), 7.87-7.93 (m, 2H), 7.64-7.72 (m, 3H), 7.52-7.58 (m, 1H), 7.44-7.49 (m, 1H); MS (ESI) m/z 358.13 [M+1]+

B. cis-4-(2-(4-(Trifluoromethyl)phenylamino)-[1,2,4]triazolo[1,5-a]pyridin-5-ylamino)cyclohexanol. To an orange solution of 5-bromo-N-(4-(trifluoromethyl)phenyl)-[1,2,4]triazolo[1,5-a]pyridin-2-amine (0.300 g, 0.840 mmol) in dioxane (15 mL) was added cis-4-aminocyclohexanol hydrochloride (0.255 g, 1.680 mmol), sodium tert-butoxide (0.242 g, 2.52 mmol), 4,5-bis(diphenylphosphino)-9,9-dimethylxanthene (0.097 g, 0.168 mmol) and tris(dibezylideneacetone)dipalladium (0) (0.081 g, 0.088 mmol) at room temperature under nitrogen. The reaction mixture was heated at 100° C. for 1 h under nitrogen. Upon completion of reaction as indicated by LCMS the reaction mixture was poured into water/brine, and extracted with ethyl acetate several times. The combined organic layer was dried over anhydrous magnesium sulfate and concentrated. The crude mixture was purified by silica gel column chromatography (eluting with 0-100% ethyl acetate in hexanes) to give the title compound as a brownish yellow solid (100% pure, 0.078 g, 24% yield). $^1$H-NMR (400 MHz, DMSO-$d_6$) δ (ppm) 10.03 (s, 1H), 7.90-7.98 (m, 2H), 7.58-7.66 (m, 2H), 7.44 (t, J=8.27 Hz, 1H), 6.77 (dd, J=1.00, 8.57 Hz, 1H), 6.19-6.26 (m, 2H), 4.51 (d, J=3.17

Hz, 1H), 3.80 (d, J=2.54 Hz, 1H), 3.55-3.66 (m, 1H), 1.83-1.96 (m, 2H), 1.56-1.78 (m, 6H); MS (ESI) m/z 392.39 [M+1]+

Example 15

(S)-4-(5-(Piperidin-3-ylamino)-[1,2,4]triazolo[1,5-a]pyridin-2-ylamino)benzamide

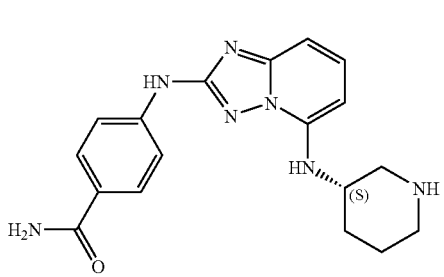

A. (S)-tert-Butyl 3-(2-(4-cyanophenylamino)-[1,2,4]triazolo[1,5-a]pyridin-5-ylamino)piperidine-1-carboxylate. To an orange solution of 4-(5-bromo-[1,2,4]triazolo[1,5-a]pyridin-2-ylamino)benzonitrile (0.250 g, 0.796 mmol) in dioxane (10 mL) was added (S)-tert-butyl 3-aminopiperidine-1-carboxylate (0.319 g, 1.592 mmol), cesium carbonate (0.519 g, 1.592 mmol), 4,5-bis(diphenylphosphino)-9,9-dimethylxanthene (0.092 g, 0.159 mmol) and tris(dibezylideneacetone) palladium (0.077 g, 0.084 mmol) at room temperature under nitrogen. The reaction mixture was heated at 100° C. for 1.5 h under nitrogen. Upon completion of the reaction as indicated by LCMS the reaction mixture was poured into brine, and extracted with ethyl acetate several times. The combined organic layers were dried over anhydrous magnesium sulfate and concentrated. The crude mixture was purified by column chromatography (eluting with 0-80% ethyl acetate in hexanes) to give the title compound as a tan solid (0.122 g, 35% yield). MS (ESI) m/z 434.51 [M+1]+.

B. (S)-4-(5-(Piperidin-3-ylamino)-[1,2,4]triazolo[1,5-a]pyridin-2-ylamino)benzamide. A pale yellow solution of (S)-tert-butyl 3-(2-(4-cyanophenylamino)-[1,2,4]triazolo[1,5-a]pyridin-5-ylamino)piperidine-1-carboxylate (0.118 g, 0.272 mmol) in 85% phosphoric acid (7 mL) was heated at 100° C. for 4 h. Upon completion of the reaction as indicated by LCMS the reaction mixture was run through a 5 g stratta column to remove the phosphoric acid to give a pale yellow foam which was purified by silica gel chromatography (eluting with 0-20% saturated methanolic ammonia in chloroform) to give the title compound as a white solid (92.1% pure, 100% ee, 0.053 g, 55% yield). $^1$H NMR (400 MHz, DMSO-d$_6$) δ (ppm) 9.88 (s, 1H), 7.80-7.85 (m, 2H), 7.73-7.79 (m, 3H), 7.44 (t, J=8.27 Hz, 1H), 7.12 (br s, 1H), 6.78 (dd, J=0.63, 8.49 Hz, 1H), 6.45 (d, J=8.78 Hz, 1H), 6.21 (d, J=7.71 Hz, 1H), 3.65-3.73 (m, 1H), 3.03 (d, J=14.40 Hz, 1H), 2.71-2.79 (m, 2H), 2.62-2.70 (m, 1H), 1.80-1.89 (m, 1H), 1.70-1.80 (m, 1H), 1.59-1.68 (m, 1H), 1.42-1.53 (m, 1H); MS (ESI) m/z 352.41 [M+1]+.

Example 16 cis-4-(5-(4-Aminocyclohexylamino)-[1,2,4]triazolo[1,5-a]pyridin-2-ylamino)benzamide

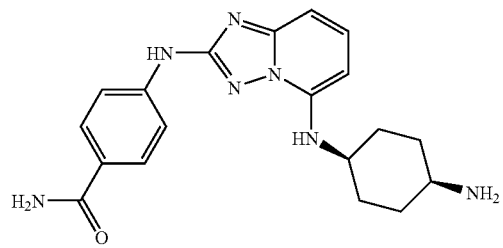

A. tert-Butyl cis-4-(2-(4-cyanophenylamino)-[1,2,4]triazolo[1,5-a]pyridin-5-ylamino)cyclohexylcarbamate. To an orange solution of 4-(5-bromo-[1,2,4]triazolo[1,5-a]pyridin-2-ylamino)benzonitrile (0.200 g, 0.637 mmol) in dioxane (10 mL) was added tert-butyl cis-4-aminocyclohexylcarbamate (0.273 g, 1.273 mmol), cesium carbonate (0.415 g, 1.273 mmol), 4,5-bis(diphenylphosphino)-9,9-dimethylxanthene (0.074 g, 0.127 mmol) and tris(dibezylideneacetone)palladium (0.061 g, 0.0669 mmol) at room temperature under nitrogen. The reaction mixture was heated at 100° C. for 1 h under nitrogen. Upon completion of the reaction, as indicated by LCMS, the reaction mixture was poured into brine, and extracted with ethyl acetate several times. The combined organic layers were dried over anhydrous magnesium sulfate and concentrated. The crude mixture was purified by column chromatography (eluting with 0-80% ethyl acetate in hexanes) to give the title compound as a tan solid (0.082 g, 29% yield). $^1$H NMR (400 MHz, DMSO-d$_6$) δ (ppm) 10.22 (s, 1H), 7.89 (d, 2H, J=8 Hz), 7.73 (d, 2H, J=8 Hz), 7.46 (t, 1H, J=8 Hz), 6.81 (d, 1H, J=8 Hz), 6.25 (d, 1H, J=8 Hz), 6.02 (d, 1H, J=8 Hz), 3.71-3.64 (m, 1H), 3.56-3.34 (m, 1H), 1.90-1.73 (m, 4H), 1.66-1.61 (m, 4H), 1.40 (s, 9H); MS (ESI) m/z 448.53 [M+1]+.

B. tert-Butyl cis-4-(2-(4-carbamoylphenylamino)-[1,2,4]triazolo[1,5-a]pyridin-5-ylamino)cyclohexylcarbamate. To a pale yellow solution of tert-butyl cis-4-(2-(4-cyanophenylamino)-[1,2,4]triazolo[1,5-a]pyridin-5-ylamino)cyclohexylcarbamate (0.078 g, 0.174 mmol) in ethanol (10 mL) (heated with a heat gun to get the starting material in solution) was added 3 N sodium carbonate (4 mL) and 30% w/w hydrogen peroxide (4 mL) at room temperature. The reaction mixture was stirred overnight at room temperature. Upon completion of the reaction as indicated by LCMS, the reaction mixture was poured into brine, and extracted with ethyl acetate several times. The combined organic layer was dried over anhydrous magnesium sulfate and concentrated. The crude mixture was purified by column chromatography (eluting with 0-10% saturated methanolic ammonia in chloroform) to give the title compound as a pale pink solid (0.066 g, 81% yield). $^1$H NMR (400 MHz, DMSO-d$_6$) δ (ppm) 9.86 (s, 1H), 7.84 (d, 2H, J=8 Hz), 7.76 (d, 3H, J=8 Hz), 7.44 (t, 1H, J=8 Hz), 7.12 (s, 1H), 6.78 (d, 1H, J=8 Hz), 6.22 (d, 1H, J=8 Hz), 5.96 (d, 1H, J=8 Hz), 3.73-3.65 (m, 1H), 3.58-3.51 (m, 1H), 1.91-1.82 (m, 2H), 1.81-1.73 (m, 2H), 1.69-1.58 (m, 4H), 1.40 (s, 9H); MS (ESI) m/z 466.55 [M+1]+.

C. Cis 4-(5-(4-Aminocyclohexylamino)-[1,2,4]triazolo[1,5-a]pyridin-2-ylamino)benzamide. To a clear orange solution of tert-butyl cis-4-(2-(4-carbamoylphenylamino)-[1,2,4]triazolo[1,5-a]pyridin-5-ylamino)cyclohexylcarbamate (0.057 g, 0.122 mmol) in dichloromethane (10 mL) was added trifluoroacetic acid (5 mL) at room temperture. The reaction mixture was stirred at room temperature overnight. Upon completion of the reaction as indicated by LCMS, the reaction mixture was concentrated and the residue was purified by silica gel chromatography (eluting with 0-25% saturated methanolic ammonia in chloroform) to give the title compound as a pale yellow solid. This solid was run through a stratta column to obtain the free base to yield the desired product as a pale yellow solid (98.7% pure, 0.026 g, 58% yield). $^1$H NMR (400 MHz, DMSO-d$_6$) δ (ppm) 9.86 (s, 1H), 7.84 (d, 2H, J=8 Hz), 7.77 (d, 3H, J=8 Hz), 7.44 (t, 1H, J=8 Hz), 7.12 (s, 1H), 6.78 (d, 1H, J=8 Hz), 6.21 (d, 1H, J=8 Hz), 6.07 (d, 1H, J=8 Hz), 3.71-3.63 (m, 1H), 2.95-2.92 (m, 1H), 1.95-1.85 (m, 2H), 1.74-1.63 (m, 4H), 1.50-1.43 (m, 2H); MS (ESI) m/z 366.43 [M+1]$^+$.

Example 17

N$^2$-Phenyl-N$^5$-(pyridin-2-yl)-[1,2,4]triazolo[1,5-a]pyridine-2,5-diamine

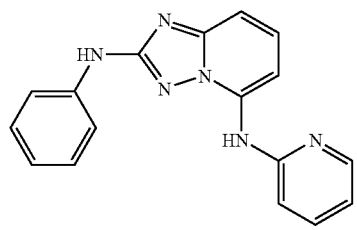

A. N$^2$-Phenyl-N$^5$-(pyridin-2-yl)-[1,2,4]triazolo[1,5-a]pyridine-2,5-diamine. A degassed mixture of 5-bromo-N-phenyl-[1,2,4]triazolo[1,5-a]pyridin-2-amine (200 mg, 0.868 mmol) and pyridin-2-amine (1.5 g, 15.96 mmol) was irradiated in the microwave (150 W) at 220° C. for 1 h, under nitrogen. The reaction mixture was diluted with ethyl acetate and washed with water and brine. The organic phase was dried over anhydrous sodium sulfate, and concentrated under reduced pressure. The residue was purified by reverse-phase preparative HPLC (30-50% acetonitrile+0.1% trifluoroacetic acid in water+0.1% trifluoroacetic acid, over 15 min) to give N$^2$-phenyl-N$^5$-(pyridin-2-yl)-[1,2,4]triazolo[1,5-a]pyridine-2,5-diamine (65 mg, 31% yield) as an oil. $^1$H NMR (400 MHz, METHANOL-d$_4$) δ (ppm) 8.35 (d, J=6.4 Hz, 1H), 8.17 (m, 1H), 8.03 (t, J=8.4 Hz, 1H), 7.91 (d, J=8.4 Hz, 1H), 7.54 (m, 3H), 7.47 (d, J=8.4 Hz, 1H), 7.36 (m, 3H), 7.12 (t, J=7.6 Hz, 1H); MS (ESI): m/z 303.0 [M+1]$^+$. Other examples were prepared following a similar procedure, changing the temperature and time of the reaction.

Example 18

N$^5$-Methyl-N$^2$, N$^5$-diphenyl-[1,2,4]triazolo[1,5-a]pyridine-2,5-diamine

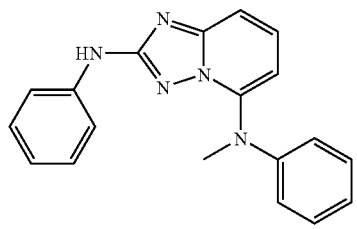

A. N$^5$-Methyl-N$^2$, N$^5$-diphenyl-[1,2,4]triazolo[1,5-a]pyridine-2,5-diamine. A mixture of 5-bromo-N-phenyl-[1,2,4]triazolo[1,5-a]pyridin-2-amine (150 mg, 0.521 mmol), 4,5-bis(diphenylphosphino)-9,9-dimethylxanthene (60 mg, 0.104 mmol), cesium carbonate (338 mg, 1.04 mmol), sodium tert-butoxide (120 mg, 1.04 mmol), methyl-phenylamine (111 mg, 1.04 mmol) and tris(dibenzylideneacetone)dipalladium(0) (48 mg, 0.052 mmol) in dioxane (5 mL) was heated at 100° C. for 1 h under nitrogen with shaking. The reaction mixture was poured into water, and the mixture was extracted with ethyl acetate. The organic layer was washed with brine, dried over anhydrous sodium sulfate, and evaporated under reduced pressure. The residue was purified by reverse-phase preparative HPLC (28-58% acetonitrile+0.1% trifluoroacetic acid in water+0.1% trifluoroacetic acid, over 20 min) to give N$^5$-methyl-N$^2$, N$^5$-diphenyl-[1,2,4]triazolo[1,5-a]pyridine-2,5-diamine as a trifluoroacetic acid salt, which was converted to a hydrochloride salt (30 mg, 18.3%) with a methanolic hydrochloride solution. $^1$H NMR (400 MHz, METHANOL-d$_4$) δ (ppm) 7.99 (m, 1H), 7.43 (m, 2H), 7.26 (m, 2H), 7.15 (m, 5H), 7.03 (m, 3H), 3.62 (s, 3H); MS (ESI): m/z 316.0 [M+1]$^+$.

The synthesis of some of the examples listed here may require the removal of one or more protecting groups such as Boc, SEM or THP groups. That deprotection was performed using standard procedures such as the one exemplified below.

Example 19

N-(Isoindolin-5-yl)-5-phenyl-[1,2,4]triazolo[1,5-a]pyridin-2-amine

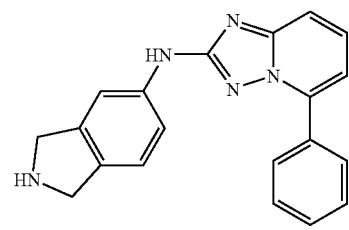

A. N-(Isoindolin-5-yl)-5-phenyl-[1,2,4]triazolo[1,5-a]pyridin-2-amine. tert-Butyl 5-(5-phenyl-[1,2,4]triazolo[1,5-a]pyridin-2-ylamino)isoindoline-2-carboxylate was prepared from tert-butyl 5-bromoisoindoline-2-carboxylate and 5-phenyl-[1,2,4]triazolo[1,5-a]pyridin-2-amine, following the procedure described for the synthesis of N-(4-morpholinophenyl)-5-phenyl-[1,2,4]triazolo[1,5-a]pyridin-2-amine. A solution of tert-butyl 5-(5-phenyl-[1,2,4]triazolo[1,5-a]pyridin-2-ylamino)isoindoline-2-carboxylate (120 mg, 0.28 mmol) in methanolic hydrochloride solution (2 M, 2 mL) was stirred at room temperature for 3 h. The solvent was removed under reduced pressure to give N-(isoindolin-5-yl)-5-phenyl-[1,2,4]triazolo[1,5-a]pyridin-2-amine (110 mg, 100% yield) as a hydrochloride salt. $^1$H NMR (300 MHz, METHANOL-$d_4$) δ (ppm) 8.24 (m, 1H), 8.03 (m, 2H), 7.80 (m, 2H), 7.77 (m, 5H), 7.64 (m, 1H), 4.60 (d, J=4.5 Hz, 4H); MS (ESI): m/z 328.1 [M+1]$^+$.

Example 20

5-(3-Aminophenyl)-N-phenyl-[1,2,4]triazolo[1,5-a]pyridin-2-amine

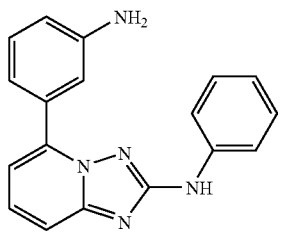

A. 5-(3-Aminophenyl)-N-phenyl-[1,2,4]triazolo[1,5-a]pyridin-2-amine. 5-(3-Nitrophenyl)-N-phenyl-[1,2,4]triazolo[1,5-a]pyridin-2-amine was prepared from 5-bromo-[1,2,4]triazolo[1,5-a]pyridin-2-amine, 3-nitro-phenylboronic acid and phenyl bromide according to the procedure described for the synthesis of 5-(furan-3-yl)-N-phenyl-[1,2,4]triazolo[1,5-a]pyridin-2-amine. A mixture of 5-(3-nitrophenyl)-N-phenyl-[1,2,4]triazolo[1,5-a]pyridin-2-amine (170 mg, 0.51 mmol), zinc dust (338 mg, 5.1 mmol), and ammonium chloride (270 mg, 5.1 mmol) in a mixture of methanol and tetrahydrofuran (v/v, 1:1, 8 mL) at room temperature overnight. The reaction mixture was filtered through celite, and the filtrate was concentrated in vacuo to give the crude product, which was washed with ethyl ether to give 5-(3-aminophenyl)-N-phenyl-[1,2,4]triazolo[1,5-a]pyridin-2-amine (79 mg, 51% yield). $^1$H NMR (400 MHz, METHANOL-$d_4$) δ (ppm) 7.62-7.59 (m, 3H), 7.44 (m, 1H), 7.37 (m, 1H), 7.30-7.24 (m, 4H), 7.08 (m, 1H), 6.89 (m, 2H); MS (ESI): m/z 302.1 [M+1]$^+$.

Example 21

5-Cyclohexyl-N-phenyl-[1,2,4]triazolo[1,5-a]pyridin-2-amine

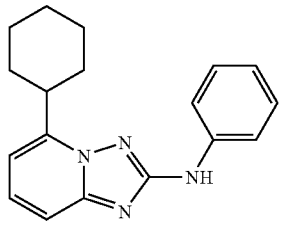

A. 5-Cyclohexyl-N-phenyl-[1,2,4]triazolo[1,5-a]pyridin-2-amine. 5-Cyclohexenyl-N-phenyl-[1,2,4]triazolo[1,5-a]pyridin-2-amine was prepared from 5-bromo-[1,2,4]triazolo[1,5-c]pyridin-2-amine, cyclohexenylboronic acid and phenyl bromide according to the procedure described for the synthesis of 5-(furan-3-yl)-N-phenyl-[1,2,4]triazolo[1,5-a]pyridin-2-amine. A mixture of 5-cyclohexenyl-N-phenyl-[1,2,4]triazolo[1,5-a]pyridin-2-amine (350 mg, 1.21 mmol) and palladium hydroxide (10% w/w, 100 mg) was hydrogenated under 1 atmosphere of hydrogen gas overnight. The catalyst was filtered off and the filtrate was concentrated. The residue was purified by silica gel column chromatography (eluting with 15-20% ethyl acetate in petroleum ether) to give 5-cyclohexyl-N-phenyl-[1,2,4]triazolo[1,5-a]pyridin-2-amine (40 mg, 11% yield). $^1$H NMR (300 MHz, METHANOL-$d_4$) δ (ppm) 7.67 (d, J=6.9 Hz, 2H), 7.55 (m, 1H), 7.33-7.26 (m, 3H), 6.94 (t, J=7.2 Hz, 1H), 6.86 (m, 1H), 3.45 (m, 1H), 2.23 (m, 2H), 1.94-1.65 (m, 3H), 1.65-1.28 (m, 5H); MS (ESI): m/z 293.2 [M+1]$^+$.

Other catalysts (such as palladium on carbon) can also be used for this type of transformation.

Example 22

5-(3-Amino-1H-indazol-5-yl)-N-phenyl-[1,2,4]triazolo[1,5-a]pyridin-2-amine

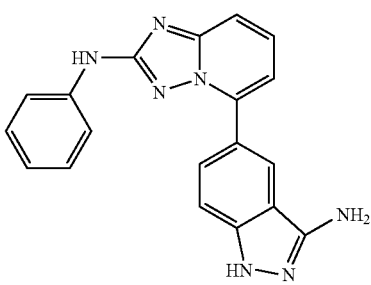

A. 5-(3-Amino-1H-indazol-5-yl)-N-phenyl-[1,2,4]triazolo[1,5-a]pyridin-2-amine. 2-Fluoro-5-(2-(phenylamino)-[1,2,4]triazolo[1,5-a]pyridin-5-yl)benzonitrile was prepared from 5-bromo-[1,2,4]triazolo[1,5-a]pyridin-2-amine, 3-cyano-4-fluorophenylboronic acid and iodobenzene following the procedure described for the synthesis of N,5-diphenyl-[1,2,4]triazolo[1,5-a]pyridin-2-amine. A suspension of 2-fluoro-5-(2-(phenylamino)-[1,2,4]triazolo[1,5-a]pyridin-5-yl)benzonitrile (0.274 g, 0.832 mmol) in water (1.5 mL) and hydrazine monohydrate (0.522 mL, 4.99 mmol) was heated to 105° C. As the reaction was not complete after 3 h, neat hydrazine monohydrate (1.5 mL) was added and heating at 105° C. maintained for 3 hours. Water was added (20 mL) and the resulting black solid was collected by filtration and washed with methanol. The solid was purified by reverse-phase semi-preparative HPLC (20-100% acetonitrile+0.1% trifluoroacetic acid in water+0.1% trifluoroacetic acid over 30 min, 4 injections). The desired fractions were combined, neutralized with a 1.75 M aqueous solution of potassium carbonate. The product precipitated as a white solid upon evaporation of acetonitrile, was collected by filtration and washed with water until neutral pH, and dried in vacuum oven overnight. 5-(3-Amino-1H-indazol-5-yl)-N-phenyl-[1,2,4]triazolo[1,5-c]pyridin-2-amine (0.092 g, 0.270 mmol, 32.4% yield) was collected as a white solid (97.2% pure). $^1$H NMR (400 MHz, DMSO-$d_6$) δ (ppm) 11.70 (br s, 1H), 9.62 (s, 1H), 8.44 (s, 1H), 7.91 (d, J=8.78 Hz, 1H), 7.71 (d, J=8.00 Hz, 2H), 7.65 (t, J=8.00 Hz, 1H), 7.54 (d, J=8.64 Hz, 1H), 7.40 (d, J=8.74 Hz, 1H), 7.25 (t, J=7.78 Hz, 2H), 7.13 (d, J=7.17 Hz, 1H), 6.85 (d, J=7.22 Hz, 1H), 5.61 (br s, 1H); MS (ESI) m/z 342 [M+1]$^+$.

Example 23

N-(5-phenyl-[1,2,4]triazolo[1,5-a]pyridin-2-yl)benzo[d]isoxazol-6-amine

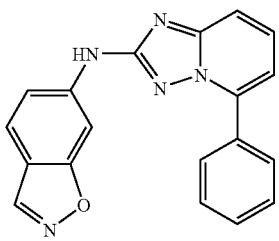

A. N-(5-Phenyl-[1,2,4]triazolo[1,5-a]pyridin-2-yl)benzo[d]isoxazol-6-amine. 2-Fluoro-4-(5-phenyl-[1,2,4]triazolo[1,5-a]pyridin-2-ylamino)benzaldehyde was prepared from 5-phenyl-[1,2,4]triazolo[1,5-a]pyridin-2-amine and 4-bromo-2-fluoro-benzaldehyde following the procedure described for the synthesis of N,5-diphenyl-[1,2,4]triazolo[1,5-a]pyridin-2-amine.

A solution of sodium hydride (60% in mineral oil, 640 mg, 16 mmol.) in N,N-dimethylformamide (5 mL) was added portion wise to a mixture of hydroxylamine hydrochloride (556 mg, 8 mmol.) in N,N-dimethylformamide (5 mL) at 0° C. One hour later, a solution of 2-fluoro-4-(5-phenyl-[1,2,4]triazolo[1,5-a]pyridin-2-ylamino)benzaldehyde (260 mg, 0.8 mmol.) in N,N-dimethylformamide (5 mL) was added, and the resulting mixture was stirred at 80° C. for about 20 hours. The mixture was filtered, and the filtrate was concentrated under reduced pressure to give crude product, which was purified by reverse-phase preparative HPLC (20 50%: acetonitrile+0.1% trifluoroacetic acid in water+0.1% trifluoroacetic acid, over 15 min) to give N-(5-phenyl-[1,2,4]triazolo[1,5-a]pyridin-2-yl)benzo[d]isoxazol-6-amine as a trifluoroacetic acid salt, which was converted to the free base (80 mg, 30% yield). $^1$H NMR (400 MHz, DMSO-$d_6$) δ (ppm) 10.15 (br s, 1H), 7.98 (m, 2H), 7.65 (m, 2H), 7.59 (m, 3H), 7.41 (m, 2H), 7.59 (m, 2H); MS (ESI): m/z 328.1 [M+1]$^+$.

Example 24

2-Fluoro-5-(5-phenyl-[1,2,4]triazolo[1,5-a]pyridin-2-ylamino)benzamide

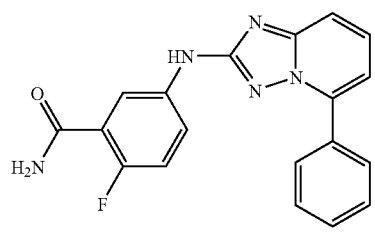

A. 2-Fluoro-5-(5-phenyl-[1,2,4]triazolo[1,5-a]pyridin-2-ylamino)benzamide. 2-Fluoro-5-(5-phenyl-[1,2,4]triazolo[1,5-a]pyridin-2-ylamino)benzonitrile was prepared from 5-phenyl-[1,2,4]triazolo[1,5-a]pyridin-2-amine and 5-bromo-2-fluorobenzonitrile following the procedure described for the synthesis of N,5-diphenyl-[1,2,4]triazolo[1,5-a]pyridin-2-amine. A mixture of 2-fluoro-5-(5-phenyl-[1,2,4]triazolo[1,5-a]pyridin-2-ylamino)benzonitrile (100 mg, 0.3 mmol), aqueous solution of hydrogen peroxide (30%, 1 mL) and potassium carbonate (123 mg, 0.9 mmol) in dimethylsulfoxide (5 mL) was stirred at room temperature overnight. The mixture was poured into ice water, and the precipitate was collected, washed with water, dried under vacuo to give 2-fluoro-5-(5-phenyl-[1,2,4]triazolo[1,5-a]pyridin-2-ylamino)benzamide (60 mg, 57% yield) as a white solid. $^1$H NMR (400 MHz, DMSO-$d_6$) δ (ppm) 9.80 (br s, 1H), 8.05 (m, 2H), 7.60 (m, 6H), 7.19 (m, 2H); MS (ESI): m/z 348.1 [M+1]$^+$.

For some examples, sodium hydroxide was used in place of potassium carbonate.

Example 25

(S)—N$^2$-(3-Amino-1H-indazol-6-yl)-N$^5$-(piperidin-3-yl)-[1,2,4]triazolo[1,5-a]pyridine-2,5-diamine

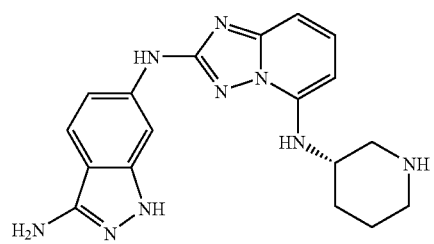

A. 4-(5-Bromo-[1,2,4]triazolo[1,5-a]pyridin-2-ylamino)-2-fluorobenzonitrile. A degassed mixture of 5-bromo-[1,2,4]triazolo[1,5-a]pyridin-2-amine (800 mg, 3.78 mmol), 2-fluoro-4-iodobenzonitrile (1.3 g, 5.29 mmol), sodium tert-butoxide (720 mg, 7.56 mmol), 4,5-bis(diphenylphosphino)-9,9-dimethylxanthene (432 mg, 0.756 mmol) and tris(dibezylideneacetone)dipalladium(0) (352 mg, 0.378 mmol) in dioxane (20 mL) was heated at 100° C. under nitrogen for 2 h. The reaction mixture was quenched by the addition of water, and the mixture was extracted with ethyl acetate for three times. The combined organic layer was dried over anhydrous sodium sulfate and concentrated. The crude material was purified on silica gel column (eluting with 0-25% ethyl acetate in petroleum ether) to give 4-(5-bromo-[1,2,4]triazolo[1,5-a]pyridin-2-ylamino)-2-fluorobenzonitrile as a brown solid (600 mg, 48.4% yield). $^1$H NMR (400 MHz, DMSO-d$_6$) δ (ppm) 10.83 (s, 1H), 7.94 (dd, J$_1$=12.8 Hz, J$_2$=1.6 Hz, 1H), 7.78 (t, J=8.0 Hz, 1H), 7.70 (d, J=8.8 Hz, 1H), 7.54 (t, J=7.6 Hz, 1H), 7.48 (t, J=6.4 Hz, 2H); MS (ESI): m/z 331.9 [M+1]$^+$ B. (S)-tert-Butyl 3-(2-(4-cyano-3-fluorophenylamino)-[1,2,4]triazolo[1,5-a]pyridin-5-ylamino)piperidine-1-carboxylate. A degassed mixture of 4-(5-bromo-[1,2,4]triazolo[1,5-a]pyridin-2-ylamino)-2-fluorobenzonitrile (300 mg, 0.9 mmol), (S)-tert-butyl 3-aminopiperidine-1-carboxylate (272 mg, 1.4 mmol), 4,5-bis(diphenylphosphino)-9,9-dimethylxanthene (105 mg, 0.18 mmol), tris(dibezylideneacetone)dipalladium(0) (83 mg, 0.09 mmol) and cesium carbonate (590 mg, 1.8 mmol) in dioxane (10 mL) was heated at 100° C. under nitrogen overnight. The reaction mixture was quenched by the addition of water, and the mixture was extracted with ethyl acetate for three times. The combined organic layer was dried over anhydrous sodium sulfate and concentrated. The crude material was purified by column chromatography on silica gel (eluting with 0-25% ethyl acetate in petroleum ether) to give (S)-tert-butyl-3-(2-(4-cyano-3-fluorophenylamino)-[1,2,4]triazolo[1,5-a]pyridin-5-ylamino)piperidine-1-carboxylate as a solid (200 mg, 49.4% yield).

C. (S)-2-Fluoro-4-(5-(piperidin-3-ylamino)-[1,2,4]triazolo[1,5-a]pyridin-2-ylamino)benzonitrile. A solution of (S)-tert-butyl 3-(2-(4-cyano-3-fluorophenylamino)-[1,2,4]triazolo[1,5-a]pyridin-5-ylamino)piperidine-1-carboxylate (200 mg, 0.44 mmol) in a methanolic hydrochloride solution (15 mL, 2 M) was stirred for 30 min. at room temperature. The solvent was removed under reduced pressure, and the residue was washed with ethyl acetate, dried under vacuum to afford (S)-2-fluoro-4-(5-(piperidin-3-ylamino)-[1,2,4]triazolo[1,5-a]pyridin-2-ylamino)benzonitrile (150 mg, 96.2%) as a hydrochloride salt.

D. (S)—N$^2$-(3-Amino-1H-indazol-6-yl)-N$^5$-(piperidin-3-yl)-[1,2,4]triazolo[1,5-a]pyridine-2,5-diamine. A solution of (S)-2-fluoro-4-(5-(piperidin-3-ylamino)-[1,2,4]triazolo[1,5-a]pyridin-2-ylamino)benzonitrile (150 mg, 0.43 mmol) and hydrazine hydrate (0.50 mL) in n-butanol (10 mL) was stirred at 120° C. under nitrogen overnight. The solvent was concentrated in vacuo to give the crude product, which was purified by reverse-phase preparative HPLC (7-37%: acetonitrile+0.1% trifluoroacetic acid in water, over 15 min) to give (S)—N$^2$-(3-amino-1H-indazol-6-yl)-N$^5$-(piperidin-3-yl)-[1,2,4]triazolo[1,5-a]pyridine-2,5-diamine as a trifluoroacetic acid salt, which was converted to the hydrochloride salt with methanolic hydrochloride solution (99.14% ee, 70 mg, 44.9% yield) as a solid. $^1$H NMR (400 M, DMSO-d$_6$) δ (ppm) 12.46 (s, 1H), 10.15 (s, 1H), 9.27 (m, 2H), 8.17 (s, 1H), 7.87 (d, J=8.8 Hz, 1H), 7.50 (t, J=8.0 Hz, 1H), 7.32 (d, J=2.0 Hz, 1H), 6.84 (d, J=8.8 Hz, 1H), 6.74 (d, J=8.8 Hz, 1H), 6.34 (d, J=8.0 Hz, 1H), 4.05 (m, 1H), 3.42 (m, 1H), 3.23 (m, 1H), 3.08 (m, 1H) 2.80 (m, 1H), 2.05 (m, 1H), 1.88 (m, 3H); MS (ESI): m/z 364.0 [M+1]$^+$.

Example 26

5-(3-(Aminomethyl)phenyl)-N-phenyl-[1,2,4]triazolo[1,5-a]pyridin-2-amine

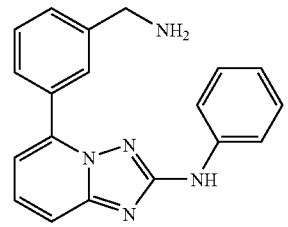

A. 5-(3-(Aminomethyl)phenyl)-N-phenyl-[1,2,4]triazolo[1,5-a]pyridin-2-amine.

A mixture of (3-(2-(phenylamino)-[1,2,4]triazolo[1,5-a]pyridin-5-yl)benzonitrile) (70 mg 0.225 mmol) and Raney Ni (100 mg) in a mixture of methanol (10 mL) and ammonia aqueous solution (0.5 mL) was hydrogenated under 1 atm of hydrogen gas at room temperature for 2 h. After the starting material was consumed (monitored by TLC), the reaction mixture was filtered, and the filtrate was evaporated. The residue was purified by reverse-phase preparative HPLC (35-65% acetonitrile+0.1% trifluoroacetic acid in water+0.1% trifluoroacetic acid, over 15 min) to give 5-(3-(aminomethyl)phenyl)-N-phenyl-[1,2,4]triazolo[1,5-a]pyridin-2-amine as a trifluoroacetic acid salt, which was converted to the corresponding hydrochloride salt with methanolic hydrochloride solution (35 mg, 49% yield). $^1$H NMR (400 MHz, METHANOL-d$_4$) δ (ppm) 8.18 (m, 1H), 8.01 (s, 1H), 8.07 (m, 1H), 7.76-7.72 (m, 3H), 7.59-7.55 (m, 3H), 7.36-7.32 (m, 2H), 7.08 (m, 1H), 4.27 (s, 2H); MS (ESI): m/z 316.1 [M+H]$^+$.

Example 27

N-(2-(Phenylamino)-[1,2,4]triazolo[1,5-a]pyridin-5-yl)acetamide

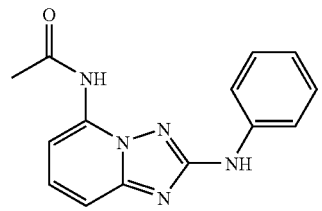

A. N-(6-Aminopyridin-2-yl)acetamide. To a mixture of pyridine-2,6-diamine (1.5 g, 13.7 mmol) and triethylamine (1.4 g, 13.8 mmol) in dichloromethane (30 mL) was added dropwise acetyl chloride (1.39 g, 13.7 mmol) at room temperature. After the addition, the reaction mixture was stirred at room temperature for 4 h. The reaction mixture was washed with water, dried over sodium sulfate, and evaporated to give N-(6-aminopyridin-2-yl)acetamide (0.95 g, 46% yield) as a white solid. $^1$H-NMR (400 MHz, DMSO-d$_6$) δ (ppm) 9.84 (s, 1H), 7.31 (t, J=7.6 Hz, 1H), 7.26 (br s, 1H), 6.15 (d, J=8.0 Hz, 1H), 5.70 (br s, 2H).

B. N-(6-(3-(Ethoxycarbonyl)thioureido)pyridin-2-yl)acetamide. A solution of N-(6-amino-pyridin-2-yl)-acetamide (0.9 g, 5.96 mmol) and ethoxycarbonyl isothiocyanate (0.94 g, 5.96 mmol) in dioxane (10 mL) was stirred at room temperature for 5 h. The solvent was removed to give N-(6-(3-(ethoxycarbonyl)thioureido) pyridin-2-yl)acetamide (1.4 g, 83.3% yield) as a solid. $^1$H-NMR (400 MHz, DMSO-d$_6$) δ (ppm) 12.10 (br s, 1H), 11.52 (br s, 1H), 10.51 (br s, 1H), 8.37 (m, 1H), 7.91 (d, J=8.0 Hz, 1H), 7.91 (t, J=8.0 Hz, 1H), 4.25 (q, J=7.2 Hz, 2H), 2.1 (s, 3H), 1.28 (t, J=7.2 Hz, 3H).

C. N-(2-Amino-[1,2,4]triazolo[1,5-a]pyridin-5-yl)acetamide. To a solution of hydroxylamine hydrochloride (1.22 g, 17.7 mmol) and N,N-ethyldiisopropylamine (1.37 g, 10.6 mmol) in a mixture of ethanol and methanol (1:1, 20 mL) was added N-(6-(3-(ethoxycarbonyl)thioureido)pyridin-2-yl)acetamide (1.00 g, 3.54 mmol). The mixture was stirred at room temperature for 2 h, and at 70° C. for 5 h. The volatiles were removed under reduced pressure, and the residue was treated with water. The resulting precipitate was washed with 20% of diethyl ether in methanol (10 mL) and diethyl ether (10 mL). After being dried under high vacuum, off-white crystals of N-(2-amino-[1,2,4]triazolo[1,5-a]pyridin-5-yl)-acetamide) (0.50 g, 62%) were obtained. $^1$H-NMR: (400 MHz, DMSO-d$_6$) δ (ppm) 10.2 (br s, 1H), 7.41 (m, 2H), 7.05 (dd, J$_1$=7.2, J$_2$=1.6 Hz, 1H), 5.94 (br s, 2H), 2.19 (s, 3H).

D. N-(2-(Phenylamino)-[1,2,4]triazolo[1,5-a]pyridin-5-yl)acetamide. To a degassed mixture of N-(2-amino-[1,2,4]triazolo[1,5-a]pyridin-5-yl)-acetamide) (300 mg 1.58 mmol), phenyl bromide (270 mg 1.74 mmol), 4,5-bis(diphenylphosphino)-9,9-dimethylxanthene (91 mg, 0.158 mmol) and cesium carbonate (1.03 g, 3.16 mmol) in dioxane (15 mL) was added tris(dibenzylideneacetone)dipalladium (0) (45 mg, 0.079 mmol) under nitrogen, and the mixture was heated at 80° C. under nitrogen overnight. The reaction mixture was quenched by the addition of water and the mixture was extracted with ethyl acetate (15 mL×3). The combined organic layer was washed with brine, dried over sodium sulfate, and concentrated. The residue was purified by reverse-phase preparative HPLC (35-68% acetonitrile+0.1% trifluoroacetic acid in water+0.1% trifluoroacetic acid, over 15 min) to give N-(2-(phenylamino)-[1,2,4]triazolo[1,5-a]pyridin-5-yl)acetamide as a trifluoroacetic acid salt, which was converted to the corresponding free base (50 mg, 12% yield). $^1$H-NMR (400 MHz, DMSO-d$_6$) δ (ppm) 10.24 (br s, 1H), 9.53 (br s, 1H), 7.76 (d, J=7.6 Hz, 2H), 7.55 (m, 2H), 7.30 (m, 3H), 6.88 (t, J=7.2 Hz, 1H), 2.27 (s, 3H); MS (ESI): m/z 267.9 [M+1]$^+$.

Example 28

N-(2-(Phenylamino)-[1,2,4]triazolo[1,5-a]pyridin-5-yl)isobutyramide

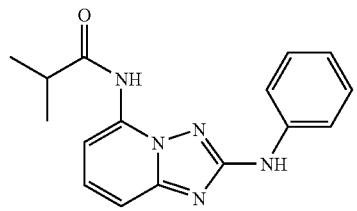

A. N$^2$-Phenyl-[1,2,4]triazolo[1,5-a]pyridine-2,5-diamine. To a suspension of copper iodide (10 mg, 0.053 mmol) in liquid ammonia (10 mL) in an autoclave at −40° C. was added 5-bromo-N-phenyl-[1,2,4]triazolo[1,5-a]pyridin-2-amine (50 mg, 0.174 mmol). The autoclave was then sealed and heated at 180° C. for 4 h. The reaction mixture was cooled, the autoclave was washed with ethyl acetate three times, and the combined organic layer was dried and evaporated. The residue was purified by silica gel column chromatography (eluting with 10-15% ethyl acetate in petroleum) to give N$^2$-phenyl-[1,2,4]triazolo[1,5-a]pyridine-2,5-diamine (30 mg, 77% yield) as a solid. MS (ESI): m/z 226.1 [M+1]$^+$.

B. N-(2-(Phenylamino)-[1,2,4]triazolo[1,5-a]pyridin-5-yl)-isobutyramide. To a solution of N$^2$-phenyl-[1,2,4]triazolo[1,5-a]pyridine-2,5-diamine (30 mg, 0.13 mmol) and triethylamine (26 mg, 0.26 mmol) in dichloromethane (5 mL) was added isobutyryl chloride (14 mg, 0.13 mmol) at 0° C., and the mixture was stirred at room temperature overnight. The reaction mixture was poured into ice-water and extracted with ethyl acetate. The organic layer was washed with brine, dried over sodium sulfate, and evaporated to dryness. The residue was purified by preparative TLC (eluting with 15-20% ethyl acetate in petroleum ether) to give N-(2-(phenylamino)-[1,2,4]triazolo[1,5-a]pyridin-5-yl)-isobutyramide (15 mg, 38% yield) as a solid. $^1$H-NMR (400 MHz, DMSO-d$_6$) δ (ppm) 7.67 (m, 3H), 7.48 (m, 1H), 7.30 (m, 3H), 6.95 (m, 1H), 2.93 (m, 1H), 1.31 (t, J=6.8 Hz, 6H); MS (ESI): m/z 296.1 [M+1]$^+$.

Example 29

N-(3-(2-(Phenylamino)-[1,2,4]triazolo[1,5-a]pyridin-5-yl)phenyl)acetamide

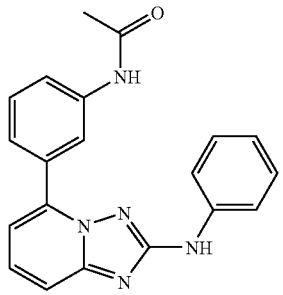

A. N-(3-(2-(Phenylamino)-[1,2,4]triazolo[1,5-a]pyridin-5-yl)phenyl)acetamide. A mixture of 5-(3-aminophenyl)-N-phenyl-[1,2,4]triazolo[1,5-a]pyridin-2-amine (50 mg, 0.17 mmol), pyridine (26.9 mg, 0.34 mmol), acetic anhydride (33.8 mg, 0.34 mmol) in dichloromethane (5 mL) was stirred at room temperature overnight. The precipitate was collected by filtration, and the filter cake was washed with water and ethyl ether to give N-[3-(2-phenylamino-[1,2,4]triazolo[1,5-a]pyridin-5-yl)-phenyl]-acetamide (40 mg, 70% yield) as a solid. $^1$H NMR (400 MHz, DMSO-d$_6$) δ (ppm) 10.15 (br s, 1H), 9.61 (br s, 1H), 8.26 (s, 1H), 7.70-7.46 (m, 7H), 7.21 (m, 2H), 7.10 (m, 1H), 6.82 (m, 1H), 2.06 (s, 3H); MS (ESI): m/z 344.1 [M+1]⁺.

Example 30

4-(5-Phenyl-[1,2,4]triazolo[1,5-a]pyridin-2-ylamino)-N-(piperidin-4-yl)benzamide

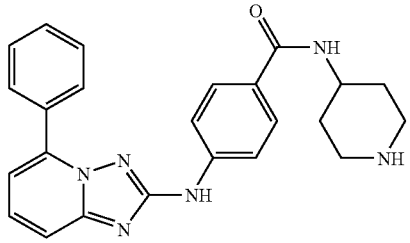

A. 4-(5-Phenyl-[1,2,4]triazolo[1,5-a]pyridin-2-ylamino) benzoic acid. A suspension of methyl 4-(5-phenyl-[1,2,4] triazolo[1,5-a]pyridin-2-ylamino)benzoate (260 mg, 0.76 mmol) (obtained from 5-phenyl-[1,2,4]triazolo[1,5-a]pyridin-2-amine and methyl 4-bromobenzoate following the procedure described for the synthesis of N,5-diphenyl-[1,2,4] triazolo[1,5-a]pyridin-2-amine) in a 10% aqueous solution of sodium hydroxide (5 mL) was refluxed overnight. After being cooled to room temperature, the reaction mixture was neutralized with 3% hydrochloric acid aqueous solution to pH=3. The precipitate was collected by filtration and washed with water to give 4-(5-phenyl-[1,2,4]triazolo[1,5-a]pyridin-2-ylamino)benzoic acid (220 mg, 88% yield) as a solid. MS (ESI): m/z 331.1 [M+1]⁺.

B. tert-Butyl 4-(4-(5-phenyl-[1,2,4]triazolo[1,5-a]pyridin-2-ylamino)benzamido) piperidine-1-carboxylate. A mixture of 4-(5-phenyl-[1,2,4]triazolo[1,5-a]pyridin-2-ylamino)benzoic acid (200 mg, 0.6 mmol), tert-butyl 4-aminopiperidine-1-carboxylate (121 mg, 0.6 mmol), 2-(3H-[1,2,3]triazolo[4,5-b]pyridin-3-yl)-1,1,3,3-tetramethylisouronium hexafluorophosphate(V) (460 mg, 1.2 mmol) and N-methylmorpholine (306 mg, 3.0 mmol) in N,N-dimethylformamide (2 mL) was stirred at room temperature overnight. Water (5 mL) was added, and the precipitate was collected by filtration and washed with water to give tert-butyl 4-(4-(5-phenyl-[1,2,4]triazolo[1,5-a]pyridin-2-ylamino)benzamido)piperidine-1-carboxylate (220 mg, 72% yield) as a solid. MS (ESI): m/z 535.1 [M+23]⁺.

C. 4-(5-Phenyl-[1,2,4]triazolo[1,5-a]pyridin-2-ylamino)-N-(piperidin-4-yl)benzamide. A solution of tert-butyl 4-(4-(5-phenyl-[1,2,4]triazolo[1,5-a]pyridin-2-ylamino)benzamido)piperidine-1-carboxylate (50 mg, 0.1 mmol) in methanolic hydrochloride solution (10 mL) was stirred at room temperature overnight. The reaction mixture was concentrated in vacuo to afford 4-(5-phenyl-[1,2,4]triazolo[1,5-a]pyridin-2-ylamino)-N-(piperidin-4-yl)benzamide (25 mg, 60% yield) as a hydrochloride salt. ¹H-NMR (300 MHz, DMSO-d₆) δ (ppm) 9.99 (br s, 1H), 8.65 (br s, 2H), 8.22 (d, J=7.5 Hz, 1H), 8.03 (d, J=6.9 Hz, 2H), 7.81-7.58 (m, 8H), 7.21 (d, J=6.9 Hz, 1H), 4.01 (m, 1H), 3.30 (m, 2H), 2.99 (m, 2H), 1.96 (m, 2H), 1.74 (m, 2H); MS (ESI): m/z 413.2 [M+1]⁺.

Example 31

5-(5-Phenyl-[1,2,4]triazolo[1,5-a]pyridin-2-ylamino)pyridine-2-ol

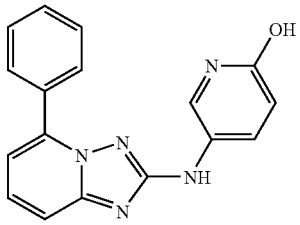

A. 5-(5-Phenyl-[1,2,4]triazolo[1,5-a]pyridin-2-ylamino)pyridine-2-ol. A mixture of N-(6-methoxypyridin-3-yl)-5-phenyl-[1,2,4]triazolo[1,5-a]pyridin-2-amine (100 mg, 0.31 mmol) (prepared following the procedure described for the synthesis of N-(4-morpholinophenyl)-5-phenyl-[1,2,4]triazolo[1,5-a]pyridin-2-amine) in a solution of hydrogen bromide in acetic acid (6 mL, 35%) was heated at 120° C. in sealed vessel for 0.5 h. After being cooled to room temperature, the mixture was made basic with a saturated aqueous solution of sodium bicarbonate to pH=7. The resulting mixture was extracted with ethyl acetate, and the combined organic layer was dried over sodium sulfate and filtered. The filtrate was evaporated under reduced pressure, and the residue was purified by reverse-phase preparative HPLC (40-70% acetonitrile+0.1% trifluoroacetic acid in water+0.1% trifluoroacetic acid, over 25 min) to give 5-(5-phenyl-[1,2,4]triazolo[1,5-a]pyridin-2-ylamino)pyridin-2-ol as a trifluoroacetic acid salt, which converted to the corresponding hydrochloride salt with methanolic hydrochloride solution (40 mg, 38% yield). ¹H-NMR (300 MHz, METHANOL-d₄) δ (ppm) 8.56 (m, 1H), 8.18 (m, 1H), 8.00 (m, 2H), 8.83 (m, 1H), 7.63-7.57 (m, 4H), 7.32 (dd, J₁=7.2 Hz, J₂=1.8 Hz, 1H), 7.09 (m, 1H); MS (ESI): m/z 304.1 [M+1]⁺.

Example 32

4-(2-(Phenylamino)-[1,2,4]triazolo[1,5-a]pyridin-5-yl)pyridin-2-ol

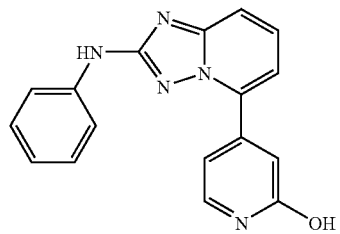

A. 4-(2-(Phenylamino)-[1,2,4]triazolo[1,5-a]pyridin-5-yl) pyridin-2-ol. A total of 60 mg of starting material was demethylated in two batches (20 mg and 40 mg) according to the procedure described below. The crude materials were then combined for purification. A suspension of 5-(2-methoxypyridin-4-yl)-N-phenyl-[1,2,4]triazolo[1,5-a]pyridin-2-amine (0.040 g, 0.126 mmol) (prepared according to the procedure described for the synthesis of N,5-diphenyl-[1,2,4]triazolo[1,5-a]pyridin-2-amine) in dichloromethane (3 mL) at room temperature was treated with boron tribromide (0.555 mL, 0.555 mmol) and stirred at room temperature for 2 days. As conversion was not complete, additional boron tribromide (0.555 mL, 0.555 mmol) was used and the reaction was stirred at room temperature for an additional 12 h. Although starting material remained unreacted, the reaction was quenched with water (1 mL) and extracted with ethyl acetate (3 times, 25 mL) then dichloromethane (3×15 mL). The combined extracts were dried over sodium sulfate and the residue obtained after evaporation of the solvent was dissolved in 10:1 DMSO:methanol and purified by semi-preparative HPLC (20-80% acetonitrile+0.1% trifluoroacetic acid in water+0.1% trifluoroacetic acid over 30 min 5 injections). The desired fractions were combined and neutralized with a 1.75 M aqueous solution of potassium carbonate. Upon removal of acetonitrile under reduced pressure, a white solid formed that was collected by filtration, washed with water until pH became neutral, and dried in a vacuum oven with mild heat. 4-(2-(Phenylamino)-[1,2,4]triazolo[1,5-a]pyridin-5-yl)pyridin-2-ol (7 mg, 12% yield overall yield) was isolated as a white solid (99.6% pure). $^1$H NMR (400 MHz, DMSO-$d_6$) δ (ppm) 8.53 (br s, 1H), 8.14 (d, J=9.47 Hz, 1H), 7.56-7.77 (m, 2H), 7.45-7.55 (m, 1H), 7.17-7.36 (m, 2H), 6.88 (m, 1H), 6.53 (d, J=9.52, 1H); MS (ESI) m/z 304 [M+1]$^+$.

Example 33

5-(3-(1H-1,2,4-Triazol-5-yl)phenyl)-N-phenyl-[1,2,4]triazolo[1,5-a]pyridin-2-amine

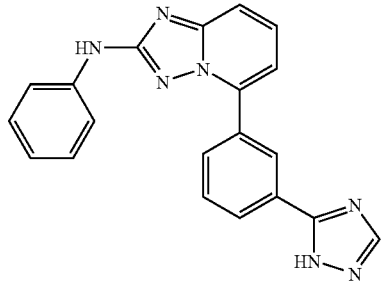

A. Ethyl 3-(2-(phenylamino)-[1,2,4]triazolo[1,5-a]pyridin-5-yl)benzimidate hydrochloride. Through a suspension of 3-(2-(phenylamino)-[1,2,4]triazolo[1,5-a]pyridin-5-yl)benzonitrile (0.115 g, 0.369 mmol) (prepared according to the procedure described for the synthesis of N,5-diphenyl-[1,2,4]triazolo[1,5-a]pyridin-2-amine) in ethanol (10 mL) was bubbled HCl gas for 10 min at 0° C. The suspension became clear immediately after introducing HCl (g) and later on partially crashed out. After 6 h, the solvent was removed under reduced pressure and used in the following step without further purification. MS (ESI) m/z 358 [M+1]$^+$.

B. 5-(3-(1H-1,2,4-Triazol-5-yl)phenyl)-N-phenyl-[1,2,4]triazolo[1,5-a]pyridin-2-amine. To a suspension of ethyl 3-(2-(phenylamino)-[1,2,4]triazolo[1,5-a]pyridin-5-yl)benzimidate hydrochloride (0.145 g, 0.369 mmol) in ethanol (10 mL) was added formohydrazide (0.111 g, 1.845 mmol) and diisopropylethylamine (0.226 mL, 1.292 mmol). The reaction was heated overnight to 120° C. in a sealed tube. The reaction mixture was cooled to room temperature and the solvent was evaporated. The residue was purified by semi-preparative HPLC (20-100% acetonitrile+0.1% trifluoroacetic acid in water+0.1% trifluoroacetic acid over 30 min, 4 injections). The desired fractions were combined and neutralized with a 1.75 M aqueous solution of potassium carbonate. A gelatinous precipitate formed upon evaporation of the acetonitrile, that was collected by filtration and washed with water until neutral pH of the washings. 5-(3-(1H-1,2,4-Triazol-5-yl)phenyl)-N-phenyl-[1,2,4]triazolo[1,5-a]pyridin-2-amine (0.033 g, 0.093 mmol, 25.3% yield) was isolated as an off-white solid (99.8% pure). $^1$H NMR (400 MHz, DMSO-$d_6$) δ (ppm) 9.65 (s, 1H), 8.87 (br s, 1H), 8.71 (br s, 1H), 8.16-8.26 (m, 1H), 7.58-7.82 (m, 6H), 7.32 (d, J=6.39 Hz, 1H), 7.16-7.25 (m, 2H), 6.79-6.89 (m, 1H); MS (ESI) m/z 354 [M+1]$^+$.

Example 34

(S)-2-(Phenylamino)-N-(piperidin-3-yl)-[1,2,4]triazolo[1,5-a]pyridine-5-carboxamide

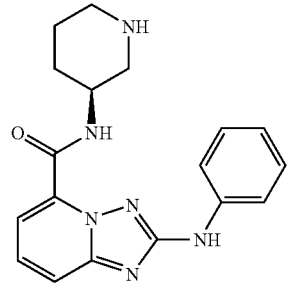

A. 2-Amino-[1,2,4]triazolo[1,5-a]pyridine-5-carbonitrile. A mixture of 5-bromo-[1,2,4]triazolo[1,5-a]pyridin-2-amine (4.26 g, 20 mmol), zinc dust (0.97 g, 15 mmol), tris(dibenzylideneacetone)dipalladium(0) (1.1 g, 1.2 mmol), 1,1'-bis(diphenylphosphino)-ferrocene (1.32 g, 2.4 mmol) and zinc cyanide (4.3 g, 39 mmol) in N,N-dimethylacetamide (60 mL) in a 250 mL round-bottle flask was degassed. Under nitrogen, the reaction mixture was heated at 100° C. overnight. When most of the solvent was removed in vacuo, a saturated sodium chloride aqueous solution was added, and the mixture was extracted with ethyl acetate. The combined organic layer was dried over sodium sulfate, filtered, and concentrated. The residue was purified by silica gel column chromatography (eluting with 10-30% ethyl acetate in petroleum ether) on silica gel to give 2-amino-[1,2,4]triazolo[1,5-a]pyridine-5-carbonitrile (910 mg, 28% yield) as a yellow solid. $^1$H NMR (400 MHz, DMSO-$d_6$) δ (ppm) 7.69 (dd, J=8.8 Hz, 1H), 7.64 (dd, J=8.8 Hz, 1H), 7.51 (t, J=8.2 Hz, 1H), 6.47 (br s, 1H).

B. 2-(Phenylamino)-[1,2,4]triazolo[1,5-a]pyridine-5-carbonitrile. To a degassed solution of 2-amino-[1,2,4]triazolo[1,5-a]pyridine-5-carbonitrile (0.9 g, 5.7 mmol), 1-bromobenzene (0.89 g, 5.7 mmol), tris(dibenzylideneacetone)dipalladium(0) (326 mg, 0.35 mmol), 4,5-bis(diphenylphosphino)-9,9-dimethylxanthene (526 mg, 0.91 mmol) and cesium carbonate (3.68 g, 12 mmol) in dioxane (20 mL) was heated at 100° C. under nitrogen overnight. After being cooled to room temperature, the reaction mixture was filtered, and the filtrate was concentrated in vacuo to give the crude product, which was purified by silica gel column chromatography (eluting with 10-30% ethyl acetate in petroleum ether) to give 2-(phenylamino)-[1,2,4]triazolo[1,5-a]pyridine-5-carbonitrile (0.7 g, 52% yield) as a solid. $^1$H NMR (400 MHz, DMSO-d$_6$) δ (ppm) 9.96 (br s, 1H), 7.93 (dd, J$_1$=8.8, J$_2$=0.8 Hz, 1H), 7.82 (dd, J$_1$=7.6, J$_2$=0.8 Hz, 1H), 7.75 (m, 3H), 7.29 (t, J=8.0 Hz, 2H), 6.90 (t, J=7.6 Hz, 1H); MS (ESI): m/z 236.1 [M+1]$^+$.

C. 2-(Phenylamino)-[1,2,4]triazolo[1,5-a]pyridine-5-carboxylic acid. A solution of 2-(phenylamino)-[1,2,4]triazolo[1,5-a]pyridine-5-carbonitrile (700 mg, 3 mmol) and sodium hydroxide (1.2 g, 30 mmol) in a mixture of ethanol (30 mL) and water (15 mL) was heated at 80° C. until TLC showed the starting material was consumed. The solvent was removed in vacuo and water was added. The mixture was washed with ethyl acetate for two times. The aqueous layer was acidified by the addition of hydrochloric acid aqueous solution to pH=3, and then the mixture was extracted with ethyl acetate. The combined organic layer was dried and concentrated to give 2-(phenylamino)-[1,2,4]triazolo[1,5-a]pyridine-5-carboxylic acid (560 mg, 73% yield) as a pale yellow solid. $^1$H NMR (400 MHz, DMSO-d$_6$) δ (ppm) 9.77 (br s, 1H), 7.72 (m, 3H), 7.60 (t, J=7.2 Hz, 1H), 7.44 (d, J=7.2 Hz, 1H), 7.25 (t, J=7.6 Hz, 2H), 6.86 (t, J=7.6 Hz, 1H); MS (ESI): m/z 255.3 [M+1]$^+$.

D. (S)-tert-Butyl 3-(2-(phenylamino)-[1,2,4]triazolo[1,5-a]pyridine-5-carboxamido)piperidine-1-carboxylate. A mixture of 2-(phenylamino)-[1,2,4]triazolo[1,5-c]pyridine-5-carboxylic acid (70 mg, 0.27 mmol), (S)-tert-butyl 3-aminopiperidine-1-carboxylate (55 mg, 0.27 mmol), 1-(3-dimethylaminopropyl)-3-ethylcarbodiimide hydrochloride (106 mg, 0.55 mmol), hydroxybenzotriazole (74 mg, 0.55 mmol) and N-methylmorpholine (75 mg, 0.55 mmol) in N,N-dimethylformamide (2 mL) was stirred at room temperature overnight. The reaction mixture was diluted with brine. The resulting precipitate was collected, washed with water and petroleum ether to give (S)-tert-butyl 3-(2-(phenylamino)-[1,2,4]triazolo[1,5-c]pyridine-5-carboxamido)piperidine-1-carboxylate (102 mg, 85% yield) as a solid, which was used in the next step without further purification.

E. (S)-2-(Phenylamino)-N-(piperidin-3-yl)-[1,2,4]triazolo[1,5-a]pyridine-5-carboxamide. A solution of (S)-tert-butyl 3-(2-(phenylamino)-[1,2,4]triazolo[1,5-a]pyridine-5-carboxamido)piperidine-1-carboxylate (102 mg, 0.24 mmol) in a methanolic hydrochloride solution (2 mL, 2 M) was stirred at room temperature until TLC showed the starting material was consumed. The solvent was evaporated under reduced pressure to give the crude product, which was purified by reverse-phase preparative HPLC (35-65% acetonitrile+0.1% trifluoroacetic acid in water+0.1% trifluoroacetic acid, over 15 min) to give (S)-2-(phenylamino)-N-(piperidin-3-yl)-[1,2,4]triazolo[1,5-a]pyridine-5-carboxamide as a trifluoroacetic acid salt, which was coverted to the corresponding hydrochloride salt (69 mg, 88% yield). $^1$H NMR (400 MHz, DMSO-d$_6$) δ (ppm) 9.95 (d, J=6.8 Hz, 1H), 9.87 (br s, 1H), 9.13 (br s, 2H), 7.78 (dd, J$_1$=8.4, J$_2$=1.2 Hz, 1H), 7.72-760 (m, 4H), 7.32 (t, J=8.0 Hz, 2H), 6.94 (t, J=7.6 Hz, 1H), 4.26 (m, 1H), 3.40 (m, 1H), 3.14 (m, 1H), 2.90 (m, 2H), 2.10 (m, 1H), 1.79 (m, 1H), 1.75 (m, 2H); MS (ESI): m/z 337.4 [M+1]$^+$.

Example 35

N-Phenyl-5-(pyridin-2-yl)-[1,2,4]triazolo[1,5-a]pyridin-2-amine

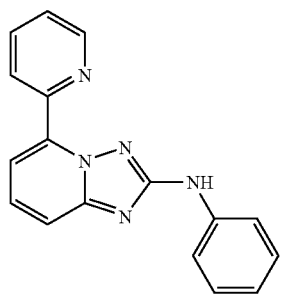

A. 2,2'-Bipyridine 1-oxide. To a solution of 2,2'-bipyridine (10 g, 64 mmol) in dichloromethane (250 mL) was added 3-chlorobenzoperoxoic acid (33 g, 192 mmol) in portions at room temperature. The mixture was stirred at room temperature for 1 hour. After the starting material was consumed, saturated aqueous sodium thiosulfate solution was added. The organic layer was washed with brine, dried over sodium sulfate, and concentrated under reduced pressure to give 2,2'-bipyridine 1-oxide (5.5 g, 50% yield) as a solid. $^1$H NMR (300 MHz, METHANOL-d$_4$) δ (ppm) 8.73 (d, J=5.1 Hz, 1H), 8.50 (d, J=5.7 Hz, 1H), 8.42 (d, J=6.3 Hz, 1H), 8.06 (dd, J$_1$=2.1 Hz, J$_2$=5.1 Hz, 1H), 7.96 (dd, J$_1$=7.2 Hz, J$_2$=9.0 Hz, 1H), 7.70 (t, J=7.5 Hz, 1H), 7.58-7.48 (m, 2H).

B. 6-Chloro-2,2'-bipyridine. A mixture of 2,2'-bipyridine 1-oxide (5.5 g, 32 mmol) and phosphoryl trichloride (20 mL) was refluxed for 4 h. Phosphoryl trichloride was distilled out and the residue was diluted with ethyl acetate. The organic layer was washed with saturated aqueous sodium bicarbonate solution and brine, and concentrated under reduced pressure. The residue was purified by column chromatography on silica gel (eluting with 10% ethyl acetate in petroleum ether) to give 6-chloro-2,2'-bipyridine (3.5 g, 57% yield) as a solid.

C. N-(4-Methoxybenzyl)-2,2'-bipyridin-6-amine. A solution of 6-chloro-2,2'-bipyridine (1 g, 5.2 mmol) in (4-methoxyphenyl)methanamine (5 mL) was stirred at 180° C. for 4 h. The mixture was purified on silica gel column (eluting with 10-80% ethyl acetate in petroleum ether) to give N-(4-methoxybenzyl)-2,2'-bipyridin-6-amine (1.2 g, 80% yield). MS (ESI): m/z 291.9 [M+1]$^+$.

D. 2,2'-Bipyridin-6-amine. A solution of N-(4-methoxybenzyl)-6-(pyridin-2-yl)pyridin-2-amine (600 mg, 2 mmol) in trifluoroacetic acid (10 mL) was stirred at 80° C. overnight. When TLC (3% dichloromethane in methanol) showed the starting material was consumed, the mixture was adjusted to pH=7 with aqueous sodium carbonate solution, and the aqueous layer was extracted with ethyl acetate. The combined organic layers were dried over sodium sulfate, and concentrated to give the crude product, which was purified on silica gel column (eluting with 0.5-1% methanol in dichloromethane) to give 2,2'-bipyridin-6-amine (280 mg, 79% yield). MS (ESI): m/z 172.1 [M+1]$^+$.

E. Ethyl 6-(pyridin-2-yl)pyridin-2-ylcarbamothioylcarbamate. To a solution of 2,2'-bipyridin-6-amine (280 mg, 1.63 mmol) in dioxane (10 mL) was added ethoxycarbonyl isothiocyanate (213 mg, 1.63 mmol) dropwise under nitrogen at room temperature, and the reaction mixture was stirred at room temperature for 2 h. The reaction mixture was monitored by TLC (50% ethyl acetate in petroleum ether), and when the starting material was consumed, the solvent was removed under reduced pressure to give crude ethyl 6-(pyridin-2-yl)pyridin-2-ylcarbamothioylcarbamate (340 mg) as a solid. MS (ESI): m/z 303.1 [M+1]$^+$.

F. 5-(Pyridin-2-yl)-[1,2,4]triazolo[1,5-a]pyridin-2-amine. To a solution of hydroxylamine hydrochloride (388 mg, 5.5 mmol) and N,N-diisopropylethylamine (435 mg, 3.3 mmol) in a mixture of methanol and ethanol (v/v, 1:1, 6 mL) was added ethyl 6-(pyridin-2-yl)pyridin-2-ylcarbamothioylcarbamate (340 mg, 1.1 mmol) in one portion at room temperature. After being stirred at room temperature for 2 h, the reaction mixture was heated at 60° C. overnight. When TLC (10% ethyl acetate in methanol) indicated the starting material was consumed, the solvent was removed under reduced pressure, and the residue was treated with water. The precipitate was collected and washed with a mixture of methanol and ethyl ether (v/v, 4:1, 8 mL) to give 5-(pyridin-2-yl)-[1,2,4]triazolo[1,5-a]pyridin-2-amine (100 mg, 51% yield) as a off-white solid. $^1$H NMR (400 MHz, DMSO-d$_6$) δ (ppm) 8.77 (d, J=8.0 Hz, 2H), 7.99 (t, J=7.6 Hz, 1H), 7.50 (m, 2H), 7.46 (m, 2H), 6.21 (br s, 2H); MS (ESI): m/z 211.9 [M+1]$^+$.

G. N-Phenyl-5-(pyridin-2-yl)-[1,2,4]triazolo[1,5-a]pyridin-2-amine. A degassed solution of 5-(pyridin-2-yl)-[1,2,4]triazolo[1,5-a]pyridin-2-amine (100 mg, 0.47 mmol), bromobenzene (81 mg, 0.52 mmol), tris(dibenzylideneacetone)dipalladium (0) (27 mg, 0.047 mmol), 4,5-bis(diphenylphosphino)-9,9-dimethylxanthene (43 mg, 0.09 mmol) and potassium tert-butoxide (100 mg, 0.9 mmol) in dioxane (5 mL) was heated at 80° C. under nitrogen overnight. After being cooled to room temperature, the reaction mixture was filtered, and the filtrate was concentrated in vacuo to give the crude product, which was purified on silica gel column (eluting with 2% methanol in dichloromethane) to give N-phenyl-5-(pyridin-2-yl)-[1,2,4]triazolo[1,5-a]pyridin-2-amine (52 mg, 38% yield). $^1$H NMR (400 MHz, METHANOL-d$_4$) δ (ppm) 8.81 (m, 2H), 8.16 (t, J=8.0 Hz, 1H), 7.76 (m, 2H), 7.64 (m, 4H), 7.31 (t, J=7.6 Hz, 2H), 6.97 (t, J=7.2 Hz, 1H); MS (ESI): m/z 288.1 [M+1]$^+$.

Example 36

N-(1H-Indazol-6-yl)-5-phenyl-[1,2,4]triazolo[1,5-a]pyridin-2-amine

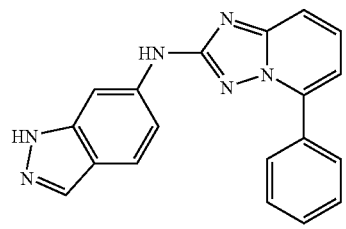

A. 2-Bromo-5-phenyl-[1,2,4]triazolo[1,5-a]pyridine. To a solution of 5-phenyl-[1,2,4]triazolo[1,5-a]pyridin-2-amine (2 g, 9.5 mmol) in a mixture of bromic acid (40% in water) and acetic acid (v/v, 2:1, 20 mL) was added sodium nitrite (3.2 g, 47.5 mmol) at room temperature, and the mixture was stirred at this temperature for 0.5 h, then stirred at 50° C. for another 0.5 h. The mixture was cooled down, and basified with sodium carbonate to pH>9, and extracted with ethyl acetate for three times. The combined organic layer was dried over anhydrous sodium sulfate and concentrated. The crude mixture was purified by column chromatography (eluting with 0-25% ethyl acetate in petroleum ether) to give 2-bromo-5-phenyl-[1,2,4]triazolo[1,5-a]pyridine (1.5 g, yield 57.7%) as a solid. $^1$H-NMR (400 MHz, DMSO-d$_6$) δ (ppm) 7.82 (m, 2H), 7.71 (m, 2H), 7.47 (m, 3H), 7.29 (m, 1H); MS (ESI): m/z 274.1 [M+1]$^+$.

B. 5-Phenyl-N-(1-(tetrahydro-2H-pyran-2-yl)-1H-indazol-6-yl)-[1,2,4]triazolo[1,5-a]pyridin-2-amine. A degassed solution of 1-(tetrahydro-2H-pyran-2-yl)-1H-indazol-6-amine (365 mg, 1.7 mmol), 2-bromo-5-phenyl-[1,2,4]triazolo[1,5-a]pyridine (460 mg, 1.7 mmol), 4,5-bis(diphenylphosphino)-9,9-dimethylxanthene (156 mg, 0.34 mmol), tris(dibenzylideneacetone)dipalladium (0) (96 mg, 0.17 mmol), and cesium carbonate (1 g, 3.4 mmol) in dioxane (10 mL) was heated at 80° C. under nitrogen overnight. After being cooled to room temperature, the reaction mixture was filtered, and the filtrate was concentrated in vacuo to give the crude product, which was purified on silica gel column (eluting with 1% methanol in dichloromethane) to give 5-phenyl-N-(1-(tetrahydro-2H-pyran-2-yl)-1H-indazol-6-yl)-[1,2,4]triazolo[1,5-a]pyridin-2-amine (100 mg, 15% yield). MS (ESI): m/z 411.0 [M+1]$^+$.

C. N-(1H-Indazol-6-yl)-5-phenyl-[1,2,4]triazolo[1,5-a]pyridin-2-amine. A mixture of 5-phenyl-N-(1-(tetrahydro-2H-pyran-2-yl)-1H-indazol-6-yl)-[1,2,4]triazolo[1,5-a]pyridin-2-amine (100 mg, 0.24 mmol) and methanolic hydrochloride solution (2 M, 5 mL) was stirred at room temperature overnight. The solvent was evaporated under reduced pressure to give N-(1H-indazol-6-yl)-5-phenyl-[1,2,4]triazolo[1,5-a]pyridin-2-amine (75 mg, 86% yield) as a hydrochloride salt. $^1$H NMR (300 MHz, DMSO-d$_6$) δ (ppm) 9.91 (br s, 1H), 8.14 (s, 1H), 8.07 (d, J=7.2 Hz, 2H), 7.73 (s, 1H), 7.72-7.54 (m, 7H), 7.25-7.21 (m, 2H); MS (ESI): m/z 327.1 [M+1]$^+$.

Example 37

5-Phenoxy-N-phenyl-[1,2,4]triazolo[1,5-a]pyridin-2-amine

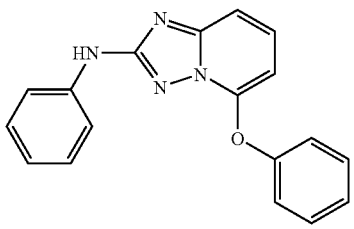

A. 2-Chloro-6-phenoxypyridine. A degassed mixture of 2,6-dichloropyridine (2.9 g, 20 mmol) (1.72 g, 10 mmol), phenol (12 g, 0.13 mmol) and sodium hydroxide (4.8 g, 0.12 mmol) in water (20 mL) was heated at 140° C. under nitrogen overnight. After being cooled down to room temperature, the reaction mixture was diluted with ethyl acetate, and the organic phase was washed with water for two times. The organic layer was dried over sodium sulfate and filtered. The filtrate was evaporated, and the residue was purified on silica gel column (eluting with 10% ethyl acetate in petroleum ether) to give 2-chloro-6-phenoxypyridine (1.7 g, 41% yield) as a white solid. $^1$H NMR (400 MHz, CHLOROFORM-d) δ

(ppm) 7.78 (t, J=8.0 Hz, 1H), 7.43 (t, J=8.0 Hz, 2H), 7.25 (t, J=7.6 Hz, 1H), 7.13 (m, 3H), 6.83 (d, J=8.0 Hz, 1H).

B. N-(4-Methoxybenzyl)-6-phenoxypyridin-2-amine. A degassed mixture of (4-methoxyphenyl)methanamine (10 mL) and 2-chloro-6-phenoxypyridine (1.7 g, 8.29 mmol) was heated at 180° C. under nitrogen with stirring for 5 h. After being cooled down to room temperature, the reaction mixture was diluted with ethyl acetate, and the mixture was washed with brine for two times. The organic layer was dried over sodium sulfate and filtered. The filtrate was evaporated, and the residue was purified on silica gel column (eluting with 10% ethyl acetate in petroleum ether) to give N-(4-methoxybenzyl)-6-phenoxypyridin-2-amine (1.5 g, 29% yield) as a white solid. MS (ESI): m/z 306.9 [M+1]$^+$.

C. 6-Phenoxypyridin-2-amine. A solution of N-(4-methoxybenzyl)-6-phenoxypyridin-2-amine (700 mg, 2.61 mmol) in a mixture of 2,2,2-trifluoroacetic acid and dichloromethane (v/v, 1/2) was refluxed for 2 h. The solvent was removed under reduced pressure, and the residue was purified on silica gel column (10% ethyl acetate in petroleum ether) to give pure 6-phenoxypyridin-2-amine (260 mg, 53% yield) as a white solid. $^1$H NMR (400 MHz, CHLOROFORM-d) δ (ppm) 7.37 (m, 3H), 7.16 (t, J=7.2 Hz, 1H), 7.04 (m, 2H), 6.24 (d, J=8.0 Hz, 1H), 5.93 (d, J=7.8 Hz, 1H); MS (ESI): m/z 186.9 [M+1]$^+$.

D. 5-Phenoxy-[1,2,4]triazolo[1,5-a]pyridin-2-amine. A mixture of 6-phenoxypyridin-2-amine (260 mg, 1.4 mmol) and ethoxycarbonyl isothiocyanate (183 mg, 1.4 mmol) in dioxane (10 mL) was stirred at room temperature for 5 h. The solvent was evaporated to afford the thioureido intermediate (440 mg, 99% yield) as a white solid, which was used in the next step without further purification.

To a solution of hydroxylamine hydrochloride (486 mg, 7.0 mmol) and N,N-diisopropylethylamine (541 mg, 4.2 mmol) in a mixture of ethanol and methanol (20 mL, 1:1) was added the thioureido intermediate (440 mg, 1.4 mmol), and the reaction mixture was stirred at room temperature for 2 h and at 70° C. for 5 h. The volatiles were removed under reduced pressure, and the residue was diluted with water. The precipitate was collected by filtration, washed with methanol (10 mL) and ethyl ether (10 mL). After being dried under vacuum, 5-phenoxy-[1,2,4]triazolo[1,5-a]pyridin-2-amine (280 mg, 88% yield) was obtained as an off-white crystalline solid. MS (ESI): m/z 226.9 [M+1]$^+$.

E. 5-Phenoxy-N-phenyl-[1,2,4]triazolo[1,5-a]pyridin-2-amine. A degassed mixture of 5-phenoxy-[1,2,4]triazolo[1,5-a]pyridin-2-amine (226 mg, 1.00 mmol), bromobenzene (156 mg, 1.00 mmol), tris(dibenzylideneacetone)dipalladium(0) (20 mg, 0.022 mmol), 4,5-bis(diphenylphosphino)-9,9-dimethylxanthene (25 mg, 0.044 mmol) and potassium tert-butoxide (244 mg, 2.00 mmol) in dioxane (5 mL) was heated at 80° C. under nitrogen overnight. The reaction mixture was quenched with water, and the aqueous layer was extracted with ethyl acetate. The organic layer was dried over sodium sulfate and filtered. The filtrate was evaporated under reduced pressure, and the residue was purified by reverse-phase preparative HPLC (38-68% acetonitrile+0.1% trifluoroacetic acid in water+0.1% trifluoroacetic acid, over 20 min.) to give 5-phenoxy-N-phenyl-[1,2,4]triazolo[1,5-a]pyridin-2-amine as a trifluoroacetic acid salt, which was converted to the hydrochloride salt with methanolic hydrochloride solution (60 mg, 20% yield) as a solid. $^1$H NMR (400 MHz, CHLOROFORM-d) δ (ppm) 7.92 (t, J=8.4 Hz, 1H), 7.57 (m, 4H), 7.42 (m, 6H), 7.12 (t, J=7.2 Hz, 1H), 6.67 (d, J=8.4 Hz, 1H); MS (ESI): m/z 303.1 [M+1]$^+$.

Example 38

5-(Cyclohexyloxy)-N-phenyl-[1,2,4]triazolo[1,5-a]pyridin-2-amine

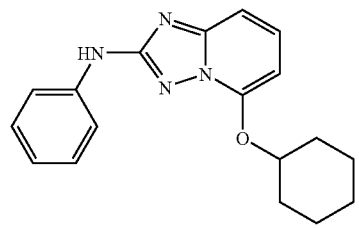

A. 2-Chloro-6-(cyclohexyloxy)pyridine. To a solution of cyclohexanol (26 g, 26 mmol) in toluene (300 mL) was added sodium (624 mg, 26 mmol) in portions, and the mixture was refluxed overnight. After being cooled down to room temperature, 2,6-dichloropyridine (29 g, 20 mmol) was added, and the resulting mixture was refluxed overnight. The reaction mixture was filtered, and the filtrate was evaporated to dryness. The crude product was purified on silica gel column (eluting with 20% ethyl acetate in petroleum ether) to give 2-chloro-6-(cyclohexyloxy)pyridine (30 g, 71% yield). $^1$HNMR (300 MHz, CHLOROFORM-d) δ (ppm) 7.46 (t, J=7.6 Hz, 1H), 6.84 (d, J=7.5 Hz, 1H), 6.59 (d, J=8.1 Hz, 1H), 5.01 (m, 1H), 1.94 (m, 2H), 1.77 (m, 2H), 1.20 (m, 6H).

B. 6-(Cyclohexyloxy)-N-(4-methoxybenzyl)pyridin-2-amine. A degassed mixture of (4-methoxyphenyl)methanamine (10 mL) and 2-chloro-6-(cyclohexyloxy)pyridine (1.0 g, 4.73 mmol) was stirred and heated at 180° C. under nitrogen for 5 h. After being cooled down to room temperature, the reaction mixture was diluted with ethyl acetate, and the mixture was washed with brine for two times. The organic layer was dried over sodium sulfate and filtered. The filtrate was evaporated, and the residue was purified on silica gel column (eluting with 10% ethyl acetate in petroleum ether) to give 6-(cyclohexyloxy)-N-(4-methoxybenzyl)pyridin-2-amine (800 mg, 54% yield) as a white solid. $^1$HNMR (400 MHz, DMSO-d$_6$) δ (ppm) 7.17 (m, 3H), 6.94 (t, J=6.0 Hz, 1H), 6.81 (d, J=8.4 Hz, 2H), 5.93 (d, J=8.0 Hz, 1H), 5.72 (d, J=8.0 Hz, 1H), 4.76 (m, 1H), 4.28 (d, J=6.0 Hz, 2H), 3.67 (s, 3H), 1.81 (m, 2H), 1.64 (m, 2H), 1.50 (m, 1H), 1.24 (m, 5H); MS (ESI): m/z 313.4 [M+1]$^+$.

C. 6-(Cyclohexyloxy)pyridin-2-amine. A solution of 6-(cyclohexyloxy)-N-(4-methoxybenzyl)pyridin-2-amine (800 mg, 2.68 mmol) in a mixture of 2,2,2-trifluoroacetic acid and dichloromethane (v/v, 1:2, 10 mL) was refluxed for 2 h. The solution was removed under reduced pressure, and the residue was purified on silica gel column (eluting with 10% ethyl acetate in petroleum ether) to give 6-(cyclohexyloxy) pyridin-2-amine (500 mg, 97% yield) as a white solid. MS (ESI): m/z 193.2 [M+1]$^+$.

D. 5-(Cyclohexyloxy)-[1,2,4]triazolo[1,5-a]pyridin-2-amine. A mixture of 6-(cyclohexyloxy)pyridin-2-amine (500 mg, 2.6 mmol) and ethoxycarbonyl isothiocyanate (341 mg, 2.6 mmol) in dioxane (15 mL) was stirred at room temperature for 5 h. The mixture was evaporated to afford the thioureido intermediate (800 mg, 90% yield), which was used in the next step without further purification.

To a solution of hydroxylamine hydrochloride (903 mg, 7.0 mmol) and N,N-diisopropylethylamine (1.00 mg, 7.8 mmol) in a mixture of ethanol and methanol (20 mL, 1:1) was added the thioureido intermediate (800 mg, 2.6 mmol), and the reaction mixture was stirred at room temperature for 2 h. The mixture was heated at 70° C. for 5 h, and the volatiles were removed under reduced pressure. The residue was diluted with water. The precipitate was washed with methanol (10 mL) and ethyl ether (10 mL). After being dried under high vacuum, 5-(cyclohexyloxy)-[1,2,4]triazolo[1,5-a]pyridin-2-amine (500 mg, 83% yield) was obtained as an off-white crystalline solid. $^1$H NMR (400 MHz, DMSO-d$_6$) δ (ppm) 7.37 (t, J=8.0 Hz, 1H), 6.86 (d, J=8.4 Hz, 1H), 6.40 (d, J=7.6 Hz, 1H), 5.92 (br s, 2H), 4.64 (m, 1H), 1.95 (m, 2H), 1.72 (m, 2H), 1.52 (m, 3H), 1.26 (m, 3H); MS (ESI): m/z 233.1 [M+1]$^+$.

E. 5-(Cyclohexyloxy)-N-phenyl-[1,2,4]triazolo[1,5-a]pyridin-2-amine. A degassed mixture of 5-(cyclohexyloxy)-[1,2,4]triazolo[1,5-a]pyridin-2-amine (150 mg, 0.64 mmol), bromobenzene (100 mg, 0.64 mmol), tris(dibenzylideneacetone)dipalladium(0) (118 mg, 0.129 mmol), 4,5-bis(diphenylphosphino)-9,9-dimethylxanthene (149 mg, 0.256 mmol) and potassium tert-butoxide (144 mg, 1.28 mmol) in dioxane (10 mL) was heated at 80° C. under nitrogen overnight. The reaction mixture was quenched with water, and the aqueous layer was extracted with ethyl acetate. The organic layer was dried over sodium sulfate and filtered. The filtrate was evaporated under reduced pressure, and the residue was purified by reverse-phase preparative HPLC (53-67%: acetonitrile+0.1% trifluoroacetic acid in water+0.1% trifluoroacetic acid, over 20 min.) to give 5-(cyclohexyloxy)-N-phenyl-[1,2,4]triazolo[1,5-a]pyridin-2-amine as a trifluoroacetic acid salt, which was converted to the hydrochloride salt with methanolic hydrochloride solution (130 mg, 65.9% yield) as a solid. $^1$H NMR (400 MHz, DMSO-d$_6$) δ (ppm) 9.62 (br s, 1H), 7.65 (d, J=8.0 Hz, 2H), 7.47 (t, J=8.0 Hz, 1H), 7.21 (t, J=8.0 Hz, 2H), 7.10 (d, J=8.0 Hz, 1H), 6.58 (d, J=8.0 Hz, 1H), 4.75 (m, 1H), 2.01 (m, 2H), 1.73 (m, 2H), 1.23 (m, 6H); MS (ESI): m/z 309.2 [M+1]$^+$.

Example 39

Phenyl(2-(phenylamino)-[1,2,4]triazolo[1,5-a]pyridin-5-yl)methanone

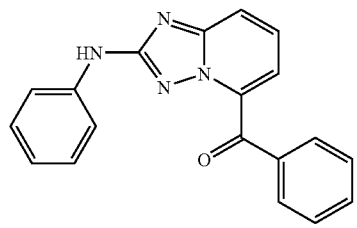

A. Phenyl(2-(phenylamino)-[1,2,4]triazolo[1,5-a]pyridin-5-yl)methanone. To a solution of 5-bromo-N-phenyl-[1,2,4]triazolo[1,5-a]pyridin-2-amine (0.1 g, 0.346 mmol) in tetrahydrofuran (1.729 mL) (colorless) at −78° C. was added n-butyllithium (2.5 M, 0.291 mL, 0.726 mmol), dropwise. The reaction mixture turned bright yellow and was maintained at low temperature for 1 h. Benzonitrile (0.039 g, 0.380 mmol) was then added neat. The reaction turned orange immediately and was allowed to slowly warm up to room temperature overnight. By LCMS, all starting material was converted with the desired product (major) and de-brominated core (side product).

The dark orange/brown solution was cooled to 0° C. and treated with 2.5 mL of a 3 N aqueous HCl solution. The reaction was stirred at 0° C. for 20 min before the layers were separated. The aqueous phase was further extracted with ethyl acetate and the combined organic extracts were dried over sodium sulfate, and evaporated to dryness (bright yellow). The residue was suspended in methanol and the resulting yellow precipitate was collected by filtration. The resulting solid was purified by semi-preparative HPLC (20-80% acetonitrile+0.1% trifluoroacetic acid in water+0.1% trifluoroacetic acid—1 injection over 30 min). The desired fraction was neutralized with a 1.75 M aqueous solution of potassium carbonate and acetonitrile was removed under reduced pressure. The bright yellow solid was collected by filtration, washed with water until pH neutral, and dried under vacuum overnight. Phenyl(2-(phenylamino)-[1,2,4]triazolo[1,5-a]pyridin-5-yl)methanone (0.021 g, 0.067 mmol, 19.32% yield) was collected as a yellow solid. $^1$H NMR (400 MHz, DMSO-d$_6$) δ (ppm) 9.67 (br s, 1H) 7.69-7.90 (m, 2H) 7.53-7.64 (m, 1H) 7.44 (d, 1H) 7.32 (d, 1H) 7.15 (t, 1H) 6.82 (1H) 2.50 (d, J=1.90 Hz, 22H); MS (ESI): m/z 315.3 [M+1]$^+$.

Example 40

5-Benzyl-N-phenyl-[1,2,4]triazolo[1,5-a]pyridin-2-amine

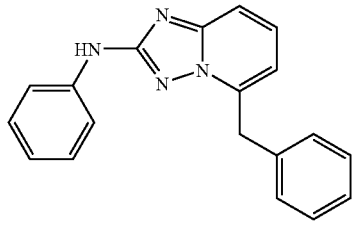

A. 5-Benzyl-N-phenyl-[1,2,4]triazolo[1,5-a]pyridin-2-amine. To a mixture of 5-bromo-N-phenyl-[1,2,4]triazolo[1,5-a]pyridin-2-amine (0.1 g, 0.346 mmol) and tetrakis(triphenylphosphine)palladium (0) (0.020 g, 0.017 mmol) at room temperature under an atmosphere of nitrogen, was added dry tetrahydrofuran (6.92 mL). The mixture became clear immediately. A 0.5 M solution of benzylzinc(II) chloride in tetrahydrofuran (1.383 mL, 0.692 mmol) was added and the reaction was stirred at 65° C. for 20 h. About 25% conversion was observed after 2.5 h, with minor reduction of the core. To drive the reaction to completion, additional reagents were added at room temperature (benzylzinc(II) chloride solution (1.383 mL, 0.692 mmol) and heating was resumed for 4 h. The reaction was quenched with ice and the crude product was extracted with ethyl acetate. The extracts were dried over sodium sulfate and evaporated to dryness. The residue was purified by semi-preparative HPLC (30-80% acetonitrile+ 0.1% trifluoroacetic acid in water+0.1% trifluoroacetic acid, over 30 min, 4 injections). The desired fractions were combined neutralized with the addition of a 1.75 M aqueous solution of potassium carbonate. A white precipitate formed upon removal of acetonitrile, that was collected by filtration and washed with water until the pH of the washings was neutral. The solid was dried overnight in a vacuum oven under mild heat. 5-Benzyl-N-phenyl-[1,2,4]triazolo[1,5-a]pyridin- 2-amine (0.090 g, 0.300 mmol, 87% yield) was collected as an off-white solid. ¹H NMR (400 MHz, DMSO-d$_6$) δ (ppm) 9.60 (br s, 1H), 7.69 (d, J=7.96 Hz, 3H), 7.49-7.57 (m, 2H), 7.44-7.49 (m, 1H), 7.38-7.43 (m, 3H), 7.32-7.37 (m, 3H), 7.20-7.30 (m, 4H), 6.84-6.91 (m, 1H), 6.77-6.83 (m, 1H), 4.44 (br s, 3H); MS (ESI): m/z 301.1 [M+1]⁺.

Example 41

5-(4-Aminobutyl)-N-phenyl-[1,2,4]triazolo[1,5-a]pyridin-2-amine

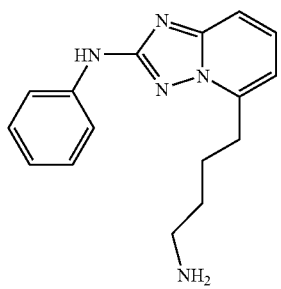

A. 2-(Phenylamino)-[1,2,4]triazolo[1,5-a]pyridine-5-carbaldehyde. To a colorless solution/suspension of 5-bromo-N-phenyl-[1,2,4]triazolo[1,5-a]pyridin-2-amine (0.2 g, 0.692 mmol) in tetrahydrofuran (3.46 mL) at −78° C. was added n-butyllithium (2.5 M, 0.581 mL, 1.453 mmol) dropwise. The reaction mixture turned bright yellow and was maintained at that temperature for 1 h. N,N-dimethylformamide (0.106 g, 1.453 mmol) was then added neat. The reaction was allowed to slowly warm up to room temperature and was stirred overnight. The reaction was quenched with the addition at 0° C. of acetic acid (1 mL) and water (10 mL). The crude product was extracted with ethyl acetate. The extracts were dried over sodium sulfate and evaporated to dryness. The residue was purified by sililca gel column chromatography (eluting with 50% ethyl acetate in hexanes) to give 2-(phenylamino)-[1,2,4]triazolo[1,5-a]pyridine-5-carbaldehyde (0.125 g, 0.525 mmol, 76% yield) as a bright yellow solid. ¹H NMR (400 MHz, METHANOL-d$_4$) δ (ppm) 7.66-7.70 (m, 2H), 7.60 (dd, J=7.27, 8.83 Hz, 1H), 7.47 (dd, J=1.27, 8.83 Hz, 1H), 7.27-7.33 (m, 2H), 7.22 (dd, J=1.17, 7.32 Hz, 1H), 6.91-6.96 (m, 1H), 6.16 (br s, 1H).

B. (E)-4-(2-(Phenylamino)-[1,2,4]triazolo[1,5-a]pyridin-5-yl)but-3-enenitrile. To a suspension of 2-(phenylamino)-[1,2,4]triazolo[1,5-a]pyridine-5-carbaldehyde (0.125 g, 0.525 mmol) in tetrahydrofuran (1.049 mL) was added diethyl 2-cyanoethylphosphonate (0.092 mL, 0.525 mmol) followed by 100 mg of a 50% aqueous solution of sodium hydroxide (0.050 g, 0.630 mmol). The suspension turned clear yellow immediately then a yellow precipitate appeared. The reaction was stirred at room temperature for 2 h. Water was added to the reaction and the product was extracted in ethyl acetate. The combined extracts were dried over sodium sulfate and evaporated to dryness. (E)-4-(2-(Phenylamino)-[1,2,4]triazolo[1,5-c]pyridin-5-yl)but-3-enenitrile was isolated as a yellow solid (0.145 g, quantitative yield). MS (ESI): m/z 276.1 [M+1]⁺.

C. 4-(2-(Phenylamino)-[1,2,4]triazolo[1,5-a]pyridin-5-yl)butanenitrile. A suspension of (E)-4-(2-(phenylamino)-[1,2,4]triazolo[1,5-a]pyridin-5-yl)but-3-enenitrile (0.145 g, 0.527 mmol) in ethanol (20 mL) was purged with nitrogen. Excess palladium on carbon (10% weight) (0.056 g, 0.527 mmol) was added and the mixture was put under an atmosphere of hydrogen. The reaction mixture was stirred at room temperature for 48 h with addition of catalyst and purging of the reaction flask with additional hydrogen overnight. Upon completion of the reaction, the catalyst was removed by filtration and washed abundantly with methanol. The filtrate was evaporated to dryness. The residue was purified by silica gel column (eluting with 50% ethyl acetate in hexanes). 4-(2-(Phenylamino)-[1,2,4]triazolo[1,5-a]pyridin-5-yl)butanenitrile (0.07 g, 0.252 mmol, 47.9% yield) was collected as a white solid. MS (ESI): m/z 278.1 [M+1]⁺.

D. 5-(4-Aminobutyl)-N-phenyl-[1,2,4]triazolo[1,5-a]pyridin-2-amine. A solution of 4-(2-(phenylamino)-[1,2,4]triazolo[1,5-a]pyridin-5-yl)butanenitrile (0.07 g, 0.252 mmol) in tetrahydrofuran (2.52 mL) was cooled to 0° C. and treated with a 1.0 M solution of lithium aluminum hydride (0.505 mL, 0.505 mmol) in tetrahydrofuran. The solution became yellow green as soon as the addition started. The reaction was stirred at 0° C. for 2.5 h. The reaction turned bright yellow and a precipitate formed. The reaction was quenched at 0° C. with a saturated solution of sodium sulfate and a 10% aqueous solution of sodium hydroxide. The supernatant solution was collected by filtration and evaporated to dryness. The residue was taken up in methanol and purified by semi-preparative HPLC (20-80% acetonitrile+0.1% trifluoroacetic acid in water+0.1% trifluoroacetic acid—3 injections). The desired fractions were combined and acetonitrile was removed under reduced pressure. The product was neutralized using an ion exchange column. The eluant was evaporated in a tared vial. After drying in a vacuum oven, 5-(4-aminobutyl)-N-phenyl-[1,2,4]triazolo[1,5-a]pyridin-2-amine (0.045 g, 0.160 mmol, 63.4% yield) was isolated as an oil that solidified upon drying (off-white solid). ¹H NMR (400 MHz, METHANOL-d$_4$) δ (ppm) 7.63-7.67 (m, 2H), 7.52 (dd, J=7.17, 9.03 Hz, 1H), 7.38 (dd, J=1.22, 8.83 Hz, 1H), 7.27-7.33 (m, 2H), 6.94 (dd, J=1.12, 7.37 Hz, 1H), 6.89 (dd, J=1.12, 7.17 Hz, 1H), 3.24-3.29 (m, 1H), 2.99 (dd, J=7.61, 13.71 Hz, 1H), 2.59-2.73 (m, 2H), 2.31-2.40 (m, 1H), 1.04 (d, J=6.78 Hz, 3H); MS (ESI): m/z 282.3 [M+1]⁺.

Example 42

5-(3-Aminopropyl)-N-phenyl-[1,2,4]triazolo[1,5-a]pyridin-2-amine

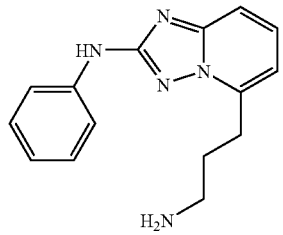

A. 3-(2-(Phenylamino)-[1,2,4]triazolo[1,5-a]pyridin-5-yl)acrylonitrile. To a solution of 2-(phenylamino)-[1,2,4]triazolo[1,5-a]pyridine-5-carbaldehyde (0.108 g, 0.453 mmol) in tetrahydrofuran (4.0 mL) was added diethyl cyanomethylphosphonate (0.080 g, 0.453 mmol) followed by 100 mg of a 50% aqueous solution of sodium hydroxide (0.044 g, 0.544 mmol). More base was added after 30 min (total of 0.5 mL in 0.1 mL increments) and the reaction was stirred for 24 h. The reaction was quenched with water and the product was extracted in ethyl acetate. The extracts were dried over sodium sulfate and evaporated to dryness. The resulting oil was purified by column chromatography (eluting with 25% ethyl acetate in hexanes). Although separable, both isomers were collected and combined (0.070 g, 84% yield). MS (ESI): m/z 262.0 [M+1]$^+$.

B. 5-(3-Aminopropyl)-N-phenyl-[1,2,4]triazolo[1,5-a]pyridin-2-amine. A solution of 3-(2-(phenylamino)-[1,2,4]triazolo[1,5-a]pyridin-5-yl)acrylonitrile (0.05 g, 0.191 mmol) in tetrahydrofuran (2.52 mL) was cooled to 0° C. and treated with a solution of lithium aluminum hydride in tetrahydrofuran (0.383 mL, 0.383 mmol). The solution became orange then brown after warming to room temperature. The reaction was then heated to 35-40° C. overnight. Another 2 equivalents of lithium aluminum hydride were added and heating to 50° C. was resumed for 9 h. The reaction was quenched at 0° C. with a saturated solution of sodium sulfate and a 10% aqueous solution of sodium hydroxide. The crude was extracted in ethyl acetate. The extracts were dried over sodium sulfate and evaporated to dryness. The residue was taken up in methanol and purified by semi-preparative HPLC (10-50% acetonitrile+0.1% trifluoroacetic acid in water+0.1% trifluoroacetic acid, over 30 min, 2 injections). The desired fractions were neutralized using an ion exchange column. The eluant was evaporated in a tared vial. 5-(3-Aminopropyl)-N-phenyl-[1,2,4]triazolo[1,5-a]pyridin-2-amine (0.006 g, 0.022 mmol, 11.73% yield) was isolated as an oil that solidified upon drying (off-white solid). $^1$H NMR (400 MHz, METHANOL-d$_4$) δ (ppm) 7.64-7.69 (m, 2H), 7.54 (dd, J=7.22, 8.83 Hz, 1H), 7.38 (dd, J=1.22, 8.83 Hz, 1H), 7.28-7.33 (m, 2H), 6.89-6.97 (m, 2H), 3.22-3.27 (m, 2H), 2.82-2.89 (m, 2H), 2.08-2.18 (m, 2H). MS (ESI): m/z 268.0 [M+1]$^+$.

Example 43

(1-Benzylpiperidin-4-yl)(2-(phenylamino)[1,2,4]triazolo[1,5-a]pyridin-5-yl)methanol

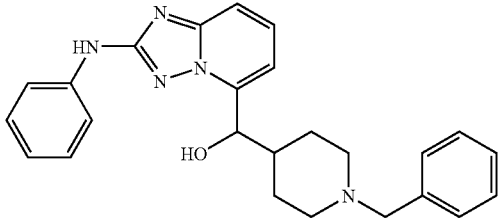

A. (1-Benzylpiperidin-4-yl)(2-(phenylamino)[1,2,4]triazolo[1,5-a]pyridin-5-yl)methanol. To a solution of 5-bromo-N-phenyl-[1,2,4]triazolo[1,5-a]pyridin-2-amine (0.270 g, 0.934 mmol) in tetrahydrofuran (4.67 mL) cooled to −78° C. was added a 2.5 M solution of n-butyllithium in hexane (0.784 mL, 1.961 mmol). The yellow solution was stirred at low temperature for 30 min before 1-benzylpiperidine-4-carbaldehyde (0.389 mL, 1.961 mmol) was added neat. The reaction was stirred at low temperature for 1.5 h. The reaction mixture was then poured into ice containing ammonium chloride. The crude was extracted with ethyl acetate and the extracts were dried over magnesium sulfate. The residue was purified by silica gel column (eluting with 0-10% methanol in ethyl acetate). (1-Benzylpiperidin-4-yl)(2-(phenylamino)-[1,2,4]triazolo[1,5-a]pyridin-5-yl)methanol contaminated with N-phenyl-[1,2,4]triazolo[1,5-c]pyridin-2-amine (0.321 g, 0.592 mmol, 63.4% yield) was collected as a light yellow oil that partially solidified under vacuum.

A portion of the residue was further purified by semi-preparative HPLC (20-80% acetonitrile+0.1% trifluoroacetic acid in water+0.1% trifluoroacetic acid, 30 min, 2 injections). The desired fractions were combined and neutralized via cation resin exchange column. (1-Benzylpiperidin-4-yl)(2-(phenylamino)-[1,2,4]triazolo[1,5-a]pyridin-5-yl)methanol (0.076 g was isolated as a white solid). $^1$H NMR (400 MHz, DMSO-d$_6$) δ (ppm) 9.64 (br s, 1H), 7.69-7.75 (m, 2H), 7.59 (dd, J=7.32, 8.78 Hz, 1H), 7.47 (dd, J=1.32, 8.74 Hz, 1H), 7.18-7.33 (m, 7H), 7.01-7.06 (m, 1H), 6.84-6.90 (m, 1H), 5.75 (d, J=5.08 Hz, 1H), 5.16 (t, J=4.78 Hz, 1H), 3.36-3.44 (m, 2H), 2.74-2.87 (m, 2H), 1.92-2.04 (m, 1H), 1.61-1.89 (m, 3H), 1.33-1.55 (m, 3H). MS (ESI): m/z 414.2 [M+1]$^+$.

Example 44

(2-(Phenylamino)-[1,2,4]triazolo[1,5-a]pyridin-5-yl)(piperidin-4-yl)methanol

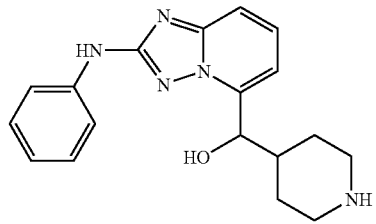

A. (2-(Phenylamino)-[1,2,4]triazolo[1,5-a]pyridin-5-yl)(piperidin-4-yl)methanol. To a degassed solution of (1-benzylpiperidin-4-yl)(2-(phenylamino)-[1,2,4]triazolo[1,5-c]pyridin-5-yl)methanol (0.245 g, 0.592 mmol) in ethanol (25 mL) was added excess palladium on carbon (10% weight) and the reaction was stirred under an atmosphere of hydrogen overnight. More catalyst and a fresh atmosphere of hydrogen were used and the reaction was stirred at room temperature for 24 h. The completion of the reaction required the addition of acetic acid (10 drops) and stirring at room temperature. The catalyst was removed under reduced pressure and washed abundantly with methanol and ethyl acetate. The filtrate was evaporated to dryness. The resulting light yellow oil was purified by semi-preparative HPLC (10-50% acetonitrile+0.1% trifluoroacetic acid in water+0.1% trifluoroacetic acid, over 30 min—4 injections). The desired fractions were combined and acetonitrile was removed under reduced pressure. The desired product was converted to its free base by eluting the aqueous solution of the salt through a STRATA-XC resin exchange column. (2-(Phenylamino)-[1,2,4]triazolo[1,5-c]pyridin-5-yl)(piperidin-4-yl)methanol (0.056 g, 0.173 mmol, 29.2% yield) was isolated as an oil that solidified under vacuum. $^1$H NMR (400 MHz, METHANOL-d$_4$) δ (ppm) 7.58-7.67 (m, 3H), 7.40 (dd, J=1.17, 8.88 Hz, 1H), 7.27-7.33 (m, 2H), 7.12 (dd, J=0.68, 7.27 Hz, 1H), 6.91-6.96 (m, 1H), 5.30 (d, J=4.64 Hz, 1H), 3.09-3.21 (m, 2H), 2.63-2.73 (m, 1H), 2.54-2.63 (m, 1H), 2.29-2.39 (m, 1H), 1.72-1.84 (m, 1H), 1.56-1.68 (m, 3H); MS (ESI): m/z 324.0 [M+1]⁺.

Example 45

N-Phenyl-5-(piperidin-4-ylmethyl)-[1,2,4]triazolo[1,5-a]pyridin-2-amine

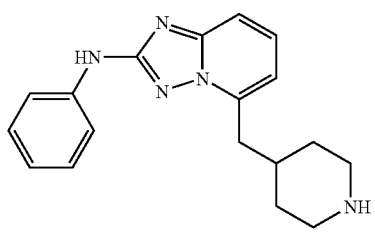

A. tert-Butyl 4-((2-(phenylamino)-[1,2,4]triazolo[1,5-a]pyridin-5-yl)methyl)piperidine-1-carboxylate. A solution of tert-butyl 4-methylenepiperidine-1-carboxylate (0.154 g, 0.778 mmol) in (1S,5S)-9-borabicyclo[3.3.1]nonane (1.038 mL, 0.519 mmol) (0.5 N in tetrahydrofuran) was heated to reflux temperature for 3 h under an atmosphere of nitrogen. The reaction was then cooled to room temperature and reacted with[1,1'-bis(diphenylphosphino)ferrocene]dichloropalladium(II) complex with dichloromethane (0.030 g, 0.036 mmol), potassium carbonate (0.072 g, 0.519 mmol) and 5-bromo-N-phenyl-[1,2,4]triazolo[1,5-a]pyridin-2-amine (0.150 g, 0.519 mmol) in N,N-dimethylformamide (2 mL). The reaction was heated to 90° C. for 36 h. Driving the reaction to completion required the use of 4 additional equivalents of borane reagent and heating for 3 h to 90° C. The reaction was quenched with water and the mixture was stirred at room temperature overnight. The organic extracts were dried over sodium sulfate and evaporated to dryness. The residue was purified by silica gel column chromatography (eluting with 50% ethyl acetate in hexanes). tert-Butyl 44(2-(phenylamino)-[1,2,4]triazolo[1,5-a]pyridin-5-yl)methyl)piperidine-1-carboxylate contaminated with N-phenyl-[1,2,4]triazolo[1,5-a]pyridin-2-amine was isolated as an oil (yield not calculated). The mixture was used without further purification in the following deprotection reaction. MS (ESI): m/z 408.5 [M+1]⁺.

B. N-Phenyl-5-(piperidin-4-ylmethyl)[1,2,4]triazolo[1,5-a]pyridin-2-amine. tert-Butyl 4-((2-(phenylamino)-[1,2,4]triazolo[1,5-a]pyridin-5-yl)methyl)piperidine-1-carboxylate was dissolved in dichloromethane (5 mL) and treated with neat trifluoroacetic acid (1.5 mL, 19.47 mmol). After 15 min at room temperature, the reaction was complete. The solvent was removed under reduced pressure and the residue was neutralized using a cation exchange resin. The free base material was dissolved in methanol and purified by semi-preparative HPLC (20-80% acetonitrile+0.1% trifluoroacetic acid in water+0.1% trifluoroacetic acid, 30 min, 2 injections). The desired fractions were neutralized using a cation resin exchange and dried under vacuum with mild heat. N-Phenyl-5-(piperidin-4-ylmethyl)-[1,2,4]triazolo[1,5-a]pyridin-2-amine (0.038 g, 0.124 mmol, 15.9% yield) was collected as an oil that solidified at room temperature after drying. ¹H NMR (400 MHz, DMSO-d₆) δ (ppm) 9.62 (s, 1H), 7.73 (dd, J=1.02, 8.64 Hz, 2H), 7.42-7.54 (m, 2H), 7.24-7.31 (m, 2H), 6.83-6.92 (m, 2H), 2.99 (d, J=7.22 Hz, 2H), 2.90 (d, J=12.05 Hz, 2H), 2.34-2.43 (m, 2H), 2.01-2.15 (m, 1H), 1.51 (d, J=11.66 Hz, 2H), 1.12-1.25 (m, 2H); MS (ESI): m/z 308.3 [M+1]⁺.

Example 46

(S)-2-Methyl-3-(2-(phenylamino)-[1,2,4]triazolo[1,5-a]pyridin-5-yl)propan-1-ol

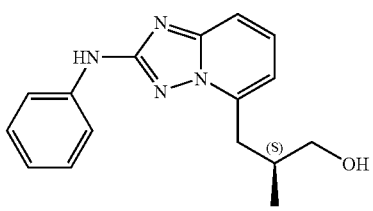

A. (S)-Methyl 2-methyl-3-(2-(phenylamino)-[1,2,4]triazolo[1,5-a]pyridin-5-yl)propanoate. To a mixture of 5-bromo-N-phenyl-[1,2,4]triazolo[1,5-a]pyridin-2-amine (0.200 g, 0.692 mmol) and tetrakis(triphenylphosphine)palladium (0) (0.200 g, 0.173 mmol) at room temperature under an atmosphere of nitrogen was added dry tetrahydrofuran (6.92 mL). The mixture became clear immediately. A 0.5 M solution of (R)-(3-ethoxy-2-methyl-3-oxopropyl)zinc(II) bromide in tetrahydrofuran (0.901 g, 3.46 mmol) was then added and the reaction was stirred at 65° C. for 2 h. The reaction was quenched with ice and the crude product was extracted with ethyl acetate. The extracts were dried over magnesium sulfate and evaporated to dryness. The residue was purified by silica gel column chromatography using 50% ethyl acetate in hexanes. The fractions were combined and evaporated to dryness. (S)-Methyl 2-methyl-3-(2-(phenylamino)-[1,2,4]triazolo[1,5-a]pyridin-5-yl)propanoate (0.21 g, 0.677 mmol, 98% yield) was isolated as a yellow solid. MS (ESI): m/z 311.1 [M+1]⁺.

B. (S)-2-Methyl-3-(2-(phenylamino)-[1,2,4]triazolo[1,5-a]pyridin-5-yl)propan-1-ol. To a solution of (S)-methyl 2-methyl-3-(2-(phenylamino)-[1,2,4]triazolo[1,5-a]pyridin-5-yl)propanoate (0.05 g, 0.161 mmol) in tetrahydrofuran (0.895 mL) at −78° C. was added a 1.0 M solution of lithium aluminum hydride in tetrahydrofuran (0.322 mL, 0.322 mmol). The reaction was then warmed to room temperature after 30 min and stirred for 30 min. The reaction was then quenched with the addition of an aqueous saturated solution of ammonium chloride and the product was extracted in ethyl acetate. The resulting light brown oil was purified by semi-preparative HPLC (20-70% acetonitrile+0.1% trifluoroacetic acid in water+0.1% trifluoroacetic acid, 30 min, 2 injections) The desired fractions were neutralized with a 1.75 N aqueous solution of potassium carbonate and acetonitrile was removed under reduced pressure. The material was extracted in ethyl acetate and the extracts were washed with water. The extracts were dried in a vacuum oven overnight. (S)-2-Methyl-3-(2-(phenylamino)-[1,2,4]triazolo[1,5-a]pyridin-5-yl)propan-1-ol (0.034 g, 0.120 mmol, 74.7% yield) was collected as a white solid. ¹H NMR (400 MHz, DMSO-d₆) δ (ppm) 9.61 (s, 1H), 7.73 (d, J=7.66 Hz, 2H), 7.48-7.55 (m, 1H), 7.41-7.46 (m, 1H), 7.24-7.31 (m, 2H), 6.83-6.92 (m, 2H), 4.61-4.67 (m, 1H), 3.35-3.42 (m, 2H), 3.18 (dd, J=6.25, 13.81 Hz, 1H), 2.85

(dd, J=8.05, 14.01 Hz, 1H), 2.24-2.35 (m, 1H), 0.90 (d, J=6.74 Hz, 3H); MS (ESI): m/z 283.2 [M+1]+.

Example 47

(S)-2-Methyl-3-(2-(phenylamino)-[1,2,4]triazolo[1,5-a]pyridin-5-yl)propanamide

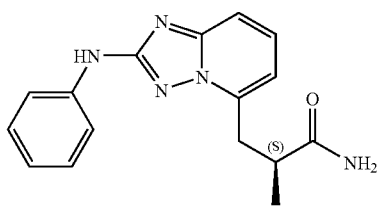

A. (S)-2-Methyl-3-(2-(phenylamino)-[1,2,4]triazolo[1,5-a]pyridin-5-yl)propanoic acid. A solution of (S)-methyl 2-methyl-3-(2-(phenylamino)-[1,2,4]triazolo[1,5-a]pyridin-5-yl)propanoate (0.11 g, 0.354 mmol) in methanol (5 mL) was treated with a 4.0 N aqueous solution of sodium hydroxide (3.90 mL, 15.60 mmol) and refluxed. After 1 h, the reaction was cooled to room temperature and pH was lowered to 2-3 with a 4 N aqueous solution of HCl. An off-white solid precipitated out, was collected by filtration and washed with water, that was dried under vacuum. (S)-2-Methyl-3-(2-(phenylamino)-[1,2,4]triazolo[1,5-a]pyridin-5-yl)propanoic acid (0.096 g, 0.324 mmol, 91% yield) was isolated as an off-white solid. MS (ESI): m/z 297.1 [M+1]+.

B. (S)-2-Methyl-3-(2-(phenylamino)-[1,2,4]triazolo[1,5-a]pyridin-5-yl)propanamide. A solution of (S)-2-methyl-3-(2-(phenylamino)-[1,2,4]triazolo[1,5-a]pyridin-5-yl)propanoic acid (0.096 g, 0.324 mmol), ammonium chloride (0.026 g, 0.486 mmol), N-methyl morpholine (0.053 mL, 0.486 mmol) in N,N-dimethylformamide (1.296 mL) was prepared at room temperature and treated with benzotriazol-1-yloxy-tris(dimethylamino)-phosphonium hexafluorophosphate (0.215 g, 0.486 mmol). The reaction was stirred at room temperature overnight. The reaction was quenched with the addition of a saturated aqueous sodium bicarbonate solution and the crude was extracted with ethyl acetate. The extracts were dried over magnesium sulfate and evaporated to dryness. The residue was purified by semi-preparative HPLC (20-80% acetonitrile+0.1% trifluoroacetic acid in water+0.1% trifluoroacetic acid, 30 min, 4 injections). The desired fractions were neutralized with a 1.75 M aqueous solution of potassium carbonate, resulting in the formation of a precipitate. Acetonitrile was removed under reduced pressure and the resulting white solid was collected by filtration and washed with water until the pH of the washings became neutral. (S)-2-Methyl-3-(2-(phenylamino)-[1,2,4]triazolo[1,5-a]pyridin-5-yl)propanamide (0.071 g, 0.240 mmol, 74.2% yield) was collected as a cotton-like white solid. $^1$H NMR (400 MHz, DMSO-d$_6$) δ (ppm) 9.64 (s, 1H), 7.74 (d, J=7.76 Hz, 2H), 7.42-7.54 (m, 2H), 7.36 (s, 1H), 7.24-7.31 (m, 2H), 6.78-6.91 (m, 3H), 3.26-3.33 (m, 1H), 2.94-3.09 (m, 2H), 1.15 (d, 3H); MS (ESI): m/z 296.1 [M+1]+.

Example 48

(S)-5-(3-Amino-2-methylpropyl)-n-phenyl-[1,2,4]triazolo[1,5-a]pyridin-2-amine

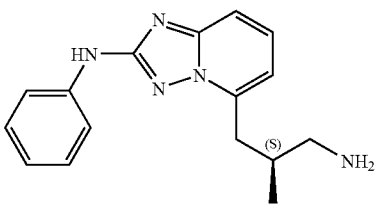

A. (S)-5-(3-Amino-2-methylpropyl)-N-phenyl-[1,2,4]triazolo[1,5-a]pyridin-2-amine. A mixture of (S)-2-methyl-3-(2-(phenylamino)-[1,2,4]triazolo[1,5-a]pyridin-5-yl)propan-1-ol (0.045 g, 0.161 mmol), phthalimide (0.047 g, 0.322 mmol), polymer-bound triphenyl phosphine (3 mmol/g, 0.107 g, 0.322 mmol) in tetrahydrofuran (1.610 mL) was treated with disisopropyl azodicarboxylate (0.063 mL, 0.322 mmol) and stirred at room temperature for 1 h. The resin was removed by filtration and the filtrate was evaporated to dryness. The residue was dissolved in ethanol (2 mL) and treated with hydrazine monohydrate (0.025 mL, 0.805 mmol). The reaction was heated to 40° C. overnight. The reaction mixture was evaporated to dryness and suspended in methanol. The filtrate was evaporated to dryness and dissolved in dimethylsulfoxide (2 mL) for purification by semi-preparative HPLC (20-100% acetonitrile+0.1% trifluoroacetic acid in water+0.1% trifluoroacetic acid, 30 min, 2 injections). The desired fractions were combined and neutralized using a cation exchange resin column (STRATA column). The residue was evaporated in a tared flask and dried in a vacuum oven. (S)-5-(3-amino-2-methylpropyl)-N-phenyl-[1,2,4]triazolo[1,5-a]pyridin-2-amine (0.023 g, 0.082 mmol, 50.8% yield) was isolated as a clear oil that solidified upon drying. $^1$H NMR (400 MHz, DMSO-d$_6$) δ (ppm) 9.61 (s, 1H), 7.69-7.77 (m, 2H), 7.47-7.53 (m, 1H), 7.41-7.46 (m, 1H), 7.23-7.31 (m, 2H), 6.83-6.92 (m, 2H), 3.20 (d, J=6.30, 13.71 Hz, 1H), 2.84

(dd, J=8.00, 13.91 Hz, 1H), 2.52-2.58 (m, 2H), 2.11-2.21 (m, 1H), 0.88 (d, J=6.74 Hz, 3H); MS (ESI): m/z 282.2 [M+1]$^+$.

Example 49

N-(6-Morpholinopyridin-3-yl)-5-phenyl-[1,2,4]triazolo[1,5-a]pyridin-2-amine

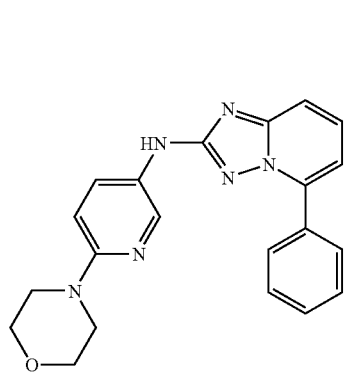

A. N-(6-Chloropyridin-3-yl)-5-phenyl-[1,2,4]triazolo[1,5-a]pyridin-2-amine. Under an atmosphere of nitrogen, to a mixture of 5-phenyl-[1,2,4]triazolo[1,5-a]pyridin-2-amine (0.3 g, 1.43 mmol), 2-chloro-5-iodopyridine (0.402 g, 1.68 mmol), palladium(II) acetate (8 mg, 0.035 mmol), 2,2'-bis(diphenylphosphino)1-1'-binaphtyl (0.021 g, 0.034 mmol), cesium carbonate (2.73 g, 8.39 mmol) was added toluene. The solution was purged with nitrogen, stirred at room temperature for 30 min and heated to 120° C. overnight. The reaction was quenched with water and extracted with ethyl acetate. The organic layer was dried over magnesium sulfate and evaporated to dryness (yellow oil). The residue was purified by column chromatography using 50% ethyl acetate in hexanes. N-(6-Chloropyridin-3-yl)-5-phenyl-[1,2,4]triazolo[1,5-a]pyridin-2-amine (0.08 g, 0.249 mmol, 14.81% yield) was isolated as a yellow solid. MS (ESI): m/z 322.0 [M+1]$^+$.

B. N-(6-Morpholinopyridin-3-yl)-5-phenyl-[1,2,4]triazolo[1,5-a]pyridin-2-amine.

A solution of N-(6-chloropyridin-3-yl)-5-phenyl-[1,2,4]triazolo[1,5-a]pyridin-2-amine (0.08 g, 0.249 mmol) in morpholine (5 mL, 57.4 mmol) was heated to 150° C. for 6 days with daily monitoring of the conversion (55% conversion). The reaction was cooled to room temperature and morpholine was removed under reduced pressure. The residue was suspended in methanol and the filtrate was purified by semi-preparative HPLC (20-100% acetonitrile+0.1% trifluoroacetic acid in water+0.1% trifluoroacetic acid, 2 injections, 30 min). The desired fractions were neutralized using a cation exchange resin, evaporated to dryness, and dried overnight in a vacuum oven. N-(6-Morpholinopyridin-3-O-5-phenyl-[1,2,4]triazolo[1,5-c]pyridin-2-amine (0.021 g, 0.056 mmol, 22.7% yield) was collected as a yellow solid. $^1$H NMR (400 MHz, DMSO-d$_6$) δ (ppm) 9.41 (s, 1H), 8.46 (d, J=2.39 Hz, 1H), 8.00-8.06 (m, 2H), 7.92 (dd, J=2.78, 9.08 Hz, 1H), 7.52-7.68 (m, 5H), 7.16 (dd, J=1.32, 7.22 Hz, 1H), 6.83 (d, J=9.08 Hz, 1H), 3.67-3.74 (m, 4H), 3.27-3.33 (m, 4H); MS (ESI): m/z 373.3 [M+1]$^+$.

Example 50

5-(5-Methylisoxazol-3-yl)-N-phenyl-[1,2,4]triazolo[1,5-a]pyridin-2-amine

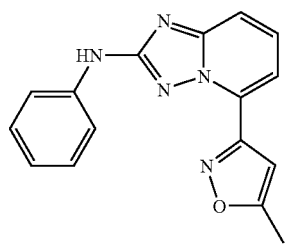

A. N-(6-Bromopyridin-2-yl)pivalamide. To a mixture of 6-bromo-pyridin-2-ylamine (100 g, 0.6 mol) and triethylamine (70.5 g, 0.72 mol) in dichloromethane (200 mL) was added dropwise pivaloyl chloride (83.5 g, 0.72 mol) at room temperature and the reaction mixture was stirred at room temperature for 4 h. The reaction mixture was washed with water, dried over sodium sulfate, and evaporated to give N-(6-bromopyridin-2-yl)pivalamide (120 g, yield 80.5%) as a white solid. $^1$H-NMR (400 MHz, DMSO-d$_6$) δ (ppm) 10.11 (s, 1H), 8.04 (d, J=8.0 Hz, 1H), 7.68 (t, J=8.0 Hz, 1H), 7.28 (d, J=7.6 Hz, 1H), 1.19 (s, 9H); MS (ESI): m/z 257.1 [M+1]$^+$.

B. N-(6-Formylpyridin-2-yl)pivalamide. A solution of N-(6-bromopyridin-2-yl)pivalamide (40 g, 0.16 mol) in toluene was cooled to 3-5° C., and a solution of isopropylmagnesium chloride in tetrahydrofuran (200 mL, 2 M) was added dropwise over a period of 1 h below 5° C. The resulting mixture was stirred at 5° C. for 12 h, and dry N,N-dimethylformamide (58.4 g, 0.8 mol) was added over 20 min at 10~15° C., and the mixture was stirred for 30 min. at 10~15° C. The reaction was quenched with water, and the resulting mixture was extracted with ethyl acetate. The combined organic layer was washed with brine, dried over sodium sulfate, and concentrated to give N-(6-formylpyridin-2-yl)pivalamide (22 g, 68.8% yield) as a solid. $^1$H-NMR (400 MHz, DMSO-d$_6$) δ (ppm) 10.16 (s, 1H), 9.90 (s, 1H), 8.29 (d, J=8.0 Hz, 1H), 7.99 (t, J=8.0 Hz, 1H), 7.64 (d, J=7.6 Hz, 1H), 1.25 (s, 9H); MS (ESI): m/z 207.1 [M+1]$^+$.

C. N-(6-((Hydroxyimino)methyl)pyridin-2-yl)pivalamide. To a solution of sodium hydroxide (3.2 g, 0.08 mol) in a mixture of water and ethanol (v/v, 5:1) was added hydroxylamine hydrochloride (5.6 g, 0.08 mol) and a solution of N-(6-formylpyridin-2-yl)pivalamide (15 g, 0.073 mol) in ethanol (50 mL) at 0° C. The mixture was stirred at 0° C. for 4 h and at room temperature for 1 h. The precipitate was collected by filtration, washed with water and ethanol to give N-(6-((hydroxyimino)methyl)pyridin-2-yl)pivalamide (15 g, 93.7% yield). $^1$H-NMR (400 MHz, DMSO-d$_6$) δ (ppm) 11.68 (s, 1H), 9.84 (s, 1H), 7.98 (m, 1H), 7.77 (t, J=8.0 Hz, 1H), 7.46 (d, J=7.6 Hz, 1H), 1.21 (s, 9H); MS (ESI): m/z 222.1 [M+1]$^+$.

D. N-(6-(5-Methylisoxazol-3-yl)pyridin-2-yl)pivalamide. N-Chlorosuccinimide (3.3 g, 0.015 mol) was added dropwise to a solution of N-(6-((hydroxyimino)methyl)pyridin-2-yl)pivalamide (5 g, 0.02 mmol) in N,N-dimethylformamide (40 mL), and the mixture was heated to 50° C. for 1 h. A mixture of prop-1-en-2-yl acetate (11 g, 0.1 mol) and triethylamine (5.7 g, 0.056 mol) was added slowly, and the reaction was stirred at 50° C. overnight. The reaction was quenched by addition of water, the mixture was extracted with ethyl acetate (15 mL×3). The combined organic layer was washed with brine, dried over sodium sulfate, and concentrated. The residue was purified by column chromatography on silica gel (eluting with 20% ethyl acetate in petroleum ether) to give N-(6-(5-methylisoxazol-3-yl)pyridin-2-yl)pivalamide (1.5 g, 25.8% yield) as a solid. $^1$H-NMR (400 MHz, DMSO-d$_6$) δ (ppm) 8.15 (d, J=8.4 Hz, 1H) 7.93 (t, J=8.0 Hz, 1H), 7.70 (d, J=7.6 Hz, 1H), 6.72 (s, 1H), 2.51 (s, 1H), 1.34 (s, 9H); MS (ESI): m/z 260.1 [M+1]$^+$.

E. 6-(5-Methylisoxazol-3-yl)pyridin-2-amine. A mixture of N-(6-(5-methylisoxazol-3-yl)pyridin-2-yl)pivalamide (1.5 g, 5.8 mmol) and potassium hydroxide aqueous solution (10 mL, 2 M) was stirred at 100° C. for 12 h. The reaction mixture was extracted with ethyl acetate, and the combined organic layer was washed with brine, dried over sodium sulfate, and concentrated under reduced pressure. The residue was purified by column chromatography on silica gel (eluting with 50% ethyl acetate in petroleum ether) to give 6-(5-methylisoxazol-3-yl)pyridin-2-amine (450 mg, 47% yield) as a white solid.

F. 5-(5-Methylisoxazol-3-yl)-[1,2,4]triazolo[1,5-a]pyridin-2-amine. A solution of 6-(5-methylisoxazol-3-yl)pyridin-2-amine (450 mg, 2.57 mmol) and ethoxycarbonyl isothiocyanate (337 mg, 2.57 mmol) in dioxane (10 mL) was stirred at room temperature for 5 h. The solvent was removed under reduced pressure to the thioureido intermediate as a solid, which was used directly without further purification.

To a solution of hydroxylamine hydrochloride (900 mg, 12.85 mmol) and N,N-ethyldiisopropylamine (994 mg, 7.71 mmol) in a mixture of ethanol and methanol (v/v, 1:1, 20 mL) was added the thioureido compound (786 mg, 2.57 mmol), and the mixture was stirred at room temperature for 2 h, at 70° C. overnight. The volatiles were removed under reduced pressure, and the residue was purified on silica gel column (eluting with 50% ethyl acetate in petroleum ether) to give 5-(5-methylisoxazol-3-yl)-[1,2,4]triazolo[1,5-a]pyridin-2-amine (200 mg, 36.2% yield) as a solid. $^1$H-NMR (400 MHz, DMSO-d$_6$) δ (ppm) 7.54 (m, 2H), 7.39 (d, J=8.8 Hz, 1H), 7.13 (s, 1H), 6.18 (s, 2H), 2.52 (s, 3H); MS (ESI): m/z 216.2 [M+1]$^+$.

G. 5-(5-Methylisoxazol-3-yl)-N-phenyl-[1,2,4]triazolo[1,5-a]pyridin-2-amine. A degassed mixture of 5-(5-methylisoxazol-3-yl)-[1,2,4]triazolo[1,5-a]pyridin-2-amine (200 mg, 0.93 mmol), iodobenzene (190 mg, 0.93 mmol), 4,5-bis(diphenylphosphino)-9,9-dimethylxanthene (108 mg, 0.186 mmol) and sodium tert-butoxide (108 mg, 1.1 mmol) in dioxane (20 mL) was added tris(dibenzylideneacetone)dipalladium(0) (84 mg, 0.093 mmol) under nitrogen, and the mixture was heated at 100° C. under nitrogen for 2 h. The reaction mixture was quenched by the addition of water, and the mixture was extracted with ethyl acetate (15 mL×3). The combined organic layer was washed with brine, dried over sodium sulfate, and concentrated. The residue was purified by reverse-phase preparative HPLC (48-68% acetonitrile+0.1% trifluoroacetic acid in water+0.1% trifluoroacetic acid, over 15 min) to give 5-(5-methylisoxazol-3-yl)-N-phenyl-[1,2,4]triazolo[1,5-a]pyridin-2-amine as a trifluoroacetic acid salt, which was converted to a hydrochloride salt with methanolic hydrochloride solution (75 mg, 27.8% yield). $^1$H-NMR (400 MHz, DMSO-d$_6$) δ (ppm) 9.73 (s, 1H), 7.71 (m, 4H), 7.56 (d, J=8.8, 1H), 7.29 (t, J=8.0, 2H), 7.22 (s, 1H), 6.88 (t, J=7.2, 1H), 2.57 (s, 3H); MS (ESI): m/z 291.9 [M+1]$^+$.

Example 51

N$^4$-(5-Phenyl-[1,2,4]triazolo[1,5-a]pyridin-2-yl)pyridine-2,4-diamine

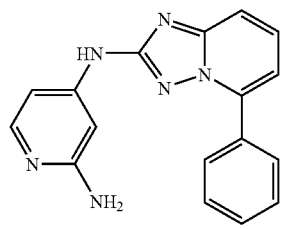

A. N-(4-(5-Phenyl-[1,2,4]triazolo[1,5-a]pyridin-2-ylamino)pyridin-2-yl)pivalamide. A degassed mixture of 5-phenyl-[1,2,4]triazolo[1,5-a]pyridin-2-amine (200 mg, 0.95 mmol), N-(4-chloropyridin-2-yl)pivalamide (244 mg, 1.15 mmol), sodium tert-butoxide (184 mg, 1.92 mmol) and (R)-(+)-2,2'-bis(diphenylphosphino)-1,1'-binaphthyl (120 mg, 0.19 mmol) in toluene (8 mL) was added tris(dibenzylideneacetone) dipalladium(0) (88 mg, 0.10 mmol) under nitrogen, and the reaction mixture was irradiated in the microwave (150 W) at 150° C. under nitrogen for 1 h. After filtration, the solvent of the filtrate was removed by rotary evaporator, and the residue was purified by reverse-phase preparative HPLC (30-60%: acetonitrile+0.1% trifluoroacetic acid in water+0.1% trifluoroacetic acid, 17.2 min.) to give N-(4-(5-phenyl-[1,2,4]triazolo[1,5-a]pyridin-2-ylamino)pyridin-2-yl)pivalamide (52 mg, 14.2% yield) as a white solid. MS (ESI): m/z 387.1 [M+1]$^+$.

B. N$^4$-(5-Phenyl-[1,2,4]triazolo[1,5-a]pyridin-2-yl)pyridine-2,4-diamine. N-(4-(5-Phenyl-[1,2,4]triazolo[1,5-a]pyridin-2-ylamino)pyridin-2-yl)pivalamide (52 mg, 0.135 mmol) was dissolved in a solution of potassium hydroxide in ethanol (2 M, 5 mL), and the mixture was stirred at 90° C. under nitrogen overnight. Ethanol was removed by rotary evaporator, and the residue was diluted with water. The aqueous layer was extracted with ethyl acetate for five times. The organic layer was combined, dried over anhydrous sodium sulfate, concentrated under high vacuum to give N$^4$-(5-phenyl-[1,2,4]triazolo[1,5-a]pyridin-2-yl)pyridine-2,4-diamine (30 mg, 75% yield) as a solid. $^1$H NMR (400 MHz, CHLO- ROFORM-d) δ (ppm) 8.02 (m, 2H), 7.91 (d, J=6.0 Hz, 1H), 7.58 (m, 6H), 7.07 (m, 2H), 6.68 (m, 1H); MS (ESI): m/z 303.1 [M+1]+.

Example 52

4-(5-(3-Hydroxyphenyl)-[1,2,4]triazolo[1,5-a]pyridin-2-ylamino)-N-methylbenzamide

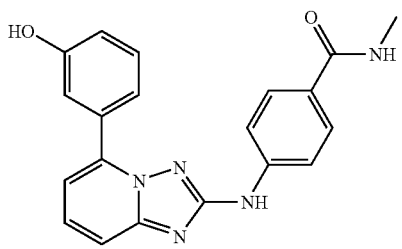

A. 4-(5-Bromo-[1,2,4]triazolo[1,5-a]pyridin-2-ylamino)-N-methylbenzamide. A degassed mixture of 5-bromo-[1,2,4]triazolo[1,5-a]pyridin-2-amine (2.12 g, 10 mmol), 4-iodo-N-methylbenzamide (2.87 g, 11 mmol), 4,5-bis(diphenylphosphino)-9,9-dimethylxanthene (1.15 g, 2.0 mmol), and sodium tert-butoxide (1.92 g, 20 mmol) in dioxane (30 mL) was added tris(dibenzylideneacetone)dipalladium (0) (913 mg, 1 mmol), and the reaction mixture was heated at 90° C. under nitrogen overnight. After being cooled down to room temperature, the reaction mixture was filtered, and the filtrate was concentrated under vacuum to give the crude product, which was purified on silica gel column (eluting with 10-80% ethyl acetate in petroleum ether) to give 4-(5-bromo-[1,2,4]triazolo[1,5-a]pyridin-2-ylamino)-N-methylbenzamide (2.2 g, 64% yield). MS (ESI): m/z 347.7 [M+1]+.

B. 4-(5-(3-Hydroxyphenyl)-[1,2,4]triazolo[1,5-a]pyridin-2-ylamino)-N-methylbenzamide. A mixture of 4-(5-bromo-[1,2,4]triazolo[1,5-a]pyridin-2-ylamino)-N-methylbenzamide (104 mg, 0.3 mmol), 3-hydroxy-phenyl boronic acid (82 mg, 0.6 mmol), triphenylphosphine (16 mg, 0.06 mmol) and potassium phosphate (127 mg, 0.6 mmol) in 1,2-dimethoxyethane (5 mL) was degassed, and palladium acetate (7 mg, 0.03 mmol) was added under nitrogen. The reaction mixture was heated to reflux at 80° C. under nitrogen overnight. After being cooled down to room temperature, the reaction mixture was partitioned between ethyl acetate (20 mL) and water (20 mL), and the aqueous layer was extracted with ethyl acetate (20 mL×3). The combined organic layer was washed with brine, dried over sodium sulfate, and evaporated. The crude product was purified by reverse-phase preparative HPLC (20-55%: acetonitrile+0.1% trifluoroacetic acid in water+0.1% trifluoroacetic acid, over 15 min) to give 4-(5-(3-hydroxyphenyl)-[1,2,4]triazolo[1,5-a]pyridin-2-ylamino)-N-methylbenzamide as a trifluoroacetic acid salt, which was converted to a hydrochloride salt (30 mg, 30% yield). 1H NMR (400 MHz, METHANOL-d4) δ (ppm) 7.97 (t, J=8.8 Hz, 1H), 7.75 (m, 2H), 7.64 (dd, J1=1.2 Hz, J2=8.8 Hz, 1H), 7.61 (m, 2H), 7.46 (dd, J1=0.8 Hz, J2=7.6 Hz, 1H), 7.38 (m, 3H), 6.96 (m, 1H), 2.81 (s, 3H). MS (ESI): m/z 360.1 [M+1]+.

Example 53

2-(2-(4-Fluorophenylamino)-[1,2,4]triazolo[1,5-a]pyridin-5-yl)-1-phenylethanol

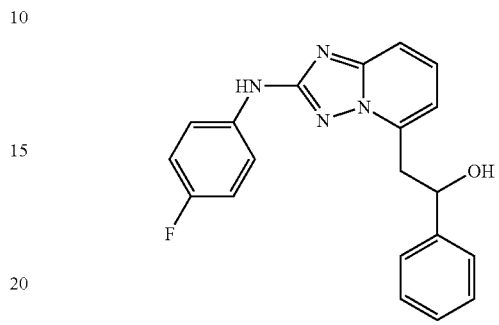

A. 2-(3-Ethoxycarbonyl-2-thioureido)-6-methylpyridine. To a solution of 6-methylpyridin-2-amine (5.0 g, 46.2 mmol) in 1,4-dioxane (185 mL) cooled to 0° C. was added ethoxycarbonyl isothiocyanate (5.23 mL, 46.2 mmol) neat dropwise. The bath was allowed to melt and the reaction was stirred at room temperature for 2 h. The reaction mixture was maintained at room temperature for 48 h. The solvent was removed under reduced pressure. 2-(3-Ethoxycarbonyl-2-thioureido)-6-methylpyridine was isolated as a light yellow solid in quantitative yield and was used with no further purification (residual solvent/reagent). MS (ESI): m/z 240.1 [M+1]+.

B. 5-Methyl-[1,2,4]triazolo[1,5-a]pyridin-2-amine. To a solution of hydroxylamine hydrochloride (16.05 g, 231 mmol) and N,N-diisopropylethyl amine (24.21 mL, 139 mmol) in a mixture of methanol (50.0 mL) and ethanol (50 mL) was added 2-(3-ethoxycarbonyl-2-thioureido)-6-methylpyridine (11.06 g, 46.2 mmol). The reaction was stirred at room temperature overnight. The solvent was removed under reduced pressure, water (50 mL) was added and the light yellow suspension was stirred at room temperature for 30 min. As all the material went in solution, the crude was extracted in ethyl acetate. The extracts were dried over magnesium sulfate and evaporated to dryness. The extracts were suspended in ethyl acetate (5 mL) and the resulting white suspension was collected by filtration. The aqueous phase also contained some amount of product contaminated with N,N-diisopropylethyl amine but attempts to further extract the aqueous phase with diethyl ether or a mixture of methanol in diethyl ether or ethyl acetate failed to yield any significant amount of material. 5-Methyl-[1,2,4]triazolo[1,5-a]pyridin-2-amine (4.05 g, 27.3 mmol, 59.2% yield) was isolated as a white solid. 1H NMR (400 MHz, METHANOL-d4) δ (ppm) 7.42 (t, 1H), 7.23 (d, J=8.20 Hz, 1H), 6.80 (d, J=7.42 Hz, 1H), 2.63 (s, 3H); MS (ESI): m/z 149.4 [M+1]+.

C. N-(4-Fluorophenyl)-5-methyl-[1,2,4]triazolo[1,5-a]pyridin-2-amine. To a suspension of 5-methyl-[1,2,4]triazolo[1,5-a]pyridin-2-amine (1 g, 6.75 mmol), 4,5-bis(diphenylphosphino)-9,9-dimethylxanthene (0.781 g, 1.350 mmol), sodium tert-butoxide (1.297 g, 13.50 mmol) and tris(dibenzylideneacetone)dipalladium(0) (0.451 g, 0.492 mmol) in 1,4-dioxane (40 mL) under an atmosphere of nitrogen, was added 1-fluoro-4-iodobenzene (1.557 mL, 13.50 mmol). The reaction mixture (dark brown suspension) was stirred at room temperature for 30 min then 40° C. for 30 min. Heating was stopped after 2 h and the reaction was quenched with water. The crude material was extracted with ethyl acetate and dried over magnesium sulfate. The extracts were evaporated to dryness (brown solid). The residue was suspended in dichloromethane and the resulting light grey solid was collected by filtration and washed with dichloromethane. The filtrate was concentrated and the resulting brown residue was suspended in a minimum volume of methanol (5 mL). The suspension was collected by filtration and rapidly washed with methanol. N-(4-Fluorophenyl)-5-methyl-[1,2,4]triazolo[1,5-a]pyridin-2-amine (0.839 g, 3.46 mmol, 51.3% yield), contaminated with about 10% of defluorinated product was isolated as an off-white solid that was dried under vacuum and used without further purification. $^1$H NMR (400 MHz, METHANOL-d$_4$) δ (ppm) 7.59-7.73 (m, 2H), 7.43-7.54 (m, 1H), 7.20-7.39 (m, 2H), 7.02 (t, J=8.59 Hz, 2H), 6.86 (d, J=7.42 Hz, 1H), 2.73 (br s, 3H); $^{19}$F NMR (400 MHz, DMSO-d$_6$) δ (ppm) -125.97; MS (ESI): m/z 243.3 [M+1]$^+$.

D. 2-(2-(4-Fluorophenylamino)-[1,2,4]triazolo[1,5-a]pyridin-5-yl)-1-phenylethanol. A suspension of N-(4-fluorophenyl)-5-methyl-[1,2,4]triazolo[1,5-a]pyridin-2-amine (0.15 g, 0.619 mmol) in diethyl ether (6.0 mL) was cooled to 0° C. A solution of n-butyl lithium in hexanes (0.508 mL, 1.269 mmol, 2.5 M) was then added dropwise. The reaction mixture turned into a brown thicker suspension. The reaction was stirred at 0° C. for 30 min followed by 30 min at room temperature. The reaction was cooled back to 0° C. before adding benzaldehyde (0.075 mL, 0.743 mmol) as a solution in diethyl ether (6.0 mL). After 1 h at 0° C., the temperature was slowly allowed to reach room temperature and the reaction was stirred overnight. No further conversion was observed after the addition of 1.1 equivalents of benzaldehyde. The reaction was quenched with water and the crude was extracted with ethyl acetate. The extracts were dried over magnesium sulfate and evaporated to dryness. The yellow residue (⅔ of the material) was purified by semi-preparative HPLC (20-80% acetonitrile+0.1% trifluoroacetic acid in water+0.1% trifluoroacetic acid, 39 min, 2 injections). The desired fractions were neutralized with a 1.75 M aqueous solution of potassium carbonate and acetonitrile was removed under reduced pressure resulting in the precipitation of the product. 2-(2-(4-Fluorophenylamino)-[1,2,4]triazolo[1,5-a]pyridin-5-yl)-1-phenylethanol (0.021 g, 0.060 mmol, 9.74% yield) was isolated as a white solid that was dried in a vacuum oven overnight. Unreacted starting material was recovered (0.030 g). $^1$H NMR (400 MHz, DMSO-d$_6$) δ (ppm) 9.66 (s, 1H), 7.72-7.82 (m, 2H), 7.41-7.55 (m, 4H), 7.34-7.40 (m, 2H), 7.28 (d, J=7.42 Hz, 1H), 7.11-7.20 (m, 2H), 6.87 (dd, J=1.56, 6.64 Hz, 1H), 5.52 (d, J=4.69 Hz, 1H), 5.25-5.34 (m, 1H), 3.38-3.48 (m, 1H), 3.23-3.31 (m, 1H); $^{19}$F NMR (376 MHz, DMSO-d$_6$) δ (ppm) -124.4; MS (ESI): m/z 349.2 [M+1]$^+$.

Example 54

4-((2-(4-Fluorophenylamino)-[1,2,4]triazolo[1,5-a]pyridin-5-yl)methyl)piperidin-4-ol

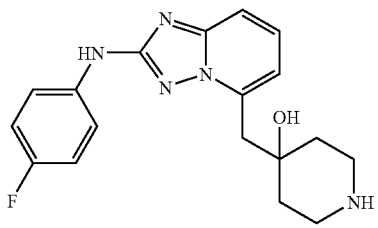

A. tert-Butyl 4-((2-(4-fluorophenylamino)-[1,2,4]triazolo[1,5-a]pyridin-5-yl)methyl)-4-hydroxypiperidine-1-carboxylate. A suspension of N-(4-fluorophenyl)-5-methyl-[1,2,4]triazolo[1,5-a]pyridin-2-amine (0.15 g, 0.619 mmol) in diethyl ether (2.064 mL) was cooled to 0° C. A solution of n-butyl lithium in hexanes (0.508 mL, 1.269 mmol) was then added dropwise. The reaction turned into a thick brown suspension. The reaction was stirred at 0° C. for 30 min followed by 30 min at room temperature. The temperature was cooled back to 0° C. before adding tert-butyl 4-oxopiperidine-1-carboxylate (0.123 g, 0.619 mmol) as a solution in diethyl ether (2.064 mL). After 30 min at 0° C., the temperature was slowly allowed to reach room temperature and the reaction was stirred overnight. The reaction was quenched with water and the crude product was extracted with ethyl acetate. The extracts were dried over sodium sulfate and evaporated to dryness. The green oily residue was purified by silica gel column chromatography (eluting with 0-50% ethyl acetate in hexanes). The desired fractions were combined and evaporated to dryness to afford tert-butyl 4-((2-(4-fluorophenylamino)-[1,2,4]triazolo[1,5-a]pyridin-5-yl)methyl)-4-hydroxypiperidine-1-carboxylate (0.109 g, 0.247 mmol, 39.9% yield) as a white solid dried under vacuum. $^1$H NMR (400 MHz, METHANOL-d$_4$) δ (ppm) 7.57-7.64 (m, 2H), 7.48-7.54 (m, 1H), 7.36 (d, J=7.42 Hz, 1H), 6.98-7.06 (m, 2H), 6.93 (d, J=7.03 Hz, 1H), 3.74-3.83 (m, 2H), 3.37-3.43 (m, 2H), 3.05-3.21 (m, 2H), 1.63-1.74 (m, 2H), 1.49-1.60 (m, 2H), 1.38-1.44 (m, 8H), 1.31-1.34 (m, 1H), 1.26-1.30 (m, 1H); MS (ESI): m/z 442.5 [M+1]$^+$.

B. 4-((2-(4-Fluorophenylamino)-[1,2,4]triazolo[1,5-a]pyridin-5-yl)methyl)piperidin-4-ol. tert-Butyl 4((2-(4-fluorophenylamino)-[1,2,4]triazolo[1,5-a]pyridin-5-yl)methyl)-4-hydroxypiperidine-1-carboxylate (0.109 g, 0.247 mmol) was dissolved in dichloromethane (5 mL) and treated at room temperature with neat trifluoroacetic acid (1.5 mL, 19.47 mmol). The reaction was stirred at room temperature for 30 min. The solvents were removed under reduced pressure yielding a yellow oil. The material was purified by semi-preparative HPLC (1 injection using 20-80 and 3 injections using 10-50% acetonitrile+0.1% trifluoroacetic acid in water+0.1% trifluoroacetic acid, 30 min). The desired fractions were combined and neutralized with a resin exchange column. 4-((2-(4-Fluorophenylamino)-[1,2,4]triazolo[1,5-a]pyridin-5-yl)methyl)piperidin-4-ol (0.073 g, 0.214 mmol, 87% yield) was isolated as a white solid. $^1$H NMR (400 MHz, DMSO-d$_6$) δ (ppm) 9.61 (s, 1H), 7.67-7.77 (m, 2H), 7.47-

7.56 (m, 1H), 7.39-7.47 (m, 1H), 7.08-7.18 (m, 2H), 6.96 (d, J=5.86 Hz, 1H), 4.64 (s, 1H), 3.29 (s, 2H), 2.69-2.79 (m, 2H), 2.57-2.69 (m, 2H), 1.42-1.55 (m, 2H), 1.32-1.42 (m, 2H); $^{19}F$ NMR (376 MHz, DMSO-$d_6$) δ (ppm)-124.5; MS (ESI): m/z 342.2 [M+1]$^+$.

Example 55

$N^1$-(4-(2-(Phenylamino)-[1,2,4]triazolo[1,5-a]pyridin-5-yl)pyridin-2-yl)ethane-1,2-diamine

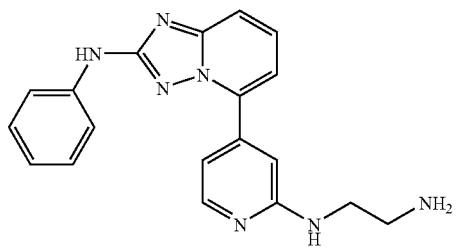

A. 5-(2-Fluoropyridin-4-yl)-N-phenyl-[1,2,4]triazolo[1,5-a]pyridin-2-amine. 5-Bromo-N-phenyl-[1,2,4]triazolo[1,5-a]pyridin-2-amine (0.44 g, 1.522 mmol), 2-fluoropyridin-4-ylboronic acid (0.257 g, 1.826 mmol), 1M sodium carbonate (4.57 mL, 4.57 mmol), dichloro[1,1'-bis(diphenylphosphino)ferrocene]palladium(II) dichloromethane adduct (0.037 g, 0.046 mmol), and dioxane (10 mL) were heated to 100° C. for 5 h under nitrogen. The reaction was cooled to room temperature, diluted with water and then filtered. The solid was rinsed with methanol to give 5-(2-fluoropyridin-4-yl)-N-phenyl-[1,2,4]triazolo[1,5-a]pyridin-2-amine (0.29 g, 62% yield) as a green solid. $^1$H NMR (400 MHz, DMSO-$d_6$) δ (ppm) 9.76 (s, 1H), 8.50 (d, J=5.1 Hz, 1H), 8.09 (d, J=5.1 Hz, 1H), 8.00 (s, 1H), 7.67-7.78 (m, 4H), 7.48 (dd, J=6.2, 2.3 Hz, 1H), 7.28 (t, J=8.0 Hz, 2H), 6.89 (t, J=7.2 Hz, 1H). MS (ESI) m/z 306.1 [M+1]$^+$.

B. $N^1$-(4-(2-(Phenylamino)-[1,2,4]triazolo[1,5-a]pyridin-5-yl)pyridin-2-yl)ethane-1,2-diamine. 5-(2-Fluoropyridin-4-yl)-N-phenyl-[1,2,4]triazolo[1,5-a]pyridin-2-amine (90 mg, 0.295 mmol), N,N-dimethylformamide (1.5 mL), and ethane-1,2-diamine (0.030 mL, 0.442 mmol) were heated to 80° C. for 16 h under nitrogen. The reaction was purified on reverse-phase HPLC (10-70% acetonitrile+0.1% trifluoroacetic acid in water+0.1% trifluoroacetic acid, over 30 min). The product fractions were past through Strata column to remove trifluoroacetic acid and then released with 2M ammonia in methanol to give $N^1$-(4-(2-(phenylamino)-[1,2,4]triazolo[1,5-a]pyridin-5-yl)pyridin-2-yl)ethane-1,2-diamine (96 mg, 32% yield) as a white solid. $^1$H NMR (400 MHz, DMSO-$d_6$) δ (ppm) 9.69 (s, 1H), 8.15 (d, J=5.5 Hz, 1H), 7.69 (dd, J=8.6, 1.2 Hz, 2H), 7.60-7.67 (m, 2H), 7.27 (t, J=7.8 Hz, 2H), 7.20 (dd, J=6.4, 2.1 Hz, 1H), 7.10 (s, 1H), 6.99-7.04 (m, 1H), 6.87 (t, J=7.2 Hz, 1H), 6.80 (t, J=5.5 Hz, 1H), 3.30 (d, J=6.4 Hz, 2H), 2.73 (t, J=6.4 Hz, 2H). MS (ESI) m/z 346.0 [M+1]$^+$.

Example 56

3-((2-(Phenylamino)-[1,2,4]triazolo[1,5-a]pyridin-5-yl)methyl)benzamide

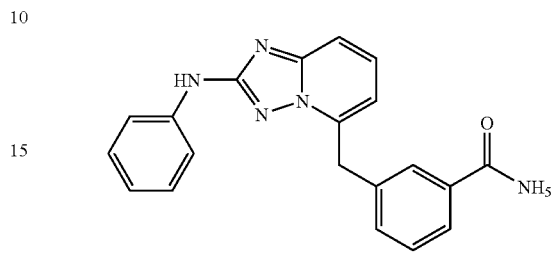

A. 3-((2-(Phenylamino)-[1,2,4]triazolo[1,5-a]pyridin-5-yl)methyl)benzonitrile. Preparation of organozinc suspension: Under an atmosphere of nitrogen, zinc powder (0.654 g, 10.000 mmol) was suspended in tetrahydrofuran (3 mL) and treated with 1,2-dibromoethane (0.080 mL, 0.865 mmol). The mixture was heated to reflux temperature for 5 min and cooled to room temperature. Trimethylsilyl chloride (0.120 mL, 0.940 mmol) was then added neat followed by a solution of 3-(bromomethyl)benzonitrile (0.980 g, 5.000 mmol) in tetrahydrofuran (20 mL) over 15 min. The reaction was stirred at room temperature for 20 min. Under an atmosphere of nitrogen was weighed palladium tetrakistriphenylphosphine (0.5 g, 0.433 mmol) and 5-bromo-N-phenyl-[1,2,4]triazolo[1,5-a]pyridin-2-amine (0.25 g, 0.865 mmol). Tetrahydrofuran (10 mL) was added followed by 20 mL of the organozinc solution described above. The reaction was stirred at 65° C. for 1 h resulting in about 50% conversion based on LCMS trace. The rest of the organozinc suspension was then added and the reaction was stirred at reflux temperature of the solvent overnight. As the conversion was complete, the reaction was quenched with saturated sodium bicarbonate and extracted with ethyl acetate. The extracts were dried over sodium sulfate and evaporated to dryness. Purification was effected by silica gel column chromatography using 50% ethyl acetate in hexanes. 3-((2-(Phenylamino)-[1,2,4]triazolo[1,5-a]pyridin-5-yl)methyl)benzonitrile (0.150 g, 0.461 mmol, 53.3% yield) contaminated with a trace amount of reduction product was isolated as a yellow oil that was used without further purification. MS (ESI): m/z 326.1 [M+1]$^+$.

B. 3-((2-(Phenylamino)-[1,2,4]triazolo[1,5-a]pyridin-5-yl)methyl)benzamide. To a suspension of 3-((2-(phenylamino)-[1,2,4]triazolo[1,5-a]pyridin-5-yl)methyl)benzonitrile (0.150 g, 0.461 mmol) in ethanol (3.0 mL) was added dropwise at room temperature hydrogen peroxide (3.0 mL, 98 mmol) and a 6.0 N aqueous solution of sodium hydroxide (0.03 mL, 0.180 mmol). The suspension was then heated to 45° C. for 2 h. The reaction was cooled to room temperature and treated with 0.05 mL of 6.0 N aqueous HCl solution. Water was added (20 mL) and the resulting precipitate was collected and washed with water. The product, dissolved in 6 mL of dimethylsulfoxide, was purified by semi-preparative HPLC (20-80% then 30-80% acetonitrile+0.1% trifluoroacetic acid in water+0.1% trifluoroacetic acid, 30 min, 4 injections). The desired fractions were neutralized with a 1.75 M aqueous solution of potassium carbonate. The product precipitated out upon removing acetonitrile. The precipitate was collected by filtration and washed with water until the pH of the washings became neutral. 3-((2-(Phenylamino)-[1,2,4]triazolo[1,5-a]pyridin-5-yl)methyl)benzamide (0.055 g, 0.160 mmol, 34.7% yield) was isolated as an off-white solid. $^1$H NMR (400 MHz, DMSO-$d_6$) δ (ppm) 9.60 (br s, 1H), 7.95 (d, J=16.40 Hz, 2H), 7.62-7.81 (m, 3H), 7.08-7.59 (m, 7H), 6.88 (d, J=6.64 Hz, 2H), 3.35 (s, 2H); MS (ESI): m/z 344.3 [M+1]$^+$.

Example 57

3-(2-(1-Methyl-1H-benzo[d][1,2,3]triazol-6-ylamino)-[1,2,4]triazolo[1,5-a]pyridin-5-yl)phenol

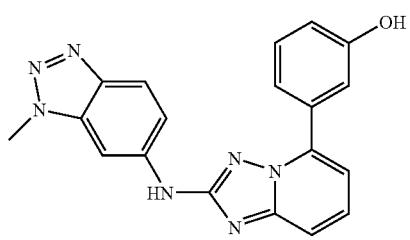

A. N-(5-(3-methoxyphenyl)-[1,2,4]triazolo[1,5-a]pyridin-2-yl)-1-methyl-1H-benzo[d][1,2,3]triazol-6-amine. A degassed mixture of 6-bromo-1-methyl-1H-benzo[d][1,2,3]triazole (126 mg 0.6 mmol), 5-(3-methoxyphenyl)-[1,2,4]triazolo[1,5-a]pyridin-2-amine (144 mg, 0.6 mmol), 4,5-bis(diphenylphosphino)-9,9-dimethyl xanthene (69 mg, 0.12 mmol) and cesium carbonate (390 mg, 1.2 mmol) in dioxane (3 mL) was added tris(dibenzylideneacetone)palladium(0) (55 mg 0.06 mmol) under nitrogen, and the mixture was heated at 100° C. with stirring under nitrogen overnight. The mixture was filtered, and washed with water (20 mL), followed by washing with methanol (20 mL) to give the crude N-(5-(3-methoxyphenyl)-[1,2,4]triazolo[1,5-a]pyridin-2-yl)-1-methyl-1H-benzo[d][1,2,3]triazol-6-amine (80 mg, 36% yield), which was used in the next step without further purification. MS (ESI): m/z 372.0 [M+1]$^+$.

B. 3-(2-(1-Methyl-1H-benzo[d][1,2,3]triazol-6-ylamino)-[1,2,4]triazolo[1,5-a]pyridin-5-yl)phenol. A mixture of N-(5-(3-methoxyphenyl)-[1,2,4]triazolo[1,5-a]pyridin-2-yl)-1-methyl-1H-benzo[d][1,2,3]triazol-6-amine (80 mg, 0.21 mmol) and sodium iodide (65 mg, 0.42 mmol) in a solution of hydrogen bromide (6 mL, 48%) was heated at 80° C. in a sealed vessel overnight. After cooling down to room temperature, the solution was neutralized to pH=7-8 with saturated sodium bicarbonate. The precipitate was collected by filtration, which was purified by a reverse-phase preparatory HPLC (28-58%: acetonitrile+0.1% trifluoroacetic acid in water+0.1% trifluoroacetic acid, over 15 min) to give 3-(2-(1-methyl-1H-benzo[d][1,2,3]triazol-6-ylamino)-[1,2,4]triazolo[1,5-a]pyridin-5-yl)phenol as a trifluoroacetic acid salt, which was converted to a hydrochloride salt. (30 mg, 39% yield). $^1$H NMR (400 MHz, METHANOL-$d_4$) δ (ppm) 8.32 (d, J=2.0 Hz, 1H), 8.04 (t, J=8.0 Hz, 1H), 7.86 (d, J=9.2 Hz, 1H), 7.72 (d, J=8.8 Hz, 1H), 7.55 (m, 2H), 7.40 (m, 3H), 7.01 (d, J=7.2 Hz, 1H), 4.19 (s, 3H); MS (ESI): m/z 358.1 [M+1]$^+$.

Example 58

5-(2-((Methylamino)methyl)benzo[d]oxazol-6-yl)-N-phenyl-[1,2,4]triazolo[1,5-a]pyridin-2-amine

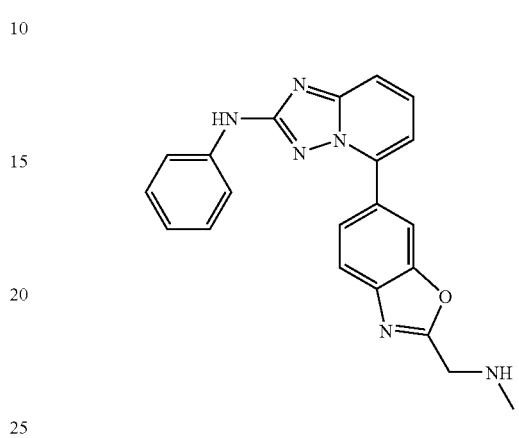

A. 5-(4-Amino-3-methoxyphenyl)-N-phenyl-[1,2,4]triazolo[1,5-a]pyridin-2-amine hydrochloride. 5-Bromo-N-phenyl-[1,2,4]triazolo[1,5-a]pyridin-2-amine (0.631 g, 2.184 mmol), 4-(tert-butoxycarbonylamino)-3-methoxyphenylboronic acid (0.7 g, 2.62 mmol), 1M sodium carbonate (6.55 mL, 6.55 mmol), dichloro[1,1'-bis(diphenylphosphino)ferrocene]palladium(II) dichloromethane adduct (0.054 g, 0.066 mmol), and dioxane (20 mL) were heated to 80° C. for 5 h under nitrogen. The reaction was concentrated and purified on silica gel column (0-70% ethyl acetate in hexanes). The product fractions were concentrated and then stirred with 4N hydrogen chloride in dioxane (4 mL) for 4 h at room temperature. The reaction was concentrated and then triturated with 10% methanol in ether to give a light yellow solid (0.56 g, 1.522 mmol, 69.7% yield). MS (ESI) m/z 332.3 [M+1]$^+$.

B. 2-Amino-5-(2-(phenylamino)-[1,2,4]triazolo[1,5-a]pyridin-5-yl)phenol. 5-(4-Amino-3-methoxyphenyl)-N-phenyl-[1,2,4]triazolo[1,5-a]pyridin-2-amine hydrochloride (0.43 g, 1.169 mmol), dichloromethane (10 mL), and 1M boron tribromide (3.51 mL, 3.51 mmol in dichloromethane) were stirred at room temperature for 20 h. The reaction was quenched with methanol and then concentrated. The residue was triturated in 10% ethyl acetate in hexanes to give a dark solid. MS (ESI) m/z 318.3 [M+1]$^+$.

C. 5-(2-((Methylamino)methyl)benzo[d]oxazol-6-yl)-N-phenyl-[1,2,4]triazolo[1,5-a]pyridin-2-amine. 2-(tert-Butoxycarbonyl(methyl)amino)acetic acid (0.143 g, 0.756 mmol), triethylamine (0.316 mL, 2.269 mmol), O-benzotriazole-N,N,N',N'-tetramethyl-uronium-hexafluoro-phosphate (0.574 g, 1.513 mmol), and N,N-dimethylformamide (3 mL) were stirred together for 15 min. Then 2-amino-5-(2-(phenylamino)-[1,2,4]triazolo[1,5-a]pyridin-5-yl)phenol (0.24 g, 0.756 mmol) was added to the reaction. The reaction was stirred at room temperature for 16 h to give the intended product already deprotected. The reaction was concentrated and then purified on silica gel column (0-100% ethyl acetate in hexanes). The product mixture was concentrated and then triturated in minimal amount of methanol and then filtered to give the intended product as a white solid (0.015 g, 0.040 mmol, 5.35% yield). $^1$H NMR (400 MHz, DMSO-$d_6$) δ

(ppm) 9.65 (s, 1H), 8.22 (d, J=1.6 Hz, 1H), 7.88 (dd, J=8.2, 1.6 Hz, 1H), 7.71 (d, J=7.8 Hz, 2H), 7.63 (d, J=7.0 Hz, 1H), 7.50-7.59 (m, 1H), 7.43 (d, J=8.2 Hz, 1H), 7.17-7.31 (m, 3H), 6.86 (t, J=7.2 Hz, 1H), 3.20 (s, 6H). MS (ESI) m/z 371.4 [M+1]⁺.

Example 59 cis-2-(4-(2-(4-(Trifluoromethyl)phenylamino)-[1,2,4]triazolo[1,5-a]pyridin-5-ylamino)cyclohexyl)propan-2-ol

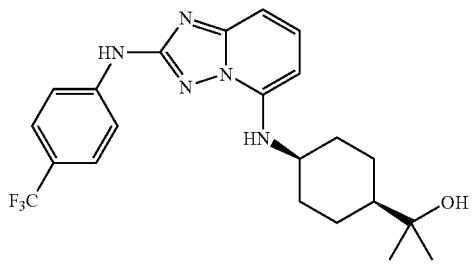

A. cis-Ethyl 4-(2-(4-(trifluoromethyl)phenylamino)-[1,2,4]triazolo[1,5-a]pyridin-5-ylamino)cyclohexanecarboxylate. 5-Bromo-N-(4-(trifluoromethyl)phenyl)-[1,2,4]triazolo[1,5-a]pyridin-2-amine (0.1 g, 0.280 mmol), cis-ethyl 4-aminocyclohexanecarboxylate hydrochloride (0.076 g, 0.364 mmol), cesium carbonate (0.274 g, 0.840 mmol), 4,5-bis(diphenylphosphino)-9,9-dimethylxanthene (0.032 g, 0.056 mmol), tris(dibezylideneacetone)palladium(0) (0.026 g, 0.028 mmol), and dioxane (5 mL) were heated to 90° C. under nitrogen for 16 h. The reaction was filtered and then concentrated. The residue was purified by silica gel chromatography (0-50% ethyl acetate in hexanes) to give a white solid (0.1 g, 0.223 mmol, 80% yield). MS (ESI) m/z 448.3 [M+1]⁺.

B. cis-2-(4-(2-(4-(Trifluoromethyl)phenylamino)-[1,2,4]triazolo[1,5-a]pyridin-5-ylamino)cyclohexyl)propan-2-ol. cis-Ethyl 4-(2-(4-(trifluoromethyl)phenylamino)-[1,2,4]triazolo[1,5-a]pyridin-5-ylamino)cyclohexanecarboxylate (0.1 g, 0.223 mmol) was dissolved in tetrahydrofuran (1 mL) and then cooled in −78° C. under nitrogen. Methylmagnesium bromide (0.745 mL, 2.235 mmol, 3M in diethyl ether) was added and the reaction was allowed to warm to room temperature over 18 h. The reaction was quenched with saturated ammonium chloride and then extracted with ethyl acetate. The organic layer was dried over magnesium sulfate, filtered, and then concentrated. The residue was purified on reverse phase HPLC (10-100% acetonitrile and water with 0.1% trifluoroacetic acid). The product fractions were past through ion-exchange column and then release with 2M ammonia in methanol. The eluent was concentrated and then triturated in hexanes to give a white solid (0.045 g, 0.104 mmol, 46.5% yield). ¹H NMR (400 MHz, DMSO-d₆) δ (ppm) 10.12 (s, 1H), 7.89 (m, J=8.6 Hz, 2H), 7.60 (m, J=8.6 Hz, 2H), 7.48 (t, J=8.4 Hz, 1H), 6.83 (d, J=8.6 Hz, 1H), 6.25 (d, J=7.8 Hz, 1H), 5.89 (d, J=8.2 Hz, 1H), 4.16 (s, 1H), 3.97 (br s, 1H), 1.98 (d, J=12.9 Hz, 2H), 1.71 (d, J=12.9 Hz, 2H), 1.62 (t, J=13.1 Hz, 2H), 1.18-1.40 (m, 3H), 1.08 (s, 6H). MS (ESI) m/z 434.5 [M+1]⁺.

Example 60

N⁶-(5-Phenyl-[1,2,4]triazolo[1,5-a]pyridin-2-yl)-N³-(piperidin-4-yl)-1H-indazole-3,6-diamine

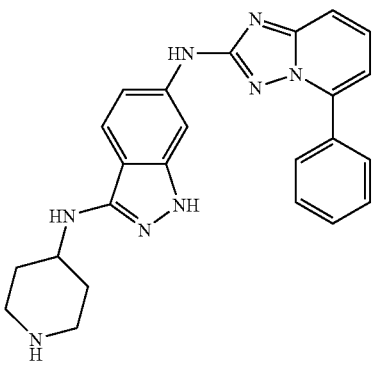

A. 2-Fluoro-4-(5-phenyl-[1,2,4]triazolo[1,5-a]pyridin-2-ylamino)benzonitrile. A mixture of 5-phenyl-[1,2,4]triazolo[1,5-a]pyridin-2-amine (300 mg, 1.43 mmol), 4-bromo-2-fluorobenzonitrile (314 mg, 1.57 mmol), cesium carbonate (928 mg, 2.86 mmol), tris(dibenzylideneacetone)dipalladium(0) (240 mg, 0.28 mmol) and 4,5-bis(diphenylphosphino)-9,9-dimethylxanthene (324 mg, 0.56 mmol) in dioxane (10 mL) was heated at 120° C. under nitrogen overnight. After cooling to room temperature, the reaction mixture was filtered, and the filtrate was evaporated under reduced pressure. The residue was purified by preparative TLC to give 2-fluoro-4-(5-phenyl-[1,2,4]triazolo[1,5-a]pyridin-2-ylamino)benzonitrile (38 mg, 8% yield) as a solid. ¹H-NMR (300 MHz, DMSO-d₆) δ (ppm) 10.66 (s, 1H), 8.00 (d, J=3.9 Hz, 2H), 7.92 (m, 1H), 7.74 (m, 3H), 7.57 (m, 3H). 7.46 (d, J=9.0 Hz, 1H), 7.27 (m, 1H); MS (ESI): m/z 330.1 [M+1]⁺.

B. N⁶-(5-Phenyl-[1,2,4]triazolo[1,5-a]pyridin-2-yl)-1H-indazole-3,6-diamine. A mixture of 2-fluoro-4-(5-phenyl-[1,2,4]triazolo[1,5-a]pyridin-2-ylamino)benzonitrile (200 mg, 0.61 mmol) and hydrazine hydrate (0.10 mL) in n-butanol (4 mL) was stirred at 120° C. under nitrogen overnight. After cooling to room temperature, the precipitate was collected by filtration, washed with methanol, and dried in vacuo to give N⁶-(5-phenyl-[1,2,4]triazolo[1,5-a]pyridin-2-yl)-1H-indazole-3,6-diamine (60 mg, 29% yield) as a white solid. ¹H NMR (400 MHz, DMSO-d₆) δ (ppm) 11.11 (br s, 1H), 9.67 (br s, 1H), 8.04 (d, J=7.2 Hz, 2H), 7.81 (s, 1H), 7.62 (m, 5H), 7.46 (d, J=6.8 Hz, 1H), 7.18 (d, J=6.8 Hz, 1H), 6.98 (d, J=8.4 Hz, 1H), 5.15 (br s, 2H); MS (ESI): m/z 341.9 [M+1]⁺.

C. tert-Butyl 4-(6-(5-phenyl-[1,2,4]triazolo[1,5-a]pyridin-2-ylamino)-1H-indazol-3-ylamino)piperidine-1-carboxylate. To a mixture of N⁶-(5-phenyl-[1,2,4]triazolo[1,5-a]pyridin-2-yl)-1H-indazole-3,6-diamine (350 mg, 1.02 mmol) in a mixture of acetic acid and methanol (1:20, 40 mL) was added tert-butyl 4-oxopiperidine-1-carboxylate (300 mg, 1.5 mmol), and the mixture was stirred at room temperature for 10 min. The mixture was chilled to 0° C., and sodium cyanoborohydride (130 mg, 2.01 mmol) was added. The reaction mixture was stirred at room temperature overnight, concentrated under reduced pressure, and purified on silica gel column (eluting with 30% ethyl acetate in petroleum ether)

and a reverse-phase preparative HPLC (30-60% acetonitrile+ 0.1% trifluoroacetic acid in water+0.1% trifluoroacetic acid) to give the desired tert-butyl 4-(6-(5-phenyl-[1,2,4]triazolo [1,5-a]pyridin-2-ylamino)-1H-indazol-3-ylamino)piperidine-1-carboxylate (70 mg, 13% yield) as a solid. MS (ESI): m/z 525.1 [M+1]$^+$.

D. N$^6$-(5-Phenyl-[1,2,4]triazolo[1,5-a]pyridin-2-yl)-N$^3$-(piperidin-4-yl)-1H-indazole-3,6-diamine. A solution of tert-butyl 4-(6-(5-phenyl-[1,2,4]triazolo[1,5-a]pyridin-2-ylamino)-1H-indazol-3-ylamino)piperidine-1-carboxylate (70 mg, 0.13 mmol) in methanolic hydrochloride solution (2 M, 5 mL) was stirred at room temperature for 1 h. The resulting mixture was concentrated under reduced pressure to give N$^6$-(5-phenyl-[1,2,4]triazolo[1,5-a]pyridin-2-yl)-N$^3$-(piperidin-4-yl)-1H-indazole-3,6-diamine as a hydrochloride salt (55 mg, 98% yield). $^1$H NMR (300 MHz, DMSO-d$_6$) δ (ppm) 12.84 (br s, 1H), 10.31 (s, 1H), 9.16 (br s, 2H), 8.07 (m, 4H), 7.73 (m, 5H), 7.28 (m, 2H), 3.41 (m, 2H), 3.03 (m, 2H), 2.19 (m, 2H), 1.73 (m, 2H); MS (ESI): m/z 425.1 [M+1]$^+$.

Example 61

N$^6$-(5-Phenyl-[1,2,4]triazolo[1,5-a]pyridin-2-yl)quinoline-2,6-diamine

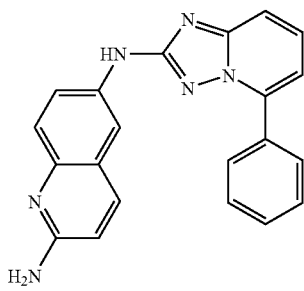

A. N$^6$-(5-Phenyl-[1,2,4]triazolo[1,5-a]pyridin-2-yl)quinoline-2,6-diamine. N$^2$-(4-methoxy-benzyl)-N$^6$-(5-phenyl-[1,2,4]triazolo[1,5-a]pyridin-2-yl)-quinoline-2,6-diamine was prepared following the same procedure as for the preparation of 5-phenyl-N-(1-(tetrahydro-2H-pyran-2-yl)-1H-indazol-6-yl)-[1,2,4]triazolo[1,5-a]pyridin-2-amine from 2-bromo-5-phenyl-[1,2,4]triazolo[1,5-a]pyridine and N$^2$-(4-methoxybenzyl)quinoline-2,6-diamine, using potassium tert-butoxide as base and heating to 100° C. A solution of N$^2$-(4-methoxy-benzyl)-N$^6$-(5-phenyl-[1,2,4]triazolo[1, 5-a]pyridin-2-yl)-quinoline-2,6-diamine (40 mg, 0.085 mmol) in trifluoroacetic acid (10 mL) was stirred at 50° C. for 1 h. The reaction mixture was evaporated under reduced pressure, and the residue was purified by a reverse-phase preparative HPLC (eluting with 31-61% acetonitrile+0.1% trifluoroacetic acid in water+0.1% trifluoroacetic acid, over 10 min) to give N$^6$-(5-phenyl-[1,2,4]triazolo[1,5-a]pyridin-2-yl)quinoline-2,6-diamine (28 mg, 93% yield), which was converted to a hydrochloride salt as a yellow solid. $^1$H NMR (400 MHz, METHANOL-d$_4$) δ (ppm) 8.22 (s, 1H), 8.16 (m, 4H), 7.91 (d, J=8.8 Hz, 1H), 7.81 (d, J=8.8 Hz, 1H), 7.69 (m, 5H), 7.11 (d, J=9.2 Hz, 1H); MS (ESI): m/z 353.1 [M+1]$^+$.

Example 62 cis-4-(2-(4-Fluorophenylamino)-[1,2,4]triazolo[1,5-a]pyridin-5-yloxy)cyclohexanol

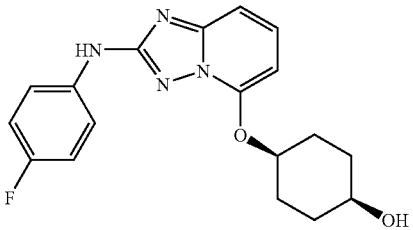

A. 2,5-Dibromo-[1,2,4]triazolo[1,5-a]pyridine. To 5-bromo-[1,2,4]triazolo[1,5-a]pyridin-2-amine (2 g, 9.39 mmol) was added 48% hydrobromic acid (20 mL). The white suspension was stirred for 5 min and cooled to 0° C. Sodium nitrate (1.943 g, 28.2 mmol) in water (9 mL) was added slowly (a brown gas was generated). After the addition was completed, the brown suspension was stirred at 0° C. for 30 min, and then allowed to warm to room temperature. Copper (I) bromide (2.69 g, 18.78 mmol) in 48% hydrobromic acid solution (10 mL) was added in and the reaction mixture turned into a black suspension. It was stirred at room temperature for 3 h and water (100 mL) was added. The reaction mixture was filtered through celite and the aqueous layer was extracted with ethyl acetate (3×100 mL). The combined organic layers were washed with sodium bicarbonate (100 mL, saturated solution) and brine (100 mL), dried over magnesium sulfate, filtered and concentrated to give 2,5-dibromo-[1,2,4]triazolo[1,5-a]pyridine (1.8 g, 69.2% yield) as a light yellow solid. $^1$H NMR (400 MHz, CHLOROFORM-d) δ (ppm) 7.70 (d, J=8.59 Hz, 1H), 7.42-7.53 (m, 1H), 7.33 (d, J=7.03 Hz, 1H). MS (ESI): m/z 278.2 [M+1]$^+$.

B. cis-2-Bromo-5-(4-(tert-butyldimethylsilyloxy)cyclohexyloxy)-[1,2,4]triazolo[1,5-a]pyridine. To a solution of cis-4-(tert-butyldimethylsilyloxy)cyclohexanol (200 mg, 0.87 mmol) in N,N-dimethylformamine (5 mL) was added sodium hydride (52 mg, 1.31 mmol) in portions at 0° C. After the addition, the mixture was stirred at room temperature for 1 h. 2,5-Dibromo-[1,2,4]triazolo[1,5-a]pyridine (239 mg, 0.87 mmol) was added, and the resulting mixture was stirred at room temperature overnight. Water was added, and the solution was extracted with ethyl acetate. The combined organic layer was concentrated, washed twice with saturated sodium chloride solution, dried over anhydrous sodium sulfate, and concentrated. The residue was purified by preparative TLC (eluting with 30% ethyl acetate in petroleum ether) to give cis-2-bromo-5-(4-(tert-butyldimethylsilyloxy)cyclohexyloxy)-[1,2,4]triazolo[1,5-c]pyridine (115 mg, 31.1% yield) as a solid. $^1$H NMR (400 MHz, DMSO-d$_6$) δ (ppm) 7.68 (t, J=8.4 Hz, 1H), 7.33 (d, J=8.8 Hz, 1H), 6.81 (d, J=8.0 Hz, 1H), 4.84 (m, 1H), 3.88 (m, 1H), 1.92 (m, 4H), 1.64 (m, 4H), 0.87 (s, 1H), 0.04 (s, 6H); MS (ESI): m/z 426.0 [M+1]$^+$.

C. cis-5-(4-(tert-Butyldimethylsilyloxy)cyclohexyloxy)-N-(4-fluorophenyl)-[1,2,4]triazolo[1,5-a]pyridin-2-amine. A mixture of cis-2-bromo-5-(4-(tert-butyldimethylsilyloxy)cyclohexyloxy)-[1,2,4]triazolo[1,5-a]pyridine (110 mg, 0.26 mmol), 4-fluoro-phenylamine (35 mg, 0.31 mmol), 4,5-bis(diphenylphosphino)-9,9-dimethylxanthene (30 mg, 0.052 mmol) and potassium tert-butoxide (58 mg, 0.52 mmol) in dioxane (10 mL) was degassed, and tris(dibenzylideneacetone)dipalladium(0) (24 mg, 0.026 mmol) was added under nitrogen. The mixture was stirred at 100° C. under nitrogen overnight. After concentration, the residue was diluted with methanol and filtered. The filtrate was concentrated under reduced pressure and purified by preparative TLC (eluting with 30% ethyl acetate in petroleum ether) to give cis-5-(4-(tert-butyldimethylsilyloxy)cyclohexyloxy)-N-(4-fluorophenyl)-[1,2,4]triazolo[1,5-c]pyridin-2-amine (110 mg, 93.2% yield) as a solid. MS (ESI): m/z 457.3 [M+1]$^+$.

D. cis-4-(2-(4-Fluorophenylamino)-[1,2,4]triazolo[1,5-a]pyridin-5-yloxy)cyclohexanol. A solution of cis-5-(4-(tert-butyldimethylsilyloxy)cyclohexyloxy)-N-(4-fluorophenyl)-[1,2,4]triazolo[1,5-a]pyridin-2-amine (100 mg, 0.22 mmol) in methanolic hydrochloride solution (2 M, 20 mL) was stirred at 50° C. for 10 min. The solution was concentrated under reduced pressure, and the residue was purified by a reverse-phase preparatory HPLC (30-60% acetonitrile+0.1% trifluoroacetic acid in water+0.1% trifluoroacetic acid, over 10 min) to give cis-4-(2-(4-fluorophenylamino)-[1,2,4]triazolo[1,5-a]pyridin-5-yloxy)cyclohexanol as a trifluoroacetic acid salt, which was converted to a hydrochloride salt (58 mg, 77.3% yield). $^1$H NMR (400 MHz, METHANOL-d$_4$) δ (ppm) 7.99 (t, J=8.4 Hz, 1H), 7.66 (m, 2H), 7.29 (d, J=8.4 Hz, 1H), 7.17 (t, J=8.8 Hz, 2H), 7.06 (d, J=8.4 Hz, 1H), 5.03 (m, 1H), 3.82 (m, 1H), 2.19 (m, 2H), 1.91 (m, 6H); MS (ESI): m/z 343.1 [M+1]$^+$.

Example 63

3-(2-(4-(Aminomethyl)phenylamino)-[1,2,4]triazolo[1,5-a]pyridin-5-yl)phenol

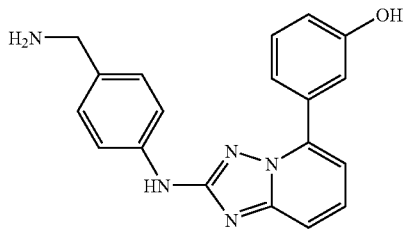

A. 4-(5-(3-Hydroxyphenyl)-[1,2,4]triazolo[1,5-a]pyridin-2-ylamino)benzonitrile. To a degassed mixture of 4-(5-bromo-[1,2,4]triazolo[1,5-a]pyridin-2-ylamino)benzonitrile (160 mg, 0.51 mmol) and 3-hydroxyphenylboronic acid (99 mg, 0.72 mmol) in dimethylsulfoxide (5 mL) were added tetrakis(triphenylphosphine)palladium(0) (59 mg, 0.05 mmol) and potassium phosphate (0.5 mL, 2 M). The mixture was refluxed under nitrogen overnight. After cooling down to room temperature, the reaction mixture was filtered, the filtrate was concentrated under reduced pressure to give the crude product, which was purified by preparative TLC (eluting with 2% methanol in dichloromethane) to give 4-(5-(3-hydroxyphenyl)-[1,2,4]triazolo[1,5-a]pyridin-2-ylamino)benzonitrile (60 mg, 36% yield) as a solid. $^1$H-NMR (400 MHz, DMSO-d$_6$) δ (ppm) 10.22 (s, 1H), 9.68 (s, 1H), 7.73 (m, 1H), 7.537 (m, 6H), 7.27 (m, 2H), 7.06 (m, 1H), 6.85 (m, 1H); MS (ESI): m/z 328.1 [M+1]$^+$.

B. 3-(2-(4-(Aminomethyl)phenylamino)-[1,2,4]triazolo[1,5-a]pyridin-5-yl)phenol.

A mixture of 4-(5-(3-hydroxyphenyl)-[1,2,4]triazolo[1,5-a]pyridin-2-ylamino)benzonitrile (60 mg, 0.18 mmol) and Raney-Ni (20 mg) in methanol (10 mL) was hydrogenated under 1 atm of hydrogen for 1 h. The catalyst was filtered off, and the filtrate was concentrated. The residue was purified by a reverse-phase preparatory HPLC (10-65% acetonitrile+0.1% trifluoroacetic acid in water+0.1% trifluoroacetic acid, over 15 min) to give 3-(2-(4-(aminomethyl)phenylamino)-[1,2,4]triazolo[1,5-a]pyridin-5-yl)phenol as a trifluoroacetic acid salt, which was converted to the hydrochloride salt (45 mg, 74% yield) with methanolic hydrochloride solution. $^1$H-NMR (400 MHz, DMSO-d$_6$) δ (ppm) 9.78 (s, 1H), 8.14 (br s, 2H), 7.70 (m, 2H), 7.57 (m, 1H), 7.63 (m, 1H), 7.39 (m, 5H), 7.13 (m, 1H), 6.95 (m, 1H), 3.91 (s, 2H); MS (ESI): m/z 332.1 [M+1]$^+$.

Example 64

N-Phenyl-5-(2-(pyrrolidin-1-ylmethyl)-1H-benzo[d]imidazol-6-yl)-[1,2,4]triazolo[1,5-a]pyridin-2-amine

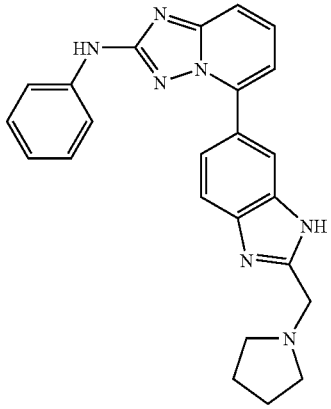

A. 2-(Pyrrolidin-1-yl)acetic acid. 2-Chloroacetic acid (3.66 g, 38.7 mmol), 1M sodium hydroxide (77 mL, 77 mmol), and pyrrolidine (3.20 mL, 38.7 mmol) were stirred together at room temperature for 3 days. The reaction was concentrated and the residue was filtered with hot ethanol. The filtrate was concentrated and then triturated with ethyl acetate to give 2-(pyrrolidin-1-yl)acetic acid (4.4 g, 88% yield) as a white solid. MS (ESI) m/z 130.1 [M+1]$^+$.

B. N-Phenyl-5-(2-(pyrrolidin-1-ylmethyl)-1H-benzo[d]imidazol-6-yl)-[1,2,4]triazolo[1,5-a]pyridin-2-amine. 2-(Pyrrolidin-1-yl)acetic acid (0.104 g, 0.806 mmol), O-benzotriazole-N,N,N',N'-tetramethyl-uronium-hexafluorophosphate (0.224 g, 0.591 mmol), triethylamine (0.225 mL, 1.612 mmol), and acetonitrile (3 mL) were stirred at room temperature for 10 min. 4-(2-(Phenylamino)-[1,2,4]triazolo[1,5-a]pyridin-5-yl)benzene-1,2-diamine (0.17 g, 0.537 mmol) was added to the reaction and then stirred at room temperature for 16 h. A solid was filtered off from the reaction, and the filtrate concentrated. The residue from the filtrate was added with 50% trifluoroacetic acid in glacial acetic acid and then heated in the microwave (200° C., 20 min). The reaction was concentrated and then purified on reverse-phase HPLC (eluting with 5-40% acetonitrile and water+0.1% trifluoroacetic acid). The product fractions were past through Strata column to remove trifluoroacetic acid. The basic product was released from the column with 2M ammonia in methanol to give N-phenyl-5-(2-(pyrrolidin-1-ylmethyl)-1H-benzo[d]imidazol-6-yl)-[1,2,4]triazolo[1,5-a]pyridin-2-amine (0.027 g, 12% yield) as a white solid. $^1$H NMR (400

MHz, DMSO-$d_6$) δ (ppm) 9.63 (s, 1H), 7.70 (dd, J=8.6, 1.2 Hz, 2H), 7.67 (d, J=7.4 Hz, 1H), 7.64 (d, J=7.0 Hz, 1H), 7.52-7.58 (m, 1H), 7.25 (t, J=7.8 Hz, 2H), 7.20 (dd, J=7.4 Hz, 1.2, 1H), 6.85 (t, J=7.2 Hz, 1H), 3.89 (s, 2H), 2.53-2.62 (m, 4H), 1.76 (ddd, J=6.4 Hz, 3.1, 2.9, 4H). MS (ESI) m/z 410.4 [M+1]$^+$.

Example 65

6-(5-Phenyl-[1,2,4]triazolo[1,5-a]pyridin-2-ylamino)quinolin-2-ol

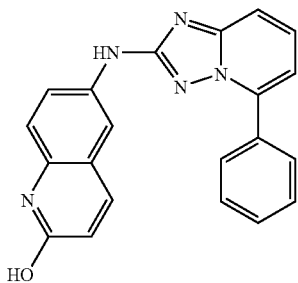

A. 6-(5-Phenyl-[1,2,4]triazolo[1,5-a]pyridin-2-ylamino)quinolin-2-ol. 2-Methoxy-N-(5-phenyl-[1,2,4]triazolo[1,5-a]pyridin-2-yl)quinolin-6-amine was synthesized from 5-phenyl-[1,2,4]triazolo[1,5-a]pyridin-2-amine and 6-bromo-2-methoxy-quinoline according to the procedure described for N-(5-diphenyl-[1,2,4]triazolo[1,5-a]pyridin-2-amine. A mixture of 2-methoxy-N-(5-phenyl-[1,2,4]triazolo[1,5-a]pyridin-2-yl)quinolin-6-amine (90 mg, 0.24 mmol) in concentrated hydrochloric acid (12 M, 20 mL) was stirred at 100° C. overnight. The mixture was evaporated in vacuo to give 6-(5-phenyl-[1,2,4]triazolo[1,5-a]pyridin-2-ylamino)quinolin-2-ol as a hydrochloride salt (66 mg, 78% yield). $^1$H NMR (400 MHz, DMSO-$d_6$) δ (ppm) 11.62 (br s, 1H), 9.72 (s, 1H), 8.06 (m, 3H), 7.73 (d, J=9.2 Hz, 1H), 7.60 (m, 6H), 7.21 (m, 2H), 6.47 (d, J=9.2 Hz, 1H); MS (ESI): m/z 354.0 [M+1]$^+$.

Example 66

4-(5-(3-Carbamoylphenyl)-[1,2,4]triazolo[1,5-a]pyridin-2-ylamino)-N-methylbenzamide

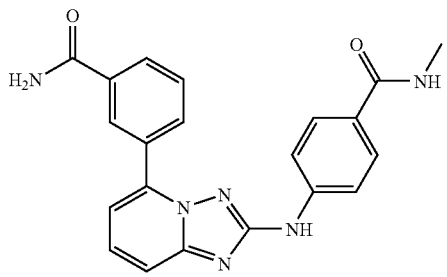

A. 4-(5-(3-Carbamoylphenyl)-[1,2,4]triazolo[1,5-a]pyridin-2-ylamino)-N-methylbenzamide. A mixture of 4-(5-bromo-[1,2,4]triazolo[1,5-a]pyridin-2-ylamino)-N-methylbenzamide (200 mg, 0.58 mmol), 3-(4,4,5,5-tetramethyl-1,3,2-dioxaborolan-2-yl)benzonitrile (102 mg, 0.69 mmol), tetrakis(triphenylphosphine) palladium (100 mg, 0.09 mmol) and aqueous sodium carbonate solution (2 M, 0.625 mL, 1.3 mmol) in 1,2-dimethoxyethane (5 mL) was degassed for three times, and stirred at 80° C. under nitrogen overnight. The solvent was removed under reduced pressure, and the residue was washed with ethyl acetate. The solid was dissolved in dimethylsulfoxide (3 mL), followed by the addition of hydrogen peroxide (1.0 mL, 30%) and potassium carbonate (160 mg, 1.16 mmol). The mixture was stirred at room temperature overnight, poured into water (20 mL), and extracted with ethyl acetate (15×3). The combined organic layer was dried over sodium sulfate, concentrated in vacuo to give the crude product, which was washed with ethyl acetate, and purified by a reverse-phase preparatory HPLC (35-65%: acetonitrile+0.1% trifluoroacetic acid in water+0.1% trifluoroacetic acid, over 10 min.) to afford 4-(5-(3-carbamoylphenyl)-[1,2,4]triazolo[1,5-a]pyridin-2-ylamino)-N-methylbenzamide as a trifluoroacetic acid salt, which was converted to the hydrochloride salt (45 mg, 20.0% yield) by using methanolic hydrochloride solution. $^1$H NMR (400 MHz, DMSO-$d_6$) δ (ppm) 10.01 (s, 1H), 8.56 (s, 1H), 8.21 (d, J=6.4 Hz, 2H), 8.14 (s, 1H), 8.06 (d, J=7.6 Hz, 1H), 7.77 (m, 7H), 7.54 (s, 1H), 7.32 (d, J=6.8 Hz, 1H), 2.76 (d, J=3.2 Hz, 3H); MS (ESI): m/z 387.16 [M+1]$^+$.

Example 67 trans-4-(2-(4-(Trifluoromethyl)phenylamino)-[1,2,4]triazolo[1,5-a]pyridin-5-yloxy)cyclohexanecarboxamide

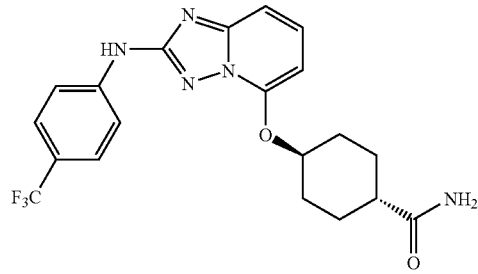

A. trans-4-(2-(4-(Trifluoromethyl)phenylamino)-[1,2,4]triazolo[1,5-a]pyridin-5-yloxy)cyclohexanecarboxylic acid. trans-Ethyl 4-(2-(4-(trifluoromethyl)phenylamino)-[1,2,4]triazolo[1,5-a]pyridin-5-yloxy)cyclohexanecarboxylate was synthesized from 2,5-dibromo-[1,2,4]triazolo[1,5-a]pyridine, trans-ethyl 4-hydroxycyclohexanecarboxylate and 4-(trifluoromethyl)aniline following the procedure described for cis-4-(2-(4-fluorophenylamino)-[1,2,4]triazolo[1,5-a]pyridin-5-yloxy)cyclohexanol. To a solution of trans-ethyl 4-(2-(4-(trifluoromethyl)phenylamino)-[1,2,4]triazolo[1,5-a]pyridin-5-yloxy)cyclohexanecarboxylate (10 mg, 0.022 mmol) in methanol (5 mL), lithium hydroxide was added (5 mg, 0.2 mmol), and the mixture was heated to reflux for 2 h. The reaction mixture was neutralized, and concentrated in vacuo. The residue was diluted with water, and extracted with ethyl acetate. The combined organic layer was dried over sodium sulfate, and evaporated to give trans-4-(2-(4-(trifluoromethyl)phenylamino)-[1,2,4]triazolo[1,5-a]pyridin-5-yloxy)cyclohexanecarboxylic acid (6 mg, 70% yield). MS (ESI): m/z 420.9 [M+1]$^+$.

B. trans-4-(2-(4-(Trifluoromethyl)phenylamino)-[1,2,4]triazolo[1,5-a]pyridin-5-yloxy)cyclohexanecarboxamide. A mixture of trans-4-(2-(4-(trifluoromethyl)phenylamino)-[1,2,4]triazolo[1,5-a]pyridin-5-yloxy)cyclohexanecarboxylic acid (6 mg, 0.014 mmol), ammonium chloride (1.5 mg, 0.03 mmol), [dimethylamino-([1,2,3]triazolo[4,5-b]pyridin-3-yloxy)-methylene]-dimethyl-ammonium hexafluoro phosphate (11 mg, 0.03 mmol), N-methylmorpholine (2 mg, 0.02 mmol) in N,N-dimethylformamine (2 mL) was stirred at room temperature overnight. The reaction mixture was concentrated, and the residue was purified by preparative TLC (eluting with 75% ethyl acetate in petroleum ether) to give trans-4-(2-(4-(trifluoromethyl)phenylamino)-[1,2,4]triazolo[1,5-a]pyridin-5-yloxy)cyclohexanecarboxamide (3 mg, 50% yield) as a solid. $^1$H NMR (400 MHz, DMSO-$d_6$) δ (ppm) 10.16 (s, 1H), 7.84 (d, J=8.4 Hz, 2H), 7.61 (d, J=8.4 Hz, 2H), 7.55 (t, J=8.4 Hz, 1H), 7.27 (d, J=8.4 Hz, 1H), 7.27 (s, 1H), 7.19 (d, J=8.4 Hz, 1H), 6.74 (s, 1H), 4.71 (m, 1H), 2.22 (m, 3H), 1.86 (m, 2H), 1.53 (m, 4H); MS (ESI): m/z 420.1 [M+1].$^+$ Example 68

5-((1-Ethylpiperidin-4-yl)methyl)-N-(4-(trifluoromethyl)phenyl)-[1,2,4]triazolo[1,5-a]pyridin-2-amine

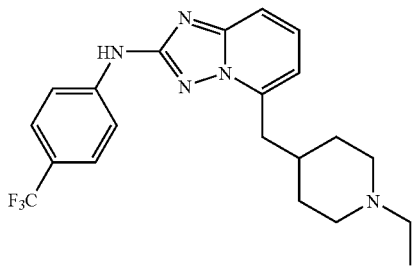

A. 5-((1-Ethylpiperidin-4-yl)methyl)-N-(4-(trifluoromethyl)phenyl)-[1,2,4]triazolo[1,5-a]pyridin-2-amine. 541-Benzylpiperidin-4-yl)methyl)-N-(4-(trifluoromethyl)phenyl)-[1,2,4]triazolo[1,5-a]pyridin-2-amine was synthesized from 1-benzyl-4-methylenepiperidine and 5-bromo-N-(4-(trifluoromethyl)phenyl)-[1,2,4]triazolo[1,5-a]pyridin-2-amine following the procedure described for N-phenyl-5-(piperidin-4-ylmethyl)-[1,2,4]triazolo[1,5-a]pyridin-2-amine. 5-((1-Benzylpiperidin-4-yl)methyl)-N-(4-(trifluoromethyl)phenyl)-[1,2,4]triazolo[1,5-a]pyridin-2-amine (0.165 g, 0.354 mmol) was dissolved in ethanol (30 mL) and treated with a catalytic amount of palladium on carbon (10 weight %). The reaction was stirred under an atmosphere of hydrogen gas overnight at room temperature. As only trace conversion was observed, a drop of acetic acid was added and the reaction was stirred at room temperature overnight. Most of the starting material was converted to the title compound contaminated with a minor amount of 5-(piperidin-4-ylmethyl)-N-(4-(trifluoromethyl)phenyl)-[1,2,4]triazolo[1,5-a]pyridin-2-amine. The catalyst was removed by filtration washed with methanol and the filtrate was concentrated under reduced pressure. The residue was purified by semi-preparative HPLC (20-70% acetonitrile+0.1% trifluoroacetic acid in water+0.1% trifluoroacetic acid, 3 injections, 30 min.). The desired fractions were combined and neutralized with a STRATA cationic resin exchange column. The eluate was concentrated under reduced pressure and dried in a vacuum oven for 5 h. 541-Ethylpiperidin-4-yl)methyl)-N-(4-(trifluoromethyl)phenyl)-[1,2,4]triazolo[1,5-a]pyridin-2-amine (0.019 g, 0.047 mmol, 13.29% yield) was isolated as a off-white solid. $^1$H NMR (400 MHz, DMSO-$d_6$) δ (ppm) 10.18 (s, 1H), 7.91 (d, J=8.59 Hz, 2H), 7.64 (d, J=8.59 Hz, 2H), 7.48-7.59 (m, 2H), 6.95 (s, 1H), 3.03 (d, J=6.64 Hz, 2H), 2.82 (br s, 2H), 2.26 (s, 2H), 1.99 (br s, 1H), 1.78 (br s, 2H), 1.55 (br s, 2H), 1.33 (br s, 2H), 0.89-1.02 (m, 3H); $^{19}$F NMR (400 MHz, DMSO-$d_6$) δ (ppm)-59.9 ppm; MS (ESI): m/z 404.2 [M+1]$^+$.

Example 69

5-(piperazin-1-ylmethyl)-N-(4-(trifluoromethyl)phenyl)-[1,2,4]triazolo[1,5-a]pyridin-2-amine

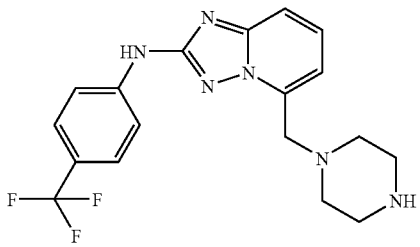

2-(4-(Trifluoromethyl)phenylamino)-[1,2,4]triazolo[1,5-a]pyridine-5-carbaldehyde. To a suspension of 5-bromo-N-(4-(trifluoromethyl)phenyl)-[1,2,4]triazolo[1,5-c]pyridin-2-amine (0.2 g, 0.560 mmol) in tetrahydrofuran (2.80 mL) (colorless) at −78° C. was added n-butyl lithium in hexanes (0.470 mL, 1.176 mmol, 2.5 M solution in hexanes) dropwise. The reaction mixture turned bright yellow and was maintained at low temperature for 1 h. N,N-Dimethylformamide (0.086 g, 1.176 mmol) was then added neat and the reaction was allowed to slowly warm up to room temperature. After 2 h, the reaction was complete and was quenched at 0° C. with the addition of 1 mL of acetic acid and 10 mL of water. The crude product was extracted with ethyl acetate and the extracts were dried over sodium sulfate and evaporated to dryness. The residue was suspended in a few mL of ethyl acetate and collected by filtration. 2-(4-(Trifluoromethyl)phenylamino)-[1,2,4]triazolo[1,5-a]pyridine-5-carbaldehyde (0.13 g, 0.424 mmol, 76% yield) was collected as a bright yellow solid and used without further purification. $^1$H NMR (400 MHz, DMSO-$d_6$) δ (ppm) 10.58 (s, 1H), 10.41 (s, 1H), 7.87-8.05 (m, 3H), 7.72-7.84 (m, 1H), 7.53-7.70 (m, 3H).

B. tert-Butyl 4-((2-(4-(trifluoromethyl)phenylamino)-[1,2,4]triazolo[1,5-a]pyridin-5-yl)methyl)piperazine-1-carboxylate. To a suspension of 2-(4-(trifluoromethyl)phenylamino)-[1,2,4]triazolo[1,5-a]pyridine-5-carbaldehyde (0.150 g, 0.490 mmol) in dichloroethane (2.449 mL) was added tert-butyl piperazine-1-carboxylate (0.100 g, 0.539 mmol). The mixture was stirred at room temperature for 30 min before sodium triacetoxyborohydride (0.114 g, 0.539 mmol) was added. The reaction was stirred at room temperature overnight. The reaction was quenched with water and the crude product was extracted with ethyl acetate. The extracts were dried over magnesium sulfate and evaporated to dryness. The residue was purified by biotage column chromatography using 5-100% ethyl acetate in hexanes. The desired fractions were combined and evaporated to dryness. tert-Butyl 4-((2-(4-(trifluoromethyl)phenylamino)-[1,2,4]triazolo[1,5-a]pyridin-5-yl)methyl)piperazine-1-carboxylate (0.142 g, 0.298 mmol, 60.8% yield) was isolated as a light yellow solid that was dried under vacuum and used without further purification. MS (ESI): m/z 477.1 [M+1]⁺.

C. 5-(piperazin-1-ylmethyl)-N-(4-(trifluoromethyl)phenyl)-[1,2,4]triazolo[1,5-a]pyridin-2-amine. A suspension of tert-butyl 4-((2-(4-(trifluoromethyl)phenylamino)-[1,2,4]triazolo[1,5-a]pyridin-5-yl)methyl)piperazine-1-carboxylate (0.233 g, 0.490 mmol) in dichloromethane (3 mL) was treated at room temperature with trifluoroacetic acid (1 mL, 12.98 mmol). The solution was stirred at room temperature for 1 h. The solvents were removed under reduced pressure and the residue was purified by preparative HPLC (10-80% acetonitrile+0.1% trifluoroacetic acid in water+0.1% trifluoroacetic acid, 30 min, 1 injection). The desired fractions were combined and neutralized with a STRATA resin exchange column. 5-(piperazin-1-ylmethyl)-N-(4-(trifluoromethyl)phenyl)-[1,2,4]triazolo[1,5-a]pyridin-2-amine (0.066 g, 0.175 mmol, 35.8% yield) was collected as a white solid. $^1$H NMR (400 MHz, DMSO-d$_6$) δ (ppm) 10.19 (s, 1H), 7.91 (d, J=8.59 Hz, 2H), 7.59-7.70 (m, 3H), 7.51-7.59 (m, 1H), 7.11 (d, J=7.03 Hz, 1H), 3.95 (s, 2H), 3.34 (br s, 4H), 2.70-2.82 (m, 4H); $^{19}$F NMR (376 MHz, DMSO-d$_6$) δ (ppm)-60.01 ppm; MS (ESI): m/z 377.2 [M+1]⁺.

Example 70 cis-3-(5-(4-Hydroxycyclohexylamino)-[1,2,4]triazolo[1,5-a]pyridin-2-ylamino)-N-methylbenzamide

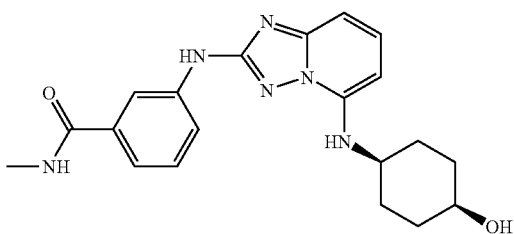

A. cis-4-(2-Bromo-[1,2,4]triazolo[1,5-a]pyridin-5-ylamino)cyclohexanol. 2,5-Dibromo-[1,2,4]triazolo[1,5-a]pyridine (4.15 g, 14.99 mmol), cis-4-aminocyclohexanol hydrochloride (3.12 g, 20.58 mmol), and potassium carbonate (4.93 g, 35.7 mmol) were added to a 200 mL flask. DMSO (15 mL) was added, and the reaction placed to stir hard in a 100° C. oil bath for 3 h. The reaction was cooled to room temperature, and water (~50 mL) was added. The mixture was stirred for 15 min, then filtered through a medium frit to collect the off-white solid, which was dried in vacuo at 60° C. for 2 h to provide the desired cis-4-(2-bromo-[1,2,4]triazolo[1,5-a]pyridin-5-ylamino)cyclohexanol (4.0438 g, 13.00 mmol, 87% yield). $^1$H NMR (300 MHz, DMSO-d$_6$) δ (ppm) 7.88 (d, J=7.97 Hz, 1H), 7.66 (s, 1H), 7.56 (t, J=8.38 Hz, 1H), 6.92 (d, J=8.52 Hz, 1H), 6.82 (d, J=7.97 Hz, 1H), 6.35 (d, J=7.97 Hz, 1H), 4.39 (br s, 1H), 3.78 (br s, 1H), 3.45-3.64 (m, 1H), 1.76-1.98 (m, 2H), 1.45-1.76 (m, 7H). (ESI): m/z 311.3 [M+1]⁺.

B. Ethyl cis-3-(5-(4-hydroxycyclohexylamino)-[1,2,4]triazolo[1,5-a]pyridin-2-ylamino)benzoate. cis-4-(2-Bromo-[1,2,4]triazolo[1,5-a]pyridin-5-ylamino)cyclohexanol (976.7 mg, 3.14 mmol), ethyl 3-aminobenzoate (734.9 mg, 4.45 mmol), tris(dibenzylideneacetone)dipalladium(0) (268.0 mg, 0.293 mmol), (9,9-dimethyl-9H-xanthene-4,5-diyl)bis(diphenylphosphine) (489.5 mg, 0.846 mmol), and potassium 2-methylpropan-2-olate (352 mg, 3.14 mmol) were weighed into a 25 mL flask. The flask was capped with a septum and flushed with nitrogen. Dioxane (4 mL) that had been freshly degassed by 5 min nitrogen bubbling was added via syringe, and the reaction was placed to stir hard in a 95° C. oil bath. After 3 h, the reaction was cooled to room temperature, filtered through celite using THF, then concentrated. The crude product was redissolved into dichloromethane/methanol and applied to a Biotage column. Flash chromatography in methanol:dichloromethane (0-7%) provided the desired ethyl cis-3-(5-(4-hydroxycyclohexylamino)-[1,2,4]triazolo[1,5-c]pyridin-2-ylamino)benzoate (0.719 g, 1.818 mmol, 57.9% yield). (ESI): m/z 396.2 [M+1]⁺.

C. cis-3-(5-(4-Hydroxycyclohexylamino)-[1,2,4]triazolo[1,5-a]pyridin-2-ylamino)benzoic acid. Ethyl cis-3-(5-(4-hydroxycyclohexylamino)-[1,2,4]triazolo[1,5-c]pyridin-2-ylamino)benzoate (0.719 g, 1.818 mmol) was treated with tetrahydrofuran (5 mL) and 1.0 M sodium hydroxide solution (2.5 mL, 2.5 mmol). The reaction was heated to 60° C. for 2 h, at which point LCMS analysis showed starting material remained. Ethanol (2 mL) was added, and heating was continued for an additional 2 h. The reaction was cooled to room temperature, diluted with ethyl acetate and dichloromethane, and washed with 1N sodium hydroxide solution. The aqueous layer was acidified with 10% potassium dihydrogen phosphate solution, extracted with ethyl acetate, and the organic solution was dried over magnesium sulfate, filtered and concentrated to provide cis-3-(5-(4-hydroxycyclohexylamino)-[1,2,4]triazolo[1,5-c]pyridin-2-ylamino)benzoic acid (299.4 mg, 0.815 mmol, 44.8% yield). $^1$H NMR (300 MHz, DMSO-d$_6$) δ (ppm) 9.83 (s, 1H), 8.35 (br s, 1H), 8.21 (d, J=6.59 Hz, 1H), 7.41-7.67 (m, 4H), 6.86 (d, J=8.52 Hz, 1H), 6.31 (d, J=7.97 Hz, 1H), 6.12 (d, J=7.97 Hz, 1H), 4.61 (br s, 1H), 3.87 (br s, 1H), 3.72 (br s, 1H), 1.59-2.07 (m, 15H). (ESI): m/z 368.5 [M+1]⁺.

D. cis-3-(5-(4-Hydroxycyclohexylamino)-[1,2,4]triazolo[1,5-a]pyridin-2-ylamino)-N-methylbenzamide. cis-3-(5-(4-hydroxycyclohexylamino)-[1,2,4]triazolo[1,5-c]pyridin-2-ylamino)benzoic acid (299.4 mg, 0.815 mmol) and methylamine hydrochloride (357.6 mg, 5.30 mmol) were treated with N,N-dimethylformamide (2 mL) in a 20 mL scintillation vial. Diisopropylethylamine (0.9 mL, 5.15 mmol) was added, followed by O-(7-azabenzotriazol-1-yl)-N,N,N',N'-tetramethyluronium hexafluorophosphate (HATU) (1.74 g, 4.58 mmol), and the reaction was stirred hard in a 50° C. aluminum block. After 1 h the reaction was cooled to room temperature, diluted with ethyl acetate and tetrahydrofuran, and washed with water. The organic layer was dried over magnesium sulfate, filtered, and concentrated. The sample was dissolved into minimum 1:1 DMSO:water and purified by semi-preparative reverse phase HPLC (0-100% acetonitrile:water with 0.1% TFA). The product was isolated as the free base by dissolution in ethyl acetate, washing with saturated sodium bicarbonate solution, drying over magnesium sulfate, then filtration and concentration to provide cis-3-(5-(4-hydroxycyclohexylamino)-[1,2,4]triazolo[1,5-c]pyridin-2-ylamino)-N-methylbenzamide (77.7 mg, 0.204 mmol, 25.06% yield) as a white solid. $^1$H NMR (300 MHz, DMSO-d$_6$) δ (ppm) 9.66 (s, 1H), 8.42 (d, J=4.40 Hz, 1H), 8.19 (s, 1H), 7.90 (d, J=7.69 Hz, 1H), 7.19-7.54 (m, 3H), 6.74 (d, J=8.52 Hz, 1H), 6.08-6.30 (m, 2H), 4.53 (br s, 1H), 3.77 (br s, 1H), 3.63 (d, J=7.69 Hz, 1H), 2.79 (d, J=4.12 Hz, 3H), 1.49-2.01 (m, 8H). (ESI): m/z 381.1 [M+1]+.

Example 71 cis-4-(2-(3-Methyl-1H-indazol-6-ylamino)[1,2,4]triazolo[1,5-a]pyridin-5-ylamino)cyclohexanol

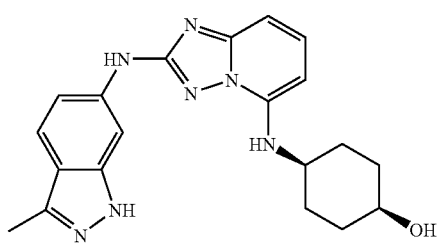

A. cis-4-(2-(3-Methyl-1-((2-(trimethylsilyl)ethoxy)methyl)-1H-indazol-6-ylamino)-[1,2,4]triazolo[1,5-a]pyridin-5-ylamino)cyclohexanol. A degassed mixture of cis-4-(2-bromo-[1,2,4]triazolo[1,5-c]pyridin-5-ylamino)cyclohexanol (160 mg, 0.5 mmol), 3-methyl-1-((2-(trimethylsilyl)ethoxy)methyl)-1H-indazol-6-amine (138 mg, 0.50 mmol), tris(dibenzylideneacetone)dipalladium(0) (46 mg, 0.05 mmol), 4,5-bis(diphenylphosphino)-9,9-dimethylxanthene (57 mg, 0.1 mmol) and potassium tert-butoxide (112 mg, 1.0 mmol) in dioxane (5 mL) was heated at 100° C. under nitrogen overnight. The reaction mixture was poured into water (20 mL), extracted ethyl acetate (15 mL×3). The combined organic layer was washed with brine (20 mL), dried over anhydrous sodium sulfate and evaporated under reduced pressure. The residue was purified on silica gel column (eluting with 5-50% ethyl acetate in petroleum ether) to give cis-4-(2-(3-methyl-1-((2-(trimethylsilyl)ethoxy)methyl)-1H-indazol-6-ylamino)-[1,2,4]triazolo[1,5-c]pyridin-5-ylamino)cyclohexanol (180 mg, 72% yield). MS (ESI): m/z 508.2 [M+1]+.

B. cis-4-(2-(3-Methyl-1H-indazol-6-ylamino)[1,2,4]triazolo[1,5-a]pyridin-5-ylamino)cyclohexanol. A mixture of cis-4-(2-(3-methyl-1-((2-(trimethylsilyl)ethoxy)methyl)-1H-indazol-6-ylamino)-[1,2,4]triazolo[1,5-c]pyridin-5-ylamino)cyclohexanol (180 mg, 0.36 mmol) and methanolic hydrochloride solution (2 M, 5 mL) was stirred at 55° C. overnight. The solvent was evaporated under reduced pressure to give the crude product, which was purified by a reverse-phase preparatory HPLC (17-43%: acetonitrile+0.1% trifluoroacetic acid in water+0.1% trifluoroacetic acid, over 20 min.) to give cis-4-(2-(3-methyl-1H-indazol-6-ylamino)-[1,2,4]triazolo[1,5-c]pyridin-5-ylamino)cyclohexanol (80 mg, 60% yield) as a hydrochloride salt. 1H NMR (400 MHz, METHANOL-$d_4$) δ (ppm) 8.06 (d, J=1.6 Hz, 1H), 7.78 (t, J=8.8 Hz, 2H), 7.24 (dd, $J_1$=8.8 Hz, $J_2$=2.0 Hz, 1H), 6.86 (d, J=8.4 Hz, 1H), 6.62 (d, J=8.0 Hz, 1H), 3.98 (m, 1H), 3.76 (m, 1H), 2.59 (s, 3H), 2.00 (m, 8H); MS (ESI): m/z 377.1 [M+1]+.

Example 72

(6-(2-(4-(Trifluoromethyl)phenylamino)-[1,2,4]triazolo[1,5-a]pyridin-5-yl)-1H-benzo[d]imidazol-2-yl)methanol

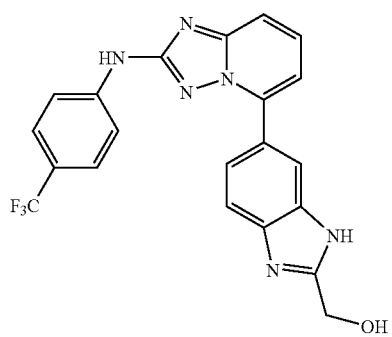

A. (6-(2-(4-(Trifluoromethyl)phenylamino)-[1,2,4]triazolo[1,5-a]pyridin-5-yl)-1H-benzo[d]imidazol-2-yl)methanol. 4-(2-(4-(Trifluoromethyl)phenylamino)-[1,2,4]triazolo[1,5-c]pyridin-5-yl)benzene-1,2-diamine was synthesized following an analogous procedure as the one described for 4-(2-phenylamino-[1,2,4]triazolo[1,5-a]pyridin-5-yl)-benzene-1,2-diamine. A mixture of 4-(2-(4-(trifluoromethyl)phenylamino)-[1,2,4]triazolo[1,5-c]pyridin-5-yl)benzene-1,2-diamine (250 mg, 0.65 mmol) and 2-hydroxyacetic acid (198 mg, 2.6 mmol) in hydrochloric acid (4N, 30 mL) was refluxed for 3 days. The mixture was evaporated under reduced pressure. The residue was purified by reverse-phase preparatory HPLC (20-50% acetonitrile+0.1% trifluoroacetic acid in water+0.1% trifluoroacetic acid, over 15 min.) to give (6-(2-(4-(trifluoromethyl)phenylamino)-[1,2,4]triazolo[1,5-c]pyridin-5-yl)-1H-benzo[d]imidazol-2-yl)methanol as a trifluoroacetic acid salt, which was converted to the hydrochloride salt (65 mg, 23.6% yield) with methanolic hydrochloride solution. 1H NMR (400 MHz, DMSO-$d_6$) δ (ppm) 10.21 (s, 1H), 8.50 (s, 1H), 8.08 (dd, $J_1$=8.4 Hz, $J_2$=1.2 Hz, 1H), 7.95 (d, J=8.8 Hz, 1H), 7.83 (d, J=8.4 Hz, 2H), 7.73-7.60 (m, 4H), 7.31 (d, J=6.0, 1H), 5.07 (s, 2H); MS (ESI): m/z 425.1 [M+1]+.

Example 73

1-(6-(2-(4-(Trifluoromethyl)phenylamino)-[1,2,4]triazolo[1,5-a]pyridin-5-yl)-1H-benzo[d]imidazol-2-yl)ethanol

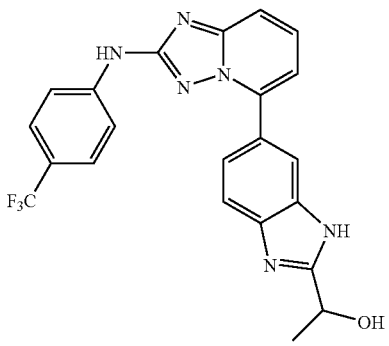

A. 1-(6-(2-(4-(Trifluoromethyl)phenylamino)-[1,2,4]triazolo[1,5-a]pyridin-5-yl)-1H-benzo[d]imidazol-2-yl)ethanol. 4-(2-(4-(Trifluoromethyl)phenylamino)-[1,2,4]triazolo[1,5-c]pyridin-5-yl)benzene-1,2-diamine was synthesized following an analogous procedure as the one described for 4-(2-phenylamino-[1,2,4]triazolo[1,5-c]pyridin-5-yl)-benzene-1,2-diamine. A mixture of 4-(2-(4-(trifluoromethyl)phenylamino)-[1,2,4]triazolo[1,5-c]pyridin-5-yl)benzene-1,2-diamine (700 mg, 1.82 mmol) and 2-hydroxypropanoic acid (328 mg, 3.65 mmol) in hydrochloric acid (4N, 30 mL) was refluxed for 48 h. The mixture was evaporated under reduced pressure. The residue was purified by reverse-phase preparatory HPLC (20-50% acetonitrile+0.1% trifluoroacetic acid in water+0.1% trifluoroacetic acid, over 15 min.) to give 1-(6-(2-(4-(trifluoromethyl)phenylamino)-[1,2,4]triazolo[1,5-c]pyridin-5-yl)-1H-benzo[d]imidazol-2-yl)ethanol (330 mg, 41.4% yield) as a trifluoroacetic acid salt, which was converted to the hydrochloride salt with methanolic hydrochloride solution. $^1$H NMR (400 MHz, METHANOL-$d_4$) δ (ppm) 8.53 (s, 1H), 8.24 (d, J=8.8 Hz, 1H), 8.08 (m, 2H), 7.82 (d, J=8.8 Hz, 1H), 7.77 (d, J=8.4 Hz, 2H), 7.66 (m, 3H), 5.42 (m, 1H), 1.78 (d, J=6.8 Hz, 3H); MS (ESI): m/z 439.1 [M+1]$^+$.

Example 74

2-(6-(2-(4-(Trifluoromethyl)phenylamino)-[1,2,4]triazolo[1,5-a]pyridin-5-yl)-1H-benzo[d]imidazol-2-yl)propan-2-ol

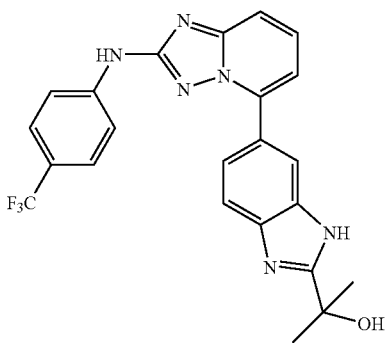

A. 1-(6-(2-(4-(Trifluoromethyl)phenylamino)-[1,2,4]triazolo[1,5-a]pyridin-5-yl)-1H-benzo[d]imidazol-2-yl)ethanone. A mixture of 1-(6-(2-(4-(trifluoromethyl)phenylamino)-[1,2,4]triazolo[1,5-c]pyridin-5-yl)-1H-benzo[d]imidazol-2-yl)ethanol (200 mg, 0.457 mmol) and manganese (IV) oxide (398 mg, 4.57 mmol) in chloroform (30 mL) was refluxed for 72 h. The mixture was filtered, and the filtrate was evaporated under reduced pressure. The residue was purified by preparative TLC to give 1-(6-(2-(4-(trifluoromethyl)phenylamino)-[1,2,4]triazolo[1,5-c]pyridin-5-yl)-1H-benzo[d]imidazol-2-yl)ethanone (100 mg, 50.3% yield) as a solid. $^1$H NMR (400 MHz, DMSO-$d_6$) δ (ppm) 13.66 (s, 1H), 10.19 (s, 1H), 8.55 (s, 1H), 8.32 (s, 1H), 8.04 (m, 1H), 7.88 (m, 2H), 7.76-7.59 (m, 4H), 7.31 (d, J=7.2 Hz, 1H), 2.74 (s, 3H); MS (ESI): m/z 437.1 [M+1]$^+$.

B. 2-(6-(2-(4-(Trifluoromethyl)phenylamino)-[1,2,4]triazolo[1,5-a]pyridin-5-yl)-1H-benzo[d]imidazol-2-yl)propan-2-ol. A mixture of 1-6-(2(4-(trifluoromethyl)phenylamino)-[1,2,4]triazolo[1,5-c]pyridin-5-yl)-1H-benzo[d]imidazol-2-yl)ethanone (100 mg, 0.23 mmol) in anhydrous tetrahydrofuran (10 mL) was stirred at 0° C. for 0.5 h. Then methylmagnesium bromide (0.5 mL, 1.6 M in diethyl ether) and methyllithium (2.0 mL, 3.0 M in diethyl ether) were added slowly, and the resulting mixture was stirred at 0° C. for 2 h, warmed to room temperature, and stirred overnight. Saturated aqueous ammonium chloride solution (15 mL) was added, and the mixture was extracted with ethyl acetate (10 mL×3). The organic layer was dried over sodium sulfate, filtered, and the filtrate was concentrated. The residue was purified by preparative TLC to afford 2464244-(trifluoromethyl)phenylamino)-[1,2,4]triazolo[1,5-c]pyridin-5-yl)-1H-benzo[d]imidazol-2-yl)propan-2-ol (28 mg, 26.9% yield) as a solid. $^1$H NMR (400 MHz, METHANOL-$d_4$) δ (ppm) 8.34 (s, 1H), 7.90 (br s, 1H), 7.81 (d, J=8.8 Hz, 2H), 7.72 (m, 2H), 7.55 (m, 3H), 7.23 (d, J=7.2 Hz, 1H), 1.74 (s, 6H); MS (ESI): m/z 453.1 [M+1]$^+$.

Example 75

6-(2-(4-(Trifluoromethyl)phenylamino)-[1,2,4]triazolo[1,5-a]pyridin-5-yl)-1H-benzo[d]imidazole-2-carboxamide

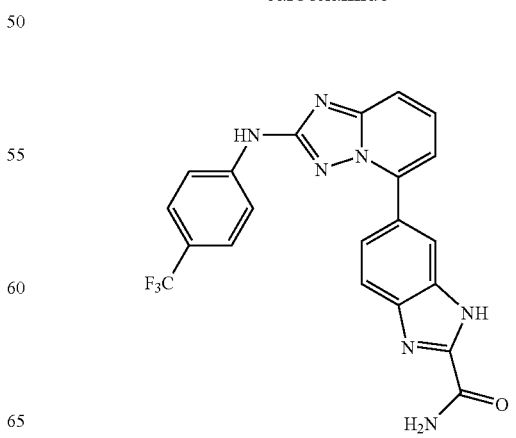

A. 5-(2-(Trichloromethyl)-1H-benzo[d]imidazol-6-yl)-N-(4-(trifluoromethyl)phenyl)-[1,2,4]triazolo[1,5-a]pyridin-2-amine. A mixture of 4-(2-4-(trifluoromethyl)phenylamino)-[1,2,4]triazolo[1,5-c]pyridin-5-yl)benzene-1,2-diamine (300 mg, 0.78 mmol) and methyl trichloroacetate (165 mg, 0.94 mmol) in acetic acid (10 mL) was stirred at room temperature for 3 h. Water (15 mL) was added to the mixture, and the precipitate was collected by filtration. The solid was washed with water, and dried under vacuum to afford 5-(2-(trichloromethyl)-1H-benzo[d]imidazol-6-yl)-N-(4-(trifluoromethyl)phenyl)-[1,2,4]triazolo[1,5-a]pyridin-2-amine (380 mg, 95.5% yield). $^1$H NMR (400 MHz, DMSO-$d_6$) δ (ppm) 10.18 (s, 1H), 8.38 (s, 1H), 7.98 (d, J=8.0 Hz, 1H), 7.86 (d, J=8.4 Hz, 3H), 7.74-7.59 (m, 4H), 7.30 (dd, $J_1$=7.2 Hz, $J_2$=1.2 Hz, 1H); MS (ESI): m/z 511.0 [M+1]$^+$.

B. 6-(2-(4-(Trifluoromethyl)phenylamino)-[1,2,4]triazolo[1,5-a]pyridin-5-yl)-1H-benzo[d]imidazole-2-carbonitrile. A solution of 5-(2-(trichloromethyl)-1H-benzo[d]imidazol-6-yl)-N-(4-(trifluoromethyl)phenyl)-[1,2,4]triazolo[1,5-c]pyridin-2-amine (380 mg, 0.745 mmol) in methanolic ammonia solution (20 mL) was stirred at 0° C. to room temperature for 2 h. The solvent was removed under reduced pressure to give crude 64244-(trifluoromethyl)phenylamino)-[1,2,4]triazolo[1,5-c]pyridin-5-yl)-1H-benzo[d]imidazole-2-carbonitrile (300 mg, 96.1% yield). MS (ESI): m/z 420.1 [M+1]$^+$.

C. 6-(2-(4-(Trifluoromethyl)phenylamino)-[1,2,4]triazolo[1,5-a]pyridin-5-yl)-1H-benzo[d]imidazole-2-carboxamide. A mixture of 6-(2-(4-(trifluoromethyl)phenylamino)-[1,2,4]triazolo[1,5-c]pyridin-5-yl)-1H-benzo[d]imidazole-2-carbonitrile (300 mg, 0.5 mmol), hydrogen peroxide (30%, 1.0 mL) and sodium hydroxide (40 mg, 1.0 mmol) in dimethylsulfoxide (5 mL) was stirred at room temperature for 3 h. The reaction mixture was poured into water (15 mL), and the mixture was extracted with ethyl acetate (15 mL×3). The combined organic layer was dried over anhydrous sodium sulfate, and evaporated under reduced pressure. The residue was purified by reverse-phase preparatory HPLC (35-65% acetonitrile+0.1% trifluoroacetic acid in water+0.1% trifluoroacetic acid, over 15 min.) to give 64244-(trifluoromethyl)phenylamino)-[1,2,4]triazolo[1,5-c]pyridin-5-yl)-1H-benzo[d]imidazole-2-carboxamide (65 mg, 29.7% yield) as a trifluoroacetic acid salt, which was converted to the hydrochloride salt with methanolic hydrochloride solution. $^1$H NMR (400 MHz, DMSO-$d_6$) δ (ppm) 10.19 (s, 1H), 8.37 (s, 1H), 7.95 (m, 5H), 7.73 (m, 4H), 7.29 (d, J=7.2 Hz, 1H); MS (ESI): m/z 438.1 [M+1]$^+$.

Example 76

5-(2-(Methoxymethyl)-1H-benzo[d]imidazol-6-yl)-N-(4-(trifluoromethyl)phenyl)-[1,2,4]triazolo[1,5-a]pyridin-2-amine

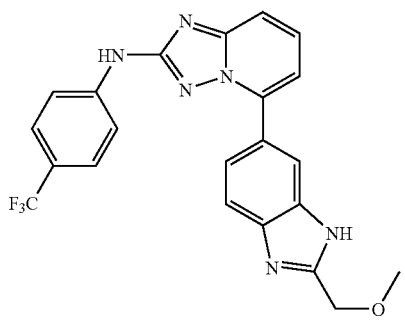

A. 5-(2-(Methoxymethyl)-1H-benzo[d]imidazol-6-yl)-N-(4-(trifluoromethyl)phenyl)-[1,2,4]triazolo[1,5-a]pyridin-2-amine. 5-(2-(Chloromethyl)-1H-benzo[d]imidazol-6-yl)-N-(4-(trifluoromethyl)phenyl)-[1,2,4]triazolo[1,5-c]pyridin-2-amine was synthesized following a procedure analogous to the one use for preparing 5-(2-(chloromethyl)-1H-benzo[d]imidazol-5-yl)-N-phenyl-[1,2,4]triazolo[1,5-c]pyridin-2-amine. A mixture of 5-(2-(chloromethyl)-1H-benzo[d]imidazol-6-yl)-N-(4-(trifluoromethyl)phenyl)-[1,2,4]triazolo[1,5-a]pyridin-2-amine (150 mg, 0.339 mmol) and sodium methanolate (55 mg, 1.02 mmol) in methanol (10 mL) was refluxed for 1 h. The solvent was removed under reduced pressure, and the residue was poured into water (10 mL). The aqueous layer was extracted with ethyl acetate (10 mL×3). The organic layer was dried over sodium sulfate, filtered, and the filtrate was concentrated. The residue was purified by reverse-phase preparatory HPLC (25-55% acetonitrile+0.1% trifluoroacetic acid in water+0.1% trifluoroacetic acid, over 15 min.) to give 5-(2-(methoxymethyl)-1H-benzo[d]imidazol-6-yl)-N-(4-(trifluoromethyl)phenyl)-[1,2,4]triazolo[1,5-c]pyridin-2-amine (55 mg, 37% yield) as a trifluoroacetic acid salt, which was converted to the hydrochloride salt with methanolic hydrochloride solution. $^1$H NMR (400 MHz, METHANOL-$d_4$) δ (ppm) 8.57 (s, 1H), 8.24 (d, J=8.8 Hz, 1H), 8.13-8.05 (m, 2H), 7.84 (d, J=8.8 Hz, 1H), 7.76 (d, J=8.4 Hz, 2H), 7.69 (d, J=7.2 Hz, 1H), 7.63 (d, J=8.4 Hz, 2H), 5.12 (s, 2H), 3.69 (s, 3H); MS (ESI): m/z 385.1 [M+1]$^+$.

Example 77

1-(2-(4-(Trifluoromethyl)phenylamino)-[1,2,4]triazolo[1,5-a]pyridin-5-yl)piperidin-4-ol

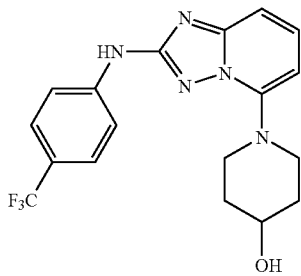

A. 1-(2-(4-(Trifluoromethyl)phenylamino)-[1,2,4]triazolo[1,5-a]pyridin-5-yl)piperidin-4-ol. 5-Bromo-N-(4-(trifluoromethyl)phenyl)-[1,2,4]triazolo[1,5-c]pyridin-2-amine (0.200 g, 0.549 mmol) and piperidin-4-ol (0.170 g, 1.680 mmol) were dissolved in N,N-dimethylformamide (2 mL) and stirred at 80° C. for 20 h. The solution was cooled to room temperature and diluted with water (8 mL) and the resulting off-white precipitate was collected and washed with water (2 mL). The material was purified using silica gel flash column chromatography (5-100% ethyl acetate in hexane) to give the product as a white solid (0.152 g, 72% yield). $^1$H NMR (400 MHz, DMSO-$d_6$) δ (ppm) 10.08 (s, 1H), 7.92 (d, J=8.59 Hz, 2H), 7.63 (d, J=8.74 Hz, 2H), 7.52 (t, J=8.20 Hz, 1H), 7.17 (d, J=8.54 Hz, 1H), 6.47 (d, J=7.76 Hz, 1H), 4.81 (d, J=4.20 Hz, 1H), 3.71-3.85 (m, 3H), 3.10 (t, J=9.59 Hz, 2H), 1.97 (d, J=11.08 Hz, 2H), 1.59-1.74 (m, 2H). MS (ESI) m/z 378.2 [M+1]$^+$.

Example 78

(S)-2-(2-(4-(Trifluoromethyl)phenylamino)-[1,2,4]triazolo[1,5-a]pyridin-5-ylamino)propan-1-ol

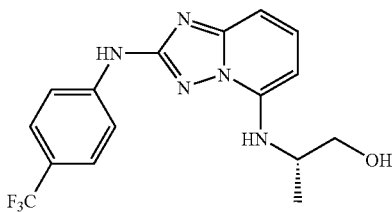

A. (S)-2-(2-(4-(Trifluoromethyl)phenylamino)-[1,2,4]triazolo[1,5-a]pyridin-5-ylamino)propan-1-ol. 5-Bromo-N-(4-(trifluoromethyl)phenyl)-[1,2,4]triazolo[1,5-c]pyridin-2-amine (0.250 g, 0.700 mmol) was suspended in (S)-2-aminopropan-1-ol (3.0 mL, 38.5 mmol) and stirred at 110° C. for 24 h. The orange solution was cooled to room temperature and added to water (20 mL) and triturated. The resulting off white precipitate was collected, rinsed with water (20 mL) and dried in vacuo at 60° C. for 12 h to give the product as an off white solid (0.210 g, 85% yield). $^1$H NMR (300 MHz, DMSO-d$_6$) δ (ppm) 10.13 (s, 1H), 8.02 (d, J=8.58 Hz, 2H), 7.72 (d, J=8.72 Hz, 2H), 7.55 (t, J=8.28 Hz, 1H), 6.88 (d, J=8.41 Hz, 1H), 6.28-6.38 (m, 2H), 5.13 (t, J=5.29 Hz, 1H), 3.83-3.95 (m, 1H), 3.65-3.72 (m, 2H), 1.37 (d, J=6.46 Hz, 3H). MS (ESI) m/z 352.2 [M+1]$^+$.

(R)-2-(2-(4-(Trifluoromethyl)phenylamino)-[1,2,4]triazolo[1,5-c]pyridin-5-ylamino)propan-1-ol was prepared following the same procedure, using (R)-2-aminopropan-1-ol as starting material.

Example 79

(S)-5-(Piperidin-3-yloxy)-N-(4-(trifluoromethyl)phenyl)-[1,2,4]triazolo[1,5-a]pyridin-2-amine

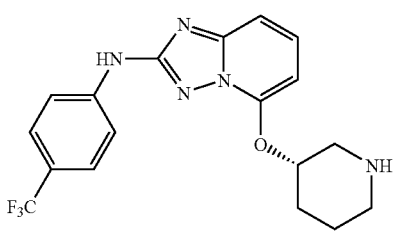

A. ((S)-tert-Butyl 3-(2-bromo-[1,2,4]triazolo[1,5-a]pyridin-5-yloxy)piperidine-1-carboxylate. To a clear colorless solution of the (S)-tert-butyl 3-hydroxypiperidine-1-carboxylate (0.262 g, 1.3 mmol) in N,N-dimethylformamide (10 mL) was added sodium hydride (0.102 g, 2.52 mmol, 60% in mineral oil) slowly portionwise at 0° C. under nitrogen. The reaction mixture was stirred at 0° C. for 1 h followed by the addition of 2,5-dibromo-[1,2,4]triazolo[1,5-a]pyridine (0.300 g, 1.083 mmol) at 0° C. The reaction mixture was stirred at room temperature overnight under nitrogen. Upon completion of reaction as indicated by LCMS the reaction mixture was poured into water/brine, and extracted with ethyl acetate several times. The combined organic layer was dried over anhydrous magnesium sulfate and concentrated. The crude mixture was purified by chromatography (eluting with 0-100% ethyl acetate in hexanes) to give (S)-tert-butyl 3-(2-bromo-[1,2,4]triazolo[1,5-c]pyridin-5-yloxy)piperidine-1-carboxylate as a white solid (0.273 g, 63% yield). $^1$H NMR (400 MHz DMSO-d$_6$) δ (ppm) 7.74 (m, 1H), 7.40 (d, J=8.69 Hz, 1H), 6.82-6.89 (m, 1H), 4.95 (br s, 1H), 4.06-4.16 (m, 1H), 3.78-3.88 (m, 1H), 3.29 (d, J=13.42 Hz, 1H), 1.92-2.08 (m, 2H), 1.79-1.92 (m, 1H), 1.48-1.58 (m, 1H), 1.33 (br s, 2H), 0.91 (br s, 6H); MS (ESI) m/z 398.27 [M+1]$^+$.

B. (S)-tert-Butyl 3-(2-(4-(trifluoromethyl)phenylamino)-[1,2,4]triazolo[1,5-a]pyridin-5-yloxy)piperidine-1-carboxylate. To a solution of (S)-tert-butyl 3-(2-bromo-[1,2,4]triazolo[1,5-c]pyridin-5-yloxy)piperidine-1-carboxylate (0.270 g, 0.680 mmol) in dioxane (10 mL) was added 4-(trifluoromethyl)aniline (0.219 g, 1.359 mmol), sodium tert-butoxide (0.131 g, 1.359 mmol), (4,5-bis(diphenylphosphino)-9,9-dimethylxanthene (0.079 g, 0.136 mmol) and tris(dibezylideneactone)palladium (0.065 g, 0.071 mmol) at room temperature under nitrogen. The reaction mixture was heated at 100° C. for 1.5 h. Upon completion of reaction as indicated by LCMS the reaction mixture was poured into water/brine, and extracted with ethyl acetate several times. The combined organic layer was dried over anhydrous magnesium sulfate and concentrated. The crude mixture was purified by chromatography (eluting with 0-100% ethyl acetate in hexanes) to give (S)-tert-butyl 3-(2-(4-(trifluoromethyl)phenylamino)-[1,2,4]triazolo[1,5-c]pyridin-5-yloxy)piperidine-1-carboxylate as a yellow solid (0.280 g, 86% yield). $^1$H NMR (400 MHz DMSO-d$_6$) δ (ppm) 10.19 (s, 1H), 7.84-7.92 (m, 2H), 7.56-7.66 (m, 3H), 7.19-7.27 (m, 1H), 6.70 (d, J=7.86 Hz, 1H), 4.92 (br s, 1H), 4.09-4.18 (m, 1H), 3.29 (br s, 1H), 2.93-3.05 (m, 1H), 1.88-2.09 (m, 1H), 1.45-1.60 (m, 1H), 1.21-1.40 (m, 4H), 0.82-0.99 (m, 6H); MS (ESI) m/z 478.48 [M+1]$^+$.

C. (S)-5-(Piperidin-3-yloxy)-N-(4-(trifluoromethyl)phenyl)-[1,2,4]triazolo[1,5-a]pyridin-2-amine. To a clear orange solution of (S)-tert-butyl 34244-(trifluoromethyl)phenylamino)-[1,2,4]triazolo[1,5-a]pyridin-5-yloxy)piperidine-1-carboxylate (0.275 g, 0.576 mmol) in methylene chloride (10 mL) was added trifluoroacetic acid (5 mL) at room temperature. The reaction mixture was stirred at room temperature overnight. Upon completion of reaction as indicated by LCMS the reaction mixture was concentrated and the residue was purified by silica gel column chromatography (eluting with of 0-15% methanolic ammonia in chloroform) and the desired fractions were run through a STRATA column to obtain the free base of the title compound as a pale yellow solid (99.8% pure, 0.176 g, 81% yield). $^1$H-NMR (400 MHz, DMSO-d$_6$) δ (ppm) 10.23 (s, 1H), 7.87 (d, J=8.49 Hz, 2H), 7.63 (d, J=8.54 Hz, 2H), 7.57 (t, J=8.32 Hz, 1H), 7.22 (d, J=8.69 Hz, 1H), 6.69 (d, J=7.86 Hz, 1H), 4.63-4.72 (m, 1H), 3.20 (d, J=13.47 Hz, 1H), 2.76-2.84 (m, 1H), 2.69 (dd, J=7.98, 12.23 Hz, 1H), 2.57 (br s, 1H), 2.13-2.21 (m, 1H), 1.63-1.79 (m, 2H), 1.46-1.57 (m, 1H); MS (ESI) m/z 378.36 [M+1]$^+$.

(R)-5-(Piperidin-3-yloxy)-N-(4-(trifluoromethyl)phenyl)-[1,2,4]triazolo[1,5-c]pyridin-2-amine was prepared following the same procedure, using (S)-tert-butyl 3-hydroxypiperidine-1-carboxylate as starting material.

Example 80

5-(Morpholinomethyl)-N-(4-(trifluoromethyl)phenyl)-[1,2,4]triazolo[1,5-a]pyridin-2-amine

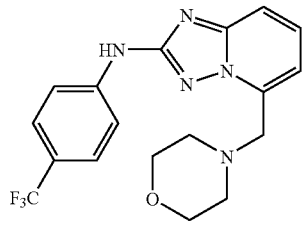

A. 5-(Morpholinomethyl)-N-(4-(trifluoromethyl)phenyl)-[1,2,4]triazolo[1,5-a]pyridin-2-amine. To a solution/suspension of 5-bromo-N-(4-(trifluoromethyl)phenyl)-[1,2,4]triazolo[1,5-a]pyridin-2-amine (300 mg, 0.8400 mmol) in dioxane (2 mL) and water (1 mL), potassium trifluoro(morpholinomethyl)borate (348 mg, 1.680 mmol), 4,5-bis(diphenylphosphino)-9,9-dimethylxanthene (24.3 mg, 0.042 mmol), palladium(II) acetate (9.43 mg, 0.042 mmol), tris(dibenzylideneacetone)dipalladium(0) (38 mg, 0.042 mmol), and potassium carbonate (348 mg, 2.52 mmol) were added under inert atmosphere. Nitrogen was bubbled through the reaction mixture for 5 min and then the reaction was heated to 100° C. for 3 hours. The reaction progress was checked by LCMS analysis. Once the starting material was consumed the reaction mixture was filtered through a cartridge filter, and the solvent was removed under vacuum. The crude was re-dissolved in dimethyl sulfoxide and purified on Semi-preparative HPLC (20-100% acetonitrile+0.1% trifluoroacetic acid in water+0.1% trifluoroacetic acid, 20 min). The fractions containing the product were loaded on a strata-X column to remove trifluoroacetic acid, then the methanol was evaporated in vacuo. The solid was dried under vacuum. 5-(Morpholinomethyl)-N-(4-(trifluoromethyl)phenyl)-[1,2,4]triazolo[1,5-c]pyridin-2-amine (20.7 mg, 0.055 mmol, 6.53% yield) was obtained as a white solid. $^1$H NMR (400 MHz, DMSO-$d_6$) δ (ppm) 10.19 (s, 1H), 7.91 (d, J=8.59 Hz, 2H), 7.48-7.73 (m, 4H), 7.12 (s, 1H), 4.00 (s, 5H), 3.58-3.74 (m, 4H), 2.59 (d, J=8.98 Hz, 4H). MS (ESI): m/z 378.2 [M+1]$^+$.

Example 81 cis-6-(5-(4-Hydroxycyclohexylamino)-[1,2,4]triazolo[1,5-a]pyridin-2-ylamino)-3,3-dimethylindolin-2-one

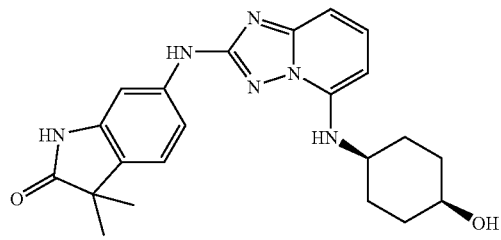

A. cis-tert-Butyl 6-(5-(4-hydroxycyclohexylamino)-[1,2,4]triazolo[1,5-a]pyridin-2-ylamino)-3,3-dimethyl-2-oxoindoline-1-carboxylate. A degassed mixture of cis-4-(2-bromo-[1,2,4]triazolo[1,5-a]pyridin-5-ylamino)cyclohexanol (225 mg, 0.72 mmol), tris(dibenzylideneacetone)dipalladium(0) (66 mg, 0.072 mmol), 4,5-bis(diphenylphosphino)-9,9-dimethylxanthene (83 mg, 0.14 mmol), cesium carbonate (476 mg, 1.45 mmol), and tert-butyl 6-amino-3,3-dimethyl-2-oxoindoline-1-carboxylate (200 mg, 0.72 mmol) in anhydrous dioxane (5 mL) was heated at 100° C. under nitrogen overnight. The reaction mixture was poured into water, and the resulting mixture was extracted ethyl acetate. The combined organic layer was washed with water and brine, dried over anhydrous sodium sulfate, and evaporated under reduced pressure. The residue was purified on silica gel column (eluting with 0-10% methanol in dichloromethane) to give cis-tert-butyl 6-(5-(4-hydroxycyclohexylamino)-[1,2,4]triazolo[1,5-c]pyridin-2-ylamino)-3,3-dimethyl-2-oxoindoline-1-carboxylate (156 mg, 42.8% yield). MS (ESI) m/z 507.3 [M+1]$^+$.

B. cis-6-(5-(4-Hydroxycyclohexylamino)-[1,2,4]triazolo[1,5-a]pyridin-2-ylamino)-3,3-dimethylindolin-2-one. A solution of cis-tert-butyl 6-(5-(4-hydroxycyclohexylamino)-[1,2,4]triazolo[1,5-c]pyridin-2-ylamino)-3,3-dimethyl-2-oxoindoline-1-carboxylate (156 mg, 0.31 mmol) in methanolic hydrochloride solution (2 M, 15 mL) was stirred at room temperature for 30 min. The solvent was evaporated under reduced pressure, the crude product was purified by a reverse-phase preparatory HPLC (17-43%: acetonitrile+0.1% trifluoroacetic acid in water+0.1% trifluoroacetic acid, over 20 min) to give cis-6-(5-(4-hydroxycyclohexylamino)-[1,2,4]triazolo[1,5-c]pyridin-2-ylamino)-3,3-dimethylindolin-2-one (80 mg, 64% yield) as a hydrochloride salt. $^1$H NMR (400 MHz, METHANOL-$d_4$) δ (ppm) 7.69 (t, J=8.4 Hz, 1H), 7.28 (d, J=2.0 Hz, 1H), 7.20 (t, J=8.0 Hz, 1H), 7.15 (dd, $J_1$=2.0 Hz, $J_2$=8.0 Hz, 1H), 6.75 (d, J=8.0 Hz, 1H), 6.54 (d, J=8.4 Hz, 1H), 3.89 (s, 1H), 3.66 (s, 1H), 1.90 (m, 8H), 1.29 (s, 6H); MS (ESI): m/z 407.3 [M+1]$^+$.

Example 82

4-((2-(4-(Trifluoromethyl)phenylamino)[1,2,4]triazolo[1,5-a]pyridin-5-yl)methyl)piperazin-2-one

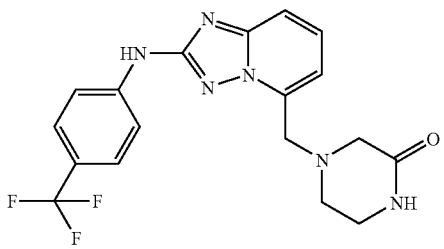

A. 2-(4-(Trifluoromethyl)phenylamino)-[1,2,4]triazolo[1,5-a]pyridine-5-carbaldehyde. To a solution/suspension of 5-bromo-N-(4-(trifluoromethyl)phenyl)-[1,2,4]triazolo[1,5-c]pyridin-2-amine (0.810 g, 2.268 mmol) in tetrahydrofuran (11.34 mL) (colorless) at −78° C. was added dropwise n-butyl lithium (1.905 mL, 4.76 mmol, 2.5 M solution in hexanes). The reaction mixture turned bright yellow and was maintained at low temperature for 1 h. N,N-dimethylformamide (0.369 mL, 4.76 mmol) was then added neat and the reaction was allowed to slowly warm up to room temperature. The reaction was checked after 1 h and was quenched at 0° C. with the addition of 1.5 mL of acetic acid and water (20 mL). The crude product was extracted with ethyl acetate and the extracts were dried over sodium sulfate and evaporated to dryness. The residue was then suspended in methanol and the resulting bright yellow precipitate was separated from an orange supernatant solution. The solid was dried under vacuum at room temperature. 2-(4-(Trifluoromethyl)phenylamino)-[1,2,4]triazolo[1,5-c]pyridine-5-carbaldehyde (0.558 g, 1.822 mmol, 80% yield) was isolated as a yellow solid. $^1$H NMR (400 MHz, DMSO-d$_6$) δ (ppm) 10.58 (s, 1H), 10.40 (br s, 1H), 7.93-8.01 (m, 3H), 7.73-7.80 (m, 1H), 7.61-7.70 (m, 3H).

B. (2-(4-(Trifluoromethyl)phenylamino)-[1,2,4]triazolo[1,5-a]pyridin-5-yl)methanol. To a suspension of 2-(4-(trifluoromethyl)phenylamino)-[1,2,4]triazolo[1,5-c]pyridine-5-carbaldehyde (0.2 g, 0.653 mmol) in 1,2-dichloroethane (2.61 mL) was added sodium triacetoxyborohydride (0.228 g, 1.077 mmol). The reaction was stirred at room temperature overnight. The reaction was quenched with water and the two phases were separated. The aqueous phase was further extracted with ethyl acetate and the combined organic phases were dried over magnesium sulfate and evaporated to dryness. Purification was effected by biotage column chromatography using 5-50% ethyl acetate in hexanes. (2-(4-(Trifluoromethyl)phenylamino)-[1,2,4]triazolo[1,5-c]pyridin-5-yl)methanol (0.172 g, 0.558 mmol, 85% yield) was isolated as a white solid and used without further purification. $^1$H NMR (400 MHz, DMSO-d$_6$) δ (ppm) 10.20 (s, 1H), 7.90 (d, J=8.59 Hz, 2H), 7.60-7.74 (m, 3H), 7.50-7.60 (m, 1H), 7.13 (d, J=7.03 Hz, 1H), 5.85 (s, 1H), 4.93 (d, 2H).

C. 5-(Bromomethyl)-N-(4-(trifluoromethyl)phenyl)-[1,2,4]triazolo[1,5-a]pyridin-2-amine. To a solution of (2-(4-(trifluoromethyl)phenylamino)-[1,2,4]triazolo[1,5-c]pyridin-5-yl)methanol (0.172 g, 0.558 mmol) in dioxane (1.006 mL) at 40° C. was added phosphorus tribromide (0.053 mL, 0.558 mmol). The reaction was stirred at 40° C. for 5 h. The reaction was quenched by adding 20 mL of a saturated aqueous solution of sodium bicarbonate and the crude was extracted with ethyl acetate. The crude was purified by biotage column chromatography using 10-60% ethyl acetate in hexanes. The desired fractions were combined and evaporated to dryness. 5-(Bromomethyl)-N-(4-(trifluoromethyl)phenyl)-[1,2,4]triazolo[1,5-c]pyridin-2-amine (0.180 g, 0.485 mmol, 87% yield) was isolated as a light yellow solid. $^1$H NMR (400 MHz, DMSO-d$_6$) δ (ppm) 10.31 (s, 1H), 7.85-8.02 (m, 2H), 7.54-7.75 (m, 4H), 7.33 (d, J=7.03 Hz, 1H), 5.10 (s, 2H); $^{19}$F NMR (376 MHz, DMSO-d$_6$) δ (ppm)-59.83 ppm.

D. 4-((2-(4-(Trifluoromethyl)phenylamino)-[1,2,4]triazolo[1,5-a]pyridin-5-yl)methyl)piperazin-2-one. A suspension of 5-(bromomethyl)-N-(4-(trifluoromethyl)phenyl)-[1,2,4]triazolo[1,5-c]pyridin-2-amine (0.075 g, 0.202 mmol) in acetonitrile (2.021 mL) was treated with piperazin-2-one (0.061 g, 0.606 mmol) and potassium carbonate (0.279 g, 2.021 mmol) and the reaction was heated to 60° C. for 20 min. The solvent was removed under reduced pressure and the crude was triturated in water. The resulting solid was collected by filtration, washed with water and dried in a vacuum oven overnight. 4-((2-(4-(Trifluoromethyl)phenylamino)-[1,2,4]triazolo[1,5-c]pyridin-5-yl)methyl)piperazin-2-one (0.075 g, 0.192 mmol, 95% yield) was collected as a white solid. $^1$H NMR (300 MHz, DMSO-d$_6$) δ (ppm) 10.18 (s, 1H), 7.89 (br s, 3H), 7.52-7.71 (m, 4H), 7.13 (d, 1H), 4.09 (s, 2H), 3.10-3.27 (m, 4H), 2.77 (br s, 2H); MS (ESI): m/z 391.2 [M+1]$^+$.

Example 83

N-methyl-4-(5-(tetrahydro-2H-pyran-4-ylamino)-[1,2,4]triazolo[1,5-a]pyridin-2-ylamino)benzamide

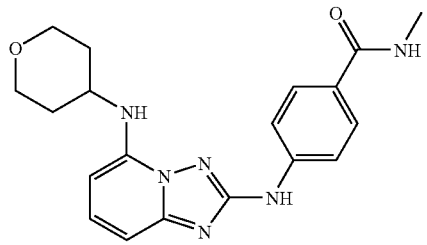

A. N-methyl-4-(5-(tetrahydro-2H-pyran-4-ylamino)-[1,2,4]triazolo[1,5-a]pyridin-2-ylamino)benzamide. A degassed mixture of 4-(5-bromo-[1,2,4]triazolo[1,5-a]pyridin-2-ylamino)-N-methylbenzamide (104 mg 0.30 mmol), tetrahydropyran-4-ylamine acetate (96.6 mg 0.6 mmol), 4,5-bis(diphenylphosphino)-9,9-dimethyl xanthene (35 mg, 0.06 mmol) and cesium carbonate (390 mg, 1.2 mmol) in dioxane (3 mL) was added tris(dibenzylideneacetone)palladium(0) (27 mg 0.03 mmol) under nitrogen, and the mixture was heated at 95° C. with stirring under nitrogen overnight. The mixture was quenched with water, and the mixture was extracted with ethyl acetate. The solvent was removed under vacuum and the residue was purified by a reverse-phase preparatory HPLC (20-50%: acetonitrile+0.1% trifluoroacetic acid in water+0.1% trifluoroacetic acid, over 15 min.) to give N-methyl-4-(5-(tetrahydro-2H-pyran-4-ylamino)-[1,2,4]triazolo[1,5-c]pyridin-2-ylamino)benzamide as a trifluoroacetic acid salt, which was converted to a hydrochloride salt (55 mg, 50% yield). $^1$H NMR (400 MHz, METHANOL-d$_4$) δ (ppm) 7.81 (m, 3H), 7.72 (m, 2H), 6.80 (d, J=8.4 Hz, 1H), 6.73 (d, J=8.8 Hz, 1H), 3.97 (dd, J$_1$=2.8 Hz, J$_2$=10.8 Hz, 2H), 3.88 (m, 1H); 3.53 (m, 2H), 2.83 (s, 3H), 1.96 (d, J=12.8 Hz, 2H); 1.83 (m, 2H); MS (ESI): m/z 367.0 [M+H]$^+$.

Example 84

5-(4-Methylisoxazol-3-yl)-N-phenyl-[1,2,4]triazolo[1,5-a]pyridin-2-amine

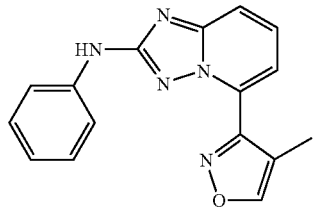

A. N-(6-(5-Ethoxy-4-methyl-4,5-dihydroisoxazol-3-yl)pyridin-2-yl)pivalamide. N-chlorosuccinimide (2 g, 0.015 mol) was added dropwise to a solution of N-(6-((hydroxyimino)methyl)pyridin-2-yl)pivalamide (3 g, 0.014 mmol) in dimethylformamide (40 mL), and the mixture was heated to 50° C. for 1 h, followed by the addition of a mixture of 1-ethoxyprop-1-ene (5.8 g,0.07 mol) and triethylamine (3.4 g, 0.035 mol) slowly. The reaction mixture was stirred at 50° C. overnight, quenched by the addition of water, and extracted with ethyl acetate (15 mL×3). The combined organic layer was washed with brine, dried over sodium sulfate, and concentrated. The residue was purified by column chromatography on silica gel (eluting with 20% ethyl acetate in petroleum ether) to yield N-(6-(5-ethoxy-4-methyl-4,5-dihydroisoxazol-3-yl)pyridin-2-yl)pivalamide (2 g, 46.8% yield) as a solid. $^1$H-NMR (400 MHz, DMSO-d$_6$) δ (ppm) 9.56 (s, 1H), 7.93 (d, J=8.4 Hz, 1H), 7.72 (t, J=8.0 Hz, 1H), 7.40 (d, J=7.6 Hz, 1H), 5.54 (d, J=7.2 Hz, 1H), 3.67 (m, 2H), 3.48 (m, 1H), 1.12 (s, 9H), 1.04 (t, J=7.2 Hz, 3H); MS (ESI): m/z 306.1 [M+1]$^+$.

B. 6-(4-Methylisoxazol-3-yl)pyridin-2-amine. A mixture of N-(6-(5-ethoxy-4-methyl-4,5-dihydroisoxazol-3-yl)pyridin-2-yl)pivalamide (1 g, 3.3 mmol) and sulfuric acid (33 mg, 0.33) in toluene was stirred at 100° C. for 12 h. The mixture was cooled down, basified with sodium carbonate, and extracted with ethyl acetate for three times. The combined organic layer was dried over anhydrous sodium sulfate and concentrated. The crude mixture was purified on silica gel column chromatography using a gradient of 0-30% ethyl acetate in petroleum ether to give 6-(4-methylisoxazol-3-yl)pyridin-2-amine (400 mg, 69.2% yield) as an oil. $^1$H-NMR (400 MHz, DMSO-d$_6$) δ (ppm) 8.72 (s, 1H), 7.47 (d, J=10.8 Hz, 1H), 6.98 (d, J=9.6 Hz, 1H), 6.52 (d, J=11.2 Hz, 1H), 6.11 (s, 2H), 2.23 (s, 3H); MS (ESI): m/z 176.1 [M+1]$^+$.

C. Intermediate A. A solution of 6-(4-methylisoxazol-3-yl)pyridin-2-amine (400 mg, 2.28 mmol) and O-ethyl carbonisothiocyanatidate (300 mg, 2.28 mmol) in dioxane (10 mL) was stirred at room temperature for 5 h. The solvent was removed under reduced pressure to give intermediate A as a solid, which was used directly without further purification.

D. 5-(4-Methylisoxazol-3-yl)[1,2,4]triazolo[1,5-a]pyridin-2-amine. To a solution of hydroxylamine hydrochloride (800 mg, 11.42 mmol) and N,N-diisopropylethylamine (884 mg, 6.85 mmol) in a mixture of ethanol and methanol (v/v, 1:1, 20 mL) was added intermediate A (699 mg, 2.28 mmol), and the mixture was stirred at room temperature for 2 h, and at 70° C. overnight. The volatiles were removed under reduced pressure, and the residue was purified on silica gel column (eluting with 40% ethyl acetate in petroleum ether) to give 5-(4-methylisoxazol-3-yl)-[1,2,4]triazolo[1,5-c]pyridin-2-amine (250 mg, 51.0%) as a solid. $^1$H-NMR (400 MHz, DMSO-d$_6$) δ (ppm) 8.78 (s, 1H), 7.41 (d, J=4.8 Hz, 1H), 6.95 (t, J=4.0 Hz, 1H), 6.03 (s, 2H), 1.85 (s, 3H); MS (ESI): m/z 216.1 [M+1]$^+$.

E. 5-(4-Methylisoxazol-3-yl)-N-phenyl-[1,2,4]triazolo[1,5-a]pyridin-2-amine. A degassed mixture of 5-(4-methylisoxazol-3-yl)-[1,2,4]triazolo[1,5-c]pyridin-2-amine (250 mg, 1.16 mmol), iodo-benzene (238 mg, 1.16 mmol), 4,5-bis(diphenylphosphino)-9,9-dimethylxanthene (135 mg, 0.116 mmol) and sodium tert-butoxide (135 mg, 1.38 mmol) in dioxane (20 mL) was added tris(dibenzylideneacetone)dipalladium(0) (105 mg, 0.116 mmol) under nitrogen, and the mixture was heated at 100° C. under nitrogen for 2 h. The reaction mixture was quenched by the addition of water, and the mixture was extracted with ethyl acetate (15 mL×3). The combined organic layer was washed with brine, dried over sodium sulfate, and concentrated. The residue was purified by a reverse-phase preparatory HPLC (40-70%: acetonitrile+0.1% trifluoroacetic acid in water+0.1% trifluoroacetic acid, over 15 min.) to give 5-(4-methylisoxazol-3-yl)-N-phenyl-[1,2,4]triazolo[1,5-c]pyridin-2-amine as a trifluoroacetic acid salt, which was converted to a hydrochloride salt with methanolic hydrochloride solution as a solid (92 mg, 27.2% yield). $^1$H-NMR (400 MHz, DMSO-d$_6$) δ (ppm) 9.77 (s, 1H), 8.99 (s, 1H), 7.79 (d, J=8.4 Hz, 1H), 7.73 (m, 3H), 7.27 (m, 3H), 6.87 (t, J=7.2 Hz, 1H), 2.04 (s, 3H); MS (ESI): m/z 291.9 [M+1]$^+$.

Example 85

2-Methyl-2-(2-(4-(trifluoromethyl)phenylamino)-[1,2,4]triazolo[1,5-a]pyridin-5-ylamino)propan-1-ol

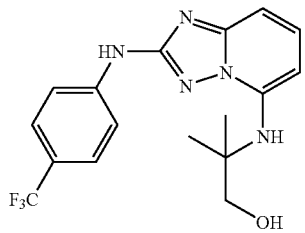

A. 2-methyl-2-(2-(4-(Trifluoromethyl)phenylamino)-[1,2,4]triazolo[1,5-a]pyridin-5-ylamino)propan-1-ol. To a solution/suspension of 5-bromo-N-(4-(trifluoromethyl)phenyl)-[1,2,4]triazolo[1,5-c]pyridin-2-amine (300 mg, 0.8400 mmol) in dioxane (7 mL) was added, 2-amino-2-methylpropan-1-ol (74.9 mg, 0.840 mmol), 4,5-bis(diphenylphosphino)-9,9-dimethylxanthene (24.3 mg, 0.042 mmol), sodium tert-butoxide (242 mg, 2.52 mmol) and tris(dibenzylideneacetone)dipalladium(0) (38 mg, 0.042 mmol) under nitrogen bubbled through the reaction mixture for 5 min and then heated to 100° C. for 3 hours. The reaction progress was checked by LCMS analysis. Once the starting material was consumed the reaction mixture was filtered through a cartridge filter, and the solvent was removed under vacuum. The crude was re-dissolved in dimethyl sulfoxide and purified on Semi-preparative HPLC (20-100% acetonitrile+0.1% trifluoroacetic acid in water+0.1% trifluoroacetic acid, 20 min). The fractions containing the product were loaded on a strata-X column to remove trifluoroacetic acid, then the methanol was evaporated in vacuo. The solid was dried under vacuum at room temperature. 2-methyl-2-(2-(4-(trifluoromethyl)phenylamino)-[1,2,4]triazolo[1,5-c]pyridin-5-ylamino)propan-1-ol (42 mg, 0.115 mmol, 13.68% yield) was obtained as an off white solid. $^1$H NMR (400 MHz, DMSO-d$_6$) δ (ppm) 10.22 (s, 1H), 7.92 (d, J=8.59 Hz, 2H), 7.46-7.74 (m, 2H), 7.24 (d, J=8.20 Hz, 1H), 6.61 (d, J=7.42 Hz, 1H), 4.08 (s, 2H), 1.22 (s, 6H); $^{19}$F NMR (376 MHz, DMSO-d$_6$) δ (ppm)-59.83 ppm. MS (ESI): m/z 366.2 [M+1]$^+$.

Example 86

4-((2-(4-(Trifluoromethyl)phenylamino)[1,2,4]triazolo[1,5-a]pyridin-5-yl)methyl)pyridin-2(1H)-one

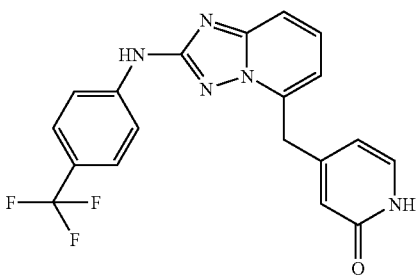

2-Methoxypyridin-4-yl)(2-(4-(trifluoromethyl)phenylamino)-[1,2,4]triazolo[1,5-a]pyridin-5-yl)methanol. The reaction was performed in two batches of starting material (0.397 g and 0.310 g) according to the following procedure and recombined for work-up and purification. A suspension of 5-bromo-N-(4-(trifluoromethyl)phenyl)-[1,2,4]triazolo[1,5-c]pyridin-2-amine (0.397 g, 1.111 mmol) in dry tetrahydrofuran (6.0 mL) was cooled to −78° C. The mixture was then reacted with n-butyl lithium (0.933 mL, 2.333 mmol, 2.5 M in hexanes). The reaction was stirred at low temperature for 1 h. A solution of 2-methoxyisonicotinaldehyde (0.32 g, 2.333 mmol) in dry tetrahydrofuran (3 mL) was then added dropwise. Low temperature was maintained for 2 h. Checked after 30 min, the reaction had progressed to a mixture of desired product contaminated with de-halogenated starting material. The reaction was quenched with water and the crude was extracted with ethyl acetate. The combined extracts were dried over magnesium sulfate and evaporated to dryness. The residue was purified by biotage column chromatography using the following gradient: 800 mL gradient 10-50% ethyl acetate in hexanes, then 1.100 L at 50% ethyl acetate in hexanes. Desired fractions were combined and evaporated to dryness. (2-Methoxypyridin-4-yl)(2-(4-(trifluoromethyl)phenylamino)-[1,2,4]triazolo[1,5-c]pyridin-5-yl)methanol (0.574 g, 1.382 mmol, 69.8% yield) was collected as a yellow oil. $^1$H NMR (400 MHz, METHANOL-d$_4$) δ (ppm) 8.04 (d, J=5.47 Hz, 1H), 7.63-7.70 (m, 3H), 7.54 (d, J=8.59 Hz, 2H), 7.47 (d, J=9.37 Hz, 1H), 7.32 (d, J=7.03 Hz, 1H), 7.04 (s, 1H), 7.01 (d, J=5.47 Hz, 1H), 6.32 (s, 1H), 3.86 (s, 3H); MS (ESI): m/z 416.2 [M+1]$^+$.

5-(Chloro(2-methoxypyridin-4-yl)methyl)-N-(4-(trifluoromethyl)phenyl)-[1,2,4]triazolo[1,5-a]pyridin-2-amine. The reaction was performed in two batches of starting material (0.250 g and 0.324 g) according to the following procedure. The crude reaction mixtures were recombined and used in the subsequent step without additional purification or characterization. To a suspension of (2-methoxypyridin-4-yl)(2-(4-(trifluoromethyl)phenylamino)-[1,2,4]triazolo[1,5-a]pyridin-5-yl)methanol (0.324 g, 0.780 mmol) in chloroform (3.90 mL) at 0° C. was added dropwise thionyl chloride (0.153 mL, 2.090 mmol). The reaction was stirred at 0° C. for 45 min then at room temperature overnight. Additional thionyl chloride (0.05 mL) and reaction time (5 h) were necessary to drive the reaction to completion. The reaction was quenched with water and neutralized with sodium carbonate. 5-(Chloro(2-methoxypyridin-4-yl)methyl)-N-(4-(trifluoromethyl)phenyl)-[1,2,4]triazolo[1,5-a]pyridin-2-amine was obtained as a yellow oil not further purified or characterized. MS (ESI): m/z 434.2 [M+1]$^+$.

5-((2-Methoxypyridin-4-yl)methyl)-N-(4-(trifluoromethyl)phenyl)-[1,2,4]triazolo[1,5-a]pyridin-2-amine. 5-(Chloro(2-methoxypyridin-4-yl)methyl)-N-(4-(trifluoromethyl)phenyl)-[1,2,4]triazolo[1,5-c]pyridin-2-amine (0.442 g, 1.019 mmol) was dissolved in acetic acid (3.90 mL) and treated with zinc dust (0.333 g, 5.09 mmol). The mixture was refluxed (117° C.) for 1 h, resulting in a conversion to the desired product with further de-methylation to 4-((2-(4-(trifluoromethyl)phenylamino)-[1,2,4]triazolo[1,5-c]pyridin-5-yl)methyl)pyridin-2(1H)-one. Although heating was maintained for a total of 6 h, the mixture remained the same. Heating was stopped. The reaction was diluted with water and neutralized with sodium carbonate. The product was then extracted in ethyl acetate. The extracts were dried over magnesium sulfate and evaporated to dryness. No purification or separation was attempted. 5-((2-Methoxypyridin-4-yl)methyl)-N-(4-(trifluoromethyl)phenyl)-[1,2,4]triazolo[1,5-a]pyridin-2-amine (0.307 g, 0.769 mmol, 75% yield) contaminated with 4-((2-(4-(trifluoromethyl)phenylamino)-[1,2,4]triazolo[1,5-a]pyridin-5-yl)methyl)pyridin-2(1H)-one was used as such in the final step. MS (ESI): m/z 400.3, 386.0 [M+1]$^+$.

4-((2-(4-(Trifluoromethyl)phenylamino)[1,2,4]triazolo[1,5-a]pyridin-5-yl)methyl)pyridin-2(1H)-one. The conversion was performed in two batches (0.215 g and 0.092 g) that were recombined prior to work-up and purification. To a suspension of 54(2-methoxypyridin-4-yl)methyl)-N-(4-(trifluoromethyl)phenyl)-[1,2,4]triazolo[1,5-a]pyridin-2-amine (0.215 g, 0.538 mmol) in acetonitrile (1.252 mL) was added trimethylsilyl chloride (0.076 mL, 0.592 mmol) and potassium iodide (0.098 g, 0.592 mmol). The reaction was heated to 60° C. overnight. The crude reaction was quenched with water. After recombining reaction mixtures, the crude was extracted in ethyl acetate, the extracts were dried over magnesium sulfate and evaporated to dryness. Upon re-suspending the evaporated extracts in ethyl acetate, a yellow solid formed that was collected by filtration and washed with methanol and water. The product was further purified by trituration in a 1:1 mixture of dimethyl sulfoxide and water. The solid was collected by filtration and washed with a 1:1 mixture of methanol and water and dried overnight in a vacuum oven. 4-((2-(4-(trifluoromethyl)phenylamino)-[1,2,4]triazolo[1,5-a]pyridin-5-yl)methyl)pyridin-2(1H)-one (0.203 g, 0.527 mmol, 68.5% yield) was collected as a white solid. $^1$H NMR (400 MHz, DMSO-d$_6$) δ (ppm) 11.50 (br s, 1H), 10.16 (s, 1H), 7.85 (d, J=8.98 Hz, 2H), 7.54-7.66 (m, 4H), 7.32 (d, J=7.42 Hz, 1H), 7.04 (dd, J=1.56, 6.64 Hz, 1H), 6.27 (s, 1H), 6.08-6.16 (m, 1H), 4.30 (s, 2H); $^{19}$F NMR (376 MHz, DMSO-d$_6$) δ (ppm) 60.09; m/z 386.1 [M+1]$^+$. A smaller batch contaminated with starting material was purified by semi-preparative HPLC (20-80% acetonitrile+0.1% trifluoroacetic acid in water+0.1% trifluoroacetic acid), resulting in isolation of the desired product in 40% yield.

Alternatively, the work-up can be modified as follows: after quenching with water, acetonitrile was removed in vacuo until approximately ⅔ of the initial volume remained. tert-Butyl methyl ether was added and the solution was washed with sodium thiosulfate. The solids were removed by filtration, washed with water, tert-butyl methyl ether, cold methanol and acetonitrile and dried under high vacuum to yield the desired product in 77% yield.

Example 87

4-(5-(3-Hydroxybenzyl)-[1,2,4]triazolo[1,5-a]pyridin-2-ylamino)-N-methylbenzamide

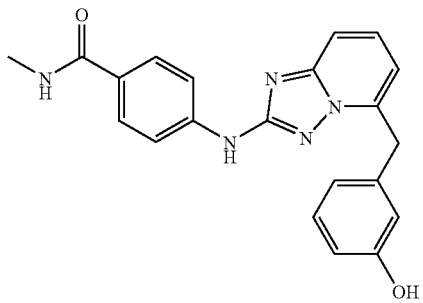

A. (2-Bromo-[1,2,4]triazolo[1,5-a]pyridin-5-yl)(3-methoxyphenyl)methanone. A mixture of 2-(3-methoxyphenyl)acetonitrile (1.17 g, 8 mmol) and sodium hydride (60% in mineral oil, 480 mg, 12 mmol) in N,N-dimethylacetamide (10 mL) was stirred at ambient temperature for 10 min., and at 45° C. 2,5-Dibromo-[1,2,4]triazolo[1,5-a]pyridine (1.1 g, 4 mmol) was added. The reaction mixture was stirred at 45° C. under 1 atmosphere of oxygen for 12 h, poured into icy-water, and extracted with ethyl acetate for three times. The combined organic layers were dried over anhydrous sodium sulfate and concentrated. The residue was purified on silica gel column (eluting with 20% ethyl acetate in petroleum ether) to give (2-bromo-[1,2,4]triazolo[1,5-c]pyridin-5-yl)(3-methoxyphenyl)methanone (780 mg, 58.6% yield) as a solid. $^1$H NMR (400 MHz, DMSO-$d_6$) δ (ppm) 8.05 (d, J=8.8 Hz, 1H), 7.88 (m, 1H), 7.55 (m, 3H), 7.38 (m, 2H), 3.82 (s, 3H).

B. (2-Bromo-[1,2,4]triazolo[1,5-a]pyridin-5-yl)(3-methoxyphenyl)methanol. A mixture of (2-bromo-[1,2,4]triazolo[1,5-c]pyridin-5-yl)(3-methoxyphenyl)methanone (660 mg, 2 mmol), sodium borohydride (76 mg, 2 mmol) in tetrahydrofuran (20 mL) was stirred at ambient temperature for 1 h. An additional sodium borohydride (76 mg, 2 mmol) was added. The mixture was stirred at ambient temperature for another 2 h and concentrated. The residue was dissolved in dichloromethane (20 mL), and the organic layer was washed with water, dried, and concentrated. The residue was purified by column chromatography on silica gel (eluting with dichloromethane) to give (2-bromo-[1,2,4]triazolo[1,5-c]pyridin-5-yl)(3-methoxyphenyl)methanol (522 mg, 78.6% yield). $^1$H NMR (400 MHz, DMSO-$d_6$) δ (ppm) 7.81 (m, 2H), 7.36 (d, J=6.8 Hz, 1H), 7.24 (t, J=8.0 Hz, 1H), 7.03 (s, 1H), 6.98 (d, J=7.6 Hz, 1H), 6.84 (dd, $J_1$=2.4 Hz, $J_2$=8.0 Hz, 1H), 6.55 (d, J=4.4 Hz, 1H), 6.28 (d, J=4.8 Hz, 1H), 3.72 (s, 3H).

C. 2-Bromo-5-(3-methoxybenzyl)[1,2,4]triazolo[1,5-a]pyridine. A mixture of (2-bromo-[1,2,4]triazolo[1,5-c]pyridin-5-yl)(3-methoxyphenyl)methanol (520 mg, 1.56 mmol) in a mixture of triethylsilane (5 mL) and trifluoroacetic acid (5 mL) was stirred at 80° C. for 10 h. When TLC indicated the starting material was consumed, the mixture was concentrated under vacuum. The residue was purified by column chromatography on silica gel (eluting with 30% petroleum ether in dimethyl chloride) to give 2-bromo-5-(3-methoxybenzyl)-[1,2,4]triazolo[1,5-c]pyridine (300 mg, 60.6% yield) as a yellow oil. $^1$H NMR (400 MHz, DMSO-$d_6$) δ (ppm) 7.75 (m, 2H), 7.26 (t, J=8.0 Hz, 1H), 6.98 (m, 2H), 6.86 (d, J=2.0 Hz, 1H), 6.84 (d, J=2.0 Hz, 1H), 4.44 (s, 2H), 3.73 (s, 3H).

D. 4-(5-(3-Hydroxybenzyl)-[1,2,4]triazolo[1,5-a]pyridin-2-ylamino)-N-methylbenzamide. A degassed mixture of 2-bromo-5-(3-methoxybenzyl)-[1,2,4]triazolo[1,5-c]pyridine (200 mg, 0.63 mmol), 4-amino-N-methylbenzamide (113 mg, 0.75 mmol), tris(dibenzylideneacetone)palladium (0) (29 mg, 0.03 mmol), 4,5-bis(diphenylphosphino)-9,9-dimethylxanthene (34 mg, 0.06 mmol), and potassium tert-butoxide (154 mg, 1.26 mmol) in dioxane (5 mL) was heated at 100° C. under nitrogen overnight. The reaction mixture was filtered, and the filtrate was concentrated in vacuo to give the crude product, which was purified on silica gel chromatography (eluting with 50% ethyl acetate in petroleum ether) to give 4-(5-(3-hydroxybenzyl)-[1,2,4]triazolo[1,5-c]pyridin-2-ylamino)-N-methylbenzamide (80 mg, 32.6% yield) as a solid. $^1$H NMR (400 MHz, DMSO-$d_6$) δ (ppm) 9.95 (s, 1H), 8.22 (m, 1H), 7.80 (m, 4H), 7.60 (m, 2H), 7.27 (t, J=8.0 Hz, 1H), 7.02 (m, 2H), 6.89 (m, 2H), 4.44 (s, 2H), 3.72 (s, 3H), 2.78 (d, J=4.4 Hz, 3H); MS (ESI): m/z 373.2 [M+1]$^+$.

Example 88

1-((2-(4-(Trifluoromethyl)phenylamino)[1,2,4]triazolo[1,5-a]pyridin-5-yl)methyl)tetrahydropyrimidin-2(1H)-one

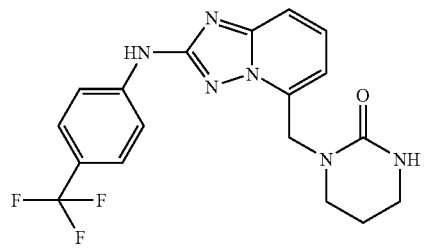

A. 5-(Azidomethyl)-N-(4-(trifluoromethyl)phenyl)-[1,2,4]triazolo[1,5-a]pyridin-2-amine. (2-(4-(Trifluoromethyl)phenylamino)-[1,2,4]triazolo[1,5-a]pyridin-5-yl)methanol (989.2 mg, 3.21 mmol) was treated with dioxane (6 mL), then diphenylphosphoryl azide (1.40 mL, 6.48 mmol) and 1,8-diazabicyclo[5.4.0]undec-7-ene (1.0 mL, 6.63 mmol). The reaction was stirred and warmed mildly in a 55° C. aluminum block for 1 min, until all solid dissolved, then left to stir at room temperature. After 18 h the reaction was diluted with ethyl acetate, water, and some sodium bicarbonate solution. The organic layer was removed, and the aqueous layer extracted with ethyl acetate. The combined organic solution was dried over magnesium sulfate, filtered and concentrated. The crude product was purified by flash chromatography over silica gel (eluting with 0-6% methanol in dichloromethane for six column volumes and then 6-8% for six column volumes) to provide 5-(azidomethyl)-N-(4-(trifluoromethyl)phenyl)-[1,2,4]triazolo[1,5-c]pyridin-2-amine (0.5473 g, 1.642 mmol, 51.2% yield) as a yellow solid. (ESI): m/z 334.5 [M+1]$^+$.

B. 5-(Aminomethyl)-N-(4-(trifluoromethyl)phenyl)-[1,2,4]triazolo[1,5-a]pyridin-2-amine. The 5-(azidomethyl)-N-(4-(trifluoromethyl)phenyl)-[1,2,4]triazolo[1,5-c]pyridin-2-amine (0.5473 g, 1.642 mmol) was treated with tetrahydrofuran (10 mL) and water (0.30 mL, 16.65 mmol). Triphenylphosphine (1.1966 g, 4.56 mmol) was added, and the homogeneous reaction was warmed to 55° C. After 3 h, the reaction was diluted with ethyl acetate and 1N hydrochloric acid, and the aqueous layer was removed. The aqueous layer was then made basic with saturated sodium bicarbonate solution, and extracted 4 times with ethyl acetate:THF, and the combined organic solution was dried over magnesium sulfate, filtered and concentrated to provide 5-(aminomethyl)-N-(4-(trifluoromethyl)phenyl)-[1,2,4]triazolo[1,5-c]pyridin-2-amine (303.1 mg, 0.986 mmol, 60.1% yield). $^1$H NMR (400 MHz, DMSO-$d_6$) δ (ppm) 10.19 (s, 1H), 7.91 (d, J=8.20 Hz, 2H), 7.59-7.70 (m, 3H), 7.50-7.57 (m, 1H), 7.15 (d, J=7.03 Hz, 1H), 4.15 (s, 2H). (ESI): m/z 308.4 [M+1]$^+$.

C. 1-((2-(4-(Trifluoromethyl)phenylamino)-[1,2,4]triazolo[1,5-a]pyridin-5-yl)methyl)tetrahydropyrimidin-2(1H)-one. 5-(Aminomethyl)-N-(4-(trifluoromethyl)phenyl)-[1,2,4]triazolo[1,5-a]pyridin-2-amine (109.1 mg, 0.355 mmol) was dissolved into tetrahydrofuran (4 mL) and 1-chloro-3-isocyanatopropane (0.060 mL, 0.585 mmol) was added. After 10 min LCMS analysis showed a strong peak for the urea, still bearing the chloride. Sodium hydride (21.0 mg, 0.831 mmol, 95%) was added to the milky suspension, giving a thick mixture. N,N-dimethylformamide (1 mL) was added to help solubilize. Another portion of sodium hydride (25.1 mg, 1.046 mmol) was added, and the reaction was left to stir at room temperature for 20 h. The sample was dissolved into water and acetonitrile using trifluoroacetic acid, and the material was then purified by reverse phase preparative HPLC (20-100% acetonitrile:water with 0.1% TFA). The product was isolated by dissolution in ethyl acetate, washing with saturated sodium bicarbonate solution, drying over magnesium sulfate, then filtration and concentration to provide 1-((2-(4-(trifluoromethyl)phenylamino)-[1,2,4]triazolo[1,5-c]pyridin-5-yl)methyl)tetrahydropyrimidin-2(1H)-one (72.8 mg, 0.186 mmol, 52.5% yield). $^1$H NMR (400 MHz, DMSO-$d_6$) δ (ppm) 10.21 (s, 1H), 7.93 (d, J=8.59 Hz, 2H), 7.59-7.69 (m, 3H), 7.53-7.58 (m, 1H), 6.85 (d, J=7.03 Hz, 1H), 6.56 (br s, 1H), 4.85 (s, 2H), 3.41 (t, J=5.66 Hz, 2H), 3.22 (br s, 2H), 1.93 (t, 2H). (ESI): m/z 391.7 [M+1]$^+$.

Example 89

4-((2-(4-(Trifluoromethyl)phenylamino)[1,2,4]triazolo[1,5-a]pyridin-5-yl)methyl)piperazine-2,6-dione

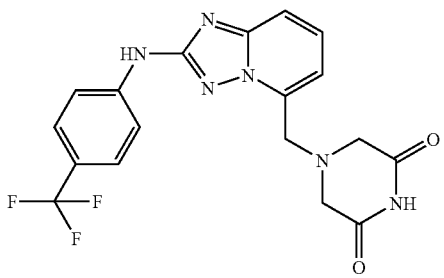

A. Dimethyl 2,2'-((2-(4-(trifluoromethyl)phenylamino)-[1,2,4]triazolo[1,5-a]pyridin-5-yl)methylazanediyl)diacetate. 5-(Aminomethyl)-N-(4-(trifluoromethyl)phenyl)-[1,2,4]triazolo[1,5-a]pyridin-2-amine (146.9 mg, 0.478 mmol) was dissolved into N,N-dimethylformamide (2.5 mL). Diisopropylethylamine (0.50 mL, 2.86 mmol) was added, and the reaction cooled to 0° C. Methyl bromoacetate (0.15 mL, 1.628 mmol) was then added in one portion, and the reaction was allowed to warm to room temperature over 20 h. The reaction was diluted with ethyl acetate and water. The organic layer was removed, and the aqueous layer extracted with ethyl acetate. The combined organic solution was dried over magnesium sulfate, filtered and concentrated. The material was purified by flash chromatography over silica gel in 2-3% ammonia-saturated methanol in dichloromethane to provide dimethyl 2,2'-((2-(4-(trifluoromethyl)phenylamino)-[1,2,4]triazolo[1,5-c]pyridin-5-yl)methylazanediyl)diacetate (189.1 mg, 0.419 mmol, 88% yield) as a yellow solid. $^1$H NMR (400 MHz, CHLOROFORM-d) δ (ppm) 7.71 (d, J=8.20 Hz, 2H), 7.60 (d, J=8.20 Hz, 2H), 7.41-7.55 (m, 3H), 7.18 (d, J=6.64 Hz, 1H), 4.47 (s, 2H), 3.77 (s, 4H), 3.71 (s, 6H). (ESI): m/z 452.4 [M+1]$^+$.

B. 4-((2-(4-(Trifluoromethyl)phenylamino)-[1,2,4]triazolo[1,5-a]pyridin-5-yl)methyl)piperazine-2,6-dione. Dimethyl 2,2'-((2-(4-(trifluoromethyl)phenylamino)-[1,2,4]triazolo[1,5-c]pyridin-5-yl)methylazanediyl)diacetate (116.9 mg, 0.259 mmol) was dissolved into formamide (4 mL, 0.259 mmol) in a pressure tube, which was capped and placed in a 120° C. oil bath. After 18 h the reaction was purified directly by reverse phase preparative HPLC (0-100% acetonitrile:water with 0.1% trifluoroacetic acid). The product was isolated as the free base by diluting some of the fractions with ethyl acetate, water, and sodium bicarbonate solution. The organic layer was removed, and the aqueous layer extracted with ethyl acetate. The combined organic solution was dried over magnesium sulfate, filtered and concentrated to provide the desired product 4-((2-(4-(trifluoromethyl)phenylamino)-[1,2,4]triazolo[1,5-a]pyridin-5-yl)methyl)piperazine-2,6-dione (10.4 mg, 0.026 mmol, 9.93% yield). $^1$H NMR (400 MHz, DMSO-$d_6$) δ (ppm) 11.23 (s, 1H), 10.19 (s, 1H), 7.90 (d, J=8.59 Hz, 2H), 7.52-7.71 (m, 6H), 7.12 (d, J=6.25 Hz, 1H), 4.22 (s, 2H), 3.56 (s, 4H). (ESI): m/z 405.1 [M+1]$^+$.

Example 90

1-((2-(4-(Trifluoromethyl)phenylamino)[1,2,4]triazolo[1,5-a]pyridin-5-yl)methyl)imidazolidine-2,4-dione

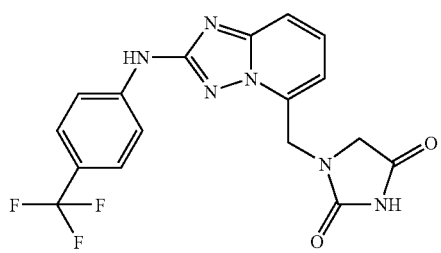

A. Ethyl 2-((2-(4-(trifluoromethyl)phenylamino)-[1,2,4]triazolo[1,5-a]pyridin-5-yl)methylamino)acetate. 2-(4-(Trifluoromethyl)phenylamino)-[1,2,4]triazolo[1,5-c]pyridine-5-carbaldehyde (308.6 mg, 1.008 mmol), ethyl aminoacetate hydrochloride (203.7 mg, 1.459 mmol), and potassium acetate (128.1 mg, 1.305 mmol) were weighed into a vial. Methanol (2 mL) was added and the vial was heated to 55° C. for 2 min. Tetrahydrofuran (2 mL) was then added to help dissolution, and the reaction cooled to room temperature. Sodium cyanoborohydride (83 mg, 1.321 mmol) was added to the reaction causing some gas evolution. After 1 h, the reaction was diluted with ethyl acetate and water. The organic layer was removed, and the aqueous layer extracted with ethyl acetate. The combined organic solution was dried over magnesium sulfate, filtered and concentrated. The crude product was purified over silica gel to provide the desired ethyl 2-(2-(4-(trifluoromethyl)phenylamino)-[1,2,4]triazolo[1,5-c]pyridin-5-yl)methylamino)acetate (0.2696 g, 0.685 mmol, 68.0% yield). $^1$H NMR (400 MHz, CHLOROFORM-d) δ (ppm) 7.73 (d, J=8.59 Hz, 2H), 7.60 (d, J=8.59 Hz, 2H), 7.44-7.50 (m, 2H), 6.96 (dd, J=5.47, 2.73 Hz, 1H), 4.30 (s, 2H), 4.18 (q, J=7.29 Hz, 2H), 3.51 (s, 2H), 1.26 (t, J=7.03 Hz, 3H). (ESI): m/z 394.4 [M+1]$^+$.

B. Ethyl 2-(1-((2-(4-(trifluoromethyl)phenylamino)-[1,2,4]triazolo[1,5-a]pyridin-5-yl)methyl)ureido)acetate. Ethyl 2-((2-(4-(trifluoromethyl)phenylamino)-[1,2,4]triazolo[1,5-c]pyridin-5-yl)methylamino)acetate (237.7 mg, 0.604 mmol) was dissolved into N,N-dimethylformamide (1 mL), and isocyanatotrimethylsilane (0.12 mL, 0.903 mmol) was added. After 18 h, LCMS analysis showed that some starting material remained. Another portion of isocyanatotrimethylsilane (0.06 mL, 0.604 mmol) was added. After 3 h the reaction was diluted with ethyl acetate and washed with water, using some methanol and tetrahydrofuran to break up the emulsion. The organic solution was removed, and the aqueous layer extracted with ethyl acetate. The combined organic solution was dried over magnesium sulfate, filtered and concentrated to provide ethyl 2-(1-((2-(4-(trifluoromethyl)phenylamino)-[1,2,4]triazolo[1,5-c]pyridin-5-yl)methyl)ureido)acetate (279.9 mg, 0.641 mmol, 106% yield) as a crude solid that was carried on directly to the next reaction (ESI): m/z 437.5 [M+1]$^+$.

C. 1-((2-(4-(Trifluoromethyl)phenylamino)-[1,2,4]triazolo[1,5-a]pyridin-5-yl)methyl)imidazolidine-2,4-dione. Ethyl 2-(1-(2-(4-(trifluoromethyl)phenylamino)-[1,2,4]triazolo[1,5-c]pyridin-5-yl)methyl)ureido)acetate (241.6 mg, 0.554 mmol) was dissolved into ethanol (2 mL), and sodium hydride (49.5 mg, 2.063 mmol) was added to give a yellow solution. Since the starting material did not completely dissolve, tetrahydrofuran (2 mL) was added. After 3 h, the reaction was quenched with water and diluted with ethyl acetate. The organic layer was removed, using some methanol to break up the emulsion, and the aqueous layer was extracted with ethyl acetate. The combined organic solution was dried over magnesium sulfate, filtered and concentrated. The solid was redissolved into dimethylsulfoxide and acetonitrile, and purified by reverse phase preparative HPLC (20-100% acetonitrile:water with 0.1% trifluoroacetic acid). The product was isolated as the free base by dissolution in ethyl acetate, washing with saturated sodium bicarbonate solution, drying over magnesium sulfate, then filtration and concentration to provide 1-((2-(4-(trifluoromethyl)phenylamino)-[1,2,4]triazolo[1,5-c]pyridin-5-yl)methyl)imidazolidine-2,4-dione (32.2 mg, 0.082 mmol, 14.90% yield). $^1$H NMR (400 MHz, DMSO-d$_6$) δ (ppm) 11.00 (s, 1H), 10.21 (s, 1H), 7.92 (d, J=8.59 Hz, 2H), 7.56-7.69 (m, 4H), 7.09 (t, J=4.10 Hz, 1H), 4.91 (s, 2H), 4.08 (s, 2H). (ESI): m/z 391.1 [M+1]$^+$.

Example 91

(1-((2-(4-(trifluoromethyl)phenylamino)[1,2,4]triazolo[1,5-a]pyridin-5-yl)methyl)piperidin-4-yl)methanol

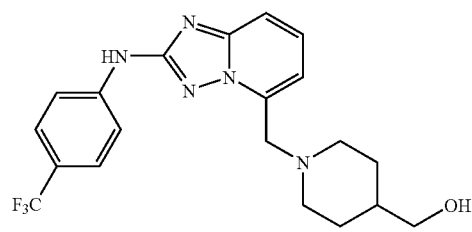

A. (1-((2-(4-(Trifluoromethyl)phenylamino)[1,2,4]triazolo[1,5-a]pyridin-5-yl)methyl)piperidin-4-yl)methanol. (2-(4-(Trifluoromethyl)phenylamino)-[1,2,4]triazolo[1,5-c]pyridin-5-yl)methanol (0.2 g, 0.649 mmol) was dissolved in ethyl acetate (5 mL) and triethylamine (0.271 mL, 1.946 mmol). Then methanesulfonyl chloride (0.101 mL, 1.298 mmol) was added and stirred at room temperature for 2 h. Piperidin-4-ylmethanol (0.224 g, 1.946 mmol) was added to the reaction and stirred at room temperature for 16 h. The reaction was concentrated and then purified by reverse phase HPLC (10-70% acetonitrile and water with 0.1% trifluoroacetic acid). The product fractions were past through ion-exchange column (Strata-XC) and released with 2M ammonia in methanol. The solution was concentrated and triturated with 5% methanol in ethyl acetate to give a white solid, (0.086 g, 0.212 mmol, 32.7% yield). $^1$H NMR (400 MHz, DMSO-d$_6$) δ (ppm) 10.18 (s, 1H), 7.91 (d, J=8.2 Hz, 2H), 7.58-7.69 (m, 3H), 7.51-7.57 (m, 1H), 7.09 (d, J=6.6 Hz, 1H), 4.45 (t, J=4.7 Hz, 1H), 3.96 (s, 2H), 3.27 (t, J=4.5 Hz, 2H), 2.98 (d, J=11.7 Hz, 2H), 2.16 (t, J=10.9 Hz, 2H), 1.68 (d, J=11.7 Hz, 2H), 1.39 (br s, 1H), 1.13-1.31 (m, 3H). MS (ESI) m/z 406.3 [M+1]$^+$.

Example 92

4-(5-(2-Hydroxy-2-(piperidin-4-yl)ethyl)[1,2,4]triazolo[1,5-a]pyridin-2-ylamino)-N-methylbenzamide

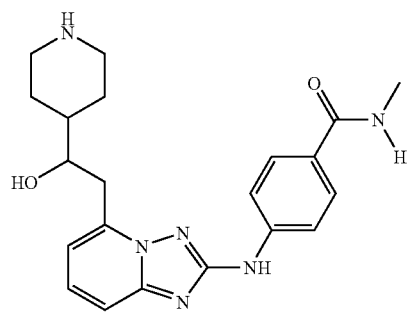

A. tert-Butyl 6-methylpyridin-2-ylcarbamate. A mixture of 6-methylpyridin-2-amine (5 g, 46 mmol), di-tert-butyl dicarbonate (20 g, 92 mmol), triethylamine (9.3 g, 92 mmol)

and N,N-dimethylpyridin-4-amine (280 mg, 2.3 mmol) in dichloromethane (20 mL) was stirred at room temperature overnight. Water was added, and the organic layer was separated, the aqueous phase was extracted with dichloromethane. The combined organic layer was washed with brine, dried over sodium sulfate and evaporated under reduced pressure. The crude product was purified on silica gel column (eluting with 10% ethyl acetate in petroleum ether) to give tert-butyl 6-methylpyridin-2-ylcarbamate (3 g, 30% yield) as a solid. $^1$H NMR (400 MHz, METHANOL-$d_4$) δ (ppm) 7.63 (t, J=8.0 Hz, 1H), 7.31 (d, J=8.0 Hz, 1H), 7.06 (d, J=7.6 Hz, 1H), 2.55 (s, 3H), 1.45 (s, 9H).

B. tert-Butyl 4-(2-(6-(tert-butoxycarbonylamino)pyridin-2-yl)acetyl)piperidine-1-carboxylate. To a stirred solution of tert-butyl 6-methylpyridin-2-ylcarbamate (1 g, 4.8 mmol) in tetrahydrofuran (10 mL) was added dropwise a solution of n-butyl lithium in hexane (4.8 mL, 2.5 M) at −78° C. under nitrogen for 1 h. After addition was complete, the reaction mixture was warmed to room temperature over 1 h, and cooled again at −78° C. A solution of tert-butyl 4-(methoxy (methyl)carbamoyl)piperidine-1-carboxylate (1.6 g, 5.7 mmol) in tetrahydrofuran (10 mL) was added dropwise into the mixture at −78° C., the reaction mixture was warmed to room temperature overnight. Aqueous ammonium chloride solution was added slowly, and the mixture was extracted with ethyl acetate (30 mL×3). The combined organic layer was washed with brine (50 mL), dried over sodium sulfate, and concentrated under reduced pressure to give the crude product, which was purified on silica gel column (eluting with 20% ethyl acetate in petroleum ether) to give tert-butyl 4-(2-(6-(tert-butoxycarbonylamino)pyridin-2-yl)acetyl)piperidine-1-carboxylate (380 mg, 19% yield) as a solid. MS (ESI): m/z 420.1 [M+1]$^+$.

C. tert-Butyl 4-(2-(6-(tert-butoxycarbonylamino)pyridin-2-yl)-1-hydroxyethyl)piperidine-1-carboxylate. A mixture of tert-butyl 4-(2-(6-(tert-butoxycarbonylamino)pyridin-2-yl) acetyl)piperidine-1-carboxylate (380 mg, 0.9 mmol) and sodium borohydride (69 mg, 1.8 mmol) in tetrahydrofuran (5 mL) was refluxed for 0.5 h. It was concentrated in vacuo, and the residue was diluted with ethyl acetate. The organic layer was washed with brine and concentrated under reduced pressure to give tert-butyl 4-(2-(6-(tert-butoxycarbonylamino)pyridin-2-yl)-1-hydroxyethyl)piperidine-1-carboxylate (320 mg, 84% yield) as a solid. MS (ESI): m/z 422.2 [M+1]$^+$.

D. 2-(6-Aminopyridin-2-yl)-1-(piperidin-4-yl)ethanol. A mixture of tert-butyl 4-(2-(6-(tert-butoxycarbonylamino)pyridin-2-yl)-1-hydroxyethyl)piperidine-1-carboxylate (320 g, 0.76 mmol) in methanolic hydrochloride solution (2 M, 5 mL) was stirred for 2 h. The reaction mixture was concentrated in vacuo to give 2-(6-amino-pyridin-2-yl)-1-piperidin-4-yl-ethanol (160 mg, 95% yield) as a solid.

E. tert-Butyl 4-(2-(6-aminopyridin-2-yl)-1-hydroxyethyl) piperidine-1-carboxylate. A mixture of methyl 2-(6-aminopyridin-2-yl)-1-(piperidin-4-yl)ethanol (160 mg, 0.72 mmol), di-tert-butyl dicarbonate (158 mg, 0.72 mmol) and triethylamine (145 mg, 1.44 mmol) in dichloromethane (5 mL) was stirred at room temperature overnight. Water was added, and the organic layer was separated. The aqueous phase was extracted with dichloromethane, and the combined organic layer was washed with brine, dried over sodium sulfate, and evaporated under reduced pressure. The crude product was purified on silica gel column (eluting with 30% ethyl acetate in petroleum ether) to give tert-butyl 4-(2-(6-aminopyridin-2-yl)-1-hydroxyethyl)piperidine-1-carboxylate (220 mg, 95% yield) as a solid. MS (ESI): m/z 322.1 [M+1]$^+$.

F. tert-Butyl 4-(2-(6-(3-(ethoxycarbonyl)thioureido)pyridin-2-yl)-1-hydroxyethyl)piperidine-1-carboxylate. A mixture of tert-butyl 4-(2-(6-aminopyridin-2-yl)-1-hydroxyethyl)piperidine-1-carboxylate (220 mg, 0.68 mmol) and ethoxycarbonyl isothiocyanate (89 mg, 0.68 mmol) in dioxane (5 mL) was stirred at room temperature for 5 h. The solvent was removed to afford tert-butyl 4-(2-(6-(3-(ethoxycarbonyl)thioureido)pyridin-2-yl)-1-hydroxyethyl)piperidine-1-carboxylate (309 mg, 99%) as a white solid, which was used in the next step without further purification.

G. tert-Butyl 4-(2-(2-amino-[1,2,4]triazolo[1,5-a]pyridin-5-yl)-1-hydroxyethyl)piperidine-1-carboxylate. To a solution of hydroxylamine hydrochloride (236 mg, 3.4 mmol) and N,N-diethylisopropyl-amine (263 mg, 2.0 mmol) in a mixture of ethanol and methanol (20 mL, v/v, 1:1) was added tert-butyl 4-(2-(6-(3-(ethoxycarbonyl)thioureido)pyridin-2-yl)-1-hydroxyethyl)piperidine-1-carboxylate (309 mg, 0.68 mmol). The reaction mixture was stirred at room temperature for 2 h and at 70° C. for 5 h. The volatiles were removed under reduced pressure, the residue was diluted with water, and the aqueous phase was extracted with dichloromethane. The combined organic layer was washed with brine, dried over sodium sulfate, and evaporated under reduced pressure to give tert-butyl 4-(2-(2-amino-[1,2,4]triazolo[1,5-c]pyridin-5-yl)-1-hydroxyethyl)piperidine-1-carboxylate (150 mg, 61% yield) as a solid. MS (ESI): m/z 362.1 [M+1]$^+$.

H. tert-Butyl 4-(1-hydroxy-2-(2-(4-(methylcarbamoyl) phenylamino)-[1,2,4]triazolo[1,5-a]pyridin-5-yl)ethyl)piperidine-1-carboxylate. A degassed mixture of tert-butyl 4-(2-(2-amino-[1,2,4]triazolo[1,5-c]pyridin-5-yl)-1-hydroxyethyl)piperidine-1-carboxylate (130 mg, 0.36 mmol), 4-iodo-N-methylbenzamide (113 mg, 0.43 mmol), tris(dibenzylideneacetone)dipalladium(0) (16 mg, 0.02 mmol), 4,5-bis(diphenylphosphino)-9,9-dimethylxanthene (21 mg, 0.044 mmol) and cesium carbonate (140 mg, 0.43 mmol) in dioxane (5 mL) was heated at 100° C. under nitrogen overnight. The reaction mixture was diluted with water, and the aqueous layer was extracted with ethyl acetate. The organic layer was dried over sodium sulfate and evaporated under reduced pressure. The residue was purified by a reverse-phase preparatory HPLC (23-43% acetonitrile+0.1% trifluoroacetic acid in water+0.1% trifluoroacetic acid, over 20 min.) to give tert-butyl 4-(1-hydroxy-2-(2-(4-(methylcarbamoyl)phenylamino)-[1,2,4]triazolo[1,5-a]pyridin-5-yl) ethyl)piperidine-1-carboxylate as a trifluoroacetic acid salt (40 mg, yield 19%). MS (ESI): m/z 495.1 [M+1]$^+$.

I. 4-(5-(2-Hydroxy-2-(piperidin-4-yl)ethyl)-[1,2,4]triazolo[1,5-a]pyridin-2-ylamino)-N-methylbenzamide. A mixture of tert-butyl 4-(1-hydroxy-2-(2-(4-(methylcarbamoyl) phenylamino)-[1,2,4]triazolo[1,5-a]pyridin-5-yl)ethyl) piperidine-1-carboxylate (40 mg, 0.08 mmol) trifluoroacetic acid salt in methanolic hydrochloride solution (2 M, 50 mL) was refluxed overnight. The reaction mixture was concentrated in vacuo to give 4-(5-(2-hydroxy-2-(piperidin-4-yl) ethyl)-[1,2,4]triazolo[1,5-c]pyridin-2-ylamino)-N-methylbenzamide (20 mg, 64% yield) as a hydrochloride salt. $^1$H NMR (400 MHz, METHANOL-$d_4$) δ (ppm) 7.97 (t, J=8.0 Hz, 1H), 7.90 (d, J=8.4 Hz, 2H), 7.76 (d, J=8.4 Hz, 2H), 7.69 (d, J=8.8 Hz, 1H), 7.40 (d, J=7.2 Hz, 1H), 4.08 (s, 1H), 3.67 (d, J=12.4 Hz, 1H), 3.48 (m, 2H), 3.17 (m, 2H), 3.06 (m, 2H), 2.94 (s, 3H), 2.23 (d, J=14.0 Hz, 1H), 2.13 (d, J=13.2 Hz, 1H), 1.73 (m, 2H); MS (ESI): m/z 394.9 [M+1]⁺.

Example 93 cis-4-(5-Phenyl-[1,2,4]triazolo[1,5-a]pyridin-2-ylamino)cyclohexanecarboxamide

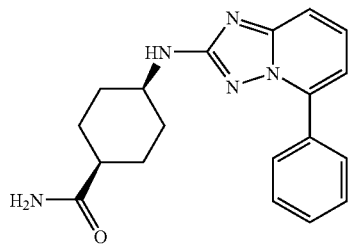

A. Ethyl 4-(5-phenyl-[1,2,4]triazolo[1,5-a]pyridin-2-ylamino)-cyclohexanecarboxylate. A solution of 5-phenyl-[1,2,4]triazolo[1,5-a]pyridin-2-amine (0.500 g, 2.378 mmol) in 1,2-dichloroethane (9.51 mL) at room temperature was treated with ethyl 4-oxocyclohexanecarboxylate (0.607 g, 3.57 mmol) and sodium triacetoxyborohydride (1.00 g, 4.76 mmol) as well as acetic acid (0.5 mL). The reaction was stirred at room temperature overnight. As unreacted starting materials were still present, additional reagents were used and stirring was pursued overnight. The reaction was quenched with water and stirred for 5 min. The organic phase was separated and dried over magnesium sulfate, and evaporated to dryness. The crude was purified by silica gel column chromatography (eluting with 10-20% ethyl acetate in hexanes). Ethyl 4-(5-phenyl-[1,2,4]triazolo[1,5-a]pyridin-2-ylamino)cyclohexanecarboxylate (0.5 g, 1.372 mmol, 57.7% yield) was used as a mixture of diastereomers in the subsequent hydrolysis step. MS (ESI) m/z 365 [M+1]⁺.

B. 4-(5-Phenyl-[1,2,4]triazolo[1,5-a]pyridin-2-ylamino)cyclohexanecarboxylic acid. Ethyl 4-(5-phenyl-[1,2,4]triazolo[1,5-a]pyridin-2-ylamino)cyclohexanecarboxylate (0.5 g, 1.372 mmol) was suspended in a 3.0 M aqueous solution of HCl (10 mL) and heated to 60° C. After 2 h, the reaction was complete and the solvents were removed under reduced pressure. Crude 4-(5-phenyl-[1,2,4]triazolo[1,5-a]pyridin-2-ylamino)cyclohexanecarboxylic acid (0.462 g, 1.372 mmol) was used without further purification. MS (ESI) m/z 337 [M+1]⁺.

C. cis-4-(5-Phenyl-[1,2,4]triazolo[1,5-a]pyridin-2-ylamino)cyclohexanecarboxamide. At room temperature, 4-(5-phenyl-[1,2,4]triazolo[1,5-a]pyridin-2-ylamino)cyclohexanecarboxylic acid (0.462 g, 1.372 mmol) was dissolved in N,N-dimethylformamide (5.49 mL) and treated with 4-methylmorpholine (0.208 g, 2.058 mmol), ammonium chloride (0.110 g, 2.058 mmol) and (1H-benzo[d][1,2,3]triazol-1-yloxy)tris(dimethylamino)phosphonium hexafluorophosphate(V) (0.910 g, 2.058 mmol). The reaction was stirred at room temperature overnight. The solvent was removed under reduced pressure and the crude was partitioned between ethyl acetate and aqueous sodium bicarbonate. The organic phase was washed with brine, dried over magnesium sulfate and evaporated to dryness. The crude was purified by silica gel column chromatography (eluting with 0-10% methanol in ethyl acetate). Full separation of the 2 diastereomers was effected by semi-preparative HPLC (10-50% acetonitrile+ 0.1% trifluoroacetic acid in water+0.1% trifluoroacetic acid over 30 min, 3 injections). The corresponding fractions were collected and neutralized with a 1.75 M aqueous solution of potassium carbonate. The most polar component was collected as a solid, by filtration after removal of acetonitrile under reduced pressure. The solid was washed with water until the pH of the washing became neutral. The material was isolated (0.015 g) as a white solid (99.8% pure) associated with the cis isomer based on its proton NMR spectrum. ¹H NMR (400 MHz, METHANOL-d₄) δ (ppm) 7.95-7.99 (m, 1H), 7.51-7.60 (m, 2H), 7.36 (dd, J=8.7, 1.2 Hz, 1H), 7.05 (dd, J=7.4, 1.3 Hz, 1H), 3.52-3.62 (m, 1H), 2.17-2.27 (m, 1H), 1.90-1.97 (m, 1H), 1.55-1.67 (m, 1H), 1.27-1.38 (m, 1H). The least polar component was extracted with ethyl acetate. The extracts were dried over magnesium sulfate and evaporated to dryness affording 0.033 g of material associated with the trans isomer (98.9% pure) based on its proton NMR spectrum. ¹H NMR (400 MHz, METHANOL-d₄) δ (ppm) 7.93-7.99 (m, 2H), 7.48-7.60 (m, 4H), 7.34-7.39 (m, 1H), 7.05 (dd, J=7.3, 1.1 Hz, 1H), 3.87-3.93 (m, 1H), 2.30-2.40 (m, 1H), 1.82-1.99 (m, 4H), 1.64-1.78 (m, 4H); MS (ESI) m/z 336 [M+1]⁺.

Example 94

(6-(2-(6-Methylpyridin-3-ylamino)-[1,2,4]triazolo[1,5-a]pyridin-5-yl)-1H-benzo[d]imidazol-2-yl)methanol

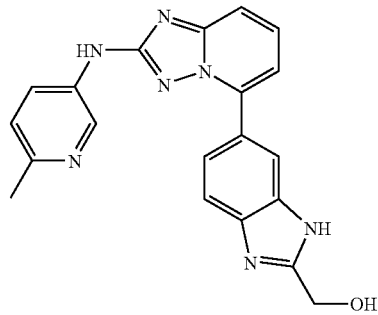

A. 4-(2-Bromo-[1,2,4]triazolo[1,5-a]pyridin-5-yl)-2-nitroaniline. A degassed mixture of 2,5-dibromo-[1,2,4]triazolo[1,5-a]pyridine (2 g, 7.28 mmol), 2-nitro-4-(4,4,5,5-tetramethyl-1,3,2-dioxaborolan-2-yl)aniline (2.3 g, 8.74 mmol), sodium carbonate (1.53 g, 14.4 mmol) and 1,1'-bis(diphenylphosphino)ferrocene palladium dichloride (534 mg, 0.728 mmol) in a mixture of dioxane and water (v/v, 3:1, 28 mL) was heated at 100° C. under nitrogen overnight. The reaction mixture was poured into water, and the mixture was extracted with ethyl acetate. The combined organic layers were dried over anhydrous sodium sulfate, and evaporated under reduced pressure. The residue was purified on silica gel column (eluting with 10-50% ethyl acetate in petroleum ether) to give 4-(2-bromo-[1,2,4]triazolo[1,5-c]pyridin-5-yl)-2-nitroaniline (1.38 g, 57% yield) as a solid. MS (ESI): m/z 333.8 [M+1]⁺.

B. tert-Butyl 4-(2-bromo-[1,2,4]triazolo[1,5-a]pyridin-5-yl)-2-nitrophenylcarbamate. A mixture of 4-(2-bromo-[1,2,4]triazolo[1,5-c]pyridin-5-yl)-2-nitroaniline (1.2 g, 3.6 mmol), di-tert-butyl dicarbonate (1.96 g, 9 mmol) and N,N-dimethylpyridin-4-amine (144 mg, 1.08 mmol) in dichloromethane (50 mL) was stirred at room temperature overnight. The solvent was removed under reduced pressure, and the residue was diluted with ethyl acetate. The organic layer was washed with water and brine, dried over anhydrous sodium sulfate, and evaporated under reduced pressure. The residue was purified on silica gel column (eluting with 10-50% ethyl acetate in petroleum ether) to give tert-butyl 4-(2-bromo-[1,2,4]triazolo[1,5-c]pyridin-5-yl)-2-nitrophenylcarbamate (1.4 g, 90% yield) as a yellow solid. MS (ESI): m/z 433.8 [M+1]+.

C. tert-Butyl 4-(2-(6-methylpyridin-3-ylamino)-[1,2,4]triazolo[1,5-a]pyridin-5-yl)-2-nitrophenylcarbamate. A degassed solution of tert-butyl 4-(2-bromo-[1,2,4]triazolo[1,5-a]pyridin-5-yl)-2-nitrophenylcarbamate (440 mg, 0.81 mmol), 6-methylpyridin-3-amine (105 mg, 0.93 mmol), tris(dibenzylideneacetone)dipalladium(0) (75 mg, 0.081 mmol), 4,5-bis(diphenylphosphino)-9,9-dimethylxanthene (92 mg, 0.162 mmol) and potassium tert-butoxide (198 mg, 1.62 mmol) in dioxane (20 mL) was heated at 110° C. under nitrogen overnight. After cooling to room temperature, the reaction mixture was concentrated, and the residue was dissolved in a mixture of dichloromethane and methanol (v/v, 1:1, 20 mL). The solids were filtrated, and the filtrate was concentrated. The residue was purified on silica gel column (eluting with 10-100% ethyl acetate in petroleum ether) to give tert-butyl 4-(2-6-methylpyridin-3-ylamino)-[1,2,4]triazolo[1,5-c]pyridin-5-yl)-2-nitrophenylcarbamate (310 mg, 77% yield). MS (ESI): m/z 462.1 [M+1]+.

D. 5-(4-Amino-3-nitrophenyl)-N-(6-methylpyridin-3-yl)-[1,2,4]triazolo[1,5-a]pyridin-2-amine. A solution of tert-butyl 4-(2-(6-methylpyridin-3-ylamino)-[1,2,4]triazolo[1,5-c]pyridin-5-yl)-2-nitrophenylcarbamate (310 mg, 0.67 mmol) in a methanolic hydrochloride solution (20 mL, 2 M) was stirred at room temperature until TLC showed the starting material was consumed. The solvent was evaporated under reduced pressure to give the crude product, which was basitified by addition of sodium bicarbonate solution to pH=8. The solution was extracted with ethyl acetate for three times, and the organic layers were dried over anhydrous sodium sulfate. After the evaporation under reduced pressure, 5-(4-amino-3-nitrophenyl)-N-(6-methylpyridin-3-yl)-[1,2,4]triazolo[1,5-a]pyridin-2-amine (190 mg, 75% yield) was obtained as a solid. MS (ESI): m/z 362.1 [M+1]+.

E. 4-(2-(6-Methylpyridin-3-ylamino)-[1,2,4]triazolo[1,5-a]pyridin-5-yl)benzene-1,2-diamine. A mixture of 5-(4-amino-3-nitrophenyl)-N-(6-methylpyridin-3-yl)-[1,2,4]triazolo[1,5-a]pyridin-2-amine (200 mg, 0.513 mmol), zinc dust (334 mg, 5.13 mmol) and ammonium chloride (277 mg, 5.13 mmol) in a mixture of tetrahydrofuran and methanol (v/v, 1:1, 40 mL) was stirred at room temperature for 2 h. The mixture was filtered, and filtrate was concentrated under reduced pressure. The residue was partitioned between water and ethyl acetate, and the aqueous solution was extracted with ethyl acetate for three times. The organic layer was washed with brine, dried over sodium sulfate, and concentrated in vacuo to give 4-(2-(6-methylpyridin-3-ylamino)-[1,2,4]triazolo[1,5-a]pyridin-5-yl)benzene-1,2-diamine (158 mg, 86% yield) as a solid. MS (ESI): m/z 332.1 [M+1]+.

F. (6-(2-(6-Methylpyridin-3-ylamino)-[1,2,4]triazolo[1,5-a]pyridin-5-yl)-1H-benzo[d]imidazol-2-yl)methanol. A mixture of 4-(2-(6-methylpyridin-3-ylamino)-[1,2,4]triazolo[1,5-a]pyridin-5-yl)benzene-1,2-diamine (158 mg, 0.48 mmol) and hydroxyacetic acid (145 mg, 1.92 mmol) in 4N hydrochloric acid (30 mL) was refluxed for 24 h. The reaction mixture was evaporated under reduced pressure. The residue was purified by reverse-phase preparatory HPLC (eluting with 7-37% acetonitrile+0.1% trifluoroacetic acid in water+0.1% trifluoroacetic acid, over 15 min.) to give (6-(2-(6-methylpyridin-3-ylamino)-[1,2,4]triazolo[1,5-a]pyridin-5-yl)-1H-benzo[d]imidazol-2-yl)methanol as a trifluoroacetic acid salt, which was converted to the hydrochloride salt (116 mg, 65% yield) as a solid. 1H NMR (400 MHz, METHANOL-d4) δ (ppm) 9.24 (s, 1H), 8.47 (s, 1H), 8.43 (m, 1H), 8.26 (d, J=9.6 Hz, 1H), 8.01 (d, J=8.8 Hz, 1H), 7.84 (m, 2H), 7.71 (d, J=9.2 Hz, 1H), 7.39 (d, J=7.6 Hz, 1H), 5.19 (s, 2H), 2.71 (s, 3H); MS (ESI): m/z 372.1 [M+1]+.

Example 95

4-(1-(2-(4-(Trifluoromethyl)phenylamino)-[1,2,4]triazolo[1,5-a]pyridin-5-yl)ethyl)piperazin-2-one

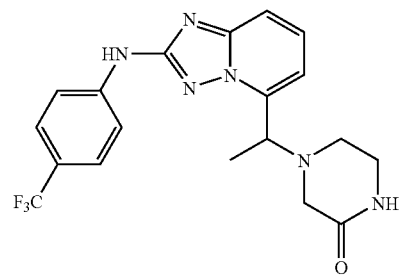

A. 1-(2-(4-(Trifluoromethyl)phenylamino)-[1,2,4]triazolo[1,5-a]pyridin-5-yl)ethanol. A suspension of 5-bromo-N-(4-(trifluoromethyl)phenyl)-[1,2,4]triazolo[1,5-c]pyridin-2-amine (1.0 g, 2.80 mmol) in tetrahydrofuran (14 mL) was cooled to −78° C. and n-butyl lithium in hexanes (2.352 mL, 5.88 mmol) was added drop wise under nitrogen. The reddish brown reaction mixture was stirred for 1 h at −78° C. and acetaldehyde (0.123 g, 0.16 mL, 2.80 mmol) was added neat to the reaction at −78° C. under nitrogen. The dry ice-bath was removed and the reaction mixture was allowed to warm up to room temperature and stirred for 1 h under nitrogen. Upon completion of reaction as indicated by LCMS the reaction mixture was quenched using acetic acid (1.5 mL) in water (20 mL), poured into water/brine, and extracted with ethyl acetate several times. The combined organic layer was dried over anhydrous magnesium sulfate and concentrated. The crude mixture was purified by chromatography using a gradient of 0-100% ethyl acetate in hexanes to give 1-(2-(4-(trifluoromethyl)phenylamino)-[1,2,4]triazolo[1,5-a]pyridin-5-yl)ethanol as a buff solid (0.384 g, 43% yield). 1H NMR (400 MHz, DMSO-d6) δ (ppm) 10.21 (s, 1H), 7.90 (d, J=8.49 Hz, 2H), 7.62-7.70 (m, 3H), 7.52-7.58 (m, 1H), 7.15 (d, J=7.17 Hz, 1H), 5.84 (d, J=4.59 Hz, 1H), 5.33 (quin, J=5.87 Hz, 1H), 1.54 (d, 3H) 10.21 (s, 1H), 7.90 (d, J=8.49 Hz, 2H), 7.62-7.70 (m, 3H), 7.52-7.58 (m, 1H), 7.15 (d, J=7.17 Hz, 1H), 5.84 (d, J=4.59 Hz, 1H), 5.33 (quin, J=5.87 Hz, 1H), 1.54 (d, 3H); MS (ESI) m/z 323.29 [M+1]+.

B. 5-(1-Bromoethyl)-N-(4-(trifluoromethyl)phenyl)-[1,2,4]triazolo[1,5-a]pyridin-2-amine. To a solution of 1-(2-(4-(trifluoromethyl)phenylamino)-[1,2,4]triazolo[1,5-c]pyridin-5-yl)ethanol (0.374 g, 1.160 mmol) in dioxane (20 mL), was added phosphorous tribromide (0.328 mL, 3.48 mmol) at room temperature. The reaction mixture was stirred at 40° C. for 22 h. Upon completion of reaction as indicated by LCMS the suspension was cooled to room temperature and poured cautiously into sodium bicarbonate solution (100 mL) and extracted with ethyl acetate (200 mL). The organic layer was separated, dried over magnesium sulfate and concentrated to give 5-(1-bromoethyl)-N-(4-(trifluoromethyl)phenyl)-[1,2,4]triazolo[1,5-a]pyridin-2-amine as a bright yellow solid (0.407 g, 91% yield). 1H NMR (400 MHz DMSO-d6) δ (ppm)

10.30 (s, 1H), 7.95 (d, J=8.78 Hz, 2H), 7.62-7.73 (m, 4H), 7.39 (dd, J=1.76, 6.93 Hz, 1H), 5.94 (q, J=6.98 Hz, 1H), 2.21 (d, 3H); MS (ESI) m/z 385/387 [M]⁺ and [M+2]⁺.

C. 4-(1-(2-(4-(Trifluoromethyl)phenylamino)-[1,2,4]triazolo[1,5-a]pyridin-5-yl)ethyl)piperazin-2-one. A yellow suspension of 5-(1-bromoethyl)-N-(4-(trifluoromethyl)phenyl)-[1,2,4]triazolo[1,5-a]pyridin-2-amine (0.150 g, 0.389 mmol), piperazin-2-one (0.117 g, 1.168 mmol) and potassium carbonate (0.538 g, 3.89 mmol) in acetonitrile (5 mL) was stirred at 60° C. for 2 h under nitrogen. Upon completion of reaction as indicated by LCMS the reaction mixture was concentrated to give a yellow solid that was treated with water (8 mL) and sonicated. The resulting pale yellow precipitate was collected, rinsed with water (2 mL) and dried to give the title compound (96.8% pure, 0.135 g, 86% yield). ¹H-NMR (400 MHz, DMSO-d₆) δ (ppm) 10.20 (s, 1H), 7.91 (d, J=8.39 Hz, 2H), 7.81 (br s, 1H), 7.54-7.69 (m, 4H), 7.15 (d, J=7.13 Hz, 1H), 4.57 (q, J=6.36 Hz, 1H), 3.02-3.26 (m, 4H), 2.68 (br s, 2H), 1.47 (d, 3H); MS (ESI) m/z 405.39 [M+1]⁺.

Example 96

(S)-1-(2-(4-(Trifluoromethyl)phenylamino)-[1,2,4]triazolo[1,5-a]pyridin-5-yl)piperidin-3-ol

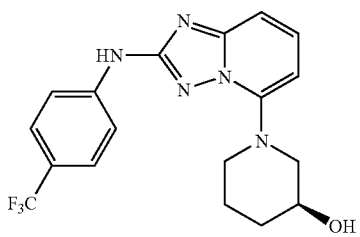

A. (S)-1-(2-(4-(Trifluoromethyl)phenylamino)-[1,2,4]triazolo[1,5-a]pyridin-5-yl)piperidin-3-ol. 5-Bromo-N-(4-(trifluoromethyl)phenyl)-[1,2,4]triazolo[1,5-a]pyridin-2-amine (0.250 g, 0.700 mmol) and (S)-piperidin-3-ol hydrochloride (0.193 g, 1.400 mmol) were suspended in 1-methyl-2-pyrrolidinone (2 mL), treated with diisopropylethylamine (0.403 mL, 2.310 mmol) and stirred at 80° C. for 2 days. The brown solution was partitioned between ethyl acetate (10 mL) and water (10 mL). The organic layer was separated and concentrated to give a brown oil that was purified using reverse-phase preparatory HPLC (20-80% acetonitrile+0.1% trifluoroacetic acid in water+0.1% trifluoroacetic acid, over 30 min). Trifluoroacetic acid was removed using a Strata cartridge to give the product as a white solid (0.077 g, 29% yield). ¹H NMR (400 MHz, DMSO-d₆) δ (ppm) 10.08 (s, 1H), 7.93 (d, J=8.54 Hz, 2H), 7.63 (d, J=8.64 Hz, 2H), 7.52 (dd, J=7.81, 8.54 Hz, 1H), 7.16 (dd, J=0.93, 8.64 Hz, 1H), 6.47 (dd, J=0.95, 7.78 Hz, 1H), 4.97 (d, J=4.69 Hz, 1H), 3.96 (dd, J=3.64, 11.88 Hz, 1H), 3.73-3.86 (m, 2H), 2.85-2.97 (m, 1H), 2.74 (dd, J=9.05, 11.01 Hz, 1H), 1.97-2.07 (m, 1H), 1.84-1.95 (m, 1H), 1.65-1.78 (m, 1H), 1.35-1.48 (m, 1H). MS (ESI) m/z 378.2 [M+1]⁺.

Example 97 cis-4-(Methyl(2-(4-(trifluoromethyl)phenylamino)-[1,2,4]triazolo[1,5-a]pyridin-5-yl)amino)cyclohexanol

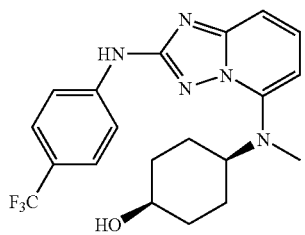

A. cis-4-(Methyl(2-(4-(trifluoromethyl)phenylamino)-[1,2,4]triazolo[1,5-a]pyridin-5-yl)amino)cyclohexanol. To a solution/suspension of cis-4-(2-(4-(trifluoromethyl)phenylamino)-[1,2,4]triazolo[1,5-a]pyridin-5-ylamino)cyclohexanol (70 mg, 0.179 mmol) in N,N-dimethylformamide (5 mL) was added sodium hydride (14.31 mg, 0.358 mmol) The reaction was stirred for 10 minutes then iodomethane (0.012 mL, 0.197 mmol) was added. The reaction was stirred overnight then it was checked by LC/MS. In addition to the desired product, a by-product (cis-N⁵-(4-methoxycyclohexyl)-N⁵-methyl-N²-(4-(trifluoromethyl)phenyl)-[1,2,4]triazolo[1,5-c]pyridine-2,5-diamine) was observed. The reaction was filtered through a cartridge filter, and the crude was purified on Dionex HPLC (30-70% acetonitrile+0.1% trifluoroacetic acid in water+0.1% trifluoroacetic acid, 35 min). The fractions containing the product were loaded on a strata-X column to remove trifluoroacetic acid, then methanol was evaporated in vacuo. The solid was dried under vacuum at room temperature. cis-4-(Methyl(2-(4-(trifluoromethyl)phenylamino)-[1,2,4]triazolo[1,5-c]pyridin-5-yl)amino)cyclohexanol (10 mg, 0.025 mmol, 13.8% yield) was isolated as a white solid. ¹H NMR (400 MHz, DMSO-d₆) δ (ppm) 7.90 (d, J=8.20 Hz, 1H), 7.69 (d, J=8.59 Hz, 1H), 7.43 (t, J=8.20 Hz, 1H), 6.76 (d, J=8.59 Hz, 1H), 6.24 (t, J=9.18 Hz, 2H), 4.48 (br s, 1H), 3.80 (br s, 1H), 3.61 (br s, 1H), 3.35 (br s, 4H), 3.15 (br s, 1H), 2.07 (br s, 1H), 1.78-1.98 (m, 3H), 1.42-1.78 (m, 6H); MS (ESI): m/z 406.2 [M+1]⁺.

Example 98

1-((2-(4-(Trifluoromethyl)phenylamino)[1,2,4]triazolo[1,5-a]pyridin-5-yl)methyl)-1,4-diazepan-5-one

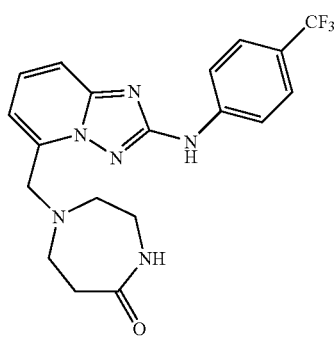

A. (2-(4-(Trifluoromethyl)phenylamino)-[1,2,4]triazolo[1,5-a]pyridin-5-yl)methyl methanesulfonate. A suspension of (2-(4-(trifluoromethyl)phenylamino)-[1,2,4]triazolo[1,5-c]pyridin-5-yl)methanol (150 mg, 0.487 mmol), in dichloroethane (3 mL) was treated with methanesulfonyl chloride (0.113 mL, 1.460 mmol), and triethylamine (0.203 mL, 1.460 mmol). The reaction mixture was left to stir for one hour and monitored by TLC. Upon consumption of the starting material, the solvent was removed in vacuo and the crude (2-(4-(trifluoromethyl)phenylamino)-[1,2,4]triazolo[1,5-a]pyridin-5-yl)methyl methanesulfonate (188 mg, 0.487 mmol, 100% yield) was used for the next step without purification.

B. 1-((2-(4-(Trifluoromethyl)phenylamino)[1,2,4]triazolo[1,5-a]pyridin-5-yl)methyl)-1,4-diazepan-5-one. A suspension of (2-(4-(trifluoromethyl)phenylamino)-[1,2,4]triazolo[1,5-c]pyridin-5-yl)methyl methanesulfonate (125 mg, 0.324 mmol) in N,N-dimethylformamide (2.5 mL) was added, 1,4-diazepan-5-one (73.9 mg, 0.647 mmol) followed by potassium carbonate (334.65 mg, 2.425 mmol). The reaction mixture was heated to 60° C. for three hours and checked by LC/MS. The reaction mixture was filtered and purified by semi-preparative HPLC (20-100% acetonitrile+0.1% trifluoroacetic acid in water+0.1% trifluoroacetic acid, 20 min). 1-((2-(4-(Trifluoromethyl)phenylamino)-[1,2,4]triazolo[1,5-c]pyridin-5-yl)methyl)-1,4-diazepan-5-one (96.5 mg, 0.239 mmol, 73.8% yield) was obtained as a white solid. $^1$H NMR (400 MHz, DMSO-$d_6$) δ (ppm) 10.18 (s, 1H), 7.91 (d, J=8.59 Hz, 2H), 7.47-7.76 (m, 6H), 7.14 (d, J=7.03 Hz, 1H), 3.98-4.24 (m, 2H), 3.14-3.26 (m, 3H), 2.68-2.80 (m, 5H). MS (ESI): m/z 420.1 [M+1]$^+$.

Example 99

4-((2-(1H-Pyrrolo[2,3-b]pyridin-5-ylamino)-[1,2,4]triazolo[1,5-a]pyridin-5-yl)methyl)piperazin-2-one

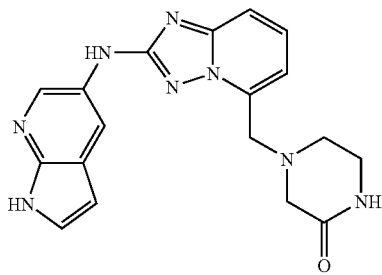

A. N,N-Di-tert-butoxycarbonyl-5-bromo-[1,2,4]triazolo[1,5-a]pyridin-2-amine. 5-Bromo-[1,2,4]triazolo[1,5-a]pyridin-2-amine (2.2 g, 10.33 mmol), di-tert-butyl dicarbonate (5.27 mL, 22.72 mmol), 4-(dimethylamino)pyridine (0.126 g, 1.033 mmol), and acetonitrile (5 mL) were heated to 60° C. for 1 h. The reaction was concentrated and then purified by silica gel chromatography (0-80% ethyl acetate in hexanes) to give N,N-di-tert-butoxycarbonyl-5-bromo-[1,2,4]triazolo[1,5-a]pyridin-2-amine (3 g, 7.26 mmol, 70.3% yield) as a white solid. $^1$H NMR (400 MHz, DMSO-$d_6$) δ (ppm) 7.87-7.95 (m, 1H), 7.65-7.74 (m, 2H), 1.42 (s, 18H); MS (ESI) m/z 415.2 [M+2]$^+$.

B. N,N-Di-tert-butoxycarbonyl-5-vinyl-[1,2,4]triazolo[1,5-a]pyridin-2-amine. N,N-Di-tert-butoxycarbonyl-5-bromo-[1,2,4]triazolo[1,5-c]pyridin-2-amine (1.66 g, 4.02 mmol), tributyl(vinyl)stannane (2.55 g, 8.03 mmol), tris(dibenzylideneacetone)dipalladium(0) (0.368 g, 0.402 mmol), tri-o-tolylphosphine (0.245 g, 0.803 mmol), triethylamine (1.680 mL, 12.05 mmol), and N,N-dimethylformamide (6 mL) were combined in a 50 mL round bottom flask with a stirbar. The atmosphere in the vial was removed and replaced with nitrogen gas three times. The resulting mixture was stirred vigorously and heated at 80° C. under nitrogen for 45 min. The resulting black mixture was purified using flash chromatography (Biotage) (5-100% ethyl acetate in hexane) to give impure N,N-di-tert-butoxycarbonyl-5-vinyl-[1,2,4]triazolo[1,5-a]pyridin-2-amine as a yellow solid which was carried on to the next step without further purification. MS (ESI) m/z 361.2 [M+1]$^+$.

C. N,N-Di-tert-butoxycarbonyl-5-hydroxymethyl-[1,2,4]triazolo[1,5-a]pyridin-2-amine. Osmium tetroxide (2.5% in tert-butanol) (1.209 mL, 0.092 mmol) was added to a stirred mixture of N,N-di-tert-butoxycarbonyl-5-vinyl-[1,2,4]triazolo[1,5-c]pyridin-2-amine (1.66 g, 4.61 mmol) and sodium periodate (2.364 g, 11.05 mmol) in 1,4-dioxane (15 mL), tert-butanol (15 mL), and water (15 mL). The resulting mixture was capped and stirred vigorously at room temperature for 3.5 h. The resulting mixture was diluted with dichloromethane and water and shaken in a separatory funnel. The layers were separated and the water layer extracted with dichloromethane. The combined organics were dried over magnesium sulfate, filtered, and concentrated on a rotary evaporator. The residue was dissolved in methanol (15 mL) and cooled to 0° C. under nitrogen. Sodium borohydride (0.261 g, 6.91 mmol) was added and the resulting mixture was stirred at 0° C. under nitrogen for 25 min. Most of the solvent was removed on a rotary evaporator. The residue was dissolved in dichloromethane and purified using flash chromatography (Biotage) (10-90% ethyl acetate in hexane) to give N,N-di-tert-butoxycarbonyl-5-hydroxymethyl-[1,2,4]triazolo[1,5-c]pyridin-2-amine (0.656 g, 1.800 mmol, 39% yield) as a colorless foam-solid. $^1$H NMR (400 MHz, DMSO-$d_6$) δ (ppm) 7.74-7.82 (m, 2H), 7.27-7.33 (m, 1H), 5.90 (br s, 1H), 4.89 (s, 2H), 1.41 (s, 18H); MS (ESI) m/z 225 [M+1]$^+$.

D. N,N-Di-tert-butoxycarbonyl-5-((3-oxopiperazinyl)methyl)-[1,2,4]triazolo[1,5-a]pyridin-2-amine. Methanesulfonic anhydride (0.374 g, 2.147 mmol) was added to a stirred solution of N,N-di-tert-butoxycarbonyl-5-hydroxymethyl-[1,2,4]triazolo[1,5-a]pyridin-2-amine (0.652 g, 1.789 mmol) and N,N-diisopropylethylamine (0.935 mL, 5.37 mmol) in dichloromethane (15 mL). The resulting light yellow solution was stirred at room temperature under nitrogen for 30 min and then piperazin-2-one (0.269 g, 2.68 mmol) was added. The resulting mixture was stirred and heated at 50° C. under a reflux condenser under nitrogen for 5.5 h. The resulting mixture was purified using flash chromatography (Biotage) (0-10% methanol in dichloromethane) to give the desired product (0.764 g, 1.711 mmol, 96% yield) as a white foam-solid. $^1$H NMR (400 MHz, DMSO-$d_6$) δ (ppm) 7.71-7.83 (m, 3H), 7.31 (dd, J=1.37, 6.83 Hz, 1H), 4.08 (s, 2H), 3.17-3.23 (m, 2H), 3.14 (s, 2H), 2.74 (t, J=5.47 Hz, 2H), 1.40 (s, 18H); MS (ESI) m/z 447.3 [M+1]$^+$.

E. 4-((2-Amino-[1,2,4]triazolo[1,5-a]pyridin-5-yl)methyl)piperazin-2-one. Trifluoroacetic acid (2.55 mL, 33.1 mmol) was added to a stirred solution of N,N-di-tert-butoxycarbonyl-5-((3-oxopiperazinyl)methyl)-[1,2,4]triazolo[1,5-a]pyridin-2-amine (0.740 g, 1.657 mmol) in dichloromethane (18.5 mL). The resulting solution was capped and stirred at room temperature for 23 h. Most of the solvent was removed on a rotary evaporator. The residue was loaded onto two 5 g Strata X—C ion exchange columns from Phenomenex. The columns were washed successively with acetonitrile, water, acetonitrile, methanol, and then 10% ammonium hydroxide in methanol. The product came off with the 10% ammonium hydroxide in methanol eluent. The 10% ammonium hydroxide in methanol eluent from both runs was concentrated on a rotary evaporator and dried under high vacuum at 40° C. to give the desired product (0.406 g, 1.649 mmol, 97%) as a white solid. $^1$H NMR (400 MHz, DMSO-d$_6$) δ (ppm) 7.82 (br s, 1H), 7.43 (dd, J=7.42, 8.59 Hz, 1H), 7.28 (d, J=8.59 Hz, 1H), 6.92 (d, J=7.03 Hz, 1H), 6.03 (s, 2H), 3.94 (s, 2H), 3.21 (br s, 2H), 3.12 (s, 2H), 2.71 (t, 2H); MS (ESI) m/z 247.3 [M+1]$^+$.

F. 4-((2-(1-Tosyl-1H-pyrrolo[2,3-b]pyridin-5-ylamino)-[1,2,4]triazolo[1,5-a]pyridin-5-yl)methyl)piperazin-2-one. A mixture of tris(dibenzylideneacetone)dipalladium(0) (0.019 g, 0.020 mmol) and 4,5-bis(diphenylphosphino)-9,9-dimethylxanthene (0.023 g, 0.041 mmol) in 1,4-dioxane (1.25 mL) was added to 5-bromo-1-tosyl-1H-pyrrolo[2,3-b]pyridine (0.086 g, 0.244 mmol), 4-((2-amino-[1,2,4]triazolo[1,5-c]pyridin-5-yl)methyl)piperazin-2-one (0.050 g, 0.203 mmol), and cesium carbonate (0.265 g, 0.812 mmol) in a 1 dram vial with a stirbar. Nitrogen was blown in to blow out air. The resulting mixture was sealed, stirred vigorously, and heated at 100° C. for 2 h 20 min. The resulting mixture was diluted with acetonitrile, filtered, and purified using reverse-phase semi-preparatory HPLC (10-70% acetonitrile+0.1% trifluoroacetic acid in water+0.1% trifluoroacetic acid, over 34 min). Fractions containing the desired product were combined and loaded onto a Strata X—C ion exchange column from Phenomenex. The column was washed successively with water, acetonitrile, methanol, and then 5% ammonium hydroxide in methanol. The product came off with the 5% ammonium hydroxide in methanol eluent and was concentrated on a rotary evaporator and dried under high vacuum at 40° C. to give the desired product (0.062 g, 0.116 mmol, 57% yield) as a white solid. $^1$H NMR (400 MHz, DMSO-d$_6$) δ (ppm) 9.91 (s, 1H), 8.59 (s, 1H), 8.48 (s, 1H), 7.97 (d, J=7.81 Hz, 2H), 7.77-7.88 (m, 2H), 7.56-7.64 (m, 1H), 7.49-7.56 (m, 1H), 7.42 (d, J=7.81 Hz, 2H), 7.10 (d, J=7.03 Hz, 1H), 6.82 (d, J=3.90 Hz, 1H), 4.08 (s, 2H), 3.13-3.27 (m, 4H), 2.77 (br s, 2H), 2.34 (s, 3H); MS (ESI) m/z 517.1 [M+1]$^+$.

G. 4-((2-(1H-Pyrrolo[2,3-b]pyridin-5-ylamino)-[1,2,4]triazolo[1,5-a]pyridin-5-yl)methyl)piperazin-2-one. Sodium hydride (0.027 g, 1.142 mmol) was added to a stirred mixture of 4-((2-(1-tosyl-1H-pyrrolo[2,3-b]pyridin-5-ylamino)-[1,2,4]triazolo[1,5-a]pyridin-5-yl)methyl)piperazin-2-one (0.059 g, 0.114 mmol) and methylamine (1.142 mL, 2.284 mmol, 2 M solution in tetrahydrofuran) in 1,4-dioxane (6 mL). The resulting cloudy mixture was heated at 40° C. under a reflux condenser under nitrogen for 2 h, then at 55° C. for 18 h, then at 70° C. for 5 h. Methanol (1 mL) and 1-methyl-2-pyrrolidinone (1 mL) were added to improve the solubility of the starting material. The resulting cloudy mixture was heated at 70° C. under a reflux condenser under nitrogen for 1 h. The resulting clear yellow solution was cooled to room temperature and trifluoroacetic acid (0.088 mL, 1.142 mmol) was added. Most of the solvent was removed on a rotary evaporator. The residue was dissolved in methanol, filtered, and purified using reverse-phase semi-preparatory HPLC (5-40% acetonitrile+0.1% trifluoroacetic acid in water+0.1% trifluoroacetic acid, over 34 min). Fractions containing the desired product were loaded onto a Strata X—C ion exchange column from Phenomenex. The column was washed successively with water, acetonitrile, methanol, and then 5% ammonium hydroxide in methanol. The product came off with the 5% ammonium hydroxide in methanol eluent and was concentrated on a rotary evaporator and dried under high vacuum at 40° C. to give the desired product (0.019 g, 0.052 mmol, 46% yield) as a white solid. $^1$H NMR (400 MHz, DMSO-d$_6$) δ (ppm) 11.42 (br s, 1H), 9.52 (s, 1H), 8.45 (d, J=2.34 Hz, 1H), 8.42 (d, J=2.34 Hz, 1H), 7.83 (s, 1H), 7.53-7.62 (m, 1H), 7.50 (d, J=8.59 Hz, 1H), 7.40 (t, J=2.73 Hz, 1H), 7.06 (d, J=7.03 Hz, 1H), 6.40 (br s, 1H), 4.08 (s, 2H), 3.23 (br s, 2H), 3.19 (s, 2H), 2.78 (t, 2H); MS (ESI) m/z 363.3 [M+1]$^+$.

Example 100

N-Methyl-4-(5-(2-(piperidin-4-yl)ethyl)[1,2,4]triazolo[1,5-a]pyridin-2-ylamino)benzamide

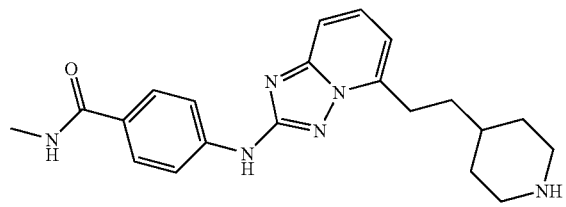

A. tert-Butyl 4-(2-(6-(tert-butoxycarbonylamino)pyridin-2-yl)-1-(methylsulfonyloxy)ethyl)piperidine-1-carboxylate. To a solution of tert-butyl 4-(2-(6-(tert-butoxycarbonylamino)pyridin-2-yl)-1-hydroxyethyl)piperidine-1-carboxylate (400 mg, 0.95 mmol) and triethylamine (191 mg, 1.9 mmol) in dichloromethane (10 mL) was added dropwise methanesulfonyl chloride (130 mg, 1.14 mmol) in ice bath, and the reaction mixture was stirred at 0° C. for 30 min. Iced water (10 mL) was added, and the organic phase was separated. The aqueous phase was extracted with dichloromethane (10 mL×2). The combined organic layers were washed with brine, dried over sodium sulfate, and evaporated under reduced pressure to give tert-butyl 4-(2-(6-(tert-butoxycarbonylamino)pyridin-2-yl)-1-(methylsulfonyloxy)ethyl)piperidine-1-carboxylate (420 mg, 88% yield) as yellow oil. MS (ESI): m/z 500.3 [M+1]$^+$.

B. tert-Butyl 4-(2-(6-(tert-butoxycarbonylamino)pyridin-2-yl)vinyl)piperidine-1-carboxylate. To a stirred solution of sodium hydride (51 mg, 1.26 mmol) in isopropanol (10 mL) was added dropwise a solution of tert-butyl 4-(2-(6-(tert-butoxycarbonylamino)pyridin-2-yl)-1-(methylsulfonyloxy)ethyl)piperidine-1-carboxylate (420 mg, 0.84 mmol) in isopropanol (10 mL) at 0° C. under nitrogen. After stirring for 30 min at 0° C., the mixture was warmed to room temperature and stirred overnight. The mixture was poured into water (50 mL), and the mixture was extracted with ethyl acetate (20 mL×4). The combined organic layers were washed with brine, dried, and concentrated to give tert-butyl 4-(2-(6-(tert-butoxycarbonylamino)pyridin-2-yl)vinyl)piperidine-1-carboxylate (300 mg, 88% yield) as an oil. MS (ESI): m/z 404.1 [M+1]$^+$.

C. tert-Butyl 4-(2-(6-(tert-butoxycarbonylamino)pyridin-2-yl)ethyl)piperidine-1-carboxylate. A mixture of tert-butyl 4-(2-(6-(tert-butoxycarbonylamino)pyridin-2-yl)vinyl)piperidine-1-carboxylate (300 mg, 0.74 mmol) and palladium on activated carbon (10% w/w, 50 mg) in methanol (5 mL) was hydrogenated under 1 atmosphere of hydrogen overnight. The catalyst was filtered off and the filtrate was concentrated to give tert-butyl 4-(2-(6-(tert-butoxycarbonylamino)pyridin-2-yl)ethyl)piperidine-1-carboxylate (250 mg, 83% yield). MS (ESI): m/z 406.0 [M+1]$^+$.

D. 6-(2-(Piperidin-4-yl)ethyl)pyridin-2-amine. A solution of tert-butyl 4-(2-(6-(tert-butoxycarbonylamino)pyridin-2-yl)ethyl)piperidine-1-carboxylate (250 mg, 0.61 mmol) in methanolic hydrochloride solution (2 M, 5 mL) was stirred for 2 h. The reaction mixture was concentrated in vacuo to give 6-(2-(piperidin-4-yl)ethyl)pyridin-2-amine, which was used in the next step without further purification.

E. tert-Butyl 4-(2-(6-aminopyridin-2-yl)ethyl)piperidine-1-carboxylate. A mixture of 6-(2-(piperidin-4-yl)ethyl)pyridin-2-amine (126 mg, 0.61 mmol), di-tert-butyl dicarbonate (132 mg, 0.61 mmol), and triethylamine (123 mg, 1.22 mmol) in dichloromethane (5 mL) was stirred at room temperature overnight. Water was added, the mixture was extracted with dichloromethane, and the combined organic layers were washed with brine, dried over sodium sulfate, and evaporated under reduced pressure. The crude product was purified on silica gel column (eluting with 50% ethyl acetate in petroleum ether) to give tert-butyl 4-(2-(6-aminopyridin-2-yl)ethyl)piperidine-1-carboxylate (150 mg, 80% yield) as a solid. $^1$H NMR (400 MHz, CHLOROFORM-d) δ (ppm) 7.33 (t, J=8.0 Hz, 1H), 6.44 (d, J=7.6 Hz, 1H), 6.31 (d, J=8.4 Hz, 1H), 4.78 (s, 2H), 4.01 (s, 2H), 2.59 (m, 4H), 1.57 (m, 4H), 1.38 (s, 10H), 1.08 (m, 2H).

F. tert-Butyl 4-(2-(6-(3-(ethoxycarbonyl)thioureido)pyridin-2-yl)ethyl)piperidine-1-carboxylate. A mixture of tert-butyl 4-(2-(6-aminopyridin-2-yl)ethyl)piperidine-1-carboxylate (150 mg, 0.49 mmol) and O-ethyl carbonisothiocyanatidate (64 mg, 0.49 mmol) in dioxane (5 mL) was stirred at room temperature for 5 h. The mixture was evaporated to afford tert-butyl 4-(2-(6-(3-(ethoxycarbonyl)thioureido)pyridin-2-yl)ethyl)piperidine-1-carboxylate (213 mg, 99% yield) as a white solid, which was used in the next step without further purification.

G. tert-Butyl 4-(2-(2-amino-[1,2,4]triazolo[1,5-a]pyridin-5-yl)ethyl)piperidine-1-carboxylate. To a solution of N,N-diethylisopropylamine (189 mg, 1.4 mmol) and hydroxylamine hydrochloride (169 mg, 2.4 mmol) in a mixture of ethanol and methanol (10 mL, 1:1) was added tert-butyl 4-(2-(6-(3-(ethoxycarbonyl)thioureido)pyridin-2-yl)ethyl)piperidine-1-carboxylate (213 mg, 0.49 mmol), and the reaction mixture was stirred at room temperature for 2 h, and at 70° C. for 5 h. The volatiles were removed under reduced pressure, and the residue was diluted with water. The aqueous phase was extracted with dichloromethane. The combined organic layers were washed with brine, dried over sodium sulfate, and evaporated under reduced pressure to give tert-butyl 4-(2-(2-amino-[1,2,4]triazolo[1,5-c]pyridin-5-yl)ethyl)piperidine-1-carboxylate (150 mg, 88% yield) as a solid. MS (ESI): m/z 346.0 [M+1]$^+$.

H. tert-Butyl 4-(2-(2-(4-(methylcarbamoyl)phenylamino)-[1,2,4]triazolo[1,5-a]pyridin-5-yl)ethyl)piperidine-1-carboxylate. A degassed mixture of tert-butyl 4-(2-(2-amino-[1,2,4]triazolo[1,5-c]pyridin-5-yl)ethyl)piperidine-1-carboxylate (120 mg, 0.36 mmol), 4-iodo-N-methylbenzamide (113 mg, 0.43 mmol), tris(dibenzylideneacetone)dipalladium(0) (16 mg, 0.02 mmol), 4,5-bis(diphenylphosphino)-9,9-dimethylxanthene (21 mg, 0.044 mmol) and cesium carbonate (87 mg, 0.72 mmol) in dioxane (5 mL) was heated at 100° C. under nitrogen overnight. The reaction mixture was quenched with water (30 mL), and the mixture was extracted with ethyl acetate (15 mL×3). The combined organic layer was dried over sodium sulfate, and filtered. The filtrate was evaporated under reduced pressure, and the residue was purified by reverse-phase preparatory HPLC (50-72% acetonitrile+0.1% trifluoroacetic acid in water+0.1% trifluoroacetic acid, over 20 min.) to give tert-butyl 4-(2-(2-(4-(methylcarbamoyl)phenylamino)-[1,2,4]triazolo[1,5-a]pyridin-5-yl)ethyl)piperidine-1-carboxylate (60 mg, 35% yield) as a solid. MS (ESI): m/z 479.0 [M+1]$^+$.

I. N-Methyl-4-(5-(2-(piperidin-4-yl)ethyl)[1,2,4]triazolo[1,5-a]pyridin-2-ylamino)benzamide. A solution of tert-butyl 4-(2-(2-(4-(methylcarbamoyl)phenylamino)-[1,2,4]triazolo[1,5-c]pyridin-5-yl)ethyl)piperidine-1-carboxylate (60 mg, 0.12 mmol) in methanolic hydrochloride solution (2 M, 5 mL) was stirred overnight. The reaction mixture was concentrated in vacuo, and the residue was washed with ethyl ether to give N-methyl-4-(5-(2-(piperidin-4-yl)ethyl)-[1,2,4]triazolo[1,5-c]pyridin-2-ylamino)benzamide (23 mg, 48% yield) as a solid. $^1$H NMR (400 MHz, METHANOL-d$_4$) δ (ppm) 7.81 (m, 4H), 7.59 (m, 1H), 7.45 (m, 1H), 6.98 (d, J=6.8 Hz, 1H), 3.42 (m, 2H), 3.02 (m, 2H), 2.94 (s, 3H), 2.15 (d, J=13.2 Hz, 2H), 1.93 (m, 2H), 1.80 (s, 1H), 1.50 (m, 2H); MS (ESI): m/z 379.2 [M+1]$^+$.

Example 101

4-(5-((3-Hydroxycyclopentyl)methyl)[1,2,4]triazolo[1,5-a]pyridin-2-ylamino)-N-methylbenzamide

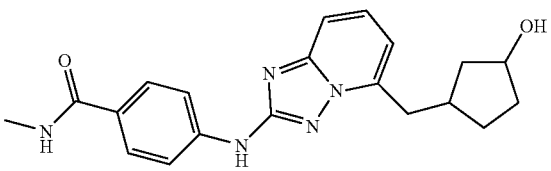

A. tert-Butyl 6-((3-oxocyclopentyl)methyl)pyridin-2-ylcarbamate. To a stirred solution of tert-butyl 6-methylpyridin-2-ylcarbamate (1.25 g, 6.01 mmol) in tetrahydrofuran (20 mL) was added dropwise a solution of n-butyl lithium in hexane (6.00 mL, 2.5 M) at −78° C. under nitrogen for 1 h. After addition was complete, the reaction mixture was warmed to room temperature over 1 h, and cooled to −78° C. A solution of cyclopent-2-enone (591 mg, 7.21 mmol) in tetrahydrofuran (10 mL) was added dropwise into the mixture at −78° C., and the reaction mixture was warmed to room temperature and stirred overnight. Aqueous ammonium chloride solution was added slowly, and the mixture was extracted with ethyl acetate (30 mL×3). The combined organic layers were washed with brine (50 mL), dried over sodium sulfate, and concentrated under reduced pressure to give the crude product, which was purified on silica gel column (eluting with 10% ethyl acetate in petroleum ether) to give tert-butyl 64(3-oxocyclopentyl)methyl)pyridin-2-ylcarbamate (750 mg, 43% yield) as an oil. $^1$H NMR (400 MHz, CHLOROFORM-d) δ (ppm) 7.75 (d, J=8.4 Hz, 1H), 7.58 (t, J=7.6 Hz, 1H), 7.18 (br s, 1H), 6.78 (d, J=7.2 Hz, 1H), 2.77 (d, J=6.0 Hz, 2H), 2.60 (m, 1H), 2.33 (m, 2H), 2.16 (m, 2H), 1.97 (m, 1H), 1.68 (m, 1H), 1.52 (s, 9H).

B. tert-Butyl 6-((3-hydroxycyclopentyl)methyl)pyridin-2-ylcarbamate. A mixture of tert-butyl 6-((3-oxocyclopentyl)methyl)pyridin-2-ylcarbamate (700 mg, 2.41 mmol) and sodium borohydride (183 mg, 4.83 mmol) in tetrahydrofuran (10 mL) was refluxed for 0.5 h. The reaction mixture was concentrated in vacuo, and the residue was diluted with ethyl acetate. The organic layer was washed with brine and concentrated under reduced pressure to give tert-butyl 6-((3-hydroxycyclopentyl)methyl)pyridin-2-ylcarbamate (580 mg, 82% yield) as a solid. $^1$H NMR (400 MHz, CHLOROFORM-d) δ (ppm) 7.71 (d, J=8.4 Hz, 1H), 7.55 (t, J=8.0 Hz, 1H), 7.18 (br s, 1H), 6.78 (dd, J$_1$=2.4 Hz, J$_2$=7.2 Hz, 1H), 4.43 (m, 1H), 2.73 (d, J=7.6 Hz, 1H), 2.64 (m, 1H), 2.60-2.30 (m, 1H), 1.76 (m, 2H), 1.69 (m, 4H), 1.50 (s, 9H), 1.42 (m, 1H).

C. 3-((6-Aminopyridin-2-yl)methyl)cyclopentanol. A solution of tert-butyl 6-((3-hydroxycyclopentyl)methyl)pyridin-2-ylcarbamate (570 mg, 1.95 mmol) in methanolic hydrochloride solution (2 M, 10 mL) was stirred for 2 h. The reaction mixture was concentrated in vacuo to give 3-((6-aminopyridin-2-yl)methyl)cyclopentanol (350 mg, 93% yield) as an oil.

D. Intermediate A. A mixture of 3-(((6-aminopyridin-2-yl) methyl)cyclopentanol (350 mg, 1.82 mmol) and O-ethyl carbonisothiocyanatidate (263 mg, 2.00 mmol) in dioxane (10 mL) was stirred at room temperature for 5 h. The solvent was removed under reduced pressure to afford intermediate A (500 mg), which was used in the next step without further purification.

E. 3-((2-Amino-[1,2,4]triazolo[1,5-a]pyridin-5-yl)methyl)cyclopentanol. To a solution of N,N-diethylisopropylamine (704 mg, 5.46 mmol) and hydroxylamine hydrochloride (628 mg, 9.1 mmol) in a mixture of ethanol and methanol (10 mL, 1:1) was added intermediate A (500 mg), and the reaction mixture was stirred at room temperature for 2 h and at 70° C. for 5 h. The volatiles were removed under reduced pressure, and the residue was diluted with water, the aqueous phase was extracted with dichloromethane. The combined organic layers were washed with brine, dried over sodium sulfate, and evaporated under reduced pressure to give 3-((2-amino-[1,2,4]triazolo[1,5-c]pyridin-5-yl)methyl)cyclopentanol (300 mg, 71% yield for two steps) as a solid. $^1$H NMR (400 MHz, CHLOROFORM-d) δ (ppm) 7.52 (m, 2H), 6.72 (d, J=7.6 Hz, 1H), 4.60 (br s, 2H), 4.45-4.35 (m, 1H), 3.33-3.05 (m, 2H), 2.85-2.56 (m, 1H), 2.01 (m, 2H), 1.80-1.53 (m, 3H), 1.40-1.32 (m, 1H).

F. 4-(5-((3-Hydroxycyclopentyl)methyl)-[1,2,4]triazolo[1,5-a]pyridin-2-ylamino)-N-methylbenzamide. A degassed mixture of 3-((2-amino-[1,2,4]triazolo[1,5-a]pyridin-5-yl) methyl)cyclopentanol (280 mg, 1.2 mmol), 4-iodo-N-methylbenzamide (473 mg, 1.81 mmol), tris(dibenzylideneacetone)dipalladium (0) (110 mg, 0.12 mmol), 4,5-bis(diphenylphosphino)-9,9-dimethylxanthene (140 mg, 0.24 mmol) and cesium carbonate (784 mg, 2.41 mmol) in dioxane (5 mL) was heated at 100° C. under nitrogen for 5 h. The reaction mixture was quenched with water, and the aqueous layer was extracted with ethyl acetate. The organic layer was dried over sodium sulfate, and filtered. The filtrate was evaporated under reduced pressure, and the residue was purified by reverse-phase preparatory HPLC (eluting with 44-74% acetonitrile+0.1% trifluoroacetic acid in water+0.1% trifluoroacetic acid, over 20 min.) to give 4-(5-((3-hydroxycyclopentyl)methyl)-[1,2,4]triazolo[1,5-c]pyridin-2-ylamino)-N-methylbenzamide as a trifluoroacetic acid salt. After preparative chiral super fluid chromatography (eluting with supercritical $CO_2$: isopropyl alcohol 55:45 at 50 mL/min, column AD 250 mm*20 mm, 10 um) two diastereomers were obtained: diastereomer 1 (20 mg, as hydrochloride salt): $^1$H NMR (400 MHz, METHANOL-$d_4$) δ (ppm) 7.82 (m, 4H), 7.57 (t, J=7.2 Hz, 1H), 7.42 (d, J=9.2 Hz, 1H), 6.94 (d, J=7.2 Hz, 1H), 4.86-4.70 (m, 1H), 3.33 (m, 2H), 2.98 (s, 3H), 2.70 (m, 1H), 2.10 (m, 1H), 2.01 (m, 1H), 1.85 (m, 2H), 1.66 (m, 1H), 1.41 (m, 1H), 1.33 (m, 1H), 1.20 (m, 1H); MS (ESI): m/z 366.1 [M+1]$^+$; and diastereomer 2 (15 mg, as hydrochloride salt): $^1$H NMR (400 MHz, METHANOL-$d_4$) δ (ppm) 8.10 (t, J=8.4 Hz, 1H), 7.93 (d, J=8.4 Hz, 2H), 7.79 (m, 3H), 7.52 (d, J=7.2 Hz, 1H), 4.41-4.22 (m, 1H), 3.41-3.21 (m, 2H), 2.95 (s, 3H), 2.68 (m, 1H), 2.20-2.00 (m, 2H), 1.90 (m, 2H), 1.62 (m, 1H), 1.49 (m, 1H); MS (ESI): m/z 366.1 [M+1]$^+$.

Example 102

4-((2-(6-(4-Hydroxypiperidin-1-yl)pyridin-3-ylamino)-[1,2,4]triazolo[1,5-a]pyridin-5-yl)methyl)piperazin-2-one

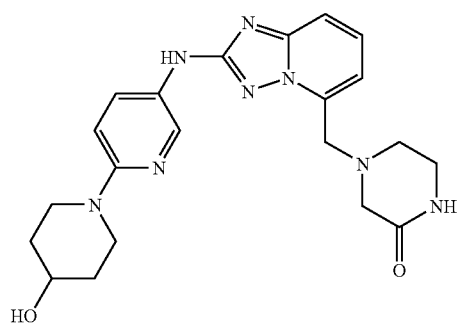

A. (2-Bromo-[1,2,4]triazolo[1,5-a]pyridin-5-yl)methanol. A stirred mixture of 2,5-dibromo-[1,2,4]triazolo[1,5-a]pyridine (0.504 g, 1.820 mmol) in tetrahydrofuran (20 mL) was heated briefly with a heat gun under nitrogen until most of the solids dissolved. The resulting light yellow mixture was cooled with a dry ice-acetone bath under nitrogen. n-Butyllithium (1.194 mL, 1.911 mmol, 1.6 M in hexane) was added dropwise slowly via syringe. During the addition the reaction became darker and darker yellow and then became red-brown colored. After 10 min N,N-dimethylformamide (1.410 mL, 18.20 mmol) was added. The cold bath was removed and the resulting mixture was warmed to 0° C. over 15 min. Water (5 mL) was added and the resulting mixture was stirred vigorously at room temperature for 15 min. The resulting red-brown mixture was diluted with water and ethyl acetate, shaken in a separatory funnel, and the layers were separated. The organics were washed with brine, dried over magnesium sulfate, filtered, and concentrated on a rotary evaporator. The residue was purified using flash chromatography (Biotage) (0-15% methanol in dichloromethane) to give an impure red-brown solid. MS (ESI) m/z 257.9 [M]$^+$, 259.7 [M+2]$^+$. A stirred mixture of impure 2-bromo-[1,2,4]triazolo[1,5-a]pyridine-5-carbaldehyde (0.233 g, 1.031 mmol) in ethanol (12 mL) was heated briefly with a heat gun until all the solids had dissolved. The resulting solution was cooled to 0° C. under nitrogen. Sodium borohydride (0.047 g, 1.237 mmol) was added and the resulting mixture was stirred vigorously at 0° C. under nitrogen for 30 min. The resulting orange mixture was purified using reverse-phase flash chromatography (Biotage) (10-100% acetonitrile in water). Fractions containing the desired product were combined and the solvent was removed on a rotary evaporator. The residue was dried under high vacuum at 40° C. to give the desired product (0.092 g, 0.403 mmol, 22% yield over two steps) as a white solid with some yellow impurity. $^1$H NMR (400 MHz, DMSO-$d_6$) δ (ppm) 7.70-7.85 (m, 2H), 7.28 (d, J=7.03 Hz, 1H), 5.92 (s, 1H), 4.90 (s, 2H); MS (ESI) m/z 228.0 [M]$^+$, 229.9 [M+2]$^+$.

B. 4-((2-Bromo-[1,2,4]triazolo[1,5-a]pyridin-5-yl)methyl)piperazin-2-one. Methanesulfonic anhydride (0.083 g, 0.479 mmol) was added to a stirred solution of (2-bromo-[1,2,4]triazolo[1,5-a]pyridin-5-yl)methanol (0.095 g, 0.417 mmol) and N,N-diisopropylethylamine (0.218 mL, 1.250 mmol) in N,N-dimethylformamide (2.5 mL). The resulting clear yellow solution was capped and stirred at room temperature. After 40 min more methanesulfonic anhydride (18 mg, 0.103 mmol) was added. The resulting clear yellow solution was capped and stirred at room temperature for an additional 30 min. piperazin-2-one (0.092 g, 0.916 mmol) was added and the resulting clear yellow solution was sealed and stirred at 50° C. for 3.5 h. The resulting mixture was purified using flash chromatography (Biotage) (0-15% methanol in dichloromethane) to give the desired product (0.121 g, 0.390 mmol, 94% yield) as a white solid with some yellow impurity. $^1$H NMR (400 MHz, DMSO-d$_6$) δ (ppm) 7.84 (br s, 1H), 7.72-7.80 (m, 2H), 7.26-7.34 (m, 1H), 4.08 (s, 2H), 3.18-3.26 (m, 2H), 3.16 (s, 2H), 2.69-2.79 (m, 2H); MS (ESI) m/z 310.0 [M]$^+$, 311.8 [M+2]$^+$.

C. 4-((2-(6-(4-Hydroxypiperidin-1-yl)pyridin-3-ylamino)-[1,2,4]triazolo[1,5-a]pyridin-5-yl)methyl)piperazin-2-one. A mixture of tris(dibenzylideneacetone)dipalladium(0) (0.035 g, 0.038 mmol) and 4,5-bis(diphenylphosphino)-9,9-dimethylxanthene (0.044 g, 0.075 mmol) in 1,4-dioxane (2.5 mL) was heated briefly with a heat gun until most of the solids had dissolved and then added to 6-(4-(tert-butyldimethylsilyloxy)piperidin-1-yl)pyridin-3-amine (0.122 g, 0.396 mmol), 4-((2-bromo-[1,2,4]triazolo[1,5-a]pyridin-5-yl)methyl)piperazin-2-one (0.117 g, 0.377 mmol), and finely ground cesium carbonate (0.504 g, 1.547 mmol) in a sealable vessel with a stirbar. Nitrogen was blown in to blow out air. The resulting mixture was sealed, stirred vigorously, and heated at 100° C. for 3.5 h. While still hot, the resulting green mixture was diluted with dimethyl sulfoxide and methanol, filtered, and concentrated on a rotary evaporator. The residue was taken up in hot dimethyl sulfoxide and methanol, filtered, and purified using reverse-phase preparatory HPLC (10-70% acetonitrile+0.1% trifluoroacetic acid in water+0.1% trifluoroacetic acid, over 30 min). Fractions containing the desired product were loaded onto a Strata X—C ion exchange column from Phenomenex. The column was washed successively with water, acetonitrile, methanol, and then 5% ammonium hydroxide in methanol. The product came off with the 5% ammonium hydroxide in methanol eluent and was concentrated on a rotary evaporator and dried under high vacuum at 40° C. 6 M HCl in water (0.206 mL, 1.239 mmol) was added to a stirred mixture of the solids from above in ethanol (10 mL) at 40° C. The resulting mixture was stirred vigorously and heated at 40° C. under a reflux condenser under nitrogen for 30 min and then at 50° C. under a reflux condenser under nitrogen for 2.5 h. The resulting mixture was cooled to room temperature. Fine solids were collected by vacuum filtration through a pipette filter, washed with methanol, and dried under high vacuum to give the desired product (0.132 g, 0.288 mmol, 97% yield as the hydrochloride salt) as an off-white solid. $^1$H NMR (400 MHz, DMSO-d$_6$ and D$_2$O) δ (ppm) 8.52 (d, J=2.73 Hz, 1H), 8.07 (dd, J=2.73, 10.15 Hz, 1H), 7.57-7.69 (m, 2H), 7.41 (d, J=9.76 Hz, 1H), 7.24 (dd, J=1.37, 6.83 Hz, 1H), 4.55 (s, 2H), 3.82 (dt, J=4.25, 8.30 Hz, 3H), 3.62 (s, 2H), 3.22-3.41 (m, 6H), 1.81-1.94 (m, 2H), 1.40-1.55 (m, 2H); MS (ESI) m/z 423.3 [M+1]$^+$.

Example 103

N$^2$-(3-methyl-1H-indazol-6-yl)-N$^5$-((tetrahydro-2H-pyran-4-yl)methyl)-[1,2,4]triazolo[1,5-a]pyridine-2,5-diamine

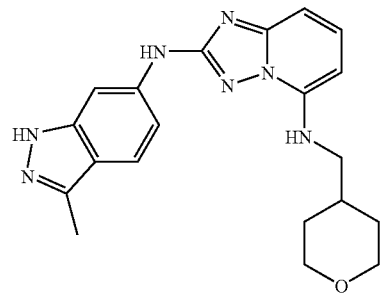

A. N$^5$-((Tetrahydro-2H-pyran-4-yl)methyl)-[1,2,4]triazolo[1,5-a]pyridine-2,5-diamine. 5-Bromo-[1,2,4]triazolo[1,5-a]pyridine-2-amine (1.00 g, 4.69 mmol), potassium carbonate (1.362 g, 9.86 mmol), and (tetrahydro-2H-pyran-4-yl)methanamine (1.081 g, 9.39 mmol) were combined in a sealable vessel with a stirbar. Nitrogen gas was blown in to blow out air. The resulting mixture was sealed, stirred vigorously, and heated at 120° C. for 18 h. Water (10 mL) was added and the resulting mixture was capped and shaken. Solids were collected by vacuum filtration, washed with water and diethyl ether, and dried under high vacuum at 40° C. to give the desired product (1.079 g, 4.36 mmol, 93% yield) as a white solid. $^1$H NMR (400 MHz, DMSO-d$_6$) δ (ppm) 7.26 (t, J=8.39 Hz, 1H), 6.44-6.57 (m, 2H), 6.00 (d, J=7.81 Hz, 1H), 5.76 (s, 2H), 3.84 (dd, J=2.73, 11.32 Hz, 2H), 3.25 (td, J=1.95, 11.52 Hz, 2H), 3.18 (t, J=6.64 Hz, 2H), 1.82-1.98 (m, 1H), 1.61 (dd, J=1.76, 12.69 Hz, 2H), 1.15-1.30 (m, 2H); MS (ESI) m/z 248.3 [M+1]$^+$.

B. N$^2$-(3-Methyl-1-tosyl-1H-indazol-6-yl)-N$^5$-((tetrahydro-2H-pyran-4-yl)methyl)-[1,2,4]triazolo[1,5-a]pyridine-2,5-diamine. A mixture of tris(dibenzylideneacetone)dipalladium(0) (0.074 g, 0.081 mmol) and 4,5-bis(diphenylphosphino)-9,9-dimethylxanthene (0.094 g, 0.162 mmol) in 1,4-dioxane (4 mL) was heated briefly with a heat gun until most of the solids had dissolved and then added to 6-bromo-3-methyl-1-tosyl-1H-indazole (0.295 g, 0.809 mmol), N$^5$-((tetrahydro-2H-pyran-4-yl)methyl)-[1,2,4]triazolo[1,5-c]pyridine-2,5-diamine (0.200 g, 0.809 mmol), and finely ground cesium carbonate (1.080 g, 3.32 mmol) in a sealable vessel with a stirbar. Nitrogen was blown in to blow out air. The resulting mixture was sealed, stirred vigorously, and heated at 100° C. for 3.5 h. The resulting green mixture was cooled to room temperature. Water (10 mL) was added with vigorous stirring. Solids were collected by vacuum filtration and washed thoroughly with water. The solids were taken up in dimethyl sulfoxide and methanol. The resulting mixture was heated with a heat gun and then quickly filtered. The filtrate was capped and let stand at room temperature for 30 min. Solids were collected by vacuum filtration, washed with methanol and diethyl ether, and dried under high vacuum at 40° C. to give the desired product (0.345 g, 0.649 mmol, 80% yield) as an off-white solid. $^1$H NMR (400 MHz, DMSO-d$_6$) δ (ppm) 10.12 (s, 1H), 8.95 (d, J=1.17 Hz, 1H), 7.78 (d, J=8.20 Hz, 2H), 7.60-7.67 (m, 1H), 7.53-7.60 (m, 1H), 7.49 (t, J=8.20 Hz, 1H), 7.38 (d, J=8.59 Hz, 2H), 6.82 (d, J=8.59 Hz, 1H), 6.20-6.31 (m, 2H), 3.76 (dd, J=3.32, 11.13 Hz, 2H), 3.29 (t, J=6.25 Hz, 2H), 3.18 (t, J=10.93 Hz, 2H), 2.41 (s, 3H), 2.31 (s, 3H), 1.87-2.03 (m, J=4.30, 7.36, 7.36, 7.36, 7.36, 11.16 Hz, 1H), 1.73 (d, J=12.49 Hz, 2H), 1.28 (qd, 2H); MS (ESI) m/z 532.2 [M+1]$^+$.

C. N$^2$-(3-Methyl-1H-indazol-6-yl)-N$^5$-((tetrahydro-2H-pyran-4-yl)methyl)-[1,2,4]triazolo[1,5-a]pyridine-2,5-diamine. Sodium hydride (0.081 g, 3.36 mmol) was added to a stirred solution of 1-methyl-2-pyrrolidinone (4 mL) and methanol (12 mL) in a sealable vessel. After 2 min N$^2$-(3-methyl-1-tosyl-1H-indazol-6-yl)-N$^5$-((tetrahydro-2H-pyran-4-yl)methyl)-[1,2,4]triazolo[1,5-c]pyridine-2,5-diamine (0.325 g, 0.611 mmol) was added. Nitrogen was blown in to blow out air. The resulting mixture was sealed, stirred vigorously, and heated at 70° C. for 15.5 h. 6 M hydrochloric acid in water (0.611 mL, 3.67 mmol) was added to neutralize the base. The resulting mixture was filtered and purified using reverse-phase preparatory HPLC (10-70% acetonitrile+0.1% trifluoroacetic acid in water+0.1% trifluoroacetic acid, over 30 min). Fractions containing the desired product were loaded onto a Strata X—C ion exchange column from Phenomenex. The column was washed successively with water, acetonitrile, methanol, and then 5% ammonium hydroxide in methanol. The product came off with the 5% ammonium hydroxide in methanol eluent and was concentrated on a rotary evaporator and dried under high vacuum to give the desired product (0.204 g, 0.536 mmol, 88% yield) as a white solid. $^1$H NMR (400 MHz, DMSO-d$_6$) δ (ppm) 12.23 (s, 1H), 9.55 (s, 1H), 8.02 (d, J=1.17 Hz, 1H), 7.53 (d, J=8.98 Hz, 1H), 7.42 (t, J=8.39 Hz, 1H), 7.31 (dd, J=1.76, 8.79 Hz, 1H), 6.75 (d, J=7.81 Hz, 1H), 6.61 (t, J=6.44 Hz, 1H), 6.20 (d, J=7.42 Hz, 1H), 3.87 (dd, J=2.73, 11.32 Hz, 2H), 3.20-3.39 (m, 4H), 2.42 (s, 3H), 1.89-2.04 (m, J=4.10, 7.33, 7.33, 7.33, 7.33, 11.09 Hz, 1H), 1.59-1.73 (m, 2H), 1.29 (qd, J=4.49, 12.30 Hz, 2H); MS (ESI) m/z 378.1 [M+1]$^+$.

Example 104

4-(1-(2-(4-(Trifluoromethyl)phenylamino)-[1,2,4]triazolo[1,5-a]pyridin-5-yl)ethyl)pyridin-2(1H)-one

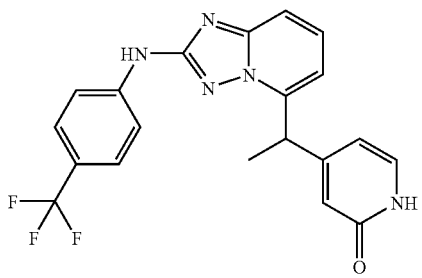

A. (2-Methoxypyridin-4-yl)(2-(4-(trifluoromethyl)phenylamino)-[1,2,4]triazolo[1,5-a]pyridin-5-yl)methanone. A stirred mixture of 5-bromo-N-(4-(trifluoromethyl)phenyl)-[1,2,4]triazolo[1,5-c]pyridin-2-amine (1.53 g, 4.28 mmol) in tetrahydrofuran (35 mL) was heated briefly with a heat gun under nitrogen until all solids dissolved. The resulting clear red solution was cooled with a dry ice acetone bath under nitrogen. n-Butyllithium (5.76 mL, 9.21 mmol, 1.6 M in hexane) was added dropwise slowly via syringe. During the addition the reaction became black-colored. After 40 min N,2-dimethoxy-N-methylisonicotinamide (4.61 mL, 9.21 mmol, 2 M in tetrahydrofuran) was added. The cold bath was removed and the resulting mixture was warmed to 0° C. over 15 min. After 30 min at 0° C., water (20 mL) was added and the resulting mixture was stirred vigorously at room temperature for 15 min. The resulting mixture was diluted with ethyl acetate and shaken in a separatory funnel. The layers were separated and the organics were washed with brine, dried over magnesium sulfate, filtered, and concentrated on a rotary evaporator. The residue was dissolved in hot ethyl acetate and purified using flash chromatography (Biotage) (10-100% ethyl acetate in hexane). Fractions containing the desired product were combined and concentrated on a rotary evaporator down to ~10 mL of ethyl acetate. Hexane (10 mL) was added. Solids were collected by vacuum filtration, washed with hexane, and dried under high vacuum to give the desired product (0.864 g, 2.090 mmol, 49% yield) as a yellow solid. $^1$H NMR (400 MHz, DMSO-d$_6$) δ (ppm) 10.23 (s, 1H), 8.43 (d, J=5.47 Hz, 1H), 7.93 (dd, J=0.98, 8.79 Hz, 1H), 7.77 (dd, J=7.42, 8.98 Hz, 1H), 7.53-7.60 (m, 2H), 7.45-7.53 (m, 3H), 7.31 (dd, J=1.37, 5.27 Hz, 1H), 7.16 (s, 1H), 3.91 (s, 3H); $^{19}$F NMR (376 MHz, DMSO-d$_6$) δ (ppm)-60.23 (s, 3F); MS (ESI) m/z 414.2 [M+1]$^+$.

B. 1-(2-Methoxypyridin-4-yl)-1-(2-(4-(trifluoromethyl)phenylamino)-[1,2,4]triazolo[1,5-a]pyridin-5-yl)ethanol. Methylmagnesium bromide (1.390 mL, 4.17 mmol, 3 M solution in diethyl ether) was added dropwise to a stirred solution of (2-methoxypyridin-4-yl)(2-(4-(trifluoromethyl)phenylamino)-[1,2,4]triazolo[1,5-c]pyridin-5-yl)methanone (0.431 g, 1.043 mmol) in tetrahydrofuran (20 mL) at 0° C. under nitrogen. The reaction instantly became red-colored upon addition of the methylmagnesium bromide but then became more yellow-colored. The resulting mixture was stirred at 0° C. under nitrogen for 50 min. Saturated aqueous ammonium chloride (2 mL) was added to quench the reaction. The resulting mixture was diluted with water and ethyl acetate and shaken in a separatory funnel. The layers were separated. The organics were washed with brine, dried over magnesium sulfate, filtered, and concentrated on a rotary evaporator. The residue was dissolved in dichloromethane and purified using flash chromatography (Biotage) (20-90% ethyl acetate in hexane) to give the desired product (0.417 g, 0.971 mmol, 93% yield) as a yellow foam-solid. $^1$H NMR (400 MHz, DMSO-d$_6$) δ (ppm) 10.01 (s, 1H), 8.06 (d, J=5.47 Hz, 1H), 7.74 (dd, J=7.42, 8.59 Hz, 1H), 7.61 (dd, J=1.17, 8.98 Hz, 1H), 7.50-7.59 (m, 4H), 7.47 (dd, J=1.17, 7.42 Hz, 1H), 6.94 (d, J=0.78 Hz, 1H), 6.86 (dd, J=1.56, 5.47 Hz, 1H), 6.44 (s, 1H), 3.82 (s, 3H), 2.03 (s, 3H); $^{19}$F NMR (376 MHz, DMSO-d$_6$) δ (ppm)-60.20 (s, 3F); MS (ESI) m/z 430.3 [M+H]$^+$.

C. 5-(1-(2-Methoxypyridin-4-yl)ethyl)-N-(4-(trifluoromethyl)phenyl)-[1,2,4]triazolo[1,5-a]pyridin-2-amine. 1-(2-Methoxypyridin-4-yl)-1-(2-(4-(trifluoromethyl)phenylamino)-[1,2,4]triazolo[1,5-c]pyridin-5-yl)ethanol (0.348 g, 0.810 mmol), methanesulfonic anhydride (0.353 g, 2.026 mmol), N,N-diisopropylethylamine (0.565 mL, 3.24 mmol), and N,N-dimethylformamide (9 mL) were combined in a sealable vessel with a stirbar. Nitrogen gas was blown in to blow out air. The resulting mixture was sealed, stirred vigorously, and heated at 100° C. for 24 h. A very large excess of both methanesulfonic anhydride and N,N-diisopropylethylamine were added in order to push the reaction to completion. The resulting mixture was sealed, stirred vigorously, and heated at 100° C. for another 1 h. The resulting mixture was diluted with ethyl acetate, saturated aqueous sodium bicarbonate, and water and shaken in a reparatory funnel. The layers were separated. The water layer was extracted with ethyl acetate. The combined organics were washed with brine, dried over magnesium sulfate, filtered, and concentrated on a rotary evaporator. The residue was dissolved in ethyl acetate and purified using flash chromatography (Biotage) (20-80% ethyl acetate in hexane) to give an impure tan solid. MS (ESI) m/z 412.0 [M+1]⁺. The tan solids were dissolved in 1-methyl-2-pyrrolidinone (3 mL) with stirring at room temperature and then diluted with ethanol (3 mL). A combination vacuum/nitrogen/hydrogen manifold was attached. The atmosphere in the flask was removed and replaced with nitrogen three times. Palladium (10 wt. % on activated carbon) (0.122 g, 0.115 mmol) was added and the atmosphere in the flask was removed and replaced with hydrogen three times. The resulting mixture was stirred vigorously under a hydrogen balloon at room temperature for 2.5 h. The atmosphere in the flask was removed and replaced with hydrogen three times. The resulting mixture was stirred vigorously under a hydrogen balloon at 50° C. for 1.5 h. The atmosphere in the flask was removed and replaced with hydrogen three times. The resulting mixture was stirred vigorously under a hydrogen balloon at 60° C. for 27 h. The resulting black mixture was filtered through Celite and purified using reverse-phase preparatory HPLC (30-100% acetonitrile+0.1% trifluoroacetic acid in water+0.1% trifluoroacetic acid, over 35 min). Fractions containing the desired product were loaded onto a Strata X—C ion exchange column from Phenomenex. The column was washed successively with water, acetonitrile, methanol, and then 5% ammonium hydroxide in methanol. The product came off with the 5% ammonium hydroxide in methanol eluent and was concentrated on a rotary evaporator and dried under high vacuum to give the desired product (0.172 g, 0.416 mmol, 51% yield over two steps) as a white solid. ¹H NMR (400 MHz, DMSO-d₆) δ (ppm) 10.08 (s, 1H), 8.08 (d, J=4.69 Hz, 1H), 7.77 (d, J=8.59 Hz, 2H), 7.64-7.71 (m, J=7.42, 8.98 Hz, 1H), 7.54-7.64 (m, 3H), 7.16 (d, J=7.03 Hz, 1H), 6.92 (dd, J=1.37, 5.27 Hz, 1H), 6.80 (s, 1H), 4.84 (q, J=7.03 Hz, 1H), 3.80 (s, 3H), 1.72 (d, 3H); ¹⁹F NMR (376 MHz, DMSO-d₆) δ (ppm)-60.10 (s, 3F); MS (ESI) m/z 414.4 [M+1]⁺.

D. 4-(1-(2-(4-(Trifluoromethyl)phenylamino)-[1,2,4]triazolo[1,5-a]pyridin-5-yl)ethyl)pyridin-2(1H)-one. Chlorotrimethylsilane (0.110 mL, 0.871 mmol) and then potassium iodide (0.145 g, 0.871 mmol) were added to a stirred solution of 5-(1-(2-methoxypyridin-4-yl)ethyl)-N-(4-(trifluoromethyl)phenyl)-[1,2,4]triazolo[1,5-c]pyridin-2-amine (0.144 g, 0.348 mmol) in acetonitrile (8 mL). The resulting mixture was stirred and heated at 60° C. under a reflux condenser under nitrogen for 14 h. The resulting yellow mixture was cooled to room temperature. Water (10 mL) was added with vigorous stirring. Solids were collected by vacuum filtration and washed thoroughly with water and diethyl ether. The solids were dissolved in DMSO and acetonitrile, filtered, and purified using reverse-phase semi-preparatory HPLC (20-80% acetonitrile+0.1% trifluoroacetic acid in water+0.1% trifluoroacetic acid, over 30 min). Fractions containing the desired product were loaded onto a Strata X—C ion exchange column from Phenomenex. The column was washed successively with water, acetonitrile, methanol, and then 5% ammonium hydroxide in methanol. The product came off with the 5% ammonium hydroxide in methanol eluent and was concentrated on a rotary evaporator and dried under high vacuum at 40° C. to give the desired product (0.089 g, 0.223 mmol, 64% yield) as a white solid. ¹H NMR (400 MHz, DMSO-d₆) δ (ppm) 11.46 (br s, 1H), 10.11 (s, 1H), 7.80 (d, J=8.59 Hz, 2H), 7.54-7.71 (m, 4H), 7.30 (d, J=6.64 Hz, 1H), 7.14 (d, J=6.64 Hz, 1H), 6.24 (d, J=1.56 Hz, 1H), 6.10 (dd, J=1.76, 6.83 Hz, 1H), 4.65 (q, J=7.03 Hz, 1H), 1.67 (d, J=7.03 Hz, 3H); ¹⁹F NMR (376 MHz, DMSO-d₆) δ (ppm)-60.01 (s, 3F); MS (ESI) m/z 400.2 [M+1]⁺.

Example 105 trans-4-((2-(3-Methyl-1H-indazol-6-ylamino)[1,2,4]
triazolo[1,5-a]pyridin-5-yl)methyl)cyclohexanol and
cis-4-((2-(3-methyl-1H-indazol-6-ylamino)-[1,2,4]
triazolo[1,5-a]pyridin-5-yl)methyl)cyclohexanol

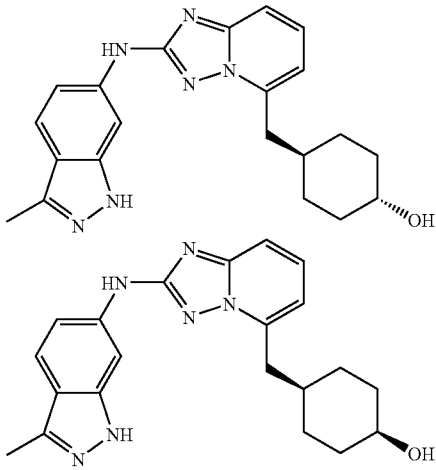

A. 4-((2-Amino-[1,2,4]triazolo[1,5-a]pyridin-5-yl)methyl)cyclohexyl 2,2,2-trifluoroacetate. A solution of tert-butyldimethyl(4-methylenecyclohexyloxy)silane (0.640 g, 2.83 mmol) in (1S,5S)-9-borabicyclo[3.3.1]nonane (5.65 mL, 2.83 mmol, 0.5 N in tetrahydrofuran) was refluxed for 3 h under an atmosphere of nitrogen. The reaction was then cooled to room temperature and reacted with [1,1'-bis(diphenylphosphino)ferrocene]-dichloropalladium(II) complex with dichloromethane (0.734 g, 0.899 mmol), potassium carbonate (0.391 g, 2.83 mmol) and N,N-di-tert-butoxycarbonyl-5-bromo-[1,2,4]triazolo[1,5-a]pyridin-2-amine (1.062 g, 2.57 mmol) in N,N-dimethylformamide (10 mL). The reaction mixture was heated to 90° C. for 3 h. The reaction was quenched with water and the crude was extracted with ethyl acetate. The organic extracts were dried over magnesium sulfate. After evaporation of the solvent, the residue was purified by Biotage column chromatography (0-30% ethyl acetate in hexanes). The 2 diastereomeric products appeared as almost resolved spots. The desired fractions were combined and evaporated to dryness. A light yellow oil was obtained that was not further characterized. The residue was dissolved in dichloromethane (5 mL) and the solution was treated with trifluoroacetic acid (0.75 mL, 9.73 mmol). The mixture was stirred at room temperature for 2 h. The solvent was removed under reduced pressure and the compound was neutralized using a saturated aqueous solution of sodium bicarbonate and extracted with ethyl acetate. The extracts were dried over magnesium sulfate and evaporated to dryness. The residue was purified by Biotage column chromatography using a rapid gradient to 100% ethyl acetate. 4-((2-Amino-[1,2,4]triazolo[1,5-a]pyridin-5-yl)methyl) cyclohexyl 2,2,2-trifluoroacetate (0.045 g, 0.131 mmol, 27.2% yield) was collected as a colorless oil. ¹H NMR (400 MHz, METHANOL-d₄) δ (ppm) 7.37-7.44 (m, 1H), 7.22 (d, J=8.59 Hz, 1H), 6.71-6.79 (m, 1H), 5.16-5.22 (m, 1H), 2.95

(dd, J=7.03, 11.71 Hz, 2H), 2.14 (ddd, J=3.51, 7.42, 10.93 Hz, 1H), 2.01-2.09 (m, 1H), 1.90-2.00 (m, 2H), 1.74-1.83 (m, 1H), 1.53-1.70 (m, 2H), 1.33-1.51 (m, 1H), 1.18-1.32 (m, 1H); MS (ESI) m/z 342.9 [M+1]+.

B. 1-(2-Fluoro-4-(5-((4-hydroxycyclohexyl)methyl)-[1,2,4]triazolo[1,5-a]pyridin-2-ylamino)phenyl)ethanone. The reaction was run in two batches. The reaction mixtures were quenched separately then combined for extraction and purification. To a suspension of 4-((2-amino-[1,2,4]triazolo[1,5-a]pyridin-5-yl)methyl)cyclohexyl 2,2,2-trifluoroacetate (0.045 g, 0.131 mmol), 4,5-bis(diphenylphosphino)-9,9-dimethylxanthene (0.015 g, 0.026 mmol), sodium tert-butoxide (0.025 g, 0.263 mmol) and tris(dibenzylideneacetone)dipalladium (0.013 g, 0.014 mmol) in dioxane (2.63 mL) under an atmosphere of nitrogen, was added 1-(4-bromo-2-fluorophenyl)ethanone (0.057 g, 0.263 mmol). The reaction mixture (dark brown) was stirred at 90° C. for 2 h. The reactions were quenched with water (10 mL), combined and extracted with ethyl acetate. The extracts (orange) slowly separated from the green emulsion. The extracts were dried over magnesium sulfate and evaporated to dryness. Purification was effected by Biotage column chromatography using 10-100% ethyl acetate in hexanes. The desired fractions were combined and evaporated to dryness. 1-(2-Fluoro-4-(5-((4-hydroxycyclohexyl)methyl)-[1,2,4]triazolo[1,5-a]pyridin-2-ylamino)phenyl)ethanone (0.060 g, 60% yield) was isolated as a yellow oil. MS (ESI) m/z 383.2 [M+1]+.

C. trans-4-((2-(3-Methyl-1H-indazol-6-ylamino)-[1,2,4]triazolo[1,5-a]pyridin-5-ylmethyl)cyclohexanol and cis-4-((2-(3-methyl-1H-indazol-6-ylamino)-[1,2,4]triazolo[1,5-a]pyridin-5-yl)methyl)cyclohexanol. 1-(2-Fluoro-4-(5-(4-hydroxycyclohexyl)methyl)-[1,2,4]triazolo[1,5-a]pyridin-2-ylamino)phenyl)ethanone (0.06 g, 0.157 mmol) was dissolved in ethanol (1.0 mL) and treated with hydrazine monohydrate (3 mL, 96 mmol). The reaction mixture was stirred at 100° C. for 48 h. Heating was stopped and water was added resulting in the formation of a white precipitate that was stirred all day. The solid was collected by filtration and washed with water. Purification was performed by semi-preparative HPLC (20-80% acetonitrile+0.1% trifluoroacetic acid in water+0.1% trifluoroacetic acid, 30 min, 2 injections). The 2 diastereomers were resolved. The desired fractions were combined and neutralized using a STRATA resin exchange column. Assignment of the stereochemistry was made based on the 1H NMR spectra. trans-4-((2-(3-Methyl-1H-indazol-6-ylamino)-[1,2,4]triazolo[1,5-c]pyridin-5-yl)methyl)cyclohexanol (0.006 g): 1H NMR (400 MHz, DMSO-d6) δ (ppm) 12.33 (s, 1H), 9.79 (s, 1H), 8.12 (s, 1H), 7.44-7.57 (m, 4H), 7.23 (d, J=8.59 Hz, 1H), 6.90 (d, J=6.64 Hz, 1H), 4.47 (br s, 1H), 3.39 (br s, 1H), 2.99 (d, J=7.03 Hz, 3H), 2.42 (s, 3H), 1.94 (br s, 1H), 1.82 (br s, 2H), 1.60-1.70 (m, 2H), 1.01-1.20 (m, 4H); MS (ESI) m/z 377.2 [M+1]+. cis-4-(2-(3-Methyl-1H-indazol-6-ylamino)-[1,2,4]triazolo[1,5-a]pyridin-5-yl)methyl)cyclohexanol (0.013 g): 1H NMR (400 MHz, DMSO-d6) δ (ppm) 12.31 (s, 1H), 9.78 (s, 1H), 8.12 (s, 1H), 7.42-7.57 (m, 3H), 7.23 (d, J=8.20 Hz, 1H), 6.90 (d, J=6.25 Hz, 1H), 4.34 (br s, 1H), 3.74 (br s, 1H), 3.04 (d, J=6.25 Hz, 2H), 2.42 (s, 3H), 2.08 (br s, 1H), 1.56-1.68 (m, 2H), 1.45-1.56 (m, 2H), 1.32-1.45 (m, 4H); MS (ESI) m/z 377.2 [M+1]+.

Example 106 cis-1-(Methoxymethyl)-4-((2-(4-(trifluoromethyl)phenylamino)-[1,2,4]triazolo[1,5-a]pyridin-5-ylmethyl)cyclohexanol

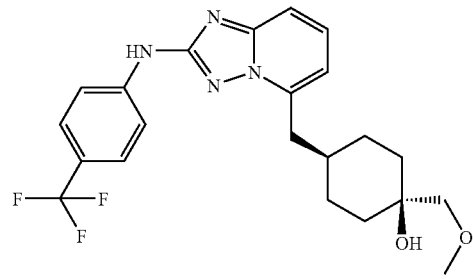

A. 5-(1,4-Dioxaspiro[4.5]decan-8-ylmethyl)-N-(4-(trifluoromethyl)phenyl)-[1,2,4]triazolo[1,5-a]pyridin-2-amine. A solution of 8-methylene-1,4-dioxaspiro[4.5]decane (1.770 g, 11.48 mmol) in (1S,5S)-9-borabicyclo[3.3.1]nonane (22.40 mL, 11.20 mmol, 0.5 N solution in tetrahydrofuran) was heated to reflux temperature for 3 h under an atmosphere of nitrogen. At room temperature, were added 5-bromo-N-(4-(trifluoromethyl)phenyl)-[1,2,4]triazolo[1,5-a]pyridin-2-amine (1.0 g, 2.80 mmol), [1,1'-bis(diphenylphosphino)ferrocene]dichloropalladium(II) complex with dichloromethane (0.800 g, 0.980 mmol), potassium carbonate (1.548 g, 11.20 mmol) and N,N-dimethylformamide (10 mL). The reaction was then heated to 90° C. overnight. The reaction was quenched with water and the crude was extracted with ethyl acetate. The organic extracts were dried over magnesium sulfate. After evaporation of the solvent, the residue was purified by Biotage column chromatography (5-50% ethyl acetate in hexanes). Fractions containing the desired product were combined and evaporated to dryness. 5-(1,4-Dioxaspiro[4.5]decan-8-ylmethyl)-N-(4-(trifluoromethyl)phenyl)-[1,2,4]triazolo[1,5-a]pyridin-2-amine (0.9 g, 2.081 mmol, 74.3% yield) was obtained as a brown oil that solidified at room temperature (contaminated with about 50% N-(4-(trifluoromethyl)phenyl)-[1,2,4]triazolo[1,5-a]pyridin-2-amine as estimated from LCMS). MS (ESI) m/z 433.5 [M+1]+.

B. 4-((2-(4-(Trifluoromethyl)phenylamino)-[1,2,4]triazolo[1,5-a]pyridin-5-ylmethyl)cyclohexanone. A solution of 5-(1,4-dioxaspiro[4.5]decan-8-ylmethyl)-N-(4-(trifluoromethyl)phenyl)-[1,2,4]triazolo[1,5-a]pyridin-2-amine (0.6 g, 1.387 mmol) in tetrahydrofuran (5 mL) was treated with a 6.0 N aqueous solution of hydrochloric acid (5 mL, 30.0 mmol) and heated to reflux temperature for 24 h. The reaction mixture was neutralized with sodium hydroxide and extracted with ethyl acetate. The residue was dried over sodium sulfate and evaporated to dryness. The residue was purified by Biotage column chromatography using 0-50% ethyl acetate in hexanes. 4-((2-(4-(Trifluoromethyl)phenylamino)-[1,2,4]triazolo[1,5-c]pyridin-5-yl)methyl)cyclohexanone (0.29 g, 0.747 mmol, 53.8% yield) was isolated as a light yellow oil that turned into a foam under vacuum. $^1$H NMR (400 MHz, DMSO-d$_6$) δ (ppm) 10.20 (s, 1H), 7.93 (d, J=8.20 Hz, 2H), 7.65 (d, J=8.20 Hz, 2H), 7.50-7.61 (m, 2H), 6.99 (d, J=6.64 Hz, 1H), 3.13 (d, J=7.42 Hz, 2H), 2.31-2.44 (m, 2H), 2.18-2.29 (m, 2H), 1.88-2.03 (m, 2H), 1.57 (br s, 2H); MS (ESI) m/z 389.4 [M+1]$^+$.

C. cis-5-(1-Oxaspiro[2.5]octan-6-ylmethyl)-N-(4-(trifluoromethyl)phenyl)-[1,2,4]triazolo[1,5-a]pyridin-2-amine. To a suspension of sodium hydride (0.011 g, 0.275 mmol) in dimethyl sulfoxide (2.75 mL) was added as a solid and in one portion, trimethylsulfoxonium iodide (0.091 g, 0.413 mmol). After 1 h, 4-((2-(4-(trifluoromethyl)phenylamino)-[1,2,4]triazolo[1,5-a]pyridin-5-yl)methyl)cyclohexanone (0.107 g, 0.275 mmol) dissolved in tetrahydrofuran (2.75 mL) was added dropwise. The reaction was stirred at room temperature for 1 h. The reaction was quenched with water and extracted with ethyl acetate (3 times). The organic phase was dried over sodium sulfate and evaporated to dryness. The residue solidified under vacuum and was used without purification in the next step. Alternatively, it can be purified by Biotage normal phase column chromatography using 5-75% ethyl acetate in hexanes. The desired fractions, combined and evaporated to dryness, afforded cis-5-(1-oxaspiro[2.5]octan-6-ylmethyl)-N-(4-(trifluoromethyl)phenyl)-[1,2,4]triazolo[1,5-c]pyridin-2-amine as a white solid in greater than 80% yield. (stereochemistry based on mechanism, $^1$H NMR (400 MHz, DMSO-d$_6$) δ (ppm) 10.18 (s, 1H), 7.92 (d, J=8.20 Hz, 3H), 7.63 (d, J=8.20 Hz, 3H), 7.49-7.60 (m, 2H), 6.98 (d, J=6.25 Hz, 1H), 3.07 (d, J=7.42 Hz, 2H), 2.15 (br s, 1H), 1.75-1.88 (m, 2H), 1.67 (d, J=12.10 Hz, 2H), 1.29-1.47 (m, 2H), 1.19 (d, J=14.06 Hz, 2H); $^{19}$F NMR (376 MHz, DMSO-d$_6$) δ (ppm)-60.03; MS (ESI) m/z 403.5 [M+H]$^+$).

D. cis-1-(Methoxymethyl)-4-((2-(4-(trifluoromethyl)phenylamino)-[1,2,4]triazolo[1,5-a]pyridin-5-yl)methyl)cyclohexanol. cis-5-(1-Oxaspiro[2.5]octan-6-ylmethyl)-N-(4-(trifluoromethyl)phenyl)-[1,2,4]triazolo[1,5-c]pyridin-2-amine was suspended in methanol (5 mL), reacted with a 6.0 N aqueous solution of potassium hydroxide (0.092 mL, 0.551 mmol) and heated to 40° C. overnight. The reaction was quenched by addition of 0.1 mL of a aqueous solution of hydrochloric acid and evaporated to dryness. The residue was purified was by semi-preparative HPLC (20-80% acetonitrile+0.1% trifluoroacetic acid in water+0.1% trifluoroacetic acid, 30 min, 2 injections). The desired fractions were combined, concentrated under reduced pressure and neutralized with a 1.75 M aqueous solution of potassium carbonate. A white solid precipitated out that was collected and dried under vacuum. cis-1-(Methoxymethyl)-4-(2-(4-(trifluoromethyl)phenylamino)-[1,2,4]triazolo[1,5-c]pyridin-5-yl)methyl)cyclohexanol (0.041 g, 0.094 mmol, 34.3% yield) was collected as a white solid. $^1$H NMR (400 MHz, DMSO-d$_6$) δ (ppm) 10.17 (s, 1H), 7.91 (d, J=8.59 Hz, 2H), 7.63 (d, J=8.59 Hz, 2H), 7.43-7.58 (m, 2H), 6.94 (d, J=6.25 Hz, 1H), 4.10 (br s, 1H), 3.22 (s, 3H), 3.06 (s, 2H), 3.00 (d, J=7.03 Hz, 2H), 1.93 (br s, 1H), 1.19-1.56 (m, 8H); $^{19}$F NMR (376 MHz, DMSO-d$_6$) δ (ppm)-60.04; MS (ESI) m/z 435.5 [M+1]$^+$.

Example 107

3'-Chloro-5'-(2-(4-(methylcarbamoyl)phenylamino)-[1,2,4]triazolo[1,5-a]pyridin-5-yl)biphenyl-2-carboxamide

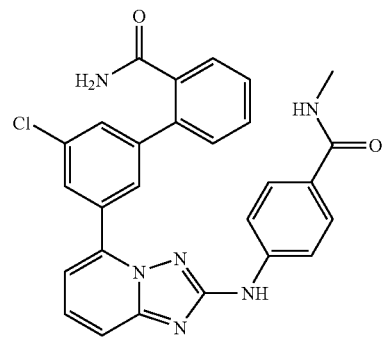

A. 4-(5-(3-Chloro-5-hydroxyphenyl)-[1,2,4]triazolo[1,5-a]pyridin-2-ylamino)-N-methylbenzamide. To a degassed solution of 3-chloro-5-hydroxyphenylboronic acid (258 mg, 1.5 mmol), 4-(5-bromo-[1,2,4]triazolo[1,5-c]pyridin-2-ylamino)-N-methylbenzamide (345 mg, 1.0 mmol), aqueous potassium phosphate (2M, 1 mL) in N,N-dimethylformamide (5 mL) was added tetrakis(triphenylphosphine)palladium (0) (115 mg, 0.1 mmol), and the reaction mixture was heated at 90° C. under nitrogen for 4 h. After cooling down to room temperature, the reaction mixture was poured into water, and extracted with ethyl acetate. The combined organic layer was washed with brine, dried over anhydrous sodium sulfate, evaporated under reduced pressure, and purified on silica gel column (eluting with 5-80% ethyl acetate in petroleum ether) to give 4-(5-(3-chloro-5-hydroxyphenyl)-[1,2,4]triazolo[1,5-c]pyridin-2-ylamino)-N-methylbenzamide (130 mg, 33% yield). $^1$H NMR (400 MHz, DMSO-d$_6$) δ (ppm) 10.33 (s, 1H), 10.03 (s, 1H), 8.24 (s, 1H), 7.78 (m, 4H), 7.67 (m, 3H), 7.37 (s, 1H), 7.25 (t, J=2.8 Hz, 1H), 7.01 (s, 1H), 7.45 (d, J=4.4 Hz, 3H).

B. 3-Chloro-5-(2-(4-(methylcarbamoyl)phenylamino)-[1,2,4]triazolo[1,5-a]pyridin-5-yl)phenyl trifluoromethanesulfonate. To a mixture of 4-(5-(3-chloro-5-hydroxyphenyl)-[1,2,4]triazolo[1,5-a]pyridin-2-ylamino)-N-methylbenzamide (120 mg, 0.30 mmol), triethylamine (303 mg, 1.0 mmol) in tetrahydrofuran (5 mL) was added dropwise trifluoromethanesulfonic anhydride (168 mg, 0.6 mmol) at 0° C. The reaction mixture was stirred at room temperature for 4 h, and concentrated, and the residue was partitioned between ethyl acetate and water. The organic layer was separated, and the aqueous layer was extracted with ethyl acetate. The combined organic layer was washed with brine, dried over anhydrous sodium sulfate, evaporated under reduced pressure, and purified on silica gel column (eluting with 5-50% ethyl acetate in petroleum ether) to give 3-chloro-5-(2-(4-(methylcarbamoyl)-phenylamino)-[1,2,4]triazolo[1,5-a]pyridin-5-yl)phenyl trifluoromethanesulfonate (120 mg, 76% yield). $^1$H NMR (400 MHz, DMSO-d$_6$) δ (ppm) 8.23 (s, 1H), 7.78 (m, 7H), 7.67 (d, J=5.6 Hz, 1H), 7.58 (s, 1H), 7.37 (s, 1H); 7.01 (s, 1H), 2.80 (d, J=4.0 Hz, 3H); MS (ESI): m/z 525.9 [M+1]$^+$.

C. 4-(5-(5-Chloro-2'-cyanobiphenyl-3-yl)-[1,2,4]triazolo[1,5-a]pyridin-2-ylamino)-N-methylbenzamide. To a degassed solution of 2-cyanophenylboronic acid (50 mg, 0.34 mmol), 3-chloro-5-(2-(4-(methylcarbamoyl)phenylamino)-[1,2,4]triazolo[1,5-a]pyridin-5-yl)phenyl trifluoromethanesulfonate (120 mg, 0.23 mmol), aqueous sodium carbonate (2 M, 1 mL) in N,N-dimethylformamide (3 mL) was added 1,1'-bis(diphenylphosphino)ferrocene palladium dichloride (17 mg, 0.023 mmol), and the reaction mixture was heated at 90° C. under nitrogen for 3 h. After cooling down to room temperature, the reaction mixture was poured into water, and the resulting mixture was extracted with ethyl acetate. The combined organic layer was washed with brine, dried over anhydrous sodium sulfate, evaporated under reduced pressure, and purified on silica gel column (eluting with 5-50% ethyl acetate in petroleum ether) to give 4-(5-(5-chloro-2'-cyanobiphenyl-3-yl)-[1,2,4]triazolo[1,5-a]pyridin-2-ylamino)-N-methylbenzamide (80 mg, 72% yield). MS (ESI): m/z 479.1 [M+1]$^+$.

D. 3'-Chloro-5'-(2-(4-(methylcarbamoyl)phenylamino)-[1,2,4]triazolo[1,5-a]pyridin-5-yl)biphenyl-2-carboxamide. To a solution of 4-(5-(5-chloro-2'-cyanobiphenyl-3-yl)-[1,2,4]triazolo[1,5-a]pyridin-2-ylamino)-N-methylbenzamide (80 mg, 0.16 mmol), and aqueous solution of sodium hydroxide (1 mL, 2 M) in dimethyl sulfoxide (5 mL) was added dropwise hydrogen peroxide (1 mL, 30%) at 0° C., and the reaction mixture was stirred at room temperature for 1 h. The reaction mixture was diluted with water, and extracted with ethyl acetate. The combined organic layer was washed with brine, dried over anhydrous sodium sulfate, evaporated under reduced pressure, and purified by a reverse-phase preparatory HPLC (eluting with 20-55%: acetonitrile+0.1% trifluoroacetic acid in water+0.1% trifluoroacetic acid, over 15 min.) to give 3'-chloro-5'-(2-(4-(methylcarbamoyl)phenylamino)-[1,2,4]triazolo[1,5-c]pyridin-5-yl)biphenyl-2-carboxamide as a trifluoroacetic acid salt, which was converted to a hydrochloride salt (20 mg, 25% yield). $^1$H NMR (400 MHz, METHANOL-d$_4$): δ (ppm) 8.25 (t, J=2.0 Hz, 1H), 8.06 (t, J=2.0 Hz, 1H), 7.99 (m, 1H), 7.83 (d, J=8.8 Hz, 2H), 7.75 (dd, J$_1$=1.2 Hz, J$_2$=8.8 Hz, 4H), 7.63 (m, 5H), 2.80 (s, 3H); MS (ESI): m/z 497.1 [M+H]$^+$.

Example 108 cis-6-(5-(4-Hydroxycyclohexylamino)-[1,2,4]triazolo[1,5-a]pyridin-2-ylamino)-1-methylindolin-2-one

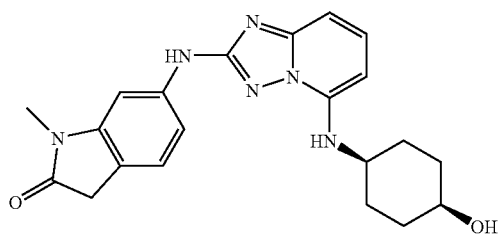

A. cis-4-(2-Amino-[1,2,4]triazolo[1,5-a]pyridin-5-ylamino)cyclohexanol. 5-Bromo-[1,2,4]triazolo[1,5-c]pyridin-2-amine (10 g, 46.9 mmol), cis-4-aminocyclohexanol hydrochloride (21.35 g, 141 mmol) and potassium carbonate (25.9 g, 188 mmol) were added to a 200 mL sealable flask. DMSO (150 mL) was added, and the reaction placed to stir vigorously in a 120° C. oil bath for 16 h. More cis-4-aminocyclohexanol hydrochloride (1.068 g, 7.04 mmol) and potassium carbonate (another 1.5 equivalents) were added and the reaction was heated to 120° C. for 18 hr. The reaction was filtered, acidified to pH=6 and purified using reverse-phase preparatory HPLC (3-30% acetonitrile+0.1% trifluoroacetic acid in water+0.1% trifluoroacetic acid, over 30 min). Fractions containing the desired product were combined and the acetonitrile removed on a rotary evaporator to afford cis-4-(2-amino-[1,2,4]triazolo[1,5-a]pyridin-5-ylamino)cyclohexanol as the trifluoroacetic acid salt as a clear oil. Fractions containing the desired product were combined and loaded onto a Strata X—C ion exchange column from Phenomenex. The column was washed successively with water, acetonitrile, methanol, and then 5% ammonium hydroxide in methanol. The product came off with the 5% ammonium hydroxide in methanol and was concentrated on a rotary evaporator and dried under high vacuum at 40° C. to give the desired product (8.5 g, 34.4 mmol, 73% yield) as a brown solid. $^1$H NMR (400 MHz, DMSO-d$_6$) δ (ppm) 7.27 (t, J=7.81 Hz, 1H), 6.55 (d, J=8.59 Hz, 1H), 6.04 (d, J=7.81 Hz, 1H), 5.85 (s, 2H), 5.77 (d, J=8.20 Hz, 1H), 4.48 (d, J=3.12 Hz, 1H), 3.72 (d, J=3.51 Hz, 1H), 3.56 (dd, J=8.00, 3.71 Hz, 1H), 1.53-1.84 (m, 8H); MS (ESI): m/z 248.3 [M+1]$^+$.

B. cis-6-(5-(4-Hydroxycyclohexylamino)-[1,2,4]triazolo[1,5-a]pyridin-2-ylamino)-1-methylindolin-2-one. A degassed solution of 6-bromo-1-methylindoline-2,3-dione (720 mg, 3 mmol), cis-4-(2-amino-[1,2,4]triazolo[1,5-c]pyridin-5-ylamino)cyclohexanol (494 mg, 2 mmol), tris(dibenzylideneacetone)dipalladium (0) (290 mg, 0.3 mmol), 4,5-bis(diphenylphosphino)-9,9-dimethylxanthene (308 mg, 0.6 mmol), and cesium carbonate (1.14 g, 3.5 mmol) in dioxane (70 mL) was heated at 100° C. under nitrogen for 2 h. After cooling to room temperature, the reaction mixture was concentrated, and the residue was purified by flash column chromatography on silica gel (eluting with 50-100% ethyl acetate in petroleum ether) to give crude cis-6-(5-(4-hydroxycyclohexylamino)-[1,2,4]triazolo[1,5-c]pyridin-2-ylamino)-1-methylindoline-2,3-dione as a yellow solid. The crude intermediate was dissolved in hydrazine hydrate (85% aqueous. solution, 10 mL), and the mixture was stirred at 140° C. for 1.5 h. When the reaction mixture turned to colorless, the solution was cooled to room temperature, and poured into water (200 mL). The precipitate was collected by filtration, and purified by a reversed-phase preparatory HPLC (45-65% acetonitrile+0.1% trifluoroacetic acid in water+0.1% trifluoroacetic acid, over 15 min) to give cis-6-(5-(4-hydroxycyclohexylamino)-[1,2,4]triazolo[1,5-c]pyridin-2-ylamino)-1-methylindolin-2-one as a trifluoroacetic acid salt, which was converted to the hydrochloride salt with a methanolic hydrochloride solution (140 mg, 16.6% yield, two steps). $^1$H NMR (400 MHz, METHANOL-d$_4$) δ (ppm) 7.87 (t, J=8.4 Hz, 1H), 7.37 (m, 3H), 6.88 (d, J=8.0, 1H), 6.76 (d, J=8.8 Hz, 1H), 3.99

(m, 1H), 3.81 (m, 1H), 3.58 (s, 2H), 3.29 (s, 3H), 2.00 (m, 8H); MS (ESI): m/z: 393.3 [M+H]⁺.

Example 109

3,3-Dimethyl-6-(5-(tetrahydro-2H-pyran-4-ylamino)-[1,2,4]triazolo[1,5-a]pyridin-2-ylamino)indolin-2-one

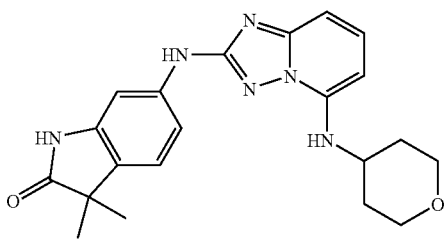

A. 2-Bromo-N-(tetrahydro-2H-pyran-4-yl)-[1,2,4]triazolo[1,5-a]pyridin-5-amine. 2,5-Dibromo-[1,2,4]triazolo[1,5-a]pyridine (511.1 mg, 1.846 mmol), tetrahydro-2H-pyran-4-amine (626 mg, 6.19 mmol), were added to a 200 mL flask. DMSO (2 mL) was added, and the reaction placed to stir hard in a 100° C. oil bath for 4 h. After 4 h LCMS analysis showed a 2:1 ratio of product to starting material. Another portion of tetrahydro-2H-pyran-4-amine (205.8 mg, 2.035 mmol) was added, and the temperature was lowered to 80° C. for 16 h. The reaction was diluted with ethyl acetate and washed with water with saturated sodium bicarbonate solution. The material was dissolved into dichloromethane and purified by column chromatography (eluting with 0-4% methanol in dichloromethane to afford 2-bromo-N-(tetrahydro-2H-pyran-4-yl)-[1,2,4]triazolo[1,5-c]pyridin-5-amine (0.5066 g, 1.705 mmol, 92% yield). ¹H NMR (400 MHz, CHLOROFORM-d) δ (ppm) 7.47 (t, J=8.39 Hz, 1H), 7.00 (d, J=8.59 Hz, 1H), 6.11 (d, J=7.81 Hz, 1H), 5.65 (d, J=7.42 Hz, 1H), 4.07 (dt, J=11.81, 3.47 Hz, 2H), 3.63-3.81 (m, 1H), 3.56 (td, J=11.62, 2.15 Hz, 2H), 2.02-2.19 (m, 2H), 1.63-1.78 (m, 2H). (ESI): m/z 297.4 [M+H]⁺.

B. tert-Butyl 3,3-dimethyl-2-oxo-6-(5-(tetrahydro-2H-pyran-4-ylamino)-[1,2,4]triazolo[1,5-a]pyridin-2-ylamino)indoline-1-carboxylate. A mixture of tris(dibenzylideneacetone)dipalladium(0) (0.099 g, 0.109 mmol) and 4,5-bis(diphenylphosphino)-9,9-dimethylxanthene (0.126 g, 0.217 mmol) in 1,4-dioxane (1.5 mL) was heated briefly with a heat gun until very hot and then added to tert-butyl 6-amino-3,3-dimethyl-2-oxoindoline-1-carboxylate (0.150 g, 0.543 mmol), 2-bromo-N-(tetrahydro-2H-pyran-4-yl)-[1,2,4]triazolo[1,5-c]pyridin-5-amine (0.161 g, 0.543 mmol) and finely ground potassium carbonate (0.308 g, 2.226 mmol) in a sealable vessel with a stirbar. Nitrogen was blown in to blow out air. The resulting mixture was sealed, stirred vigorously, and heated at 100° C. for 4 h. After cooling to room temperature the reaction mixture was diluted with hot DMSO and filtered through a syringe filter. The filter cake was washed with hot DMSO. The filtrate was diluted with methanol and purified using reverse-phase preparatory HPLC (10-80% acetonitrile+0.1% trifluoroacetic acid in water+0.1% trifluoroacetic acid, over 30 min). Fractions containing the desired product were combined, neutralized with saturated aqueous sodium bicarbonate, and the acetonitrile was removed on a rotary evaporator. The resulting mixture was extracted with ethyl acetate. The organics were dried over magnesium sulfate, filtered, concentrated on a rotary evaporator, and dried under high vacuum to give the desired product (0.148 g, 0.300 mmol, 55% yield) as a yellow solid. ¹H NMR (400 MHz, DMSO-d₆) δ (ppm) 9.63 (s, 1H), 8.47 (d, J=1.95 Hz, 1H), 7.38-7.47 (m, 2H), 7.27 (d, J=8.20 Hz, 1H), 6.74 (d, J=8.20 Hz, 1H), 6.29 (d, J=7.81 Hz, 1H), 6.07 (d, J=8.20 Hz, 1H), 3.87-3.97 (m, 2H), 3.73-3.87 (m, 1H), 3.42-3.55 (m, 2H), 2.01 (dd, J=2.34, 12.49 Hz, 2H), 1.63-1.74 (m, 2H), 1.61 (s, 9H), 1.32 (s, 6H); MS (ESI) m/z 493.2 [M+1]⁺.

C. 3,3-Dimethyl-6-(5-(tetrahydro-2H-pyran-4-ylamino)-[1,2,4]triazolo[1,5-a]pyridin-2-ylamino)indolin-2-one. A stirred solution of tert-butyl 3,3-dimethyl-2-oxo-6-(5-(tetrahydro-2H-pyran-4-ylamino)-[1,2,4]triazolo[1,5-c]pyridin-2-ylamino)indoline-1-carboxylate (0.117 g, 0.238 mmol) in acetic acid (5 mL) was heated at 110° C. under a reflux condenser under nitrogen for 2.5 h. The resulting mixture was diluted with DMSO, filtered, and purified using reverse-phase preparatory HPLC (5-50% acetonitrile+0.1% trifluoroacetic acid in water+0.1% trifluoroacetic acid, over 30 min). Fractions containing the desired product were loaded onto a Strata X—C ion exchange column from Phenomenex. The column was washed successively with water, acetonitrile, methanol, 5% ammonium hydroxide in methanol, and then 5% ammonium hydroxide in 50% methanol in dichloromethane. The product came off with the ammonium hydroxide eluent and was concentrated on a rotary evaporator and dried under high vacuum at 50° C. to give the desired product (0.072 g, 0.183 mmol, 77% yield) as a white solid. ¹H NMR (400 MHz, DMSO-d₆) δ (ppm) 10.26 (s, 1H), 9.44 (s, 1H), 7.41 (t, J=8.20 Hz, 1H), 7.35 (d, J=1.95 Hz, 1H), 7.29-7.34 (m, J=1.95, 8.20 Hz, 1H), 7.13 (d, J=8.20 Hz, 1H), 6.74 (dd, J=1.17, 8.59 Hz, 1H), 6.28 (d, J=7.42 Hz, 1H), 6.09 (d, J=8.59 Hz, 1H), 3.93 (dd, J=2.54, 8.00 Hz, 2H), 3.72-3.86 (m, 1H), 3.48 (td, J=1.95, 11.71 Hz, 2H), 1.98 (dd, J=1.95, 12.49 Hz, 2H), 1.61-1.77 (m, 2H), 1.22 (s, 6H); MS (ESI) m/z 393.2 [M+1]⁺.

Example 110

4-((2-(3-Methyl-1H-indazol-6-ylamino)[1,2,4]triazolo[1,5-a]pyridin-5-yl)methyl)piperazin-2-one

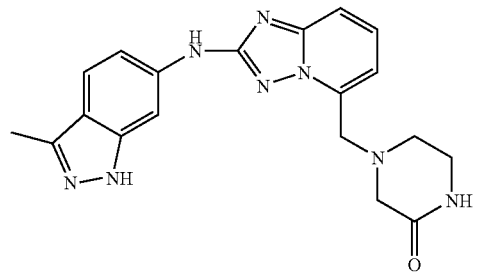

A. Methyl 2-amino-[1,2,4]triazolo[1,5-a]pyridine-5-carboxylate. A solution of O-ethyl carbonisothiocyanatidate (2.229 mL, 19.72 mmol) in dioxane (100 mL) was cooled in an ice-bath. Methyl 6-aminopicolinate (3 g, 19.72 mmol) was added in small portions and then stirred for 1 h until LCMS analysis showed that the thiourea intermediate was formed. Triethylamine (2.75 mL, 19.72 mmol) was added to the reaction followed by hydroxylamine hydrochloride (1.370 g, 19.72 mmol). The reaction was heated to 100° C. for 16 h. The reaction was cooled to room temperature, diluted with ethyl acetate, filtered, and rinsed with ethyl acetate. The filtrate was concentrated and then purified on silica gel column (0-50% methanol in ethyl acetate). The product fractions were concentrated and then triturated with 50% ethyl acetate in hexanes and then filtered to give methyl 2-amino-[1,2,4]triazolo[1,5-a]pyridine-5-carboxylate as a white solid (1.13 g, 5.88 mmol, 29.8% yield). $^1$H NMR (400 MHz, DMSO-d$_6$) δ (ppm) 7.56-7.65 (m, 1H), 7.51 (t, J=8.0 Hz, 1H), 7.38-7.45 (m, 1H), 6.25 (s, 2H), 3.93 (s, 3H); MS (ESI) m/z 193.1 [M+1]$^+$.

B. Methyl 2-(3-methyl-1-tosyl-1H-indazol-6-ylamino)-[1,2,4]triazolo[1,5-a]pyridine-5-carboxylate. 6-Bromo-3-methyl-1-tosyl-1H-indazole (0.66 g, 1.807 mmol), methyl 2-amino-[1,2,4]triazolo[1,5-c]pyridine-5-carboxylate (0.382 g, 1.988 mmol), cesium carbonate (1.766 g, 5.42 mmol), 4,5-bis(diphenylphosphino)-9,9-dimethylxanthene (0.105 g, 0.181 mmol), tris(dibezylideneacetone)palladium(0) (0.083 g, 0.090 mmol), and dioxane (20 mL) were heated to 90° C. under nitrogen for 2 h. The reaction was filtered and then concentrated. The residue was purified on silica gel column (0-100% ethyl acetate in hexanes followed by 0-20% methanol in ethyl acetate). Product fractions were concentrated and then triturated in ether to give the title compound as a bright yellow solid (0.66 g, 77% yield). $^1$H NMR (400 MHz, DMSO-d$_6$) δ (ppm) 10.35 (s, 1H), 8.75 (d, J=1.6 Hz, 1H), 7.83 (d, J=8.6 Hz, 2H), 7.70-7.75 (m, 1H), 7.63-7.68 (m, 2H), 7.37 (d, J=8.2 Hz, 2H), 4.03 (s, 3H), 2.42 (s, 3H), 2.30 (s, 3H). MS (ESI) m/z 477.5 [M+1]$^+$.

C. (2-(3-Methyl-1-tosyl-1H-indazol-6-ylamino)-[1,2,4]triazolo[1,5-a]pyridin-5-yl)methanol. Methyl 2-(3-methyl-1-tosyl-1H-indazol-6-ylamino)-[1,2,4]triazolo[1,5-c]pyridine-5-carboxylate (0.66 g, 1.385 mmol) was added with ethanol (25 mL). Sodium borohydride (0.157 g, 4.16 mmol) was added in three portions. The reaction was heated to 50° C. for 4 h. The reaction was concentrated and then triturated in water, filtered, and then triturated again in 10% methanol in ethyl acetate to give the title compound as a grey solid, (0.22 g, 35.4% yield). MS (ESI) m/z 449.5 [M+H]$^+$.

D. 4-((2-(3-Methyl-1H-indazol-6-ylamino)[1,2,4]triazolo[1,5-a]pyridin-5-yl)methyl)piperazin-2-one. (2-(3-Methyl-1-tosyl-1H-indazol-6-ylamino)-[1,2,4]triazolo[1,5-a]pyridin-5-yl)methanol (0.22 g, 0.491 mmol), N,N-dimethylformamide (1 mL), methanesulfonic anhydride (0.51 g, 2.94 mmol), and triethylamine (0.684 mL, 4.91 mmol) were stirred together for 4 h. piperazin-2-one (0.147 g, 1.472 mmol) was added to the reaction and heated at 60° C. for 16 h. The reaction was purified via reverse phase HPLC (10-70% acetonitrile+0.1% trifluoroacetic acid in water+0.1% trifluoroacetic acid). The product fractions were past through ion-exchange column (Strata-XC) and then released with 2M ammonia in methanol. The solution was concentrated and triturated with 5% methanol in ethyl acetate to give a white solid. The solid was taken up in methanol (20 mL) and then added with 25% sodium methoxide in methanol. The reaction was heated in the microwave (120° C., 30 min). The reaction was concentrated, neutralized with 1M sodium hydroxide, and then filtered to give a tan color solid. The solid was purified via reverse phase HPLC (10-70% acetonitrile+0.1% trifluoroacetic acid in water+0.1% trifluoroacetic acid). The product fractions were past through ion-exchange column (Strata-XC) and then released with 2M ammonia in methanol. The solution was concentrated and then triturated with 10% methanol in ether to give the title compound as a white solid, (0.043 g, 23.29% yield). $^1$H NMR (400 MHz, DMSO-d$_6$) δ (ppm) 12.32 (s, 1H), 9.81 (s, 1H), 8.13 (d, J=1.6 Hz, 1H), 7.85 (s, 1H), 7.57-7.63 (m, 1H), 7.54-7.56 (m, 1H), 7.51-7.54 (m, 1H), 7.20 (dd, J=1.8, 8.8 Hz, 1H), 7.06-7.14 (m, 1H), 4.11 (s, 2H), 3.18-3.27 (m, 4H), 2.79 (t, J=5.5 Hz, 2H), 2.42 (s, 3H). MS (ESI) m/z 377.1 [M+1]$^+$.

Example 111

1-(3-Methyl-1H-indazol-6-yl)-4-((2-(3-methyl-1H-indazol-6-ylamino)-[1,2,4]triazolo[1,5-a]pyridin-5-yl)methyl)piperazin-2-one

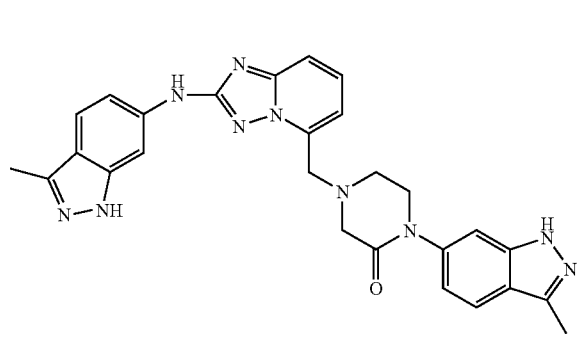

A. N,N-Di-tert-butoxycarbonyl-5-methyl-[1,2,4]triazolo[1,5-a]pyridin-2-amine. To a solution of 5-methyl-[1,2,4]triazolo[1,5-a]pyridin-2-amine (5 g, 33.7 mmol) in acetonitrile (50 mL) was added 4-(dimethylamino)pyridine (0.412 g, 3.37 mmol), and di-tert-butyl dicarbonate (19.59 mL, 84 mmol). The reaction was heated to 70° C. for 4 h. The reaction was concentrated and purified via silica gel chromatography (0-50% ethyl acetate in hexanes) to give a white solid, (7.9 g, 67% yield). MS (ESI) m/z 349.4 [M+1]$^+$.

B. N,N-Di-tert-butoxycarbonyl-5-(bromomethyl)-[1,2,4]triazolo[1,5-a]pyridin-2-amine. N,N-Di-tert-butoxycarbonyl-5-methyl-[1,2,4]triazolo[1,5-a]pyridin-2-amine (2 g, 5.74 mmol) was dissolved in acetonitrile (50 mL) and then purged with nitrogen for 10 min. N-Bromosuccimide (1.226 g, 6.89 mmol) and 2,2'-azobis(2-methylpropionitrile) (0.094 g, 0.574 mmol) were added to the solution and then heated to 70° C. The reaction was recharged with fresh N-Bromosuccimide and 2,2'-azobis(2-methylpropionitrile) once every 24 h for the first two days. The reaction was heated for a total of 5 d. The reaction was concentrated and then extracted with water and ethyl acetate. The organic layer was dried over anhydrous magnesium sulfate, filtered, and then concentrated. The residue was purified via silica gel chromatography (0-50% ethyl acetate in hexanes) to give a white solid (1.05 g, 42.8% yield), MS (ESI) m/z 427.2 [M]$^+$.

C. 4-((2-Amino-[1,2,4]triazolo[1,5-a]pyridin-5-yl)methyl)piperazin-2-one hydrochloride. N,N-Di-tert-butoxycarbonyl-5-(bromomethyl)-[1,2,4]triazolo[1,5-a]pyridin-2-amine (1 g, 2.340 mmol), piperazin-2-one (0.293 g, 2.93 mmol), potassium carbonate (0.970 g, 7.02 mmol), and acetonitrile (10 mL) were heated in the microwave (120° C., 10 min). The reaction was concentrated and then purified on silica gel column (0-100% ethyl acetate in hexanes). Product fractions were concentrated and then treated with 4N hydrogen chloride in dioxane (5 mL) for 1 h. The reaction was concentrated and then triturated with ethyl acetate to give a white solid, (0.8 g, 91% yield). MS (ESI) m/z 247.3 [M+1]$^+$.

D. 1-(3-Methyl-1H-indazol-6-yl)-4-((2-(3-methyl-1H-indazol-6-ylamino)-[1,2,4]triazolo[1,5-a]pyridin-5-yl)methyl)piperazin-2-one. 6-Bromo-3-methyl-1-(tetrahydro-2H-pyran-2-yl)-1H-indazole (0.240 g, 0.812 mmol), 4-((2-amino-[1,2,4]triazolo[1,5-c]pyridin-5-yl)methyl)piperazin-2-one (0.2 g, 0.812 mmol), sodium tert-butoxide (0.234 g, 2.4 mmol), 4,5-bis(diphenylphosphino)-9,9-dimethylxanthene (0.047 g, 0.081 mmol), tris(dibezylideneacetone)palladium (0) (0.037 g, 0.041 mmol), and dioxane (8 mL) were heated to 100° C. under nitrogen for 16 h. The reaction was filtered and then treated with 4N hydrogen chloride (5 mL) for 2 h. The reaction was concentrated and purified on reverse phase HPLC (10-70% acetonitrile+0.1% trifluoroacetic acid in water+0.1% trifluoroacetic acid). Product fractions were past through Strata-XC ion-exchange column and then released with 2M ammonia in methanol to give a white solid, (5 mg, 1.2% yield). $^1$H NMR (400 MHz, DMSO-d$_6$) δ (ppm) 12.68 (s, 1H), 12.33 (s, 1H), 9.84 (s, 1H), 8.15 (d, J=1.6 Hz, 1H), 7.69 (d, J=8.2 Hz, 1H), 7.50-7.66 (m, 3H), 7.40 (d, J=1.2 Hz, 1H), 7.17-7.26 (m, 2H), 7.04 (dd, J=2.0, 8.6 Hz, 1H), 4.21 (s, 2H), 3.79 (t, J=5.5 Hz, 2H), 3.49 (s, 2H), 3.06 (t, J=5.5 Hz, 2H), 2.48 (s, 3H), 2.42 (s, 3H). MS (ESI) m/z 507.4 [M+1]$^+$.

Example 112

(2-(3-Methyl-1H-indazol-6-ylamino)[1,2,4]triazolo [1,5-a]pyridin-5-yl(tetrahydro-2H-pyran-4-ylmethanol and N-(3-methyl-1H-indazol-6-yl-5-((tetrahydro-2H-pyran-4-yl)methyl)-[1,2,4]triazolo[1,5-a]pyridin-2-amine

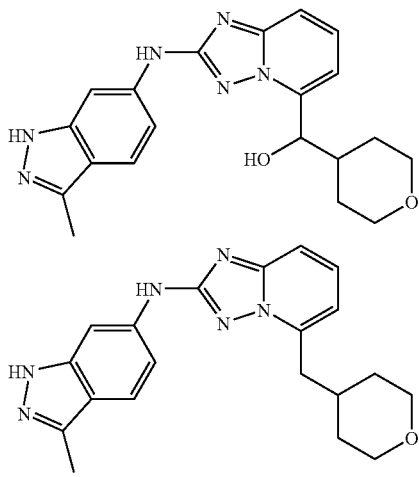

A. N-(3-methyl-1-tosyl-1H-indazol-6-yl)[1,2,4]triazolo [1,5-a]pyridin-2-amine. [1,2,4]Triazolo[1,5-c]pyridin-2-amine was synthesized following the same procedure used for 5-bromo-[1,2,4]triazolo[1,5-c]pyridin-2-amine, using pyridin-2-amine as starting material. A mixture of tris(dibenzylideneacetone)dipalladium(0) (0.341 g, 0.373 mmol) and 4,5-bis(diphenylphosphino)-9,9-dimethylxanthene (0.431 g, 0.745 mmol) in 1,4-dioxane (6 mL) was heated briefly with a heat gun until most of the solids had dissolved and then added to 6-bromo-3-methyl-1-tosyl-1H-indazole (1.361 g, 3.73 mmol), [1,2,4]triazolo[1,5-a]pyridin-2-amine (0.500 g, 3.73 mmol), finely ground cesium carbonate (4.98 g, 15.28 mmol), and 1,4-dioxane (6 mL) in a sealable vessel with a stirbar. Nitrogen was blown in to blow out air. The resulting mixture was sealed, stirred vigorously, and heated at 120° C. for 2 h. After cooling to room temperature the resulting mixture was diluted with water and ethyl acetate and filtered through a fritted funnel. The filter cake was washed thoroughly with hot 5% methanol in ethyl acetate to wash all of the desired product through. The layers of the filtrate were separated and the organics were washed once with brine, dried over magnesium sulfate, filtered, and concentrated on a rotary evaporator. The residue was triturated with diethyl ether. Solids were collected by vacuum filtration, washed with diethyl ether, and dried under high vacuum at 40° C. to give the desired product (1.49 g, 3.56 mmol, 96% yield) as a yellow solid. $^1$H NMR (400 MHz, DMSO-d$_6$) δ (ppm) 10.14 (s, 1H), 8.84 (d, J=6.64 Hz, 1H), 8.65 (s, 1H), 7.79 (d, J=8.59 Hz, 2H), 7.57-7.70 (m, 4H), 7.38 (d, J=8.20 Hz, 2H), 7.09 (td, J=1.95, 6.64 Hz, 1H), 2.42 (s, 3H), 2.31 (s, 3H); MS (ESI) m/z 419.3 [M+1]$^+$.

B. (2-(3-Methyl-1-tosyl-1H-indazol-6-ylamino)-[1,2,4] triazolo[1,5-a]pyridin-5-yl)(tetrahydro-2H-pyran-4-yl) methanol. Tetrahydro-2H-pyran-4-carbaldehyde was stored in THF over 3 A molecular sieves overnight at 0° C. N-(3-methyl-1-tosyl-1H-indazol-6-yl)-[1,2,4]triazolo[1,5-a]pyridin-2-amine was dried under high vacuum at 40° C. overnight in a reaction flask with stirbar. A stirred mixture of N-(3-methyl-1-tosyl-1H-indazol-6-yl)-[1,2,4]triazolo[1,5-c]pyridin-2-amine (0.681 g, 1.627 mmol) in tetrahydrofuran (25 mL) was heated briefly with a heat gun under nitrogen until all solids dissolved. The resulting yellow solution was cooled with a dry ice acetone bath under nitrogen. n-Butyllithium (2.187 mL, 3.50 mmol, 1.6 M in hexanes) was added dropwise slowly via syringe. After 45 min tetrahydro-2H-pyran-4-carbaldehyde (4.07 mL, 4.07 mmol, 1 M in tetrahydrofuran) was added. The cold bath was removed and the resulting mixture was warmed to 0° C. over 15 min. Water (5 mL) was added and the resulting mixture was stirred vigorously at room temperature for 15 min. The resulting mixture was diluted with water and ethyl acetate and shaken in a separatory funnel. The layers were separated and the organics were washed with water and then brine and then dried over magnesium sulfate, filtered, and concentrated on a rotary evaporator nearly to dryness. The residue was purified using flash chromatography (Biotage) (20-100% ethyl acetate in hexane) to give the desired product (0.525 g, 0.986 mmol, 61% yield) as a yellow solid. $^1$H NMR (400 MHz, DMSO-d$_6$) δ (ppm) 10.25 (s, 1H), 8.97 (s, 1H), 7.78 (d, J=8.20 Hz, 2H), 7.60-7.71 (m, 2H), 7.54 (d, J=8.59 Hz, 1H), 7.42 (dd, J=1.56, 8.98 Hz, 1H), 7.37 (d, 8.20 Hz, 2H), 7.12 (d, J=7.03 Hz, 1H), 5.86 (d, J=5.08 Hz, 1H), 5.39 (t, J=4.88 Hz, 1H), 3.73-3.85 (m, 2H), 3.09-3.27 (m, 2H), 2.41 (s, 3H), 2.31 (s, 3H), 2.18-2.28 (m, 1H), 1.74 (qd, J=4.10, 12.43 Hz, 1H), 1.50-1.62 (m, 1H), 1.47 (d, J=12.49 Hz, 1H), 1.34 (d, 1H); MS (ESI) m/z 533.4 [M+H]$^+$.

C. (2-(3-Methyl-1-tosyl-1H-indazol-6-ylamino)-[1,2,4] triazolo[1,5-a]pyridin-5-yl)(tetrahydro-2H-pyran-4-yl)methyl acetate and N-(3-methyl-1-tosyl-1H-indazol-6-yl-5-((tetrahydro-2H-pyran-4-yl)methyl)-[1,2,4]triazolo[1,5-a] pyridin-2-amine. Thionyl chloride (0.231 mL, 3.18 mmol) was added to a stirred mixture of (2-(3-methyl-1-tosyl-1H-indazol-6-ylamino)-[1,2,4]triazolo[1,5-a]pyridin-5-yl)(tetrahydro-2H-pyran-4-yl)methanol (0.423 g, 0.794 mmol) and N,N-diisopropylethylamine (1.176 mL, 6.75 mmol) in chloroform (20 mL). The resulting dark-colored mixture was stirred at room temperature under nitrogen for 3 h and then the solvent was removed on a rotary evaporator. Acetic acid (10 mL) was added followed by zinc dust (<10 micron) (1.038 g, 15.88 mmol). The resulting mixture was stirred and heated at 100° C. under a reflux condenser under nitrogen for 18 h. The resulting mixture was filtered through Celite and the filter cake washed thoroughly with methanol. The filtrate was purified using reverse-phase preparatory HPLC (20-100% acetonitrile+0.1% trifluoroacetic acid in water+0.1% trifluoroacetic acid, over 30 min). Fractions containing the desired product were combined, neutralized with saturated aqueous sodium bicarbonate, and the acetonitrile was removed on a rotary evaporator. The residue was extracted three times with ethyl acetate. The organic extracts were washed with brine, concentrated on a rotary evaporator, and dried under high vacuum to give a 24:76 mixture of (2-(3-methyl-1-tosyl-1H-indazol-6-ylamino)-[1,2,4]triazolo[1,5-c]pyridin-5-yl)(tetrahydro-2H-pyran-4-yl)methyl acetate to N-(3-methyl-1-tosyl-1H-indazol-6-yl)-5-((tetrahydro-2H-pyran-4-yl)methyl)-[1,2,4]triazolo[1,5-c]pyridin-2-amine (0.176 g) as a tan solid. This material was carried on to the next step without further purification.

D. (2-(3-Methyl-1H-indazol-6-ylamino)[1,2,4]triazolo[1,5-a]pyridin-5-yl)(tetrahydro-2H-pyran-4-ylmethanol and N-(3-methyl-1H-indazol-6-yl)-5-((tetrahydro-2H-pyran-4-yl)methyl)-[1,2,4]triazolo[1,5-a]pyridin-2-amine. A mixture of (2-(3-methyl-1-tosyl-1H-indazol-6-ylamino)-[1,2,4]triazolo[1,5-a]pyridin-5-yl)(tetrahydro-2H-pyran-4-yl)methyl acetate and N-(3-methyl-1-tosyl-1H-indazol-6-yl)-5-((tetrahydro-2H-pyran-4-yl)methyl)-[1,2,4]triazolo[1,5-c]pyridin-2-amine (0.175 g, 0.339 mmol) was dissolved in 1-methyl-2-pyrrolidinone (2 mL) with stirring at room temperature and then diluted with methanol (4 mL). Sodium hydride (0.041 g, 1.694 mmol) was added under nitrogen and the resulting mixture was stirred and heated at 70° C. under a reflux condenser under nitrogen for 17 h. The resulting mixture was cooled to room temperature and trifluoroacetic acid (0.209 mL, 2.71 mmol) was added. The resulting mixture was filtered and purified using reverse-phase semi-preparatory HPLC (5-60% acetonitrile+0.1% trifluoroacetic acid in water+0.1% trifluoroacetic acid, over 30 min). Fractions containing the desired products were loaded onto separate Strata X—C ion exchange columns from Phenomenex. The columns were washed successively with water, acetonitrile, methanol, and then 10% ammonium hydroxide in 70% methanol in dichloromethane. The product came off with the 10% ammonium hydroxide in 70% methanol in dichloromethane eluent and was concentrated on a rotary evaporator and dried under high vacuum at 40° C. to give the desired product (2-(3-methyl-1H-indazol-6-ylamino)-[1,2,4]triazolo[1,5-c]pyridin-5-yl)(tetrahydro-2H-pyran-4-yl)methanol (0.016 g, 0.042 mmol, 12% yield) as an off-white solid. $^1$H NMR (400 MHz, DMSO-$d_6$) δ (ppm) 12.36 (s, 1H), 9.82 (s, 1H), 8.12 (d, J=1.17 Hz, 1H), 7.62 (dd, J=7.42, 8.59 Hz, 1H), 7.47-7.57 (m, 2H), 7.21 (dd, J=1.76, 8.79 Hz, 1H), 7.07 (d, J=7.03 Hz, 1H), 5.83 (d, J=4.69 Hz, 1H), 5.22 (t, J=4.69 Hz, 1H), 3.77-3.92 (m, 2H), 3.24 (t, J=10.93 Hz, 1H), 3.09-3.20 (m, 1H), 2.42 (s, 3H), 2.16-2.29 (m, J=3.86, 3.86, 7.91, 11.71 Hz, 1H), 1.72 (qd, J=4.49, 12.56 Hz, 1H), 1.53 (qd, J=4.69, 12.49 Hz, 1H), 1.43 (d, J=11.71 Hz, 1H), 1.30 (d, 1H); MS (ESI) m/z 379.2 [M+1]$^+$ and N-(3-methyl-1H-indazol-6-yl)-5-((tetrahydro-2H-pyran-4-yl)methyl)-[1,2,4]triazolo[1,5-c]pyridin-2-amine (0.051 g, 0.141 mmol, 42% yield) as an off-white solid. $^1$H NMR (400 MHz, DMSO-$d_6$) δ (ppm) 12.34 (s, 1H), 9.80 (s, 1H), 8.14 (d, J=1.56 Hz, 1H), 7.44-7.57 (m, 3H), 7.21 (dd, J=1.56, 8.59 Hz, 1H), 6.92 (dd, J=1.37, 6.83 Hz, 1H), 3.84 (dd, J=2.54, 11.52 Hz, 2H), 3.26 (t, J=10.93 Hz, 2H), 3.07 (d, J=7.03 Hz, 2H), 2.42 (s, 3H), 2.19-2.36 (m, 1H), 1.54 (d, J=11.32 Hz, 2H), 1.29-1.45 (m, 2H); MS (ESI) m/z 363.3 [M+1]$^+$.

Example 113 cis-6-(5-(4-Hydroxycyclohexylamino)-[1,2,4]triazolo[1,5-a]pyridin-2-ylamino)-1H-pyrrolo[3,2-b]pyridin-2(3H)-one

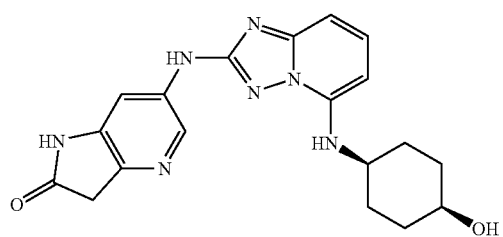

A. Diethyl cis-2-(3-amino-5-(5-(4-hydroxycyclohexylamino)-[1,2,4]triazolo[1,5-a]pyridin-2-ylamino)pyridin-2-yl)malonate. A mixture of cis-4-(2-amino-[1,2,4]triazolo[1,5-c]pyridin-5-ylamino)cyclohexanol (600 mg, 2.43 mmol), diethyl 2-(5-bromo-3-nitropyridin-2-yl)malonate (835 mg, 2.31 mmol), tris(dibenzylideneacetone)dipalladium (423 mg, 0.46 mmol), cesium carbonate (1.5 g, 4.62 mmol), and 4,5-bis(diphenylphosphino)-9,9-dimethylxanthene (267 mg, 0.46 mmol) in dioxane (10 mL) was degassed under nitrogen, the mixture was refluxed overnight. The mixture was poured into water (30 mL), and extracted with ethyl acetate. The organic layer was dried, concentrated, and purified on silica gel column (eluting with 0.5-1.5% dichloromethane in methanol) to give diethyl cis-2-(3-amino-5-(5-(4-hydroxycyclohexylamino)-[1,2,4]triazolo[1,5-c]pyridin-2-ylamino)pyridin-2-yl)malonate (120.0 mg, 10% yield).

B. Methyl cis-2-(3-amino-5-(5-(4-hydroxycyclohexylamino)-[1,2,4]triazolo[1,5-a]pyridin-2-ylamino)pyridin-2-yl)acetate. To a mixture of diethyl cis-2-(3-amino-5-(5-(4-hydroxycyclohexylamino)-[1,2,4]triazolo[1,5-c]pyridin-2-ylamino)pyridin-2-yl)malonate (120.0 mg, 0.23 mmol) in a mixture of dichloromethane (10 mL) and methanol (50 mL) was added Raney nickel (100 mg), and the mixture was stirred under hydrogen at room temperature for 24 hours. LCMS analysis showed that the major product was the desired product (if the reaction was not completed, just kept the hydrogenation until the reaction was completed). The mixture was filtered, concentrated under reduced pressure, and purified on silica gel column (eluting with 1-2% dichloromethane in methanol) to give methyl cis-2-(3-amino-5-(5-(4-hydroxycyclohexylamino)-[1,2,4]triazolo[1,5-c]pyridin-2-ylamino)pyridin-2-yl)acetate.

C. cis-6-(5-(4-Hydroxycyclohexylamino)-[1,2,4]triazolo[1,5-a]pyridin-2-ylamino)-1H-pyrrolo[3,2-b]pyridin-2(3H)-one. To a mixture of methyl cis-2-(3-amino-5-(5-(4-hydroxycyclohexylamino)-[1,2,4]triazolo[1,5-c]pyridin-2-ylamino)pyridin-2-yl)acetate (130 mg, 0.32 mmol) in ethyl acetate (10 mL) was added concentrated hydrochloride acid solution (0.5 mL), and the mixture was refluxed for 1 hour. The mixture was neutralized with saturated aqueous sodium carbonate solution to pH=9, and extracted with ethyl acetate. The combined organic layer was washed with water and saturated aqueous sodium chloride solution, dried, concentrated under reduced pressure, and purified on silica gel column (eluting with 2-5% dichloromethane in methanol) to give cis-6-(5-(4-hydroxycyclohexylamino)-[1,2,4]triazolo[1,5-a]pyridin-2- ylamino)-1H-pyrrolo[3,2-b]pyridine-2(3H)-one (15 mg, 17.9%). ¹H NMR (300 MHz, DMSO-d₆) δ (ppm) 10.48 (s, 1H), 9.69 (s, 1H), 8.40 (s, 1H), 7.73 (s, 1H), 7.44 (t, J=7.8 Hz, 1H), 6.76 (d, J=8.7 Hz, 1H), 6.23 (d, J=8.1 Hz, 1H), 5.96 (d, J=7.8 Hz, 1H), 4.52 (s, 1H), 3.78 (s, 2H), 1.84-1.65 (m, 8H); MS (ESI): m/z 380.3 [M+1]⁺.

Example 114

4-((2-(3-(Trifluoromethyl)-1H-indazol-6-ylamino)-[1,2,4]triazolo[1,5-a]pyridin-5-yl)methyl)piperazin-2-one

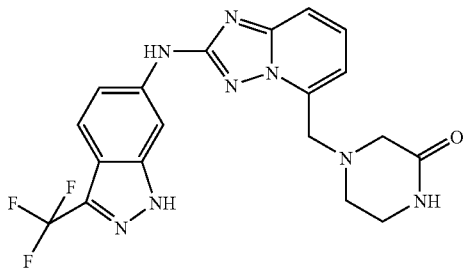

A. Methyl 2-bromo-[1,2,4]triazolo[1,5-a]pyridine-5-carboxylate. To a solution of 2-amino-[1,2,4]triazolo[1,5-a]pyridine-5-carboxylic acid methyl ester (4.0 g, 21 mmol) in a mixture of hydrobromic acid (40% in water) and acetic acid (v/v, 2:1, 150 mL) was added sodium nitrite (8.7 g, 126 mmol) at room temperature, and the mixture was stirred at room temperature overnight. When the starting material was consumed, the reaction mixture was basified with sodium bicarbonate to pH>9. The solid was washed by water, and dried to give methyl 2-bromo-[1,2,4]triazolo[1,5-a]pyridine-5-carboxylate (4.2 g, 78% yield) as a solid. ¹H NMR (400 MHz, CHLOROFORM-d) δ (ppm) 7.88 (m, 1H), 7.75 (m, 1H), 7.61 (m, 1H), 4.06 (s, 3H); MS (ESI): m/z 255.8 [M+1]⁺.

B. 2-Bromo-[1,2,4]triazolo[1,5-a]pyridine-5-carboxylic acid. A mixture of methyl 2-bromo-[1,2,4]triazolo[1,5-a]pyridine-5-carboxylate (3.38 g, 13.2 mmol) and lithium hydroxide (3.17 g, 132 mmol) in a mixture of tetrahydrofurane and water (v/v, 1:1, 70 mL) was heated at 80° C. overnight. When the starting material was consumed, the organic layer was separated. The aqueous layer was neutralized with hydrochloric acid to pH=6, and extracted with ethyl acetate. The combined organic layer was dried over sodium sulfate, and evaporated in vacuo to give 2-bromo-[1,2,4]triazolo[1,5-a]pyridine-5-carboxylic acid (2.9 g, 91% yield) as a solid. ¹H NMR (400 MHz, DMSO-d₆) δ (ppm) 8.06 (m, 1H), 7.81 (m, 2H); MS (ESI): m/z 241.9 [M+H]⁺.

C. (2-Bromo-[1,2,4]triazolo[1,5-a]pyridin-5-yl)-methanol. A solution of 2-bromo-[1,2,4]triazolo[1,5-c]pyridine-5-carboxylic acid (2.9 g, 12.2 mmol) in tetrahydrofurane (40 mL) was added dropwise a solution of borane dimethyl sulfide complex (9.27 g, 122 mmol) in tetrahydrofuran (10 mL) at room temperature. When TLC indicated the starting material was consumed, methanol was added to quench the reaction, and the mixture was concentrated in vacuo to give the crude product (2-bromo-[1,2,4]triazolo[1,5-a]pyridin-5-yl)-methanol (2.6 g, 94% yield). MS (ESI): m/z 229.9 [M+1]⁺.

D. 2-Bromo-5-(bromomethyl)[1,2,4]triazolo[1,5-a]pyridine. To a solution of (2-bromo-[1,2,4]triazolo[1,5-a]pyridin-5-yl)-methanol (2.6 g, 11.45 mmol) in dioxane (20 mL) was added phosphorus tribromide (1.6 mL, 17.18 mmol) at 0° C., and the reaction mixture was stirred at 40° C. overnight. When the starting material was consumed, the reaction was quenched by the addition of saturated sodium bicarbonate aqueous solution, and extracted with ethyl acetate. The combined organic layer was dried over anhydrous sodium sulfate, evaporated under reduced pressure, and purified on silica gel column (eluting with 10-11% ethyl acetate in petroleum ether) to give 2-bromo-5-(bromomethyl)-[1,2,4]triazolo[1,5-c]pyridine (2.0 g, 61% yield) as a solid. MS (ESI): m/z 291.9 [M+1]⁺.

E. 4-(2-Bromo-[1,2,4]triazolo[1,5-a]pyridin-5-ylmethyl)-piperazin-2-one. A suspension of 2-bromo-5-(bromomethyl)-[1,2,4]triazolo[1,5-c]pyridine (0.6 g, 2.1 mmol), piperazin-2-one (0.63 g, 6.3 mmol) and potassium carbonate (3.0 g, 21 mmol) in acetonitrile (20 mL) was heated at 60° C. When the starting material was consumed, the solvent was removed under reduced pressure, and the residue was treated with water. The precipitate was collected by filtration, washed with water, and dried under high vacuum to give 4-(2-bromo-[1,2,4]triazolo[1,5-c]pyridin-5-ylmethyl)-piperazin-2-one (0.49 g, 75% yield) as a solid. ¹H NMR (400 MHz, DMSO-d₆) δ (ppm) 7.84 (s, 1H), 7.76 (m, 2H), 7.30 (m, 1H), 4.08 (s, 2H), 3.22 (s, 2H), 3.16 (s, 2H), 2.74 (m, 2H); MS (ESI): m/z 309.9 [M+1]⁺.

F. 4-((2-(3-(Trifluoromethyl)-1-((2-(trimethylsilyl)ethoxy)methyl)-1H-indazol-6-ylamino)-[1,2,4]triazolo[1,5-a]pyridin-5-yl)methyl)piperazin-2-one. A degassed mixture of 4-(2-bromo-[1,2,4]triazolo[1,5-c]pyridin-5-ylmethyl)-piperazin-2-one (380 mg, 1.23 mmol), 3-(trifluoromethyl)-1-((2-(trimethylsilyl)ethoxy)methyl)-1H-indazol-6-amine (410 mg, 1.23 mmol), tris(dibenzylideneacetone)palladium (0) (110 mg, 0.123 mmol), 4,5-bis(diphenylphosphino)-9,9-dimethylxanthene (140 mg, 0.246 mmol), and cesium carbonate (920 mg, 2.46 mmol) in dioxane (20 mL) was heated at 100° C. under nitrogen overnight. The reaction mixture was concentrated in vacuo, and purified on silica gel column (eluting with 0.5-2% methanol in dichloromethane) to give 4-((2-(3-(trifluoromethyl)-1-((2-(trimethylsilyl)ethoxy)methyl)-1H-indazol-6-ylamino)-[1,2,4]triazolo[1,5-c]pyridin-5-yl)methyl)piperazin-2-one (510 mg, 74% yield). ¹H NMR (400 MHz, CHLOROFORM-d) δ (ppm) 8.32 (s, 1H), 8.12 (br s, 1H), 7.72 (m, 1H), 7.50 (m, 2H), 7.26 (m, 1H), 7.04 (d, J=8.0 Hz, 1H), 6.46 (br s, 1H), 5.78 (s, 2H), 4.19 (s, 2H), 3.59 (m, 2H), 3.46 (m, 2H), 3.43 (s, 2H), 2.95 (m, 2H), 0.89 (m, 2H), −0.09 (s, 9H).

G. 4-((2-(3-(Trifluoromethyl)-1H-indazol-6-ylamino)-[1,2,4]triazolo[1,5-a]pyridin-5-yl)methyl)piperazin-2-one. A mixture of 4-((2-(3-(trifluoromethyl)-1-((2-(trimethylsilyl)ethoxy)methyl)-1H-indazol-6-ylamino)-[1,2,4]triazolo[1,5-c]pyridin-5-yl)methyl)piperazin-2-one (250 mg, 0.446 mmol) in a mixture of dichloromethane and trifluoroacetic acid (v/v, 3:1, 15 mL) was stirred at room temperature for 2 h. When the starting material was consumed, the solvent was removed, and the residue was dissolved in a mixture of methanol (20 mL) and aqueous ammonium hydroxide. When the material was consumed, the solvent was removed, and the residue was washed with water and methanol to give 4-((2-(3-(trifluoromethyl)-1H-indazol-6-ylamino)-[1,2,4]triazolo[1,5-c]pyridin-5-yl)methyl)piperazin-2-one as a hydrochloride salt (100 mg, 52% yield). ¹H NMR (400 MHz, METHANOL-d₄) δ (ppm) 8.40 (s, 1H), 7.67 (m, 2H), 7.51 (d, J=8.8 Hz, 1H), 7.33 (d, J=9.6 Hz, 1H), 7.17 (m, 1H), 4.26 (s, 2H), 3.45 (s, 2H), 3.41 (m, 2H), 2.96 (m, 2H); MS (ESI): m/z 431.3 [M+1]+.

Example 115

3,3-Dimethyl-6-(5-(piperidin-4-ylmethyl)[1,2,4]triazolo[1,5-a]pyridin-2-ylamino)indolin-2-one

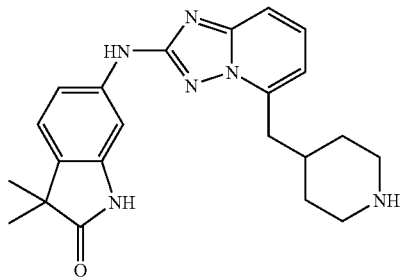

A. 6-(5-Bromo-[1,2,4]triazolo[1,5-a]pyridin-2-ylamino)-3,3-dimethyl-1-((2-(trimethylsilyl)ethoxy)methyl)indolin-2-one. A degassed mixture of 5-bromo-[1,2,4]triazolo[1,5-c]pyridin-2-amine (1.0 g, 4.72 mmol), 6-iodo-3,3-dimethyl-1-((2-(trimethylsilyl)ethoxy)methyl)indolin-2-one (2.15 g, 5.19 mmol), 4,5-bis(diphenylphosphino)-9,9-dimethylxanthene (546 mg, 0.95 mmol), tris(dibenzylideneacetone)palladium (0) (430 mg, 0.47 mmol), and cesium carbonate (4.6 g, 14.2 mmol) in dioxane (30 mL) was heated at 80° C. under nitrogen for 2 h. The reaction mixture was poured into water (20 mL), extracted with ethyl acetate (15 mL×3), dried over anhydrous sodium sulfate, evaporated under reduced pressure, and purified by silica gel column (eluting with 10-16% ethyl acetate in petrol ether) to afford 6-(5-bromo-[1,2,4]triazolo[1,5-c]pyridin-2-ylamino)-3,3-dimethyl-1-((2-(trimethylsilyl)ethoxy)methyl)indolin-2-one (600 mg, 26%). 1H NMR (400 MHz, DMSO-d6) δ (ppm) 9.87 (s, 1H), 7.63 (m, 2H), 7.53 (d, J=7.2 Hz, 1H), 7.42 (m, 2H), 7.29 (d, J=8.0 Hz, 1H), 5.10 (s, 2H), 3.56 (t, J=8.0 Hz, 2H), 1.31 (s, 6H), 0.89 (t, J=8.0 Hz, 2H), −0.06 (s, 9H); MS (ESI): m/z 504.1 [M+H]+.

B. tert-Butyl 4-((2-(3,3-dimethyl-2-oxo-1-((2-(trimethylsilyl)ethoxy)methyl)indolin-6-ylamino)-[1,2,4]triazolo[1,5-a]pyridin-5-yl)methyl)piperidine-1-carboxylate. To a solution of tert-butyl 4-methylenepiperidine-1-carboxylate (480 mg 2.4 mmol) in tetrahydrofuran (10 mL) was added 9-borabicyclo[3.3.1]nonane (6 mL, 0.5 M in tetrahydrofuran) at room temperature under nitrogen, and the resulting mixture was heated at 75° C. for 3 h. A mixture of 6-(5-bromo-[1,2,4]triazolo[1,5-c]pyridin-2-ylamino)-3,3-dimethyl-1-((2-(trimethylsilyl)ethoxy)methyl)indolin-2-one (600 mg, 1.2 mmol), [1,1'-bis(diphenylphosphino)ferrocene]dichloropalladium(II) (90 mg, 0.12 mmol), and potassium carbonate (498 mg, 3.6 mmol) in a mixture of N,N-dimethylformamide (10 mL) and water (1 mL) was stirred at 60° C. for 4 h. After cooling down to room temperature, the reaction mixture was diluted with water (50 mL), and the mixture was extracted with ethyl acetate (50 mL×3). The combined organic layer was dried over anhydrous sodium sulfate, and concentrated under reduced pressure to give crude product, which was purified by a reverse-phase preparatory HPLC (70-100% acetonitrile+0.75% trifluoroacetic acid in water, over 15 min) to give tert-butyl 4-((2-(3,3-dimethyl-2-oxo-1-((2-(trimethylsilyl)ethoxy)methyl)indolin-6-ylamino)-[1,2,4]triazolo[1,5-a]pyridin-5-yl)methyl)piperidine-1-carboxylate (250 mg, 34% yield). MS (ESI): m/z 621.2 [M+1]+.

C. 3,3-Dimethyl-6-(5-(piperidin-4-ylmethyl)-[1,2,4]triazolo[1,5-a]pyridin-2-ylamino)indolin-2-one. To a solution of tert-butyl 4-((2-(3,3-dimethyl-2-oxo-1-((2-(trimethylsilyl)ethoxy)methyl)indolin-6-ylamino)-[1,2,4]triazolo[1,5-a]pyridin-5-yl)methyl)piperidine-1-carboxylate (250 mg, 0.4 mmol) in dichloromethane (15 mL) was added trifluoroacetic acid (5 mL), and the mixture was stirred at room temperature for 1 h. The reaction mixture was concentrated under reduced pressure, and the residue was dissolved in a mixture of methanol (5 mL) and ammonia hydrate solution (2 mL). The mixture was stirred at room temperature for about 18 h, concentrated under reduced pressure, and purified by a reverse-phase preparatory HPLC (37-57% acetonitrile+0.75% trifluoroacetic acid in water, over 15 min) to give 3,3-dimethyl-6-(5-(piperidin-4-ylmethyl)-[1,2,4]triazolo[1,5-a]pyridin-2-ylamino)indolin-2-one as a trifluoroacetic acid salt, which was converted to the hydrochloride salt (85 mg, 57% yield). 1H NMR (400 MHz, METHANOL-d4) δ (ppm) 7.77 (t, J=7.6 Hz, 1H), 7.52 (d, J=8.8 Hz, 1H), 7.30 (s, 1H), 7.17 (m, 3H), 3.32 (d, J=8.8 Hz, 2H), 3.18 (d, J=7.2 Hz, 2H), 2.90 (t, J=8.0 Hz, 2H), 2.33 (s, 1H), 1.89 (d, J=8.8 Hz, 2H), 1.57 (m, 2H), 1.28 (s, 6H); MS (ESI): m/z 391.3 [M+1]+.

Example 116

1-Methyl-N3-(piperidin-4-yl)-N6-(5-((tetrahydro-2H-pyran-4-yl)methyl)-[1,2,4]triazolo[1,5-a]pyridin-2-yl)-1H-indazole-3,6-diamine

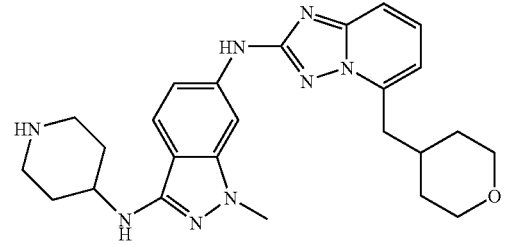

A. tert-Butyl 6-((tetrahydro-2H-pyran-4-yl)methyl)pyridin-2-ylcarbamate. Under nitrogen, to a solution of 4-methylenetetrahydro-2H-pyran (3.42 g, 34.9 mmol) in tetrahydrofuran (10 mL) was added 9-borabicyclo[3.3.1]nonane (70 mL, 34.9 mmol), and the mixture was stirred at 75° C. for 2 h. To the mixture was added tert-butyl 6-bromopyridin-2-ylcarbamate (6.5 g, 23.9 mmol), potassium carbonate (7.29 g, 52.4 mmol), 1,1'-bis(diphenylphosphino)ferrocene palladium dichloride (2.55 g, 3.49 mmol), N,N-dimethylformamide (80 mL), and water (20 mL). The resulting mixture was stirred at 60° C. for 3 h, cooled to room temperature, filtered, concentrated under reduced pressure, and purified by column chromatography on silica gel (eluting with 10-20% ethyl acetate in petroleum ether) to give tert-butyl 6-((tetrahydro-2H-pyran-4-yl)methyl)pyridin-2-ylcarbamate (6.0 g, 86% yield). 1H NMR (400 MHz, CHLOROFORM-d) δ (ppm) 7.75 (d, J=8.4 Hz, 1H), 7.31 (t, J=8.4 Hz, 1H), 7.35 (br s, 1H), 6.77 (d, J=7.2 Hz, 1H), 3.95 (dd, J1=4.0 Hz, J2=11.6 Hz, 2H), 3.37 (t, J=11.2 Hz, 2H), 2.58 (d, J=7.2 Hz, 2H), 1.93 (m, 1H), 1.85 (m, 2H), 1.51 (s, 9H), 1.37 (m, 2H).

B. 6-((Tetrahydro-2H-pyran-4-yl)methyl)pyridin-2-amine. A solution of tert-butyl 6-((tetrahydro-2H-pyran-4-yl)methyl)pyridin-2-ylcarbamate (6.0 g, 20.5 mmol) in methanolic hydrochloride solution (80 mL, 2 M) was stirred at 50° C. for 2 h. When the starting material was consumed, the reaction mixture was concentrated in vacuo to give the desired product as a hydrochloride salt. The residue was dissolved in ethyl acetate, and the mixture was washed with saturated sodium dicarbonate solution and dried over sodium sulfate. The solvent was removed to give 6-((tetrahydro-2H-pyran-4-yl)methyl)pyridin-2-amine (3.6 g, 91.5% yield). $^{1}$H NMR (300 MHz, CHLOROFORM-d) δ (ppm) 7.34 (t, J=7.2 Hz, 1H), 6.46 (d, J=7.5 Hz, 1H), 6.33 (d, J=7.1 Hz, 1H), 4.45 (br s, 2H), 3.95 (dd, $J_1$=4.0 Hz, $J_2$=11.6 Hz, 2H), 3.38 (t, J=11.2 Hz, 2H), 2.52 (d, J=7.2 Hz, 1H), 1.93 (m, 1H), 1.85 (m, 2H), 1.37 (m, 2H).

C. 5-((Tetrahydro-2H-pyran-4-yl)methyl)-[1,2,4]triazolo[1,5-a]pyridin-2-amine. A mixture of 6-((tetrahydro-2H-pyran-4-yl)methyl)pyridin-2-amine (3.6 g, 18.8 mmol) and O-ethyl carbonisothiocyanatidate (2.5 g, 18.8 mmol) in dioxane (40 mL) was stirred at room temperature. When the starting material was consumed, the mixture was concentrated in vacuo. The residue was dissolved in a mixture of methanol (25 mL) and ethanol (25 mL), hydroxylamine hydrochloride (6.5 g, 93.8 mmol) and N,N-diethylisopropylamine (7.26 g, 56.3 mmol) were added, and the mixture was stirred at room temperature for 2 h and 75° C. for 3 h. The mixture was concentrated in vacuo, and purified by column chromatography on silica gel (eluting with 20-50% ethyl acetate in petroleum ether) to give 5-((tetrahydro-2H-pyran-4-yl)methyl)-[1,2,4]triazolo[1,5-c]pyridin-2-amine (3.6 g, 82% yield) as a white solid. $^{1}$H NMR (400 MHz, DMSO-$d_6$) δ (ppm) 7.36 (t, J=8.4 Hz, 1H), 7.22 (d, J=8.4 Hz, 1H), 6.72 (d, J=6.8 Hz, 1H), 6.00 (br s, 2H), 3.81 (d, J=9.2 Hz, 2H), 3.22 (t, J=10.8 Hz, 2H), 2.90 (d, J=7.2 Hz, 2H), 2.19 (m, 1H), 1.44 (m, 2H), 1.32 (m, 2H).

D. tert-Butyl 4-(1-methyl-6-(5-((tetrahydro-2H-pyran-4-yl)methyl)-[1,2,4]triazolo[1,5-a]pyridin-2-ylamino)-1H-indazol-3-ylamino)piperidine-1-carboxylate. A degassed solution of tert-butyl 4-(6-bromo-1-methyl-1H-indazol-3-ylamino)piperidine-1-carboxylate (723 mg, 1.77 mmol), tris(dibenzylidene acetone)dipalladium (0) (147 mg, 0.16 mmol), 4,5-bis(diphenylphosphino)-9,9-dimethyl xanthene (185 mg, 0.32 mmol), 5-((tetrahydro-2H-pyran-4-yl)methyl)-[1,2,4]triazolo[1,5-c]pyridin-2-amine (374 mg, 1.61 mmol), and cesium carbonate (1.05 g, 3.22 mmol) in dioxane (40 mL) was heated at 100° C. under nitrogen for 3 h. After cooling to room temperature, the reaction mixture was concentrated, and the residue was dissolved in 20 mL of a mixture of dichloromethane and methanol (v/v, 1:1). The reaction mixture was filtered, concentrated, and purified on silica gel column (eluting with 10-100% ethyl acetate in petroleum ether) and a reverse-phase preparatory HPLC (33-63%: acetonitrile+0.075% trifluoroacetic acid in water+0.075% trifluoroacetic acid, over 15 min) to give tert-butyl 4-(1-methyl-6-(5-((tetrahydro-2H-pyran-4-yl)methyl)-[1,2,4]triazolo[1,5-c]pyridin-2-ylamino)-1H-indazol-3-ylamino)piperidine-1-carboxylate (400 mg, 44% yield) as a solid. MS (ESI): m/z 561.3 [M+H]$^+$.

E. 1-Methyl-$N^3$-(piperidin-4-yl)-$N^6$-(5-((tetrahydro-2H-pyran-4-yl)methyl)-[1,2,4]triazolo[1,5-a]pyridin-2-yl)-1H-indazole-3,6-diamine. A solution of tert-butyl 441-methyl-6-(5-((tetrahydro-2H-pyran-4-yl)methyl)-[1,2,4]triazolo[1,5-c]pyridin-2-ylamino)-1H-indazol-3-ylamino)piperidine-1-carboxylate (400 mg, 0.714 mmol) in a methanolic hydrochloride solution (20 mL, 2 M) was stirred at room temperature until TLC showed the starting material was consumed. The solvent was evaporated under reduced pressure to give 1-methyl-$N^3$-(piperidin-4-yl)-$N^6$-(5-((tetrahydro-2H-pyran-4-yl)methyl)-[1,2,4]triazolo[1,5-c]pyridin-2-yl-1H-indazole-3,6-diamine as a hydrochloride salt (305 mg, 93% yield). $^{1}$H NMR (400 MHz, METHANOL-$d_4$) δ (ppm) 8.04 (m, 2H), 7.93 (m, 1H), 7.69 (d, J=8.8 Hz, 1H), 7.35 (m 2H), 3.97 (m, 2H), 3.86 (s, 3H), 3.57 (m, 2H), 3.32 (m, 4H), 2.41 (m, 3H), 2.01 (m, 2H), 1.66 (m, 2H), 1.55 (2H); MS (ESI): m/z 461.4 [M+1]$^+$.

Example 117

(S)-3,3-Dimethyl-6-(5-(piperidin-3-ylamino)-[1,2,4]triazolo[1,5-a]pyridin-2-ylamino)indolin-2-one

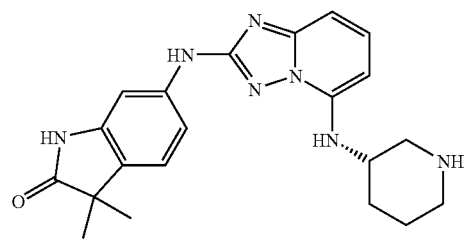

A. (S)-tert-Butyl 3-(2-bromo-[1,2,4]triazolo[1,5-a]pyridin-5-ylamino)piperidine-1-carboxylate. 2,5-Dibromo-[1,2,4]triazolo[1,5-a]pyridine (0.500 g, 1.806 mmol), potassium carbonate (0.998 g, 7.22 mmol), and (S)-tert-butyl 3-aminopiperidine-1-carboxylate (1.085 g, 5.42 mmol) were combined in a sealable vessel with a stirbar under nitrogen atmosphere. Dimethylsulfoxide (3 mL) was added and the resulting mixture was sealed, stirred vigorously, and heated at 100° C. for 14 hours. The resulting suspension was filtered and concentrated in vacuo to give a dark oil, which was purified by flash chromatography (0-50% ethyl acetate in hexanes) to afford (S)-tert-butyl 3-(2-bromo-[1,2,4]triazolo[1,5-a]pyridin-5-ylamino)piperidine-1-carboxylate (0.529 g, 1.335 mmol, 73.9% yield). MS (ESI) m/z 396.2 [M]$^+$.

B. (S)-tert-butyl 6-(5-(1-(tert-butoxycarbonyl)piperidin-3-ylamino)-[1,2,4]triazolo[1,5-a]pyridin-2-ylamino)-3,3-dimethyl-2-oxoindoline-1-carboxylate. A mixture of tris(dibenzylideneacetone)dipalladium(0) (0.244 g, 0.267 mmol) and 4,5-bis(diphenylphosphino)-9,9-dimethylxanthene (0.309 g, 0.534 mmol) in 1,4-dioxane (1.5 mL) was heated briefly with a heat gun until very hot and then added to tert-butyl 6-amino-3,3-dimethyl-2-oxoindoline-1-carboxylate (0.369 g, 1.335 mmol), (S)-tert-butyl 3-(2-bromo-[1,2,4]triazolo[1,5-a]pyridin-5-ylamino)piperidine-1-carboxylate (0.529 g, 1.335 mmol) and finely ground potassium carbonate (0.756 g, 5.47 mmol) in a sealable vessel with a stirbar. Nitrogen was blown in to blow out air. The resulting mixture was sealed, stirred vigorously, and heated at 100° C. for 5 h. After cooling to room temperature, the solid was removed by filtration and the solvent was removed under reduced pressure. The residue was purified by silica gel chromatography (0-4% ammonia saturated methanol in methylenechloride) to give (S)-tert-butyl 6-(5-(1-(tert-butoxycarbonyl)piperidin-3-ylamino)-[1,2,4]triazolo[1,5-a]pyridin-2-ylamino)-3,3-dimethyl-2-oxoindoline-1-carboxylate (0.462 g, 0.781 mmol, 58.5% yield). MS (ESI) m/z 592.7 [M+1]$^+$.

C. (S)-3,3-Dimethyl-6-(5-(piperidin-3-ylamino)-[1,2,4]triazolo[1,5-a]pyridin-2-ylamino)indolin-2-one. To a stirred mixture of (S)-tert-butyl 6-(5-(1-(tert-butoxycarbonyl)piperidin-3-ylamino)-[1,2,4]triazolo[1,5-a]pyridin-2-ylamino)-3,3-dimethyl-2-oxoindoline-1-carboxylate (0.462 g, 0.781 mmol) in ethanol (30 mL) was added hydrogen chloride (4 N in dioxane, 1.952 mL, 7.81 mmol). The resulting mixture was heated at 50° C. under nitrogen for 16 h. The resulting suspension was concentrated by half on a rotary evaporator, filtered and washed with a small amount of ethanol to afford (S)-3,3-dimethyl-6-(5-(piperidin-3-ylamino)-[1,2,4]triazolo[1,5-c]pyridin-2-ylamino)indolin-2-one dihydrochloride (0.300 g, 0.646 mmol, 83% yield) as a yellow-white solid. $^1$H NMR (400 MHz, DMSO-d$_6$) δ (ppm) 10.38 (s, 1H), 9.85 (br s, 1H), 9.18-9.36 (m, 2H), 7.51-7.61 (m, 2H), 7.31 (dd, J=2.15, 8.00 Hz, 1H), 7.17 (d, J=8.20 Hz, 1H), 6.82-6.93 (m, 2H), 6.44 (d, J=8.20 Hz, 1H), 4.10 (br s, 1H), 3.37 (d, J=11.32 Hz, 1H), 3.27 (d, J=12.89 Hz, 1H), 3.13 (q, J=9.89 Hz, 1H), 2.82 (d, J=10.15 Hz, 1H), 2.05 (br s, 1H), 1.82-1.97 (m, 2H), 1.23 (s, 6H); MS (ESI) m/z 392.6 [M+1]$^+$.

Example 118

5-(5-((2-Hydroxypyridin-4-yl)methyl)[1,2,4]triazolo[1,5-a]pyridin-2-ylamino)isoindolin-1-one

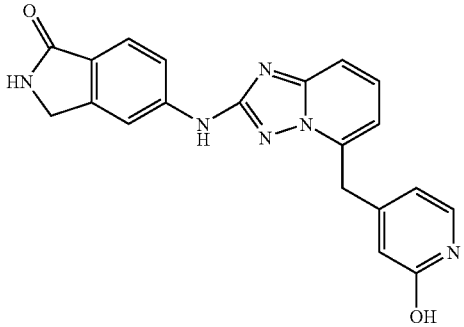

A. (2-Amino-[1,2,4]triazolo[1,5-a]pyridin-5-yl)(2-methoxypyridin-4-yl)methanone. 5-Bromo-[1,2,4]triazolo[1,5-a]pyridin-2-amine (10 g, 46.9 mmol) was suspended in anhydrous tetrahydrofuran (300 mL) and cooled to −78° C. n-Butyl lithium (64.5 mL, 103 mmol) was added over 30 minutes and the solution was allowed to stir for 1 h (brown suspension). N,2-dimethoxy-N-methylisonicotinamide (9.21 g, 46.9 mmol) dissolved in tetrahydrofuran (50 mL, dried over molecular sieves) was added dropwise via syringe (brown suspension). The reaction was stirred for 1 h and allowed to slowly warm to room temperature for 3 h (reaction became a clear solution as it warmed up to room temperature). LCMS analysis showed the desired product. The reaction was quenched by dropwise addition of water (20 mL) and then neutralized with aqueous hydrochloric acid to pH=7. Flash chromatography (30-100% ethyl acetate in hexane) gave the desired product as a light yellow solid (6.5 g, 24.14 mmol, 51.4% yield). MS (ESI) m/z 270.2 [M+1]$^+$.

B. 5-((2-Methoxypyridin-4-yl)methyl)[1,2,4]triazolo[1,5-a]pyridin-2-amine.

To a solution of (2-amino-[1,2,4]triazolo[1,5-c]pyridin-5-yl)(2-methoxypyridin-4-yl)methanone (3.5 g, 13.00 mmol) in ethylene glycol (50 mL) was added hydrazine monohydrate (3.5 mL, 112 mmol) and stirred for 5 min until a clear solution was obtained. Solid potassium hydroxide (0.729 g, 13.00 mmol) dissolved in ethylene glycol (20 mL) was added and heated at 130° C. for 16 h. Water (100 mL) was added to the reaction, and was then neutralized to pH=7 with trifluoroacetic acid. The reaction was then extracted with ethyl acetate (2×200 mL). The combined organics were dried over magnesium sulfate, filtered and concentrated on a rotary evaporator. Flash chromatography (50-100% ethyl acetate in hexane) gave the desired product as a white solid (3.2 g, 12.54 mmol, 96% yield). MS (ESI) m/z 256.3 [M+1]$^+$.

C. 2-Bromo-5-((2-methoxypyridin-4-yl)methyl)-[1,2,4]triazolo[1,5-a]pyridine. 5-((2-Methoxypyridin-4-yl)methyl)-[1,2,4]triazolo[1,5-c]pyridin-2-amine (3 g, 11.75 mmol) was suspended in cold hydrobromic acid (50 mL, 48% solution) and then cooled in an ice-bath. Sodium nitrite (1.216 g, 17.63 mmol) dissolved in cold water (20 mL) was added dropwise and allowed to stirred at 0° C. for 1 h. Copper (I) bromide (2.023 g, 14.10 mmol) dissolved in 48% hydrobromic acid (10 mL) was added and the reaction was allowed to warm up to room temperature and was stirred for 16 h. The reaction mixture was then cooled to 0° C., neutralized with sodium hydroxide (1N aq) and extracted with ethyl acetate. The aqueous layer was evaporated to dryness and the crude material was crystallized from ethyl acetate to give 2-bromo-5-((2-methoxypyridin-4-yl)methyl)-[1,2,4]triazolo[1,5-c]pyridine as a white solid (2.5 g, 7.83 mmol, 66.7% yield). MS (ESI) m/z 320.9 [M+2]$^+$.

D. 5-(5-((2-Hydroxypyridin-4-yl)methyl)-[1,2,4]triazolo[1,5-a]pyridin-2-ylamino)isoindolin-1-one. A mixture of tris(dibenzylideneacetone)dipalladium(0) (0.192 g, 0.210 mmol) and 4,5-bis(diphenylphosphino)-9,9-dimethylxanthene (0.091 g, 0.157 mmol) in 1,4-dioxane (5 mL) was added to 5-amino-2-(2,4-dimethoxybenzyl)isoindolin-1-one (0.234 g, 0.783 mmol), 2-bromo-5-((2-methoxypyridin-4-yl)methyl)-[1,2,4]triazolo[1,5-c]pyridine (0.250 g, 0.783 mmol) and potassium carbonate (0.433 g, 3.13 mmol) in a sealable vessel with a stir bar. Nitrogen was blown in to blow out air. The resulting mixture was sealed, and heated at 110° C. for 3 h. The resulting mixture was filtered and saturated aqueous sodium bicarbonate was added and was extracted with ethyl acetate (2×100 mL). The combined organics were dried over magnesium sulfate, filtered, and concentrated on a rotary evaporator to dryness and purified using reverse-phase semi-preparatory HPLC (10-70% acetonitrile+0.1% trifluoroacetic acid in water+0.1% trifluoroacetic acid, over 34 min). The solvent was removed on a rotary evaporator, saturated aqueous sodium bicarbonate was added and was extracted with ethyl acetate (2×100 mL). The combined organics were dried over magnesium sulfate, filtered, and concentrated on a rotary evaporator to dryness to give 2-(2,4-dimethoxybenzyl)-5-(5-((2-methoxypyridin-4-yl)methyl)-[1,2,4]triazolo[1,5-c]pyridin-2-ylamino)isoindolin-1-one as a white solid (0.2 g, 0.373 mmol, 47.6% yield). The white solid was dissolved in ethanol: water (100 mL) at room temperature and aqueous hydrochloric acid (5 mL, 6M) was added. This solution was stirred for 3 h. The solvent was removed on a rotary evaporator and the crude was purified using reverse-phase semi-preparatory HPLC (5-40% acetonitrile+0.1% trifluoroacetic acid in water+0.1% trifluoroacetic acid, over 39 min). Fractions containing the desired product were loaded onto a Strata X—C ion exchange column from Phenomenex. The column was washed successively with water, acetonitrile, methanol, and then hot 10% ammonium hydroxide in methanol. The product eluted with the 10% ammonium hydroxide in methanol, was concentrated on a rotary evaporator to dryness, crystallized from ethyl acetate:hexane and dried under high vacuum at 40° C. to give the desired product as a white solid (0.05 g, 0.134 mmol, 17%). $^1$H NMR (400 MHz, DMSO-d$_6$) δ (ppm) 10.36 (s, 1H), 8.23 (br s, 3H), 8.03 (d, J=8.59 Hz, 1H), 7.91 (d, J=1.95 Hz, 1H), 7.74 (dd, J=8.79, 2.15 Hz, 1H), 7.50-7.70 (m, 2H), 7.35 (d, J=6.64 Hz, 1H), 7.12 (d, J=7.03 Hz, 1H), 6.49 (s, 1H), 6.19 (dd, J=6.64, 1.56 Hz, 1H), 4.36 (s, 2H), 4.31 (d, 1H). MS (ESI) m/z 373.2 [M+1]+.

Example 119

N-(2-(methoxymethyl)-1H-benzo[d]imidazol-6-yl-5-((tetrahydro-2H-pyran-4-yl)methyl)-[1,2,4]triazolo[1,5-a]pyridin-2-amine

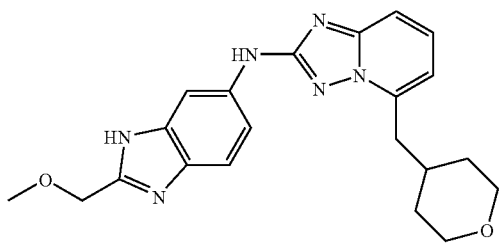

A. (2-Amino-[1,2,4]triazolo[1,5-a]pyridin-5-yl)(tetrahydro-2H-pyran-4-yl)methanone. 5-Bromo-[1,2,4]triazolo[1,5-a]pyridin-2-amine (11.07 g, 52.0 mmol) was suspended in anhydrous tetrahydrofuran (200 mL) and cooled to −78° C. n-Butyllithium (71.4 mL, 114 mmol) was added over 30 min and the solution was allowed to stir for 2 h (brown suspension) at −78° C. N-methoxy-N-methyltetrahydro-2H-pyran-4-carboxamide (9 g, 52.0 mmol) dissolved in tetrahydrofuran (50 mL, dried over molecular sieves) was added dropwise via syringe. The reaction was stirred for 1 h at −78° C. and allowed slowly warm to room temperature for 3 h (reaction became clear solution as it warmed up to room temperature.). LCMS analysis showed the desired product. The reaction was quenched with saturated sodium bicarbonate solution. The layers were separated and the aqueous was extracted with ethyl acetate (2×200 mL). The organics were dried with sodium sulfate, and the volatiles removed in vacuo. The crude was purified by crystallization from ethyl acetate to give (2-amino-[1,2,4]triazolo[1,5-a]pyridin-5-yl)(tetrahydro-2H-pyran-4-yl)methanone (8.4 g, 34.1 mmol, 65.6% yield) as a yellow solid. MS (ESI) m/z 247.0 [M+1]+.

B. 5-((Tetrahydro-2H-pyran-4-yl)methyl)[1,2,4]triazolo[1,5-a]pyridin-2-amine. To a solution of (2-amino-[1,2,4]triazolo[1,5-a]pyridin-5-yl)(tetrahydro-2H-pyran-4-yl)methanone (8 g, 32.5 mmol) in ethylene glycol (100 mL) was added hydrazine monohydrate (8.16 mL, 260 mmol) and the reaction mixture was stirred for 5 min until a clear solution was obtained. Solid potassium hydroxide (3.65 g, 65.0 mmol) dissolved in ethylene glycol (20 mL) was added and the reaction mixture was heated at 160° C. for 16 h. Water (100 mL) was added to the reaction, and it was neutralized to pH=7 with hydrochloric acid. The reaction was then extracted with ethyl acetate (2×400 mL). The combined organics were dried over magnesium sulfate, filtered, concentrated on a rotary evaporator to give the desired product (7 g, 30.1 mmol, 93% yield) as an off white solid. MS (ESI) m/z 233.2 [M+1]+. This material was used without further purification in the next step.

C. 2-Bromo-5-((tetrahydro-2H-pyran-4-yl)methyl)-[1,2,4]triazolo[1,5-a]pyridine. 5-((Tetrahydro-2H-pyran-4-yl)methyl)-[1,2,4]triazolo[1,5-a]pyridin-2-amine (7 g, 30.1 mmol) was suspended in cold hydrobromic acid (60 mL, 48% solution) and then cooled in an ice-bath. Sodium nitrite (3.12 g, 45.2 mmol) dissolved in cold water (40 mL) was added dropwise and allowed to stir at 0° C. for 1 h. Copper(I) bromide (5.19 g, 36.2 mmol) dissolved in hydrobromic acid (20 mL, 48% solution) was added dropwise and the reaction mixture was allowed to warm up to room temperature and further stirred for 1 h. The reaction was cooled to 0° C., neutralized with sodium hydroxide (6N aqueous), and extracted with ethyl acetate. The crude product was purified via flash chromatography (eluting with 30-60% ethyl acetate in hexane) to afford 2-bromo-5-((tetrahydro-2H-pyran-4-yl)methyl)-[1,2,4]triazolo[1,5-a]pyridine as a purple oil (3.4 g, 11.48 mmol, 38.1% yield). This compound was further purified by crystallization from methanol (3 mL) to give the title compound as a pink solid (3.0 g). MS (ESI) m/z 298.3 [M+1]+.

D. N-(2-(methoxymethyl)-1H-benzo[d]imidazol-6-yl)-5-((tetrahydro-2H-pyran-4-yl)methyl)-[1,2,4]triazolo[1,5-a]pyridin-2-amine. To a mixture of tris(dibenzylideneacetone)dipalladium(0) (0.077 g, 0.084 mmol) and 4,5-bis(diphenylphosphino)-9,9-dimethylxanthene (0.098 g, 0.169 mmol) in 1,4-dioxane (10 mL) was added 2-(methoxymethyl)-1-tosyl-1H-benzo[d]imidazol-5-amine (0.280 g, 0.844 mmol), 2-bromo-5-((tetrahydro-2H-pyran-4-yl)methyl)-[1,2,4]triazolo[1,5-a]pyridine (0.25 g, 0.844 mmol) and finely ground potassium carbonate (0.35 g, 2.53 mmol) in a sealable vessel with a stir bar. Nitrogen was blown in to blow out air. The resulting mixture was sealed, stirred, and heated at 120° C. LCMS after 3 h shows complete conversion to desired product. The resulting mixture was filtered. Saturated aqueous sodium bicarbonate was added and extracted with ethyl acetate (2×100 mL). The combined organics were dried over magnesium sulfate, filtered, and concentrated on a rotary evaporator to dryness and purified using reverse-phase preparatory HPLC (eluting with 20-70% acetonitrile+0.1% trifluoroacetic acid in water+0.1% trifluoroacetic acid, over 39 min). Fractions containing the desired product were concentrated on a rotary evaporator and aqueous hydrochloric acid (25 mL, 6M) was added and heated to 70° C. overnight. The solvent was removed on a rotary evaporator and purified using reverse-phase semi-preparatory HPLC (eluting with 5-40% acetonitrile+0.1% trifluoroacetic acid in water+0.1% trifluoroacetic acid, over 39 min). Fractions containing the desired product were loaded onto a Strata X—C ion exchange column from Phenomenex. The column was washed successively with water, acetonitrile, methanol, and then hot 10% ammonium hydroxide in methanol. The product eluted with the 10% ammonium hydroxide in methanol and was concentrated on a rotary evaporator to dryness. This material was crystallized from 20% ethyl acetate in hexane and dried under high vacuum at 40° C. to give the desired product as a white solid (0.130 g, 0.331 mmol, 39.2% yield). $^1$H NMR (400 MHz, DMSO-$d_6$) δ (ppm) 12.30 (br s, 1H), 9.56 (br s, 1H), 8.14 (s, 1H), 7.30-7.55 (m, 4H), 6.89 (d, J=5.86 Hz, 1H), 4.58 (s, 2H), 3.84 (dd, J=11.32, 2.73 Hz, 2H), 3.36 (s, 3H), 3.26 (t, J=10.93 Hz, 2H), 3.06 (d, J=7.03 Hz, 2H), 2.19-2.36 (m, 1H), 1.54 (d, J=11.32 Hz, 2H), 1.29-1.45 (m, 2H); MS (ESI) m/z 393.2 [M+1]⁺.

Example 120

6-(5-(Hydroxy(tetrahydro-2H-pyran-4-yl)methyl)-[1,2,4]triazolo[1,5-a]pyridin-2-ylamino)-3,3-dimethylindolin-2-one and 3,3-dimethyl-6-(5-((tetrahydro-2H-pyran-4-yl)methyl)-[1,2,4]triazolo[1,5-a]pyridin-2-ylamino)indolin-2-one

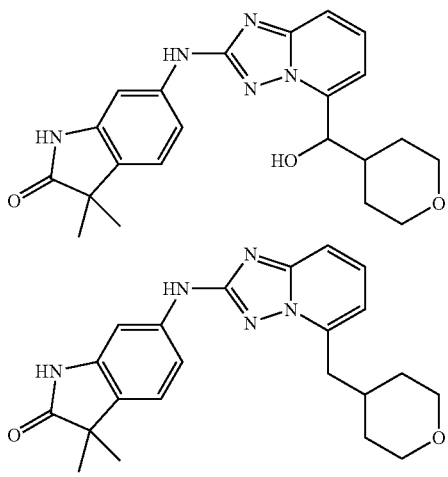

A. (2-Bromo-[1,2,4]triazolo[1,5-a]pyridin-5-yl)(tetrahydro-2H-pyran-4-yl)methanol. A solution of tetrahydro-2H-pyran-4-carbaldehyde in tetrahydrofuran was dried over 3 A molecular sieves prior to use. 2,5-dibromo-[1,2,4]triazolo[1,5-a]pyridine was dried under high vacuum in the reaction flask with a stirbar at 40° C. overnight prior to use. n-Butyllithium (2.70 mL, 4.32 mmol, 1.6 M in hexane) was added slowly dropwise to a stirred solution of 2,5-dibromo-[1,2,4]triazolo[1,5-a]pyridine (1.14 g, 4.12 mmol) in tetrahydrofuran (30 mL) cooled with a dry ice/acetone bath under nitrogen. During the addition the reaction became darker yellow. After 10 min tetrahydro-2H-pyran-4-carbaldehyde (4.53 mL, 4.53 mmol, 1 M in tetrahydrofuran) was added. The cold bath was removed and the resulting mixture was warmed to 0° C. over ±15 min. The resulting mixture was diluted with methanol (1 mL) and most of the solvent was removed on a rotary evaporator. The residue was purified using flash chromatography (Biotage) (eluting with 10-100% ethyl acetate in hexane) to give the desired product (0.792 g, 2.54 mmol, 62% yield) as a white foam-solid. MS (ESI) m/z 312.1 [M]⁺, 314.2 [M+2]⁺.

B. tert-Butyl 6-(5-(hydroxy(tetrahydro-2H-pyran-4-yl)methyl)-[1,2,4]triazolo[1,5-a]pyridin-2-ylamino)-3,3-dimethyl-2-oxoindoline-1-carboxylate. A mixture of tris(dibenzylideneacetone)dipalladium(0) (0.101 g, 0.110 mmol) and 4,5-bis(diphenylphosphino)-9,9-dimethylxanthene (0.128 g, 0.221 mmol) in 1,4-dioxane (1.5 mL) was heated briefly with a heat gun until very hot and then added to tert-butyl 6-amino-3,3-dimethyl-2-oxoindoline-1-carboxylate (0.305 g, 1.104 mmol), (2-bromo-[1,2,4]triazolo[1,5-a]pyridin-5-yl)(tetrahydro-2H-pyran-4-yl)methanol (0.345 g, 1.104 mmol), 1,4-dioxane (2 mL) and finely ground potassium carbonate (0.625 g, 4.53 mmol) in a sealable vessel with a stirbar. Nitrogen was blown in to blow out air. The resulting mixture was sealed, stirred vigorously, and heated at 100° C. for 2.5 h. After cooling to room temperature the reaction mixture was filtered through a syringe filter. The filter cake was washed with DMSO. The filtrate was diluted with 0.1% trifluoroacetic acid in acetonitrile and methanol and purified using reverse-phase preparatory HPLC (15-75% acetonitrile+0.1% trifluoroacetic acid in water+0.1% trifluoroacetic acid, over 30 min). Fractions containing the desired product were combined, neutralized with saturated aqueous sodium bicarbonate, and the acetonitrile was removed on a rotary evaporator. The resulting mixture was extracted with ethyl acetate. The organics were dried over magnesium sulfate, filtered, concentrated on a rotary evaporator, and dried under high vacuum to give the desired product (0.442 g, 0.871 mmol, 79% yield) as a yellow solid. MS (ESI) m/z 507.7 [M+1]⁺.

C. 6-(5-(Hydroxy(tetrahydro-2H-pyran-4-yl)methyl)-[1,2,4]triazolo[1,5-a]pyridin-2-ylamino)-3,3-dimethylindolin-2-one and 3,3-dimethyl-6-(5-((tetrahydro-2 1-/- pyran-4-yl)methyl)-[1,2,4]triazolo[1,5-a]pyridin-2-ylamino)indolin-2-one. Thionyl chloride (0.095 mL, 1.303 mmol) in chloroform (1.5 mL) was added to a stirred solution of tert-butyl 6-(5-(hydroxy(tetrahydro-2H-pyran-4-yl)methyl)-[1,2,4]triazolo[1,5-c]pyridin-2-ylamino)-3,3-dimethyl-2-oxoindoline-1-carboxylate (0.441 g, 0.869 mmol) and N,N-diisopropylethylamine (1.286 mL, 7.39 mmol) in chloroform (20 mL) at −45° C. The resulting yellow solution was stirred while slowly warming to 0° C. over 30 min. The resulting yellow solution was recooled to −45° C. More thionyl chloride (0.019 mL, 0.261 mmol) in chloroform (0.3 mL) was added. The resulting yellow solution was stirred while slowly warming to 0° C. over 30 min. The resulting yellow-orange solution was transferred to a separatory funnel with dichloromethane and shaken with saturated aqueous sodium bicarbonate. The layers were separated and the water layer extracted again with dichloromethane. The combined organics were washed with 0.5 M sodium bisulfate in water (2×10 mL), then brine, and then dried over magnesium sulfate, filtered, and concentrated on a rotary evaporator. The residue was dissolved in acetic acid (10 mL) with stirring at room temperature. Zinc dust (<10 micron) (1.136 g, 17.38 mmol) was added. The resulting gray and orange mixture was stirred and heated at 110° C. under a reflux condenser under nitrogen for 1.5 h. The resulting mixture was filtered through Celite and the filter cake washed with 20% methanol in dichloromethane. The filtrate was concentrated on a rotary evaporator. The residue was dissolved in DMSO/methanol, filtered, and purified using reverse-phase preparatory HPLC (15-65% acetonitrile+0.1% trifluoroacetic acid in water+0.1% trifluoroacetic acid, over 30 min). Fractions containing the desired products were loaded onto Strata X—C ion exchange columns from Phenomenex. The columns were washed successively with water, acetonitrile, methanol, and then 5% ammonium hydroxide in methanol. The products came off with the 5% ammonium hydroxide in methanol eluent and were concentrated on a rotary evaporator and dried under high vacuum at 50° C. to give 645-(hydroxy(tetrahydro-2H-pyran-4-yl)methyl)-[1,2,4]triazolo[1,5-a]pyridin-2-ylamino)-3,3-dimethylindolin-2-one (0.148 g, 0.363 mmol, 42% yield) as an off-white solid. ¹H NMR (400 MHz, DMSO-d₆) δ (ppm) 10.34 (s, 1H), 9.65 (s, 1H), 7.60 (dd, J=7.42, 8.59 Hz, 1H), 7.46 (dd, J=1.37, 8.79 Hz, 1H), 7.41 (d, J=1.95 Hz, 1H), 7.26 (dd, J=1.95, 8.20 Hz, 1H), 7.14 (d, J=8.20 Hz, 1H), 7.05 (d, J=7.03 Hz, 1H), 5.80 (d, J=5.08 Hz, 1H), 5.18 (t, J=4.88 Hz, 1H), 3.84 (ddd, J=3.12, 11.71, 15.23 Hz, 2H), 3.20-3.30 (m, 1H), 3.16 (td, J=1.95, 11.71 Hz, 1H), 2.19 (tq, J=3.86, 11.79 Hz, 1H), 1.70 (qd, J=4.30, 12.49 Hz, 1H), 1.51 (qd, J=4.49, 12.43 Hz, 1H), 1.39 (d, J=11.71 Hz, 1H), 1.31 (d, J=12.49 Hz, 1H), 1.23 (s, 6H); MS (ESI) m/z 408.3 [M+1]⁺. 3,3-Dimethyl-6-(5-((tetrahydro-2H-pyran-4-yl)methyl)-[1,2,4]triazolo[1,5-a]pyridin-2-ylamino)indolin-2-one (0.055 g, 0.140 mmol, 16% yield) was also isolated as a white solid. $^1$H NMR (400 MHz, DMSO-d$_6$) δ (ppm) 10.33 (s, 1H), 9.63 (s, 1H), 7.47-7.54 (m, 1H), 7.43 (dd, J=1.37, 11.52 Hz, 2H), 7.27 (dd, J=1.95, 8.20 Hz, 1H), 7.14 (d, J=7.81 Hz, 1H), 6.91 (d, J=7.03 Hz, 1H), 3.84 (dd, J=2.34, 11.32 Hz, 2H), 3.26 (t, J=10.93 Hz, 2H), 3.04 (d, J=7.42 Hz, 2H), 2.16-2.31 (m, 1H), 1.52 (d, J=11.32 Hz, 2H), 1.36 (qd, J=4.30, 12.10 Hz, 2H), 1.23 (s, 6H); MS (ESI) m/z 392.3 [M+1]⁺.

Example 121

3,3-Dimethyl-6-(5-(1-(tetrahydro-2H-pyran-4-yl)ethyl)-[1,2,4]triazolo[1,5-a]pyridin-2-ylamino)indolin-2-one

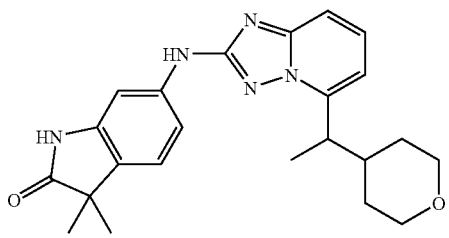

A. (2-Bromo-[1,2,4]triazolo[1,5-a]pyridin-5-yl)(tetrahydro-2H-pyran-4-yl)methanone. A solution of N-methoxy-N-methyltetrahydro-2H-pyran-4-carboxamide in tetrahydrofuran was dried over 3 A molecular sieves prior to use. 2,5-Dibromo-[1,2,4]triazolo[1,5-a]pyridine was dried under high vacuum in the reaction flask with a stirbar at 40° C. overnight prior to use. n-Butyllithium (2.96 mL, 4.74 mmol, 1.6 M in hexane) was added slowly dropwise to a stirred solution of 2,5-dibromo-[1,2,4]triazolo[1,5-a]pyridine (1.25 g, 4.51 mmol) in tetrahydrofuran (25 mL) cooled with a dry ice/acetone bath under nitrogen. During the addition the reaction became darker yellow and then dark red-colored. After 10 min N-methoxy-N-methyltetrahydro-2H-pyran-4-carboxamide (4.97 mL, 4.97 mmol, 1M solution in tetrahydrofuran) was added. The cold bath was removed and the resulting mixture was warmed to 0° C. over ±15 min. The resulting mixture was diluted with methanol (1 mL) and most of the solvent was removed on a rotary evaporator. The residue was purified using flash chromatography (Biotage) (10-100% ethyl acetate in hexane). Fractions containing the desired product were combined and most of the solvent removed on a rotary evaporator. The residue was triturated with 20% ethyl acetate in hexane. Solids were collected by vacuum filtration, washed with hexane, and dried under high vacuum to give the desired product (0.658 g, 2.122 mmol, 47% yield) as a white solid. $^1$H NMR (400 MHz, DMSO-d$_6$) δ (ppm) 8.08 (dd, J=1.17, 8.98 Hz, 1H), 7.86 (dd, J=7.42, 8.98 Hz, 1H), 7.74 (dd, J=1.17, 7.03 Hz, 1H), 3.84-3.96 (m, 3H), 3.42 (td, J=2.15, 11.42 Hz, 2H), 1.80 (dd, J=1.56, 12.89 Hz, 2H), 1.52-1.66 (m, 2H); MS (ESI) m/z 310.2 [M]⁺312.1 [M+2]⁺.

B. tert-Butyl 3,3-dimethyl-2-oxo-6-(5-(tetrahydro-2H-pyran-4-carbonyl)-[1,2,4]triazolo[1,5-a]pyridin-2-ylamino)indoline-1-carboxylate. A mixture of tris(dibenzylideneacetone)dipalladium(0) (0.050 g, 0.054 mmol) and 4,5-bis(diphenylphosphino)-9,9-dimethylxanthene (0.063 g, 0.109 mmol) in 1,4-dioxane (2 mL) was heated briefly with a heat gun until very hot and then added to tert-butyl 6-amino-3,3-dimethyl-2-oxoindoline-1-carboxylate (0.150 g, 0.543 mmol), (2-bromo-[1,2,4]triazolo[1,5-a]pyridin-5-yl)(tetrahydro-2H-pyran-4-yl)methanone (0.168 g, 0.543 mmol) and finely ground potassium carbonate (0.308 g, 2.226 mmol) in a sealable vessel with a stirbar. Nitrogen was blown in to blow out air. The resulting mixture was sealed, stirred vigorously, and heated at 100° C. for 1.5 h. After cooling to room temperature the reaction mixture was diluted with ethyl acetate and water with vigorous stirring. The resulting mixture was filtered through a syringe filter and the filter cake washed with ethyl acetate. The layers of the filtrate were separated in a reparatory funnel and the organics were concentrated on a rotary evaporator. The residue was taken up in dichloromethane and purified using flash chromatography (Biotage) (20-80% ethyl acetate in hexane) to give the desired product (0.183 g, 0.362 mmol, 67% yield) as a yellow solid. MS (ESI) m/z 506.2 [M+1]⁺.

C. 3,3-Dimethyl-6-(5-(1-(tetrahydro-2H-pyran-4-yl)vinyl)-[1,2,4]triazolo[1,5-a]pyridin-2-ylamino)indolin-2-one. (Trimethylsilylmethyl)-magnesium chloride (0.700 mL, 0.700 mmol, 1 M in diethyl ether) was added dropwise slowly to a stirred solution of tert-butyl 3,3-dimethyl-2-oxo-6-(5-(tetrahydro-2H-pyran-4-carbonyl)-[1,2,4]triazolo[1,5-c]pyridin-2-ylamino)indoline-1-carboxylate (0.118 g, 0.233 mmol) in tetrahydrofuran (10 mL) at −70° C. under nitrogen. The reaction mixture became dark red-colored upon addition of the Grignard reagent. The resulting mixture was stirred under nitrogen while slowly warming to 0° C. over 2 h. More (trimethylsilylmethyl)-magnesium chloride (0.233 mL, 0.233 mmol, 1 M in diethyl ether) was added and the resulting red solution was stirred at 0° C. under nitrogen for 35 min. More (trimethylsilylmethyl)-magnesium chloride (0.350 mL, 0.350 mmol, 1 M in diethyl ether) was added and the resulting mixture was stirred at 0° C. under nitrogen for 1.5 h. More (trimethylsilylmethyl)-magnesium chloride (0.350 mL, 0.350 mmol, 1 M in diethyl ether) was added and the resulting mixture was stirred at 0° C. under nitrogen for 1 h. Saturated aqueous ammonium chloride was added to quench the reaction. The resulting mixture was diluted with ethyl acetate and water and shaken in a separatory funnel. The layers were separated and the organics were washed with brine, dried over magnesium sulfate, filtered, and concentrated on a rotary evaporator. The residue was taken up in dichloromethane and purified using flash chromatography (Biotage) (20-100% ethyl acetate in hexane) to an impure white solid. MS (ESI) m/z 594.5 [M+H]⁺. To the white solids was added acetic acid (5 mL). The resulting mixture was stirred and heated at 120° C. under a reflux condenser for 85 h. The resulting mixture was filtered and purified using reverse-phase preparatory HPLC (10-60% acetonitrile+0.1% trifluoroacetic acid in water+0.1% trifluoroacetic acid, over 30 min). Fractions containing the desired product were loaded onto a Strata X—C ion exchange column from Phenomenex. The column was washed successively with water, acetonitrile, methanol, and then a mixture of 5% ammonium hydroxide, 45% methanol, and 50% dichloromethane. The product came off with the ammonium hydroxide eluent and was concentrated on a rotary evaporator and dried under high vacuum to give the desired product (0.035 g, 0.087 mmol, 64% yield) as an off-white solid. MS (ESI) m/z 404.5 [M+1]⁺.

D. 3,3-Dimethyl-6-(5-(1-(tetrahydro-2H-pyran-4-yl)ethyl)-[1,2,4]triazolo[1,5-a]pyridin-2-ylamino)indolin-2-one. A mixture of 3,3-dimethyl-6-(5-(1-(tetrahydro-2H-pyran-4-yl)vinyl)-[1,2,4]triazolo[1,5-c]pyridin-2-ylamino) indolin-2-one (0.035 g, 0.087 mmol) in ethanol (6 mL) with stirring was prepared. A combination vacuum/nitrogen/hydrogen manifold was attached. The atmosphere in the flask was removed and replaced with nitrogen three times. Palladium (10 wt. % on activated carbon) (4.62 mg, 4.34 mmol) was added and the atmosphere in the flask was removed and replaced with hydrogen three times. The resulting mixture was stirred vigorously under a hydrogen balloon at 50° C. for 2 h. 1-Methyl-2-pyrrolidinone (1 mL) was added to improve solubility of the starting material and the resulting mixture was stirred vigorously under a hydrogen balloon at 70° C. for 10 h. The resulting mixture was filtered through a syringe filter and loaded onto a Strata X—C ion exchange column from Phenomenex. The column was washed successively with water, acetonitrile, methanol, and then a mixture of 5% ammonium hydroxide, 45% methanol, and 50% dichloromethane. The product came off with the ammonium hydroxide eluent and was concentrated on a rotary evaporator and dried under high vacuum at 50° C. to give the desired product (0.034 g, 0.084 mmol, 97% yield) as an off-white solid. $^1$H NMR (400 MHz, DMSO-$d_6$) δ (ppm) 10.35 (s, 1H), 9.60 (s, 1H), 7.53 (dd, J=7.22, 8.79 Hz, 1H), 7.38-7.45 (m, 2H), 7.26 (dd, J=1.95, 8.20 Hz, 1H), 7.14 (d, J=7.81 Hz, 1H), 6.91 (d, J=7.42 Hz, 1H), 3.90 (dd, J=3.12, 11.32 Hz, 1H), 3.77 (dd, J=2.54, 11.52 Hz, 1H), 3.50 (quip, J=7.32 Hz, 1H), 3.13-3.31 (m, 2H), 2.07-2.21 (m, 1H), 1.70 (d, J=13.28 Hz, 1H), 1.36 (d, J=7.03 Hz, 3H), 1.25-1.34 (m, 3H), 1.23 (s, 6H); MS (ESI) m/z 406.2 [M+1]$^+$.

Example 122 trans-6-(5-((4-Hydroxy-4-methylcyclohexyl)methyl)-[1,2,4]triazolo[1,5-a]pyridin-2-ylamino)-3,3-dimethylindolin-2-one and cis-6-(5-((4-hydroxy-4-methylcyclohexyl)methyl)-[1,2,4]triazolo[1,5-a]pyridin-2-ylamino)-3,3-dimethylindolin-2-one

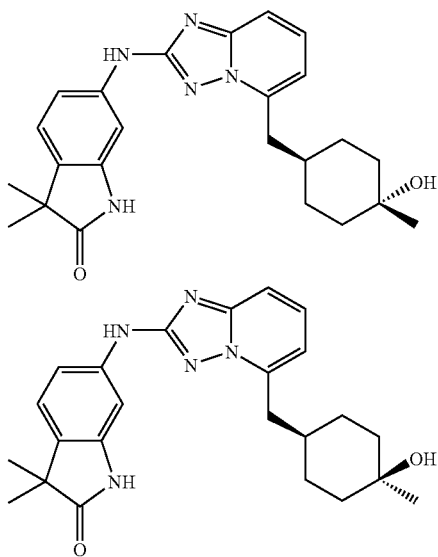

A. 2-Bromo-[1,2,4]triazolo[1,5-a]pyridine. A suspension of [1,2,4]triazolo[1,5-a]pyridin-2-amine (0.500 g, 3.73 mmol, obtained from pyridin-2-amine following an analogous procedure as the one described for 5-bromo-[1,2,4]triazolo[1,5-a]pyridin-2-amine) in 48% HBr (5 mL) was cooled to 0° C. and slowly treated with a solution of sodium nitrite (0.386 g, 5.59 mmol) in water (2 mL) resulting in a dark brown suspension with brown gas evolution. The mixture was stirred for 1 h. A dark purple solution of copper(I) bromide (0.642 g, 4.47 mmol) in 48% HBr (2 mL) was added and the reaction mixture was stirred overnight at room temperature. The purple suspension was poured into water (15 mL) and the resulting yellow-orange suspension was collected and dried to give an orange solid which was further purified by column chromatography (eluting with 100% dicholomethane) to afford 2-bromo-[1,2,4]triazolo[1,5-a]pyridine (0.455 g, 61% yield). $^1$H NMR (400 MHz, DMSO-$d_6$) δ (ppm) 8.96 (dt, 1H), 7.81-7.91 (m, 1H), 7.68-7.79 (m, 1H), 7.27 (td, J=1.37, 6.93 Hz, 1H); MS (ESI) m/z 197.9 [M]$^+$ and 200.1 [M+2]$^+$.

B. 6-([1,2,4]Triazolo[1,5-a]pyridin-2-ylamino)-3,3-dimethylindolin-2-one. A mixture of tris(dibenzylideneacetone)dipalladium(0) (0.116 g, 0.126 mmol), 4,5-bis(diphenylphosphino)-9,9-dimethylxanthene (0.146 g, 0.252 mmol), 2-bromo-[1,2,4]triazolo[1,5-a]pyridine (0.25 g, 1.262 mmol), cesium carbonate (1.687 g, 5.18 mmol), and tert-butyl 6-amino-3,3-dimethyl-2-oxoindoline-1-carboxylate (0.349 g, 1.262 mmol) in 1,4-dioxane (4 mL) was put under an atmosphere of nitrogen and heated to 75° C. for 3.5 h then to 65° C. overnight. As starting material was left unreacted, the mixture was heated to 75° C. for an additional 3 h. After cooling to room temperature, the reaction mixture was diluted with 20% methanol in dichloromethane with vigorous stirring. The resulting mixture was filtered through Celite and the filter cake washed with 20% methanol in dichloromethane. The filtrate was concentrated on a rotary evaporator and purified by biotage column chromatography (eluting with 5-75% ethyl acetate in hexanes). Both LCMS and $^1$HNMR showed that the Boc protecting group was cleaved during the purification step. 6-([1,2,4]Triazolo[1,5-a]pyridin-2-ylamino)-3,3-dimethylindolin-2-one (0.202 g, 0.689 mmol, 54.5% yield) was isolated as a yellow solid. $^1$H NMR (400 MHz, DMSO-$d_6$) δ (ppm) 10.29 (s, 1H), 9.56 (s, 1H), 8.69-8.75 (m, 1H), 7.52-7.60 (m, 2H), 7.36 (d, J=1.95 Hz, 1H), 7.19-7.25 (m, 1H), 7.10-7.16 (m, 1H), 6.98-7.05 (m, 1H), 1.18-1.26 (m, 6H); MS (ESI) m/z 294.2 [M+1]$^+$.

C. 6-(5-Bromo-[1,2,4]triazolo[1,5-a]pyridin-2-ylamino)-3,3-dimethylindolin-2-one. A solution of 6-([1,2,4]triazolo[1,5-a]pyridin-2-ylamino)-3,3-dimethylindolin-2-one (0.200 g, 0.682 mmol) in dry tetrahydrofuran (2.73 mL) was cooled to −78° C. and treated with n-butyl lithium (1.321 mL, 2.114 mmol, 1.6 M in hexanes). After 30 min at low temperature, 1,2-dibromo-1,1,2,2-tetrafluoroethane (0.549 g, 2.114 mmol) was added. After 20 min, the cold bath was removed and the reaction was stirred overnight. More than 50% conversion was observed in the clean LCMS trace. Water (10 mL) was added to the reaction and the crude was extracted with ethyl acetate. The extracts were dried over sodium sulfate and evaporated to dryness. The residue was loaded in a mixture of dimethyl formamide/methanol on a silica gel biotage column and the compound was eluted with 5-100% ethyl acetate in hexanes. All fractions containing the product were combined, evaporated to dryness, and had to be re-purified by biotage column chromatography using 10-75% ethyl acetate in hexanes. 6-(5-Bromo-[1,2,4]triazolo[1,5-c]pyridin-2-ylamino)-3,3-dimethylindolin-2-one (0.091 g, 0.244 mmol, 35.9% yield) was isolated as a yellow solid. MS (ESI) m/z 372.1 [M+1]$^+$.

D. 6-(5-(1,4-Dioxaspiro[4.5]decan-8-ylmethyl)-[1,2,4]triazolo[1,5-a]pyridin-2-ylamino)-3,3-dimethylindolin-2-one. A solution of 8-methylene-1,4-dioxaspiro[4.5]decane (0.117 g, 0.758 mmol) in a 0.5 M solution of (1S,5S)-9-borabicyclo[3.3.1]nonane in tetrahydrofuran (1.467 mL, 0.733 mmol) was heated to reflux temperature for 2 h under an atmosphere of nitrogen. The reaction was then cooled to room temperature and reacted with [1,1'-bis(diphenylphosphino)

ferrocene]dichloropalladium(II) complex with dichloromethane (0.070 g, 0.086 mmol), potassium carbonate (0.101 g, 0.733 mmol) and 6-(5-bromo-[1,2,4]triazolo[1,5-c]pyridin-2-ylamino)-3,3-dimethylindolin-2-one (0.091 g, 0.244 mmol) in dimethyl formamide (2.445 mL). The reaction mixture was heated to 90° C. overnight. LCMS analysis showed more than 50% conversion to the desired M+1, contaminated with reduced starting material 6-([1,2,4]triazolo[1,5-c]pyridin-2-ylamino)-3,3-dimethylindolin-2-one. The reaction was quenched with water and the crude was extracted with ethyl acetate. The organic extracts were dried over sodium sulfate and after evaporation of the solvent, the residue was purified by silica gel biotage column chromatography (50-100% ethyl acetate in hexanes). Fractions containing the desired M+1 were combined and evaporated to dryness. A light yellow oil was obtained. MS (ESI) m/z 448.6 [M+1]$^+$.

E. 3,3-Dimethyl-6-(5-((4-oxocyclohexyl)methyl)-[1,2,4]triazolo[1,5-a]pyridin-2-ylamino)indolin-2-one. A solution of 6-(5-(1,4-dioxaspiro[4.5]decan-8-ylmethyl)-[1,2,4]triazolo[1,5-c]pyridin-2-ylamino)-3,3-dimethylindolin-2-one (0.081 g, 0.181 mmol) contaminated with 6-([1,2,4]triazolo[1,5-c]pyridin-2-ylamino)-3,3-dimethylindolin-2-one in dry tetrahydrofuran (1.810 mL), was treated with a 6.0 N aqueous hydrochloric acid (0.5 mL, 3.00 mmol) and heated to 50° C. for 1 h. After 2 h, the conversion monitored by LCMS had not progressed so additional acid was used: 0.5 mL of 6.0 N solution of hydrochloric acid was added and the temperature was increased to reflux and maintained overnight. Although the deprotection was still not complete, the reaction was worked up. The mixture was neutralized with an aqueous solution of sodium hydroxide and extracted with ethyl acetate. The residue was dried over sodium sulfate and evaporated to dryness. The crude was purified by silica gel biotage column chromatography (0-100% ethyl acetate in hexanes). 3,3-Dimethyl-6-(5-((4-oxocyclohexyl)methyl)-[1,2,4]triazolo[1,5-c]pyridin-2-ylamino)indolin-2-one (0.048 g, 0.119 mmol, 65.7% yield) contaminated with 6-([1,2,4]triazolo[1,5-a]pyridin-2-ylamino)-3,3-dimethylindolin-2-one was isolated as a colorless solid that was used without further purification. MS (ESI) m/z 404.4 [M+H]$^+$.

F. trans-6-(5-((4-Hydroxy-4-methylcyclohexyl)methyl)-[1,2,4]triazolo[1,5-a]pyridin-2-ylamino)-3,3-dimethylindolin-2-one and cis-6-(5-((4-hydroxy-4-methylcyclohexyl)methyl)-[1,2,4]triazolo[1,5-a]pyridin-2-ylamino)-3,3-dimethylindolin-2-one. 3,3-Dimethyl-6-(5((4-oxocyclohexyl)methyl)-[1,2,4]triazolo[1,5-c]pyridin-2-ylamino)indolin-2-one (0.052 g, 0.129 mmol) was dissolved in dry tetrahydrofuran (1.289 mL) and treated with a 3.0 M commercial solution of methyl magnesium bromide in diethyl ether (0.133 mL, 0.400 mmol) at room temperature. The reaction mixture became bright yellow immediately and a solid formed. The reaction monitored by LCMS analysis showed an incomplete conversion after 1 h. An additional 0.03 mL of methyl magnesium bromide solution was used at room temperature. The reaction was quenched after 3 h with a slow addition of water and the crude was extracted in ethyl acetate. The extracts were dried over sodium sulfate and evaporated to dryness. The colorless solid residue was purified by semi-preparative HPLC (20-100% acetonitrile+0.1% trifluoroacetic acid+0.1% trifluoroacetic acid in water, 1 injection, 30 min). The 2 diastereomers were separated. The corresponding fractions containing the desired M+1 were combined separately, acetonitrile was removed under reduced pressure, and the pH was neutralized with the addition of a 1.75 M aqueous solution of potassium carbonate. The stereochemistry was assigned based on chemical shifts. trans-6-(54(4-Hydroxy-4-methylcyclohexyl)methyl)-[1,2,4]triazolo[1,5-c]pyridin-2-ylamino)-3,3-dimethylindolin-2-one (0.006 g, 0.014 mmol, 11.10% yield) was isolated as a white solid: $^1$H NMR (400 MHz, DMSO-d$_6$) δ (ppm) 10.31 (s, 1H), 9.61 (s, 1H), 7.46-7.55 (m, 1H), 7.37-7.45 (m, 2H), 7.28 (d, J=7.81 Hz, 1H), 7.13 (d, J=8.59 Hz, 1H), 6.87 (d, J=7.03 Hz, 1H), 4.21 (s, 1H), 3.01 (d, J=6.64 Hz, 2H), 2.01 (br s, 1H), 1.49-1.65 (m, 4H), 1.27-1.39 (m, 2H), 1.16-1.26 (m, 8H), 1.12 (s, 3H); MS (ESI) m/z 420 [M+1]$^+$. cis-6-(5-((4-hydroxy-4-methylcyclohexyl)methyl)-[1,2,4]triazolo[1,5-a]pyridin-2-ylamino)-3,3-dimethylindolin-2-one (0.006 g, 0.014 mmol, 11.10% yield): $^1$H NMR (400 MHz, DMSO-d$_6$) δ (ppm) 10.30 (s, 1H), 9.61 (s, 1H), 7.45-7.55 (m, 1H), 7.36-7.45 (m, 2H), 7.28 (d, J=6.64 Hz, 1H), 7.13 (d, J=8.20 Hz, 1H), 6.88 (d, J=6.25 Hz, 1H), 3.96 (s, 1H), 2.98 (d, J=6.25 Hz, 2H), 1.92 (br s, 1H), 1.41-1.59 (m, 4H), 1.30-1.40 (m, 2H), 1.22 (s, 8H), 1.06 (s, 3H); MS (ESI) m/z 420 [M+1]$^+$.

Example 123

4-((2-(3-Methyl-1H-indazol-6-ylamino)[1,2,4]triazolo[1,5-a]pyridin-5-yl)methyl)pyridin-2(1H)-one

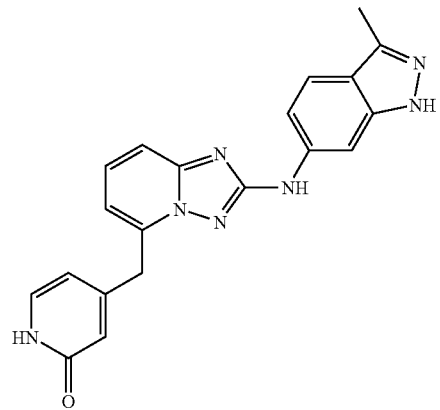

A. N-(3-methyl-1-(tetrahydro-2H-pyran-2-yl)-1H-indazol-6-yl)-[1,2,4]triazolo[1,5-a]pyridin-2-amine. To a solution/suspension of [1,2,4]triazolo[1,5-a]pyridin-2-amine (500 mg, 3.73 mmol) in dioxane (4 mL) and water (4.00 μl) was added sodium tert-butoxide (853 mg, 8.87 mmol), 6-bromo-3-methyl-1-(tetrahydro-2H-pyran-2-yl)-1H-indazole (1048 mg, 3.55 mmol), tris(dibenzylideneacetone)dipalladium (81 mg, 0.089 mmol), and 4,5-bis(diphenylphosphino)-9,9-dimethylxanthene (103 mg, 0.177 mmol). The reaction mixture was bubbled with nitrogen and the reaction was stirred overnight at 100° C. Water was added to the reaction mixture and the product was extracted with 10% methanol in dichloromethane, then it was washed with brine. The crude product was purified on the biotage eluting with 0-20% methanol in dichloromethane to afford N-(3-methyl-1-(tetrahydro-2H-pyran-2-yl)-1H-indazol-6-yl)-[1,2,4]triazolo[1,5-a]pyridin-2-amine (800 mg, 2.296 mmol, 64.7% yield). $^1$H NMR (400 MHz, DMSO-d$_6$) δ (ppm) 9.82 (s, 1H), 8.81 (d, J=6.64 Hz, 1H), 8.14 (d, J=1.56 Hz, 1H), 7.47-7.72 (m, 3H), 7.34 (dd, J=1.95, 8.59 Hz, 1H), 6.94-7.15 (m, 1H), 5.60 (dd, J=2.54, 9.96 Hz, 1H), 3.94 (d, J=12.49 Hz, 2H), 3.71 (ddd, J=6.05, 7.81, 11.52 Hz, 2H), 2.42 (s, 3H), 2.06 (d, J=13.28 Hz, 1H), 1.95 (dd, J=2.73, 13.28 Hz, 1H), 1.78 (br s, 1H), 1.50-1.67 (m, 2H).

B. (2-Methoxypyridin-4-yl)(2-(3-methyl-1-(tetrahydro-2H-pyran-2-yl-1H-indazol-6-ylamino)-[1,2,4]triazolo[1,5-a]pyridin-5-yl)methanone. A solution/suspension of N-(3-methyl-1-(tetrahydro-2H-pyran-2-yl)-1H-indazol-6-yl)-[1,2,4]triazolo[1,5-c]pyridin-2-amine (600 mg, 1.722 mmol) in tetrahydrofuran (15 mL) was cooled to −78° C. and n-butyl lithium (1.292 mL, 2.067 mmol) was added dropwise. The reaction mixture became deep red. The reaction was stirred for 15 min, then a solution of N,2-dimethoxy-N-methylisonicotinamide (405 mg, 2.067 mmol) in tetrahydrofuran (2 mL) was added dropwise. The reaction mixture was allowed to warm up to room temperature and stirred for 2 hours. LC/MS shows product. The reaction mixture was quenched with water, then 1N HCl was added (2 mL). The reaction changed color. The product was extracted with ethyl acetate twice then it was washed with brine. The crude product was purified by column chromatography (eluting with 12-100% ethyl acetate in hexanes in the Biotage) to yield (2-methoxypyridin-4-yl)(2-(3-methyl-1-(tetrahydro-2H-pyran-2-yl)-1H-indazol-6-ylamino)-[1,2,4]triazolo[1,5-c]pyridin-5-yl)methanone (670 mg, 1.386 mmol, 80% yield). MS (ESI): m/z 484.4 [M+H]$^+$.

C. (2-Methoxypyridin-4-yl)(2-(3-methyl-1H-indazol-6-ylamino)-[1,2,4]triazolo[1,5-a]pyridin-5-yl)methanone. To a solution/suspension of (2-methoxypyridin-4-yl)(2-(3-methyl-1-(tetrahydro-2H-pyran-2-yl)-1H-indazol-6-ylamino)-[1,2,4]triazolo[1,5-c]pyridin-5-yl)methanone (670 mg, 1.386 mmol) in dioxane was added hydrogen chloride (2 mL, 4 M in dioxane). The reaction was stirred at 45° C. for 2 hours. The solvent was then removed in vacuo and this crude was taken to the next step without further purification. MS (ESI): m/z 400.4 [M+1]$^+$.

D. 4-((2-(3-methyl-1H-indazol-6-ylamino)-[1,2,4]triazolo[1,5-a]pyridin-5-ylmethyl)pyridin-2(1H)-one. To a solution/suspension of (2-methoxypyridin-4-yl)(2-(3-methyl-1H-indazol-6-ylamino)-[1,2,4]triazolo[1,5-c]pyridin-5-yl)methanone (400 mg, 0.847 mmol), in a 50 mL pressure vial, hydrazine hydrate (1.232 mL, 25.4 mmol), and potassium hydroxide (1188 mg, 21.17 mmol) were added followed by ethylene glycol (10 mL). The reaction mixture was heated to 190° C., and was left to stir overnight, then checked by LCMS. Once the reaction was complete, water was added to the crude mixture and the product was extracted with ethyl acetate three times. The organics were washed with brine and dried over sodium sulfate. The crude was purified on semi-preparative HPLC (20-100% acetonitrile+0.1% trifluoroacetic acid in water+0.1% trifluoroacetic acid, 20 min). The fractions containing the product were loaded on a strata-X column to remove trifluoroacetic acid, then methanol was evaporated in vacuo. 4-((2-(3-methyl-1H-indazol-6-ylamino)-[1,2,4]triazolo[1,5-a]pyridin-5-yl)methyl)pyridin-2-ol (15 mg, 0.040 mmol, 4.77% yield) was obtained as a white solid. $^1$H NMR (400 MHz, DMSO-d$_6$) δ (ppm) 12.38 (s, 1H), 11.70 (br s, 1H), 9.76 (s, 1H), 8.07 (d, J=1.17 Hz, 1H), 7.56-7.65 (m, 1H), 7.49-7.55 (m, 2H), 7.34 (d, J=6.64 Hz, 1H), 7.08 (td, J=1.56, 7.81 Hz, 2H), 6.53 (d, J=0.78 Hz, 1H), 6.19 (dd, J=1.56, 6.64 Hz, 1H), 4.31 (s, 2H), 2.43 (s, 3H); MS (ESI): m/z 371.7 [M+1]$^+$.

Example 124

6-(5-(3-Hydroxy-3-methylazetidin-1-yl)-[1,2,4]triazolo[1,5-a]pyridin-2-ylamino)-3,3-dimethylindolin-2-one

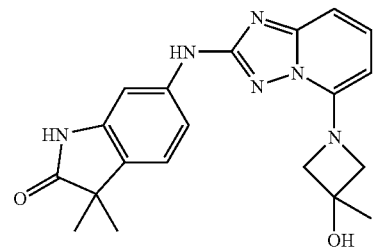

A. 1-(2-Bromo-[1,2,4]triazolo[1,5-a]pyridin-5-yl)-3-methylazetidin-3-ol. 2,5-Dibromo-[1,2,4]triazolo[1,5-a]pyridine (0.500 g, 1.806 mmol), 3-methylazetidin-3-ol hydrochloride (0.446 g, 3.61 mmol), potassium carbonate (0.749 g, 5.42 mmol), and dimethylsulfoxide (2.86 mL) were added to a microwave vial and heated to 100° C. for 16 h. The reaction was extracted with water and ethyl acetate. The organic layer was dried over magnesium sulfate, filtered, and dried. The residue was purified via silica gel chromatography (0-100% ethyl acetate in hexanes) over 1.2 L. The desired fractions were concentrated and then triturated in hexanes to afford 1-(2-bromo-[1,2,4]triazolo[1,5-a]pyridin-5-yl)-3-methylazetidin-3-ol (298.8 mg, 1.055 mmol, 58.4% yield) as a white solid. MS (ESI) m/z 283.1 [M]$^+$, 285.1 [M+2]$^+$.

B. 6-(5-(3-Hydroxy-3-methylazetidin-1-yl)-[1,2,4]triazolo[1,5-a]pyridin-2-ylamino)-3,3-dimethylindolin-2-one. A mixture of tris(dibenzylideneacetone)dipalladium(0) (133.0 mg, 0.145 mmol) and 4,5-bis(diphenylphosphino)-9,9-dimethylxanthene (168.0 mg, 0.290 mmol) in 1,4-dioxane (1.5 mL) was heated briefly with a heat gun until very hot and then added tert-butyl 6-amino-3,3-dimethyl-2-oxoindoline-1-carboxylate (200.0 mg, 0.724 mmol), 1-(2-bromo-[1,2,4]triazolo[1,5-c]pyridin-5-yl)-3-methylazetidin-3-ol (205.0 mg, 0.724 mmol) and finely ground potassium carbonate (410.0 mg, 2.97 mmol) in a sealable vessel with a stirbar. The vessel was purged with nitrogen. The resulting mixture was sealed, stirred vigorously, and heated to 110° C. for 16 h. The reaction mixture was cooled to room temperature, diluted with hot dimethylsulfoxide, and filtered through a syringe filter. The filter cake was washed with hot dimethylsulfoxide. The filtrate was diluted with methanol and purified using reverse-phase preparatory HPLC (10-70% acetonitrile+0.1% trifluoroacetic acid in water+0.1% trifluoroacetic acid, over 30 min). Fractions containing the desired product were combined and organic volatiles removed under reduced pressure. Ethyl acetate and saturated sodium bicarbonate were added and the product extracted. Organic layer was dried over magnesium sulfate. Organic volatiles were removed under reduced pressure. The residue was treated with 4M hydrochloric acid in dioxane (1.0 mL) and dioxane (2.0 mL) and the solution heated to 60° C. for 1 h. Organic volatiles were removed under reduced pressure. The residue was triturated in hexanes, sonicated, filtered, and dried in vacuo to afford 6-(5-(3-hydroxy-3-methylazetidin-1-yl)-[1,2,4]triazolo[1,5-c]pyridin-2-ylamino)-3,3-dimethylindolin-2-one as a hydrochloride salt (1.12 mg, 2.70 mmol, 0.373% yield). $^1$H NMR (400 MHz, DMSO-$d_6$) δ (ppm) 10.43 (s, 1H), 9.44 (s, 1H), 7.39 (t, J=8.2 Hz, 1H), 7.34 (d, J=2.0 Hz, 1H), 7.19-7.23 (m, 1H), 7.13-7.16 (m, 1H), 6.80 (d, J=7.8 Hz, 1H), 5.93 (d, J=7.0 Hz, 1H), 4.25 (d, J=8.6 Hz, 2H), 4.11 (d, J=7.8 Hz, 2H), 1.54 (s, 3H), 1.22 (s, 6H). MS (ESI) m/z 379.3 [M+1]$^+$.

Example 125

(R)-3,3-Dimethyl-6-(5-(methyl(tetrahydrofuran-3-yl)amino)-[1,2,4]triazolo[1,5-a]pyridin-2-ylamino)indolin-2-one

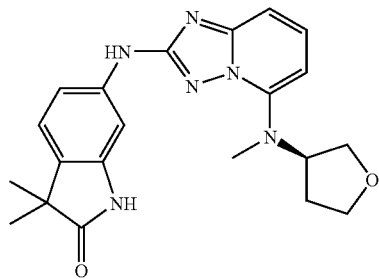

A. (R)-2-Bromo-N-(tetrahydrofuran-3-yl)-[1,2,4]triazolo[1,5-a]pyridin-5-amine. 2,5-Dibromo-[1,2,4]triazolo[1,5-c]pyridine (1.5 g, 5.42 mmol), (R)-tetrahydrofuran-3-amine hydrochloride (0.669 g, 5.42 mmol), potassium carbonate (2.246 g, 16.25 mmol), and dimethylsulfoxide (8.57 mL) were heated in a microwave vial at 100° C. for 16 h. The reaction was cooled to room temperature and extracted with water and ethyl acetate. The organic layer was then washed with brine, dried over magnesium sulfate, filtered, and dried in vacuo. The residue was treated with ethyl acetate (4 mL) and dichloromethane (4 mL) and purified using silica gel chromatography (5-100% ethyl acetate in hexanes) over 1.2 L. The desired fractions were combined and organic volatiles removed under reduced pressure. The residue was triturated in 10% ethyl acetate in hexanes, filtered, washed with hexanes and dried en vacuo to afford (R)-2-bromo-N-(tetrahydrofuran-3-yl)-[1,2,4]triazolo[1,5-a]pyridin-5-amine (602.0 mg, 2.126 mmol, 39.3% yield) as a white solid. MS (ESI) m/z 283.1 [M]$^+$, 285.1 [M+2]$^+$.

B. (R)-2-Bromo-N-methyl-N-(tetrahydrofuran-3-yl-[1,2,4]triazolo[1,5-a]pyridin-5-amine. (R)-2-Bromo-N-(tetrahydrofuran-3-yl)-[1,2,4]triazolo[1,5-a]pyridin-5-amine (500.0 mg, 1.766 mmol) was suspended in 1,2-dimethoxyethane (8.83 mL) and cooled to 0° C. The reaction was purged with nitrogen followed by the addition of sodium hydride (89.0 mg, 3.53 mmol, 95%). The mixture was allowed to stir for 10 min. Iodomethane (330.0 μL, 5.30 mmol) was added dropwise and the reaction mixture was allowed to warm to room temperature and stir for 16 h. Ethyl acetate was added to the reaction and allowed to stir for 1 min followed by an extraction with ethyl acetate and water. The organics were washed with brine and dried with magnesium sulfate. Organic volatiles were removed under reduced pressure and purified using silica gel chromatography on an Emrys Biotage SP1 (10-100% ethyl acetate in hexanes) over 1.2 L. The desired fractions were combined and organic volatiles removed under reduced pressure to afford (R)-2-bromo-N-methyl-N-(tetrahydrofuran-3-yl)-[1,2,4]triazolo[1,5-a]pyridin-5-amine (373.8 mg, 1.258 mmol, 71.2% yield). MS (ESI) m/z 297.1 [M]$^+$, 299.1 [M+2]$^+$.

C. (R)-3,3-Dimethyl-6-(5-(methyl(tetrahydrofuran-3-yl)amino)-[1,2,4]triazolo[1,5-a]pyridin-2-ylamino)indolin-2-one. A mixture of tris(dibenzylideneacetone)dipalladium(0) (230.0 mg, 0.251 mmol) and 4,5-bis(diphenylphosphino)-9,9-dimethylxanthene (291.0 mg, 0.502 mmol) in 1,4-dioxane (1.5 mL) was heated briefly with a heat gun until very hot and then added to tert-butyl 6-amino-3,3-dimethyl-2-oxoindoline-1-carboxylate (347.0 mg, 1.255 mmol), (R)-2-bromo-N-methyl-N-(tetrahydrofuran-3-yl)-[1,2,4]triazolo[1,5-a]pyridin-5-amine (373.0 mg, 1.255 mmol) and cesium carbonate (1227.0 mg, 3.77 mmol) in a sealable vessel with a stirbar. The vessel was purged with nitrogen. The resulting mixture was sealed, stirred vigorously, and heated at 80° C. for 16 h. After cooling to room temperature the reaction mixture was diluted with ethyl acetate and extracted using ethyl acetate and water, followed by brine, and dried on magnesium sulfate. Organic volatiles were removed under reduced pressure and the residue was dissolved in minimal ethyl acetate and purified using silica gel chromatography (0-100% ethyl acetate in hexanes) over 1.2 L. The desired fractions were combined, and organic volatiles removed under reduced pressure. The residue was treated with dioxanes (4.0 mL) and 4N HCl in dioxanes (1.0 mL) and heated to 70° C. for 6 h. Organic volatiles were removed under reduced pressure. Solids were taken up in hexanes, filtered, washed with hexanes, and dried in vacuo to afford (R)-3,3-dimethyl-6-(5-(methyl(tetrahydrofuran-3-yl)amino)-[1,2,4]triazolo[1,5-a]pyridin-2-ylamino)indolin-2-one as a hydrochloride salt (222.2 mg, 0.518 mmol, 41.3% yield, ee 100%). $^1$H NMR (400 MHz, DMSO-$d_6$) δ (ppm) 10.34 (s, 1H), 9.58 (s, 1H), 7.49 (dd, J=8.6, 7.8 Hz, 1H), 7.37 (d, J=2.0 Hz, 1H), 7.26 (dd, J=8.0, 2.1 Hz, 1H), 7.15 (d, J=8.2 Hz, 1H), 7.10 (dd, J=8.6, 1.2 Hz, 1H), 6.46 (dd, J=7.6, 1.0 Hz, 1H), 4.89-4.97 (m, 1H), 3.99 (td, J=8.5, 4.9 Hz, 1H), 3.86-3.92 (m, 1H), 3.80-3.86 (m, 1H), 3.61-3.68 (m, 1H), 2.96 (s, 3H), 2.15-2.25 (m, 1H), 1.98-2.08 (m, 1H), 1.23 (s, 6H). MS (ESI) m/z 393.2 [M+1]$^+$.

Example 126

6-(5-(Difluoro(tetrahydro-2H-pyran-4-yl)methyl)-[1,2,4]triazolo[1,5-a]pyridin-2-ylamino)-3,3-dimethylindolin-2-one

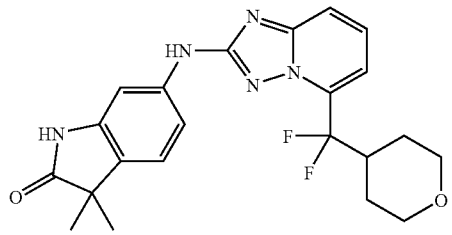

A. 2-Bromo-5-(difluoro(tetrahydro-2H-pyran-4-yl)methyl)-[1,2,4]triazolo[1,5-a]pyridine. (Diethylamino)sulfur trifluoride (0.845 mL, 6.45 mmol) was added to a stirred solution of (2-bromo-[1,2,4]triazolo[1,5-a]pyridin-5-yl)(tetrahydro-2H-pyran-4-yl)methanone (0.400 g, 1.290 mmol) in chloroform (5 mL) in a sealable vessel. Nitrogen was blown in to blow out air. The reaction mixture was sealed and heated at 50° C. for 4 h and then at 40° C. for 12 h. The resulting mixture was poured onto acetonitrile (20 mL) with stirring and then diluted with methanol (10 mL). The resulting yellow solution was concentrated on a rotary evaporator and then purified using flash chromatography (Biotage) (5-50% ethyl acetate in hexane) to give 2-bromo-5-(difluoro(tetrahydro-2H-pyran-4-yl)methyl)-[1,2,4]triazolo[1,5-a]pyridine (0.317 g, 0.954 mmol, 74% yield) as a light yellow solid. $^1$H NMR (400 MHz, DMSO-d$_6$) δ (ppm) 8.04 (d, J=8.98 Hz, 1H), 7.85 (dd, J=7.42, 8.98 Hz, 1H), 7.51 (dd, J=1.17, 7.42 Hz, 1H), 3.82-3.92 (m, 2H), 3.28 (td, J=3.71, 11.03 Hz, 2H), 3.06-3.24 (m, 1H), 1.42-1.58 (m, 4H); $^{19}$F NMR (376 MHz, DMSO-d$_6$) δ (ppm)-109.11 (d, J=14.93 Hz, 2F); MS (ESI) m/z 332.2 [M]$^+$, 334.2 [M+2]$^+$.

B. tert-Butyl 6-(5-(difluoro(tetrahydro-2H-pyran-4-yl)methyl)-[1,2,4]triazolo[1,5-a]pyridin-2-ylamino)-3,3-dimethyl-2-oxoindoline-1-carboxylate. A mixture of tris(dibenzylideneacetone)dipalladium(0) (0.085 g, 0.093 mmol) and 4,5-bis(diphenylphosphino)-9,9-dimethylxanthene (0.108 g, 0.187 mmol) in 1,4-dioxane (1.5 mL) was heated briefly with a heat gun until very hot and then added to tert-butyl 6-amino-3,3-dimethyl-2-oxoindoline-1-carboxylate (0.284 g, 1.027 mmol), 2-bromo-5-(difluoro(tetrahydro-2H-pyran-4-yl)methyl)-[1,2,4]triazolo[1,5-a]pyridine (0.310 g, 0.933 mmol), finely ground potassium carbonate (0.529 g, 3.83 mmol), and 1,4-dioxane (2 mL) in a sealable vessel with a stirbar. Nitrogen was blown in to blow out air. The resulting mixture was sealed, stirred vigorously, and heated at 100° C. for 2.5 h. After cooling to room temperature the resulting mixture was diluted with water and ethyl acetate, filtered through Celite, and the filter cake washed thoroughly with ethyl acetate. The layers of the filtrate were separated in a reparatory funnel. The organics were washed with brine, dried over magnesium sulfate, filtered, and concentrated on a rotary evaporator. The residue was taken up in dichloromethane and purified using flash chromatography (Biotage) (20-80% ethyl acetate in hexane) to give tert-butyl 645-(difluoro(tetrahydro-2H-pyran-4-yl)methyl)-[1,2,4]triazolo[1,5-a]pyridin-2-ylamino)-3,3-dimethyl-2-oxoindoline-1-carboxylate (0.423 g, 0.802 mmol, 86% yield) as a yellow foam-solid. $^1$H NMR (400 MHz, DMSO-d$_6$) δ (ppm) 9.97 (s, 1H), 8.22 (d, J=1.56 Hz, 1H), 7.72-7.77 (m, 1H), 7.68 (dd, J=7.03, 8.59 Hz, 1H), 7.50 (dd, J=1.95, 8.20 Hz, 1H), 7.32 (d, J=8.20 Hz, 1H), 7.29 (dd, J=1.17, 7.03 Hz, 1H), 3.85-3.95 (m, 2H), 3.36-3.54 (m, 1H), 3.27 (td, J=2.34, 11.32 Hz, 2H), 1.62 (s, 9H), 1.44-1.58 (m, 4H), 1.32 (s, 6H); $^{19}$F NMR (376 MHz, DMSO-d$_6$) δ (ppm)-109.47 (s, 2F); MS (ESI) m/z 528.4 [M+1]$^+$.

C. 6-(5-(Difluoro(tetrahydro-2H-pyran-4-yl)methyl)-[1,2,4]triazolo[1,5-a]pyridin-2-ylamino)-3,3-dimethylindolin-2-one. A stirred solution of tert-butyl 6-(5-(difluoro(tetrahydro-2H-pyran-4-yl)methyl)-[1,2,4]triazolo[1,5-c]pyridin-2-ylamino)-3,3-dimethyl-2-oxoindoline-1-carboxylate (0.416 g, 0.789 mmol) in acetic acid (7 mL) was heated at 110° C. under a reflux condenser under nitrogen for 4.5 h. The resulting yellow solution was loaded onto a Strata X—C ion exchange column from Phenomenex. The column was washed successively with water, acetonitrile, methanol, and then a mixture of 5% ammonium hydroxide, 45% methanol, and 50% dichloromethane. The product came off with the ammonium hydroxide eluent and was concentrated on a rotary evaporator and dried under high vacuum at 45° C. to give 6-(5-(difluoro(tetrahydro-2H-pyran-4-yl)methyl)-[1,2,4]triazolo[1,5-c]pyridin-2-ylamino)-3,3-dimethylindolin-2-one (0.141 g, 0.330 mmol, 42% yield) as a slightly yellow solid. $^1$H NMR (400 MHz, DMSO-d$_6$) δ (ppm) 10.35 (s, 1H), 9.81 (s, 1H), 7.76 (d, J=8.20 Hz, 1H), 7.67 (dd, J=7.22, 8.79 Hz, 1H), 7.34 (d, J=1.95 Hz, 1H), 7.24-7.32 (m, 2H), 7.17 (d, J=7.81 Hz, 1H), 3.86-3.96 (m, 2H), 3.36-3.51 (m, 1H), 3.27 (td, J=2.54, 11.42 Hz, 2H), 1.42-1.62 (m, 4H), 1.23 (s, 6H); $^{19}$F NMR (376 MHz, DMSO-d$_6$) δ (ppm)-109.47 (d, J=14.93 Hz, 2F); MS (ESI) m/z 428.3 [M+H]$^+$.

Example 127

4-((2-(3-(Methoxymethyl)-1H-indazol-6-ylamino)-[1,2,4]triazolo[1,5-a]pyridin-5-ylmethyl)piperazin-2-one

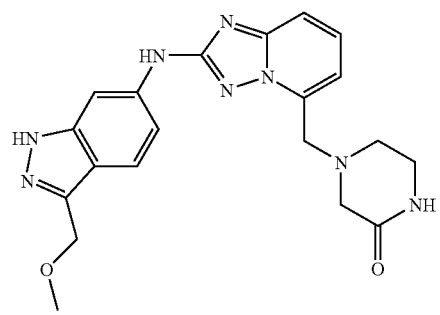

A. 4-((2-(3-(Methoxymethyl)-1-((2-(trimethylsilyl)ethoxy)methyl)-1H-indazol-6-ylamino)-[1,2,4]triazolo[1,5-a]pyridin-5-yl)methyl)piperazin-2-one. A mixture of tris(dibenzylideneacetone)dipalladium(0) (0.074 g, 0.081 mmol) and 4,5-bis(diphenylphosphino)-9,9-dimethylxanthene (0.094 g, 0.163 mmol) in 1,4-dioxane (1.5 mL) was heated briefly with a heat gun until very hot and then added to 3-(methoxymethyl)-1-((2-(trimethylsilyl)ethoxy)methyl)-1H-indazol-6-amine (0.250 g, 0.813 mmol), 4-((2-bromo-[1,2,4]triazolo[1,5-c]pyridin-5-yl)methyl)piperazin-2-one (0.252 g, 0.813 mmol), finely ground potassium carbonate (0.461 g, 3.33 mmol), and 1,4-dioxane (2 mL) in a sealable vessel with a stirbar. Nitrogen was blown in to blow out air. The resulting mixture was sealed, stirred vigorously, and heated at 100° C. for 5.5 h. After cooling to room temperature the reaction mixture was diluted with 20% methanol in dichloromethane with vigorous stirring. The resulting mixture was filtered through Celite and the filter cake washed with 20% methanol in dichloromethane. The filtrate was concentrated on a rotary evaporator, dissolved in DMSO and methanol, filtered, and purified using reverse-phase preparatory HPLC (15-70% acetonitrile+0.1% trifluoroacetic acid in water+0.1% trifluoroacetic acid, over 30 min). Fractions containing the desired product were loaded onto a Strata X—C ion exchange column from Phenomenex. The column was washed successively with water, acetonitrile, methanol, and then 5% ammonium hydroxide in methanol. The product came off with the 5% ammonium hydroxide in methanol eluent and was concentrated on a rotary evaporator and dried under high vacuum at 45° C. to give 4-((2-(3-(methoxymethyl)-1-((2-(trimethylsilyl)ethoxy)methyl)-1H-indazol-6-ylamino)-[1,2,4]triazolo[1,5-c]pyridin-5-yl)methyl)piperazin-2-one (0.133 g at 90% purity, 0.223 mmol, 27% yield) as a yellow solid.

B. 4-((2-(3-(Methoxymethyl)-1H-indazol-6-ylamino)-[1,2,4]triazolo[1,5-a]pyridin-5-yl)methyl)piperazin-2-one. 6 M HCl in water (0.410 mL, 2.459 mmol) was added to a stirred mixture of 4-((2-(3-(methoxymethyl)-1-((2-(trimethylsilyl)ethoxy)methyl)-1H-indazol-6-ylamino)-[1,2,4]triazolo[1,5-c]pyridin-5-yl)methyl)piperazin-2-one (0.132 g, 0.246 mmol) in ethanol (5 mL) at 60° C. The resulting mixture was stirred vigorously and heated at 60° C. under a reflux condenser under nitrogen for 12 h. The solvent was removed on a rotary evaporator. The residue was dissolved in hot DMSO, diluted with methanol, filtered, and purified using reverse-phase semi-preparatory HPLC (5-30% acetonitrile+0.1% trifluoroacetic acid in water+0.1% trifluoroacetic acid, over 30 min). Fractions containing the desired product were loaded onto a Strata X—C ion exchange column from Phenomenex. The column was washed successively with water, acetonitrile, methanol, and then 5% ammonium hydroxide in methanol. The product came off with the 5% ammonium hydroxide in methanol eluent and was concentrated on a rotary evaporator and dried under high vacuum at 45° C. to give the desired product (0.012 g, 0.030 mmol, 12% yield) as a white solid. $^1$H NMR (400 MHz, DMSO-d$_6$) δ (ppm) 12.67 (s, 1H), 9.86 (s, 1H), 8.19 (d, J=1.17 Hz, 1H), 7.86 (s, 1H), 7.51-7.65 (m, 3H), 7.24 (dd, J=1.76, 8.79 Hz, 1H), 7.11 (d, J=7.03 Hz, 1H), 4.66 (s, 2H), 4.11 (s, 2H), 3.29 (s, 3H), 3.17-3.27 (m, 4H), 2.80 (t, J=5.27 Hz, 2H); MS (ESI) m/z 407.5 [M+1]$^+$.

Example 128

(R)-3,3-Dimethyl-6-(5-((tetrahydrofuran-3-yl)methyl)-[1,2,4]triazolo[1,5-a]pyridin-2-ylamino)indolin-2-one and (S)-3,3-dimethyl-6-(5-((tetrahydrofuran-3-yl)methyl)-[1,2,4]triazolo[1,5-a]pyridin-2-ylamino)indolin-2-one

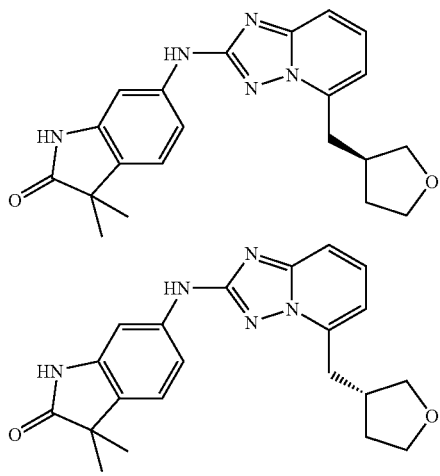

A. N-(6-(Tetrahydrofuran-3-carbonyl)pyridin-2-yl)pivalamide. A solution of N-(6-bromopyridin-2-yl)pivalamide (5.0 g, 19.5 mol) in toluene was cooled to 3-5° C., and a solution of isopropyl magnesium chloride in tetrahydrofuran (24.4 mL, 2 M) was added dropwise over a period of 1 h while maintaining the temperature below 5° C. After the resulting mixture was stirred at 5° C. for 12 h, dry N-methoxy-N-methyltetrahydrofuran-3-carboxamide (4.65 g, 29.3 mol) was added over 20 min at 10-15° C., and the mixture was stirred for 30 min at that temperature. The reaction mixture was quenched with water, and the resulting mixture was extracted with ethyl acetate. The combined organic layer was washed with brine, dried over sodium sulfate, concentrated, and purified on silica gel column (eluting with 5-50% ethyl acetate in petroleum ether) to give N-(6-(tetrahydrofuran-3-carbonyl)pyridin-2-yl)pivalamide (4.8 g, 89% yield) as a solid. $^1$H NMR (400 MHz, CHLOROFORM-d) δ (ppm) 8.46 (d, J=7.8 Hz, 1H), 8.00 (br s, 1H), 7.87 (m, 2H), 4.45 (m, 1H), 4.22 (t, J=7.8 Hz, 1H), 3.94 (m, 3H), 2.33 (m, 1H), 2.16 (m, 1H), 1.36 (s, 9H).

B. N-(6-(Hydroxy(tetrahydrofuran-3-yl)methyl)pyridin-2-yl)pivalamide. To a solution of N-(6-(tetrahydrofuran-3-carbonyl)pyridin-2-yl)pivalamide (4.7 g, 17.0 mmol) in ethanol (30 mL) was added sodium borohydride (1.30 g, 34.0 mmol) in portions at room temperature. When the starting material was consumed, the reaction mixture was quenched with water, and concentrated. The residue was washed with water and dried to give N-(6-(hydroxy(tetrahydrofuran-3-yl)methyl)pyridin-2-yl)pivalamide (4.0 g, 85% yield). $^1$H NMR (400 MHz, CHLOROFORM-d) δ (ppm) 8.16 (dd, J$_1$=2.0 Hz, J$_2$=8.4 Hz, 1H), 8.02 (br s, 1H), 7.71 (t, J=8.0 Hz, 1H), 7.00 (d, J=7.6 Hz, 1H), 4.59 (m, 1H), 4.12-3.68 (m, 6H), 2.63 (m, 1H), 1.32 (s, 9H).

C. N-(6-((Tetrahydrofuran-3-yl)methyl)pyridin-2-yl)pivalamide. To a solution of N-(6-(hydroxy(tetrahydrofuran-3-yl)methyl)pyridin-2-yl)pivalamide (3.95 g, 14.2 mmol) and triethylamine (1.44 g, 14.2 mmol) in dichloromethane (15 mL) was added methanesulfonyl chloride (1.62 g, 14.2 mmol) at 0° C., and the resulting solution was stirred at 0° C. for 30 min. The reaction mixture was evaporated under reduced pressure, and the residue was dissolved in acetic acid (5 mL). Zinc dust (4.62 g, 71 mmol) was added, and the mixture was stirred at 40° C. overnight under nitrogen. The reaction mixture was concentrated, diluted with ethyl acetate (50 mL) and water (10 mL), and neutralized to pH=9 with aqueous sodium hydroxide solution (5N). The organic layer was separated, and the aqueous layer was extracted with ethyl acetate (10 mL×3). The combined organic layer was dried, concentrated, and purified on silica gel column (eluting with 10-50% ethyl acetate in petroleum ether) to give N-(6-((tetrahydrofuran-3-yl)methyl)pyridin-2-yl)pivalamide (2.8 g, 75% yield). $^1$H NMR (400 MHz, CHLOROFORM-d) δ (ppm) 8.08 (d, J=8.1 Hz, 1H), 7.95 (br s, 1H), 7.62 (t, J=8.1 Hz, 1H), 6.87 (d, J=7.5 Hz, 1H), 3.91 (m, 3H), 3.50 (m, 1H), 2.76 (m, 3H), 2.03 (m, 1H), 1.66 (m, 1H), 1.32 (s, 9H).

D. 6-((Tetrahydrofuran-3-yl)methyl)pyridin-2-amine. A mixture of N-(6-((tetrahydrofuran-3-yl)methyl)pyridin-2-yl)pivalamide (2.8 g, 10.7 mmol) and potassium hydroxide in aqueous solution (10 mL, 2 M) was stirred at 100° C. for 12 h. The reaction mixture was extracted with ethyl acetate. The combined organic layer was washed with brine, dried over sodium sulfate, concentrated under reduced pressure, and purified by column chromatography on silica gel (eluting with 50% ethyl acetate in petroleum ether) to give 6-((tetrahydrofuran-3-yl)methyl)pyridin-2-amine (1.5 g, 78% yield). $^1$H NMR (400 MHz, CHLOROFORM-d) δ (ppm) 8.08 (t, J=8.0 Hz, 1H), 6.48 (d, J=8.0 Hz, 1H), 6.33 (d, J=8.0 Hz, 1H), 4.42 (br s, 2H), 3.91 (m, 2H), 3.77 (m, 1H), 3.47 (m, 1H), 2.67 (m, 3H), 2.04 (m, 1H), 1.66 (s, 1H).

E. 5-((Tetrahydrofuran-3-yl)methyl)-[1,2,4]triazolo[1,5-a]pyridin-2-amine. A solution of 6-((tetrahydrofuran-3-yl)methyl)pyridin-2-amine (1.5 g, 8.4 mmol) and O-ethyl carbonisothiocyanatidate (1.1 g, 8.4 mmol) in dioxane (20 mL) was stirred at room temperature for 5 h. When the starting material was consumed, the mixture was concentrated in vacuo. The residue was dissolved in a mixture of methanol (15 mL) and ethanol (15 mL). A mixture solution of hydroxylamine hydrochloride solution (2.9 g, 42 mmol) and N,N-ethyldiisopropylamine (3.26 g, 25.3 mmol) in a mixture of ethanol and methanol (v/v, 1:1, 20 mL) was added, and the mixture was stirred at room temperature for 2 h, at 70° C. overnight. The volatiles were removed under reduced pressure, and the residue was purified on silica gel column (eluting with 50% ethyl acetate in petroleum ether) to give 5-((tetrahydrofuran-3-yl)methyl)-[1,2,4]triazolo[1,5-c]pyridin-2-amine (1.7 g, 93% yield) as a solid. $^1$H NMR (400 MHz, CHLOROFORM-d) δ (ppm) 7.34 (m, 2H), 6.64 (dd, J$_1$=1.6

Hz, J₂=6.4 Hz, 1H), 4.56 (br s, 2H), 3.95 (m, 1H), 3.91 (m, 1H), 3.80 (m, 1H), 3.55 (m, 1H), 3.08 (d, J=7.6 Hz, 1H), 2.96 (m, 1H), 2.08 (m, 1H), 1.69 (s, 1H).

F. 3,3-Dimethyl-6-(5-((tetrahydrofuran-3-yl)methyl)-[1,2,4]triazolo[1,5-a]pyridin-2-ylamino)-1-((2-(trimethylsilyl)ethoxy)methyl)indolin-2-one. A degassed mixture of 5-((tetrahydrofuran-3-yl)methyl)-[1,2,4]triazolo[1,5-c]pyridin-2-amine (700 mg, 3.21 mmol), 6-iodo-3,3-dimethyl-1-((2-(trimethylsilyl)ethoxy)methyl)indolin-2-one (1.6 g, 3.85 mmol), tris(dibenzylideneacetone)dipalladium(0) (294 mg, 0.32 mmol), 4,5-bis(diphenylphosphino)-9,9-dimethylxanthene (372 mg, 0.64 mmol), and cesium carbonate (2.09 g, 6.42 mmol) in dioxane (20 mL) was stirred under nitrogen. The mixture was heated at 100° C. under nitrogen for 1 h, quenched by the addition of water, and extracted with ethyl acetate (15 mL x3). The combined organic layer was washed with brine, dried over sodium sulfate, and concentrated. The volatiles were removed under reduced pressure, and the residue was purified on silica gel column (eluting with 50% ethyl acetate in petroleum ether) to afford 3,3-dimethyl-6-(5-((tetrahydrofuran-3-yl)methyl)-[1,2,4]triazolo[1,5-a]pyridin-2-ylamino)-1-((2-(trimethylsilyl)ethoxy)methyl)indolin-2-one (500 mg, 31% yield). MS (ESI): m/z 508.4 [M+H]⁺.

G. (R)-3,3-Dimethyl-6-(5-((tetrahydrofuran-3-yl)methyl)-[1,2,4]triazolo[1,5-a]pyridin-2-ylamino)indolin-2-one and (S)-3,3-dimethyl-6-(5-((tetrahydrofuran-3-yl)methyl)-[1,2,4]triazolo[1,5-a]pyridin-2-ylamino)indolin-2-one. To a solution of 3,3-dimethyl-6-(5-((tetrahydrofuran-3-yl)methyl)-[1,2,4]triazolo[1,5-c]pyridin-2-ylamino)-1-((2-(trimethylsilyl)ethoxy)methyl)indolin-2-one (500 mg, 0.95 mmol) in dichloromethane (10 mL) was added 2,2,2-trifluoroacetic acid (3 mL), and the mixture was stirred for 2 h. The solution was concentrated under vacuum, and the residue was dissolved in a mixture of dioxane (10 mL) and aqueous ammonia solution (10 mL). The mixture was stirred for 30 min., the solvent was removed, and the residue was extracted with ethyl acetate. The solvent was removed, and the residue was purified by a reverse-phase preparatory HPLC (eluting with 24-54% acetonitrile+0.1% trifluoroacetic acid in water+0.1% trifluoroacetic acid, over 13 min) to give to give 3,3-dimethyl-6-(5-((tetrahydrofuran-3-yl)methyl)-[1,2,4]triazolo[1,5-c]pyridin-2-ylamino)indolin-2-one (200 mg, 54% yield) as a trifluoroacetic acid salt. The two enantiomers were separated by chiral supercritical fluid chromatography (Instrument: Berger MultiGram™ SFC, Mettler Toledo Co, Ltd; Column: OJ 250 mm*20 mm, 5um; Mobile phase: A: Supercritical CO₂, B: EtOH , A:B=65:35 at 40 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The first enantiomer eluted at 8.42 min (35 mg, 96.14% ee): ¹H NMR (400 MHz, METHANOL-d₄) δ (ppm) 7.55 (m, 2H), 7.47 (s, 1H), 7.39 (d, J=8.8 Hz, 1H), 7.22 (d, J=7.6 Hz, 1H), 7.17 (d, J=8.4 Hz, 1H), 6.93 (d, J=6.8 Hz, 1H), 3.98 (m, 2H), 3.82 (m, 1H), 3.63 (m, 1H), 3.25 (m, 2H), 3.04 (m, 1H), 2.12 (m, 1H), 1.79 (m, 1H), 1.34 (m, 6H); MS (ESI): m/z 378.2 [M+1]⁺. The second enantiomer eluted at 8.90 min (36 mg, 100% ee): ¹H NMR (400 MHz, METHANOL-d₄) δ (ppm) 7.57 (t, J=8.4 Hz, 2H), 7.50 (s, 1H), 7.41 (d, J=8.8 Hz, 1H), 7.24 (d, J=7.6 Hz, 1H), 7.17 (d, J=8.4 Hz, 1H), 6.93 (d, J=6.8 Hz, 1H), 3.98 (m, 2H), 3.82 (m, 1H), 3.63 (m, 1H), 3.25 (m, 2H), 3.04 (m, 1H), 2.12 (m, 1H), 1.79 (m, 1H), 1.34 (m, 6H); MS (ESI): m/z 378.2 [M+H]⁺.

Example 129 cis-6-(5-(4-Hydroxy-4-methylcyclohexylamino)-[1,2,4]triazolo[1,5-a]pyridin-2-ylamino)-3,3-dimethylindolin-2-one

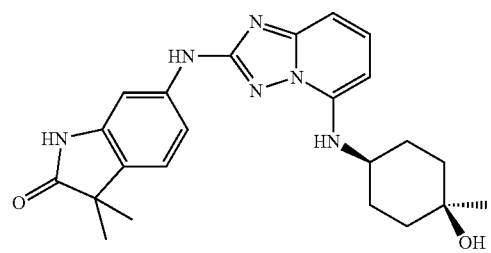

A. cis-4-(2-Bromo-[1,2,4]triazolo[1,5-a]pyridin-5-ylamino)-1-methylcyclohexanol. A mixture of 2,5-dibromo-[1,2,4]triazolo[1,5-a]pyridine (639 mg, 2.3 mmol), cis-4-amino-1-methylcyclohexanol (300 mg, 2.3 mmol), and triethylamine (464 mg, 4.6 mmol) in N,N-dimethylacetamide (10 mL) was stirred at 125° C. overnight. The reaction mixture was cooled to room temperature, poured into water, and extracted with ethyl acetate. The organic layer was concentrated under reduced pressure, and purified on silica gel column (eluting with 50% ethyl acetate in petroleum ether) to give cis-4-(2-bromo-[1,2,4]triazolo[1,5-a]pyridin-5-ylamino)-1-methylcyclohexanol (150 mg, 53% yield). ¹H NMR (300 MHz, METHANOL-d₄) δ (ppm) 7.56 (t, J=8.1 Hz, 1H), 6.83 (t, J=8.4 Hz, 1H), 6.28 (d, J=7.5 Hz, 1H), 3.42 (m, 1H), 1.70 (m, 8H), 1.20 (s, 3H); MS (ESI): m/z 326.6 [M+1]⁺.

B. cis-6-(5-(4-Hydroxy-4-methylcyclohexylamino)-[1,2,4]triazolo[1,5-a]pyridin-2-ylamino)-3,3-dimethylindolin-2-one. A mixture of cis-4-(2-bromo-[1,2,4]triazolo[1,5-c]pyridin-5-ylamino)-1-methylcyclohexanol (400 mg, 1.2 mmol), tert-butyl 6-amino-3,3-dimethyl-2-oxoindoline-1-carboxylate (340 mg, 1.2 mmol), 4,5-bis(diphenylphosphino)-9,9-dimethylxanthene (69 mg, 0.12 mmol), and cesium carbonate (585 mg, 1.8 mmol) in dioxane (10 mL) was degassed, then tris(dibenzylideneacetone)dipalladium (0) (55 mg, 0.06 mmol) was added under nitrogen, and the reaction mixture was stirred at 100° C. under nitrogen overnight. Dioxane was removed under reduced pressure, and the residue was purified on silica gel column (eluting with 50% ethyl acetate in petroleum ether) to give cis-6-(5-(4-hydroxy-4-methylcyclohexylamino)-[1,2,4]triazolo[1,5-c]pyridin-2-ylamino)-3,3-dimethylindolin-2-one (100 mg, 20% yield). ¹H NMR (400 MHz, METHANOL-d₄) δ (ppm) 7.47 (m, 2H), 7.16 (s, 2H), 6.71 (d, J=8.4 Hz, 1H), 6.19 (d, J=8.0 Hz, 1H), 3.51 (s, 1H), 1.99 (m, 2H), 1.82 (m, 4H), 1.63 (m, 2H), 1.28 (m, 11H); MS (ESI): m/z 421.3 [M+1]$^+$.

Example 130

5-(Difluoro(tetrahydro-2H-pyran-4-yl)methyl)-N-(3-methyl-1H-indazol-6-yl)-[1,2,4]triazolo[1,5-a]pyridin-2-amine

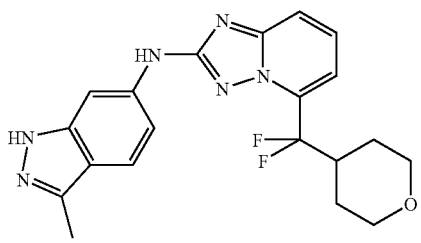

A. 2-Bromo-5-(difluoro(tetrahydro-2H-pyran-4-yl)methyl)-[1,2,4]triazolo[1,5-a]pyridine. (Diethylamino)sulfur trifluoride (4.26 mL, 32.2 mmol) was added to a stirred solution of (2-bromo-[1,2,4]triazolo[1,5-c]pyridin-5-yl)(tetrahydro-2H-pyran-4-yl)methanone (2 g, 6.45 mmol) in chloroform (40 mL) in a high pressure flask under nitrogen. The flask was sealed and heated at 50° C. for 16 h. The reaction was quenched with methanol (1 mL). The resulting mixture was diluted with ethyl acetate (200 mL) and washed with saturated aqueous sodium bicarbonate. The organics were washed with brine and then dried over magnesium sulfate, filtered, and concentrated on a rotary evaporator. The residue was purified using flash chromatography (5-50% ethyl acetate in hexane), to give the desired product (1.7 g, 5.12 mmol, 79% yield) as a light yellow solid. MS (ESI) m/z 334.2 [M+2]$^+$.

B. 5-(Difluoro(tetrahydro-2H-pyran-4-yl)methyl)-N-(3-methyl-1H-indazol-6-yl)-[1,2,4]triazolo[1,5-a]pyridin-2-amine. To a mixture of tris(dibenzylideneacetone)dipalladium(0) (0.082 g, 0.090 mmol) and 4,5-bis(diphenylphosphino)-9,9-dimethylxanthene (0.105 g, 0.181 mmol) in 1,4-dioxane (10 mL) was added 3-methyl-1-(tetrahydro-2H-pyran-2-yl)-1H-indazol-6-amine (0.209 g, 0.903 mmol), 2-bromo-5-(difluoro(tetrahydro-2H-pyran-4-yl)methyl)-[1,2,4]triazolo[1,5-a]pyridine (0.3 g, 0.903 mmol) and finely ground potassium carbonate (0.372 g, 2.69 mmol). The resulting mixture was sealed and stirred at 120° C. for 3 h. The resulting mixture was diluted with ethyl acetate (20 mL) and filtered. Saturated aqueous sodium bicarbonate was added and extracted with ethyl acetate (2×100 mL). The combined organics were dried over magnesium sulfate, filtered, and concentrated on a rotary evaporator to dryness. The residue was dissolved in 50% methanol in dimethylsulfoxide and purified using reverse-phase preparatory HPLC (20-70% acetonitrile+0.1% trifluoroacetic acid in water+0.1% trifluoroacetic acid, over 39 min). Fractions containing the desired product were concentrated on a rotary evaporator and aqueous hydrochloric acid 6M (25 mL) was added and stirred for 5 h. The solvent was removed on a rotary evaporator and residue was purified using reverse-phase semi-preparatory HPLC (5-40% acetonitrile+0.1% trifluoroacetic acid in water+0.1% trifluoroacetic acid, over 39 min). Fractions containing the desired product were loaded onto a Strata X—C ion exchange column from Phenomenex. The column was washed successively with water, acetonitrile, methanol, and then hot 10% ammonium hydroxide in methanol. The product came off with the 10% ammonium hydroxide in methanol and was concentrated on a rotary evaporator to dryness. The residue was crystallized from ethyl acetate in hexane and dried under high vacuum at 40° C. to give the desired product (0.165 g, 0.414 mmol, 45.9% yield) as a white solid. $^1$H NMR (400 MHz, DMSO-d$_6$) δ (ppm) 12.41 (s, 1H) 10.00 (s, 1H) 8.10 (s, 1H) 7.81 (d, J=8.59 Hz, 1H) 7.62-7.75 (m, 1H) 7.56 (d, J=8.59 Hz, 1H) 7.30 (d, J=7.42 Hz, 1H) 7.24 (dd, J=8.79, 1.76 Hz, 1H) 3.92 (d, J=10.93 Hz, 2H) 3.38-3.58 (m, 1H) 3.27 (td, J=11.13, 3.12 Hz, 2H) 2.44 (s, 3H) 1.40-1.66 (m, 4H). MS (ESI) m/z 399.2 [M+1]$^+$.

Example 131

(S)-2-Methyl-3-(2-(3-methyl-1H-indazol-6-ylamino)-[1,2,4]triazolo[1,5-a]pyridin-5-yl)propan-1-ol

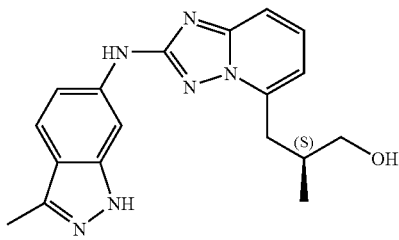

A. (S)-Methyl 3-(2-(bis(tert-butoxycarbonyl)amino)-[1,2,4]triazolo[1,5-a]pyridin-5-yl)-2-methylpropanoate. To a mixture of N,N-di-tert-butoxycarbonyl-5-bromo-[1,2,4]triazolo[1,5-c]pyridin-2-amine (3.0 g, 7.26 mmol) and tetrakistriphenylphosphine palladium (0) (2.097 g, 1.815 mmol) under an atmosphere of nitrogen was added at room temperature dry tetrahydrofuran (12.10 mL). A 0.5 M solution of (R)-(3-ethoxy-2-methyl-3-oxopropyl)zinc(II) bromide in tetrahydrofuran (43.6 mL, 21.78 mmol) was then added neat and the reaction was stirred at 65° C. for 3 h. The reaction was quenched with ice and the crude product was extracted with ethyl acetate. A large amount of salts slowly separated from the bright yellow extracts. The extracts were dried over magnesium sulfate. The extracts were evaporated to dryness. The residue was suspended in a small volume of dichloromethane, the solid was removed by filtration, and the filtrate purified by normal phase column chromatography (5-100% ethyl acetate in hexanes followed by 10% methanol in ethyl acetate). The product eluted as a mixture of mono-Boc-protected and deprotected product, contaminated with triphenyl phosphine oxide. The desired fractions were combined and evaporated to a yellow oil that turned into a foam under vacuum. (S)-Methyl 3-(2-(bis(tert-butoxycarbonyl)amino)-[1,2,4]triazolo[1,5-c]pyridin-5-yl)-2-methylpropanoate (3.6 g, 8.29 mmol, >95% yield) contaminated with (S)-methyl 3-(2-(tert-butoxycarbonylamino)-[1,2,4]triazolo[1,5-a]pyridin-5-yl)-2-methylpropanoate and triphenyl phosphine oxide was isolated without further attempt to remove the contaminant; MS (ESI) m/z 235.2 [M+1-Boc]$^+$.

B. (S)-Methyl 3-(2-amino-[1,2,4]triazolo[1,5-a]pyridin-5-yl)-2-methylpropanoate 2,2,2-trifluoroacetate. A suspension of a mixture of (S)-methyl 3-(2-(bis(tert-butoxycarbonyl)amino)-[1,2,4]triazolo[1,5-a]pyridin-5-yl)-2-methylpropanoate and (S)-methyl 3-(2-(tert-butoxycarbonylamino)-[1, 2,4]triazolo[1,5-c]pyridin-5-yl)-2-methylpropanoate (1.1 g, 3.29 mmol) in dichloromethane (5 mL) was treated at room temperature with trifluoroacetic acid (5.0 mL, 64.9 mmol) and the reaction was stirred at room temperature for 3 h. The solvents were removed under reduced pressure and the resulting orange oil was suspended in methanol (3 mL). The solid was removed by filtration and the filtrate was purified by preparative reverse HPLC (10-65% acetonitrile+0.1% trifluoroacetic acid in water+0.1% trifluoroacetic acid, 30 min, 1 run). The desired fractions were combined and evaporated to dryness. (S)-Methyl 3-(2-amino-[1,2,4]triazolo[1,5-a]pyridin-5-yl)-2-methylpropanoate 2,2,2-trifluoroacetate (0.511 g, 1.467 mmol, 44.6% yield) was isolated as a white solid. $^1$H NMR (400 MHz, METHANOL-d$_4$) δ (ppm) 7.76 (ddt, J=1.00, 7.80, 9.76 Hz, 1H), 7.48 (d, J=8.98 Hz, 1H), 7.16 (d, J=7.42 Hz, 1H), 3.59 (s, 3H), 3.39-3.47 (m, 1H), 3.15-3.26 (m, 2H), 1.19-1.25 (m, 3H); MS (ESI) m/z 235.3 [M+H]$^+$.

C. (2S)-Methyl 2-methyl-3-(2-(3-methyl-1-(tetrahydro-2H-pyran-2-yl)-1H-indazol-6-ylamino)-[1,2,4]triazolo[1,5-a]pyridin-5-yl)propanoate. A suspension of (S)-methyl 3-(2-amino-[1,2,4]triazolo[1,5-a]pyridin-5-yl)-2-methylpropanoate 2,2,2-trifluoroacetate (0.25 g, 0.718 mmol), 6-bromo-3-methyl-1-(tetrahydro-2H-pyran-2-yl)-1H-indazole (0.254 g, 0.861 mmol), 4,5-bis(diphenylphosphino)-9,9-dimethylxanthene (0.083 g, 0.144 mmol), tris(dibenzylideneacetone)dipalladium (0.066 g, 0.072 mmol), and cesium carbonate (1.403 g, 4.31 mmol) in dioxane (4 mL) under an atmosphere of nitrogen was heated to 75° C. After 1 h, the reaction was cooled to room temperature, quenched with water, and extracted with ethyl acetate. The residue was purified by biotage column chromatography (5-100% ethyl acetate in hexanes). The desired fractions were combined and evaporated to dryness. (2S)-Methyl 2-methyl-3-(2-(3-methyl-1-(tetrahydro-2H-pyran-2-yl)-1H-indazol-6-ylamino)-[1,2,4]triazolo[1,5-c]pyridin-5-yl)propanoate (0.201 g, 0.448 mmol, 62.4% yield) was isolated as a yellow solid. $^1$H NMR (400 MHz, DMSO-d$_6$) δ (ppm) 9.89 (d, J=1.56 Hz, 1H), 8.24 (dd, J=1.17, 5.47 Hz, 1H), 7.46-7.60 (m, 3H), 7.18-7.28 (m, 1H), 6.88-6.97 (m, 1H), 5.55-5.68 (m, 1H), 3.92 (d, J=11.32 Hz, 1H), 3.69 (d, J=2.73 Hz, 1H), 3.54 (d, J=5.86 Hz, 3H), 3.48 (dd, J=6.64, 10.15 Hz, 1H), 3.21-3.32 (m, 3H), 2.38-2.45 (m, 3H), 2.01-2.11 (m, 1H), 1.91-2.01 (m, 1H), 1.79 (br s, 1H), 1.59 (br s, 2H), 1.22 (dd, J=1.95, 6.64 Hz, 3H); MS (ESI) m/z 449.6 [M+1]$^+$.

D. (2S)-2-Methyl-3-(2-(3-methyl-1-(tetrahydro-2H-1-pyran-2-yl)-1H-indazol-6-ylamino)-[1,2,4]triazolo[1,5-a]pyridin-5-yl)propan-1-ol. A suspension of (2S)-methyl 2-methyl-3-(2-(3-methyl-1-(tetrahydro-2H-pyran-2-yl)-1H-indazol-6-ylamino)-[1,2,4]triazolo[1,5-c]pyridin-5-yl)propanoate (0.2 g, 0.446 mmol) in dry tetrahydrofuran (1.784 mL) was cooled to −78° C. and reacted with a 1.0 M solution of lithium aluminum hydride in tetrahydrofuran/heptane (0.892 mL, 0.892 mmol). After 30 min at low temperature, the reaction was warmed to room temperature and was stirred for an additional 30 min. The reaction was quenched with a saturated aqueous solution of ammonium chloride and the product was extracted with ethyl acetate. The extracts were dried over sodium sulfate and evaporated to dryness. (2S)-2-M ethyl-3-(2-(3-methyl-1-(tetrahydro-2H-pyran-2-yl)-1H-indazol-6-ylamino)-[1,2,4]triazolo[1,5-c]pyridin-5-yl)propan-1-ol (0.191 g, 0.454 mmol, quantitative yield) was isolated as a tan solid, that was used without further purification. $^1$H NMR (400 MHz, DMSO-d$_6$) δ (ppm) 9.85 (s, 1H), 8.25 (d, J=7.42 Hz, 1H), 7.49-7.61 (m, 2H), 7.42-7.49 (m, 1H), 7.23 (d, J=8.59 Hz, 1H), 6.92 (d, J=7.42 Hz, 1H), 5.61 (d, J=7.81 Hz, 1H), 4.64-4.73 (m, 1H), 3.88-3.98 (m, J=12.00 Hz, 1H), 3.71 (br s, 1H), 3.36-3.50 (m, 2H), 3.22-3.31 (m, 1H), 2.86-3.02 (m, 1H), 2.30-2.47 (m, 5H), 2.02-2.11 (m, 1H), 1.92-2.02 (m, 1H), 1.78 (br s, 1H), 1.58 (br s, 2H), 0.87-1.00 (m, 3H); MS (ESI) m/z 221.3 [M+H]$^+$.

E. (S)-2-Methyl-3-(2-(3-methyl-1H-indazol-6-ylamino)-[1,2,4]triazolo[1,5-a]pyridin-5-yl)propan-1-ol. A suspension of (2S)-2-methyl-3-(2-(3-methyl-1-(tetrahydro-2H-pyran-2-yl)-1H-indazol-6-ylamino)-[1,2,4]triazolo[1,5-c]pyridin-5-yl)propan-1-ol (0.111 g, 0.264 mmol) in methanol (2.0 mL) was treated at room temperature with a 6.0 N aqueous solution of hydrochloric acid (1.0 mL, 6.00 mmol) and the reaction was stirred at 40° C. for 30 min. The solvent was then removed under reduced pressure affording an off-white solid. The residue was purified by semi-preparative HPLC (10-60% acetonitrile+0.1% trifluoroacetic acid in water+0.1% trifluoroacetic acid, 2 runs, 30 min). The desired fractions were combined and neutralized with a 1.75 M aqueous solution of potassium carbonate. Upon removal of the organic solvent, a white precipitate formed that was collected by filtration and washed with water until neutral pH. The solid was dried under high vacuum for 2 h. (S)-2-Methyl-3-(2-(3-methyl-1H-indazol-6-ylamino)-[1,2,4]triazolo[1,5-c]pyridin-5-yl)propan-1-ol (0.056 g, 0.166 mmol, 63.1% yield) was isolated as a white solid. $^1$H NMR (400 MHz, DMSO-d$_6$) δ (ppm) 12.31 (s, 1H), 9.77 (s, 1H), 8.12 (s, 1H), 7.40-7.58 (m, 3H), 7.22 (d, J=8.98 Hz, 1H), 6.91 (d, J=6.64 Hz, 1H), 4.56-4.67 (m, 1H), 3.36-3.46 (m, 2H), 3.14-3.25 (m, 1H), 2.84-2.95 (m, 1H), 2.42 (s, 3H), 2.32 (d, J=7.03 Hz, 1H), 0.92 (d, J=6.64 Hz, 3H); MS (ESI) m/z 337.0 [M+1]$^+$.

Example 132 cis-6-(5-(4-Hydroxycyclohexylamino)-[1,2,4]triazolo[1,5-a]pyridin-2-ylamino)-1,4-dimethylindolin-2-one

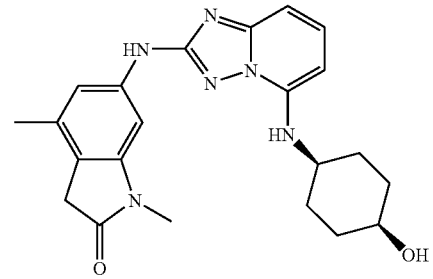

A. cis-6-(5-(4-Hydroxycyclohexylamino)-[1,2,4]triazolo[1,5-a]pyridin-2-ylamino)-1,4-dimethylindoline-2,3-dione. A mixture of 6-bromo-1,4-dimethylindoline-2,3-dione (0.34 g, 1.338 mmol), cis-4-(2-amino-[1,2,4]triazolo[1,5-a]pyridin-5-ylamino)cyclohexanol (0.446 g, 1.804 mmol), cesium carbonate (1.308 g, 4.01 mmol), tris(dibenzylideneacetone)dipalladium(0) (0.245 g, 0.268 mmol) and 4,5-bis(diphenylphosphino)-9,9-dimethylxanthene (0.310 g, 0.535 mmol) in 1,4-dioxane (6 mL) was degassed for 2 min and then stirred at 90° C. for 17 h. The cooled reaction solution was filtered through Celite and the filter cake was washed with dichloromethane and methanol. The solvent was removed under reduced pressure. Purification by column chromatography (eluting with 0-10% methanol in dichloromethane) provided the title compound as a yellow solid (0.22 g, 39.1% yield). MS (ESI) m/z 421.5 [M+H]$^+$.

B. cis-6-(5-(4-Hydroxycyclohexylamino)-[1,2,4]triazolo[1,5-a]pyridin-2-ylamino)-1,4-dimethylindolin-2-one. A suspension of cis-6-(5-(4-hydroxycyclohexylamino)-[1,2,4]triazolo[1,5-c]pyridin-2-ylamino)-1,4-dimethylindoline-2,3-dione (200 mg, 0.476 mmol) in hydrazine hydrate (4.6 mL, 95 mmol) was heated to 140° C. in a microwave for 2.25 h. The reaction was cooled to room temperature and the crude was purified by column chromatography (eluting with 0-10% methanol in dichloromethane). The resulting solid was triturated with methanol and ethanol, to give the title product as yellow solid (60 mg, 31% yield). $^1$H NMR (400 MHz, DMSO-d$_6$) δ (ppm) 9.53 (br s, 1H), 7.43 (t, J=8.20 Hz, 1H), 7.38 (s, 1H), 7.09 (d, J=1.56 Hz, 1H), 6.74 (d, J=8.20 Hz, 1H), 6.22 (d, J=7.81 Hz, 1H), 3.70-3.76 (m, 1H), 3.40 (s, 1H), 3.14 (s, 3H), 2.20 (s, 3H), 1.80-1.92 (m, 2H), 1.69-1.78 (m, 2H), 1.55-1.69 (m, 4H). MS (ESI) m/z 407.1 [M+1]$^+$.

Example 133

6-(5-(2-Methoxypyridin-4-yl)-[1,2,4]triazolo[1,5-a]pyridin-2-ylamino)-3,3-dimethylindolin-2-one

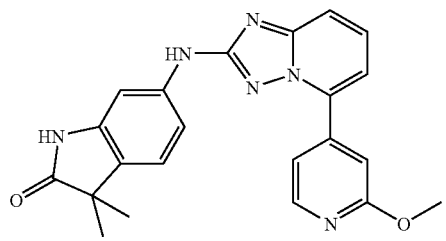

A. 2-Bromo-5-(2-methoxypyridin-4-yl)-[1,2,4]triazolo[1,5-a]pyridine. A degassed solution of 2,5-dibromo-[1,2,4]triazolo[1,5-a]pyridine (540 mg, 1.96 mmol), 2-methoxypyridin-4-ylboronic acid (300 mg, 1.96 mmol), saturated sodium carbonate solution (3.92 mL), and 1,1'-bis(diphenylphosphino)ferrocene palladium dichloride (143 mg, 0.196 mmol) in dioxane (10 mL) was heated at 100° C. for 5 hrs. After cooling to room temperature, the reaction mixture was concentrated under reduced pressure, and the residue was purified on silica gel column (eluting with 5-25% ethyl acetate in petroleum ether) to give 2-bromo-5-(2-methoxypyridin-4-yl)-[1,2,4]triazolo[1,5-c]pyridine (340 mg, 57% yield). $^1$H NMR (300 MHz, CHLOROFORM-d) δ (ppm) 8.28 (d, J=7.2 Hz, 1H), 7.70 (m, 1H), 7.59 (m, 1H), 7.34 (m, 1H), 7.25 (s, 1H), 7.15 (m, 1H), 3.95 (s, 3H); MS (ESI): m/z 304.9 [M+H]$^+$.

B. tert-Butyl 6-(5-(2-methoxypyridin-4-yl)-[1,2,4]triazolo[1,5-a]pyridin-2-ylamino)-3,3-dimethyl-2-oxoindoline-1-carboxylate. A mixture of 2-bromo-5-(2-methoxypyridin-4-yl)-[1,2,4]triazolo[1,5-c]pyridine (334 mg, 1.1 mmol), tert-butyl 6-amino-3,3-dimethyl-2-oxoindoline-1-carboxylate (303 mg, 1.1 mmol), cesium carbonate (717 mg, 2.2 mmol), 4,5-bis(diphenylphosphino)-9,9-dimethylxanthene (127 mg, 0.22 mmol), and tris(dibenzylideneacetone)dipalladium(0) (101 mg, 0.11 mmol) in dioxane (20 mL) was heated at 100° C. under nitrogen for 1.5 h. The solvent was removed, and the residue was purified on silica gel column (eluting with 5-100% ethyl acetate in petroleum ether) to give tert-butyl 64542-methoxypyridin-4-yl)-[1,2,4]triazolo[1,5-c]pyridin-2-ylamino)-3,3-dimethyl-2-oxoindoline-1-carboxylate (230 mg, 42% yield) as a solid. MS (ESI): m/z 501.1 [M+1]$^+$.

C. 6-(5-(2-Methoxypyridin-4-yl)-[1,2,4]triazolo[1,5-a]pyridin-2-ylamino)-3,3-dimethylindolin-2-one. A solution of tert-butyl 6-(5-(2-methoxypyridin-4-yl)-[1,2,4]triazolo[1,5-c]pyridin-2-ylamino)-3,3-dimethyl-2-oxoindoline-1-carboxylate (230 mg, 0.46 mmol) in a methanolic hydrochloride solution (10 mL, 2 M) was stirred at room temperature until LCMS analysis showed the starting material was consumed. The reaction mixture was evaporated under reduced pressure, and purified by a reverse-phase preparatory HPLC (eluting with 35-65%: acetonitrile+0.075% trifluoroacetic acid in water+0.075% trifluoroacetic acid, over 15 min) to give 6-(5-(2-methoxypyridin-4-yl)-[1,2,4]triazolo[1,5-c]pyridin-2-ylamino)-3,3-dimethylindolin-2-one as a trifluoroacetic acid salt, which was converted to a hydrochloride salt (102 mg, 55.4% yield). $^1$H-NMR (400 MHz, METHANOL-d$_4$) δ (ppm) 8.53 (d, J=5.6 Hz, 1H), 8.11 (m, 1H), 7.91 (m, 4H), 7.26 (m, 3H), 4.21 (s, 3H), 1.37 (s, 6H); MS (ESI): m/z 401.2 [M+H]$^+$.

5.2 Biological Examples 5.2.1 Syk HTRF Assay Protocol

Test compounds were prepared at a concentration of 1.5 mM in DMSO followed by 3-fold dilutions in Greiner 394 well polypropylene plates. A 1:4 dilution of compounds by 8 µL/well transfer from the polypropylene plates to 24 µL/well Assay Buffer in Costar 3710 384 well black plates was then performed. Kinases (13 µL/well) or Assay Buffer only (background controls; 50 mM HEPES pH 7.6, 1 mM DTT, 10 mM MgCl$_2$, 0.01% Triton X100, 0.01% BSA and 0.1 mM EDTA) were added to Costar 3710 384-well black plates for the HTRF assays (Carna Biosciences) and compound was added from the 1:4 dilution plate. Syk start mix (87.5 µM ATP, 80 nM Substrate Peptide (American Peptide Company 332722) was added and the mixture was incubated at room temperature for 1 hour. Syk Stop Solution (120 mM EDTA in dilution buffer) was then added to the Syk HTRF assay plate and incubated at room temperature on a shaker for 2 minutes. Syk Antibody Mix (4.86 µg/mL DyLight 647 Streptavidin (Pierce 21824); 1 µg/mL Lance Eu-Anti-Phosphotyrosine (PerkinElmer AD0069)) was added to the Syk HTRF assay plate and the mixture was further incubated at room temperature for >4 h. Time resolved fluorescence was read in assay plates on a PerkinElmer EnVision. HTRF assays were performed using 320 nm excitation, 60 µs delay, 665 nm and 615 nm emission. Data was expressed by division of 665 nm by 615 nm emissions.

5.2.2 HTRF-Ulight PLK1 Enzyme Assay

The assay described below is designed to measure the activity of PLK1 kinase via the transfer of phosphate to a peptide substrate. The PLK1 kinase assay was carried out in a 384-well black plate (Corning cat#3710) at a final volume of 25 pt. ATP was used at a final concentration of 3 µM, 1× the apparent Km. PLK1 kinase was purchased from Carna Biosciences (cat #05-157) and was diluted in Assay Buffer (50 mM HEPES pH 7.6, 1 mM DTT, mM MgCl$_2$, 0.01% triton X-100, 0.01% BSA, 0.1 mM EDTA) to give a final assay concentration of 15 ng/well (11 nM). The peptide substrate, ULight-p70 S6K (Thr389) Peptide and Europium-anti-phospho-p70 S6K (Thr389) Antibody were purchased from PerkinElmer (cat #TRF0126, TRF0214). Test compound was diluted in 100% DMSO and 0.5 µL was added to 14.5 µL kinase. Enzyme and compound were allowed to equilibrate at room temperature for minutes. The reaction was started with the addition of 10 µl 2.5×ATP and 2.5×ULight-p70S6K peptide (25 nM final assay condition) in Assay Buffer. Reactions were allowed to proceed for 90 minutes before addition of 10

µL Stop Solution/Detection mix (14 mM EDTA, 0.5 nM Eu-anti-phos-p70 AB final). After 30 minute incubation at room temperature, the reactions were read on the Envision (excitation at 330 nM and emission filters at 665 nM and 615 nM).

Heteroaryl Compounds as described herein have, or are expected to have an $IC_{50}$ value of <10 µM, with some compounds having an $IC_{50}$ of <1 µM, and others an $IC_{50}$ of <0.1 µM.

5.2.3 FLT3 HTRF Assay Protocol

Test compounds were prepared at a concentration of 1.5 mM in DMSO followed by 3-fold dilutions in Greiner 394 well polypropylene plates. A 1:4 dilution of compounds by 8 µL/well transfer from the polypropylene plates to 24 µL/well Assay Buffer (50 mM HEPES pH 7.6, 1 mM DTT, 10 mM $MgCl_2$, 0.01% Triton X100, 0.01% BSA and 0.1 mM EDTA) in Costar 3573 384 well black plates was then performed. Kinase (13 µL/well of 154 ng/mL FLT3, SignalChem F12-11G-05) or Assay Buffer only (background controls) were added to Costar 3573 384-well black plates and compound (2 µL/well) was added from the 1:4 dilution plate. Substrate/detection mixture (10 µL/well) (1250 µM ATP, 500 nM Gastin Precursor (Tyr 87) Biotinylated Peptide (Cell Signaling Technology 1310), 1.65 µg/mL (30 nM) DyLight 649 Streptavidin (Pierce 21845), 750 ng/mL Lance Eu-Anti-Phosphotyrosine (PerkinElmer AD0069)) was added and the mixture was incubated at room temperature for 1 hour. 10 µL/well of a mixture of 60 mM EDTA/0.01% Triton X100 was then added to the FLT3 HTRF assay plate and mixed on a shaker for 2 minutes. The mixture was further incubated at room temperature for >1 h. Time resolved fluorescence was read in assay plates on a PerkinElmer EnVision. HTRF assays were performed using 320 nm excitation, 60 µs delay, 665 nm and 615 nm emission. Data was expressed by division of 665 nm by 615 nm emissions.

Heteroaryl Compounds as described herein were shown to have, or will be shown to have an $IC_{50}$ value of <10 µM, with some compounds having an $IC_{50}$ of <1 µM, and others an $IC_{50}$ of <0.1 µM.

5.2.4 JAK2 HTRF Assay Protocol

Test compounds were prepared at a concentration of 1.5 mM in DMSO followed by 3-fold dilutions in Greiner 394 well polypropylene plates. A 1:4 dilution of compounds by 8 µL/well transfer from the polypropylene plates to 24 µL/well Assay Buffer (50 mM HEPES pH 7.6, 1 mM DTT, 10 mM $MgCl_2$, 0.01% Triton X100, 0.01% BSA and 0.1 mM EDTA) in Costar 3573 384 well black plates was then performed. Kinase (13 µL/well of 4.6 ng/mL JAK2, Millipore 14-511) or Assay Buffer only (background controls) were added to Costar 3573 384-well black plates and compound (2 µL/well) was added from the 1:4 dilution plate. Substrate/detection mixture (10 µL/well) (30 nM DyLight 647-Streptavidin (Pierce 21824), 750 ng/mL Eu-anti-phospho-Tyrosine PerkinElmer AD0069), 37.5 µM ATP and 500 nM FLT3 (Tyr 589) Biotinylated Peptide (Cell Signaling Techology 1305) was added and the mixture was incubated at room temperature for 1 hour. 10 µL/well of a mixture of 60 mM EDTA/0.01% Triton X100 was then added to the JAK2 HTRF assay plate and mixed on a shaker for 2 minutes. The mixture was further incubated at room temperature for >1 h. Time resolved fluorescence was read in assay plates on a PerkinElmer EnVision. HTRF assays were performed using 320 nm excitation, 60 µs delay, 665 nm and 615 nm emission. Data was expressed by division of 665 nm by 615 nm emissions.

Heteroaryl Compounds as described herein were shown to have, or will be shown to have an $IC_{50}$ value of <10 µM, with some compounds having an $IC_{50}$ of <1 µM, and others an $IC_{50}$ of <0.1 µM.

5.2.5 Syk Functional Assay Protocol:CD69 Expression in anti-IgM Stimulated Primary B-Cells Primary B-cells were purified from Buffy coat cell preparations obtained from healthy human donors at San Diego Blood Bank (SDBB). Cells were maintained in RPMI/10% FBS. Cells were counted and the cell density was adjusted to 1 min/mL in RPMI growth media. A compound pretreatment plate in a 96 well round-bottom format was prepared with enough cell volume to cover the desired number of wells, assuming 50 µL cells/well in the treatment plate. In a separate 96 well plate, compounds were diluted 1:50 into RPMI growth media. 22 µL of the diluted compound solution was added to 200 µL cells in the compound pretreatment plate. The mixture was placed in a tissue culture incubator for 30-60 minutes. 20 µg/mL anti-IgM solution in RPMI growth media was prepared and 50 µL was added per well into a new 96 well round bottom plate (cell stimulation plate). 50 µL of compound pretreated cells were added to the anti-IgM containing plate using a multichannel pipettor and the mixture was incubated for 12-14 hours at 37° C. Following incubation, the plate was spun at 1200 rpm for 5 minutes and the media was removed. 100 µL of CD69 antibody solution per well was added, the plate was gently tapped to mix, then incubated in the dark at room temperature for 30 minutes. Following 30 minutes of incubation the plate was spun, and washed once with 250 µL stain buffer then spun to retrieve the final cell pellet which was resuspended in 100 µL stain buffer and read on the cytometer for % positive.

Heteroaryl Compounds as described herein have, or are expected to have an $IC_{50}$ value of <10 µM, with some compounds having an $IC_{50}$ of <1 µM, and others an $IC_{50}$ of <0.1 µM.

5.2.6 Syk Functional Assay: IgE-dependent Beta-hexosaminidase Secretion from the LAD2 Human Mast Cell Line LAD2 cells (NIH; Kirshenbaum, et al., Leukemia Research 27:677-682, 2003) were plated into a 96 well format, sensitized through FccR with NP-IgE, and degranulated by crosslinking with $NP_{16}$—BSA. The supernatants were collected and the secretory granule components including beta-hexosaminidase were measured in various colorimetric assays.

Briefly, LAD2 cells were gently dislodged from a culture flask, collected, and spun down at 1200 rpm for 5 minutes. The spent culture media was removed and saved and the cells were resuspended at 0.8-1 million/mL in spent culture media. 100 µL of 0.5 ug/mL NP-IgE was plated in the spent culture media into a round bottom 96 well plate. 100 µL cells were added to the plate and placed back in a tissue culture incubator for 12-14 hours to sensitize the cells and load the FccR receptors. Following a 12-14 hour incubation the plate was spun at 1200 rpm for 5 minutes. The media was removed with a multichannel pipetor and the cell pellets were resuspended in 100 µL, Modified Tyrode's buffer. The cells were allowed to rest for 3.5 hours in a tissue culture incubator. The compounds were diluted 1:50 in Modified Tyrode's buffer and then 11 µL of compound solution was added to each well (giving a 0.2%

DMSO final concentration). The compound was pre-incubated for 30-60 minutes in a tissue culture incubator. Following pre-incubation 12 μL of 1.0 μg/mL $NP_{16}$—BSA diluted in Modified Tyrode's buffer was added, making the total volume in the well 123 μL. Ionomycin at 100 nM final can be added instead of NP—BSA as a Syk-independent control for stimulation. The plate was incubated in a tissue culture incubator for 90 minutes. Following incubation the plate was spun at 1200 rpm for 5 minutes, and 75 μL of supernatant (SN) was transferred to an empty 96 well plate for storage. The remaining SN was removed from the cell plate and discarded. 125 μL 0.1% triton X-100 in Modified Tyrode's buffer was added to the cell pellet, pipetted up/down to lyse the cells and the mixture was incubated on ice for 15 min. 30 μL SN from the storage plate or 5 μL cell pellet lysate plus 25 μL 0.1% Triton solution was added to a new 96 well flat-bottom plate in identical layout for the final plate read. 150 μL PNAG substrate was added to all wells and the plate was incubated at 37° C. for 1 hour. 50 μL stop solution (0.32 M glycine, 2.4 g/100 mL; 0.2 M sodium carbonate, 2.5 g/100 mL) was added to each well and the plate was read immediately at 405 nm. Data is expressed as % release per well (after subtracting background from all wells)=100×(SN/(SN+6× cell lysate)).

Heteroaryl Compounds as described herein have, or are expected to have an $IC_{50}$ value of <10 μM, with some compounds having an $IC_{50}$ of <1 μM, and others an $IC_{50}$ of <0.1 μM.

5.2.7 CD14+Derived Macrophage Cell Based Assay

Cryopreserved human CD14+ monocytic cells were isolated from peripheral blood of screened, healthy donors given G-CSF (Neupogen) for 4 days to mobilize cells to the peripheral blood (Lonza). CD14+ Monocytes were isolated using positive immunomagnetic selection directed against CD14. Cells were cultured in growth media containing RPMI 1640, 10% FBS and Penicillin+Streptomycin and were then plated at 50,000 cells/200 μL/well of Growth Medium supplemented with 100 ng/mL GM-CSF (Pepro Tech) for 5 days in 5% $CO_2$ and 37° C. incubator to differentiate the cells into macrophages. Following differentiation, CD14+ derived macrophages were pretreated with compound for 30 minutes and stimulated with Biotin-SP conjugated goat anti-human IgG (Jackson ImmunoResearch Labs) for 8 hours in a 96-well format in 5% $CO_2$ and 37° C. incubator. Following incubation, 100 μl/well supernatant was collected and transferred to a new 96 well U bottom plate for measurement of TNF-α using the Mesoscale Discovery human TNF-α cytokine assay.

Heteroaryl Compounds as described herein have, or are expected to have an $IC_{50}$ value of <10 μM, with some compounds having an $IC_{50}$ of <1 μM, and others an $IC_{50}$ of <0.1 μM.

5.2.8 Syk Biomarker Assay Protocol:phosphoBLNK Measurement by PhosFlow in anti-IgM Stimulated Ramos Ramos B-cell lymphoma (clone RA1, CRL1596; ATCC) cells were suspended at 1 min/mL in spent culture media. A compound pretreatment plate was prepared in a 96 well round-bottom format with enough cell volume to cover the desired number of wells, assuming 50 μL cells/well in the treatment plate (e.g. for 4 wells 200 μL cells was added). In a separate 96 well plate, compounds were diluted 1:50 into spent culture media. 22 μL of diluted compound was added to 200 μL cells in the compound pretreatment plate and the plate was placed back in the tissue culture incubator for 30-60 minutes. 50 μL of anti-IgM (AffiniPure F(ab') fragment goat anti-human IgM (Jackson, cat. 109-006-129, 1.3 mg/mL) (40 μg/mL in spent culture media) per well was added into a new 96 well round bottom plate (cell stimulation plate). Using a multichannel pipettor, 50 μL of compound pretreated cells were quickly added to the anti-IgM containing plate, and the plate was placed back in the tissue culture incubator for 10 minutes. An equal volume (100 μL) of prewarmed CytoFix reagent was added to all wells of the cell stimulation plate and the plate was placed back into the tissue culture incubator for 10 minutes, then spun at 1200 rpm for 5 minutes. The media was gently dumped out and the plate was blotted dry. Perm/Wash Buffer (100 μL) was added to all wells and the plate was left at room temperature for 10 minutes, then spun at 1200 rpm for 5 minutes. The media was gently dumped out and the plate was blotted dry. The cells were then washed three times with 200 μL BSA Stain Buffer (BD Pharmingen, cat 554657), the plate was spun and the supernatant was removed. 100 μL of pBLNK antibody solution (PE mouse anti-phosphoBLNK (pY84, BD Pharmingen, cat. 558442) per well was added to the plate, gently mixed and then incubated in the dark at room temperature for 30 minutes. The plate was washed once with 200 μL BSA Stain buffer, spun and the supernatant was removed. The final cell pellet was resuspended in 100 μL BSA Stain buffer and read on a cytometer.

Heteroaryl Compounds have, or are expected to have, an $IC_{50}$ below 30 μM in this assay, with some compounds having an $IC_{50}$ below 10 μM, and others having an $IC_{50}$ below 1 μM.

5.2.9 Syk Biomarker Assay Protocol: pSyk (Y525/526) Expression in tetracycline Induced TEL-Syk Expressing HEK 293 Cells by In-Cell Western A stable clone expressing the Tel-Syk protein, containing N-terminal Tel (a.a. 1-336) fused to the catalytic domain (a.a. 341-612) of Syk, was generated in the HEK 293 T-REx™ cell line. Cells are maintained in DMEM/10% tetracycline free FBS with 0.5 mg/mL zeocin and 5 μg/mL blasticidin. Cells are seeded at 50,000 per well in a black poly-D-lysine coated 96-well plate and rested overnight at 37° C., 5% $CO_2$. Tel-Syk expression is induced with 1 μg/mL tetracycline for 6 hours at 37° C., 5% $CO_2$. Following the induction, cells are treated with diluted compounds for 90 minutes. After compound incubation, the cells are fixed in 150 μl of 4% formaldehyde for 20 min, then permeabilized in PBS+0.1% Triton X-100 by washing five times for 5 min for a total of 25 minutes. The plate is blocked with 100 μl Odyssey blocking buffer (Licor) for at least 90 min, then incubated in 100 μl of primary antibody solution (rabbit anti-Syk pY525/526 at 1:1000, and mouse anti-V5 at 1:2500 in Odyssey blocking buffer) overnight at 4° C. on a rocking platform. The plate is washed 5 times for 5 min with PBS+0.1% Tween-20 (PBST) on a shaker at room temperature. The secondary antibody solution (anti-rabbit AF680 at 1:1000, and anti-mouse IR800 at 1:1000 in Odyssey blocking buffer) is added at 100 μl per well and the plate is incubated for one hour at room temperature, shaking. The plate is then washed 5 times for 5 minutes with PBST and the buffer removed by aspiration after the final wash. The plate is scanned on the Licor Odyssey and the pSyk expression is normalized to V5.

Heteroaryl Compounds have, or are expected to have, an $IC_{50}$ below 30 μM in this assay, with some compounds having an $IC_{50}$ below 10 μM, and others having an $IC_{50}$ below 1 μM.

5.2.10 Syk Functional Assay:Cell-Titer Glo Viability Assay in SU-DHL-4, SU-DHL-5 and Pfeiffer Cells The assay was designed to measure cytotoxic activity of the Heteroaryl Compounds in DLBCL cells. SU-DHL-4, SU-DHL-5 and Pfeiffer cells were obtained from DSMZ (German Collection of Microorganisms and Cell Cultures). Culture medium was RPMI-1640 supplemented with 10% fetal bovine serum (FBS) and 100 units/mL penicillin/100 µg/mL streptomycin.

Briefly, 100 µL of a cell suspension containing 10,000 cells was plated into each well of 96-well opaque-walled plates. Compounds and controls were serially diluted in DMSO and culture medium according to standard compound dilution protocol. 11 µL of compound dilutions, including the DMSO control, was added in triplicate to the cells using a repeat pipettor. This yielded final concentrations of 30 µM, 10 µM, 3 µM, 1 µM, and 0.3 µM containing 0.2% DMSO in each well. After 72 h of compound treatment, the cell viability was determined with CellTiter-Glo Reagent according to the manufacturer's protocol. Briefly, 100 µL of reconstituted CellTiter-Glo Reagent was added to each well of the 96-well plate. Luminescence signals were measured using the Victor 2 microplate reader. For each cell line, $IC_{50}$ was calculated using vehicle DMSO control as 100%.

Heteroaryl Compounds have, or are expected to have, an $IC_{50}$ below 30 µM in this assay, with some compounds having an $IC_{50}$ below 10 µM, and others having an $IC_{50}$ below 1 µM.

5.2.11 Cancer Cell Screening Assay

All hematological and solid cancer cell lines, unless otherwise noted, were obtained from commercial sources (ATCC, DMSZ, NCl, or CellTrends). OCI-LY-3 and OCI-LY-10 were obtained from Dr. Louis Staudt. All hematological cancer cell lines, unless otherwise noted, were maintained in RPMI 1640 supplemented with 10% fetal bovine serum. OCI-LY-3, OCI-LY-7, OCI-LY-10 were maintained in IMDM+20% human plasma and 55 µM B-mercaptoethanol. All breast cancer cell lines, unless otherwise noted, were maintained in RPMI 1640 supplemented with 10% fetal bovine serum. BT-20, CAL-120, CAL-51, CAL-85-1, CAMA-1, KPL-1, MDA-MB-134-VI, MDA-MB-157, MDA-MB-361, MDA-MB-415, MDA-MB-436, MDA-MB-453, MDA-MB-468, UACC-812 were maintained in DMEM supplemented with 10% fetal bovine serum. MCF-12A was maintained in DMEM/F12+5% horse serum, 20 ng/mL EGF, 100 ng/mL cholera toxin, 0.01 mg/mL insulin, and 500 ng/mL hydrocortisone.

All cancer cell lines were optimized for density and time in 384-well plates. For hematological cancer cell lines, 40 µL of cells were plated at a optimal density and allowed to grow overnight at 37° C./5% $CO_2$ and then treated with a serial dilution of Heteroaryl Compound. After 72 hours, cell viability was measured using CellTiterGlo (Promega) and read for luminescence. For breast cancer cell lines, serial dilutions of Compound were spotted via an acoustic dispenser into empty 384-well plates, sealed, and stored at −20° C. for up to 1 month. Forty µL of cells were then plated and allowed to grow for 96 hours at 37° C./5% $CO_2$. After 96 hours, cell viability was measured using CellTiterGlo (Promega) and read for luminescence. Results were expressed as an $IC_{50}$, which is the compound concentration required to inhibit 50% of the untreated control cells. Results were also expressed as a $GI_{50}$, which is the compound concentration required to inhibit the growth of the untreated control cells during the 96 hours of compound treatment.

Some of the typical human cancer cell lines that can be used in the above assay are: AU565, BT-20, BT-474, BT-483, BT-549, CAL-120, CAL-51, CAL-85-1, CAMA-1, DU4475, EFM-19, EFM-192A, HCC1143, HCC1187, HCC1428, HCC1500, HCC1569, HCC1937, HCC1954, HCC202, HCC2157, HCC38, HCC70, HS578T, KPL-1, MCF10A, MCF12A, MCF7, MDA-MB-134-VI, MDA-MB-157, MDA-MB-175-VII, MDA-MB-231, MDA-MB-361, MDA-MB-415, MDA-MB-435, MDA-MB-436 MDA-MB-453, MDA-MB-468, NCI/ADR-RES, SK-BR-3, T47D, UACC-812, ZR-75-1, ZR-75-30 as representatives of breast cancer cell lines; and BL-41, CCRF-CEM, Daudi, DG-75, DOHH-2, EHEB, Farage, GRANTA-519, HL-60, HT, JEKO-1, JIY-OYE, JVMO2, K562, KARPAS-1106P, Karpas-231, KARPAS-299, Karpas-422, Kasumi-1, Kasumi-2, Kasumi-3, KG-1, KM-H2, KMS-12-PE, KOPN-8, L-1236, L-363, LP-1, MEC-1, MHH-PREB-1, Mino, MN-60, MOLM-13, Molt-4, NALM-19, Namalwa, Namalwa.CSN/70, NCI-H929, OCI-LY-10, OCI-LY-19, OCI-LY-3, OCI-LY-7, OPM-2, Pfeiffer, RAMOS, RC-K8, REC-1, RI-1, RL, RPMI-8226, SC-1, SK-MM-2, SR, SU-DHL-1, SU-DHL-10, SU-DHL-16, SU-DHL-4, SU-DHL-5, SU-DHL-6, U-DHL-8, Tanoue, THP-1, $TOLED_0$, U266B1, U-698-M, WSU-DLCL2, WSU-FSCCL, WSU-NHL as representatives of hematological cancer cell lines.

Heteroaryl Compounds as described herein have, or are expected to have, an $IC_{50}$ or $GI_{50}$ value of <10 µM, with some compounds having an $IC_{50}$ or $GI_{50}$ of <1 µM, and others an $IC_{50}$ or $GI_{50}$ of <0.1 µM.

5.2.12 Cytotoxic Activity in CLL Cells

Frozen PBMC from CLL patients (Conversant Healthcare Systems, Inc.) were thawed, washed once and suspended in RPMI (Invitrogen) supplemented with 10% FBS (HyClone) at 1 million cells/mL. Typically, PBMC presenting more than 90% CD19+CD5+ blasts cells as assessed by flow cytometry (using BD Biosciences antibodies) were used for the assays. Cells (100 µL) were plated in 96 well plates. Heteroaryl Compounds were added in 100 µL of medium in concentrations varying from 0.001 to 10 µM. Compounds can be added alone or in combination with other agents (e.g. lenalidomide at 0.1 to 10 µM, fludarabine at 0.01 to 10 µM, or CD40L (Invitrogen) at 1 to 100 ng/mL). Cells were incubated for 3 days.

Alternatively, the cells can be pre-treated overnight with the second active agents in 50 µL (dosing as above) and then treated with Heteroaryl Compounds (0.001 to 10 µM) and incubated for an additional 3 days.

Cytotoxic activity was measured by Annexin V/7AAD (BD Pharmingen) using the FACSArray flow cytometer. The data was analyzed using FlowJo software. Results were expressed either as percentage of apoptotic cells (Annexin V positive cells) or percentage of viable cells (Annexin V negative cells).

Heteroaryl Compounds as described herein have or are expected to have an $IC_{50}$ value of <10 µM, with some compounds having an $IC_{50}$ of <1 µM, and others an $IC_{50}$ of <0.1 µM.

5.2.13 In Vivo Passive Cutaneous Anaphylaxis and passive Arthus Reaction in the Rat Intradermal injection of antibodies specific to dinitrophenol (DNP; rat-antiDNP IgE (PCA) or anti-DNP IgG (Arthus reaction)) followed by intravenous (IV) injection of antigen (DNP—BSA) causes a rapid inflammatory response characterized by mast cell degranulation, vascular leakage and immune complex deposition at the injection sites. In this model system, test compounds are administered at several timepoints prior to administration of antigen. A solution of rat anti-DNP IgE or IgG (1:1000 dilution) is injected intradermally. Twenty four hours later an intravenous injection of DNP conjugated to bovine serum albumin (DNP—BSA; 1 mg/kg of body weight) in solution containing 2% Evans blue dye is administered. The degree of edema is measured in the dorsal skin of CD/IGS rats using Evan's blue dye as an indicator of local tissue edema. Dye is extracted from the tissue following formamide incubation and the absorbance of this extract is read at 610 nm.

Heteroaryl Compounds as described herein have, or are expected to have, an $ED_{50}$ value of <100 mg/kg, with some compounds having an $ED_{50}$ of <10 mg/kg, and others an $ED_{50}$ of <1 mg/kg.

5.2.14 In Vivo Collagen Induced Arthritis (CIA) Model in the Rat

Rheumatoid arthritis (RA) is characterized by chronic joint inflammation eventually leading to irreversible cartilage destruction. IgG-containing immune complexes are abundant in the synovial tissue of subjects with RA. CIA is a widely accepted animal model of RA that results in chronic inflammatory synovitis characterized by pannus formation and joint degradation. In this model, intradermal immunization with native type II collagen, emulsified with incomplete Freund's adjuvant, results in an inflammatory polyarthritis within 10 or 11 days and subsequent joint destruction in 3 to 4 weeks.

Briefly, Porcine type II collagen is emulsified 1:1 with incomplete Freunds adjuvant and female Lewis rats are injected intradermally at 10 sites in the dorsal area, using 100 µL of collagen per site on day 0. Beginning on the day of arthritis onset (Day 10) animals are dosed either with vehicle control or compound. Hind limbs are scored daily for clinical arthritis severity using a standardized method based on the degree of joint inflammation. Radiographs of hind limbs are obtained at the conclusion of the study and these limbs are analyzed for histopathologic changes. IgG antibodies to native collagen can be measured.

Heteroaryl Compounds as described herein have, or are expected to have an $ED_{50}$ value of <100 mg/kg, with some compounds having an $ED_{50}$ of <10 mg/kg, and others an $ED_{50}$ of <1 mg/kg.

5.2.15 Xenograft Cancer Model

Human cancer cell lines are injected into athymic nude mice. For cells maintained in vitro, tumors are generated by injecting precisely determined numbers of cells into mice. For tumors which are best propagated in vivo, tumor fragments from donor mice are implanted into small numbers of mice for maintenance, or larger numbers of mice for study initiation. A typical efficacy study design involves administering one or more drugs to tumor-bearing mice. Additionally, reference chemotherapeutic agents (positive control) and negative controls are similarly administered and maintained. Routes of administration can include subcutaneous (SC), intraperitoneal (IP), intravenous (IV), intramuscular (IM) and oral (PO). Tumor measurements and body weights are taken over the course of the study and morbidity and mortality are recorded. Necropsy, histopathology, bacteriology, parasitology, serology and PCR can also be performed to enhance understanding of disease and drug action.

Some of the typical human cancer cell lines that can be used in the above xenograft models are: the MDA MB-231, MCF7, MDA-MB-435, and T-47D cell lines for breast cancer; the KM 12, HCT-15, COLO 205, HCT-116 and HT29 cell lines for colon cancer; the NCI-H460 and A549 cell lines for lung cancer; the CRW22, LNCAP, PC-3, PCC-3, and DU-145 cell lines for prostate cancer; the LOX-IMVI and A375 cell line for melanoma; the SK-O V-3 and A2780 cell lines for ovarian cancer; and the CAKI-I, A498, SN12C cell lines for renal cancer U-87MG cell line for glioma cancer, and SU-DHL-4 cell line for hematological cancer.

Heteroaryl Compounds as described herein have, or are expected to have an $ED_{50}$ value of <100 mg/kg, with some compounds having an $ED_{50}$ of <10 mg/kg, and others an $ED_{50}$ of <1 mg/kg.

5.2.16 Rat anti-GBM glomerulonephritis a Model for Goodpasture's Disease

Inbred Sprague-Dawley rats were immunized with 5 mg (subcutaneous) sheep IgG in Freund's complete adjuvant followed 5 days later (termed day 0) by intravenous injection of sheep anti-rat glomerular basement membrane (GBM) serum (10 mg). Neutrophil and macrophage accumulation in the kidneys was measured by immunohistochemistry (IHC) at 3 h, 6 h and 24 h post IV injection of sheep anti-rat GBM. After 24 h, the disease was progressive with increasing severity of proteinuria and the development of significant glomerular and tubulointerstitial damage by day 14. This was measured by histology, serum creatinine and urine was collected for urinary protein levels as assessed by the benzethonium chloride method (McDowell T L, Benzethonium Chloride method for proteins adapted to centrifugal analysis, Clin Chem 31 (6); 864 (1985). Animals are dosed with either vehicle control or compound, either prior to or at designated timepoints post IV injection of sheep anti-rat GBM serum.

Heteroaryl Compounds as described herein have or are expected to have an $ED_{50}$ value of <100 mg/kg, with some compounds having an $ED_{50}$ of <10 mg/kg, and others an $ED_{50}$ of <1 mg/kg.

5.3 Heteroaryl Compound Activity

Each of the compounds in Table 1 was tested in the Syk HTRF assay and was found to have activity therein, with all of the compounds having an $IC_{50}$ below 10 µM in the assay, with some compounds having an $IC_{50}$ between 0.005 nM and 250 nM (activity level D), some an $IC_{50}$ between 250 nM and 500 nM (activity level C), some an $IC_{50}$ between 500 nM and 1 µM (activity level B), and others having an $IC_{50}$ between 1 µM and 10 µM (activity level A).

TABLE 1

| Cmpd. No. | Structure | Cmpd. Name | MH+ (Obs.) | Activity Level |
|---|---|---|---|---|
| 1 | 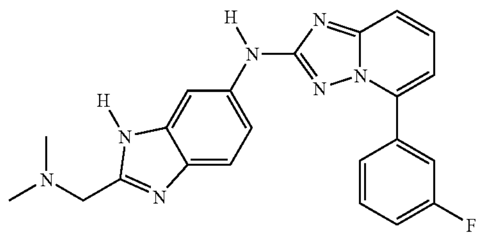 | N-(2-((dimethylamino)methyl)-1H-benzo[d]imidazol-6-yl)-5-(3-fluorophenyl)-[1,2,4]triazolo[1,5-a]pyridin-2-amine | 401.2 | D |
| 2 | 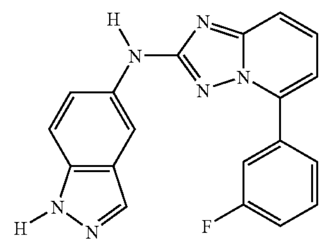 | 5-(3-fluorophenyl)-N-(1H-indazol-5-yl)-[1,2,4]triazolo[1,5-a]pyridin-2-amine | 344.1 | D |
| 3 | 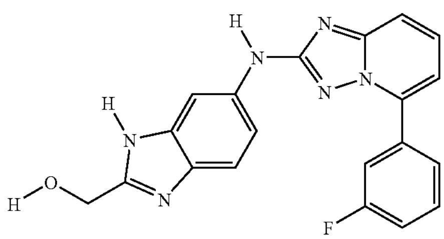 | (6-(5-(3-fluorophenyl)-[1,2,4]triazolo[1,5-a]pyridin-2-ylamino)-1H-benzo[d]imidazol-2-yl)methanol | 375.1 | D |
| 4 | 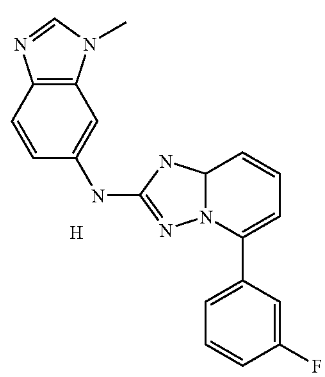 | 5-(3-fluorophenyl)-N-(1-methyl-1H-benzo[d]imidazol-6-yl)-[1,2,4]triazolo[1,5-a]pyridin-2-amine | 359.1 | D |
| 5 | 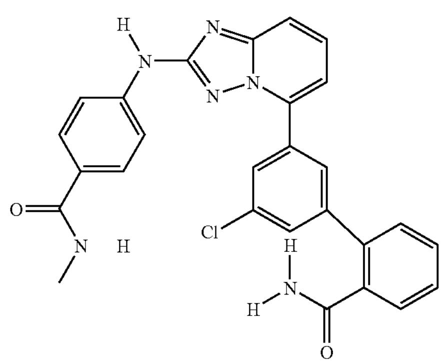 | 3'-chloro-5'-(2-(4-(methylcarbamoyl)phenylamino)-[1,2,4]triazolo[1,5-a]pyridin-5-yl)biphenyl-2-carboxamide | 497.1 | D |

TABLE 1-continued

| Cmpd. No. | Structure | Cmpd. Name | MH+ (Obs.) | Activity Level |
|---|---|---|---|---|
| 6 | 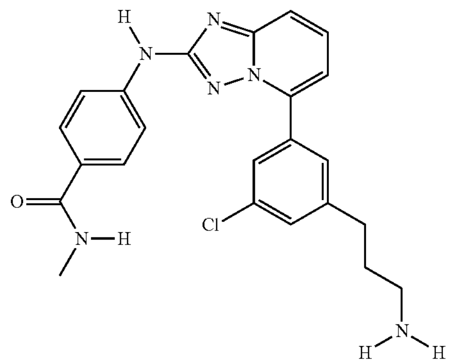 | 4-(5-(3-(3-aminopropyl)-5-chlorophenyl)-[1,2,4]triazolo-[1,5-a]pyridin-2-ylamino)-N-methylbenzamide | 435.2 | D |
| 7 | 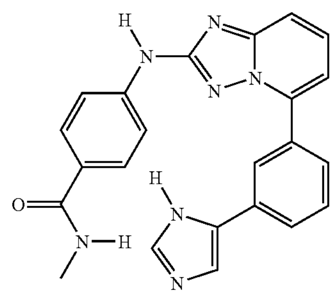 | 4-(5-(3-(1H-imidazol-5-yl)phenyl)-[1,2,4]triazolo[1,5-a]pyridin-2-ylamino)-N-methylbenzamide | 410.1 | D |
| 8 | 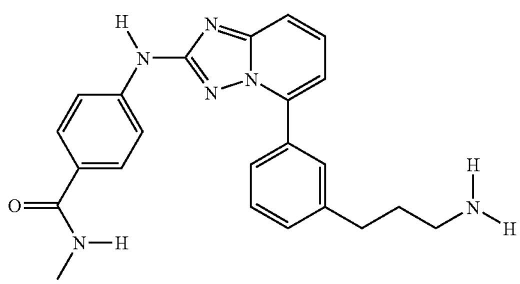 | 4-(5-(3-(3-aminopropyl)phenyl)-[1,2,4]triazolo[1,5-a]pyridin-2-ylamino)-N-methylbenzamide | 401.5 | D |
| 9 | 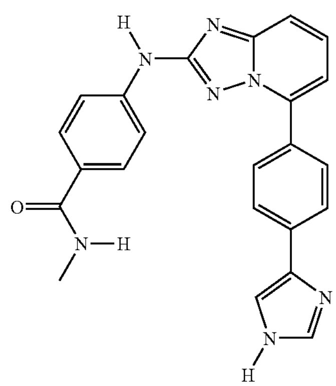 | 4-(5-(4-(1H-imidazol-4-yl)phenyl)-[1,2,4]triazolo[1,5-a]pyridin-2-ylamino)-N-methylbenzamide | 410.1 | D |
| 10 | 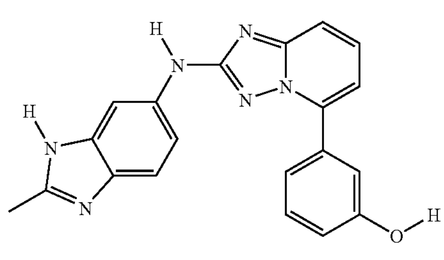 | 3-(2-(2-methyl-1H-benzo[d]imidazol-6-ylamino)-[1,2,4]triazolo[1,5-a]pyridin-5-yl)phenol | 357.1 | D |

TABLE 1-continued

| Cmpd. No. | Structure | Cmpd. Name | MH+ (Obs.) | Activity Level |
|---|---|---|---|---|
| 11 | 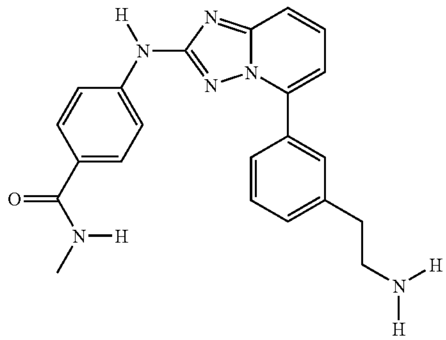 | 4-(5-(3-(2-aminoethyl)phenyl)-[1,2,4]triazolo[1,5-a]pyridin-2-ylamino)-N-methylbenzamide | 387.1 | C |
| 12 | 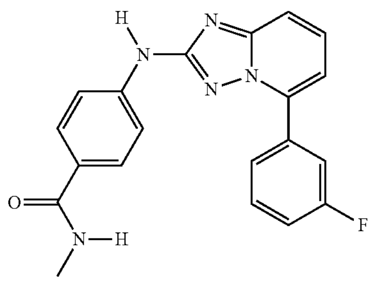 | 4-(5-(3-fluorophenyl)-[1,2,4]triazolo[1,5-a]pyridin-2-ylamino)-N-methylbenzamide | 362.3 | C |
| 13 | 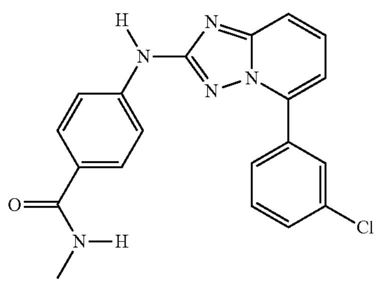 | 4-(5-(3-chlorophenyl)-[1,2,4]triazolo[1,5-a]pyridin-2-ylamino)-N-methylbenzamide | 378.2 | D |
| 14 | 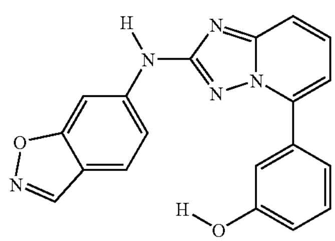 | 3-(2-(benzo[d]isoxazol-6-ylamino)-[1,2,4]triazolo[1,5-a]pyridin-5-yl)phenol | 343.9 | D |
| 15 | 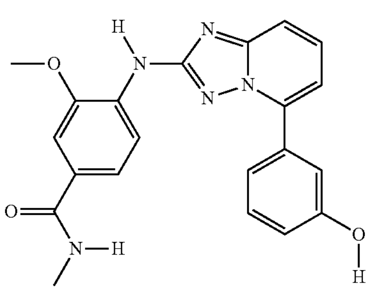 | 4-(5-(3-hydroxyphenyl)-[1,2,4]triazolo[1,5-a]pyridin-2-ylamino)-3-methoxy-N-methylbenzamide | 390.2 | B |

TABLE 1-continued

| Cmpd. No. | Cmpd. Name | MH+ (Obs.) | Activity Level |
|---|---|---|---|
| 16 | 3-(2-(4-(1H-imidazol-2-yl)phenylamino)-[1,2,4]triazolo[1,5-a]pyridin-5-yl)phenol | 368.9 | D |
| 17 | $N^6$-(5-phenyl-[1,2,4]triazolo[1,5-a]pyridin-2-yl)quinoline-2,6-diamine | 353.1 | D |
| 18 | 4-(5-(3-carbamoylphenyl)-[1,2,4]triazolo[1,5-a]pyridin-2-ylamino)-N-methylbenzamide | 387.2 | B |
| 19 | 3-(2-(1-methyl-1H-indazol-6-ylamino)-[1,2,4]triazolo[1,5-a]pyridin-5-yl)phenol | 357.1 | D |

TABLE 1-continued

| Cmpd. No. | Cmpd. Name | MH+ (Obs.) | Activity Level |
|---|---|---|---|
| 20 | 4-(5-(3-methoxyphenyl)-[1,2,4]triazolo[1,5-a]pyridin-2-ylamino)-N-methylbenzamide | 374.1 | C |
| 21 | 4-(5-(2-fluorophenyl)-[1,2,4]triazolo[1,5-a]pyridin-2-ylamino)-N-methylbenzamide | 362 | B |
| 22 | 4-(5-(2-chlorophenyl)-[1,2,4]triazolo[1,5-a]pyridin-2-ylamino)-N-methylbenzamide | 378 | A |
| 23 | N6-(5-phenyl-[1,2,4]triazolo[1,5-a]pyridin-2-yl)-N3-(piperidin-4-yl)-1H-indazole-3,6-diamine | 425.1 | D |

TABLE 1-continued

| Cmpd. No. | Structure | Cmpd. Name | MH+ (Obs.) | Activity Level |
|---|---|---|---|---|
| 24 | 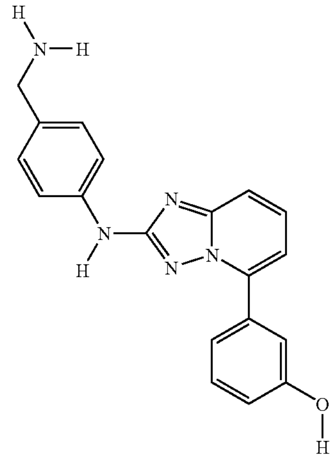 | 3-(2-(4-(aminomethyl)phenylamino)-[1,2,4]triazolo[1,5-a]pyridin-5-yl)phenol | 332.1 | C |
| 25 | 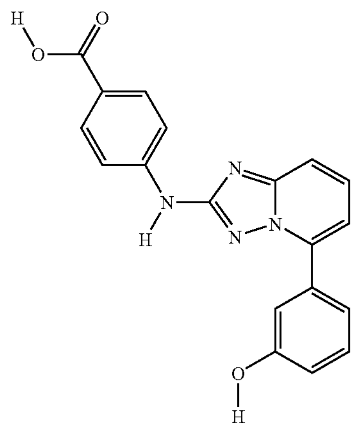 | 4-(5-(3-hydroxyphenyl)-[1,2,4]triazolo[1,5-a]pyridin-2-ylamino)benzoic acid | 347.1 | D |
| 26 | 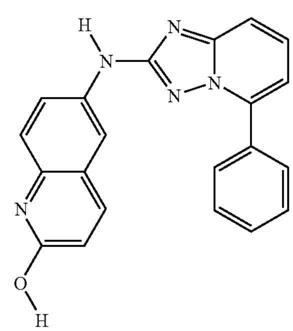 | 6-(5-phenyl-[1,2,4]triazolo[1,5-a]pyridin-2-ylamino)quinolin-2-ol | 354 | D |

TABLE 1-continued
| Cmpd. No. | Structure | Cmpd. Name | MH+ (Obs.) | Activity Level |
|---|---|---|---|---|
| 27 | 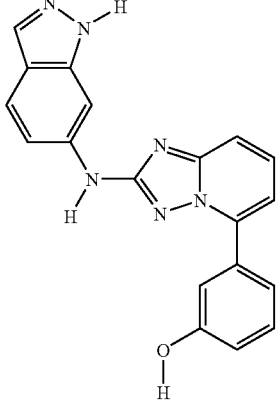 | 3-(2-(1H-indazol-6-ylamino)-[1,2,4]triazolo[1,5-a]pyridin-5-yl)phenol | 343.13 | D |
| 28 | 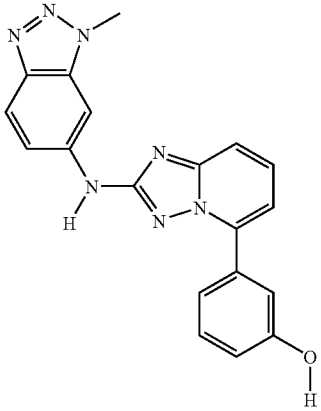 | 3-(2-(1-methyl-1H-benzo[d][1,2,3]triazol-6-ylamino)-[1,2,4]triazolo[1,5-a]pyridin-5-yl)phenol | 358.1 | D |
| 29 | 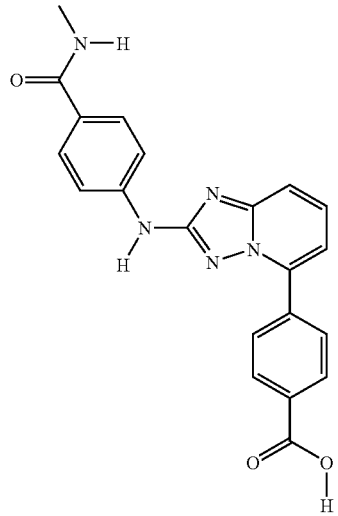 | 4-(2-(4-(methylcarbamoyl)phenylamino)-[1,2,4]triazolo[1,5-a]pyridin-5-yl)benzoic acid | 387.9 | A |

TABLE 1-continued

| Cmpd. No. | Structure | Cmpd. Name | MH+ (Obs.) | Activity Level |
|---|---|---|---|---|
| 30 | 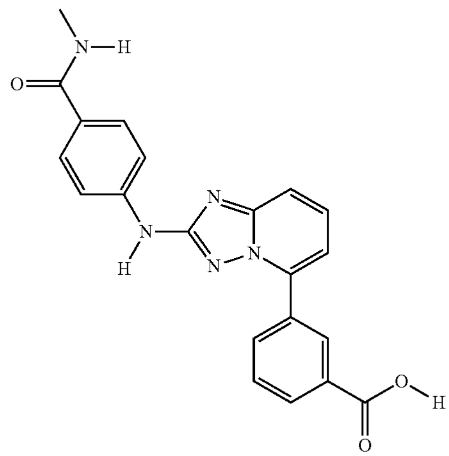 | 3-(2-(4-(methylcarbamoyl)phenylamino)-[1,2,4]triazolo[1,5-a]pyridin-5-yl)benzoic acid | 388.1 | A |
| 31 | 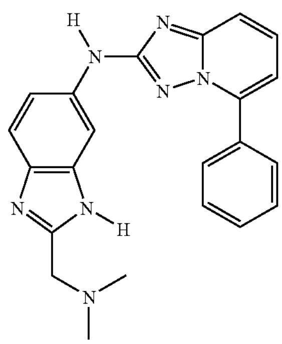 | N-(2-((dimethylamino)methyl)-1H-benzo[d]imidazol-6-yl)-5-phenyl-[1,2,4]triazolo[1,5-a]pyridin-2-amine | 384.1 | D |
| 32 | 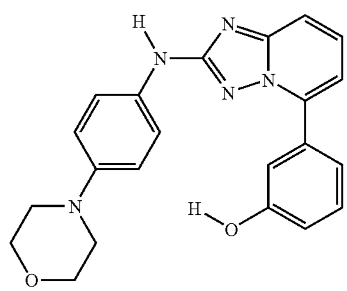 | 3-(2-(4-morpholinophenylamino)-[1,2,4]triazolo[1,5-a]pyridin-5-yl)phenol | 388.0 | D |
| 33 | 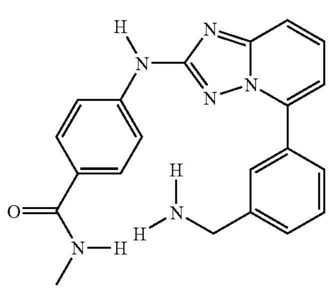 | 4-(5-(3-(aminomethyl)phenyl)-[1,2,4]triazolo[1,5-a]pyridin-2-ylamino)-N-methylbenzamide | 395.2 [M + 23]+ | D |

TABLE 1-continued

| Cmpd. No. | Cmpd. Name | MH+ (Obs.) | Activity Level |
|---|---|---|---|
| 34 | 4-(5-(3-hydroxyphenyl)-[1,2,4]triazolo[1,5-a]pyridin-2-ylamino)-N-(1-methylpiperidin-4-yl)benzamide | 443 | D |
| 35 | 1-methyl-$N^6$-(5-phenyl-[1,2,4]triazolo[1,5-a]pyridin-2-yl)-1H-indazole-3,6-diamine | 356.1 | D |
| 36 | 4-(5-(3-hydroxyphenyl)-[1,2,4]triazolo[1,5-a]pyridin-2-ylamino)-N-methylbenzamide | 360.1 | D |
| 37 | N-(5-phenyl-[1,2,4]triazolo[1,5-a]pyridin-2-yl)-2,3-dihydrobenzo[d]isothiazol-6-amine dione | 377.9 | D |
| 38 | N-(5-methoxypyridin-3-yl)-5-phenyl-[1,2,4]triazolo[1,5-a]pyridin-2-amine | 318.1 | B |

TABLE 1-continued

| Cmpd. No. | Structure | Cmpd. Name | MH+ (Obs.) | Activity Level |
|---|---|---|---|---|
| 39 | 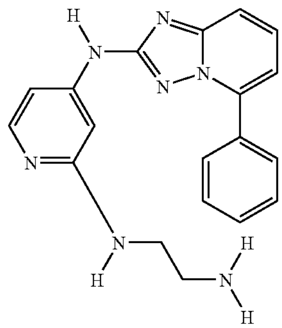 | $N^2$-(2-aminomethyl)-$N^4$-(5-phenyl-[1,2,4]triazolo[1,5-a]pyridin-2-yl)pyridine-2,4-dimaine | 346.1 | C |
| 40 | 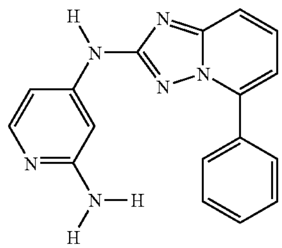 | $N^4$-(5-phenyl-[1,2,4]triazolo[1,5-a]pyridin-2-yl)pyridine-2,4-diamine | 303.1 | B |
| 41 | 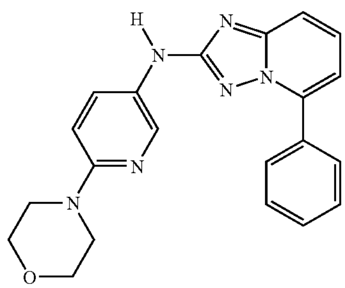 | N-(6-morpholinopyridin-3-yl)-5-phenyl-[1,2,4]triazolo[1,5-a]pyridin-2-amine | 373.3 | D |
| 42 | 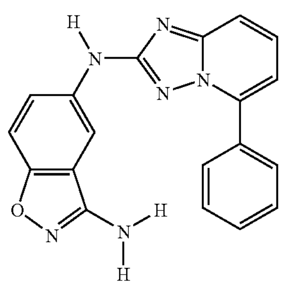 | $N^5$-(5-phenyl-[1,2,4]triazolo[1,5-a]pyridin-2-yl)benzo[d]isoxazole-3,5-diamine | 343.1 | D |
| 43 | 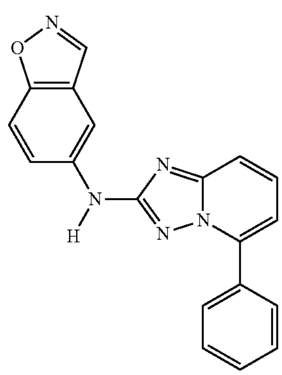 | N-(5-phenyl-[1,2,4]triazolo[1,5-a]pyridin-2-yl)benzo[d]isoxazol-5-amine | 328.1 | D |

TABLE 1-continued

| Cmpd. No. | Structure | Cmpd. Name | MH+ (Obs.) | Activity Level |
|---|---|---|---|---|
| 44 | 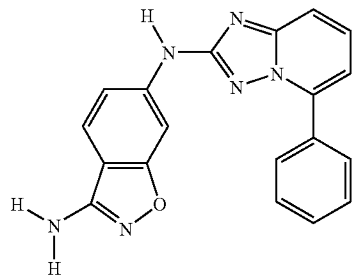 | N6-(5-phenyl-[1,2,4]triazolo[1,5-a]pyridin-2-yl)benzo[d]isoxazole-3,6-diamine | 343.1 | C |
| 45 | 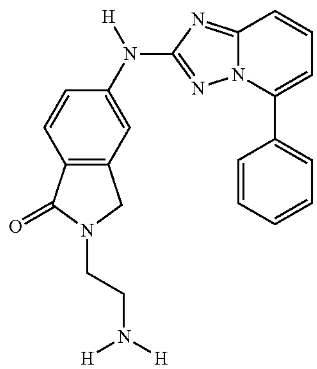 | 2-(2-aminoethyl)-5-(5-phenyl-[1,2,4]triazolo[1,5-a]pyridin-2-ylamino)isoindolin-1-one | 385.1 | C |
| 46 | 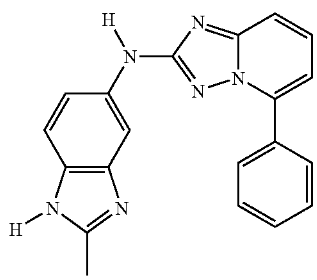 | N-(2-methyl-1H-benzo[d]imidazol-5-yl)-5-phenyl-[1,2,4]triazolo[1,5-a]pyridin-2-amine | 341.1 | D |
| 47 | 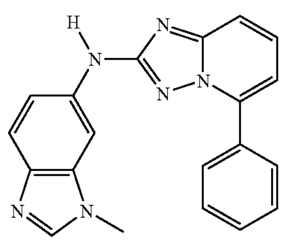 | N-(1-methyl-1H-benzo[d]imidazol-6-yl)-5-phenyl-[1,2,4]triazolo[1,5-a]pyridin-2-amine | 341.1 | D |
| 48 | 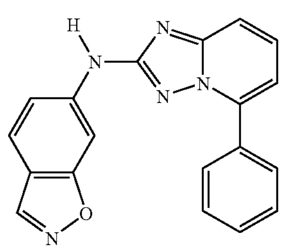 | N-(5-phenyl-[1,2,4]triazolo[1,5-a]pyridin-2-yl)benzo[d]isoxazol-6-amine | 328.1 | A |

TABLE 1-continued

| Cmpd. No. | Structure | Cmpd. Name | MH+ (Obs.) | Activity Level |
|---|---|---|---|---|
| 49 | 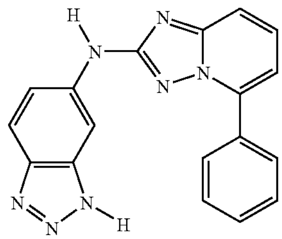 | N-(5-phenyl-[1,2,4]triazolo[1,5-a]pyridin-2-yl)-1H-benzo[d][1,2,3]triazol-6-amine | 328.1 | D |
| 50 | 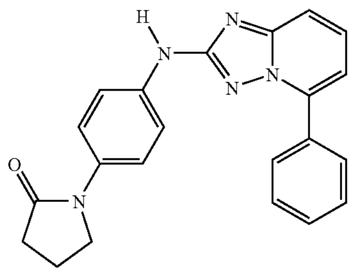 | 1-(4-(5-phenyl-[1,2,4]triazol[1,5-a]pyridin-2-ylamino)phenyl)pyrrolidin-2-one | 370.5 | D |
| 51 | 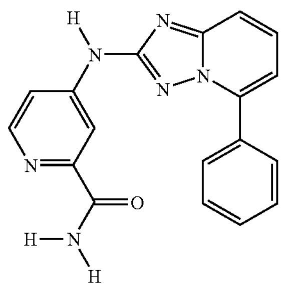 | 4-(5-phenyl-[1,2,4]triazolo[1,5-a]pyridin-2-ylamino)picolinamide | 331.1 | A |
| 52 | 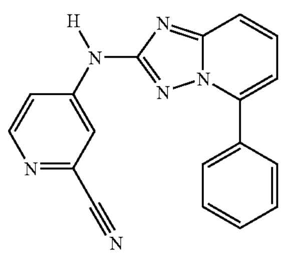 | 4-(5-phenyl-[1,2,4]triazolo[1,5-a]pyridin-2-ylamino)picolinamide | 313.1 | A |
| 53 | 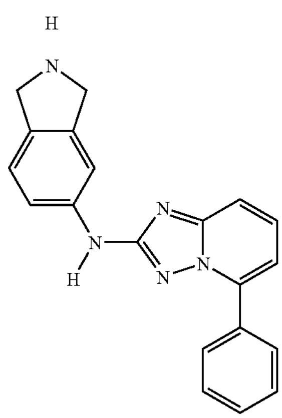 | N-(isoquinolin-5-yl)-5-phenyl-[1,2,4]triazolo[1,5-a]pyridin-2-amine | 328.1 | D |

TABLE 1-continued

| Cmpd. No. | Structure | Cmpd. Name | MH+ (Obs.) | Activity Level |
|---|---|---|---|---|
| 54 | 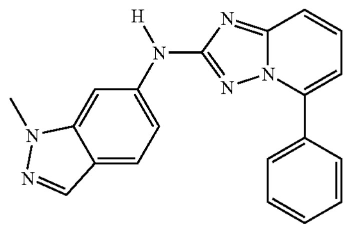 | N-(1-methyl-1H-indazol-6-yl)-5-phenyl-[1,2,4]triazolo[1,5-a]pyridin-2-amine | 341.1 | D |
| 55 | 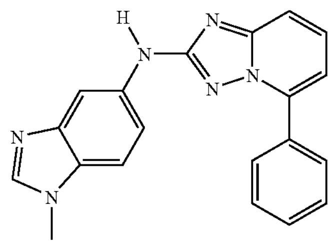 | N-(1-methyl-1H-benzo[d]imidazol-5-yl)-5-phenyl-[1,2,4]triazolo[1,5-a]pyridin-2-amine | 341.1 | C |
| 56 | 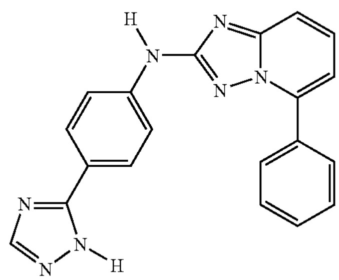 | N-(4-(1H-1,2,4-triazol-5-yl)phenyl)-5-phenyl-[1,2,4]triazolo[1,5-a]pyridin-2-amine | 354.2 | D |
| 57 | 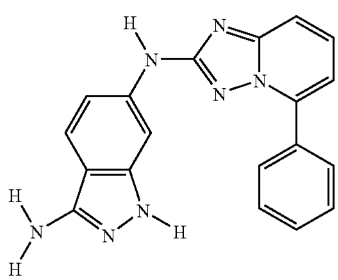 | $N^6$-(5-phenyl-[1,2,4]triazolo[1,5-a]pyridin-2-yl)-1H-indazole-3,6-diamine | 341.9 | D |
| 58 | 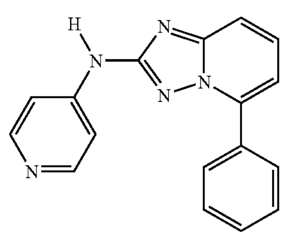 | 5-phenyl-N-(pyridin-4-yl)-[1,2,4]triazolo[1,5-a]pyridin-2-amine | 288 | B |
| 59 | 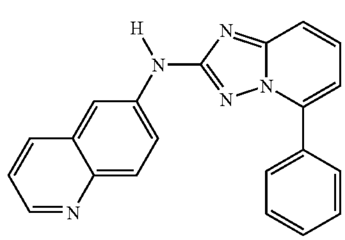 | N-(5-phenyl-[1,2,4]triazolo[1,5-a]pyridin-2-yl)quinolin-6-amine | 338.2 | D |

TABLE 1-continued

| Cmpd. No. | Structure | Cmpd. Name | MH+ (Obs.) | Activity Level |
|---|---|---|---|---|
| 60 | 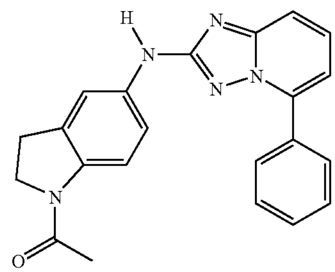 | 1-(5-(5-phenyl-[1,2,4]triazolo[1,5-a]pyridin-2-ylamino)indolin-1-yl)ethanone | 370.1 | D |
| 61 | 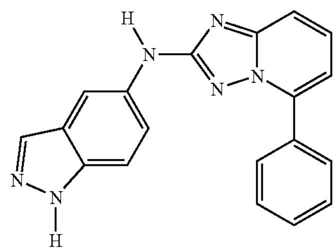 | N-(1H-indazol-5-yl)-5-phenyl-[1,2,4]triazolo]1,5-a]pyridin-2-amine | 327.1 | D |
| 62 | 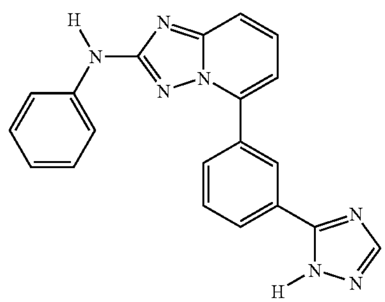 | 5-(3-(1H-1,2,4-triazol-5-yl)phenyl)-N-phenyl-[1,2,4]triazolo[1,5-a]pyridin-2-amine | 354 | C |
| 63 | 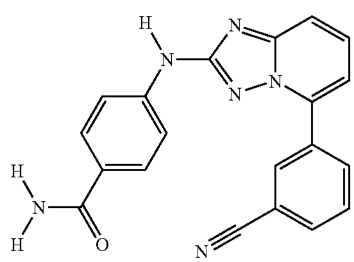 | 4-(5-(3-cyanophenyl)-[1,2,4]triazolo[1,5-a]pyridin-2-ylamino)benzamide | 355.4 | C |
| 64 | 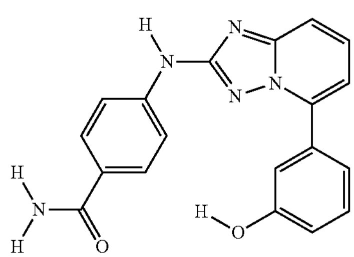 | 4-(5-(3-hydroxyphenyl)-[1,2,4]triazolo[1,5-a]pyridin-2-ylamino)benzamide | 346.3 | D |
| 65 | 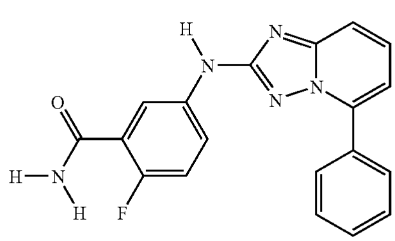 | 2-fluoro-5-(5-phenyl-[1,2,4]triazolo[1,5-a]pyridin-2-ylamino)benzamide | 348.1 | A |

TABLE 1-continued

| Cmpd. No. | Structure | Cmpd. Name | MH+ (Obs.) | Activity Level |
|---|---|---|---|---|
| 66 | 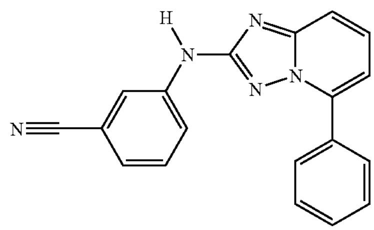 | 3-(5-phenyl-[1,2,4]triazolo[1,5-a]pyridin-2-ylamino)benzonitrile | 312.3 | A |
| 67 | 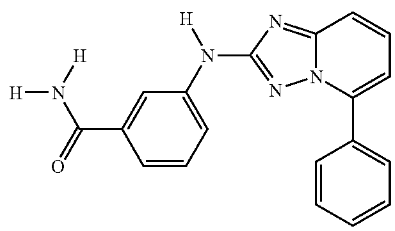 | 3-(5-phenyl-[1,2,4]triazolo[1,5-a]pyridin-2-ylamino)benzamide | 330.1 | B |
| 68 | 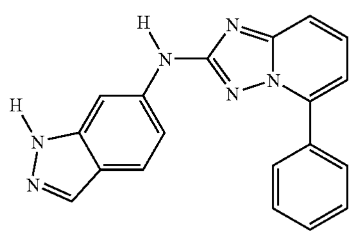 | N-(1H-indazol-6-yl)-5-phenyl-[1,2,4]triazol[1,5-a]pyridin-2-amine | 327.1 | D |
| 69 | 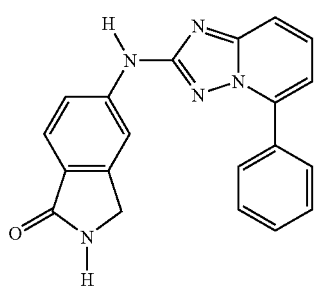 | 5-(5-phenyl-[1,2,4]triazolo[1,5-a]pyridin-2-ylamino)isoindolin-1-one | 342.1 | C |
| 70 | 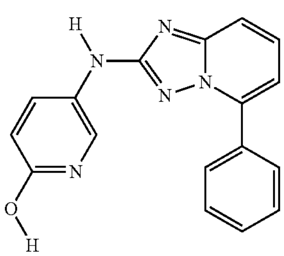 | 5-(5-phenyl-[1,2,4]triazolo[1,5-a]pyridin-2-ylamino)pyridine-2-ol | 304.1 | A |
| 71 | 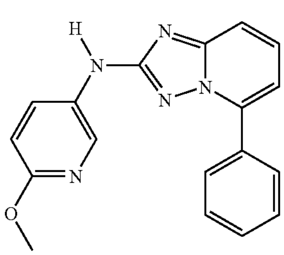 | N-(6-methoxypyridin-3-yl)-5-phenyl-[1,2,4]triazolo[1,5-a]pyridin-2-amine | 318.1 | A |

TABLE 1-continued

| Cmpd. No. | Structure | Cmpd. Name | MH+ (Obs.) | Activity Level |
|---|---|---|---|---|
| 72 | 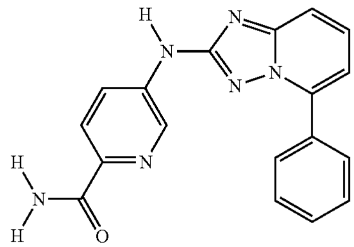 | 5-(5-phenyl-[1,2,4]triazolo[1,5-a]pyridin-2-ylamino)picolinamide | 331.1 | A |
| 73 | 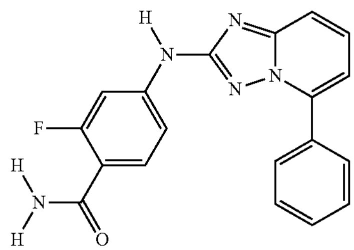 | 2-fluoro-4-(5-phenyl-[1,2,4]triazolo[1,5-a]pyridin-2-ylamino)benzamide | 348.1 | A |
| 74 | 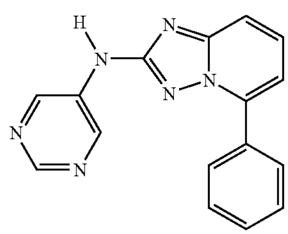 | 5-phenyl-N-(pyrimidin-5-yl)-[1,2,4]triazolo[1,5-a]pyridin-2-amine | 288.9 | A |
| 75 | 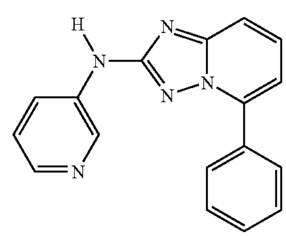 | 5-phenyl-N-(pyridin-3-yl)-[1,2,4]triazolo[1,5-a]pyridin-2-amine | 288.1 | B |
| 76 | 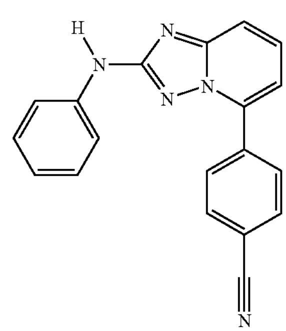 | 4-(2-(phenylamino)-[1,2,4]triazolo[1,5-a]pyridin-5-yl)benzonitrile | 311.9 | A |

TABLE 1-continued

| Cmpd. No. | Structure | Cmpd. Name | MH+ (Obs.) | Activity Level |
|---|---|---|---|---|
| 77 | 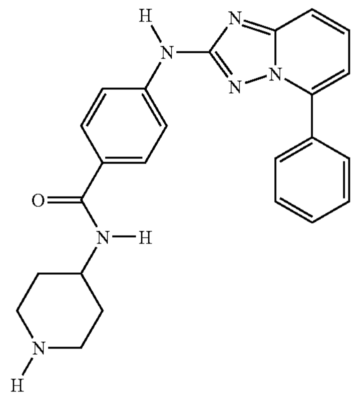 | 4-(5-phenyl-[1,2,4]triazolo[1,5-a]pyridin-2-ylamino)-N-(piperidin-4-yl)benzamide | 413.2 | D |
| 78 | 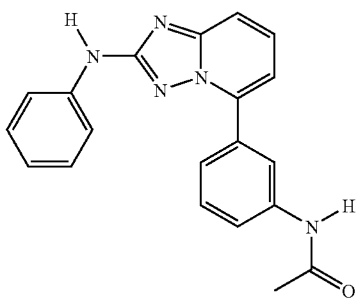 | N-(3-(2-(phenylamino)-[1,2,4]triazolo[1,5-a]pyridin-5-yl)phenyl)acetamide | 344.1 | A |
| 79 | 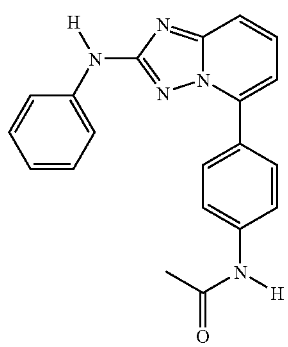 | N-(4-(2-(phenylamino)-[1,2,4]triazolo[1,5-a]pyridin-5-yl)phenyl)acetamide | 344.1 | C |
| 80 | 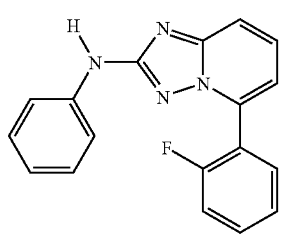 | 5-(2-fluorophenyl)-N-phenyl-[1,2,4]triazolo[1,5-a]pyridin-2-amine | 305.1 | A |
| 81 | 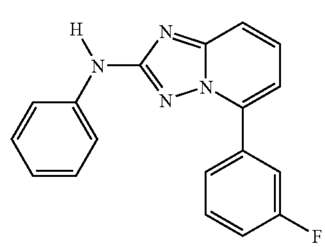 | 5-(3-fluorophenyl)-N-phenyl-[1,2,4]triazolo[1,5-a]pyridin-2-amine | 305.1 | B |

TABLE 1-continued

| Cmpd. No. | Cmpd. Name | MH+ (Obs.) | Activity Level |
|---|---|---|---|
| 82 | 5-(4-aminophenyl)-N-phenyl-[1,2,4]triazolo[1,5-a]pyridin-2-amine | 302.1 | C |
| 83 | 3-(2-(phenylamino)-[1,2,4]triazolo[1,5-a]pyridin-5-yl)benzonitrile | 311.9 | A |
| 84 | 5-(3-(aminomethyl)phenyl)-N-phenyl-[1,2,4]triazolo[1,5-a]pyridin-2-amine | 316.1 | D |
| 85 | 4-(2-(phenylamino)-[1,2,4]triazolo[1,5-a]pyridin-5-yl)benzamide | 352.1 | D |
| 86 | 3-(2-(phenylamino)-[1,2,4]triazolo[1,5-a]pyridin-5-yl)benzamide | 329.9 | D |

TABLE 1-continued

| Cmpd. No. | Structure | Cmpd. Name | MH+ (Obs.) | Activity Level |
|---|---|---|---|---|
| 87 | 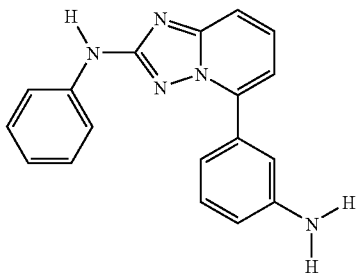 | 5-(3-aminophenyl)-N-phenyl-[1,2,4]triazolo[1,5-a]pyridin-2-amine | 302.1 | D |
| 88 | 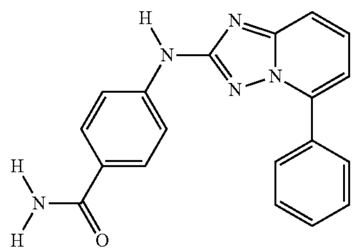 | 4-(5-phenyl-[1,2,4]triazolo[1,5-a]pyridin-2-ylamino)benzamide | 330.1 | D |
| 89 | 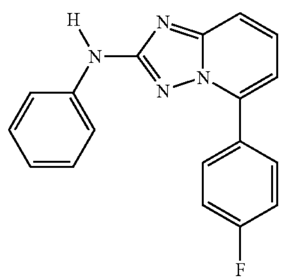 | 5-(4-fluorophenyl)-N-phenyl-[1,2,4]triazolo[1,5-a]pyridin-2-amine | 305.1 | C |
| 90 | 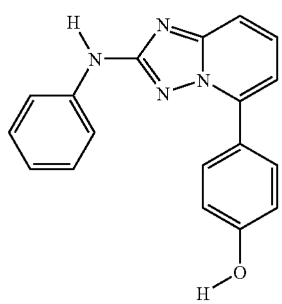 | 4-(2-(phenylamnino)-[1,2,4]triazolo[1,5-a]pyridin-5-yl)phenol | 303 | A |
| 91 | 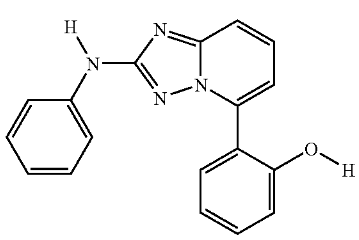 | 2-(2-(phenylamino)-[1,2,4]triazolo[1,5-a]pyridin-5-yl)phenol | 303 | C |

TABLE 1-continued

| Cmpd. No. | Structure | Cmpd. Name | MH+ (Obs.) | Activity Level |
|---|---|---|---|---|
| 92 | 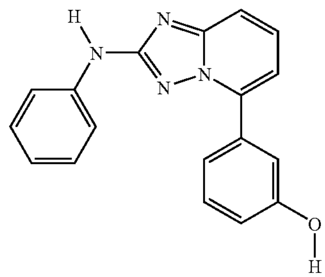 | 3-(2-(phenylamino)[1,2,4]triazolo[1,5-a]pyridin-5-yl)phenol | 303 | D |
| 93 | 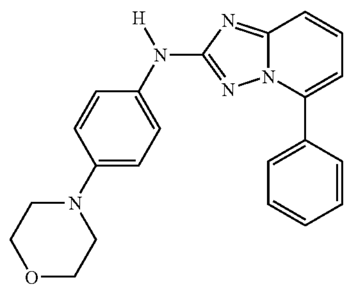 | N-(4-morpholinophenyl)-5-phenyl-[1,2,4]triazolo[1,5-a]pyridin-2-amine | 372.2 | D |
| 94 | 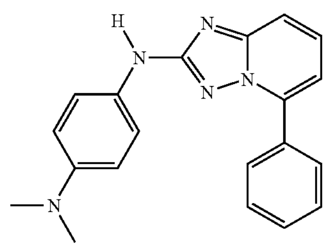 | $N^1,N^1$-dimethyl-$N^4$-(5-phenyl-[1,2,4]triazolo[1,5-a]pyridin-2-yl)benzene-1,4-diamine | 330.2 | D |
| 95 | 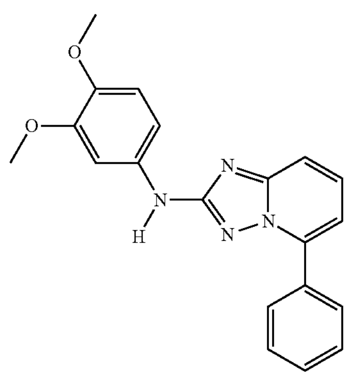 | N-(3,4-dimethoxyphenyl)-5-phenyl-[1,2,4]triazolo[1,5-a]pyridin-2-amine | 347.1 | D |
| 96 | 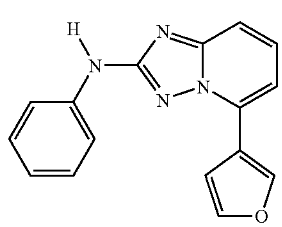 | 5-(furan-3-yl)-N-phenyl-[1,2,4]triazolo[1,5-a]pyridin-2-amine | 277.2 | C |

TABLE 1-continued

| Cmpd. No. | Cmpd. Name | MH+ (Obs.) | Activity Level |
|---|---|---|---|
| 97 | 5-(3-chlorophenyl)-N-phenyl-[1,2,4]triazolo[1,5-a]pyridin-2-amine | 320.9 | A |
| 98 | N,5-diphenyl-[1,2,4]triazolo[1,5-a]pyridin-2-amine | 286.9 | B |
| 99 | 1-methyl-$N^3$-(tetrahydro-2H-pyran-4-yl)-$N^6$-(5-((tetrahydro-2H-pyran-4-yl)methyl)-[1,2,4]triazolo[1,5-a]pyridin-2-yl)-1H-indazole-3,6-diamine | 462.4 | A |
| 100 | $N^3$-(tetrahydro-2H-pyran-4-yl)-$N^6$-(5-((tetrahydro-2H-pyran-4-yl)methyl)-[1,2,4]triazolo[1,5-a]pyridin-2-yl)-1H-indazole-3,6-diamine | 448.4 | D |

TABLE 1-continued

| Cmpd. No. | Structure | Cmpd. Name | MH+ (Obs.) | Activity Level |
|---|---|---|---|---|
| 101 | 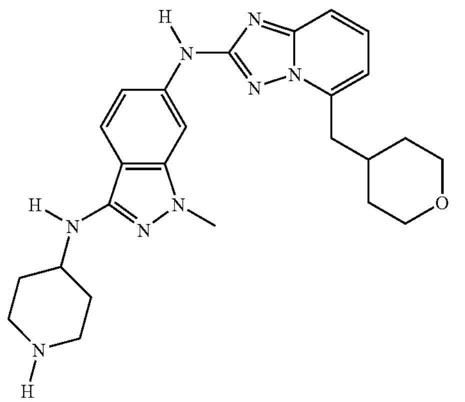 | 1-methyl-N³-(piperidin-4-yl)-N⁶-(5-((tetrahydro-2H-pyran-4-yl)methyl)-[1,2,4]triazolo[1,5-a]pyridin-2-yl)-1H-indazole-3,6-diamine | 461.4 | A |
| 102 | 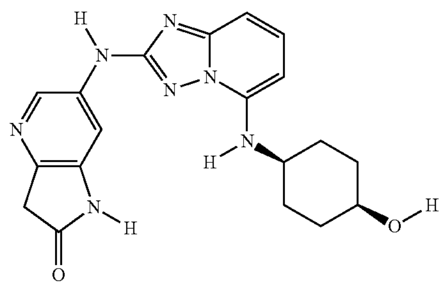 | cis-6-(5-(4-hydroxycyclohexylamino)-[1,2,4]triazolo[1,5-a]pyridin-2-ylamino)-1H-pyrrolo[3,2-b]pyridin-2(3H)-one | 379.3 | B |
| 103 | 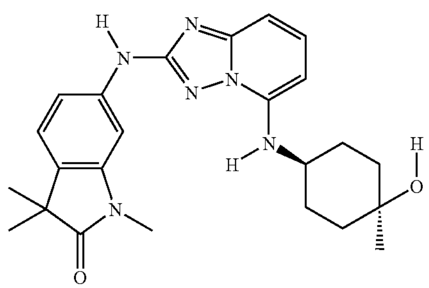 | cis-6-(5-(4-hydroxy-4-methylcyclohexylamino)-[1,2,4]triazolo[1,5-a]pyridin-2-ylamino)-1,3,3-trimethylindolin-2-one | 435.1 | D |
| 104 | 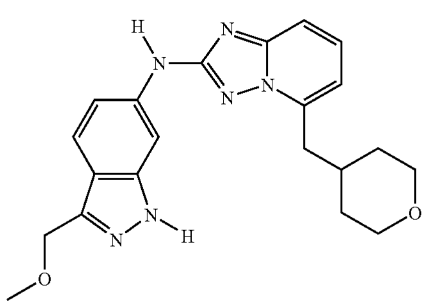 | N-(3-(methoxymethyl)-1H-indazol-6-yl)-5-((tetrahydro-2H-pyran-4-yl)methyl)-[1,2,4]triazolo[1,5-a]pyridin-2-amine | 393 | D |
| 105 | 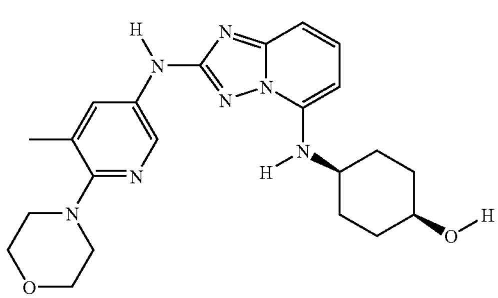 | cis-4-(2-(5-methyl-6-morpholinopyridin-3-ylamino)-[1,2,4]triazolo[1,5-a]pyridin-5-ylamino)cyclohexanol | 424.5 | D |

TABLE 1-continued

| Cmpd. No. | Structure | Cmpd. Name | MH+ (Obs.) | Activity Level |
|---|---|---|---|---|
| 106 | 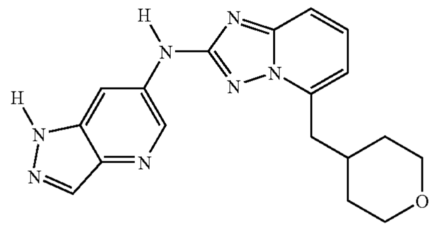 | N-(5-((tetrahydro-2H-pyran-4-yl)methyl)-[1,2,4]triazolo[1,5-a]pyridin-2-yl)-1H-pyrazolo[4,3-b]pyridin-6-amine | 350.2 | B |
| 107 | 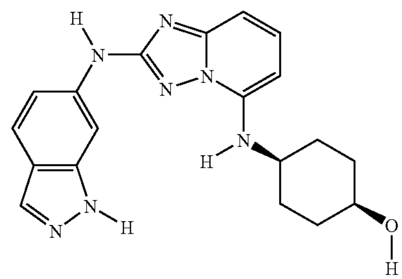 | cis-4-(2-(1H-pyrazolo[4,3-b]pyridin-6-ylamino)-[1,2,4]triazolo[1,5-a]pyridin-5-ylamino)cyclohexanol | 365.3 | D |
| 108 | 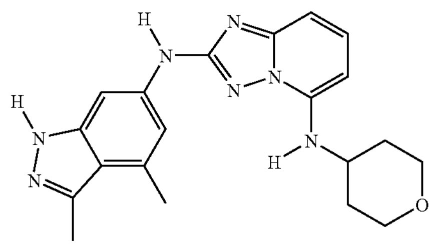 | $N^2$-(3,4-dimethyl-1H-indazol-6-yl)-$N^5$-(tetrahydro-2H-pyran-4-yl)-[1,2,4]triazolo[1,5-a]pyridin-2,5-diamine | 378.7 | D |
| 109 | 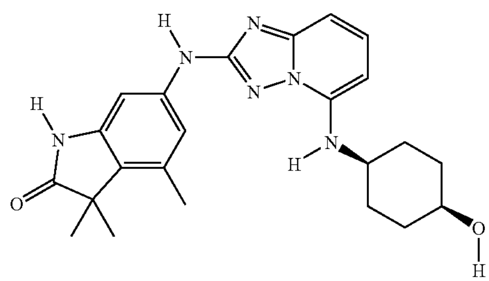 | cis-6-(5-(4-hydroxycyclohexylamino)-[1,2,4]triazolo[1,5-a]pyridin-2-ylamino)-3,3,4-trimethylindolin-2-one | 421.4 | D |
| 110 | 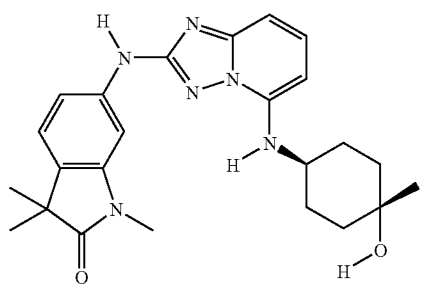 | trans-6-(5-(4-hydroxy-4-methylcyclohexylamino)-[1,2,4]triazolo[1,5-a]pyridin-2-ylamino)-1,3-3-trimethylindolin-2-one | 435.1 | D |
| 111 | 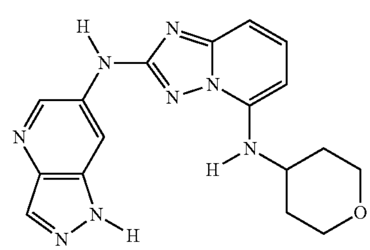 | $N^2$-(1H-pyrazolo[4,3-b]pyridin-6-yl)-$N^5$-(tetrahydro-2H-pyran-4-yl)-[1,2,4]triazolo[1,5-a]pyridine-2,5-diamine | 351.4 | A |

TABLE 1-continued

| Cmpd. No. | Structure | Cmpd. Name | MH+ (Obs.) | Activity Level |
|---|---|---|---|---|
| 112 | 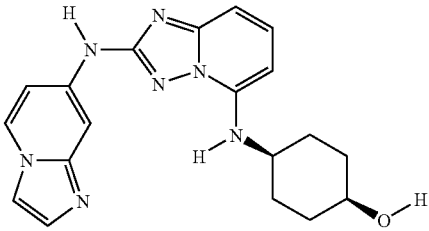 | cis-4-(2-(imidazo[1,2-a]pyridin-7-ylamino)-[1,2,4]triazolo[1,5-a]pyridin-5-ylamino)cyclohexanol | 364.6 | A |
| 113 | 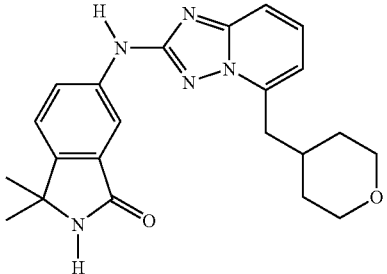 | 3,3-dimethyl-6-(5-((tetrahydro-2H-pyran-4-yl)methyl)-[1,2,4]triazolo[1,5-a]pyridin-2-ylamino)isoindolin-1-one | 392.1 | A |
| 114 | 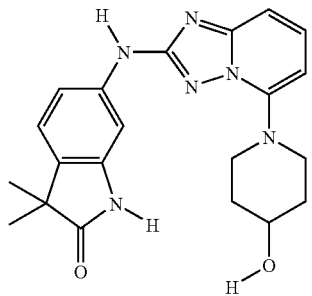 | 6-(5-(4-hydroxypiperidin-1-yl)-[1,2,4]triazolo[1,5-a]pyridin-2-ylamino)-3,3-dimethylindolin-2-one | 393.45 | D |
| 115 | 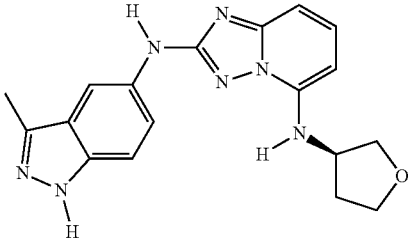 | (R)-$N^2$-(3-methyl-1H-indazol-5-yl)-$N^5$-(tetrahydrofuran-3-yl)-[1,2,4]triazolo[1,5-a]pyridin-2,5-diamine | 350.1 | C |
| 116 | 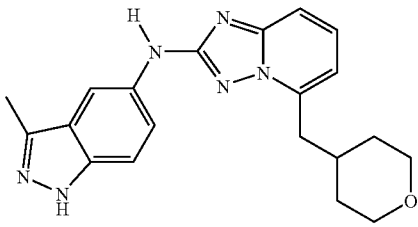 | N-(3-methyl-1H-indazol-5-yl)-5-((tetrahydro-2H-pyran-4-yl)methyl)-[1,2,4]triazolo[1,5-a]pyridin-2-amine | 363.2 | D |
| 117 | 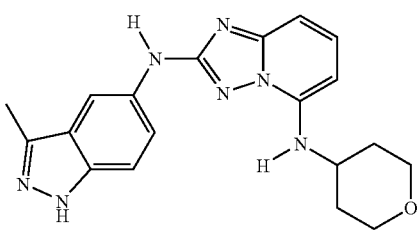 | $N^2$-(3-methyl-1H-indazol-5-yl)-$N^5$-(tetrahydro-2H-pyran-4-yl)-[1,2,4]triazolo[1,5-a]pyridine-2,5-diamine | 364.1 | B |

TABLE 1-continued

| Cmpd. No. | Cmpd. Name | MH+ (Obs.) | Activity Level |
|---|---|---|---|
| 118 | 1-methyl-6-(5-((tetrahydro-2H-pyran-4-yl)methyl)-[1,2,4]triazolo[1,5-a]pyridin-2-ylamino)indolin-2-one | 378 | A |
| 119 | 1-methyl-6-(5-(tetrahydro-2H-pyran-4-ylamino)-[1,2,4]triazolo[1,5-a]pyridin-2-ylamino)indolin-2-one | 379 | A |
| 120 | cis-6-(5-(4-hydroxycyclohexylamino)-[1,2,4]triazolo[1,5-a]pyridin-2-ylamino)-3,3-dimethylisoindolin-1-one | 407.1 | C |
| 121 | (S)-3,3-dimethyl-6-(5-(methyl(tetrahydrofuran-3-yl)amino)-[1,2,4]triazolo[1,5-a]pyridin-2-ylamino)indolin-2-one | 393.2 | D |
| 122 | (R)-3,3-dimethyl-6-(5-(methyl(tetrahydrofuran-3-yl)amino)-[1,2,4]triazolo[1,5-a]pyridin-2-ylamino)indolin-2-one | 393.2 | D |

TABLE 1-continued

| Cmpd. No. | Structure | Cmpd. Name | MH+ (Obs.) | Activity Level |
|---|---|---|---|---|
| 123 | 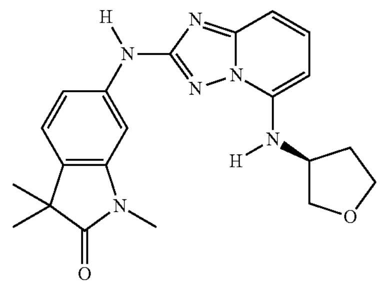 | (R)-1,3,3-trimethyl-6-(5-(tetrahydrofuran-3-ylamino)-[1,2,4]triazolo[1,5-a]pyridin-2-ylamino)indolin-2-one | 393.2 | D |
| 124 | 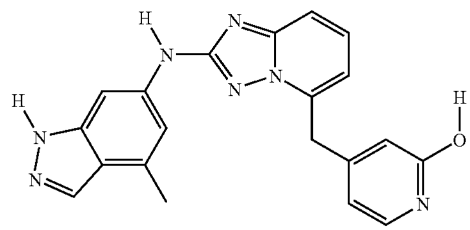 | 4-((2-(4-methyl-1H-indazol-6-ylamino)-[1,2,4]triazolo[1,5-a]pyridin-5-yl)methyl)pyridine-2-ol | 372.1 | D |
| 125 | 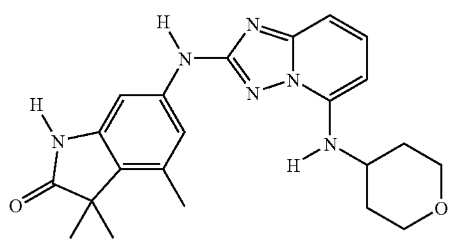 | 3,3,4-trimethyl-6-(5-(tetrahydro-2H-pyran-4-ylamino)-[1,2,4]triazolo[1,5-a]pyridin-2-ylamino)indolin-2-one | 407.1 | D |
| 126 | 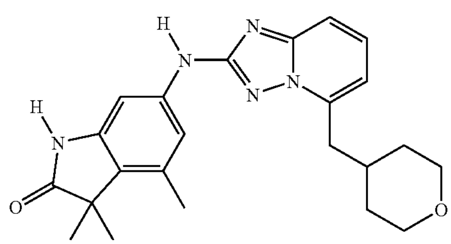 | 3,3,4-trimethyl-6-(5-((tetrahydro-2H-pyran-4-yl)methyl)-[1,2,4]triazolo[1,5-a]pyridin-22-ylamino)indolin-2-one | 406.2 | D |
| 127 | 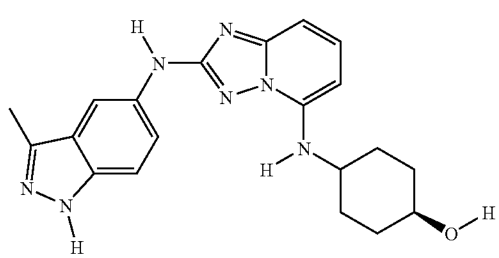 | trans-4-(2-(3-methyl-1H-indazol-5-ylamino)-[1,2,4]triazolo[1,5-a]pyridin-5-ylamino)cyclohexanol | 378.2 | D |
| 128 | 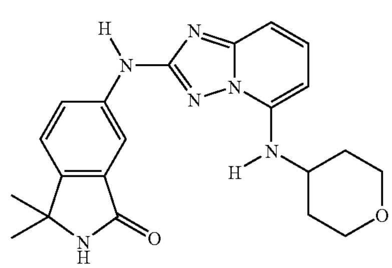 | 3,3-dimethyl-6-(5-(tetrahydro-2H-pyran-4-ylamino)-[1,2,4]triazolo[1,5-a]pyridin-2-ylamino)isoindolin-1-one | 393.1 | B |

TABLE 1-continued

| Cmpd. No. | Structure | Cmpd. Name | MH+ (Obs.) | Activity Level |
|---|---|---|---|---|
| 129 | 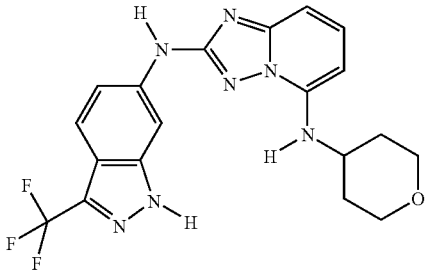 | N5-(tetrahydro-2H-pyran-4-yl)-N2-(3-(trifluoromethyl)-1H-indazol-6-yl)-[1,2,4]triazolo[1,5-a]pyridin-2,5-diamine | 418.3 | C |
| 130 | 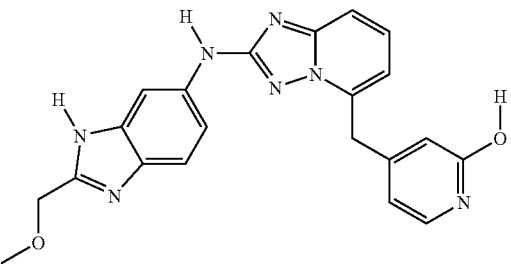 | 4-((2-(2-(methoxymethyl)-1H-benzo[d]imidazol-6-ylamino)-[1,2,4]triazolo[1,5-a]pyridin-5-yl)methyl)pyridin-2-ol | 402.3 | D |
| 131 | 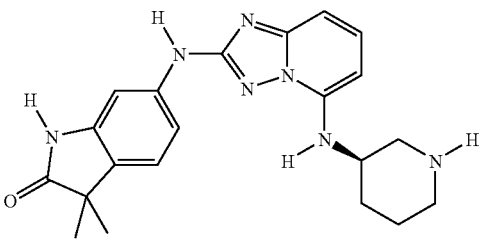 | (R)-3,3-dimethyl-6-(5-(piperidin-3-ylamino)-[1,2,4]triazolo[1,5-a]pyridin-2-ylamino)indolin-2-one | 392.6 | D |
| 132 | 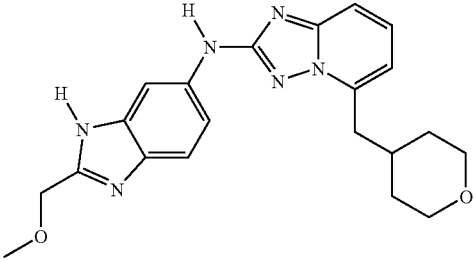 | N-(2-(methoxymethyl)-1H-benzo[d]imidazol-6-yl)-5-((tetrahydro-2H-pyran-4-yl)methyl)-[1,2,4]triazolo[1,5-a]pyridin-2-amine | 393.2 | D |
| 133 | 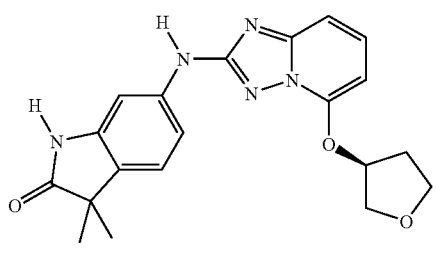 | (S)-3,3-dimethyl-6-(5-(tetrahydrofuran-3-yloxy)-[1,2,4]triazolo[1,5-a]pyridin-2-ylamino)indolin-2-one | 380.3 | C |
| 134 | 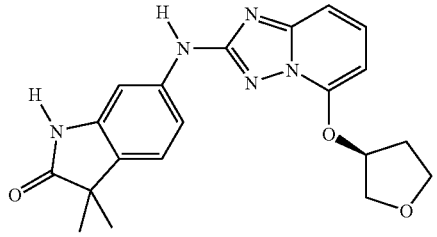 | (R)-3,3-dimethyl-6-(5-(tetrahydrofuran-3-yloxy)-[1,2,4]triazolo[1,5-a]pyridin-2-ylamino)indolin-2-one | 380.3 | D |

TABLE 1-continued

| Cmpd. No. | Structure | Cmpd. Name | MH+ (Obs.) | Activity Level |
|---|---|---|---|---|
| 135 | 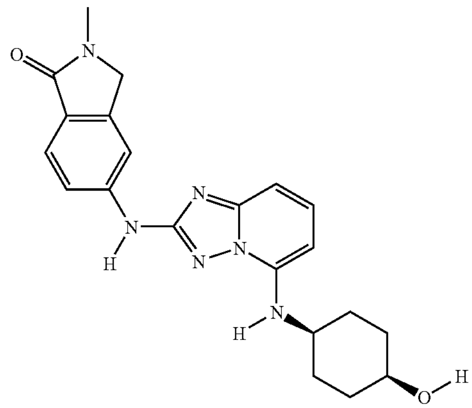 | cis-5-(5-(4-hydroxycyclohexylamino)-[1,2,4]triazolo[1,5-a]pyridin-2-ylamino)-2-methylisoindolin-1-one | 393.2 | D |
| 136 | 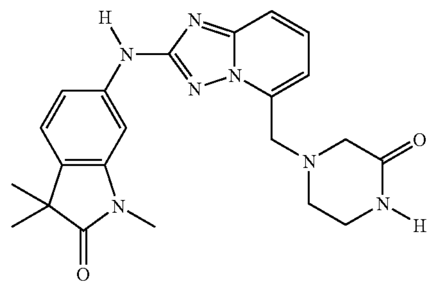 | 1,3,3-trimethyl-6-(5-((3-oxopiperazin-1-yl)methyl)-[1,2,4]triazolo[1,5-a]pyridin-2-ylamino)inolin-2-one | 420 | D |
| 137 | 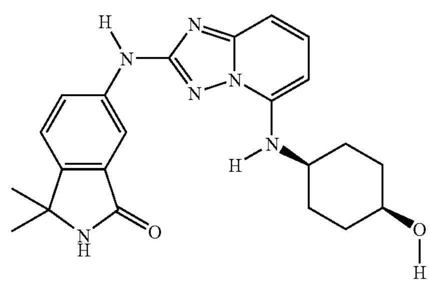 | trans-6-(5-(4-hydroxycyclohexylamino)-[1,2,4]triazolo[1,5-a]pyridin-2-ylamino)-3,3-dimethylisoindolin-1-one | 407.1 | B |
| 138 | 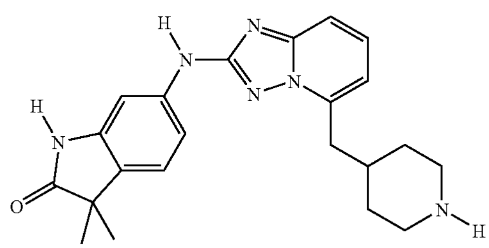 | 3,3-dimethyl-6-(5-(piperidin-4-ylmethyl)-[1,2,4]triazolo[1,5-a]pyridin-2-ylamino)indolin-2-one | 391.3 | D |
| 139 | 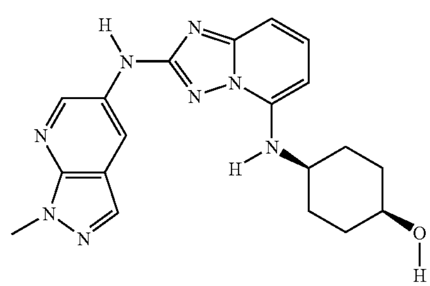 | cis-4-(2-(1-methyl-1H-pyrazolo[3,4-b]pyridin-5-ylamino)-[1,2,4]triazolo[1,5-a]pyridin-5-ylamino)cyclohexanol | 379.3 | D |

TABLE 1-continued

| Cmpd. No. | Structure | Cmpd. Name | MH+ (Obs.) | Activity Level |
|---|---|---|---|---|
| 140 | 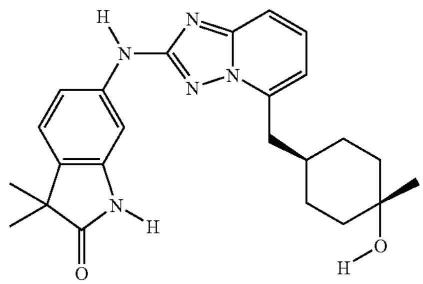 | cis-6-(5-((4-hydroxy-4-methylcyclohexyl)methyl)-[1,2,4]triazolo[1,5-a]pyridin-2-ylamino)-3,3-dimethylindolin-2-one | 420 | D |
| 141 | 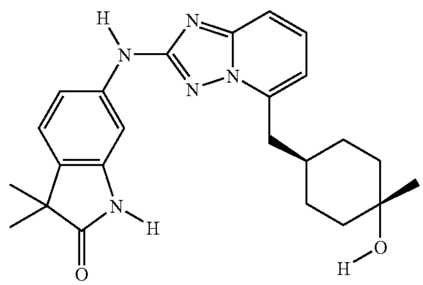 | trans-6-(5-((4-hydroxy-4-methylcyclohexyl)methyl)-[1,2,4]triazolo[1,5-a]pyridin-2-ylamino)-3,3-dimethylindolin-2-one | 420 | D |
| 142 | 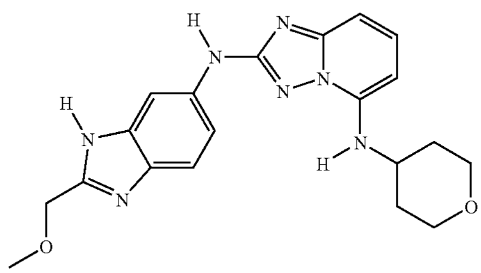 | $N^2$-(2-(methoxymethyl)-1H-benzo[d]imidazol-6-yl)-$N^5$-(tetrahydro-2H-pyran-4-yl)-[1,2,4]triazolo[1,5-a]pyridine-2,5-diamine | 394.3 | C |
| 143 | 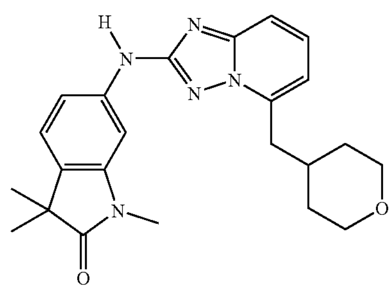 | 1,3,3-trimethyl-6-(5-((tetrahydro-2H-pyran-4-yl)methyl)-[1,2,4]triazolo[1,5-a]pyridin-2-ylamino)indolin-2-one | 406.4 | D |
| 144 | 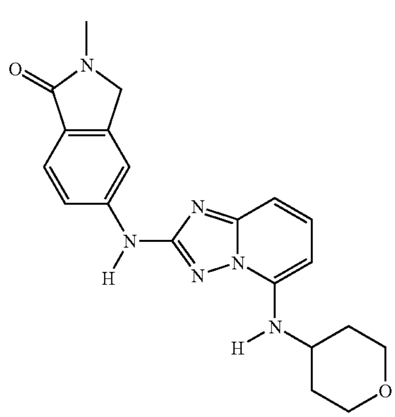 | 2-methyl-5-(5-(tetrahydro-2H-pyran-4-ylamino)-[1,2,4]triazolo[1,5-a]pyridin-2-ylamino)isoinoldin-1-one | 379 | A |

TABLE 1-continued

| Cmpd. No. | Structure | Cmpd. Name | MH+ (Obs.) | Activity Level |
|---|---|---|---|---|
| 145 | 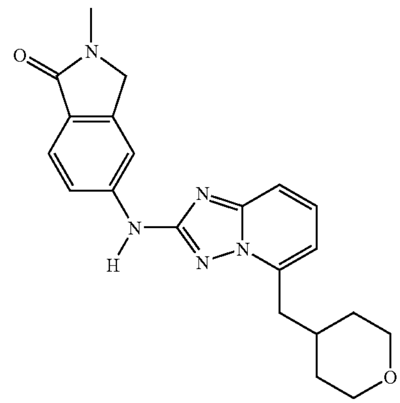 | 2-methyl-5-(5-((tetrahydro-2H-pyran-4-yl)methyl)-[1,2,4]triazolo[1,5-a]pyridin-2-ylamino)isoinoldin-1-one | 378.1 | B |
| 146 | 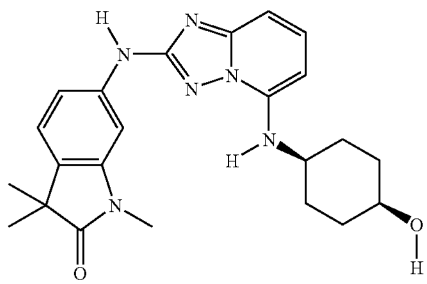 | trans-6-(5-(4-hydroxycyclohexylamino)-[1,2,4]triazolo[1,5-a]pyridin-2-ylamino)-1,3,3-trimethylindolin-2-one | 421.2 | D |
| 147 | 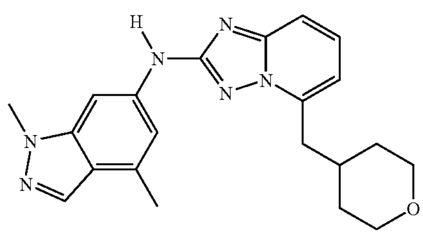 | N-(1,4-dimethyl-1H-indazol-6-yl)-5-((tetrahydro-2H-pyran-4-yl)methyl)-[1,2,4]triazolo[1,5-a]pyridin-2-amine | 377.1 | D |
| 148 | 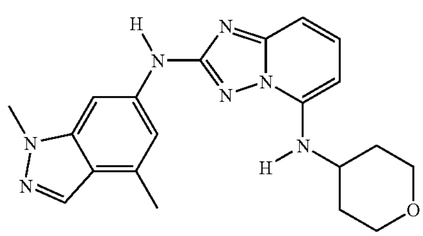 | $N^2$-(1,4-dimethyl-1H-indazol-6-yl)-$N^5$-(tetrahydro-2H-pyran-4-yl)-[1,2,4]triazolo[1,5-a]pyridin-2,5-diamine | 378.2 | D |
| 149 | 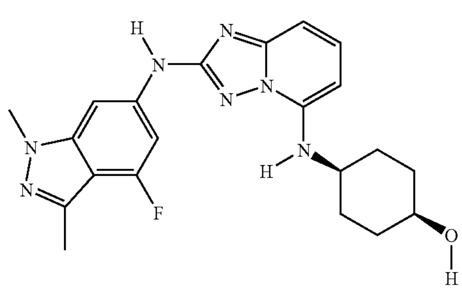 | cis-4-(2-(4-fluoro-1,3-dimethyl-1H-indazol-6-ylamino)-[1,2,4]triazolo[1,5-a]pyridin-5-ylamino)cyclohexanol | 410.3 | D |

TABLE 1-continued

| Cmpd. No. | Structure | Cmpd. Name | MH+ (Obs.) | Activity Level |
|---|---|---|---|---|
| 150 | 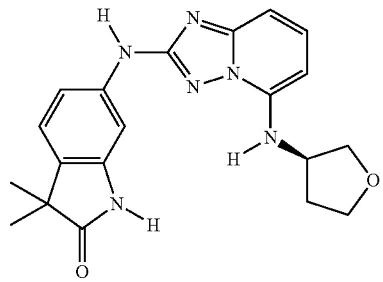 | (R)-3,3-dimethyl-6-(5-(tetrahydrofuran-4-ylamino)-[1,2,4]triazolo[1,5-a]pyridin-2-ylamino)indolin-2-one | 379.5 | D |
| 151 | 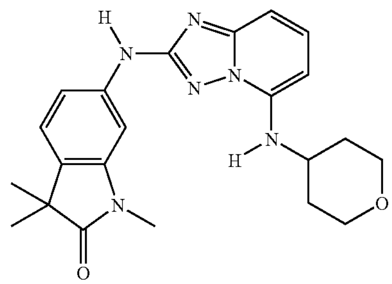 | 1,3,3-trimethyl-6-(5-(tetrahydro-2H-pyran-4-ylamino)-[1,2,4]triazolo[1,5-a]pyridin-2-ylamino)indolin-2-one | 406.4 | D |
| 152 | 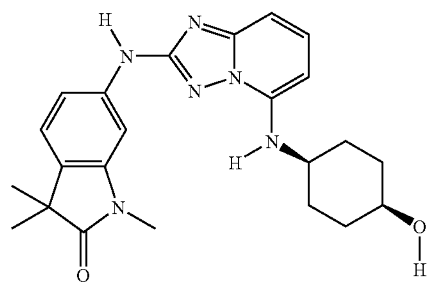 | cis-6-(5-(4-hydroxycyclohexylamino)-[1,2,4]triazolo[1,5-a]pyridin-2-ylamino)-1,3-3-trimethylindolin-2-one | 421.2 | D |
| 153 | 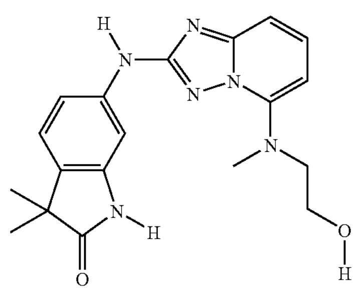 | 6-(5-((2-hydroxyethyl)(methyl)amino)-[1,2,4]triazolo[1,5-a]pyridin-2-ylamino)-3,3-dimethylindolin-2-one | 367 | D |
| 154 | 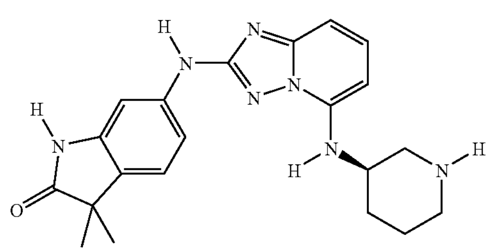 | (S)-3,3-dimethyl-6-(5-(piperidin-3-ylamino)-[1,2,4]triazolo[1,5-a]pyridin-2-ylamino)indolin-2-one | 392.6 | D |

| Cmpd. No. | Structure | Cmpd. Name | MH+ (Obs.) | Activity Level |
|---|---|---|---|---|
| 155 | 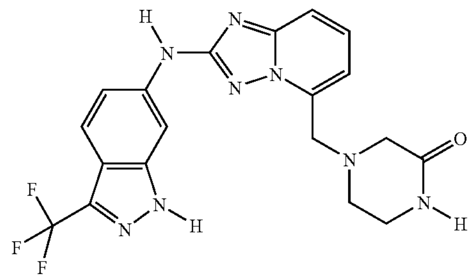 | 4-((2-(3-(trifluoromethyl)-1H-indazol-6-ylamino)-[1,2,4]triazolo[1,5-a]pyridin-5-yl)methyl)piperazin-2-one | 431.3 | D |
| 156 | 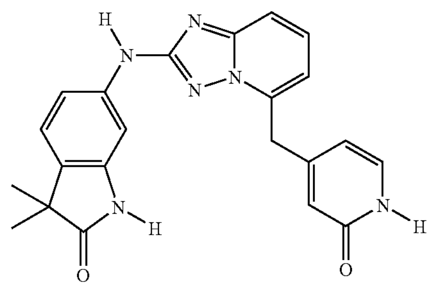 | 3,3-dimethyl-6-(5-((2-oxo-1,2-dihydropyridin-4-yl)methyl)-[1,2,4]triazolo[1,5-a]pyridin-2-ylamino)indolin-2-one | 401.4 | D |
| 157 | 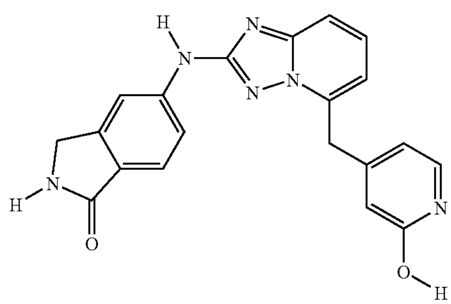 | 5-(5-((2-hydroxypyridin-4-yl)methyl)-[1,2,4]triazolo[1,5-a]pyridin-2-ylamino)isoindolin-1-one | 373.2 | D |
| 158 | 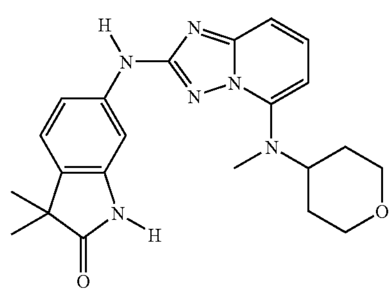 | 3,3-dimethyl-6-(5-(methyl(tetrahydro-2H-pyran-4-yl)amino)-[1,2,4]triazolo[1,5-a]pyridin-2-ylamino)indolin-2-one | 407.1 | D |
| 159 | 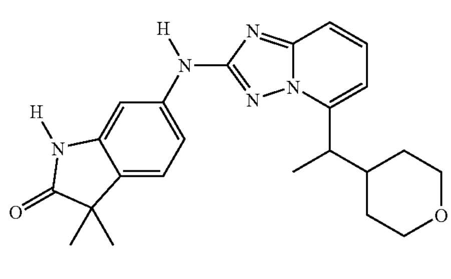 | 3,3-dimethyl-6-(5-(1-(tetrahydro-2H-pyran-4-yl)ethyl)-[1,2,4]triazolo[1,5-a]pyridin-2-ylamino)indolin-2-one | 406.2 | D |

TABLE 1-continued

| Cmpd. No. | Structure | Cmpd. Name | MH+ (Obs.) | Activity Level |
|---|---|---|---|---|
| 160 | 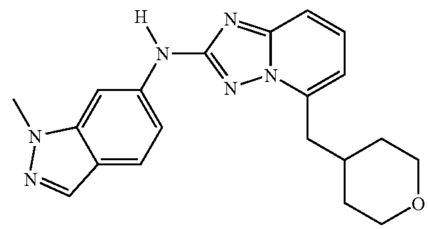 | N-(1-methyl-1H-indazol-6-yl)-5-((tetrahydro-2H-pyran-4-yl)methyl)-[1,2,4]triazolo[1,5-a]pyridin-2-amine | 363.3 | D |
| 161 | 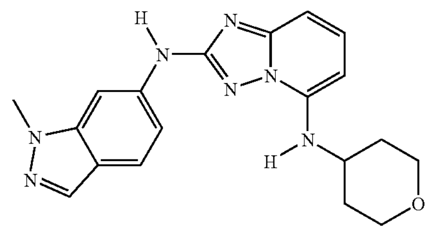 | $N^2$-(1-methyl-1H-indazol-6-yl)-$N^5$-(tetrahydro-2H-pyran-4-yl)-[1,2,4]triazolo[1,5-a]pyridin-2,5-diamine | 364.2 | D |
| 162 | 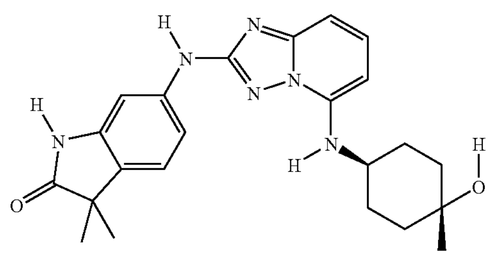 | trans-6-(5-(4-hydroxy-4-methylcyclohexylamino)-[1,2,4]triazolo[1,5-a]pyridin-2-ylamino)-3,3-dimethylindolin-2-one | 421.2 | D |
| 163 | 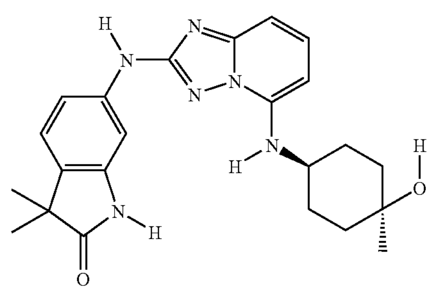 | cis-6-(5-(4-hydroxy-4-methylcyclohexylamino)-[1,2,4]triazolo[1,5-a]pyridin-2-ylamino)-3,3-dimethylindolin-2-one | 421.3 | D |
| 164 | 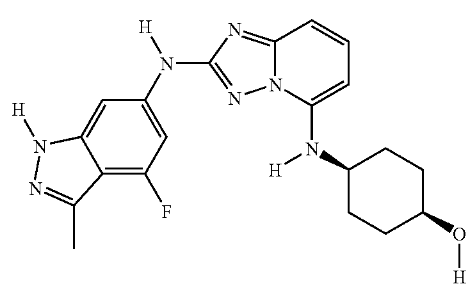 | cis-4-(2-(4-fluoro-3-methyl-1H-indazol-6-ylamino)-[1,2,4]triazolo[1,5-a]pyridin-5-ylamino)cyclohexanol | 396.3 | D |
| 165 | 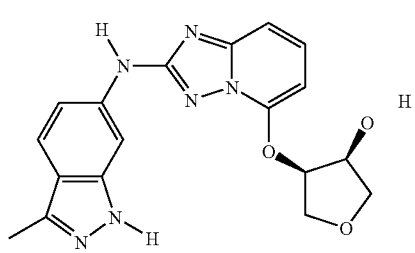 | (±)-cis-4-(2-(3-methyl-1H-indazol-6-ylamino)-[1,2,4]triazolo[1,5-a]pyridin-5-yloxy)tetrahydrofuran-3-ol | 367.37 | C |

TABLE 1-continued

| Cmpd. No. | Cmpd. Name | MH+ (Obs.) | Activity Level |
|---|---|---|---|
| 166 | (±)-trans-4-(2-(3-methyl-1H-indazol-6-ylamino)-[1,2,4]-triazolo[1,5-a]pyridin-5-ylamino)tetrahydrofuran-3-ol | 366.39 | D |
| 167 | (R)-N$^2$-(3-methyl-1H-indazol-6-yl)-N$^5$-(tetrahydrofuran-3-yl)-[1,2,4]triazolo[1,5-a]pyridin-2,5-diamine | 350.6 | D |
| 168 | 3,3-dimethyl-6-(5-(tetrahydro-2H-pyran-4-yloxy)-[1,2,4]triazolo[1,5-a]pyridin-2-ylamino)indolin-2-one | 394.3 | D |
| 169 | 3-methyl-1-((2-(3-methyl-1H-indazol-6-ylamino)-[1,2,4]triazolo[1,5-a]pyridin-5-yl)methyl)azetidin-3-ol | 364.3 | C |
| 170 | 6-(5-(3-hydroxyazetidin-1-yl)-[1,2,4]triazolo[1,5-a]pyridin-2-ylamino)-3,3-dimethylindolin-2-one | 365.1 | D |

TABLE 1-continued

| Cmpd. No. | Cmpd. Name | MH+ (Obs.) | Activity Level |
|---|---|---|---|
| 171 | 6-(5-(3-hydroxy-3-methylazetidin-1-yl)-[1,2,4]triazolo[1,5-a]pyridin-2-ylamino)-3,3-dimethylindolin-2-one | 379.3 | D |
| 172 | 3,3-dimethyl-6-(5-((3-oxopiperazin-1-yl)methyl)-[1,2,4]triazolo[1,5-a]pyridin-2-ylamino)indolin-2-one | 406.2 | D |
| 173 | 6-(5-(hydroxy(tetrahydro-2H-pyran-4-yl)methyl)-[1,2,4]triazolo[1,5-a]pyridin-2-ylamino)-3,3-dimethylindolin-2-one | 408.3 | C |
| 174 | cis-5-(5-(4-hydroxycyclohexylamino)-[1,2,4]triazolo[1,5-a]pyridin-2-ylamino)-2-(2-methoxyethyl)isoindolin-1-one | 437.3 | D |
| 175 | trans-6-(5-(4-hydroxycyclohexylamino)-[1,2,4]triazolo[1,5-a]pyridin-2-ylamino)-3,3-dimethylindolin-2-one | 407.3 | D |
| 176 | 3,3-dimethyl-6-(5-((tetrahydro-2H-pyran-4-yl)methyl)-[1,2,4]triazolo[1,5-a]pyridin-2-ylamino)indolin-2-one | 392.3 | D |

TABLE 1-continued

| Cmpd. No. | Structure | Cmpd. Name | MH+ (Obs.) | Activity Level |
|---|---|---|---|---|
| 177 | 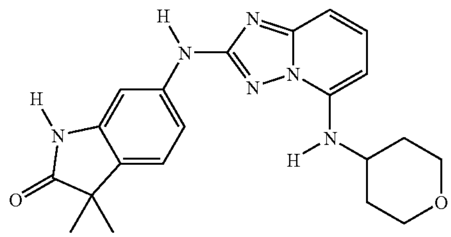 | 3,3-dimethyl-6-(5-(tetrahydro-2H-pyran-4-ylamino)-[1,2,4]triazolo[1,5-a]pyridin-2-ylamino)indolin-2-one | 393.2 | D |
| 178 | 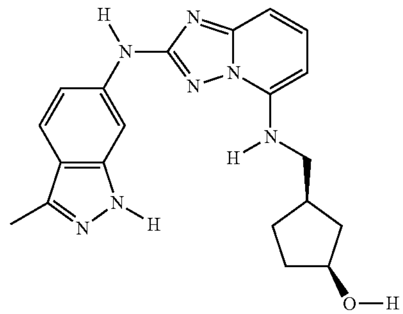 | (1S,3R)-3-((2-(3-methyl-1H-indazol-6-ylamino)-[1,2,4]triazolo[1,5-a]pyridin-5-ylamino)methyl)cyclopentanol | 378.5 | D |
| 179 | 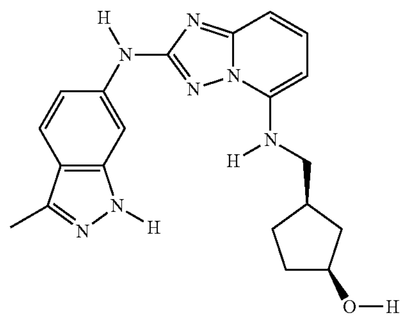 | (1R,3R)-3-((2-(3-methyl-1H-indazol-6-ylamino)-[1,2,4]triazolo[1,5-a]pyridin-5-ylamino)methyl)cyclopentanol | 378.5 | D |
| 180 | 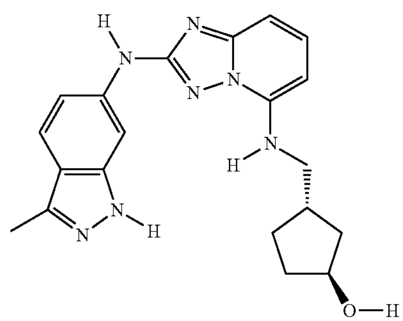 | (1R,3S)-3-((2-(3-methyl-1H-indazol-6-ylamino)-[1,2,4]triazolo[1,5-a]pyridin-5-ylamino)methyl)cyclopentanol | 377.9 | D |
| 181 | 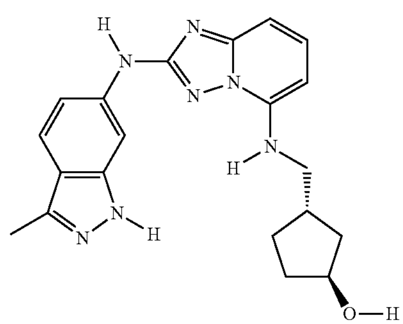 | (1S,3S)-3-((2-(3-methyl-1H-indazol-6-ylamino)-[1,2,4]triazolo[1,5-a]pyridin-5-ylamino)methyl)cyclopentanol | 378.3 | D |

TABLE 1-continued

| Cmpd. No. | Structure | Cmpd. Name | MH+ (Obs.) | Activity Level |
|---|---|---|---|---|
| 182 | 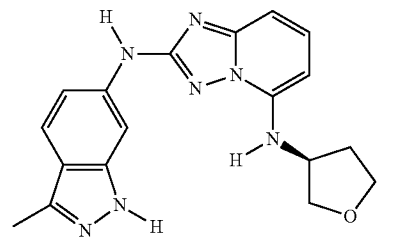 | (S)-N²-(3-methyl-1H-indazol-6-yl)-N⁵-(tetrahydrofuran-3-yl)-[1,2,4]triazolo[1,5-a]pyridin-2,5-diamine | 349.8 | C |
| 183 | 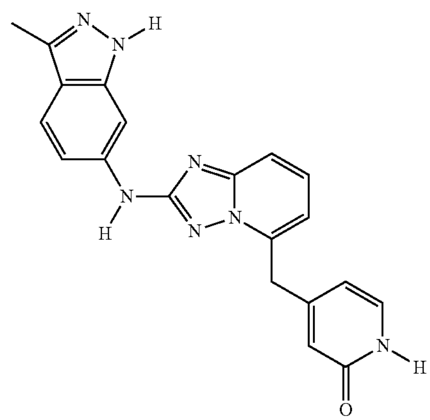 | 4-((2-(3-methyl-1H-indazol-6-ylamino)-[1,2,4]triazolo[1,5-a]pyridin-5-yl)methyl)pyridin-2(1H)-one | 371.7 | D |
| 184 | 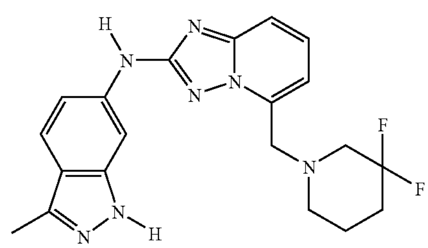 | 5-((3,3-difluoropiperidin-1-yl)methyl)-N-(3-methyl-1H-indazol-6-yl)-[1,2,4]triazolo[1,5-a]pyridin-2-amine | 398.3 | D |
| 185 | 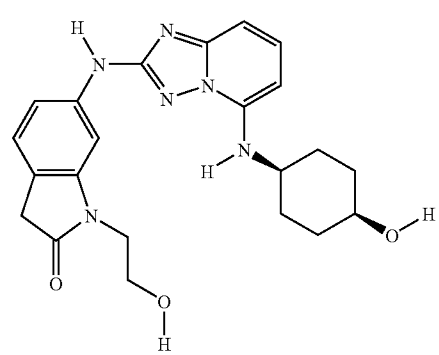 | cis-6-(5-(4-hydroxycyclohexylamino)-[1,2,4]triazolo[1,5-a]pyridin-2-ylamino)-1-(2-hydroxyethyl)indolin-2-one | 423.2 | C |
| 186 | 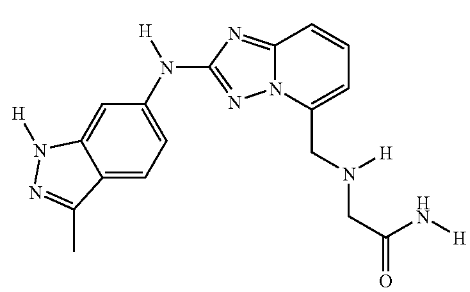 | 2-((2-(3-methyl-1H-indazol-6-ylamino)-[1,2,4]triazolo[1,5-a]pyridin-5-yl)methylamino)acetamide | 351.5 | D |

TABLE 1-continued

| Cmpd. No. | Structure | Cmpd. Name | MH+ (Obs.) | Activity Level |
|---|---|---|---|---|
| 187 | 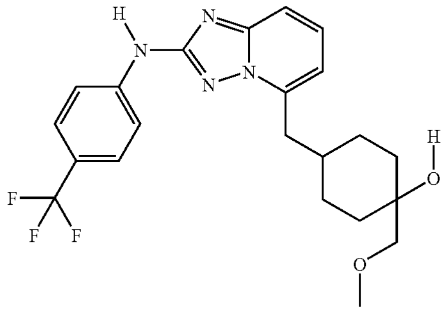 | cis-1-(methoxymethyl)-4-((2-(4-(trifluoromethyl)phenylamino)-[1,2,4]triazolo[1,5-a]pyridin-5-yl)methyl)cyclohexanol | 435.5 | B |
| 188 | 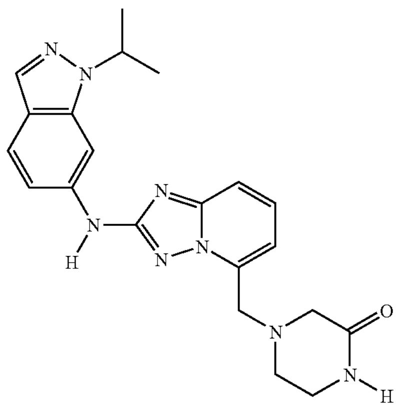 | 4-((2-(1-isopropyl-1H-indazol-6-ylamino)-[1,2,4]triazolo[1,5-a]pyridin-5-yl)methyl)piperazin-2-one | 405.4 | D |
| 189 | 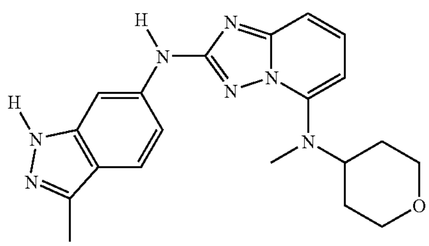 | $N^5$-methyl-$N^2$-(3-methyl-1H-indazol-6-yl)-$N^5$-(tetrahydro-2H-pyran-4-yl)-[1,2,4]triazolo[1,5-a]pyridin-2,5-diamine | 378.2 | D |
| 190 | 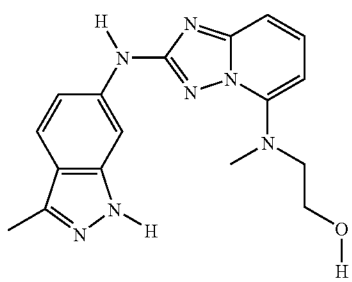 | 2-(methyl(2-(3-methyl-1H-indazol-6-ylamino)-[1,2,4]triazolo[1,5-a]pyridin-5-yl)amino)ethanol | 338.3 | D |
| 191 | 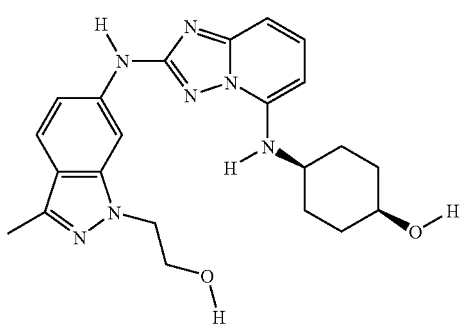 | cis-4-(2-(1-(2-hydroxyethyl)-3-methyl-1H-indazol-6-ylamino)-[1,2,4]triazolo[1,5-a]pyridin-5-ylamino)cyclohexanol | 422.3 | D |

TABLE 1-continued

| Cmpd. No. | Cmpd. Name | MH+ (Obs.) | Activity Level |
|---|---|---|---|
| 192 | cis-6-(5-(4-hydroxycyclohexylamino)-[1,2,4]triazolo[1,5-a]pyridin-2-ylamino)-1-methylindolin-2-one | 393.3 | D |
| 193 | 6-(hydroxy(2-(4-(trifluoromethyl)phenylamino)-[1,2,4]triazolo[1,5-a]pyridin-5-yl)methyl)pyrimidin-4(3H)-one | 402.7 | D |
| 194 | cis-4-(2-(1-(2-methoxyethyl)-3-methyl-1H-indazol-6-ylamino)-[1,2,4]triazolo[1,5-a]pyridin-5-ylamino)cyclohexanol | 436.3 | C |
| 195 | cis-4-(2-(2-(hydroxymethyl)-1H-benzo[d]imidazol-6-ylamino)-[1,2,4]triazolo[1,5-a]pyridin-5-ylamino)cyclohexanol | 394.3 | D |
| 196 | cis-4-(2-(2-(methoxymethyl)-1H-benzo[d]imidazol-6-ylamino)-[1,2,4]triazolo[1,5-a]pyridin-5-ylamino)cyclohexyl | 408.3 | D |

TABLE 1-continued

| Cmpd. No. | Structure | Cmpd. Name | MH+ (Obs.) | Activity Level |
|---|---|---|---|---|
| 197 | 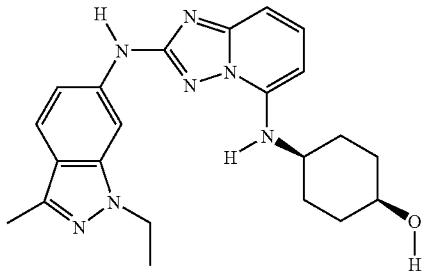 | cis-4-(2-(1-ethyl-3-methyl-1H-indazol-6-ylamino)-[1,2,4]triazolo[1,5-a]pyridin-5-ylamino)cyclohexanol | 406.3 | D |
| 198 | 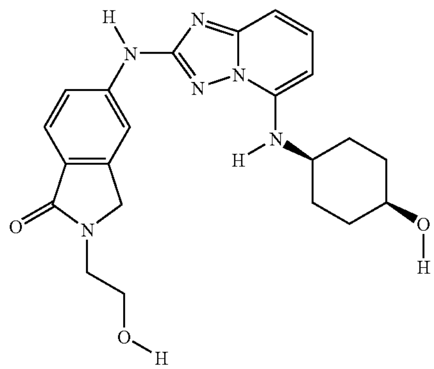 | cis-5-(5-(4-hydroxycyclohexylamino)-[1,2,4]triazolo[1,5-a]pyridin-2-ylamino)-2-(2-hydroxyethyl)isoindolin-1-one | 423.3 | D |
| 199 | 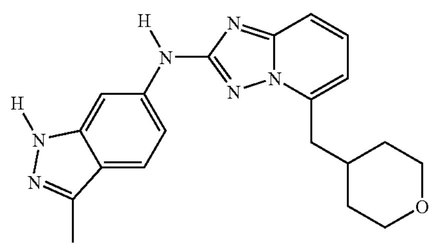 | N-(3-methyl-1H-indazol-6-yl)-5-((tetrahydro-2H-pyran-4-yl)methyl)-[1,2,4]triazolo[1,5-a]pyridin-2-amine | 363.3 | D |
| 200 | 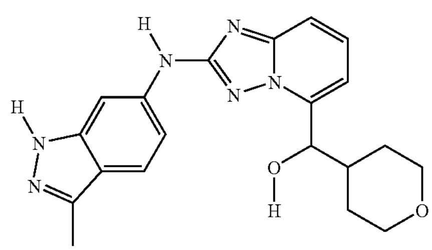 | (2-(3-methyl-1H-indazol-6-ylamino)-[1,2,4]triazolo[1,5-a]pyridin-5-yl)(tetrahydro-2H-pyran-4-yl)methanol | 379.2 | B |
| 201 | 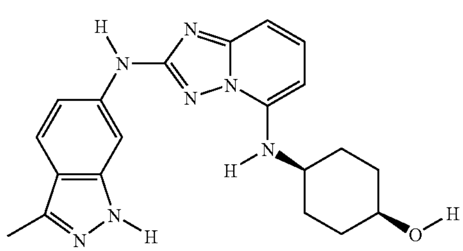 | trans-4-(2-(3-methyl-1H-indazol-6-ylamino)-[1,2,4]triazolo[1,5-a]pyridin-5-ylamino)cyclohexanol | 378.2 | D |

TABLE 1-continued

| Cmpd. No. | Structure | Cmpd. Name | MH+ (Obs.) | Activity Level |
|---|---|---|---|---|
| 202 | 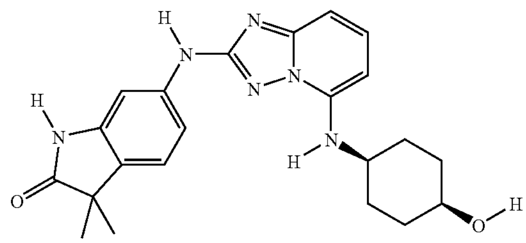 | cis-6-(5-(4-hydroxycyclohexylamino)-[1,2,4]triazolo[1,5-a]pyridin-2-ylamino)-3,3-dimethylindolin-2-one | 407.3 | D |
| 203 | 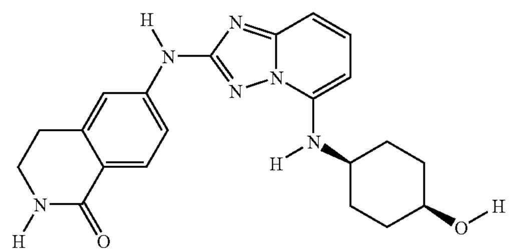 | cis-6-(5-(4-hydroxycyclohexylamino)-[1,2,4]triazolo[1,5-a]pyridin-2-ylamino)-3,4-dihydroisoquinolin-1(2H)-one | 393.2 | D |
| 204 | 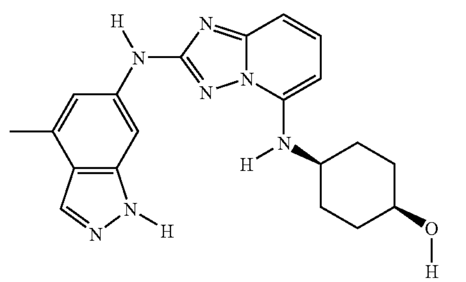 | cis-4-(2-(4-methyl-1H-indazol-6-ylamino)-[1,2,4]triazolo[1,5-a]pyridin-5-ylamino)cyclohexanol | 378.44 | D |
| 205 | 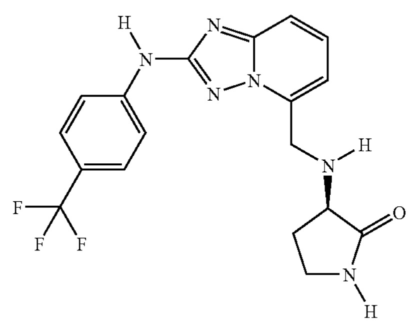 | (R)-3-((2-(4-(trifluoromethyl)phenylamino)-[1,2,4]triazolo[1,5-a]pyridin-5-yl)methylamino)pyrrolidin-2-one | 391 | A |
| 206 | 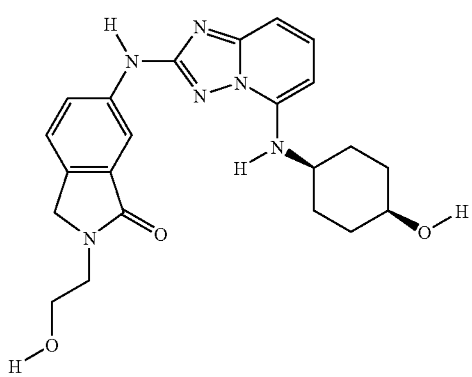 | cis-6-(5-(4-hydroxycyclohexylamino)-[1,2,4]triazolo[1,5-a]pyridin-2-ylamino)-2-(2-hydroxyethyl)isoindolin-1-one | 423.3 | A |

TABLE 1-continued

| Cmpd. No. | Structure | Cmpd. Name | MH+ (Obs.) | Activity Level |
|---|---|---|---|---|
| 207 | 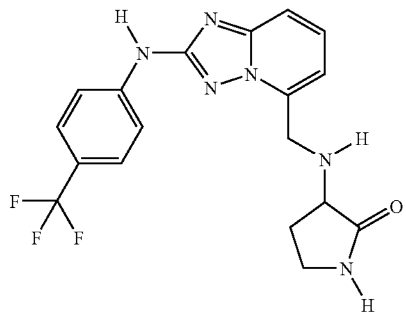 | (±)-3-((2-(4-(trifluoromethyl)phenylamino)-[1,2,4]triazolo[1,5-a]pyridin-5-yl)methylamino)pyrrolidin-2-one | 391.1 | A |
| 208 | 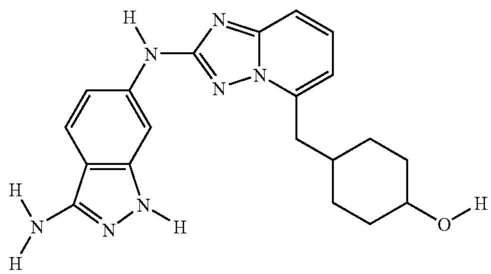 | 4-((2-(3-amino-1H-indazol-6-ylamino)-[1,2,4]triazolo[1,5-a]pyridin-5-yl)methyl)cyclohexanol | 378.3 | D |
| 209 | 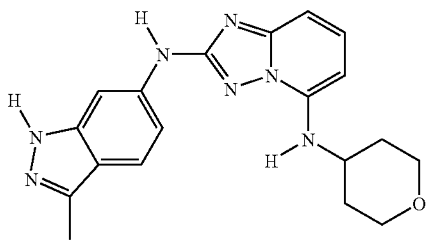 | $N^2$-(3-methyl-1H-indazol-6-yl)-$N^5$-(tetrahydro-2H-pyran-4-yl)-[1,2,4]triazolo[1,5-a]pyridin-2,5-diamine | 364.2 | D |
| 210 | 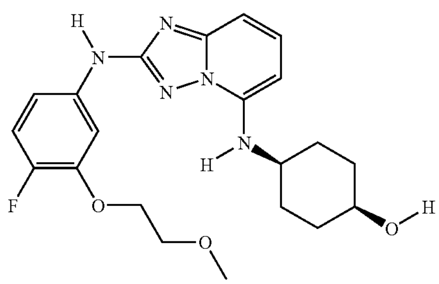 | cis-4-(2-(4-fluoro-3-(2-methoxyethoxy)phenylamino)-[1,2,4]triazolo[1,5-a]pyridin-5-ylamino)cyclohexanol | 416.2 | D |
| 211 | 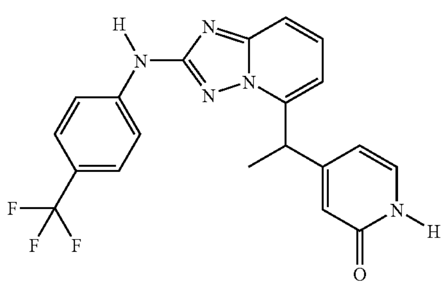 | 4-(1-(2-(4-(trifluoromethyl)phenylamino)-[1,2,4]triazolo[1,5-a]pyridin-5-yl)ethyl)pyridin-2(1H)-one | 400.2 | D |

TABLE 1-continued

| Cmpd. No. | Cmpd. Name | MH+ (Obs.) | Activity Level |
|---|---|---|---|
| 212 | (1S,2S)-2-(2-(3-methyl-1H-indazol-6-ylamino)-[1,2,4]triazolo[1,5-a]pyridin-5-ylamino)cyclopentanol | 364.3 | D |
| 213 | N-methyl-2-((2-(4-(trifluoromethyl)phenylamino)-[1,2,4]triazolo[1,5-a]pyrridin-5-yl)methylamino)acetamide | 379.1 | A |
| 214 | 4-(5-((3-hydroxycyclopentyl)methyl)-[1,2,4]triazolo[1,5-a]pyridin-2-ylamino)-N-methylbenzamide (diastereomer 2) | 366.1 | A |
| 215 | 1-(2-(3-methyl-1H-indazol-6-ylamino)-[1,2,4]triazolo[1,5-a]pyridin-5-yl)azetidin-3-ol | 336.2 | D |

TABLE 1-continued

| Cmpd. No. | Structure | Cmpd. Name | MH+ (Obs.) | Activity Level |
|---|---|---|---|---|
| 216 | 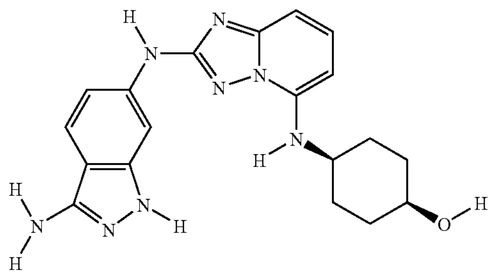 | cis-4-(2-(3-amino-1H-indazol-6-ylamino)-[1,2,4]triazolo[1,5-a]pyridin-5-ylamino)cyclohexanol | 379.4 | D |
| 217 | 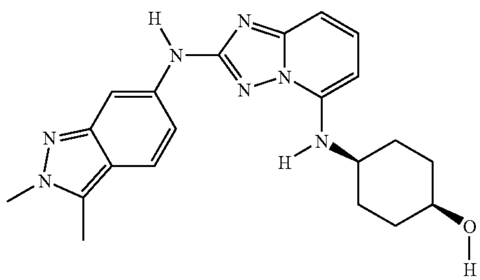 | cis-4-(2-(2,3-dimethyl-2H-indazol-6-ylamino)-[1,2,4]triazolo[1,5-a]pyridin-5-ylamino)cyclohexanol | 392.47 | D |
| 218 | 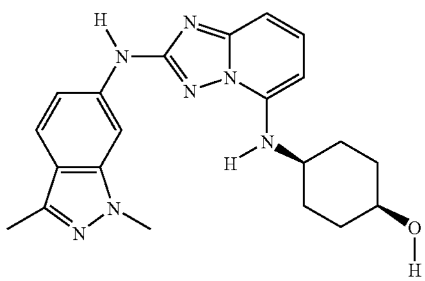 | cis-4-(2-(1,3-dimethyl-1H-indazol-6-ylamino)-[1,2,4]triazolo[1,5-a]pyridin-5-ylamino)cyclohexanol | 392.47 | D |
| 219 | 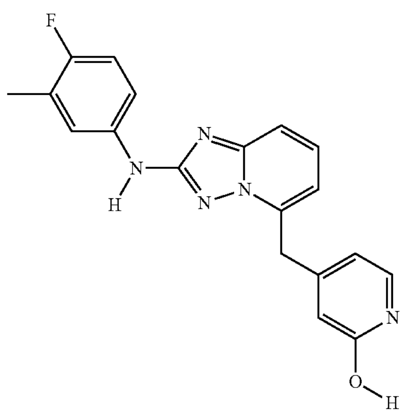 | 4-((2-(4-fluoro-3-methylphenylamino)-[1,2,4]triazolo[1,5-a]pyridin-5-yl)methyl)pyridin-2-ol | 348.9 | D |
| 220 | 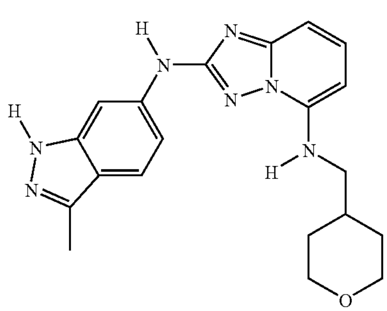 | $N^2$-(3-methyl-1H-indazol-6-yl)-$N^5$-((tetrahydro-2H-pyran-4-yl)methyl)-[1,2,4]triazolo[1,5-a]pyridin-2,5-diamine | 378.1 | C |

TABLE 1-continued

| Cmpd. No. | Structure | Cmpd. Name | MH+ (Obs.) | Activity Level |
|---|---|---|---|---|
| 221 | 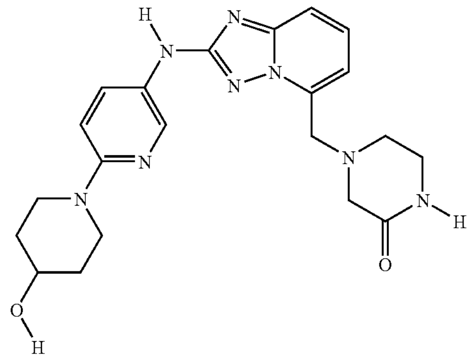 | 4-((2-(6-(4-hydroxypiperidin-1-yl)pyridin-3-ylamino)-[1,2,4]triazolo[1,5-a]pyridin-5-yl)methyl)piperazin-2-one | 423.3 | B |
| 222 | 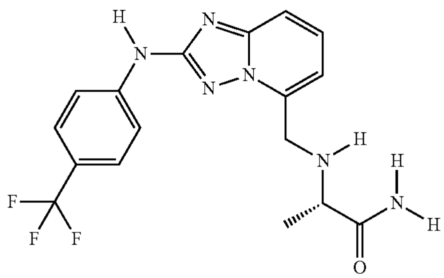 | (S)-2-((2-(4-(trifluoromethyl)phenylamino)-[1,2,4]triazolo[1,5-a]pyridin-5-yl)methylamino)propanamide | 379 | A |
| 223 | 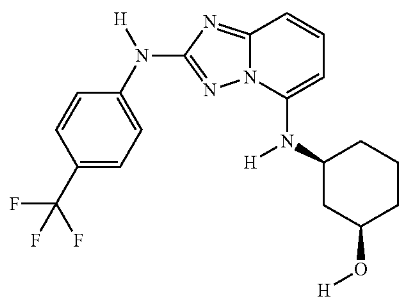 | cis-3-(2-(4-(trifluoromethyl)phenylamino)-[1,2,4]triazolo[1,5-a]pyridin-5-ylamino)cyclohexanol (enantiomer 1) | 392.2 | A |
| 224 | 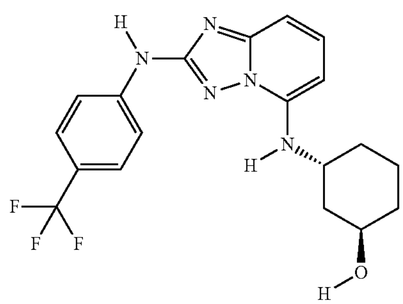 | cis-3-(2-(4-(trifluoromethyl)phenylamino)-[1,2,4]triazolo[1,5-a]pyridin-5-ylamino)cyclohexanol (enantiomer 2) | 392.2 | A |
| 225 | 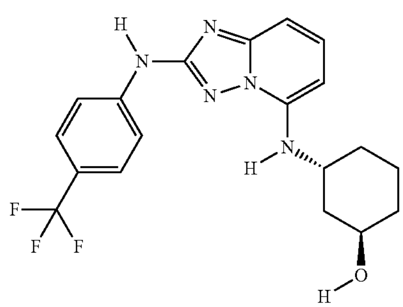 | trans-3-(2-(4-(trifluoromethyl)phenylamino)-[1,2,4]triazolo[1,5-a]pyridin-5-ylamino)cyclohexanol (enantiomer 1) | 392.2 | D |

| Cmpd. No. | Structure | Cmpd. Name | MH+ (Obs.) | Activity Level |
|---|---|---|---|---|
| 226 | 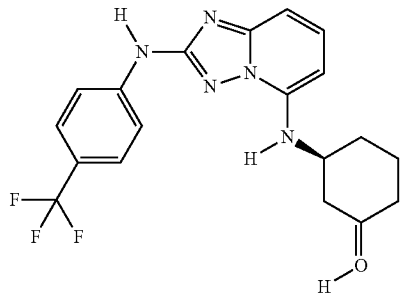 | trans-3-(2-(4-(trifluoromethyl)(phenylamino)-[1,2,4]triazolo[1,5-a]pyridin-5-ylamino)cyclohexanol (enantiomer 2) | 392.2 | B |
| 227 | 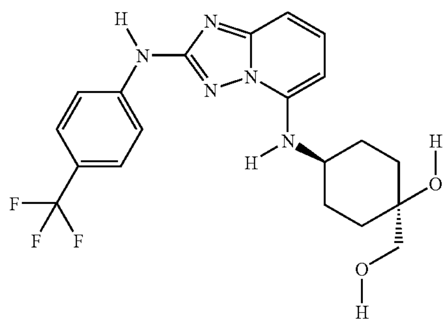 | cis-1-(hydroxymethyl)-4-(2-(4-(trifluoromethyl)phenylamino)-[1,2,4]triazolo[1,5-a]pyridin-5-ylamino)cyclohexanol | 422.2 | D |
| 228 | 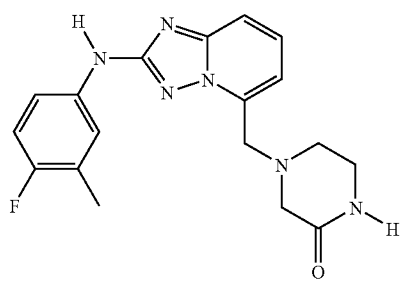 | 4-((2-(4-fluoro-3-methylphenylamino)-[1,2,4]triazolo[1,5-a]pyridin-5-yl)methyl)piperazin-2-one | 355.2 | C |
| 229 | 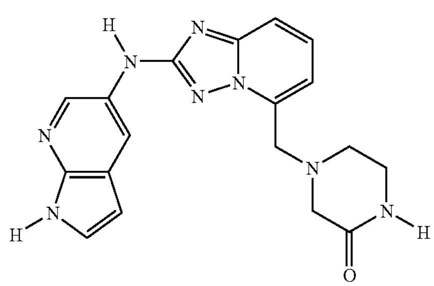 | 4-((2-(1H-pyrrolo[2,3-b]pyridin-5-ylamino)-[1,2,4]triazolo[1,5-a]pyridin-5-yl)methyl)piperazin-2-one | 363.3 | D |
| 230 | 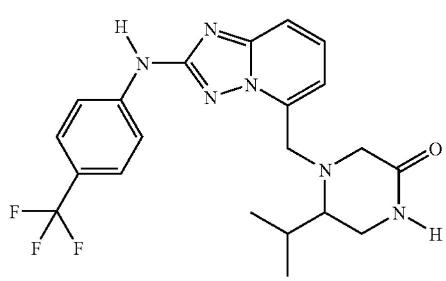 | (±)-5-isopropyl-4-((2-(4-(trifluoromethyl)phenylamino)-[1,2,4]triazolo[1,5-a]pyridin-5-yl)methyl)piperazin-2-one | 433.2 | A |

TABLE 1-continued

| Cmpd. No. | Structure | Cmpd. Name | MH+ (Obs.) | Activity Level |
|---|---|---|---|---|
| 231 | 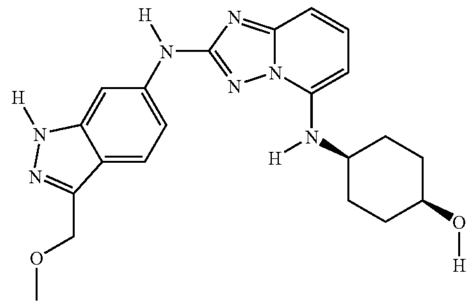 | cis-4-(2-(3-(methoxymethyl)-1H-indazol-6-ylamino)-[1,2,4]triazolo[1,5-a]pyridin-5-ylamino)cyclohexanol | 408.2 | D |
| 232 | 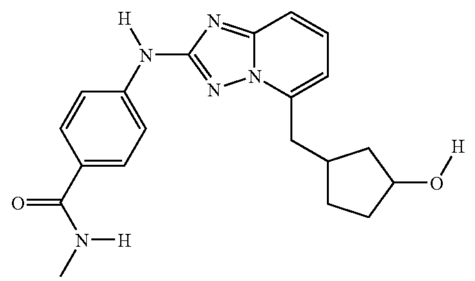 | 4-(5-((3-hydroxycyclopentyl)methyl)-[1,2,4]triazolo[1,5-a]pyridin-2-ylamino)-N-methylbenzamide (diastereomer 1) | 366.1 | A |
| 233 | 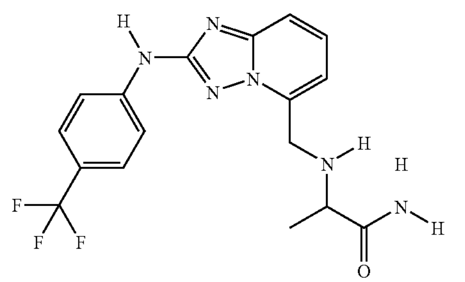 | (±)-2-((2-(4-(trifluoromethyl)phenylamino)-[1,2,4]triazolo[1,5-a]pyridin-5-yl)methylamino)propanamide | 379.2 | B |
| 234 | 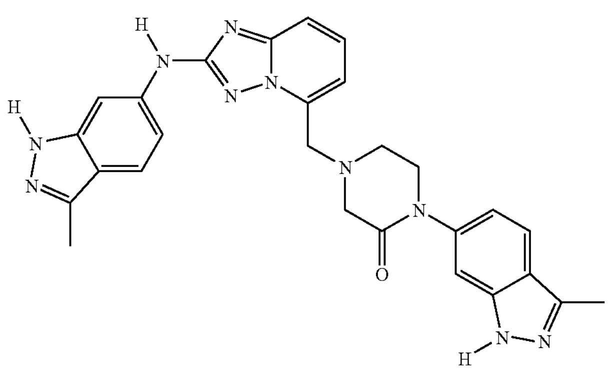 | 1-(3-methyl-1H-indazol-6-yl)-4-((2-(3-methyl-1H-indazol-6-ylamino)-[1,2,4]triazolo[1,5-a]pyridin-5-yl)methyl)piperazin-2-one | 507.4 | A |
| 235 | 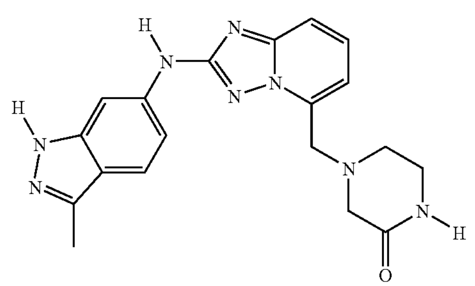 | 4-((2-(3-methyl-1H-indazol-6-ylamino)-[1,2,4]triazolo[1,5-a]pyridin-5-yl)methyl)piperazin-2-one | 377.1 | D |

TABLE 1-continued

| Cmpd. No. | Structure | Cmpd. Name | MH+ (Obs.) | Activity Level |
|---|---|---|---|---|
| 236 | 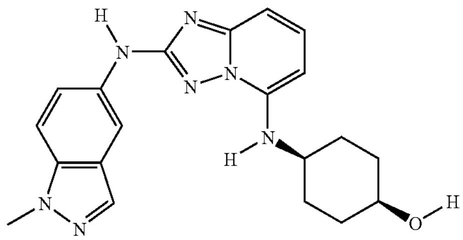 | cis-4-(2-(1-methyl-1H-indazol-5-ylamino)-[1,2,4]triazolo[1,5-a]pyridin-5-ylamino)cyclohexanol | 378.2 | D |
| 237 | 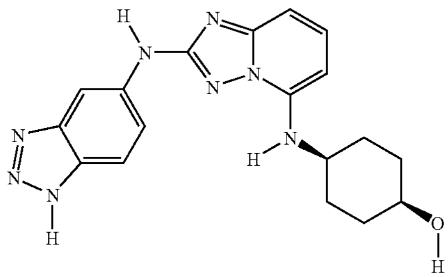 | cis-4-(2-(1H-benzo[d][1,2,3]triazolo-5-ylamino)-[1,2,4]triazolo[1,5-a]pyridin-5-ylamino)cyclohexanol | 365.1 | D |
| 238 | 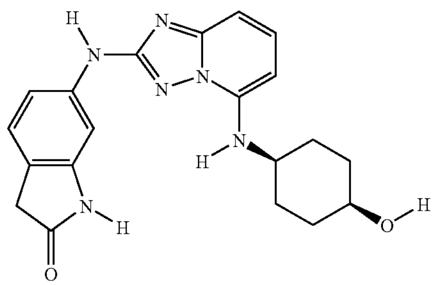 | cis-6-(5-(4-hydroxycyclohexylamino)-[1,2,4]triazolo[1,5-a]pyridin-2-ylamino)indolin-2-one | 379.2 | D |
| 239 | 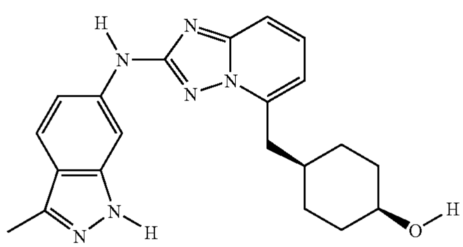 | cis-4-((2-(3-methyl-1H-indazol-6-ylamino)-[1,2,4]triazolo[1,5-a]pyridin-5-yl)methyl)cyclohexanol | 377.2 | D |
| 240 | 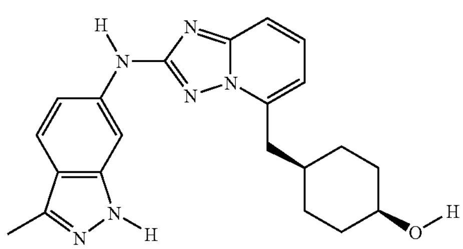 | trans-4-((2-(3-methyl-1H-indazol-6-ylamino)-[1,2,4]triazolo[1,5-a]pyridin-5-yl)methyl)cyclohexanol | 377.2 | D |
| 241 | 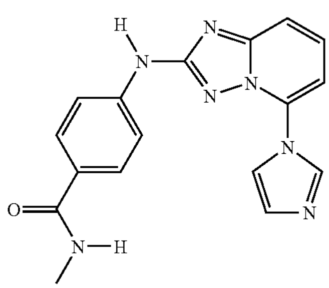 | 4-(5-(1H-imidazol-1-yl)-[1,2,4]triazolo[1,5-a]pyridin-2-ylamino)-N-methylbenzamide | 334.2 | A |

TABLE 1-continued

| Cmpd. No. | Structure | Cmpd. Name | MH+ (Obs.) | Activity Level |
|---|---|---|---|---|
| 242 | 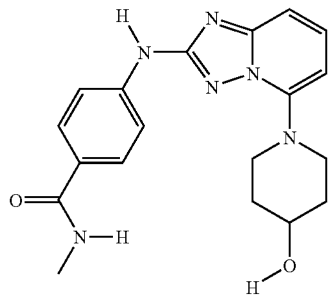 | 4-(5-(4-hydroxypiperidin-1-yl)-[1,2,4]triazolo[1,5-a]pyridin-2-ylamino)-N-methylbenzamide | 367.2 | A |
| 243 | 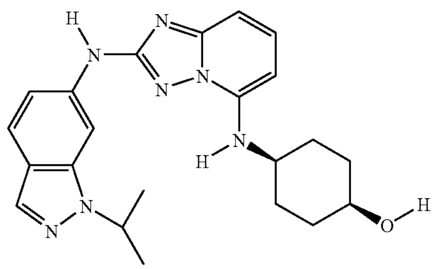 | cis-4-(2-(1-isopropyl-1H-indazol-6-ylamino)-[1,2,4]triazolo[1,5-a]pyridin-5-ylamino)cyclohexanol | 406.2 | D |
| 244 | 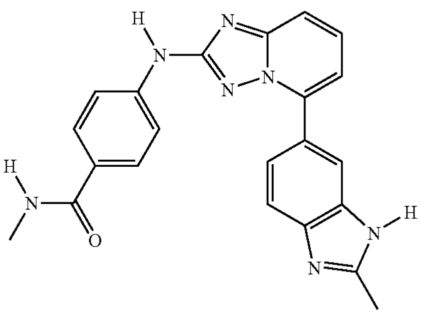 | N-methyl-4-(5-(2-methyl-1H-benzo[d]imidazol-6-yl)-[1,2,4]triazolo[1,5-a]pyridin-2-ylamino)benzamide | 398.1 | D |
| 245 | 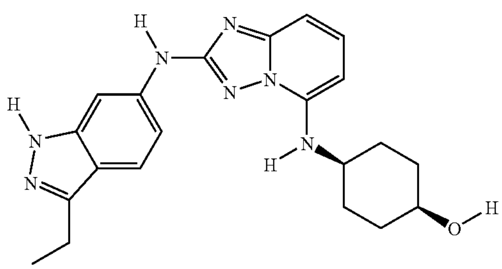 | cis-4-(2-(3-ethyl-1H-indazol-6-ylamino)-[1,2,4]triazolo[1,5-a]pyridin-5-ylamino)cyclohexanol | 392.2 | D |
| 246 | 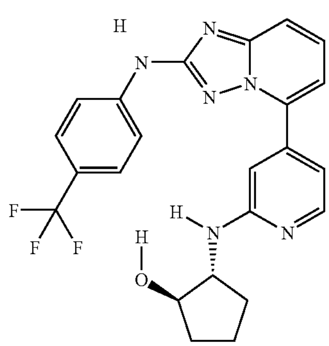 | (1R,2R)-2-(4-(2-(4-(trifluoromethyl)phenylamino)-[1,2,4]triazolo[1,5-a]pyridin-5-yl)pyridin-2-ylamino)cyclopentanol | 455.1 | B |

TABLE 1-continued

| Cmpd. No. | Cmpd. Name | MH+ (Obs.) | Activity Level |
|---|---|---|---|
| 247 | N-methyl-4-(5-(piperidin-1-yl)-[1,2,4]triazolo[1,5-a]pyridin-2-ylamino)benzamide | 351.3 | B |
| 248 | (±)-trans-3-(2-(4-(trifluoromethyl)phenylamino)-[1,2,4]triazolo[1,5-a]pyridin-5-ylamino)cyclohexanol | 392.2 | D |
| 249 | (S)-4-(5-(3-hydroxypyrrolidin-1-yl)-[1,2,4]triazolo[1,5-a]pyridin-2-ylamino)-N-methylbenzamide | 353.1 | B |
| 250 | (R)-4-(5-(3-hydroxypyrrolidin-1-yl)-[1,2,4]triazolo[1,5-a]pyridin-2-ylamino)-N-methylbenzamide | 353.1 | B |
| 251 | N-methyl-4-(5-(pyrrolidin-1-yl)-[1,2,4]triazolo[1,5-a]pyridin-2-ylamino)benzamide | 337.2 | C |

TABLE 1-continued

| Cmpd. No. | Cmpd. Name | MH+ (Obs.) | Activity Level |
|---|---|---|---|
| 252 | 1-((2-(4-(trifluoromethyl)phenylamino)-[1,2,4]triazolo[1,5-a]pyridin-5-yl)methyl)imidazolidine-2,4-dione | 391.1 | A |
| 253 | cis-5-(5-(4-hydroxycyclohexylamino)-[1,2,4]triazolo[1,5-a]pyridin-2-ylamino)isoindolin-1-one | 379.2 | D |
| 254 | N-methyl-4-(5-(2-(piperidin-4-yl)ethyl)-[1,2,4]triazolo[1,5-a]pyridin-2-ylamino)benzamide | 379.2 | B |
| 255 | cis-4-(5-(4-hydroxycyclohexylamino)-[1,2,4]triazolo[1,5-a]pyridin-2-ylamino)picolinamide | 368.3 | A |
| 256 | cis-4-(5-(4-hydroxycyclohexylamino)-[1,2,4]triazolo[1,5-a]pyridin-2-ylamino)picolinonitrile | 350.1 | B |

TABLE 1-continued

| Cmpd. No. | Structure | Cmpd. Name | MH+ (Obs.) | Activity Level |
|---|---|---|---|---|
| 257 | 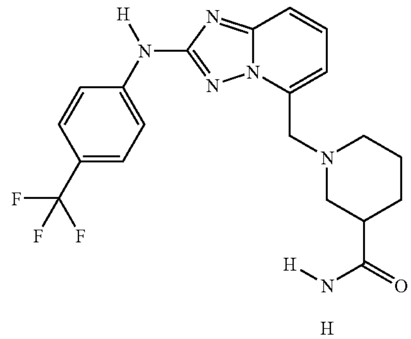 | 1-((2-(4-(trifluoromethyl)phenylamino)-[1,2,4]triazolo[1,5-a]pyridin-5-yl)methyl)piperidine-3-carboxamide | 419.2 | A |
| 258 | 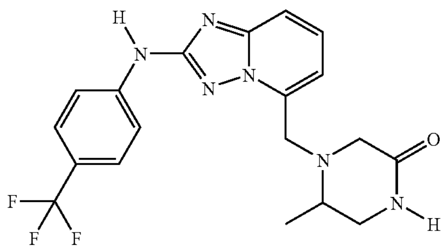 | 5-methyl-4-((2-(4-(trifluoromethyl)phenylamino)-[1,2,4]triazolo[1,5-a]pyridin-5-yl)methyl)piperazin-2-one | 405.39 | B |
| 259 | 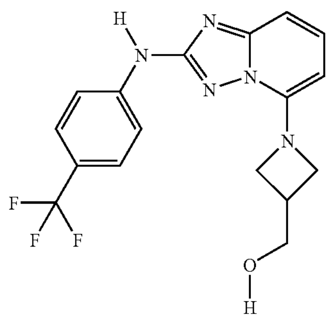 | (1-(2-(4-(trifluoromethyl)phenylamino)-[1,2,4]triazolo[1,5-a]pyridin-5-yl)azetidin-3-yl)methanol | 364.2 | D |
| 260 | 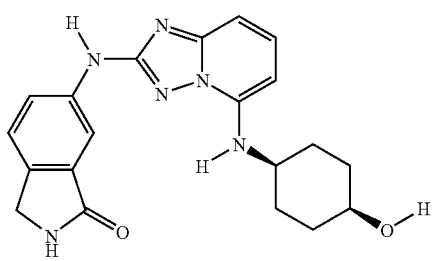 | cis-6-(5-(4-hydroxycyclohexylamino)-[1,2,4]triazolo[1,5-a]pyridin-2-ylamino)isoindolin-2-one | 379.2 | B |
| 261 | 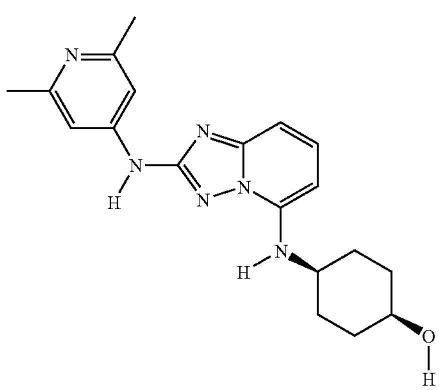 | cis-4-(2-(2,6-dimethylpyridin-4-ylamino)-[1,2,4]triazolo[1,5-a]pyridin-5-ylamino)cyclohexanol | 353.2 | B |

TABLE 1-continued

| Cmpd. No. | Structure | Cmpd. Name | MH+ (Obs.) | Activity Level |
|---|---|---|---|---|
| 262 | 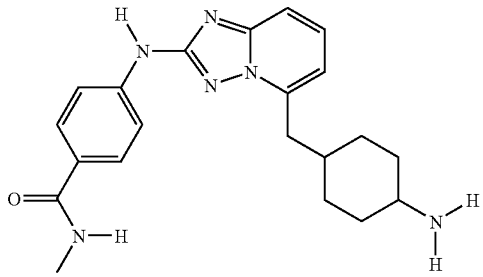 | 4-(5-((4-aminocyclohexyl)methyl)-[1,2,4]triazolo[1,5-a]pyridin-2-ylamino)-N-methylbenzamide | 378.2 | D |
| 263 | 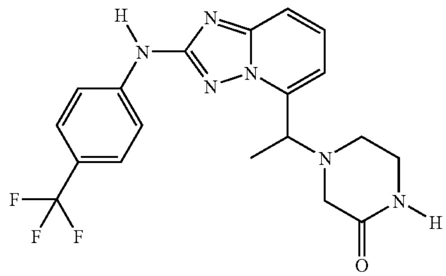 | 4-(1-(2-(4-(trifluoromethyl)phenylamino)-[1,2,4]triazolo[1,5-a]pyridin-5-yl)ethyl)piperazin-2-one | 405.39 | D |
| 264 | 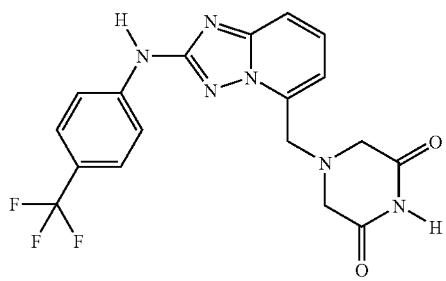 | 4-((2-(4-(trifluoromethyl)phenylamino)-[1,2,4]triazolo[1,5-a]pyridin-5-yl)methyl)piperazine-2,6-dione | 405.1 | D |
| 265 | 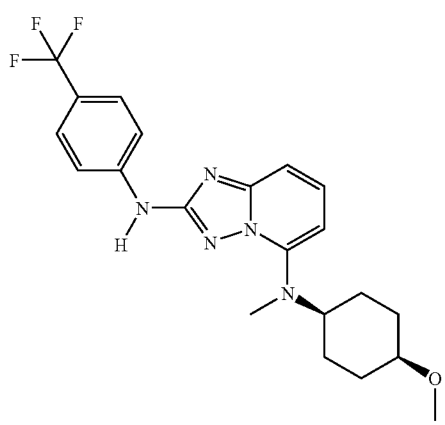 | cis-$N^5$-(4-methoxycyclohexyl)-$N^5$-methyl-$N^2$-(4-(trifluoromethyl)phenyl)-[1,2,4]triazolo[1,5-a]pyridine-2,5-diamine | 420.1 | A |

TABLE 1-continued

| Cmpd. No. | Structure | Cmpd. Name | MH+ (Obs.) | Activity Level |
|---|---|---|---|---|
| 266 | 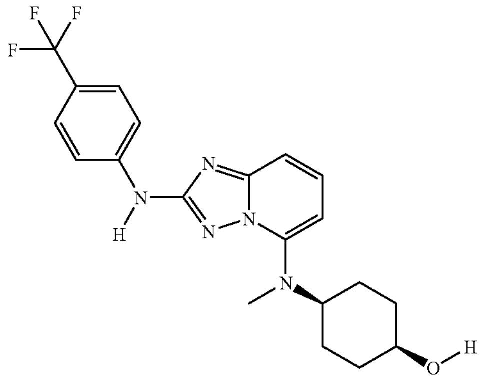 | cis-4-(methyl(2-(4-(trifluoromethyl)phenylamino)-[1,2,4]triazolo[1,5-a]pyridin-5-yl)amino)cyclohexanol | 406.2 | A |
| 267 | 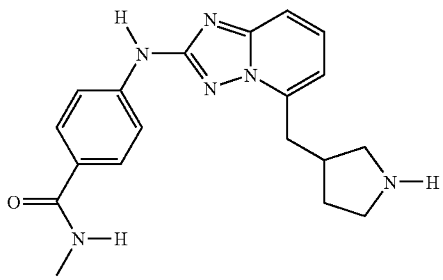 | N-methyl-4-(5-(pyrrolidin-3-ylmethyl)-[1,2,4]triazolo[1,5-a]pyridin-2-ylamino)benzamide | 351.2 | B |
| 268 | 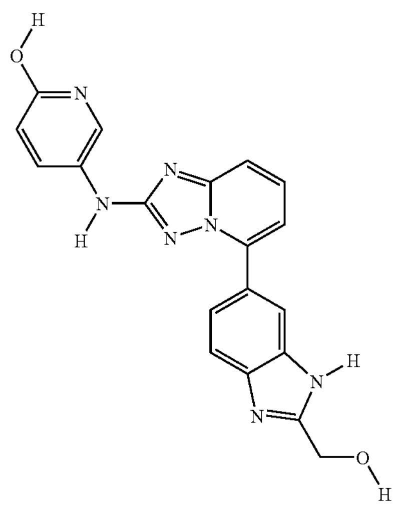 | 5-(5-(2-(hydroxyethyl)-1H-benzo[d]imidazol-6-yl)-[1,2,4]triazolo[1,5-a]pyridin-2-ylamino)pyridin-2-ol | 373.2 | C |
| 269 | 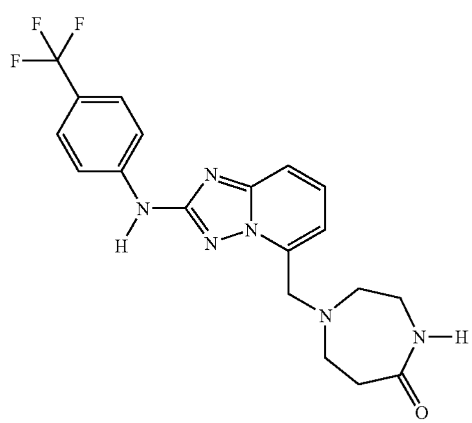 | 1-((2-(4-(trifluoromethyl)phenylamino)-[1,2,4]triazolo[1,5-a]pyridin-5-yl)methyl)-1,4-diazepan-5-one | 420.1 | B |

TABLE 1-continued

| Cmpd. No. | Structure | Cmpd. Name | MH+ (Obs.) | Activity Level |
|---|---|---|---|---|
| 270 | 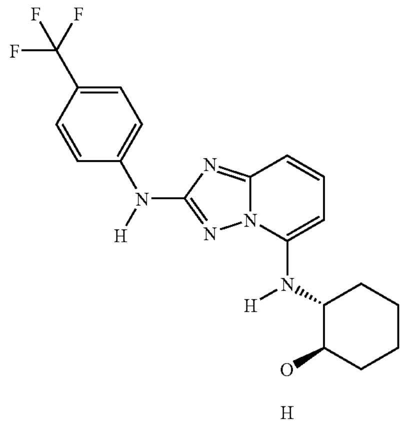 | (1S,2R)-2-(2-(4-(trifluoromethyl)phenylamino)-[1,2,4]triazolo[1,5-a]pyridin-5-ylamino)cyclohexanol | 392.1 | A |
| 271 | 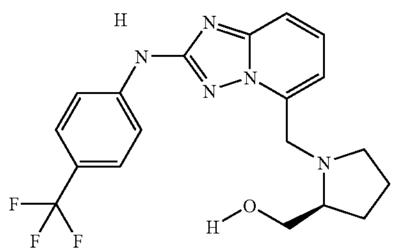 | (S)-(1-((2-(4-(trifluoromethyl)phenylamino)-[1,2,4]triazolo[1,5-a]pyridin-5-yl)methyl)pyrrolidin-2-yl)methanol | 392.4 | A |
| 272 | 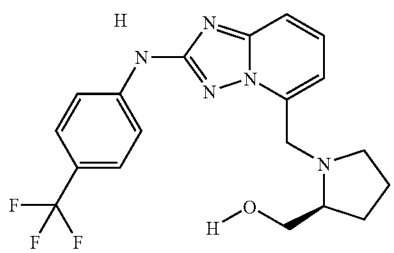 | (R)-(1-((2-(4-(trifluoromethyl)phenylamino)-[1,2,4]triazolo[1,5-a]pyridin-5-yl)methyl)pyrrolidin-2-yl)methanol | 392.4 | A |
| 273 | 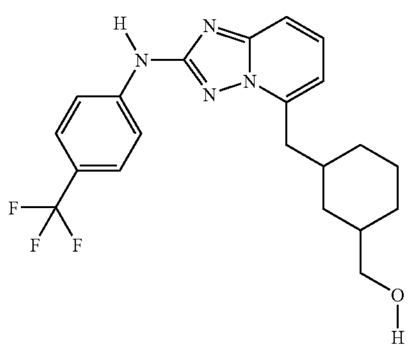 | (1-((2-(4-(trifluoromethyl)phenylamino)-[1,2,4]triazolo[1,5-a]pyridin-5-yl)methyl)piperidin-3-yl)methanol | 406.3 | A |
| 274 | 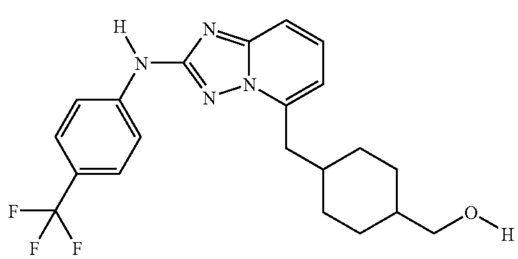 | (1-((2-(4-(trifluoromethyl)phenylamino)-[1,2,4]triazolo[1,5-a]pyridin-5-yl)methyl)piperidin-4-yl)methanol | 406.3 | A |

TABLE 1-continued

| Cmpd. No. | Structure | Cmpd. Name | MH+ (Obs.) | Activity Level |
|---|---|---|---|---|
| 275 | 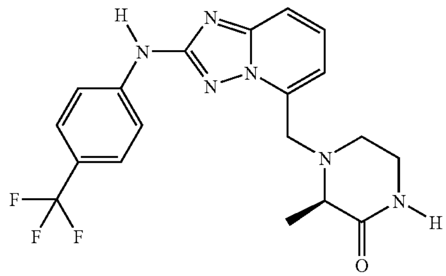 | (S)-3-methyl-4-((2-(4-(trifluoromethyl)phenylamino)-[1,2,4]triazolo[1,5-a]pyridin-5-yl)methyl)piperazin-2-one | 405.39 | D |
| 276 | 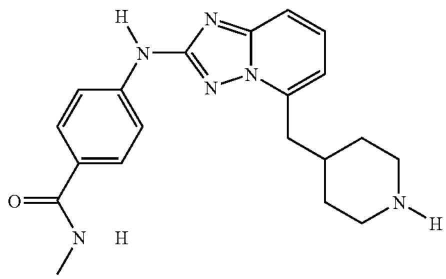 | N-methyl-4-(5-(piperazin-4-ylmethyl)-[1,2,4]triazolo[1,5-a]pyridin-2-ylamino)benzamide | 365.2 | D |
| 277 | 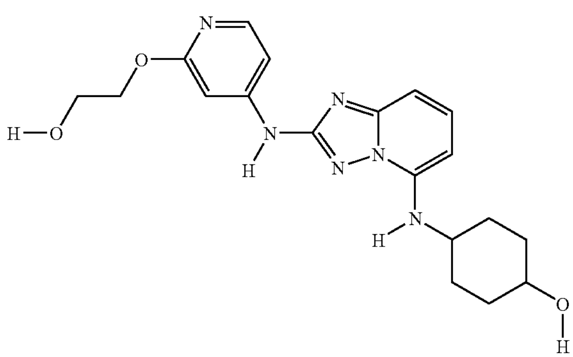 | cis-4-(2-(2-(2-hydroxyethoxy)pyridin-4-ylamino)-[1,2,4]triazolo[1,5-a]pyridin-5-ylamino)cyclohexanol | 385.2 | D |
| 278 | 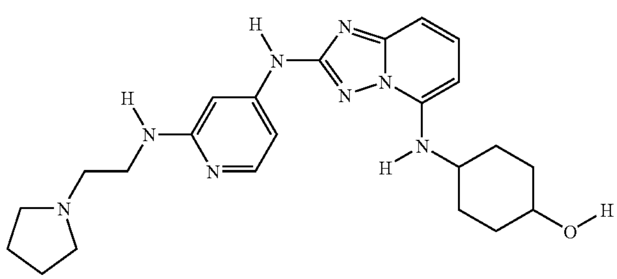 | cis-4-(2-(2-(2-(pyrrolidin-1-yl)ethylamino)pyridin-4-ylamino)-[1,2,4]triazolo[1,5-a]pyridin-5-ylamino)cyclohexanol | 437.1 | D |
| 279 | 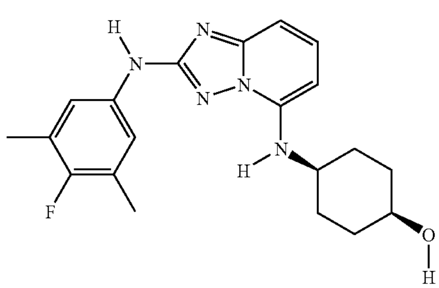 | cis-4-(2-(4-fluoro-3,5-dimethylphenylamino)-[1,2,4]triazolo[1,5-a]pyridin-5-ylamino)cyclohexanol | 370.2 | D |

TABLE 1-continued

| Cmpd. No. | Structure | Cmpd. Name | MH+ (Obs.) | Activity Level |
|---|---|---|---|---|
| 280 | 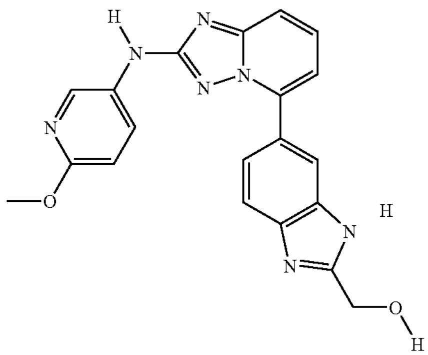 | (6-(2-(6-methoxypyridin-3-ylamino)-[1,2,4]triazolo[1,5-a]pyridin-5-yl)-1H-benzo[d]imidazol-2-yl)methanol | 388.2 | C |
| 281 | 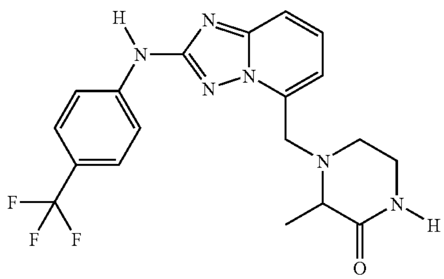 | 3-methyl-4-((2-(4-(trifluoromethyl)phenylamino)-[1,2,4]triazolo[1,5-a]pyridin-5-yl)methyl)piperazin-2-one | 405.39 | D |
| 282 | 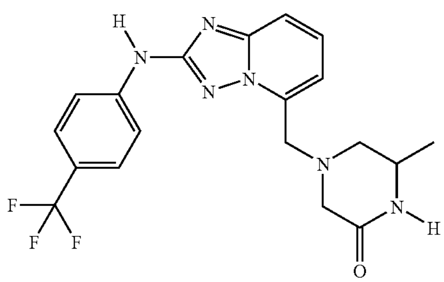 | 6-methyl-4-((2-(4-(trifluoromethyl)phenylamino)-[1,2,4]triazolo[1,5-a]pyridin-5-yl)methyl)piperazin-2-one | 405.39 | A |
| 283 | 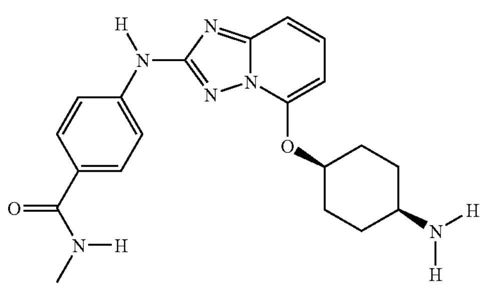 | cis-4-(5-(4-aminocyclohexyloxy)-[1,2,4]triazolo[1,5-a]pyridin-2-ylamino)-N-methylbenzamide | 381.1 | A |
| 284 | 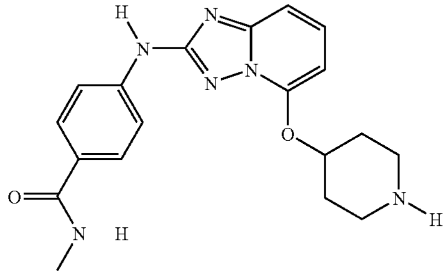 | N-methyl-4-(5-(piperidin-4-yloxy)-[1,2,4]triazolo[1,5-a]pyridin-2-ylamino)benzamide | 367.1 | A |

TABLE 1-continued

| Cmpd. No. | Structure | Cmpd. Name | MH+ (Obs.) | Activity Level |
|---|---|---|---|---|
| 285 | 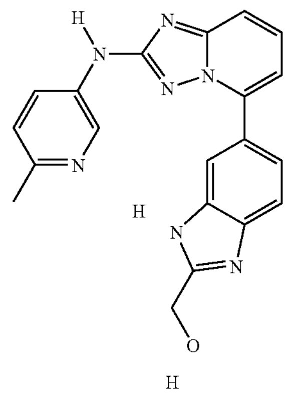 | (6-(2-(6-methylpyridin-3-ylamino)-[1,2,4]triazolo[1,5-a]pyridin-5-yl)-1H-benzo[d]imidazol-2-yl)methanol | 372.1 | D |
| 286 | 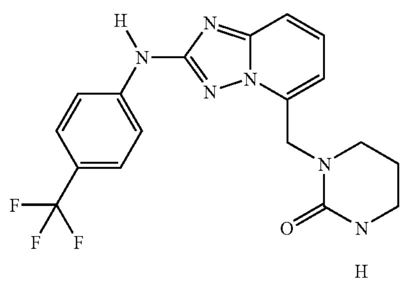 | 1-((2-(4-(trifluoromethyl)phenylamino)-[1,2,4]triazolo[1,5-a]pyridin-5-yl)methyl)tetrahydropyrimidin-2(1H)-one | 391.7 | A |
| 287 | 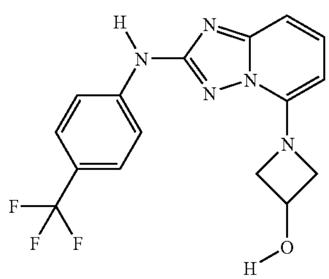 | 1-(2-(4-(trifluoromethyl)phenylamino)-[1,2,4]triazolo[1,5-a]pyridin-5-yl)azetidin-3-ol | 350.1 | D |
| 288 | 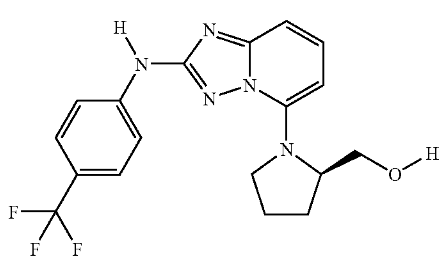 | (R)-(1-(2-(4-(trifluoromethyl)phenylamino)-[1,2,4]triazolo[1,5-a]pyridin-5-yl)pyrrolidin-2-yl)methanol | 378.4 | C |
| 289 | 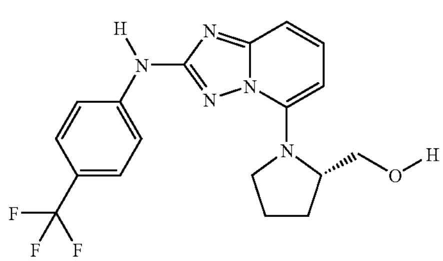 | (S)-(1-(2-(4-(trifluoromethyl)phenylamino)-[1,2,4]triazolo[1,5-a]pyridin-5-yl)pyrrolidin-2-yl)methanol | 378.4 | A |

TABLE 1-continued

| Cmpd. No. | Structure | Cmpd. Name | MH+ (Obs.) | Activity Level |
|---|---|---|---|---|
| 290 | 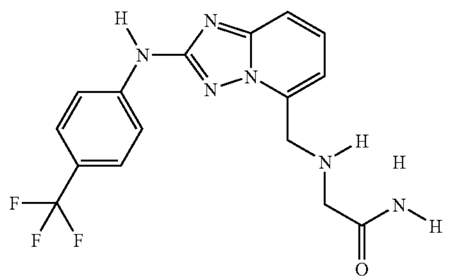 | 2-((2-(4-(trifluoromethyl)phenylamino)-[1,2,4]triazolo[1,5-a]pyridin-5-yl)methylamino)acetamide | 365.1 | D |
| 291 | 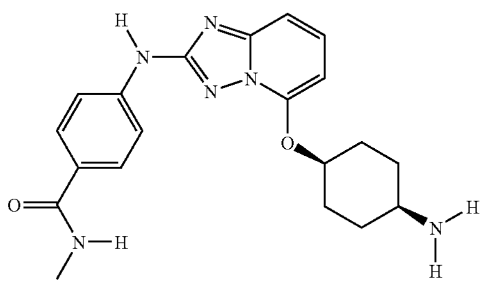 | trans-4-(5-(4-aminocyclohexyloxy)-[1,2,4]triazolo[1,5-a]pyridin-2-ylamino)-N-methylbenzamide | 381.1 | C |
| 292 | 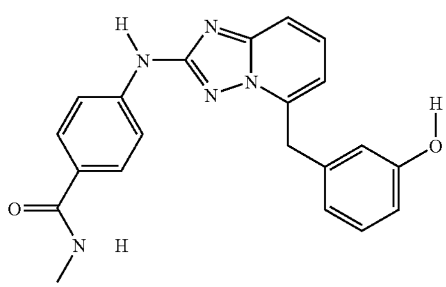 | 4-(5-(3-hydroxybenzyl)-[1,2,4]triazolo[1,5-a]pyridin-2-ylamino)-N-methylbenzamide | 373.2 | D |
| 293 | 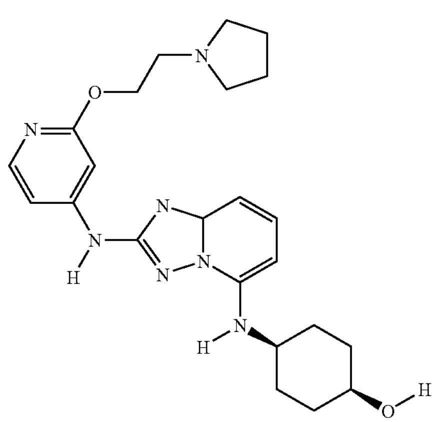 | cis-4-(2-(2-(2-(pyrrolidiun-1-yl)ethoxy)pyridin-4-ylamino)-[1,2,4]triazolo[1,5-a]pyridin-5-ylamino)cyclohexanol | 438.1 | B |

TABLE 1-continued

| Cmpd. No. | Structure | Cmpd. Name | MH+ (Obs.) | Activity Level |
|---|---|---|---|---|
| 294 | 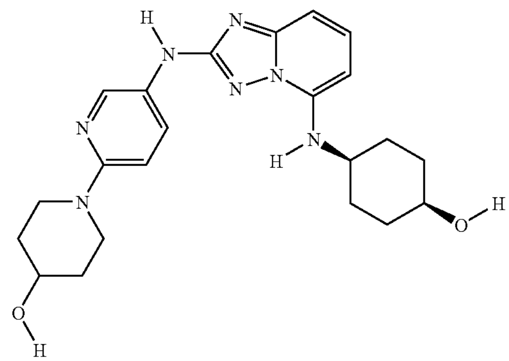 | cis-1-(5-(5-(4-hydroxycyclohexylamino)-[1,2,4]triazolo[1,5-a]pyridin-2-ylamino)pyridin-2-yl)piperidin-4-ol | 424.1 | D |
| 295 | 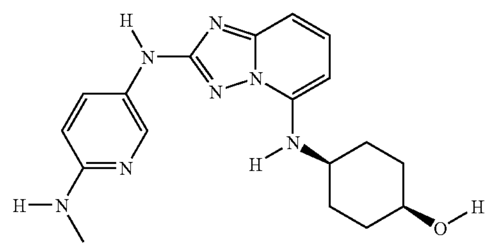 | cis-4-(2-(6-(methylamino)pyridin-3-ylamino)-[1,2,4]triazolo[1,5-a]pyridin-5-ylamino)cyclohexanol | 354.1 | D |
| 296 | 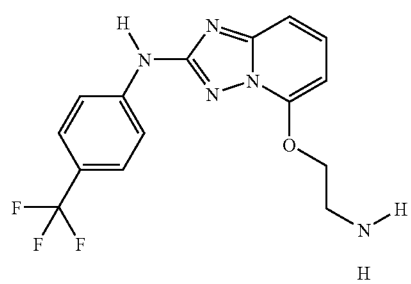 | 5-(2-aminoethoxy)-N-(4-(trifluoromethyl)phenyl)-[1,2,4]triazolo[1,5-a]pyridin-2-amine | 338.1 | B |
| 297 | 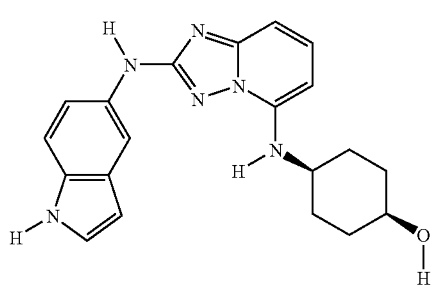 | cis-4-(2-(1H-pyrrolo[2,3-b]pyridin-5-ylamino)-[1,2,4]triazolo[1,5-a]pyridin-5-ylamino)cyclohexanol | 364.2 | D |
| 298 | 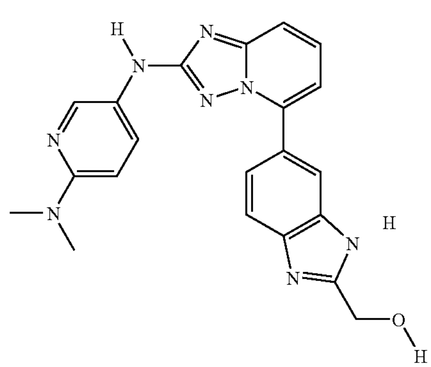 | (6-(2-(6-(dimethylamino)pyridin-3-ylamino)-[1,2,4]triazolo[1,5-a]pyridin-5-yl)-1H-benzo[d]imidazol-2-yl)methanol | 401.2 | D |

TABLE 1-continued

| Cmpd. No. | Cmpd. Name | MH+ (Obs.) | Activity Level |
|---|---|---|---|
| 299 | (R)-1-((2-(4-(trifluoromethyl)phenylamino)-[1,2,4]triazolo[1,5-a]pyridin-5-yl)methyl)piperidin-3-ol | 392.1 | A |
| 300 | (S)-1-((2-(4-(trifluoromethyl)phenylamino)-[1,2,4]triazolo[1,5-a]pyridin-5-yl)methyl)piperidin-3-ol | 392.1 | A |
| 301 | 1-((2-(4-(trifluoromethyl)phenylamino)-[1,2,4]triazolo[1,5-a]pyridin-5-yl)methyl)imidazolidin-4-one | 377.1 | A |
| 302 | (R)-5-(pyrrolidin-2-ylmethoxy)-N-(4-(trifluoromethyl)phenyl)-[1,2,4]triazolo[1,5-a]pyridin-2-amine | 378 | A |
| 303 | (S)-5-(pyrrolidin-2-ylmethoxy)-N-(4-(trifluoromethyl)phenyl)-[1,2,4]triazolo[1,5-a]pyridin-2-amine | 378 | A |

TABLE 1-continued

| Cmpd. No. | Structure | Cmpd. Name | MH+ (Obs.) | Activity Level |
|---|---|---|---|---|
| 304 | 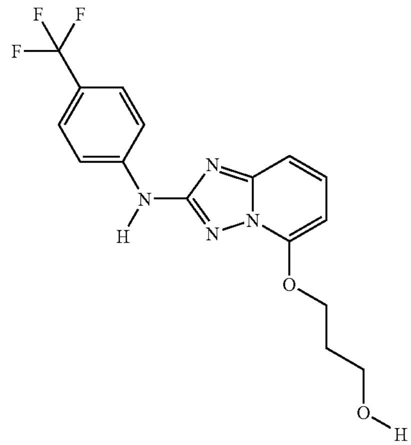 | 3-(2-(4-(trifluoromethyl)phenylamino)-[1,2,4]triazolo[1,5-a]pyridin-5-yloxy)propan-1-ol | 353.1 | A |
| 305 | 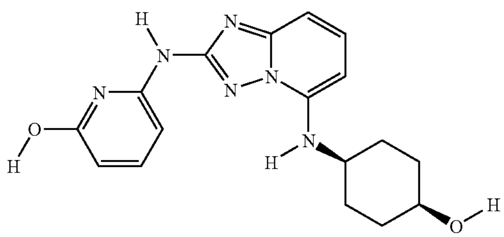 | cis-6-(5-(4-hydroxycyclohexylamino)-[1,2,4]triazolo[1,5-a]pyridin-2-ylamino)pyridin-2-ol | 341.2 | A |
| 306 | 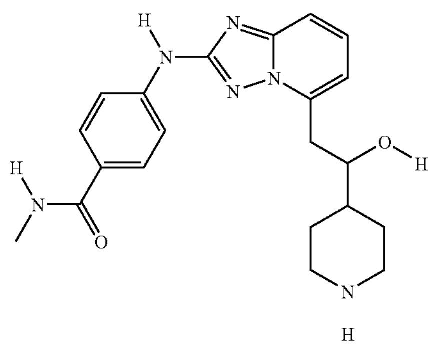 | 4-(5-(2-hydroxy-2-(piperidin-4-yl)ethyl)-[1,2,4]triazolo[1,5-a]pyridin-2-ylamino)-N-methylbenzamide | 394.9 | A |
| 307 | 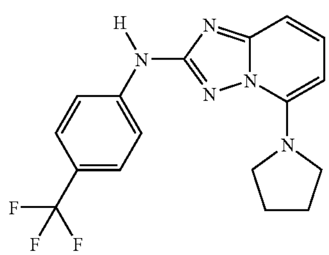 | 5-(pyrrolidin-1-yl)-N-(4-(trifluoromethyl)phenyl)-[1,2,4]triazolo[1,5-a]pyridin-2-amine | 348.2 | A |
| 308 | 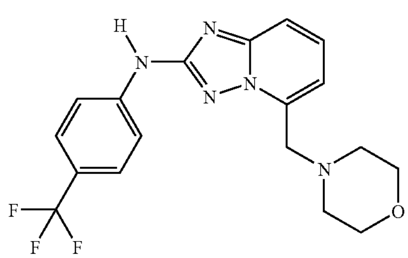 | 5-(morpholinomethyl)-N-(4-(trifluoromethyl)phenyl)-[1,2,4]triazolo[1,5-a]pyridin-2-amine | 378.2 | A |

TABLE 1-continued

| Cmpd. No. | Structure | Cmpd. Name | MH+ (Obs.) | Activity Level |
|---|---|---|---|---|
| 309 | 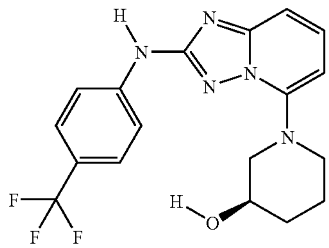 | (R)-1-(2-(4-(trifluoromethyl)phenylamino)-[1,2,4]triazolo[1,5-a]pyridin-5-yl)piperidin-3-ol | 378.2 | B |
| 310 | 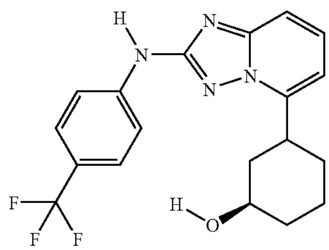 | (S)-1-(2-(4-(trifluoromethyl)phenylamino)-[1,2,4]triazolo[1,5-a]pyridin-5-yl)piperidin-3-ol | 378.2 | C |
| 311 | 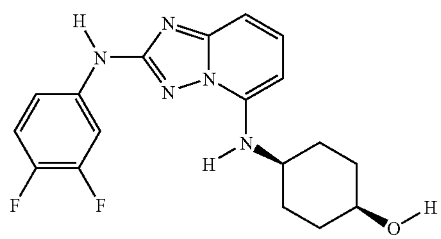 | cis-4-(2-(3,4-difluorophenylamino)-[1,2,4]triazolo[1,5-a]pyridin-5-ylamino)cyclohexanol | 360.1 | C |
| 312 | 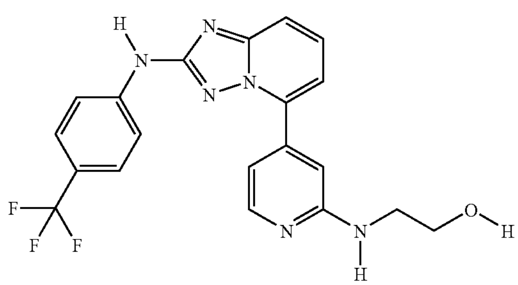 | 2-(4-(2-(4-(trifluoromethyl)phenylamino)-[1,2,4]triazolo[1,5-a]pyridin-5-yl)pyridin-2-ylamino)ethanol | 415.1 | D |
| 313 | 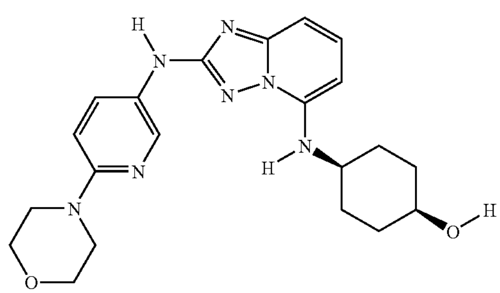 | cis-4-(2-(6-morpholinopyridin-3-ylamino)-[1,2,4]triazolo[1,5-a]pyridin-5-ylamino)cyclohexanol | 410.2 | D |
| 314 | 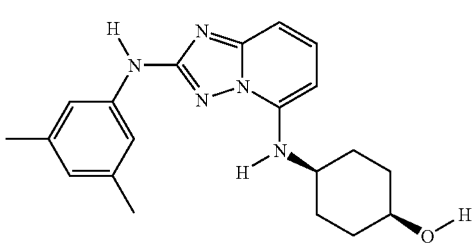 | cis-4-(2-(3,5-dimethylphenylamino)-[1,2,4]triazolo[1,5-a]pyridin-5-ylamino0)cyclohexaol | 352 | D |

TABLE 1-continued

| Cmpd. No. | Cmpd. Name | MH+ (Obs.) | Activity Level |
|---|---|---|---|
| 315 | 2-(2-(4-(trifluoromethyl)phenylamino)-[1,2,4]triazolo[1,5-a]pyridin-5-yloxy)ethanol | 339.1 | A |
| 316 | cis-3-(5-(4-hydroxycyclohexylamino)-[1,2,4]triazolo[1,5-a]pyridin-2-ylamino)-N-methylbenzamide | 381.1 | C |
| 317 | 4-((2-(4-(trifluoromethyl)phenylamino)-[1,2,4]triazolo[1,5-a]pyridin-5-yl)methyl)pyridin-2(1H)-one | 386.1 | D |
| 318 | cis-2-fluoro-5-(5-(4-hydroxycyclohexylamino)-[1,2,4]triazolo[1,5-a]pyridin-2-ylamino)benzamide | 385.2 | A |
| 319 | cis-4-(2-(4-fluorophenylamino)-[1,2,4]triazolo[1,5-a]pyridin-5-ylamino)cyclohexanol | 342.1 | D |

TABLE 1-continued

| Cmpd. No. | Structure | Cmpd. Name | MH+ (Obs.) | Activity Level |
|---|---|---|---|---|
| 320 | 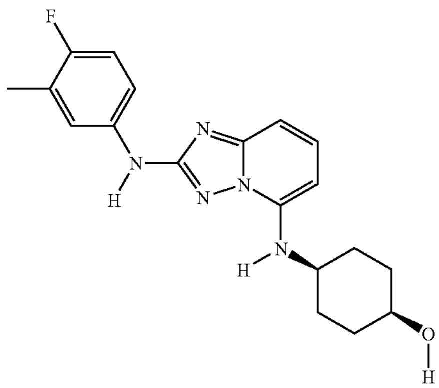 | cis-4-(2-(4-fluoro-3-methylphenylamino)-[1,2,4]triazolo[1,5-a]pyridin-5-ylamino)cyclohexanol | 356.2 | D |
| 321 | 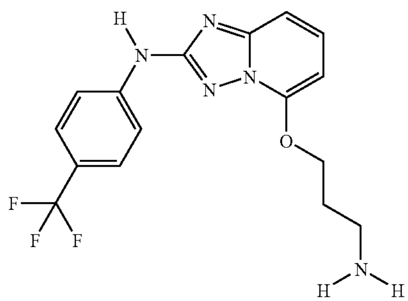 | 5-(3-aminopropoxy)-N-(4-(trifluoromethyl)phenyl)-[1,2,4]triazolo[1,5-a]pyridin-2-amine | 351.1 | A |
| 322 | 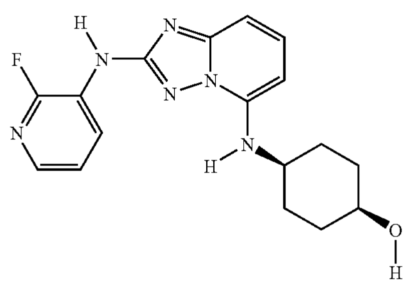 | cis-4-(2-(2-fluoropyridin-3-ylamino)-[1,2,4]triazolo[1,5-a]pyridin-5-ylamino)cyclohexanol | 343 | A |
| 323 | 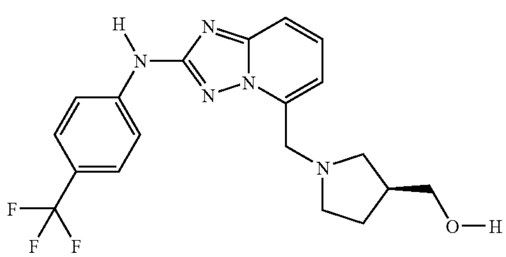 | (R)-(1-((2-(4-(trifluoromethyl)phenylamino)-[1,2,4]triazolo[1,5-a]pyridin-5-yl)methyl)pyrrolidin-3-yl)methanol | 392.3 | A |
| 324 | 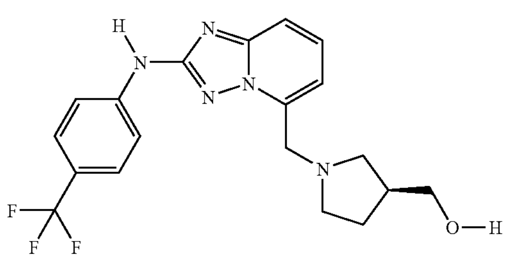 | (S)-(1-((2-(4-(trifluoromethyl)phenylamino)-[1,2,4]triazolo[1,5-a]pyridin-5-yl)methyl)pyrrolidin-3-yl)methanol | 392.3 | A |

| Cmpd. No. | Structure | Cmpd. Name | MH+ (Obs.) | Activity Level |
|---|---|---|---|---|
| 325 | 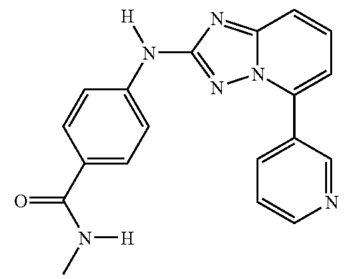 | N-methyl-4-(5-(pyridin-3-yl)-[1,2,4]triazolo[1,5-a]pyridin-2-ylamino)benzamide | 345.2 | B |
| 326 | 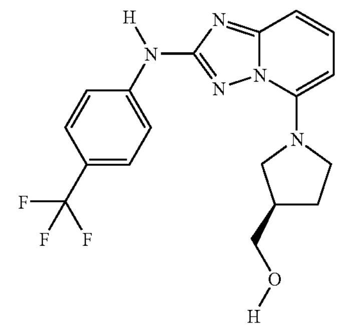 | (R)-(1-(2-(4-(trifluoromethyl)phenylamino)-[1,2,4]triazolo[1,5-a]pyridin-5-yl)pyrrolidin-3-yl)methanol | 378.2 | C |
| 327 | 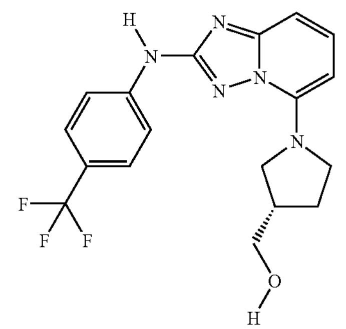 | (S)-(1-(2-(4-(trifluoromethyl)phenylamino)-[1,2,4]triazolo[1,5-a]pyridin-5-yl)pyrrolidin-3-yl)methanol | 378.2 | C |
| 328 | 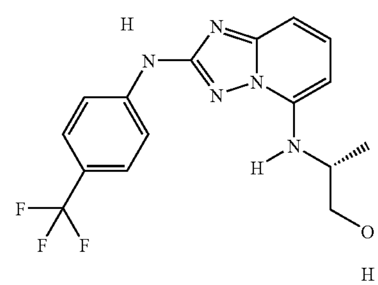 | (R)-2-(2-(4-(trifluoromethyl)phenylamino)-[1,2,4]triazolo[1,5-a]pyridin-5-ylamino)propan-1-ol | 352.2 | A |
| 329 | 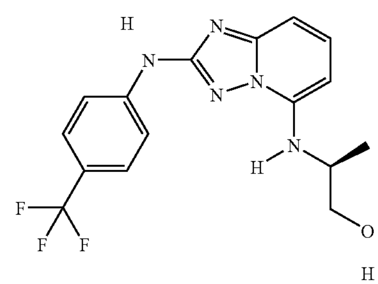 | (S)-2-(2-(4-(trifluoromethyl)phenylamino)-[1,2,4]triazolo[1,5-a]pyridin-5-ylamino)propan-1-ol | 352.2 | B |

TABLE 1-continued

| Cmpd. No. | Structure | Cmpd. Name | MH+ (Obs.) | Activity Level |
|---|---|---|---|---|
| 330 | 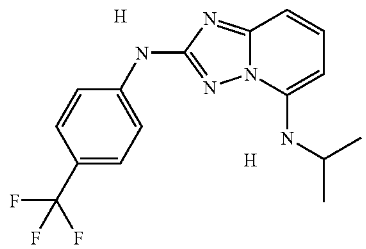 | $N^5$-isopropyl-$N^2$-(4-(trifluoromethyl)phenyl)-[1,2,4]triazolo[1,5-a]pyridin-2,5-diamine | 336.2 | A |
| 331 | 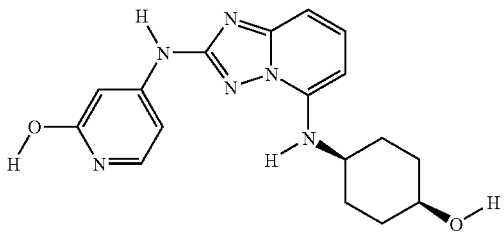 | cis-4-(5-(4-hydroxycyclohexylamino)-[1,2,4]triazolo[1,5-a]pyridin-2-ylamino)pyridin-2-ol | 341.2 | A |
| 332 | 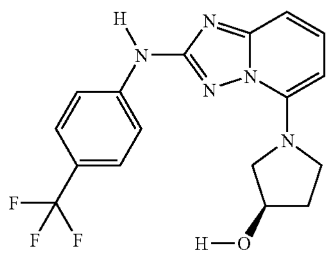 | (R)-1-(2-(4-(trifluoromethyl)phenylamino)-[1,2,4]triazolo[1,5-a]pyridin-5-yl)pyrrolidin-3-ol | 364.2 | B |
| 333 | 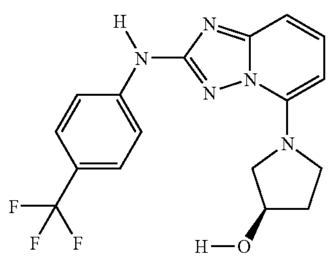 | (S)-1-(2-(4-(trifluoromethyl)phenylamino)-[1,2,4]triazolo[1,5-a]pyridin-5-yl)pyrrolidin-3-ol | 364.2 | C |
| 334 | 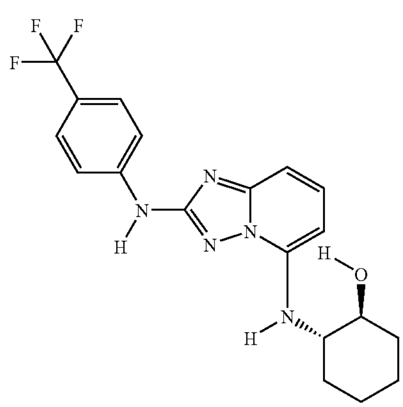 | (1S,2S)-2-(2-(4-(trifluoromethyl)phenylamino)-[1,2,4]triazolo[1,5-a]pyridin-5-ylamino)cyclohexanol | 392.3 | A |

TABLE 1-continued

| Cmpd. No. | Structure | Cmpd. Name | MH+ (Obs.) | Activity Level |
|---|---|---|---|---|
| 335 | 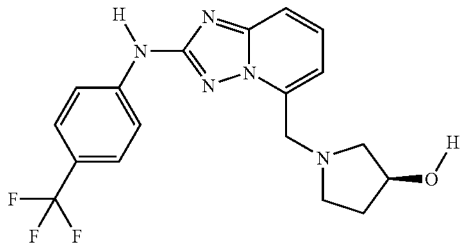 | (R)-1-((2-(4-(trifluoromethyl)phenylamino)-[1,2,4]triazolo[1,5-a]pyridin-5-yl)methyl)pyrrolidin-3-ol | 378.2 | A |
| 336 | 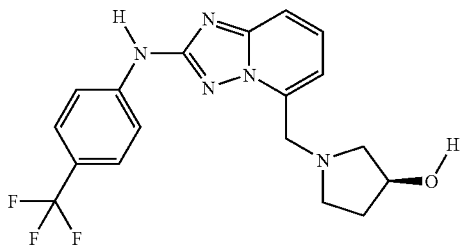 | (S)-1-((2-(4-(trifluoromethyl)phenylamino)-[1,2,4]triazolo[1,5-a]pyridin-5-yl)methyl)pyrrolidin-3-ol | 378.2 | A |
| 337 | 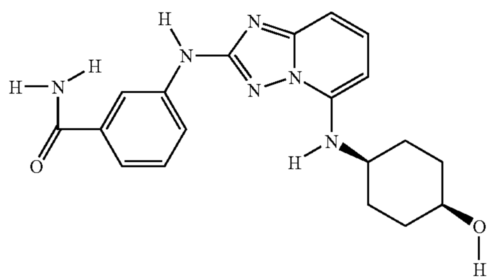 | cis-3-(5-(4-hydroxycyclohexylamino)-[1,2,4]triazolo[1,5-a]pyridin-2-ylamino)benzamide | 367.2 | C |
| 338 | 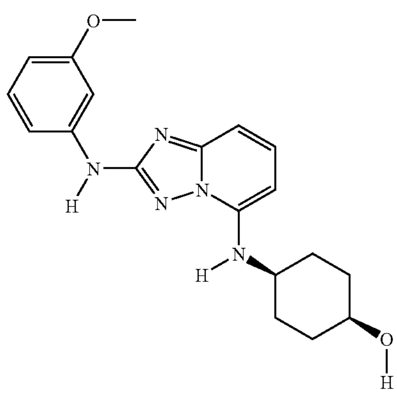 | cis-4-(2-(3-methoxyphenylamino)-[1,2,4]triazolo[1,5-a]pyridin-5-ylamino)cyclohexanol | 354.1 | D |
| 339 | 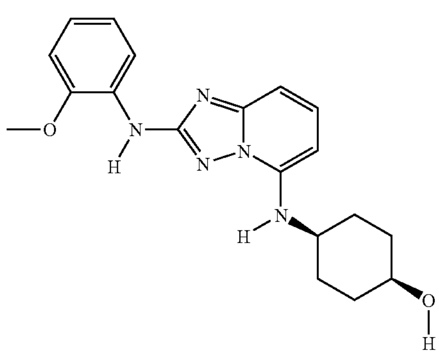 | cis-4-(2-(2-methoxyphenylamino)-[1,2,4]triazolo[1,5-a]pyridin-5-ylamino)cyclohexanol | 354.1 | A |

TABLE 1-continued

| Cmpd. No. | Structure | Cmpd. Name | MH+ (Obs.) | Activity Level |
|---|---|---|---|---|
| 340 | 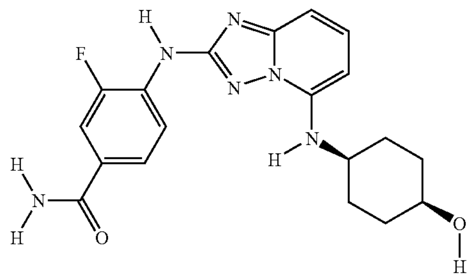 | cis-3-fluoro-4-(5-(4-hydroxycyclohexylamino)-[1,2,4]triazolo[1,5-a]pyridin-2-ylamino)benzamide | 385.1 | A |
| 341 | 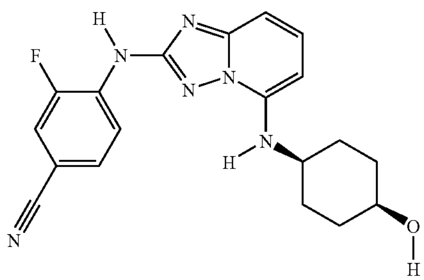 | cis-3-fluoro-4-(5-(4-hydroxycyclohexylamino)-[1,2,4]triazolo[1,5-a]pyridin-2-ylamino)benzonitrile | 367.1 | A |
| 342 | 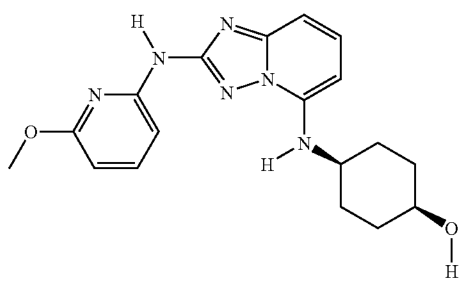 | cis-4-(2-(6-methoxypyridin-2-ylamino)-[1,2,4]triazolo[1,5-a]pyridin-5-ylamino)cyclohexanol | 355.1 | A |
| 343 | 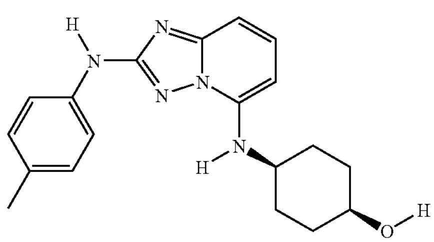 | cis-4-(2-(p-tolylamino)-[1,2,4]triazolo[1,5-a]pyridin-5-ylamino)cyclohexanol | 338.1 | D |
| 344 | 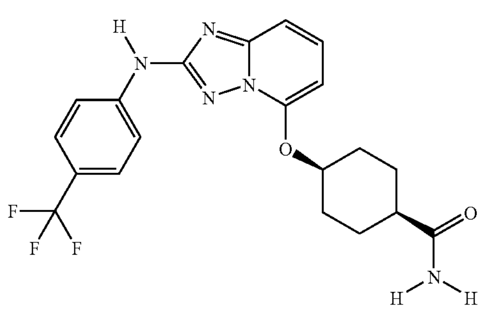 | cis-4-(2-(4-(trifluoromethyl)phenylamino)-[1,2,4]triazolo[1,5-a]pyridin-5-yloxy)cyclohexanecarboxamide | 420.1 | B |

TABLE 1-continued

| Cmpd. No. | Structure | Cmpd. Name | MH+ (Obs.) | Activity Level |
|---|---|---|---|---|
| 345 | 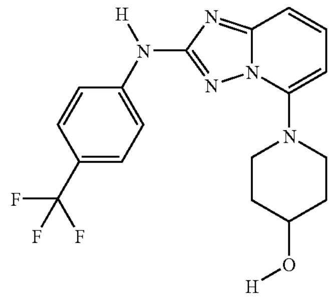 | 1-(2-(4-(trifluoromethyl)phenylamino)-[1,2,4]triazolo[1,5-a]pyridin-5-yl)piperidin-4-ol | 378.2 | B |
| 346 | 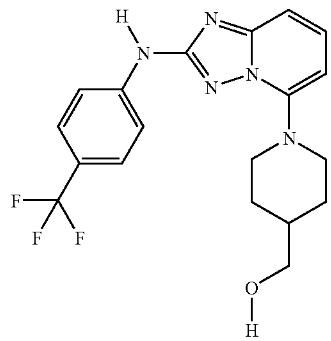 | (1-(2-(4-(trifluoromethyl)phenylamino)-[1,2,4]triazolo[1,5-a]pyridin-5-yl)piperidin-4-yl)methanol | 392.3 | A |
| 347 | 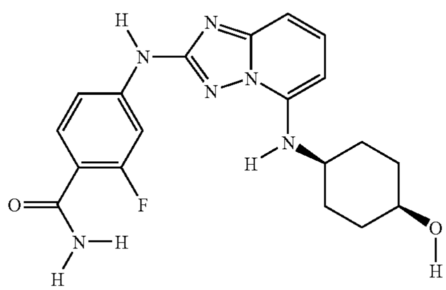 | cis-2-fluoro-4-(5-(4-hydroxycyclohexylamino)-[1,2,4]triazolo[1,5-a]pyridin-2-ylamino)benzamide | 385.1 | D |
| 348 | 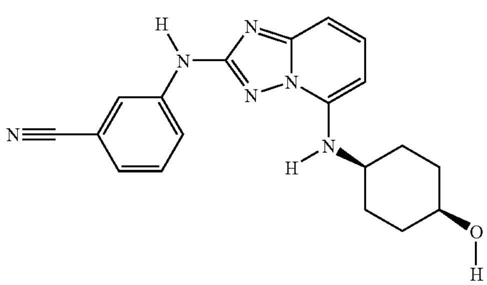 | cis-3-(5-(4-hydroxycyclohexylamino)-[1,2,4]triazolo[1,5-a]pyridin-2-ylamino)benzonitrile | 349.2 | C |
| 349 | 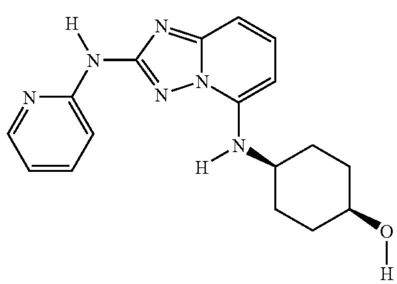 | cis-4-(2-(pyridin-2-ylamino)-[1,2,4]triazolo[1,5-a]pyridin-5-ylamino)cyclohexanol | 325.1 | A |

TABLE 1-continued

| Cmpd. No. | Structure | Cmpd. Name | MH+ (Obs.) | Activity Level |
|---|---|---|---|---|
| 350 | 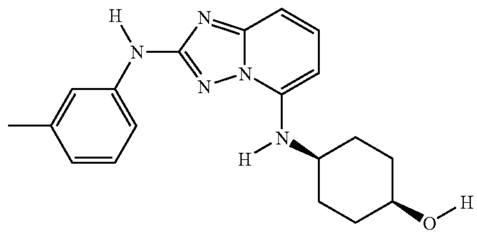 | cis-4-(2-(m-tolylamino)-[1,2,4]triazolo[1,5-a]pyridin-5-ylamino)cyclohexanol | 338.2 | D |
| 351 | 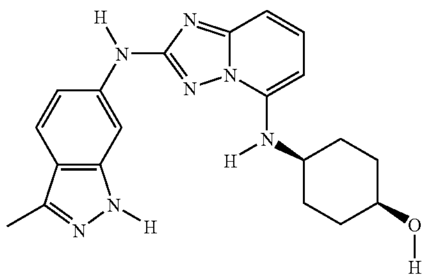 | cis-4-(2-(3-methyl-1H-indazol-6-ylamino)-[1,2,4]triazolo[1,5-a]pyridin-5-ylamino)cyclohexanol | 377.1 | D |
| 352 | 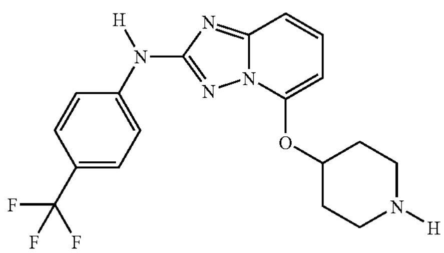 | 5-(piperidin-4-yloxy)-N-(4-(trifluoromethyl)phenyl)-[1,2,4]triazolo[1,5-a]pyridin-2-amine | 378.4 | A |
| 353 | 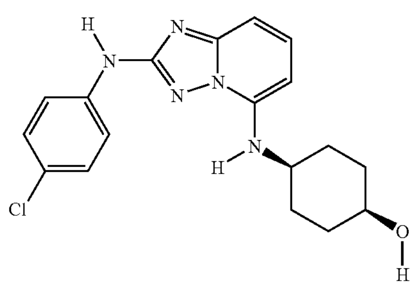 | cis-4-(2-(4-chlorophenylamino)-[1,2,4]triazolo[1,5-a]pyridin-5-ylamino)cyclohexanol | 358.2 | D |
| 354 | 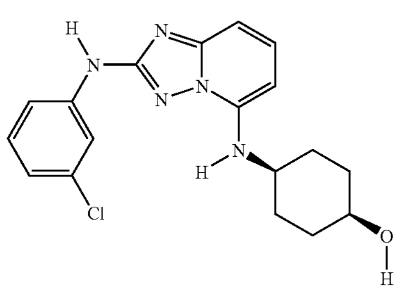 | cis-4-(2-(3-chlorophenylamino)-[1,2,4]triazolo[1,5-a]pyridin-5-ylamino)cyclohexanol | 358.2 | D |

TABLE 1-continued

| Cmpd. No. | Structure | Cmpd. Name | MH+ (Obs.) | Activity Level |
|---|---|---|---|---|
| 355 | 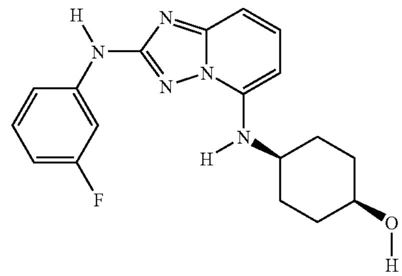 | cis-4-(2-(3-fluorophenylamino)-[1,2,4]triazolo[1,5-a]pyridin-5-ylamino)cyclohexanol | 342.1 | D |
| 356 | 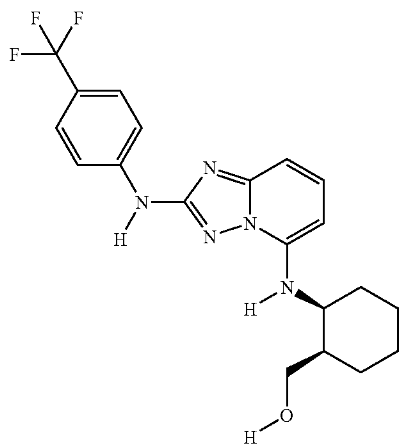 | (1S,2R)-(2-(2-(4-(trifluoromethyl)phenylamino)-[1,2,4]triazolo[1,5-a]pyridin-5-ylamino)cyclohexyl)methanol | 406.2 | A |
| 357 | 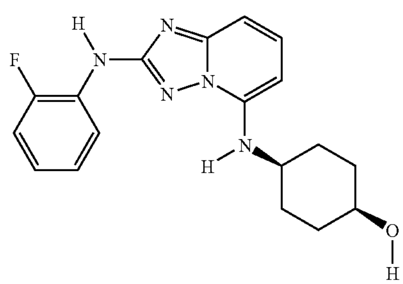 | cis-4-(2-(2-fluorophenylamino)-[1,2,4]triazolo[1,5-a]pyridin-5-ylamino)cyclohexanol | 342.1 | A |
| 358 | 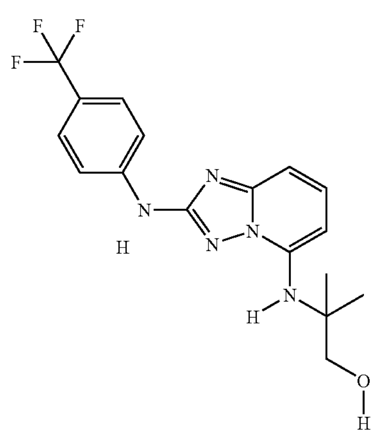 | 2-methyl-2-(2-(4-(trifluoromethyl)phenylamino)-[1,2,4]triazolo[1,5-a]pyridin-5-ylamino)propan-1-ol | 366.2 | A |

TABLE 1-continued

| Cmpd. No. | Structure | Cmpd. Name | MH+ (Obs.) | Activity Level |
|---|---|---|---|---|
| 359 | 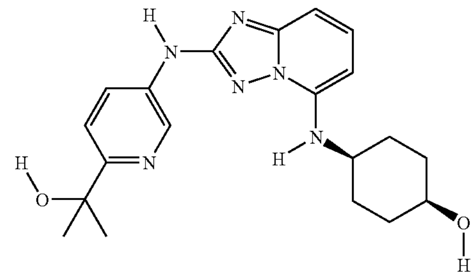 | cis-4-(2-(6-(2-hydroxypropan-2-yl)pyridin-3-ylamino)-[1,2,4]triazolo[1,5-a]pyridin-5-ylamino)cyclohexanol | 383.5 | A |
| 360 | 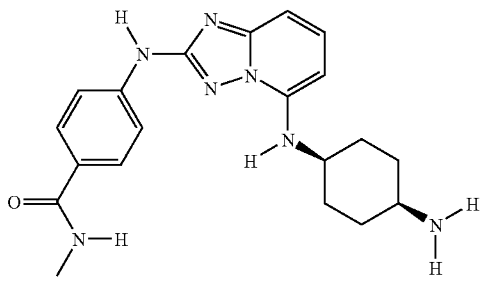 | 4-(5-(cis-4-aminocyclohexylamino)-[1,2,4]triazolo[1,5-a]pyridin-2-ylamino)-N-methylbenzamide | 380.5 | B |
| 361 | 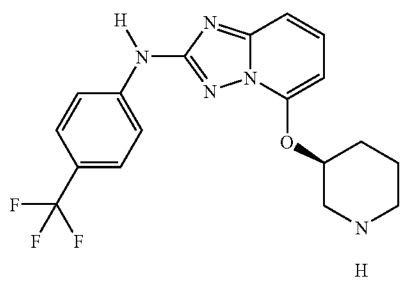 | (R)-5-(piperidin-3-yloxy)-N-(4-(trifluoromethyl)phenyl)-[1,2,4]triazolo[1,5-a]pyridin-2-amine | 378.4 | A |
| 362 | 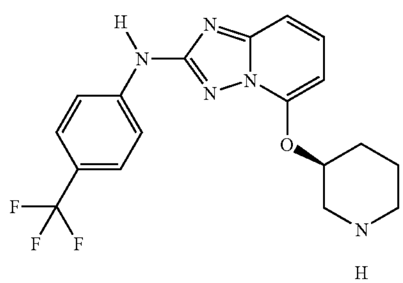 | (S)-5-(piperidin-3-yloxy)-N-(4-(trifluoromethyl)phenyl)-[1,2,4]triazolo[1,5-a]pyridin-2-amine | 378.36 | A |
| 363 | 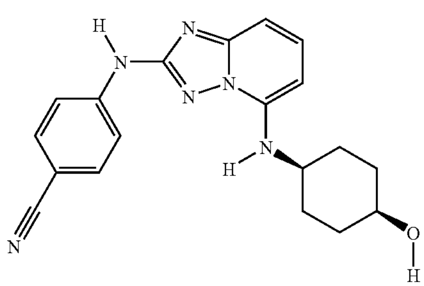 | 4-(5-(cis-4-hydroxycyclohexylamino)-[1,2,4]triazolo[1,5-a]pyridin-2-ylamino)benzonitrile | 349.2 | D |

TABLE 1-continued

| Cmpd. No. | Structure | Cmpd. Name | MH+ (Obs.) | Activity Level |
|---|---|---|---|---|
| 364 | 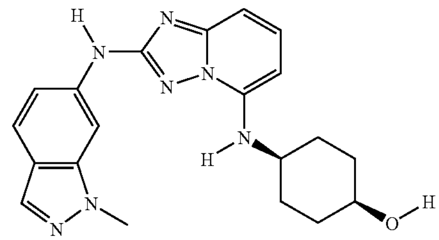 | cis-4-(2-(1-methyl-1H-indazol-6-ylamino)-[1,2,4]triazolo[1,5-a]pyridin-5-ylamino)cyclohexanol | 378.2 | D |
| 365 | 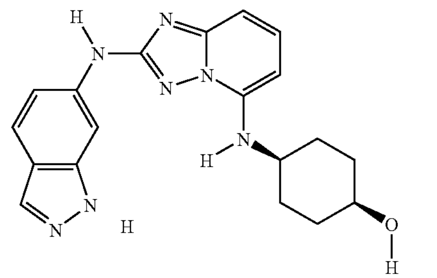 | cis-4-(2-(1H-indazol-6-ylamino)-[1,2,4]triazolo[1,5-a]pyridin-5-ylamino)cyclohexanol | 364.1 | D |
| 366 | 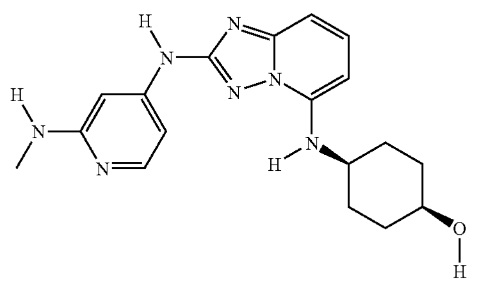 | cis-4-(2-(2-(methylamino)pyridin-4-ylamino)-[1,2,4]triazolo[1,5-a]pyridin-5-ylamino)cyclohexanol | 354.3 | D |
| 367 | 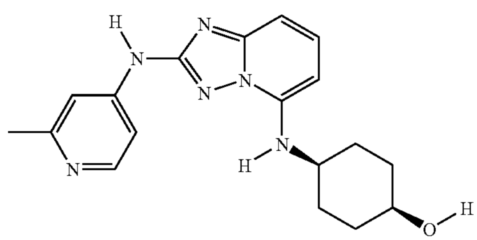 | cis-4-(2-(2-methylpyridin-4-ylamino)-[1,2,4]triazolo[1,5-a]pyridin-5-ylamino)cyclohexanol | 339.1 | B |
| 368 | 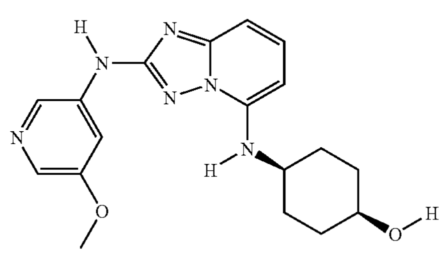 | cis-4-(2-(5-methoxypyridin-3-ylamino)-[1,2,4]triazolo[1,5-a]pyridin-5-ylamino)cyclohexanol | 355 | B |
| 369 | 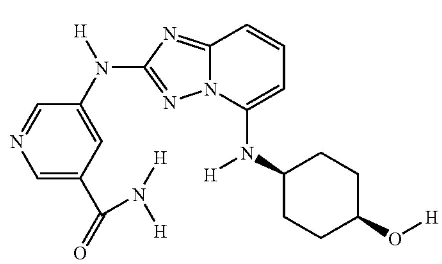 | cis-5-(5-(4-hydroxycyclohexylamino)-[1,2,4]triazolo[1,5-a]pyridin-2-ylamino)nicotinamide | 368 | A |

TABLE 1-continued

| Cmpd. No. | Cmpd. Name | MH+ (Obs.) | Activity Level |
|---|---|---|---|
| 370 | cis-5-(5-(4-hydroxycyclohexylamino)-[1,2,4]triazolo[1,5-a]pyridin-2-ylamino)picolinamide | 368.2 | B |
| 371 | cis-5-(5-(4-hydroxycyclohexylamino)-[1,2,4]triazolo[1,5-a]pyridin-2-ylamino)pyridin-2-ol | 341.1 | A |
| 372 | 5-(pyridin-4-ylmethyl)-N-(4-(trifluoromethyl)phenyl)-[1,2,4]triazolo[1,5-a]pyridin-2-amine | 370.2 | A |
| 373 | (±)trans-3-(2-(4-(trifluoromethyl)phenylamino)-[1,2,4]triazolo[1,5-a]pyridin-5-ylamino)cyclohexanol | 392.5 | B |
| 374 | (1S,2S)-2-(2-(4-(trifluoromethyl)phenylamino)-[1,2,4]triazolo[1,5-a]pyridin-5-ylamino)cyclopentanol | 378.2 | D |

TABLE 1-continued

| Cmpd. No. | Structure | Cmpd. Name | MH+ (Obs.) | Activity Level |
|---|---|---|---|---|
| 375 | 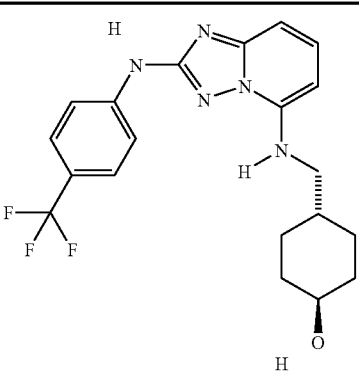 | trans-4-((2-(4-(trifluoromethyl)phenylamino)-[1,2,4]triazolo[1,5-a]pyridin-5-ylamino)methyl)cyclohexanol | 406.2 | A |
| 376 | 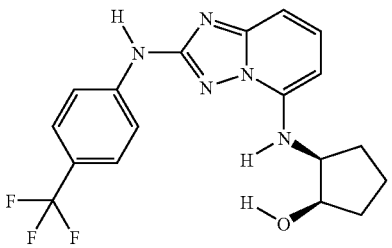 | (1S,2R)-2-(2-(4-(trifluoromethyl)phenylamino)-[1,2,4]triazolo[1,5-a]pyridin-5-ylamino)cyclopentanol | 378.2 | A |
| 377 | 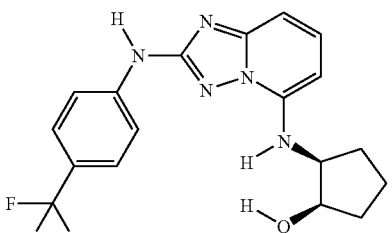 | (1R,2R)-2-(2-(4-(trifluoromethyl)phenylamino)-[1,2,4]triazolo[1,5-a]pyridin-5-ylamino)cyclopentanol | 378.2 | D |
| 378 | 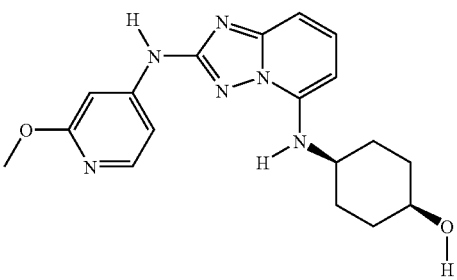 | cis-4-(2-(2-methoxypyridin-4-ylamino)-[1,2,4]triazolo[1,5-a]pyridin-5-ylamino)cyclohexanol | 355.2 | D |
| 379 | 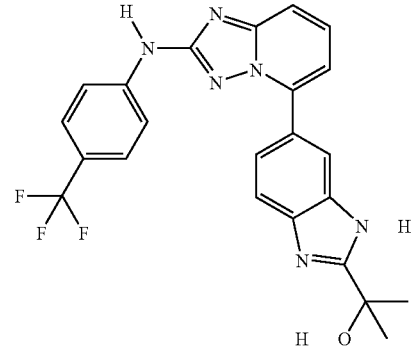 | 2-(6-(2-(4-(trifluoromethyl)phenylamino)-[1,2,4]triazolo[1,5-a]pyridin-5-yl)-1H-benzo[d]imidazol-2-yl)propan-2-ol | 453.1 | C |

TABLE 1-continued

| Cmpd. No. | Structure | Cmpd. Name | MH+ (Obs.) | Activity Level |
|---|---|---|---|---|
| 380 | 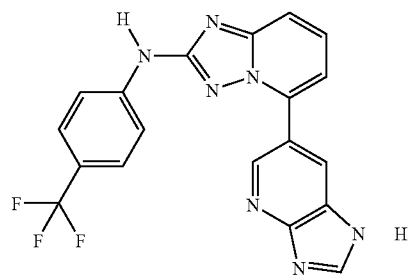 | 5-(1H-imidazo[4,5-b]pyridin-6-yl)-N-(4-(trifluoromethyl)phenyl)-[1,2,4]triazolo[1,5-a]pyridin-2-amine | 396.1 | D |
| 381 | 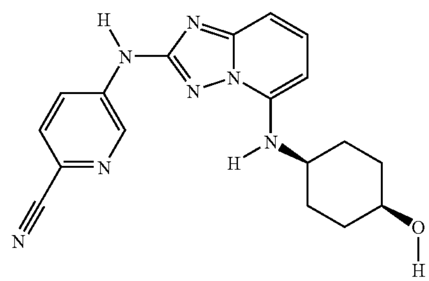 | cis-5-(5-(4-hydroxycyclohexylamino)-[1,2,4]triazolo[1,5-a]pyridin-2-ylamino)picolinamide | 350.2 | A |
| 382 | 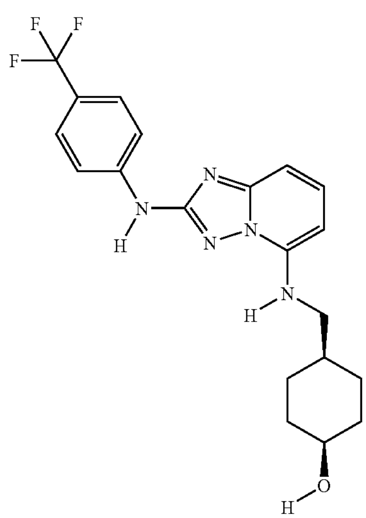 | cis-4-((2-(4-(trifluoromethyl)phenylamino)-[1,2,4]triazolo[1,5-a]pyridin-5-ylamino)methyl)cyclohexanol | 406.2 | A |
| 383 | 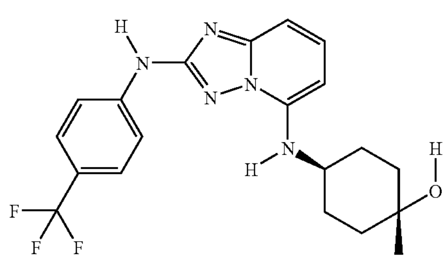 | trans-1-methyl-4-(2-(4-(trifluoromethyl)phenylamino)-[1,2,4]triazolo[1,5-a]pyridin-5-ylamino)cyclohexanol | 406.2 | B |

TABLE 1-continued

| Cmpd. No. | Cmpd. Name | MH+ (Obs.) | Activity Level |
|---|---|---|---|
| 384 | cis-1-methyl-4-(2-(4-(trifluoromethyl)phenylamino)-[1,2,4]triazolo[1,5-a]pyridin-5-ylamino)cyclohexanol | 406.2 | D |
| 385 | cis-2-(4-(2-(4-(trifluoromethyl)phenylamino)-[1,2,4]triazolo[1,5-a]pyridin-5-ylamino)cyclohexyl)propan-2-ol | 434.5 | B |
| 386 | cis-4-(5-(4-hydroxycyclohexylamino)-[1,2,4]triazolo[1,5-a]pyridin-2-ylamino)-N-methylbenzamide | 381.5 | B |
| 387 | trans-4-(5-(4-hydroxycyclohexylamino)-[1,2,4]triazolo[1,5-a]pyridin-2-ylamino)-N-methylbenzamide | 381.5 | A |
| 388 | 4-((2-(4-(trifluoromethyl)phenylamino)-[1,2,4]-triazolo[1,5-a]pyridin-5-yl)methyl)piperazin-2-one | 391.2 | D |

TABLE 1-continued

| Cmpd. No. | Cmpd. Name | MH+ (Obs.) | Activity Level |
|---|---|---|---|
| 389 | cis-4-(2-(pyridin-4-ylamino)-[1,2,4]triazolo[1,5-a]pyridin-5-ylamino)cyclohexanol | 325.2 | A |
| 390 | cis-4-(2-(5-methylpyridin-3-ylamino)-[1,2,4]triazolo[1,5-a]pyridin-5-ylamino)cyclohexanol | 339.1 | C |
| 391 | cis-4-(2-(6-methoxypyridin-3-ylamino)-[1,2,4]triazolo[1,5-a]pyridin-5-ylamino)cyclohexanol | 355.1 | B |
| 392 | cis-4-(2-(6-(dimethylamino)pyridin-3-ylamino)-[1,2,4]triazolo[1,5-a]pyridin-5-ylamino)cyclohexanol | 368.3 | C |
| 393 | 5-(piperazin-1-ylmethyl)-N-(4-(trifluoromethyl)phenyl)-[1,2,4]triazolo[1,5-a]pyridin-2-amine | 377.2 | D |

TABLE 1-continued

| Cmpd. No. | Cmpd. Name | MH+ (Obs.) | Activity Level |
|---|---|---|---|
| 394 | trans-4-(5-(4-aminocyclohexylamino)-[1,2,4]triazolo[1,5-a]pyridin-2-ylamino)-N-methylbenzamide | 380.5 | C |
| 395 | 5-(piperidin-4-ylmethyl)-N-(4-(trifluoromethyl)phenyl)-[1,2,4]triazolo[1,5-a]pyridin-2-amine | 376.2 | D |
| 396 | 1-((2-(4-(trifluoromethyl)phenylamino)-[1,2,4]triazolo[1,5-a]pyridin-5-yl)methyl)piperidin-4-ol | 392.3 | A |
| 397 | trans-2-(4-(2-(4-(trifluoromethyl)phenylamino)-[1,2,4]triazolo[1,5-a]pyridin-5-ylamino)cyclohexyl)propan-2-ol | 434.5 | A |
| 398 | trans-4-((2-(4-(trifluoromethyl)phenylamino)-[1,2,4]triazolo[1,5-a]pyridin-5-yl)methyl)cyclohexanol | 391.2 | D |
| 399 | cis-4-((2-(4-(trifluoromethyl)phenylamino)-[1,2,4]triazolo[1,5-a]pyridin-5-yl)methyl)cyclohexanol | 391.2 | D |

TABLE 1-continued

| Cmpd. No. | Structure | Cmpd. Name | MH+ (Obs.) | Activity Level |
|---|---|---|---|---|
| 400 | 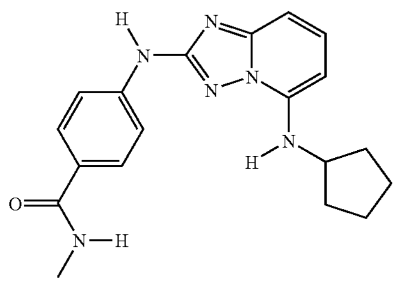 | 4-(5-(cyclopentylamino)-[1,2,4]triazolo[1,5-a]pyridin-2-ylamino)-N-methylbenzamide | 351.1 | D |
| 401 | 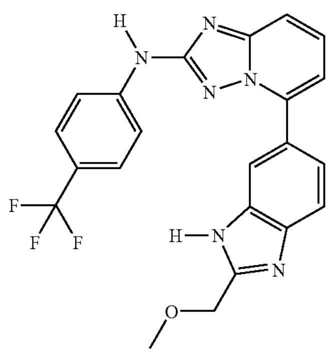 | 5-(2-(methoxymethyl)-1H-benzo[d]imidazol-6-yl)-N-(4-(trifluoromethyl)phenyl)-[1,2,4]triazolo[1,5-a]pyridin-2-amine | 439.2 | D |
| 402 | 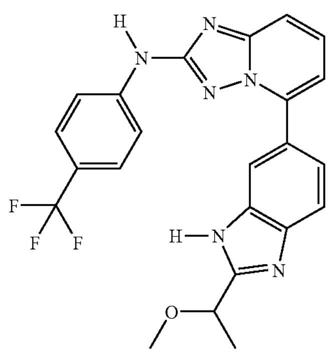 | 1-(6-(2-(4-(trifluoromethyl)phenylamino)-[1,2,4]triazolo[1,5-a]pyridin-5-yl)-1H-benzo[d]imidazol-2-yl)ethanol | 439.1 | D |
| 403 | 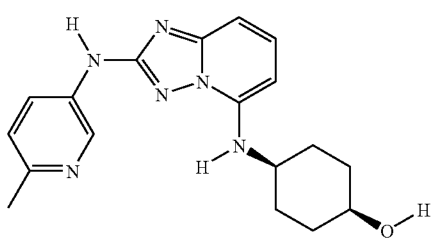 | cis-4-(2-(6-methylpyridin-3-ylamino)-[1,2,4]triazolo[1,5-a]pyridin-5-ylamino)cyclohexanol | 339.1 | D |
| 404 | 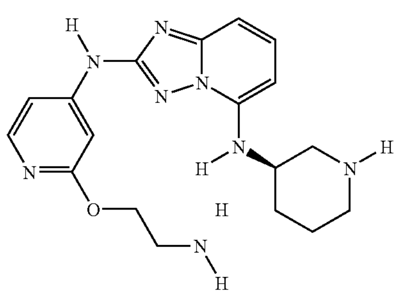 | (S)-N²-(2-(2-aminoethoxy)pyridin-4-yl)-N⁵-(piperidin-3-yl)-[1,2,4]triazolo[1,5-a]pyridine-2,5-diamine | 369.1 | D |

TABLE 1-continued

| Cmpd. No. | Structure | Cmpd. Name | MH+ (Obs.) | Activity Level |
|---|---|---|---|---|
| 405 | 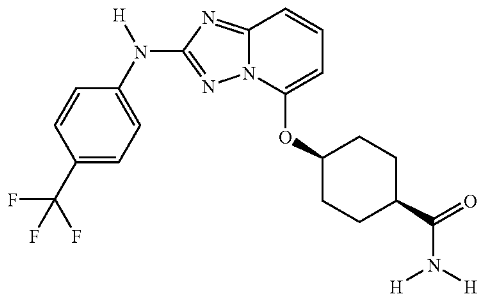 | trans-4-(2-(4-(trifluoromethyl)phenylamino)-[1,2,4]triazolo[1,5-a]pyridin-5-yloxy)cyclohexanecarboxamide | 420.1 | A |
| 406 | 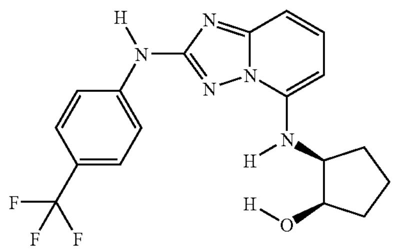 | (1R,2S)-2-(2-(4-(trifluoromethyl)phenylamino)-[1,2,4]triazolo[1,5-a]pyridin-5-ylamino)cyclopentanol | 378.2 | B |
| 407 | 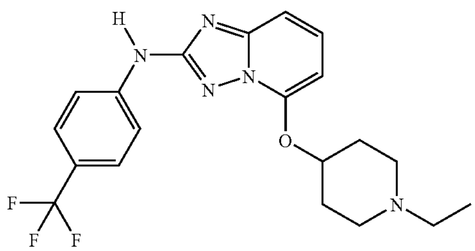 | 5-((1-ethylpiperidin-4-yl)methyl)-N-(4-(trifluoromethyl)phenyl)-[1,2,4]triazolo[1,5-a]pyridin-2-amine | 404.2 | B |
| 408 | 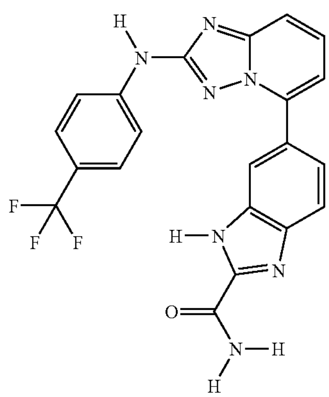 | 6-(2-(4-(trifluoromethyl)phenylamino)-[1,2,4]triazolo[1,5-a]pyridin-5-yl)-1H-benzo[d]imidazole-2-carboxamide | 438.1 | D |
| 409 | 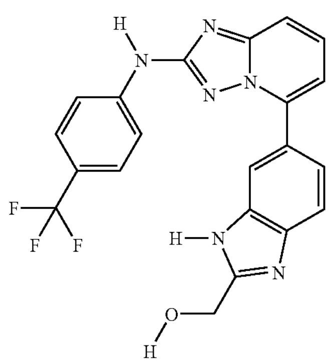 | (6-(2-(4-(trifluoromethyl)phenylamino)-[1,2,4]triazolo[1,5-a]pyridin-5-yl)-1H-benzo[d]imidazol-2-yl)methanol | 425.1 | D |

TABLE 1-continued

| Cmpd. No. | Structure | Cmpd. Name | MH+ (Obs.) | Activity Level |
|---|---|---|---|---|
| 410 | 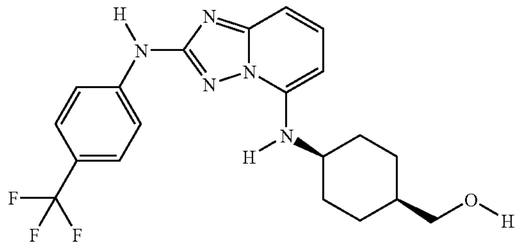 | cis-(4-(2-(4-(trifluoromethyl)phenylamino)-[1,2,4]triazolo[1,5-a]pyrridin-5-ylamino)cyclohexyl)methanol | 406.5 | D |
| 411 | 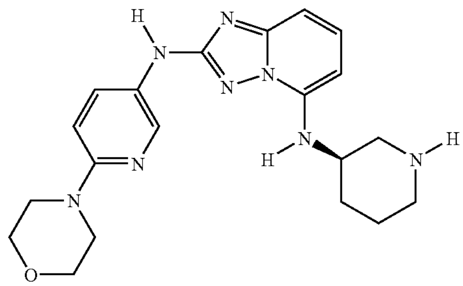 | (S)-N$^2$-(6-morpholinopyridin-3-yl)-N$^5$-(piperidin-3-yl)-[1,2,4]triazolo[1,5-a]pyridine-2,5-diamine | 395.2 | D |
| 412 | 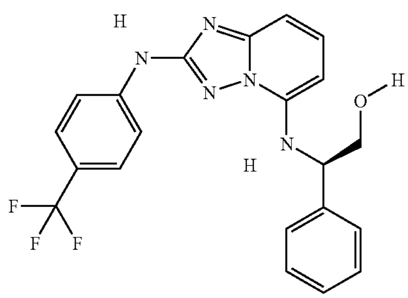 | (R)-2-phenyl-2-(2-(4-(trifluoromethyl)phenylamino)-[1,2,4]triazolo[1,5-a]pyridin-5-ylamino)ethanol | 414.4 | A |
| 413 | 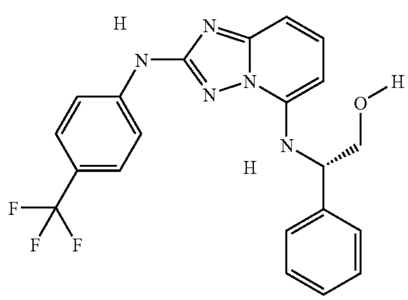 | (S)-2-phenyl-2-(2-(4-(trifluoromethyl)phenylamino)-[1,2,4]triazolo[1,5-a]pyridin-5-ylamino)ethanol | 414.4 | A |
| 414 | 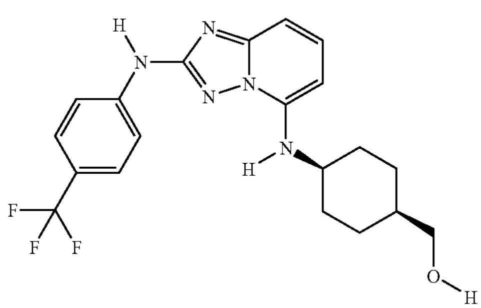 | trans-(4-(2-(4-(trifluoromethyl)phenylamino)-[1,2,4]triazolo[1,5-a]pyridin-5-ylamino)cyclohexyl)methanol | 406.6 | B |

TABLE 1-continued

| Cmpd. No. | Cmpd. Name | MH+ (Obs.) | Activity Level |
|---|---|---|---|
| 415 | 4-(2-(4-(trifluoromethyl)phenylamino)-[1,2,4]triazolo[1,5-a]pyridin-5-ylamino)pyridin-2-ol | 387.5 | A |
| 416 | 4-(2-(4-fluorophenylamino)-[1,2,4]triazolo[1,5-a]pyridin-5-yl)picolinamide | 349.15 | A |
| 417 | cis-4-(2-(4-fluorophenylamino)-[1,2,4]triazolo[1,5-a]pyridin-5-yloxy)cyclohexanol | 343.1 | A |
| 418 | (1S,3R)-3-(2-(4-(trifluoromethyl)phenylamino)-[1,2,4]triazolo[1,5-a]pyridin-5-ylamino)cyclopentanol | 378.5 | D |
| 419 | (1S,3S)-3-(2-(4-(trifluoromethyl)phenylamino)-[1,2,4]triazolo[1,5-a]pyridin-5-ylamino)cyclopentanol | 378.5 | C |

TABLE 1-continued

| Cmpd. No. | Structure | Cmpd. Name | MH+ (Obs.) | Activity Level |
|---|---|---|---|---|
| 420 | 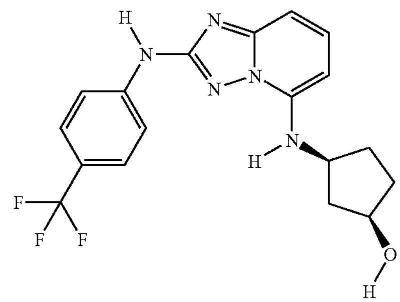 | (1R,3R)-3-(2-(4-(trifluoromethyl)phenylamino)-[1,2,4]triazolo[1,5-a]pyridin-5-ylamino)cyclopentanol | 378.5 | C |
| 421 | 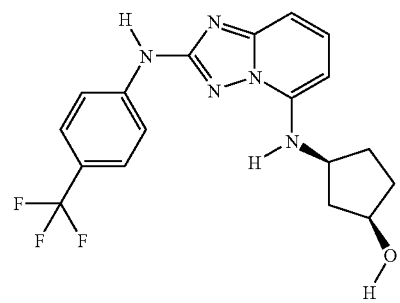 | (1R,3S)-3-(2-(4-(trifluoromethyl)phenylamino)-[1,2,4]triazolo[1,5-a]pyridin-5-ylamino)cyclopentanol | 378.5 | C |
| 422 | 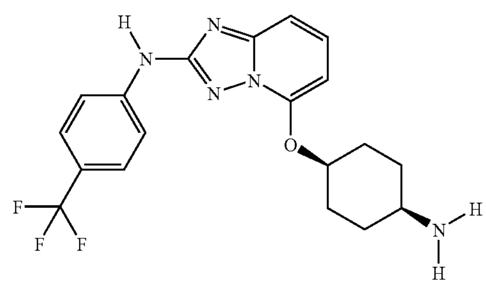 | trans-5-(4-aminocyclohexyloxy)-N-(4-(trifluoromethyl)phenyl)-[1,2,4]triazolo[1,5-a]pyridin-2-amine | 392.1 | D |
| 423 | 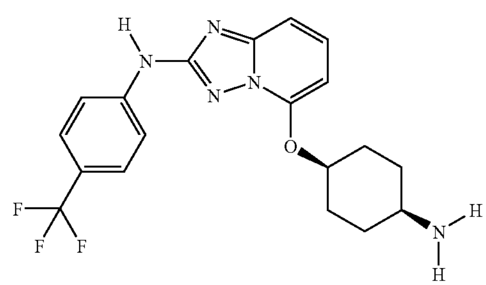 | cis-5-(4-aminocyclohexyloxy)-N-(4-(trifluoromethyl)phenyl)-[1,2,4]triazolo[1,5-a]pyridin-2-amine | 392.1 | B |
| 424 | 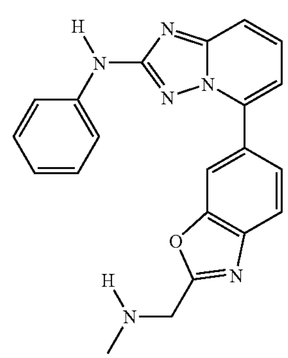 | 5-(2-((methylamino)methyl)benzo[d]oxazol-6-yl)-N-phenyl-[1,2,4]triazolo[1,5-a]pyridin-2-amine | 371.4 | B |

TABLE 1-continued

| Cmpd. No. | Structure | Cmpd. Name | MH+ (Obs.) | Activity Level |
|---|---|---|---|---|
| 425 | 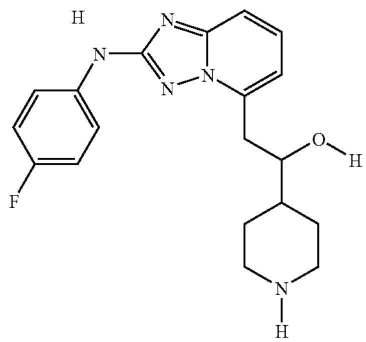 | 2-(2-(4-fluorophenylamino)-[1,2,4]triazolo[1,5-a]pyridin-5-yl)-1-(piperidin-4-yl)ethanol | 356.1 | A |
| 426 | 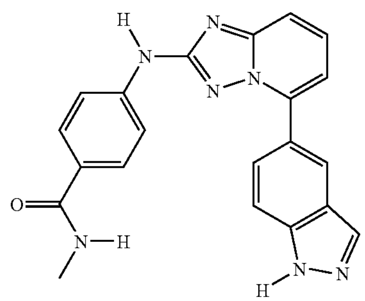 | 4-(5-(1H-indazol-5-yl)-[1,2,4]triazolo[1,5-a]pyridin-2-ylamino)-N-methylbenzamide | 384.2 | D |
| 427 | 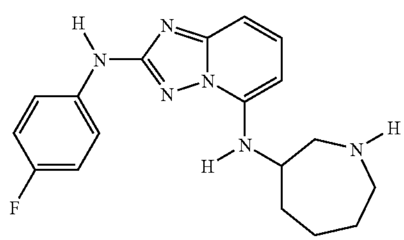 | $N^5$-(azepan-3-yl)-$N^2$-(4-fluorophenyl)-[1,2,4]triazolo[1,5-a]pyridine-2,5-diamine | 341.2 | C |
| 428 | 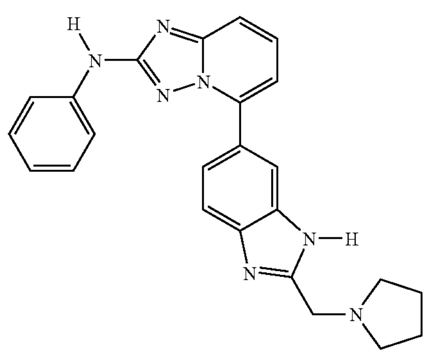 | N-phenyl-5-(2-(pyrrolidin-1-ylmethyl)-1H-benzo[d]imidazol-6-yl)-[1,2,4]triazolo[1,5-a]pyridin-2-amine | 410.4 | D |
| 429 | 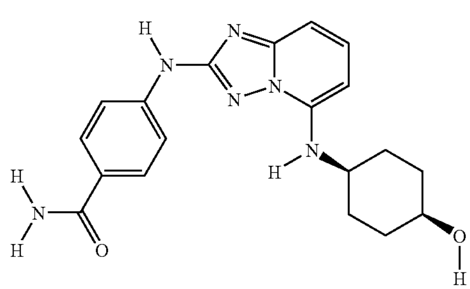 | cis-4-(5-(4-hydroxycyclohexylamino)-[1,2,4]triazolo[1,5-a]pyridin-2-ylamino)benzamide | 349.4 | D |

TABLE 1-continued

| Cmpd. No. | Structure | Cmpd. Name | MH+ (Obs.) | Activity Level |
|---|---|---|---|---|
| 430 | 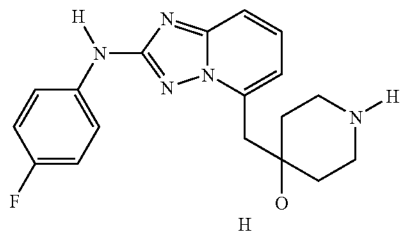 | 4-((2-(4-fluorophenylamino)-[1,2,4]triazolo[1,5-a]pyridin-5-yl)methyl)piperidin-4-ol | 342.2 | A |
| 431 | 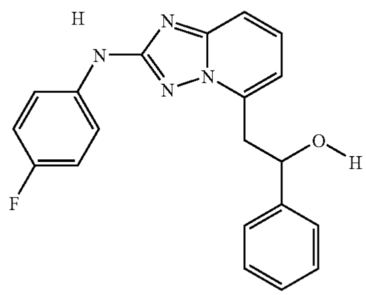 | 2-(2-(4-fluorophenylamino)-[1,2,4]triazolo[1,5-a]pyridin-5-yl)-1-phenylethanol | 349.2 | C |
| 432 | 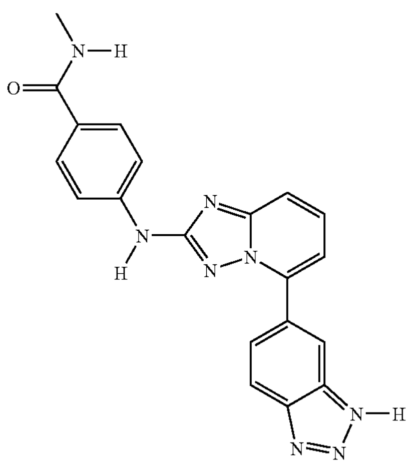 | 4-(5-(1H-benzo[d][1,2,3]triazol-6-yl)-[1,2,4]triazolo[1,5-a]pyridin-2-ylamino)-N-methylbenzamide | 385.1 | D |
| 433 | 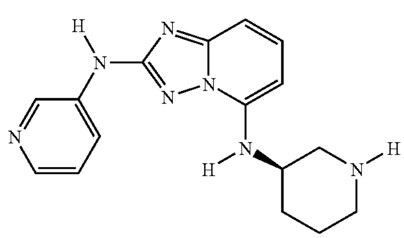 | (S)-N5-(piperidin-3-yl)-N2-(pyridin-3-yl)-[1,2,4]triazolo[1,5-a]pyridin-2,5-diamine | 310.1 | D |
| 434 | 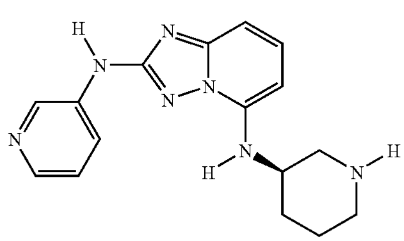 | (R)-N5-(piperidin-3-yl)-N2-(pyridin-3-yl)-[1,2,4]triazolo[1,5-a]pyridine-2,5-diamine | 310.1 | A |

TABLE 1-continued

| Cmpd. No. | Structure | Cmpd. Name | MH+ (Obs.) | Activity Level |
|---|---|---|---|---|
| 435 | 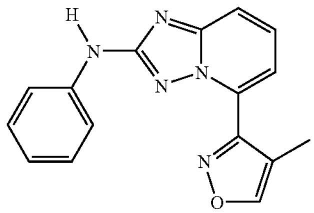 | 5-(4-methylisoxazol-3-yl)-N-phenyl-[1,2,4]triazolo[1,5-a]pyridin-2-amine | 291.9 | A |
| 436 | 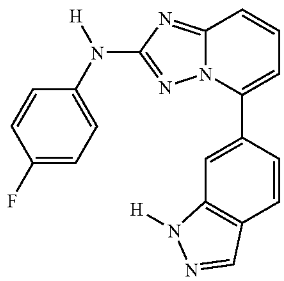 | N-(4-fluorophenyl)-5-(1H-indazol-6-yl)-[1,2,4]triazolo[1,5-a]pyridin-2-amine | 345.1 | D |
| 437 | 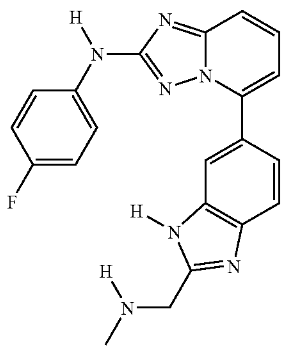 | N-(4-fluorophenyl)-5-(2-((methylamino)methyl)-1H-benzo[d]imidazol-6-yl)-[1,2,4]triazolo[1,5-a]pyridin-2-amine | 388.1 | D |
| 438 | 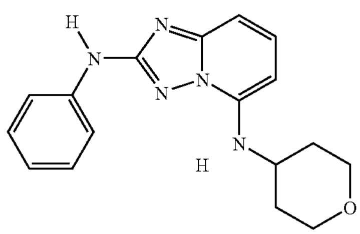 | $N^2$-phenyl-$N^5$-(tetrahydro-2H-pyran-4-yl)-[1,2,4]triazolo[1,5-a]pyridine-2,5-diamine | 310.2 | A |
| 439 | 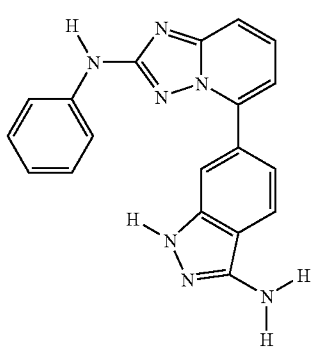 | 5-(3-amino-1H-indazol-6-yl)-N-phenyl-[1,2,4]triazolo[1,5-a]pyridin-2-amine | 342.0 | D |

TABLE 1-continued

| Cmpd. No. | Structure | Cmpd. Name | MH+ (Obs.) | Activity Level |
|---|---|---|---|---|
| 440 | 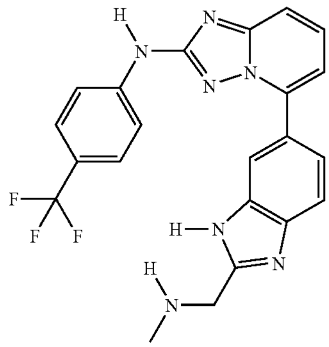 | 5-(2-((methylamino)methyl)-1H-benzo[d]imidazol-6-yl)-N-(4-(trifluoromethyl)phenyl)-[1,2,4]triazolo[1,5-a]pyridin-2-amine | 438.1 | D |
| 441 | 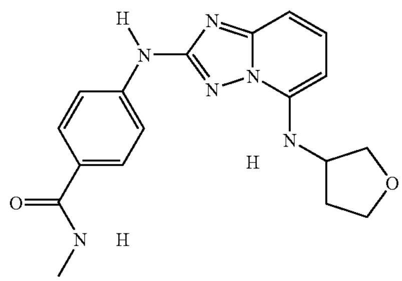 | N-methyl-4-(5-(tetrahydrofuran-3-ylamino)-[1,2,4]triazolo[1,5-a]pyridin-2-ylamino)benzamide | 353.2 | A |
| 442 | 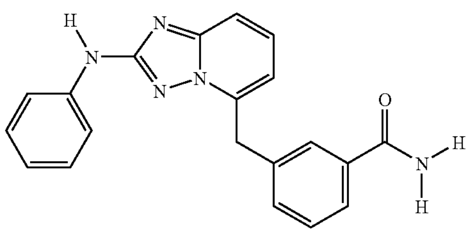 | 3-((2-(phenylamino)-[1,2,4]triazolo[1,5-a]pyridin-5-yl)methyl)benzamide | 344.3 | C |
| 443 | 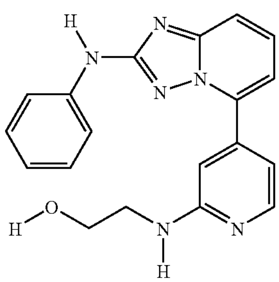 | 2-(4-(2-(phenylamino)-[1,2,4]triazolo[1,5-a]pyridin-5-yl)pyridin-2-ylamino)ethanol | 347.1 | D |
| 444 | 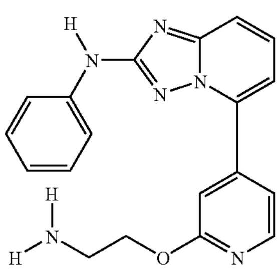 | 5-(2-(2-aminoethoxy)pyridin-4-yl)-N-phenyl-[1,2,4]triazolo[1,5-a]pyridin-2-amine | 347.3 | C |

TABLE 1-continued

| Cmpd. No. | Cmpd. Name | MH+ (Obs.) | Activity Level |
|---|---|---|---|
| 445 | 5-(2-aminopyridin-4-yl)-N-phenyl-[1,2,4]triazolo[1,5-a]pyridin-2-amine | 303.4 | D |
| 446 | 5-(2-(dimethylamino)pyridin-4-yl)-N-phenyl-[1,2,4]triazolo[1,5-a]pyridin-2-amine | 331.3 | C |
| 447 | N¹-(4-(2-(phenylamino)-[1,2,4]triazolo[1,5-a]pyridin-5-yl)pyridin-2-yl)ethane-1,2-diamine | 346 | D |
| 448 | (R)-N²-(isoindolin-5-yl)-N⁵-(piperidin-3-yl)-[1,2,4]triazolo[1,5-a]pyridin-2,5-diamine | 350.1 | A |
| 449 | (S)-N²-(isoindol-5-yl)-N⁵-(piperidin-3-yl)-[1,2,4]triazolo[1,5-a]pyridine-2,5-diamine | 350.1 | D |

TABLE 1-continued

| Cmpd. No. | Structure | Cmpd. Name | MH+ (Obs.) | Activity Level |
|---|---|---|---|---|
| 450 | 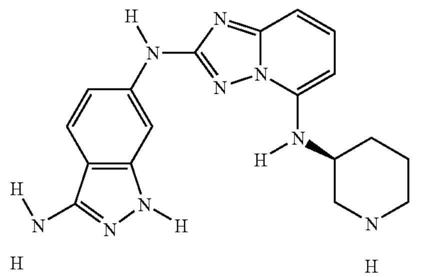 | (R)-N$^2$-(3-amino-1H-indazol-6-yl)-N$^5$-(piperidin-3-yl)-[1,2,4]triazolo[1,5-a]pyridin-2,5-diamine | 364 | D |
| 451 | 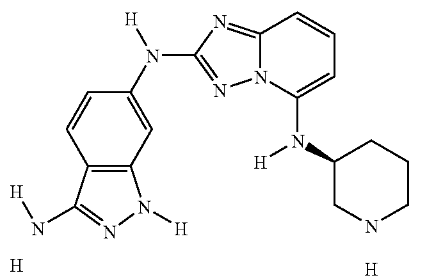 | (S)-N$^2$-(3-amino-1H-indazol-6-yl)-N$^5$-(piperidin-3-yl)-[1,2,4]triazolo[1,5-a]pyridine-2,5-diamine | 364 | D |
| 452 | 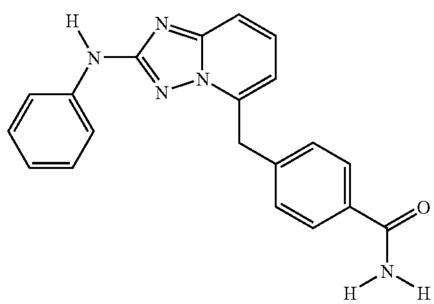 | 4-((2-(phenylamino)-[1,2,4]triazolo[1,5-a]pyridin-5-yl)methyl)benzamide | 344.1 | A |
| 453 | 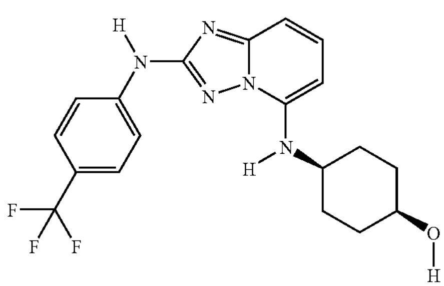 | cis-4-(2-(4-(trifluoromethyl)phenylamino)-[1,2,4]triazolo[1,5-a]pyridin-5-ylamino)cyclohexanol | 392.4 | D |
| 454 | 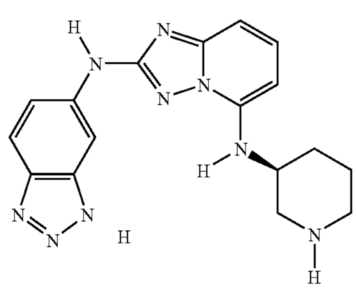 | (S)-N$^2$-(1H-benzo[d][1,2,3]triazol-6-yl)-N$^5$-(piperidin-3-yl)-[1,2,4]triazolo[1,5-a]pyridine-2,5-diamine | 349.1 | D |

TABLE 1-continued

| Cmpd. No. | Structure | Cmpd. Name | MH+ (Obs.) | Activity Level |
|---|---|---|---|---|
| 455 | 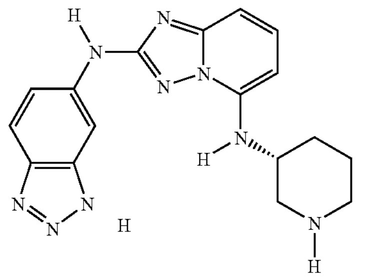 | (R)-N²-(1H-benzo[d][1,2,3]triazol-6-yl)-N⁵-(piperidin-3-yl)-[1,2,4]triazolo[1,5-a]pyridine-2,5-diamine | 350.2 | C |
| 456 | 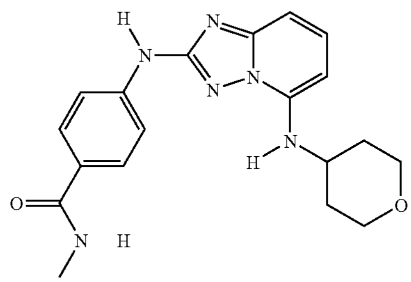 | N-methyl-4-(5-(tetrahydro-2H-pyran-4-ylamino)-[1,2,4]triazolo[1,5-a]pyridin-2-ylamino)benzamide | 367.0 | A |
| 457 | 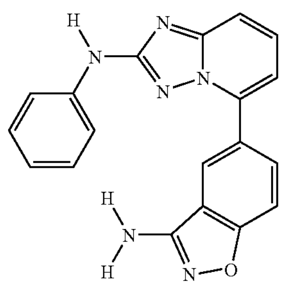 | 5-(2-(phenylamino)-[1,2,4]triazolo[1,5-a]pyridin-5-yl)benzo[d]isoxazol-3-amine | 343 | D |
| 458 | 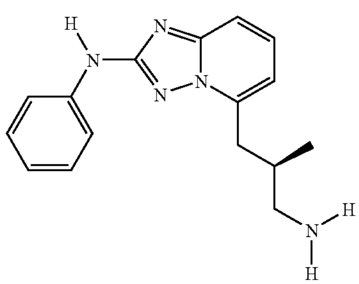 | (R)-5-(3-amino-2-methylpropyl)-N-phenyl-[1,2,4]triazolo[1,5-a]pyridin-2-amine | 282.2 | A |
| 459 | 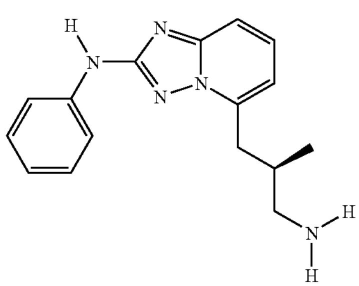 | (S)-5-(3-amino-2-methylpropyl)-N-phenyl-[1,2,4]triazolo[1,5-a]pyridin-2-amine | 282.2 | A |

| Cmpd. No. | Structure | Cmpd. Name | MH+ (Obs.) | Activity Level |
|---|---|---|---|---|
| 460 | 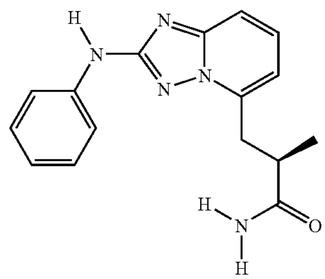 | (R)-2-methyl-3-(2-(phenylamino)-[1,2,4]triazolo[1,5-a]pyridin-5-yl)propanamide | 296.1 | A |
| 461 | 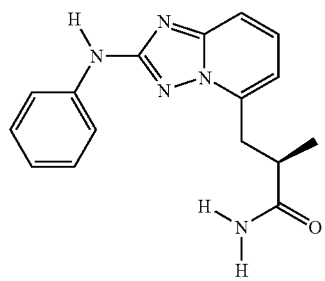 | (S)-2-methyl-3-(2-(phenylamino)-[1,2,4]triazolo[1,5-a]pyridin-5-yl)propanamide | 296.1 | A |
| 462 | 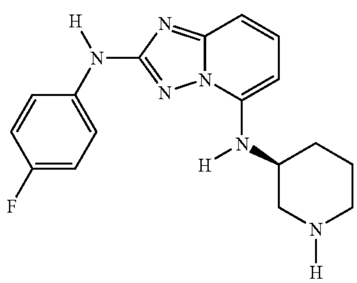 | (R)-N2-(4-fluorophenyl)-N5-(piperidin-3-yl)-[1,2,4]triazolo[1,5-a]pyridin-2,5-diamine | 327.1 | A |
| 463 | 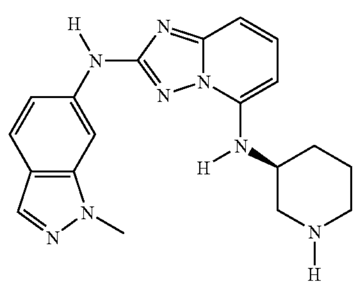 | (R)-N2-(1-methyl-1H-indazol-6-yl)-N5-(piperidin-3-yl)-[1,2,4]triazolo[1,5-a]pyridin-2,5-diamine | 363.2 | B |
| 464 | 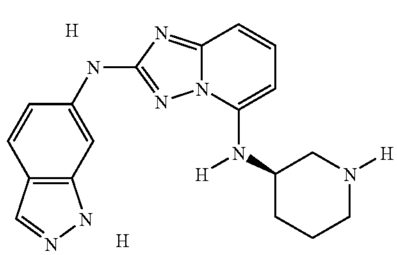 | (S)-N2-(1H-indazol-6-yl)-N5-(piperidin-3-yl)-[1,2,4]triazolo[1,5-a]pyridine-2,5-diamine | 349.1 | D |

TABLE 1-continued

| Cmpd. No. | Cmpd. Name | MH⁺ (Obs.) | Activity Level |
|---|---|---|---|
| 465 | (S)-$N^2$-(4-fluorophenyl)-$N^5$-(piperidin-3-yl)-[1,2,4]triazolo[1,5-a]pyridine-2,5-diamine | 327.1 | D |
| 466 | (S)-$N^2$-(1-methyl-1H-indazol-6-yl)-$N^5$-(piperidin-3-yl)-[1,2,4]triazolo[1,5-a]pyridine-2,5-diamine | 363.2 | D |
| 467 | (R)-$N^2$-(1H-indazol-6-yl)-$N^5$-(piperidin-3-yl)-[1,2,4]triazolo[1,5-a]pyridin-2,5-diamine | 349.1 | D |
| 468 | (R)-$N^5$-(piperidin-3-yl)-$N^2$-(4-(trifluoromethyl)phenyl)-[1,2,4]triazolo[1,5-a]pyridin-2,5-diamine | 377.0 | B |
| 469 | (S)-$N^5$-(piperidin-3-yl)-$N^2$-(4-(trifluoromethyl)phenyl)-[1,2,4]triazolo[1,5-a]pyridin-2,5-diamine | 377.0 | D |

TABLE 1-continued

| Cmpd. No. | Cmpd. Name | MH+ (Obs.) | Activity Level |
|---|---|---|---|
| 470 | trans-4-(2-(phenylamino)-[1,2,4]triazolo[1,5-a]pyridin-5-ylamino)cyclohexanol | 324.39 | A |
| 471 | cis-4-(2-(phenylamino)-[1,2,4]triazolo[1,5-a]pyridin-5-ylamino)cyclohexanol | 324.39 | D |
| 472 | $N^5$-methyl-$N^2$,$N^5$-diphenyl-[1,2,4]triazolo[1,5-a]pyridin-2,5-diamine | 316 | A |
| 473 | 5-(5-methylisoxazol-3-yl)-N-phenyl-[1,2,4]triazolo[1,5-a]pyridin-2-amine | 291.9 | B |
| 474 | (R)-$N^2$-phenyl-$N^5$-(pyrrolidin-3-yl)-[1,2,4]triazolo[1,5-a]pyridin-2,5-diamine | 295.35 | B |
| 475 | (S)-$N^2$-phenyl-$N^5$-(pyrrolidin-3-yl)-[1,2,4]triazolo[1,5-a]pyridin-2,5-diamine | 295.35 | C |

TABLE 1-continued

| Cmpd. No. | Structure | Cmpd. Name | MH+ (Obs.) | Activity Level |
|---|---|---|---|---|
| 476 | 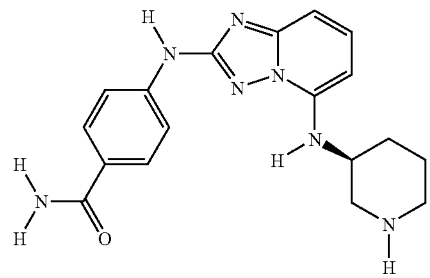 | (R)-4-(5-(piperidin-3-ylamino)-[1,2,4]triazolo[1,5-a]pyridin-2-ylamino)benzamide | 352.41 | A |
| 477 | 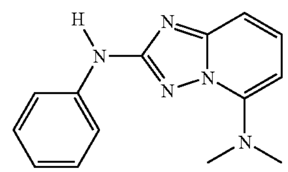 | $N^5,N^5$-dimethyl-$N^2$-phenyl-[1,2,4]triazolo[1,5-a]pyridin-2,5-diamine | 254.1 | A |
| 478 | 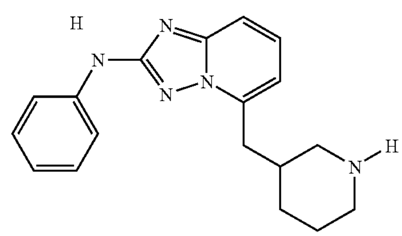 | N-phenyl-5-(piperidin-3-ylmethyl)-[1,2,4]triazolo[1,5-a]pyridin-2-amine | 308.3 | C |
| 479 | 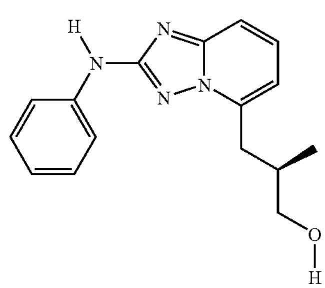 | (R)-2-methyl-3-(2-(phenylamino)-[1,2,4]triazolo[1,5-a]pyridin-5-yl)propan-1-ol | 283.2 | B |
| 480 | 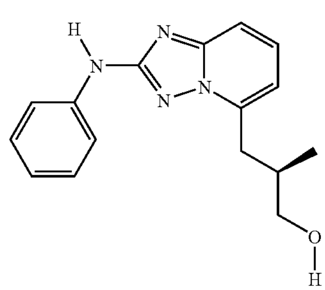 | (S)-2-methyl-3-(2-(phenylamino)-[1,2,4]triazolo[1,5-a]pyridin-5-yl)propan-1-ol | 283.2 | C |

TABLE 1-continued

| Cmpd. No. | Structure | Cmpd. Name | MH+ (Obs.) | Activity Level |
|---|---|---|---|---|
| 481 | 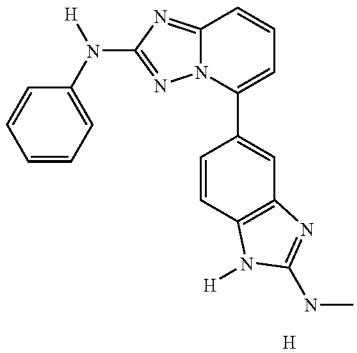 | 5-(2-(methylamino)-1H-benzo[d]imidazol-5-yl)-N-phenyl-[1,2,4]triazolo[1,5-a]pyridin-2-amine | 356.2 | D |
| 482 | 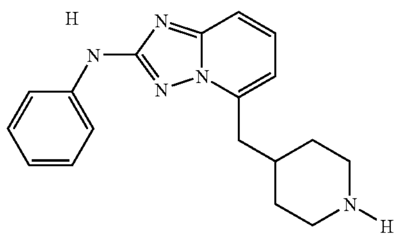 | N-phenyl-5-(piperidin-4-ylmethyl)-[1,2,4]triazolo[1,5-a]pyridin-2-amine | 308.3 | D |
| 483 | 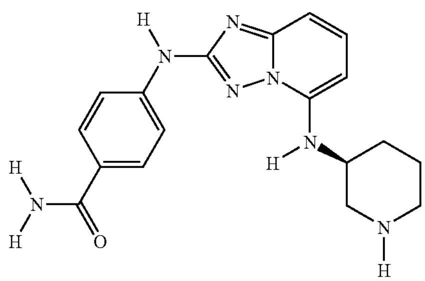 | (S)-4-(5-(piperidin-3-ylamino)-[1,2,4]triazolo[1,5-a]pyridin-2-ylamino)benzamide | 352.4 | D |
| 484 | 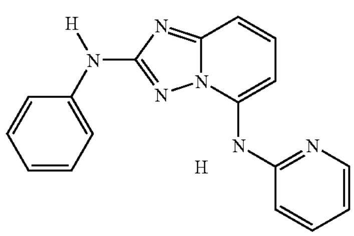 | N²-phenyl-N⁵-(pyridin-2-yl)-[1,2,4]triazolo[1,5-a]pyridin-2,5-diamine | 303 | B |
| 485 | 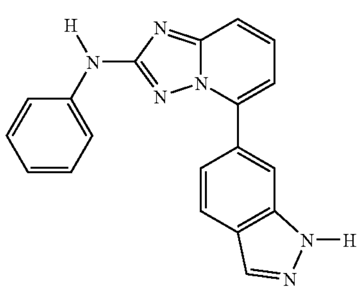 | 5-(1H-indazol-6-yl)-N-phenyl-[1,2,4]triazolo[1,5-a]pyridin-2-amine | 327.1 | D |

TABLE 1-continued
| Cmpd. No. | Structure | Cmpd. Name | MH+ (Obs.) | Activity Level |
|---|---|---|---|---|
| 486 | 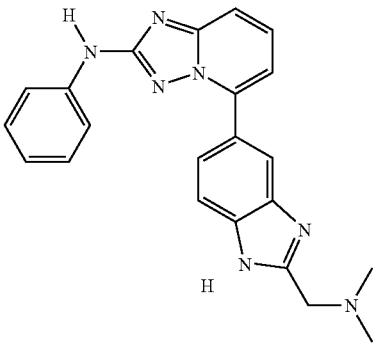 | 5-(2-((dimethylamino)methyl)-1H-benzo[d]imidazol-5-yl)-N-phenyl-[1,2,4]triazolo[1,5-a]pyridin-2-amine | 384.3 | D |
| 487 | 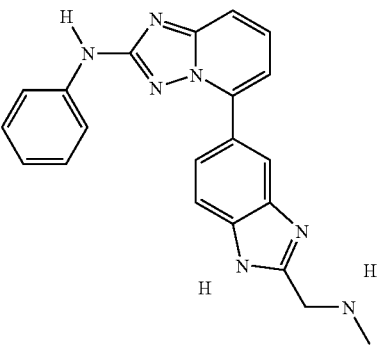 | 5-(2-((methylamino)methyl)-1H-benzo[d]imidazol-5-yl)-N-phenyl-[1,2,4]triazolo[1,5-a]pyridin-2-amine | 370.1 | D |
| 488 | 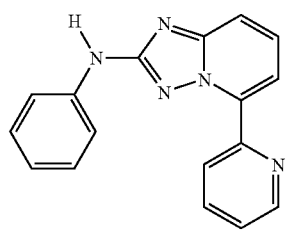 | N-phenyl-5-(pyridin-2-yl)-[1,2,4]triazolo[1,5-a]pyridin-2-amine | 288.1 | A |
| 489 | 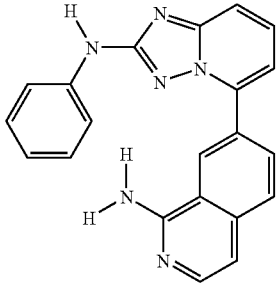 | 7-(2-(phenylamino)-[1,2,4]triazolo[1,5-a]pyridin-5-yl)isoquinolin-1-amine | 353.1 | B |

TABLE 1-continued

| Cmpd. No. | Structure | Cmpd. Name | MH+ (Obs.) | Activity Level |
|---|---|---|---|---|
| 490 | 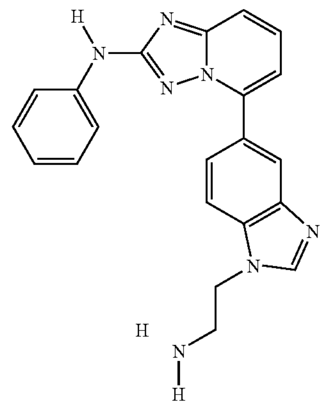 | 5-(1-(2-aminoethyl)-1H-benzo[d]imidazol-5-yl)-N-phenyl-[1,2,4]triazolo[1,5-a]pyridin-2-amine | 370.1 | A |
| 491 | 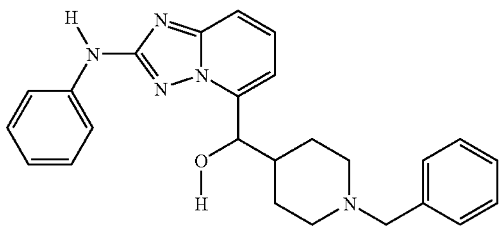 | (1-benzylpiperidin-4-yl)(2-(phenylamino)-[1,2,4]triazolo[1,5-a]pyridin-5-yl)methanol | 414.2 | A |
| 492 | 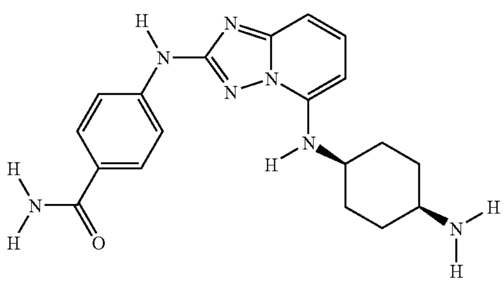 | trans-4-(5-(4-aminocyclohexylamino)-[1,2,4]triazolo[1,5-a]pyridin-2-ylamino)benzamide | 366.43 | D |
| 493 | 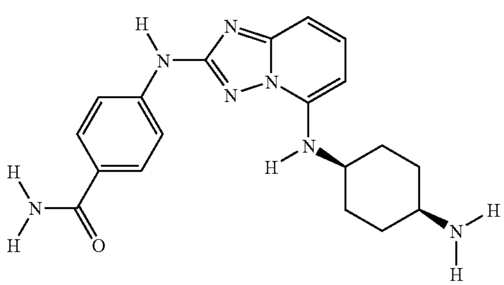 | cis-4-(5-(4-aminocyclohexylamino)-[1,2,4]triazolo[1,5-a]pyridin-2-ylamino)benzamide | 366.4 | D |
| 494 | 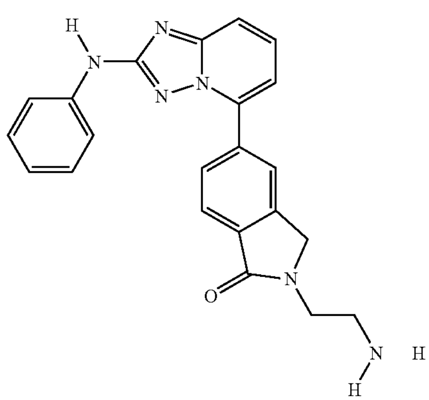 | 2-(2-aminoethyl)-5-(2-(phenylamino)-[1,2,4]triazolo[1,5-a]pyridin-5-yl)isoindolin-1-one | 385.3 | B |

TABLE 1-continued
| Cmpd. No. | Structure | Cmpd. Name | MH+ (Obs.) | Activity Level |
|---|---|---|---|---|
| 495 | 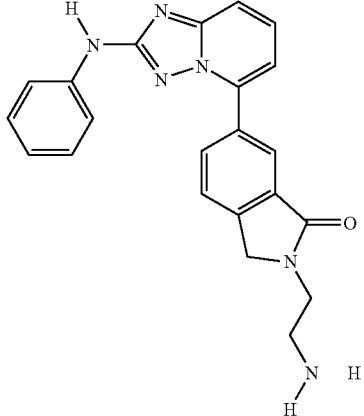 | 2-(2-aminoethyl)-6-(2-(phenylamino)-[1,2,4]triazolo[1,5-a]pyridin-5-yl)isoindolin-1-one | 385.2 | A |
| 496 | 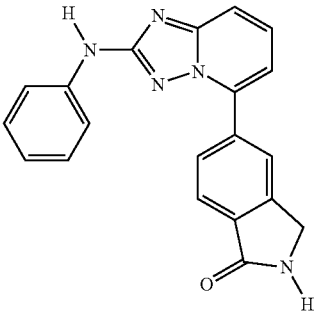 | 5-(2-(phenylamino)-[1,2,4]triazolo[1,5-a]pyridin-5-yl)isoindolin-1-one | 342.1 | C |
| 497 | 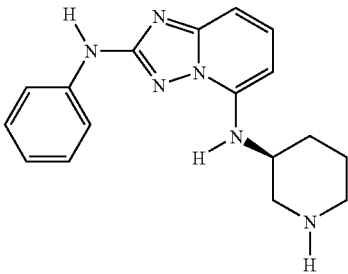 | (R)-$N^2$-phenyl-$N^5$-(piperidin-3-yl)-[1,2,4]triazolo[1,5-a]pyridin-2,5-diamine | 309.38 | A |
| 498 | 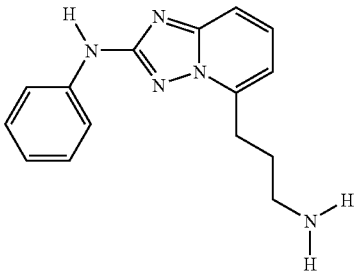 | 5-(3-aminopropyl)-N-phenyl-[1,2,4]triazolo[1,5-a]pyridin-2-amine | 268 | A |

TABLE 1-continued

| Cmpd. No. | Cmpd. Name | MH+ (Obs.) | Activity Level |
|---|---|---|---|
| 499 | 4-(2-(phenylamino)-[1,2,4]triazolo[1,5-a]pyridin-5-yl)-isoindolin-1-one | 342.3 | A |
| 500 | 6-(2-(phenylamino)-[1,2,4]triazolo[1,5-a]pyridin-5-yl)-isoindolin-1-one | 342.3 | B |
| 501 | (2-(phenylamino)-[1,2,4]triazolo[1,5-a]pyridin-5-yl)(pyridin-3-yl)methanol | 318 | C |
| 502 | (2-(phenylamino)-[1,2,4]triazolo[1,5-a]pyridin-5-yl)(piperidin-4-yl)methanol | 324 | C |
| 503 | 5-phenoxy-N-phenyl-[1,2,4]triazolo[1,5-a]pyridin-2-amine | 303.1 | A |

TABLE 1-continued

| Cmpd. No. | Cmpd. Name | MH+ (Obs.) | Activity Level |
|---|---|---|---|
| 504 | (S)-2-(phenylamino)-N-(piperidin-3-yl)-[1,2,4]triazolo[1,5-a]pyridine-5-carboxamide | 337.4 | A |
| 505 | 5-(4-aminobutyl)-N-phenyl-[1,2,4]triazolo[1,5-a]pyridin-2-amine | 282.3 | B |
| 506 | 5-benzyl-N-phenyl-[1,2,4]triazolo[1,5-a]pyridin-2-amine | 301.1 | A |
| 507 | (S)-$N^2$-phenyl-$N^5$-(piperidin-3-yl)-[1,2,4]triazolo[1,5-a]pyridin-2,5-diamine | 309.4 | D |
| 508 | cis-$N^5$-(4-aminocyclohexyl)-$N^2$-phenyl-[1,2,4]triazolo[1,5-a]pyridine-2,5-diamine | 323.41 | C |

TABLE 1-continued

| Cmpd. No. | Structure | Cmpd. Name | MH+ (Obs.) | Activity Level |
|---|---|---|---|---|
| 509 | 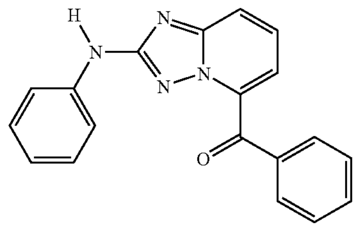 | phenyl(2-(phenylamino)-[1,2,4]triazolo[1,5-a]pyridin-5-yl)methanone | 315.3 | A |
| 510 | 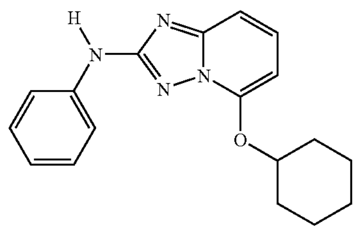 | 5-(cyclohexyl)-N-phenyl-[1,2,4]triazolo[1,5-a]pyridin-2-amine | 309.2 | A |
| 511 | 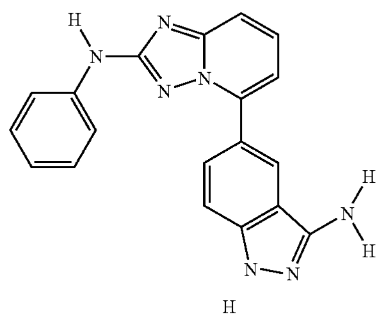 | 5-(3-amino-1H-indazol-5-yl)-N-phenyl-[1,2,4]triazolo[1,5-a]pyridin-2-amine | 342 | C |
| 512 | 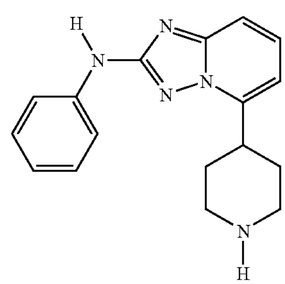 | N-phenyl-5-(piperidin-4-yl)-[1,2,4]triazolo[1,5-a]pyridin-2-amine | 294 | A |
| 513 | 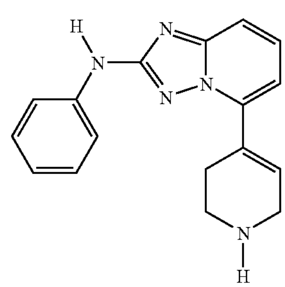 | N-phenyl-5-(1,2,3,6-tetrahydropyridin-4-yl)-[1,2,4]triazolo[1,5-a]pyridin-2-amine | 292 | A |

TABLE 1-continued

| Cmpd. No. | Cmpd. Name | MH+ (Obs.) | Activity Level |
|---|---|---|---|
| 514 | 5-(1H-benzo[d]imidazol-6-yl)-N-phenyl-[1,2,4]triazolo[1,5-a]pyridin-2-amine | 327.2 | D |
| 515 | 5-(1-(2-aminoethyl)-1H-benzo[d]imidazol-6-yl)-N-phenyl-[1,2,4]triazolo[1,5-a]pyridin-2-amine | 370.2 | A |
| 516 | 4-(5-(piperidin-4-ylamino)-[1,2,4]triazolo[1,5-a]pyridin-2-ylamino)benzamide | 352.41 | A |
| 517 | 4-(2-(phenylamino)-[1,2,4]triazolo[1,5-a]pyridin-5-yl)pyridin-2-ol | 304 | A |
| 518 | trans-$N^5$-(4-aminocyclohexyl)-$N^2$-phenyl-[1,2,4]triazolo[1,5-a]pyridine-2,5-diamine | 323.4 | B |

TABLE 1-continued

| Cmpd. No. | Structure | Cmpd. Name | MH+ (Obs.) | Activity Level |
|---|---|---|---|---|
| 519 | 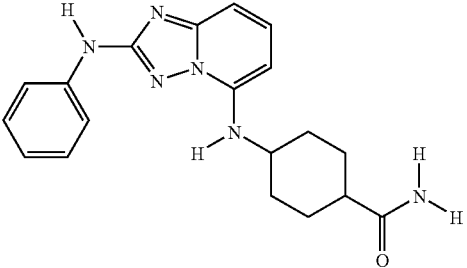 | cis-4-(2-(phenylamino)-[1,2,4]triazolo[1,5-a]pyrridin-5-ylamino)cyclohexanecarboxamide | 351.42 | A |
| 520 | 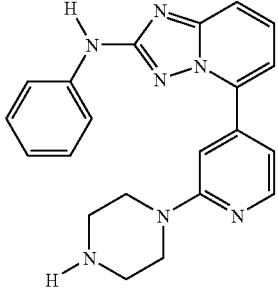 | N-phenyl-5-(2-(piperazin-1-yl)pyridin-4-yl)-[1,2,4]triazolo[1,5-a]pyridin-2-amine | 372 | A |
| 521 | 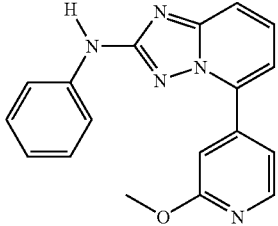 | 5-(2-(methoxypyridin-4-yl)-N-phenyl-[1,2,4]triazolo[1,5-a]pyridin-2-amine | 318 | B |
| 522 | 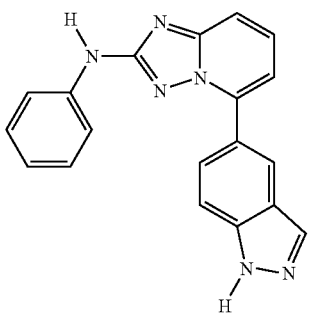 | 5-(1H-indazol-5-yl)-N-phenyl-[1,2,4]triazolo[1,5-a]pyridin-2-amine | 327.1 | B |
| 523 | 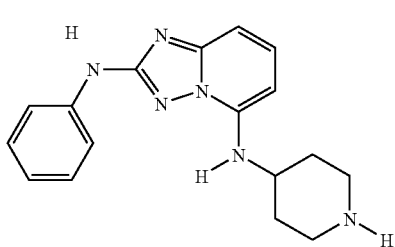 | $N^2$-phenyl-$N^5$-(piperidin-4-yl)-[1,2,4]triazolo[1,5-a]pyridine-2,5-diamine | 309.38 | B |

TABLE 1-continued

| Cmpd. No. | Structure | Cmpd. Name | MH+ (Obs.) | Activity Level |
|---|---|---|---|---|
| 524 | 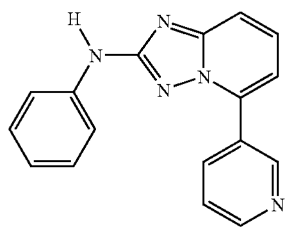 | N-phenyl-5-(pyridin-3-yl)-[1,2,4]triazolo[1,5-a]pyridin-2-amine | 288.1 | A |
| 525 | 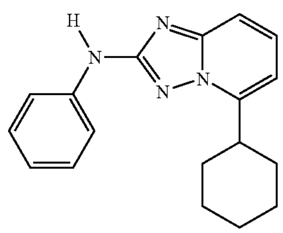 | 5-cyclohexyl-N-phenyl-[1,2,4]triazolo[1,5-a]pyridin-2-amine | 293.2 | A |
| 526 | 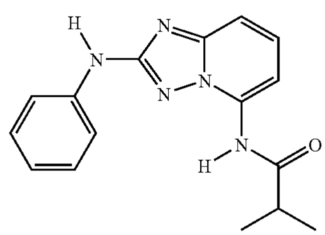 | N-(2-(phenylamino)-[1,2,4]triazolo[1,5-a]pyridin-5-yl)isobutyramide | 296.1 | A |
| 527 | 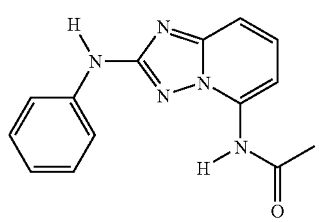 | N-(2-(phenylamino)-[1,2,4]triazolo[1,5-a]pyridin-5-yl)acetamide | 267.9 | B |
| 528 | 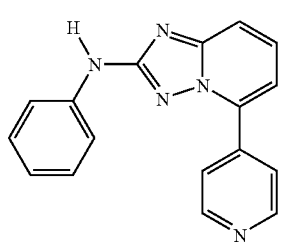 | N-phenyl-5-(pyridin-4-yl)-[1,2,4]triazolo[1,5-a]pyridin-2-amine | 288.1 | C |
| 529 | 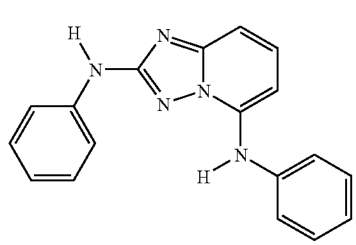 | $N^2,N^5$-diphenyl-[1,2,4]triazolo[1,5-a]pyridine-2,5-diamine | 302.1 | C |

TABLE 1-continued

| Cmpd. No. | Cmpd. Name | MH+ (Obs.) | Activity Level |
|---|---|---|---|
| 530 | $N^5$-isopropyl-$N^2$-phenyl-[1,2,4]triazolo[1,5-a]pyrridine-2,5-diamine | 268.2 | B |
| 531 | $N^2$-(3-methylbenzo[d]isoxazol-6-yl)-$N^5$-(tetrahydro-2H-pyran-4-yl)-[1,2,4]triazolo[1,5-a]pyridine-2,5-diamine | 365.2 | A |
| 532 | 1-methyl-5-(5-((tetrahydro-2H-pyran-4-yl)methyl)-[1,2,4]triazolo[1,5-a]pyridin-2-ylamino)-1H-benzo[d]imidazol-2(3H)-one | 379.2 | D |
| 533 | 4-((2-(3-(methoxymethyl)-1H-indazol-6-ylamino)-[1,2,4]triazolo[1,5-a]pyridin-5-yl)methyl)piperazin-2-one | 407.5 | D |
| 534 | $N^2$-(3-methyl-[1,2,4]triazolo[4,3-a]pyridin-7-yl)-$N^5$-(tetrahydro-2H-pyran-4-yl)-[1,2,4]triazolo[1,5-a]pyridine-2,5-diamine | 365.6 | A |
| 535 | N-(5-methyl-6-morpholinopyridin-3-yl)-5-((tetrahydro-2H-pyran-4-yl)methyl)-[1,2,4]triazolo[1,5-a]pyridin-2-amine | 409.6 | B |

TABLE 1-continued

| Cmpd. No. | Cmpd. Name | MH+ (Obs.) | Activity Level |
|---|---|---|---|
| 536 | 6-(5-(difluoro(tetrahydro-2H-pyran-4-yl)methyl)-[1,2,4]triazolo[1,5-a]pyridin-2-ylamino)-3,3-dimethylindolin-2-one | 428.3 | D |
| 537 | 3-methyl-N-(5-((tetrahydro-2H-pyran-4-yl)methyl)-[1,2,4]triazolo[1,5-a]pyridin-2-yl)benzo[d]isoxazol-6-amine | 364.1 | B |
| 538 | 3-methyl-N-(5-((tetrahydro-2H-pyran-4-yl)methyl)-[1,2,4]triazolo[1,5-a]pyridin-2-yl)-[1,2,4]triazolo[4,3-a]pyridin-7-amine | 364.6 | A |
| 539 | N2-(3-methyl-1H-pyrazolo[3,4-b]pyridin-5-yl)-N5-(tetrahydro-2H-pyran-4-yl)-[1,2,4]triazolo[1,5-a]pyridin-2,5-diamine | 365.3 | A |
| 540 | 5-((tetrahydro-2H-pyran-4-yl)methyl)-N-(3-(trifluoromethyl)-1H-indazol-6-yl)-[1,2,4]triazolo[1,5-a]pyridin-2-amine | 417.2 | D |
| 541 | cis-4-(2-(3-methyl-1H-pyrazolo[3,4-b]pyridin-5-ylamino)-[1,2,4]triazolo[1,5-a]pyridin-5-ylamino)cyclohexanol | 379.1 | D |

TABLE 1-continued

| Cmpd. No. | Cmpd. Name | MH+ (Obs.) | Activity Level |
|---|---|---|---|
| 542 | N5-methyl-N2-(1-methyl-1H-indazol-5-yl)-N5-(tetrahydro-2H-pyran-4-yl)-[1,2,4]triazolo[1,5-a]pyridine-2,5-diamine | 378 | D |
| 543 | cis-4-(2-(3-methylbenzo[d]isoxazol-6-ylamino)-[1,2,4]triazolo[1,5-a]pyridin-5-ylamino)cyclohexanol | 379.4 | D |
| 544 | 3-methyl-N-(5-((tetrahydro-2H-pyran-4-yl)methyl)-[1,2,4]triazolo[1,5-a]pyridin-2-yl)-1H-pyrazolo[3,4-b]pyridin-5-amine | 364.2 | B |
| 545 | cis-tert-butyl 6-(5-(4-hydroxycyclohexylamino)-[1,2,4]triazolo[1,5-a]pyridin-2-ylamino)-3,3-dimethyl-2-oxoindoline-1-carboxylate | 508.2 | D |
| 546 | 3,3,4-trimethyl-6-(5-((3-oxopiperazin-1-yl)methyl)-[1,2,4]triazolo[1,5-a]pyridin-2-ylamino)indolin-2-amine | 420 | D |

TABLE 1-continued

| Cmpd. No. | Structure | Cmpd. Name | MH+ (Obs.) | Activity Level |
|---|---|---|---|---|
| 547 | 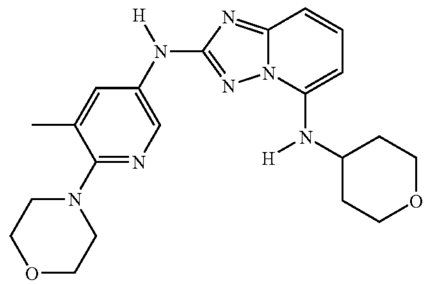 | $N^2$-(5-methyl-6-morpholinopyridin-3-yl)-$N^5$-(tetrahydro-2H-pyran-4-yl)-[1,2,4]triazolo[1,5-a]pyrridine-2,5-diamine | 410.1 | B |
| 548 | 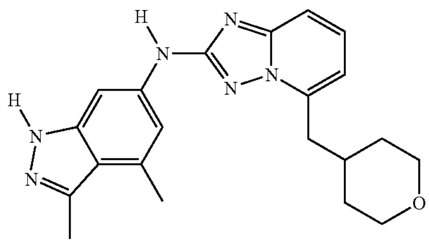 | N-(3,4-dimethyl-1H-indazol-6-yl)-5-((tetrahydro-2H-pyran-4-yl)methyl)-[1,2,4]triazolo[1,5-a]pyridin-2-amine | 377.7 | D |
| 549 | 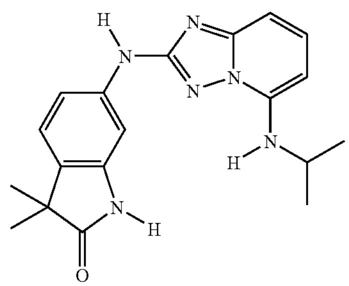 | 6-(5-(isopropylamino)-[1,2,4]triazolo[1,5-a]pyridin-2-ylamino)-3,3-dimethylindolin-2-one | 351 | D |
| 550 | 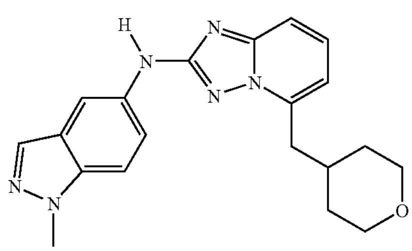 | N-(1-methyl-1H-indazol-5-yl)-5-((tetrahydro-2H-pyran-4-yl)methyl)-[1,2,4]triazolo[1,5-a]pyridin-2-amine | 363.4 | D |
| 551 | 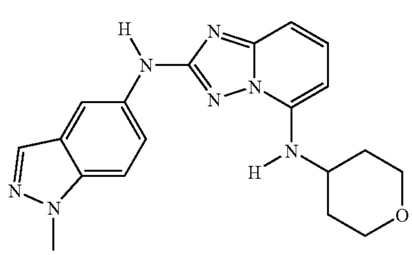 | $N^2$-(1-methyl-1H-indazol-5-yl)-$N^5$-(tetrahydro-2H-pyran-4-yl)-[1,2,4]triazolo[1,5-a]pyridine-2,5-diamine | 364.1 | D |

TABLE 1-continued

| Cmpd. No. | Structure | Cmpd. Name | MH+ (Obs.) | Activity Level |
|---|---|---|---|---|
| 552 | 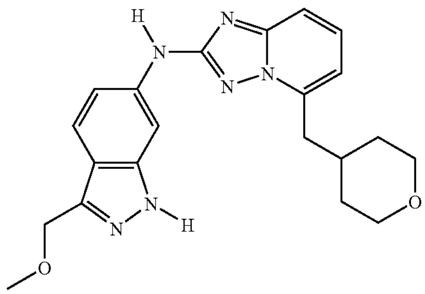 | N-(3-(methoxymethyl)-1H-indazol-6-yl)-5-((tetrahydro-2H-pyran-4-yl)methyl)-[1,2,4]triazolo[1,5-a]pyridin-2-amine | 393 | D |
| 553 | 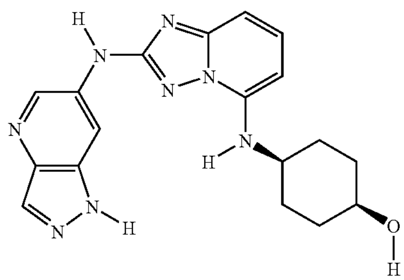 | cis-4-(2-(1H-pyrazolo-[4,3-b]pyridin-6-ylamino)-[1,2,4]triazolo[1,5-a]pyridin-5-ylamino)cyclohexanol | 365.3 | D |
| 554 | 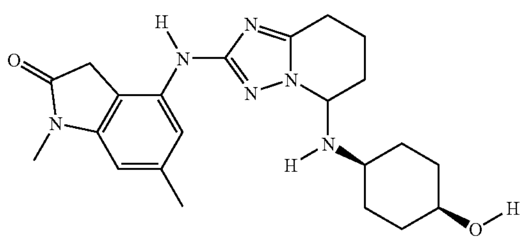 | cis-4-(5-(4-hydroxycyclohexylamino)-[1,2,4]triazolo[1,5-a]pyridin-2-ylamino)-1,6-dimethylindolin-2-one | 407.1 | B |
| 555 | 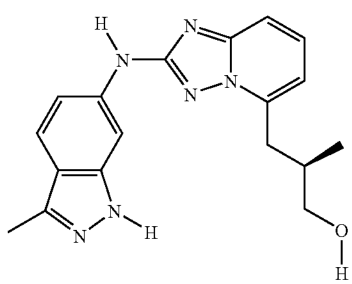 | (S)-2-methyl-3-(2-(3-methyl-1H-indazol-6-ylamino)-[1,2,4]triazolo[1,5-a]pyridin-5-yl)propan-1-ol | 337.0 | D |
| 556 | 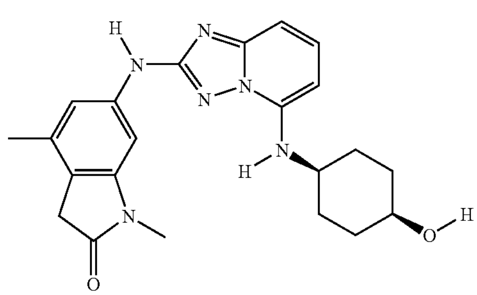 | cis-6-(5-(4-hydroxycyclohexylamino)-[1,2,4-triazolo[1,5-a]pyridin-2-ylamino)-1,4-dimethylindolin-2-one | 407.1 | D |

TABLE 1-continued

| Cmpd. No. | Cmpd. Name | MH+ (Obs.) | Activity Level |
|---|---|---|---|
| 557 | N-(4-(1H-1,2,4-triazolo-3-yl)phenyl)-5-((tetrahydro-2H-pyran-4-yl)methyl)-[1,2,4]triazolo[1,5-a]pyridin-2-amine | 376.5 | B |
| 558 | 3,3-dimethyl-6-(5-((tetrahydrofuran-3-yl)methyl)-[1,2,4]triazolo[1,5-a]pyridin-2-ylamino)indolin-2-one (enantiomer 2) | 378.2 | D |
| 559 | 6-(5-(2-methoxypyridin-4-yl)-[1,2,4]triazolo[1,5-a]pyridin-2-ylamino)-3,3-dimethylindolin-2-one | 401.2 | D |
| 560 | 4-(5-(cyclohexylamino)-[1,2,4]triazolo[1,5-a]pyridin-2-ylamino)benzamide | 351.3 | B |
| 561 | 3,3-dimethyl-6-(5-((tetrahydrofuran-3-yl)methyl)-[1,2,4]triazolo[1,5-a]pyridin-2-ylamino)indolin-2-one (enantiomer 1) | 378.2 | D |

TABLE 1-continued

| Cmpd. No. | Cmpd. Name | MH+ (Obs.) | Activity Level |
|---|---|---|---|
| 562 | 5-(difluoro(tetrahydro-2H-pyran-4-yl)methyl)-N-(3-methyl-1H-indazol-6-yl)-[1,2,4]triazolo[1,5-a]pyridin-2-amine | 399.2 | D |
| 563 | 5-((1,4-dioxan-2-yl)difluoromethyl)-N-(3-methyl-1H-indazol-6-yl)-[1,2,4]triazolo[1,5-a]pyridin-2-amine | 401.4 | D |
| 564 | 3,3-dimethyl-6-(5-methyl-[1,2,4]triazolo[1,5-a]pyridin-2-ylamino)indolin-2-amine | 308.2 | D |
| 565 | $N^2$-(4-(1H-1,2,4-triazol-3-yl)phenyl)-$N^5$-(tetrahydro-2H-pyran-4-yl)-[1,2,4]triazolo[1,5-a]pyridine-2,5-diamine | 377.4 | A |
| 566 | 6-(5-(dimethylamino)-[1,2,4]triazolo[1,5-a]pyridin-2-ylamino)-3,3-dimethylindolin-2-one | 337.0 | D |

TABLE 1-continued

| Cmpd. No. | Cmpd. Name | MH+ (Obs.) | Activity Level |
|---|---|---|---|
| 567 | cis-4-(2-(4-(1H-1,2,4-triazol-3-yl)phenylamino)-[1,2,4]triazolo[1,5-a]pyrridin-5-ylamino)cyclohexanol | 391.0 | D |
| 568 | cis-4-(2-(3-methyl-[1,2,4]triazolo[4,3-a]pyridin-7-ylamino)-[1,2,4]triazolo[1,5-a]pyridin-5-ylamino)cyclohexanol | 379.7 | D |
| 569 | 1-methyl-5-(5-(tetrahydro-2H-pyran-4-ylamino)-[1,2,4-]triazolo[1,5-a]pyridin-2-ylamino)-1H-benzo[d]imidazol-2(3H)-one | 380.4 | D |
| 570 | cis-5-(5-(4-hydroxycyclohexylamino)-[1,2,4]triazolo[1,5-a]pyridin-2-ylamino)-1-methyl-1H-benzo[d]imidazol-2(3H)-one | 394.4 | D |
| 571 | 3,3-dimethyl-6-(5-morpholino-[1,2,4]triazolo[1,5-a]pyridin-2-ylamino)indolin-2-one | 379.0 | D |

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A compound of formula (I):

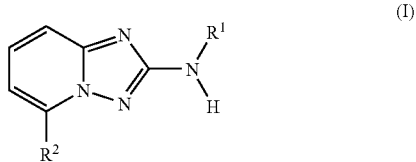

(I)

or pharmaceutically acceptable salt, tautomer, or stereoisomer thereof, wherein:

$R^1$ is a substituted or unsubstituted aryl, or a substituted or unsubstituted heterocyclyl;

$R^2$ is a substituted $C_{1-8}$ alkyl, an unsubstituted non-aromatic cycloalkyl, an unsubstituted non-aromatic heterocyclylalkyl, an unsubstituted aralkyl, —$NR^3R^4$, —$OR^3$, —C(=O)$R^5$, —C(=O)$NR^3R^4$, —NHC(=O)$R^3$, —$(CH_2)_{0-2}CR^6(OR^3)R^4$, or an unsubstituted heterocyclyl selected from azetidinyl, pyrrolidyl, morpholinyl, 1,2,3,6-tetrahydropyridyl, isoxazolyl, imidazolyl, indazolyl, benzimidazolyl, benzisoxazolyl, benzo[d]oxazolyl, isoindolin-1-onyl, isoquinolinyl, or quinolyl;

$R^3$ and $R^4$ are at each occurrence independently —H, a substituted or unsubstituted $C_{1-8}$ alkyl, a substituted or unsubstituted aryl, a substituted or unsubstituted heteroaryl, a substituted or unsubstituted cycloalkyl, a substituted or unsubstituted heterocyclyl, a substituted or unsubstituted aralkyl, or a substituted or unsubstituted heterocyclylalkyl;

$R^5$ is substituted or unsubstituted $C_{1-8}$ alkyl, a substituted or unsubstituted aryl, a substituted or unsubstituted heteroaryl, a substituted or unsubstituted cycloalkyl, a substituted or unsubstituted heterocyclyl, a substituted or unsubstituted aralkyl, or a substituted or unsubstituted heterocyclylalkyl; and $R^6$ is —H, or a substituted or unsubstituted $C_{1-8}$ alkyl, or together with $R^4$ and the atoms to which they are attached form a substituted or unsubstituted heterocyclyl;

provided the compound is not $N^5$-cyclopentyl-$N^2$-(4-(2-(pyrrolidin-1-yl)ethoxy)phenyl)-[1,2,4]triazolo[1,5-a]pyridine-2,5-diamine.

2. The compound of claim 1, wherein $R^1$ is a substituted or unsubstituted aryl.

3. The compound of claim 2, wherein $R^1$ is a substituted or unsubstituted phenyl.

4. The compound of claim 3, wherein $R^1$ is phenyl, substituted with one or more substituted or unsubstituted $C_{1-4}$ alkyl, substituted or unsubstituted heterocyclyl, halogen, hydroxyl, alkoxy, carboxy, —CN, —$(C_{0-4}$alkyl)$NR_2$, —O($C_{1-4}$alkyl)$NR_2$, —$NR_2$, or —C(=O)$NR_2$, wherein each R is independently H, a substituted or unsubstituted $C_{1-6}$ alkyl, or a substituted or unsubstituted heterocyclyl.

5. The compound of claim 3, wherein $R^1$ is phenyl, substituted with one or more —F, —Cl, —$CF_3$, —CN, hydroxyl, carboxy, methyl, —$(C_{0-4}$alkyl)$NH_2$, —$(C_{0-4}$alkyl)NH($C_{1-4}$alkyl), —O($C_{1-4}$alkyl), —O($C_{1-4}$alkyl)O($C_{1-4}$alkyl), —O($C_{1-4}$alkyl)$NH_2$, —N($C_{1-4}$alkyl)$_2$, —C(=O)$NH_2$, —C(=O)NH($C_{1-4}$alkyl), —C(=O)NH (substituted or unsubstituted piperidyl), or a substituted or unsubstituted heterocyclyl selected from morpholinyl, triazolyl, pyrrolidyl, imidazolyl or pyrrolidinonyl.

6. The compound of claim 1, wherein $R^1$ is a substituted or unsubstituted heterocyclyl.

7. The compound of claim 6, wherein $R^1$ is a substituted or unsubstituted heterocyclyl selected from isoindolin-1-onyl, pyridyl, pyrimidyl, indazolyl, indolinyl, isoindolinyl, indolin-2-onyl, quinolinyl, dihydroisoquinolin-1-onyl, benzotriazolyl, benzimidazolyl, 1H-pyrazolo[3,4-b]pyridyl, 1H-pyrazolo[4,3-b]pyridyl, 1H-benzo[d]imidazol-2(3H)-onyl, benzisoxazolyl, isoquinolinyl, dihydrobenzisothiazole-1,1-dionyl or pyrrolopyridyl.

8. The compound of claim 6, wherein $R^1$ is substituted with one or more substituted or unsubstituted $C_{1-4}$ alkyl, substituted or unsubstituted heterocyclyl, halogen, hydroxyl, hydroxyalkyl, alkoxy, —CN, —OR, —$NR_2$, —($C_{1-4}$ alkyl)$NR_2$, —C(=O)$NR_2$ or —C(O)R, wherein each R is independently —H, a substituted or unsubstituted $C_{1-6}$ alkyl, a substituted or unsubstituted heterocyclyl or a substituted or unsubstituted heterocyclylalkyl.

9. The compound of claim 6, wherein $R^1$ is

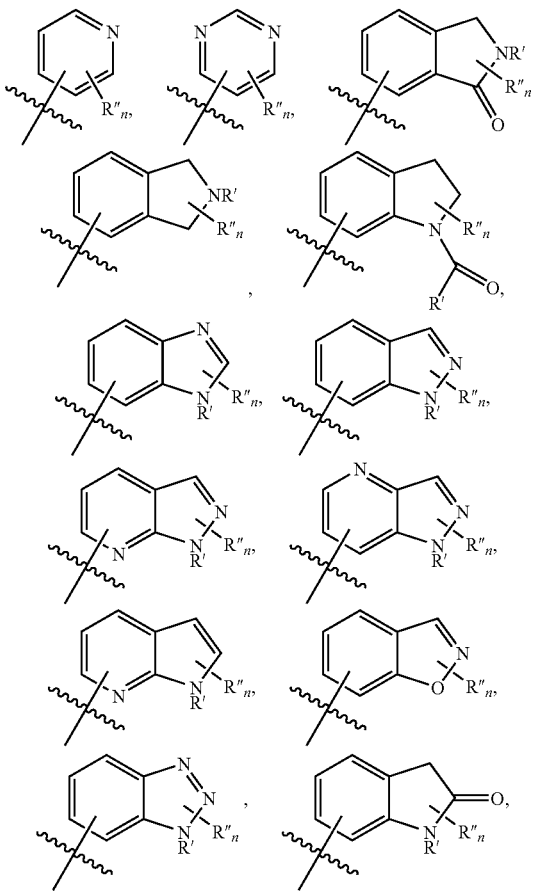

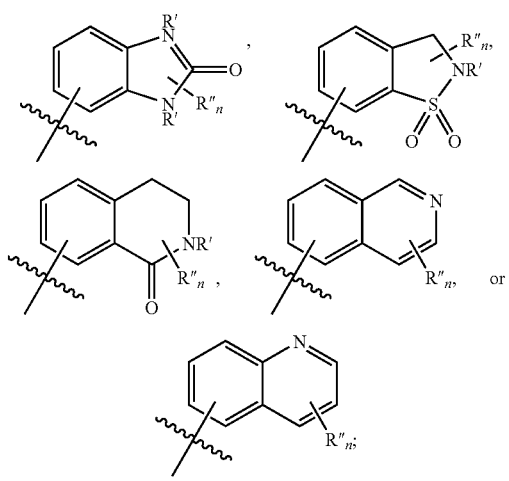

wherein R' is —H, or a substituted or unsubstituted $C_{1-6}$ alkyl; each R" is independently a substituted or unsubstituted $C_{1-4}$ alkyl, substituted or unsubstituted heterocyclyl, substituted or unsubstituted heterocyclylalkyl, hydroxyl, halogen, alkoxy, —CN, —OR, —NR$_2$, —($C_{1-4}$ alkyl)NR$_2$, —C(=O)NR$_2$, wherein each R is independently —H, a substituted or unsubstituted $C_{1-6}$ alkyl, a substituted or unsubstituted heterocyclyl or a substituted or unsubstituted heterocyclylalkyl; and n is 0-2.

10. The compound of claim 9, wherein $R^1$ is

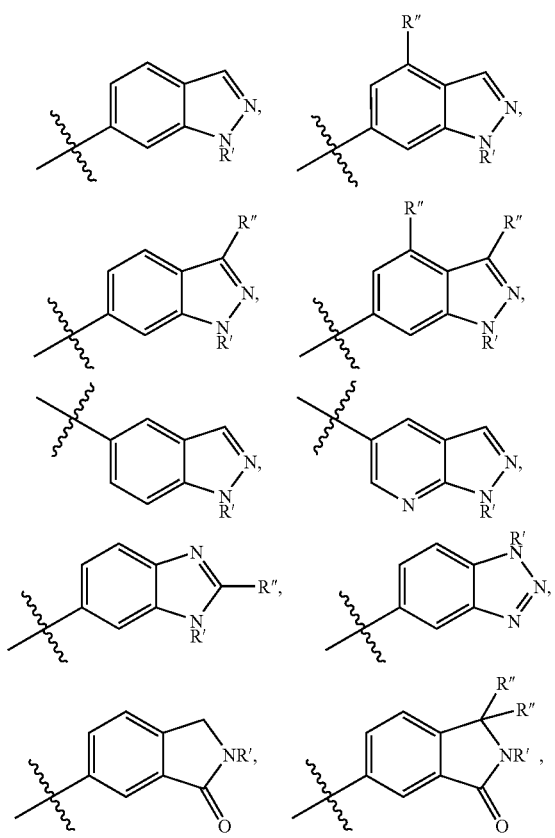

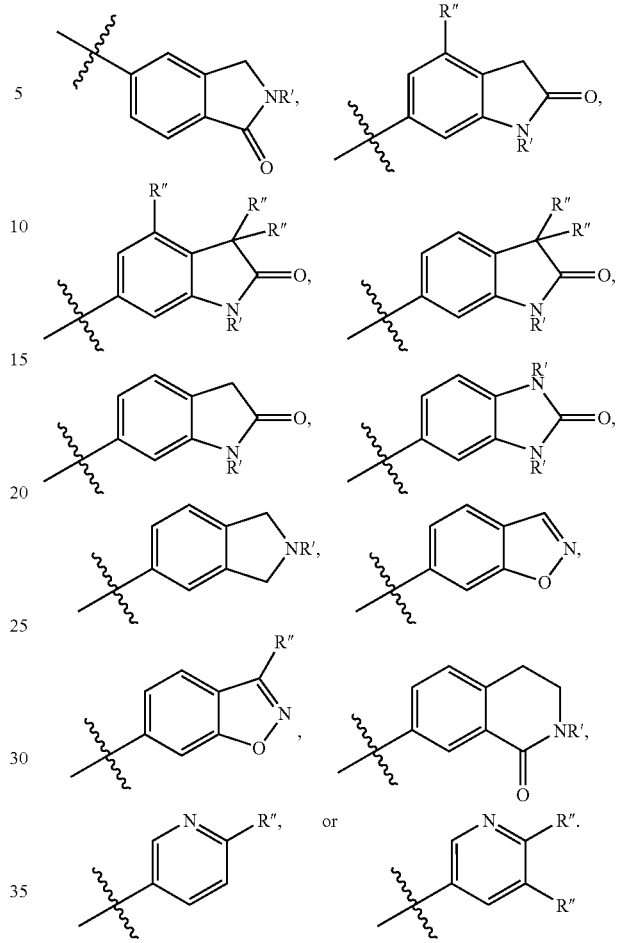

11. The compound of claim 9, wherein R' is —H, —CH$_3$, —CH$_2$CH$_3$, isopropyl, —(CH$_2$)$_2$OH, —(CH$_2$)$_2$NH$_2$, or —(CH$_2$)$_2$OCH$_3$.

12. The compound of claim 9, wherein R" is —F, —CH$_3$, —CH$_2$CH$_3$, isopropyl, —NH($C_{1-3}$ alkyl)NH$_2$, —NH(CH$_2$)$_2$OH, —CF$_3$, —OH, —OCH$_3$, —O(CH$_2$)$_2$OCH$_3$, —O(CH$_2$)$_2$OH, —O(CH$_2$)$_2$NH$_2$, —O(CH$_2$)$_2$pyrrolidyl, —CH$_2$OH, —(CH$_2$)$_2$OH, —CH$_2$OCH$_3$, —(CH$_2$)$_2$OCH$_3$, —CH$_2$NH$_2$, —CH$_2$NHCH$_3$, —CH$_2$N(CH$_3$)$_2$, —C(CH$_3$)$_2$OH, —CN, —NH$_2$, —NHCH$_3$, —N(CH$_3$)$_2$, —NH(CH$_2$)$_2$NH$_2$, —C(=O)NH$_2$, —C(=O)NHCH$_3$, —NH(CH$_2$)$_2$pyrrolidyl, —NH(substituted or unsubstituted piperidyl), substituted or unsubstituted piperidyl, —NH(substituted or unsubstituted tetrahydropyranyl), or substituted or unsubstituted morpholinyl.

13. The compound of claim 1, wherein $R^2$ is a substituted $C_{1-6}$ alkyl.

14. The compound of claim 13, wherein $R^2$ is methyl, ethyl, n-propyl, isopropyl, n-butyl, sec-butyl, isobutyl, or tert-butyl, substituted with one or more —OH, —C(O)NH$_2$, —NH$_2$, alkylamino, —NHCH$_2$C(=O)NH$_2$, cyclopentyl, cyclopentanol, cyclohexyl, cyclohexanol, or 1-methylcyclohexanol-4-yl.

15. The compound of claim 1, wherein $R^2$ is an unsubstituted heterocyclylalkyl.

16. The compound of claim 15, wherein $R^2$ is a heterocyclylalkyl selected from —CH$_2$-azetidinyl, —CH$_2$-piperidyl, —CH$_2$-pyridin-2(1H)-onyl, —CH$_2$-pyridyl, —CH$_2$-piperazin-2-onyl, —CH$_2$-piperazin-2,6-dionyl, —CH$_2$-piperazinyl, —CH$_2$-pyrrolidyl, —CH$_2$-1,4-dioxanyl, —CH$_2$-piperidin-2,6-dionyl, —CH$_2$-imidazolidinyl, —CH$_2$-imidazolidin-4-onyl, —CH$_2$-morpholinyl, —CH$_2$-tetrahydropyrimidin-2(1H)-onyl, —CH$_2$-1,4-diazepan-5-onyl, —CH$_2$-tetrahydro-2H-pyranyl or —CH$_2$-imidazolidin-2,4-dionyl.

17. The compound of claim 1, wherein R$^2$ is —NR$^3$R$^4$.

18. The compound of claim 17, wherein R$^2$ is —NH(C$_{1-6}$ alkyl), —N(C$_{1-6}$ alkyl)$_2$, —N(C$_{1-6}$ alkyl) (cycloalkyl), —NH(aryl), —NH(heteroaryl), —NH(cycloalkyl), —NH(cycloalkylalkyl), —NH(heterocyclyl), —N(C$_{1-6}$ alkyl)(heterocyclyl), or —NH(heterocyclylalkyl), wherein each alkyl, aryl, heteroaryl, cycloalkyl, cycloalkylalkyl, heterocyclyl and heterocyclylalkyl is independently substituted or unsubstituted.

19. The compound of claim 17, wherein R$^2$ is —NH(methyl), —N(methyl)$_2$, —N(methyl) (ethyl), —NH(ethyl), —NH(propyl), —NH(isopropyl), —NH(cyclopentyl), —NH(cyclohexyl), —N(cyclohexyl)(methyl), —NHCH$_2$(cyclopentyl), —NHCH$_2$(cyclohexyl), —NH(phenyl), —NH(pyridyl), —NH(piperidyl), —NH(tetrahydro-2H-pyranyl), —N(methyl)(tetrahydro-2H-pyranyl), —NH(azepanyl), —NH(tetrahydrofuranyl), —N(methyl)(tetrahydrofuranyl), —NH(pyrrolidyl), or —NHCH$_2$(tetrahydro-2H -pyranyl), wherein each methyl, ethyl, propyl, isopropyl, cyclopentyl, cyclohexyl, phenyl, pyridyl, piperidyl, pyrrolidyl, tetrahydro-2H-pyranyl, azepanyl, or tetrahydrofuranyl is independently substituted or unsubstituted.

20. The compound of claim 19, wherein the methyl, ethyl, propyl, isopropyl, cyclopentyl, cyclohexyl, phenyl, pyridyl, piperidyl, pyrrolidyl, tetrahydro-2H -pyranyl, azepanyl, or tetrahydrofuranyl, is substituted with one or more phenyl, C$_{1-4}$alkyl, hydroxyalkyl, —NR$_2$, —OR, or —C(=O)NR$_2$, wherein each R is independently —H, a substituted or unsubstituted C$_{1-6}$ alkyl, a substituted or unsubstituted heterocyclyl or a substituted or unsubstituted heterocyclylalkyl.

21. The compound of claim 1, wherein R$^2$ is —OR$^3$.

22. The compound of claim 21, wherein R$^3$ is cyclohexyl, methyl, ethyl, propyl, piperidyl, tetrahydro-2H-pyranyl, tetrahydrofuranyl, —CH$_2$(pyrrolidyl), or phenyl.

23. The compound of claim 1, wherein R$^2$ is —(CH$_2$)$_{0-2}$CR$^6$(OR$^3$)R$^4$.

24. The compound of claim 23, wherein R$^2$ is —CH(OR$^3$)R$^4$.

25. The compound of claim 24, wherein R$^3$ is H and R$^4$ is phenyl, piperidyl, pyridyl, pyrimidin-4(3H)-onyl, or tetrahydrofuranyl.

26. The compound of claim 23, wherein R$^3$ is —H, and R$^4$ and R$^6$, together with the atoms to which they are bound, form a piperidyl.

27. The compound of claim 1, wherein R$^2$ is an unsubstituted heterocyclyl selected from azetidinyl, pyrrolidyl, morpholinyl, 1,2,3,6-tetrahydropyridyl, isoxazolyl, imidazolyl, indazolyl, benzimidazolyl, benzisoxazolyl, benzo[d]oxazolyl, isoindolin-1-onyl, quinolinyl, or isoquinolinyl.

28. The compound of claim 1, wherein the compound at a concentration of 10 µM inhibits Syk by at least about 50%.

29. A compound, wherein the compound is
1-methyl-N$^3$-(tetrahydro-2H-pyran-4-yl)-N$^6$-(5-((tetrahydro-2H-pyran-4-yl)methyl)-[1,2,4]triazolo[1,5-a]pyridin-2-yl)-1H-indazole-3,6-diamine;
N$^3$-(tetrahydro-2H-pyran-4-yl)-N$^6$-(5-((tetrahydro-2H-pyran-4-yl)methyl)-[1,2,4]triazolo[1,5-a]pyridin-2-yl)-1H-indazole-3,6-diamino;
1-methyl-N$^3$-(piperidin-4-yl)-N$^6$-(5-((tetrahydro-2H-pyran-4-yl)methyl)-[1,2,4]triazolo[1,5-a]pyridin-2-yl)-1H-indazole-3,6-diamino;
cis-6-(5-(4-hydroxycyclohexylamino)-[1,2,4]triazolo[1,5-a]pyridin-2-ylamino)-1H-pyrrolo[3,2-b]pyridin-2(3H)-one;
cis-6-(5-(4-hydroxy-4-methylcyclohexylamino)-[1,2,4]triazolo[1,5-a]pyridin-2-ylamino)-1,3,3-trimethylindolin-2-one;
N-(3-(methoxymethyl)-1H-indazol-6-yl)-5-((tetrahydro-2H-pyran-4-yl)methyl)-[1,2,4]triazolo[1,5-a]pyridin-2-amine;
cis-4-(2-(5-methyl-6-morpholinopyridin-3-ylamino)-[1,2,4]triazolo[1,5-a]pyridin-5-ylamino)cyclohexanol;
N-(5-((tetrahydro-2H-pyran-4-yl)methyl)-[1,2,4]triazolo[1,5-a]pyridin-2-yl)-1H-pyrazolo[4,3-b]pyridin-6-amine;
cis-4-(2-(1H-pyrazolo[4,3-b]pyridin-6-ylamino)-[1,2,4]triazolo[1,5-a]pyridin-5-ylamino)cyclohexanol;
N$^2$-(3,4-dimethyl-1H-indazol-6-yl)-N$^5$-(tetrahydro-2H-pyran-4-yl)-[1,2,4]triazolo[1,5-a]pyridine-2,5-diamine;
cis-6-(5-(4-hydroxycyclohexylamino)-[1,2,4]triazolo[1,5-a]pyridin-2-ylamino)-3,3,4-trimethylindolin-2-one;
trans-6-(5-(4-hydroxy-4-methylcyclohexylamino)-[1,2,4]triazolo[1,5-a]pyridin-2-ylamino)-1,3,3-trimethylindolin-2-one;
N$^2$-(1H-pyrazolo[4,3-b]pyridin-6-yl)-N$^5$-(tetrahydro-2H-pyran-4-yl)-[1,2,4]triazolo[1,5-a]pyridine-2,5-diamine;
cis-4-(2-(imidazo[1,2-a]pyridin-7-ylamino)-[1,2,4]triazolo[1,5-a]pyridin-5-ylamino)cyclohexanol;
3,3-dimethyl-6-(5-((tetrahydro-2H-pyran-4-yl)methyl)-[1,2,4]triazolo[1,5-a]pyridin-2-ylamino)isoindolin-1-one;
6-(5-(4-hydroxypiperidin-1-yl)-[1,2,4]triazolo[1,5-a]pyridin-2-ylamino)-3,3-dimethylindolin-2-one;
(R)—N$^2$-(3-methyl-1H-indazol-5-yl)-N$^5$-(tetrahydrofuran-3-yl)-[1,2,4]triazolo[1,5-a]pyridine-2,5-diamine;
N-(3-methyl-1H-indazol-5-yl)-5-((tetrahydro-2H-pyran-4-yl)methyl)-[1,2,4]triazolo[1,5-a]pyridin-2-amine;
N$^2$-(3-methyl-1H-indazol-5-yl)-N$^5$-(tetrahydro-2H-pyran-4-yl)-[1,2,4]triazolo[1,5-a]pyridine-2,5-diamine;
1-methyl-6-(5-((tetrahydro-2H-pyran-4-yl)methyl)-[1,2,4]triazolo[1,5-a]pyridin-2-ylamino)indolin-2-one;
1-methyl-6-(5-(tetrahydro-2H-pyran-4-ylamino)-[1,2,4]triazolo[1,5-a]pyridin-2-ylamino)indolin-2-one;
cis-6-(5-(4-hydroxycyclohexylamino)-[1,2,4]triazolo[1,5-a]pyridin-2-ylamino)-3,3-dimethylisoindolin-1-one;
(S)-3,3-dimethyl-6-(5-(methyl(tetrahydrofuran-3-yl)amino)-[1,2,4]triazolo[1,5-a]pyridin-2-ylamino)indolin-2-one;
(R)-3,3-dimethyl-6-(5-(methyl(tetrahydrofuran-3-yl)amino)-[1,2,4]triazolo[1,5-a]pyridin-2-ylamino)indolin-2-one;
(R)-1,3,3-trimethyl-6-(5-(tetrahydrofuran-3-ylamino)-[1,2,4]triazolo[1,5-a]pyridin-2-ylamino)indolin-2-one;
4-((2-(4-methyl-1H-indazol-6-ylamino)-[1,2,4]triazolo[1,5-a]pyridin-5-yl)methyl)pyridine-2-ol;
3,3,4-trimethyl-6-(5-(tetrahydro-2H-pyran-4-ylamino)-[1,2,4]triazolo[1,5-a]pyridin-2-ylamino)indolin-2-one;
3,3,4-trimethyl-6-(5-((tetrahydro-2H-pyran-4-yl)methyl)-[1,2,4]triazolo[1,5-a]pyridin-2-ylamino)indolin-2-one;
trans-4-(2-(3-methyl-1H-indazol-5-ylamino)-[1,2,4]triazolo[1,5-a]pyridin-5-ylamino)cyclohexanol;
3,3-dimethyl-6-(5-(tetrahydro-2H-pyran-4-ylamino)-[1,2,4]triazolo[1,5-a]pyridin-2-ylamino)isoindolin-1-one;
N$^5$-(tetrahydro-2H-pyran-4-yl)-N$^2$-(3-(trifluoromethyl)-1H-indazol-6-yl)-[1,2,4]triazolo[1,5-a]pyridine-2,5-diamine;

4-((2-(2-(methoxymethyl)-1H-benzo[d]imidazol-6-ylamino)-[1,2,4]triazolo[1,5-a]pyridin-5-yl)methyl)pyridine-2-ol;
(R)-3,3-dimethyl-6-(5-(piperidin-3-ylamino)-[1,2,4]triazolo[1,5-a]pyridin-2-ylamino)indolin-2-one;
N-(2-(methoxymethyl)-1H-benzo[d]imidazol-6-yl)-5-((tetrahydro-2H-pyran-4-yl)methyl)-[1,2,4]triazolo[1,5-a]pyridin-2-amine;
(S)-3,3-dimethyl-6-(5-(tetrahydrofuran-3-yloxy)-[1,2,4]triazolo[1,5-a]pyridin-2-ylamino)indolin-2-one;
(R)-3,3-dimethyl-6-(5-(tetrahydrofuran-3-yloxy)-[1,2,4]triazolo[1,5-a]pyridin-2-ylamino)indolin-2-one;
cis-5-(5-(4-hydroxycyclohexylamino)-[1,2,4]triazolo[1,5-a]pyridin-2-ylamino)-2-methylisoindolin-1-one;
1,3,3-trimethyl-6-(5-((3-oxopiperazin-1-yl)methyl)-[1,2,4]triazolo[1,5-a]pyridin-2-ylamino)indolin-2-one;
trans-6-(5-(4-hydroxycyclohexylamino)-[1,2,4]triazolo[1,5-a]pyridin-2-ylamino)-3,3-dimethylisoindolin-1-one;
3,3-dimethyl-6-(5-(piperidin-4-ylmethyl)-[1,2,4]triazolo[1,5-a]pyridin-2-ylamino)indolin-2-one;
cis-4-(2-(1-methyl-1H-pyrazolo[3,4-b]pyridin-5-ylamino)-[1,2,4]triazolo[1,5-a]pyridin-5-ylamino)cyclohexanol;
cis-6-(5-((4-hydroxy-4-methylcyclohexyl)methyl)-[1,2,4]triazolo[1,5-a]pyridin-2-ylamino)-3,3-dimethylindolin-2-one;
trans-6-(5-((4-hydroxy-4-methylcyclohexyl)methyl)-[1,2,4]triazolo[1,5-a]pyridin-2-ylamino)-3,3-dimethylindolin-2-one;
$N^2$-(2-(methoxymethyl)-1H-benzo[d]imidazol-6-yl)-$N^5$-(tetrahydro-2H-pyran-4-yl)-[1,2,4]triazolo[1,5-a]pyridine-2,5-diamine;
1,3,3-trimethyl-6-(5-((tetrahydro-2H-pyran-4-yl)methyl)-[1,2,4]triazolo[1,5-a]pyridin-2-ylamino)indolin-2-one;
2-methyl-5-(5-(tetrahydro-2H-pyran-4-ylamino)-[1,2,4]triazolo[1,5-a]pyridin-2-ylamino)isoindolin-1-one;
2-methyl-5-(5-((tetrahydro-2H-pyran-4-yl)methyl)-[1,2,4]triazolo[1,5-a]pyridin-2-ylamino)isoindolin-1-one;
trans-6-(5-(4-hydroxycyclohexylamino)-[1,2,4]triazolo[1,5-a]pyridin-2-ylamino)-1,3,3-trimethylindolin-2-one;
N-(1,4-dimethyl-1H-indazol-6-yl)-5-((tetrahydro-2H-pyran-4-yl)methyl)-[1,2,4]triazolo[1,5-a]pyridin-2-amine;
$N^2$-(1,4-dimethyl-1H-indazol-6-yl)-$N^5$-(tetrahydro-2H-pyran-4-yl)-[1,2,4]triazolo[1,5-a]pyridine-2,5-diamine;
cis-4-(2-(4-fluoro-1,3-dimethyl-1H-indazol-6-ylamino)-[1,2,4]triazolo[1,5-a]pyridin-5-ylamino)cyclohexanol;
(R)-3,3-dimethyl-6-(5-(tetrahydrofuran-3-ylamino)-[1,2,4]triazolo[1,5-a]pyridin-2-ylamino)indolin-2-one;
1,3,3-trimethyl-6-(5-(tetrahydro-2H-pyran-4-ylamino)-[1,2,4]triazolo[1,5-a]pyridin-2-ylamino)indolin-2-one;
cis-6-(5-(4-hydroxycyclohexylamino)-[1,2,4]triazolo[1,5-a]pyridin-2-ylamino)-1,3,3-trimethylindolin-2-one;
6-(5-((2-hydroxyethyl)(methyl)amino)-[1,2,4]triazolo[1,5-a]pyridin-2-ylamino)-3,3-dimethylindolin-2-one;
(S)-3,3-dimethyl-6-(5-(piperidin-3-ylamino)-[1,2,4]triazolo[1,5-a]pyridin-2-ylamino)indolin-2-one;
4-((2-(3-(trifluoromethyl)-1H-indazol-6-ylamino)-[1,2,4]triazolo[1,5-a]pyridin-5-yl)methyl)piperazin-2-one;
3,3-dimethyl-6-(5-((2-oxo-1,2-dihydropyridin-4-yl)methyl)-[1,2,4]triazolo[1,5-a]pyridin-2-ylamino)indolin-2-one;
5-(5-((2-hydroxypyridin-4-yl)methyl)-[1,2,4]triazolo[1,5-a]pyridin-2-ylamino)isoindolin-1-one;
3,3-dimethyl-6-(5-(methyl(tetrahydro-2H-pyran-4-yl)amino)-[1,2,4]triazolo[1,5-a]pyridin-2-ylamino)indolin-2-one;
3,3-dimethyl-6-(5-(1-(tetrahydro-2H-pyran-4-yl)ethyl)-[1,2,4]triazolo[1,5-a]pyridin-2-ylamino)indolin-2-one;
N-(1-methyl-1H-indazol-6-yl)-5-((tetrahydro-2H-pyran-4-yl)methyl)-[1,2,4]triazolo[1,5-a]pyridin-2-amine;
$N^2$-(1-methyl-1H-indazol-6-yl)-$N^5$-(tetrahydro-2H-pyran-4-yl)-[1,2,4]triazolo[1,5-a]pyridine-2,5-diamine;
trans-6-(5-(4-hydroxy-4-methylcyclohexylamino)-[1,2,4]triazolo[1,5-a]pyridin-2-ylamino)-3,3-dimethylindolin-2-one;
cis-6-(5-(4-hydroxy-4-methylcyclohexylamino)-[1,2,4]triazolo[1,5-a]pyridin-2-ylamino)-3,3-dimethylindolin-2-one;
cis-4-(2-(4-fluoro-3-methyl-1H-indazol-6-ylamino)-[1,2,4]triazolo[1,5-a]pyridin-5-ylamino)cyclohexanol;
(±)-cis-4-(2-(3-methyl-1H-indazol-6-ylamino)-[1,2,4]triazolo[1,5-a]pyridin-5-yloxy)tetrahydrofuran-3-ol;
(±)-trans-4-(2-(3-methyl-1H-indazol-6-ylamino)-[1,2,4]triazolo[1,5-a]pyridin-5-ylamino)tetrahydrofuran-3-ol;
(R)—$N^2$-(3-methyl-1H-indazol-6-yl)-$N^5$-(tetrahydrofuran-3-yl)-[1,2,4]triazolo[1,5-a]pyridine-2,5-diamine;
3,3-dimethyl-6-(5-(tetrahydro-2H-pyran-4-yloxy)-[1,2,4]triazolo[1,5-a]pyridin-2-ylamino)indolin-2-one;
3-methyl-1-((2-(3-methyl-1H-indazol-6-ylamino)-[1,2,4]triazolo[1,5-a]pyridin-5-yl)methyl)azetidin-3-ol;
6-(5-(3-hydroxyazetidin-1-yl)-[1,2,4]triazolo[1,5-a]pyridin-2-ylamino)-3,3-dimethylindolin-2-one;
6-(5-(3-hydroxy-3-methylazetidin-1-yl)-[1,2,4]triazolo[1,5-a]pyridin-2-ylamino)-3,3-dimethylindolin-2-one;
3,3-dimethyl-6-(5-((3-oxopiperazin-1-yl)methyl)-[1,2,4]triazolo[1,5-a]pyridin-2-ylamino)indolin-2-one;
6-(5-(hydroxy(tetrahydro-2H-pyran-4-yl)methyl)-[1,2,4]triazolo[1,5-a]pyridin-2-ylamino)-3,3-dimethylindolin-2-one;
cis-5-(5-(4-hydroxycyclohexylamino)-[1,2,4]triazolo[1,5-a]pyridin-2-ylamino)-2-(2-methoxyethyl)isoindolin-1-one;
trans-6-(5-(4-hydroxycyclohexylamino)-[1,2,4]triazolo[1,5-a]pyridin-2-ylamino)-3,3-dimethylindolin-2-one;
3,3-dimethyl-6-(5-((tetrahydro-2H-pyran-4-yl)methyl)-[1,2,4]triazolo[1,5-a]pyridin-2-ylamino)indolin-2-one;
3,3-dimethyl-6-(5-(tetrahydro-2H-pyran-4-ylamino)-[1,2,4]triazolo[1,5-a]pyridin-2-ylamino)indolin-2-one;
(1S,3R)-3-((2-(3-methyl-1H-indazol-6-ylamino)-[1,2,4]triazolo[1,5-a]pyridin-5-ylamino)methyl)cyclopentanol;
(1R,3R)-3-((2-(3-methyl-1H-indazol-6-ylamino)-[1,2,4]triazolo[1,5-a]pyridin-5-ylamino)methyl)cyclopentanol;
(1R,3S)-3-((2-(3-methyl-1H-indazol-6-ylamino)-[1,2,4]triazolo[1,5-a]pyridin-5-ylamino)methyl)cyclopentanol;
(1S,3S)-3-((2-(3-methyl-1H-indazol-6-ylamino)-[1,2,4]triazolo[1,5-a]pyridin-5-ylamino)methyl)cyclopentanol;
(S)—$N^2$-(3-methyl-1H-indazol-6-yl)-$N^5$-(tetrahydrofuran-3-yl)-[1,2,4]triazolo[1,5-a]pyridine-2,5-diamine;
4-((2-(3-methyl-1H-indazol-6-ylamino)-[1,2,4]triazolo[1,5-a]pyridin-5-yl)methyl)pyridin-2(1H)-one;
5-((3,3-difluoropiperidin-1-yl)methyl)-N-(3-methyl-1H-indazol-6-yl)-[1,2,4]triazolo[1,5-a]pyridin-2-amine;
cis-6-(5-(4-hydroxycyclohexylamino)-[1,2,4]triazolo[1,5-a]pyridin-2-ylamino)-1-(2-hydroxyethyl)indolin-2-one;

2-((2-(3-methyl-1H-indazol-6-ylamino)-[1,2,4]triazolo[1,5-a]pyridin-5-yl)methylamino)acetamide;
cis-1-(methoxymethyl)-4-((2-(4-(trifluoromethyl)phenylamino)-[1,2,4]triazolo[1,5-a]pyridin-5-yl)methyl)cyclohexanol;
4-((2-(1-isopropyl-1H-indazol-6-ylamino)-[1,2,4]triazolo[1,5-a]pyridin-5-yl)methyl)piperazin-2-one;
$N^5$-methyl-$N^2$-(3-methyl-1H-indazol-6-yl)-$N^5$-(tetrahydro-2H-pyran-4-yl)-[1,2,4]triazolo[1,5-a]pyridine-2,5-diamine;
2-(methyl(2-(3-methyl-1H-indazol-6-ylamino)-[1,2,4]triazolo[1,5-a]pyridin-5-yl)amino)ethanol;
cis-4-(2-(1-(2-hydroxyethyl)-3-methyl-1H-indazol-6-ylamino)-[1,2,4]triazolo[1,5-a]pyridin-5-ylamino)cyclohexanol;
cis-6-(5-(4-hydroxycyclohexylamino)-[1,2,4]triazolo[1,5-a]pyridin-2-ylamino)-1-methylindolin-2-one;
6-(hydroxy(2-(4-(trifluoromethyl)phenylamino)-[1,2,4]triazolo[1,5-a]pyridin-5-yl)methyl)pyrimidin-4(3H)-one;
cis-4-(2-(1-(2-methoxyethyl)-3-methyl-1H-indazol-6-ylamino)-[1,2,4]triazolo[1,5-a]pyridin-5-ylamino)cyclohexanol;
cis-4-(2-(2-(hydroxymethyl)-1H-benzo[d]imidazol-6-ylamino)-[1,2,4]triazolo[1,5-a]pyridin-5-ylamino)cyclohexanol;
cis-4-(2-(2-(methoxymethyl)-1H-benzo[d]imidazol-6-ylamino)-[1,2,4]triazolo[1,5-a]pyridin-5-ylamino)cyclohexanol;
cis-4-(2-(1-ethyl-3-methyl-1H-indazol-6-ylamino)-[1,2,4]triazolo[1,5-a]pyridin-5-ylamino)cyclohexanol;
cis-5-(5-(4-hydroxycyclohexylamino)-[1,2,4]triazolo[1,5-a]pyridin-2-ylamino)-2-(2-hydroxyethyl)isoindolin-1-one;
N-(3-methyl-1H-indazol-6-yl)-5-((tetrahydro-2H-pyran-4-yl)methyl)-[1,2,4]triazolo[1,5-a]pyridin-2-amine;
(2-(3-methyl-1H-indazol-6-ylamino)-[1,2,4]triazolo[1,5-a]pyridin-5-yl)(tetrahydro-2H-pyran-4-yl)methanol;
trans-4-(2-(3-methyl-1H-indazol-6-ylamino)-[1,2,4]triazolo[1,5-a]pyridin-5-ylamino)cyclohexanol;
cis-6-(5-(4-hydroxycyclohexylamino)-[1,2,4]triazolo[1,5-a]pyridin-2-ylamino)-3,3-dimethylindolin-2-one;
cis-6-(5-(4-hydroxycyclohexylamino)-[1,2,4]triazolo[1,5-a]pyridin-2-ylamino)-3,4-dihydroisoquinolin-1(2H)-one;
cis-4-(2-(4-methyl-1H-indazol-6-ylamino)-[1,2,4]triazolo[1,5-a]pyridin-5-ylamino)cyclohexanol;
(R)-3-((2-(4-(trifluoromethyl)phenylamino)-[1,2,4]triazolo[1,5-a]pyridin-5-yl)methylamino)pyrrolidin-2-one;
cis-6-(5-(4-hydroxycyclohexylamino)-[1,2,4]triazolo[1,5-a]pyridin-2-ylamino)-2-(2-hydroxyethyl)isoindolin-1-one;
(±)-3-((2-(4-(trifluoromethyl)phenylamino)-[1,2,4]triazolo[1,5-a]pyridin-5-yl)methylamino)pyrrolidin-2-one;
4-((2-(3-amino-1H-indazol-6-ylamino)-[1,2,4]triazolo[1,5-a]pyridin-5-yl)methyl)cyclohexanol;
$N^2$-(3-methyl-1H-indazol-6-yl)-$N^5$-(tetrahydro-2H-pyran-4-yl)-[1,2,4]triazolo[1,5-a]pyridine-2,5-diamine;
cis-4-(2-(4-fluoro-3-(2-methoxyethoxy)phenylamino)-[1,2,4]triazolo[1,5-a]pyridin-5-ylamino)cyclohexanol;
4-(1-(2-(4-(trifluoromethyl)phenylamino)-[1,2,4]triazolo[1,5-a]pyridin-5-yl)ethyl)pyridin-2(1H)-one;
(1S,2S)-2-(2-(3-methyl-1H-indazol-6-ylamino)-[1,2,4]triazolo[1,5-a]pyridin-5-ylamino)cyclopentanol;
N-methyl-2-(2-(4-(trifluoromethyl)phenylamino)-[1,2,4]triazolo[1,5-a]pyridin-5-yl)methylamino)acetamide;
4-(5-((3-hydroxycyclopentyl)methyl)-[1,2,4]triazolo[1,5-a]pyridin-2-ylamino)-N-methylbenzamide (diastereomer 2);
1-(2-(3-methyl-1H-indazol-6-ylamino)-[1,2,4]triazolo[1,5-a]pyridin-5-yl)azetidin-3-ol;
cis-4-(2-(3-amino-1H-indazol-6-ylamino)-[1,2,4]triazolo[1,5-a]pyridin-5-ylamino)cyclohexanol;
cis-4-(2-(2,3-dimethyl-2H-indazol-6-ylamino)-[1,2,4]triazolo[1,5-a]pyridin-5-ylamino)cyclohexanol;
cis-4-(2-(1,3-dimethyl-1H-indazol-6-ylamino)-[1,2,4]triazolo[1,5-a]pyridin-5-ylamino)cyclohexanol;
4-((2-(4-fluoro-3-methylphenylamino)-[1,2,4]triazolo[1,5-a]pyridin-5-yl)methyl)pyridin-2-ol;
$N^2$-(3-methyl-1H-indazol-6-yl)-$N^5$-((tetrahydro-2H-pyran-4-yl)methyl)-[1,2,4]triazolo[1,5-a]pyridine-2,5-diamine;
4-((2-(6-(4-hydroxypiperidin-1-yl)pyridin-3-ylamino)-[1,2,4]triazolo[1,5-a]pyridin-5-yl)methyl)piperazin-2-one;
(S)-2-((2-(4-(trifluoromethyl)phenylamino)-[1,2,4]triazolo[1,5-a]pyridin-5-yl)methylamino)propanamide;
cis-3-(2-(4-(trifluoromethyl)phenylamino)-[1,2,4]triazolo[1,5-a]pyridin-5-ylamino)cyclohexanol (enantiomer 1);
cis-3-(2-(4-(trifluoromethyl)phenylamino)-[1,2,4]triazolo[1,5-a]pyridin-5-ylamino)cyclohexanol (enantiomer 2);
trans-3-(2-(4-(trifluoromethyl)phenylamino)-[1,2,4]triazolo[1,5-a]pyridin-5-ylamino)cyclohexanol (enantiomer 1);
trans-3-(2-(4-(trifluoromethyl)phenylamino)-[1,2,4]triazolo[1,5-a]pyridin-5-ylamino)cyclohexanol (enantiomer 2);
cis-1-(hydroxymethyl)-4-(2-(4-(trifluoromethyl)phenylamino)-[1,2,4]triazolo[1,5-a]pyridin-5-ylamino)cyclohexanol;
4-((2-(4-fluoro-3-methylphenylamino)-[1,2,4]triazolo[1,5-a]pyridin-5-yl)methyl)piperazin-2-one;
4-((2-(1H-pyrrolo[2,3-b]pyridin-5-ylamino)-[1,2,4]triazolo[1,5-a]pyridin-5-yl)methyl)piperazin-2-one;
(±)-5-isopropyl-4-(2-(4-(trifluoromethyl)phenylamino)-[1,2,4]triazolo[1,5-a]pyridin-5-yl)methyl)piperazin-2-one;
cis-4-(2-(3-(methoxymethyl)-1H-indazol-6-ylamino)-[1,2,4]triazolo[1,5-a]pyridin-5-ylamino)cyclohexanol;
4-(5-((3-hydroxycyclopentyl)methyl)-[1,2,4]triazolo[1,5-a]pyridin-2-ylamino)-N-methylbenzamide (diastereomer 1);
(±)-2-((2-(4-(trifluoromethyl)phenylamino)-[1,2,4]triazolo[1,5-a]pyridin-5-yl)methylamino)propanamide;
1-(3-methyl-1H-indazol-6-yl)-4((2-(3-methyl-1H-indazol-6-ylamino)-[1,2,4]triazolo[1,5-a]pyridin-5-yl)methyl)piperazin-2-one;
4-((2-(3-methyl-1H-indazol-6-ylamino)-[1,2,4]triazolo[1,5-a]pyridin-5-yl)methyl)piperazin-2-one;
cis-4-(2-(1-methyl-1H-indazol-5-ylamino)-[1,2,4]triazolo[1,5-a]pyridin-5-ylamino)cyclohexanol;
cis-4-(2-(1H-benzo[d][1,2,3]triazol-5-ylamino)-[1,2,4]triazolo[1,5-a]pyridin-5-ylamino)cyclohexanol;
cis-6-(5-(4-hydroxycyclohexylamino)-[1,2,4]triazolo[1,5-a]pyridin-2-ylamino)indolin-2-one;
cis-4-((2-(3-methyl-1H-indazol-6-ylamino)-[1,2,4]triazolo[1,5-a]pyridin-5-yl)methyl)cyclohexanol;
trans-4-((2-(3-methyl-1H-indazol-6-ylamino)-[1,2,4]triazolo[1,5-a]pyridin-5-yl)methyl)cyclohexanol;
4-(5-(1H-imidazol-1-yl)-[1,2,4]triazolo[1,5-a]pyridin-2-ylamino)-N-methylbenzamide;

4-(5-(4-hydroxypiperidin-1-yl)-[1,2,4]triazolo[1,5-a]pyridin-2-ylamino)-N-methylbenzamide;
cis-4-(2-(1-isopropyl-1H-indazol-6-ylamino)-[1,2,4]triazolo[1,5-a]pyridin-5-ylamino)cyclohexanol;
N-methyl-4-(5-(2-methyl-1H-benzo[d]imidazol-6-yl)-[1,2,4]triazolo[1,5-a]pyridin-2-ylamino)benzamide;
cis-4-(2-(3-ethyl-1H-indazol-6-ylamino)-[1,2,4]triazolo[1,5-a]pyridin-5-ylamino)cyclohexanol;
(1R,2R)-2-(4-(2-(4-(trifluoromethyl)phenylamino)-[1,2,4]triazolo[1,5-a]pyridin-5-yl)pyridin-2-ylamino)cyclopentanol;
N-methyl-4-(5-(piperidin-1-yl)-[1,2,4]triazolo[1,5-a]pyridin-2-ylamino)benzamide;
(±)-trans-3-(2-(4-(trifluoromethyl)phenylamino)-[1,2,4]triazolo[1,5-a]pyridin-5-ylamino)cyclohexanol;
(S)-4-(5-(3-hydroxypyrrolidin-1-yl)-[1,2,4]triazolo[1,5-a]pyridin-2-ylamino)-N-methylbenzamide;
(R)-4-(5-(3-hydroxypyrrolidin-1-yl)-[1,2,4]triazolo[1,5-a]pyridin-2-ylamino)-N-methylbenzamide;
N-methyl-4-(5-(pyrrolidin-1-yl)-[1,2,4]triazolo[1,5-a]pyridin-2-ylamino)benzamide;
1-((2-(4-(trifluoromethyl)phenylamino)-[1,2,4]triazolo[1,5-a]pyridin-5-yl)methyl)imidazolidine-2,4-dione;
cis-5-(5-(4-hydroxycyclohexylamino)-[1,2,4]triazolo[1,5-a]pyridin-2-ylamino)isoindolin-1-one;
N-methyl-4-(5-(2-(piperidin-4-yl)ethyl)-[1,2,4]triazolo[1,5-a]pyridin-2-ylamino)benzamide;
cis-4-(5-(4-hydroxycyclohexylamino)-[1,2,4]triazolo[1,5-a]pyridin-2-ylamino)picolinamide;
cis-4-(5-(4-hydroxycyclohexylamino)-[1,2,4]triazolo[1,5-a]pyridin-2-ylamino)picolinonitrile;
1-((2-(4-(trifluoromethyl)phenylamino)-[1,2,4]triazolo[1,5-a]pyridin-5-yl)methyl)piperidine-3-carboxamide;
5-methyl-4-((2-(4-(trifluoromethyl)phenylamino)-[1,2,4]triazolo[1,5-a]pyridin-5-yl)methyl)piperazin-2-one;
(1-(2-(4-(trifluoromethyl)phenylamino)-[1,2,4]triazolo[1,5-a]pyridin-5-yl)azetidin-3-yl)methanol;
cis-6-(5-(4-hydroxycyclohexylamino)-[1,2,4]triazolo[1,5-a]pyridin-2-ylamino)isoindolin-1-one;
cis-4-(2-(2,6-dimethylpyridin-4-ylamino)-[1,2,4]triazolo[1,5-a]pyridin-5-ylamino)cyclohexanol;
4-(5-((4-aminocyclohexyl)methyl)-[1,2,4]triazolo[1,5-a]pyridin-2-ylamino)-N-methylbenzamide;
4-(1-(2-(4-(trifluoromethyl)phenylamino)-[1,2,4]triazolo[1,5-a]pyridin-5-yl)ethyl)piperazin-2-one;
4-((2-(4-(trifluoromethyl)phenylamino)-[1,2,4]triazolo[1,5-a]pyridin-5-yl)methyl)piperazine-2,6-dione;
cis-N$^5$-(4-methoxycyclohexyl)-N$^5$-methyl-N$^2$-(4-(trifluoromethyl)phenyl)-[1,2,4]triazolo[1,5-a]pyridine-2,5-diamine;
cis-4-(methyl(2-(4-(trifluoromethyl)phenylamino)-[1,2,4]triazolo[1,5-a]pyridin-5-yl)amino)cyclohexanol;
N-methyl-4-(5-(pyrrolidin-3-ylmethyl)-[1,2,4]triazolo[1,5-a]pyridin-2-ylamino)benzamide;
5-(5-(2-(hydroxymethyl)-1H-benzo[d]imidazol-6-yl)-[1,2,4]triazolo[1,5-a]pyridin-2-ylamino)pyridin-2-ol;
1-((2-(4-(trifluoromethyl)phenylamino)-[1,2,4]triazolo[1,5-a]pyridin-5-yl)methyl)-1,4-diazepan-5-one;
(1S,2R)-2-(2-(4-(trifluoromethyl)phenylamino)-[1,2,4]triazolo[1,5-a]pyridin-5-ylamino)cyclohexanol;
(S)-(1-((2-(4-(trifluoromethyl)phenylamino)-[1,2,4]triazolo[1,5-a]pyridin-5-yl)methyl)pyrrolidin-2-yl)methanol;
(R)-(1-((2-(4-(trifluoromethyl)phenylamino)-[1,2,4]triazolo[1,5-a]pyridin-5-yl)methyl)pyrrolidin-2-yl)methanol;
(1-((2-(4-(trifluoromethyl)phenylamino)-[1,2,4]triazolo[1,5-a]pyridin-5-yl)methyl)piperidin-3-yl)methanol;
(1-((2-(4-(trifluoromethyl)phenylamino)-[1,2,4]triazolo[1,5-a]pyridin-5-yl)methyl)piperidin-4-yl)methanol;
(S)-3-methyl-4-((2-(4-(trifluoromethyl)phenylamino)-[1,2,4]triazolo[1,5-a]pyridin-5-yl)methyl)piperazin-2-one;
N-methyl-4-(5-(piperidin-4-ylmethyl)-[1,2,4]triazolo[1,5-a]pyridin-2-ylamino)benzamide;
cis-4-(2-(2-(2-hydroxyethoxy)pyridin-4-ylamino)-[1,2,4]triazolo[1,5-a]pyridin-5-ylamino)cyclohexanol;
cis-4-(2-(2-(2-(pyrrolidin-1-yl)ethylamino)pyridin-4-ylamino)-[1,2,4]triazolo[1,5-a]pyridin-5-ylamino)cyclohexanol;
cis-4-(2-(4-fluoro-3,5-dimethylphenylamino)-[1,2,4]triazolo[1,5-a]pyridin-5-ylamino)cyclohexanol;
(6-(2-(6-methoxypyridin-3-ylamino)-[1,2,4]triazolo[1,5-a]pyridin-5-yl)-1H-benzo[d]imidazol-2-yl)methanol;
3-methyl-4-((2-(4-(trifluoromethyl)phenylamino)-[1,2,4]triazolo[1,5-a]pyridin-5-yl)methyl)piperazin-2-one;
6-methyl-4-((2-(4-(trifluoromethyl)phenylamino)-[1,2,4]triazolo[1,5-a]pyridin-5-yl)methyl)piperazin-2-one;
cis-4-(5-(4-aminocyclohexyloxy)-[1,2,4]triazolo[1,5-a]pyridin-2-ylamino)-N-methylbenzamide;
N-methyl-4-(5-(piperidin-4-yloxy)-[1,2,4]triazolo[1,5-a]pyridin-2-ylamino)benzamide;
(6-(2-(6-methylpyridin-3-ylamino)-[1,2,4]triazolo[1,5-a]pyridin-5-yl)-1H-benzo[d]imidazol-2-yl)methanol;
1-(2-(4-(trifluoromethyl)phenylamino)-[1,2,4]triazolo[1,5-a]pyridin-5-yl)methyl)tetrahydropyrimidin-2(1H)-one;
1-(2-(4-(trifluoromethyl)phenylamino)-[1,2,4]triazolo[1,5-a]pyridin-5-yl)azetidin-3-ol;
(R)-(1-(2-(4-(trifluoromethyl)phenylamino)-[1,2,4]triazolo[1,5-a]pyridin-5-yl)pyrrolidin-2-yl)methanol;
(S)-(1-(2-(4-(trifluoromethyl)phenylamino)-[1,2,4]triazolo[1,5-a]pyridin-5-yl)pyrrolidin-2-yl)methanol;
2-((2-(4-(trifluoromethyl)phenylamino)-[1,2,4]triazolo[1,5-a]pyridin-5-yl)methylamino)acetamide;
trans-4-(5-(4-aminocyclohexyloxy)-[1,2,4]triazolo[1,5-a]pyridin-2-ylamino)-N-methylbenzamide;
4-(5-(3-hydroxybenzyl)-[1,2,4]triazolo[1,5-a]pyridin-2-ylamino)-N-methylbenzamide;
cis-4-(2-(2-(2-(pyrrolidin-1-yl)ethoxy)pyridin-4-ylamino)-[1,2,4]triazolo[1,5-a]pyridin-5-ylamino)cyclohexanol;
cis-1-(5-(5-(4-hydroxycyclohexylamino)-[1,2,4]triazolo[1,5-a]pyridin-2-ylamino)pyridin-2-yl)piperidin-4-ol;
cis-4-(2-(6-(methylamino)pyridin-3-ylamino)-[1,2,4]triazolo[1,5-a]pyridin-5-ylamino)cyclohexanol;
5-(2-aminoethoxy)-N-(4-(trifluoromethyl)phenyl)-[1,2,4]triazolo[1,5-a]pyridin-2-amine;
cis-4-(2-(1H-pyrrolo[2,3-b]pyridin-5-ylamino)-[1,2,4]triazolo[1,5-a]pyridin-5-ylamino)cyclohexanol;
(6-(2-(6-(dimethylamino)pyridin-3-ylamino)-[1,2,4]triazolo[1,5-a]pyridin-5-yl)-1H-benzo[d]imidazol-2-yl)methanol;
(R)-1-((2-(4-(trifluoromethyl)phenylamino)-[1,2,4]triazolo[1,5-a]pyridin-5-yl)methyl)piperidin-3-ol;
(S)-1-((2-(4-(trifluoromethyl)phenylamino)-[1,2,4]triazolo[1,5-a]pyridin-5-yl)methyl)piperidin-3-ol;
1-((2-(4-(trifluoromethyl)phenylamino)-[1,2,4]triazolo[1,5-a]pyridin-5-yl)methyl)imidazolidin-4-one;
(R)-5-(pyrrolidin-2-ylmethoxy)-N-(4-(trifluoromethyl)phenyl)-[1,2,4]triazolo[1,5-a]pyridin-2-amine;
(S)-5-(pyrrolidin-2-ylmethoxy)-N-(4-(trifluoromethyl)phenyl)-[1,2,4]triazolo[1,5-a]pyridin-2-amine;

3-(2-(4-(trifluoromethyl)phenylamino)-[1,2,4]triazolo[1,5-a]pyridin-5-yloxy)propan-1-ol;
cis-6-(5-(4-hydroxycyclohexylamino)-[1,2,4]triazolo[1,5-a]pyridin-2-ylamino)pyridin-2-ol;
4-(5-(2-hydroxy-2-(piperidin-4-yl)ethyl)-[1,2,4]triazolo[1,5-a]pyridin-2-ylamino)-N-methylbenzamide;
5-(pyrrolidin-1-yl)-N-(4-(trifluoromethyl)phenyl)-[1,2,4]triazolo[1,5-a]pyridin-2-amine;
5-(morpholinomethyl)-N-(4-(trifluoromethyl)phenyl)-[1,2,4]triazolo[1,5-a]pyridin-2-amine;
(R)-1-(2-(4-(trifluoromethyl)phenylamino)-[1,2,4]triazolo[1,5-a]pyridin-5-yl)piperidin-3-ol;
(S)-1-(2-(4-(trifluoromethyl)phenylamino)-[1,2,4]triazolo[1,5-a]pyridin-5-yl)piperidin-3-ol;
cis-4-(2-(3,4-difluorophenylamino)-[1,2,4]triazolo[1,5-a]pyridin-5-ylamino)cyclohexanol;
2-(4-(2-(4-(trifluoromethyl)phenylamino)-[1,2,4]triazolo[1,5-a]pyridin-5-yl)pyridin-2-ylamino)ethanol;
cis-4-(2-(6-morpholinopyridin-3-ylamino)-[1,2,4]triazolo[1,5-a]pyridin-5-ylamino)cyclohexanol;
cis-4-(2-(3,5-dimethylphenylamino)-[1,2,4]triazolo[1,5-a]pyridin-5-ylamino)cyclohexanol;
2-(2-(4-(trifluoromethyl)phenylamino)-[1,2,4]triazolo[1,5-a]pyridin-5-yloxy)ethanol;
cis-3-(5-(4-hydroxycyclohexylamino)-[1,2,4]triazolo[1,5-a]pyridin-2-ylamino)-N-methylbenzamide;
4-((2-(4-(trifluoromethyl)phenylamino)-[1,2,4]triazolo[1,5-a]pyridin-5-yl)methyl)pyridin-2(1H)-one;
cis-2-fluoro-5-(5-(4-hydroxycyclohexylamino)-[1,2,4]triazolo[1,5-a]pyridin-2-ylamino)benzamide;
cis-4-(2-(4-fluorophenylamino)-[1,2,4]triazolo[1,5-a]pyridin-5-ylamino)cyclohexanol;
cis-4-(2-(4-fluoro-3-methylphenylamino)-[1,2,4]triazolo[1,5-a]pyridin-5-ylamino)cyclohexanol;
5-(3-aminopropoxy)-N-(4-(trifluoromethyl)phenyl)-[1,2,4]triazolo[1,5-a]pyridin-2-amine;
cis-4-(2-(2-fluoropyridin-3-ylamino)-[1,2,4]triazolo[1,5-a]pyridin-5-ylamino)cyclohexanol;
(R)-(1-((2-(4-(trifluoromethyl)phenylamino)-[1,2,4]triazolo[1,5-a]pyridin-5-yl)methyl)pyrrolidin-3-yl)methanol;
(S)-(1-((2-(4-(trifluoromethyl)phenylamino)-[1,2,4]triazolo[1,5-a]pyridin-5-yl)methyl)pyrrolidin-3-yl)methanol;
N-methyl-4-(5-(pyridin-3-yl)-[1,2,4]triazolo[1,5-a]pyridin-2-ylamino)benzamide;
(R)-(1-(2-(4-(trifluoromethyl)phenylamino)-[1,2,4]triazolo[1,5-a]pyridin-5-yl)pyrrolidin-3-yl)methanol;
(S)-(1-(2-(4-(trifluoromethyl)phenylamino)-[1,2,4]triazolo[1,5-a]pyridin-5-yl)pyrrolidin-3-yl)methanol;
(R)-2-(2-(4-(trifluoromethyl)phenylamino)-[1,2,4]triazolo[1,5-a]pyridin-5-ylamino)propan-1-ol;
(S)-2-(2-(4-(trifluoromethyl)phenylamino)-[1,2,4]triazolo[1,5-a]pyridin-5-ylamino)propan-1-ol;
$N^5$-isopropyl-$N^2$-(4-(trifluoromethyl)phenyl)-[1,2,4]triazolo[1,5-a]pyridine-2,5-diamine;
cis-4-(5-(4-hydroxycyclohexylamino)-[1,2,4]triazolo[1,5-a]pyridin-2-ylamino)pyridin-2-ol;
(R)-1-(2-(4-(trifluoromethyl)phenylamino)-[1,2,4]triazolo[1,5-a]pyridin-5-yl)pyrrolidin-3-ol;
(S)-1-(2-(4-(trifluoromethyl)phenylamino)-[1,2,4]triazolo[1,5-a]pyridin-5-yl)pyrrolidin-3-ol;
(1S,2S)-2-(2-(4-(trifluoromethyl)phenylamino)-[1,2,4]triazolo[1,5-a]pyridin-5-ylamino)cyclohexanol;
(R)-1-((2-(4-(trifluoromethyl)phenylamino)-[1,2,4]triazolo[1,5-a]pyridin-5-yl)methyl)pyrrolidin-3-ol;
(S)-1-((2-(4-(trifluoromethyl)phenylamino)-[1,2,4]triazolo[1,5-a]pyridin-5-yl)methyl)pyrrolidin-3-ol;
cis-3-(5-(4-hydroxycyclohexylamino)-[1,2,4]triazolo[1,5-a]pyridin-2-ylamino)benzamide;
cis-4-(2-(3-methoxyphenylamino)-[1,2,4]triazolo[1,5-a]pyridin-5-ylamino)cyclohexanol;
cis-4-(2-(2-methoxyphenylamino)-[1,2,4]triazolo[1,5-a]pyridin-5-ylamino)cyclohexanol;
cis-3-fluoro-4-(5-(4-hydroxycyclohexylamino)-[1,2,4]triazolo[1,5-a]pyridin-2-ylamino)benzamide;
cis-3-fluoro-4-(5-(4-hydroxycyclohexylamino)-[1,2,4]triazolo[1,5-a]pyridin-2-ylamino)benzonitrile;
cis-4-(2-(6-methoxypyridin-2-ylamino)-[1,2,4]triazolo[1,5-a]pyridin-5-ylamino)cyclohexanol;
cis-4-(2-(p-tolylamino)-[1,2,4]triazolo[1,5-a]pyridin-5-ylamino)cyclohexanol;
cis-4-(2-(4-(trifluoromethyl)phenylamino)-[1,2,4]triazolo[1,5-a]pyridin-5-yloxy)cyclohexanecarboxamide;
1-(2-(4-(trifluoromethyl)phenylamino)-[1,2,4]triazolo[1,5-a]pyridin-5-yl)piperidin-4-ol;
(1-(2-(4-(trifluoromethyl)phenylamino)-[1,2,4]triazolo[1,5-a]pyridin-5-yl)piperidin-4-yl)methanol;
cis-2-fluoro-4-(5-(4-hydroxycyclohexylamino)-[1,2,4]triazolo[1,5-a]pyridin-2-ylamino)benzamide;
cis-3-(5-(4-hydroxycyclohexylamino)-[1,2,4]triazolo[1,5-a]pyridin-2-ylamino)benzonitrile;
cis-4-(2-(pyridin-2-ylamino)-[1,2,4]triazolo[1,5-a]pyridin-5-ylamino)cyclohexanol;
cis-4-(2-(m-tolylamino)-[1,2,4]triazolo[1,5-a]pyridin-5-ylamino)cyclohexanol;
cis-4-(2-(3-methyl-1H-indazol-6-ylamino)-[1,2,4]triazolo[1,5-a]pyridin-5-ylamino)cyclohexanol;
5-(piperidin-4-yloxy)-N-(4-(trifluoromethyl)phenyl)-[1,2,4]triazolo[1,5-a]pyridin-2-amine;
cis-4-(2-(4-chlorophenylamino)-[1,2,4]triazolo[1,5-a]pyridin-5-ylamino)cyclohexanol;
cis-4-(2-(3-chlorophenylamino)-[1,2,4]triazolo[1,5-a]pyridin-5-ylamino)cyclohexanol;
cis-4-(2-(3-fluorophenylamino)-[1,2,4]triazolo[1,5-a]pyridin-5-ylamino)cyclohexanol;
(1S,2R)-(2-(2-(4-(trifluoromethyl)phenylamino)-[1,2,4]triazolo[1,5-a]pyridin-5-ylamino)cyclohexyl)methanol;
cis-4-(2-(2-fluorophenylamino)-[1,2,4]triazolo[1,5-a]pyridin-5-ylamino)cyclohexanol;
2-methyl-2-(2-(4-(trifluoromethyl)phenylamino)-[1,2,4]triazolo[1,5-a]pyridin-5-ylamino)propan-1-ol;
cis-4-(2-(6-(2-hydroxypropan-2-yl)pyridin-3-ylamino)-[1,2,4]triazolo[1,5-a]pyridin-5-ylamino)cyclohexanol;
4-(5-(cis-4-aminocyclohexylamino)-[1,2,4]triazolo[1,5-a]pyridin-2-ylamino)-N-methylbenzamide;
(R)-5-(piperidin-3-yloxy)-N-(4-(trifluoromethyl)phenyl)-[1,2,4]triazolo[1,5-a]pyridin-2-amine;
(S)-5-(piperidin-3-yloxy)-N-(4-(trifluoromethyl)phenyl)-[1,2,4]triazolo[1,5-a]pyridin-2-amine;
4-(5-(cis-4-hydroxycyclohexylamino)-[1,2,4]triazolo[1,5-a]pyridin-2-ylamino)benzonitrile;
cis-4-(2-(1-methyl-1H-indazol-6-ylamino)-[1,2,4]triazolo[1,5-a]pyridin-5-ylamino)cyclohexanol;
cis-4-(2-(1H-indazol-6-ylamino)-[1,2,4]triazolo[1,5-a]pyridin-5-ylamino)cyclohexanol;
cis-4-(2-(2-(methylamino)pyridin-4-ylamino)-[1,2,4]triazolo[1,5-a]pyridin-5-ylamino)cyclohexanol;
cis-4-(2-(2-methylpyridin-4-ylamino)-[1,2,4]triazolo[1,5-a]pyridin-5-ylamino)cyclohexanol;
cis-4-(2-(5-methoxypyridin-3-ylamino)-[1,2,4]triazolo[1,5-a]pyridin-5-ylamino)cyclohexanol;

cis-5-(5-(4-hydroxycyclohexylamino)-[1,2,4]triazolo[1,5-a]pyridin-2-ylamino)nicotinamide;
cis-5-(5-(4-hydroxycyclohexylamino)-[1,2,4]triazolo[1,5-a]pyridin-2-ylamino)picolinamide;
cis-5-(5-(4-hydroxycyclohexylamino)-[1,2,4]triazolo[1,5-a]pyridin-2-ylamino)pyridin-2-ol;
5-(pyridin-4-ylmethyl)-N-(4-(trifluoromethyl)phenyl)-[1,2,4]triazolo[1,5-a]pyridin-2-amine;
(±)-trans-3-(2-(4-(trifluoromethyl)phenylamino)-[1,2,4]triazolo[1,5-a]pyridin-5-ylamino)cyclohexanol;
(1S,2S)-2-(2-(4-(trifluoromethyl)phenylamino)-[1,2,4]triazolo[1,5-a]pyridin-5-ylamino)cyclopentanol;
trans-4-((2-(4-(trifluoromethyl)phenylamino)-[1,2,4]triazolo[1,5-a]pyridin-5-ylamino)methyl)cyclohexanol;
(1S,2R)-2-(2-(4-(trifluoromethyl)phenylamino)-[1,2,4]triazolo[1,5-a]pyridin-5-ylamino)cyclopentanol;
(1R,2R)-2-(2-(4-(trifluoromethyl)phenylamino)-[1,2,4]triazolo[1,5-a]pyridin-5-ylamino)cyclopentanol;
cis-4-(2-(2-methoxypyridin-4-ylamino)-[1,2,4]triazolo[1,5-a]pyridin-5-ylamino)cyclohexanol;
2-(6-(2-(4-(trifluoromethyl)phenylamino)-[1,2,4]triazolo[1,5-a]pyridin-5-yl)-1H-benzo[d]imidazol-2-yl)propan-2-ol;
5-(1H-imidazo[4,5-b]pyridin-6-yl)-N-(4-(trifluoromethyl)phenyl)-[1,2,4]triazolo[1,5-a]pyridin-2-amine;
cis-5-(5-(4-hydroxycyclohexylamino)-[1,2,4]triazolo[1,5-a]pyridin-2-ylamino)picolinonitrile;
cis-4-(2-(4-(trifluoromethyl)phenylamino)-[1,2,4]triazolo[1,5-a]pyridin-5-ylamino)methyl)cyclohexanol;
trans-1-methyl-4-(2-(4-(trifluoromethyl)phenylamino)-[1,2,4]triazolo[1,5-a]pyridin-5-ylamino)cyclohexanol;
cis-1-methyl-4-(2-(4-(trifluoromethyl)phenylamino)-[1,2,4]triazolo[1,5-a]pyridin-5-ylamino)cyclohexanol;
cis-2-(4-(2-(4-(trifluoromethyl)phenylamino)-[1,2,4]triazolo[1,5-a]pyridin-5-ylamino)cyclohexyl)propan-2-ol;
cis-4-(5-(4-hydroxycyclohexylamino)-[1,2,4]triazolo[1,5-a]pyridin-2-ylamino)-N-methylbenzamide;
trans-4-(5-(4-hydroxycyclohexylamino)-[1,2,4]triazolo[1,5-a]pyridin-2-ylamino)-N-methylbenzamide;
4-((2-(4-(trifluoromethyl)phenylamino)-[1,2,4]triazolo[1,5-a]pyridin-5-yl)methyl)piperazin-2-one;
cis-4-(2-(pyridin-4-ylamino)-[1,2,4]triazolo[1,5-a]pyridin-5-ylamino)cyclohexanol;
cis-4-(2-(5-methylpyridin-3-ylamino)-[1,2,4]triazolo[1,5-a]pyridin-5-ylamino)cyclohexanol;
cis-4-(2-(6-methoxypyridin-3-ylamino)-[1,2,4]triazolo[1,5-a]pyridin-5-ylamino)cyclohexanol;
cis-4-(2-(6-(dimethylamino)pyridin-3-ylamino)-[1,2,4]triazolo[1,5-a]pyridin-5-ylamino)cyclohexanol;
5-(piperazin-1-ylmethyl)-N-(4-(trifluoromethyl)phenyl)-[1,2,4]triazolo[1,5-a]pyridin-2-amine;
trans-4-(5-(4-aminocyclohexylamino)-[1,2,4]triazolo[1,5-a]pyridin-2-ylamino)-N-methylbenzamide;
5-(piperidin-4-ylmethyl)-N-(4-(trifluoromethyl)phenyl)-[1,2,4]triazolo[1,5-a]pyridin-2-amine;
1-((2-(4-(trifluoromethyl)phenylamino)-[1,2,4]triazolo[1,5-a]pyridin-5-yl)methyl)piperidin-4-ol;
trans-2-(4-(2-(4-(trifluoromethyl)phenylamino)-[1,2,4]triazolo[1,5-a]pyridin-5-ylamino)cyclohexyl)propan-2-ol;
trans-4-((2-(4-(trifluoromethyl)phenylamino)-[1,2,4]triazolo[1,5-a]pyridin-5-yl)methyl)cyclohexanol;
cis-4-(2-(4-(trifluoromethyl)phenylamino)-[1,2,4]triazolo[1,5-a]pyridin-5-yl)methyl)cyclohexanol;
4-(5-(cyclopentylamino)-[1,2,4]triazolo[1,5-a]pyridin-2-ylamino)-N-methylbenzamide;
5-(2-(methoxymethyl)-1H-benzo[d]imidazol-6-yl)-N-(4-(trifluoromethyl)phenyl)-[1,2,4]triazolo[1,5-a]pyridin-2-amine;
1-(6-(2-(4-(trifluoromethyl)phenylamino)-[1,2,4]triazolo[1,5-a]pyridin-5-yl)-1H-benzo[d]imidazol-2-yl)ethanol;
cis-4-(2-(6-methylpyridin-3-ylamino)-[1,2,4]triazolo[1,5-a]pyridin-5-ylamino)cyclohexanol;
(S)—N²-(2-(2-aminoethoxy)pyridin-4-yl)-N⁵-(piperidin-3-yl)-[1,2,4]triazolo[1,5-a]pyridine-2,5-diamine;
trans-4-(2-(4-(trifluoromethyl)phenylamino)-[1,2,4]triazolo[1,5-a]pyridin-5-yloxy)cyclohexanecarboxamide;
(1R,2S)-2-(2-(4-(trifluoromethyl)phenylamino)-[1,2,4]triazolo[1,5-a]pyridin-5-ylamino)cyclopentanol;
5-((1-ethylpiperidin-4-yl)methyl)-N-(4-(trifluoromethyl)phenyl)-[1,2,4]triazolo[1,5-a]pyridin-2-amine;
6-(2-(4-(trifluoromethyl)phenylamino)-[1,2,4]triazolo[1,5-a]pyridin-5-yl)-1H-benzo[d]imidazole-2-carboxamide;
(6-(2-(4-(trifluoromethyl)phenylamino)-[1,2,4]triazolo[1,5-a]pyridin-5-yl)-1H-benzo[d]imidazol-2-yl)methanol;
cis-(4-(2-(4-(trifluoromethyl)phenylamino)-[1,2,4]triazolo[1,5-a]pyridin-5-ylamino)cyclohexyl)methanol;
(S)—N²-(6-morpholinopyridin-3-yl)-N⁵-(piperidin-3-yl)-[1,2,4]triazolo[1,5-a]pyridine-2,5-diamine;
(R)-2-phenyl-2-(2-(4-(trifluoromethyl)phenylamino)-[1,2,4]triazolo[1,5-a]pyridin-5-ylamino)ethanol;
(S)-2-phenyl-2-(2-(4-(trifluoromethyl)phenylamino)-[1,2,4]triazolo[1,5-a]pyridin-5-ylamino)ethanol;
trans-(4-(2-(4-(trifluoromethyl)phenylamino)-[1,2,4]triazolo[1,5-a]pyridin-5-ylamino)cyclohexyl)methanol;
4-(2-(4-(trifluoromethyl)phenylamino)-[1,2,4]triazolo[1,5-a]pyridin-5-ylamino)pyridin-2-ol;
4-(2-(4-fluorophenylamino)-[1,2,4]triazolo[1,5-a]pyridin-5-yl)picolinamide;
cis-4-(2-(4-fluorophenylamino)-[1,2,4]triazolo[1,5-a]pyridin-5-yloxy)cyclohexanol;
(1S,3R)-3-(2-(4-(trifluoromethyl)phenylamino)-[1,2,4]triazolo[1,5-a]pyridin-5-ylamino)cyclopentanol;
(1S,3S)-3-(2-(4-(trifluoromethyl)phenylamino)-[1,2,4]triazolo[1,5-a]pyridin-5-ylamino)cyclopentanol;
(1R,3R)-3-(2-(4-(trifluoromethyl)phenylamino)-[1,2,4]triazolo[1,5-a]pyridin-5-ylamino)cyclopentanol;
(1R,3S)-3-(2-(4-(trifluoromethyl)phenylamino)-[1,2,4]triazolo[1,5-a]pyridin-5-ylamino)cyclopentanol;
trans-5-(4-aminocyclohexyloxy)-N-(4-(trifluoromethyl)phenyl)-[1,2,4]triazolo[1,5-a]pyridin-2-amine;
cis-5-(4-aminocyclohexyloxy)-N-(4-(trifluoromethyl)phenyl)-[1,2,4]triazolo[1,5-a]pyridin-2-amine;
5-(2-((methylamino)methyl)benzo[d]oxazol-6-yl)-N-phenyl-[1,2,4]triazolo[1,5-a]pyridin-2-amine;
2-(2-(4-fluorophenylamino)-[1,2,4]triazolo[1,5-a]pyridin-5-yl)-1-(piperidin-4-yl)ethanol;
4-(5-(1H-indazol-5-yl)-[1,2,4]triazolo[1,5-a]pyridin-2-ylamino)-N-methylbenzamide;
N⁵-(azepan-3-yl)-N²-(4-fluorophenyl)-[1,2,4]triazolo[1,5-a]pyridine-2,5-diamine;
N-phenyl-5-(2-(pyrrolidin-1-ylmethyl)-1H-benzo[d]imidazol-6-yl)-[1,2,4]triazolo[1,5-a]pyridin-2-amine;
cis-4-(5-(4-hydroxycyclohexylamino)-[1,2,4]triazolo[1,5-a]pyridin-2-ylamino)benzamide;
4-((2-(4-fluorophenylamino)-[1,2,4]triazolo[1,5-a]pyridin-5-yl)methyl)piperidin-4-ol;
2-(2-(4-fluorophenylamino)-[1,2,4]triazolo[1,5-a]pyridin-5-yl)-1-phenylethanol;
4-(5-(1H-benzo[d][1,2,3]triazol-6-yl)-[1,2,4]triazolo[1,5-a]pyridin-2-ylamino)-N-methylbenzamide;

(S)—N⁵-(piperidin-3-yl)-N²-(pyridin-3-yl)-[1,2,4]triazolo[1,5-a]pyridine-2,5-diamine;
(R)—N⁵-(piperidin-3-yl)-N²-(pyridin-3-yl)-[1,2,4]triazolo[1,5-a]pyridine-2,5-diamine;
5-(4-methylisoxazol-3-yl)-N-phenyl-[1,2,4]triazolo[1,5-a]pyridin-2-amine;
N-(4-fluorophenyl)-5-(1H-indazol-6-yl)-[1,2,4]triazolo[1,5-a]pyridin-2-amine;
N-(4-fluorophenyl)-5-(2-((methylamino)methyl)-1H-benzo[d]imidazol-6-yl)-[1,2,4]triazolo[1,5-a]pyridin-2-amine;
N²-phenyl-N⁵-(tetrahydro-2H-pyran-4-yl)-[1,2,4]triazolo[1,5-a]pyridine-2,5-diamine;
5-(3-amino-1H-indazol-6-yl)-N-phenyl-[1,2,4]triazolo[1,5-a]pyridin-2-amine;
5-(2-((methylamino)methyl)-1H-benzo[d]imidazol-6-yl)-N-(4-(trifluoromethyl)phenyl)-[1,2,4]triazolo[1,5-a]pyridin-2-amine;
N-methyl-4-(5-(tetrahydrofuran-3-ylamino)-[1,2,4]triazolo[1,5-a]pyridin-2-ylamino)benzamide;
3-((2-(phenylamino)-[1,2,4]triazolo[1,5-a]pyridin-5-yl)methyl)benzamide;
2-(4-(2-(phenylamino)-[1,2,4]triazolo[1,5-a]pyridin-5-yl)pyridin-2-ylamino)ethanol;
5-(2-(2-aminoethoxy)pyridin-4-yl)-N-phenyl-[1,2,4]triazolo[1,5-a]pyridin-2-amine;
5-(2-aminopyridin-4-yl)-N-phenyl-[1,2,4]triazolo[1,5-a]pyridin-2-amine;
5-(2-(dimethylamino)pyridin-4-yl)-N-phenyl-[1,2,4]triazolo[1,5-a]pyridin-2-amine;
N¹-(4-(2-(phenylamino)-[1,2,4]triazolo[1,5-a]pyridin-5-yl)pyridin-2-yl)ethane-1,2-diamine;
(R)—N²-(isoindolin-5-yl)-N⁵-(piperidin-3-yl)-[1,2,4]triazolo[1,5-a]pyridine-2,5-diamine;
(S)—N²-(isoindolin-5-yl)-N⁵-(piperidin-3-yl)-[1,2,4]triazolo[1,5-a]pyridine-2,5-diamine;
(R)—N²-(3-amino-1H-indazol-6-yl)-N⁵-(piperidin-3-yl)-[1,2,4]triazolo[1,5-a]pyridine-2,5-diamine;
(S)—N²-(3-amino-1H-indazol-6-yl)-N⁵-(piperidin-3-yl)-[1,2,4]triazolo[1,5-a]pyridine-2,5-diamine;
4-((2-(phenylamino)-[1,2,4]triazolo[1,5-a]pyridin-5-yl)methyl)benzamide;
cis-4-(2-(4-(trifluoromethyl)phenylamino)-[1,2,4]triazolo[1,5-a]pyridin-5-ylamino)cyclohexanol;
(S)—N²-(1H-benzo[d][1,2,3]triazol-6-yl)-N⁵-(piperidin-3-yl)-[1,2,4]triazolo[1,5-a]pyridine-2,5-diamine;
(R)—N²-(1H-benzo[d][1,2,3]triazol-6-yl)-N⁵-(piperidin-3-yl)-[1,2,4]triazolo[1,5-a]pyridine-2,5-diamine;
N-methyl-4-(5-(tetrahydro-2H-pyran-4-ylamino)-[1,2,4]triazolo[1,5-a]pyridin-2-ylamino)benzamide;
5-(2-(phenylamino)-[1,2,4]triazolo[1,5-a]pyridin-5-yl)benzo[d]isoxazol-3-amine;
(R)-5-(3-amino-2-methylpropyl)-N-phenyl-[1,2,4]triazolo[1,5-a]pyridin-2-amine;
(S)-5-(3-amino-2-methylpropyl)-N-phenyl-[1,2,4]triazolo[1,5-a]pyridin-2-amine;
(R)-2-methyl-3-(2-(phenylamino)-[1,2,4]triazolo[1,5-a]pyridin-5-yl)propanamide;
(S)-2-methyl-3-(2-(phenylamino)-[1,2,4]triazolo[1,5-a]pyridin-5-yl)propanamide;
(R)—N²-(4-fluorophenyl)-N⁵-(piperidin-3-yl)-[1,2,4]triazolo[1,5-a]pyridine-2,5-diamine;
(R)—N²-(1-methyl-1H-indazol-6-yl)-N⁵-(piperidin-3-yl)-[1,2,4]triazolo[1,5-a]pyridine-2,5-diamine;
(S)—N²-(1H-indazol-6-yl)-N⁵-(piperidin-3-yl)-[1,2,4]triazolo[1,5-a]pyridine-2,5-diamine;
(S)—N²-(4-fluorophenyl)-N⁵-(piperidin-3-yl)-[1,2,4]triazolo[1,5-a]pyridine-2,5-diamine;
(S)—N²-(1-methyl-1H-indazol-6-yl)-N⁵-(piperidin-3-yl)-[1,2,4]triazolo[1,5-a]pyridine-2,5-diamine;
(R)—N²-(1H-indazol-6-yl)-N⁵-(piperidin-3-yl)-[1,2,4]triazolo[1,5-a]pyridine-2,5-diamine;
(R)—N⁵-(piperidin-3-yl)-N²-(4-(trifluoromethyl)phenyl)-[1,2,4]triazolo[1,5-a]pyridine-2,5-diamine;
(S)—N⁵-(piperidin-3-yl)-N²-(4-(trifluoromethyl)phenyl)-[1,2,4]triazolo[1,5-a]pyridine-2,5-diamine;
trans-4-(2-(phenylamino)-[1,2,4]triazolo[1,5-a]pyridin-5-ylamino)cyclohexanol;
cis-4-(2-(phenylamino)-[1,2,4]triazolo[1,5-a]pyridin-5-ylamino)cyclohexanol;
N⁵-methyl-N², N⁵-diphenyl-[1,2,4]triazolo[1,5-a]pyridine-2,5-diamine;
5-(5-methylisoxazol-3-yl)-N-phenyl-[1,2,4]triazolo[1,5-a]pyridin-2-amine;
(R)—N²-phenyl-N⁵-(pyrrolidin-3-yl)-[1,2,4]triazolo[1,5-a]pyridine-2,5-diamine;
(S)—N²-phenyl-N⁵-(pyrrolidin-3-yl)-[1,2,4]triazolo[1,5-a]pyridine-2,5-diamine;
(R)-4-(5-(piperidin-3-ylamino)-[1,2,4]triazolo[1,5-a]pyridin-2-ylamino)benzamide;
N⁵, N⁵-dimethyl-N²-phenyl-[1,2,4]triazolo[1,5-a]pyridine-2,5-diamine;
N-phenyl-5-(piperidin-3-ylmethyl)-[1,2,4]triazolo[1,5-a]pyridin-2-amine;
(R)-2-methyl-3-(2-(phenylamino)-[1,2,4]triazolo[1,5-a]pyridin-5-yl)propan-1-ol;
(S)-2-methyl-3-(2-(phenylamino)-[1,2,4]triazolo[1,5-a]pyridin-5-yl)propan-1-ol;
5-(2-(methylamino)-1H-benzo[d]imidazol-5-yl)-N-phenyl-[1,2,4]triazolo[1,5-a]pyridin-2-amine;
N-phenyl-5-(piperidin-4-ylmethyl)-[1,2,4]triazolo[1,5-a]pyridin-2-amine;
(S)-4-(5-(piperidin-3-ylamino)-[1,2,4]triazolo[1,5-a]pyridin-2-ylamino)benzamide;
N²-phenyl-N⁵-(pyridin-2-yl)-[1,2,4]triazolo[1,5-a]pyridine-2,5-diamine;
5-(1H-indazol-6-yl)-N-phenyl-[1,2,4]triazolo[1,5-a]pyridin-2-amine;
5-(2-((dimethylamino)methyl)-1H-benzo[d]imidazol-5-yl)-N-phenyl-[1,2,4]triazolo[1,5-a]pyridin-2-amine;
5-(2-((methylamino)methyl)-1H-benzo[d]imidazol-5-yl)-N-phenyl-[1,2,4]triazolo[1,5-a]pyridin-2-amine;
N-phenyl-5-(pyridin-2-yl)-[1,2,4]triazolo[1,5-a]pyridin-2-amine;
7-(2-(phenylamino)-[1,2,4]triazolo[1,5-a]pyridin-5-yl)isoquinolin-1-amine;
5-(1-(2-aminoethyl)-1H-benzo[d]imidazol-5-yl)-N-phenyl-[1,2,4]triazolo[1,5-a]pyridin-2-amine;
(1-benzylpiperidin-4-yl)(2-(phenylamino)-[1,2,4]triazolo[1,5-a]pyridin-5-yl)methanol;
trans-4-(5-(4-aminocyclohexylamino)-[1,2,4]triazolo[1,5-a]pyridin-2-ylamino)benzamide;
cis-4-(5-(4-aminocyclohexylamino)-[1,2,4]triazolo[1,5-a]pyridin-2-ylamino)benzamide;
2-(2-aminoethyl)-5-(2-(phenylamino)-[1,2,4]triazolo[1,5-a]pyridin-5-yl)isoindolin-1-one;
2-(2-aminoethyl)-6-(2-(phenylamino)-[1,2,4]triazolo[1,5-a]pyridin-5-yl)isoindolin-1-one;
5-(2-(phenylamino)-[1,2,4]triazolo[1,5-a]pyridin-5-yl)isoindolin-1-one;
(R)—N²-phenyl-N⁵-(piperidin-3-yl)-[1,2,4]triazolo[1,5-a]pyridine-2,5-diamine;

5-(3-aminopropyl)-N-phenyl-[1,2,4]triazolo[1,5-a]pyridin-2-amine;
4-(2-(phenylamino)-[1,2,4]triazolo[1,5-a]pyridin-5-yl)isoindolin-1-one;
6-(2-(phenylamino)-[1,2,4]triazolo[1,5-a]pyridin-5-yl)isoindolin-1-one;
(2-(phenylamino)-[1,2,4]triazolo[1,5-a]pyridin-5-yl)(pyridin-3-yl)methanol;
(2-(phenylamino)-[1,2,4]triazolo[1,5-a]pyridin-5-yl)(piperidin-4-yl)methanol;
5-phenoxy-N-phenyl-[1,2,4]triazolo[1,5-a]pyridin-2-amine;
(S)-2-(phenylamino)-N-(piperidin-3-yl)-[1,2,4]triazolo[1,5-a]pyridine-5-carboxamide;
5-(4-aminobutyl)-N-phenyl-[1,2,4]triazolo[1,5-a]pyridin-2-amine;
5-benzyl-N-phenyl-[1,2,4]triazolo[1,5-a]pyridin-2-amine;
(S)—$N^2$-phenyl-$N^5$-(piperidin-3-yl)-[1,2,4]triazolo[1,5-a]pyridine-2,5-diamine;
cis-$N^5$-(4-aminocyclohexyl)-$N^2$-phenyl-[1,2,4]triazolo[1,5-a]pyridine-2,5-diamine;
phenyl(2-(phenylamino)-[1,2,4]triazolo[1,5-a]pyridin-5-yl)methanone;
5-(cyclohexyloxy)-N-phenyl-[1,2,4]triazolo[1,5-a]pyridin-2-amine;
5-(3-amino-1H-indazol-5-yl)-N-phenyl-[1,2,4]triazolo[1,5-a]pyridin-2-amine;
N-phenyl-5-(piperidin-4-yl)-[1,2,4]triazolo[1,5-a]pyridin-2-amine;
N-phenyl-5-(1,2,3,6-tetrahydropyridin-4-yl)-[1,2,4]triazolo[1,5-a]pyridin-2-amine;
5-(1H-benzo[d]imidazol-6-yl)-N-phenyl-[1,2,4]triazolo[1,5-a]pyridin-2-amine;
5-(1-(2-aminoethyl)-1H-benzo[d]imidazol-6-yl)-N-phenyl-[1,2,4]triazolo[1,5-a]pyridin-2-amine;
4-(5-(piperidin-4-ylamino)-[1,2,4]triazolo[1,5-a]pyridin-2-ylamino)benzamide;
4-(2-(phenylamino)-[1,2,4]triazolo[1,5-a]pyridin-5-yl)pyridin-2-ol;
trans-$N^5$-(4-aminocyclohexyl)-$N^2$-phenyl-[1,2,4]triazolo[1,5-a]pyridine-2,5-diamine;
cis-4-(2-(phenylamino)-[1,2,4]triazolo[1,5-a]pyridin-5-ylamino)cyclohexanecarboxamide;
N-phenyl-5-(2-(piperazin-1-yl)pyridin-4-yl)-[1,2,4]triazolo[1,5-a]pyridin-2-amine;
5-(2-methoxypyridin-4-yl)-N-phenyl-[1,2,4]triazolo[1,5-a]pyridin-2-amine;
5-(1H-indazol-5-yl)-N-phenyl-[1,2,4]triazolo[1,5-a]pyridin-2-amine;
$N^2$-phenyl-$N^5$-(piperidin-4-yl)-[1,2,4]triazolo[1,5-a]pyridine-2,5-diamine;
N-phenyl-5-(pyridin-3-yl)-[1,2,4]triazolo[1,5-a]pyridin-2-amine;
5-cyclohexyl-N-phenyl-[1,2,4]triazolo[1,5-a]pyridin-2-amine;
N-(2-(phenylamino)-[1,2,4]triazolo[1,5-a]pyridin-5-yl)isobutyramide;
N-(2-(phenylamino)-[1,2,4]triazolo[1,5-a]pyridin-5-yl)acetamide;
N-phenyl-5-(pyridin-4-yl)-[1,2,4]triazolo[1,5-a]pyridin-2-amine;
$N^2$, $N^5$-diphenyl-[1,2,4]triazolo[1,5-a]pyridine-2,5-diamine;
$N^5$-isopropyl-$N^2$-phenyl-[1,2,4]triazolo[1,5-a]pyridine-2,5-diamine;
$N^2$-(3-methylbenzo[d]isoxazol-6-yl)-$N^5$-(tetrahydro-2H-pyran-4-yl)-[1,2,4]triazolo[1,5-a]pyridine-2,5-diamine;
1-methyl-5-(5-((tetrahydro-2H-pyran-4-yl)methyl)-[1,2,4]triazolo[1,5-a]pyridin-2-ylamino)-1H-benzo[d]imidazol-2(3H)-one;
4-((2-(3-(methoxymethyl)-1H-indazol-6-ylamino)-[1,2,4]triazolo[1,5-a]pyridin-5-yl)methyl)piperazin-2-one;
$N^2$-(3-methyl-[1,2,4]triazolo[4,3-a]pyridin-7-yl)-$N^5$-(tetrahydro-2H-pyran-4-yl)-[1,2,4]triazolo[1,5-a]pyridine-2,5-diamine;
N-(5-methyl-6-morpholinopyridin-3-yl)-5-((tetrahydro-2H-pyran-4-yl)methyl)-[1,2,4]triazolo[1,5-a]pyridin-2-amine;
6-(5-(difluoro(tetrahydro-2H-pyran-4-yl)methyl)-[1,2,4]triazolo[1,5-a]pyridin-2-ylamino)-3,3-dimethylindolin-2-one;
3-methyl-N-(5-((tetrahydro-2H-pyran-4-yl)methyl)-[1,2,4]triazolo[1,5-a]pyridin-2-yl)benzo[d]isoxazol-6-amine;
3-methyl-N-(5-((tetrahydro-2H-pyran-4-yl)methyl)-[1,2,4]triazolo[1,5-a]pyridin-2-yl)-[1,2,4]triazolo[4,3-a]pyridin-7-amine;
$N^2$-(3-methyl-1H-pyrazolo[3,4-b]pyridin-5-yl)-$N^5$-(tetrahydro-2H-pyran-4-yl)-[1,2,4]triazolo[1,5-a]pyridine-2,5-diamine;
5-((tetrahydro-2H-pyran-4-yl)methyl)-N-(3-(trifluoromethyl)-1H-indazol-6-yl)-[1,2,4]triazolo[1,5-a]pyridin-2-amine;
cis-4-(2-(3-methyl-1H-pyrazolo[3,4-b]pyridin-5-ylamino)-[1,2,4]triazolo[1,5-a]pyridin-5-ylamino)cyclohexanol;
$N^5$-methyl-$N^2$-(1-methyl-1H-indazol-5-yl)-$N^5$-(tetrahydro-2H-pyran-4-yl)-[1,2,4]triazolo[1,5-a]pyridine-2,5-diamine;
cis-4-(2-(3-methylbenzo[d]isoxazol-6-ylamino)-[1,2,4]triazolo[1,5-a]pyridin-5-ylamino)cyclohexanol;
3-methyl-N-(5-((tetrahydro-2H-pyran-4-yl)methyl)-[1,2,4]triazolo[1,5-a]pyridin-2-yl)-1H-pyrazolo[3,4-b]pyridin-5-amine;
cis-tert-butyl 6-(5-(4-hydroxycyclohexylamino)-[1,2,4]triazolo[1,5-a]pyridin-2-ylamino)-3,3-dimethyl-2-oxoindoline-1-carboxylate;
3,3,4-trimethyl-6-(5(((3-oxopiperazin-1-yl)methyl)-[1,2,4]triazolo[1,5-a]pyridin-2-ylamino)indolin-2-one;
$N^2$-(5-methyl-6-morpholinopyridin-3-yl)-$N^5$-(tetrahydro-2H-pyran-4-yl)-[1,2,4]triazolo[1,5-a]pyridine-2,5-diamine;
N-(3,4-dimethyl-1H-indazol-6-yl)-5-((tetrahydro-2H-pyran-4-yl)methyl)-[1,2,4]triazolo[1,5-a]pyridin-2-amine;
6-(5-(isopropylamino)-[1,2,4]triazolo[1,5-a]pyridin-2-ylamino)-3,3-dimethylindolin-2-one;
N-(1-methyl-1H-indazol-5-yl)-5-((tetrahydro-2H-pyran-4-yl)methyl)-[1,2,4]triazolo[1,5-a]pyridin-2-amine;
$N^2$-(1-methyl-1H-indazol-5-yl)-$N^5$-(tetrahydro-2H-pyran-4-yl)-[1,2,4]triazolo[1,5-a]pyridine-2,5-diamine;
N-(3-(methoxymethyl)-1H-indazol-6-yl)-5-((tetrahydro-2H-pyran-4-yl)methyl)-[1,2,4]triazolo[1,5-a]pyridin-2-amine;
cis-4-(2-(1H-pyrazolo[4,3-b]pyridin-6-ylamino)-[1,2,4]triazolo[1,5-a]pyridin-5-ylamino)cyclohexanol;
cis-4-(5-(4-hydroxycyclohexylamino)-[1,2,4]triazolo[1,5-a]pyridin-2-ylamino)-1,6-dimethylindolin-2-one;
(S)-2-methyl-3-(2-(3-methyl-1H-indazol-6-ylamino)-[1,2,4]triazolo[1,5-a]pyridin-5-yl)propan-1-ol;

cis-6-(5-(4-hydroxycyclohexylamino)-[1,2,4]triazolo[1,5-a]pyridin-2-ylamino)-1,4-dimethylindolin-2-one;
N-(4-(1H-1,2,4-triazol-3-yl)phenyl)-5-((tetrahydro-2H-pyran-4-yl)methyl)-[1,2,4]triazolo[1,5-a]pyridin-2-amine;
3,3-dimethyl-6-(5-((tetrahydrofuran-3-yl)methyl)-[1,2,4]triazolo[1,5-a]pyridin-2-ylamino)indolin-2-one;
6-(5-(2-methoxypyridin-4-yl)-[1,2,4]triazolo[1,5-a]pyridin-2-ylamino)-3,3-dimethylindolin-2-one;
4-(5-(cyclohexylamino)-[1,2,4]triazolo[1,5-a]pyridin-2-ylamino)benzamide 3,3-dimethyl-6-(5-((tetrahydrofuran-3-yl)methyl)-[1,2,4]triazolo[1,5-a]pyridin-2-ylamino)indolin-2-one;
5-(difluoro(tetrahydro-2H-pyran-4-yl)methyl)-N-(3-methyl-1H-indazol-6-yl)-[1,2,4]triazolo[1,5-a]pyridin-2-amine;
5-((1,4-dioxan-2-yl)difluoromethyl)-N-(3-methyl-1H-indazol-6-yl)-[1,2,4]triazolo[1,5-a]pyridin-2-amine;
3,3-dimethyl-6-(5-methyl-[1,2,4]triazolo[1,5-a]pyridin-2-ylamino)indolin-2-one
$N^2$-(4-(1H-1,2,4-triazol-3-yl)phenyl)-$N^5$-(tetrahydro-2H-pyran-4-yl)-[1,2,4]triazolo[1,5-a]pyridine-2,5-diamine;
6-(5-(dimethylamino)-[1,2,4]triazolo[1,5-a]pyridin-2-ylamino)-3,3-dimethylindolin-2-one cis-4-(2-(4-(1H-1,2,4-triazol-3-yl)phenylamino)-[1,2,4]triazolo[1,5-a]pyridin-5-ylamino)cyclohexanol;
cis-4-(2-(3-methyl-[1,2,4]triazolo[4,3-a]pyridin-7-ylamino)-[1,2,4]triazolo[1,5-a]pyridin-5-ylamino)cyclohexanol;
1-methyl-5-(5-(tetrahydro-2H-pyran-4-ylamino)-[1,2,4]triazolo[1,5-a]pyridin-2-ylamino)-1H-benzo[d]imidazol-2(3H)-one;
cis-5-(5-(4-hydroxycyclohexylamino)-[1,2,4]triazolo[1,5-a]pyridin-2-ylamino)-1-methyl-1H-benzo[d]imidazol-2(3H)-one; or
3,3-dimethyl-6-(5-morpholino-[1,2,4]triazolo[1,5-a]pyridin-2-ylamino)indolin-2-one.

30. A compound or pharmaceutically acceptable salt, tautomer, or stereoisomer, thereof, wherein the compound is
N-(2-((dimethylamino)methyl)-1H-benzo[d]imidazol-6-yl)-5-(3-fluorophenyl)-[1,2,4]triazolo[1,5-a]pyridin-2-amine;
5-(3-fluorophenyl)-N-(1H-indazol-5-yl)-[1,2,4]triazolo[1,5-a]pyridin-2-amine;
(6-(5-(3-fluorophenyl)-[1,2,4]triazolo[1,5-a]pyridin-2-ylamino)-1H-benzo[d]imidazol-2-yl)methanol;
5-(3-fluorophenyl)-N-(1-methyl-1H-benzo[d]imidazol-6-yl)-[1,2,4]triazolo[1,5-a]pyridin-2-amine;
3'-chloro-5'-(2-(4-(methylcarbamoyl)phenylamino)-[1,2,4]triazolo[1,5-a]pyridin-5-yl)biphenyl-2-carboxamide;
4-(5-(3-(3-aminopropyl)-5-chlorophenyl)-[1,2,4]triazolo[1,5-a]pyridin-2-ylamino)-N-methylbenzamide;
4-(5-(3-(1H-imidazol-5-yl)phenyl)-[1,2,4]triazolo[1,5-a]pyridin-2-ylamino)-N-methylbenzamide;
4-(5-(3-(3-aminopropyl)phenyl)-[1,2,4]triazolo[1,5-a]pyridin-2-ylamino)-N-methylbenzamide;
4-(5-(4-(1H-imidazol-4-yl)phenyl)-[1,2,4]triazolo[1,5-a]pyridin-2-ylamino)-N-methylbenzamide;
3-(2-(2-methyl-1H-benzo[d]imidazol-6-ylamino)-[1,2,4]triazolo[1,5-a]pyridin-5-yl)phenol;
4-(5-(3-(2-aminoethyl)phenyl)-[1,2,4]triazolo[1,5-a]pyridin-2-ylamino)-N-methylbenzamide;
4-(5-(3-fluorophenyl)-[1,2,4]triazolo[1,5-a]pyridin-2-ylamino)-N-methylbenzamide;
4-(5-(3-chlorophenyl)-[1,2,4]triazolo[1,5-a]pyridin-2-ylamino)-N-methylbenzamide;
3-(2-(benzo[d]isoxazol-6-ylamino)-[1,2,4]triazolo[1,5-a]pyridin-5-yl)phenol;
4-(5-(3-hydroxyphenyl)-[1,2,4]triazolo[1,5-a]pyridin-2-ylamino)-3-methoxy-N-methylbenzamide;
3-(2-(4-(1H-imidazol-2-yl)phenylamino)-[1,2,4]triazolo[1,5-a]pyridin-5-yl)phenol;
$N^6$-(5-phenyl-[1,2,4]triazolo[1,5-a]pyridin-2-yl)quinoline-2,6-diamine;
4-(5-(3-carbamoylphenyl)-[1,2,4]triazolo[1,5-a]pyridin-2-ylamino)-N-methylbenzamide;
3-(2-(1-methyl-1H-indazol-6-ylamino)-[1,2,4]triazolo[1,5-a]pyridin-5-yl)phenol;
4-(5-(3-methoxyphenyl)-[1,2,4]triazolo[1,5-a]pyridin-2-ylamino)-N-methylbenzamide;
4-(5-(2-fluorophenyl)-[1,2,4]triazolo[1,5-a]pyridin-2-ylamino)-N-methylbenzamide;
4-(5-(2-chlorophenyl)-[1,2,4]triazolo[1,5-a]pyridin-2-ylamino)-N-methylbenzamide;
$N^6$-(5-phenyl-[1,2,4]triazolo[1,5-a]pyridin-2-yl)-$N^3$-(piperidin-4-yl)-1H-indazole-3,6-diamine;
3-(2-(4-(aminomethyl)phenylamino)-[1,2,4]triazolo[1,5-a]pyridin-5-yl)phenol;
4-(5-(3-hydroxyphenyl)-[1,2,4]triazolo[1,5-a]pyridin-2-ylamino)benzoic acid;
6-(5-phenyl-[1,2,4]triazolo[1,5-a]pyridin-2-ylamino)quinolin-2-ol;
3-(2-(1H-indazol-6-ylamino)-[1,2,4]triazolo[1,5-a]pyridin-5-yl)phenol;
3-(2-(1-methyl-1H-benzo[d][1,2,3]triazol-6-ylamino)-[1,2,4]triazolo[1,5-a]pyridin-5-yl)phenol;
4-(2-(4-(methylcarbamoyl)phenylamino)-[1,2,4]triazolo[1,5-a]pyridin-5-yl)benzoic acid;
3-(2-(4-(methylcarbamoyl)phenylamino)-[1,2,4]triazolo[1,5-a]pyridin-5-yl)benzoic acid;
N-(2-((dimethylamino)methyl)-1H-benzo[d]imidazol-6-yl)-5-phenyl-[1,2,4]triazolo[1,5-a]pyridin-2-amine;
3-(2-(4-morpholinophenylamino)-[1,2,4]triazolo[1,5-a]pyridin-5-yl)phenol;
4-(5-(3-(aminomethyl)phenyl)-[1,2,4]triazolo[1,5-a]pyridin-2-ylamino)-N-methylbenzamide;
4-(5-(3-hydroxyphenyl)-[1,2,4]triazolo[1,5-a]pyridin-2-ylamino)-N-(1-methylpiperidin-4-yl)benzamide;
1-methyl-$N^6$-(5-phenyl-[1,2,4]triazolo[1,5-a]pyridin-2-yl)-1H-indazole-3,6-diamine;
4-(5-(3-hydroxyphenyl)-[1,2,4]triazolo[1,5-a]pyridin-2-ylamino)-N-methylbenzamide;
N-(5-phenyl-[1,2,4]triazolo[1,5-a]pyridin-2-yl)-2,3-dihydrobenzo[d]isothiazol-6-amine dione;
N-(5-methoxypyridin-3-yl)-5-phenyl-[1,2,4]triazolo[1,5-a]pyridin-2-amine;
$N^2$-(2-aminoethyl)-$N^4$-(5-phenyl-[1,2,4]triazolo[1,5-a]pyridin-2-yl)pyridine-2,4-diamine;
$N^4$-(5-phenyl-[1,2,4]triazolo[1,5-a]pyridin-2-yl)pyridine-2,4-diamine;
N-(6-morpholinopyridin-3-yl)-5-phenyl-[1,2,4]triazolo[1,5-a]pyridin-2-amine;
$N^5$-(5-phenyl-[1,2,4]triazolo[1,5-a]pyridin-2-yl)benzo[d]isoxazole-3,5-diamine;
N-(5-phenyl-[1,2,4]triazolo[1,5-a]pyridin-2-yl)benzo[d]isoxazol-5-amine;
$N^6$-(5-phenyl-[1,2,4]triazolo[1,5-a]pyridin-2-yl)benzo[d]isoxazole-3,6-diamine;
2-(2-aminoethyl)-5-(5-phenyl-[1,2,4]triazolo[1,5-a]pyridin-2-ylamino)isoindolin-1-one;
N-(2-methyl-1H-benzo[d]imidazol-5-yl)-5-phenyl-[1,2,4]triazolo[1,5-a]pyridin-2-amine;

N-(1-methyl-1H-benzo[d]imidazol-6-yl)-5-phenyl-[1,2,4]triazolo[1,5-a]pyridin-2-amine;
N-(5-phenyl-[1,2,4]triazolo[1,5-a]pyridin-2-yl)benzo[d]isoxazol-6-amine;
N-(5-phenyl-[1,2,4]triazolo[1,5-a]pyridin-2-yl)-1H-benzo[d][1,2,3]triazol-6-amine;
1-(4-(5-phenyl-[1,2,4]triazolo[1,5-a]pyridin-2-ylamino)phenyl)pyrrolidin-2-one;
4-(5-phenyl-[1,2,4]triazolo[1,5-a]pyridin-2-ylamino)picolinamide;
4-(5-phenyl-[1,2,4]triazolo[1,5-a]pyridin-2-ylamino)picolinonitrile;
N-(isoindolin-5-yl)-5-phenyl-[1,2,4]triazolo[1,5-a]pyridin-2-amine;
N-(1-methyl-1H-indazol-6-yl)-5-phenyl-[1,2,4]triazolo[1,5-a]pyridin-2-amine;
N-(1-methyl-1H-benzo[d]imidazol-5-yl)-5-phenyl-[1,2,4]triazolo[1,5-a]pyridin-2-amine;
N-(4-(1H-1,2,4-triazol-5-yl)phenyl)-5-phenyl-[1,2,4]triazolo[1,5-a]pyridin-2-amine;
$N^6$-(5-phenyl-[1,2,4]triazolo[1,5-a]pyridin-2-yl)-1H-indazole-3,6-diamine;
5-phenyl-N-(pyridin-4-yl)-[1,2,4]triazolo[1,5-a]pyridin-2-amine;
N-(5-phenyl-[1,2,4]triazolo[1,5-a]pyridin-2-yl)quinolin-6-amine;
1-(5-(5-phenyl-[1,2,4]triazolo[1,5-a]pyridin-2-ylamino)indolin-1-yl)ethanone;
N-(1H-indazol-5-yl)-5-phenyl-[1,2,4]triazolo[1,5-a]pyridin-2-amine;
5-(3-(1H-1,2,4-triazol-5-yl)phenyl)-N-phenyl-[1,2,4]triazolo[1,5-a]pyridin-2-amine;
4-(5-(3-cyanophenyl)-[1,2,4]triazolo[1,5-a]pyridin-2-ylamino)benzamide;
4-(5-(3-hydroxyphenyl)-[1,2,4]triazolo[1,5-a]pyridin-2-ylamino)benzamide;
2-fluoro-5-(5-phenyl-[1,2,4]triazolo[1,5-a]pyridin-2-ylamino)benzamide;
3-(5-phenyl-[1,2,4]triazolo[1,5-a]pyridin-2-ylamino)benzonitrile;
3-(5-phenyl-[1,2,4]triazolo[1,5-a]pyridin-2-ylamino)benzamide;
N-(1H-indazol-6-yl)-5-phenyl-[1,2,4]triazolo[1,5-a]pyridin-2-amine;
5-(5-phenyl-[1,2,4]triazolo[1,5-a]pyridin-2-ylamino)isoindolin-1-one;
5-(5-phenyl-[1,2,4]triazolo[1,5-a]pyridin-2-ylamino)pyridine-2-ol;
N-(6-methoxypyridin-3-yl)-5-phenyl-[1,2,4]triazolo[1,5-a]pyridin-2-amine;
5-(5-phenyl-[1,2,4]triazolo[1,5-a]pyridin-2-ylamino)picolinamide;
2-fluoro-4-(5-phenyl-[1,2,4]triazolo[1,5-a]pyridin-2-ylamino)benzamide;
5-phenyl-N-(pyrimidin-5-yl)-[1,2,4]triazolo[1,5-a]pyridin-2-amine;
5-phenyl-N-(pyridin-3-yl)-[1,2,4]triazolo[1,5-a]pyridin-2-amine;
4-(2-(phenylamino)-[1,2,4]triazolo[1,5-a]pyridin-5-yl)benzonitrile;
4-(5-phenyl-[1,2,4]triazolo[1,5-a]pyridin-2-ylamino)-N-(piperidin-4-yl)benzamide;
N-(3-(2-(phenylamino)-[1,2,4]triazolo[1,5-a]pyridin-5-yl)phenyl)acetamide;
N-(4-(2-(phenylamino)-[1,2,4]triazolo[1,5-a]pyridin-5-yl)phenyl)acetamide;
5-(2-fluorophenyl)-N-phenyl-[1,2,4]triazolo[1,5-a]pyridin-2-amine;
5-(3-fluorophenyl)-N-phenyl-[1,2,4]triazolo[1,5-a]pyridin-2-amine;
5-(4-aminophenyl)-N-phenyl-[1,2,4]triazolo[1,5-a]pyridin-2-amine;
3-(2-(phenylamino)-[1,2,4]triazolo[1,5-a]pyridin-5-yl)benzonitrile;
5-(3-(aminomethyl)phenyl)-N-phenyl-[1,2,4]triazolo[1,5-a]pyridin-2-amine;
4-(2-(phenylamino)-[1,2,4]triazolo[1,5-a]pyridin-5-yl)benzamide;
3-(2-(phenylamino)-[1,2,4]triazolo[1,5-a]pyridin-5-yl)benzamide;
5-(3-aminophenyl)-N-phenyl-[1,2,4]triazolo[1,5-a]pyridin-2-amine;
4-(5-phenyl-[1,2,4]triazolo[1,5-a]pyridin-2-ylamino)benzamide;
5-(4-fluorophenyl)-N-phenyl-[1,2,4]triazolo[1,5-a]pyridin-2-amine;
4-(2-(phenylamino)-[1,2,4]triazolo[1,5-a]pyridin-5-yl)phenol;
2-(2-(phenylamino)-[1,2,4]triazolo[1,5-a]pyridin-5-yl)phenol;
3-(2-(phenylamino)-[1,2,4]triazolo[1,5-a]pyridin-5-yl)phenol;
N-(4-morpholinophenyl)-5-phenyl-[1,2,4]triazolo[1,5-a]pyridin-2-amine;
$N^1$,$N^1$-dimethyl-$N^4$-(5-phenyl-[1,2,4]triazolo[1,5-a]pyridin-2-yl)benzene-1,4-diamine;
N-(3,4-dimethoxyphenyl)-5-phenyl-[1,2,4]triazolo[1,5-a]pyridin-2-amine;
5-(furan-3-yl)-N-phenyl-[1,2,4]triazolo[1,5-a]pyridin-2-amine;
5-(3-chlorophenyl)-N-phenyl-[1,2,4]triazolo[1,5-a]pyridin-2-amine; or
N,5-diphenyl-[1,2,4]triazolo[1,5-a]pyridin-2-amine.

31. A pharmaceutical composition comprising an effective amount of a compound of claim 1 or 30, or a pharmaceutically acceptable salt, tautomer, or stereoisomer thereof, and a pharmaceutically acceptable carrier, excipient or vehicle.

\* \* \* \* \*